United States Patent
Henderson et al.

(10) Patent No.: US 11,407,732 B1
(45) Date of Patent: Aug. 9, 2022

(54) TRICYCLIC DEGRADERS OF IKAROS AND AIOLOS

(71) Applicant: C4 Therapeutics, Inc., Watertown, MA (US)

(72) Inventors: James A. Henderson, Weston, MA (US); Minsheng He, Andover, MA (US); Andrew Charles Good, Watertown, MA (US); Andrew John Phillips, Arlington, MA (US)

(73) Assignee: C4 Therapeutics, Inc., Watertown, MA (US)

( * ) Notice: Subject to any disclaimer, the term of this patent is extended or adjusted under 35 U.S.C. 154(b) by 54 days.

(21) Appl. No.: 17/498,617

(22) Filed: Oct. 11, 2021

Related U.S. Application Data

(63) Continuation of application No. PCT/US2020/027678, filed on Apr. 10, 2020.

(60) Provisional application No. 62/833,107, filed on Apr. 12, 2019.

(51) Int. Cl.
*C07D 401/04* (2006.01)

(52) U.S. Cl.
CPC ................. *C07D 401/04* (2013.01)

(58) Field of Classification Search
None
See application file for complete search history.

(56) References Cited

U.S. PATENT DOCUMENTS

| | | |
|---|---|---|
| 5,635,517 A | 6/1997 | Muller et al. |
| 8,648,096 B2 | 2/2014 | Muller et al. |
| 9,732,064 B2 | 8/2017 | Muller et al. |
| 9,796,698 B2 | 10/2017 | Muller et al. |
| 9,801,868 B2 | 10/2017 | Muller et al. |
| 9,834,538 B2 | 12/2017 | Muller et al. |
| 9,920,027 B2 | 3/2018 | Ruchelman et al. |
| 11,185,543 B2 | 11/2021 | Alexander et al. |
| 2002/0147343 A1 | 10/2002 | Chen et al. |
| 2009/0298882 A1 | 12/2009 | Muller et al. |
| 2014/0356322 A1 | 12/2014 | Crews et al. |
| 2014/0377293 A1 | 12/2014 | Zeldis |
| 2018/0008574 A1 | 1/2018 | Xu et al. |
| 2019/0328722 A1 | 10/2019 | Ge et al. |
| 2020/0000776 A1 | 1/2020 | Ge et al. |
| 2020/0061033 A1 | 2/2020 | Lee et al. |
| 2021/0206743 A1 | 7/2021 | Lee et al. |

FOREIGN PATENT DOCUMENTS

| | | |
|---|---|---|
| WO | WO 2008/027542 A2 | 3/2008 |
| WO | WO 2008/033567 A1 | 3/2008 |
| WO | WO 2008/039489 A2 | 4/2008 |
| WO | WO 2008/115516 A2 | 9/2008 |
| WO | WO 2009/042177 A1 | 4/2009 |
| WO | WO 2009/139880 A1 | 11/2009 |
| WO | WO 2009/145899 A1 | 12/2009 |
| WO | WO 2010/053732 A1 | 5/2010 |
| WO | WO 2012/175481 A1 | 12/2012 |
| WO | WO 2015/085172 A2 | 6/2015 |
| WO | WO 2017/197056 A1 | 11/2017 |
| WO | WO 2017/201069 A1 | 11/2017 |
| WO | WO 2019/038717 A1 | 2/2019 |
| WO | WO 2019/148055 A1 | 8/2019 |
| WO | WO 2019/191112 A1 | 10/2019 |
| WO | WO 2019/241274 A1 | 12/2019 |
| WO | WO 2020/006233 A1 | 1/2020 |
| WO | WO 2020/006262 A1 | 1/2020 |
| WO | WO 2020/006265 A1 | 1/2020 |
| WO | WO 2020/010177 A1 | 1/2020 |
| WO | WO 2020/010227 A1 | 1/2020 |
| WO | WO 2020/012334 A1 | 1/2020 |
| WO | WO 2021/041664 A1 | 3/2021 |
| WO | WO 2021/127586 A1 | 6/2021 |

OTHER PUBLICATIONS

Agafonov, Roman et al.; "Quantitative and high throughput method for measuring complex formation between target proteins and E3 ubiquitin ligase," C4 Therapeutics Presentation (2017).
Bartlett, et al. "The evolution of thalidomide and its IMiD derivatives as anticancer agents." Nat Rev Cancer 2004, 4(4):312-322.
Berndsen et al. "New insights into ubiquitin E3 ligase mechanism" Nat. Struct. Mol. Biol. 2014, 21:301-307.
C4 Therapeutics Presentation—S. Fisher, "Degrader Drugs: From cellular activity to in vivo pharmacology Discovery on Target," 21 pages, Sep. 18, 2019.
C4 Therapeutics Presentation—Huang et al., "CAMD Methods Development in Protein Degrader Space," 41 pages; Sep. 17, 2019.
C4 Therapeutics Presentation—C. Nasveschuk, "Degrader Drug Space: What Rules?" HT-ADME Conference Cambridge, MA. Jun. 20, 2019.
Chamberlain et al. "Structure of the human cereblon-DDB1-lenalidomide complex reveals basis for responsiveness to thalidomide analogs" Nature Structural and Molecule Biology, 2014, 21(9):803-809.
Chang, X. and Stewart, K. A. "What is the functional role of the thalidomide binding protein cereblon?" Int J Biochem Mol Bio. 2011, 2(3):287-294.
Contino-Pepin, et al., "Preliminary biological evaluations of new thalidomide analogues for multiple sclerosis application", Bioorganic & Medicinal Chemistry Letters, 2009, 19(3), 878-881.
Deshaies et al. "Ring domain E3 ubiquitin ligases." Ann. Rev. Biochem. 2009, 78:399-434.
Fischer et al. "Structure of the DDB1-CRBN E3 ubiquitin ligase in complex with thalidomide" Nature 2014, 512:49-53.
Fischer et al. "The Molecular Basis of CRL4DDB2/CSA Ubiquitin Ligase Architecture, Targeting, and Activation," Cell 2011, 147:1024-1039.
Fisher, Stewart L., et al.; "Targeted protein degradation and the enzymology of degraders," Elsevier, Chemical Biology, 2018, 44:47-55.

(Continued)

*Primary Examiner* — Heidi Reese
(74) *Attorney, Agent, or Firm* — Knowles Intellectual Property Strategies, LLC

(57) ABSTRACT

Tricyclic cereblon binders for the degradation of Ikaros or Aiolos by the ubiquitin proteasome pathway for therapeutic applications are described.

30 Claims, No Drawings

(56) References Cited

OTHER PUBLICATIONS

International Application No. PCT/US2020/027678, filed Apr. 10, 2020; International Search Report and Written Opinion, dated Jul. 28, 2020 pp. 11.
Ito et al., "Identification of a Primary Target of thalidomide teratogenicity", Science, 2010, 327(5971), 1345-1350, XP0055062167.
Jacques et al. "Differentiation of anti-inflammatory and antitumorigenic properties of stabilized enantiomers of thalidomide analogs" PNAS 2015, 112:E1471-E1479.
Kronke et al. "Lenalidomide Causes Selective Degradation of IKZF1 and IKZF3 in Multiple Myeloma Cells" Science 2014, 343(6168):301-305.
Kronke et al. "Lenalidomide induces ubiquitination and degradation of CDK1 [alpha] in del(5q) MDS" Nature 2015, 523(7559):183-188.
Lu et al. "The myeloma drug lenalidomide promotes the cereblon-dependent destruction of Ikaros proteins" Science 2014, 343:305-309.
Ruchelman et al. "Isosteric analogs of lenalidomide and pomalidomide: Synthesis and biological activity" Bioorganic and Medicinal Chemistry Letters 2012, 23:360-365.
Schneekloth et al. "Chemical approaches to controlling intracellular protein degradation" Chembiochem 2005, 6(1):40-46.
Schneekloth et al. "Chemical Genetic Control of Protein Levels: Selective in Vivo Targeted Degradation" Journal of the American Chemical Society 2004, 126(12):3748-3754.
Schneekloth et al. "Targeted Intracellular Protein Degradation Induced by a Small Molecule: En Route to Chemical Proteomics" Bioorganic and Medicinal Chemistry Letters 2008, 18:5904-5908.
C4 Therapeutics Presentation—Zeid, Rhamy; Targeted protein degradation as a novel therapeutic approach, High throughput chemistry & chemical biology Gordon Research Conference; pp. 40 (2017).
Zhou et al. "Harnessing the Ubiquitination Machinery to Target the Degradation of Specific Cellular Proteins" Molecular Cell 2000, 6:751-756.
U.S. Pat. No. 10,646,575 B2, U.S. Appl. No. 16/186,339, Phillips et al., May 12, 2020.
U.S. Pat. No. 10,660,968 B2, U.S. Appl. No. 16/186,334, Phillips et al., May 26, 2020.
U.S. Pat. No. 10,849,982 B2, U.S. Appl. No. 16/186,341, Phillips et al., Dec. 1, 2020.
U.S. Pat. No. 10,905,768 B2, U.S. Appl. No. 16/872,225, Phillips et al., Feb. 2, 2021.
2019/0076539 A1, U.S. Appl. No. 16/186,333, Phillips et al., Mar. 14, 2019.
2020/0140456 A1, U.S. Appl. No. 16/721,650, Phillips et al., May 7, 2020.
2020/0207764 A1, U.S. Appl. No. 16/809,325, Norcross et al., Jul. 2, 2020.
2020/0207783 A1, U.S. Appl. No. 16/809,336, Norcross et al., Jul. 2, 2020.
2020/0207733 A1, U.S. Appl. No. 16/809,345, Norcross et al., Jul. 2, 2020.
2020/0308171 A1, U.S. Appl. No. 16/903,237, Jaeschke et al., Oct. 1, 2020.
2020/0361930 A1, U.S. Appl. No. 16/984,987, Duplessis et al., Nov. 19, 2020.
2021/0009559 A1, U.S. Appl. No. 17/031,550, Henderson et al, Jan. 14, 2021.
2021/0032245 A1, U.S. Appl. No. 17/072,896, Nasveschuk et al, Feb. 4, 2021.
2021/0070763 A1, U.S. Appl. No. 17/103,621, Nasveschuk et al, Mar. 11, 2021.
2021/0106688 A1, U.S. Appl. No. 16/882,236, Phillips et al., Apr. 15, 2021.
2021/0198256 A1, U.S. Appl. No. 17/192,634, Nasveschuk et al, Jul. 1, 2021.
U.S. Appl. No. 16/874,475, Phillips et al., filed May 14, 2020.
U.S. Appl. No. 17/107,781, Phillips et al., filed Nov. 30, 2020.
U.S. Appl. No. 17/121,389, Phillips et al., filed Dec. 14, 2020.
U.S. Appl. No. 17/164,446, Phillips et al., filed Feb. 1, 2021.
U.S. Appl. No. 17/351,935, Phillips et al., filed Jun. 18, 2021.
U.S. Appl. No. 17/465,583, Nasveschuk et al, filed Sep. 2, 2021.
Hansen, Joshua D., et al.; "Discovery of CRBN E3 Ligase Modulator CC-92480 for the Treatment of Relapsed and Refractory Multiple Myeloma," Journal of Medicinal Chemistry, J. Med. Chem. 2020, 63, 6648-6676, American Chemical Society, ACS Publications, 2020.
Matyskiela, Mary E.; et al.; "A Cereblon Modulator (CC-220) with Improved Degradation of Ikaros and Aiolos," Journal of Medicinal Chemistry, DOI: 10.1021/acs.jmedchem.6b01921, J. Med. Chem. 2018, 61, 535-542, ACS Publications, 2017.
Rok Frlan et al.; "Evaluation of US 2016/0115161A1: Isoindoline compounds and methods of their use," Expert Opinion on Therapeutic Patents, 27:6, 637-641, 2017.

TRICYCLIC DEGRADERS OF IKAROS AND AIOLOS

CROSS REFERENCE TO RELATED APPLICATIONS

This application is a continuation of International Application No. PCT/US2020/027678, filed in the U.S. Receiving Office on Apr. 10, 2020, which claims priority to U.S. Provisional Application 62/833,107, filed on Apr. 12, 2019. The entirety of each of these applications is incorporated herein for all purposes.

FIELD OF THE INVENTION

The invention provides cereblon binders for the degradation of Ikaros (IKZF1) or Aiolos (IKZF3) by the ubiquitin proteasome pathway for therapeutic applications as described further herein.

BACKGROUND

Protein degradation is a highly regulated and essential process that maintains cellular homeostasis. The selective identification and removal of damaged, misfolded, or excess proteins is achieved via the ubiquitin-proteasome pathway (UPP). The UPP is central to the regulation of almost all cellular processes, including antigen processing, apoptosis, biogenesis of organelles, cell cycling, DNA transcription and repair, differentiation and development, immune response and inflammation, neural and muscular degeneration, morphogenesis of neural networks, modulation of cell surface receptors, ion channels and the secretory pathway, the response to stress and extracellular modulators, ribosome biogenesis and viral infection.

Covalent attachment of multiple ubiquitin molecules by an E3 ubiquitin ligase to a terminal lysine residue marks the protein for proteasome degradation, where the protein is digested into small peptides and eventually into its constituent amino acids that serve as building blocks for new proteins. Defective proteasomal degradation has been linked to a variety of clinical disorders including Alzheimer's disease, Parkinson's disease, Huntington's disease, muscular dystrophies, cardiovascular disease, and cancer among others.

The Ikaros ("IKZF") family is a series of zinc-finger protein transcription factors that are important for certain physiological processes, particularly lymphocyte development (see Fan, Y. and Lu, D. "The Ikaros family of zinc-finger proteins" Acta Pharmaceutica Sinica B, 2016, 6:513-521). Ikaros ("IKZF1") was first discovered in 1992 (see Georgopoulos, K. et al. "Ikaros, an early lymphoid-specific transcription factor and a putative mediator for T cell commitment" Science, 1992, 258:802-812), and over the subsequent two decades four additional homologs have been identified: Helios ("IKZF2"), Aiolos ("IKZF3"), Eos ("IKZF4"), and Pegasus ("IKZF5") (see John, L. B., and Ward, A. C. The Ikaros gene family: transcriptional regulators of hematopoiesis and immunity" Mol Immunol, 2011, 48:1272-1278). Each homolog gene can produce several protein isoforms through alternative splicing, theoretically allowing for the generation of a large number of protein complexes through different combinations of the various homologs. Highly conserved among members of this family is a set of two $Cys_2His_2$ zinc finger motifs at the C-terminus that mediates protein interactions among various members of the protein family. Up to four zinc finger motifs at the N-terminus are present for recognition of DNA sequences; with the number of these N-terminal zinc fingers varying due to alternative splicing. Isoforms without these N-terminal zinc fingers show a dominant negative effect on transcriptional activation (see Winandy, S. et al. "A dominant mutation in the Ikaros gene leads to rapid development of leukemia and lymphoma" Cell, 1995, 83:289-299).

The distribution of various members of the Ikaros protein family within the body varies significantly. Ikaros, Helios, and Aiolos are mainly present in lymphoid cells and their corresponding progenitors, with Ikaros additionally also detected in the brain, and Ikaros and Helios also detected in erythroid cells. Eos and Pegasus are more widely spread, and found in skeletal muscle, the liver, the brain, and the heart (see Perdomo, J. et al. "Eos and Pegasus, two members of the Ikaros family of proteins with distinct DNA binding activities: J Biol Chem, 2000, 275:38347-38354; Schmitt, C. et al. "Aiolos and Ikaros: regulators of lymphocyte development, homeostasis and lymphoproliferation" Apoptosis, 2002, 7:277-284; Yoshida, T. and Georgopoulos, K. "Ikaros fingers on lymphocyte differentiation" Int J Hematol, 2014, 100:220-229).

Ikaros is important for proper lymphocyte development. Deletion of the exons encoding the first three N-terminal zinc fingers leads to mice lacking T-cells, B-cells, natural killer (NK) cells, and their progenitors. Genetic alterations in Ikaros are correlated with a poor outcome in the treatment of acute lymphoblastic leukemia (ALL). Ikaros and Aiolos are involved in the proliferation of multiple myeloma cells, suggesting a potential role in malignancy.

The drug thalidomide and its analogs lenalidomide and pomalidomide have garnered interest as immunomodulators and antineoplastics, especially in multiple myeloma (see Martiniani, R. et al. "Biological activity of lenalidomide and its underlying therapeutic effects in multiple myeloma" Adv Hematol, 2012, 2012:842945; and Terpos, E. et al. "Pomalidomide: a novel drug to treat relapsed and refractory multiple myeloma" Oncotargets and Therapy, 2013, 6:531). While the exact therapeutic mechanism of action of thalidomide, lenalidomide and pomalidomide is unknown, the compounds are used in the treatment of some cancers including multiple myeloma. There are also clinical and preclinical studies related to the treatment of renal cell carcinoma, glioblastoma, prostate cancer, melanoma, colorectal cancer, crohns disease, rheumatoid arthritis, Bechet's syndrome, breast cancer, head and neck cancer, ovarian cancer, chronic heart failure, graft-versus-host disease, and tuberculous meningitis.

Thalidomide and its analogues have been found to bind to the ubiquitin ligase cereblon and redirect its ubiquitination activity (see Ito, T. et al. "Identification of a primary target of thalidomide teratogenicity" Science, 2010, 327:1345). Cereblon forms part of an E3 ubiquitin ligase complex which interacts with damaged DNA binding protein 1, forming an E3 ubiquitin ligase complex with Cullin 4 and the E2-binding protein ROC1 (known as RBX1) where it functions as a substrate receptor to select proteins for ubiquitination.

The binding of lenalidomide to cereblon facilitates subsequent binding of cereblon to Ikaros and Aiolos, leading to their ubiquitination and degradation by the proteasome (see Lu, G. et al. "The myeloma drug lenalidomide promotes the cereblon-dependent destruction of Ikaros proteins" Science, 2014, 343:305-309; Krönke, J. et al. "Lenalidomide causes selective degradation of IKZF1 and IKZF3 in multiple myeloma cells" Science, 2014, 343:301-305).

The disclosure that thalidomide binds to the cereblon E3 ubiquitin ligase led to research to investigate incorporating thalidomide and certain derivatives into compounds for the targeted destruction of proteins. Celgene has disclosed imids for similar uses, including those in U.S. Pat. Nos. 6,045,501; 6,315,720; 6,395,754; 6,561,976; 6,561,977; 6,755,784; 6,869,399; 6,908,432; 7,141,018; 7,230,012; 7,820,697; 7,874,984; 7,959,566; 8,204,763; 8,315,886; 8,589,188; 8,626,531; 8,673,939; 8,735,428; 8,741,929; 8,828,427; 9,056,120; 9,101,621; and 9,101,622.

WO 2020/006262 filed by Dana Farber Cancer Institute discloses cereblon modulators.

PCT/US19/24094 filed by C4 Therapeutics, Inc. discloses cereblon binders for degradation of Ikaros.

It is an object of the present invention to provide new compounds, uses and processes of manufacture that cause the degradation of Ikaros or Aiolos for medical therapy, including for the treatment of hematopoietic disorders that involve abnormal cellular proliferation, including tumors and cancers.

SUMMARY OF THE INVENTION

New compounds are provided, along with their uses and manufacture that bind cereblon. It is believed that binding of the disclosed compounds to cereblon results in increased interaction of cereblon with Ikaros (IKZF1) or Aiolos (IKZF3), leading to their subsequent ubiquitination and degradation in the proteasome. Decreased levels of Ikaros or Aiolos leads to changes in transcriptional regulation of their downstream proteins. The selected compounds are found to be both potent binders of cereblon as well as showing potent inhibition of multiple myeloma cell proliferation as compared to pomalidomide.

A selected compound disclosed herein, its pharmaceutically acceptable salt, or its pharmaceutically acceptable composition can be used to can be used to treat a disorder mediated by Ikaros or Aiolos, for example, a hematopoietic malignancy such as multiple myeloma, leukemia, acute myeloid leukemia, acute lymphoblastic leukemia, chronic lymphoblastic leukemia, a myelodysplastic syndrome, or other target indications. Therefore, in one embodiment a method to treat a host (typically a human) with a disorder mediated by Ikaros or Aiolos is provided that includes administering an effective amount of the disclosed compound or its pharmaceutically acceptable salt described herein to the host, optionally as a pharmaceutically acceptable composition.

In one aspect, a compound is provided of Formula I:

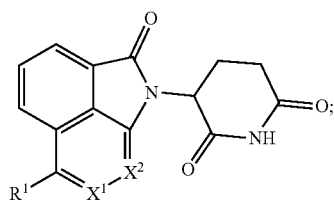

(I)

or a pharmaceutically acceptable salt, N-oxide, isotopic derivative, or prodrug thereof, optionally in a pharmaceutically acceptable carrier to form a composition;

wherein:

$X^1$ and $X^2$ are independently selected from CH and N;

$R^1$ is selected from hydrogen, halogen, cyano, nitro, alkyl, haloalkyl, —$NR^2R^{2'}$, —$OR^2$, —$NR^2R^4$, —$OR^4$, —$NR^2R^5$, —$OR^5$, —$(CR^3R^{3'})$—$R^4$, —$(CR^3R^{3'})$—$R^5$, —$(CR^3R^{3'})$—$NR^2R^4$, —$(CR^3R^{3'})$—$NR^2R^5$, —$(CR^3R^{3'})$—$OR^4$, —$(CR^3R^{3'})$—$OR^5$, —$C(O)R^4$, —$SR^4$, —$SR^5$, —$S(O)R^4$, and —$S(O)_2R^4$;

$R^2$ and $R^{2'}$ are independently selected at each occurrence from hydrogen, alkyl, haloalkyl, cycloalkyl, heterocycle, aryl, heteroaryl, —$C(O)R^8$, —$C(O)OR^8$, —$C(O)$—$NR^8R^{8'}$, —$S(O)R^8$, —$SO_2R^8$, —$SO_2$—$OR^8$, and —$SO_2$—$NR^8R^{8'}$;

$R^3$ is selected from hydrogen, halogen, alkyl, haloalkyl, —$OR^8$, and —$NR^8R^{8'}$;

$R^{3'}$ is selected from hydrogen, halogen, alkyl, and haloalkyl;

or $R^3$ and $R^{3'}$ can be brought together with the carbon to which they are attached to form a 3- to 6-membered cycloalkyl ring;

$R^4$ is selected from cycloalkyl, heterocycle, aryl, and heteroaryl, wherein each $R^4$ is optionally substituted with one group selected from $R^6$, and wherein each $R^4$ is also optionally substituted with 1, 2, 3, or 4 groups independently selected from $R^7$;

$R^5$ is —$C(O)R^6$;

$R^6$ is selected from alkyl, cycloalkyl, heterocycle, aryl, and heteroaryl, wherein each $R^6$ is optionally substituted with 1, 2, 3, or 4 groups independently selected from $R^9$;

or $R^6$ is selected from alkyl, cycloalkyl, heterocycle, aryl, heteroaryl, —CO-alkyl, —CO-cycloalkyl, —CO-heterocycle, —CO-aryl, —CO-heteroaryl, —O-alkyl, —O-cycloalkyl, —O-heterocycle, —O-aryl, —O-heteroaryl, —$NR^2$-alkyl, —$NR^2$-cycloalkyl, —$NR^2$-heterocycle, —$NR^2$-aryl, and —$NR^2$-heteroaryl, wherein each $R^6$ is optionally substituted with 1, 2, 3, or 4 groups independently selected from $R^9$;

$R^7$ is independently selected at each occurrence from hydrogen, halogen, hydroxyl, cyano, nitro, alkyl, haloalkyl, alkenyl, alkynyl, cycloalkyl, heterocycle, aryl, heteroaryl, —$OR^8$, —$NR^8R^{8'}$, —$C(O)R^8$, —$C(O)OR^8$, —$C(O)$—$NR^8R^{8'}$, —$OC(O)R^8$, —$NR^2$—$C(O)R^8$, —$S(O)R^8$, —$SO_2R^8$, —$SO_2$—$OR^8$, and —$SO_2$—$NR^8R^{8'}$;

or two $R^7$ on the same carbon may be brought together to form an oxo group;

$R^8$ and $R^{8'}$ are independently selected at each occurrence from hydrogen, alkyl, haloalkyl, alkenyl, alkynyl, cycloalkyl, heterocycle, aryl, and heteroaryl;

$R^9$ is independently selected at each occurrence from hydrogen, halogen, cyano, nitro, $R^{10}$, —$CH_2R^{10}$, —$OR^{10}$, —$NR^2R^{10}$, —$C(O)R^{10}$, —$C(O)CH_2R^{10}$, —$C(O)CH_2OR^{10}$, —$C(O)CH_2NR^2R^{10}$, —$OC(O)R^{10}$, —$NR^2$—$C(O)R^{10}$, —$C(O)OR^{10}$, —$C(O)NR^2R^{10}$, —$S(O)R^{10}$, —$SO_2R^{10}$, $SO_2CH_2R^{10}$, —$SO_2CH_2OR^{10}$, —$SO_2CH_2NR^2R^{10}$, —$NR^2SO_2R^{10}$, —$SO_2$—$OR^{10}$, and —$SO_2$—$NR^2R^{10}$, $R^{10}$ is selected from alkyl, haloalkyl, alkenyl, alkynyl, cycloalkyl, heterocycle, aryl, and heteroaryl, wherein each $R^{10}$ is optionally substituted with 1, 2, 3, or 4 groups independently selected from $R^{11}$; and $R^{11}$ is selected from: hydrogen; halogen; hydroxyl; cyano; nitro; alkyl; haloalkyl; alkenyl optionally substituted with an aryl or heteroaryl group; alkynyl optionally substituted with an aryl or heteroaryl group; cycloalkyl; heterocycle; aryl optionally substituted with 1, 2, 3, or 4 halogen, alkyl, or —$OR^8$ groups; heteroaryl optionally substituted with 1, 2, 3, or 4 halogen, alkyl, or —$OR^8$ groups; —$CH_2$aryl optionally substituted with 1, 2, 3, or 4 halogen, alkyl, or —$OR^8$ groups; —$CH_2$heteroaryl optionally substituted with 1, 2, 3, or 4 halogen, alkyl, or —$OR^8$ groups; —$OR^8$; —$NR^8R^{8'}$; —$C(O)R^8$; —$C(O)OR^8$; —$C(O)$—$NR^8R^{8'}$; —$C(O)CH_2R^8$;

—C(O)CH$_2$OR$^8$; —C(O)CH$_2$—NR$^8$R$^{8'}$; —OC(O)R$^8$; —NR$^2$—C(O)R$^8$; —CH$_2$—OC(O)R$^8$; —CH$_2$—NR$^2$—C(O)R$^8$; —S(O)R$^8$; —SO$_2$R$^8$; —SO$_2$—OR$^8$; and —SO$_2$—NR$^8$R$^{8'}$;

or two R$^{11}$ groups on the same carbon may be brought together to form an oxo group.

or R$^{11}$ is independently selected at each occurrence from: halogen; hydroxyl; cyano; nitro; alkyl; haloalkyl; alkenyl; alkynyl; cycloalkyl; heterocycle; aryl; heteroaryl; —CH$_2$aryl; —CH$_2$heteroaryl; —OR; —NR$^8$R$^{8'}$; —C(O)R$^8$; —C(O)OR$^8$; —C(O)—NR$^8$R$^{8'}$; —C(O)CH$_2$R$^8$; —C(O)CH$_2$OR$^8$; —C(O)CH$_2$—NR$^8$R$^{8'}$; —OC(O)R$^8$; —NR$^2$—C(O)R$^8$; —CH$_2$—OC(O)R$^8$; —CH$_2$—NR$^2$—C(O)R$^8$; —S(O)R$^8$; —SO$_2$R$^8$; —SO$_2$—OR$^8$; oxo, and —SO$_2$—NR$^8$R$^{8'}$; each of which R$^{11}$ groups is optionally substituted with 1, 2, 3, or 4, groups independently selected from R$^{12}$; and R$^{12}$ is independently selected at each occurrence from: halogen; hydroxyl; cyano; nitro; alkyl; haloalkyl; alkenyl; alkynyl; cycloalkyl; heterocycle; aryl; heteroaryl; —CH$_2$aryl; —CH$_2$heteroaryl; —OR$^8$; —NR$^8$R$^{8'}$; —C(O)R$^8$; —C(O)OR$^8$; —C(O)—NR$^8$R$^{8'}$; —C(O)CH$_2$R$^8$; —C(O)CH$_2$OR$^8$; —C(O)CH$_2$—NR$^8$R$^{8'}$; —OC(O)R$^8$; —NR$^2$—C(O)R$^8$; —CH$_2$—OC(O)R$^8$; —CH$_2$—NR$^2$—C(O)R$^8$; —S(O)R$^8$; —SO$_2$R$^8$; —SO$_2$—OR$^8$; and —SO$_2$—NR$^8$R$^{8'}$.

In one embodiment, the compound of Formula I is selected from Formula I-a, Formula I-b, and Formula I-c:

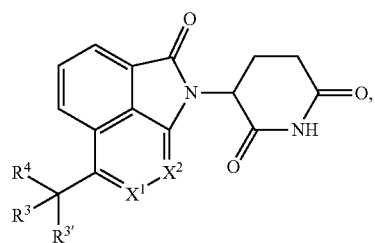

(I-a)

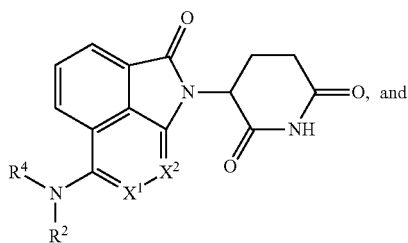

(I-b)

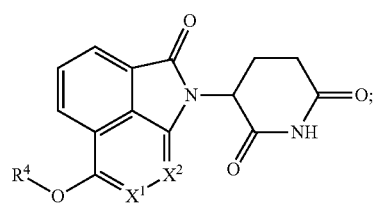

(I-c)

wherein all variables are as defined herein.

In another embodiment, the compound of Formula I is selected from Formula I-d, Formula I-e, Formula I-f, and Formula I-g:

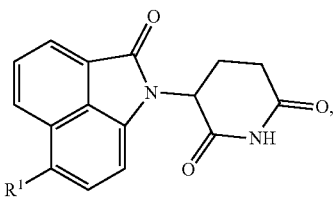

(I-d)

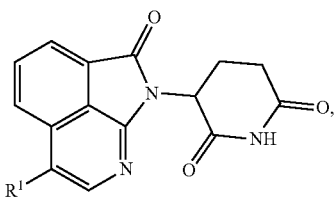

(I-e)

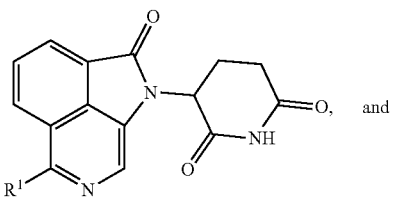

(I-f)

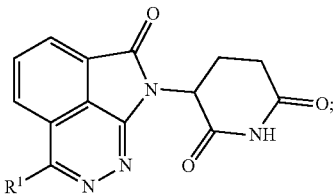

(I-g)

wherein all variables are as defined herein.

In another aspect, the compound of Formula I is selected from Formula I-h:

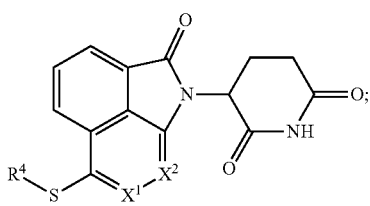

(I-h)

wherein all variables are as defined herein.

In one aspect a compound of Formula (II) is provided:

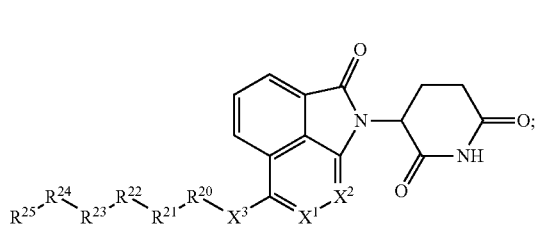

(II)

or a pharmaceutically acceptable salt, N-oxide, isotopic derivative, or prodrug thereof, optionally in a pharmaceutically acceptable carrier to form a composition;

wherein:

$X^3$ is selected from bond, $NR^2$, $C(R^3R^{3'})$, O, C(O), C(S), S, S(O), and $S(O)_2$; $R^{20}$, $R^{21}$, $R^{22}$, $R^{23}$, and $R^{24}$ are independently at each occurrence selected from the group consisting of a bond, alkyl, —C(O)—, —C(O)O—, —OC(O)—, —SO$_2$—, —S(O)—, —C(S)—, —C(O)NR$^2$—, —NR$^2$C(O)—, —O—, —S—, —NR$^2$—, —P(O)(R$^{28}$)—, —P(O)—, alkene, alkyne, haloalkyl, aryl, heterocycle, heteroaryl, bicycle, and carbocycle; each of which is optionally substituted with 1, 2, 3, or 4 substituents independently selected from $R^{40}$; and wherein $R^{20}$, $R^{21}$, $R^2$, $R^{23}$, and $R^{24}$ cannot be selected in such a way that i. —C(O)—, —C(O)O—, —OC(O)—, —SO$_2$—, —S(O)—, —P(O)(R$^{28}$)—, —P(O)—, and —C(S)— moieties are adjacent to each other; or ii. —O—, —S—, or —NR$^2$— moieties are adjacent to each other; or iii. moieties are otherwise selected in an order that an unstable molecule results (as defined as producing a molecule that has a shelf life at ambient temperature of less than about four months (or alternatively less than about six or five months) due to decomposition caused by the selection and order of the moieties $R^{20}$, $R^{21}$, $R^2$, $R^{23}$, and $R^{24}$);

$R^{25}$ is selected from hydrogen, alkyl, alkene, alkyne, halogen, hydroxyl, alkoxy, azide, amino, cyano, —OR$^2$, —NR$^2$R$^{2'}$, —NR$^2$SO$_2$R$^{28}$, —OSO$_2$R$^{28}$, —SO$_2$R$^{28}$, haloalkyl, aryl, heteroaryl, heterocycle, bicycle, and cycloalkyl; each of which $R^{21}$ groups is optionally substituted with 1, 2, 3, or 4 groups independently selected from $R^{12}$;

$R^{28}$ independently selected at each occurrence from hydrogen, —NR$^2$R$^{2'}$, —OR$^2$, —SR$^2$, alkyl, haloalkyl, alkenyl, alkynyl, cycloalkyl, heterocycle, aryl, and heteroaryl;

$R^{40}$ is independently at each occurrence selected from the group consisting of hydrogen, alkyl, alkene, alkyne, halogen, hydroxyl, alkoxy, azide, amino, cyano, —NR$^2$R$^{2'}$, —NR$^2$SO$_2$R$^{28}$, —OSO$_2$R$^{28}$, —SO$_2$R$^{28}$, haloalkyl, aryl, heteroaryl, heterocycle, and cycloalkyl; each of which $R^{40}$ groups is optionally substituted with 1, 2, 3, or 4 groups independently selected from $R^{12}$;

or two $R^{40}$s together form an oxo group;

and wherein all other variables are as defined herein.

In one embodiment, the compounds described herein bind to cereblon, increasing the interaction between cereblon and Ikaros (IKZF1) or Aiolos (IKZF3) and leading to the subsequent ubiquitination and degradation of the protein in the proteasome.

In one embodiment, the compound of the present invention selectively degrades IKZF1 and/or 3 over one or more of IKZF2 and/or 4 and/or 5.

In some embodiments, therefore, based on this discovery, compounds and methods are provided for the treatment of a patient with a disorder mediated by Ikaros (IKZF1) or Aiolos (IKZF3). Ikaros (IKZF1) or Aiolos (IKZF3) are targeted for selective degradation by a method that includes administering an effective amount of a selective compound as described herein alone or in combination with another active agent to a patient (typically a human) in need thereof, optionally in a pharmaceutically acceptable carrier to form a composition. In one embodiment, the disorder is a lymphoid disorder. In one embodiment, the disorder is a leukemia. In one embodiment, the disorder is a lymphoid leukemia. In one embodiment, the disorder is a lymphoblastic leukemia. In some embodiments, the disorder is a hematological malignancy, for example multiple myeloma, a myelodysplastic syndrome such as 5q-syndrome, acute lymphoblastic leukemia, chronic lymphocytic leukemia, Hodgkin's lymphoma, non-Hodgkin's lymphoma, or chronic lymphocytic leukemia. In another embodiment, a selected compound of the present invention is administered to achieve immunomodulation and to reduce angiogenesis.

In other embodiments, compounds and methods are presented for the treatment of a disorder including, but not limited to, benign growth, neoplasm, tumor, cancer, abnormal cellular proliferation, immune disorders, inflammatory disorders, graft-versus-host rejection, viral infection, bacterial infection, an amyloid-based proteinopathy, a proteinopathy, or a fibrotic disorder. Further, other disorders are described below which can be treated with an effective amount of a compound described herein.

In certain embodiments, any of the compounds described herein have at least one desired isotopic substitution of an atom, at an amount about the natural abundance of the isotope, i.e., enriched. In one embodiment, the compound includes a deuterium or multiple deuterium atoms.

Other features and advantages of the present invention will be apparent from the following detailed description and claims.

Thus, the present invention includes at least the following features:

(a) a compound of Formula I or Formula II as described herein, or a pharmaceutically acceptable salt, isotopic derivative (including a deuterated derivative), or prodrug thereof, (b) a compound of Formula I or Formula II as described herein, or a pharmaceutically acceptable salt, isotopic derivative, or prodrug thereof, for the treatment of a disorder that is mediated by Ikaros or Aiolos;

(c) use of a compound of Formula I or Formula II as described herein, or a pharmaceutically acceptable salt, isotopic derivative, or prodrug thereof, in an effective amount in the treatment of a patient, typically a human, with any one of the disorders described herein, including those mediated by Ikaros or Aiolos;

(d) use of a compound of Formula I or Formula II as described herein, or a pharmaceutically acceptable salt, isotopic derivative, or prodrug thereof in the manufacture of a medicament for the treatment of a medical disorder sensitive to the compound, as further described herein;

(e) a method of manufacturing a medicament for the treatment of a disorder described herein in a host characterized in that a compound of Formula I or Formula II is used in the manufacture;

(f) a compound of Formula I or Formula II as described herein, or a pharmaceutically acceptable salt, isotopic derivative, or prodrug thereof, for the treatment of cancer in a host, including any of the cancers described herein;

(g) use of a compound of Formula I or Formula II as described herein, or a pharmaceutically acceptable salt, isotopic derivative, or prodrug thereof in the manufacture of a medicament for the treatment of cancer, including any of the cancers described herein;

(h) a method of manufacturing a medicament for the treatment of cancer in a host, including any of the cancers described herein, characterized in that a compound of Formula I or Formula II is used in the manufacture;

(i) a compound of Formula I or Formula II as described herein, or a pharmaceutically acceptable salt, isotopic derivative, or prodrug thereof, for the treatment of a tumor in a host, including any of the tumors described herein;

(j) use of a compound of Formula I or Formula II as described herein, or a pharmaceutically acceptable salt, isotopic derivative, or prodrug thereof in the manufacture of a medicament for the treatment of a tumor, including any of the tumors described herein;

(k) a method of manufacturing a medicament for the treatment of a tumor in a host, including any of the tumors described herein, characterized in that a compound of Formula I or Formula II is used in the manufacture;

(l) a compound of Formula I or Formula II as described herein, or a pharmaceutically acceptable salt, isotopic derivative, or prodrug thereof, for the treatment of an immune, autoimmune, or inflammatory disorder in a host;

(m) use of a compound of Formula I or Formula II as described herein, or a pharmaceutically acceptable salt, isotopic derivative, or prodrug thereof in the manufacture of a medicament for the treatment of an immune, autoimmune, or inflammatory disorder;

(n) a method of manufacturing a medicament for the treatment of an immune, autoimmune, or inflammatory disorder in a host characterized in that a compound of Formula I or Formula II is used in the manufacture;

(o) a compound of Formula I or Formula II as described herein, or a pharmaceutically acceptable salt, isotopic derivative, or prodrug thereof, for the treatment of a hematological malignancy such as multiple myeloma, leukemia, lymphoblastic leukemia, chronic lymphocytic leukemia, Hodgkin's lymphoma, or non-Hodgkin's lymphoma;

(p) use of a compound of Formula I or Formula II as described herein, or a pharmaceutically acceptable salt, isotopic derivative, or prodrug thereof in the manufacture of a medicament for the treatment of a hematological malignancy such as multiple myeloma, leukemia, lymphoblastic leukemia, chronic lymphocytic leukemia, Hodgkin's lymphoma, or non-Hodgkin's lymphoma;

(q) a method of manufacturing a medicament for the treatment of a hematological malignancy in a host such as multiple myeloma, leukemia, lymphoblastic leukemia, chronic lymphocytic leukemia, Hodgkin's lymphoma, or non-Hodgkin's lymphoma, characterized in that a compound of Formula I or Formula II is used in the manufacture;

(r) a pharmaceutical composition comprising an effective host-treating amount of a compound of Formula I or Formula II as described herein or a pharmaceutically acceptable salt, isotopic derivative, or prodrug thereof with a pharmaceutically acceptable carrier or diluent;

(s) a compound a described herein as a mixture of enantiomers or diastereomers (as relevant), including the racemate;

(t) a compound as described herein in enantiomerically or diastereomerically (as relevant) enriched form, including an isolated enantiomer or diastereomer (i.e. greater than 85, 90, 95, 97, or 99% pure); and (u) a process for the e of therapeutic products that contain an effective amount of a compound of Formula I or Formula II as described herein.

DETAILED DESCRIPTION OF THE INVENTION

I. Definitions

Unless otherwise defined, all technical and scientific terms used herein have the same meaning as commonly understood by one of ordinary skill in the art to which this application belongs. In the specification, singular forms also include the plural unless the context clearly dictates otherwise. Although methods and materials similar or equivalent to those described herein can be used in the practice and testing of the present application, suitable methods and materials are described below. All publications, patent applications, patents, and other references mentioned herein are incorporated by reference. The references cited herein are not admitted to be prior art to the claimed application. In the case of conflict, the present specification, including definitions, will control. In addition, the materials, methods, and examples are illustrative only and are not intended to be limiting.

Compounds are described using standard nomenclature. Unless defined otherwise, all technical and scientific terms used herein have the same meaning as is commonly understood by one of skill in the art to which this invention belongs.

In one embodiment of each compound described herein, the compound may be in the form of a racemate, enantiomer, mixture of enantiomers, diastereomer, mixture of diastereomers, tautomer, N-oxide, or isomer, such as a rotamer, as if each is specifically described unless specifically excluded by context.

The terms "a" and "an" do not denote a limitation of quantity, but rather denote the presence of at least one of the referenced item. The term "or" means "and/or". Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of examples, or exemplary language (e.g., "such as"), is intended merely to better illustrate the invention and does not pose a limitation on the scope of the invention unless otherwise claimed.

The present invention includes compounds described herein with at least one desired isotopic substitution of an atom, at an amount above the natural abundance of the isotope, i.e., enriched. Isotopes are atoms having the same atomic number but different mass numbers, i.e., the same number of protons but a different number of neutrons. If isotopic substitutions are used, the common replacement is at least one deuterium for hydrogen.

More generally, examples of isotopes that can be incorporated into compounds of the invention include isotopes of hydrogen, carbon, nitrogen, oxygen, fluorine, and chlorine such as $^2$H, $^3$H, $^{11}$C, $^{13}$C, $^{14}$C, $^{15}$N, $^{17}$O, $^{18}$O, $^{18}$F, $^{35}$S, and $^{36}$Cl respectively. In one non-limiting embodiment, isotopically labelled compounds can be used in metabolic studies (with, for example $^{14}$C), reaction kinetic studies (with, for example $^2$H or $^3$H), detection or imaging techniques, such as positron emission tomography (PET) or single-photon emission computed tomography (SPECT) including drug or substrate tissue distribution assays, or in radioactive treatment of patients. Additionally, any hydrogen atom present in the compound of the invention may be substituted with an $^{18}$F atom, a substitution that may be particularly desirable for PET or SPECT studies. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

By way of general example and without limitation, isotopes of hydrogen, for example, deuterium ($^2H$) and tritium ($^3H$) may be used anywhere in described structures that achieves the desired result. Alternatively or in addition, isotopes of carbon, e.g., $^{13}C$ and $^{14}C$, may be used.

Isotopic substitutions, for example deuterium substitutions, can be partial or complete. Partial deuterium substitution means that at least one hydrogen is substituted with deuterium. In certain embodiments, the isotope is 90, 95 or 99% or more enriched in an isotope at any location of interest. In one non-limiting embodiment, deuterium is 90, 95 or 99% enriched at a desired location.

In one non-limiting embodiment, the substitution of a hydrogen atom for a deuterium atom can be provided in any compound described herein. For example, when any of the groups are, or contain for example through substitution, methyl, ethyl, or methoxy, the alkyl residue may be deuterated (in non-limiting embodiments, $CDH_2$, $CD_2H$, $CD_3$, $CH_2CD_3$, $CD_2CD_3$, $CHDCH_2D$, $CH_2CD_3$, $CHDCHD_2$, $OCDH_2$, $OCD_2H$, or $OCD_3$ etc.). In certain other embodiments, when two substituents are combined to form a cycle the unsubstituted carbons may be deuterated. In one embodiment, at least one deuterium is placed on an atom that has a bond which is broken during metabolism of the compound in vivo, or is one, two or three atoms remote form the metabolized bond (e.g., which may be referred to as an α, β or γ, or primary, secondary or tertiary isotope effect).

The compounds of the present invention may form a solvate with a solvent (including water). Therefore, in one non-limiting embodiment, the invention includes a solvated form of the compounds described herein. The term "solvate" refers to a molecular complex of a compound of the present invention (including a salt thereof) with one or more solvent molecules. Non-limiting examples of solvents are water, ethanol, isopropanol, dimethyl sulfoxide, acetone and other common organic solvents. The term "hydrate" refers to a molecular complex comprising a compound of the invention and water. Pharmaceutically acceptable solvates in accordance with the invention include those wherein the solvent may be isotopically substituted, e.g. $D_2O$, $d_6$-acetone, $d_6$-DMSO. A solvate can be in a liquid or solid form.

A dash ("-") that is not between two letters or symbols is used to indicate a point of attachment for a substituent. For example, —(C═O)NH$_2$ is attached through carbon of the keto (C═O) group.

"Alkyl" is a branched or straight chain saturated aliphatic hydrocarbon group. In one non-limiting embodiment, the alkyl group contains from 1 to about 12 carbon atoms, more generally from 1 to about 6 carbon atoms or from 1 to about 4 carbon atoms. In one non-limiting embodiment, the alkyl contains from 1 to about 8 carbon atoms. In certain embodiments, the alkyl is $C_1$-$C_2$, $C_1$-$C_3$, $C_1$-$C_4$, $C_1$-$C_6$, or $C_1$-$C_6$. The specified ranges as used herein indicate an alkyl group having each member of the range described as an independent species. For example, the term $C_1$-$C_6$ alkyl as used herein indicates a straight or branched alkyl group having from 1, 2, 3, 4, 5, or 6 carbon atoms and is intended to mean that each of these is described as an independent species.

For example, the term $C_1$-$C_4$ alkyl as used herein indicates a straight or branched alkyl group having from 1, 2, 3, or 4 carbon atoms and is intended to mean that each of these is described as an independent species. Examples of alkyl include, but are not limited to, methyl, ethyl, n-propyl, isopropyl, n-butyl, isobutyl, sec-butyl, t-butyl, n-pentyl, isopentyl, tert-pentyl, neopentyl, n-hexyl, 2-methylpentane, 3-methylpentane, 2,2-dimethylbutane, and 2,3-dimethylbutane.

"Alkenyl" is a linear or branched aliphatic hydrocarbon groups having one or more carbon-carbon double bonds that may occur at a stable point along the chain. The specified ranges as used herein indicate an alkenyl group having each member of the range described as an independent species, as described above for the alkyl moiety. In one non-limiting embodiment, the alkenyl contains from 2 to about 12 carbon atoms, more generally from 2 to about 6 carbon atoms or from 2 to about 4 carbon atoms. In certain embodiments the alkenyl is $C_2$, $C_2$-$C_3$, $C_2$-$C_4$, $C_2$-$C_5$, or $C_2$-$C_6$. Examples of alkenyl radicals include, but are not limited to ethenyl, propenyl, allyl, propenyl, butenyl and 4-methylbutenyl. The term "alkenyl" also embodies "cis" and "trans" alkenyl geometry, or alternatively, "E" and "Z" alkenyl geometry. The term "Alkenyl" also encompasses cycloalkyl or carbocyclic groups possessing at least one point of unsaturation.

"Alkynyl" is a branched or straight chain aliphatic hydrocarbon group having one or more carbon-carbon triple bonds that may occur at any stable point along the chain. The specified ranges as used herein indicate an alkynyl group having each member of the range described as an independent species, as described above for the alkyl moiety. In one non-limiting embodiment, the alkynyl contains from 2 to about 12 carbon atoms, more generally from 2 to about 6 carbon atoms or from 2 to about 4 carbon atoms. In certain embodiments the alkynyl is $C_2$, $C_2$-$C_3$, $C_2$-$C_4$, $C_2$-$C_5$, or $C_2$-$C_6$. Examples of alkynyl include, but are not limited to, ethynyl, propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl and 5-hexynyl.

"Halo" and "Halogen" is independently fluorine, chlorine, bromine or iodine.

"Haloalkyl" is a branched or straight-chain alkyl groups substituted with 1 or more halo atoms described above, up to the maximum allowable number of halogen atoms. Examples of haloalkyl groups include, but are not limited to, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Perhaloalkyl" means an alkyl group having all hydrogen atoms replaced with halogen atoms. Examples include but are not limited to, trifluoromethyl and pentafluoroethyl.

As used herein, "aryl" refers to a radical of a monocyclic or polycyclic (e.g., bicyclic or tricyclic) 4n+2 aromatic ring system (e.g., having 6, 10, or 14 x electrons shared in a cyclic array) having 6-14 ring carbon atoms and zero heteroatoms provided in the aromatic ring system ("$C_{6-14}$ aryl"). In some embodiments, an aryl group has 6 ring carbon atoms ("$C_6$aryl"; e.g., phenyl). In some embodiments, an aryl group has 10 ring carbon atoms ("$C_{10}$ aryl"; e.g., naphthyl such as 1-naphthyl and 2-naphthyl). In some embodiments, an aryl group has 14 ring carbon atoms ("$C_{14}$ aryl"; e.g., anthracyl). "Aryl" also includes ring systems wherein the aryl ring, as defined above, is fused with one or more cycloalkyl or heterocycle groups wherein the radical or point of attachment is on the aryl ring, and in such instances, the number of carbon atoms continue to designate the number of carbon atoms in the aryl ring system. The one or more fused cycloalkyl or heterocycle groups can be a 4 to 7-membered saturated or partially unsaturated cycloalkyl or heterocycle groups.

The term "heterocycle" denotes saturated and partially saturated heteroatom-containing ring radicals, wherein there are 1, 2, 3, or 4 heteroatoms independently selected from nitrogen, sulfur, boron, silicone, and oxygen. Heterocyclic rings may comprise monocyclic 3-10 membered rings, as well as 5-16 membered bicyclic ring systems (which can include bridged, fused, and spiro-fused bicyclic ring systems). It does not include rings containing —O—O—, —O—S— or —S—S— portions. Examples of saturated heterocycle groups include saturated 3- to 6-membered heteromonocyclic groups containing 1 to 4 nitrogen atoms [e.g. pyrrolidinyl, imidazolidinyl, piperidinyl, pyrrolinyl, piperazinyl]; saturated 3 to 6-membered heteromonocyclic group containing 1 to 2 oxygen atoms and 1 to 3 nitrogen atoms [e.g. morpholinyl]; saturated 3 to 6-membered heteromonocyclic group containing 1 to 2 sulfur atoms and 1 to 3 nitrogen atoms [e.g., thiazolidinyl]. Examples of partially saturated heterocycle radicals include but are not limited to, dihydrothienyl, dihydropyranyl, dihydrofuryl, and dihydrothiazolyl. Examples of partially saturated and saturated heterocycle groups include but are not limited to, pyrrolidinyl, imidazolidinyl, piperidinyl, pyrrolinyl, pyrazolidinyl, piperazinyl, morpholinyl, tetrahydropyranyl, thiazolidinyl, dihydrothienyl, 2,3-dihydro-benzo[1,4]dioxanyl, indolinyl, isoindolinyl, dihydrobenzothienyl, dihydrobenzofuryl, isochromanyl, chromanyl, 1,2-dihydroquinolyl, 1,2,3,4-tetrahydro-isoquinolyl, 1,2,3,4-tetrahydro-quinolyl, 2,3,4,4a,9,9a-hexahydro-1H-3-aza-fluorenyl, 5,6,7-trihydro-1,2,4-triazolo[3,4-a]isoquinolyl, 3,4-dihydro-2H-benzo[1,4]oxazinyl, benzo[1,4]dioxanyl, 2,3-dihydro-1H-1λ'-benzo[d]isothiazol-6-yl, dihydropyranyl, dihydrofuryl and dihydrothiazolyl.

"Heterocycle" also includes groups wherein the heterocyclic radical is fused/condensed with an aryl or carbocycle radical, wherein the point of attachment is the heterocycle ring. "Heterocycle" also includes groups wherein the heterocyclic radical is substituted with an oxo group (i.e.

). For example a partially unsaturated condensed heterocyclic group containing 1 to 5 nitrogen atoms, for example, indoline or isoindoline; a partially unsaturated condensed heterocyclic group containing 1 to 2 oxygen atoms and 1 to 3 nitrogen atoms; a partially unsaturated condensed heterocyclic group containing 1 to 2 sulfur atoms and 1 to 3 nitrogen atoms; and a saturated condensed heterocyclic group containing 1 to 2 oxygen or sulfur atoms.

The term "heterocycle" also includes "bicyclic heterocycle". The term "bicyclic heterocycle" denotes a heterocycle as defined herein wherein there is one bridged, fused, or spirocyclic portion of the heterocycle. The bridged, fused, or spirocyclic portion of the heterocycle can be a carbocycle, heterocycle, or aryl group as long as a stable molecule results. Unless excluded by context the term "heterocycle" includes bicyclic heterocycles. Bicyclic heterocycle includes groups wherein the fused heterocycle is substituted with an oxo group. Non-limiting examples of bicyclic heterocycles include:

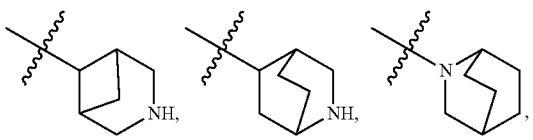

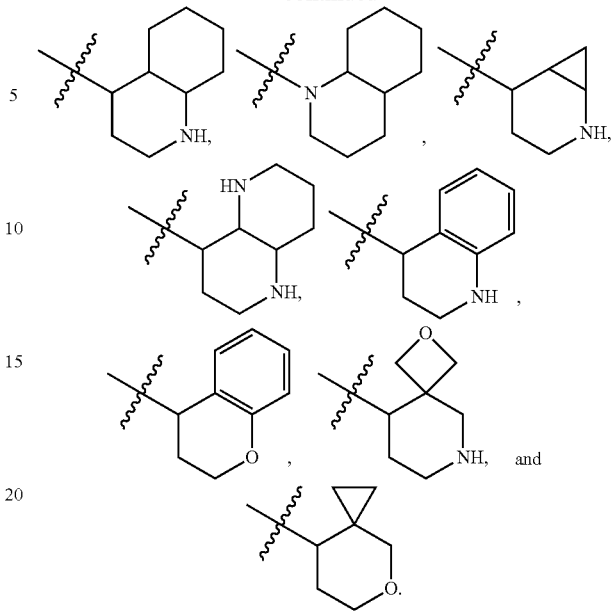

The term "heteroaryl" denotes stable aromatic ring systems that contain 1, 2, 3, or 4 heteroatoms independently selected from O, N, and S, wherein the ring nitrogen and sulfur atom(s) are optionally oxidized, and nitrogen atom(s) are optionally quaternized. Examples include but are not limited to, unsaturated 5 to 6 membered heteromonocyclyl groups containing 1 to 4 nitrogen atoms, such as pyrrolyl, imidazolyl, pyrazolyl, 2-pyridyl, 3-pyridyl, 4-pyridyl, pyrimidyl, pyrazinyl, pyridazinyl, triazolyl [e.g., 4H-1,2,4-triazolyl, 1H-1,2,3-triazolyl, 2H-1,2,3-triazolyl]; unsaturated 5- to 6-membered heteromonocyclic groups containing an oxygen atom, for example, pyranyl, 2-furyl, 3-furyl, etc.; unsaturated 5 to 6-membered heteromonocyclic groups containing a sulfur atom, for example, 2-thienyl, 3-thienyl, etc.; unsaturated 5- to 6-membered heteromonocyclic groups containing 1 to 2 oxygen atoms and 1 to 3 nitrogen atoms, for example, oxazolyl, isoxazolyl, oxadiazolyl [e.g., 1,2,4-oxadiazolyl, 1,3,4-oxadiazolyl, 1,2,5-oxadiazolyl]; unsaturated 5 to 6-membered heteromonocyclic groups containing 1 to 2 sulfur atoms and 1 to 3 nitrogen atoms, for example, thiazolyl, thiadiazolyl [e.g., 1,2,4-thiadiazolyl, 1,3,4-thiadiazolyl, 1,2,5-thiadiazolyl]. In one embodiment the "heteroaryl" group is a 8, 9, or 10 membered bicyclic ring system. Examples of 8, 9, or 10 membered bicyclic heteroaryl groups include benzofurazanyl, benzothiophenyl, benzothiazolyl, benzoxazolyl, quinazolinyl, quinoxalinyl, naphthyridinyl, quinolinyl, isoquinolinyl, benzofuranyl, indolyl, indazolyl, and benzotriazolyl.

As used herein, "carbocyclic", "carbocycle" or "cycloalkyl" includes a saturated or partially unsaturated (i.e., not aromatic) group containing all carbon ring atoms and from 3 to 14 ring carbon atoms ("$C_{3-14}$ cycloalkyl") and zero heteroatoms in the non-aromatic ring system. In some embodiments, a cycloalkyl group has 3 to 10 ring carbon atoms ("$C_{3-10}$ cycloalkyl"). In some embodiments, a cycloalkyl group has 3 to 9 ring carbon atoms ("$C_{3-9}$ cycloalkyl"). In some embodiments, a cycloalkyl group has 3 to 8 ring carbon atoms ("$C_{3-8}$ cycloalkyl"). In some embodiments, a cycloalkyl group has 3 to 7 ring carbon atoms ("$C_{3-7}$ cycloalkyl"). In some embodiments, a cycloalkyl group has 3 to 6 ring carbon atoms ("$C_{3-6}$ cycloalkyl").

In some embodiments, a cycloalkyl group has 4 to 6 ring carbon atoms ("$C_{4-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Exemplary $C_{3-6}$ cycloalkyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ cycloalkyl groups include, without limitation, the aforementioned $C_{3-6}$ cycloalkyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), and the like. Exemplary $C_{3-10}$ cycloalkyl groups include, without limitation, the aforementioned $C_{3-8}$ cycloalkyl groups as well as cyclononyl ($C_9$), cyclononenyl ($C_9$), cyclodecyl ($C_{10}$), cyclodecenyl ($C_{10}$), and the like. As the foregoing examples illustrate, in certain embodiments, the cycloalkyl group can be saturated or can contain one or more carbon-carbon double bonds. The term "cycloalkyl" also includes ring systems wherein the cycloalkyl ring, as defined above, is fused with one heterocycle, aryl or heteroaryl ring wherein the point of attachment is on the cycloalkyl ring, and in such instances, the number of carbons continue to designate the number of carbons in the carbocyclic ring system. The term "cycloalkyl" also includes ring systems wherein the cycloalkyl ring, as defined above, has a spirocyclic heterocycle, aryl or heteroaryl ring wherein the point of attachment is on the cycloalkyl ring, and in such instances, the number of carbons continue to designate the number of carbons in the carbocyclic ring system. The term "cycloalkyl" also includes bicyclic or polycyclic fused, bridged, or spiro ring systems that contain from 5 to 14 carbon atoms and zero heteroatoms in the non-aromatic ring system. Representative examples of "cycloalkyl" include, but are not limited to,

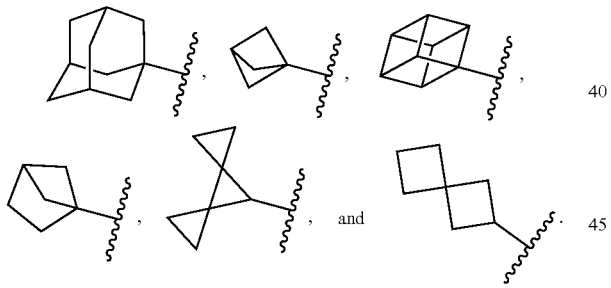

The term "bicycle" refers to a ring system wherein two rings are fused together and each ring is independently selected from carbocycle, heterocycle, aryl, and heteroaryl. Non-limiting examples of bicycle groups include:

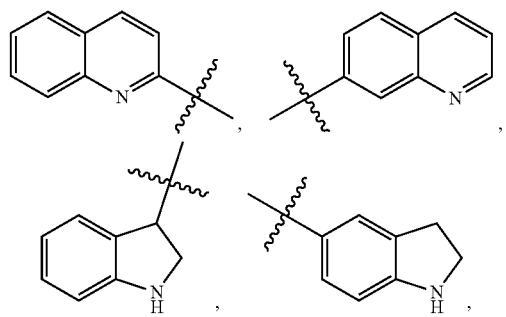

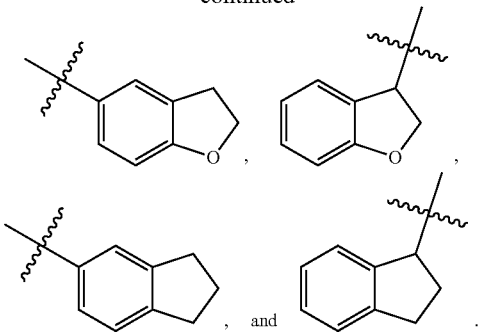

When the term "bicycle" is used in the context of a bivalent residue such as $R^{20}$, $R^{21}$, $R^2$, $R^{23}$, or $R^{24}$, the attachment points can be on separate rings or on the same ring. In certain embodiments both attachment points are on the same ring. In certain embodiments both attachment points are on different rings. Non-limiting examples of bivalent bicycle groups include:

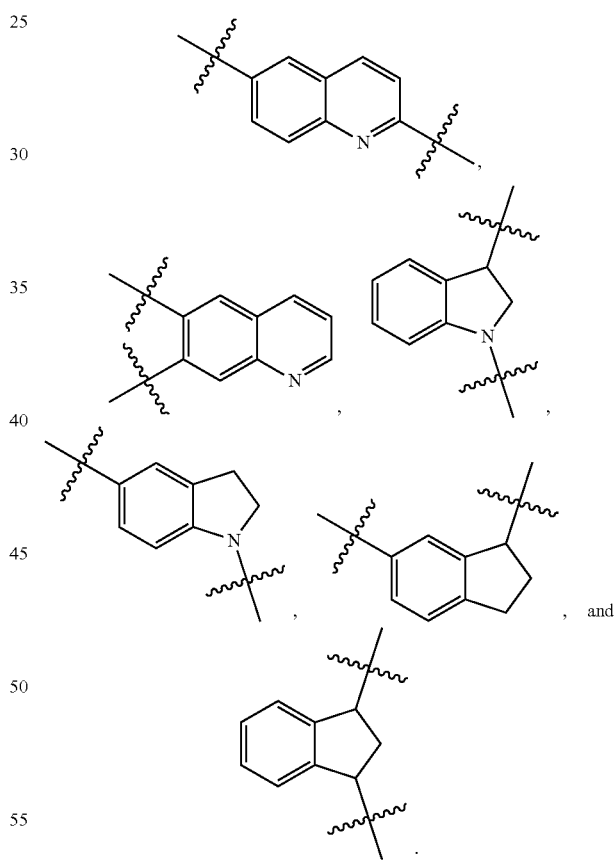

A "dosage form" means a unit of administration of an active agent. Examples of dosage forms include tablets, capsules, injections, suspensions, liquids, emulsions, implants, particles, spheres, creams, ointments, suppositories, inhalable forms, transdermal forms, buccal, sublingual, topical, gel, mucosal, and the like. A "dosage form" can also include an implant, for example an optical implant.

As used herein "endogenous" refers to any material from or produced inside an organism, cell, tissue or system.

As used herein, the term "exogenous" refers to any material introduced from or produced outside an organism, cell, tissue or system.

By the term "modulating," as used herein, is meant mediating a detectable increase or decrease in the level of a response in a subject compared with the level of a response in the subject in the absence of a treatment or compound, and/or compared with the level of a response in an otherwise identical but untreated subject. The term encompasses perturbing and/or affecting a native signal or response thereby mediating a beneficial therapeutic response in a subject, preferably, a human.

"Parenteral" administration of a compound includes, e.g., subcutaneous (s.c.), intravenous (i.v.), intramuscular (i.m.), or intrasternal injection, or infusion techniques.

As used herein, "pharmaceutical compositions" is a composition comprising at least one active agent such as a selected active compound as described herein, and at least one other substance, such as a carrier. "Pharmaceutical combinations" are combinations of at least two active agents which may be combined in a single dosage form or provided together in separate dosage forms with instructions that the active agents are to be used together to treat any disorder described herein.

As used herein, a "pharmaceutically acceptable salt" is a derivative of the disclosed compound in which the parent compound is modified by making inorganic and organic, acid or base addition salts thereof with a biologically acceptable lack of toxicity. The salts of the present compounds can be synthesized from a parent compound that contains a basic or acidic moiety by conventional chemical methods. Generally, such salts can be prepared by reacting free acid forms of these compounds with a stoichiometric amount of the appropriate base (such as Na, Ca, Mg, or K hydroxide, carbonate, bicarbonate, or the like), or by reacting free base forms of these compounds with a stoichiometric amount of the appropriate acid. Such reactions are typically carried out in water or in an organic solvent, or in a mixture of the two. Generally, non-aqueous media like ether, ethyl acetate, ethanol, isopropanol, or acetonitrile are typical, where practicable. Salts of the present compounds further include solvates of the compounds and of the compound salts.

Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts and the quaternary ammonium salts of the parent compound formed, for example, from non-toxic inorganic or organic acids. For example, conventional non-toxic acid salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, mesylic, esylic, besylic, sulfanilic, 2-acetoxybenzoic, fumaric, toluenesulfonic, methanesulfonic, ethane disulfonic, oxalic, isethionic, $HOOC-(CH_2)_n-COOH$ where n is 0-4, and the like, or using a different acid that produces the same counterion. Lists of additional suitable salts may be found, e.g., in *Remington's Pharmaceutical Sciences,* 17th ed., Mack Publishing Company, Easton, Pa., p. 1418 (1985).

The term "carrier" means a diluent, excipient, or vehicle that an active agent is used or delivered in.

A "pharmaceutically acceptable excipient" means an excipient that is useful in preparing a pharmaceutical composition/combination that is generally safe, and neither biologically nor otherwise inappropriate for administration to a host, typically a human. In one embodiment, an excipient is used that is acceptable for veterinary use.

A "patient" or "host" or "subject" is a human or non-human animal in need of treatment, of any of the disorders as specifically described herein. Typically, the host is a human. A "host" may alternatively refer to for example, a mammal, primate (e.g., human), cow, sheep, goat, horse, dog, cat, rabbit, rat, mice, fish, bird and the like.

A "therapeutically effective amount" of a pharmaceutical composition/combination of this invention means an amount effective, when administered to a host, to provide a therapeutic benefit such as an amelioration of symptoms or reduction or diminution of the disease itself.

Throughout this disclosure, various aspects of the invention can be presented in a range format. It should be understood that the description in range format is merely for convenience and should not be construed as a limitation on the scope of the invention. The description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

II. Compounds of the Present Invention

Embodiments of "Alkyl"

In one embodiment "alkyl" is a $C_1$-$C_{10}$alkyl, $C_1$-$C_9$alkyl, $C_1$-$C_8$alkyl, $C_1$-$C_7$alkyl, $C_1$-$C_6$alkyl, $C_1$-$C_5$alkyl, $C_1$-$C_4$alkyl, $C_1$-$C_3$alkyl, or $C_1$-$C_2$alkyl.

In one embodiment "alkyl" has one carbon.
In one embodiment "alkyl" has two carbons.
In one embodiment "alkyl" has three carbons.
In one embodiment "alkyl" has four carbons.
In one embodiment "alkyl" has five carbons.
In one embodiment "alkyl" has six carbons.

Non-limiting examples of "alkyl" include: methyl, ethyl, propyl, butyl, pentyl, and hexyl.

Additional non-limiting examples of "alkyl" include: isopropyl, isobutyl, isopentyl, and isohexyl.

Additional non-limiting examples of "alkyl" include: sec-butyl, sec-pentyl, and sec-hexyl.

Additional non-limiting examples of "alkyl" include: tert-butyl, tert-pentyl, and tert-hexyl.

Additional non-limiting examples of "alkyl" include: neopentyl, 3-pentyl, and active pentyl.

Embodiments of "Haloalkyl"

In one embodiment "haloalkyl" is a $C_1$-$C_{10}$haloalkyl, $C_1$-$C_9$haloalkyl, $C_1$-$C_8$haloalkyl, $C_1$-$C_7$haloalkyl, $C_1$-$C_6$haloalkyl, $C_1$-$C_5$haloalkyl, $C_1$-$C_4$haloalkyl, $C_1$-$C_3$haloalkyl, and $C_1$-$C_2$haloalkyl.

In one embodiment "haloalkyl" has one carbon.
In one embodiment "haloalkyl" has one carbon and one halogen.
In one embodiment "haloalkyl" has one carbon and two halogens.
In one embodiment "haloalkyl" has one carbon and three halogens.
In one embodiment "haloalkyl" has two carbons.
In one embodiment "haloalkyl" has three carbons.

In one embodiment "haloalkyl" has four carbons.
In one embodiment "haloalkyl" has five carbons.
In one embodiment "haloalkyl" has six carbons.
Non-limiting examples of "haloalkyl" include:

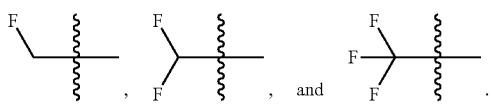

Additional non-limiting examples of "haloalkyl" include:

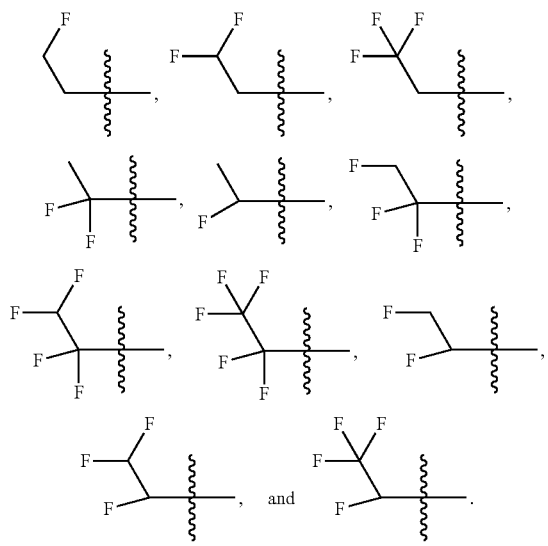

Additional non-limiting examples of "haloalkyl" include:

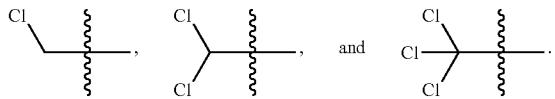

Additional non-limiting examples of "haloalkyl" include:

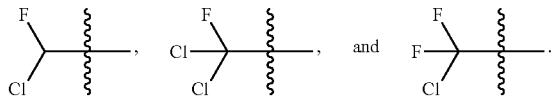

Embodiments of "Aryl"

In one embodiment "aryl" is a 6 carbon aromatic group (phenyl)

In one embodiment "aryl" is a 10 carbon aromatic group (napthyl)

In one embodiment "aryl" is a 6 carbon aromatic group fused to a heterocycle wherein the point of attachment is the aryl ring. Non-limiting examples of "aryl" include indoline, tetrahydroquinoline, tetrahydroisoquinoline, and dihydrobenzofuran wherein the point of attachment for each group is on the aromatic ring.

For example,

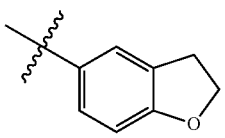 [SMILES: *c1ccc2c(c1)CCO2]

is an "aryl" group.
However,

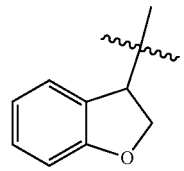 [SMILES: *C1COc2ccccc21]

is a "heterocycle" group.

In one embodiment "aryl" is a 6 carbon aromatic group fused to a cycloalkyl wherein the point of attachment is the aryl ring. Non-limiting examples of "aryl" include dihydroindene and tetrahydronaphthalene wherein the point of attachment for each group is on the aromatic ring.

For example,

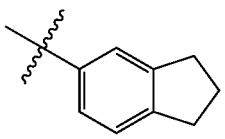 [SMILES: *c1ccc2c(c1)CCC2]

is an "aryl" group.
However,

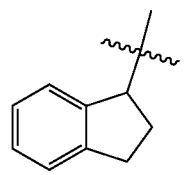 [SMILES: *C1CCc2ccccc21]

is a "cycloalkyl" group.

Embodiments of "Heteroaryl"

In one embodiment "heteroaryl" is a 5 membered aromatic group containing 1, 2, 3, or 4 nitrogen atoms.

Non-limiting examples of 5 membered "heteroaryl" groups include pyrrole, furan, thiophene, pyrazole, imidazole, triazole, tetrazole, isoxazole, oxazole, oxadiazole, oxatriazole, isothiazole, thiazole, thiadiazole, and thiatriazole.

Additional non-limiting examples of 5 membered "heteroaryl" groups include:

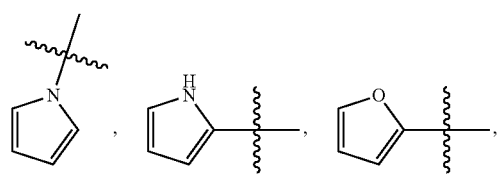

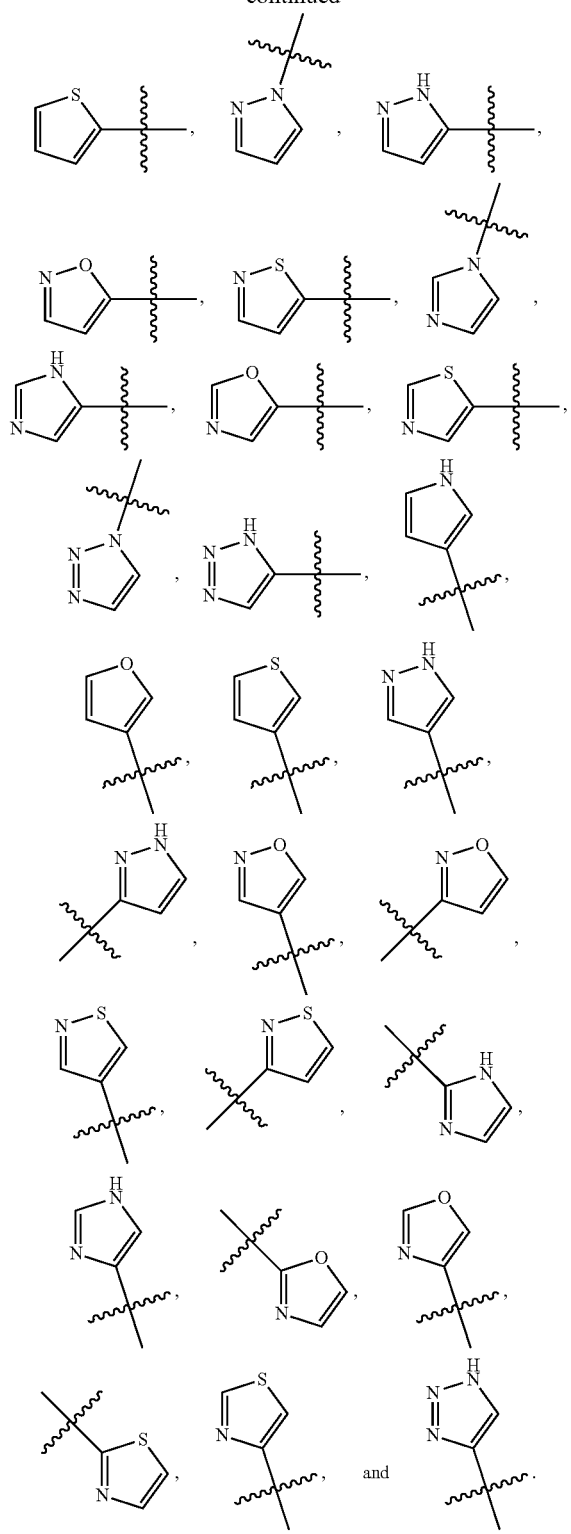

In one embodiment "heteroaryl" is a 6 membered aromatic group containing 1, 2, or 3 nitrogen atoms (i.e. pyridinyl, pyridazinyl, triazinyl, pyrimidinyl, and pyrazinyl).

Non-limiting examples of 6 membered "heteroaryl" groups with 1 or 2 nitrogen atoms include:

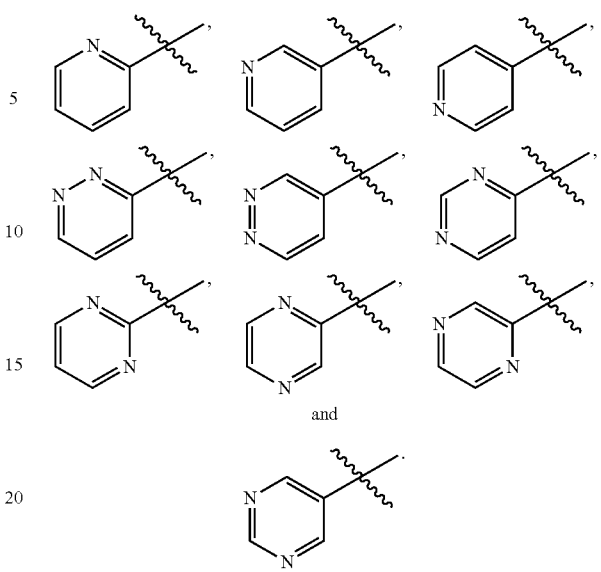

and

In one embodiment "heteroaryl" is a 9 membered bicyclic aromatic group containing 1 or 2 atoms selected from nitrogen, oxygen, and sulfur.

Non-limiting examples of "heteroaryl" groups that are bicyclic include indole, benzofuran, isoindole, indazole, benzimidazole, azaindole, azaindazole, purine, isobenzofuran, benzothiophene, benzoisoxazole, benzoisothiazole, benzooxazole, and benzothiazole.

Additional non-limiting examples of "heteroaryl" groups that are bicyclic include:

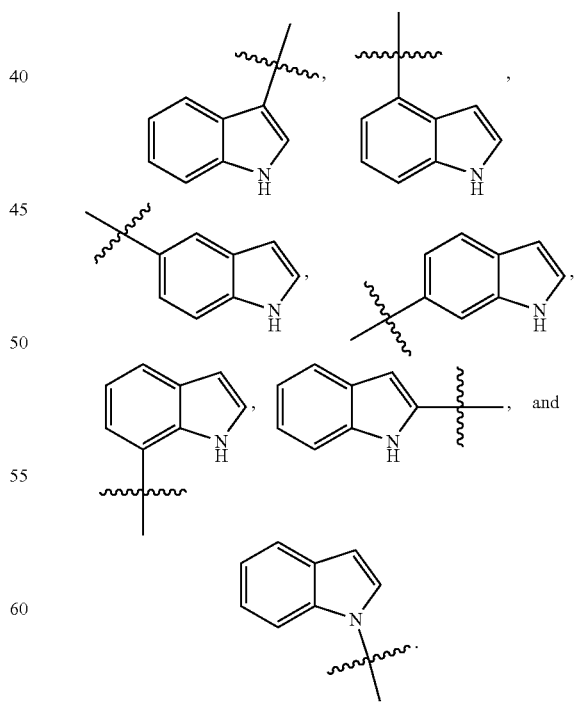

Additional non-limiting examples of "heteroaryl" groups that are bicyclic include:

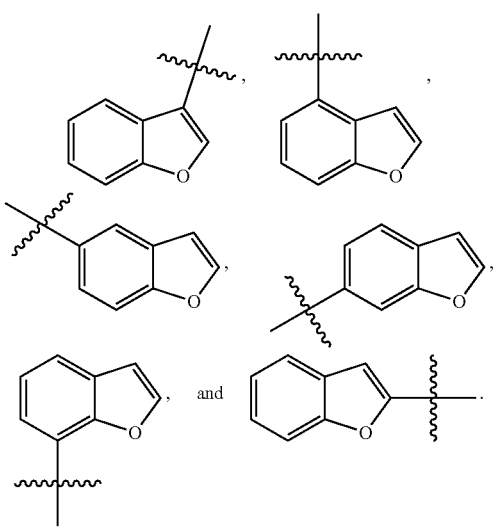

Additional non-limiting examples of "heteroaryl" groups that are bicyclic include:

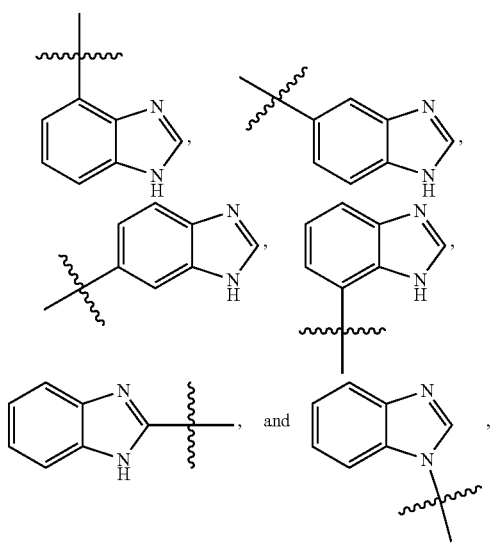

In one embodiment "heteroaryl" is a 10 membered bicyclic aromatic group containing 1 or 2 atoms selected from nitrogen, oxygen, and sulfur.

Non-limiting examples of "heteroaryl" groups that are bicyclic include quinoline, isoquinoline, quinoxaline, phthalazine, quinazoline, cinnoline, and naphthyridine.

Additional non-limiting examples of "heteroaryl" groups that are bicyclic include:

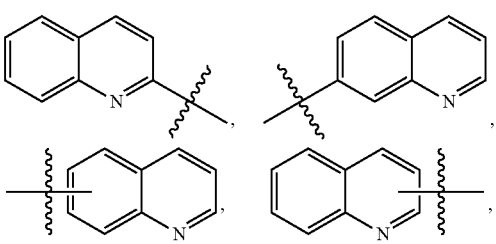

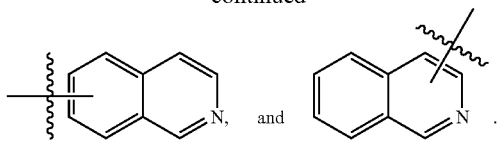

Embodiments of "Cycloalkyl"

In one embodiment "cycloalkyl" is a $C_3$-$C_8$cycloalkyl, $C_3$-$C_7$cycloalkyl, $C_3$-$C_6$cycloalkyl, $C_3$-$C_5$cycloalkyl, $C_3$-$C_4$cycloalkyl, $C_4$-$C_8$cycloalkyl, $C_5$-$C_8$cycloalkyl, or $C_6$-$C_8$cycloalkyl.

In one embodiment "cycloalkyl" has three carbons.
In one embodiment "cycloalkyl" has four carbons.
In one embodiment "cycloalkyl" has five carbons.
In one embodiment "cycloalkyl" has six carbons.
In one embodiment "cycloalkyl" has seven carbons.
In one embodiment "cycloalkyl" has eight carbons.
In one embodiment "cycloalkyl" has nine carbons.
In one embodiment "cycloalkyl" has ten carbons.

Non-limiting examples of "cycloalkyl" include: cyclopropyl, cyclobutyl, cyclopentyl, cyclohexyl, cycloheptyl, cyclooctyl, and cyclodecyl.

Additional non-limiting examples of "cycloalkyl" include dihydro-indene and tetrahydronaphthalene wherein the point of attachment for each group is on the cycloalkyl ring.

For example

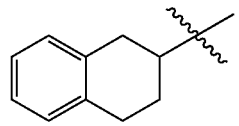 [SMILES: *C1CCc2ccccc2C1]

is an "cycloalkyl" group.

However,

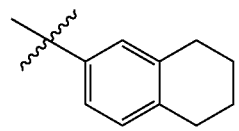 [SMILES: *c1ccc2c(c1)CCCC2]

is an "aryl" group.

Additional examples of "cycloalkyl" groups include

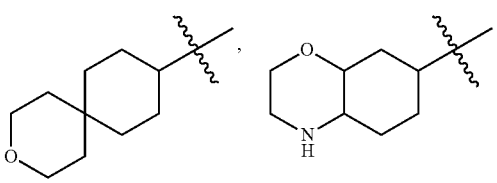

and

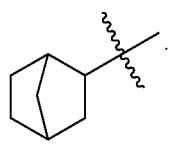 [SMILES: *C1CC2CCC1C2]

Embodiments of "Heterocycle"

In one embodiment "heterocycle" refers to a cyclic ring with one nitrogen and 3, 4, 5, 6, 7, or 8 carbon atoms.

In one embodiment "heterocycle" refers to a cyclic ring with one nitrogen and one oxygen and 3, 4, 5, 6, 7, or 8 carbon atoms.

In one embodiment "heterocycle" refers to a cyclic ring with two nitrogens and 3, 4, 5, 6, 7, or 8 carbon atoms.

In one embodiment "heterocycle" refers to a cyclic ring with one oxygen and 3, 4, 5, 6, 7, or 8 carbon atoms.

In one embodiment "heterocycle" refers to a cyclic ring with one sulfur and 3, 4, 5, 6, 7, or 8 carbon atoms.

Non-limiting examples of "heterocycle" include aziridine, oxirane, thiirane, azetidine, 1,3-diazetidine, oxetane, and thietane.

Additional non-limiting examples of "heterocycle" include pyrrolidine, 3-pyrroline, 2-pyrroline, pyrazolidine, and imidazolidine.

Additional non-limiting examples of "heterocycle" include tetrahydrofuran, 1,3-dioxolane, tetrahydrothiophene, 1,2-oxathiolane, and 1,3-oxathiolane.

Additional non-limiting examples of "heterocycle" include piperidine, piperazine, tetrahydropyran, 1,4-dioxane, thiane, 1,3-dithiane, 1,4-dithiane, morpholine, and thiomorpholine.

Additional non-limiting examples of "heterocycle" include indoline, tetrahydroquinoline, tetrahydroisoquinoline, and dihydrobenzofuran wherein the point of attachment for each group is on the heterocyclic ring.

For example,

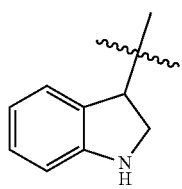 [SMILES: *C1CNc2ccccc21]

is a "heterocycle" group.

However,

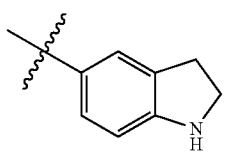 [SMILES: *c1ccc2c(c1)CCN2]

is an "aryl" group.

Non-limiting examples of "heterocycle" also include:

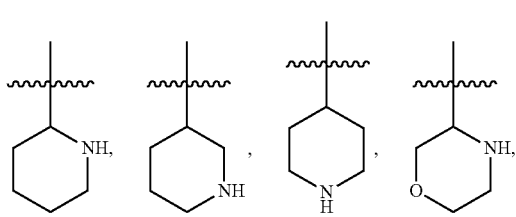

-continued

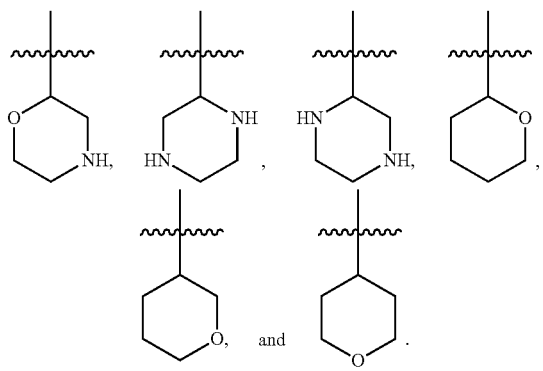

Additional non-limiting examples of "heterocycle" include:

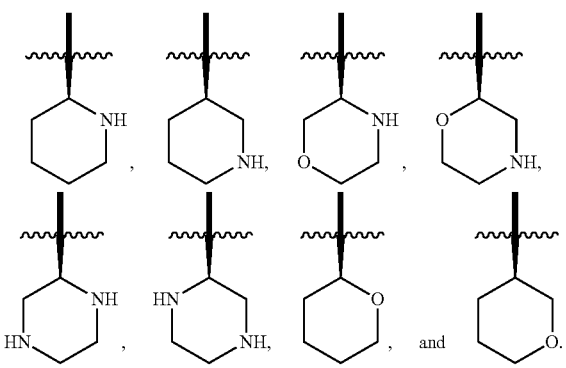

Additional non-limiting examples of "heterocycle" include:

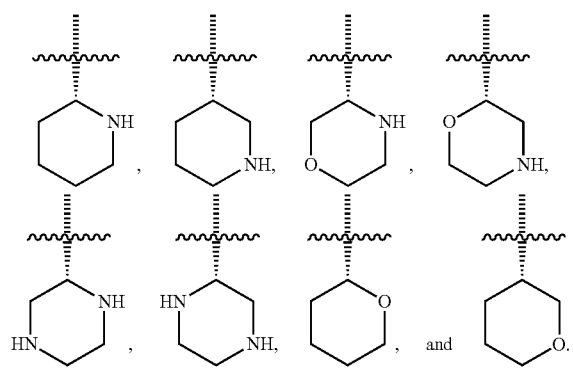

Non-limiting examples of "heterocycle" also include:

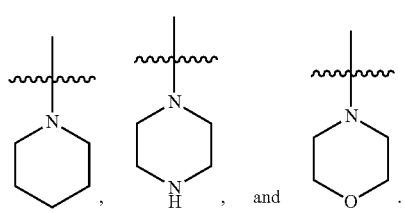

Non-limiting examples of "heterocycle" also include:

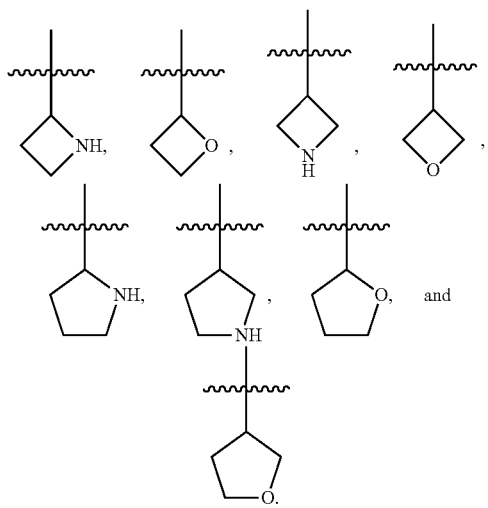

Additional non-limiting examples of "heterocycle" include:

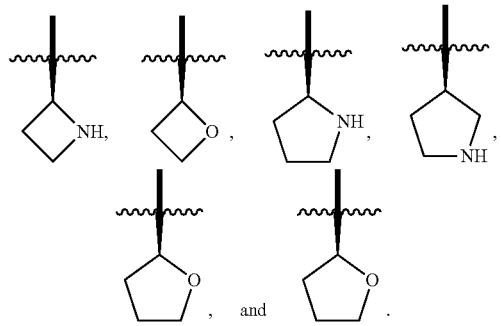

Additional non-limiting examples of "heterocycle" include:

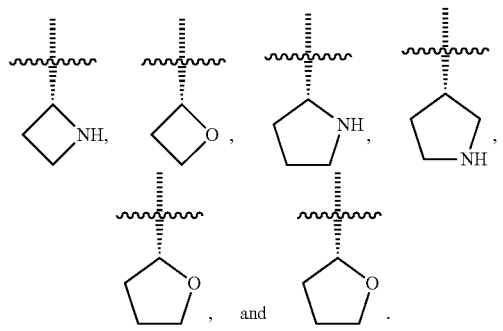

Optional Substituents

In one embodiment a moiety described herein that can be substituted with 1, 2, 3, or 4 substituents is substituted with one substituent.

In one embodiment a moiety described herein that can be substituted with 1, 2, 3, or 4 substituents is substituted with two substituents.

In one embodiment a moiety described herein that can be substituted with 1, 2, 3, or 4 substituents is substituted with three substituents.

In one embodiment a moiety described herein that can be substituted with 1, 2, 3, or 4 substituents is substituted with four substituents.

Non-limiting Embodiments of the Tricyclic Core

The tricyclic core moiety has 1, 2, or 3 nitrogens.

In one embodiment, the compound of Formula I is selected from:

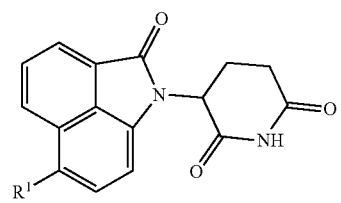

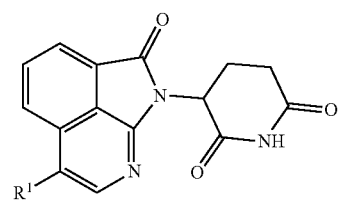

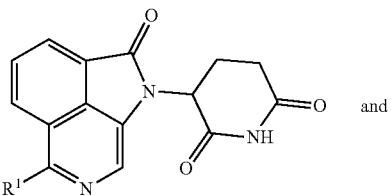

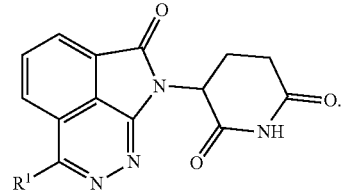

Non-Limiting Embodiments of Formula I:

In certain embodiments the compound of the present invention is selected from Formula:

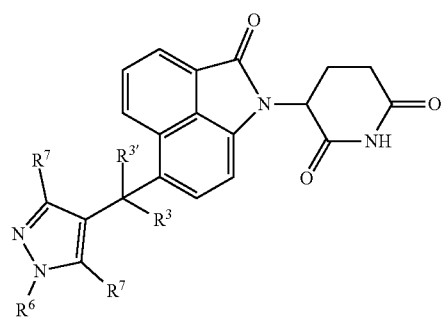

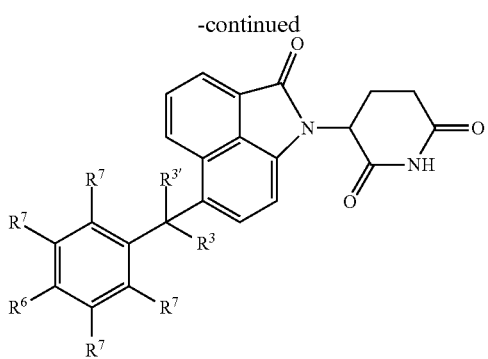
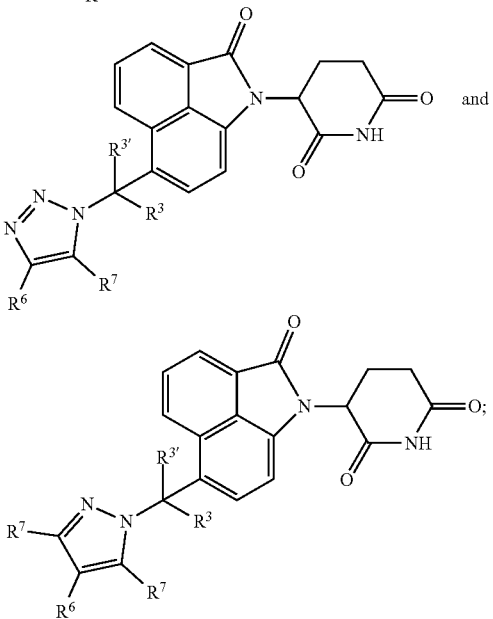
or a pharmaceutically acceptable salt thereof.
In certain embodiments the compound of the present invention is selected from Formula:
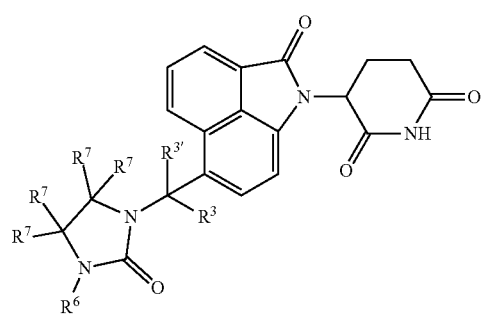
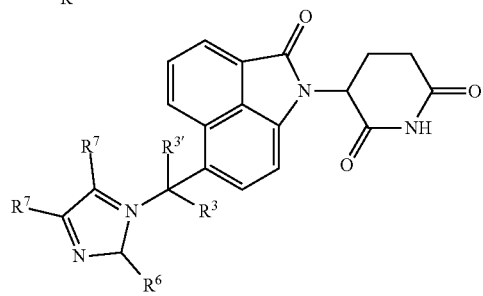
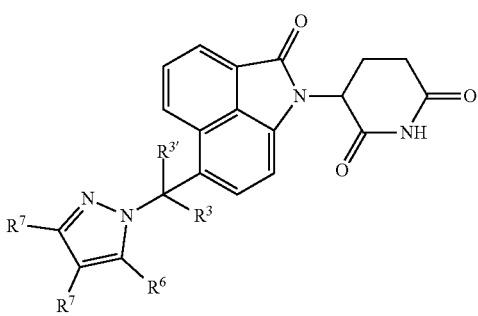
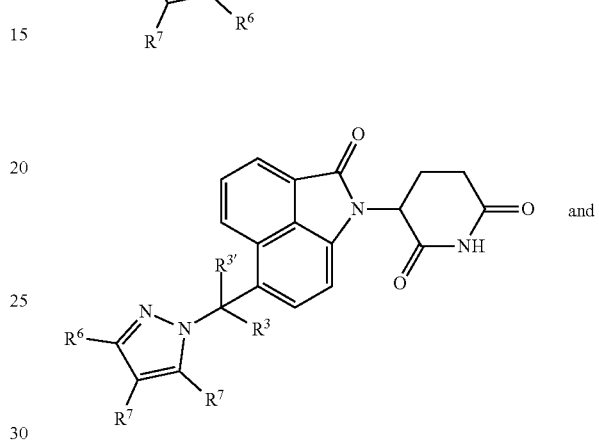
or a pharmaceutically acceptable salt thereof.
In certain embodiments the compound of the present invention is selected from Formula:
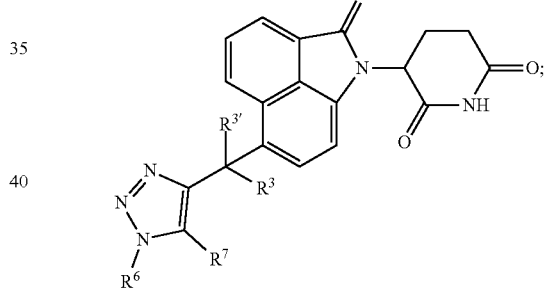
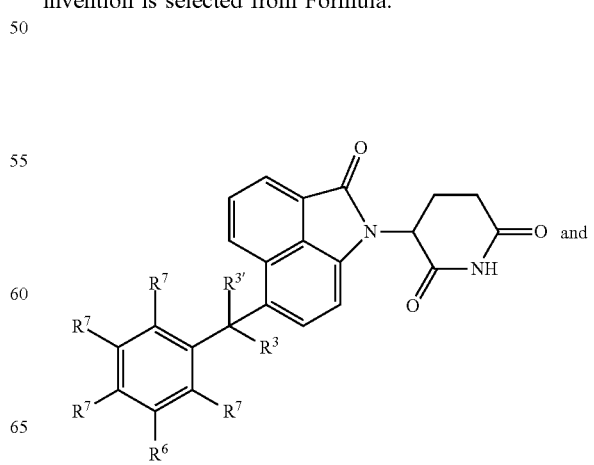

31
-continued
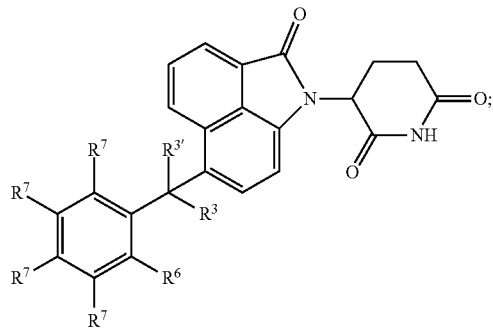
or a pharmaceutically acceptable salt thereof.
In certain embodiments the compound of the present invention is selected from Formula:
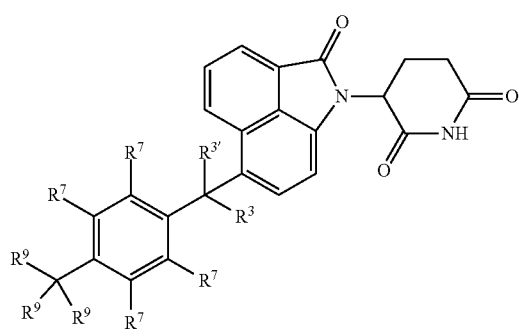
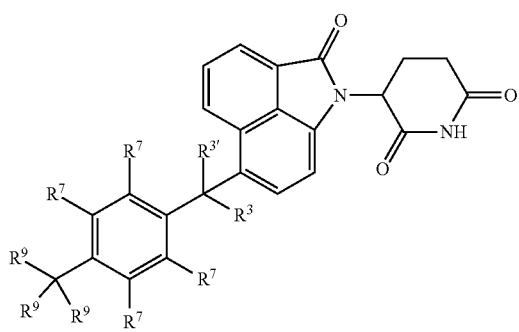
32
-continued
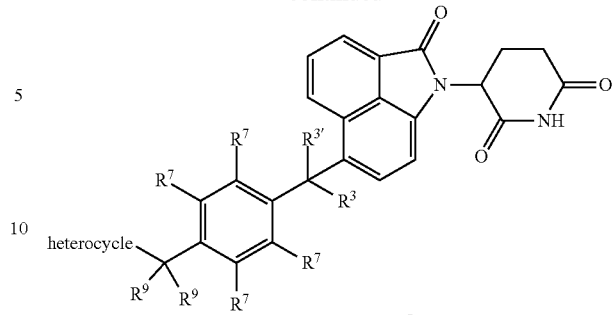
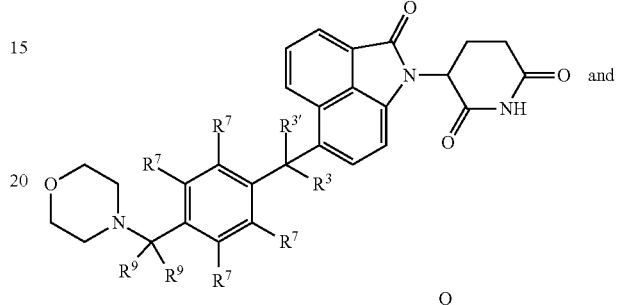
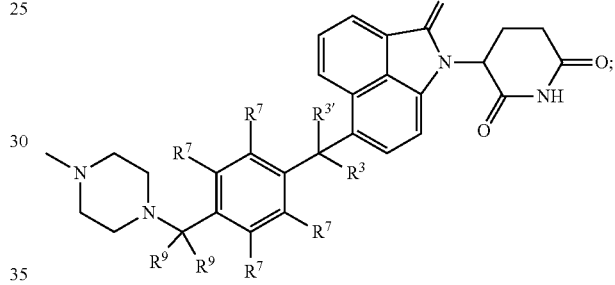 and
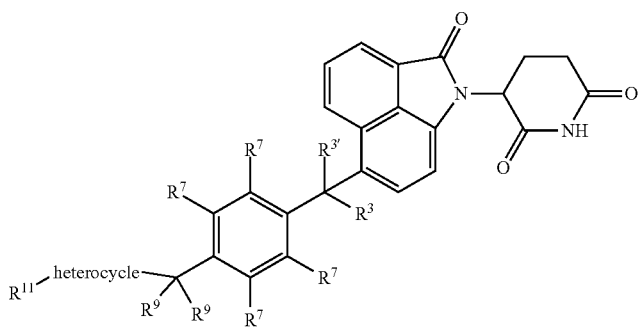
or a pharmaceutically acceptable salt thereof.
In certain embodiments the compound of the present invention is selected from Formula:

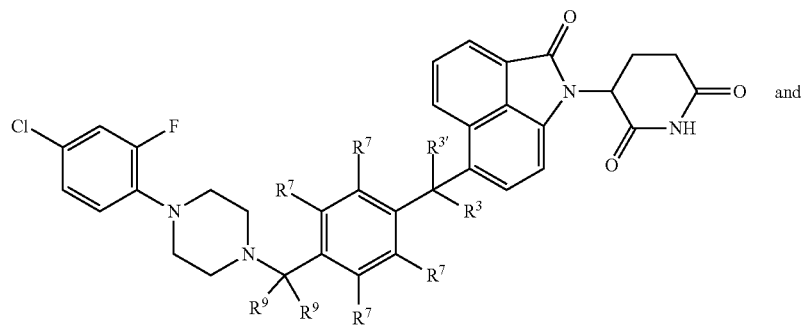
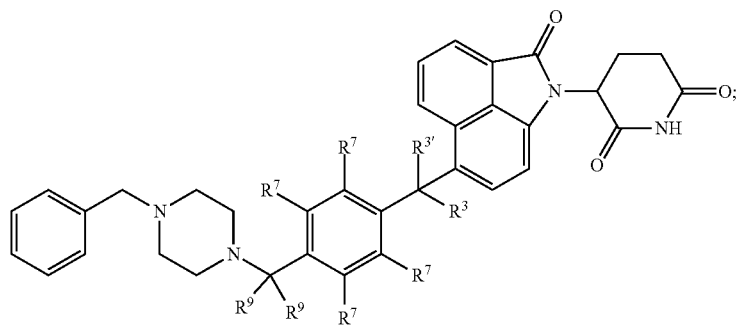
or a pharmaceutically acceptable salt thereof.
In certain embodiments the compound of the present invention is selected from Formula:
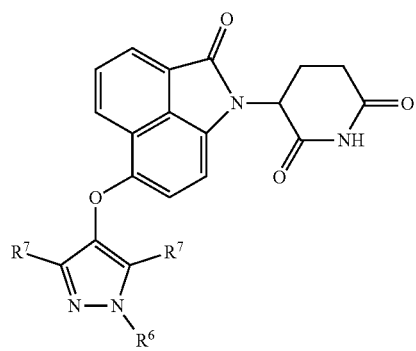
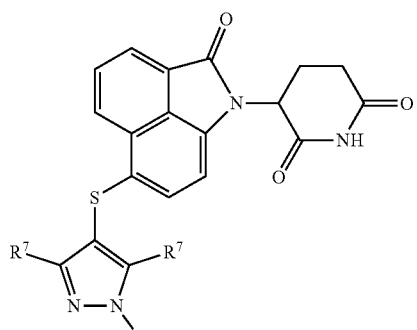
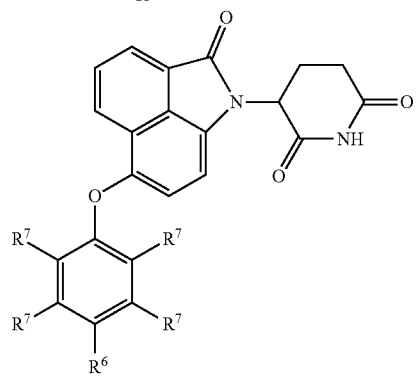
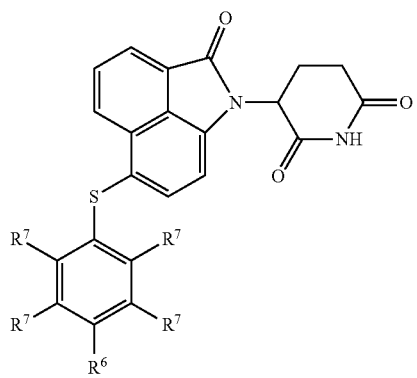

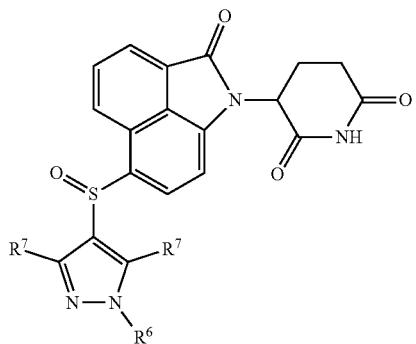
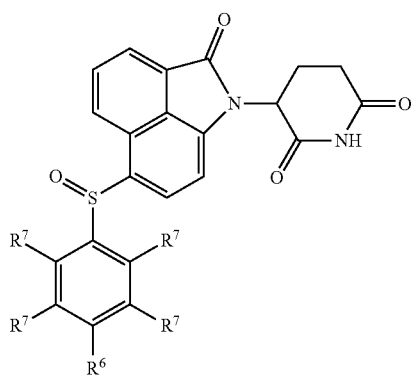
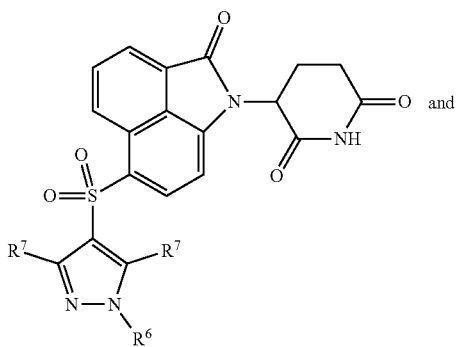
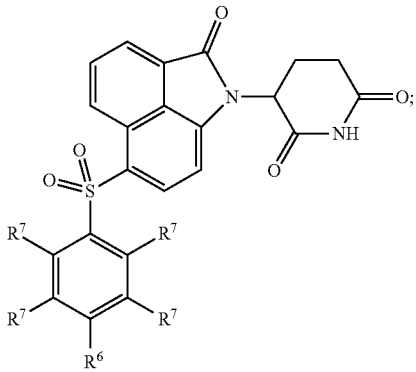
or a pharmaceutically acceptable salt thereof.
In certain embodiments the compound of the present invention is selected from Formula:
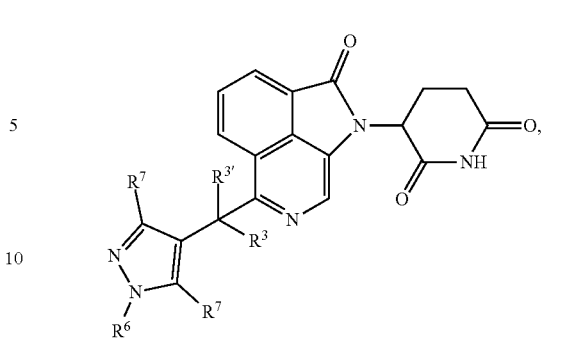
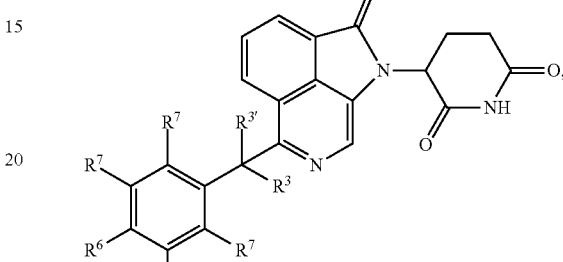
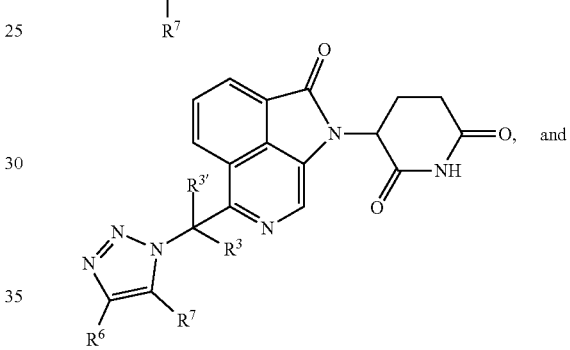
or a pharmaceutically acceptable salt thereof.
In certain embodiments the compound of the present invention is selected from Formula:
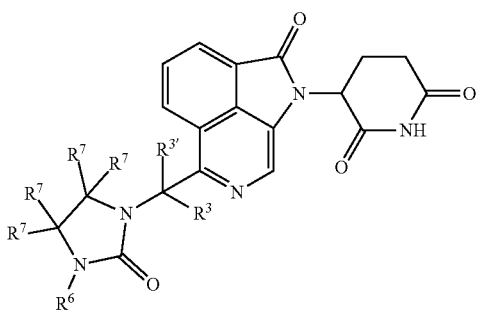

-continued
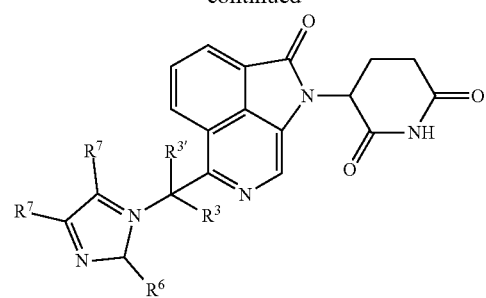
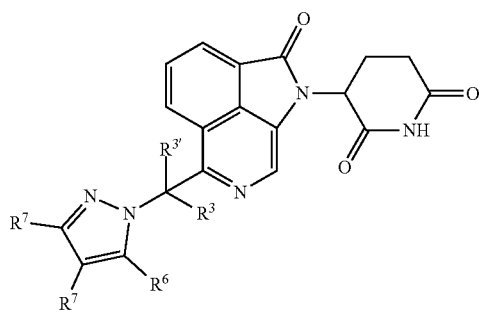
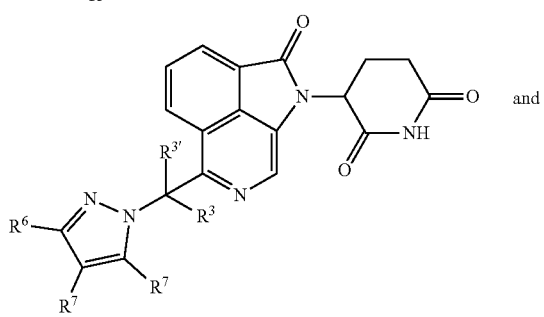
and
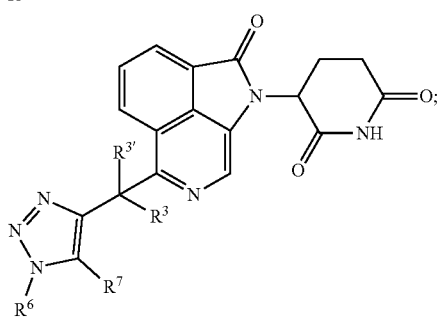
or a pharmaceutically acceptable salt thereof.
In certain embodiments the compound of the present invention is selected from Formula:
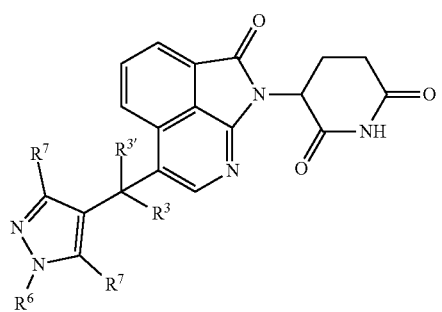
-continued
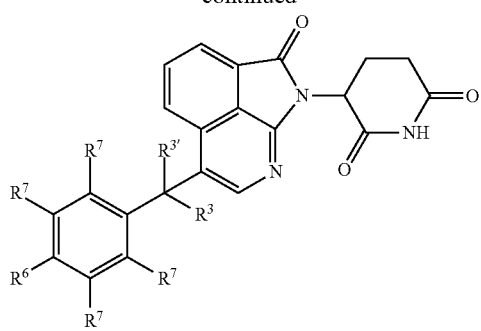
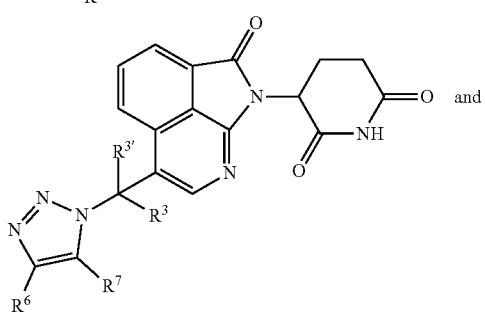
and
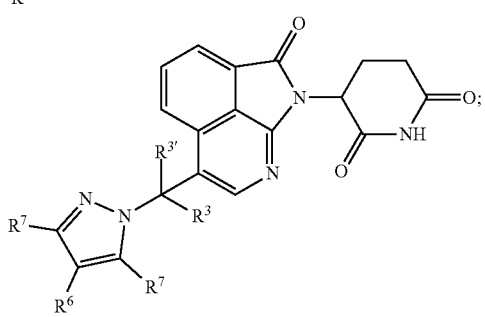
or a pharmaceutically acceptable salt thereof.
In certain embodiments the compound of the present invention is selected from Formula:
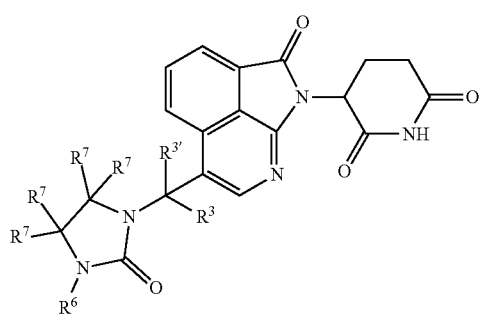
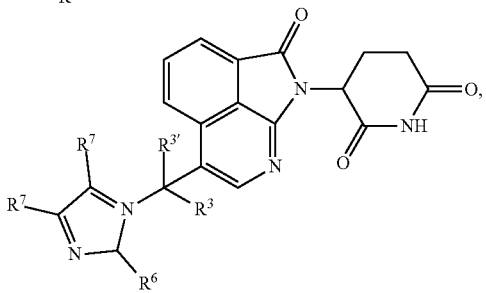

39
-continued
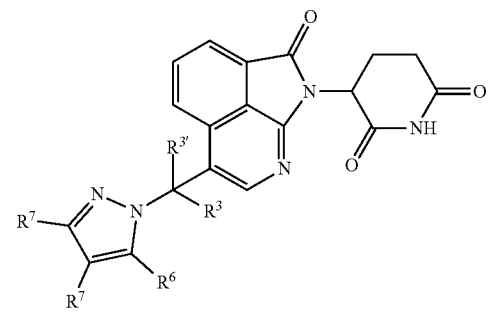
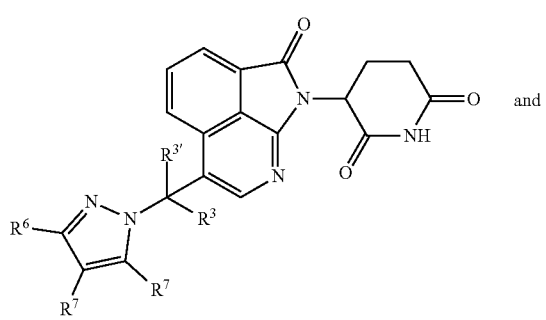
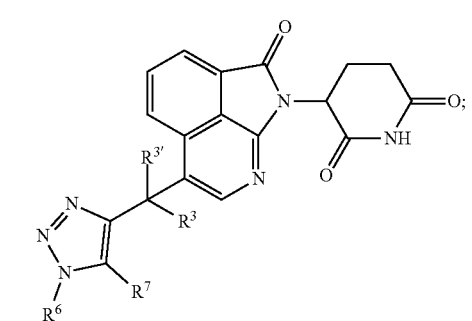
or a pharmaceutically acceptable salt thereof.
In certain embodiments the compound of the present invention is selected from:
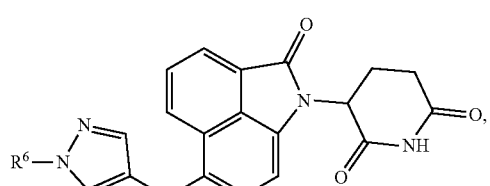
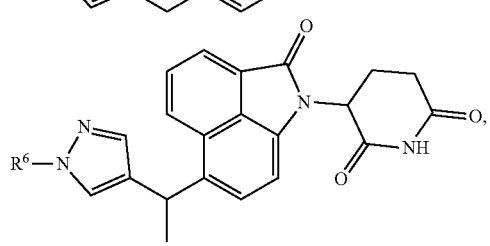
40
-continued
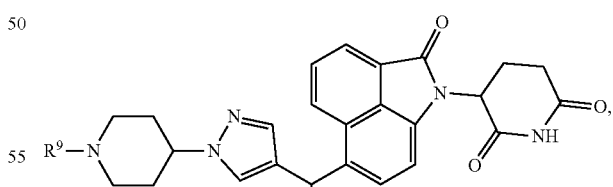
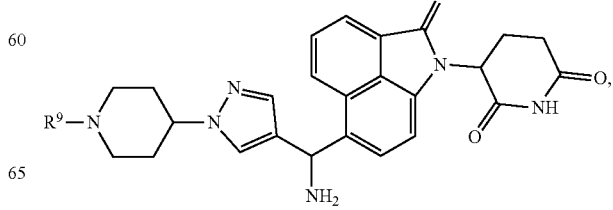

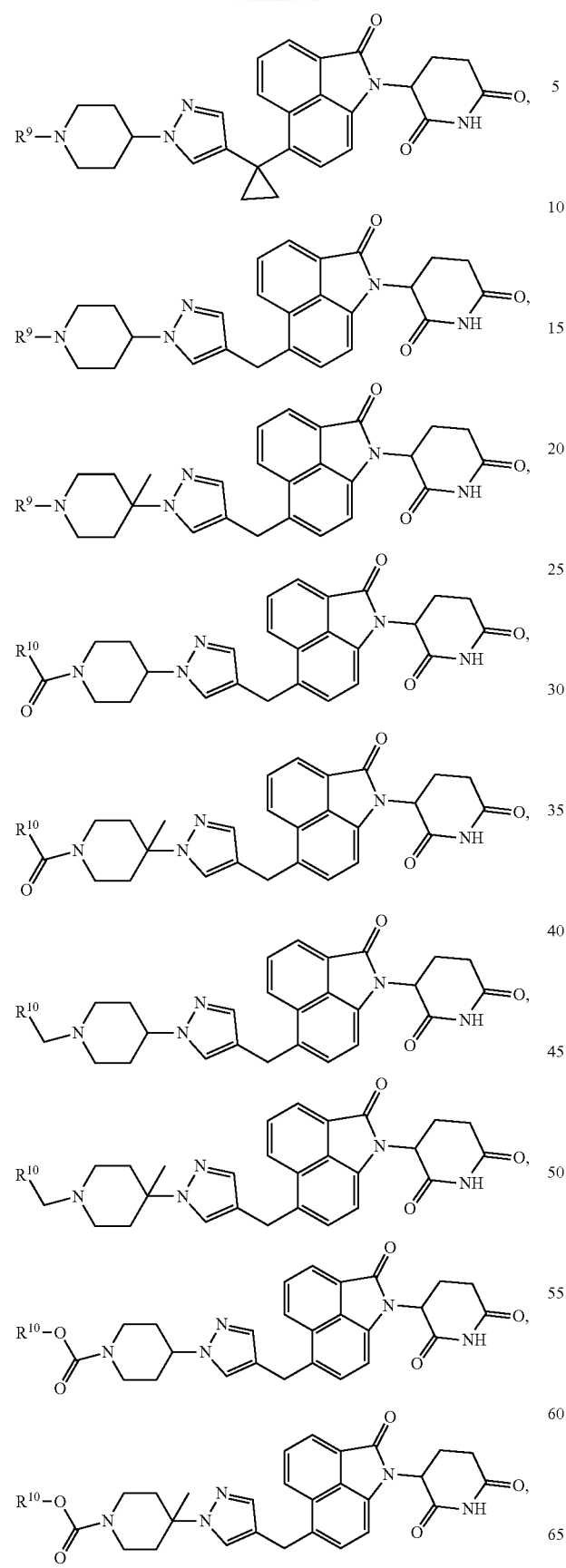
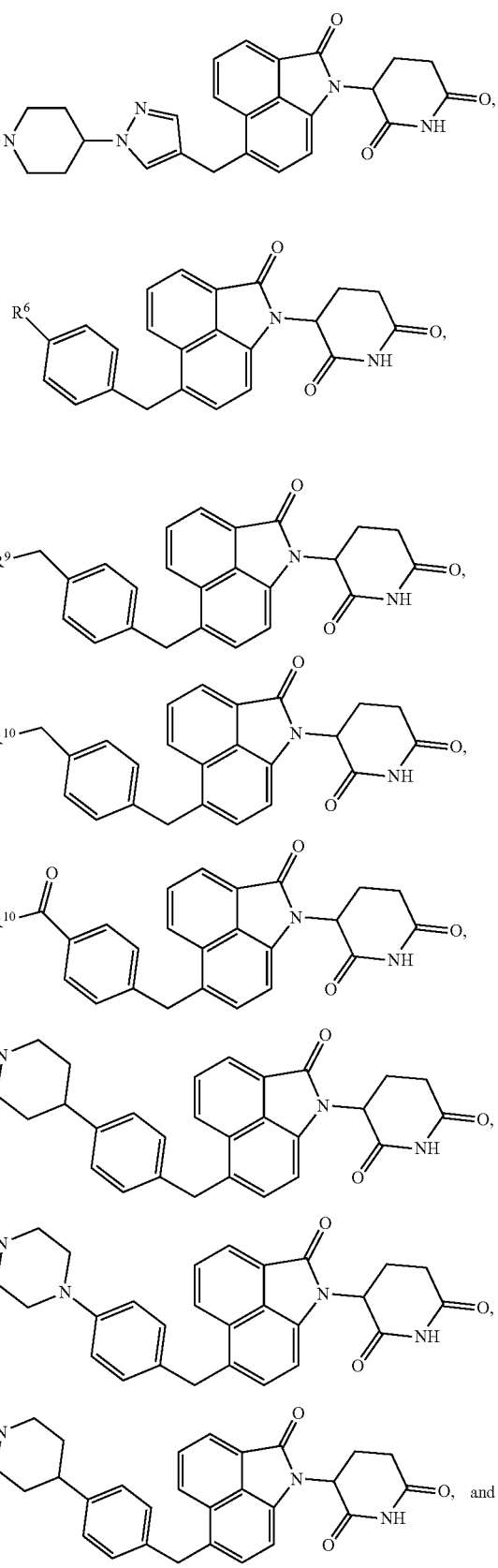

-continued
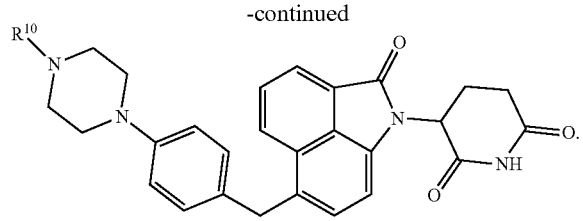
In one embodiment, the compound of Formula I is selected from:
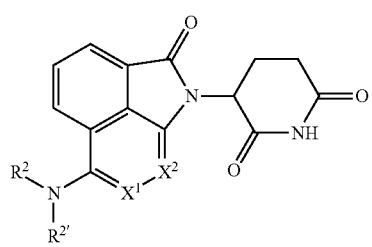
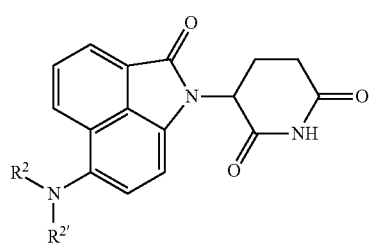
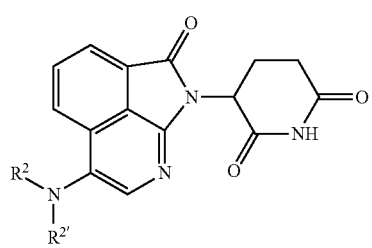
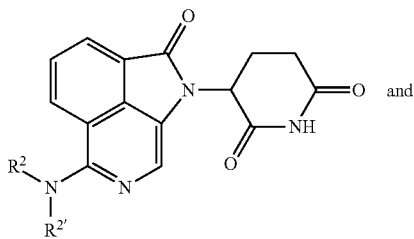 and
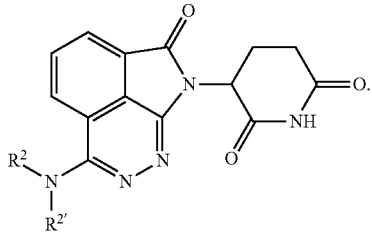
In one embodiment, the compound of Formula I is selected from:
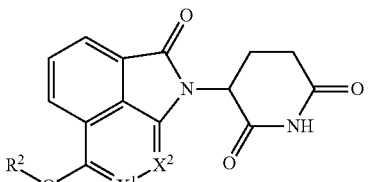
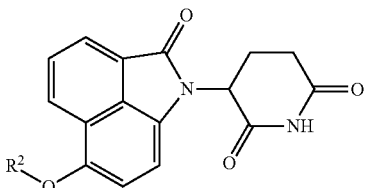
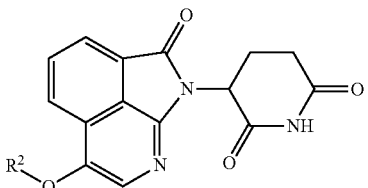
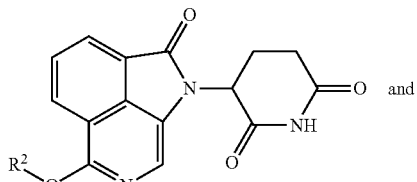 and
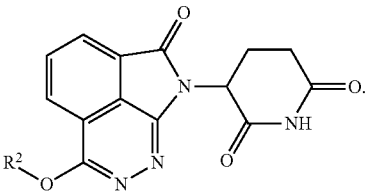
In one embodiment, the compound of Formula I is selected from:
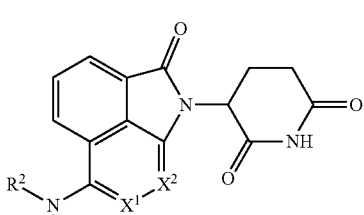
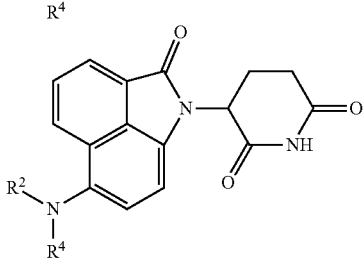

In one embodiment, the compound of Formula I is selected from:

In one embodiment, the compound of Formula I is selected from:

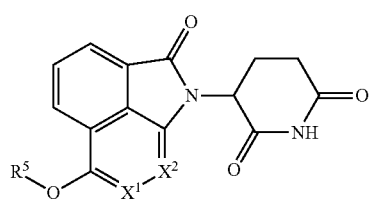
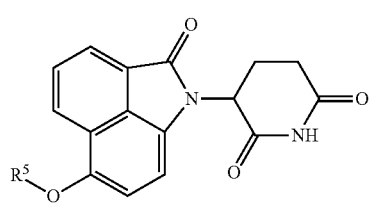
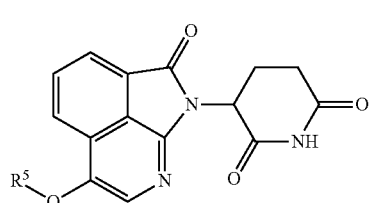
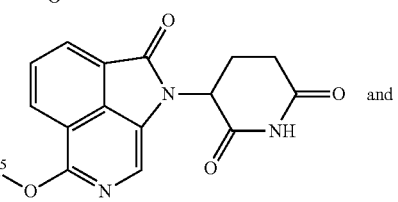
and
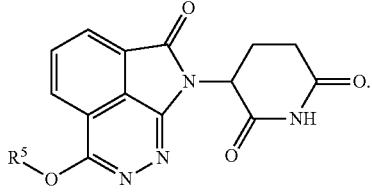
In one embodiment, the compound of Formula I is selected from:
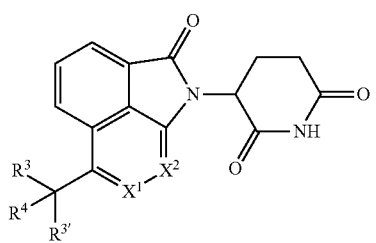
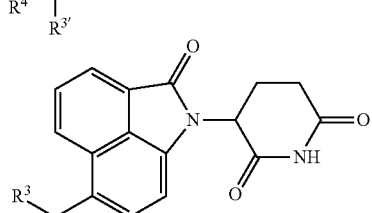
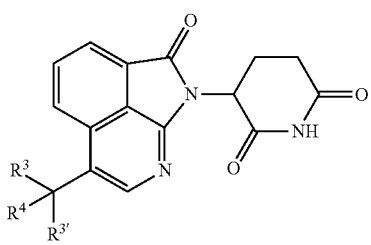
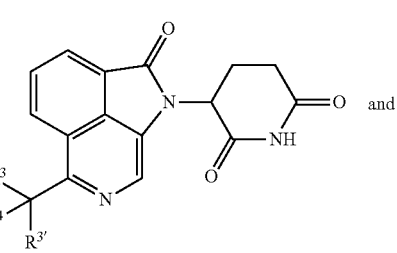
and
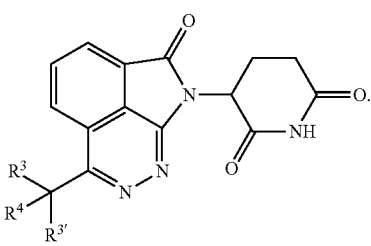
In one embodiment, the compound of Formula I is selected from:
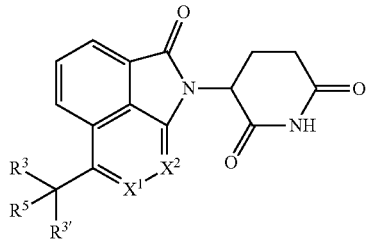
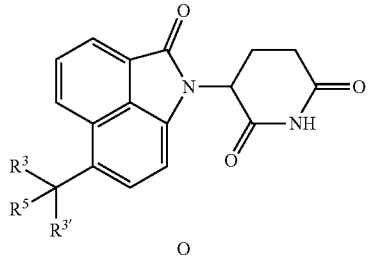
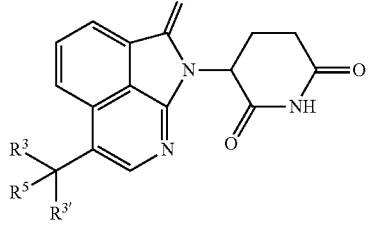

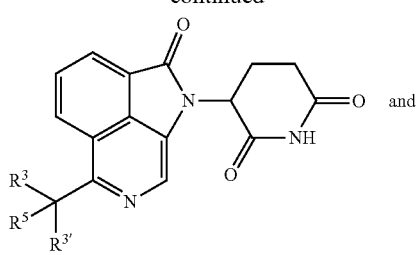
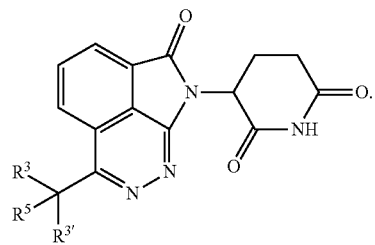
In one embodiment, the compound of Formula I is selected from:
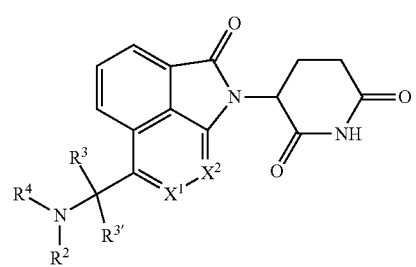
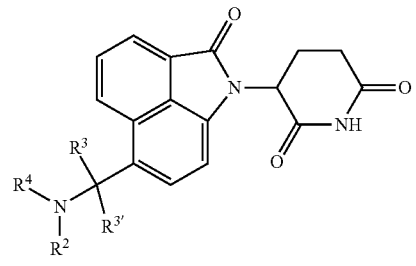
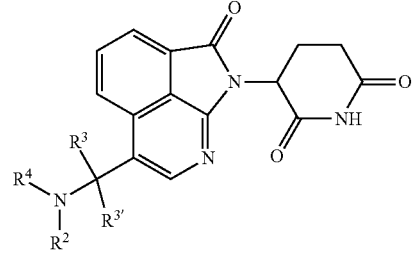
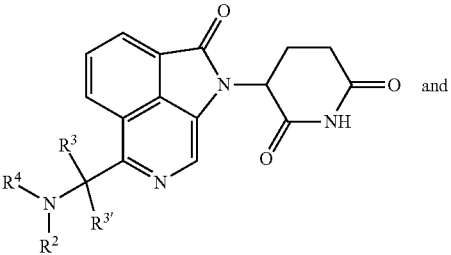
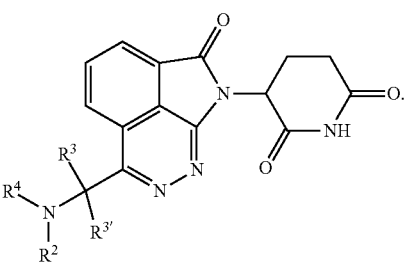
In one embodiment, the compound of Formula I is selected from:
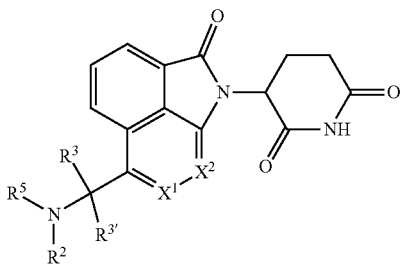
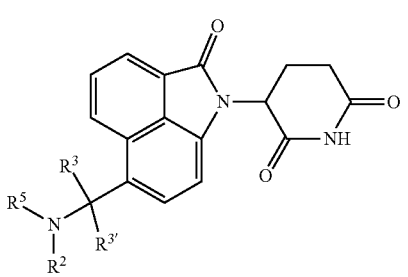
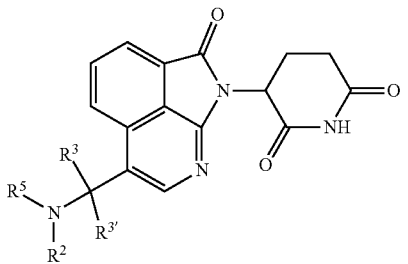
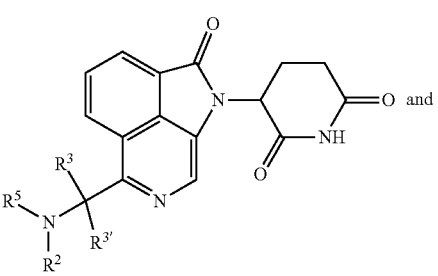

-continued
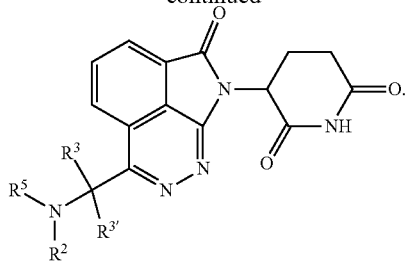
In one embodiment, the compound of Formula I is selected from:
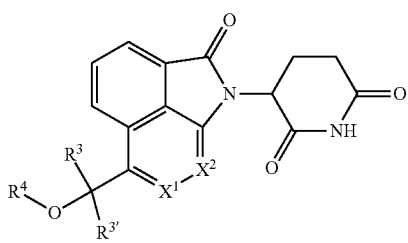
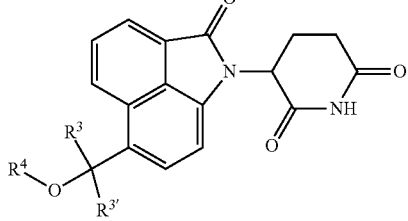
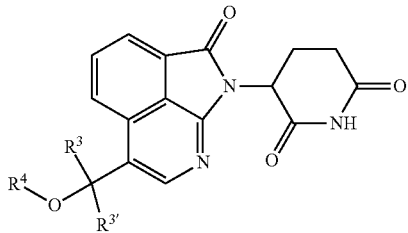
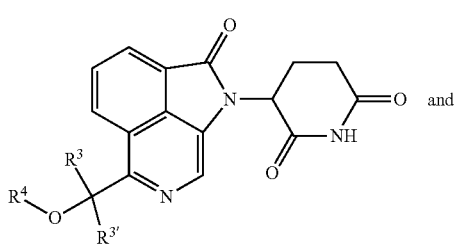 and
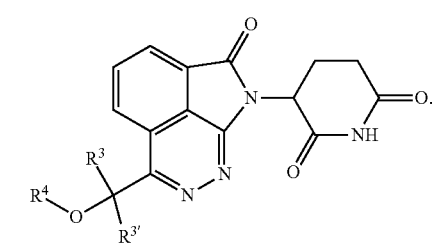
In one embodiment, the compound of Formula I is selected from:
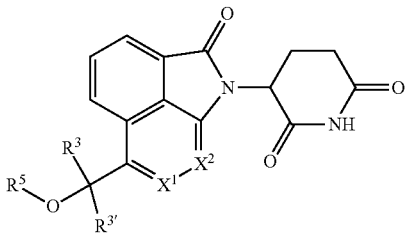
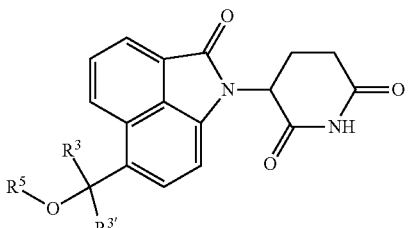
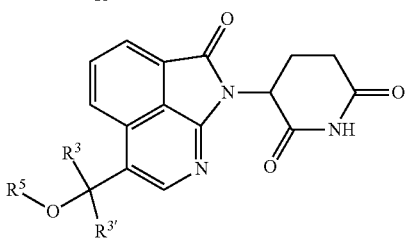
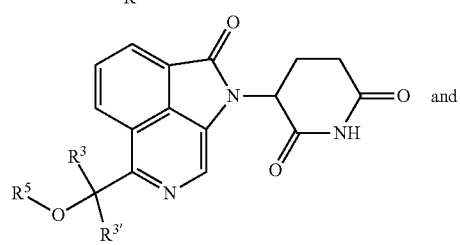 and
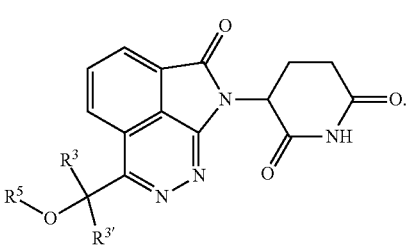
In one embodiment, the compound of Formula I is selected from:
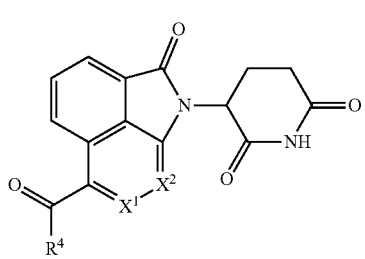

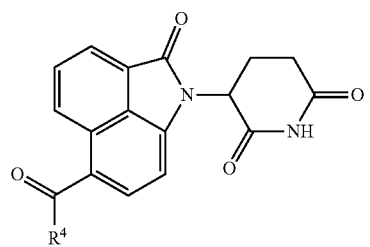
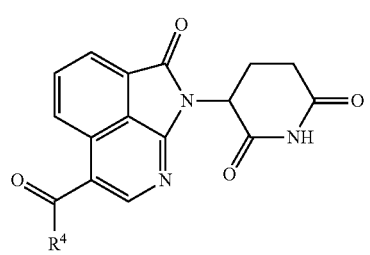
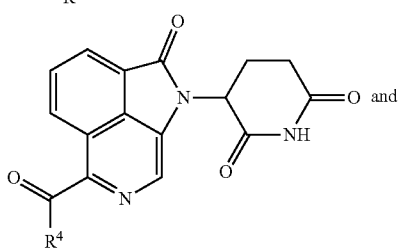
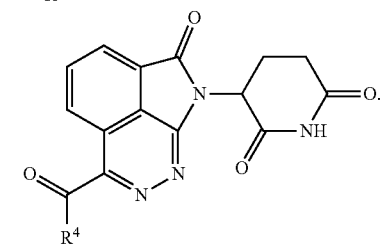
In one embodiment, the compound of Formula I is selected from:
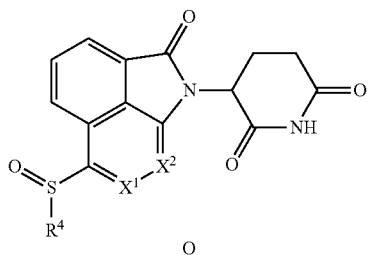
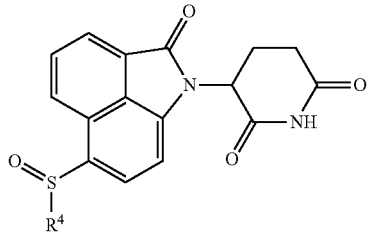
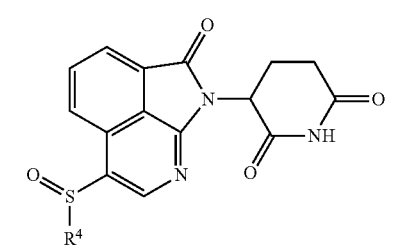
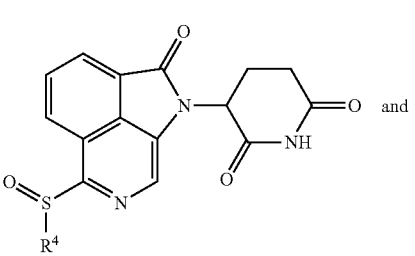
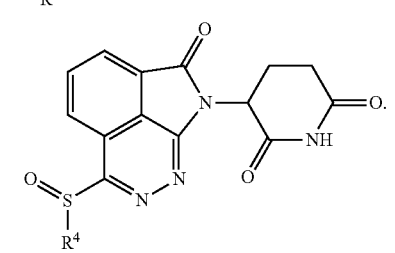
In one embodiment, the compound of Formula I is selected from:
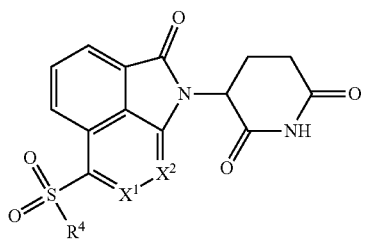
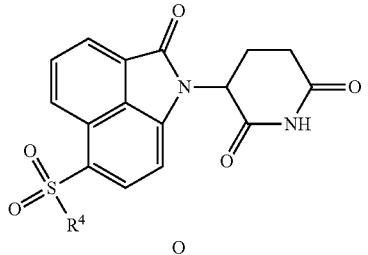
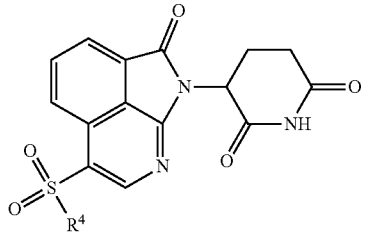

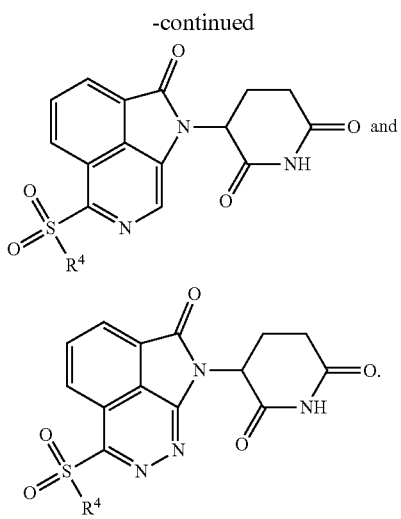

In one embodiment, the compound of Formula I is selected from:

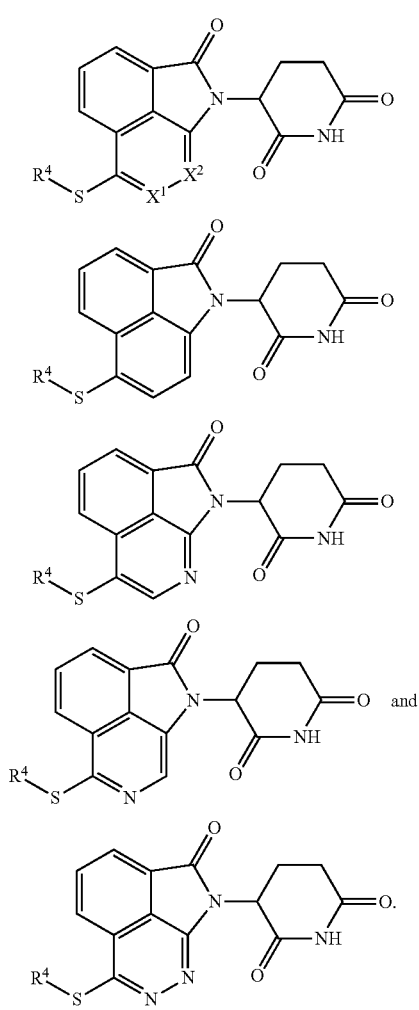

In one embodiment, the compound of Formula I is selected from:

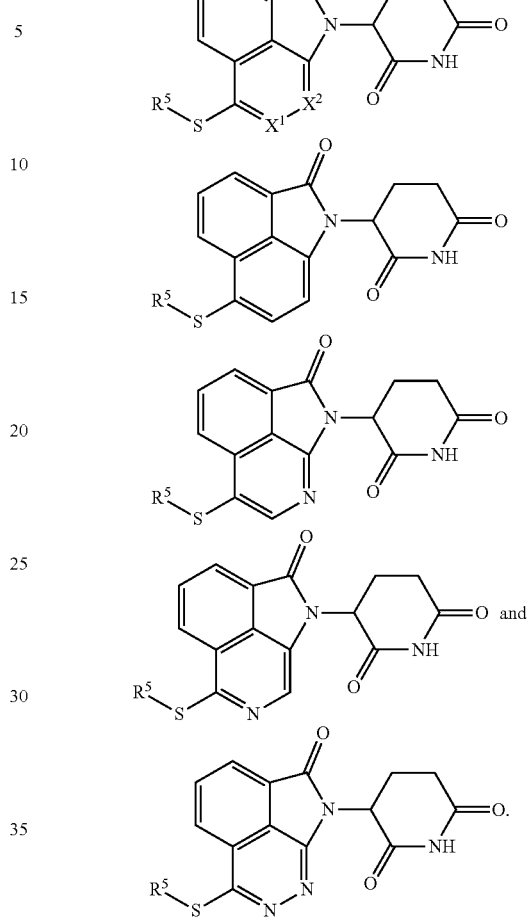

Non-Limiting Embodiments of $R^1$

In one embodiment of Formula I, $R^1$ is selected from —NH(cycloalkyl substituted with $R^6$). In one embodiment of Formula I, $R^1$ is selected from —NH(heterocycle substituted with $R^6$). In one embodiment of Formula I, $R^1$ is selected from —NH(aryl substituted with $R^6$). In one embodiment of Formula I, $R^1$ is selected from —NH(heteroaryl substituted with $R^6$). In one embodiment of Formula I, $R^1$ is selected from —N(CH$_3$)(cycloalkyl substituted with $R^6$). In one embodiment of Formula I, $R^1$ is selected from —N(CH$_3$)(heterocycle substituted with $R^6$). In one embodiment of Formula I, $R^1$ is selected from —N(CH$_3$)(aryl substituted with $R^6$). In one embodiment of Formula I, $R^1$ is selected from —N(CH$_3$)(heteroaryl substituted with $R^6$).

In one embodiment of Formula I, $R^1$ is selected from —O(cycloalkyl substituted with $R^6$). In one embodiment of Formula I, $R^1$ is selected from —O(heterocycle substituted with $R^6$). In one embodiment of Formula I, $R^1$ is selected from —O(aryl substituted with $R^6$). In one embodiment of Formula I, $R^1$ is selected from —O(heteroaryl substituted with $R^6$).

In one embodiment of Formula I, $R^1$ is selected from —S(cycloalkyl substituted with $R^6$). In one embodiment of Formula I, $R^1$ is selected from —S(heterocycle substituted with $R^6$). In one embodiment of Formula I, $R^1$ is selected from —S(aryl substituted with $R^6$). In one embodiment of Formula I, $R^1$ is selected from —S(heteroaryl substituted with $R^6$).

In one embodiment of Formula I, $R^1$ is selected from —NH—C(O)-(alkyl). In one embodiment of Formula I, $R^1$ is selected from —NH—C(O)-(cycloalkyl). In one embodiment of Formula I, $R^1$ is selected from —NH—C(O)-(heterocycle). In one embodiment of Formula I, $R^1$ is selected from —NH—C(O)-(aryl). In one embodiment of Formula I, $R^1$ is selected from —NH—C(O)-(heteroaryl). In one embodiment of Formula I, $R^1$ is selected from —N(CH$_3$)—C(O)-(alkyl). In one embodiment of Formula I, $R^1$ is selected from —N(CH$_3$)—C(O)-(cycloalkyl). In one embodiment of Formula I, $R^1$ is selected from —N(CH$_3$)—C(O)-(heterocycle). In one embodiment of Formula I, $R^1$ is selected from —N(CH$_3$)—C(O)-(aryl). In one embodiment of Formula I, $R^1$ is selected from —N(CH$_3$)—C(O)-(heteroaryl).

In one embodiment of Formula I, $R^1$ is selected from —O—C(O)-(alkyl). In one embodiment of Formula I, $R^1$ is selected from —O—C(O)-(cycloalkyl). In one embodiment of Formula I, $R^1$ is selected from —O—C(O)-(heterocycle). In one embodiment of Formula I, $R^1$ is selected from —O—C(O)-(aryl). In one embodiment of Formula I, $R^1$ is selected from —O—C(O)-(heteroaryl).

In one embodiment of Formula I, $R^1$ is selected from —S—C(O)-(alkyl). In one embodiment of Formula I, $R^1$ is selected from —S—C(O)-(cycloalkyl). In one embodiment of Formula I, $R^1$ is selected from —S—C(O)-(heterocycle). In one embodiment of Formula I, $R^1$ is selected from —S—C(O)-(aryl). In one embodiment of Formula I, $R^1$ is selected from —S—C(O)-(heteroaryl).

In one embodiment of Formula I, $R^1$ is selected from —CH$_2$(cycloalkyl substituted with $R^6$). In one embodiment of Formula I, $R^1$ is selected from —CH$_2$(heterocycle substituted with $R^6$). In one embodiment of Formula I, $R^1$ is selected from —CH$_2$(aryl substituted with $R^6$). In one embodiment of Formula I, $R^1$ is selected from —CH$_2$(heteroaryl substituted with $R^6$). In one embodiment of Formula I, $R^1$ is selected from —CF$_2$(cycloalkyl substituted with $R^6$). In one embodiment of Formula I, $R^1$ is selected from —CF$_2$(heterocycle substituted with $R^6$). In one embodiment of Formula I, $R^1$ is selected from —CF$_2$(aryl substituted with $R^6$). In one embodiment of Formula I, $R^1$ is selected from —CF$_2$(heteroaryl substituted with $R^6$). In one embodiment of Formula I, $R^1$ is selected from —CH(OH)(cycloalkyl substituted with $R^6$). In one embodiment of Formula I, $R^1$ is selected from —CH(OH)(heterocycle substituted with $R^6$). In one embodiment of Formula I, $R^1$ is selected from —CH(OH)(aryl substituted with $R^6$). In one embodiment of Formula I, $R^1$ is selected from —CH(OH)(heteroaryl substituted with $R^6$).

In one embodiment of Formula I, $R^1$ is selected from —CH$_2$—C(O)-(alkyl). In one embodiment of Formula I, $R^1$ is selected from —CH$_2$—C(O)-(cycloalkyl). In one embodiment of Formula I, $R^1$ is selected from —CH$_2$—C(O)-(heterocycle). In one embodiment of Formula I, $R^1$ is selected from —CH$_2$—C(O)-(aryl). In one embodiment of Formula I, $R^1$ is selected from —CH$_2$—C(O)-(heteroaryl). In one embodiment of Formula I, $R^1$ is selected from —CF$_2$—C(O)-(alkyl). In one embodiment of Formula I, $R^1$ is selected from —CF$_2$—C(O)-(cycloalkyl). In one embodiment of Formula I, $R^1$ is selected from —CF$_2$—C(O)-(heterocycle). In one embodiment of Formula I, $R^1$ is selected from —CF$_2$—C(O)-(aryl). In one embodiment of Formula I, $R^1$ is selected from —CF$_2$—C(O)-(heteroaryl). In one embodiment of Formula I, $R^1$ is selected from —CH(OH)—C(O)-(alkyl). In one embodiment of Formula I, $R^1$ is selected from —CH(OH)—C(O)-(cycloalkyl). In one embodiment of Formula I, $R^1$ is selected from —CH(OH)—C(O)-(heterocycle). In one embodiment of Formula I, $R^1$ is selected from —CH(OH)—C(O)-(aryl). In one embodiment of Formula I, $R^1$ is selected from —CH(OH)—C(O)-(heteroaryl).

In one embodiment of Formula I, $R^1$ is selected from —CH$_2$—NH(cycloalkyl substituted with $R^6$). In one embodiment of Formula I, $R^1$ is selected from —CH$_2$—NH(heterocycle substituted with $R^6$). In one embodiment of Formula I, $R^1$ is selected from —CH$_2$—NH(aryl substituted with $R^6$). In one embodiment of Formula I, $R^1$ is selected from —CH$_2$—NH(heteroaryl substituted with $R^6$). In one embodiment of Formula I, $R^1$ is selected from —CH$_2$—N(CH$_3$)(cycloalkyl substituted with $R^6$). In one embodiment of Formula I, $R^1$ is selected from —CH$_2$—N(CH$_3$)(heterocycle substituted with $R^6$). In one embodiment of Formula I, $R^1$ is selected from —CH$_2$—N(CH$_3$)(aryl substituted with $R^6$). In one embodiment of Formula I, $R^1$ is selected from —CH$_2$—N(CH$_3$)(heteroaryl substituted with $R^6$).

In one embodiment of Formula I, $R^1$ is selected from —CH$_2$—O(cycloalkyl substituted with $R^6$). In one embodiment of Formula I, $R^1$ is selected from —CH$_2$—O(heterocycle substituted with $R^6$). In one embodiment of Formula I, $R^1$ is selected from —CH$_2$—O(aryl substituted with $R^6$). In one embodiment of Formula I, $R^1$ is selected from —CH$_2$—O(heteroaryl substituted with $R^6$).

In one embodiment of Formula I, $R^1$ is selected from —CH$_2$—NH—C(O)-(alkyl). In one embodiment of Formula I, $R^1$ is selected from —CH$_2$—NH—C(O)-(cycloalkyl). In one embodiment of Formula I, $R^1$ is selected from —CH$_2$—NH—C(O)-(heterocycle). In one embodiment of Formula I, $R^1$ is selected from —CH$_2$—NH—C(O)-(aryl). In one embodiment of Formula I, $R^1$ is selected from —CH$_2$—NH—C(O)-(heteroaryl). In one embodiment of Formula I, $R^1$ is selected from —CH$_2$—N(CH$_3$)—C(O)-(alkyl). In one embodiment of Formula I, $R^1$ is selected from —CH$_2$—N(CH$_3$)—C(O)-(cycloalkyl). In one embodiment of Formula I, $R^1$ is selected from —CH$_2$—N(CH$_3$)—C(O)-(heterocycle). In one embodiment of Formula I, $R^1$ is selected from —CH$_2$—N(CH$_3$)—C(O)-(aryl). In one embodiment of Formula I, $R^1$ is selected from —CH$_2$—N(CH$_3$)—C(O)-(heteroaryl).

In one embodiment of Formula I, $R^1$ is selected from —CH$_2$—O—C(O)-(alkyl). In one embodiment of Formula I, $R^1$ is selected from —CH$_2$—O—C(O)-(cycloalkyl). In one embodiment of Formula I, $R^1$ is selected from —CH$_2$—O—C(O)-(heterocycle). In one embodiment of Formula I, $R^1$ is selected from —CH$_2$—O—C(O)-(aryl). In one embodiment of Formula I, $R^1$ is selected from —CH$_2$—O—C(O)-(heteroaryl).

In one embodiment of Formula I, $R^1$ is selected from —C(O)-(cycloalkyl substituted with $R^6$). In one embodiment of Formula I, $R^1$ is selected from —C(O)-(heterocycle substituted with $R^6$). In one embodiment of Formula I, $R^1$ is selected from —C(O)-(aryl substituted with $R^6$). In one embodiment of Formula I, $R^1$ is selected from —C(O)-(heteroaryl substituted with $R^6$).

In one embodiment of Formula I, $R^1$ is selected from —S(O)-(cycloalkyl substituted with $R^6$). In one embodiment of Formula I, $R^1$ is selected from —S(O)-(heterocycle substituted with $R^6$). In one embodiment of Formula I, $R^1$ is selected from —S(O)-(aryl substituted with $R^6$). In one embodiment of Formula I, $R^1$ is selected from —S(O)-(heteroaryl substituted with $R^6$).

In one embodiment of Formula I, $R^1$ is selected from —S(O)$_2$-(cycloalkyl substituted with $R^6$). In one embodiment of Formula I, $R^1$ is selected from —S(O)$_2$-(heterocycle substituted with $R^6$). In one embodiment of Formula I, $R^1$ is selected from —S(O)$_2$-(aryl substituted with R$^6$). In one embodiment of Formula I, R$^1$ is selected from —S(O)$_2$-(heteroaryl substituted with R$^6$).

In one embodiment of Formula I, R$^1$ is selected from:

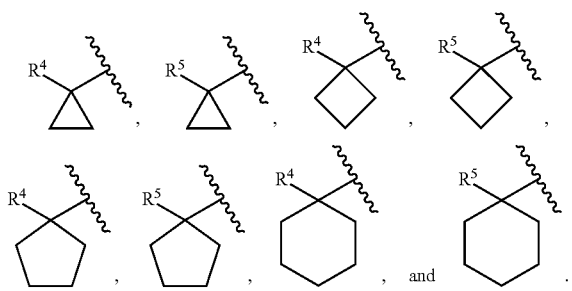

In certain embodiments, R$^1$ is selected from halogen, hydrogen, amino, or cyano. In one embodiment, R$^1$ is bromine.

In certain embodiments, R$^1$ is —(CH$_2$)—R$^4$ wherein R$^4$ is heteroaryl optionally substituted with R$^6$ and R$^6$ is heterocycle optionally substituted with 1 or 2 groups selected from R$^9$. In a further embodiment, R$^9$ is selected from hydrogen and alkyl. Non-limiting examples of this embodiment include:

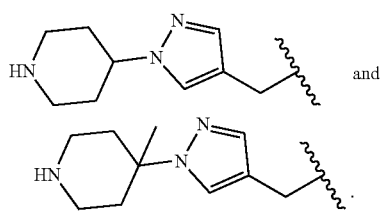

In certain embodiments, R$^1$ is —(CH$_2$)—R$^4$ wherein R$^4$ is heteroaryl optionally substituted with R$^6$ and R$^6$ is heterocycle optionally substituted with 1 or 2 groups selected from R$^9$. In a further embodiment, R$^9$ is selected from alkyl and —C(O)R$^{10}$ wherein R$^{10}$ is heterocycle. Non-limiting examples of this embodiment include:

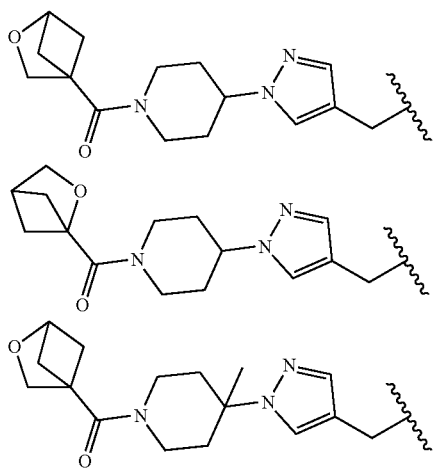

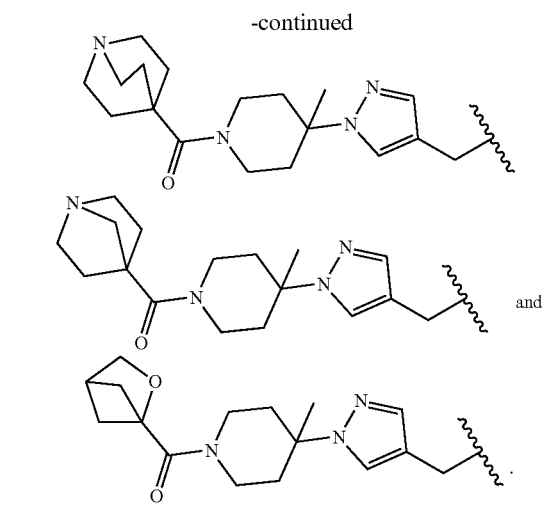

In certain embodiments, R$^1$ is —(CH$_2$)—R$^4$ wherein R$^4$ is heteroaryl optionally substituted with R$^6$ and R$^6$ is heterocycle optionally substituted with 1 or 2 groups selected from R$^9$. In a further embodiment, R$^9$ is selected from alkyl and —C(O)R$^{10}$ wherein R$^{10}$ is heterocycle optionally substituted with R$^{11}$ and R$^{11}$ is alkyl. Non-limiting examples of this embodiment include:

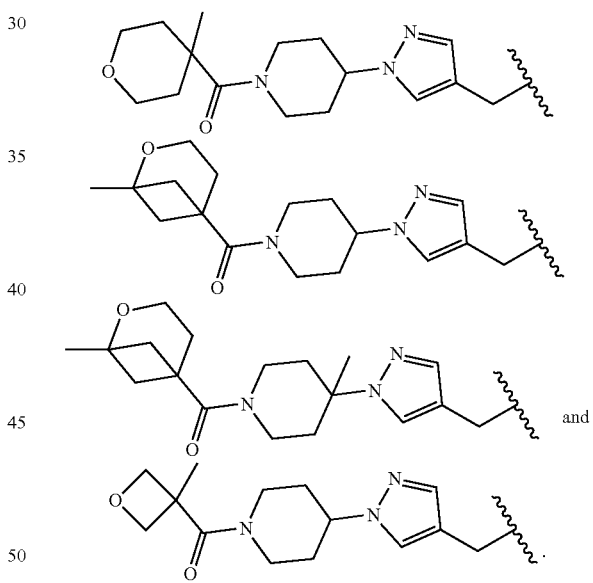

In certain embodiments, R$^1$ is —(CH$_2$)—R$^4$ wherein R$^4$ is heteroaryl optionally substituted with R$^6$ and R$^6$ is heterocycle optionally substituted with 1 or 2 groups selected from R$^9$. In a further embodiment, R$^9$ is selected from alkyl and —C(O)R$^{10}$ wherein R$^{10}$ is cycloalkyl. Non-limiting examples of this embodiment include:

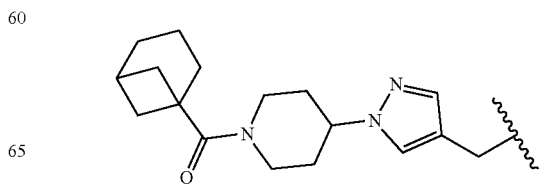

61

-continued

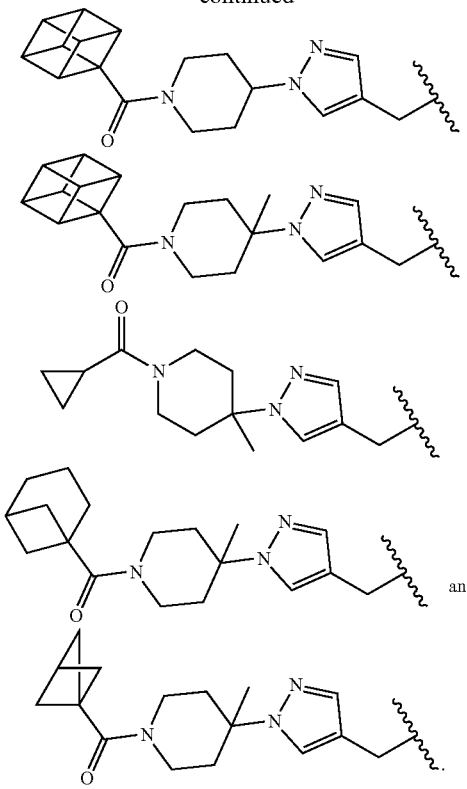

In certain embodiments, $R^1$ is —$(CH_2)$—$R^4$ wherein $R^4$ is heteroaryl optionally substituted with $R^6$ and $R^6$ is heterocycle optionally substituted with 1 or 2 groups selected from $R^9$. In a further embodiment, $R^9$ is selected from alkyl and —$C(O)R^{10}$ wherein $R^{10}$ is cycloalkyl optionally substituted with $R^{11}$ and $R^{11}$ is cyano. Non-limiting examples of this embodiment include:

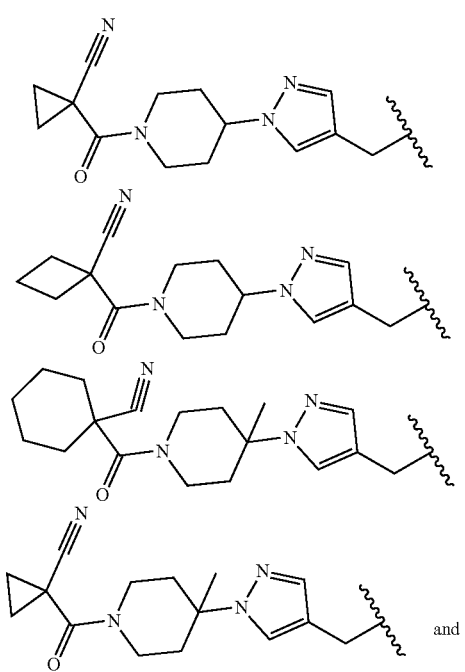

62

-continued

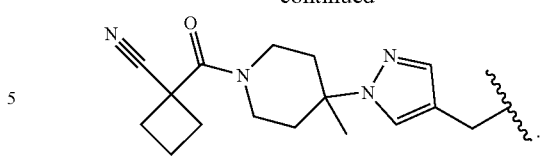

In certain embodiments, $R^1$ is —$(CH_2)$—$R^4$ wherein $R^4$ is heteroaryl optionally substituted with $R^6$ and $R^6$ is heterocycle optionally substituted with 1 or 2 groups selected from $R^9$. In a further embodiment, $R^9$ is selected from alkyl and —$C(O)R^{10}$ wherein $R^{10}$ is cycloalkyl optionally substituted with $R^{11}$ and $R^{11}$ is alkyl. Non-limiting examples of this embodiment include:

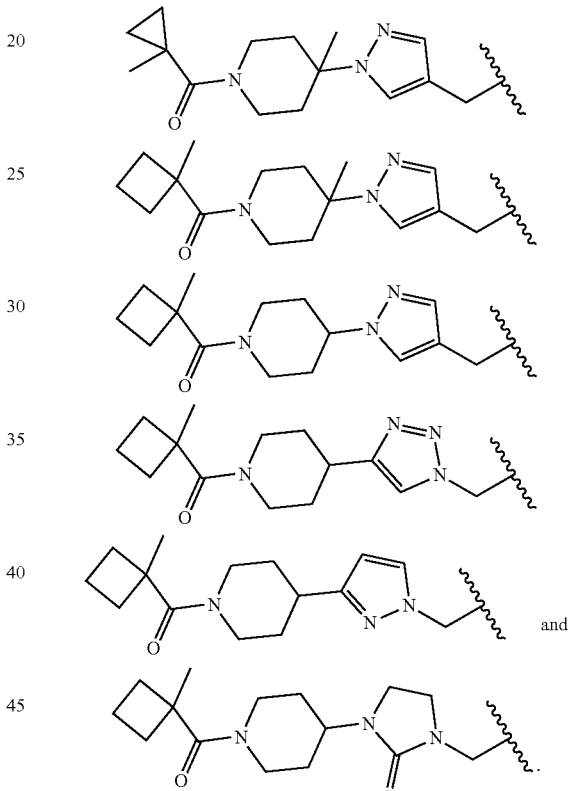

In certain embodiments, $R^1$ is —$(CH_2)$—$R^4$ wherein $R^4$ is heteroaryl optionally substituted with $R^6$ and $R^6$ is heterocycle optionally substituted with 1 or 2 groups selected from $R^9$. In a further embodiment, $R^9$ is selected from alkyl and —$C(O)R^{10}$ wherein $R^{10}$ is cycloalkyl optionally substituted with $R^{11}$ and $R^{11}$ is haloalkyl. Non-limiting examples of this embodiment include:

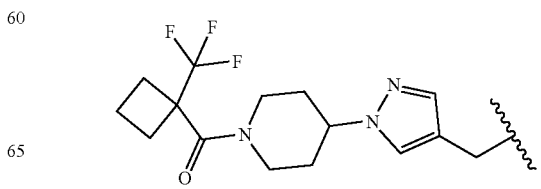

-continued

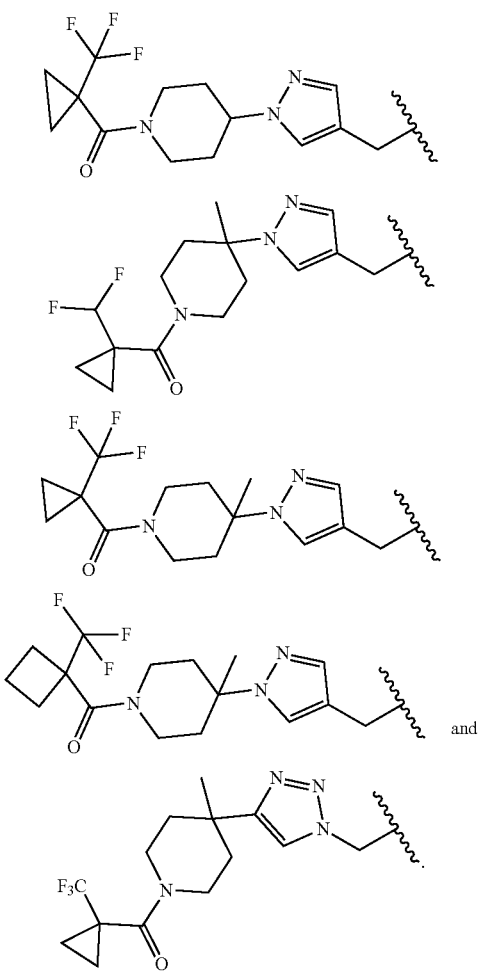

In certain embodiments, $R^1$ is —(CH$_2$)—$R^4$ wherein $R^4$ is heteroaryl optionally substituted with $R^6$ and $R^6$ is heterocycle optionally substituted with 1 or 2 groups selected from $R^9$. In a further embodiment, $R^9$ is selected from alkyl and —C(O)R$^{10}$ wherein $R^{10}$ is alkyl optionally substituted with $R^{11}$ and $R^{11}$ is selected from hydrogen, hydroxyl, and cyano. Non-limiting examples of this embodiment include:

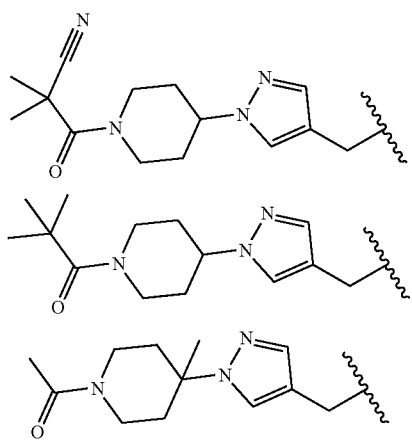

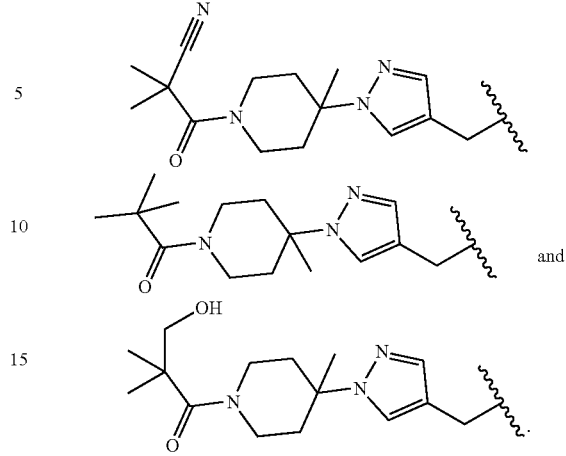

In certain embodiments, $R^1$ is —(CH$_2$)—$R^4$ wherein $R^4$ is heteroaryl optionally substituted with $R^6$ and $R^6$ is heterocycle optionally substituted with 1 or 2 groups selected from $R^9$. In a further embodiment, $R^9$ is selected from alkyl and —C(O)R$^{10}$ wherein $R^{10}$ is haloalkyl. Non-limiting examples of this embodiment include:

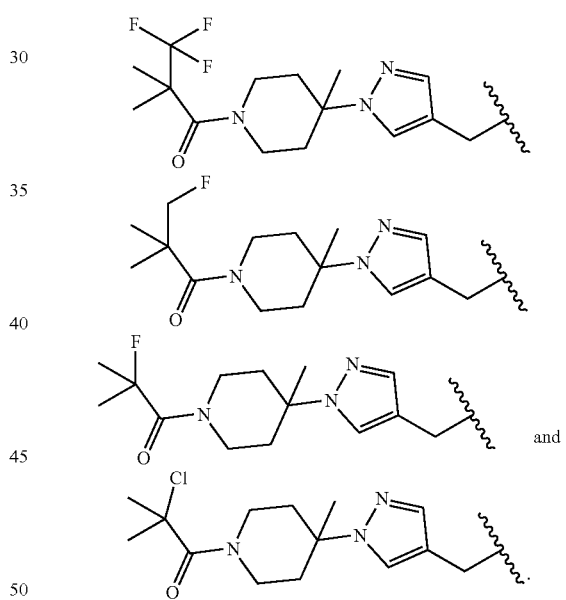

In certain embodiments, $R^1$ is —(CH$_2$)—$R^4$ wherein $R^4$ is heteroaryl optionally substituted with $R^6$ and $R^6$ is heterocycle optionally substituted with 1 or 2 groups selected from $R^9$. In a further embodiment, $R^9$ is selected from alkyl and —C(O)R$^{10}$ wherein $R^{10}$ is alkyl optionally substituted with $R^{11}$ and $R^{11}$ is OR$^8$. Non-limiting examples of this embodiment include:

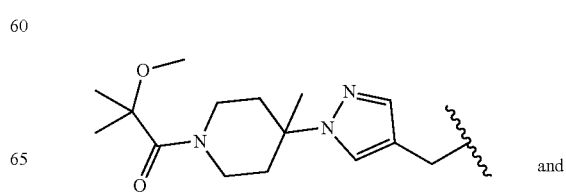

-continued

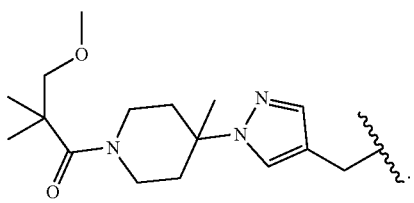

In certain embodiments, $R^1$ is —$(CH_2)$—$R^4$ wherein $R^4$ is heteroaryl optionally substituted with $R^6$ and $R^6$ is heterocycle optionally substituted with $R^9$. In a further embodiment, $R^9$ is —$C(O)R^{10}$ wherein $R^{10}$ is heteroaryl or aryl optionally substituted with $R^{11}$ and $R^{11}$ is selected from hydrogen and alkyl. Non-limiting examples of this embodiment include:

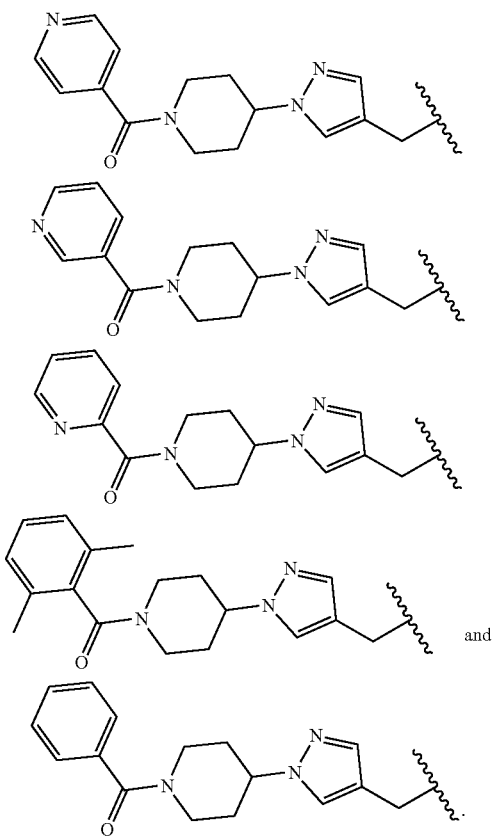

In certain embodiments, $R^1$ is —$(CH_2)$—$R^4$ wherein $R^4$ is heteroaryl optionally substituted with $R^6$ and $R^6$ is heterocycle optionally substituted with $R^9$. In a further embodiment, $R^9$ is —$C(O)NR^1R^{10}$ or —$C(O)OR^{10}$ wherein $R^{10}$ is alkyl. Non-limiting examples of this embodiment include:

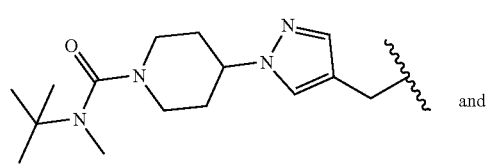 and

-continued

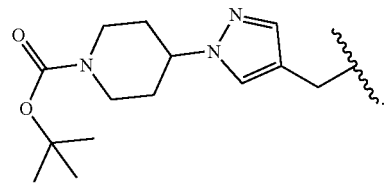

In certain embodiments, $R^1$ is —$(CH_2)$—$R^4$ wherein $R^4$ is heteroaryl optionally substituted with $R^6$ and $R^6$ is heterocycle optionally substituted with 1 or 2 groups selected from $R^9$. In a further embodiment, $R^9$ is selected from alkyl and —$CH_2R^{10}$ wherein $R^{10}$ is cycloalkyl optionally substituted with $R^{11}$ and $R^{11}$ is alkyl. Non-limiting examples of this embodiment include:

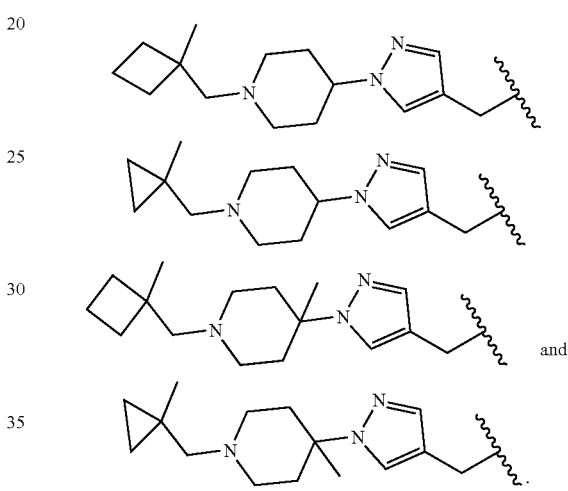

and

In certain embodiments, $R^1$ is —$(CH_2)$—$R^4$ wherein $R^4$ is heteroaryl optionally substituted with $R^6$ and $R^6$ is heterocycle optionally substituted with 1 or 2 groups selected from $R^9$. In a further embodiment, $R^9$ is selected from alkyl and —$CH_2R^{10}$ wherein $R^{10}$ is cycloalkyl optionally substituted with $R^{11}$ and $R^{11}$ is selected from haloalkyl or cyano. Non-limiting examples of this embodiment include:

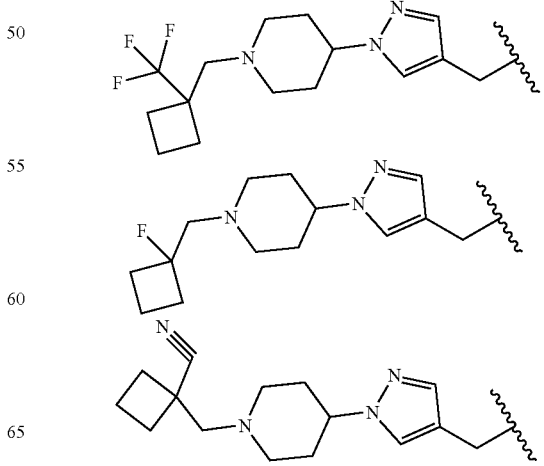

-continued

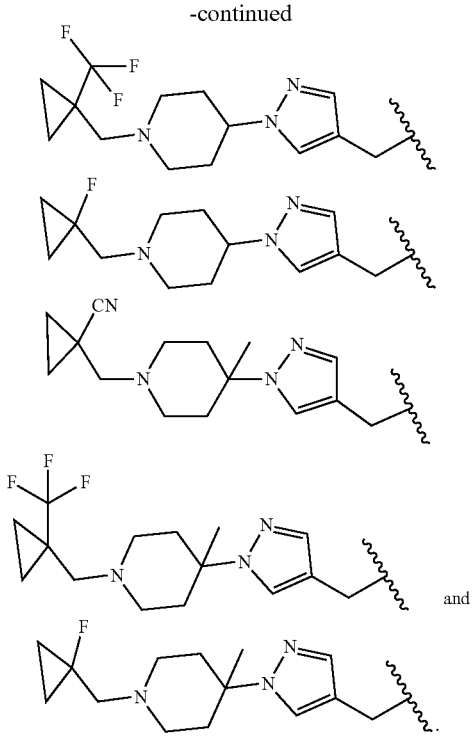

In certain embodiments, $R^1$ is —(CH$_2$)—$R^4$ wherein $R^4$ is heteroaryl optionally substituted with $R^6$ and $R^6$ is heterocycle optionally substituted with 1 or 2 groups selected from $R^9$. In a further embodiment, $R^9$ is selected from alkyl and —CH$_2$R$^{10}$ wherein $R^{10}$ is cycloalkyl optionally substituted with $R^{11}$ and $R^{11}$ is OR$^8$. Non-limiting examples of this embodiment include:

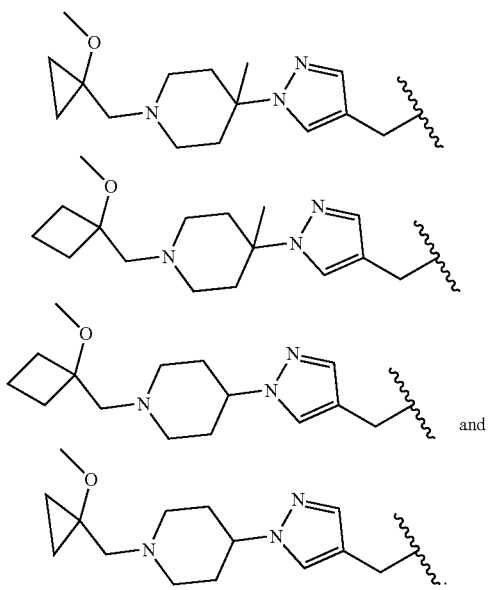

In certain embodiments, $R^1$ is —(CH$_2$)—$R^4$ wherein $R^4$ is heteroaryl optionally substituted with $R^6$ and $R^6$ is heterocycle optionally substituted with 1 or 2 groups selected from $R^9$. In a further embodiment, $R^9$ is selected from alkyl and —CH$_2$R$^{10}$ wherein $R^{10}$ is alkyl optionally substituted with $R^{11}$ and $R^{11}$ is selected from hydrogen, cyano, and OR$^8$. Non-limiting examples of this embodiment include:

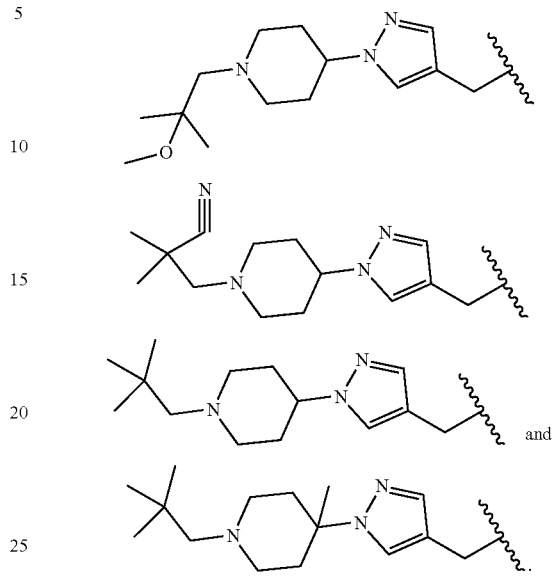

In certain embodiments, $R^1$ is —(CH$_2$)—$R^4$ wherein $R^4$ is heteroaryl optionally substituted with $R^6$ and $R^6$ is heterocycle optionally substituted with $R^9$. In a further embodiment, $R^9$ is $R^{10}$ and $R^{10}$ is cycloalkyl. Non-limiting examples of this embodiment include:

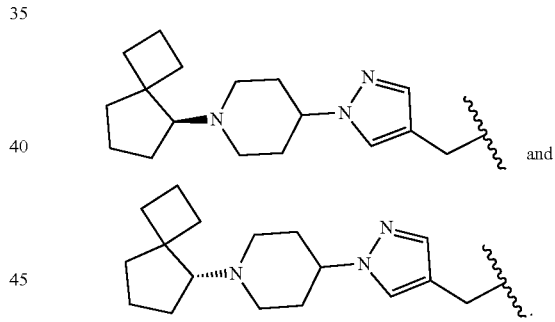

In certain embodiments, $R^1$ is —(CH$_2$)—$R^4$ wherein $R^4$ is heteroaryl substituted with $R^7$ and substituted with $R^6$ wherein $R^6$ is heterocycle optionally substituted with 1 or 2 groups selected from $R^9$. In a further embodiment, $R^9$ is selected from alkyl and —C(O)R$^{10}$ and $R^{10}$ is cycloalkyl optionally substituted with $R^{11}$ and $R^{11}$ is alkyl. A non-limiting example of this embodiment includes:

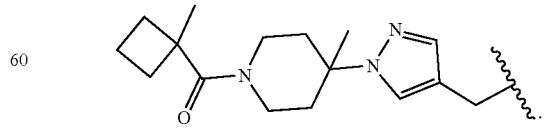

In certain embodiments, $R^1$ is —(CH$_2$)—$R^4$ wherein $R^4$ is heteroaryl optionally substituted with $R^6$ and $R^6$ is cycloalkyl. A non-limiting example of this embodiment includes:

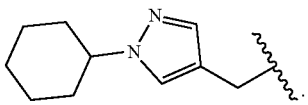 [SMILES: *Cc1cnn(C2CCCCC2)c1]

In certain embodiments, $R^1$ is —C(O)$R^4$ wherein $R^4$ is heteroaryl optionally substituted with $R^6$ and $R^6$ is heterocycle. In a further embodiment, $R^6$ is optionally substituted with $R^9$ and $R^9$ is —C(O)O$R^{10}$ wherein $R^{10}$ is alkyl. A non-limiting example of this embodiment includes:

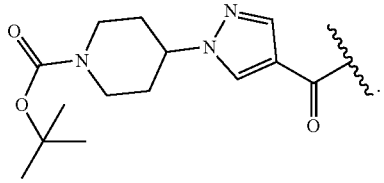 [SMILES: *C(=O)c1cnn(C2CCN(C(=O)OC(C)(C)C)CC2)c1]

In certain embodiments, $R^1$ is —CH(CH$_3$)$R^4$ wherein $R^4$ is heteroaryl optionally substituted with $R^6$ and $R^6$ is heterocycle. In a further embodiment, $R^6$ is optionally substituted with $R^9$ and $R^9$ is —C(O)O$R^{10}$ or —C(O)$R^{10}$ wherein $R^{10}$ is alkyl or cycloalkyl optionally substituted with $R^{11}$ and $R^{11}$ is selected from alkyl and hydrogen. Non-limiting examples of this embodiment include:

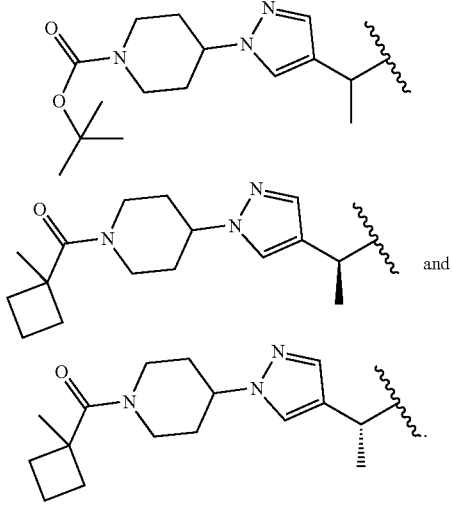

In certain embodiments, $R^1$ is —CH(NH$_2$)$R^4$ wherein $R^4$ is heteroaryl optionally substituted with $R^6$ and $R^6$ is heterocycle. In a further embodiment, $R^6$ is optionally substituted with $R^9$ and $R^9$ is —C(O)O$R^{10}$ or —C(O)$R^{10}$ wherein $R^{10}$ is alkyl or cycloalkyl optionally substituted with $R^{11}$ and $R^{11}$ is selected from alkyl and hydrogen. Non-limiting examples of this embodiment include:

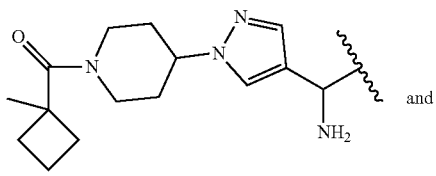

-continued

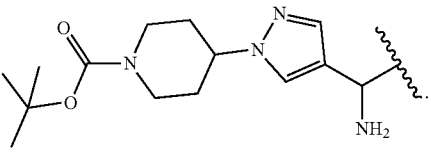

In certain embodiments, $R^1$ is —S$R^4$, —S(O)$R^4$, or —S(O)$_2R^4$ wherein $R^4$ is heteroaryl optionally substituted with $R^6$ and $R^6$ is heterocycle optionally substituted with $R^9$. In a further embodiment, $R^9$ is —C(O)$R^{10}$ wherein $R^{10}$ is cycloalkyl optionally substituted with $R^{11}$ and $R^{11}$ is alkyl. Non-limiting examples of this embodiment include:

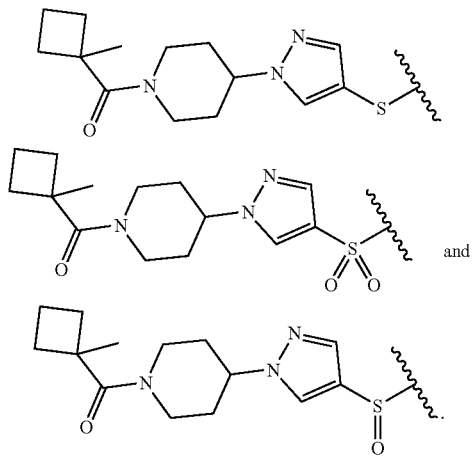

In certain embodiments, $R^1$ is —(CH$_2$)—$R^4$ wherein $R^4$ is heteroaryl optionally substituted with $R^6$ and $R^6$ is cycloalkyl optionally substituted with $R^9$. In a further embodiment, $R^9$ is selected from —O$R^{10}$ wherein $R^{10}$ is alkyl optionally substituted with $R^{11}$ and $R^{11}$ is aryl. A non-limiting example of this embodiment includes:

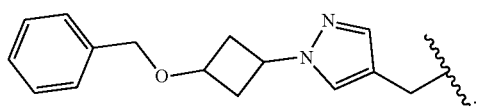 [SMILES: *Cc1cnn(C2CC(OCc3ccccc3)C2)c1]

In certain embodiments, $R^1$ is —(C$R^3R^{3'}$)—$R^4$ wherein $R^3$ and $R^{3'}$ are brought together with the carbon to which they are attached to form a 3-membered cycloalkyl ring and $R^4$ is heteroaryl optionally substituted with $R^6$ wherein $R^6$ is heterocycle optionally substituted with $R^9$. In a further embodiment, $R^9$ is —C(O)$R^{10}$ or —CH$_2R^{10}$ wherein $R^{10}$ is cycloalkyl optionally substituted with $R^{11}$ and $R^{11}$ is alkyl. Non-limiting examples of this embodiment include:

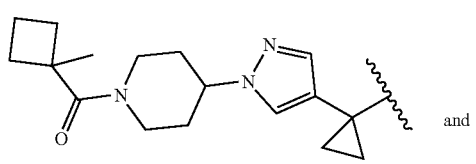

-continued

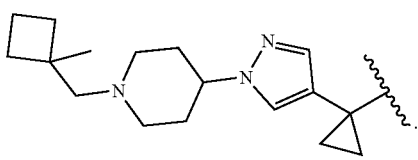

In certain embodiments, $R^1$ is —(CH$_2$)—$R^4$ wherein $R^4$ is aryl substituted with $R^6$ and $R^6$ is alkyl optionally substituted with $R^9$. In a further embodiment, $R^9$ is $R^{10}$ and $R^{10}$ is heterocycle optionally substituted with $R^{11}$ wherein $R^{11}$ is —C(O)OR$^8$, —C(O)R$^8$, or —SO$_2$R$^8$ and $R^8$ is alkyl, cycloalkyl, haloalkyl, or aryl. Non-limiting examples of this embodiment include:

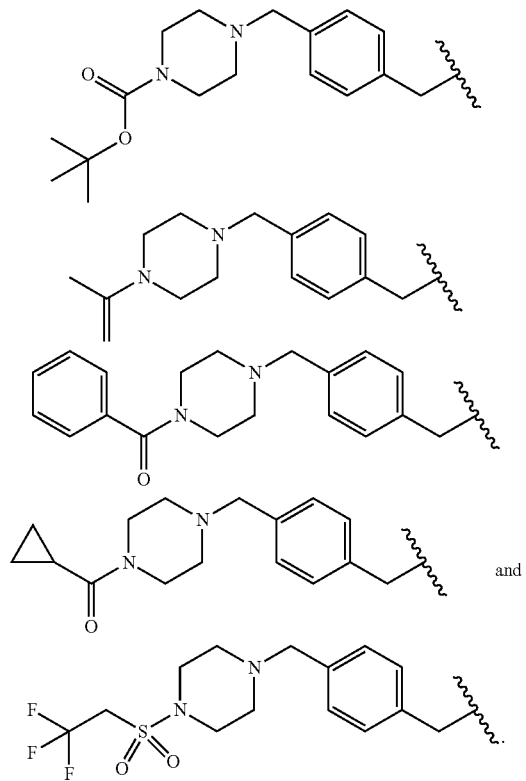

In certain embodiments, $R^1$ is —(CH$_2$)—$R^4$ wherein $R^4$ is aryl substituted with $R^6$ and $R^6$ is alkyl optionally substituted with $R^9$. In a further embodiment, $R^9$ is $R^{10}$ and $R^{10}$ is heterocycle or heteroaryl. Non-limiting examples of this embodiment include:

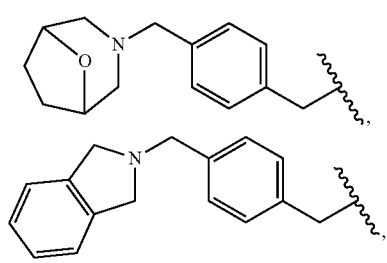

-continued

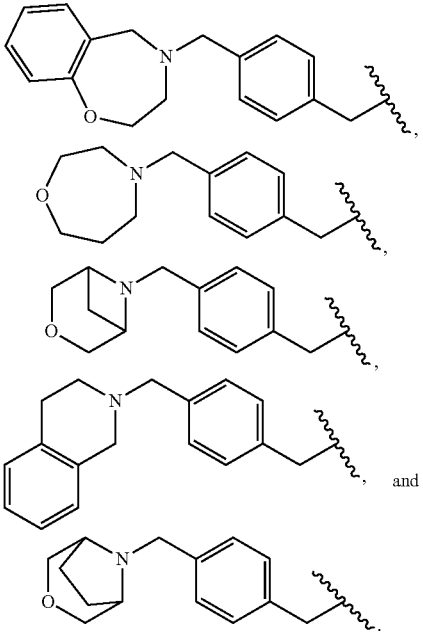

In certain embodiments, $R^1$ is —(CH$_2$)—$R^4$ wherein $R^4$ is aryl substituted with $R^6$ and $R^6$ is alkyl optionally substituted with $R^9$. In a further embodiment, $R^9$ is $R^{10}$ and $R^{10}$ is heterocycle or heteroaryl optionally substituted with $R^{11}$ wherein $R^{11}$ is selected from hydrogen, alkyl or haloalkyl. In one embodiment, two $R^{11}$ groups on the same carbon are brought together to form an oxo group. Non-limiting examples of this embodiment include:

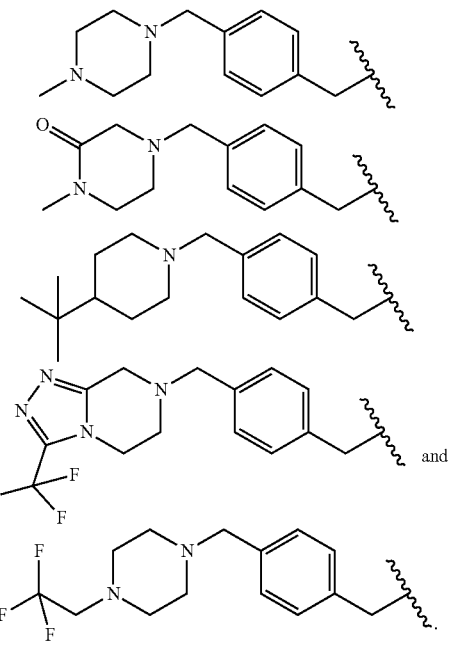

In certain embodiments, $R^1$ is —CH$_2$—$R^4$ wherein $R^4$ is aryl optionally substituted with $R^6$ and $R^6$ is alkyl optionally substituted with $R^9$. In a further embodiment, $R^9$ is $R^{10}$ wherein $R^{10}$ is heterocycle optionally substituted with $R^{11}$ and R[11] is —CH₂aryl optionally substituted with halogen. Non-limiting examples of this embodiment include:

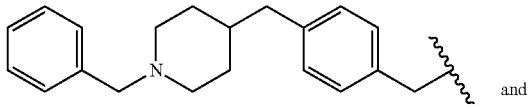 and

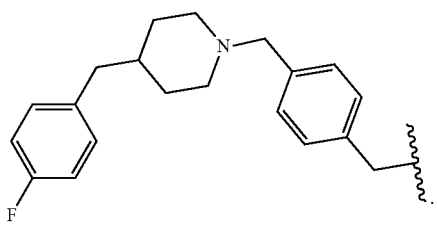

In certain embodiments, R[1] is —CH₂—R[4] wherein R[4] is aryl optionally substituted with R[6] and R[6] is alkyl optionally substituted with R[9]. In a further embodiment, R[9] is R[10] wherein R[10] is heterocycle optionally substituted with R[11] and R[11] is aryl optionally substituted with halogen. A non-limiting example of this embodiment includes:

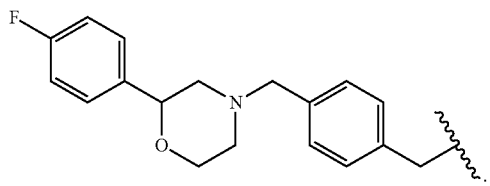 [SMILES: *Cc1ccc(CN2CCOC(c3ccc(F)cc3)C2)cc1]

In certain embodiments, R[1] is —CH₂—R[4] wherein R[4] is aryl optionally substituted with R[6] and R[6] is heterocycle optionally substituted with R[9]. In a further embodiment, R[9] is —CH₂R[10] or —C(O)R[10] wherein R[10] is cycloalkyl optionally substituted with R[11] and R[11] is hydrogen or alkyl. Non-limiting examples of this embodiment include:

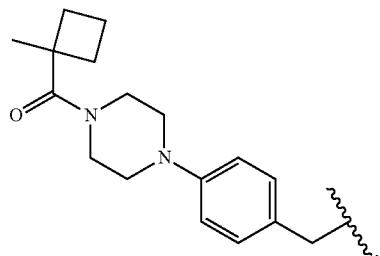

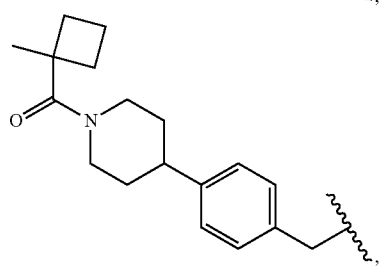

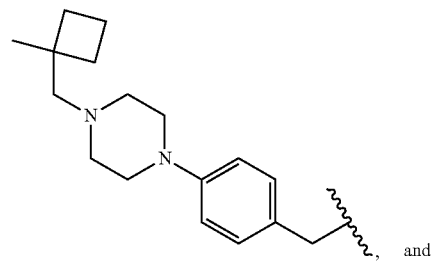, and

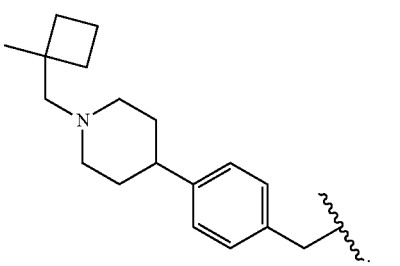

In certain embodiments, R[1] is —(CH₂)—R[4] wherein R[4] is heteroaryl optionally substituted with R[6] and R[6] is heterocycle optionally substituted with R[9]. In a further embodiment, R[9] is selected from R[10] wherein R[10] is heteroaryl optionally substituted with R[11] groups selected from halogen and hydrogen. Non-limiting examples of this embodiment include:

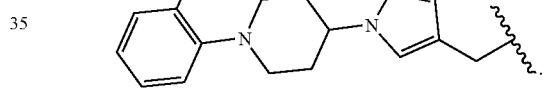

In certain embodiments, R[1] is selected from

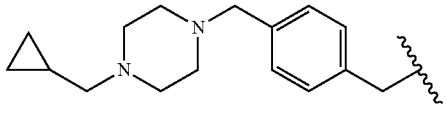

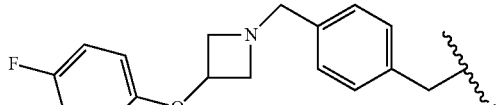

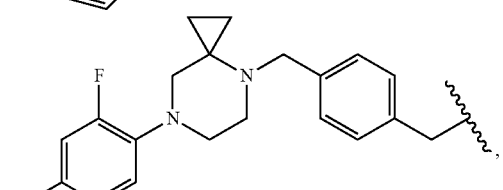

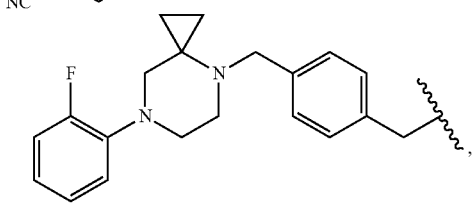

75
-continued
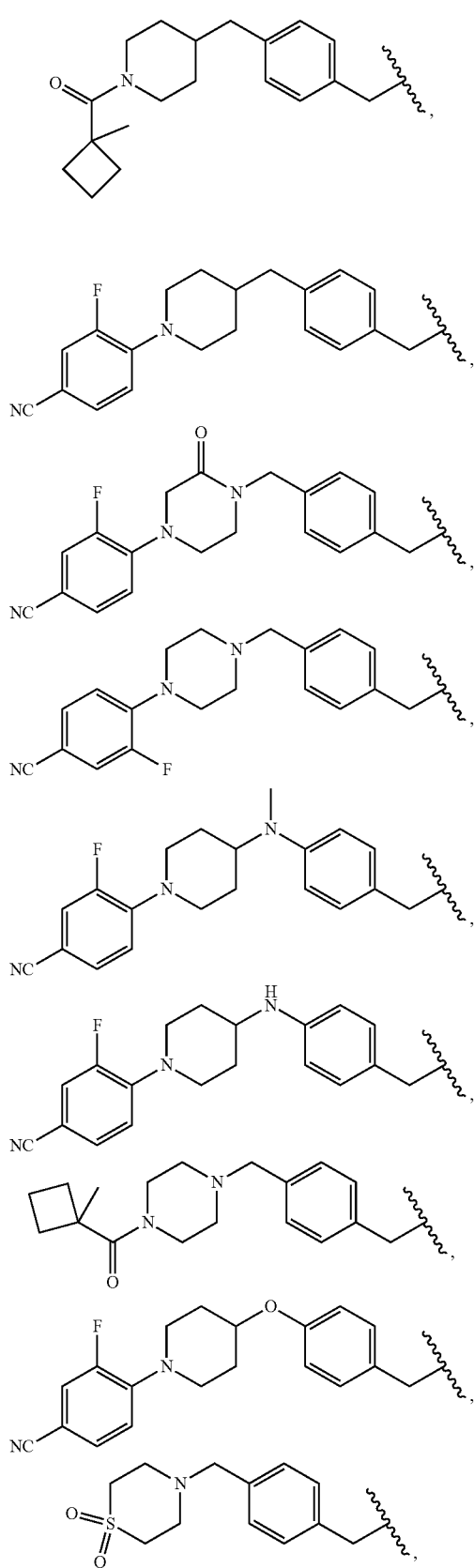
76
-continued
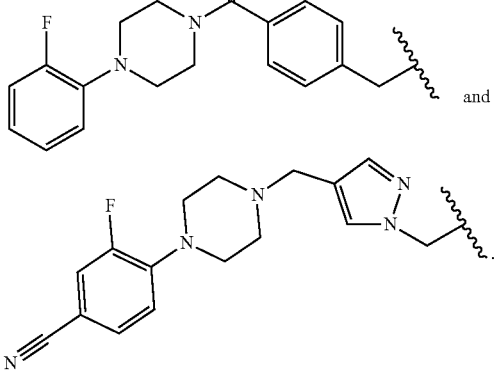
Non-limiting Embodiments of $R^4$
In one embodiment of Formula I, $R^4$ is selected from:
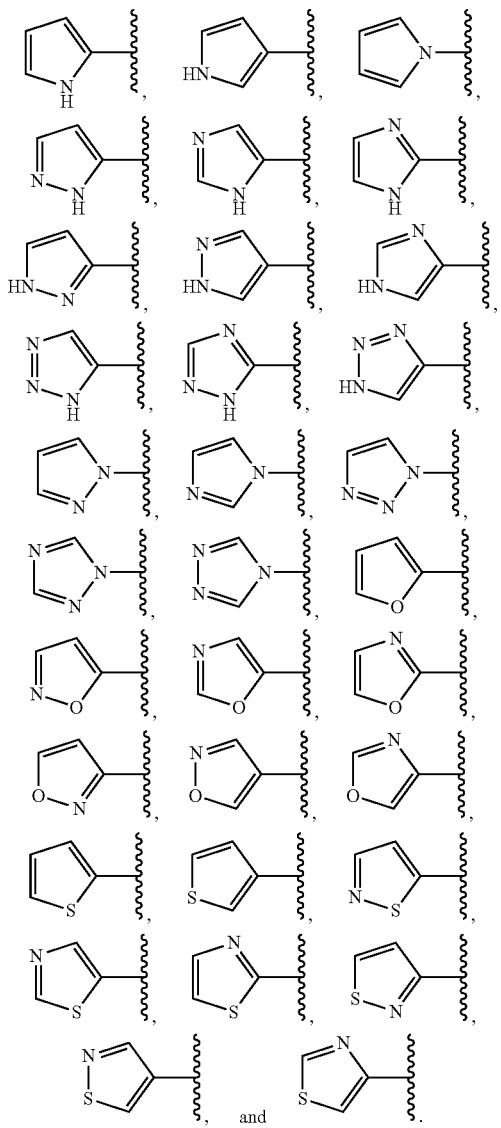

In one embodiment of Formula I, $R^4$ is selected from:
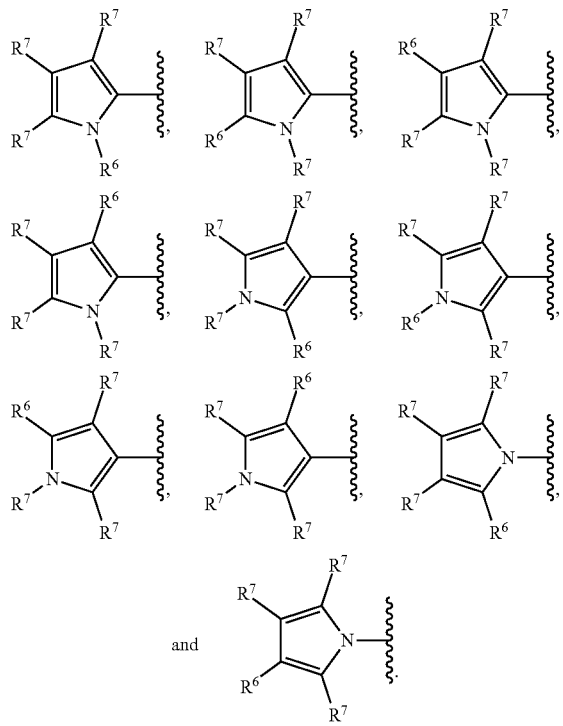
and
In one embodiment of Formula I, $R^4$ is selected from:
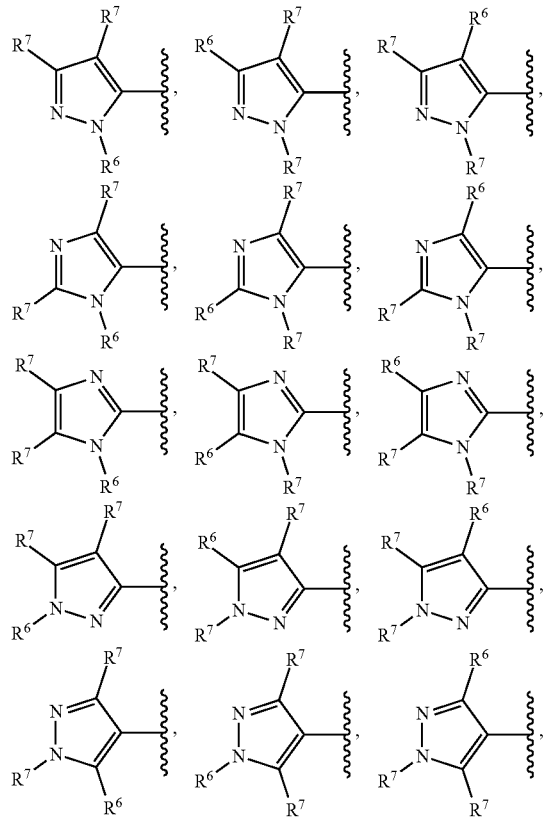
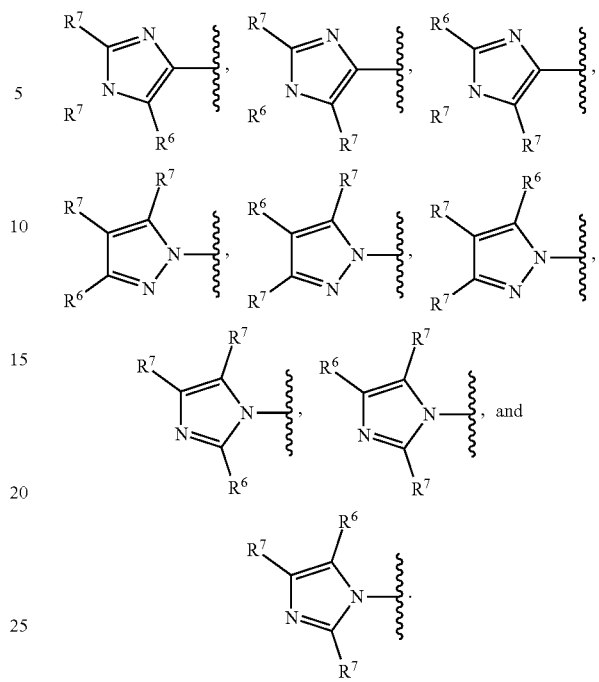
and
In one embodiment of Formula I, $R^4$ is selected from:
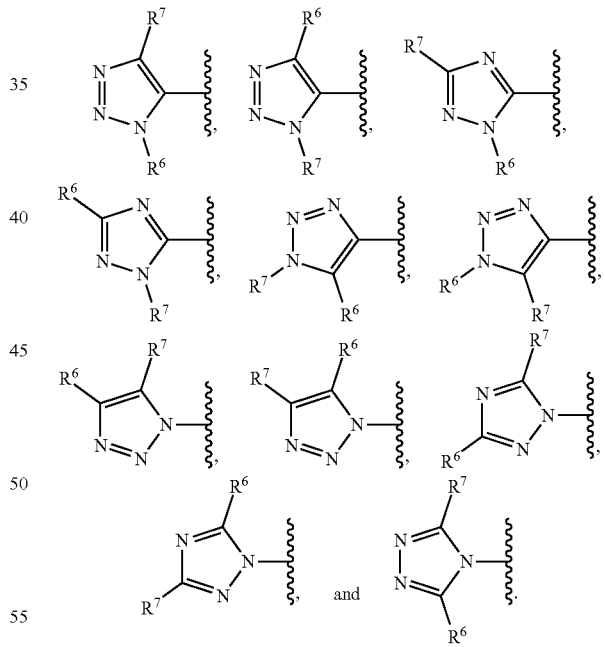
and
In one embodiment of Formula I, $R^4$ is selected from:
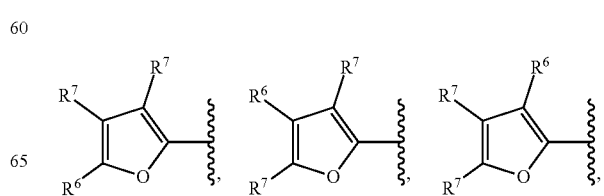

-continued
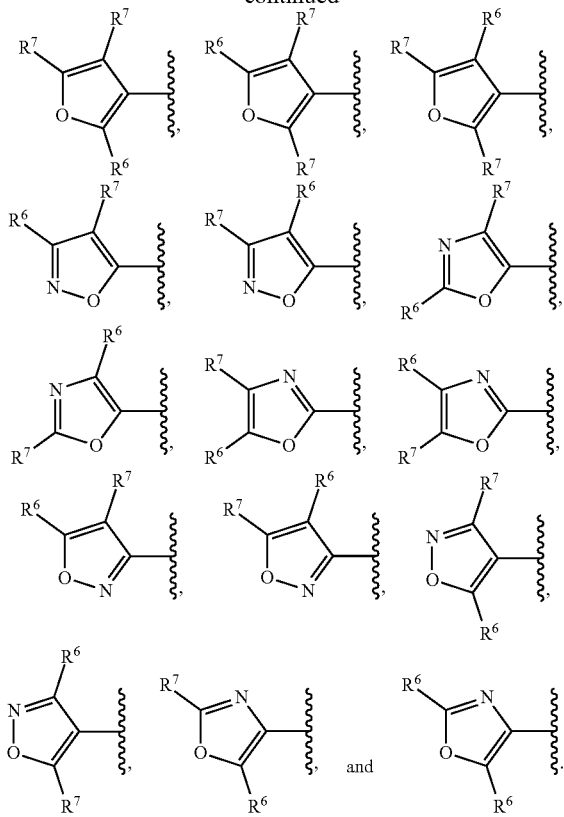
In one embodiment of Formula I, R⁴ is selected from:
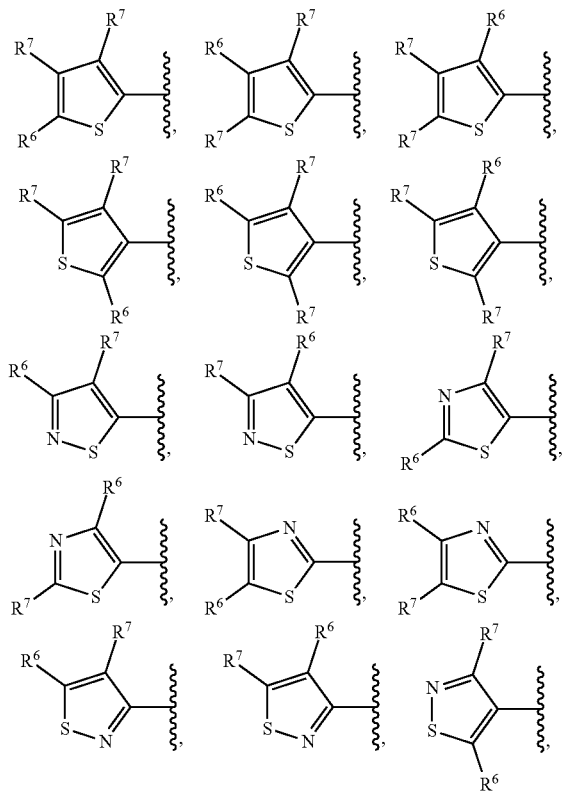
-continued
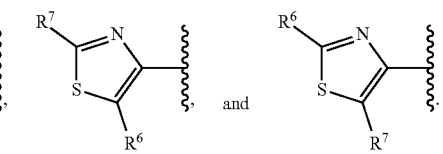
In one embodiment of Formula I, R⁴ is selected from:
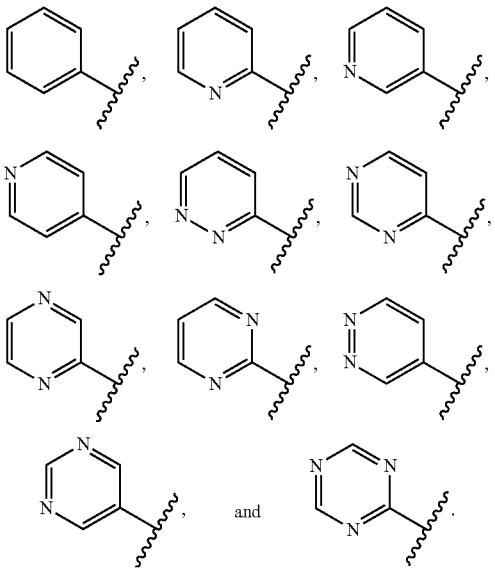
In one embodiment of Formula I, R⁴ is selected from:
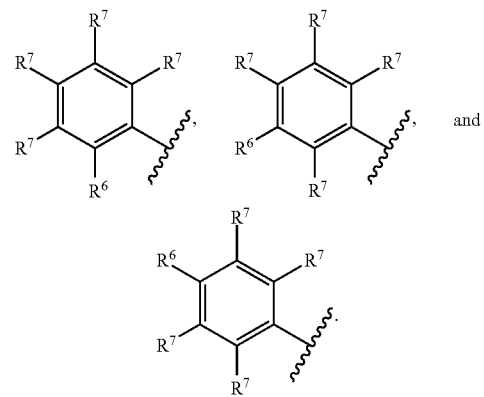
In one embodiment of Formula I, R⁴ is selected from:
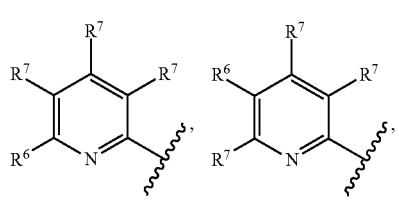

-continued
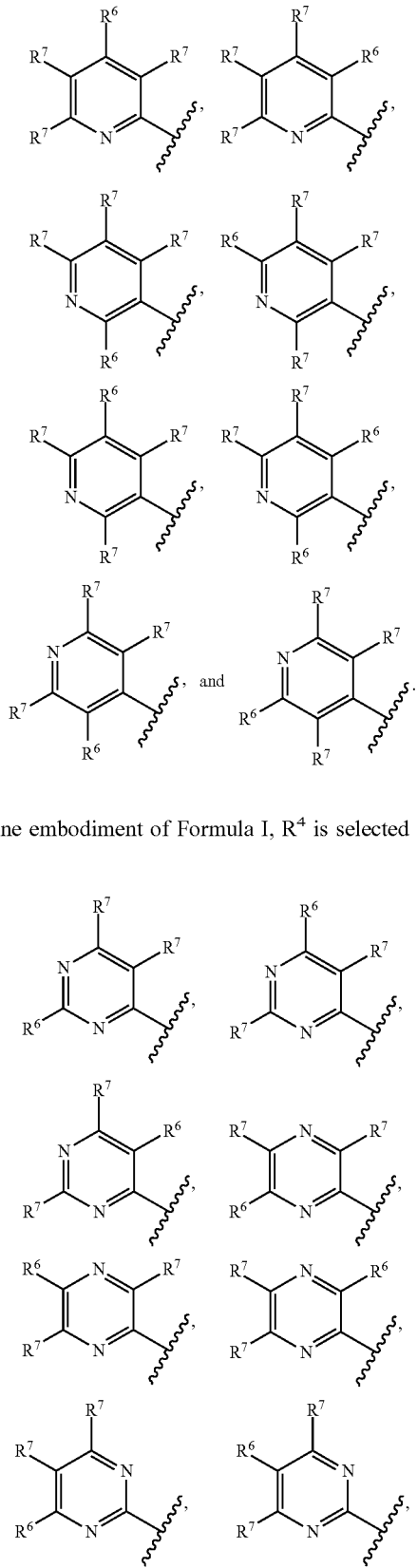
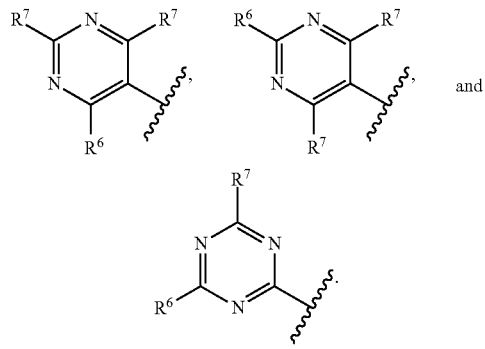
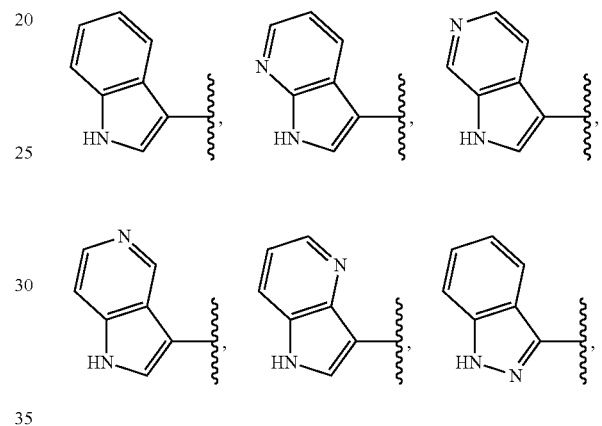
In one embodiment of Formula I, R⁴ is selected from:
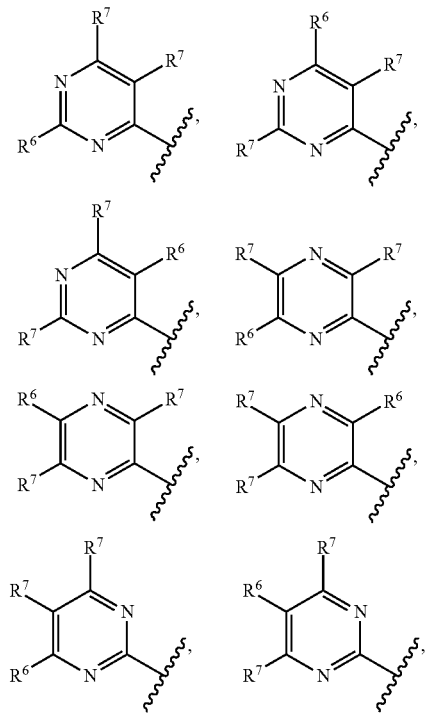
In one embodiment of Formula I, R⁴ is selected from:
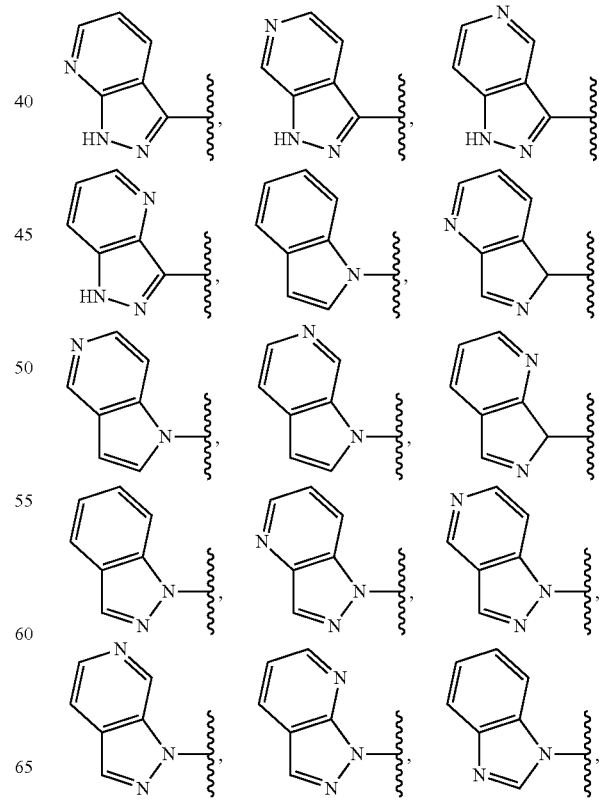

-continued
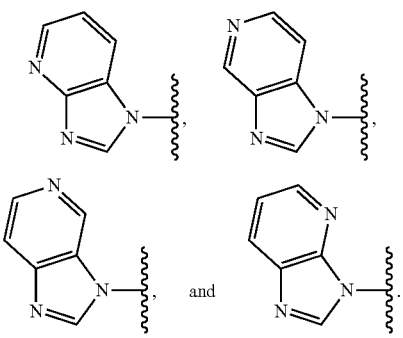
In one embodiment of Formula I, R⁴ is selected from:
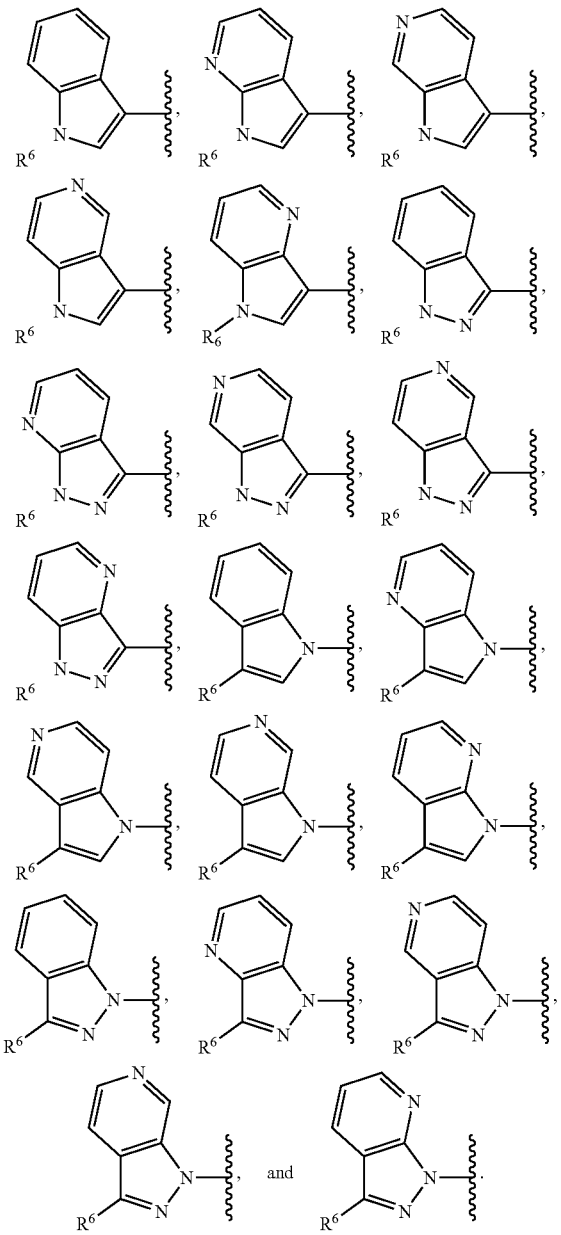
In certain embodiments R⁴ is selected from:
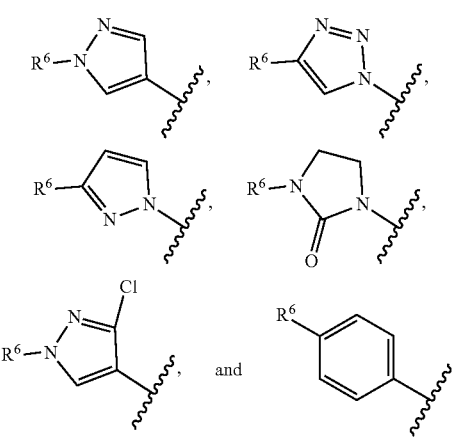
In one embodiment, a compound of Formula I is selected from:
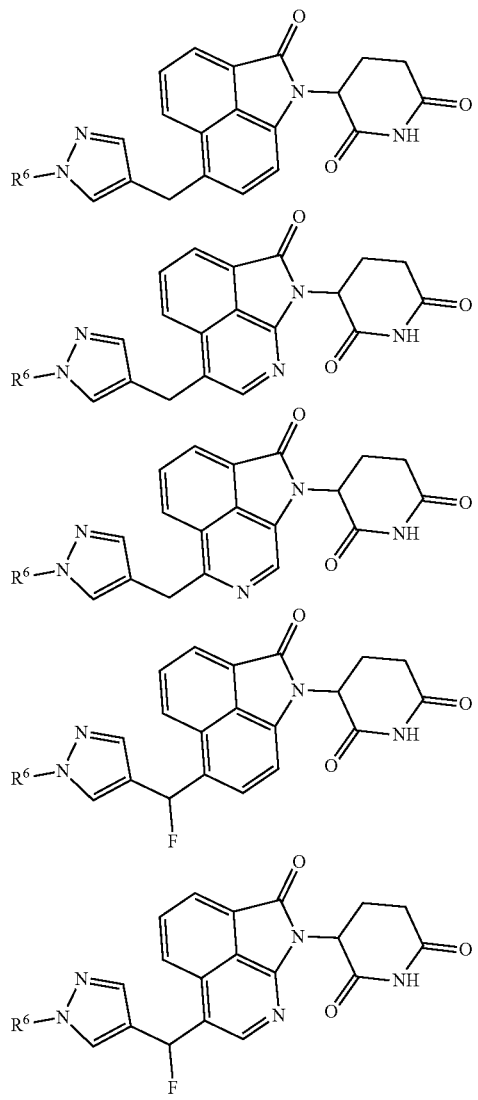

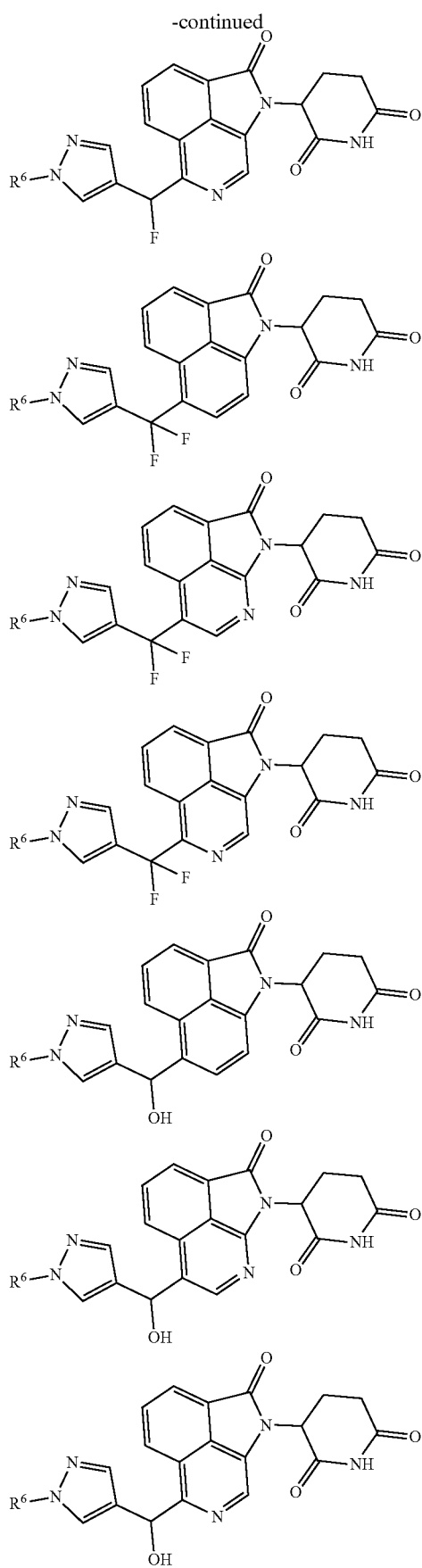
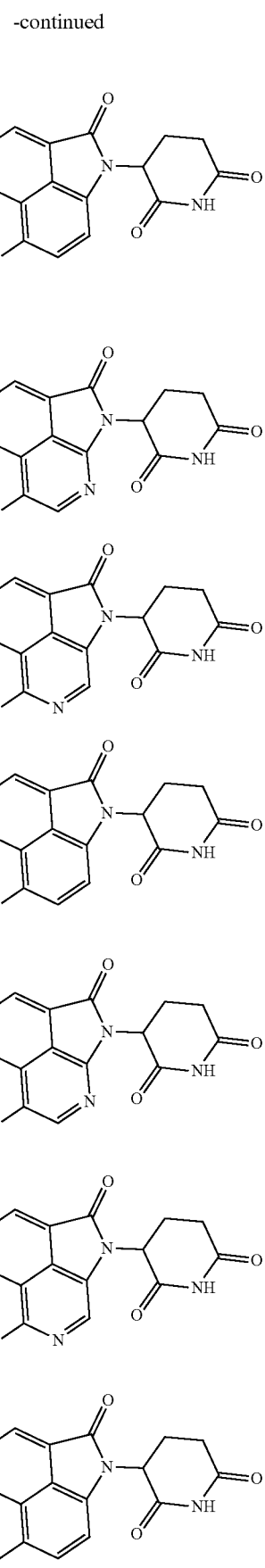

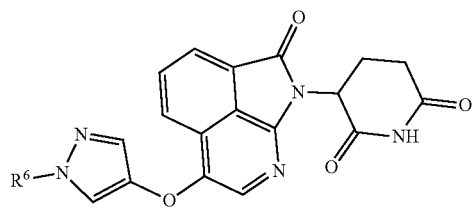
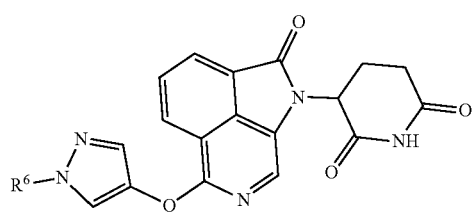
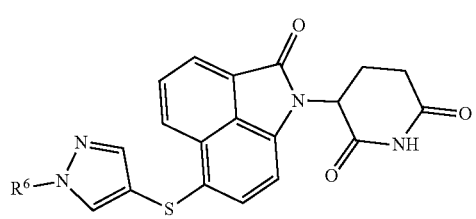
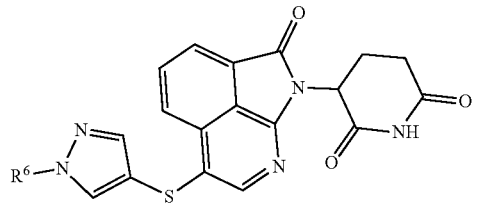
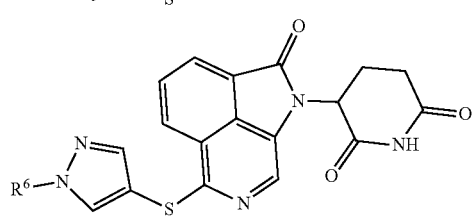

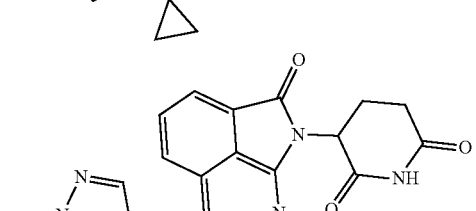
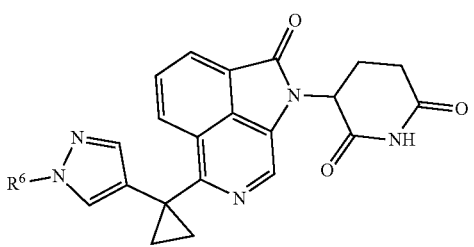
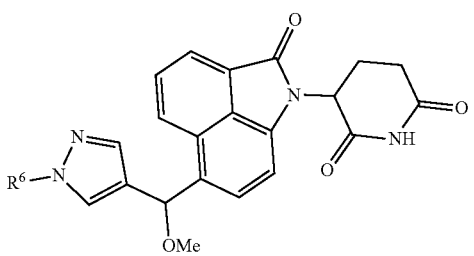
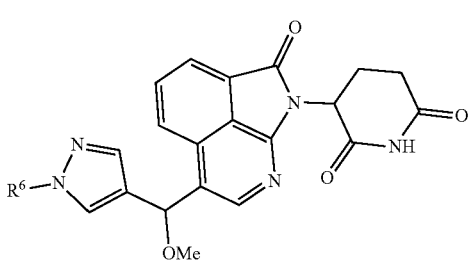
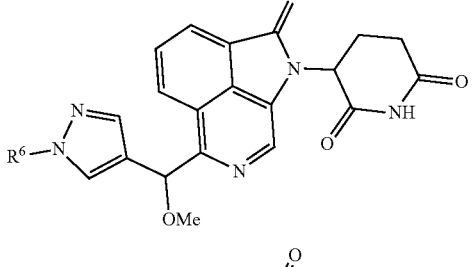
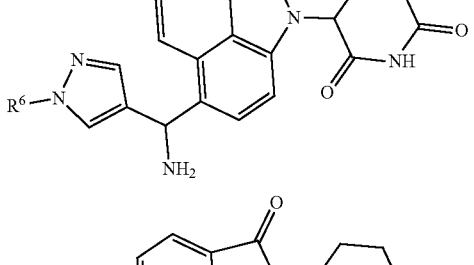
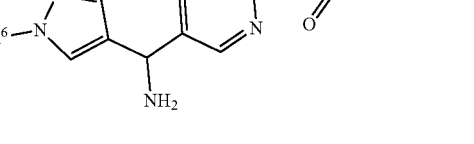
and

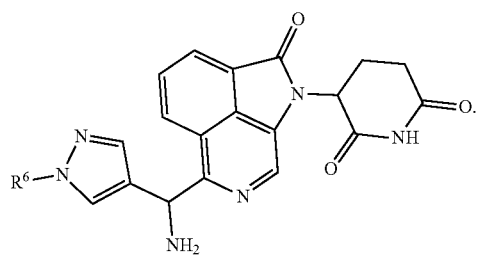
In one embodiment, a compound of Formula I is selected from:
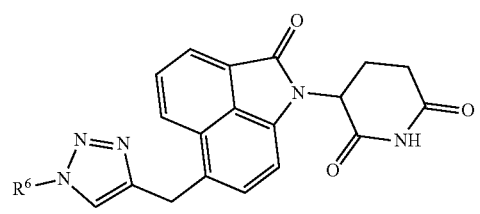
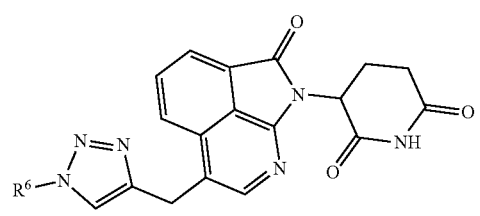
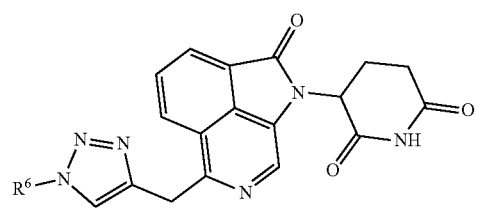
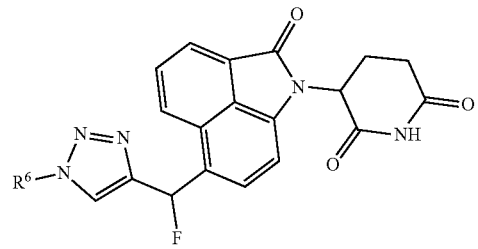
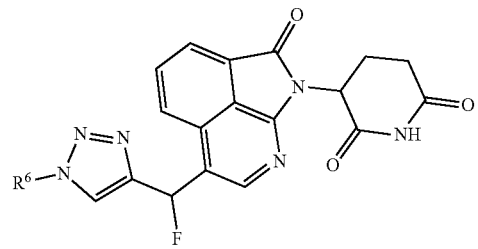
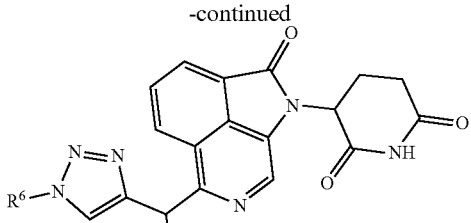
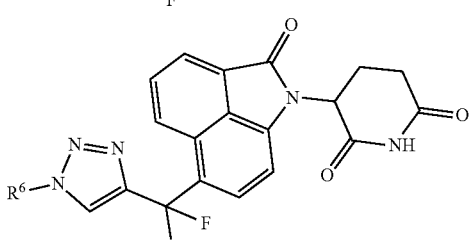
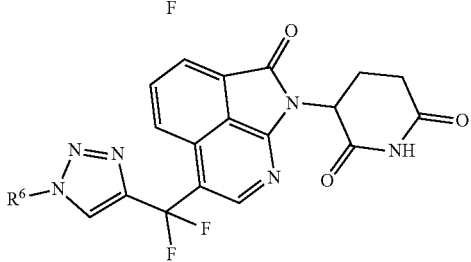
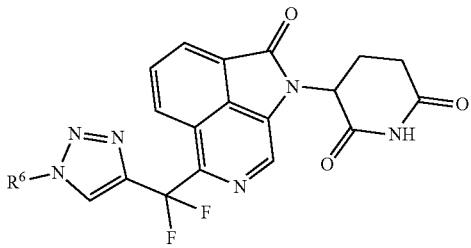
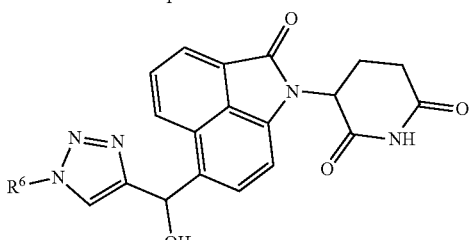
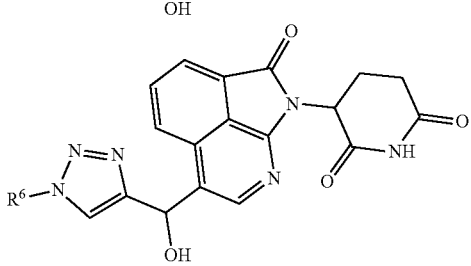
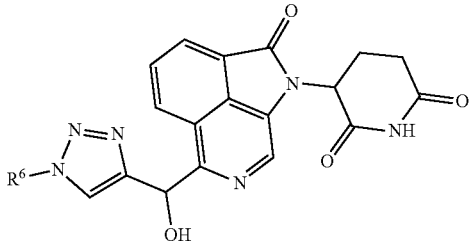

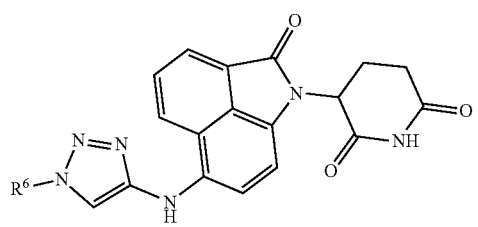
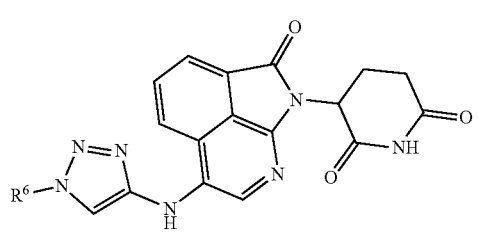
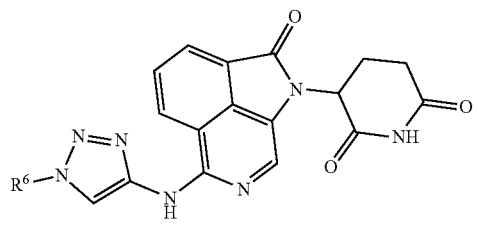
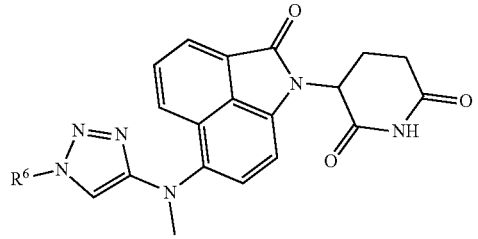
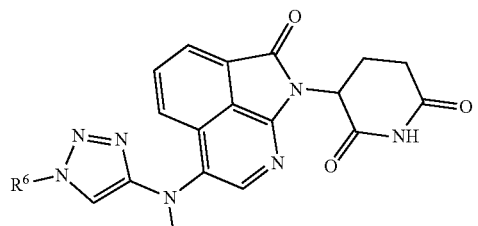
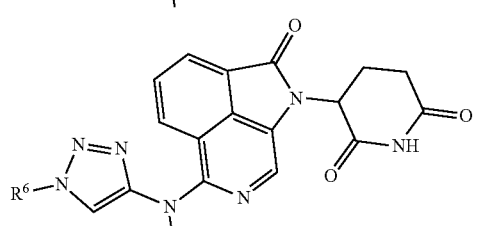
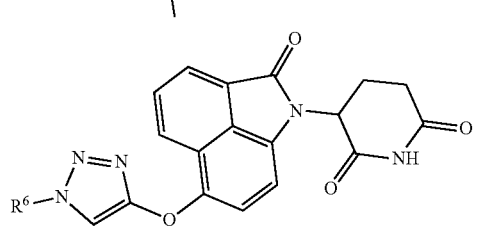
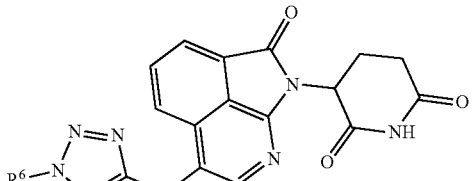
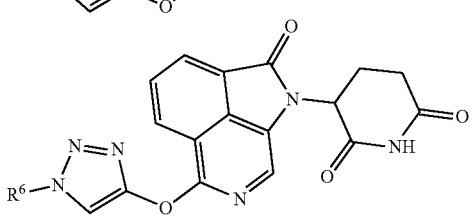
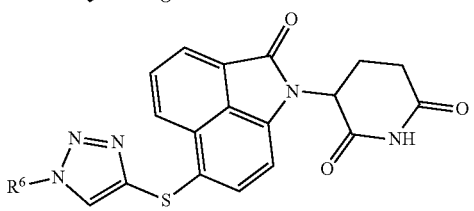
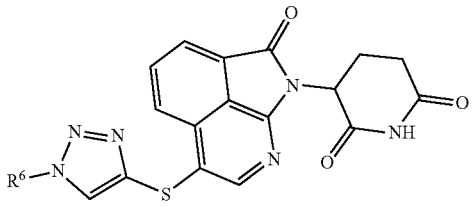
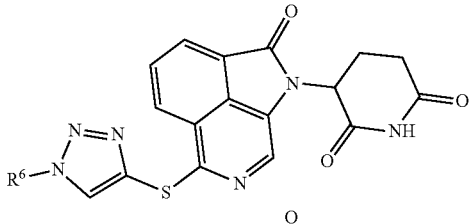
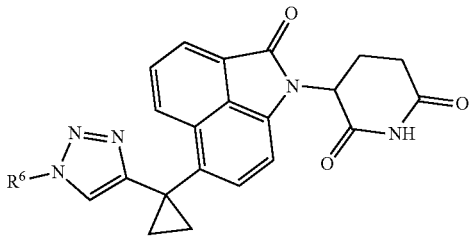
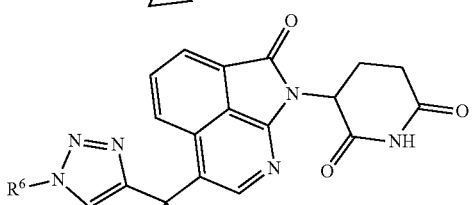
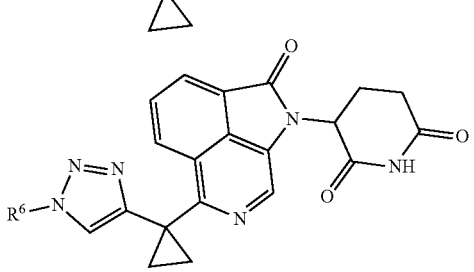

-continued
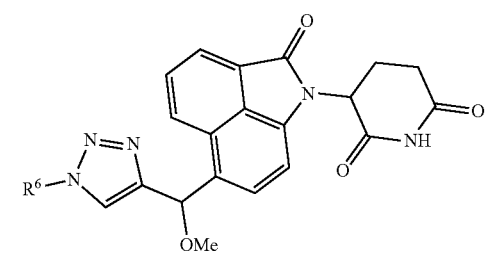
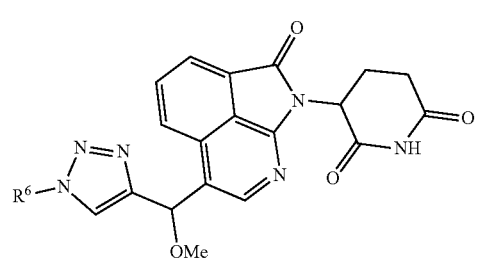
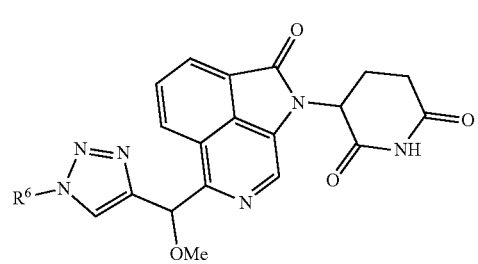
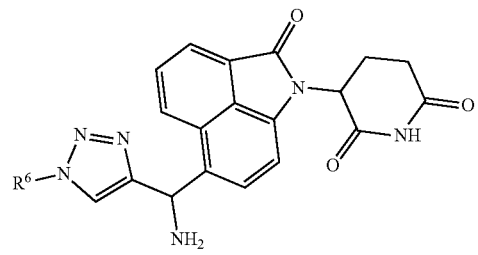
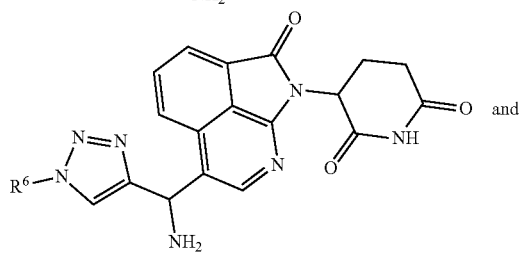 and
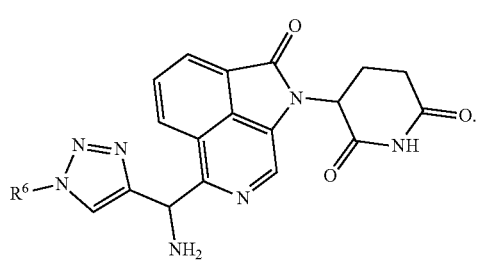.
In one embodiment, a compound of Formula I is selected from:
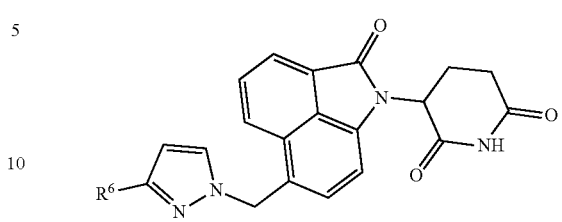
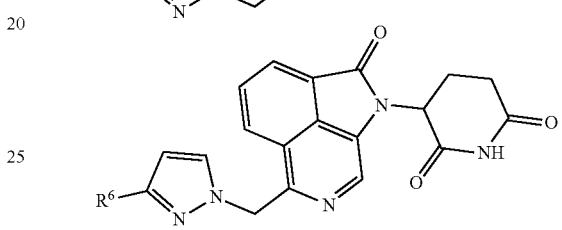
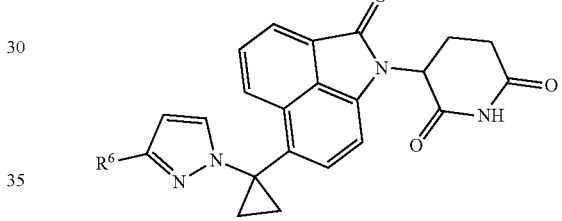
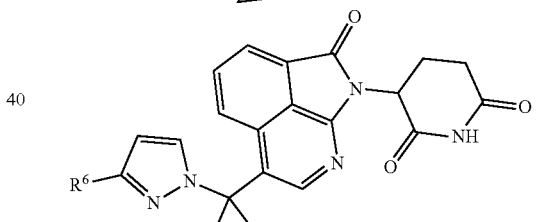
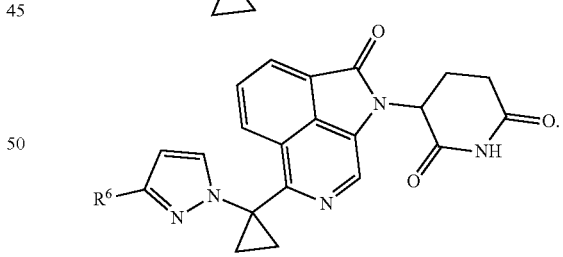 and
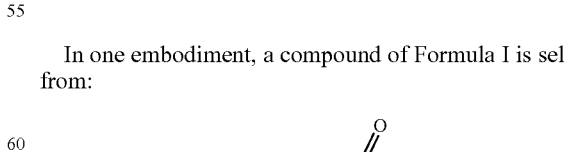.
In one embodiment, a compound of Formula I is selected from:
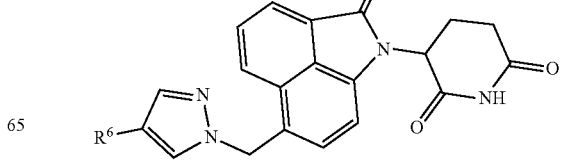

-continued
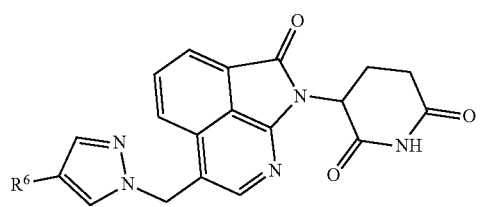

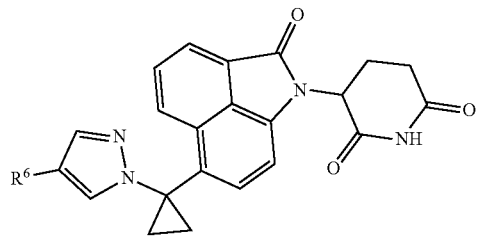
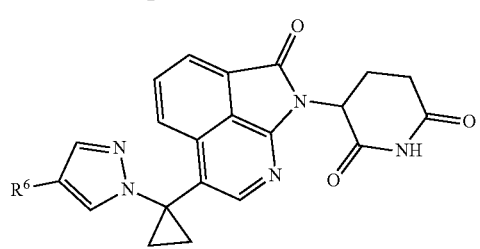
and
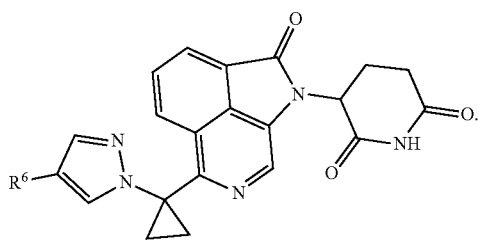
In one embodiment, a compound of Formula I is selected from:
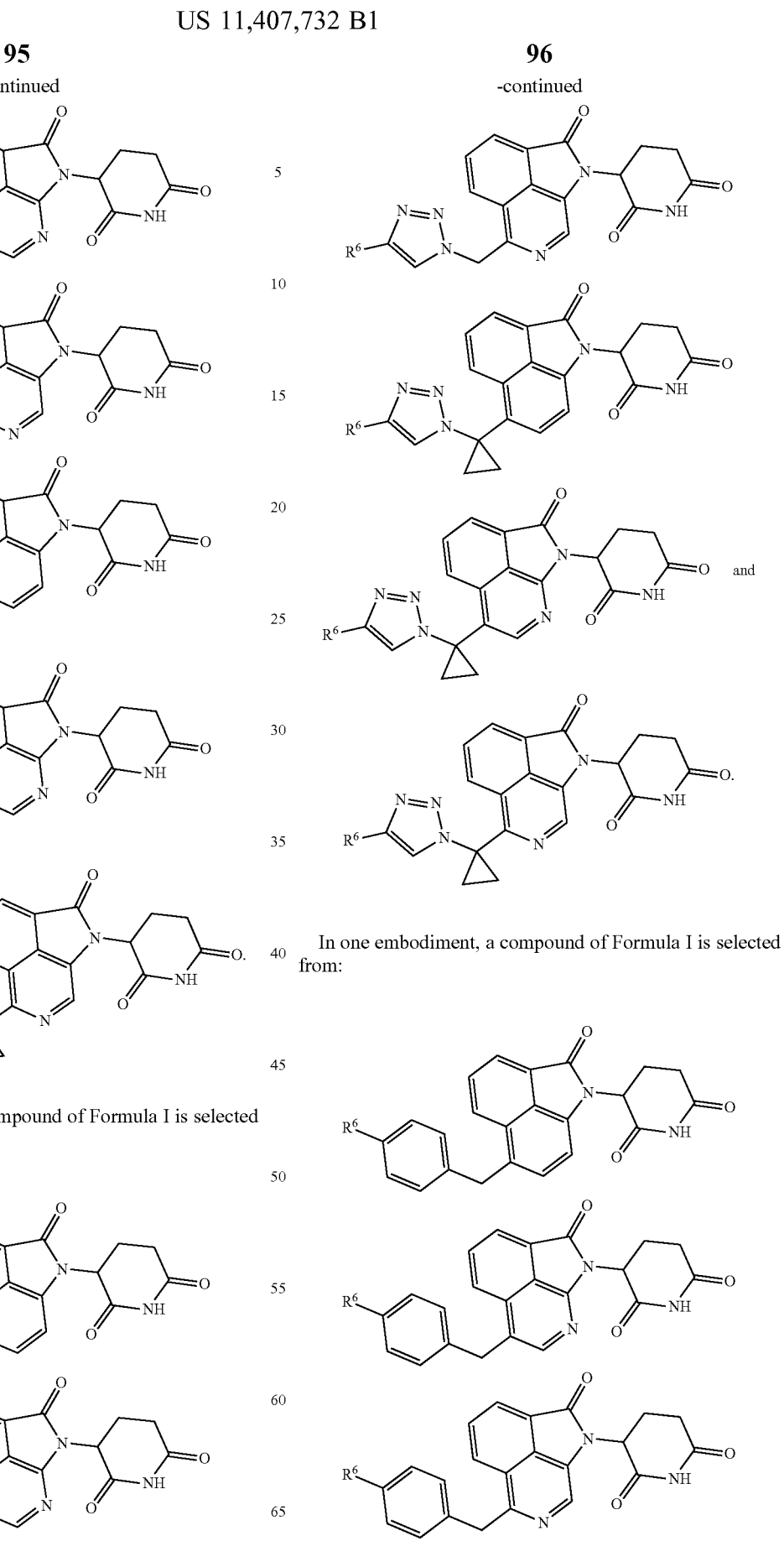
In one embodiment, a compound of Formula I is selected from:

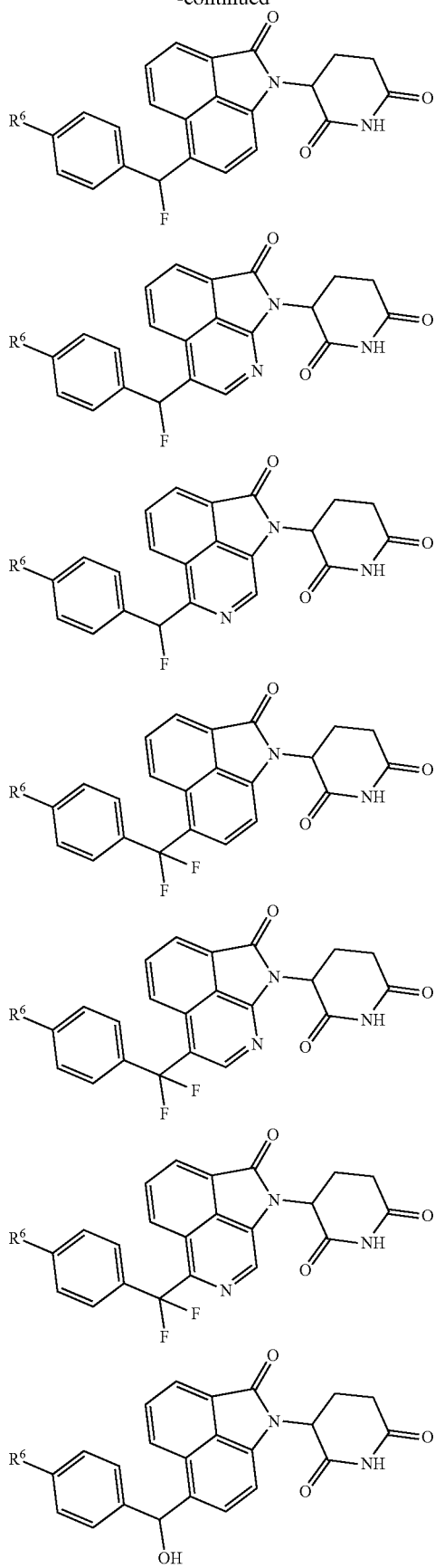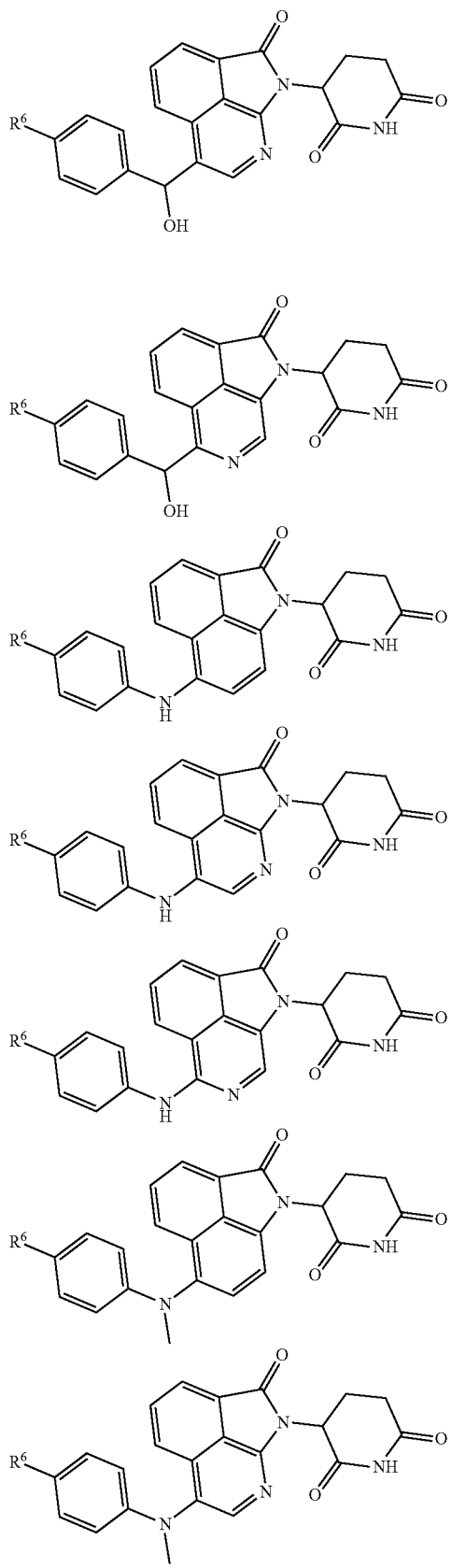

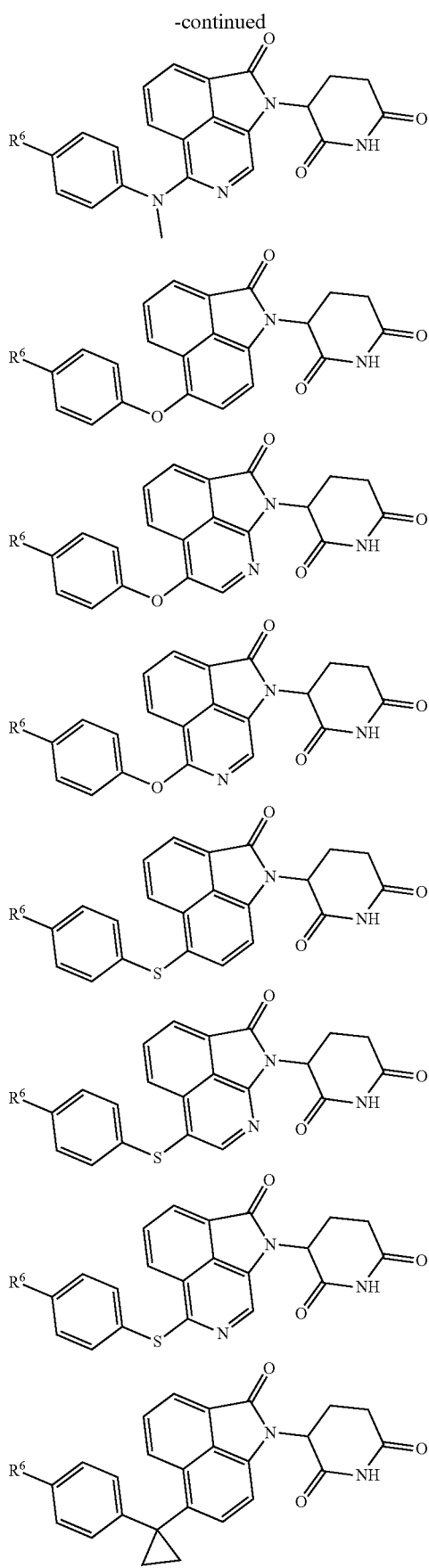
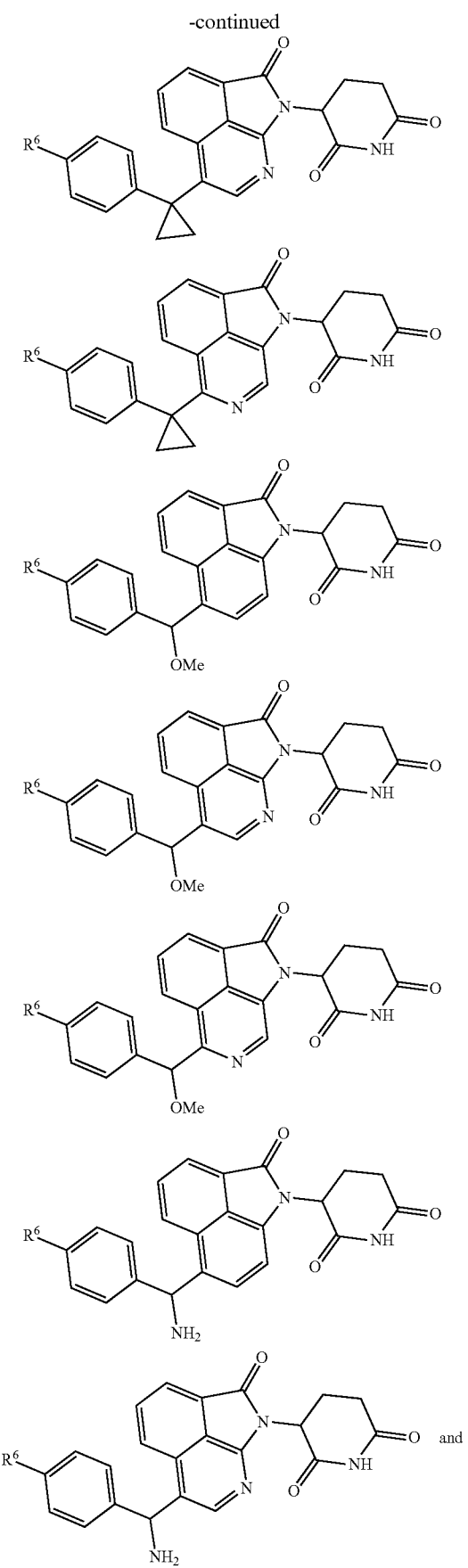

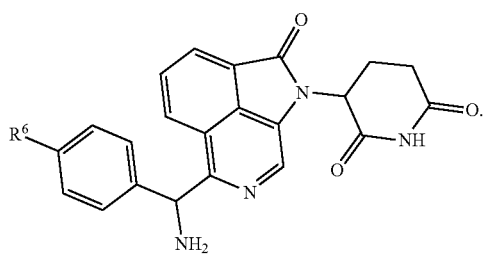
In one embodiment, the compound of Formula I is selected from:
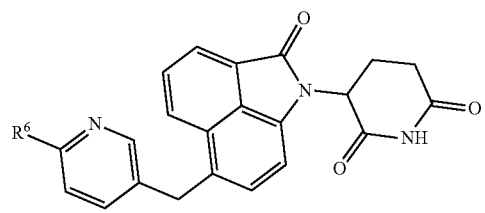
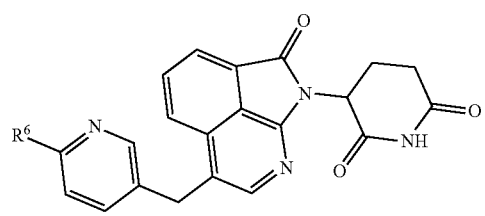
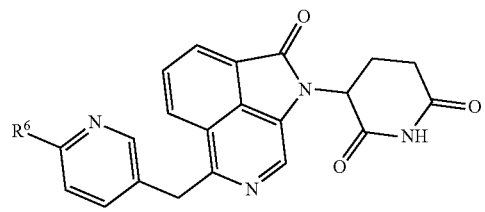
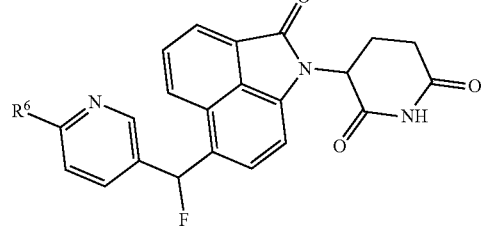
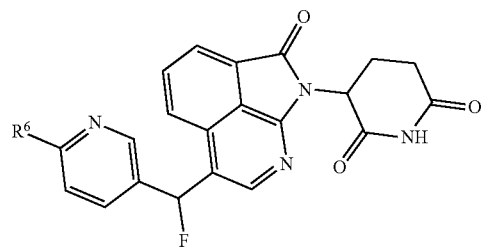
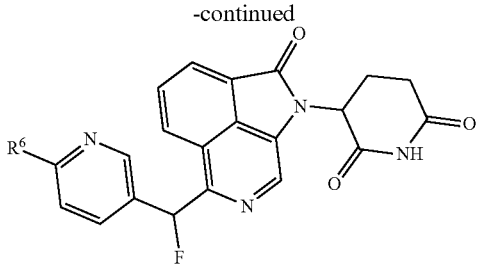
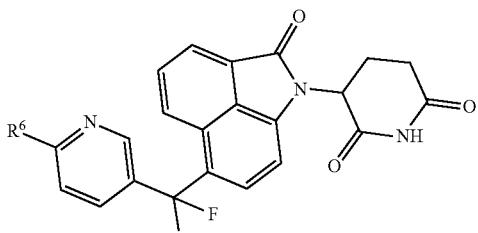
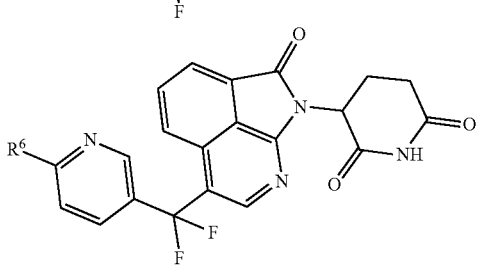
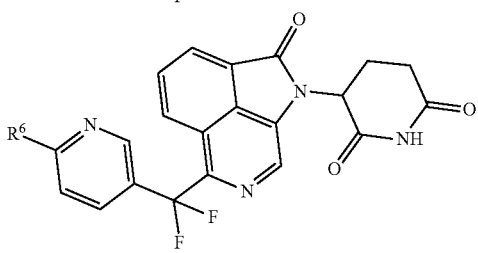
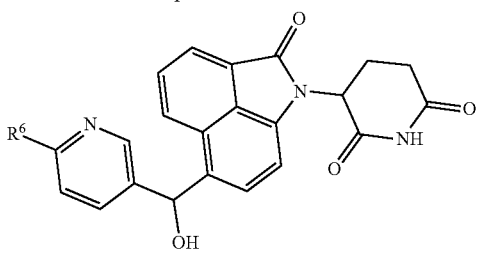
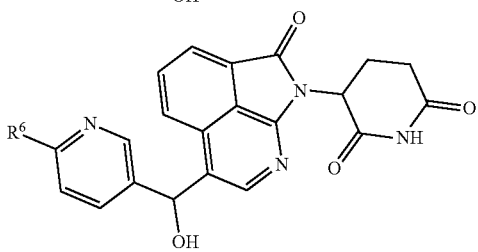
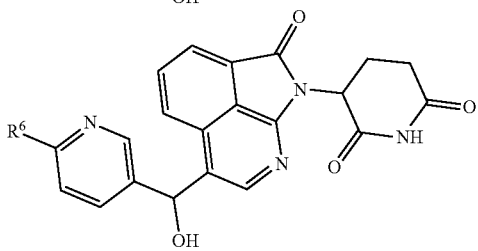

103
-continued
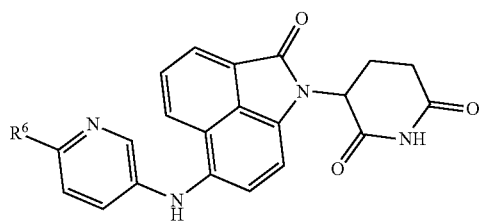
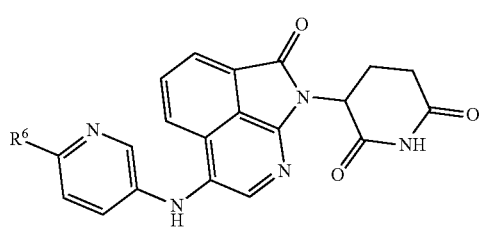
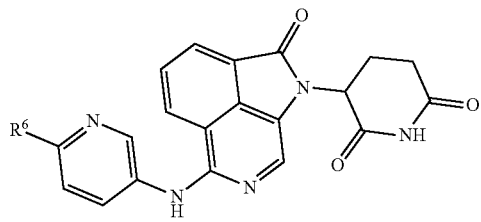
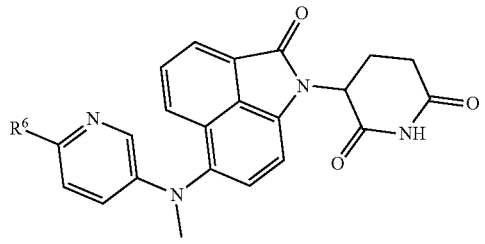
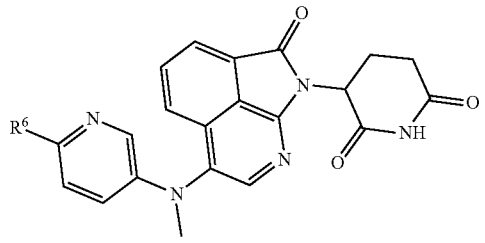
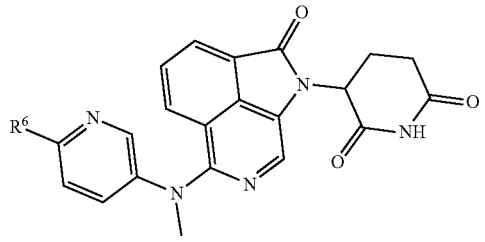
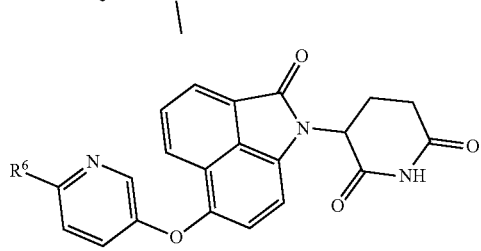
104
-continued
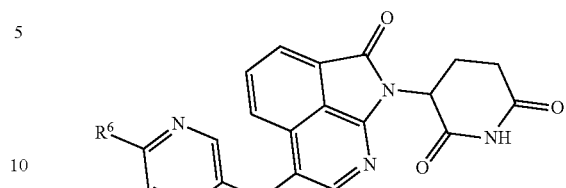
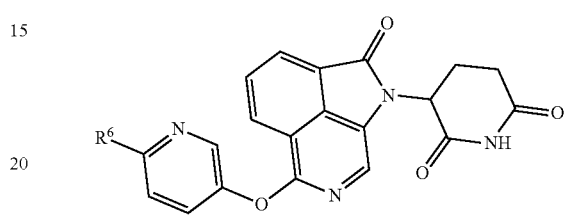
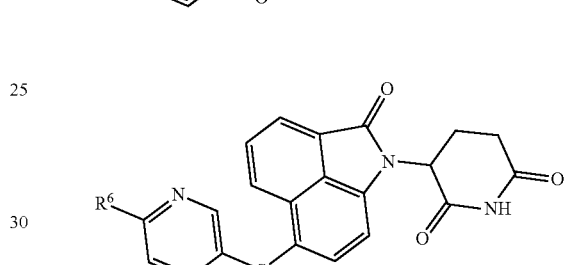
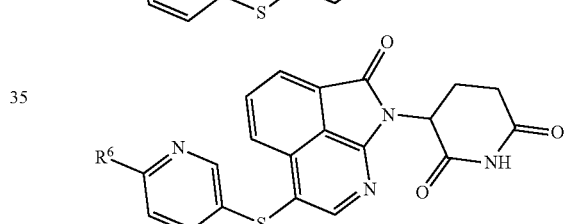
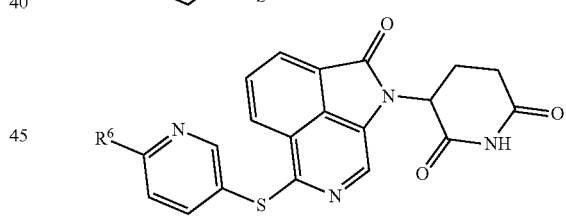
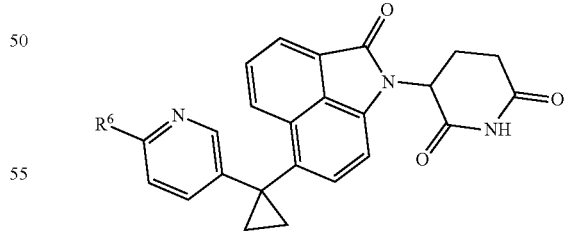
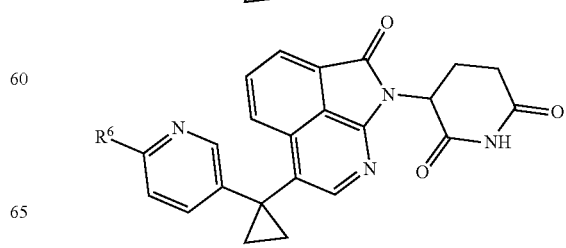

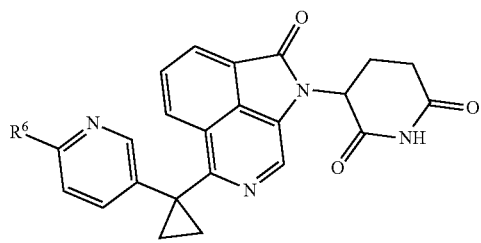
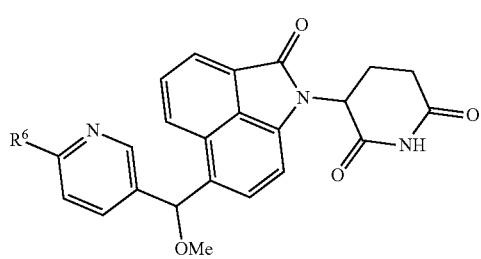
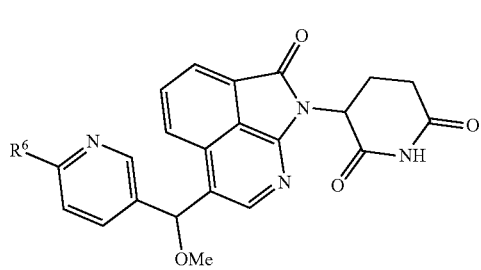
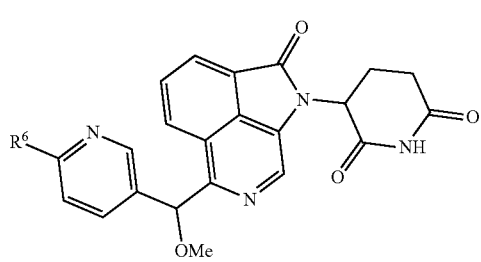
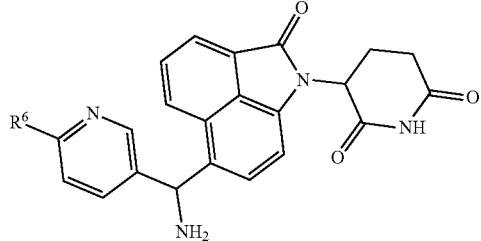
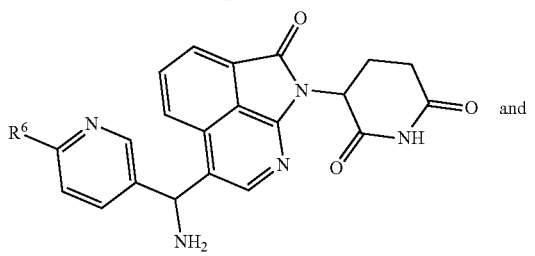
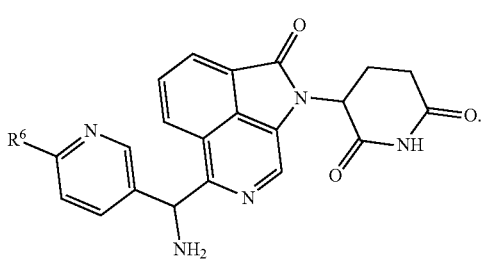
In one embodiment, a compound of Formula I is selected from:
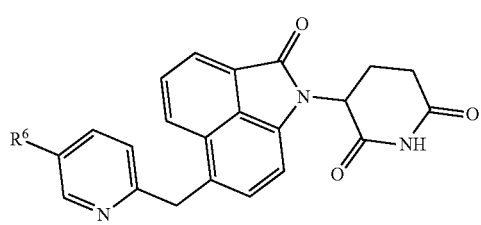
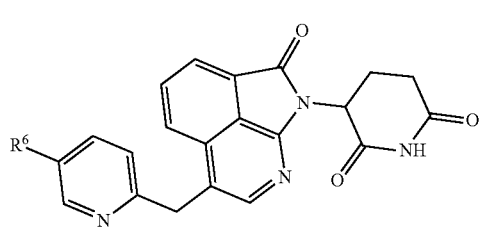
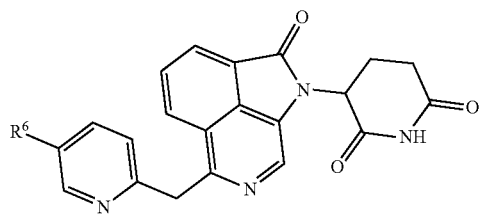
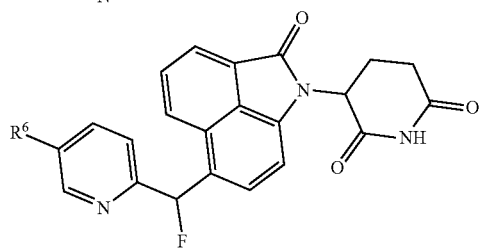
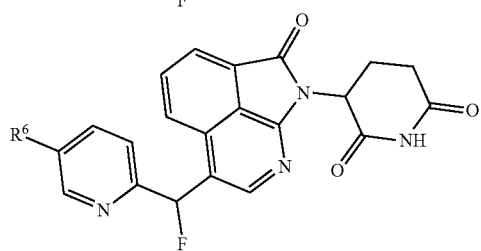

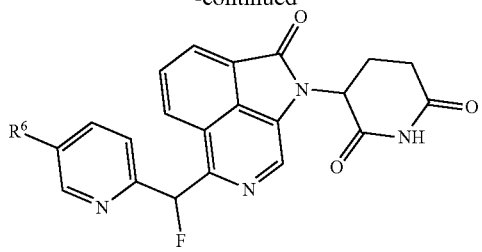
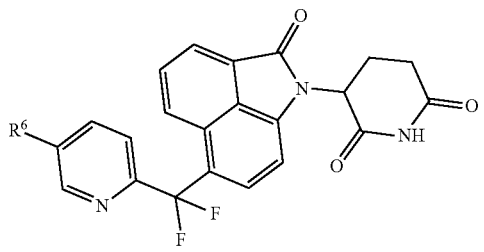
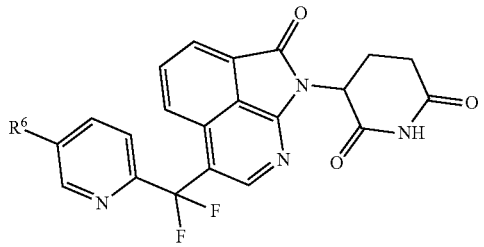
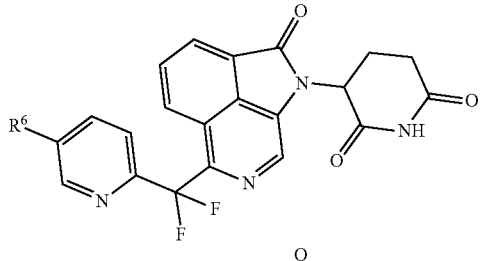
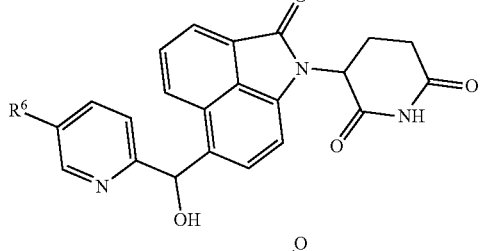
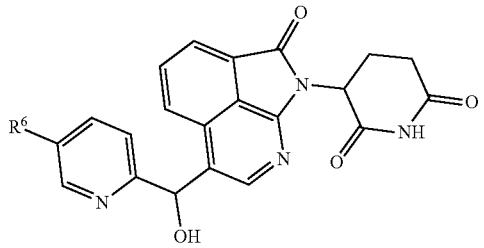
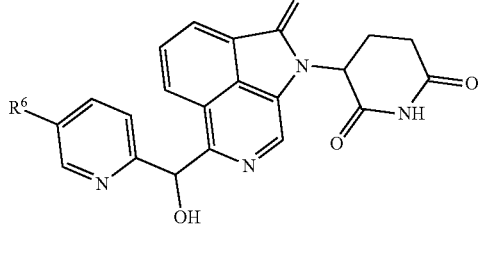
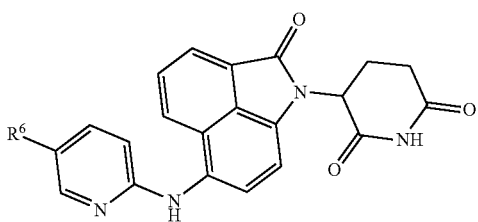
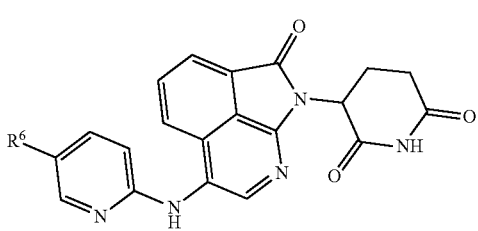
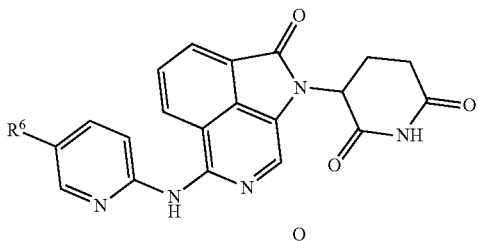
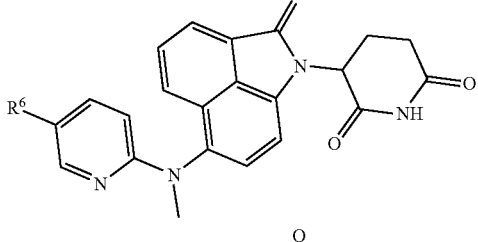
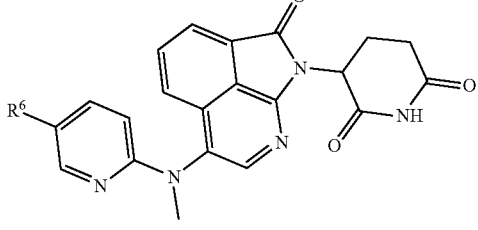
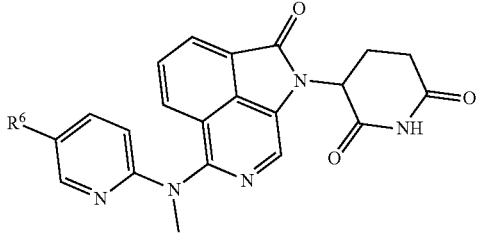
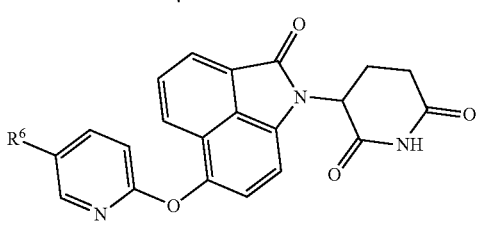

109
-continued
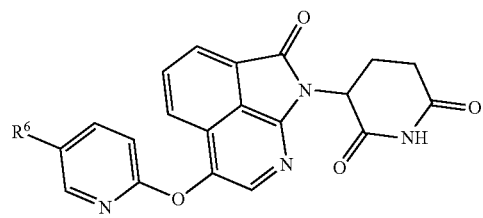
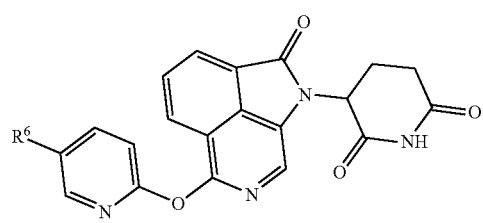
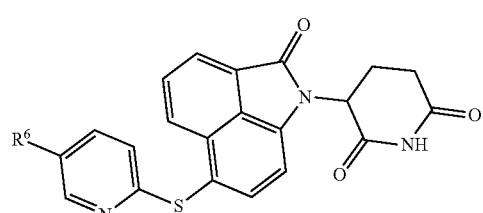
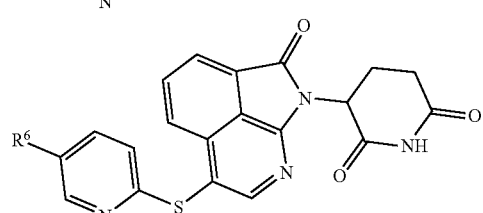
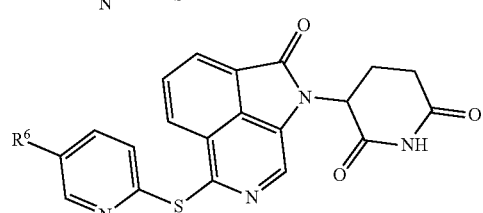
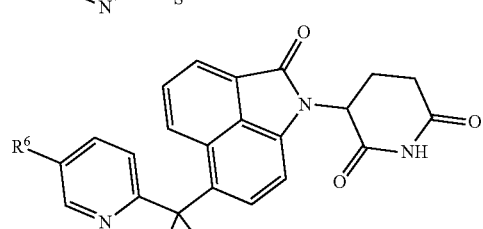
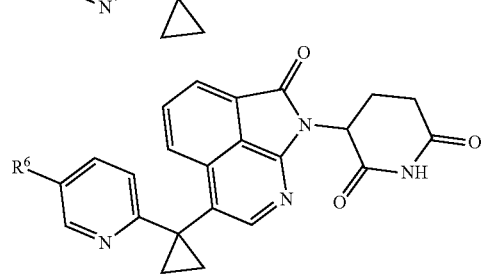
110
-continued
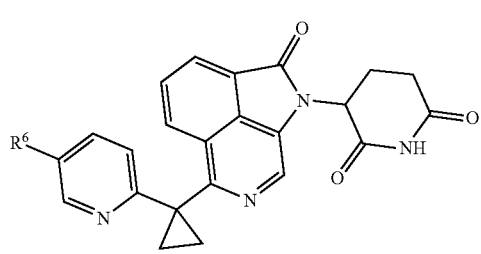
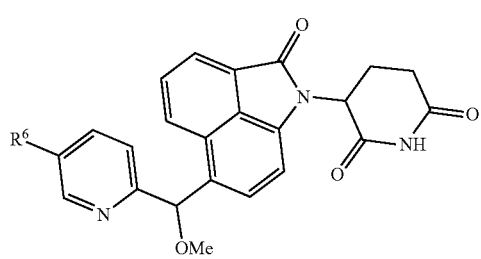
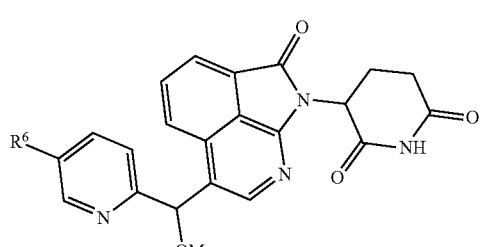
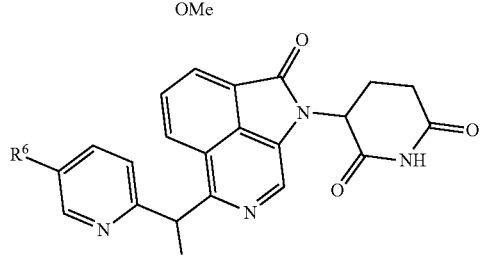
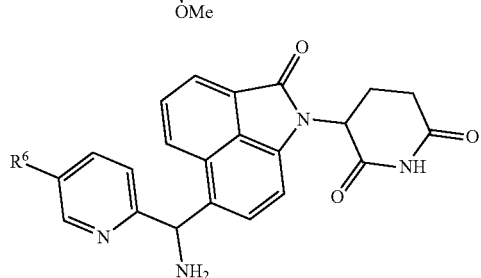
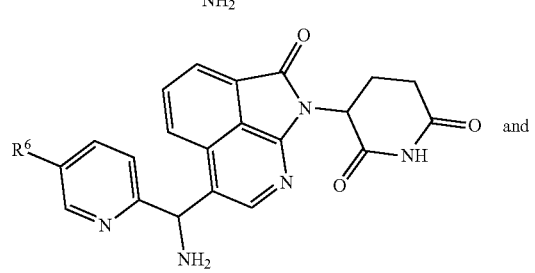
and

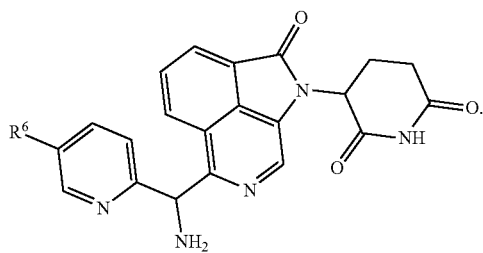
In one embodiment, the compound of Formula I is selected from:
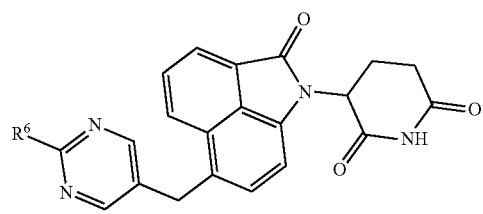
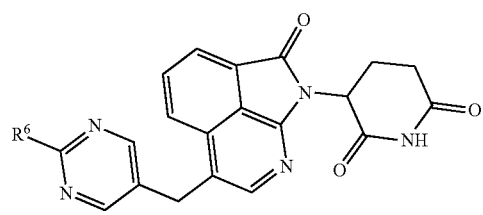
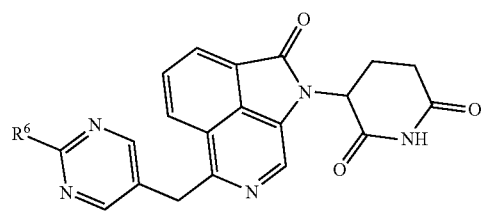
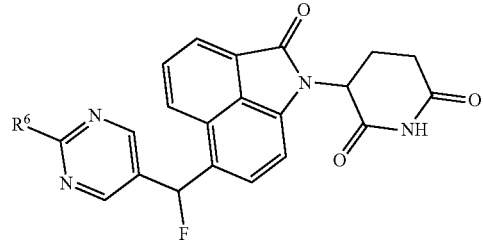
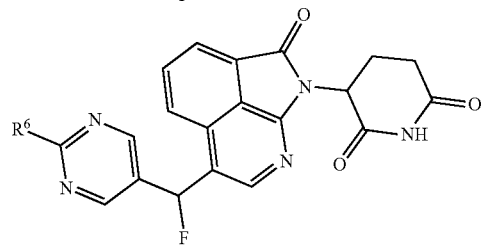
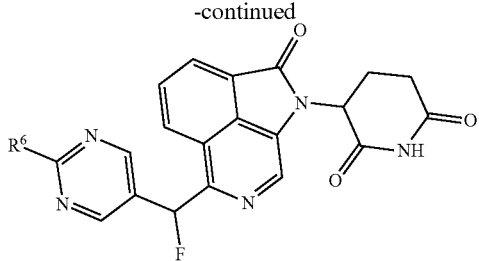
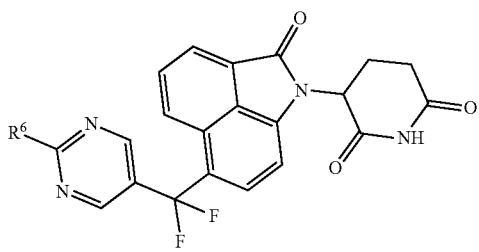
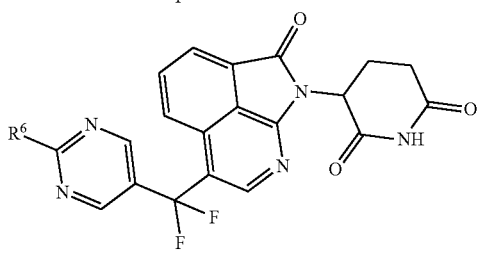
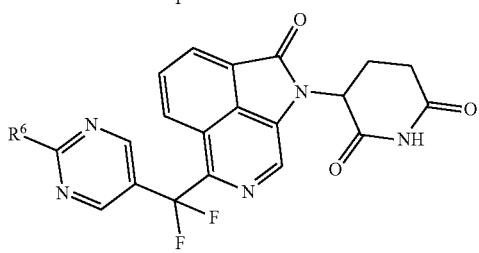
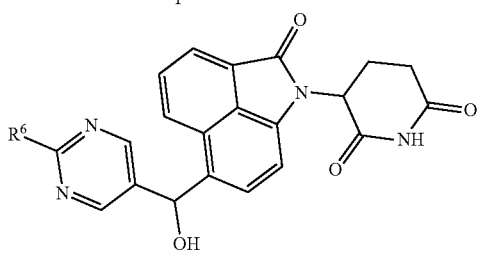
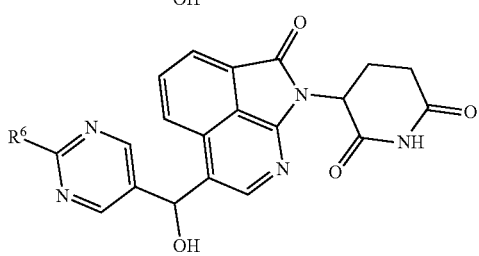
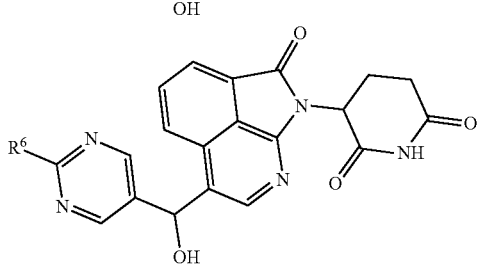

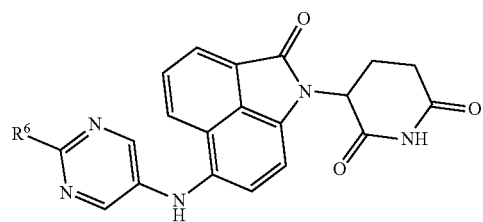
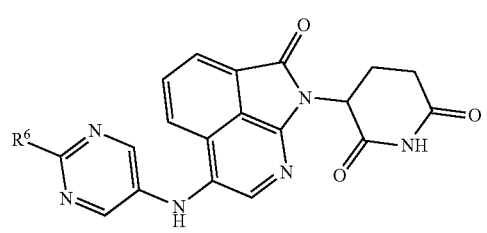
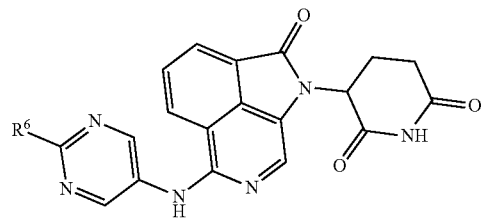
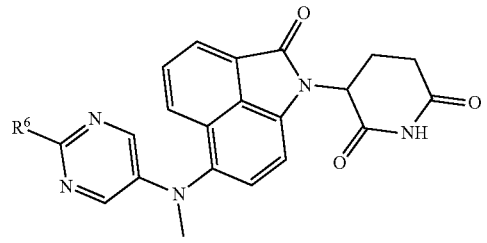
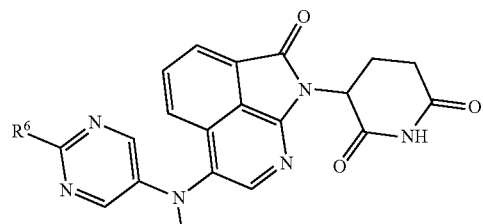
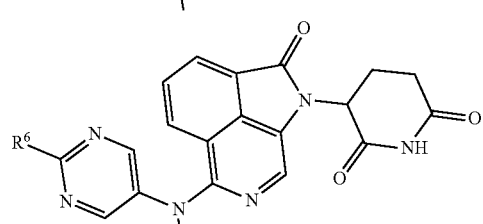
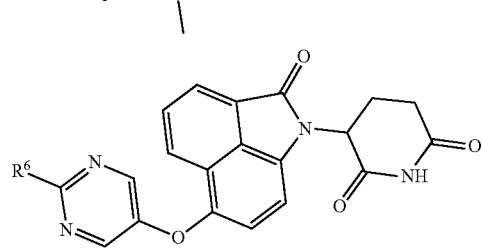
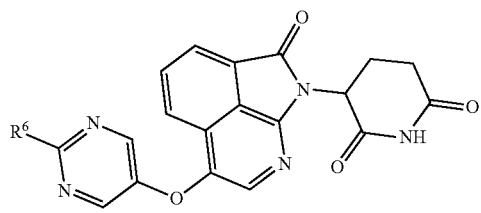
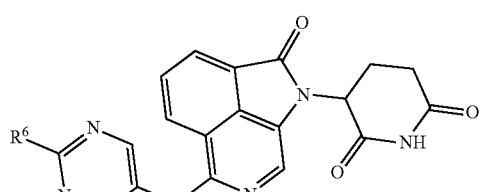
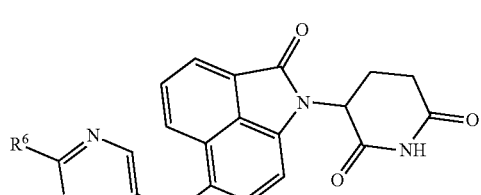
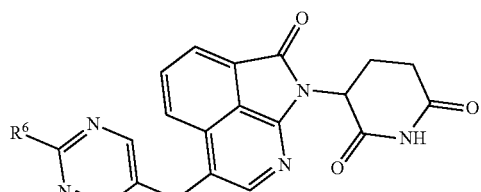
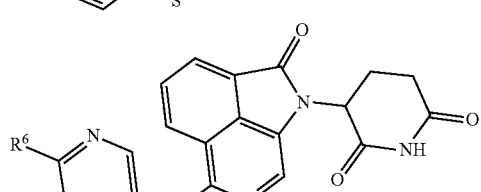
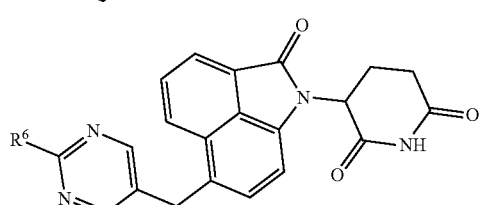
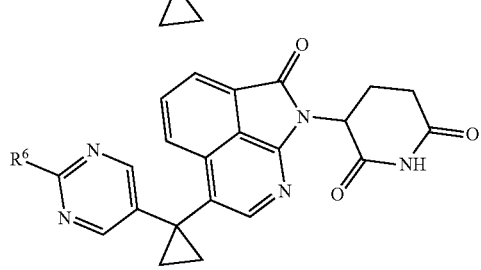

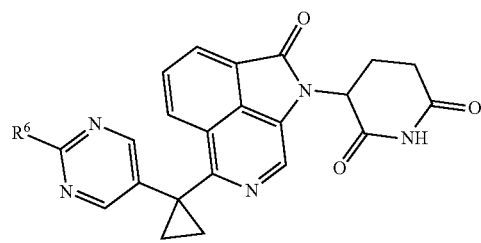
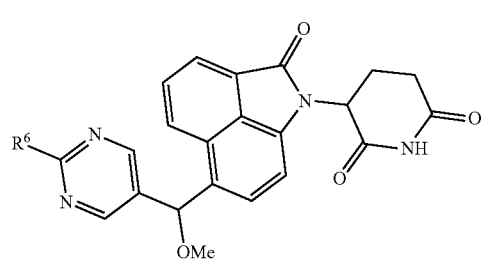

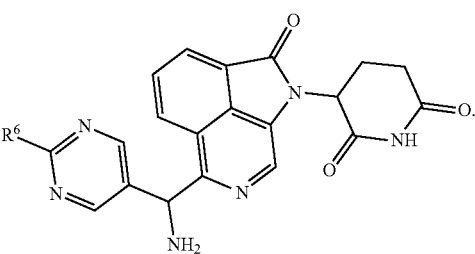
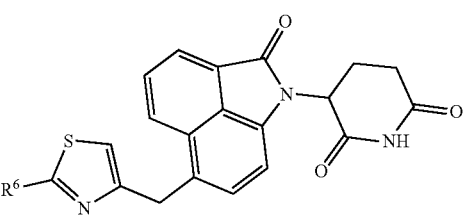
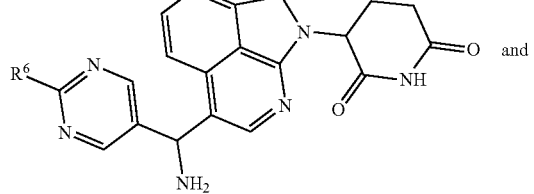
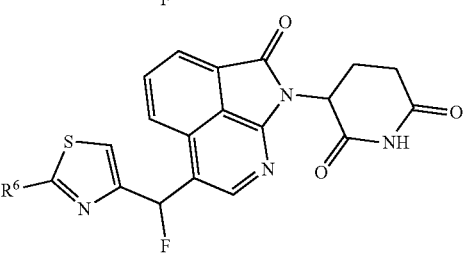
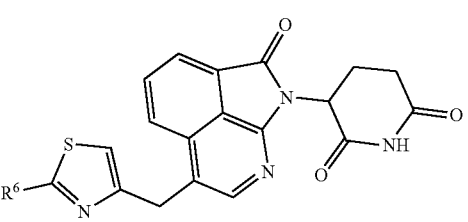
In one embodiment, the compound of Formula I is selected from:
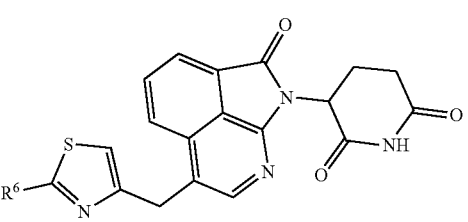
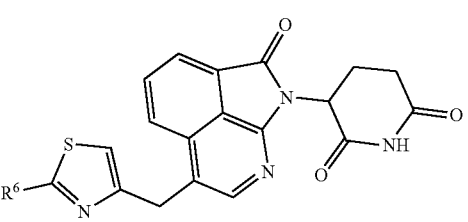
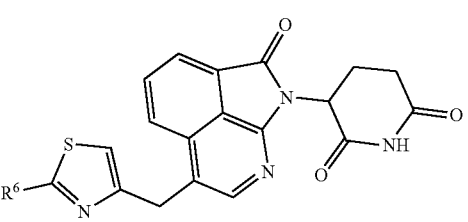
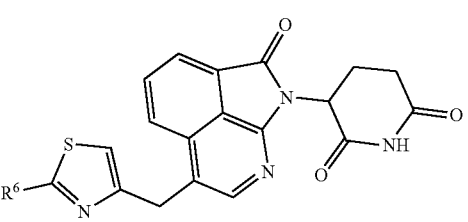
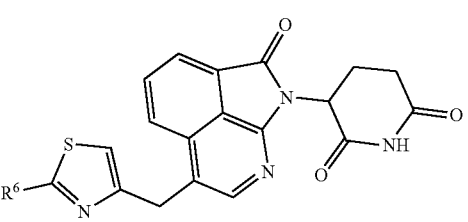

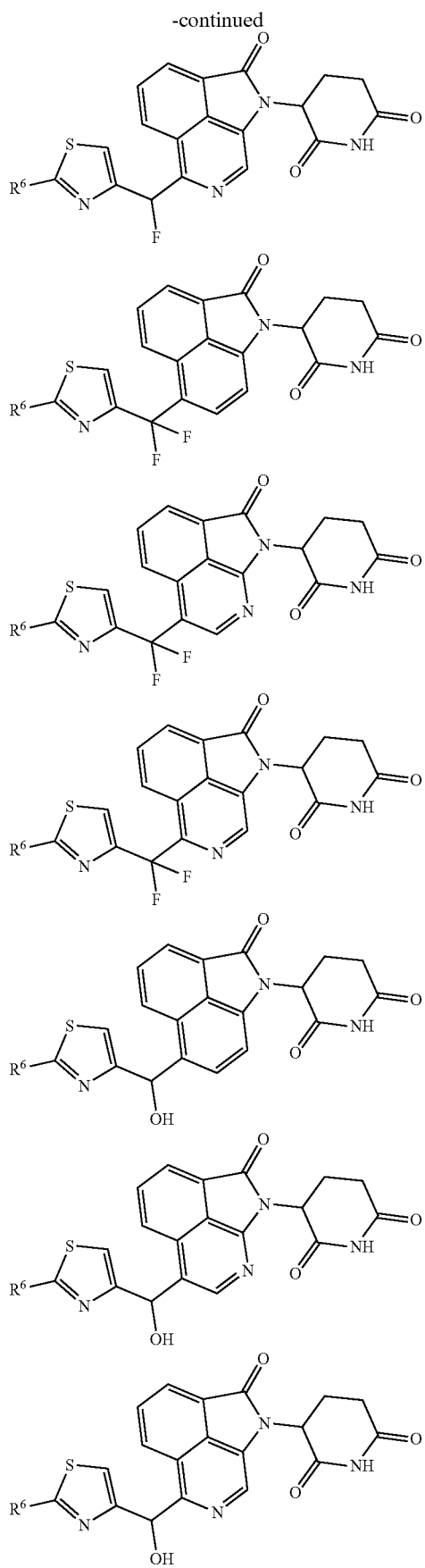
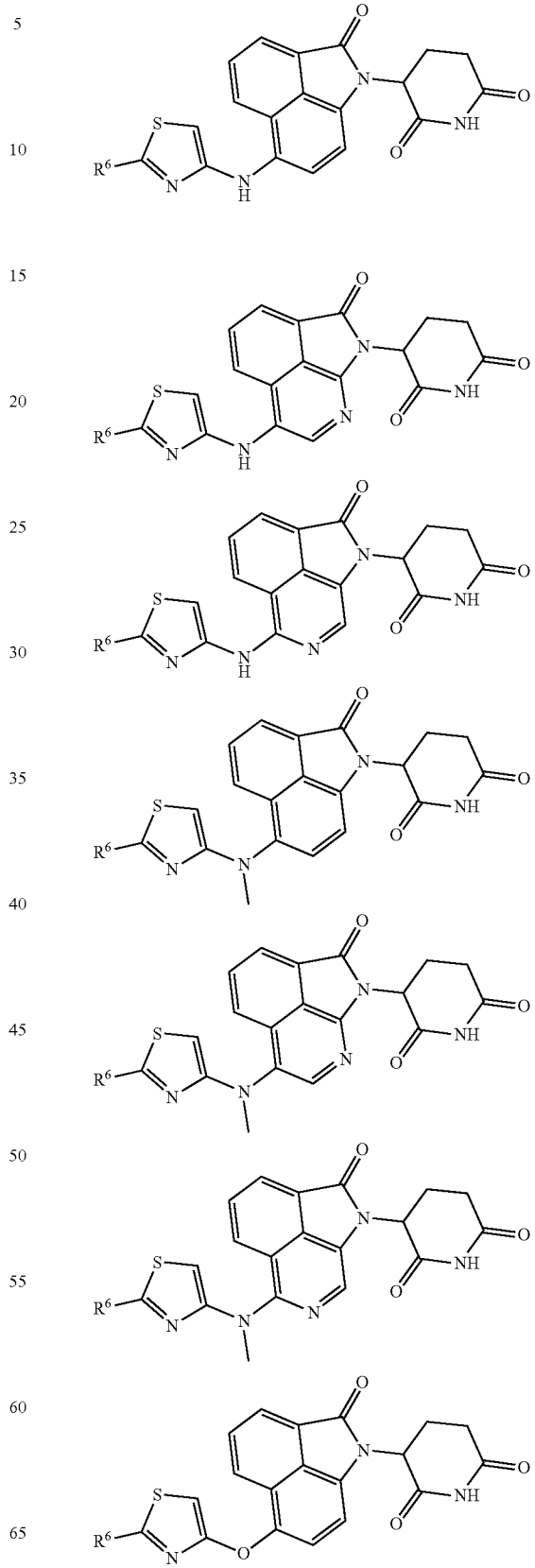

119
-continued
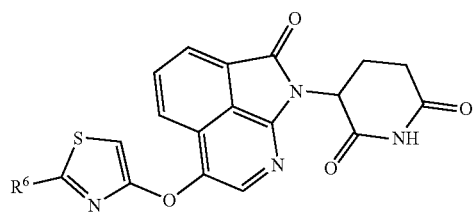
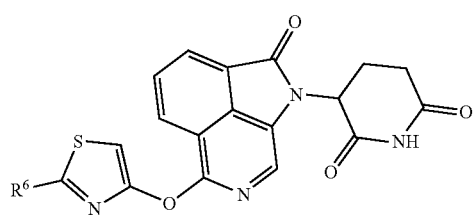
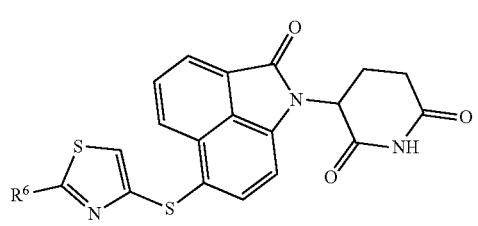
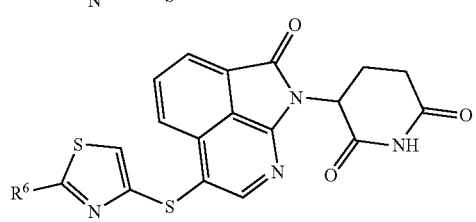
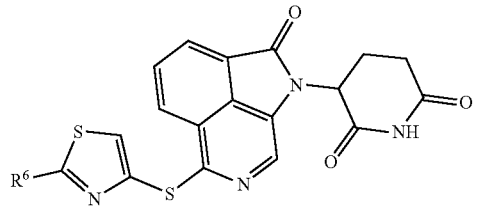
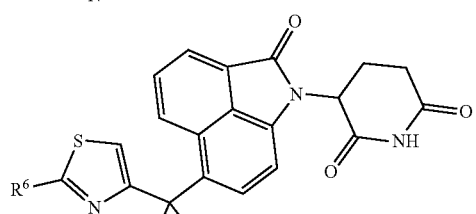
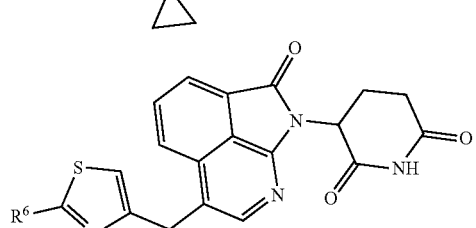
120
-continued
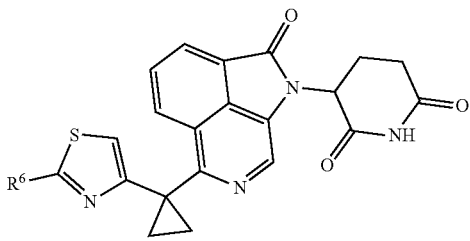
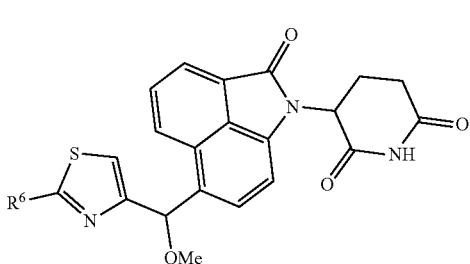
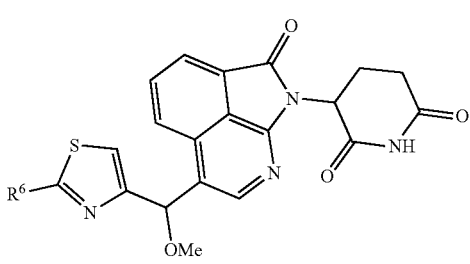
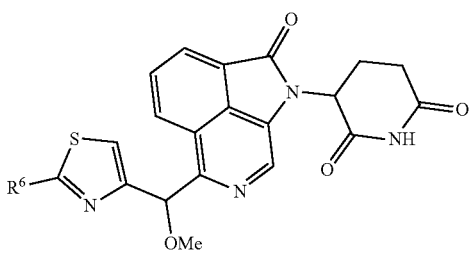
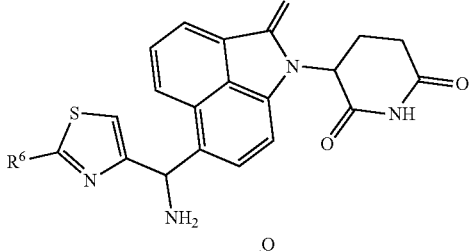
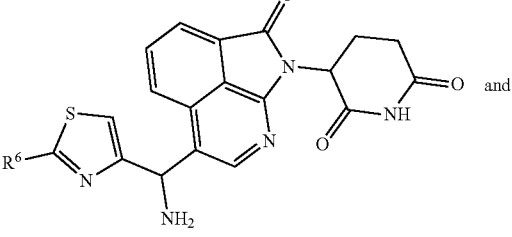 and

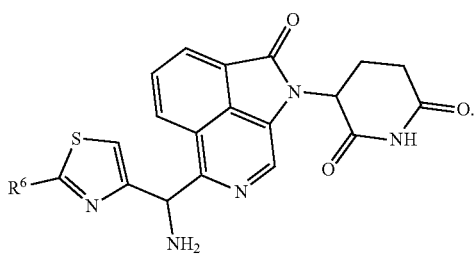
In one embodiment, the compound of Formula I is selected from:
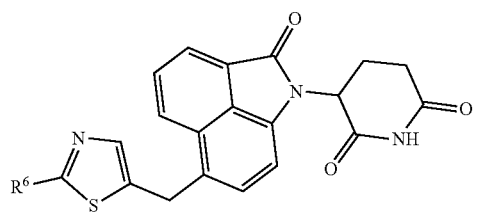
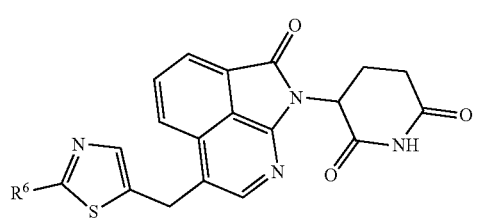
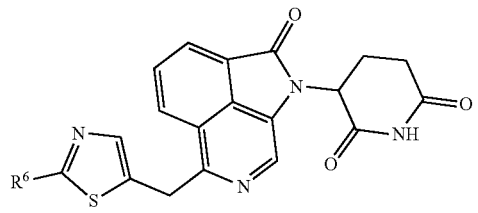
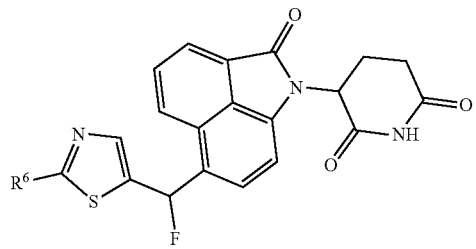
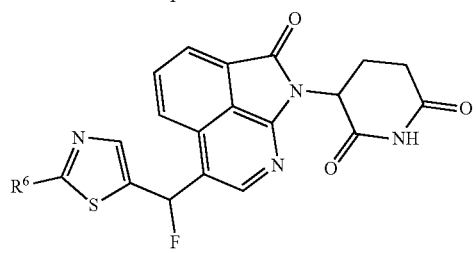
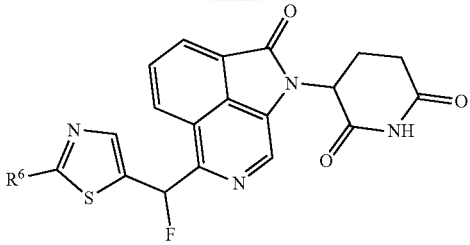
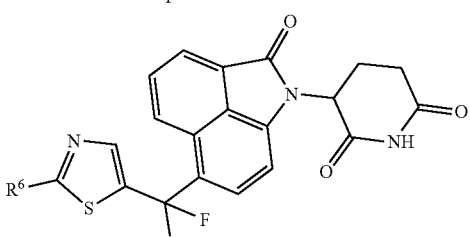
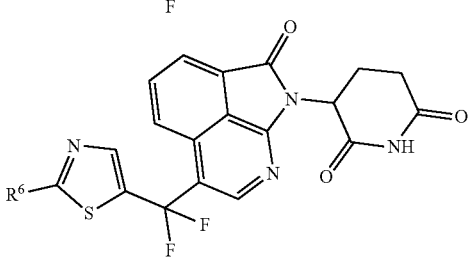
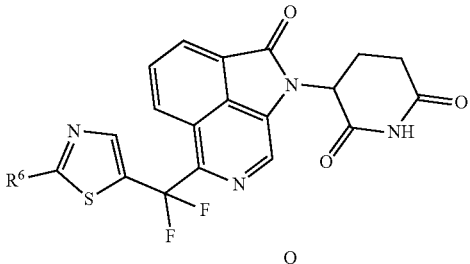
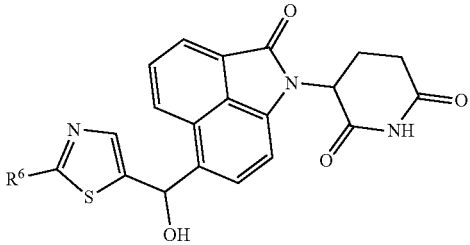
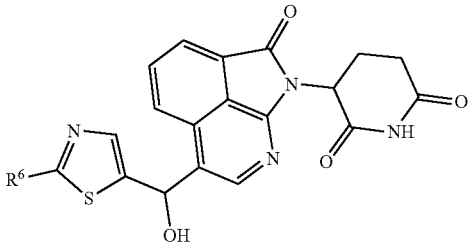
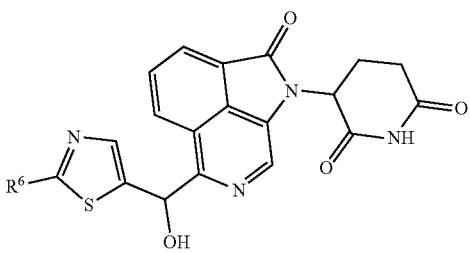

-continued
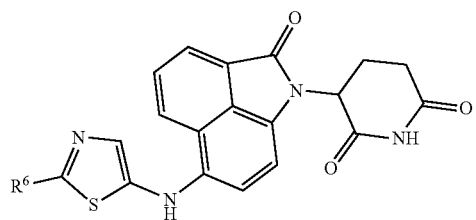
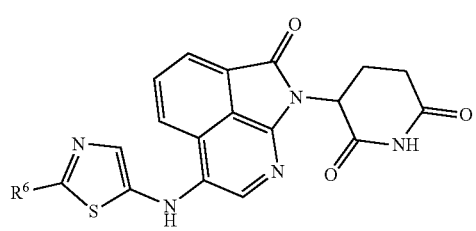
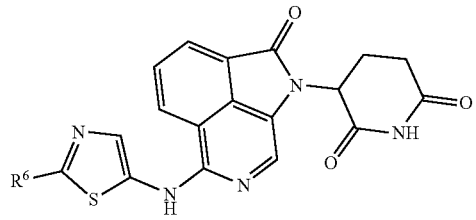
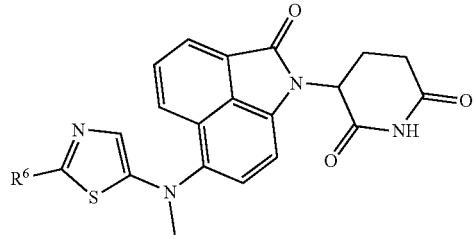
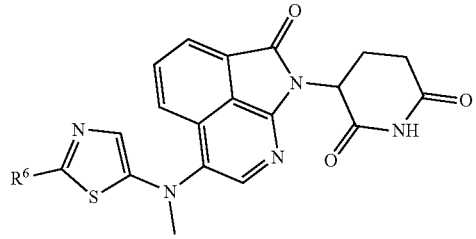
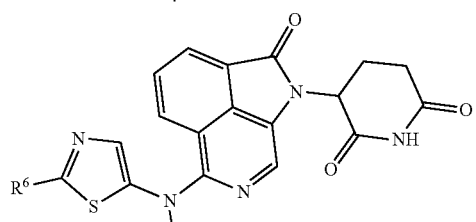
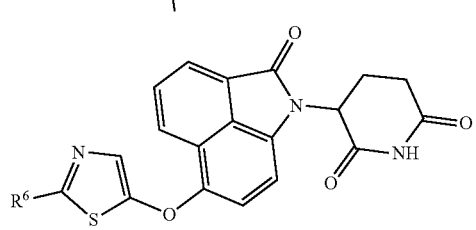
-continued
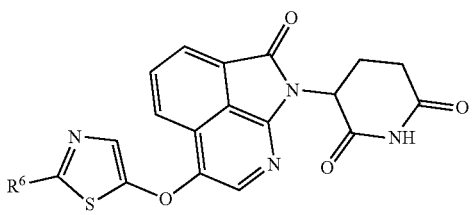
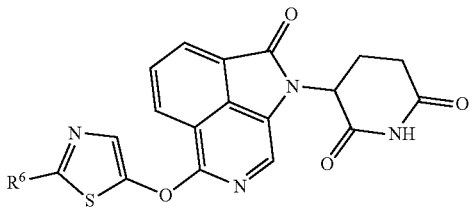
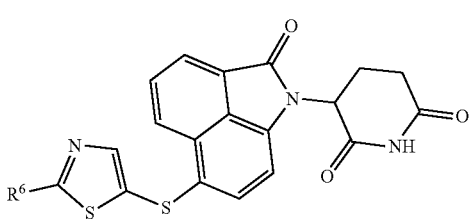
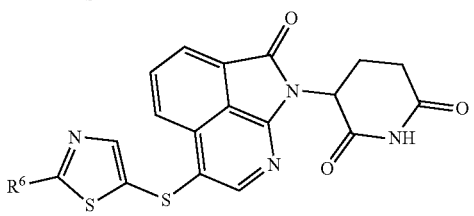
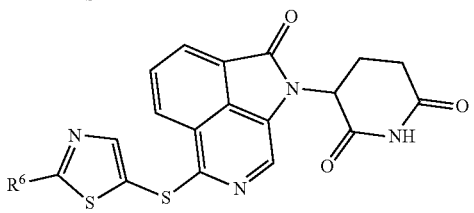
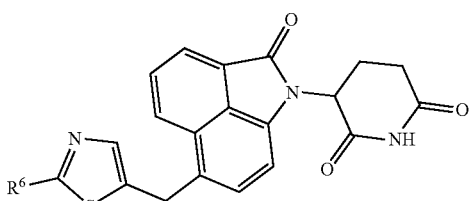
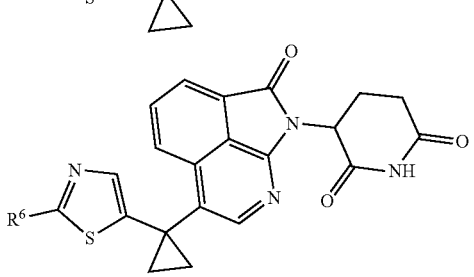

125
-continued
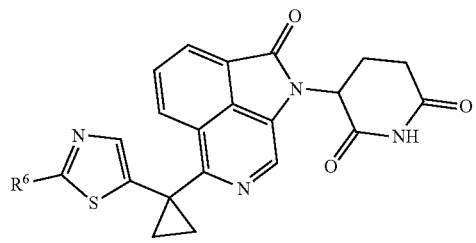
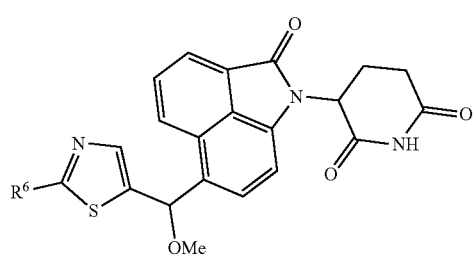
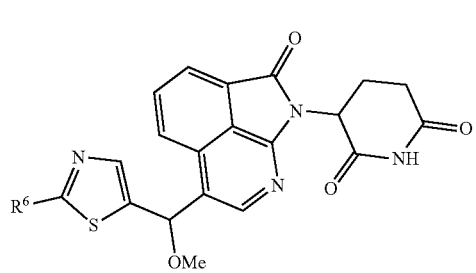
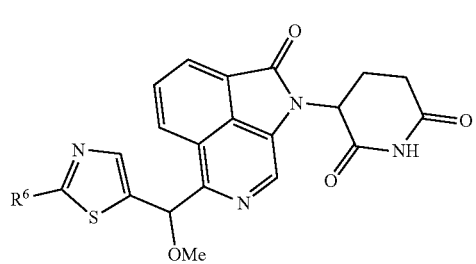
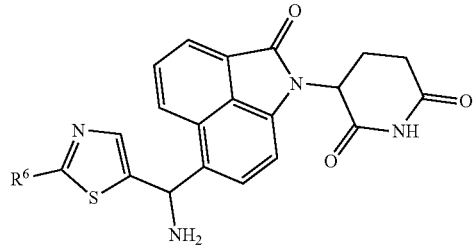
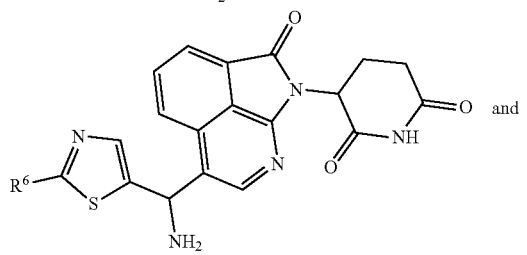
and
126
-continued
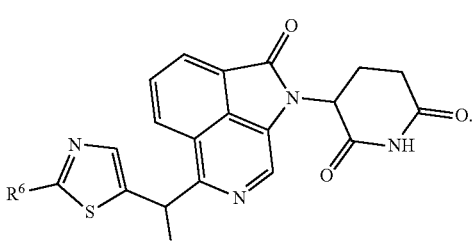
In one embodiment, a compound of Formula I is selected from:
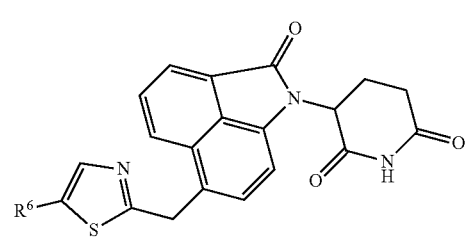
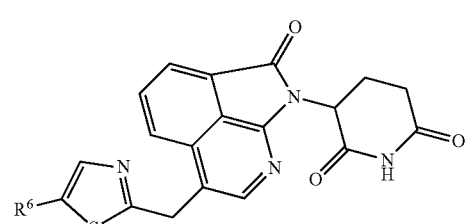
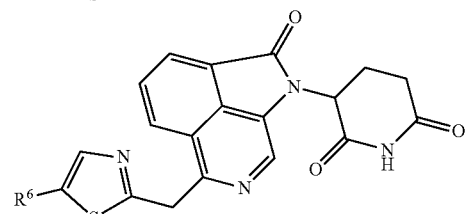
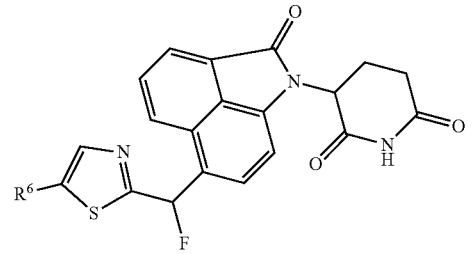
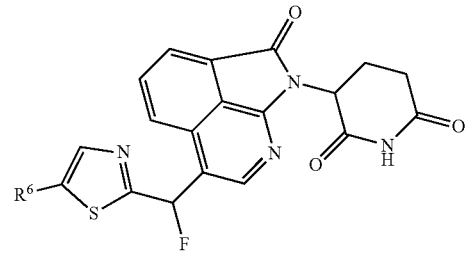

127
-continued
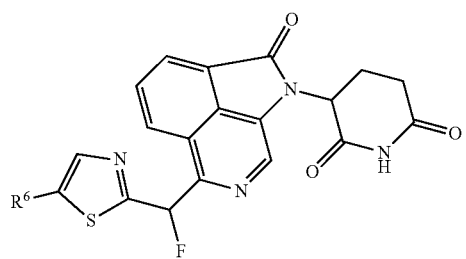
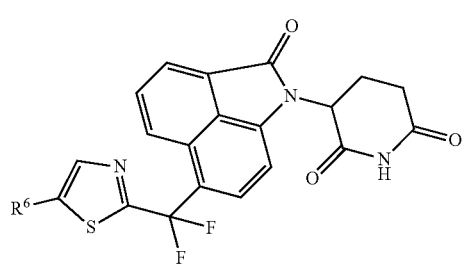
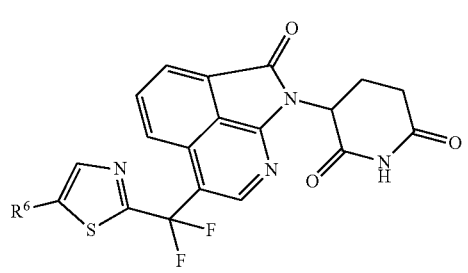
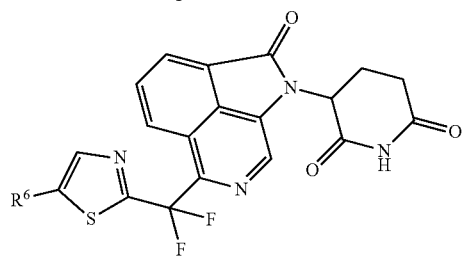
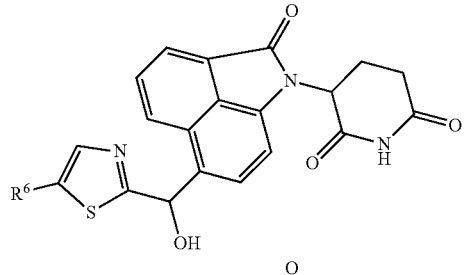
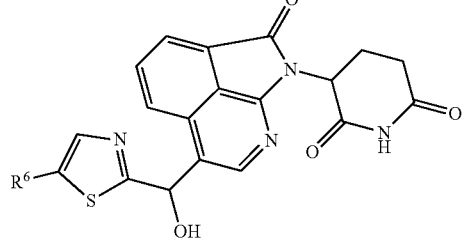
128
-continued
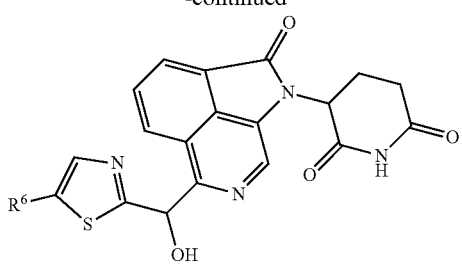
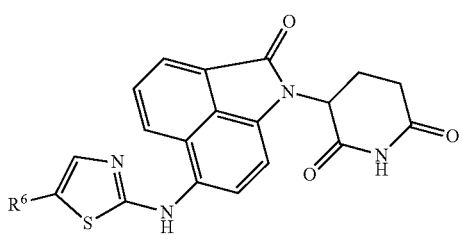
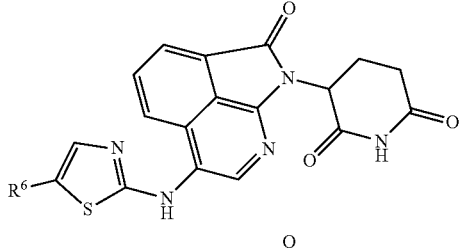
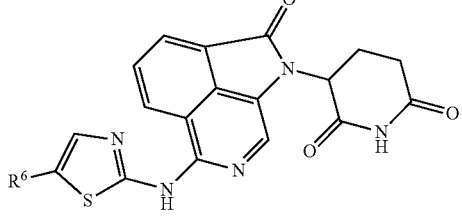
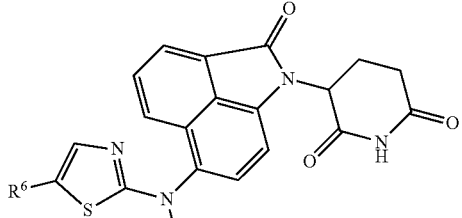
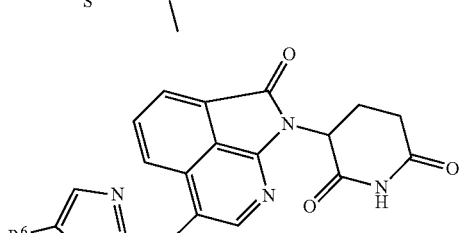
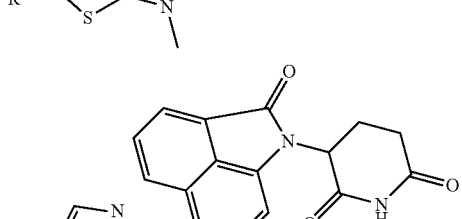
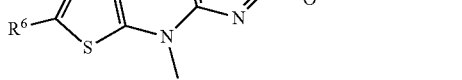

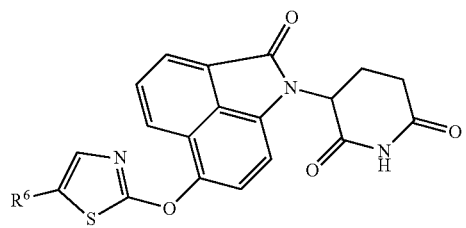
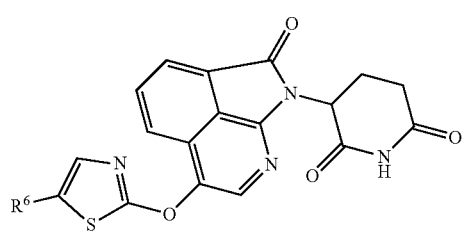
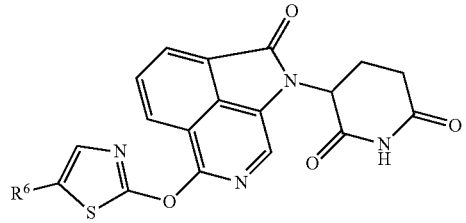
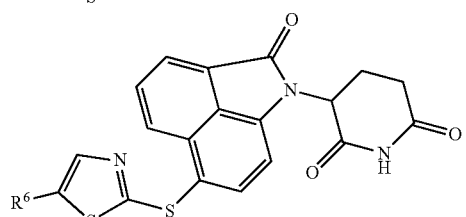
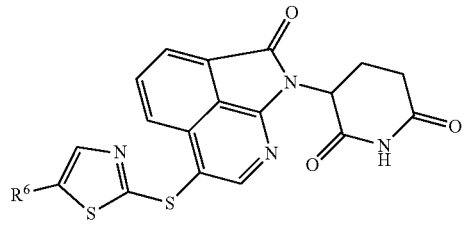
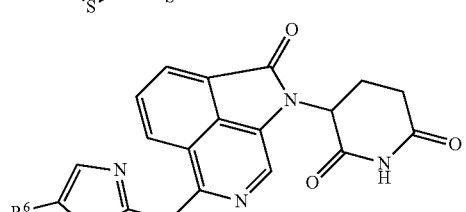
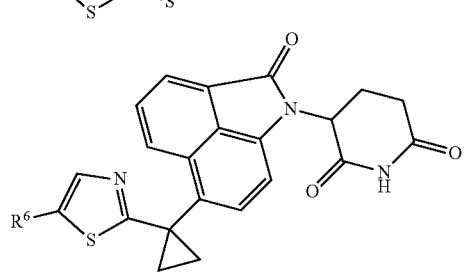
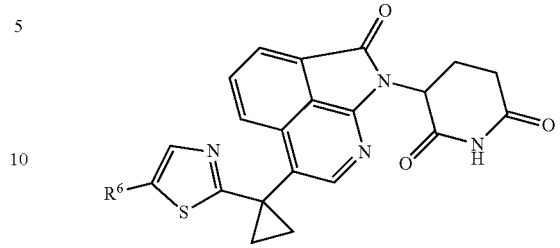
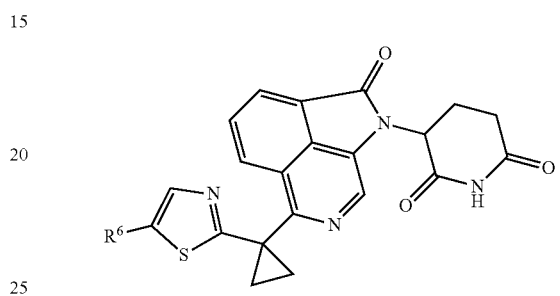
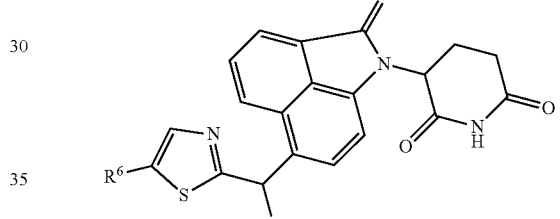
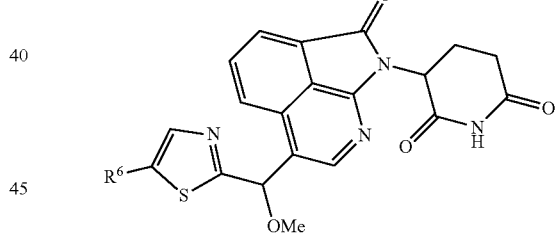
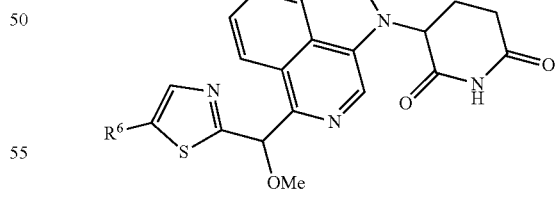
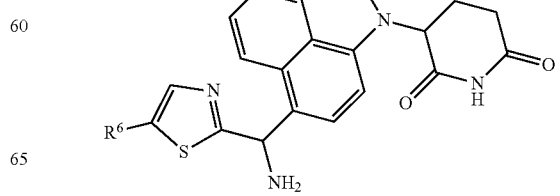

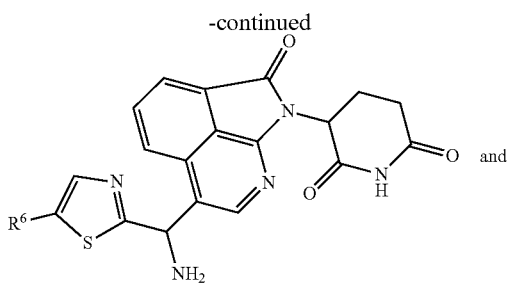
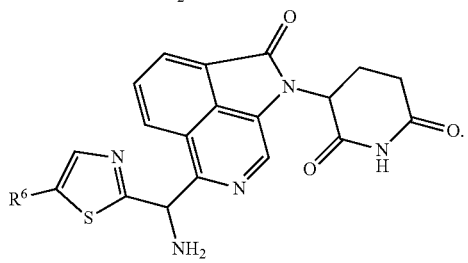
In one embodiment, the compound of Formula I is selected from:
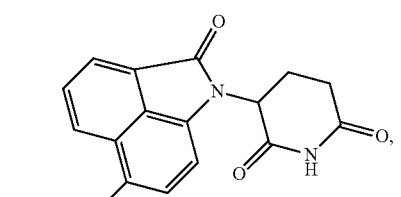
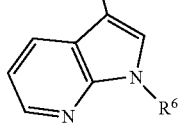
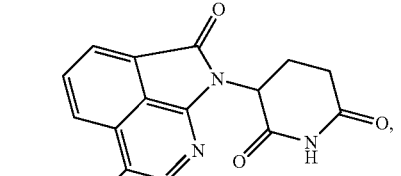
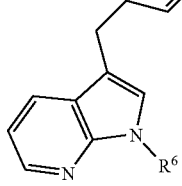
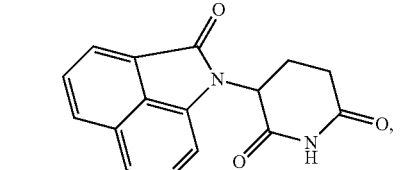
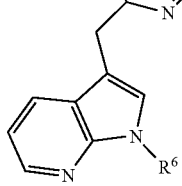
and
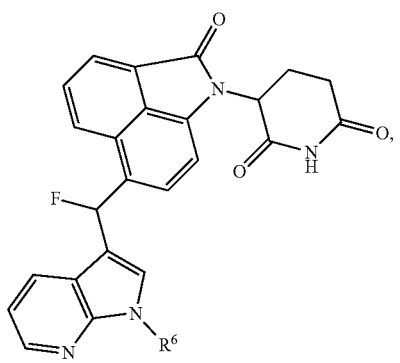
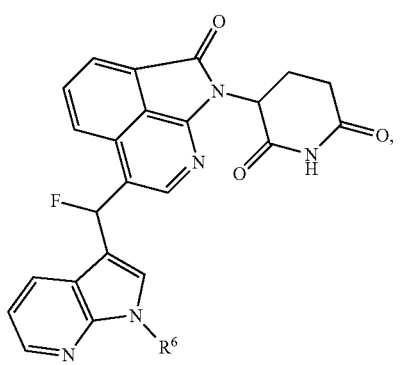
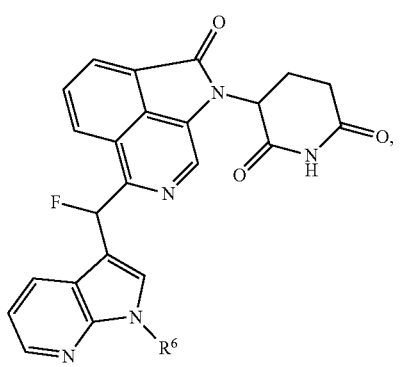
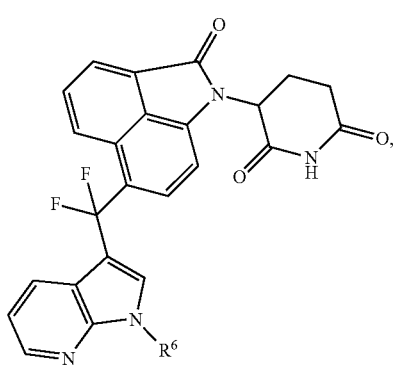

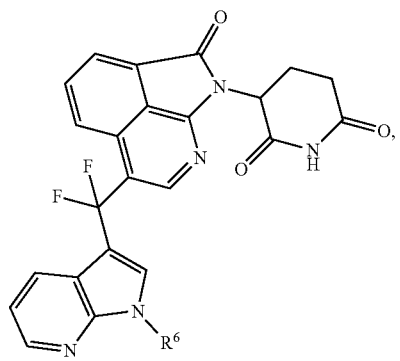
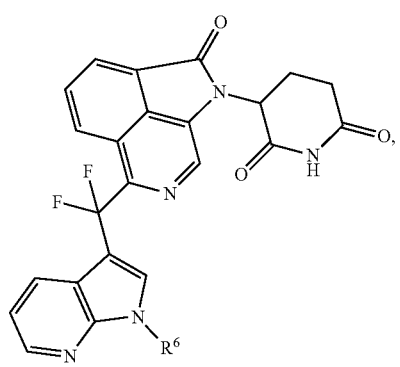
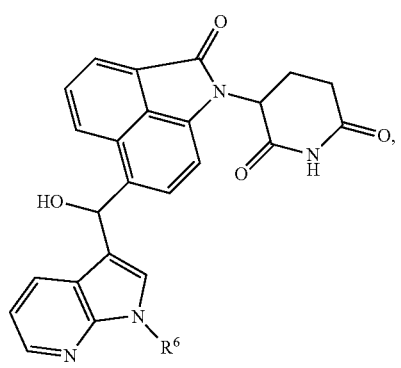
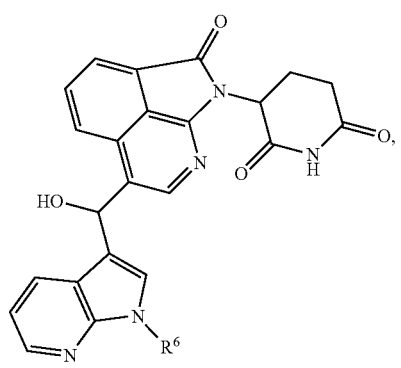
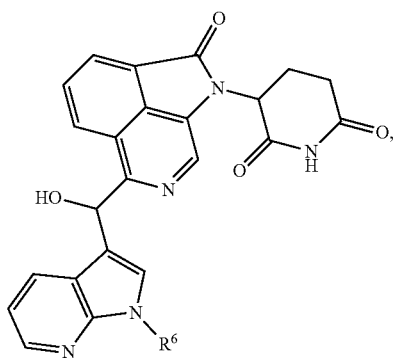
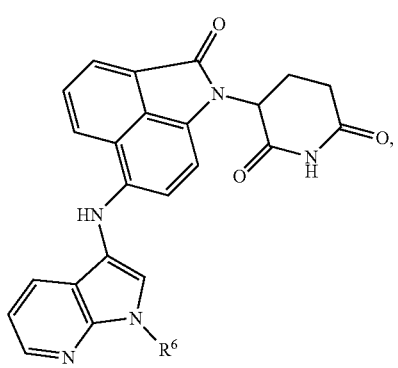
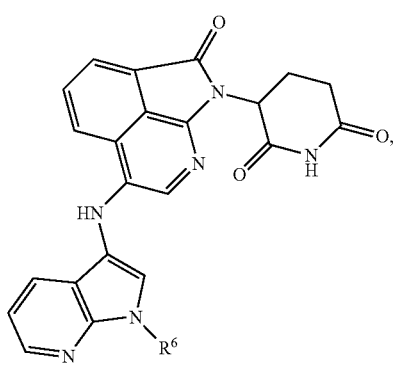
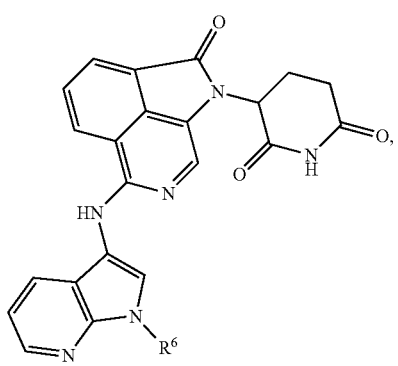

135
-continued
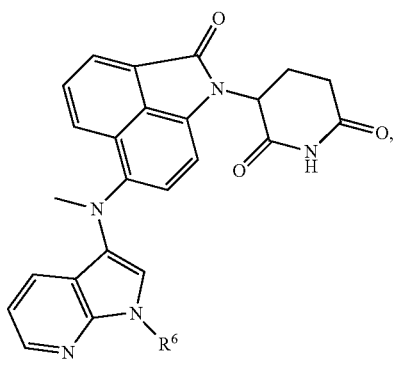
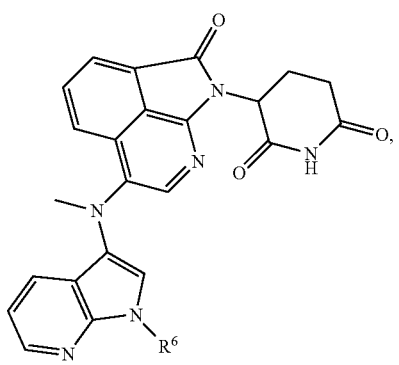

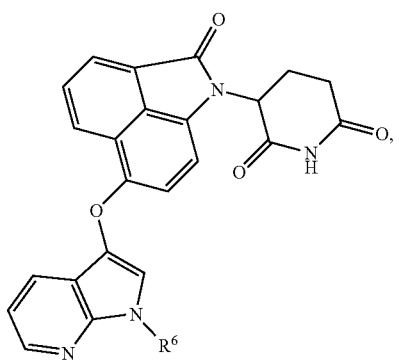
136
-continued
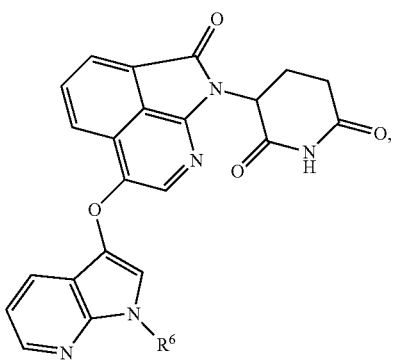
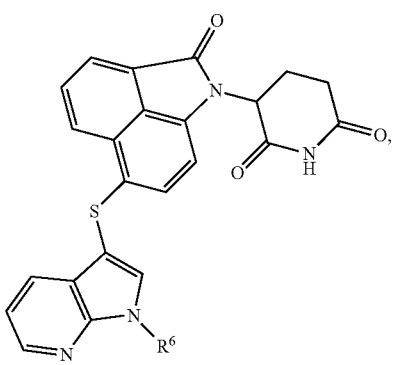
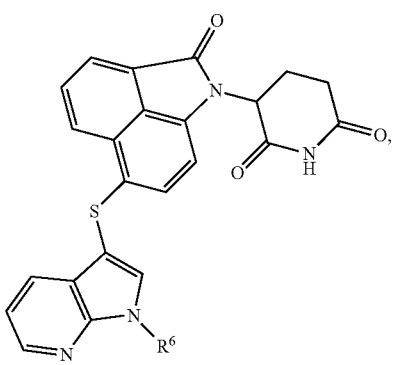
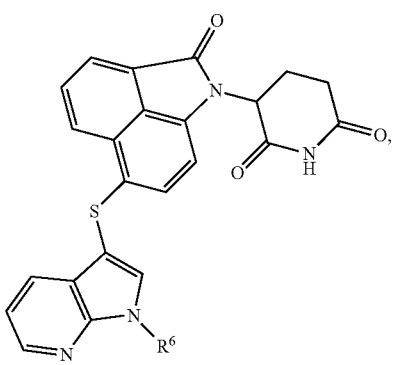

137
-continued
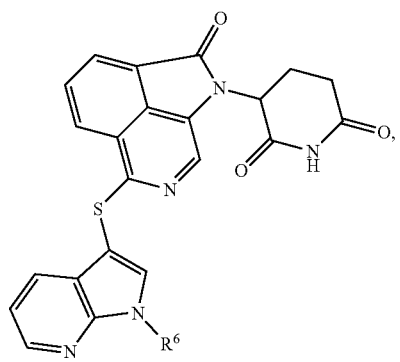
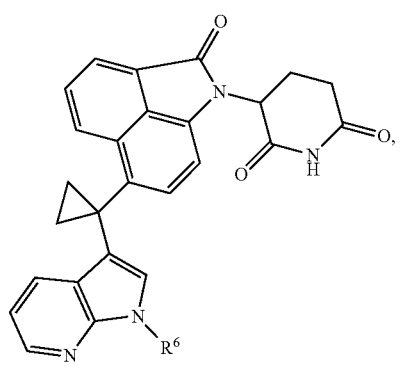
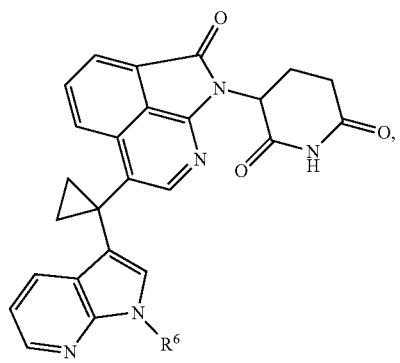
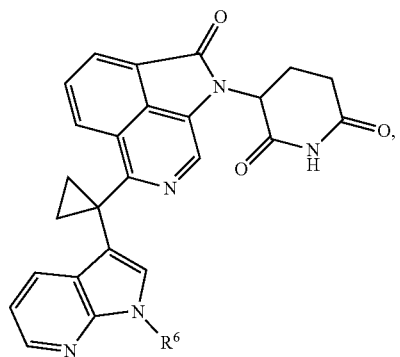
138
-continued
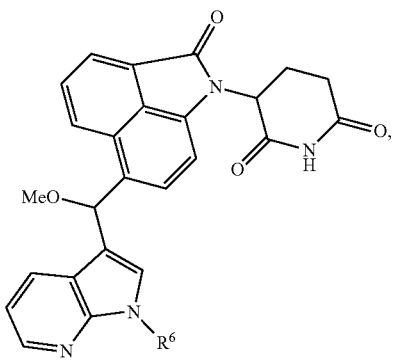
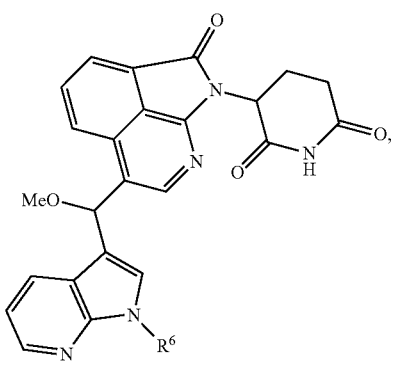
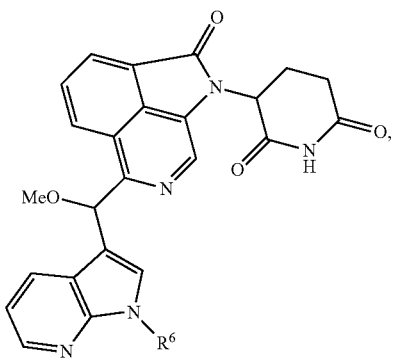
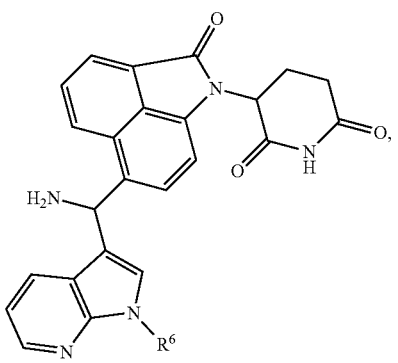

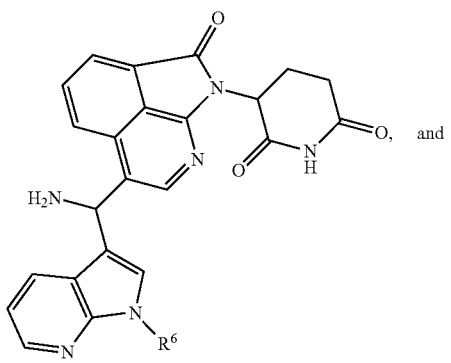
, and
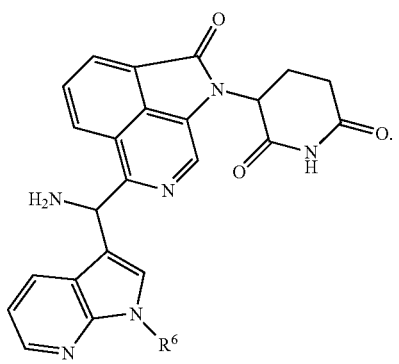
.
In one embodiment, the compound of Formula I is selected from:
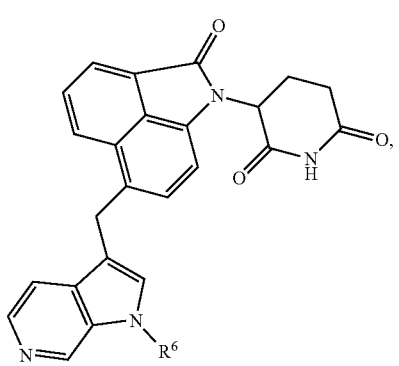
,
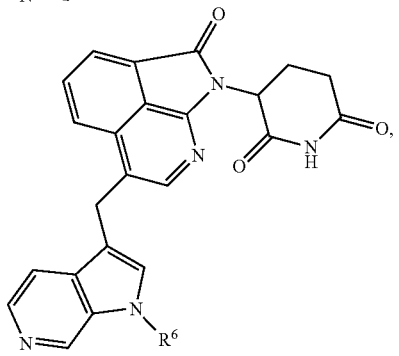
,
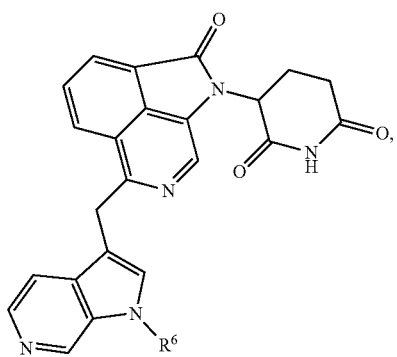
,
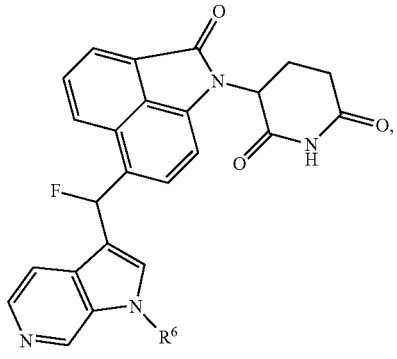
,
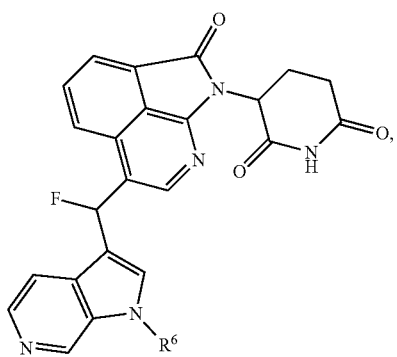
,
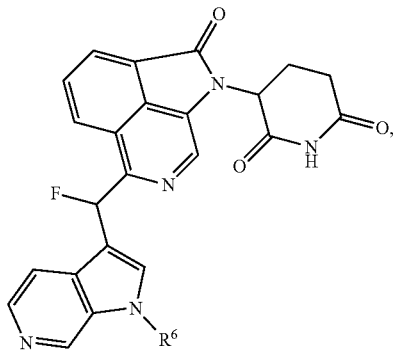
,

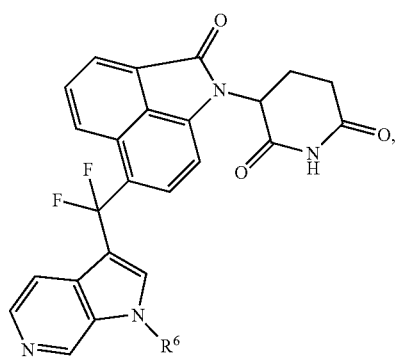
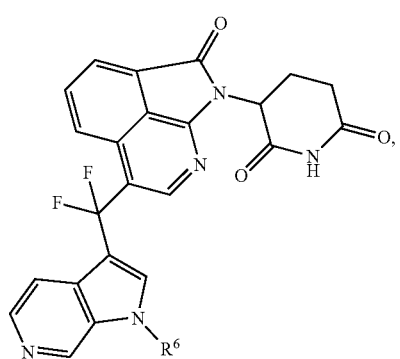
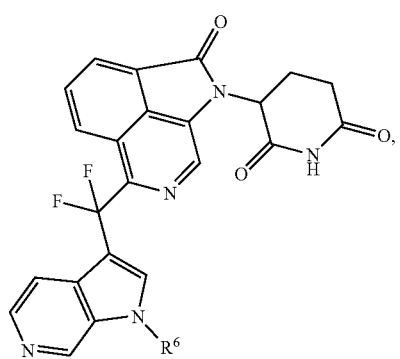
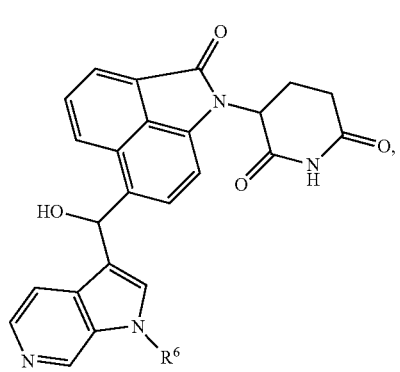
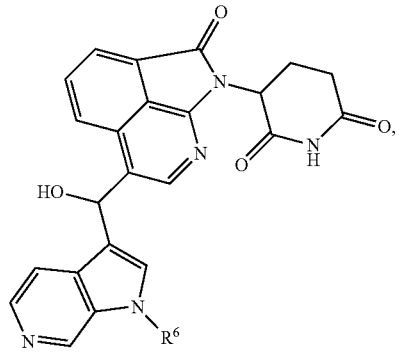
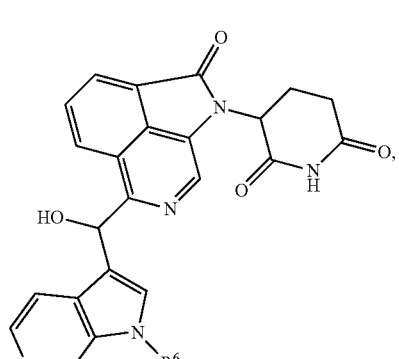
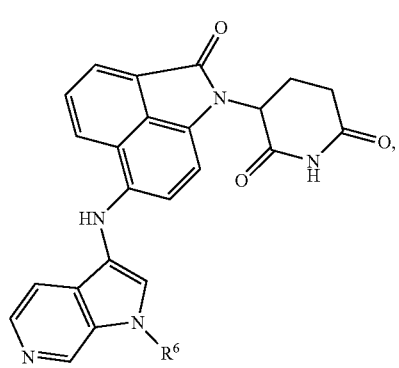
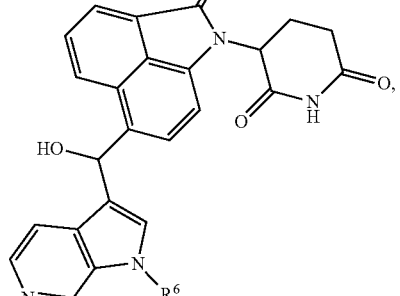

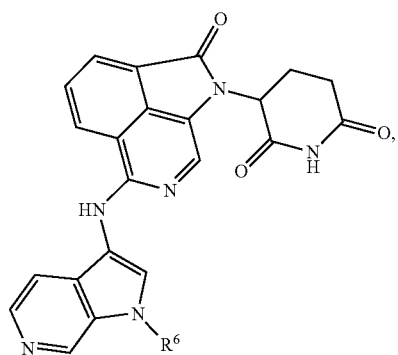
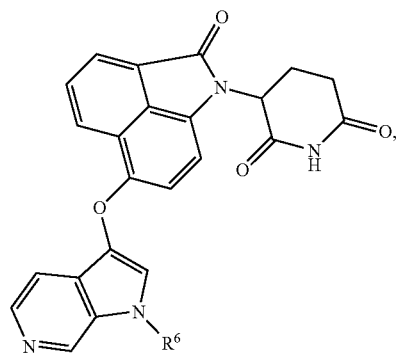
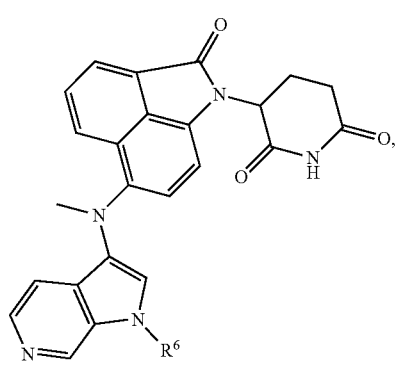
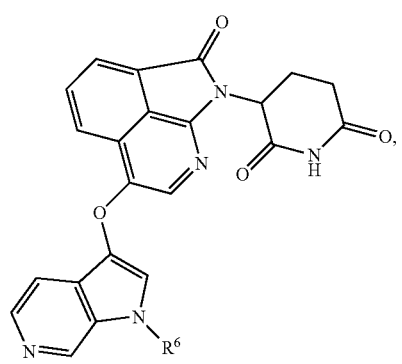
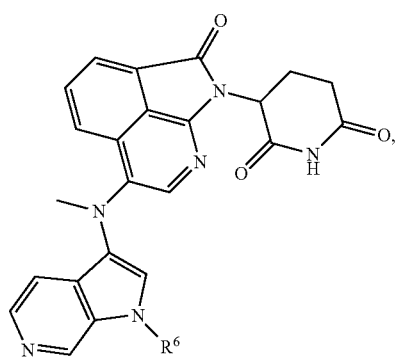
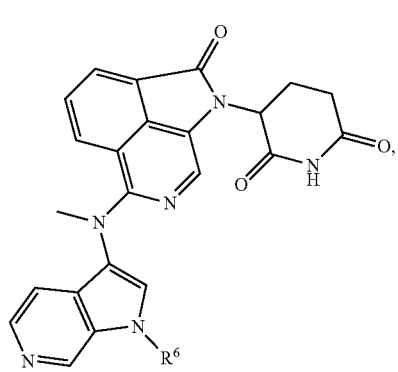
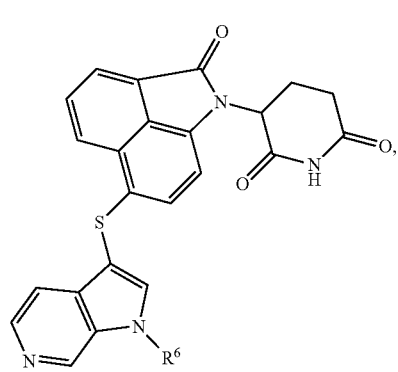

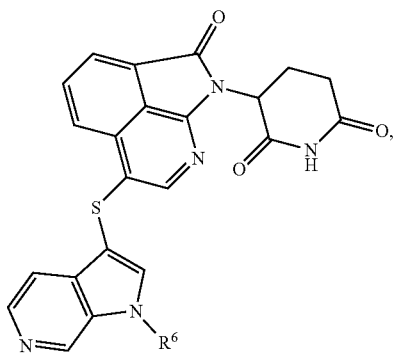
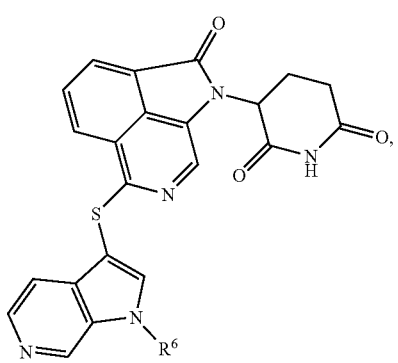
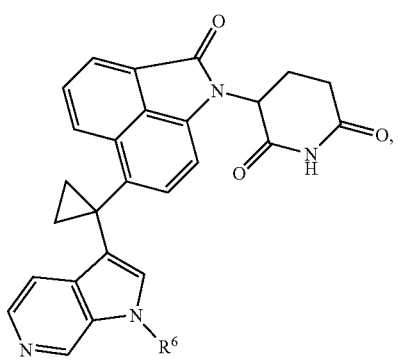
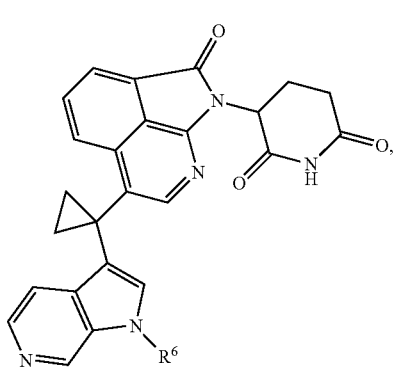
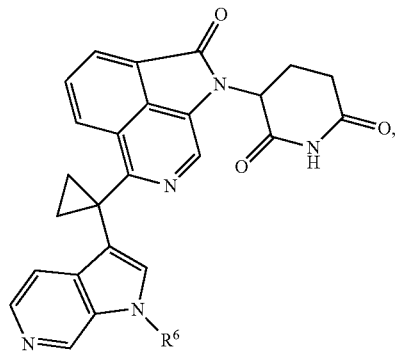
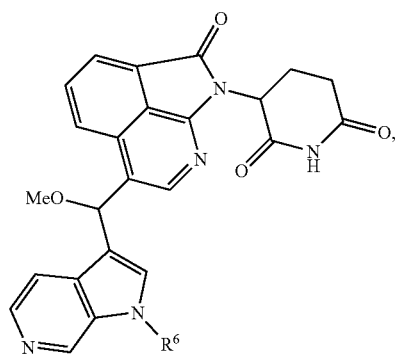
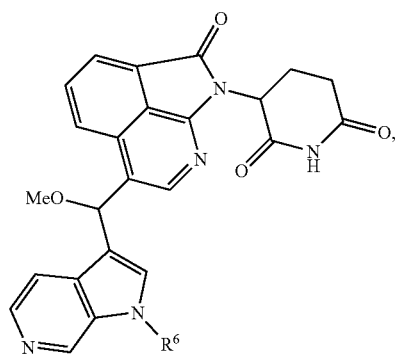
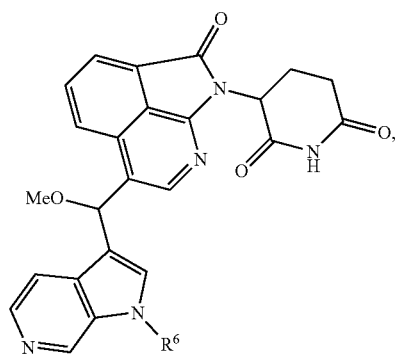

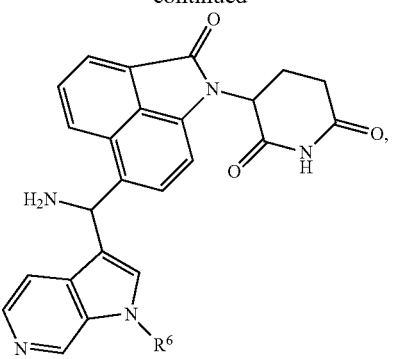
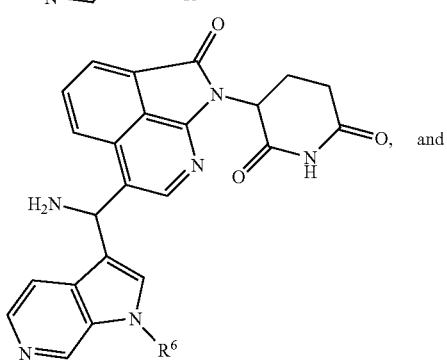
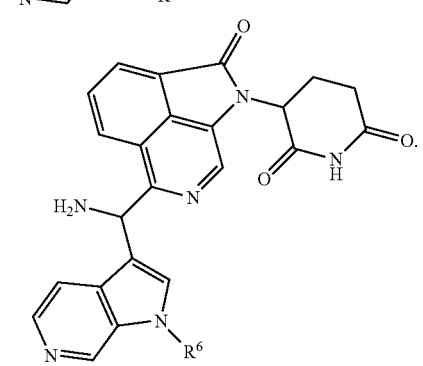
In one embodiment, the compound of Formula I is selected from:
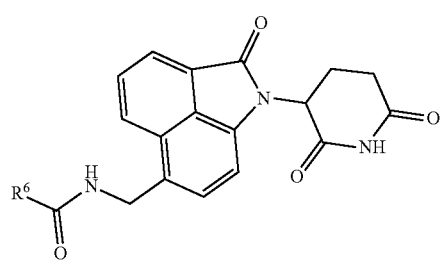
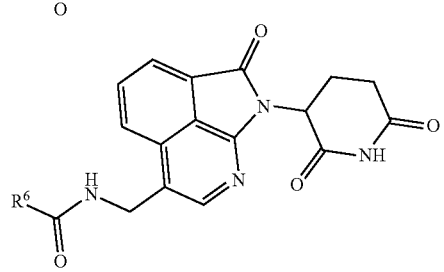
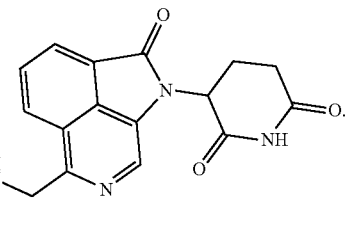
and
In one embodiment, the compound of Formula I is selected from:
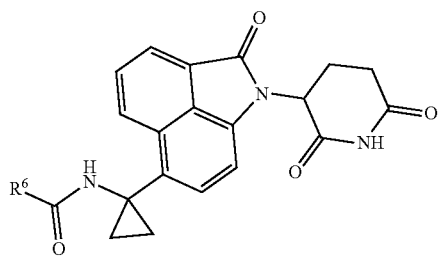
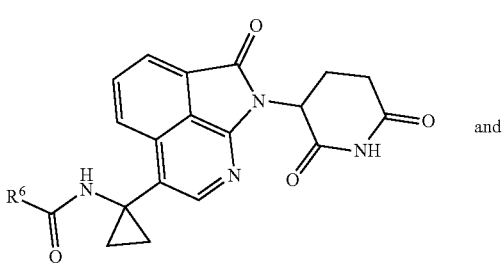
and
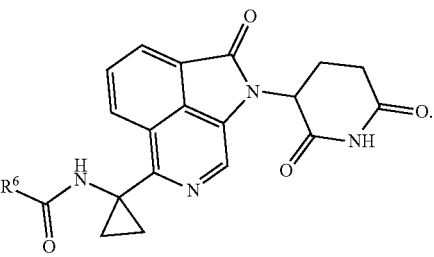
In one embodiment, the compound of Formula I is selected from:
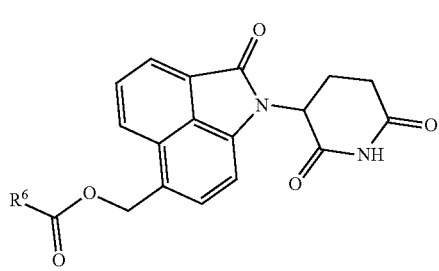

-continued
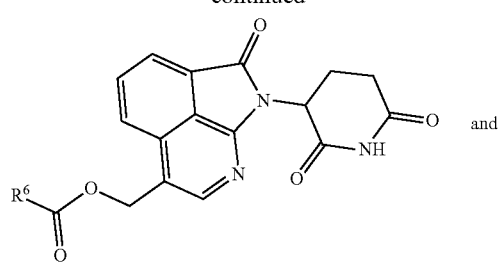 and
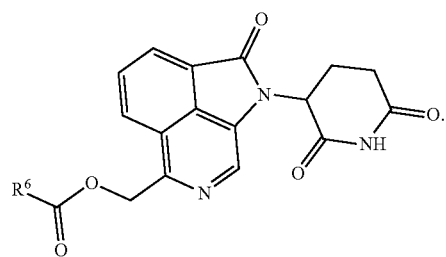
In one embodiment, the compound of Formula I is selected from:
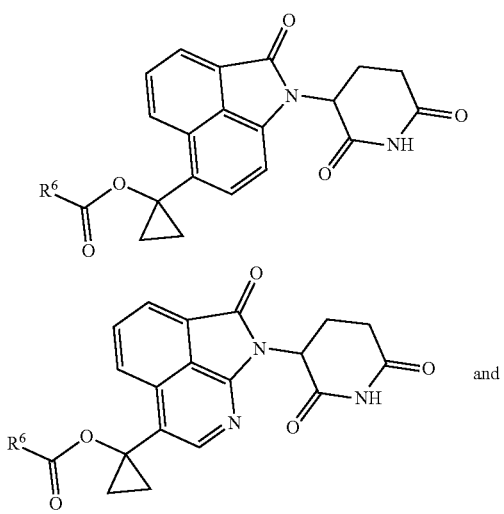
and
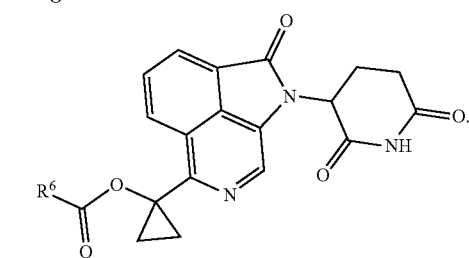
Non-Limiting Embodiments of $R^6$
In one embodiment of Formula I, $R^6$ is selected from:
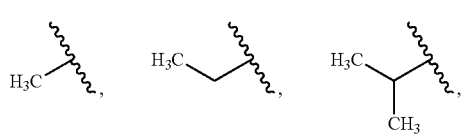
-continued
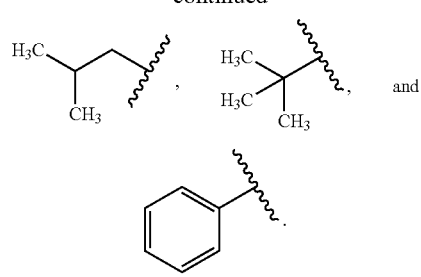
In one embodiment of Formula I, $R^6$ is selected from:
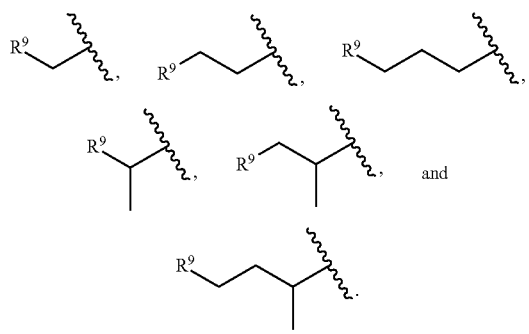
In one embodiment of Formula I, $R^6$ is selected from:
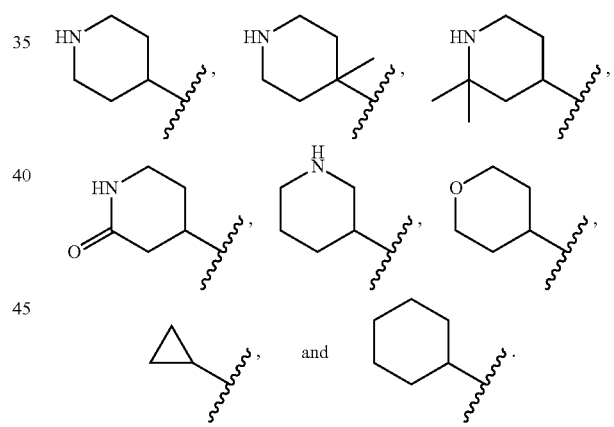
In one embodiment of Formula I, $R^6$ is selected from:
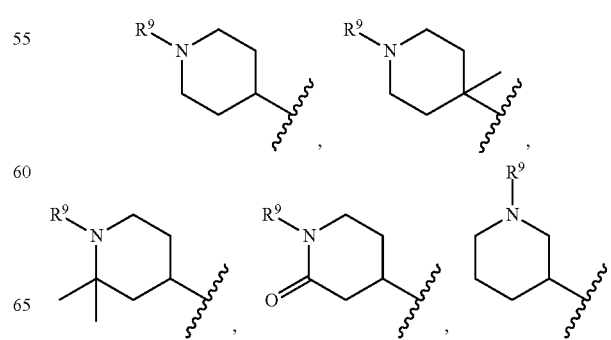

-continued
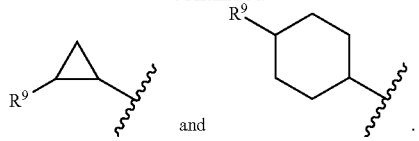
and
In one embodiment of Formula I, $R^6$ is selected from:
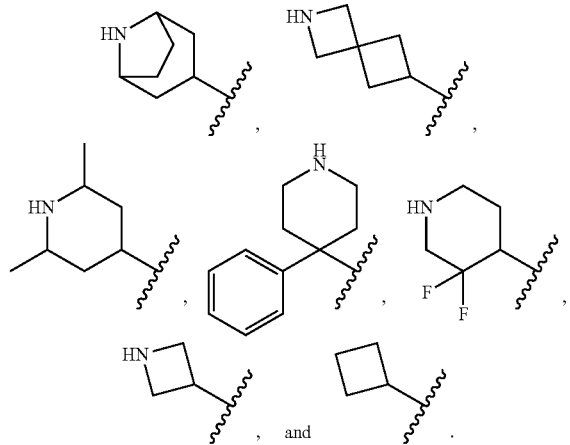
and
In one embodiment of Formula I, $R^6$ is selected from:
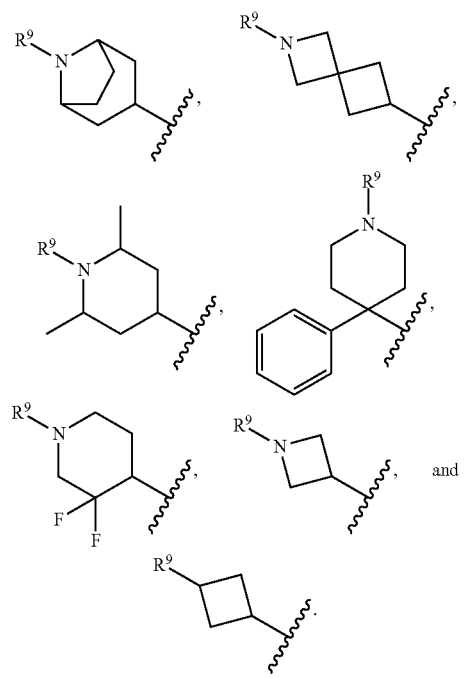
In certain embodiments $R^6$ is selected from:
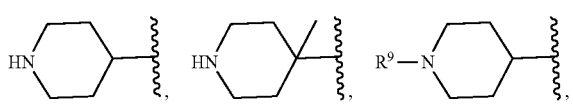
-continued
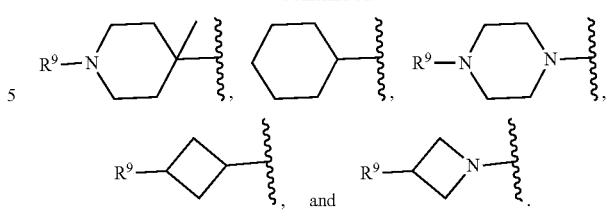
and
Non-Limiting Embodiments of $R^9$
In one embodiment, $R^9$ is selected from:
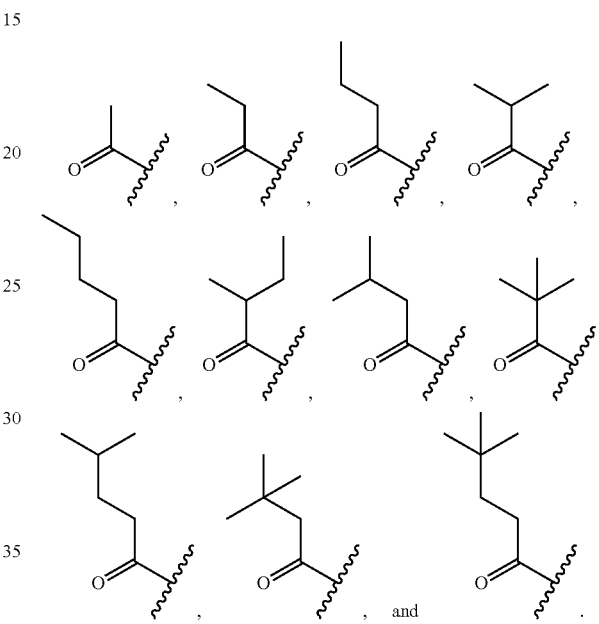
, and
In one embodiment, $R^9$ is selected from:
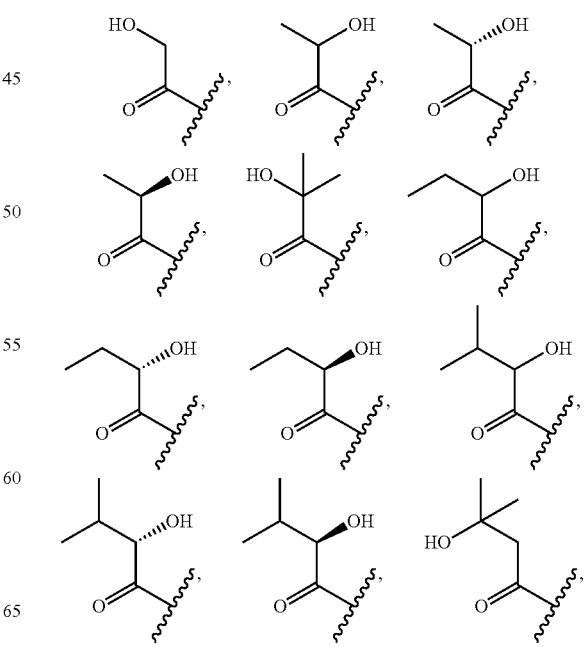

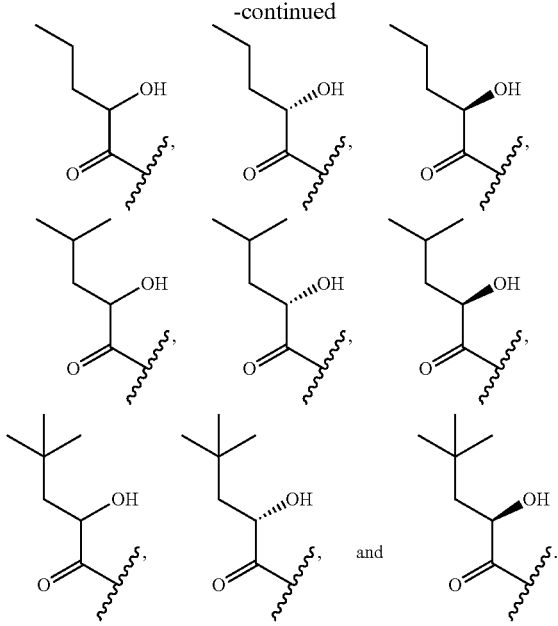
In one embodiment, $R^9$ is selected from:
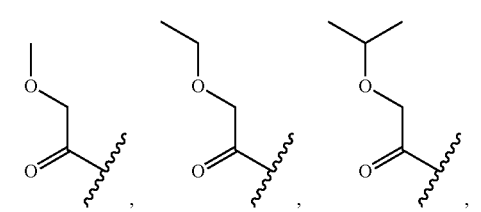
In one embodiment, $R^9$ is selected from:
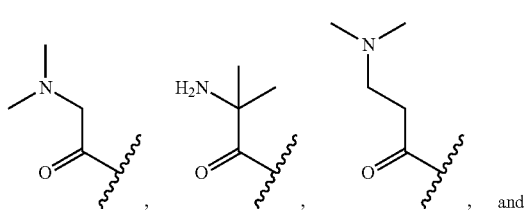
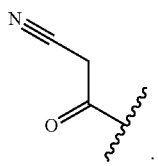 [SMILES: *C(=O)CC#N]
In one embodiment, $R^9$ is
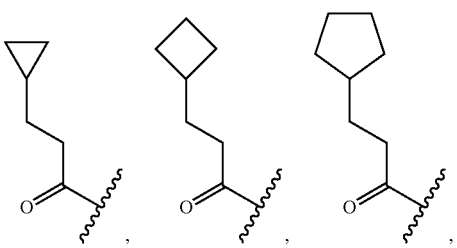
In one embodiment, $R^9$ is selected from:
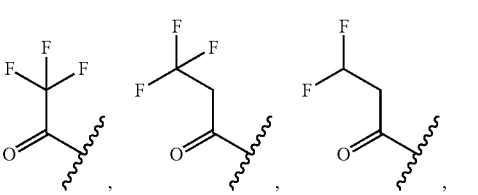
In one embodiment, $R^9$ is selected from:
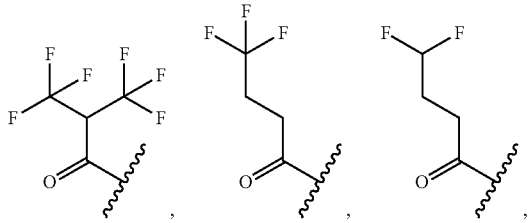

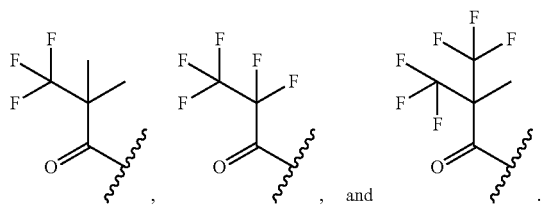
In one embodiment, R⁹ is selected from:
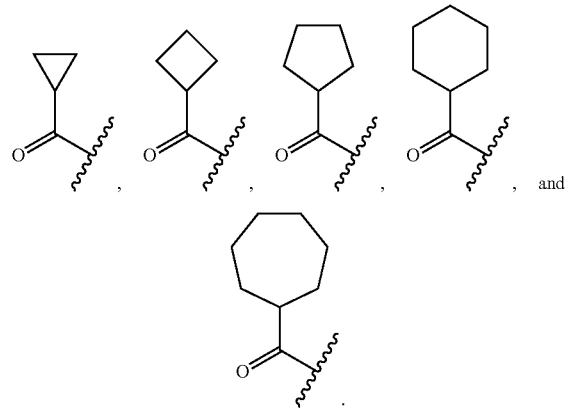
In one embodiment, R⁹ is selected from:
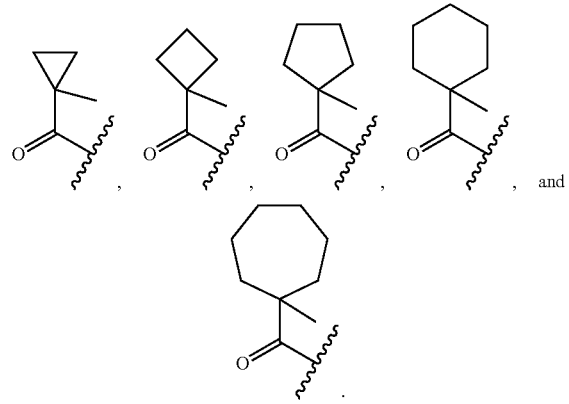
In one embodiment, R⁹ is selected from:
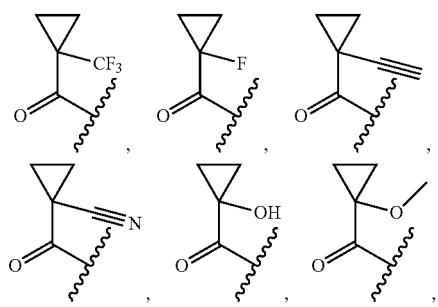
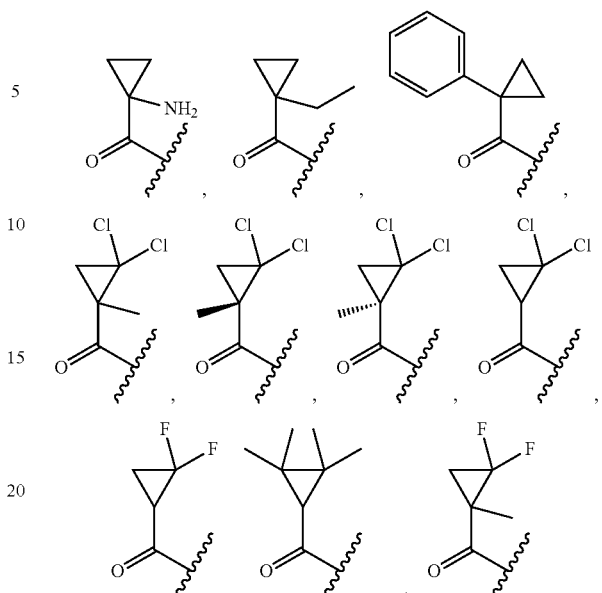
In one embodiment, R⁹ is selected from:
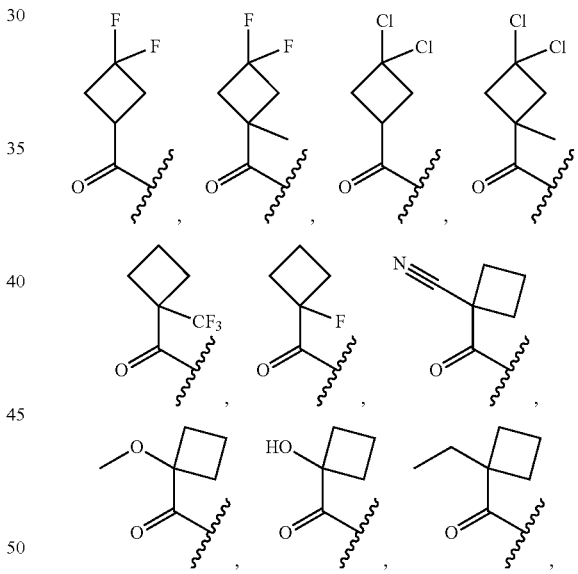
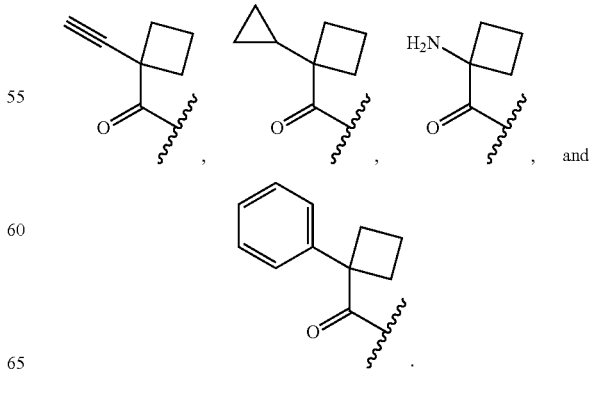

In one embodiment, $R^9$ is selected from:
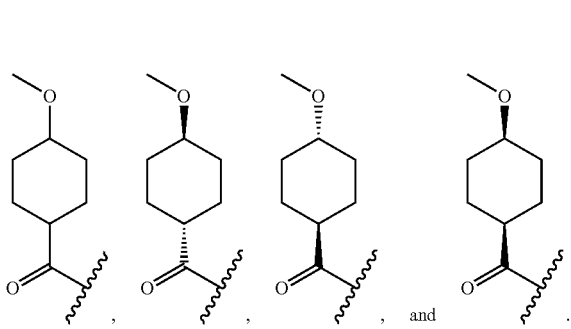 [SMILES: *C(=O)C1CCC(OC)CC1 ; *C(=O)[C@H]1CC[C@H](OC)CC1 ; *C(=O)[C@H]1CC[C@H](OC)CC1 ; *C(=O)[C@H]1CC[C@@H](OC)CC1]
In one embodiment, $R^9$ is selected from:
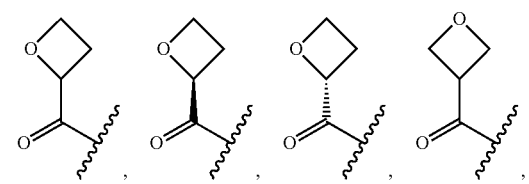
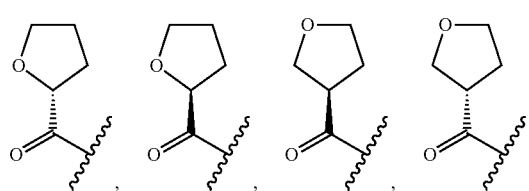
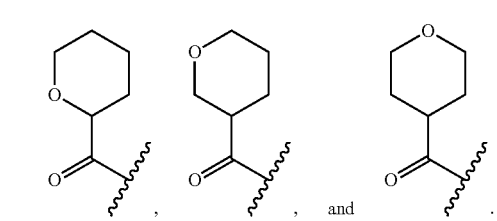
In one embodiment, $R^9$ is selected from:
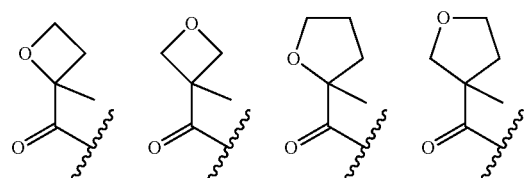
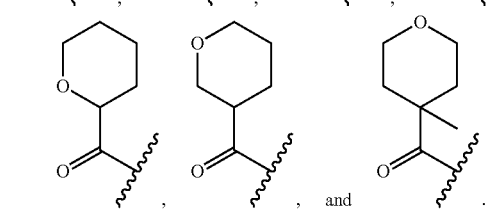
In one embodiment, $R^9$ is selected from:
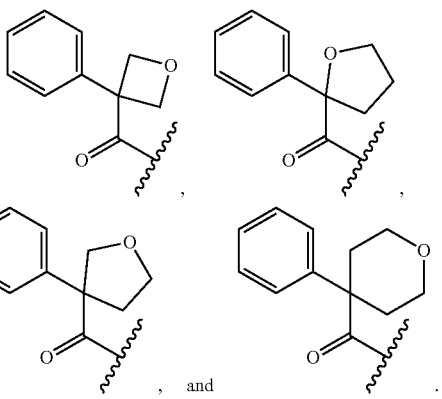
In one embodiment, $R^9$ is selected from:
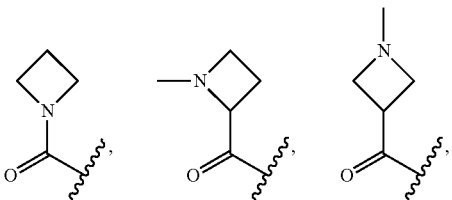
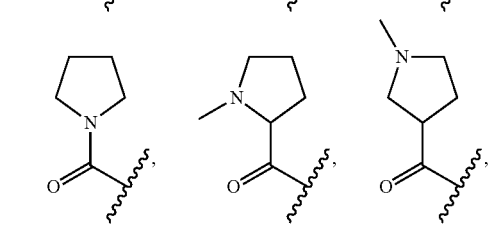
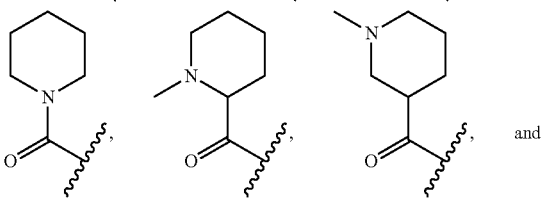
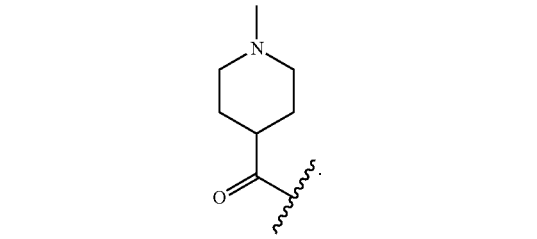
In one embodiment, $R^9$ is selected from:
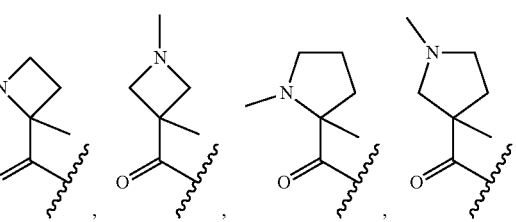

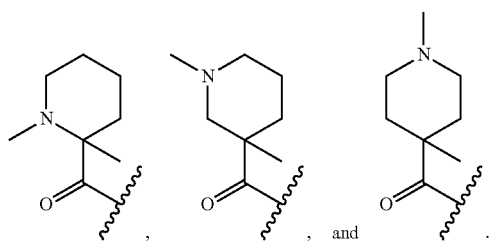
In one embodiment, $R^9$ is
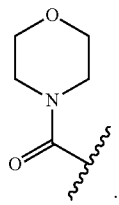
In one embodiment, $R^9$ is O
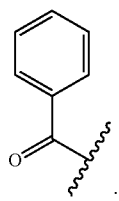
In one embodiment, $R^9$ is selected from:
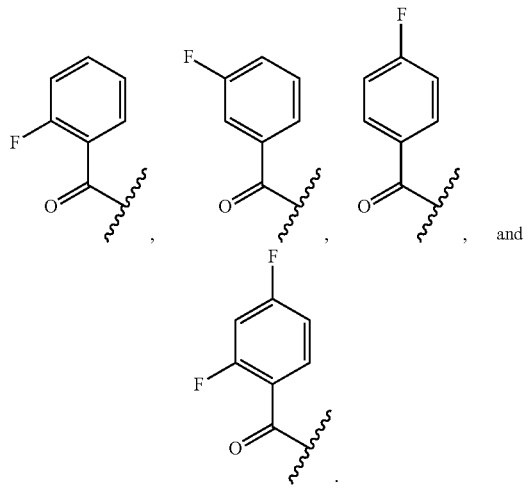
In one embodiment, $R^9$ is
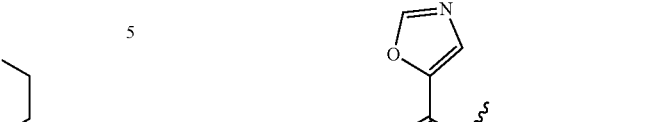
In one embodiment, $R^9$ is selected from
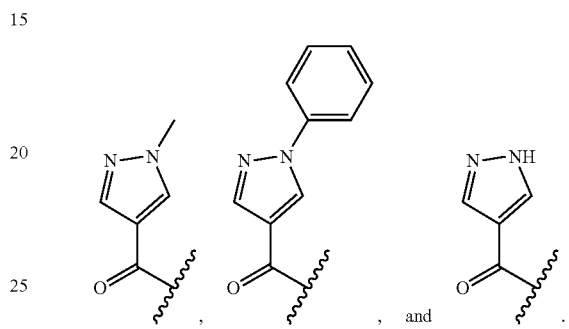
In one embodiment, $R^9$ is selected from
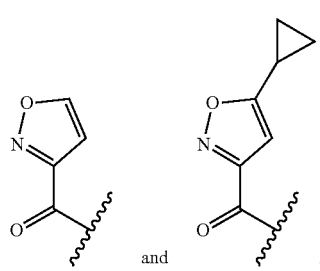
and
In one embodiment, $R^9$ is
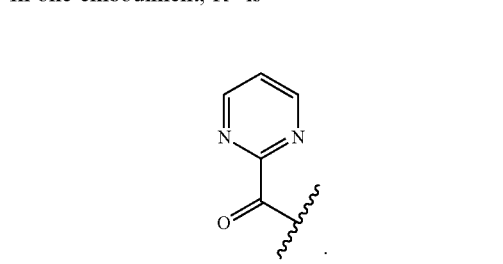
In on embodiment, $R^9$ is
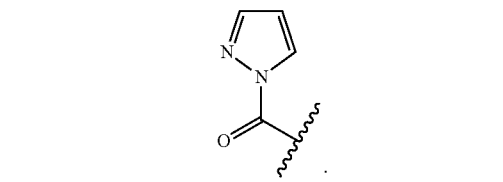

In one embodiment, $R^9$ is
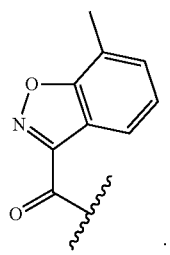 [SMILES: *C(=O)c1noc2c(C)cccc12]
In one embodiment, $R^9$ is
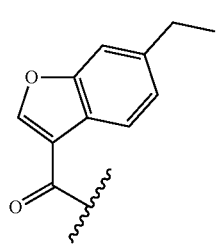
In one embodiment, $R^9$ is
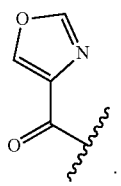
In one embodiment, $R^9$ is
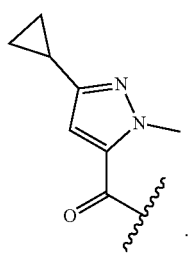 [SMILES: *C(=O)c1cc(C2CC2)nn1C]
In one embodiment, $R^9$ is selected from:
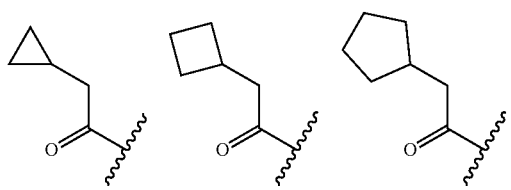
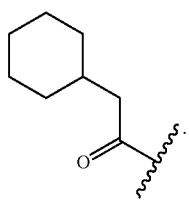
In one embodiment, $R^9$ is selected from:
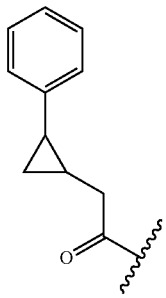 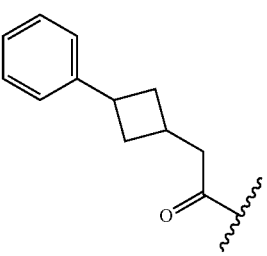
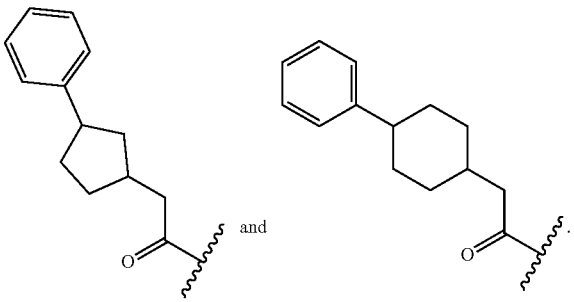
In one embodiment, $R^9$ is
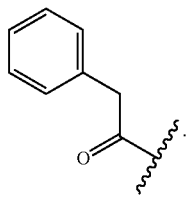 [SMILES: *C(=O)Cc1ccccc1]
In one embodiment, $R^9$ is selected from:
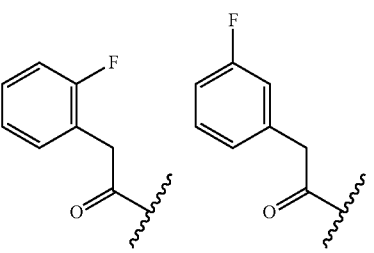

-continued
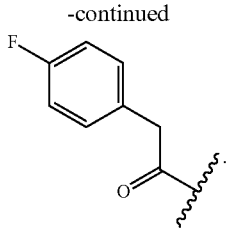
In one embodiment, R⁹ is selected from:
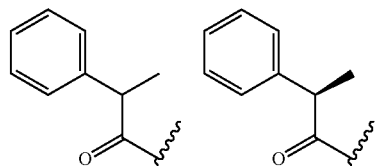
and
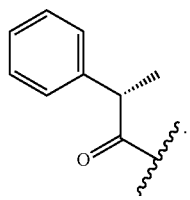
In one embodiment, R⁹ is
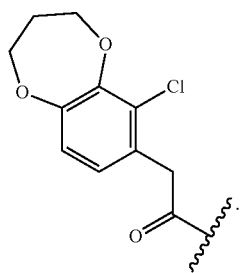 [SMILES: *C(=O)Cc1ccc2c(c1Cl)OCCCO2]
In one embodiment, R⁹ is selected from:
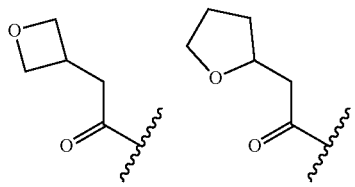
and
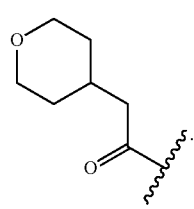
In one embodiment, R⁹ is selected from:
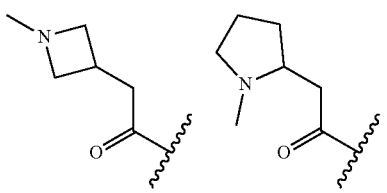
and
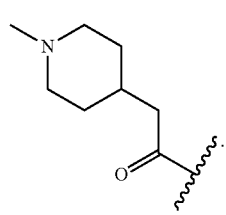
In one embodiment, R⁹ is
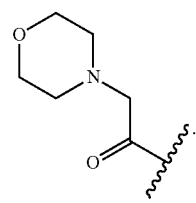 [SMILES: *C(=O)CN1CCOCC1]
In one embodiment, R⁹ is selected from:
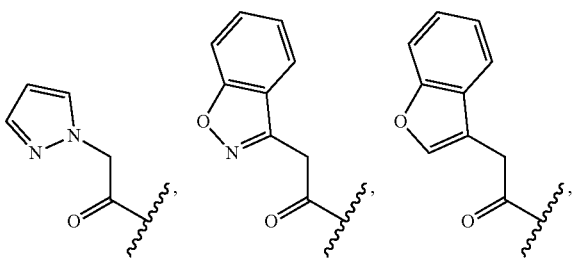
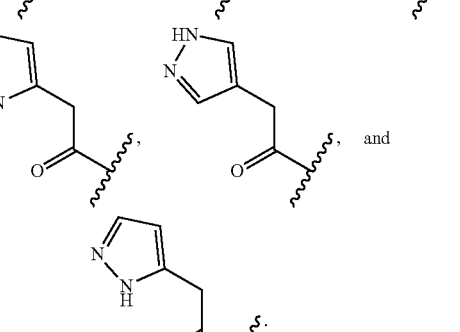
and
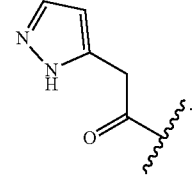

In one embodiment, R⁹ is selected from:
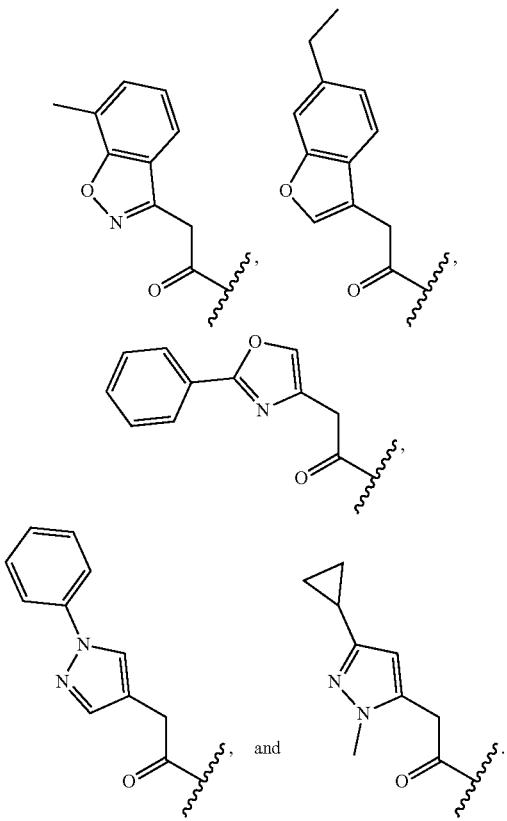
In one embodiment, R⁹ is selected from:
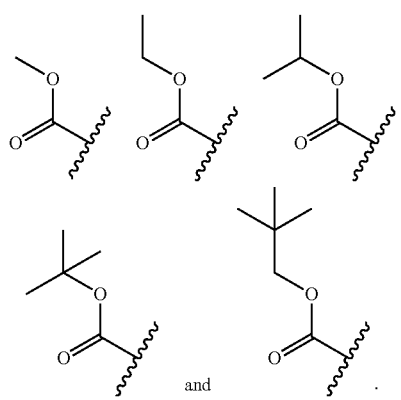
and
In one embodiment, R⁹ is selected from:
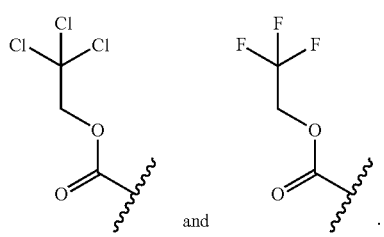 [SMILES: *C(=O)OCC(Cl)(Cl)Cl ; *C(=O)OCC(F)(F)F]
and
In one embodiment, R⁹ is
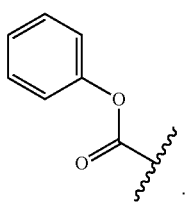 [SMILES: *C(=O)Oc1ccccc1]
In one embodiment, R⁹ is
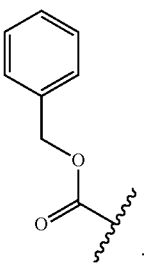 [SMILES: *C(=O)OCc1ccccc1]
In one embodiment, R⁹ is selected from:
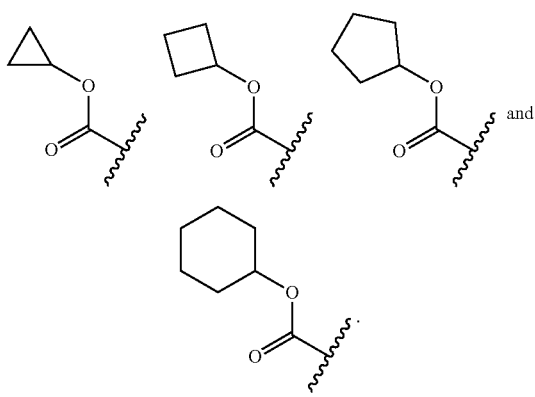
In one embodiment, R⁹ is selected from:
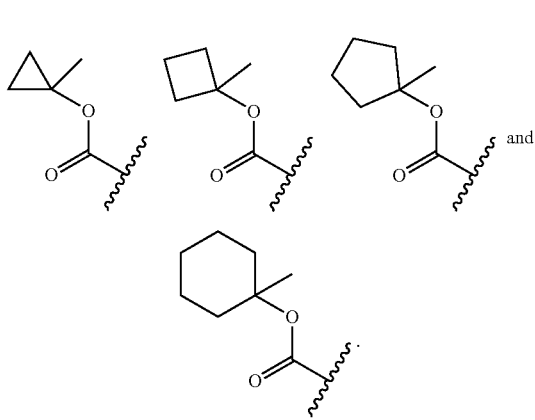

In one embodiment, $R^9$ is selected from:
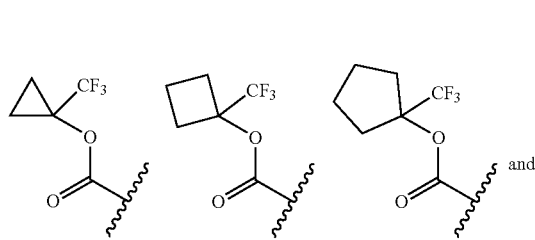
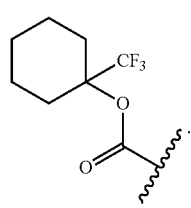
In one embodiment, $R^9$ is selected from:
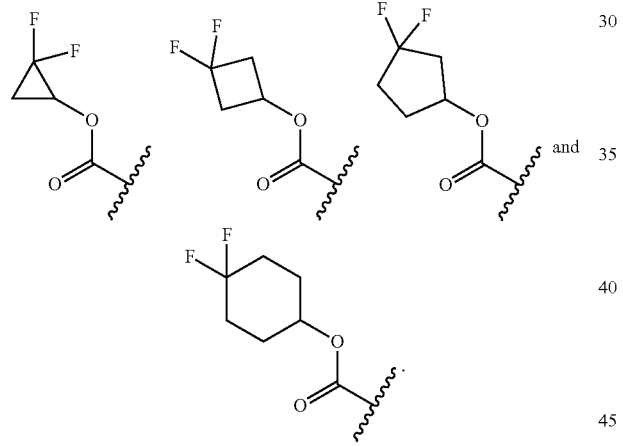
In one embodiment, $R^9$ is selected from:
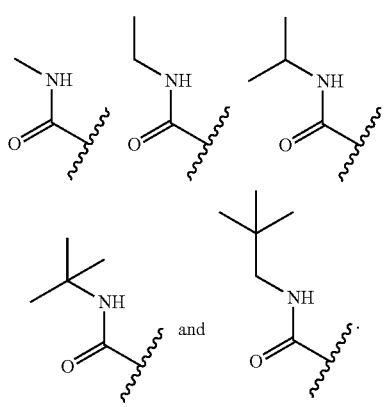
In one embodiment, $R^9$ is selected from:
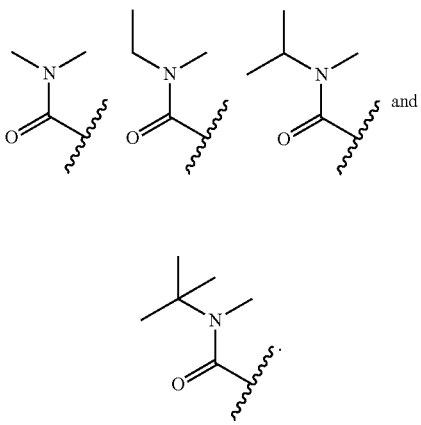
In one embodiment, $R^9$ is
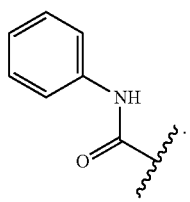 [SMILES: *C(=O)Nc1ccccc1]
In one embodiment, $R^9$ is
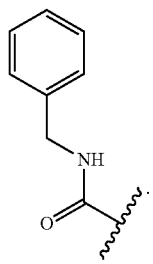 [SMILES: *C(=O)NCc1ccccc1]
In one embodiment, $R^9$ is selected from:
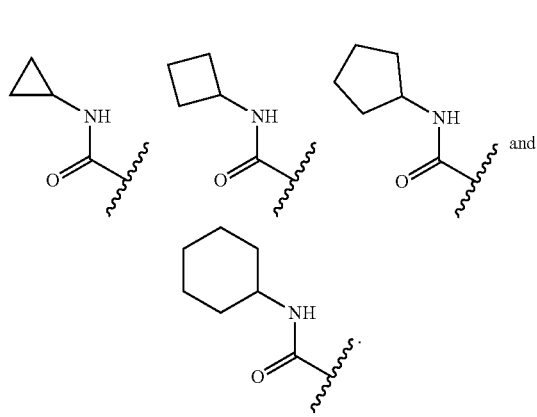

In one embodiment, $R^9$ is selected from:
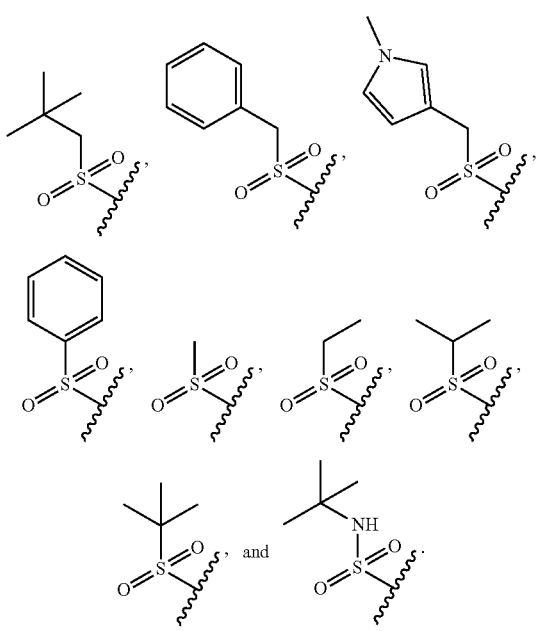
In one embodiment, $R^9$ is
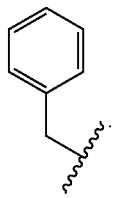 [SMILES: *Cc1ccccc1]
In one embodiment, $R^9$ is selected from:
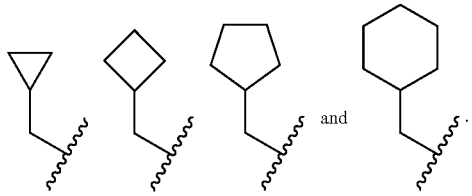
In one embodiment, $R^9$ is selected from:
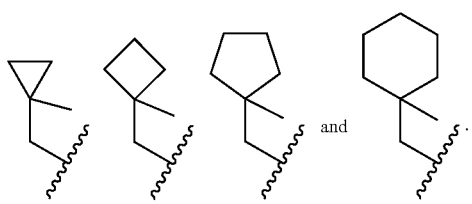
In one embodiment, $R^9$ is selected from:
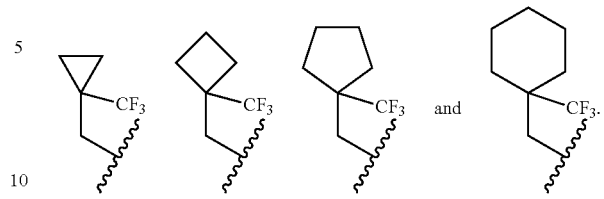
In one embodiment, $R^9$ is selected from:
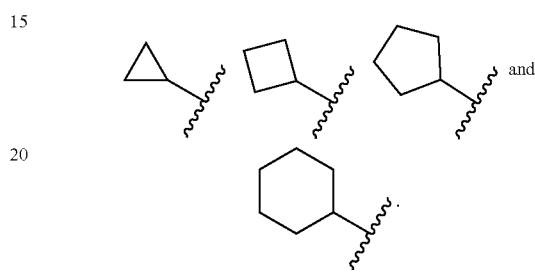
In one embodiment, $R^9$ is selected from:
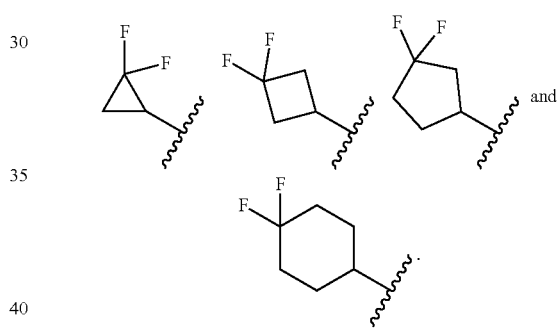
In one embodiment, $R^9$ is selected from:
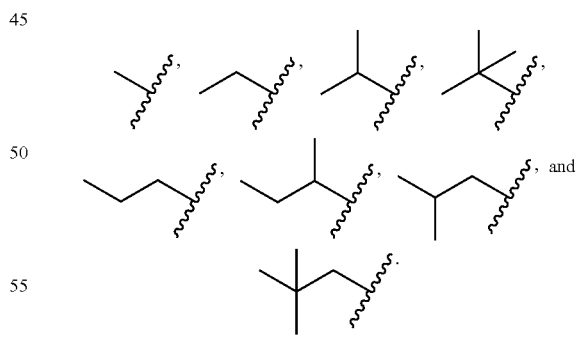
In one embodiment, $R^9$ is
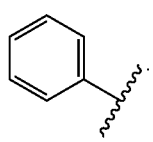

In one embodiment, $R^9$ is
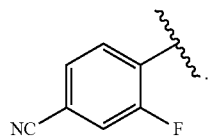
In one embodiment, $R^9$ is selected from:
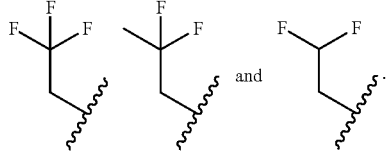
In one embodiment, $R^9$ is
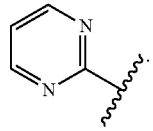
In one embodiment, $R^9$ is selected from:
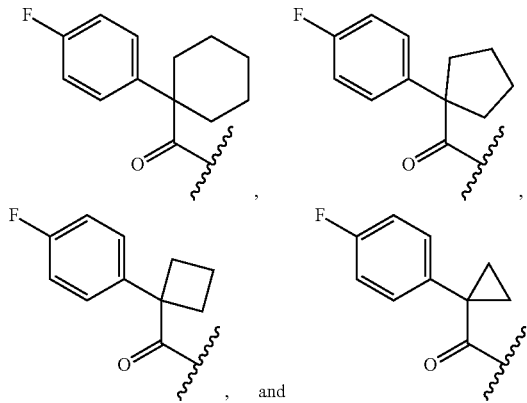
In one embodiment, $R^9$ is selected from:
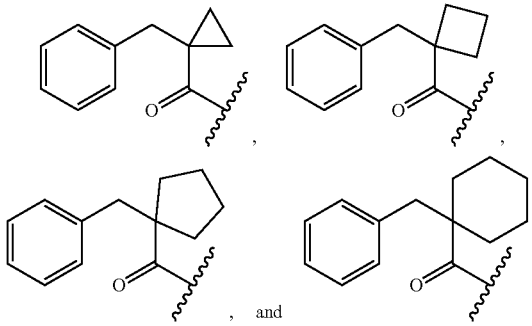
In one embodiment, $R^9$ is selected from:
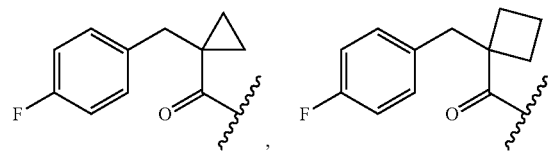
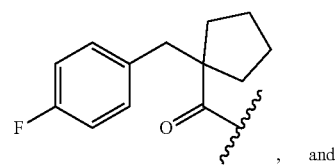
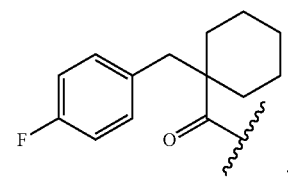
In one embodiment, $R^9$ is
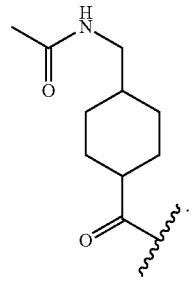 [SMILES: *C(=O)C1CCC(CNC(C)=O)CC1]
In one embodiment, $R^9$ is selected from:
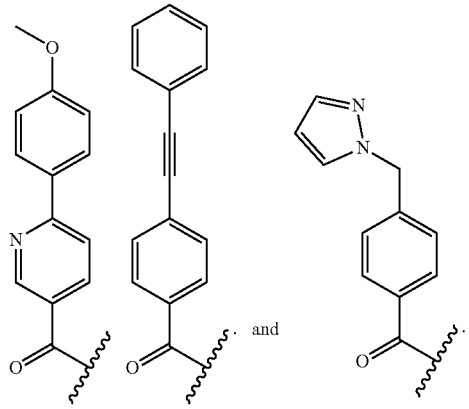

In one embodiment, $R^9$ is selected from:
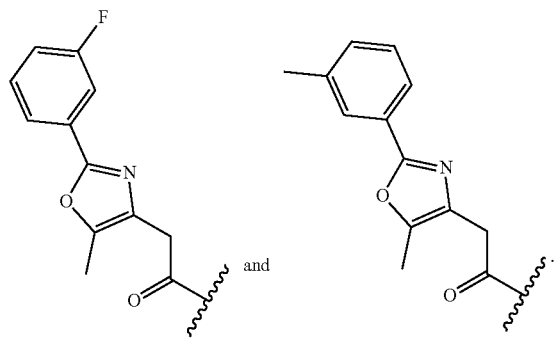 [SMILES: *C(=O)Cc1nc(-c2cccc(F)c2)oc1C ; *C(=O)Cc1nc(-c2cccc(C)c2)oc1C]
and
In one embodiment, $R^9$ is
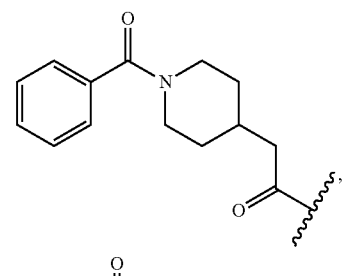
In one embodiment, $R^9$ is selected from:
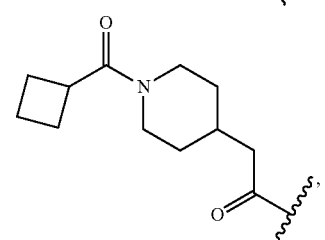
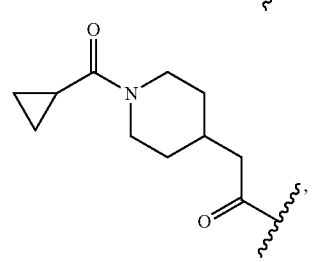
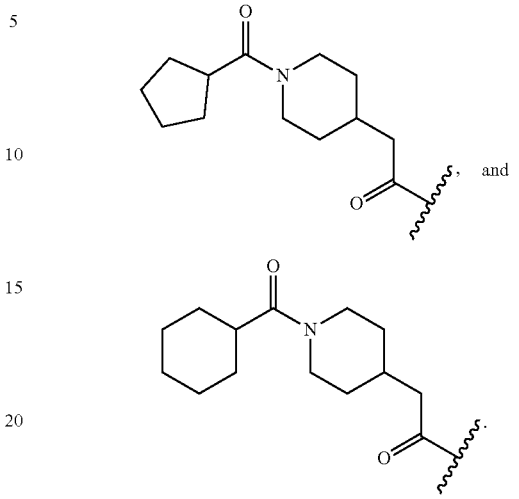
In one embodiment, $R^9$ is selected from:
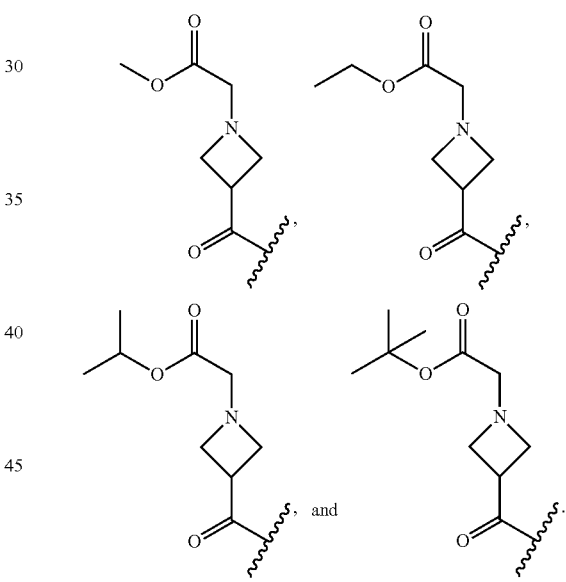
In one embodiment, $R^9$ is selected from:
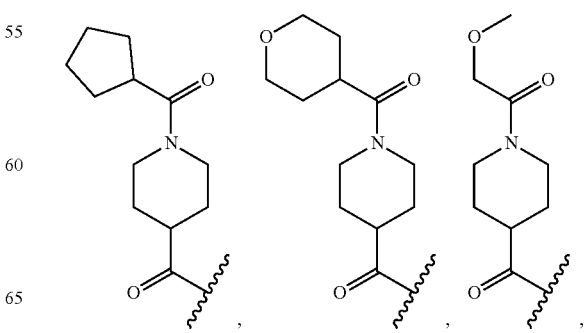

-continued
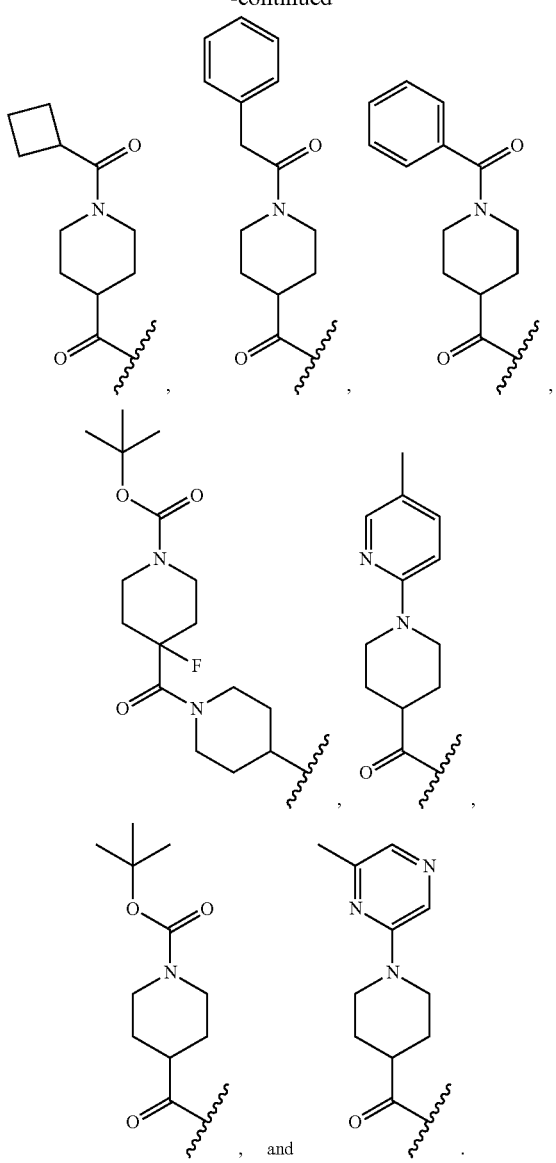
In one embodiment, $R^9$ is selected from:
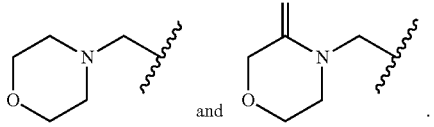
and
In one embodiment, $R^9$ is selected from:
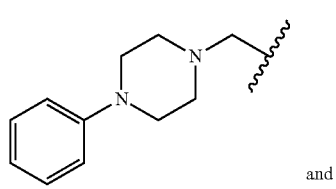
and
-continued
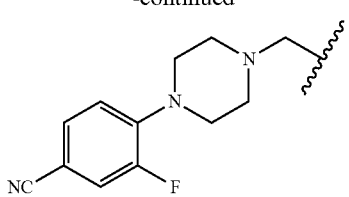
In one embodiment, $R^9$ is selected from:
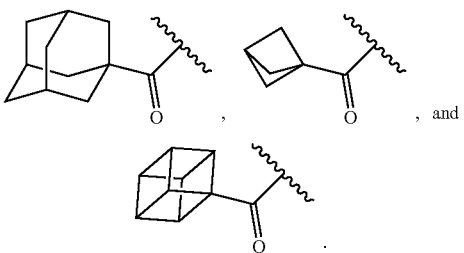
, and
Non-Limiting Embodiments of $R^{10}$
Non-limiting examples of —C(O)$R^{10}$ include:
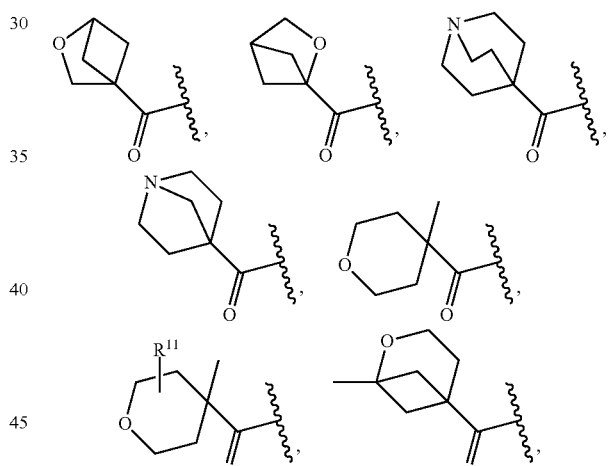
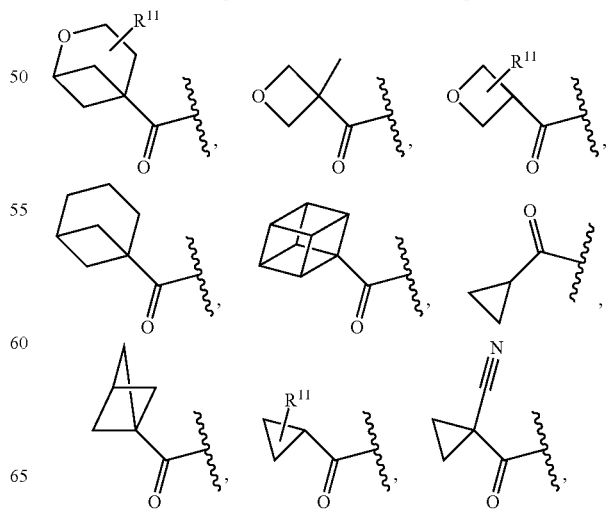

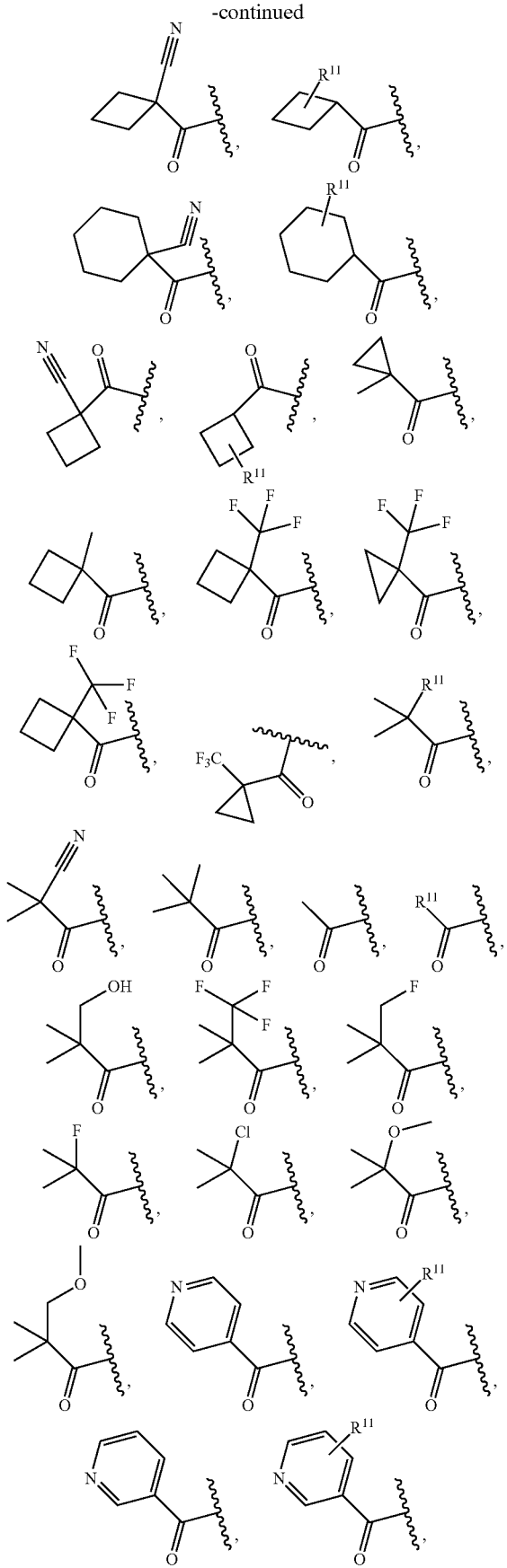
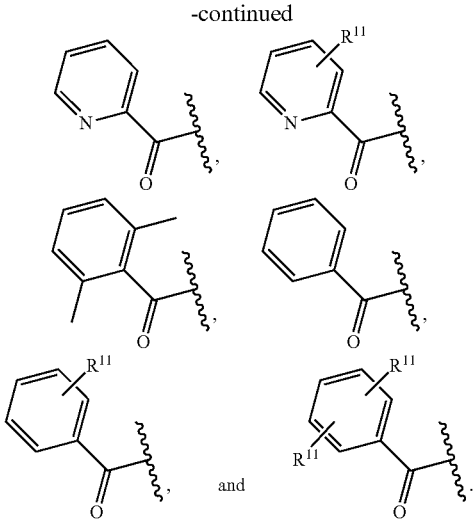
and
Non-limiting examples of —CH$_2$R$^{10}$ include:
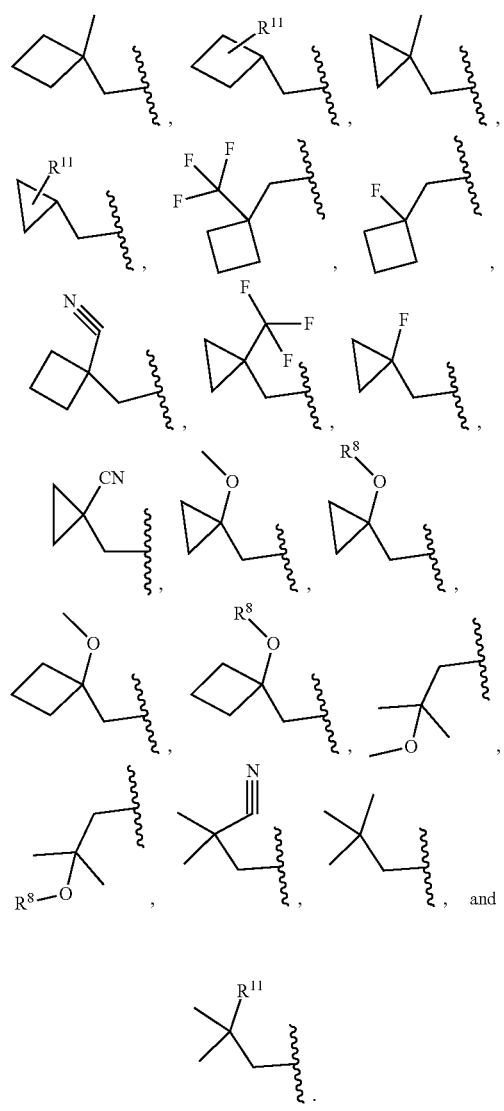

Non-limiting examples of $R^{10}$ include:
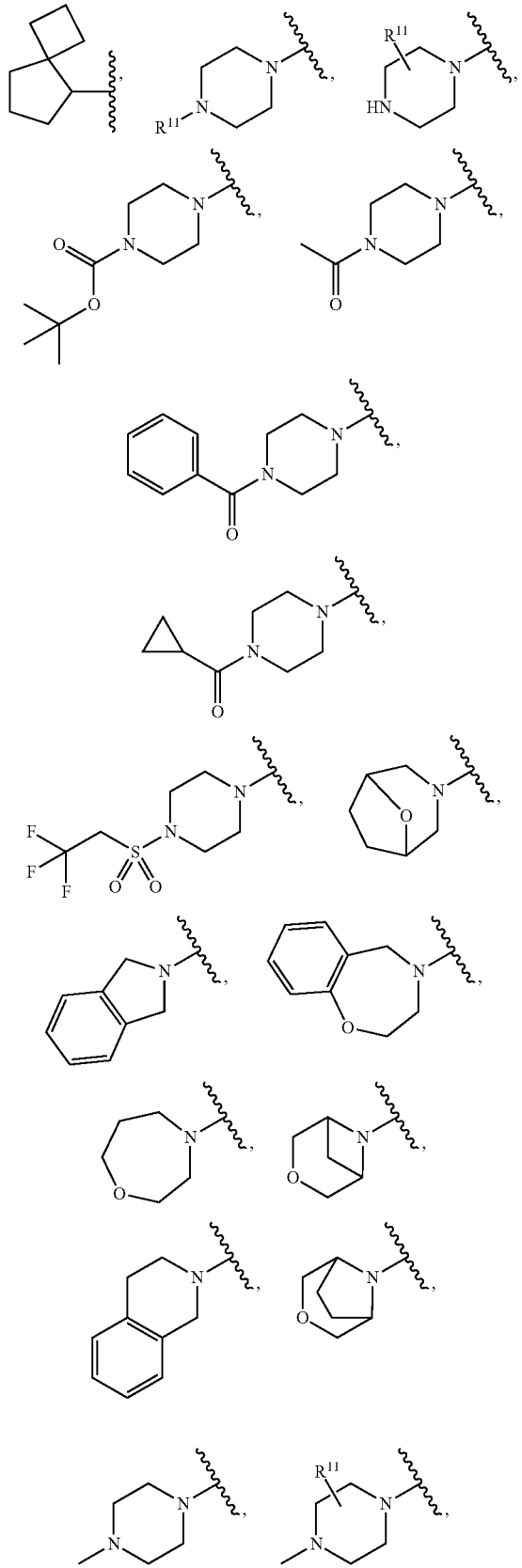
-continued
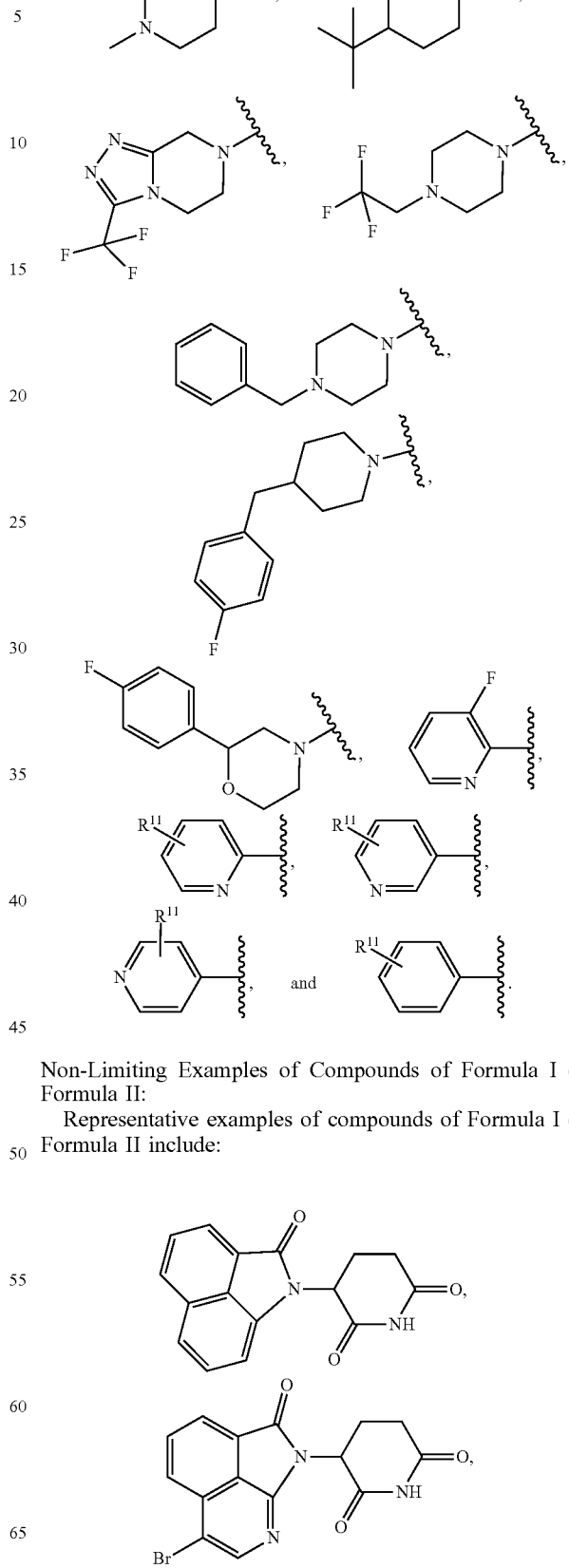
Non-Limiting Examples of Compounds of Formula I or Formula II:
Representative examples of compounds of Formula I or Formula II include:

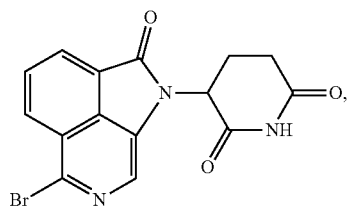
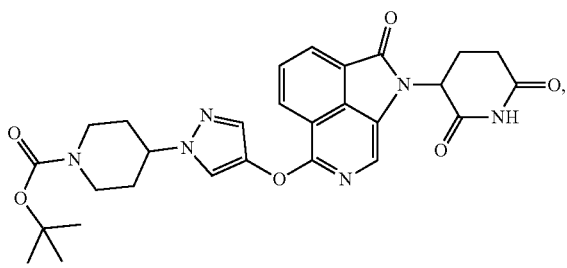
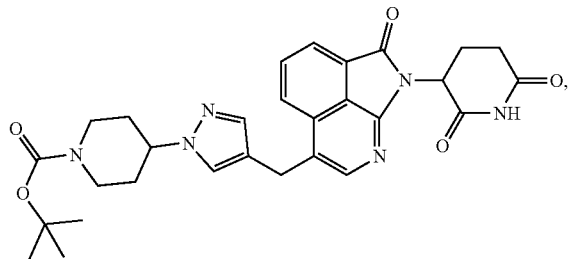
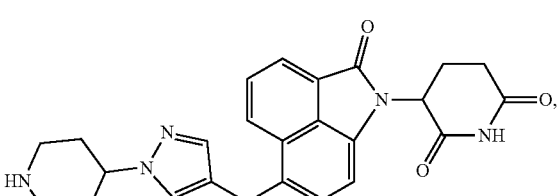
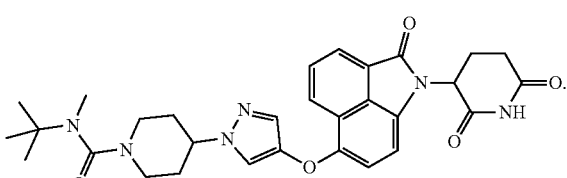
and
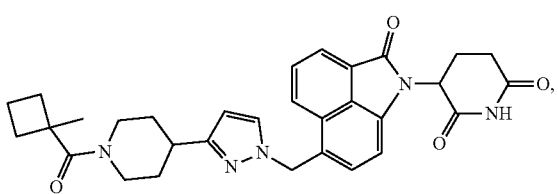
Additional representative examples of compounds of Formula I or Formula II include:
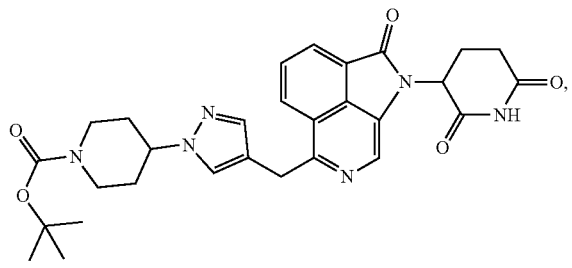
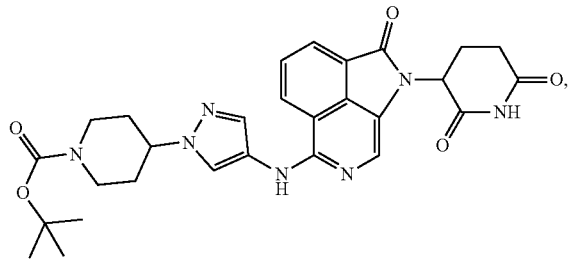
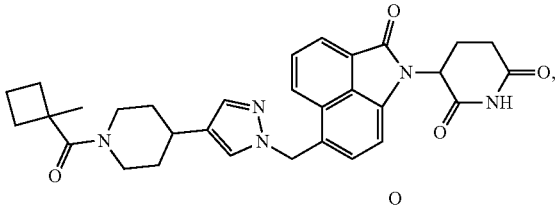
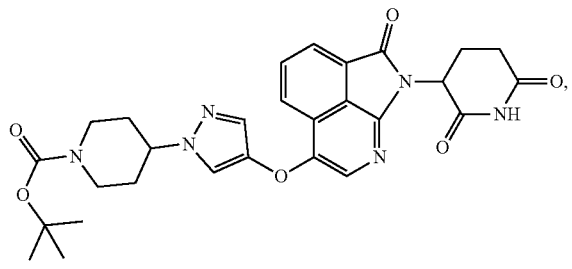
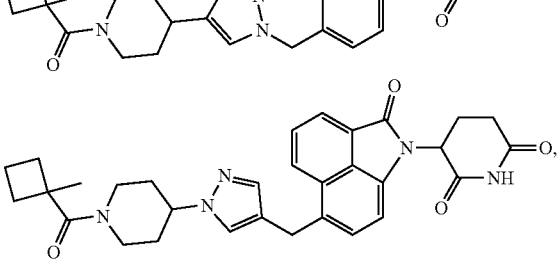

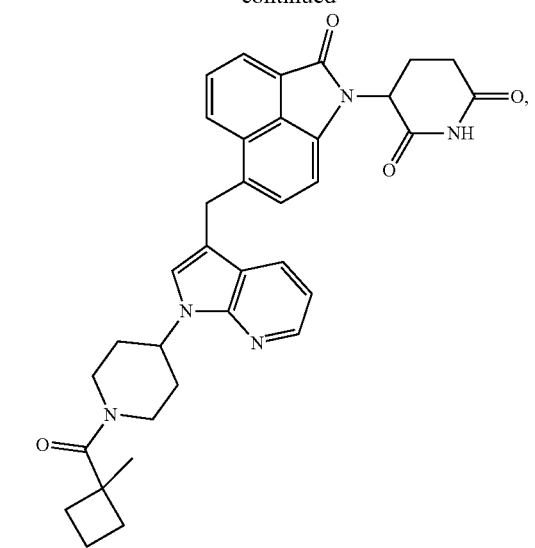
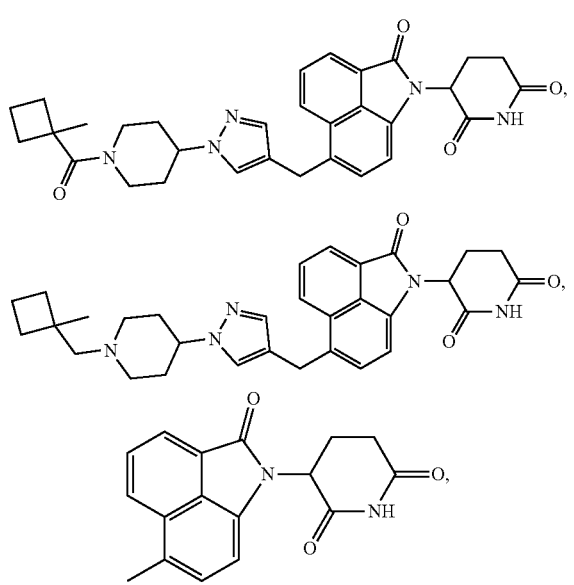
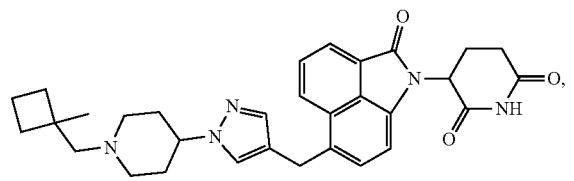
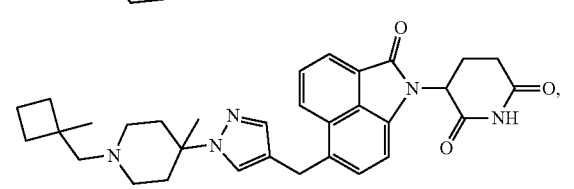
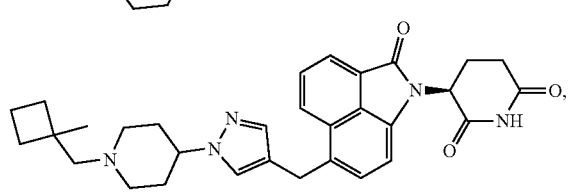
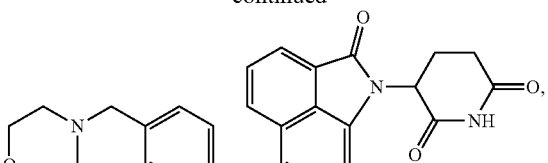
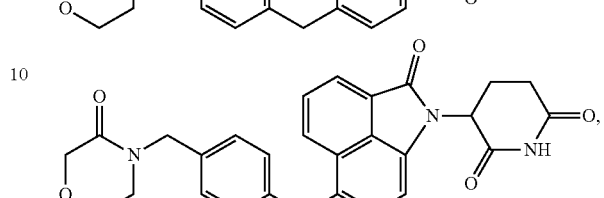
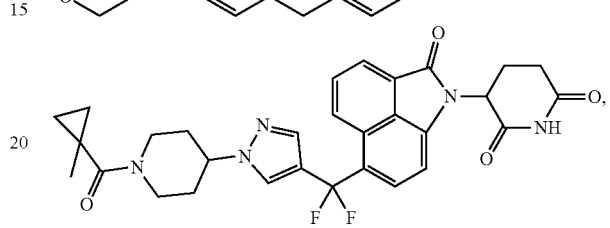
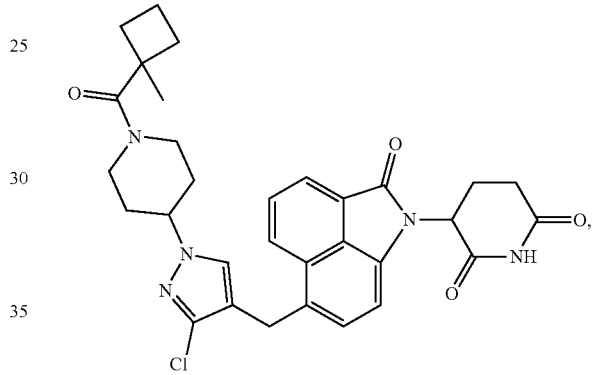
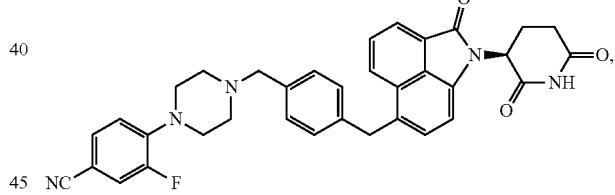
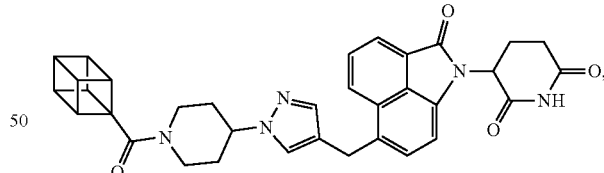
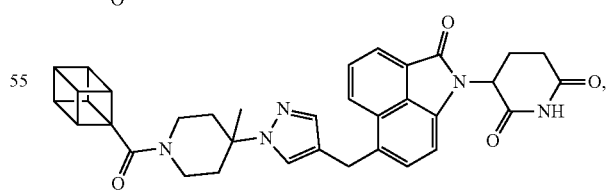
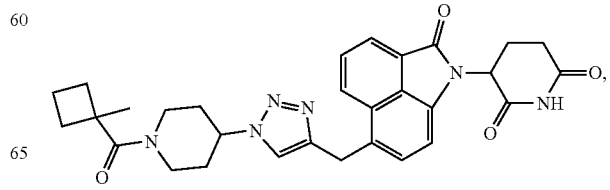

185
-continued
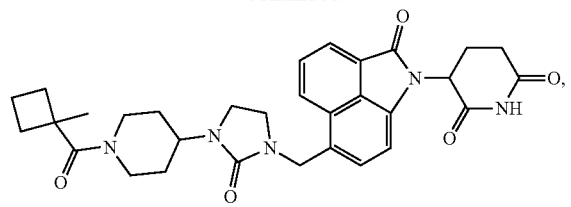
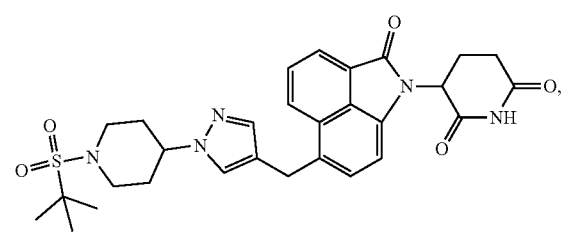
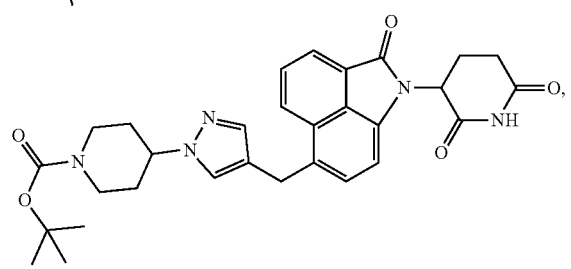
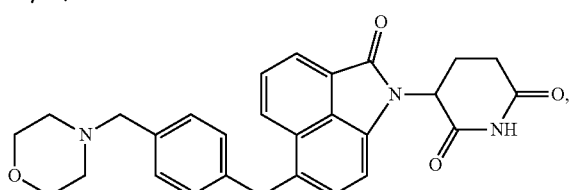
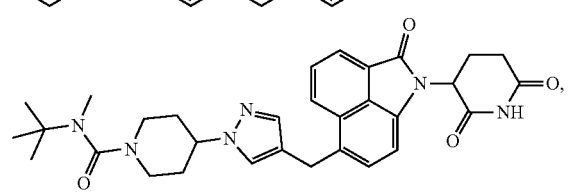
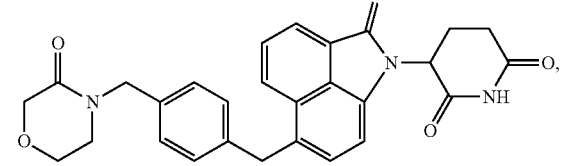
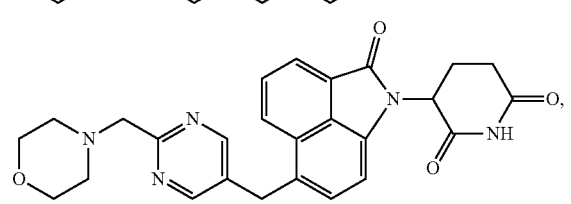
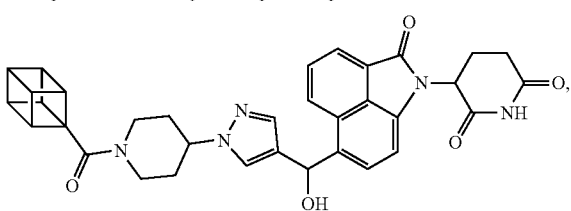
186
-continued
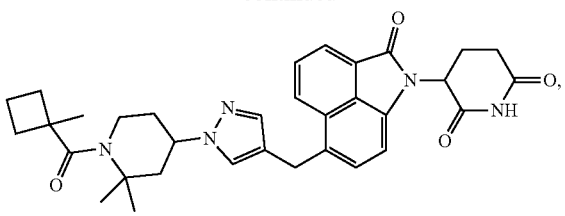
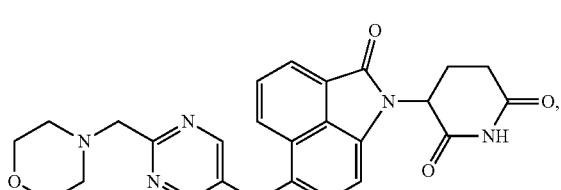
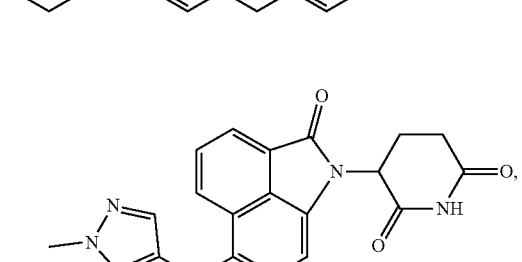
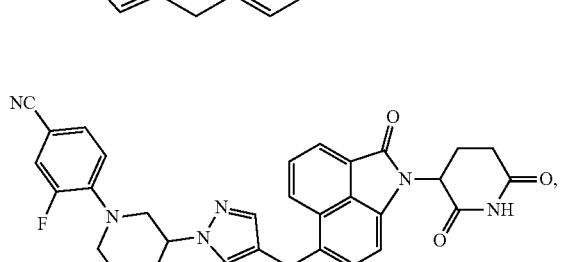
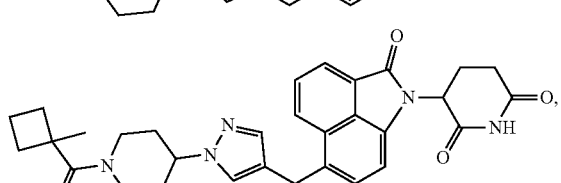
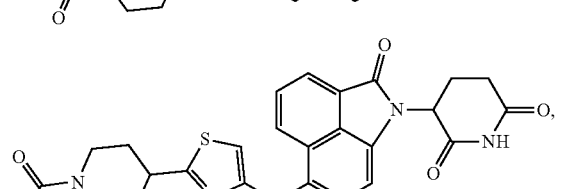
and
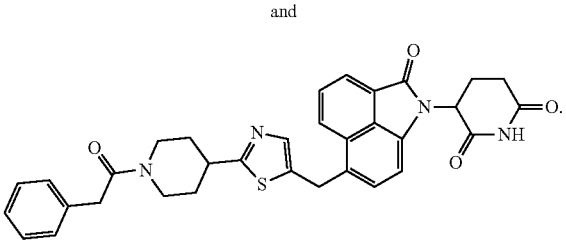

Additional representative examples of compounds of Formula I or Formula II include:
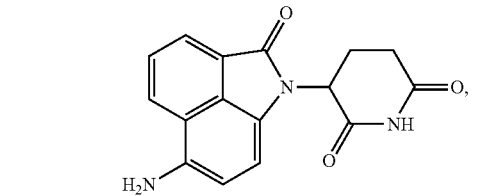
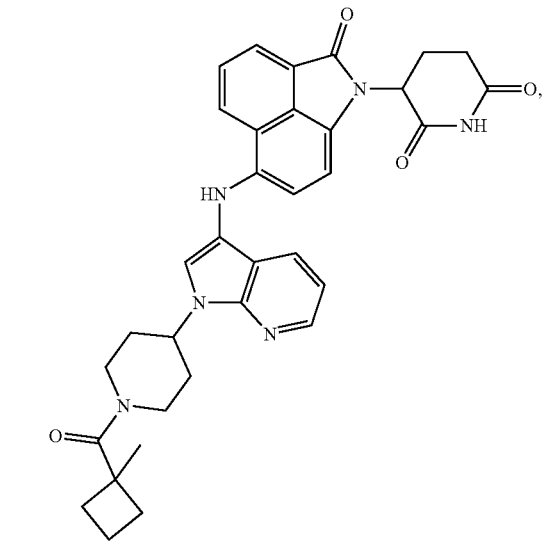
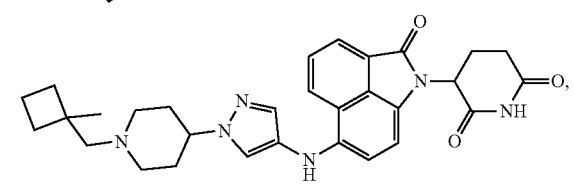
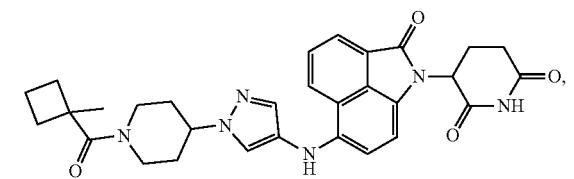
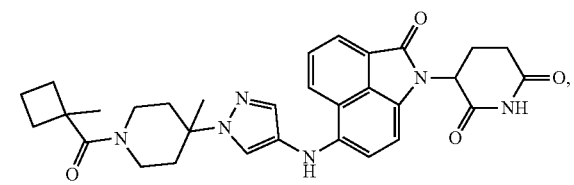
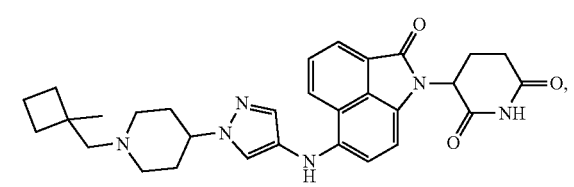
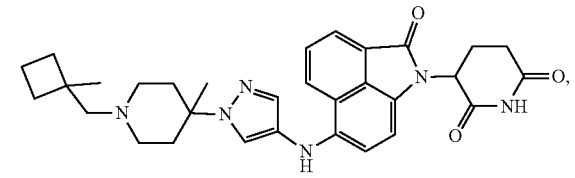
-continued
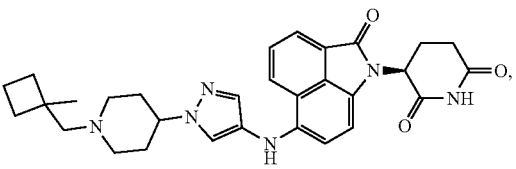
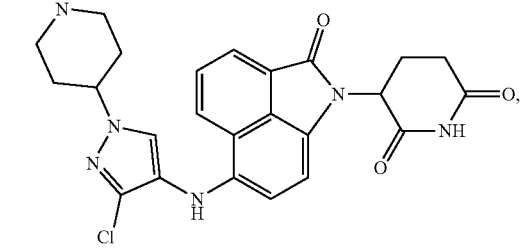
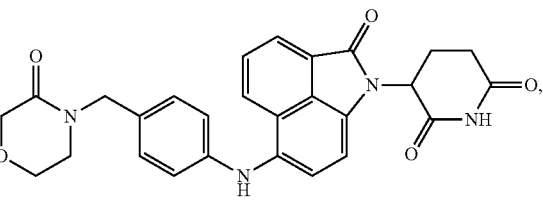
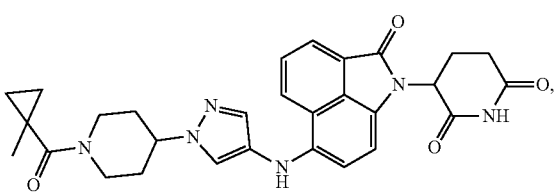
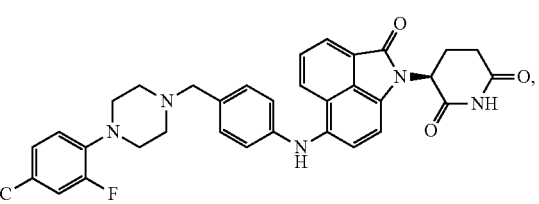
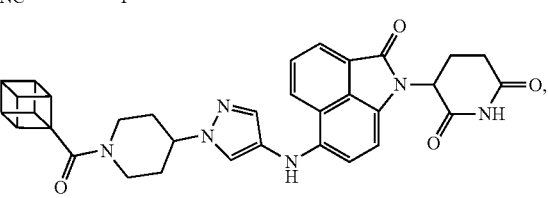

-continued
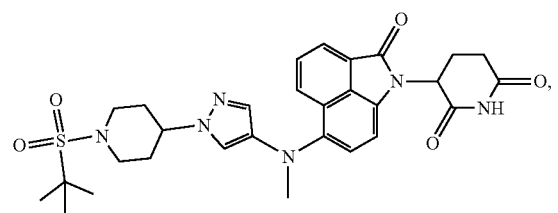
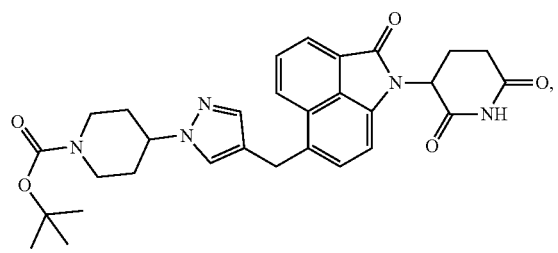
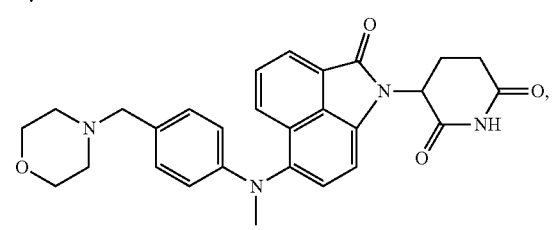
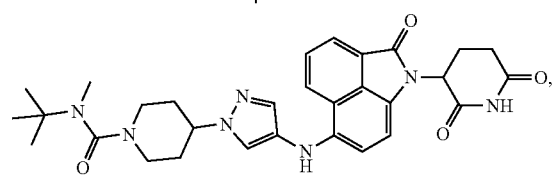
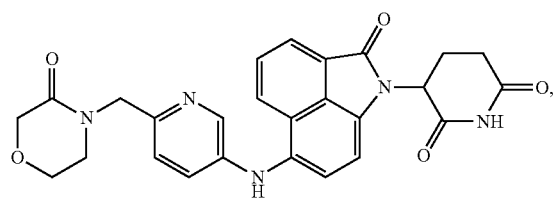
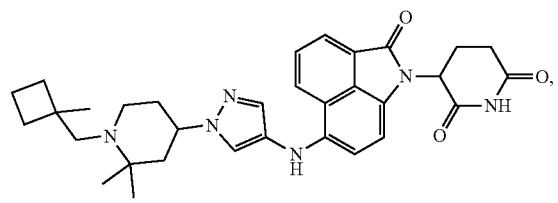
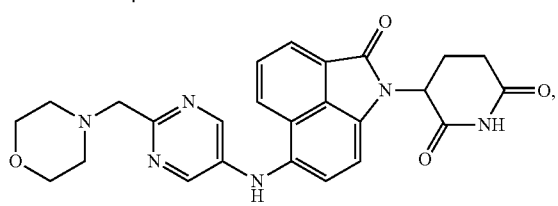
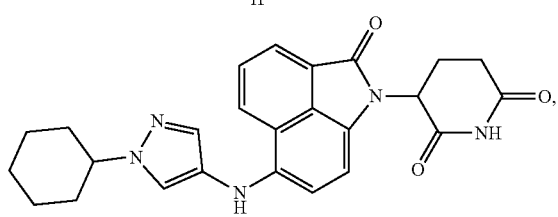
-continued
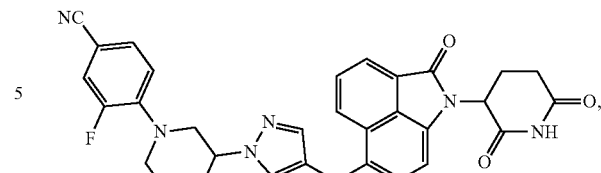
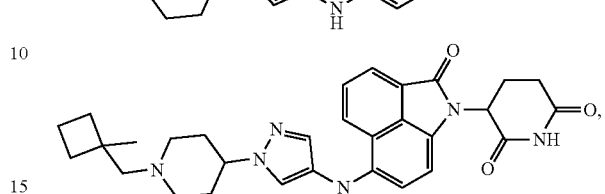
and
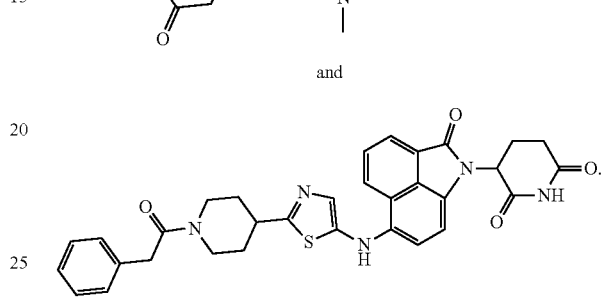
In certain embodiments the compound of the present invention is selected from:
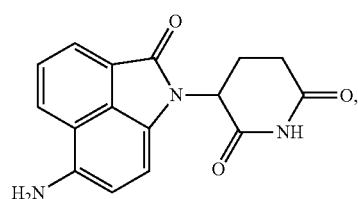
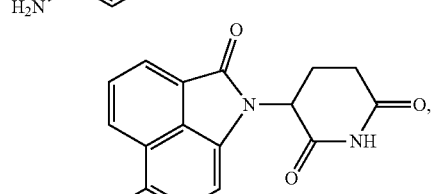

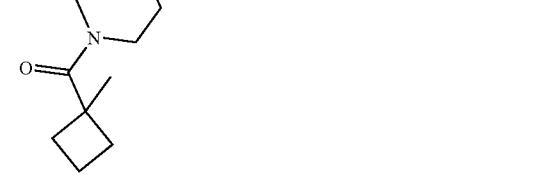
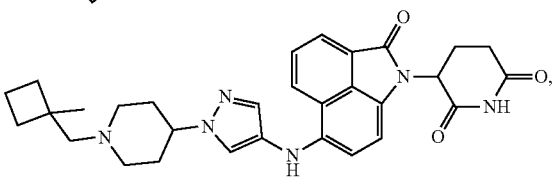

191
-continued
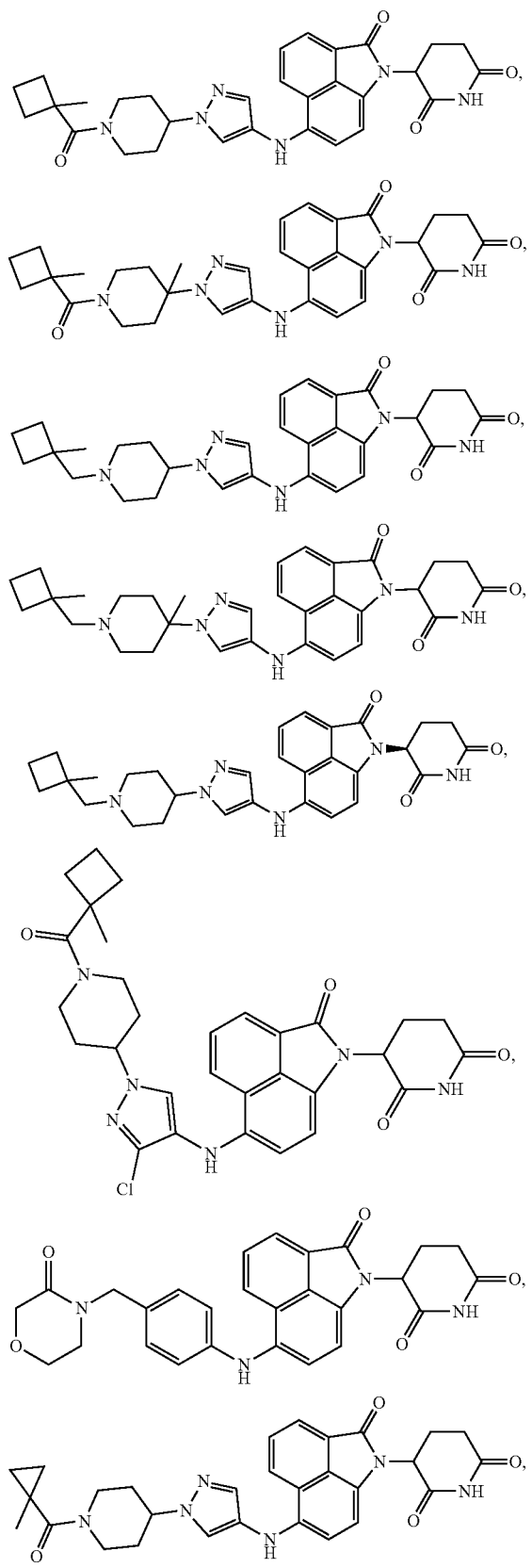
192
-continued
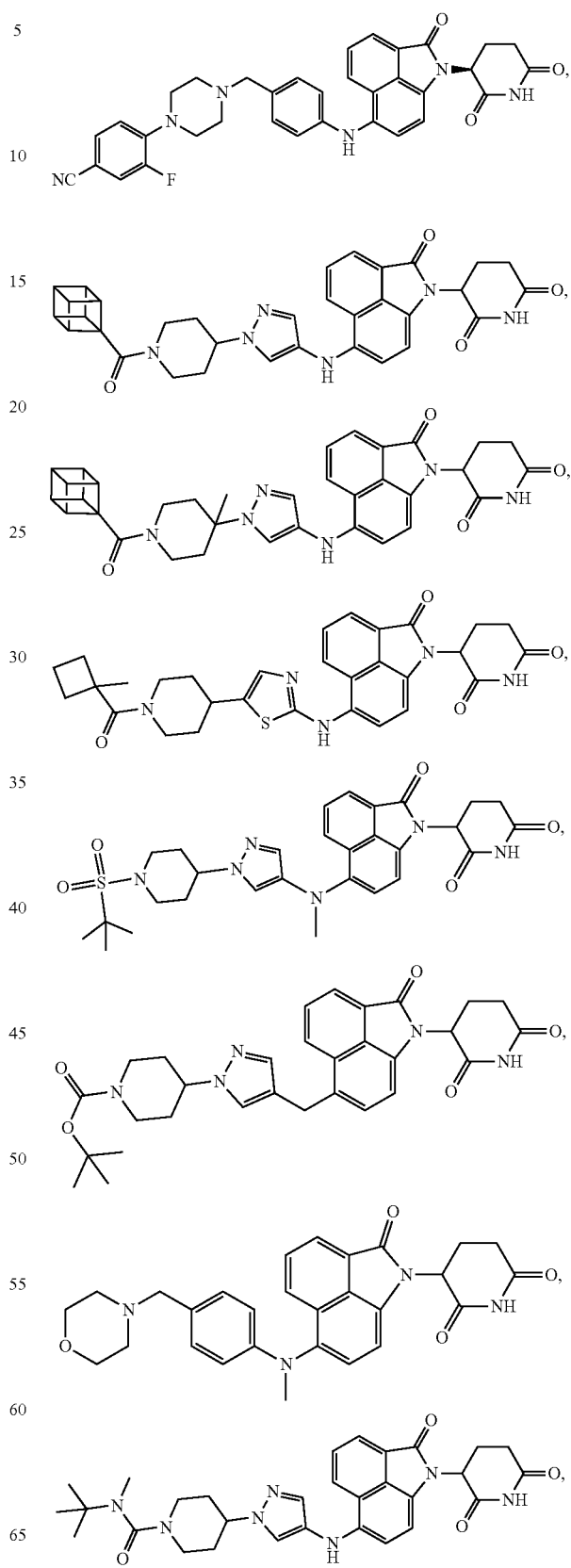

-continued

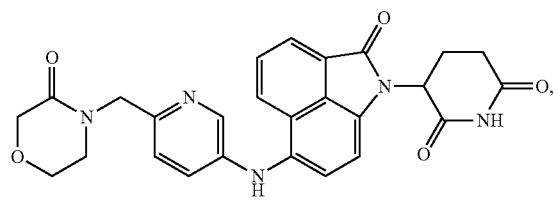

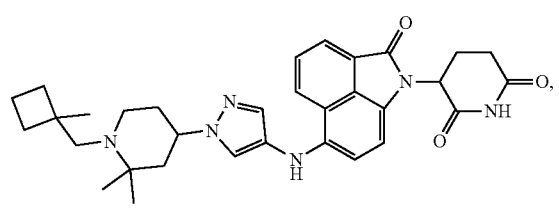

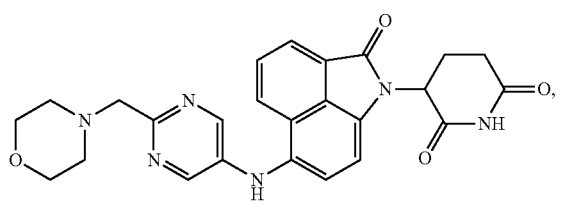

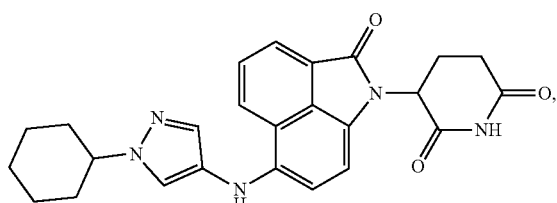

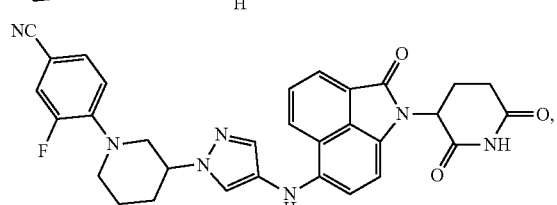

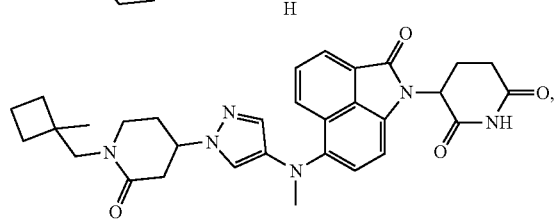

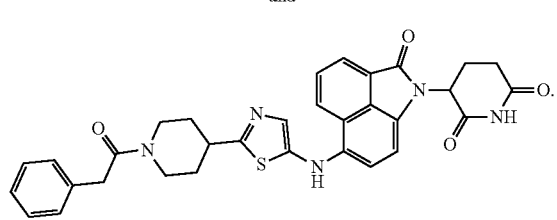

In one embodiment the compound of the present invention is:

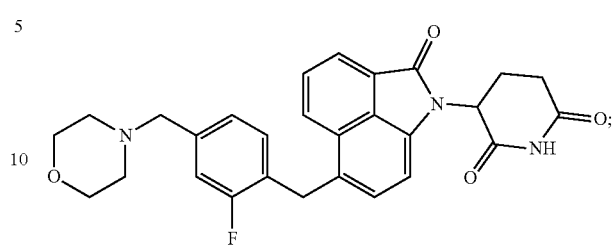

or a pharmaceutically acceptable salt thereof.

Non-Limiting Isotopic Embodiments

In one embodiment the compound is isotopically labeled. In one embodiment at least one R group independently selected from $R^1$, $R^2$, $R^3$, $R^{3'}$, $R^4$, $R^5$, $R^6$, $R^7$, $R^8$, $R^9$, $R^{10}$, $R^{11}$, $R^{12}$, $R^{20}$, $R^{21}$, $R^{22}$, $R^{23}$, $R^{24}$, $R^{25}$, $R^{26}$, $R^{28}$, or $R^{40}$ is isotopically labeled with 1, 2, or more isotopes as allowed by valence. In one embodiment the isotopic label is deuterium. In one embodiment, at least one deuterium is placed on an atom that has a bond which is broken during metabolism of the compound in vivo, or is one, two or three atoms remote form the metabolized bond (e.g., which may be referred to as an α, β or γ, or primary, secondary or tertiary isotope effect). In another embodiment the isotopic label is $^{13}C$. In another embodiment the isotopic label is $^{18}F$.

In certain embodiments the compound of the present invention is selected from:

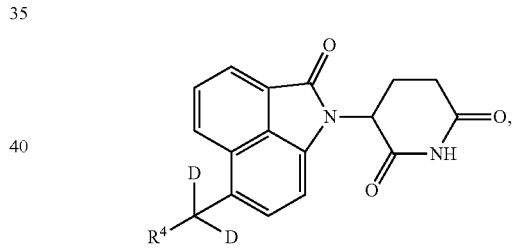

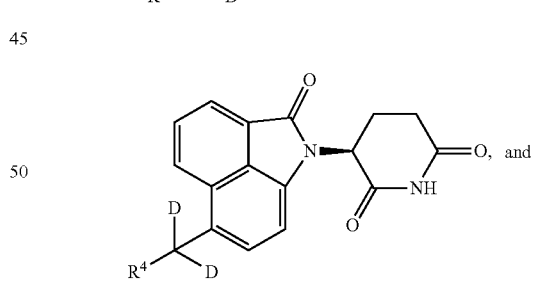

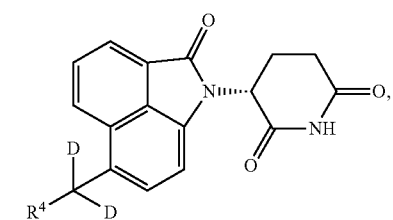

or a pharmaceutically acceptable salt thereof.

In certain embodiments the compound of the present invention is selected from:
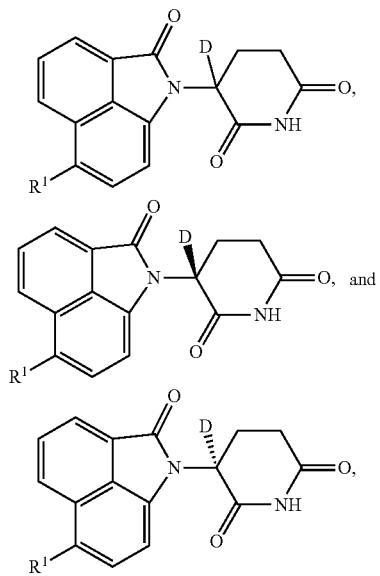
or a pharmaceutically acceptable salt thereof.
In certain embodiments the compound of the present invention is selected from:
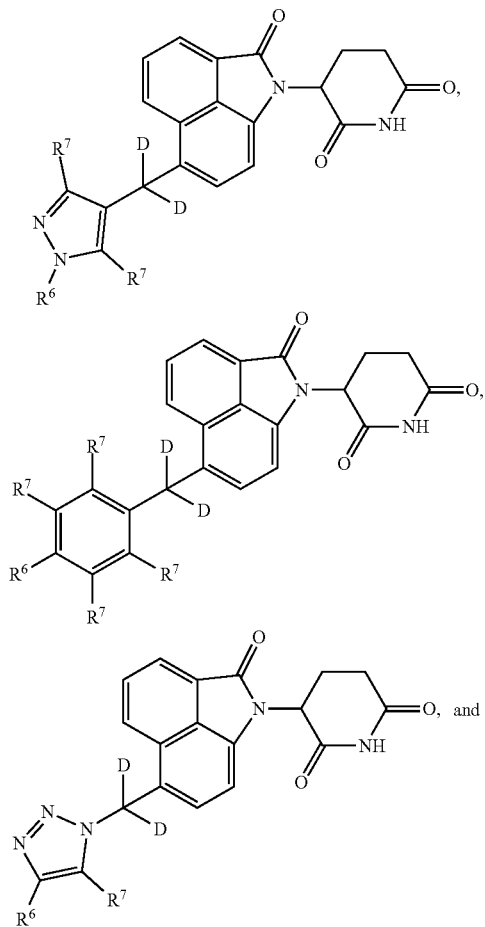
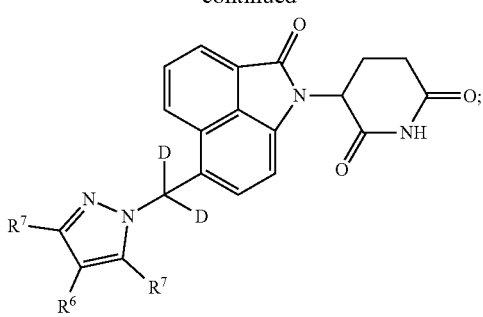
or a pharmaceutically acceptable salt thereof.
In certain embodiments the compound of the present invention is selected from Formula:
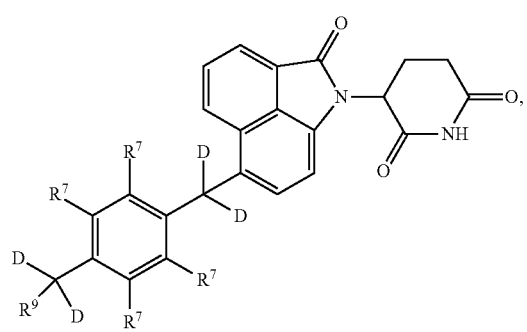
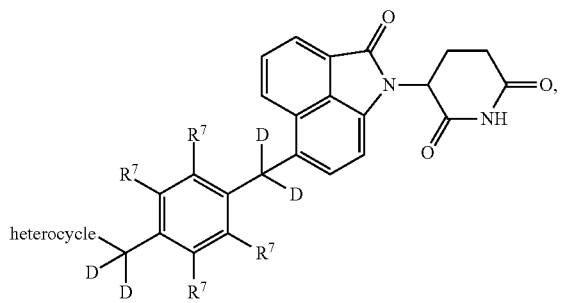
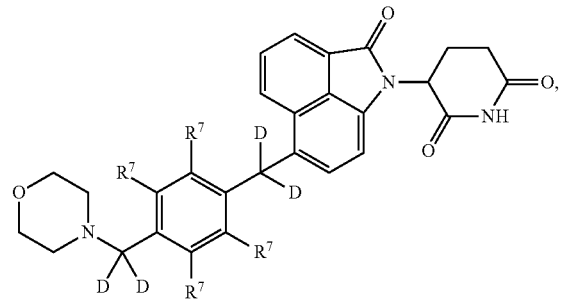
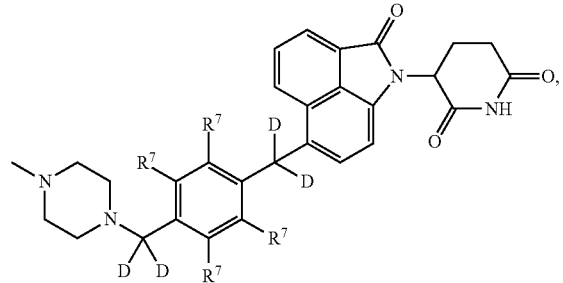

197
-continued
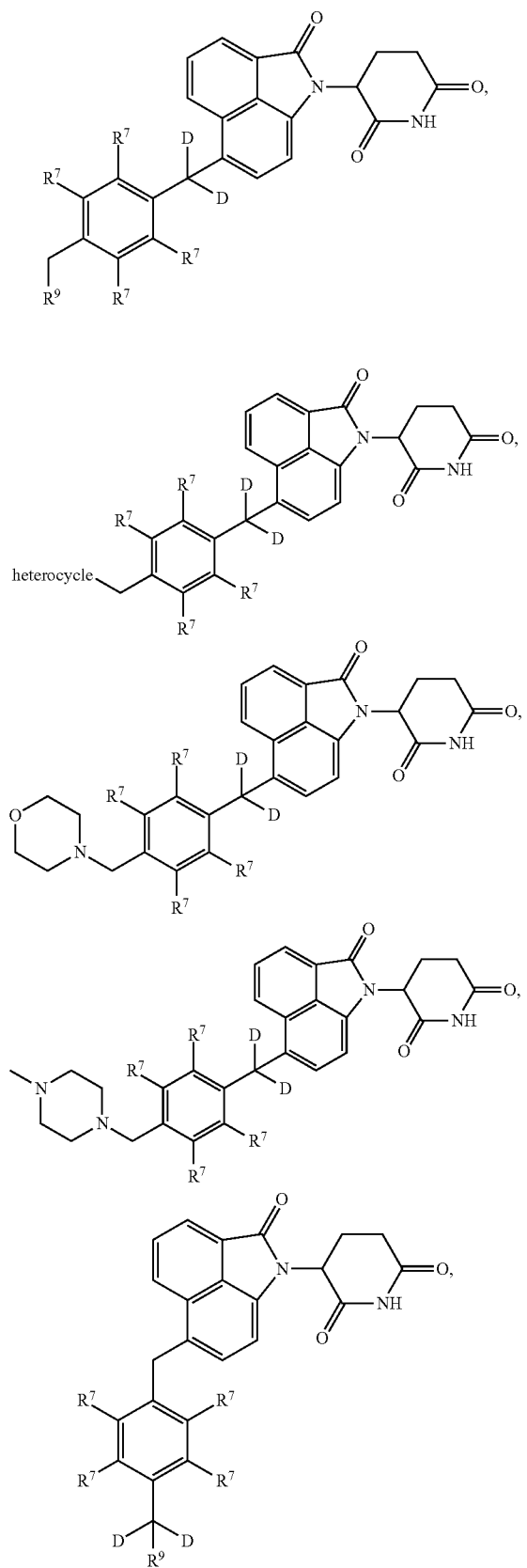
198
-continued
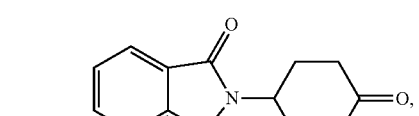
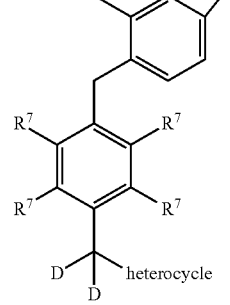
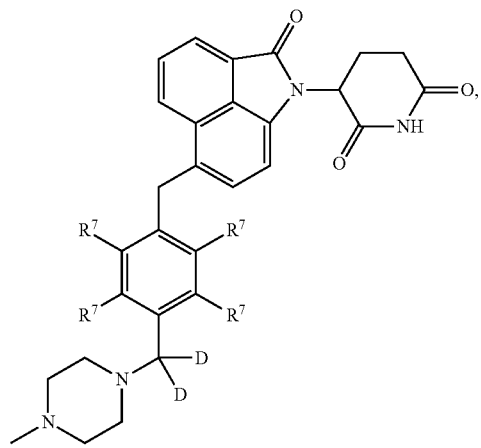
or a pharmaceutically acceptable salt thereof.
In certain embodiments the compound of the present invention is selected from Formula:

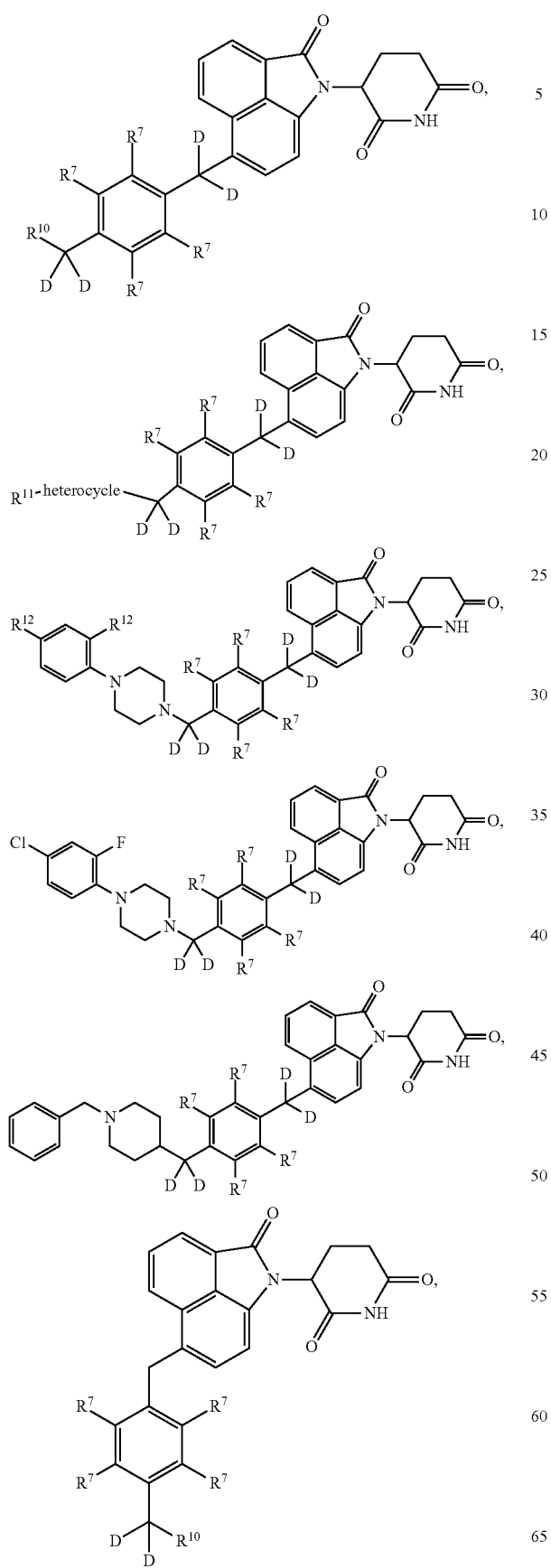

-continued
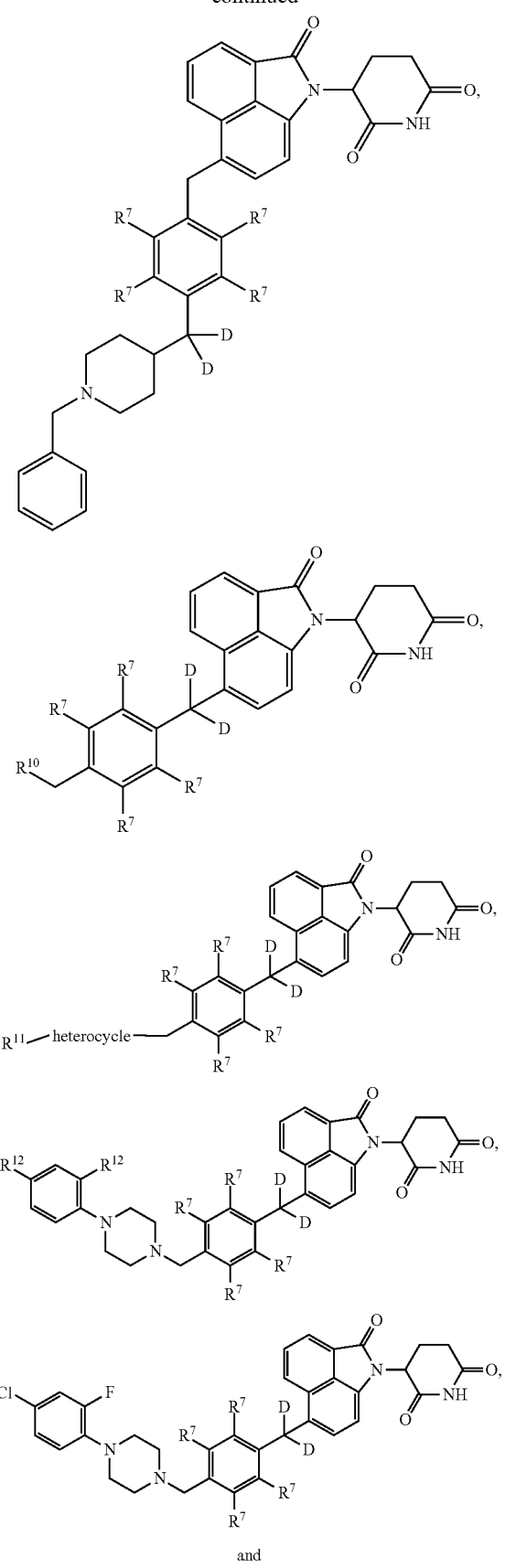
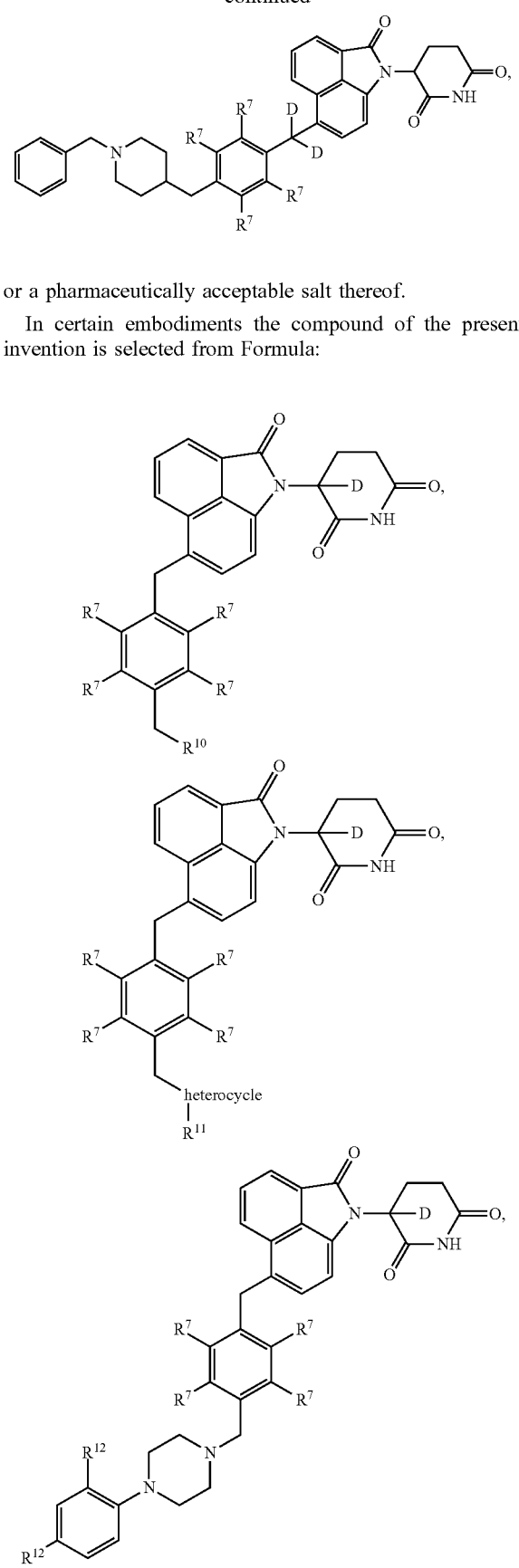
or a pharmaceutically acceptable salt thereof.
In certain embodiments the compound of the present invention is selected from Formula:

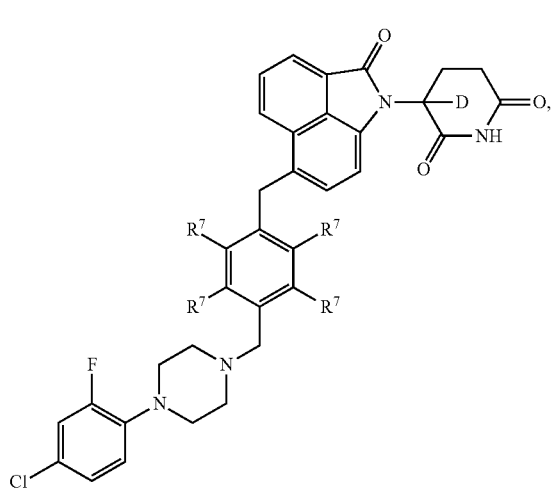
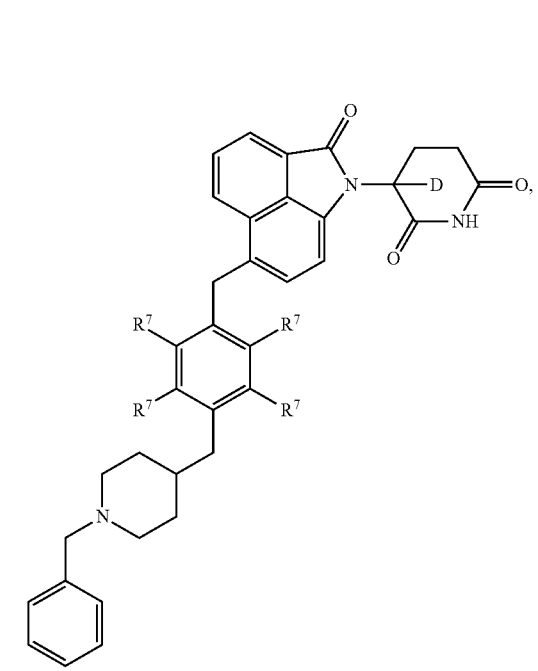
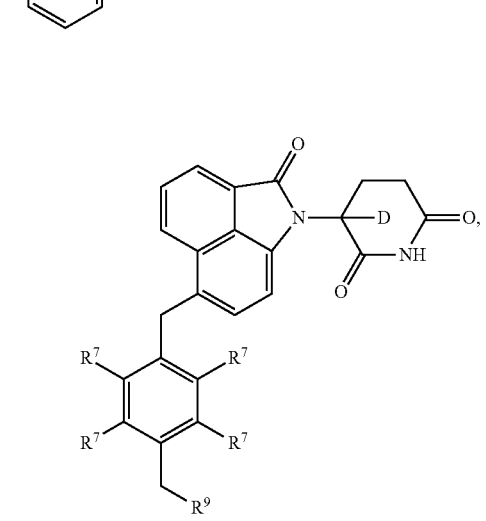
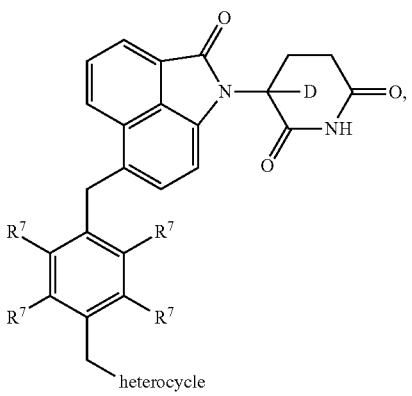
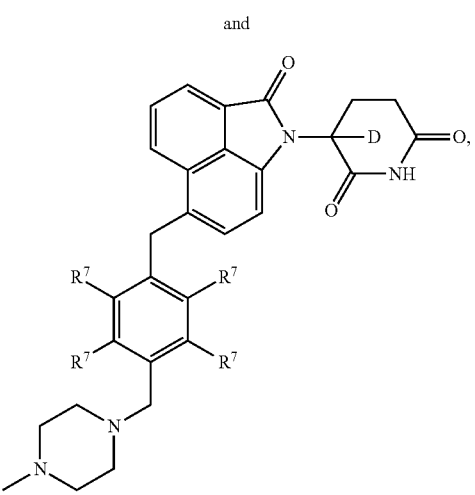
or a pharmaceutically acceptable salt thereof.
In certain embodiments the compound of the present invention is selected from:

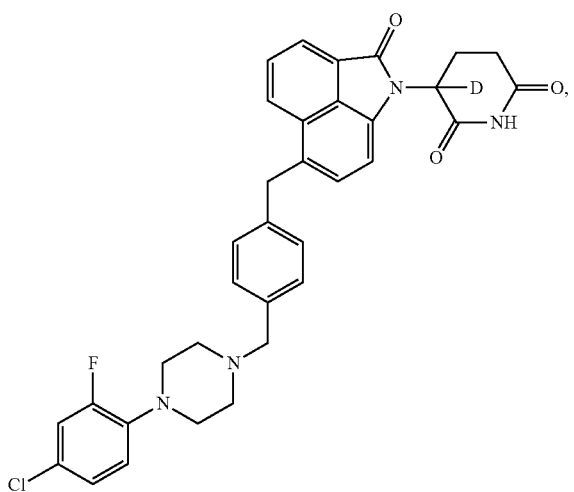
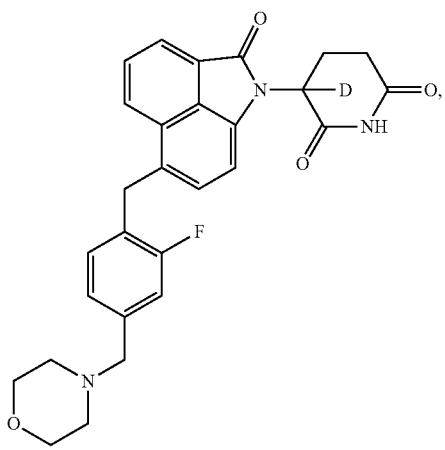
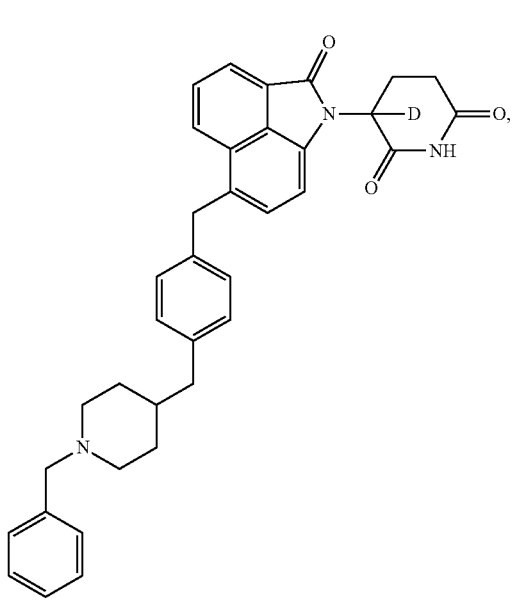
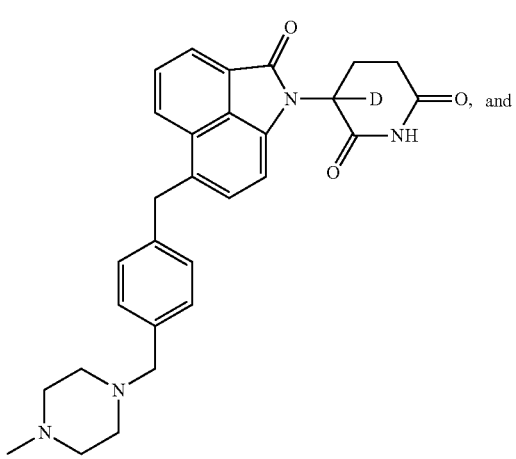
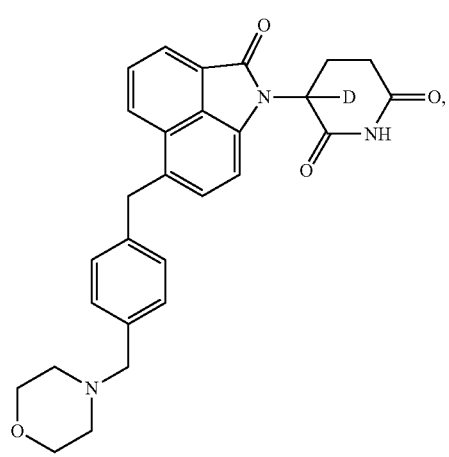
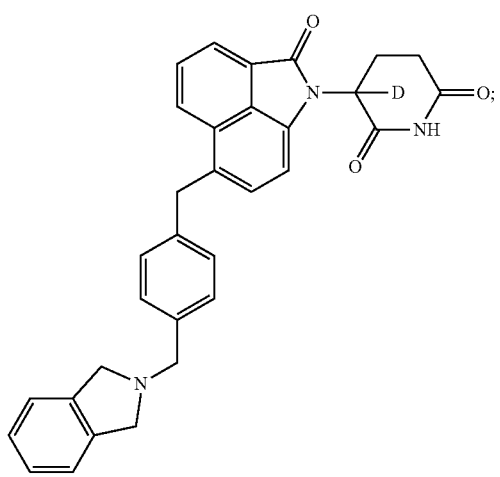
or a pharmaceutically acceptable salt thereof.
In certain embodiments the compound of the present invention is selected from:

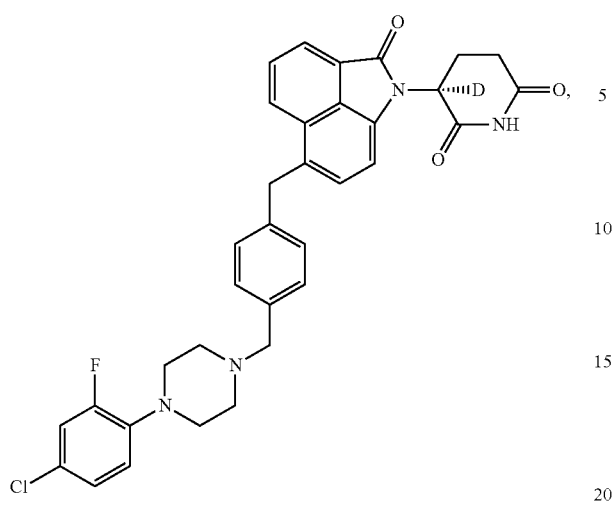
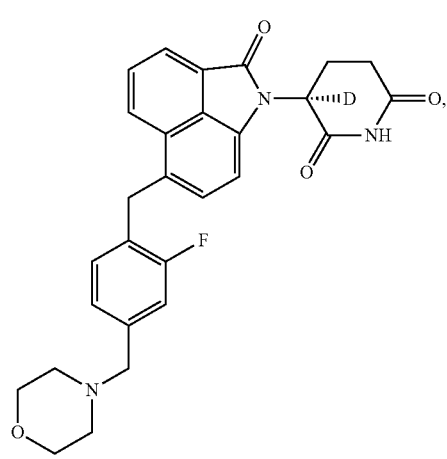
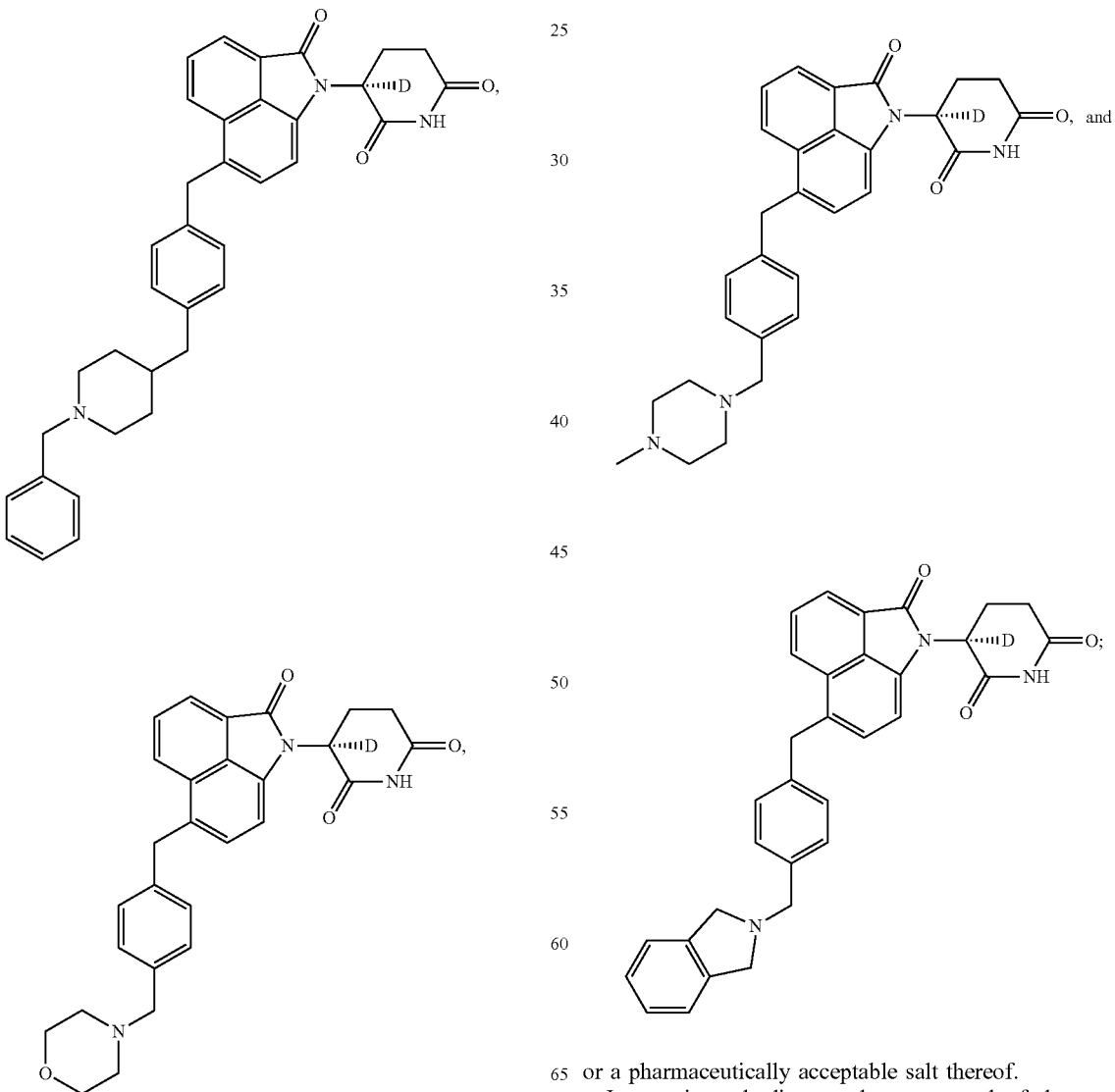
or a pharmaceutically acceptable salt thereof.
In certain embodiments the compound of the present invention is selected from:

209
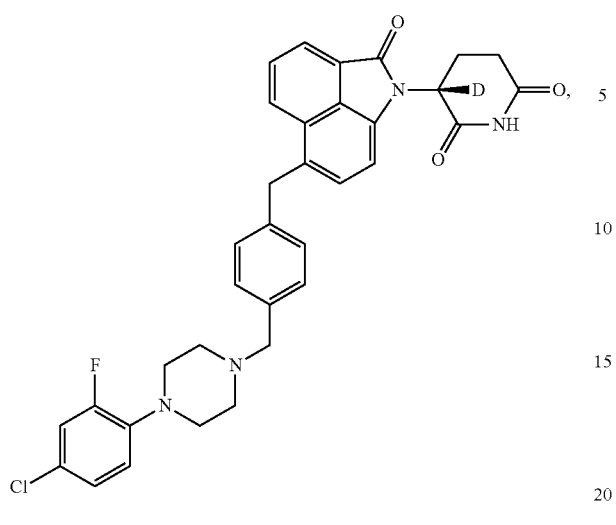
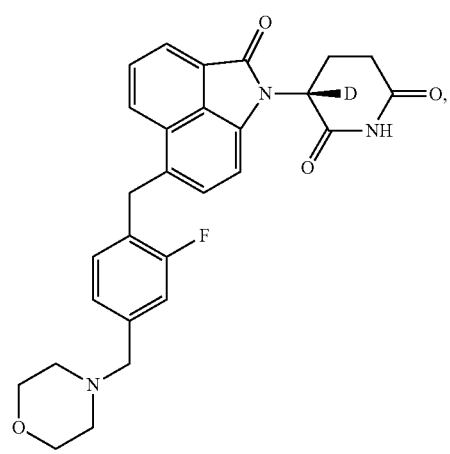
210
-continued
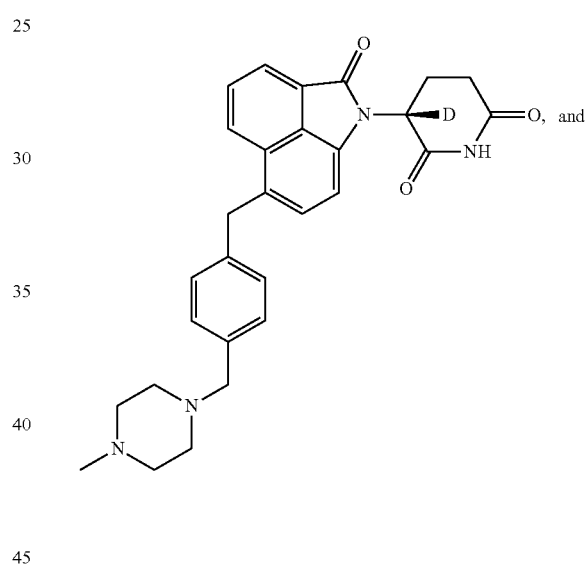
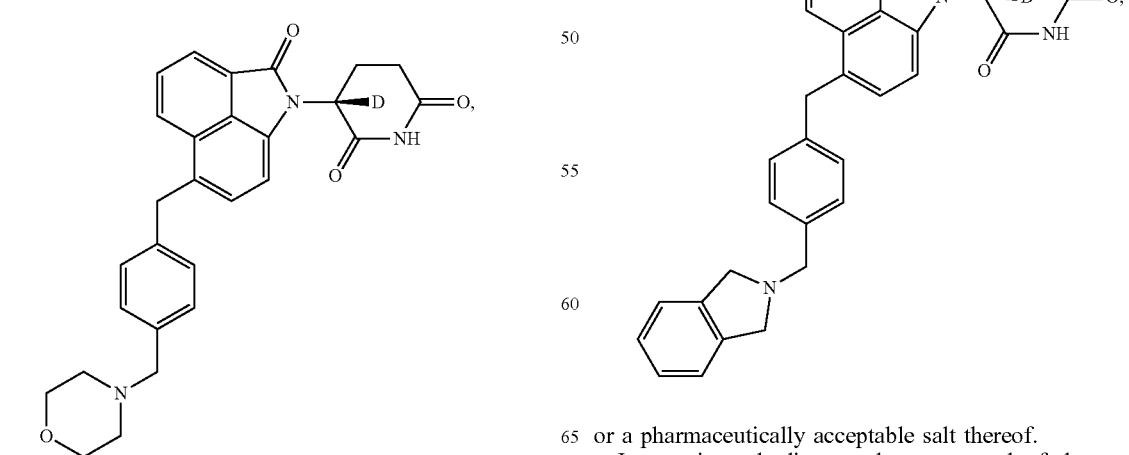
or a pharmaceutically acceptable salt thereof.
In certain embodiments the compound of the present invention is selected from:

211
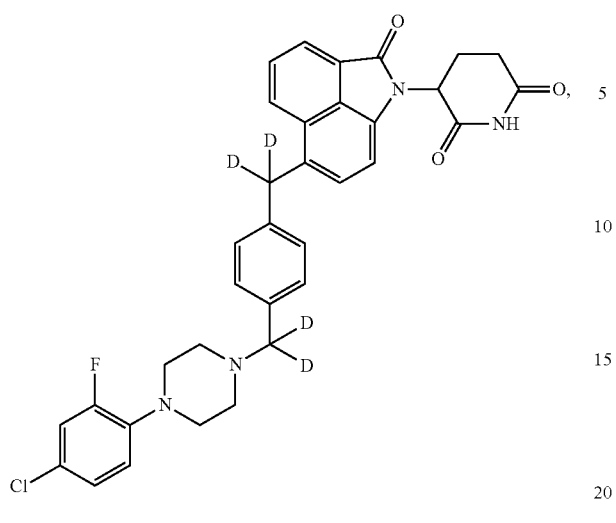
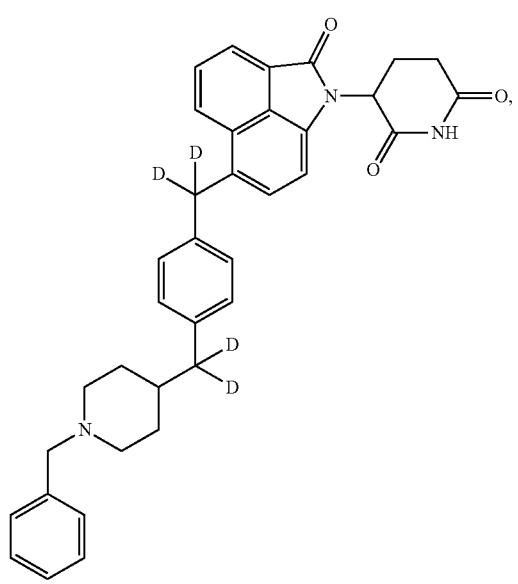
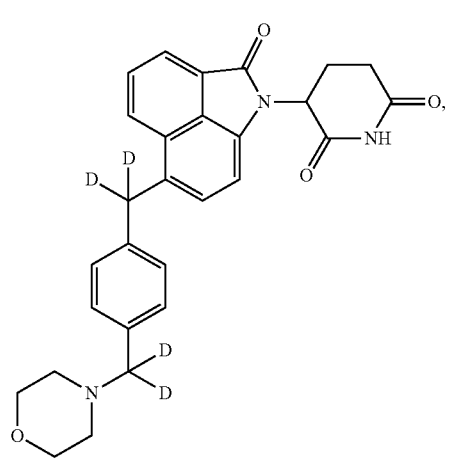
212
-continued
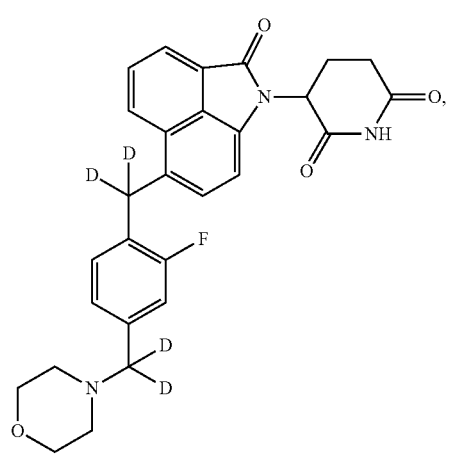
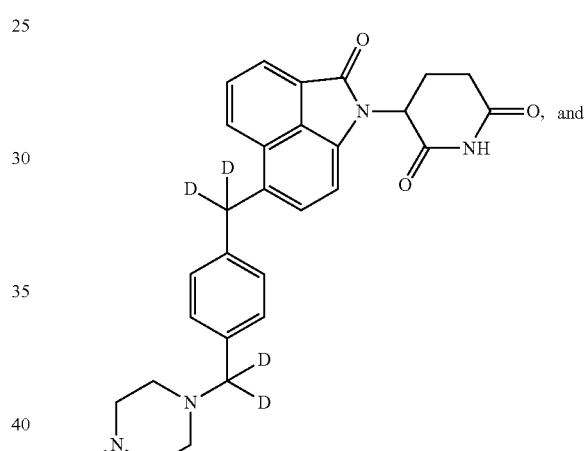
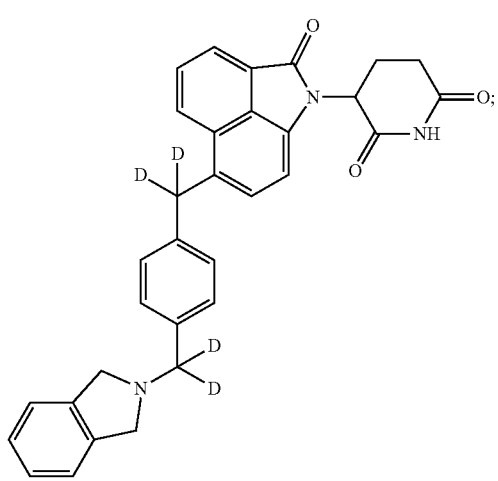
or a pharmaceutically acceptable salt thereof.
In certain embodiments the compound of the present invention is selected from:

213
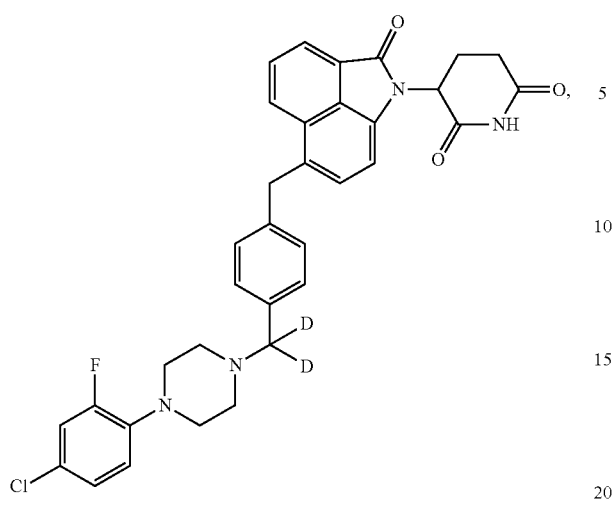
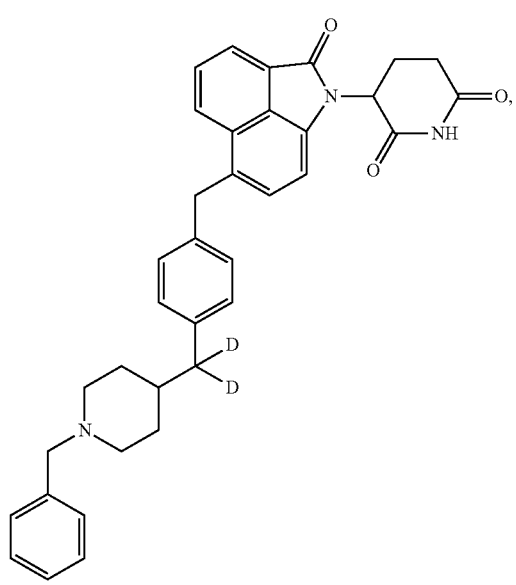
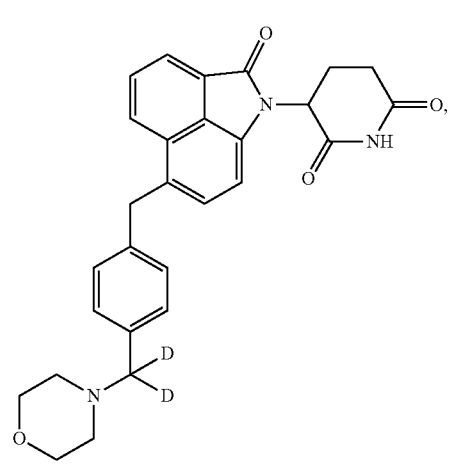
214
-continued
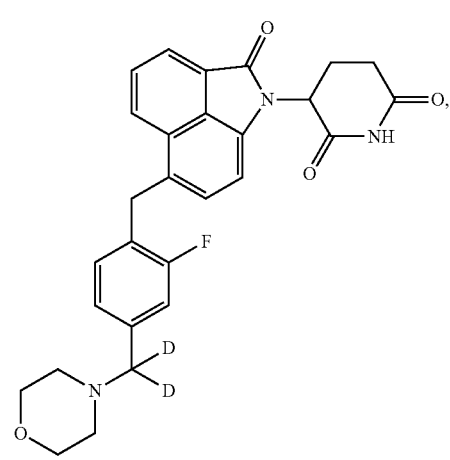
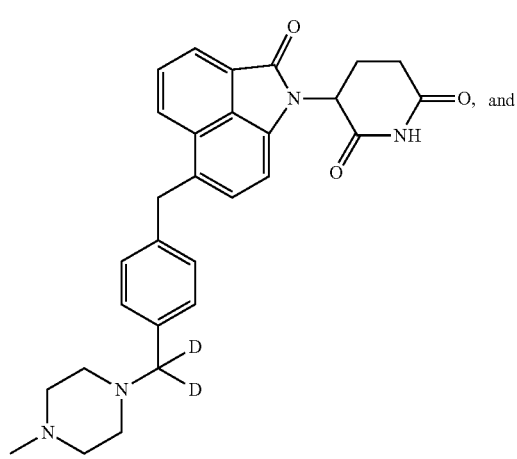
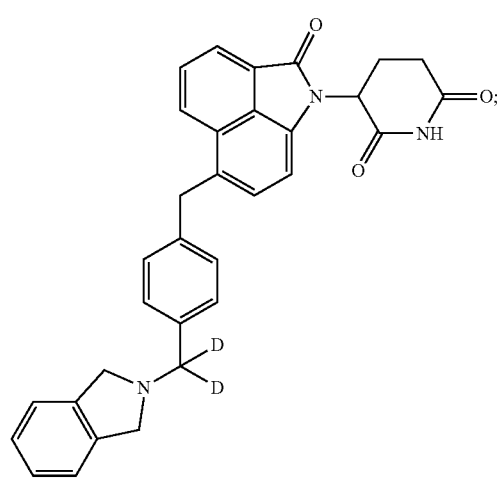
or a pharmaceutically acceptable salt thereof.
In certain embodiments the compound of the present invention is selected from:

215
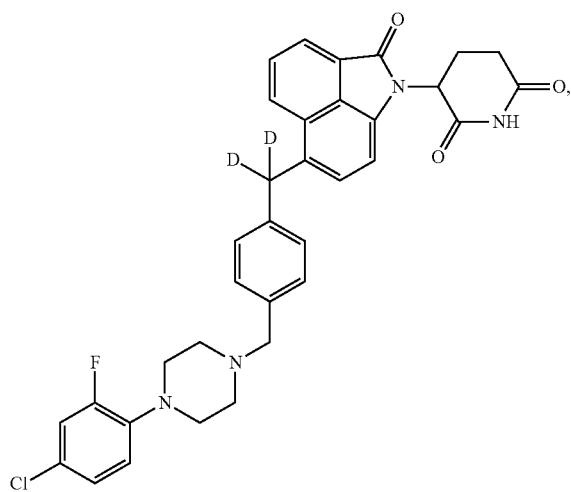
216
-continued
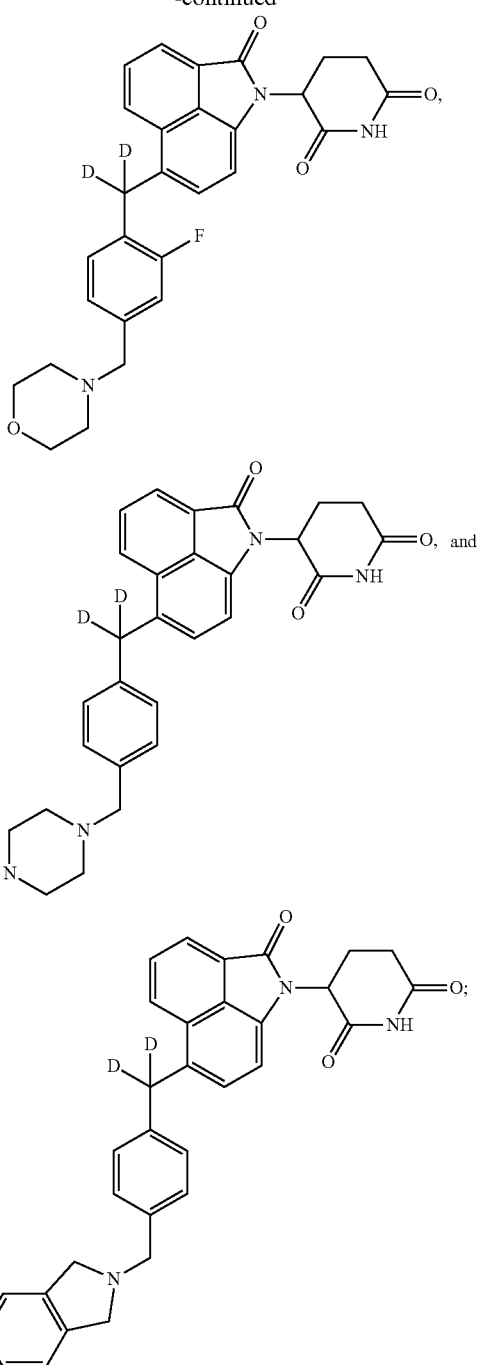
or a pharmaceutically acceptable salt thereof.
In certain embodiments the compound of the present invention is selected from:
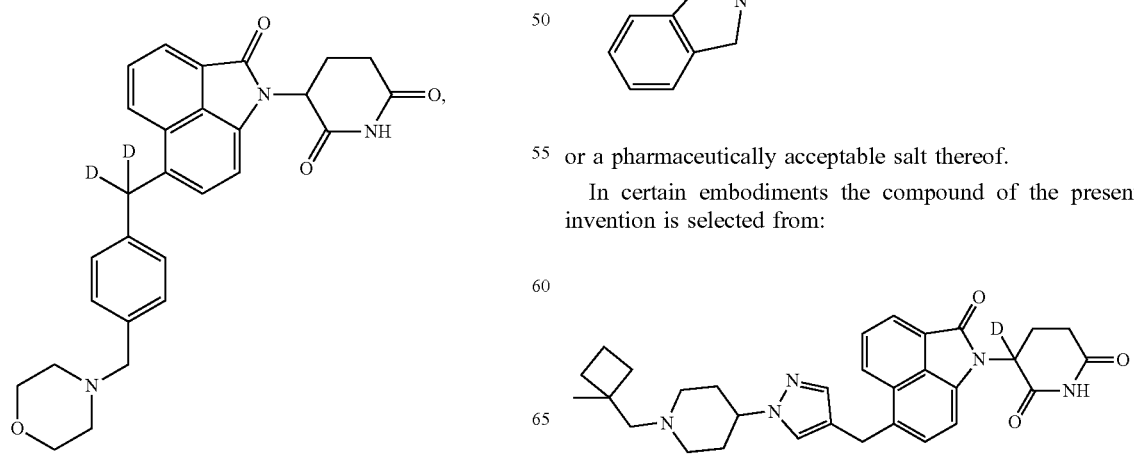

217
-continued
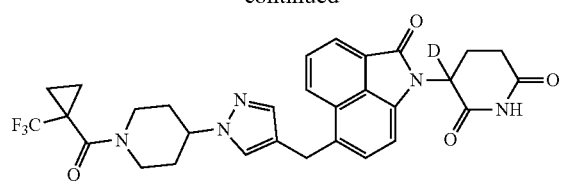
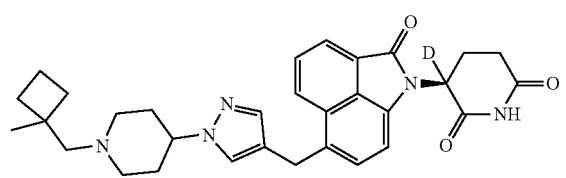
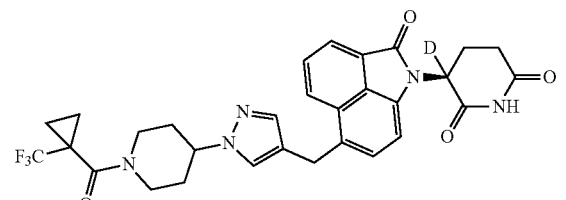
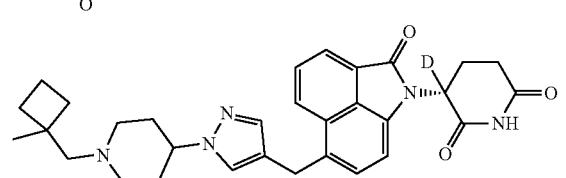
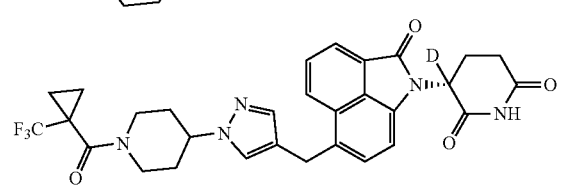
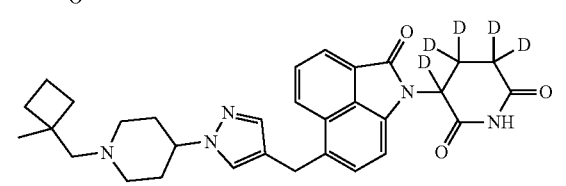
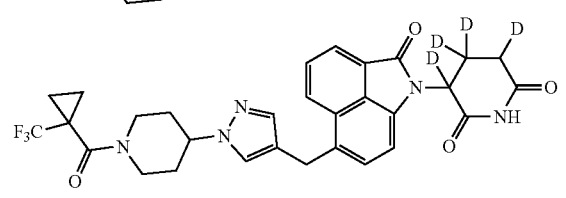
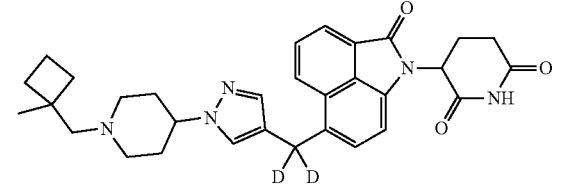
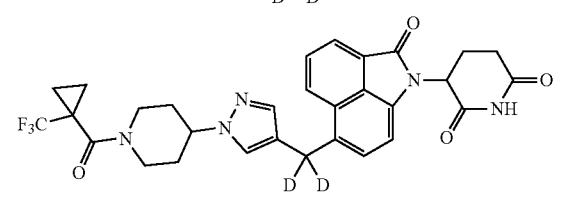
218
-continued
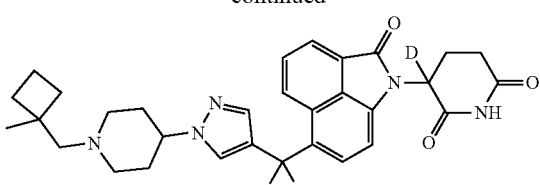
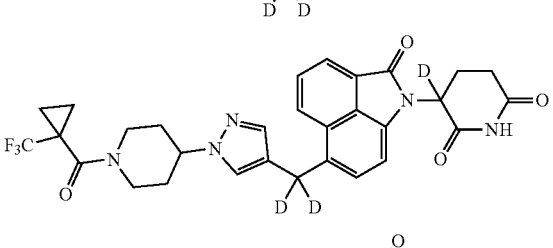
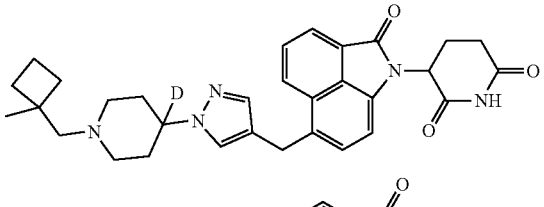
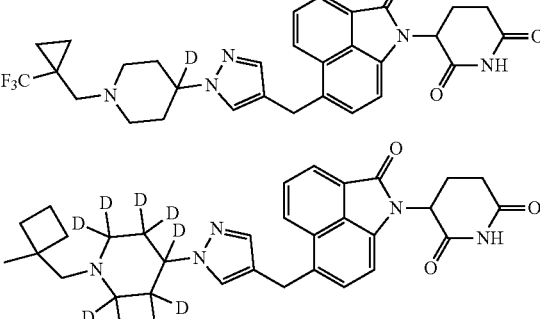
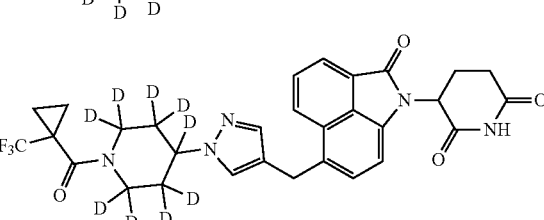
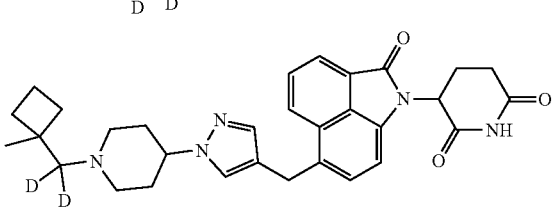
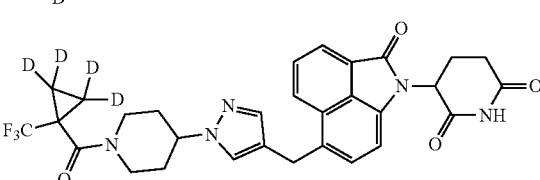
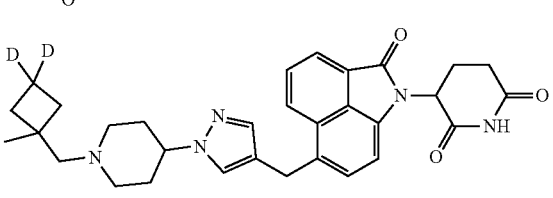

219
-continued
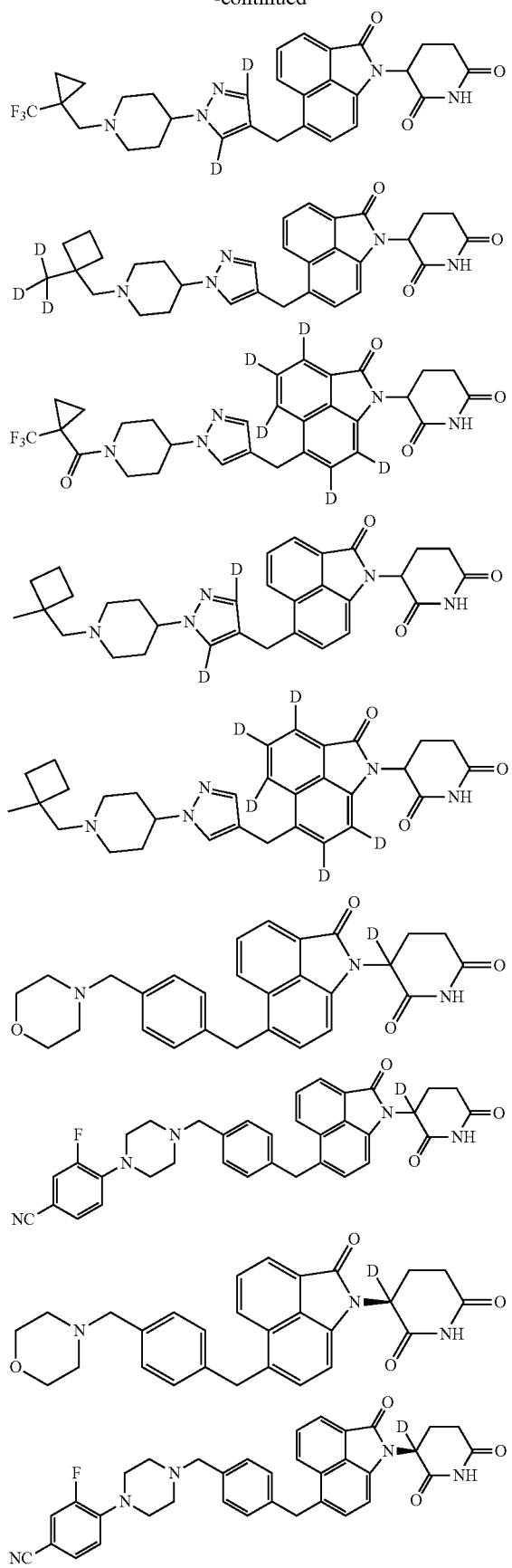
220
-continued
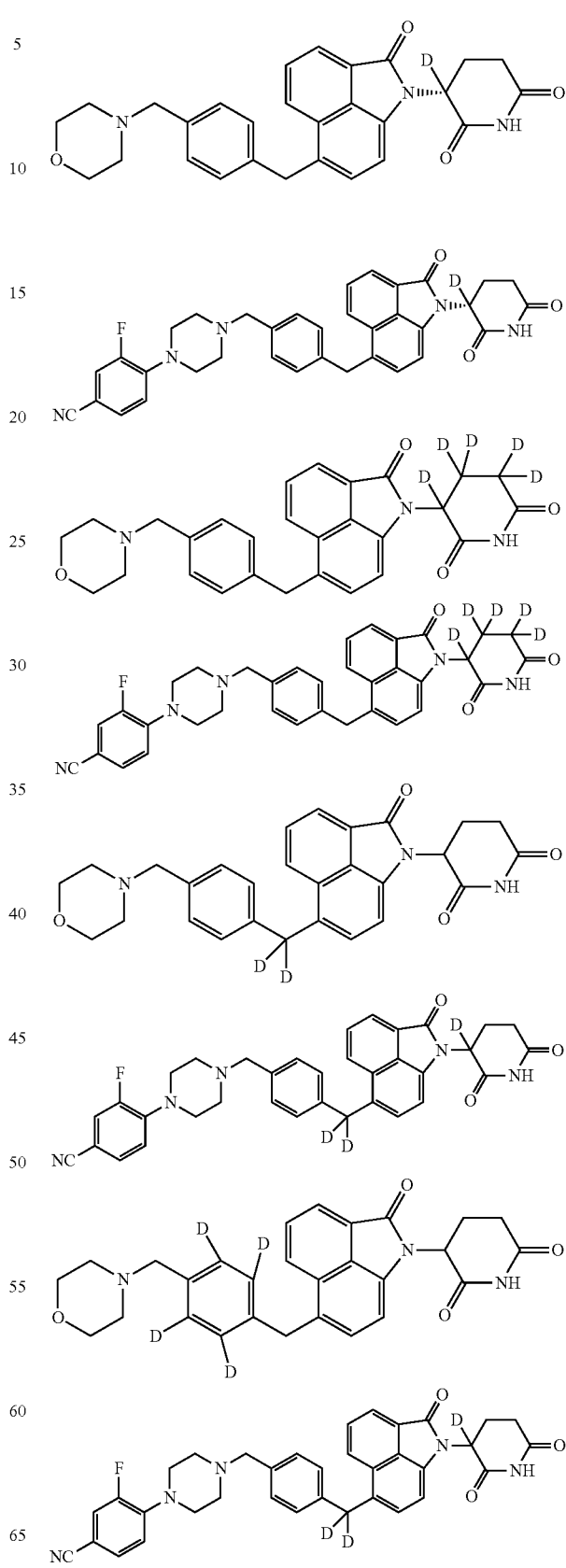

221
-continued
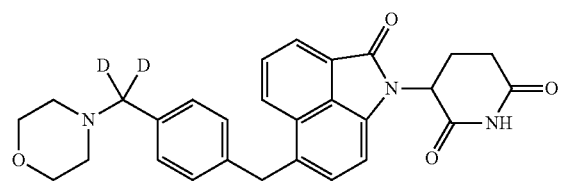
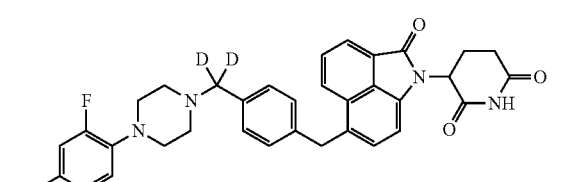
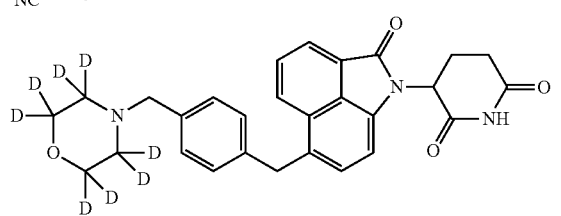
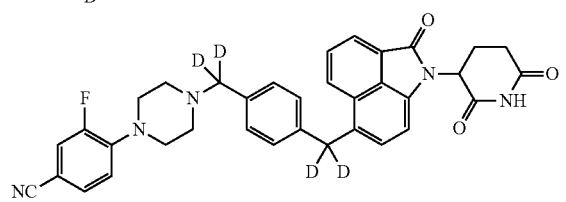
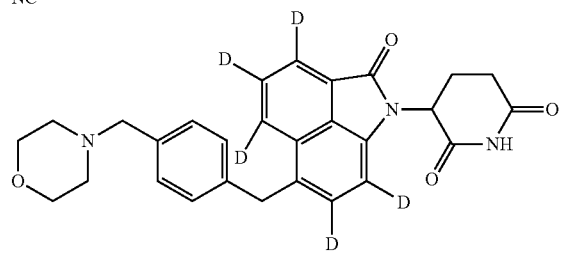
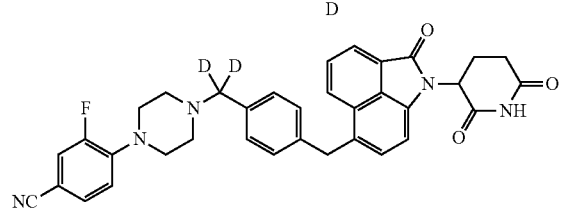
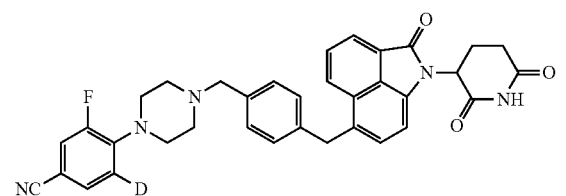
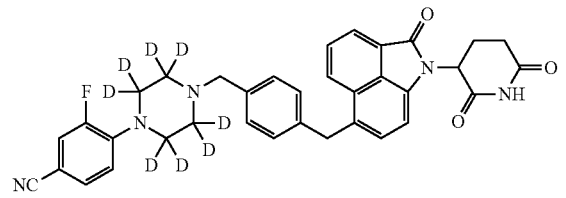
222
-continued
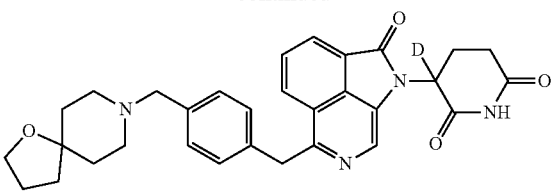
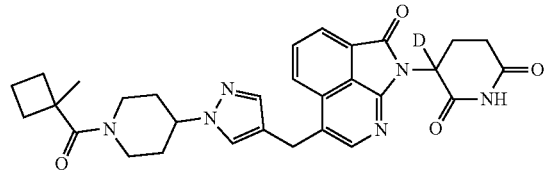
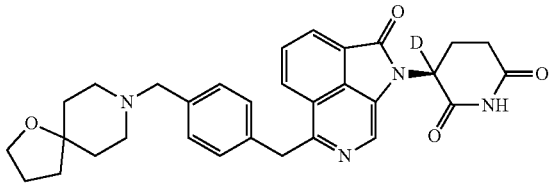
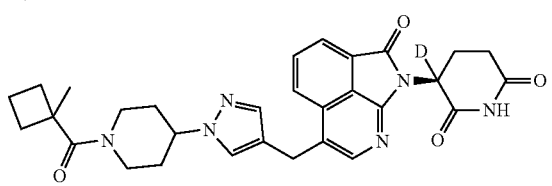
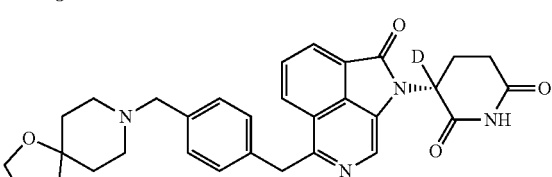
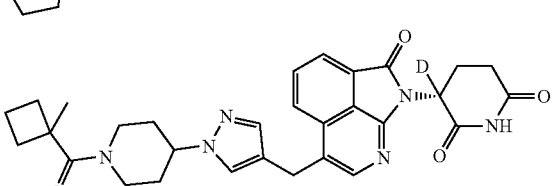
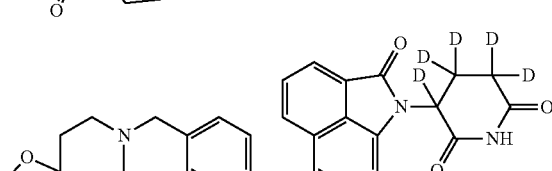
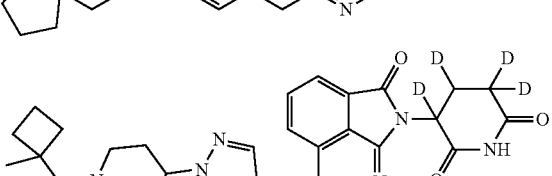
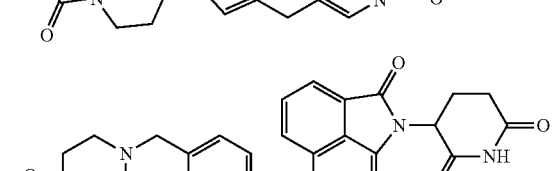
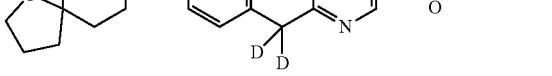

223
-continued
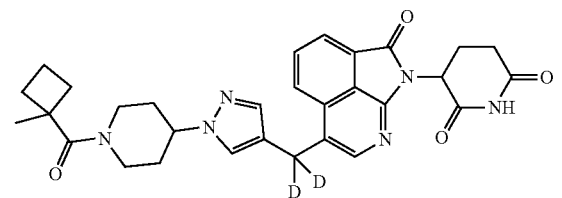
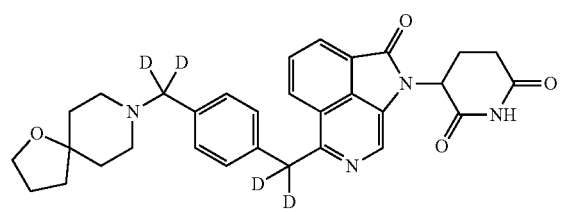
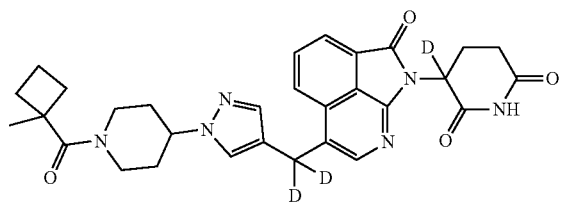
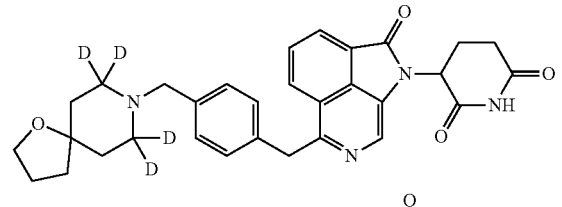
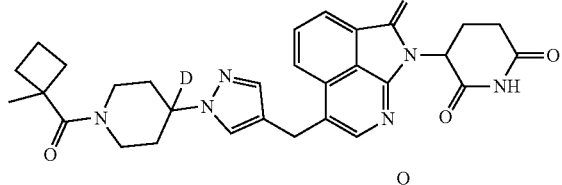
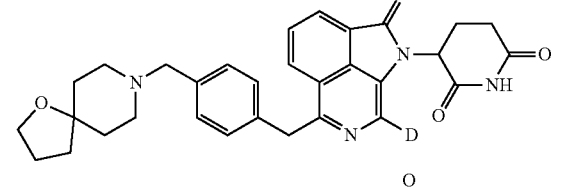
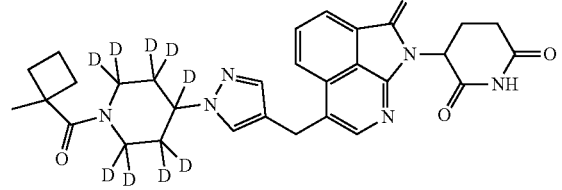
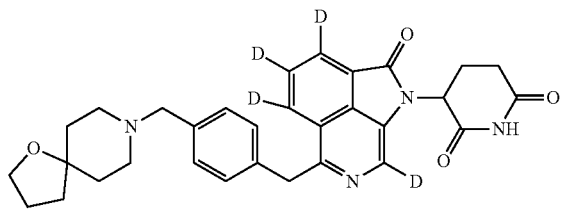
224
-continued
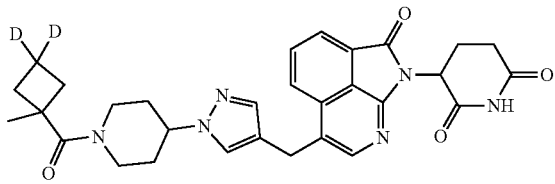
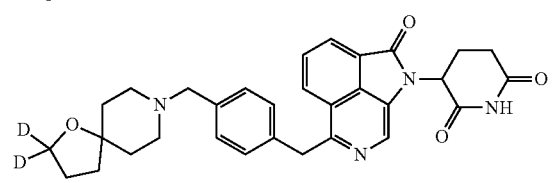
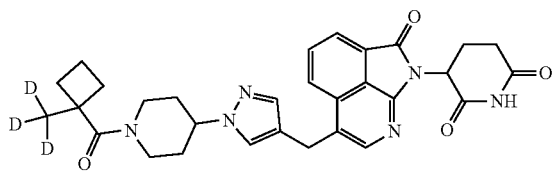
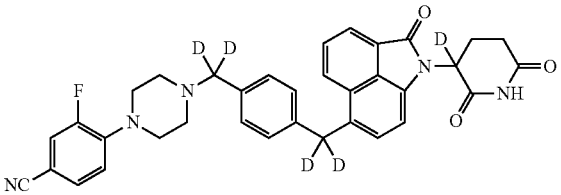
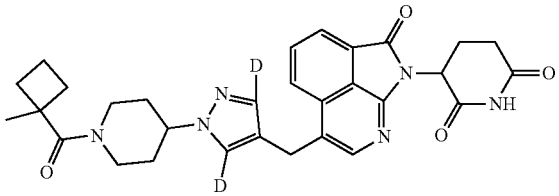
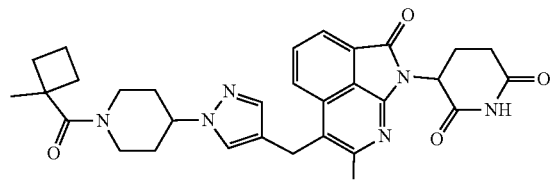
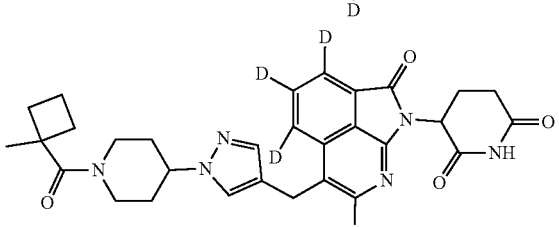
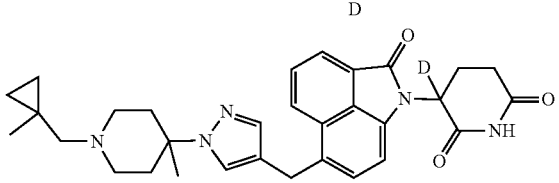
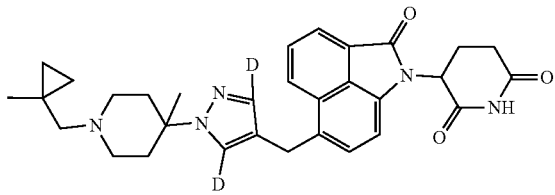

225
-continued

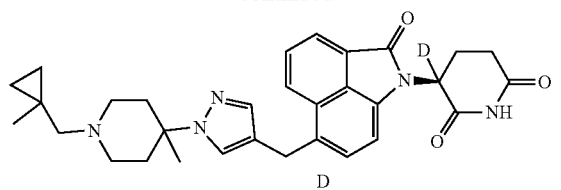
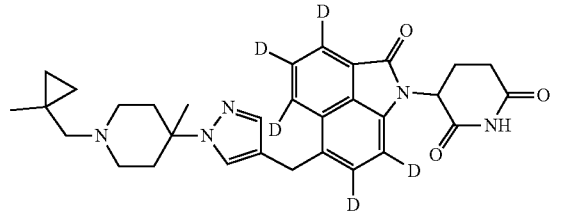
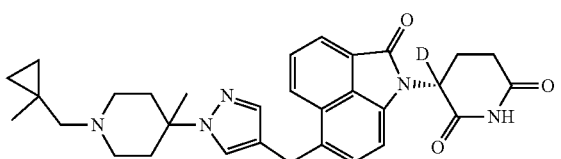
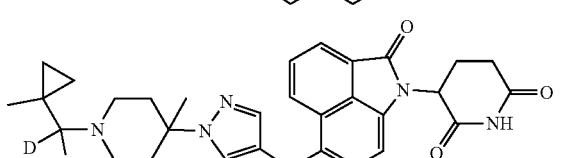
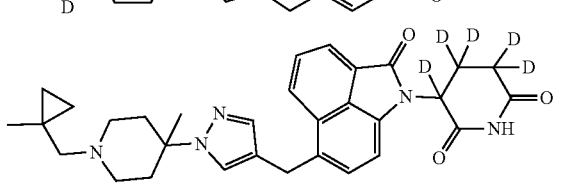
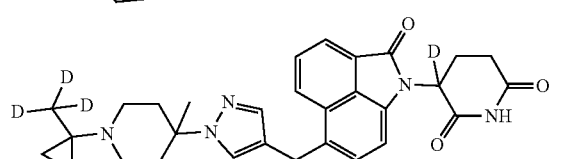
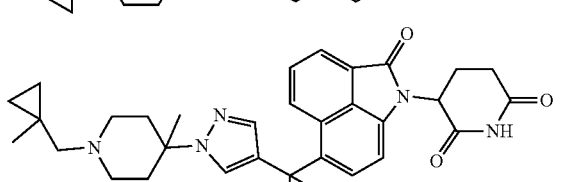
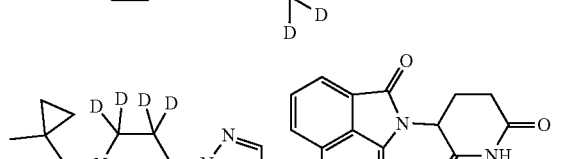
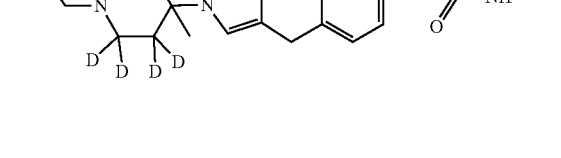
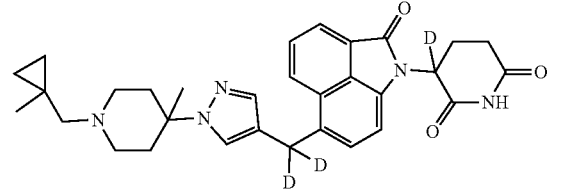

226
-continued

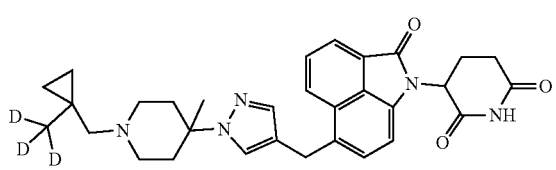
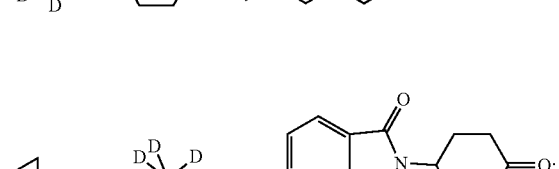
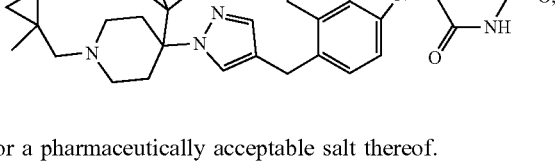

or a pharmaceutically acceptable salt thereof.

In certain embodiments the compound of the present invention is selected from:

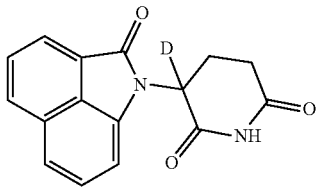
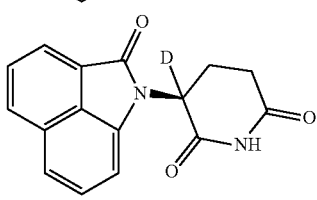
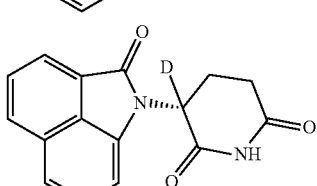
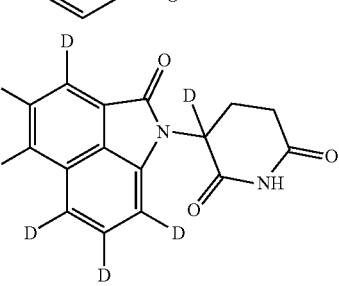

or a pharmaceutically acceptable salt thereof.

In any of the above structures where there are two deuterium on a methylene the same molecule with one deuterium at that position is envisioned. In any of the above structures where there are three deuterium on a methyl the same molecule with one or two deuterium at that position is envisioned.

Additional Embodiments

1. In certain embodiments a compound is provided of Formula I or Formula II

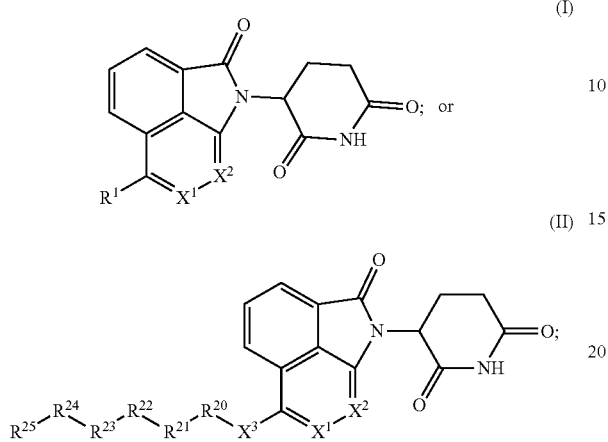

or a pharmaceutically acceptable salt, N-oxide, isotopic derivative, or prodrug thereof,
wherein:
$X^1$ and $X^2$ are independently selected from CH and N;
$X^3$ is selected from bond, $NR^2$, $C(R^3R^{3'})$, O, C(O), C(S), S, S(O), and $S(O)_2$;
$R^1$ is selected from hydrogen, halogen, cyano, nitro, alkyl, haloalkyl, $-NR^2R^{2'}$, $-OR^2$, $-NR^2R^4$, $-OR^4$, $-NR^2R^5$, $-OR^3$, $-(CR^3R^{3'})-R^4$, $-(CR^3R^{3'})-R^5$, $-(CR^3R^{3'})-NR^2R^4$, $-(CR^3R^{3'})-NR^2R^5$, $-(CR^3R^{3'})-OR^4$, $-(CR^3R^{3'})-OR^5$, $-C(O)R^4$, $-SR^4$, $-SR^5$, $-S(O)R^4$, and $-S(O)_2R^4$;
$R^2$ and $R^{2'}$ are independently selected at each occurrence from hydrogen, alkyl, haloalkyl, cycloalkyl, heterocycle, aryl, heteroaryl, $-C(O)R^8$, $-C(O)OR^8$, $-C(O)-NR^8R^{8'}$, $-S(O)R^8$, $-SO_2R^8$, $-SO_2-OR^8$, and $-SO_2-NR^8R^{8'}$;
$R^3$ is selected from hydrogen, halogen, alkyl, haloalkyl, $-OR^8$, and $-NR^8R^{8'}$;
$R^{3'}$ is selected from hydrogen, halogen, alkyl, and haloalkyl;
or $R^3$ and $R^{3'}$ can be brought together with the carbon to which they are attached to form a 3- to 6-membered cycloalkyl ring;
$R^4$ is selected from cycloalkyl, heterocycle, aryl, and heteroaryl, wherein each $R^4$ is optionally substituted with one group selected from $R^6$, and wherein each $R^4$ is also optionally substituted with 1, 2, 3, or 4 groups independently selected from $R^7$;
$R^5$ is $-C(O)R^6$;
$R^6$ is selected from alkyl, cycloalkyl, heterocycle, aryl, and heteroaryl, wherein each $R^6$ is optionally substituted with 1, 2, 3, or 4 groups independently selected from $R^9$;
or $R^6$ is selected from alkyl, cycloalkyl, heterocycle, aryl, heteroaryl, —CO-alkyl, —CO-cycloalkyl, —CO-heterocycle, —CO-aryl, —CO-heteroaryl, —O-alkyl, —O-cycloalkyl, —O-heterocycle, —O-aryl, —O-heteroaryl, $-NR^2$-alkyl, $-NR^2$-cycloalkyl, $-NR^2$-heterocycle, $-NR^2$-aryl, and $-NR^2$-heteroaryl, wherein each $R^6$ is optionally substituted with 1, 2, 3, or 4 groups independently selected from $R^1$;
$R^7$ is independently selected at each occurrence from hydrogen, halogen, hydroxyl, cyano, nitro, alkyl, haloalkyl, alkenyl, alkynyl, cycloalkyl, heterocycle, aryl, heteroaryl, $-OR^8$, $-NR^8R^{8'}$, $-C(O)R^8$, $-C(O)OR^8$, $-C(O)-NR^8R^{8'}$, $-OC(O)R^8$, $-NR^2-C(O)R^8$, $-S(O)R^8$, $-SO_2R^8$, $-SO_2-OR^8$, and $-SO_2-NR^8R^{8'}$;
or two $R^7$ on the same carbon may be brought together to form an oxo group;
$R^8$ and $R^{8'}$ are independently selected at each occurrence from hydrogen, alkyl, haloalkyl, alkenyl, alkynyl, cycloalkyl, heterocycle, aryl, and heteroaryl;
$R^9$ is independently selected at each occurrence from hydrogen, halogen, cyano, nitro, $R^{10}$, $-CH_2R^{10}$, $-OR^{10}$, $-NR^2R^{10}$, $-C(O)R^{10}$, $-C(O)CH_2R^{10}$, $-C(O)CH_2OR^{10}$, $-C(O)CH_2NR^2R^{10}$, $-OC(O)R^{10}$, $-NR^2-C(O)R^{10}$, $-C(O)OR^{10}$, $-C(O)NR^2R^{10}$, $-S(O)R^{10}$, $-SO_2R^{10}$, $SO_2CH_2R^{10}$, $-SO_2CH_2OR^{10}$, $-SO_2CH_2NR^2R^{10}$, $-NR^2SO_2R^{10}$, $-SO_2-OR^{10}$, and $-SO_2-NR^2R^{10}$;
$R^{10}$ is selected from alkyl, haloalkyl, alkenyl, alkynyl, cycloalkyl, heterocycle, aryl, and heteroaryl, wherein each $R^{10}$ is optionally substituted with 1, 2, 3, or 4 groups independently selected from $R^{11}$; and
$R^{11}$ is selected from: hydrogen; halogen; hydroxyl; cyano; nitro; alkyl; haloalkyl; alkenyl optionally substituted with an aryl or heteroaryl group; alkynyl optionally substituted with an aryl or heteroaryl group; cycloalkyl; heterocycle; aryl optionally substituted with 1, 2, 3, or 4 halogen, alkyl, or $-OR^8$ groups; heteroaryl optionally substituted with 1, 2, 3, or 4 halogen, alkyl, or $-OR^8$ groups; $-CH_2$aryl optionally substituted with 1, 2, 3, or 4 halogen, alkyl, or $-OR^8$ groups; $-CH_2$heteroaryl optionally substituted with 1, 2, 3, or 4 halogen, alkyl, or $-OR^8$ groups; $-OR^8$; $-NR^8R^{8'}$; $-C(O)R^8$; $-C(O)OR^8$; $-C(O)-NR^8R^{8'}$; $-C(O)CH_2R^8$; $-C(O)CH_2OR^8$; $-C(O)CH_2-NR^8R^{8'}$; $-OC(O)R^8$; $-NR^2-C(O)R^8$; $-CH_2-OC(O)R^8$; $-CH_2-NR^2-C(O)R^8$; $-S(O)R^8$; $-SO_2R$; $-SO_2-OR^8$; and $-SO_2-NR^8R^{8'}$;
or two $R^{11}$ groups on the same carbon may be brought together to form an oxo group.
or $R^{11}$ is independently selected at each occurrence from: halogen; hydroxyl; cyano; nitro; alkyl; haloalkyl; alkenyl; alkynyl; cycloalkyl; heterocycle; aryl; heteroaryl; $-CH_2$aryl; $-CH_2$heteroaryl; $-OR^8$; $-NR^8R^{8'}$; $-C(O)R^8$; $-C(O)OR^8$; $-C(O)-NR^8R^{8'}$; $-C(O)CH_2R^8$; $-C(O)CH_2OR^8$; $-C(O)CH_2-NR^7R^{8'}$; $-OC(O)R^8$; $-NR^2-C(O)R^8$; $-CH_2-OC(O)R^8$; $-CH_2-NR^2-C(O)R^8$; $-S(O)R^8$; $-SO_2R^8$; $-SO_2-OR^8$; oxo, and $-SO_2-NR^8R^{8'}$; each of which $R^{11}$ groups is optionally substituted with 1, 2, 3, or 4, groups independently selected from $R^{12}$;
$R^{12}$ is independently selected at each occurrence from: halogen; hydroxyl; cyano; nitro; alkyl; haloalkyl; alkenyl; alkynyl; cycloalkyl; heterocycle; aryl; heteroaryl; $-CH_2$aryl; $-CH_2$heteroaryl; $-OR^8$; $-NR^8R^{8'}$; $-C(O)R^8$; $-C(O)OR^8$; $-C(O)-NR^8R^{8'}$; $-C(O)CH_2R^8$; $-C(O)CH_2OR^8$; $-C(O)CH_2-NR^8R^{8'}$; $-OC(O)R^8$; $-NR^2-C(O)R^8$;

—CH$_2$—OC(O)R$^8$; —CH$_2$—NR$^2$—C(O)R$^8$; —S(O)R$^8$; —SO$_2$R$^8$; —SO$_2$—OR$^8$; oxo; and —SO$_2$—NR$^8$R$^{8'}$;

R$^{20}$, R$^{21}$, R$^{22}$, R$^{23}$, and R$^{24}$ are independently at each occurrence selected from the group consisting of a bond, alkyl, —C(O)—, —C(O)O—, —OC(O)—, —SO$_2$—, —S(O)—, —C(S)—, —C(O)NR$^2$—, —NR$^2$C(O)—, —O—, —S—, —NR$^2$—, —P(O)(R$^{28}$)—, —P(O)—, alkene, alkyne, haloalkyl, aryl, heterocycle, heteroaryl, bicycle, and carbocycle; each of which is optionally substituted with 1, 2, 3, or 4 substituents independently selected from R$^8$; and wherein R$^{20}$, R$^{21}$, R$^{22}$, R$^{23}$, and R$^{24}$ cannot be selected in such a way that i. —C(O)—, —C(O)O—, —OC(O)—, —SO$_2$—, —S(O)—, —P(O)(R$^{28}$)—, —P(O)—, and —C(S)— moieties are adjacent to each other; or ii. —O—, —S—, or —NR$^2$— moieties are adjacent to each other; or iii. moieties are otherwise selected in an order that an unstable molecule results (as defined as producing a molecule that has a shelf life at ambient temperature of less than about four months (or alternatively less than about six or five months) due to decomposition caused by the selection and order of the moieties R$^{20}$, R$^{21}$, R$^2$, R$^{23}$, and R$^{24}$);

R$^{25}$ is selected from hydrogen, alkyl, alkene, alkyne, halogen, hydroxyl, alkoxy, azide, amino, cyano, —OR$^2$, —NR$^2$R$^{2'}$, —NR$^2$SO$_2$R$^{28}$, —OSO$_2$R$^{28}$, —SO$_2$R$^{28}$, haloalkyl, aryl, heteroaryl, heterocycle, bicycle, and cycloalkyl; each of which R$^{23}$ groups is optionally substituted with 1, 2, 3, or 4 groups independently selected from R$^{12}$;

R$^{28}$ independently selected at each occurrence from hydrogen, —NR$^2$R$^{2'}$, —OR$^2$, —SR$^2$, alkyl, haloalkyl, alkenyl, alkynyl, cycloalkyl, heterocycle, aryl, and heteroaryl;

R$^{40}$ is independently at each occurrence selected from the group consisting of hydrogen, alkyl, alkene, alkyne, halogen, hydroxyl, alkoxy, azide, amino, cyano, —NR$^2$R$^{2'}$, —NR$^2$SO$_2$R$^{28}$, —OSO$_2$R$^{28}$, —SO$_2$R$^{28}$, haloalkyl, aryl, heteroaryl, heterocycle, oxo, and cycloalkyl; each of which R$^{40}$ groups is optionally substituted with 1, 2, 3, or 4 groups independently selected from R$^{12}$.

2. The compound of embodiment 1 of Formula:

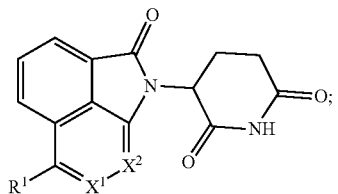

(I)

or a pharmaceutically acceptable salt, N-oxide, isotopic derivative, or prodrug thereof.

3. The compound of embodiment 2, wherein:
R$^6$ is selected from alkyl, cycloalkyl, heterocycle, aryl, and heteroaryl, wherein each R$^6$ is optionally substituted with 1, 2, 3, or 4 groups independently selected from R$^9$; and
R$^{11}$ is selected from: hydrogen; halogen; hydroxyl; cyano; nitro; alkyl; haloalkyl; alkenyl optionally substituted with an aryl or heteroaryl group; alkynyl optionally substituted with an aryl or heteroaryl group; cycloalkyl; heterocycle; aryl optionally substituted with 1, 2, 3, or 4 halogen, alkyl, or —OR$^8$ groups; heteroaryl optionally substituted with 1, 2, 3, or 4 halogen, alkyl, or —OR$^8$ groups; —CH$_2$aryl optionally substituted with 1, 2, 3, or 4 halogen, alkyl, or —OR$^8$ groups; —CH$_2$heteroaryl optionally substituted with 1, 2, 3, or 4 halogen, alkyl, or —OR$^8$ groups; —OR$^8$. —NR$^8$R$^{8'}$; —C(O)R$^8$; —C(O)OR$^8$; —C(O)—NR$^8$R$^{8'}$; —C(O)CH$_2$R$^8$; —C(O)CH$_2$OR$^8$; —C(O)CH$_2$—NR$^8$R$^{8'}$; —OC(O)R$^8$; —NR$^2$—C(O)R$^8$; —CH$_2$—OC(O)R$^8$; —CH$_2$—NR$^2$—C(O)R$^8$; —S(O)R$^8$; —SO$_2$R$^8$; —SO$_2$—OR$^8$; and —SO$_2$—NR$^8$R$^{8'}$;

or two R$^1$ groups on the same carbon may be brought together to form an oxo group.

4. The compound of embodiment 1 or embodiment 2, wherein R$^{12}$ is selected from halogen, alkyl, and haloalkyl.

5. The compound of embodiment 1 or embodiment 2, wherein R$^{12}$ is selected from hydroxyl, cyano, nitro, alkenyl, alkynyl, cycloalkyl, heterocycle, aryl, and heteroaryl.

6. The compound of embodiment 1 or embodiment 2, wherein R$^{12}$ is selected from —CH$_2$aryl; —CH$_2$heteroaryl; —OR$^8$; —NR$^8$R$^{8'}$; —C(O)R$^8$; —C(O)OR$^8$; —C(O)—NR$^8$R$^{8'}$; —C(O)CH$_2$R$^8$; —C(O)CH$_2$OR$^8$; —C(O)CH$_2$—NR$^8$R$^{8'}$; —OC(O)R$^8$; —NR$^2$—C(O)R$^8$; —CH$_2$—OC(O)R$^8$; —CH$_2$—NR$^2$—C(O)R$^8$; —S(O)R$^8$; —SO$_2$R$^8$; —SO$_2$—OR$^8$; oxo; and —SO$_2$—NR$^8$R$^{8'}$.

7. The compound of embodiment 1 or 2, wherein one R$^{12}$ substituent is halogen.

8. The compound of embodiment 1 or 2, wherein two R$^2$ substituents are halogen.

9. The compound of embodiment 1 or 2, wherein one R$^{12}$ substituent is alkyl.

10. The compound of embodiment 1 or 2, wherein two R$^{12}$ substituents are alkyl.

11. The compound of embodiment 1 or 2, wherein one R$^{12}$ substituent is haloalkyl.

12. The compound of embodiment 1 or 2, wherein one R$^{12}$ substituent is cycloalkyl.

13. The compound of any one of embodiments 4-12, wherein R$^{11}$ is alkyl optionally substituted with 1, 2, 3, or 4 substituents selected from R$^{12}$.

14. The compound of any one of embodiments 4-12, wherein R$^{11}$ is cycloalkyl optionally substituted with 1, 2, 3, or 4 substituents selected from R$^{12}$.

15. The compound of any one of embodiments 4-12, wherein R$^{11}$ is heterocycle optionally substituted with 1, 2, 3, or 4 substituents selected from R$^{12}$.

16. The compound of any one of embodiments 4-12, wherein R$^{11}$ is aryl optionally substituted with 1, 2, 3, or 4 substituents selected from R$^{12}$.

17. The compound of any one of embodiments 4-12, wherein R$^{11}$ is heteroaryl optionally substituted with 1, 2, 3, or 4 substituents selected from R$^{12}$.

18. The compound of any one of embodiments 1-12, wherein R$^{11}$ is alkyl.

19. The compound of any one of embodiments 1-12, wherein R$^{11}$ is cyano.

20. The compound of any one of embodiments 1-12, wherein R$^{11}$ is haloalkyl.

21. The compound of any one of embodiments 1-12, wherein R$^{11}$ is hydrogen.

22. The compound of any one of embodiments 1-12, wherein $R^{11}$ is hydroxyl.
23. The compound of any one of embodiments 1-12, wherein $R^{11}$ is $OR^8$.
24. The compound of any one of embodiments 1-12, wherein $R^{11}$ is aryl.
25. The compound of any one of embodiments 1-12, wherein $R^{11}$ is heteroaryl.
26. The compound of any one of embodiments 1-12, wherein $R^{11}$ is —C(O)OR$^8$, —C(O)R$^8$, or —SO$_2$R$^8$.
27. The compound of any one of embodiments 1-12, wherein $R^{11}$ is —CH$_2$aryl.
28. The compound of any one of embodiments 1-27, wherein $R^1$ is —NR$^2$R$^4$.
29. The compound of any one of embodiments 1-27, wherein $R^1$ is —OR$^4$.
30. The compound of any one of embodiments 1-27, wherein $R^1$ is —C(O)R$^4$.
31. The compound of any one of embodiments 1-27, wherein $R^1$ is —SR$^4$.
32. The compound of any one of embodiments 1-27, wherein $R^1$ is —S(O)R$^4$.
33. The compound of any one of embodiments 1-27, wherein $R^1$ is and —S(O)$_2$R$^4$.
34. The compound of any one of embodiments 1-27, wherein the compound is of Formula:

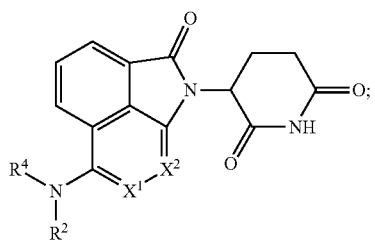

(I-b)

or a pharmaceutically acceptable salt thereof.
35. The compound of any one of embodiments 1-27, wherein the compound is of Formula:

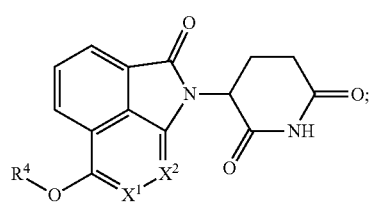

(I-c)

or a pharmaceutically acceptable salt thereof.
36. The compound of any one of embodiments 1-27, wherein the compound is of Formula:

(I-h)

or a pharmaceutically acceptable salt thereof.

37. The compound of any one of embodiments 1-27, wherein the compound is of Formula:

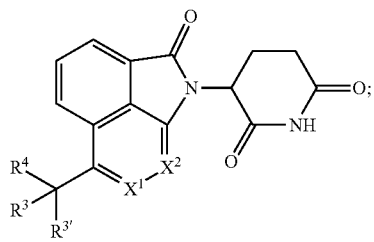

(I-a)

or a pharmaceutically acceptable salt thereof.
38. The compound of any one of embodiments 1-27, wherein $R^1$ is —(CR$^3$R$^{3'}$)—R$^5$.
39. The compound of embodiment 37 or 38, wherein $R^3$ is hydrogen.
40. The compound of embodiment 37 or 38, wherein $R^3$ is —NR$^8$R$^{8'}$.
41. The compound of embodiment 37 or 38, wherein $R^3$ is alkyl.
42. The compound of any one of embodiments 37-41, wherein $R^{3'}$ is hydrogen.
43. The compound of any one of embodiments 1-27, wherein $R^1$ is —NR$^2$R$^5$.
44. The compound of any one of embodiments 1-27, wherein $R^1$ is —OR$^5$.
45. The compound of any one of embodiments 38-44, wherein $R^5$ is —C(O)alkyl optionally substituted with 1, 2, 3, or 4 groups independently selected from $R^9$.
46. The compound of any one of embodiments 38-44, wherein $R^5$ is —C(O)heterocycle optionally substituted with 1, 2, 3, or 4 groups independently selected from $R^9$.
47. The compound of any one of embodiments 38-44, wherein $R^5$ is —C(O)aryl optionally substituted with 1, 2, 3, or 4 groups independently selected from $R^9$.
48. The compound of any one of embodiments 38-44, wherein $R^5$ is —C(O)heteroaryl optionally substituted with 1, 2, 3, or 4 groups independently selected from $R^9$.
49. The compound of any one of embodiments 1-48, wherein the compound is of Formula:

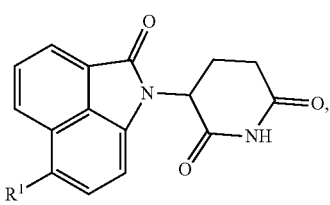

(I-d)

or a pharmaceutically acceptable salt thereof.
50. The compound of any one of embodiments 1-48, wherein the compound is of Formula:

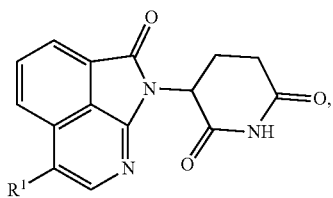

(I-e)

or a pharmaceutically acceptable salt thereof.
51. The compound of any one of embodiments 1-48, wherein the compound is of Formula:

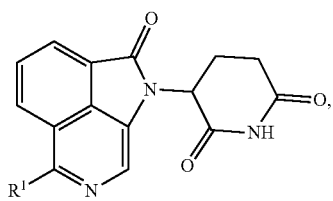

(I-f)

or a pharmaceutically acceptable salt thereof.
52. The compound of any one of embodiments 49-51, wherein $R^4$ is cycloalkyl substituted with one group selected from $R^6$, and optionally substituted with 1, 2, 3, or 4 groups independently selected from $R^7$.
53. The compound of any one of embodiments 49-51, wherein $R^4$ is heterocycle substituted with one group selected from $R^6$, and optionally substituted with 1, 2, 3, or 4 groups independently selected from $R^7$.
54. The compound of any one of embodiments 49-51, wherein $R^4$ is aryl substituted with one group selected from $R^6$, and optionally substituted with 1, 2, 3, or 4 groups independently selected from $R^7$.
55. The compound of any one of embodiments 49-51, wherein $R^4$ is heteroaryl substituted with one group selected from $R^6$, and optionally substituted with 1, 2, 3, or 4 groups independently selected from $R^7$.
56. The compound of any one of embodiments 49-51, wherein $R^4$ is

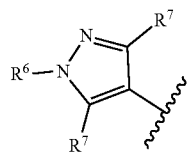

57. The compound of any one of embodiments 49-51, wherein $R^4$ is

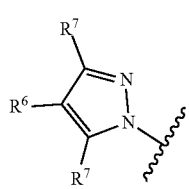

58. The compound of any one of embodiments 49-51, wherein $R^4$ is

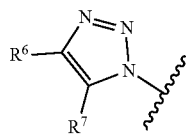

59. The compound of any one of embodiments 49-51, wherein $R^4$ is

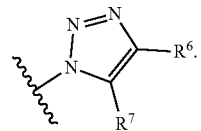

60. The compound of any one of embodiments 49-51, wherein $R^4$ is

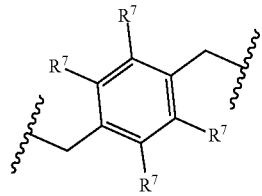

61. The compound of any one of embodiments 1-60, wherein $R^7$ is selected from hydrogen, halogen, hydroxyl, cyano, nitro, alkyl, haloalkyl, alkenyl, alkynyl, cycloalkyl, heterocycle, aryl, heteroaryl, —$OR^8$, and —$NR^8R^{8'}$.
62. The compound of any one of embodiments 1-60, wherein $R^7$ is selected from hydrogen, halogen, alkyl, haloalkyl, —$C(O)R^8$, —$C(O)OR^8$, —$C(O)$—$NR^8R^{8'}$, —$OC(O)R^8$, —$NR^2$—$C(O)R^8$, —$S(O)R^8$, —$SO_2R^8$, —$SO_2$—$OR^8$, and —$SO_2$—$NR^8R^{8'}$.
63. The compound of any one of embodiments 1-60, wherein one $R^7$ is hydrogen.
64. The compound of any one of embodiments 1-60, wherein two $R^7$s are hydrogen.
65. The compound of any one of embodiments 1-60, wherein three $R^7$s are hydrogen.
66. The compound of any one of embodiments 1-65, wherein one $R^7$ is halogen.
67. The compound of any one of embodiments 1-64, wherein two $R^7$s are halogen.
68. The compound of any one of embodiments 1-65, wherein one $R^7$ is alkyl.
69. The compound of any one of embodiments 1-64, wherein two $R^7$s are alkyl.
70. The compound of any one of embodiments 1-65, wherein one $R^7$ is haloalkyl.
71. The compound of any one of embodiments 1-64, wherein two $R^7$s are haloalkyl.
72. The compound of any one of embodiments 1-71, wherein $R^6$ is selected from:

-continued

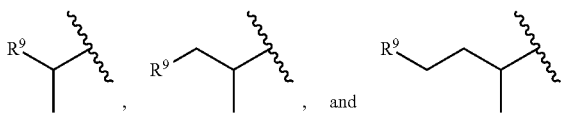

73. The compound of any one of embodiments 1-71, wherein $R^6$ is selected from:

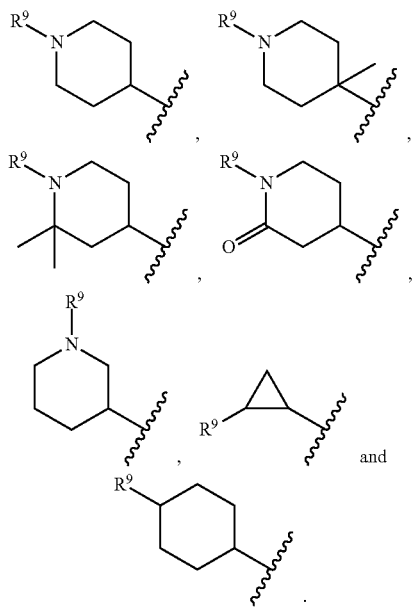

74. The compound of any one of embodiments 1-71, wherein $R^6$ is selected from:

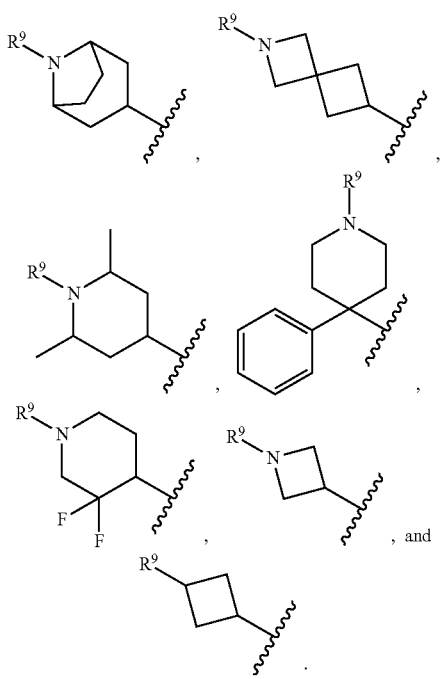

75. The compound of any one of embodiments 1-71, wherein $R^6$ is alkyl optionally substituted with 1, 2, 3, or 4 groups independently selected from $R^9$.
76. The compound of any one of embodiments 1-71, wherein $R^6$ is cycloalkyl optionally substituted with 1, 2, 3, or 4 groups independently selected from $R^9$.
77. The compound of any one of embodiments 1-71, wherein $R^6$ is heterocycle optionally substituted with 1, 2, 3, or 4 groups independently selected from $R^9$.
78. The compound of any one of embodiments 1-71, wherein $R^6$ is aryl optionally substituted with 1, 2, 3, or 4 groups independently selected from $R^9$.
79. The compound of any one of embodiments 1-71, wherein $R^6$ is heteroaryl optionally substituted with 1, 2, 3, or 4 groups independently selected from $R^9$.
80. The compound of any one of embodiments 75-79, wherein $R^6$ is not substituted.
81. The compound of any one of embodiments 75-79, wherein $R^6$ is substituted with 1 group selected from $R^9$.
82. The compound of any one of embodiments 75-79, wherein $R^6$ is substituted with 2 groups independently selected from $R^9$.
83. The compound of any one of embodiments 75-79, wherein $R^6$ is substituted with 3 groups independently selected from $R^9$.
84. The compound of any one of embodiments 75-79, wherein $R^6$ is substituted with 4 groups independently selected from $R^9$.
85. The compound of any one of embodiments 1-84, wherein $R^9$ is selected from hydrogen, halogen, alkyl, haloalkyl, cyano, and nitro.
86. The compound of any one of embodiments 1-84, wherein $R^9$ is selected from $R^{10}$.
87. The compound of any one of embodiments 1-84, wherein $R^9$ is selected from $-CH_2R^{10}$, $-OR^{10}$, $-NR^2R^{10}$, $-C(O)R^{10}$, $-C(O)CH_2R^{10}$, $-C(O)CH_2OR^{10}$, $-C(O)CH_2NR^2R^{10}$, $-OC(O)R^{10}$, $-NR^2-C(O)R^{10}$, $-C(O)OR^{10}$, $-C(O)NR^2R^{10}$, $-S(O)R^{10}$, $-SO_2R^{10}$, $SO_2CH_2R^{10}$, $-SO_2CH_2OR^{10}$, $-SO_2CH_2NR^2R^{10}$, $-NR^2SO_2R^{10}$, $-SO_2-OR^{10}$, and $-SO_2-NR^2R^{10}$.
88. The compound of embodiment 86 or 87, wherein $R^{10}$ is alkyl optionally substituted with 1, 2, 3, or 4 groups independently selected from $R^{11}$.
89. The compound of embodiment 86 or 87, wherein $R^{10}$ is haloalkyl optionally substituted with 1, 2, 3, or 4 groups independently selected from $R^{11}$.
90. The compound of embodiment 86 or 87, wherein $R^{10}$ is alkenyl optionally substituted with 1, 2, 3, or 4 groups independently selected from $R^{11}$.
91. The compound of embodiment 86 or 87, wherein $R^{10}$ is alkynyl optionally substituted with 1, 2, 3, or 4 groups independently selected from $R^{11}$.
92. The compound of embodiment 86 or 87, wherein $R^{10}$ is cycloalkyl optionally substituted with 1, 2, 3, or 4 groups independently selected from $R^{11}$.
93. The compound of embodiment 86 or 87, wherein $R^{10}$ heterocycle optionally substituted with 1, 2, 3, or 4 groups independently selected from $R^{11}$.
94. The compound of embodiment 86 or 87, wherein $R^{10}$ is aryl optionally substituted with 1, 2, 3, or 4 groups independently selected from $R^{11}$.
95. The compound of embodiment 86 or 87, wherein $R^{10}$ is heteroaryl optionally substituted with 1, 2, 3, or 4 groups independently selected from $R^{11}$.

96. The compound of any one of embodiments 88-95, wherein R$^{10}$ is not substituted.

97. The compound of any one of embodiments 88-95, wherein R$^{10}$ is substituted with 1 group selected from R$^{11}$.

98. The compound of any one of embodiments 88-95, wherein R$^{10}$ is substituted with 2 groups independently selected from R$^{11}$.

99. The compound of any one of embodiments 88-95, wherein R$^{10}$ is substituted with 3 groups independently selected from R$^{11}$.

100. The compound of any one of embodiments 88-95, wherein R$^{10}$ is substituted with 4 groups independently selected from R$^{11}$.

101. The compound of any one of embodiments 1-100, wherein R$^2$, R$^8$, and R$^{8'}$ are hydrogen.

102. The compound of any one of embodiments 1-100, wherein R$^2$, R$^8$, and R$^{8'}$ are alkyl.

103. The compound of any one of embodiments 1-71, wherein R$^6$ is selected from:

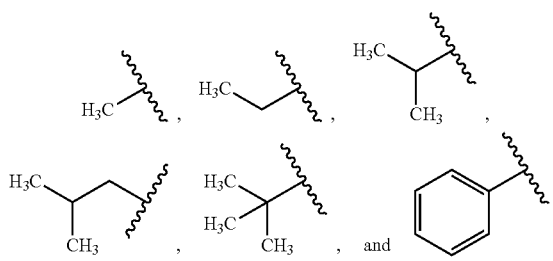

104. The compound of any one of embodiments 1-71, wherein R$^6$ is selected from:

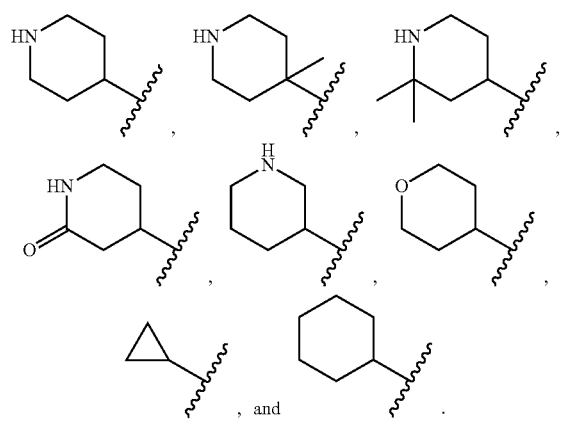

105. The compound of any one of embodiments 1-71, wherein R$^6$ is selected from:

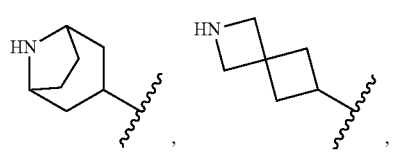

-continued

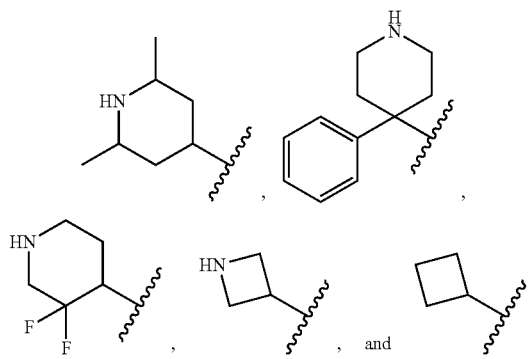

106. The compound of embodiment 1, wherein the compound is of Formula:

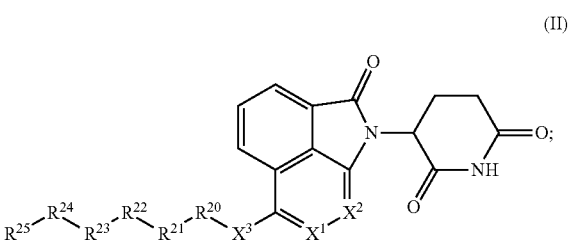

or a pharmaceutically acceptable salt, N-oxide, isotopic derivative, or prodrug thereof.

107. The compound of embodiment 106, wherein the compound is of Formula:

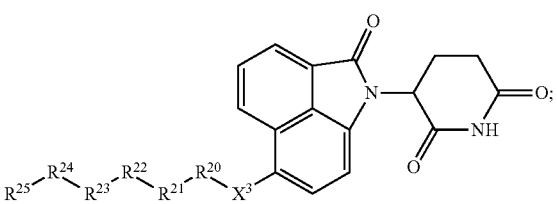

or a pharmaceutically acceptable salt, N-oxide, isotopic derivative, or prodrug thereof.

108. The compound of embodiment 106, wherein the compound is of Formula:

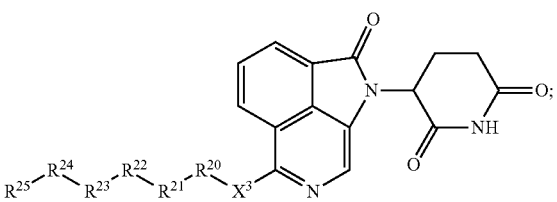

or a pharmaceutically acceptable salt, N-oxide, isotopic derivative, or prodrug thereof.

109. The compound of embodiment 106, wherein the compound is of Formula:

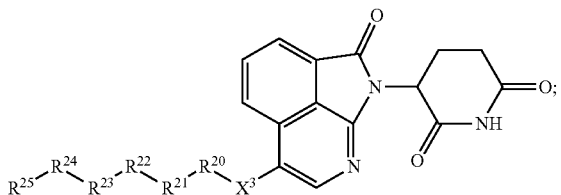

or a pharmaceutically acceptable salt, N-oxide, isotopic derivative, or prodrug thereof.

110. The compound of any one of embodiments 106-109, wherein $X^3$ is bond.
111. The compound of any one of embodiments 106-109, wherein $X^3$ is $C(R^3R^3)$.
112. The compound of any one of embodiments 106-109, wherein $X^3$ is $C(O)$.
113. The compound of any one of embodiments 106-109, wherein $X^3$ is $C(S)$.
114. The compound of any one of embodiments 106-109, wherein $X^3$ is $S(O)$.
115. The compound of any one of embodiments 106-109, wherein $X^3$ is $S(O)_2$
116. The compound of any one of embodiments 106-109, wherein $X^3$ is $NR^2$.
117. The compound of any one of embodiments 106-109, wherein $X^3$ is O.
118. The compound of any one of embodiments 106-109, wherein $X^3$ is $NR^2$
119. The compound of any one of embodiments 106-109, wherein $X^3$ is O.
120. The compound of any one of embodiments 106-109, wherein $X^3$ is S.
121. The compound of any one of embodiments 106-120, wherein $R^{20}$ is bond.
122. The compound of any one of embodiments 106-120, wherein $R^{20}$ is alkyl optionally substituted with 1, 2, 3, or 4 substituents independently selected from $R^{40}$.
123. The compound of any one of embodiments 106-120, wherein $R^{20}$ is alkene or alkyne optionally substituted with 1, 2, 3, or 4 substituents independently selected from $R^{40.}$
124. The compound of any one of embodiments 106-120, wherein $R^{20}$ is haloalkyl optionally substituted with 1, 2, 3, or 4 substituents independently selected from $R^{40}$.
125. The compound of any one of embodiments 106-120, wherein $R^{20}$ is aryl optionally substituted with 1, 2, 3, or 4 substituents independently selected from $R^{40}$.
126. The compound of any one of embodiments 106-120, wherein $R^{20}$ is heteroaryl optionally substituted with 1, 2, 3, or 4 substituents independently selected from $R^{40}$.
127. The compound of any one of embodiments 106-120, wherein $R^{20}$ is heterocycle optionally substituted with 1, 2, 3, or 4 substituents independently selected from $R^{40}$.
128. The compound of any one of embodiments 106-120, wherein $R^{20}$ is bicycle optionally substituted with 1, 2, 3, or 4 substituents independently selected from $R^{40}$.
129. The compound of any one of embodiments 106-115, wherein $R^{20}$ is —O—.
130. The compound of any one of embodiments 106-115, wherein $R^{20}$ is —S—.
131. The compound of any one of embodiments 106-115, wherein $R^{20}$ is —NR$^2$—.
132. The compound of any one of embodiments 106-111, wherein $R^{20}$ is —C(O)—, —C(O)O—, —OC(O)—, —SO$_2$—, —S(O)—, —C(S)—, —C(O)NR$^2$—, —P(O)(R$^{28}$)—, or —P(O)—.

133. The compound of any one of embodiments 106-132, wherein $R^{21}$ is bond.
134. The compound of any one of embodiments 106-132, wherein $R^{21}$ is alkyl optionally substituted with 1, 2, 3, or 4 substituents independently selected from $R^{40}$.
135. The compound of any one of embodiments 106-132, wherein $R^{21}$ is alkene or alkyne optionally substituted with 1, 2, 3, or 4 substituents independently selected from $R^{40.}$
136. The compound of any one of embodiments 106-132, wherein $R^{21}$ is haloalkyl optionally substituted with 1, 2, 3, or 4 substituents independently selected from $R^{40}$.
137. The compound of any one of embodiments 106-132, wherein $R^{21}$ is aryl optionally substituted with 1, 2, 3, or 4 substituents independently selected from $R^{40}$.
138. The compound of any one of embodiments 106-132, wherein $R^{21}$ is heteroaryl optionally substituted with 1, 2, 3, or 4 substituents independently selected from $R^{40}$.
139. The compound of any one of embodiments 106-132, wherein $R^{21}$ is heterocycle optionally substituted with 1, 2, 3, or 4 substituents independently selected from $R^{40}$.
140. The compound of any one of embodiments 106-132, wherein $R^{21}$ is bicycle optionally substituted with 1, 2, 3, or 4 substituents independently selected from $R^{40}$.
141. The compound of any one of embodiments 106-128, wherein $R^{21}$ is —O—.
142. The compound of any one of embodiments 106-128, wherein $R^{21}$ is —S—.
143. The compound of any one of embodiments 106-128, wherein $R^{21}$ is —NR$^2$—.
144. The compound of any one of embodiments 106-131, wherein $R^{21}$ is —C(O)—, —C(O)O—, —OC(O)—, —SO$_2$—, —S(O)—, —C(S)—, —C(O)NR$^2$—, P(OX)(R$^{28}$), or —P(O)—.
145. The compound of any one of embodiments 106-144, wherein $R^{22}$ is bond.
146. The compound of any one of embodiments 106-144, wherein $R^{22}$ is alkyl optionally substituted with 1, 2, 3, or 4 substituents independently selected from $R^{40}$.
147. The compound of any one of embodiments 106-144, wherein $R^{22}$ is alkene or alkyne optionally substituted with 1, 2, 3, or 4 substituents independently selected from $R^{40.}$
148. The compound of any one of embodiments 106-144, wherein $R^{22}$ is haloalkyl optionally substituted with 1, 2, 3, or 4 substituents independently selected from $R^{40}$.
149. The compound of any one of embodiments 106-144, wherein $R^{22}$ is aryl optionally substituted with 1, 2, 3, or 4 substituents independently selected from $R^{40}$.
150. The compound of any one of embodiments 106-144, wherein $R^{22}$ is heteroaryl optionally substituted with 1, 2, 3, or 4 substituents independently selected from $R^{40}$.
151. The compound of any one of embodiments 106-144, wherein $R^{22}$ is heterocycle optionally substituted with 1, 2, 3, or 4 substituents independently selected from $R^{40}$.
152. The compound of any one of embodiments 106-144, wherein $R^{22}$ is bicycle optionally substituted with 1, 2, 3, or 4 substituents independently selected from $R^{40}$.
153. The compound of any one of embodiments 106-143, wherein $R^{22}$ is —C(O)—, —C(O)O—, —OC(O)—, —SO$_2$—, —S(O)—, —C(S)—, —C(O)NR$^2$—, —P(O)(R$^{28}$)—, or —P(O)—.

154. The compound of any one of embodiments 106-140, wherein $R^{22}$ is —O—.
155. The compound of any one of embodiments 106-140, wherein $R^{22}$ is —S—.
156. The compound of any one of embodiments 106-140, wherein $R^{22}$ is —$NR^2$—.
157. The compound of any one of embodiments 106-156, wherein $R^{23}$ or $R^{24}$ is bond.
158. The compound of any one of embodiments 106-156, wherein $R^{23}$ or $R^{24}$ is alkyl optionally substituted with 1, 2, 3, or 4 substituents independently selected from $R^{40}$.
159. The compound of any one of embodiments 106-156, wherein $R^{23}$ or $R^{24}$ is alkene or alkyne optionally substituted with 1, 2, 3, or 4 substituents independently selected from $R^{40}$.
160. The compound of any one of embodiments 106-156, wherein $R^{23}$ or $R^{24}$ is haloalkyl optionally substituted with 1, 2, 3, or 4 substituents independently selected from $R^{40}$.
161. The compound of any one of embodiments 106-156, wherein $R^{23}$ or $R^{24}$ is aryl optionally substituted with 1, 2, 3, or 4 substituents independently selected from $R^{40}$.
162. The compound of any one of embodiments 106-156, wherein $R^{23}$ or $R^{24}$ is heteroaryl optionally substituted with 1, 2, 3, or 4 substituents independently selected from $R^{40}$.
163. The compound of any one of embodiments 106-156, wherein $R^{23}$ or $R^{24}$ is heterocycle optionally substituted with 1, 2, 3, or 4 substituents independently selected from $R^{40}$.
164. The compound of any one of embodiments 106-156, wherein $R^{23}$ or $R^{24}$ is bicycle optionally substituted with 1, 2, 3, or 4 substituents independently selected from $R^{40}$.
165. The compound of any one of embodiments 106-156, wherein $R^{23}$ or $R^{24}$ is —C(O)—, —C(O)O—, —OC(O)—, —$SO_2$—, —S(O)—, —C(S)—, —C(O)$NR^2$—, —P(O)($R^{28}$)—, or —P(O)—.
166. The compound of any one of embodiments 106-156, wherein $R^{23}$ or $R^{24}$ is —O—.
167. The compound of any one of embodiments 106-156, wherein $R^{23}$ or $R^{24}$ is —S—.
168. The compound of any one of embodiments 106-156, wherein $R^{23}$ or $R^{24}$ is —$NR^2$—.
169. The compound of any one of embodiments 106-168, wherein $R^{21}$ is hydrogen.
170. The compound of any one of embodiments 106-168, wherein $R^{21}$ is halogen.
171. The compound of any one of embodiments 106-168, wherein $R^2$ is alkyl optionally substituted with 1, 2, 3, or 4 groups independently selected from $R^{12}$.
172. The compound of any one of embodiments 106-168, wherein $R^{25}$ is selected from alkene, alkyne, hydroxyl, alkoxy, azide, amino, cyano, —$OR^2$, —$NR^2R^{2'}$, —$NR^2SO_2R^{28}$, —$OSO_2R^{28}$, —$SO_2R^{28}$, haloalkyl, aryl, heteroaryl, heterocycle, bicycle, and cycloalkyl; each of which $R^{21}$ groups is optionally substituted with 1, 2, 3, or 4 groups independently selected from $R^{12}$.
173. The compound of anyone one of embodiments 106-172, wherein $R^{40}$ is selected from alkyl, alkene, alkyne, halogen, hydroxyl, alkoxy, azide, amino, cyano, haloalkyl, aryl, heteroaryl, heterocycle, oxo, and cycloalkyl; each of which $R^{40}$ groups is optionally substituted with 1, 2, 3, or 4 groups independently selected from $R^{12}$.
174. The compound of embodiment 173, wherein $R^{40}$ is not substituted.
175. The compound of embodiment 1, wherein the compound is selected from:

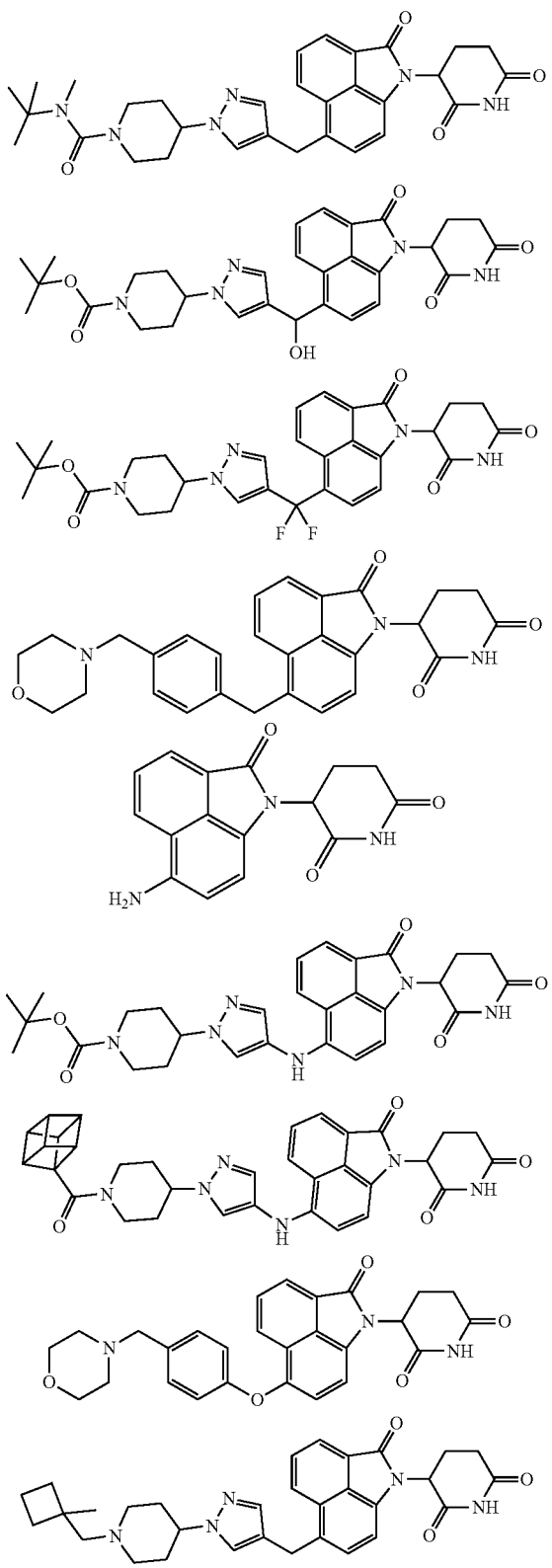

243
-continued
244
-continued
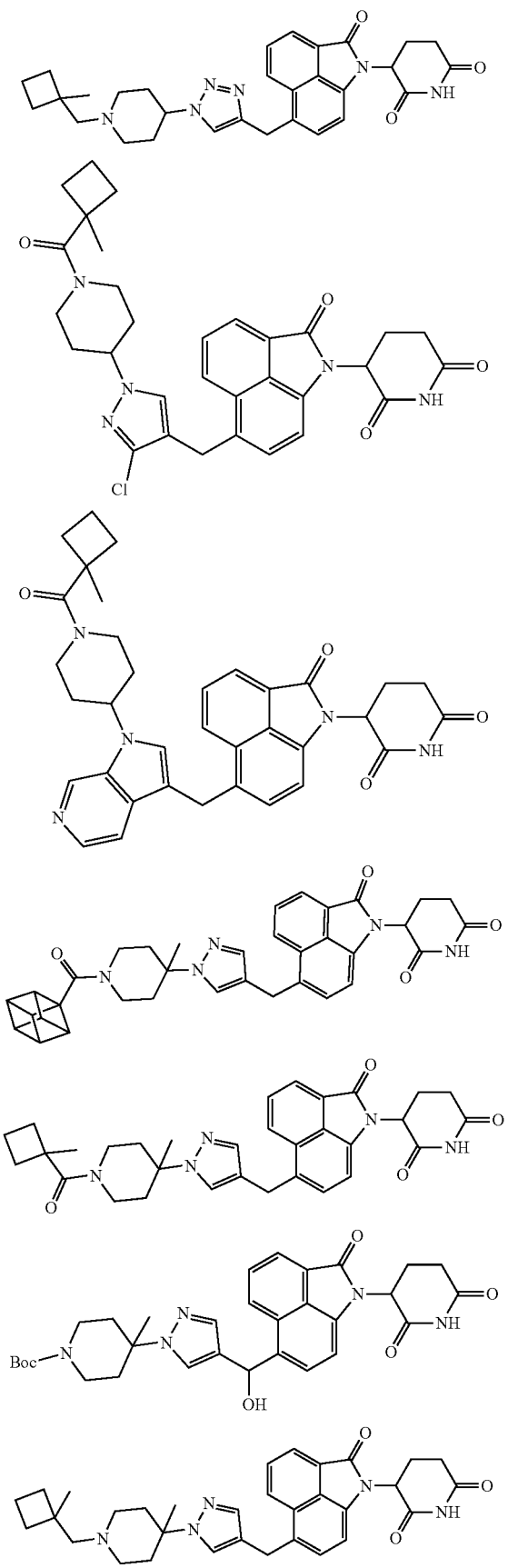
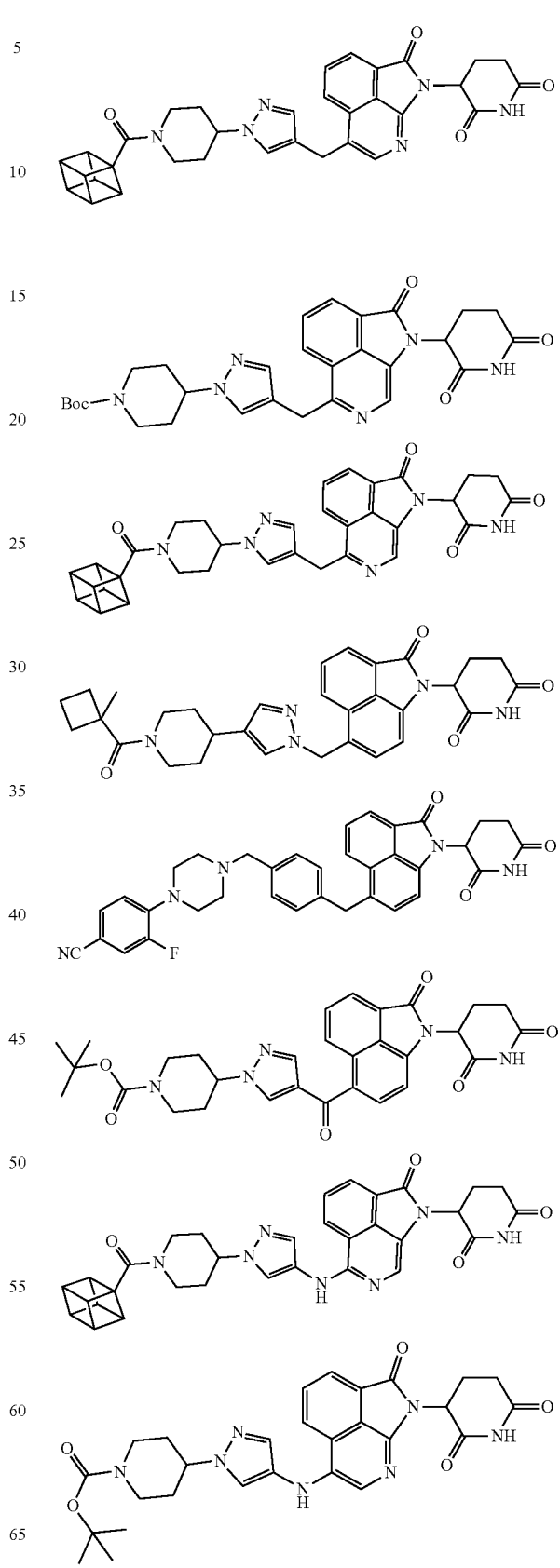

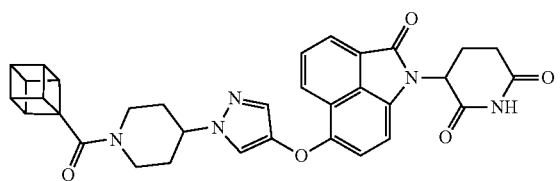

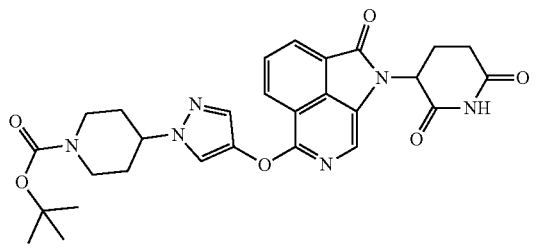

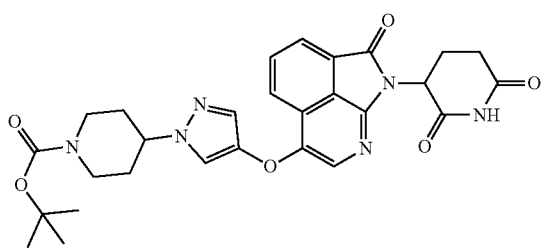

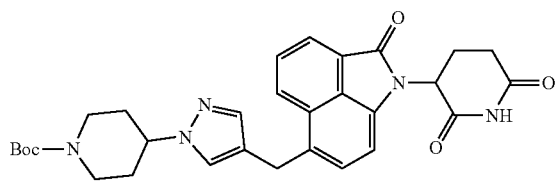

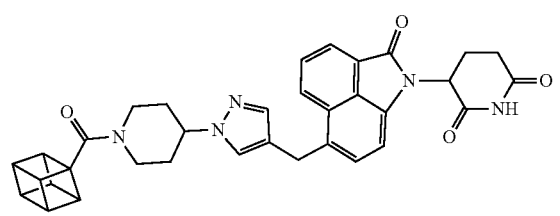

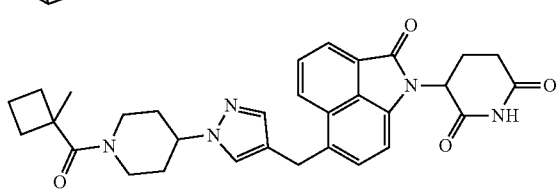

and

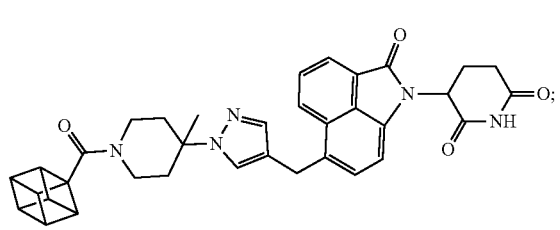

or a pharmaceutically acceptable salt thereof.

176. The compound of embodiment 1, wherein the compound is selected from Table 2 or a pharmaceutically acceptable salt thereof.

177. The compound of embodiment 1, wherein the compound is of structure:

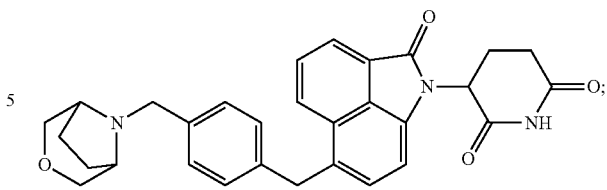

or a pharmaceutically acceptable salt thereof.

178. The compound of embodiment 1, wherein the compound is of structure:

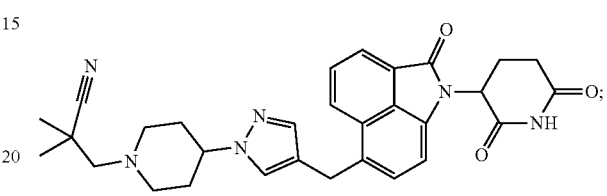

or a pharmaceutically acceptable salt thereof.

179. The compound of embodiment 1, wherein the compound is of structure:

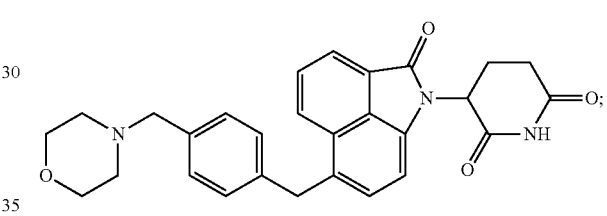

or a pharmaceutically acceptable salt thereof.

180. The compound of embodiment 1, wherein the compound is of structure:

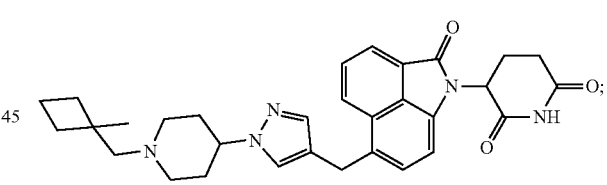

or a pharmaceutically acceptable salt thereof.

181. The compound of embodiment 1, wherein the compound is of structure:

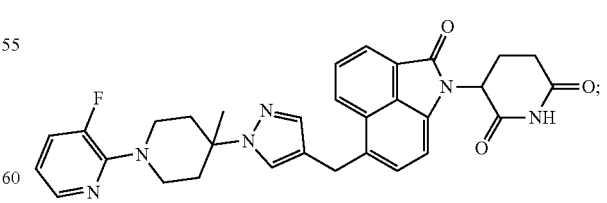

or a pharmaceutically acceptable salt thereof.

182. In certain embodiments a pharmaceutical composition comprising a compound of any one of embodiments 1-181 or a pharmaceutical salt thereof and a pharmaceutically acceptable excipient is provided.

183. In certain embodiments a method of treating a disorder mediated by cereblon in a human comprising administering an effective dose of a compound of any one of embodiments 1-181 or a pharmaceutically acceptable salt or composition thereof to a human in need thereof is provided.
184. The method of embodiment 183, wherein the disorder is mediated by Ikaros or Aiolos.
185. The method of embodiment 183 or 184, wherein the disorder is a cancer.
186. The method of embodiment 183 or 184, wherein the disorder is a tumor.
187. The method of embodiment 183 or 184, wherein the disorder is an immune, autoimmune, or inflammatory disorder.
188. The method of embodiment 183 or 184, wherein the disorder is a hematological malignancy.
189. The method of embodiment 183 or 184, wherein the disorder is multiple myeloma, leukemia, lymphoblastic leukemia, chronic lymphocytic leukemia, Hodgkin's lymphoma, or non-Hodgkin's lymphoma.
190. In certain embodiments a compound for use in the manufacture of a medicament to treat a disorder mediated by cereblon in a human wherein the compound is selected any one of embodiments 1-181 or a pharmaceutically acceptable salt or composition thereof is provided.
191. The compound for use of embodiment 190, wherein the disorder is mediated by Ikaros or Aiolos.
192. The compound for use of embodiment 190 or 191, wherein the disorder is a cancer.
193. The compound for use of embodiment 190 or 191, wherein the disorder is a tumor.
194. The compound for use of embodiment 190 or 191, wherein the disorder is an immune, autoimmune, or inflammatory disorder.
195. The compound for use of embodiment 190 or 191, wherein the disorder is a hematological malignancy.
196. The compound for use of embodiment 190 or 191, wherein the disorder is multiple myeloma, leukemia, lymphoblastic leukemia, chronic lymphocytic leukemia, Hodgkin's lymphoma, or non-Hodgkin's lymphoma.
197. In certain embodiments a use of a compound in the treatment of a disorder mediated by cereblon in a human wherein the compound is selected any one of embodiments 1-181 or a pharmaceutically acceptable salt or composition thereof is provided.
198. The use of embodiment 197, wherein the disorder is mediated by Ikaros or Aiolos.
199. The use of embodiment 197 or 198, wherein the disorder is a cancer.
200. The use of embodiment 197 or 198, wherein the disorder is a tumor.
201. The use of embodiment 197 or 198, wherein the disorder is an immune, autoimmune, or inflammatory disorder.
202. The use of embodiment 197 or 198, wherein the disorder is a hematological malignancy.
203. The use of embodiment 197 or 198, wherein the disorder is multiple myeloma, leukemia, lymphoblastic leukemia, chronic lymphocytic leukemia, Hodgkin's lymphoma, or non-Hodgkin's lymphoma.

III. Methods of Treatment

Any of the compounds described herein can be used in an effective amount to treat a host, including a human, in need thereof, optionally in a pharmaceutically acceptable carrier to treat any of the disorders described herein. In certain embodiments, the method comprises administering an effective amount of the active compound or its salt as described herein, optionally including a pharmaceutically acceptable excipient, carrier, or adjuvant (i.e., a pharmaceutically acceptable composition), optionally in combination or alternation with an additional therapeutically active agent or combination of agents.

In one embodiment, the compound of the present invention selectively degrades IKZF1 and/or 3 over one or more of IKZF2 and/or 4 and/or 5.

In one embodiment a compound of Formula I is used to treat a disorder described herein.

In one embodiment a compound of Formula II is used to treat a disorder described herein.

In one embodiment a compound of Formula I-a is used to treat a disorder described herein.

In one embodiment a compound of Formula I-b is used to treat a disorder described herein.

In one embodiment a compound of Formula I-c is used to treat a disorder described herein.

In one embodiment a compound of Formula I-d is used to treat a disorder described herein.

In one embodiment a compound of Formula I-e is used to treat a disorder described herein.

In one embodiment a compound of Formula I-f is used to treat a disorder described herein.

In one embodiment a compound of Formula I-g is used to treat a disorder described herein.

In one embodiment the disorder treated by a compound of the present invention is an immunomodulatory disorder. In one embodiment the disorder treated by a compound of the present invention is mediated by angiogenesis. In one embodiment the disorder treated by a compound of the present invention is related to the lymphatic system.

In one embodiment a compound of the present invention pharmaceutical salt thereof, optionally in a pharmaceutical composition as described herein is used to degrade Ikaros or Aiolos, which is a mediator of the disorder affecting the patient, such as a human. The control of protein level afforded by any of the compounds of the present invention provides treatment of a disease state or condition, which is modulated through Ikaros or Aiolos by lowering the level of that protein in the cell, e.g., cell of a patient, or by lowering the level of downstream proteins in the cell. In certain embodiments, the method comprises administering an effective amount of the compound as described herein, optionally including a pharmaceutically acceptable excipient, carrier, adjuvant (i.e., a pharmaceutically acceptable composition), optionally in combination or alternation with an additional therapeutically active agent or combination of agents.

In one embodiment, a compound of the present invention is used to treat a disorder including, but not limited to, benign growth, neoplasm, tumor, cancer, abnormal cellular proliferation, immune disorder, inflammatory disorder, graft-versus-host rejection, viral infection, bacterial infection, an amyloid-based proteinopathy, a proteinopathy, or a fibrotic disorder.

The term "disease state" or "condition" when used in connection with any of the compounds is meant to refer to any disease state or condition that is mediated by Ikaros or Aiolos, such as cellular proliferation, or by proteins that are downstream of Ikaros or Aiolos, and where degradation of such protein in a patient may provide beneficial therapy or relief of symptoms to a patient in need thereof. In certain instances, the disease state or condition may be cured.

In one embodiment, a compound or its corresponding pharmaceutically acceptable salt, isotopic derivative, or prodrug as described herein can be used in an effective amount to treat a host, for example a human, with a lymphoma or lymphocytic or myelocytic proliferation disorder or abnormality. For example, a compound as described herein can be administered to a host suffering from a Hodgkin Lymphoma or a Non-Hodgkin Lymphoma. For example, the host can be suffering from a Non-Hodgkin Lymphoma such as, but not limited to: an AIDS-Related Lymphoma; Anaplastic Large-Cell Lymphoma; Angioimmunoblastic Lymphoma; Blastic NK-Cell Lymphoma; Burkitt's Lymphoma; Burkitt-like Lymphoma (Small Non-Cleaved Cell Lymphoma); diffuse small-cleaved cell lymphoma (DSCCL); Chronic Lymphocytic Leukemia/Small Lymphocytic Lymphoma; Cutaneous T-Cell Lymphoma; Diffuse Large B-Cell Lymphoma; Enteropathy-Type T-Cell Lymphoma; Follicular Lymphoma; Hepatosplenic Gamma-Delta T-Cell Lymphoma; Lymphoblastic Lymphoma; Mantle Cell Lymphoma; Marginal Zone Lymphoma; Nasal T-Cell Lymphoma; Pediatric Lymphoma; Peripheral T-Cell Lymphomas; Primary Central Nervous System Lymphoma; T-Cell Leukemias; Transformed Lymphomas; Treatment-Related T-Cell Lymphomas; Langerhans cell histiocytosis; or Waldenstrom's Macroglobulinemia.

In another embodiment, a compound or its corresponding pharmaceutically acceptable salt, isotopic derivative, or prodrug as described herein can be used in an effective amount to treat a host, for example a human, with a Hodgkin lymphoma, such as, but not limited to: Nodular Sclerosis Classical Hodgkin's Lymphoma (CHL); Mixed Cellularity CHL; Lymphocyte-depletion CHL; Lymphocyte-rich CHL; Lymphocyte Predominant Hodgkin Lymphoma; or Nodular Lymphocyte Predominant HL.

In another embodiment, a compound or its corresponding pharmaceutically acceptable salt, isotopic derivative, or prodrug as described herein can be used in an effective amount to treat a host, for example a human, with an immunomodulatory condition. Non-limiting examples of immunomodulatory conditions include: arthritis, lupus, celiac disease, Sjogren's syndrome, polymyalgia rheumatia, multiple sclerosis, ankylosing spondylitis, type 1 diabetes, alopecia areata, vasculitis, and temporal arteritis.

In certain embodiments, the condition treated with a compound of the present invention is a disorder related to abnormal cellular proliferation. Abnormal cellular proliferation, notably hyperproliferation, can occur as a result of a wide variety of factors, including genetic mutation, infection, exposure to toxins, autoimmune disorders, and benign or malignant tumor induction.

Abnormal proliferation of B-cells, T-cells, and/or NK cells can result in a wide range of diseases such as cancer, proliferative disorders and inflammatory/immune diseases. A host, for example a human, afflicted with any of these disorders can be treated with an effective amount of a compound as described herein to achieve a decrease in symptoms (palliative agent) or a decrease in the underlying disease (a disease modifying agent).

In one embodiment, a compound or its corresponding pharmaceutically acceptable salt, isotopic derivative, or prodrug as described herein can be used in an effective amount to treat a host, for example a human, with a specific B-cell lymphoma or proliferative disorder such as, but not limited to: multiple myeloma; Diffuse large B cell lymphoma; Follicular lymphoma; Mucosa-Associated Lymphatic Tissue lymphoma (MALT); Small cell lymphocytic lymphoma; diffuse poorly differentiated lymphocytic lymphoma; Mediastinal large B cell lymphoma; Nodal marginal zone B cell lymphoma (NMZL); Splenic marginal zone lymphoma (SMZL); Intravascular large B-cell lymphoma; Primary effusion lymphoma; or Lymphomatoid granulomatosis; B-cell prolymphocytic leukemia; Hairy cell leukemia; Splenic lymphoma/leukemia, unclassifiable; Splenic diffuse red pulp small B-cell lymphoma; Hairy cell leukemia-variant; Lymphoplasmacytic lymphoma; Heavy chain diseases, for example, Alpha heavy chain disease, Gamma heavy chain disease, Mu heavy chain disease; Plasma cell myeloma; Solitary plasmacytoma of bone; Extraosseous plasmacytoma; Primary cutaneous follicle center lymphoma; T cell/histiocyte rich large B-cell lymphoma; DLBCL associated with chronic inflammation; Epstein-Barr virus (EBV)+ DLBCL of the elderly; Primary mediastinal (thymic) large B-cell lymphoma; Primary cutaneous DLBCL, leg type; ALK+ large B-cell lymphoma; Plasmablastic lymphoma; Large B-cell lymphoma arising in HHV8-associated multicentric; Castleman disease; B-cell lymphoma, unclassifiable, with features intermediate between diffuse large B-cell lymphoma; or B-cell lymphoma, unclassifiable, with features intermediate between diffuse large B-cell lymphoma and classical Hodgkin lymphoma.

In one embodiment, a compound or its corresponding pharmaceutically salt, isotopic derivative, or prodrug as described herein can be used in an effective amount to treat a host, for example a human, with a T-cell or NK-cell lymphoma such as, but not limited to: anaplastic lymphoma kinase (ALK) positive, ALK negative anaplastic large cell lymphoma, or primary cutaneous anaplastic large cell lymphoma; angioimmunoblastic lymphoma; cutaneous T-cell lymphoma, for example mycosis fungoides, Sézary syndrome, primary cutaneous anaplastic large cell lymphoma, primary cutaneous CD30+ T-cell lymphoproliferative disorder; primary cutaneous aggressive epidermotropic CD8+ cytotoxic T-cell lymphoma; primary cutaneous gamma-delta T-cell lymphoma; primary cutaneous small/medium CD4+ T-cell lymphoma, and lymphomatoid papulosis; Adult T-cell Leukemia/Lymphoma (ATLL); Blastic NK-cell Lymphoma; Enteropathy-type T-cell lymphoma; Hematosplenic gamma-delta T-cell Lymphoma; Lymphoblastic Lymphoma; Nasal NK/T-cell Lymphomas; Treatment-related T-cell lymphomas; for example lymphomas that appear after solid organ or bone marrow transplantation; T-cell prolymphocytic leukemia; T-cell large granular lymphocytic leukemia; Chronic lymphoproliferative disorder of NK-cells; Aggressive NK cell leukemia; Systemic EBV+ T-cell lymphoproliferative disease of childhood (associated with chronic active EBV infection); Hydroa vacciniforme-like lymphoma; Adult T-cell leukemia/lymphoma; Enteropathy-associated T-cell lymphoma; Hepatosplenic T-cell lymphoma; or Subcutaneous panniculitis-like T-cell lymphoma.

In one embodiment, a compound or its corresponding pharmaceutically acceptable salt, isotopic derivative, or prodrug as described herein can be used to treat a host, for example a human, with leukemia. For example, the host may be suffering from an acute or chronic leukemia of a lymphocytic or myelogenous origin, such as, but not limited to: Acute lymphoblastic leukemia (ALL); Acute myelogenous leukemia (AML); Chronic lymphocytic leukemia (CLL); Chronic myelogenous leukemia (CML); juvenile myelomonocytic leukemia (JMML); hairy cell leukemia (HCL); acute promyelocytic leukemia (a subtype of AML); large granular lymphocytic leukemia; or Adult T-cell chronic leukemia. In one embodiment, the patient suffers from an acute myelogenous leukemia, for example an undifferentiated AML (M0); myeloblastic leukemia (M1; with/without minimal cell maturation); myeloblastic leukemia (M2; with cell maturation); promyelocytic leukemia (M3 or M3 variant [M3V]); myelomonocytic leukemia (M4 or M4 variant with eosinophilia [M4E]); monocytic leukemia (M5); erythroleukemia (M6); or megakaryoblastic leukemia (M7).

There are a number of skin disorders associated with cellular hyperproliferation. Psoriasis, for example, is a benign disease of human skin generally characterized by plaques covered by thickened scales. The disease is caused by increased proliferation of epidermal cells of unknown cause. Chronic eczema is also associated with significant hyperproliferation of the epidermis.

Other diseases caused by hyperproliferation of skin cells include atopic dermatitis, lichen planus, warts, pemphigus vulgaris, actinic keratosis, basal cell carcinoma and squamous cell carcinoma.

Other hyperproliferative cell disorders include blood vessel proliferation disorders, fibrotic disorders, autoimmune disorders, graft-versus-host rejection, tumors and cancers.

Blood vessel proliferative disorders include angiogenic and vasculogenic disorders. Proliferation of smooth muscle cells in the course of development of plaques in vascular tissue cause, for example, restenosis, retinopathies and atherosclerosis. Both cell migration and cell proliferation play a role in the formation of atherosclerotic lesions.

Fibrotic disorders are often due to the abnormal formation of an extracellular matrix. Examples of fibrotic disorders include hepatic cirrhosis and mesangial proliferative cell disorders. Hepatic cirrhosis is characterized by the increase in extracellular matrix constituents resulting in the formation of a hepatic scar. Hepatic cirrhosis can cause diseases such as cirrhosis of the liver. An increased extracellular matrix resulting in a hepatic scar can also be caused by viral infection such as hepatitis. Lipocytes appear to play a major role in hepatic cirrhosis.

Mesangial disorders are brought about by abnormal proliferation of mesangial cells. Mesangial hyperproliferative cell disorders include various human renal diseases, such as glomerulonephritis, diabetic nephropathy, malignant nephrosclerosis, thrombotic micro-angiopathy syndromes, transplant rejection, and glomerulopathies.

Another disease with a proliferative component is rheumatoid arthritis. Rheumatoid arthritis is generally considered an autoimmune disease that is thought to be associated with activity of autoreactive T cells, and to be caused by autoantibodies produced against collagen and IgE.

Other disorders that can include an abnormal cellular proliferative component include Bechet's syndrome, acute respiratory distress syndrome (ARDS), ischemic heart disease, post-dialysis syndrome, leukemia, acquired immune deficiency syndrome, vasculitis, lipid histiocytosis, septic shock and inflammation in general.

A compound or its pharmaceutically acceptable salt, isotopic analog, or prodrug as described herein can be used in an effective amount to treat a host, for example a human, with a proliferative condition such as myeloproliferative disorder (MPD), polycythemia vera (PV), essential thrombocythemia (ET), myeloid metaplasia with myelofibrosis (MMM), chronic myelomonocytic leukemia (CMML), hypereosinophilic syndrome (HES), system mast cell disease (SMCD), and the like. In another embodiment, a compound provided herein is useful for the treatment of primary myelofibrosis, post-polycythemia vera myelofibrosis, post-essential thrombocythemia myelofibrosis, and secondary acute myelogenous leukemia.

In one embodiment, a compound or its pharmaceutically acceptable salt, isotopic analog, or prodrug as described herein can be used in an effective amount to treat a host, for example a human, with a myelodysplastic syndrome (MDS) such as, but not limited to: refractory cytopenia with unilineage dysplasia, refractory anemia with ring sideroblasts (RARS), refractory anemia with ring sideroblasts-thrombocytosis (RARS-t), refractory cytopenia with multilineage dyslplasia (RCMD) including RCMD with multilineage dysplasia and ring sideroblasts (RCMD-RS), Refractory amenias with excess blasts I (RAEB-I) and II (RAEB-II), 5q-syndrome, refractory cytopenia of childhood, and the like.

In one embodiment a compound of the present invention can provide a therapeutic effect by direct degradation of Ikaros or Aiolos which may change the transcriptional regulation of a protein downstream of Ikaros or Aiolos.

The term "neoplasia" or "cancer" is used to refer to the pathological process that results in the formation and growth of a cancerous or malignant neoplasm, i.e., abnormal tissue that grows by cellular proliferation, often more rapidly than normal and continues to grow after the stimuli that initiated the new growth cease. Malignant neoplasms show partial or complete lack of structural organization and functional coordination with the normal tissue and most invade surrounding tissues, metastasize to several sites, and are likely to recur after attempted removal and to cause the death of the patient unless adequately treated. As used herein, the term neoplasia is used to describe all cancerous disease states and embraces or encompasses the pathological process associated with malignant hematogenous, ascitic and solid tumors. Exemplary cancers which may be treated by the present compounds either alone or in combination with at least one additional anti-cancer agent include squamous-cell carcinoma, basal cell carcinoma, adenocarcinoma, hepatocellular carcinomas, and renal cell carcinomas, cancer of the bladder, bowel, breast, cervix, colon, esophagus, head, kidney, liver, lung, neck, ovary, pancreas, prostate, and stomach; leukemias; benign and malignant lymphomas, particularly Burkitt's lymphoma and Non-Hodgkin's lymphoma; benign and malignant melanomas; myeloproliferative diseases; sarcomas, including Ewing's sarcoma, hemangiosarcoma, Kaposi's sarcoma, liposarcoma, myosarcomas, peripheral neuroepithelioma, synovial sarcoma, gliomas, astrocytomas, oligodendrogliomas, ependymomas, gliobastomas, neuroblastomas, ganglioneuromas, gangliogliomas, medulloblastomas, pineal cell tumors, meningiomas, meningeal sarcomas, neurofibromas, and Schwannomas; bowel cancer, breast cancer, prostate cancer, cervical cancer, uterine cancer, lung cancer, ovarian cancer, testicular cancer, thyroid cancer, astrocytoma, esophageal cancer, pancreatic cancer, stomach cancer, liver cancer, colon cancer, melanoma; carcinosarcoma, Hodgkin's disease, Wilms' tumor and teratocarcinomas. Additional cancers which may be treated using compounds according to the present invention include, for example, T-lineage Acute lymphoblastic Leukemia (T-ALL), T-lineage lymphoblastic Lymphoma (T-LL), Peripheral T-cell lymphoma, Adult T-cell Leukemia, Pre-B ALL, Pre-B Lymphomas, Large B-cell Lymphoma, Burkitts Lymphoma, B-cell ALL, Philadelphia chromosome positive ALL and Philadelphia chromosome positive CML.

Additional cancers which may be treated using the disclosed compounds according to the present invention include, for example, acute granulocytic leukemia, acute lymphocytic leukemia (ALL), acute myelogenous leukemia (AML), adenocarcinoma, adenosarcoma, adrenal cancer, adrenocortical carcinoma, anal cancer, anaplastic astrocytoma, angiosarcoma, appendix cancer, astrocytoma, Basal cell carcinoma, B-Cell lymphoma, bile duct cancer, bladder cancer, bone cancer, bone marrow cancer, bowel cancer, brain cancer, brain stem glioma, breast cancer, triple (estrogen, progesterone and HER-2) negative breast cancer, double negative breast cancer (two of estrogen, progesterone and HER-2 are negative), single negative (one of estrogen, progesterone and HER-2 is negative), estrogen-receptor positive, HER2-negative breast cancer, estrogen receptor-negative breast cancer, estrogen receptor positive breast cancer, metastatic breast cancer, luminal A breast cancer, luminal B breast cancer, Her2-negative breast cancer, HER2-positive or negative breast cancer, progesterone receptor-negative breast cancer, progesterone receptor-positive breast cancer, recurrent breast cancer, carcinoid tumors, cervical cancer, cholangiocarcinoma, chondrosarcoma, chronic lymphocytic leukemia (CLL), chronic myelogenous leukemia (CML), colon cancer, colorectal cancer, craniopharyngioma, cutaneous lymphoma, cutaneous melanoma, diffuse astrocytoma, ductal carcinoma in situ (DCIS), endometrial cancer, ependymoma, epithelioid sarcoma, esophageal cancer, ewing sarcoma, extrahepatic bile duct cancer, eye cancer, fallopian tube cancer, fibrosarcoma, gallbladder cancer, gastric cancer, gastrointestinal cancer, gastrointestinal carcinoid cancer, gastrointestinal stromal tumors (GIST), germ cell tumor glioblastoma multiforme (GBM), glioma, hairy cell leukemia, head and neck cancer, hemangioendothelioma, Hodgkin lymphoma, hypopharyngeal cancer, infiltrating ductal carcinoma (IDC), infiltrating lobular carcinoma (ILC), inflammatory breast cancer (IBC), intestinal Cancer, intrahepatic bile duct cancer, invasive/infiltrating breast cancer, Islet cell cancer, jaw cancer, Kaposi sarcoma, kidney cancer, laryngeal cancer, leiomyosarcoma, leptomeningeal metastases, leukemia, lip cancer, liposarcoma, liver cancer, lobular carcinoma in situ, low-grade astrocytoma, lung cancer, lymph node cancer, lymphoma, male breast cancer, medullary carcinoma, medulloblastoma, melanoma, meningioma, Merkel cell carcinoma, mesenchymal chondrosarcoma, mesenchymous, mesothelioma metastatic breast cancer, metastatic melanoma metastatic squamous neck cancer, mixed gliomas, monodermal teratoma, mouth cancer mucinous carcinoma, mucosal melanoma, multiple myeloma, Mycosis Fungoides, myelodysplastic syndrome, nasal cavity cancer, nasopharyngeal cancer, neck cancer, neuroblastoma, neuroendocrine tumors (NETs), non-Hodgkin's lymphoma, non-small cell lung cancer (NSCLC), oat cell cancer, ocular cancer, ocular melanoma, oligodendroglioma, oral cancer, oral cavity cancer, oropharyngeal cancer, osteogenic sarcoma, osteosarcoma, ovarian cancer, ovarian epithelial cancer ovarian germ cell tumor, ovarian primary peritoneal carcinoma, ovarian sex cord stromal tumor, Paget's disease, pancreatic cancer, papillary carcinoma, paranasal sinus cancer, parathyroid cancer, pelvic cancer, penile cancer, peripheral nerve cancer, peritoneal cancer, pharyngeal cancer, pheochromocytoma, pilocytic astrocytoma, pineal region tumor, pineoblastoma, pituitary gland cancer, primary central nervous system (CNS) lymphoma, prostate cancer, rectal cancer, renal cell carcinoma, renal pelvis cancer, rhabdomyosarcoma, salivary gland cancer, soft tissue sarcoma, bone sarcoma, sarcoma, sinus cancer, skin cancer, small cell lung cancer (SCLC), small intestine cancer, spinal cancer, spinal column cancer, spinal cord cancer, squamous cell carcinoma, stomach cancer, synovial sarcoma, T-cell lymphoma, testicular cancer, throat cancer, thymoma/thymic carcinoma, thyroid cancer, tongue cancer, tonsil cancer, transitional cell cancer, tubal cancer, tubular carcinoma, undiagnosed cancer, ureteral cancer, urethral cancer, uterine adenocarcinoma, uterine cancer, uterine sarcoma, vaginal cancer, vulvar cancer, T-cell lineage acute lymphoblastic leukemia (T-ALL), T-cell lineage lymphoblastic lymphoma (T-LL), peripheral T-cell lymphoma, Adult T-cell leukemia, Pre-B ALL, Pre-B lymphomas, large B-cell lymphoma, Burkitts lymphoma, B-cell ALL, Philadelphia chromosome positive ALL, Philadelphia chromosome positive CML, juvenile myelomonocytic leukemia (JMML), acute promyelocytic leukemia (a subtype of AML), large granular lymphocytic leukemia, Adult T-cell chronic leukemia, diffuse large B cell lymphoma, follicular lymphoma; Mucosa-Associated Lymphatic Tissue lymphoma (MALT), small cell lymphocytic lymphoma, mediastinal large B cell lymphoma, nodal marginal zone B cell lymphoma (NMZL); splenic marginal zone lymphoma (SMZL); intravascular large B-cell lymphoma; primary effusion lymphoma; or lymphomatoid granulomatosis; B-cell prolymphocytic leukemia; splenic lymphoma/leukemia, unclassifiable, splenic diffuse red pulp small B-cell lymphoma; lymphoplasmacytic lymphoma; heavy chain diseases, for example, Alpha heavy chain disease, Gamma heavy chain disease, Mu heavy chain disease, plasma cell myeloma, solitary plasmacytoma of bone; extraosseous plasmacytoma; primary cutaneous follicle center lymphoma, T cell/histocyte rich large B-cell lymphoma, DLBCL associated with chronic inflammation; Epstein-Barr virus (EBV)+ DLBCL of the elderly; primary mediastinal (thymic) large B-cell lymphoma, primary cutaneous DLBCL, leg type, ALK+ large B-cell lymphoma, plasmablastic lymphoma; large B-cell lymphoma arising in HHV8-associated multicentric, Castleman disease; B-cell lymphoma, unclassifiable, with features intermediate between diffuse large B-cell lymphoma, or B-cell lymphoma, unclassifiable, with features intermediate between diffuse large B-cell lymphoma and classical Hodgkin lymphoma. In one embodiment the disorder is adenoid cystic carcinoma. In one embodiment the disorder is NUT midline carcinoma.

In another embodiment, a compound or its pharmaceutically acceptable salt, isotopic derivative or prodrug as described herein can be used in an effective amount to treat a host, for example a human, with an autoimmune disorder. Examples include, but are not limited to: Acute disseminated encephalomyelitis (ADEM); Addison's disease; Agammaglobulinemia; Alopecia areata; Amyotrophic lateral sclerosis (Also Lou Gehrig's disease; Motor Neuron Disease); Ankylosing Spondylitis; Antiphospholipid syndrome; Antisynthetase syndrome; Atopic allergy; Atopic dermatitis; Autoimmune aplastic anemia; Autoimmune arthritis; Autoimmune cardiomyopathy; Autoimmune enteropathy; Autoimmune granulocytopenia; Autoimmune hemolytic anemia; Autoimmune hepatitis; Autoimmune hypoparathyroidism; Autoimmune inner ear disease; Autoimmune lymphoproliferative syndrome; Autoimmune myocarditis; Autoimmune pancreatitis; Autoimmune peripheral neuropathy; Autoimmune ovarian failure; Autoimmune polyendocrine syndrome; Autoimmune progesterone dermatitis; Autoimmune thrombocytopenic purpura; Autoimmune thyroid disorders; Autoimmune urticarial; Autoimmune uveitis; Autoimmune vasculitis; Balo disease/Balo concentric sclerosis; Behçet's disease; Berger's disease; Bickerstaff s encephalitis; Blau syndrome; Bullous pemphigoid; Cancer; Castleman's disease; Celiac disease; Chagas disease; Chronic inflammatory demyelinating polyneuropathy; Chronic inflammatory demyelinating polyneuropathy; Chronic obstructive pulmonary disease; Chronic recurrent multifocal osteomyelitis; Churg-Strauss syndrome; Cicatricial pemphigoid; Cogan syndrome; Cold agglutinin disease; Complement component 2 deficiency; Contact dermatitis; Cranial arteritis; CREST syndrome; Crohn's disease; Cushing's Syndrome; Cutaneous leukocytoclastic angiitis; Dego's disease; Dercum's disease; Dermatitis herpetiformis; Dermatomyositis; Diabetes mellitus type 1; Diffuse cutaneous systemic sclerosis; Discoid lupus erythematosus; Dressler's syndrome; Drug-induced lupus; Eczema; Endometriosis; Enthesitis-related arthritis; Eosinophilic fasciitis; Eosinophilic gastroenteritis; Eosinophilic pneumonia; Epidermolysis bullosa acquisita; Erythema nodosum; Erythroblastosis fetalis; Essential mixed cryoglobulinemia; Evan's syndrome; Extrinsic and intrinsic reactive airways disease (asthma); Fibrodysplasia ossificans progressive; Fibrosing alveolitis (or Idiopathic pulmonary fibrosis); Gastritis; Gastrointestinal pemphigoid; Glomerulonephritis; Goodpasture's syndrome; Graves' disease; Guillain-Barre syndrome (GBS); Hashimoto's encephalopathy; Hashimoto's thyroiditis; Hemolytic anemia; Henoch-Schonlein purpura; Herpes gestationis (Gestational Pemphigoid); Hidradenitis suppurativa; Hughes-Stovin syndrome; Hypogammaglobulinemia; Idiopathic inflammatory demyelinating diseases; Idiopathic pulmonary fibrosis; Idiopathic thrombocytopenic purpura; IgA nephropathy; Immune glomerulonephritis; Immune nephritis; Immune pneumonitis; Inclusion body myositis; inflammatory bowel disease; Interstitial cystitis; Juvenile idiopathic arthritis aka Juvenile rheumatoid arthritis; Kawasaki's disease; Lambert-Eaton myasthenic syndrome; Leukocytoclastic vasculitis; Lichen planus; Lichen sclerosus; Linear IgA disease (LAD); Lupoid hepatitis aka Autoimmune hepatitis; Lupus erythematosus; Majeed syndrome; microscopic polyangiitis; Miller-Fisher syndrome; mixed connective tissue disease; Morphea; Mucha-Habermann disease aka Pityriasis lichenoides et varioliformis acuta; Multiple sclerosis; Myasthenia gravis; Myositis; Ménière's disease; Narcolepsy; Neuromyelitis optica (also Devic's disease); Neuromyotonia; Occular cicatricial pemphigoid; Opsoclonus myoclonus syndrome; Ord's thyroiditis; Palindromic rheumatism; PANDAS (pediatric autoimmune neuropsychiatric disorders associated with *streptococcus*); Paraneoplastic cerebellar degeneration; Paroxysmal nocturnal hemoglobinuria (PNH); Parry Romberg syndrome; Pars planitis; Parsonage-Turner syndrome; Pemphigus vulgaris; Perivenous encephalomyelitis; Pernicious anaemia; POEMS syndrome; Polyarteritis nodosa; Polymyalgia rheumatic; Polymyositis; Primary biliary cirrhosis; Primary sclerosing cholangitis; Progressive inflammatory neuropathy; Psoriasis; Psoriatic arthritis; pure red cell aplasia; Pyoderma gangrenosum; Rasmussen's encephalitis; Raynaud phenomenon; Reiter's syndrome; relapsing polychondritis; restless leg syndrome; retroperitoneal fibrosis; rheumatic fever; rheumatoid arthritis; Sarcoidosis; Schizophrenia; Schmidt syndrome; Schnitzler syndrome; Scleritis; Scleroderma; Sclerosing cholangitis; serum sickness; Sjögren's syndrome; Spondyloarthropathy; Stiff person syndrome; Still's disease; Subacute bacterial endocarditis (SBE); Susac's syndrome; Sweet's syndrome; Sydenham chorea; sympathetic ophthalmia; systemic lupus erythematosus; Takayasu's arteritis; temporal arteritis (also known as "giant cell arteritis"); thrombocytopenia; Tolosa-Hunt syndrome; transverse myelitis; ulcerative colitis; undifferentiated connective tissue disease; undifferentiated spondyloarthropathy; urticarial vasculitis; vasculitis; vitiligo; viral diseases such as Epstein Barr Virus (EBV), Hepatitis B, Hepatitis C, HIV, HTLV 1, Varicella-Zoster Virus (VZV) and Human Papilloma Virus (HPV); or Wegener's granulomatosis. In some embodiments, the autoimmune disease is an allergic condition, including those from asthma, food allergies, atopic dermatitis, chronic pain, and rhinitis.

Cutaneous contact hypersensitivity and asthma are just two examples of immune responses that can be associated with significant morbidity. Others include atopic dermatitis, eczema, Sjogren's Syndrome, including keratoconjunctivitis sicca secondary to Sjogren's Syndrome, alopecia areata, allergic responses due to arthropod bite reactions, Crohn's disease, aphthous ulcer, iritis, conjunctivitis, keratoconjunctivitis, ulcerative colitis, cutaneous lupus erythematosus, scleroderma, vaginitis, proctitis, and drug eruptions. These conditions may result in any one or more of the following symptoms or signs: itching, swelling, redness, blisters, crusting, ulceration, pain, scaling, cracking, hair loss, scarring, or oozing of fluid involving the skin, eye, or mucosal membranes.

In atopic dermatitis, and eczema in general, immunologically mediated leukocyte infiltration (particularly infiltration of mononuclear cells, lymphocytes, neutrophils, and eosinophils) into the skin importantly contributes to the pathogenesis of these diseases. Chronic eczema also is associated with significant hyperproliferation of the epidermis. Immunologically mediated leukocyte infiltration also occurs at sites other than the skin, such as in the airways in asthma and in the tear producing gland of the eye in keratoconjunctivitis sicca.

A compound or its pharmaceutically acceptable salt, isotopic variant, or prodrug as described herein can be used in an effective amount to treat a host, for example a human, with a skin disorder such as psoriasis (for example, psoriasis vulgaris), atopic dermatitis, skin rash, skin irritation, skin sensitization (e.g., contact dermatitis or allergic contact dermatitis). For example, certain substances including some pharmaceuticals when topically applied can cause skin sensitization. In some embodiments, the skin disorder is treated by topical administration of compounds known in the art in combination with the compounds disclosed herein. In one non-limiting embodiment compounds of the present invention are used as topical agents in treating contact dermatitis, atopic dermatitis, eczematous dermatitis, psoriasis, Sjogren's Syndrome, including keratoconjunctivitis sicca secondary to Sjogren's Syndrome, alopecia areata, allergic responses due to arthropod bite reactions, Crohn's disease, aphthous ulcer, iritis, conjunctivitis, keratoconjunctivitis, ulcerative colitis, asthma, allergic asthma, cutaneous lupus erythematosus, scleroderma, vaginitis, proctitis, and drug eruptions. The novel method may also be useful in reducing the infiltration of skin by malignant leukocytes in diseases such as mycosis fungoides.

Disease states of conditions which may be treated using compounds according to the present invention include, for example, asthma, autoimmune diseases such as multiple sclerosis, various cancers, ciliopathies, cleft palate, diabetes, heart disease, hypertension, inflammatory bowel disease, mental retardation, mood disorder, obesity, refractive error, infertility, Angelman syndrome, Canavan disease, Coeliac disease, Charcot-Marie-Tooth disease, Cystic fibrosis, Duchenne muscular dystrophy, Haemochromatosis, Haemophilia, Klinefelter's syndrome, Neurofibromatosis, Phenylketonuria, Polycystic kidney disease 1 (PKD1) or 2 (PKD2) Prader-Willi syndrome, Sickle-cell disease, Tay-Sachs disease, Turner syndrome.

Further disease states or conditions which may be treated by compounds according to the present invention include Alzheimer's disease, Amyotrophic lateral sclerosis (Lou Gehrig's disease), Anorexia nervosa, Anxiety disorder, Atherosclerosis, Attention deficit hyperactivity disorder, Autism, Bipolar disorder, Chronic fatigue syndrome, Chronic obstructive pulmonary disease, Crohn's disease, Coronary heart disease, Dementia, Depression, Diabetes mellitus type 1, Diabetes mellitus type 2, Epilepsy, Guillain-Barre syndrome, Irritable bowel syndrome, Lupus, Metabolic syndrome, Multiple sclerosis, Myocardial infarction, Obesity, Obsessive-compulsive disorder, Panic disorder, Parkinson's disease, Psoriasis, Rheumatoid arthritis, Sarcoidosis, Schizophrenia, Stroke, Thromboangiitis obliterans, Tourette syndrome, Vasculitis.

Still additional disease states or conditions which can be treated by compounds according to the present invention include aceruloplasminemia, Achondrogenesis type II, achondroplasia, Acrocephaly, Gaucher disease type 2, acute intermittent porphyria, Canavan disease, Adenomatous Polyposis Coli, ALA dehydratase deficiency, adenylosuccinate lyase deficiency, Adrenogenital syndrome, Adrenoleukodystrophy, ALA-D porphyria, ALA dehydratase deficiency, Alkaptonuria, Alexander disease, Alkaptonuric ochronosis, alpha 1-antitrypsin deficiency, alpha-1 proteinase inhibitor, emphysema, amyotrophic lateral sclerosis Alström syndrome, Alexander disease, Amelogenesis imperfecta, ALA dehydratase deficiency, Anderson-Fabry disease, androgen insensitivity syndrome, Anemia Angiokeratoma Corporis Diffusum, Angiomatosis retinae (von Hippel-Lindau disease) Apert syndrome, Arachnodactyly (Marfan syndrome), Stickler syndrome, Arthrochalasis multiplex congenital (Ehlers-Danlos syndrome #arthrochalasia type) ataxia telangiectasia, Rett syndrome, primary pulmonary hypertension, Sandhoff disease, neurofibromatosis type II, Beare-Stevenson cutis gyrata syndrome, Mediterranean fever, familial, Benjamin syndrome, beta-thalassemia, Bilateral Acoustic Neurofibromatosis (neurofibromatosis type II), factor V Leiden thrombophilia, Bloch-Sulzberger syndrome (incontinentia pigmenti), Bloom syndrome, X-linked sideroblastic anemia, Bonnevie-Ullrich syndrome (Turner syndrome), Bourneville disease (tuberous sclerosis), prion disease, Birt-Hogg-Dubé syndrome, Brittle bone disease (osteogenesis imperfecta), Broad Thumb-Hallux syndrome (Rubinstein-Taybi syndrome), Bronze Diabetes/Bronzed Cirrhosis (hemochromatosis), Bulbospinal muscular atrophy (Kennedy's disease), Burger-Grutz syndrome (lipoprotein lipase deficiency), CGD Chronic granulomatous disorder, Campomelic dysplasia, biotinidase deficiency, Cardiomyopathy (Noonan syndrome), Cri du chat, CAVD (congenital absence of the vas deferens), Caylor cardiofacial syndrome (CBAVD), CEP (congenital erythropoietic porphyria), cystic fibrosis, congenital hypothyroidism, Chondrodystrophy syndrome (achondroplasia), otospondylomegaepiphyseal dysplasia, Lesch-Nyhan syndrome, galactosemia, Ehlers-Danlos syndrome, Thanatophoric dysplasia, Coffin-Lowry syndrome, Cockayne syndrome, (familial adenomatous polyposis), Congenital erythropoietic porphyria, Congenital heart disease, Methemoglobinemia/Congenital methaemoglobinaemia, achondroplasia, X-linked sideroblastic anemia, Connective tissue disease, Conotruncal anomaly face syndrome, Cooley's Anemia (beta-thalassemia), Copper storage disease (Wilson's disease), Copper transport disease (Menkes disease), hereditary coproporphyria, Cowden syndrome, Craniofacial dysarthrosis (Crouzon syndrome), Creutzfeldt-Jakob disease (prion disease), Cockayne syndrome, Cowden syndrome, Curschmann-Batten-Steinert syndrome (myotonic dystrophy), Beare-Stevenson cutis gyrata syndrome, primary hyperoxaluria, spondyloepimetaphyseal dysplasia (Strudwick type), muscular dystrophy, Duchenne and Becker types (DBMD), Usher syndrome, Degenerative nerve diseases including de Grouchy syndrome and Dejerine-Sottas syndrome, developmental disabilities, distal spinal muscular atrophy, type V, androgen insensitivity syndrome, Diffuse Globoid Body Sclerosis (Krabbe disease), Di George's syndrome, Dihydrotestosterone receptor deficiency, androgen insensitivity syndrome, Down syndrome, Dwarfism, erythropoietic protoporphyria Erythroid 5-aminolevulinate synthetase deficiency, Erythropoietic porphyria, erythropoietic protoporphyria, erythropoietic uroporphyria, Friedreich's ataxia-familial paroxysmal polyserositis, porphyria cutanea tarda, familial pressure sensitive neuropathy, primary pulmonary hypertension (PPH), Fibrocystic disease of the pancreas, fragile X syndrome, galactosemia, genetic brain disorders, Giant cell hepatitis (Neonatal hemochromatosis), Gronblad-Strandberg syndrome (pseudoxanthoma elasticum), Gunther disease (congenital erythropoietic porphyria), haemochromatosis, Hallgren syndrome, sickle cell anemia, hemophilia, hepatoerythropoietic porphyria (HEP), Hippel-Lindau disease (von Hippel-Lindau disease), Huntington's disease, Hutchinson-Gilford progeria syndrome (progeria), Hyperandrogenism, Hypochondroplasia, Hypochromic anemia, Immune system disorders, including X-linked severe combined immunodeficiency, Insley-Astley syndrome, Jackson-Weiss syndrome, Joubert syndrome, Lesch-Nyhan syndrome, Jackson-Weiss syndrome, Kidney diseases, including hyperoxaluria, Klinefelter's syndrome, Kniest dysplasia, Lacunar dementia, Langer-Saldino achondrogenesis, ataxia telangiectasia, Lynch syndrome, Lysyl-hydroxylase deficiency, Machado-Joseph disease, Metabolic disorders, including Kniest dysplasia, Marfan syndrome, Movement disorders, Mowat-Wilson syndrome, cystic fibrosis, Muenke syndrome, Multiple neurofibromatosis, Nance-Insley syndrome, Nance-Sweeney chondrodysplasia, Niemann-Pick disease, Noack syndrome (Pfeiffer syndrome), Osler-Weber-Rendu disease, Peutz-Jeghers syndrome, Polycystic kidney disease, polyostotic fibrous dysplasia (McCune-Albright syndrome), Peutz-Jeghers syndrome, Prader-Labhart-Willi syndrome, hemochromatosis, primary hyperuricemia syndrome (Lesch-Nyhan syndrome), primary pulmonary hypertension, primary senile degenerative dementia, prion disease, progeria (Hutchinson Gilford Progeria Syndrome), progressive chorea, chronic hereditary (Huntington) (Huntington's disease), progressive muscular atrophy, spinal muscular atrophy, propionic acidemia, protoporphyria, proximal myotonic dystrophy, pulmonary arterial hypertension, PXE (pseudoxanthoma elasticum), Rb (retinoblastoma), Recklinghausen disease (neurofibromatosis type I), Recurrent polyserositis, Retinal disorders, Retinoblastoma, Rett syndrome, RFALS type 3, Ricker syndrome, Riley-Day syndrome, Roussy-Levy syndrome, severe achondroplasia with developmental delay and acanthosis nigricans (SADDAN), Li-Fraumeni syndrome, sarcoma, breast, leukemia, and adrenal gland (SBLA) syndrome, sclerosis tuberose (tuberous sclerosis), SDAT, SED congenital (spondyloepiphyseal dysplasia congenita), SED Strudwick (spondyloepimetaphyseal dysplasia, Strudwick type), SEDc (spondyloepiphyseal dysplasia congenita) SEMD, Strudwick type (spondyloepimetaphyseal dysplasia, Strudwick type), Shprintzen syndrome, Skin pigmentation disorders, Smith-Lemli-Opitz syndrome, South-African genetic porphyria (variegate porphyria), infantile-onset ascending hereditary spastic paralysis, Speech and communication disorders, sphingolipidosis, Tay-Sachs disease, spinocerebellar ataxia, Stickler syndrome, stroke, androgen insensitivity syndrome, tetrahydrobiopterin deficiency, beta-thalassemia, Thyroid disease, Tomaculous neuropathy (hereditary neuropathy with liability to pressure palsies), Treacher Collins syndrome, Triplo X syndrome (triple X syndrome), Trisomy 21 (Down syndrome), Trisomy X, VHL syndrome (von Hippel-Lindau disease), Vision impairment and blindness (Alström syndrome), Vrolik disease, Waardenburg syndrome, Warburg Sjo Fledelius Syndrome, Wolf-Hirschhorn syndrome, Wolff Periodic disease, Weissenbacher-Zweymuller syndrome and Xeroderma pigmentosum, among others.

In one embodiment, a method is provided for treating multiple myeloma comprising administering to a patient an effective amount of a compound of Formula I or Formula II, or a pharmaceutically acceptable salt, isotopic analog, or prodrug thereof, optionally in a pharmaceutically acceptable carrier to form a composition. In another embodiment, a compound of Formula I or Formula II, or a pharmaceutically acceptable salt, isotopic analog, or prodrug thereof, optionally in a pharmaceutically acceptable carrier to form a composition, for use in a method of treating multiple myeloma, wherein the method comprises administering the compound to a patient.

In one embodiment, a method is provided for managing the progression of multiple myeloma comprising administering to a patient an effective amount of a compound of Formula I or Formula II, or a pharmaceutically acceptable salt, isotopic analog, or prodrug thereof, optionally in a pharmaceutically acceptable carrier to form a composition. In another embodiment, a compound of Formula I or Formula II, or a pharmaceutically acceptable salt, isotopic analog, or prodrug thereof, optionally in a pharmaceutically acceptable carrier to form a composition, for use in a method of managing the progression of multiple myeloma, wherein the method comprises administering the compound to a patient.

In one embodiment, a method is provided for inducing a therapeutic response as assessed by the International Uniform Response Criteria (IURC) for Multiple Myeloma (described in Durie B. G. M; et al. "International uniform response criteria for multiple myeloma. *Leukemia* 2006, 10(10):1-7) in a patient having multiple myeloma comprising administering to the patient an effective amount of a compound of Formula I or Formula II, or a pharmaceutically acceptable salt, isotopic analog, or prodrug thereof, optionally in a pharmaceutically acceptable carrier to form a composition.

In another embodiment, a method is provided to achieve a stringent complete response, complete response, or very good partial response, as assessed by the IURC for Multiple Myeloma in a patient having multiple myeloma comprising administering to the patient an effective amount of a compound of Formula I or Formula II, or a pharmaceutically acceptable salt, isotopic analog, or prodrug thereof, optionally in a pharmaceutically acceptable carrier to form a composition.

In another embodiment, a method is provided to achieve an increase in overall survival, progression-free survival, event-free survival, time to process, or disease-free survival in a patient having multiple myeloma comprising administering to the patient an effective amount of a compound of Formula I or Formula II, or a pharmaceutically acceptable salt, isotopic analog, or prodrug thereof, optionally in a pharmaceutically acceptable carrier to form a composition.

In another embodiment, a method is provided to achieve an increase in overall survival in a patient having multiple myeloma comprising administering to the patient an effective amount of a compound of Formula I or Formula II, or a pharmaceutically acceptable salt, isotopic analog, or prodrug thereof, optionally in a pharmaceutically acceptable carrier to form a composition.

In another embodiment, a method is provided to achieve an increase in progression-free survival in a patient having multiple myeloma comprising administering to the patient an effective amount of a compound of Formula I or Formula II, or a pharmaceutically acceptable salt, isotopic analog, or prodrug thereof, optionally in a pharmaceutically acceptable carrier to form a composition.

In another embodiment, a method is provided to achieve an increase in event-free survival in a patient having multiple myeloma comprising administering to the patient an effective amount of a compound of Formula I or Formula II, or a pharmaceutically acceptable salt, isotopic analog, or prodrug thereof, optionally in a pharmaceutically acceptable carrier to form a composition.

In another embodiment, a method is provided to achieve an increase in time to progression in a patient having multiple myeloma comprising administering to the patient an effective amount of a compound of Formula I or Formula II, or a pharmaceutically acceptable salt, isotopic analog, or prodrug thereof, optionally in a pharmaceutically acceptable carrier to form a composition.

In another embodiment, a method is provided to achieve an increase in disease-free survival in a patient having multiple myeloma comprising administering to the patient an effective amount of a compound of Formula I or Formula II, or a pharmaceutically acceptable salt, isotopic analog, or prodrug thereof, optionally in a pharmaceutically acceptable carrier to form a composition.

Methods are also provided to treat patients who have been previously treated for multiple myeloma but are non-responsive to standard therapies in addition to those who have not been previously treated. Additional methods are provided to treat patients who have undergone surgery in an attempt to treat multiple myeloma in addition to those who have not undergone surgery. Methods are also provided to treat patients who have previously undergone transplant therapy in addition to those who have not.

The compounds described herein may be used in the treatment or management of multiple myeloma that is relapsed, refractory, or resistant. In some embodiments, the multiple myeloma is primary, secondary, tertiary, quadruply or quintuply relapsed. In one embodiment, the compounds described herein may be used to reduce, maintain, or eliminate minimal residual disease (MRD).

The types of multiple myeloma that may be treated with the compounds described herein include, but are not limited to: monoclonal gammopathy of undetermined significance (MGUS); low risk, intermediate risk, or high risk multiple myeloma; newly diagnosed multiple myeloma, including low risk, intermediate risk, or high risk newly diagnosed multiple myeloma); transplant eligible and transplant ineligible multiple myeloma; smoldering (indolent) multiple myeloma (including low risk, intermediate risk, or high risk smoldering multiple myeloma); active multiple myeloma; solitary plasmocytoma; plasma cell leukemia; central nervous system multiple myeloma; light chain myeloma; non-secretory myeloma; Immunoglobulin D myeloma; and Immunoglobulin E myeloma.

In some embodiments, the compounds described herein may be used in the treatment or management of multiple myeloma characterized by genetic abnormalities, for example but not limited to: Cyclin D translocations (for example, t(11;14)(q13;q32); t(6;14)(p21;32); t(12;14)(p13; q32); or t(6;20);); MMSET translocations (for example t(4;14)(p16;q32); MAF translocations (for example t(14;16)

(q32;a32); t(20;22); t(16;22)(q11;q13); or t(14;20)(q32; q11); or other chromosome factors (for example deletion of 17p13 or chromosome 13; del(17/17p), nonhyperdiploidy, and gain (1q)).

In one embodiment, a method is provided for treating or managing multiple myeloma comprising administering to a patient an effective amount of a compound of Formula I or Formula II, or a pharmaceutically acceptable salt, isotopic analog, or prodrug thereof, optionally in a pharmaceutically acceptable carrier to form a composition, as induction therapy.

In one embodiment, a method is provided for treating or managing multiple myeloma comprising administering to a patient an effective amount of a compound of Formula I or Formula II, or a pharmaceutically acceptable salt, isotopic analog, or prodrug thereof, optionally in a pharmaceutically acceptable carrier to form a composition, as consolidation therapy.

In one embodiment, a method is provided for treating or managing multiple myeloma comprising administering to a patient an effective amount of a compound of Formula I or Formula II, or a pharmaceutically acceptable salt, isotopic analog, or prodrug thereof, optionally in a pharmaceutically acceptable carrier to form a composition, as maintenance therapy.

In one embodiment, the multiple myeloma is plasma cell leukemia.

In one embodiment, the multiple myeloma is high risk multiple myeloma. In some embodiments, the high risk multiple myeloma is relapsed or refractory. In one embodiment, the high risk multiple myeloma has relapsed within 12 months of the first treatment. In another embodiment, the high risk multiple myeloma is characterized by genetic abnormalities, for example, one or more of del(17/17p) and t(14;16)(q32;q32). In some embodiments, the high risk multiple myeloma is relapsed or refractory to one, two or three previous treatments.

In one embodiment, the multiple myeloma has a p53 mutation. In one embodiment, the p53 mutation is a Q331 mutation. In one embodiment, the p53 mutation is a R273H mutation. In one embodiment, the p53 mutation is a K132 mutation. In one embodiment, the p53 mutation is a K132N mutation. In one embodiment, the p53 mutation is a R337 mutation. In one embodiment, the p53 mutation is a R337L mutation. In one embodiment, the p53 mutation is a W146 mutation. In one embodiment, the p53 mutation is a S261 mutation. In one embodiment, the p53 mutation is a S261T mutation. In one embodiment, the p53 mutation is a E286 mutation. In one embodiment, the p53 mutation is a E286K mutation. In one embodiment, the p53 mutation is a R175 mutation. In one embodiment, the p53 mutation is a R175H mutation. In one embodiment, the p53 mutation is a E258 mutation. In one embodiment, the p53 mutation is a E258K mutation. In one embodiment, the p53 mutation is a A161 mutation. In one embodiment, the p53 mutation is a A161T mutation.

In one embodiment, the multiple myeloma has a homozygous deletion of p53. In one embodiment, the multiple myeloma has a homozygous deletion of wild-type p53. In one embodiment, the multiple myeloma has wild-type p53.

In one embodiment, the multiple myeloma shows activation of one or more oncogenic drivers. In one embodiment, the one or more oncogenic drivers are selected from the group consisting of C-MAF, MAFB, FGFR3, MMset, Cyclin D1, and Cyclin D. In one embodiment, the multiple myeloma shows activation of C-MAF. In one embodiment, the multiple myeloma shows activation of MAFB. In one embodiment, the multiple myeloma shows activation of FGFR3 and MMset. In one embodiment, the multiple myeloma shows activation of C-MAF, FGFR3, and MMset. In one embodiment, the multiple myeloma shows activation of Cyclin D1. In one embodiment, the multiple myeloma shows activation of MAFB and Cyclin D1. In one embodiment, the multiple myeloma shows activation of Cyclin D.

In one embodiment, the multiple myeloma has one or more chromosomal translocations. In one embodiment, the chromosomal translocation is t(14;16). In one embodiment, the chromosomal translocation is t(14;20). In one embodiment, the chromosomal translocation is t(4; 14). In one embodiment, the chromosomal translocations are t(4;14) and t(14;16). In one embodiment, the chromosomal translocation is t(11;14). In one embodiment, the chromosomal translocation is t(6;20). In one embodiment, the chromosomal translocation is t(20;22). In one embodiment, the chromosomal translocations are t(6;20) and t(20;22). In one embodiment, the chromosomal translocation is t(16;22). In one embodiment, the chromosomal translocations are t(14; 16) and t(16;22). In one embodiment, the chromosomal translocations are t(14;20) and t(11;14).

In one embodiment, the multiple myeloma has a Q331 p53 mutation, activation of C-MAF, and a chromosomal translocation at t(14; 16). In one embodiment, the multiple myeloma has homozygous deletion of p53, activation of C-MAF, and a chromosomal translocation at t(14; 16). In one embodiment, the multiple myeloma has a K132N p53 mutation, activation of MAFB, and a chromosomal translocation at t(14;20). In one embodiment, the multiple myeloma has wild type p53, activation of FGFR3 and MMset, and a chromosomal translocation at t(4; 14). In one embodiment, the multiple myeloma has wild type p53, activation of C-MAF, and a chromosomal translocation at t(14;16). In one embodiment, the multiple myeloma has homozygous deletion of p53, activation of FGFR3, MMset, and C-MAF, and chromosomal translocations at t(4;14) and t(14;16). In one embodiment, the multiple myeloma has homozygous deletion of p53, activation of Cyclin D1, and a chromosomal translocation at t(11;14). In one embodiment, the multiple myeloma has a R337L p53 mutation, activation of Cyclin D1, and a chromosomal translocation at t(11;14). In one embodiment, the multiple myeloma has a W146 p53 mutation, activation of FGFR3 and MMset, and a chromosomal translocation at t(4; 14). In one embodiment, the multiple myeloma has a S261T p53 mutation, activation of MAFB, and chromosomal translocations at t(6;20) and t(20;22). In one embodiment, the multiple myeloma has a E286K p53 mutation, by activation of FGFR3 and MMset, and a chromosomal translocation at t(4; 14). In one embodiment, the multiple myeloma has a R175H p53 mutation, activation of FGFR3 and MMset, and a chromosomal translocation at t(4; 14). In one embodiment, the multiple myeloma has a E258K p53 mutation, activation of C-MAF, and chromosomal translocations at t(14;16) and t(16;22). In one embodiment, the multiple myeloma has wild type p53, activation of MAFB and Cyclin D1, and chromosomal translocations at t(14;20) and t(11;14). In one embodiment, the multiple myeloma has a A161T p53 mutation, activation of Cyclin D, and a chromosomal translocation at t(11;14).

In some embodiments, the multiple myeloma is transplant eligible newly diagnosed multiple myeloma. In other embodiments, the multiple myeloma is transplant ineligible newly diagnosed multiple myeloma.

In some embodiments, the multiple myeloma shows early progression (for example less than 12 months) following initial treatment. In other embodiments, the multiple myeloma shows early progression (for example less than 12 months) following autologous stem cell transplant. In another embodiment, the multiple myeloma is refractory to lenalidomide. In another embodiment, the multiple myeloma is refractory to pomalidomide. In some such embodiments, the multiple myeloma is predicted to be refractory to pomalidomide (for example, by molecular characterization). In another embodiment, the multiple myeloma is relapsed or refractory to 3 or more treatments and was exposed to a proteasome inhibitor (for example, bortezomib, carfilzomib, ixazomib, oprozomib, or marizomib) and an immunomodulatory compound (for example thalidomide, lenalidomide, pomalidomide, iberdomide, or avadomide), or double refractory to a proteasome inhibitor and an immunomodulatory compound. In still other embodiments, the multiple myeloma is relapsed or refractory to 3 or more prior therapies, including for example, a CD38 monoclonal antibody (CD38 mAb, for example, daratumumab or isatuximab), a proteasome inhibitor (for example, bortezomib, carfilzomib, ixazomib, or marizomib), and an immunomodulatory compound (for example thalidomide, lenalidomide, pomalidomide, iberdomide, or avadomide) or double refractory to a proteasome inhibitor or immunomodulatory compound and a CD38 mAb. In still other embodiments, the multiple myeloma is triple refractory, for example, the multiple myeloma is refractory to a proteasome inhibitor (for example, bortezomib, carfilzomib, ixazomib, oprozomib or marizomib), an immunomodulatory compound (for example thalidomide, lenalidomide, pomalidomide, iberdomide, or avadomide), and one other active agent, as described herein.

In one embodiment, a method is provided for treating or managing relapsed or refractory multiple myeloma in patients with impaired renal function or a symptom thereof comprising administering to a patient an effective amount of a compound of Formula I or Formula II, or a pharmaceutically acceptable salt, isotopic analog, or prodrug thereof, optionally in a pharmaceutically acceptable carrier to form a composition.

In another embodiment, a method is provided for treating or managing relapsed or refractory multiple myeloma in frail patients comprising administering to a patient an effective amount of a compound of Formula I or Formula II, or a pharmaceutically acceptable salt, isotopic analog, or prodrug thereof, optionally in a pharmaceutically acceptable carrier to form a composition, wherein the frail patient is characterized by ineligibility for induction therapy or intolerance to dexamethasone treatment. In other embodiments, the frail patient is elderly, for example, older than 65 years old.

In another embodiment, a method is provided for treating or managing fourth line relapsed or refractory multiple myeloma comprising administering to a patient an effective amount of a compound of Formula I or Formula II, or a pharmaceutically acceptable salt, isotopic analog, or prodrug thereof, optionally in a pharmaceutically acceptable carrier to form a composition.

In another embodiment, a method is provided for treating or managing newly diagnosed, transplant-ineligible multiple myeloma comprising administering to a patient an effective amount of a compound of Formula I or Formula II, or a pharmaceutically acceptable salt, isotopic analog, or prodrug thereof, optionally in a pharmaceutically acceptable carrier to form a composition.

In another embodiment, a method is provided for treating or managing newly diagnosed, transplant-ineligible multiple myeloma comprising administering to a patient an effective amount of a compound of Formula I or Formula II, or a pharmaceutically acceptable salt, isotopic analog, or prodrug thereof, optionally in a pharmaceutically acceptable carrier to form a composition, as maintenance therapy after another therapy or transplant.

In another embodiment, a method is provided for treating or managing high risk multiple myeloma that is relapsed or refractory to one, two, or three previous treatments comprising administering to a patient an effective amount of a compound of Formula I or Formula II, or a pharmaceutically acceptable salt, isotopic analog, or prodrug thereof, optionally in a pharmaceutically acceptable carrier to form a composition.

In some embodiments, the patient to be treated by one of the compounds described herein has not be treated with multiple myeloma therapy prior to administration. In some embodiments, the patient to be treated by one of the compounds described herein has been treated by multiple myeloma therapy prior to administration. In some embodiments, the patient to be treated by one of the compounds described herein has developed drug resistant to the multiple myeloma therapy.

In some embodiments, the patient to be treated by one of the compounds described herein has developed resistance to one, two, or three multiple myeloma therapies, wherein the therapies are selected from a CD38 antibody (CD38 mAB, for example, daratumumab or isatuximab), a proteasome inhibitor (for example, bortezomib, carfilzomib, ixazomib, or marizomib), and an immunomodulatory compound (for example thalidomide, lenalidomide, pomalidomide, iberdomide, or avodomide).

The compounds described herein can be used to treat a patient regardless of patient's age.

In some embodiments, the subject is 18 years or older. In other embodiments, the subject is more than 18, 25, 35, 40, 45, 50, 55, 60, 65, or 70 years old. In other embodiments, the patient is less than 65 years old. In other embodiments, the patient is more than 65 years old. In one embodiment, the patient is an elderly multiple myeloma patient, such as a patient older than 65 years old. In one embodiment, the patient is an elderly multiple myeloma patient, such as a patient older than 75 years old.

IV. Combination Therapy

Any of the compounds described herein can be used in an effective amount alone or in combination to treat a host such as a human with a disorder as described herein.

The term "bioactive agent" or "additional therapeutically active agent" is used to describe an agent, other than the compound according to the present invention, which can be used in combination or alternation with a compound of the present invention to achieve a desired result of therapy. In one embodiment, the compound of the present invention and the additional therapeutically active agent are administered in a manner that they are active in vivo during overlapping time periods, for example, have time-period overlapping Cmax, Tmax, AUC or other pharmacokinetic parameter. In another embodiment, the compound of the present invention and the additional therapeutically active agent are administered to a host in need thereof that do not have overlapping pharmacokinetic parameter, however, one has a therapeutic impact on the therapeutic efficacy of the other.

In one aspect of this embodiment, the additional therapeutically active agent is an immune modulator, including but not limited to a checkpoint inhibitor, including as non-limiting examples, a PD-1 inhibitor, PD-L1 inhibitor, PD-L2 inhibitor, CTLA-4 inhibitor, LAG-3 inhibitor, TIM-3 inhibitor, V-domain Ig suppressor of T-cell activation (VISTA) inhibitors, small molecule, peptide, nucleotide, or other inhibitor. In certain aspects, the immune modulator is an antibody, such as a monoclonal antibody.

PD-1 inhibitors that blocks the interaction of PD-1 and PD-L1 by binding to the PD-1 receptor, and in turn inhibit immune suppression include, for example, nivolumab (Opdivo), pembrolizumab (Keytruda), pidilizumab, AMP-224 (AstraZeneca and MedImmune), PF-06801591 (Pfizer), MEDI0680 (AstraZeneca), PDR001 (Novartis), REGN2810 (Regeneron), SHR-12-1 (Jiangsu Hengrui Medicine Company and Incyte Corporation), TSR-042 (Tesaro), and the PD-L1/VISTA inhibitor CA-170 (Curis Inc.). PD-L1 inhibitors that block the interaction of PD-1 and PD-L1 by binding to the PD-L1 receptor, and in turn inhibits immune suppression, include for example, atezolizumab (Tecentriq), durvalumab (AstraZeneca and MedImmune), KN035 (Alphamab), and BMS-936559 (Bristol-Myers Squibb). CTLA-4 checkpoint inhibitors that bind to CTLA-4 and inhibits immune suppression include, but are not limited to, ipilimumab, tremelimumab (AstraZeneca and MedImmune), AGEN1884 and AGEN2041 (Agenus). LAG-3 checkpoint inhibitors, include, but are not limited to, BMS-986016 (Bristol-Myers Squibb), GSK2831781 (GlaxoSmithKline), IMP321 (Prima BioMed), LAG525 (Novartis), and the dual PD-1 and LAG-3 inhibitor MGD013 (MacroGenics). An example of a TIM-3 inhibitor is TSR-022 (Tesaro). In one embodiment, the PD-1 inhibitor is BGB-A317. In one embodiment, the PD-L1 inhibitor is MED14736. In one embodiment, the PD-L2 inhibitor is rHIgM12B7A.

In one embodiment, the checkpoint inhibitor is a B7 inhibitor, for example a B7-H3 inhibitor or a B7-H4 inhibitor. In one embodiment, the B7-H3 inhibitor is MGA271.

In one embodiment, the checkpoint inhibitor is an OX40 agonist. In one embodiment, the checkpoint inhibitor is an anti-OX40 antibody, for example anti-OX-40 or MEDI6469.

In one embodiment, the checkpoint inhibitor is a GITR agonist. In one embodiment, the GITR agonist is an anti-GITR antibody, for example TRX518.

In one embodiment, the checkpoint inhibitor is a CD137 agonist. In one embodiment, the CD137 agonist is an anti-CD137 antibody, for example PF-05082566.

In one embodiment, the checkpoint inhibitor is a CD40 agonist. In one embodiment, the CD40 agonist is an anti-CD40 antibody, for example CF-870,893.

In one embodiment, the checkpoint inhibitor is an IDO inhibitor, for example INCB24360 or indoximod.

In another embodiment, an active compounds described herein can be administered in an effective amount for the treatment of abnormal tissue of the male reproductive system such as prostate or testicular cancer, in combination or alternation with an effective amount of an androgen (such as testosterone) inhibitor including but not limited to a selective androgen receptor modulator, a selective androgen receptor degrader, a complete androgen receptor degrader, or another form of partial or complete androgen antagonist. In one embodiment, the prostate or testicular cancer is androgen-resistant. Non-limiting examples of anti-androgen compounds are provided in WO 2011/156518 and U.S. Pat. Nos. 8,455,534 and 8,299,112. Additional non-limiting examples of anti-androgen compounds include: enzalutamide, apalutamide, cyproterone acetate, chlormadinone acetate, spironolactone, canrenone, drospirenone, ketoconazole, topilutamide, abiraterone acetate, and cimetidine.

In one embodiment, the additional therapeutically active agent is an ALK inhibitor. Examples of ALK inhibitors include but are not limited to Crizotinib, Alectinib, ceritinib, TAE684 (NVP-TAE684), GSK1838705A, AZD3463, ASP3026, PF-06463922, entrectinib (RXDX-101), and AP26113.

In one embodiment, the additional therapeutically active agent is an EGFR inhibitor. Examples of EGFR inhibitors include erlotinib (Tarceva), gefitinib (Iressa), afatinib (Gilotrif), rociletinib (CO-1686), osimertinib (Tagrisso), olmutinib (Olita), naquotinib (ASP8273), nazartinib (EGF816), PF-06747775 (Pfizer), icotinib (BPI-2009), neratinib (HKI-272; PB272); avitinib (AC0010), EAI045, tarloxotinib (TH-4000; PR-610), PF-06459988 (Pfizer), tesevatinib (XL647; EXEL-7647; KD-019), transtinib, WZ-3146, WZ8040, CNX-2006, and dacomitinib (PF-00299804; Pfizer).

In one embodiment, the additional therapeutically active agent is an HER-2 inhibitor. Examples of HER-2 inhibitors include trastuzumab, lapatinib, ado-trastuzumab emtansine, and pertuzumab.

In one embodiment, the additional therapeutically active agent is a CD20 inhibitor. Examples of CD20 inhibitors include obinutuzumab, rituximab, fatumumab, ibritumomab, tositumomab, and ocrelizumab.

In one embodiment, the additional therapeutically active agent is a JAK3 inhibitor. Examples of JAK3 inhibitors include tasocitinib.

In one embodiment, the additional therapeutically active agent is a BCL-2 inhibitor. Examples of BCL-2 inhibitors include venetoclax, ABT-199 (4-[4-[[2-(4-Chlorophenyl)-4,4-dimethylcyclohex-1-en-1-yl]methyl]piperazin-1-yl]-N-[[3-nitro-4-[[(tetrahydro-2H-pyran-4-yl)methyl]amino]phenyl]sulfonyl]-2-[(1H-pyrrolo[2,3-b]pyridin-5-yl)oxy] benzamide), ABT-737 (4-[4-[[2-(4-chlorophenyl)phenyl]methyl]piperazin-1-yl]-N-[4-[[(2R)-4-(dimethylamino)-1-phenylsulfanylbutan-2-yl] amino]-3-nitrophenyl] sulfonylbenzamide) (navitoclax), ABT-263 ((R)-4-(4-((4'-chloro-4,4-dimethyl-3,4,5,6-tetrahydro-[1, 1'-biphenyl]-2-yl)methyl)piperazin-1-yl)-N-((4-((4-morpholino-1-(phenylthio)butan-2-yl)amino)-3((trifluoromethyl)sulfonyl) phenyl)sulfonyl)benzamide), GX15-070 (obatoclax mesylate, (2Z)-2-[(5Z)-5-[(3,5-dimethyl-1H-pyrrol-2-yl)methylidene]-4-methoxypyrrol-2-ylidene]indole; methanesulfonic acid))), 2-methoxy-antimycin A3, YC137 (4-(4,9-dioxo-4,9-dihydronaphtho[2,3-d]thiazol-2-ylamino)-phenyl ester), pogosin, ethyl 2-amino-6-bromo-4-(1-cyano-2-ethoxy-2-oxoethyl)-4H-chromene-3-carboxylate, Nilotinib-d3, TW-37 (N-[4-[[2-(1,1-Dimethylethyl)phenyl]sulfonyl]phenyl]-2,3,4-trihydroxy-5-[[2-(1-methylethyl)phenyl]methyl]benzamide), Apogossypolone (ApoG2), HA14-1, AT101, sabutoclax, gambogic acid, or G3139 (Oblimersen).

In one embodiment, the additional therapeutically active agent is a kinase inhibitor. In one embodiment, the kinase inhibitor is selected from a phosphoinositide 3-kinase (PI3K) inhibitor, a Bruton's tyrosine kinase (BTK) inhibitor, or a spleen tyrosine kinase (Syk) inhibitor, or a combination thereof.

Examples of PI3 kinase inhibitors include but are not limited to Wortmannin, demethoxyviridin, perifosine, idelalisib, Pictilisib, Palomid 529, ZSTK474, PWT33597, CUDC-907, and AEZS-136, duvelisib, GS-9820, BKM120, GDC-0032 (Taselisib) (2-[4-[2-(2-Isopropyl-5-methyl-1,2,4-triazol-3-yl)-5,6-dihydroimidazo[1,2-d][1,4]benzoxazepin-9-yl]pyrazol-1-yl]-2-methylpropanamide), MLN-1117 ((2R)-1-Phenoxy-2-butanyl hydrogen (S)-methylphosphonate; or Methyl(oxo) {[(2R)-1-phenoxy-2-butanyl]

oxy}phosphonium)), BYL-719 ((2S)—N1-[4-Methyl-5-[2-(2,2,2-trifluoro-1,1-dimethylethyl)-4-pyridinyl]-2-thiazolyl]-1,2-pyrrolidinedicarboxamide), GSK2126458 (2,4-Difluoro-N-{2-(methyloxy)-5-[4-(4-pyridazinyl]-6-quinolinyl]-3-pyridinyl)benzenesulfonamide) (omipalisib), TGX-221 ((±)-7-Methyl-2-(morpholin-4-yl)-9-(1-phenylaminoethyl)-pyrido[1,2-a]-pyrimidin-4-one), GSK2636771 (2-Methyl-1-(2-methyl-3-(trifluoromethyl)benzyl)-6-morpholino-1H-benzo[d]imidazole-4-carboxylic acid dihydrochloride), KIN-193 ((R)-2-((1-(7-methyl-2-morpholino-4-oxo-4H-pyrido[1,2-a]pyrimidin-9-yl)ethyl)amino)benzoic acid), TGR-1202/RP5264, GS-9820 ((S)-1-(4-((2-(2-aminopyrimidin-5-yl)-7-methyl-4-mohydroxypropan-1-one), GS-1101 (5-fluoro-3-phenyl-2-([S]-1-[9H-purin-6-ylamino]-propyl)-3H-quinazolin-4-one), AMG-319, GSK-2269557, SAR245409 (N-(4-(N-(3-((3,5-dimethoxyphenyl)amino)quinoxalin-2-yl)sulfamoyl)phenyl)-3-methoxy-4 methylbenzamide), BAY80-6946 (2-amino-N-(7-methoxy-8-(3-morpholinopropoxy)-2,3-dihydroimidazo[1,2-c]quinaz), AS 252424 (5-[l-[5-(4-Fluoro-2-hydroxy-phenyl)-furan-2-yl]-meth-(Z)-ylidene]-thiazolidine-2,4-dione), CZ 24832 (5-(2-amino-8-fluoro-[1,2,4]triazolo[1,5-a]pyridin-6-yl)-N-tert-butylpyridine-3-sulfonamide), Buparlisib (5-[2,6-Di(4-morpholinyl)-4-pyrimidinyl]-4-(trifluoromethyl)-2-pyridinamine), GDC-0941 (2-(1H-Indazol-4-yl)-6-[[4-(methylsulfonyl)-1-piperazinyl]methyl]-4-(4-morpholinyl)thieno[3,2-d]pyrimidine), GDC-0980 ((S)-1-(4-((2-(2-aminopyrimidin-5-yl)-7-methyl-4-morpholinothieno[3,2-d]pyrimidin-6 yl)methyl)piperazin-1-yl)-2-hydroxypropan-1-one (also known as RG7422)), SF1126 ((8S,14S,17S)-14-(carboxymethyl)-8-(3-guanidinopropyl)-17-(hydroxymethyl)-3,6,9,12, 15-pentaoxo-1-(4-(4-oxo-8-phenyl-4H-chromen-2-yl)morpholino-4-ium)-2-oxa-7,10,13,16-tetraazaoctadecan-18-oate), PF-05212384 (N-[4-[[4-(Dimethylamino)-1-piperidinyl]carbonyl]phenyl]-N'-[4-(4,6-di-4-morpholinyl-1,3,5-triazin-2-yl)phenyl]urea) (gedatolisib), LY3023414, BEZ235 (2-Methyl-2-{4-[3-methyl-2-oxo-8-(quinolin-3-yl)-2,3-dihydro-1H-imidazo[4,5-c]quinolin-1-yl]phenyl}propanenitrile) (dactolisib), XL-765 (N-(3-(N-(3-(3, 5-dimethoxyphenylamino)quinoxalin-2-yl)sulfamoyl)phenyl)-3-methoxy-4-methylbenzamide), and GSK1059615 (5-[[4-(4-Pyridinyl)-6-quinolinyl]methylene]-2,4-thiazolidenedione), PX886 ([(3aR,6E,9S,9aR,10R,11aS)-6-[[bis(prop-2-enyl)amino]methylidene]-5-hydroxy-9-(methoxymethyl)-9a,11a-dimethyl-1,4,7-trioxo-2,3,3a,9,10, 11-hexahydroindeno[4,5h]isochromen-10-yl] acetate (also known as sonolisib)), LY294002, AZD8186, PF-4989216, pilaralisib, GNE-317, PI-3065, PI-103, NU7441 (KU-57788), HS 173, VS-5584(SB2343), CZC24832, TG100-115, A66, YM201636, CAY10505, PIK-75, PIK-93, AS-605240, BGT226 (NVP-BGT226), AZD6482, voxtalisib, alpelisib, IC-87114, TGI100713, CH5132799, PKI-402, copanlisib (BAY 80-6946), XL 147, PIK-90, PIK-293, PIK-294, 3-MA (3-methyladenine), AS-252424, AS-604850, apitolisib (GDC-0980; RG7422), and the structure described in WO2014/071109.

Examples of BTK inhibitors include ibrutinib (also known as PCI-32765) (Imbruvica™) (1-[(3R)-3-[4-amino-3-(4-phenoxy-phenyl)pyrazolo[3,4-d]pyrimidin-1-yl]piperidin-1-yl]prop-2-en-1-one), dianilinopyrimidine-based inhibitors such as AVL-101 and AVL-291/292 (N-(3-((5-fluoro-2-((4-(2-methoxyethoxy)phenyl)amino)pyrimidin-4-yl)amino)phenyl)acrylamide) (Avila Therapeutics) (see US Patent Publication No 2011/0117073, incorporated herein in its entirety), Dasatinib ([N-(2-chloro-6-methylphenyl)-2-(6-(4-(2-hydroxyethyl)piperazin-1-yl)-2-methylpyrimidin-4-ylamino)thiazole-5-carboxamide], LFM-A13 (alpha-cyano-beta-hydroxy-beta-methyl-N-(2,5-ibromophenyl) propenamide), GDC-0834 ([R—N-(3-(6-(4-(1,4-dimethyl-3-oxopiperazin-2-yl)phenylamino)-4-methyl-5-oxo-4,5-dihydropyrazin-2-yl)-2-methylphenyl)-4,5,6,7-tetrahydrobenzo[b]thiophene-2-carboxamide], CGI-560 4-(tert-butyl)-N-(3-(8-(phenylamino)imidazo[1,2-a]pyrazin-6-yl)phenyl)benzamide, CGI-1746 (4-(tert-butyl)-N-(2-methyl-3-(4-methyl-6-((4-(morpholine-4-carbonyl)phenyl)amino)-5-oxo-4,5-dihydropyrazin-2-yl)phenyl)benzamide), CNX-774 (4-(4-((4-((3-acrylamidophenyl)amino)-5-fluoropyrimidin-2-yl)amino)phenoxy)-N-methylpicolinamide), CTA056 (7-benzyl-1-(3-(piperidin-1-yl)propyl)-2-(4-(pyridin-4-yl)phenyl)-1H-imidazo[4,5-g] quinoxalin-6(5H)-one), GDC-0834 ((R)—N-(3-(6-((4-(1,4-dimethyl-3-oxopiperazin-2-yl)phenyl)amino)-4-methyl-5-oxo-4,5-dihydropyrazin-2-yl)-2-methylphenyl)-4,5,6,7-tetrahydrobenzo[b]thiophene-2-carboxamide), GDC-0837 ((R)—N-(3-(6-((4-(1,4-dimethyl-3-oxopiperazin-2-yl)phenyl)amino)-4-methyl-5-oxo-4,5-dihydropyrazin-2-yl)-2-methylphenyl)-4,5,6,7-tetrahydrobenzo[b]thiophene-2-carboxamide), HM-71224, ACP-196, ONO-4059 (Ono Pharmaceuticals), PRT062607 (4-((3-(2H-1,2,3-triazol-2-yl)phenyl)amino)-2-(((1R,2S)-2-aminocyclohexyl)amino) pyrimidine-5-carboxamide hydrochloride), QL-47 (1-(1-acryloylindolin-6-yl)-9-(1-methyl-1H-pyrazol-4-yl)benzo [h][1,6]naphthyridin-2(1H)-one), and RN486 (6-cyclopropyl-8-fluoro-2-(2-hydroxymethyl-3-{1-methyl-5-[5-(4-methyl-piperazin-1-yl)-pyridin-2-ylamino]-6-oxo-1,6-dihydro-pyridin-3-yl}-phenyl)-2H-isoquinolin-1-one), and other molecules capable of inhibiting BTK activity, for example those BTK inhibitors disclosed in Akinleye et ah, Journal of Hematology & Oncology, 2013, 6:59, the entirety of which is incorporated herein by reference.

Syk inhibitors include, for example, Cerdulatinib (4-(cyclopropylamino)-2-((4-(4-(ethylsulfonyl)piperazin-1-yl) phenyl)amino)pyrimidine-5-carboxamide), entospletinib (6-(1H-indazol-6-yl)-N-(4-morpholinophenyl)imidazo[1,2-a] pyrazin-8-amine), fostamatinib ([6-({5-Fluoro-2-[(3,4,5-trimethoxyphenyl)amino]-4-pyrimidinyl}amino)-2,2-dimethyl-3-oxo-2,3-dihydro-4H-pyrido[3,2-b][1,4]oxazin-4-yl]methyl dihydrogen phosphate), fostamatinib disodium salt (sodium (6-((5-fluoro-2-((3,4,5-trimethoxyphenyl) amino)pyrimidin-4-yl)amino)-2,2-dimethyl-3-oxo-2H-pyrido[3,2-b][1,4]oxazin-4(3H)-yl)methyl phosphate), BAY 61-3606 (2-(7-(3,4-Dimethoxyphenyl)-imidazo[1,2-c]pyrimidin-5-ylamino)-nicotinamide HCl), RO9021 (6-[(1R, 2S)-2-Amino-cyclohexylamino]-4-(5,6-dimethyl-pyridin-2-ylamino)-pyridazine-3-carboxylic acid amide), imatinib (Gleevac; 4-[(4-methylpiperazin-1-yl)methyl]-N-(4-methyl-3-{[4-(pyridin-3-yl)pyrimidin-2-yl]amino}phenyl)benzamide), staurosporine, GSK143 (2-(((3R,4R)-3-aminotetrahydro-2H-pyran-4-yl)amino)-4-(p-tolylamino)pyrimidine-5-carboxamide), PP2 (1-(tert-butyl)-3-(4-chlorophenyl)-1H-pyrazolo[3,4-d]pyrimidin-4-amine), PRT-060318 (2-(((1R, 2S)-2-aminocyclohexyl)amino)-4-(m-tolylamino) pyrimidine-5-carboxamide), PRT-062607 (4-((3-(2H-1,2,3-triazol-2-yl)phenyl)amino)-2-(((1R,2S)-2-aminocyclohexyl)amino)pyrimidine-5-carboxamide hydrochloride), R112 (3,3'-((5-fluoropyrimidine-2,4-diyl) bis(azanediyl))diphenol), R348 (3-Ethyl-4-methylpyridine), R406 (6-((5-fluoro-2-((3,4,5-trimethoxyphenyl)amino)pyrimidin-4-yl)amino)-2,2-dimethyl-2H-pyrido[3,2-b][1,4] oxazin-3(4H)-one), piceatannol (3-Hydroxyresveratol), YM193306(see Singh et al. Discovery and Development of Spleen Tyrosine Kinase (SYK) Inhibitors, J. Med. Chem. 2012, 55, 3614-3643), 7-azaindole, piceatannol, ER-27319

(see Singh et al. Discovery and Development of Spleen Tyrosine Kinase (SYK) Inhibitors, J. Med. Chem. 2012, 55, 3614-3643 incorporated in its entirety herein), Compound D (see Singh et al. Discovery and Development of Spleen Tyrosine Kinase (SYK) Inhibitors, J. Med. Chem. 2012, 55, 3614-3643 incorporated in its entirety herein), PRT060318 (see Singh et al. Discovery and Development of Spleen Tyrosine Kinase (SYK) Inhibitors, J. Med. Chem. 2012, 55, 3614-3643 incorporated in its entirety herein), luteolin (see Singh et al. Discovery and Development of Spleen Tyrosine Kinase (SYK) Inhibitors, J. Med. Chem. 2012, 55, 3614-3643 incorporated in its entirety herein), apigenin (see Singh et al. Discovery and Development of Spleen Tyrosine Kinase (SYK) Inhibitors, J. Med. Chem. 2012, 55, 3614-3643 incorporated in its entirety herein), quercetin (see Singh et al. Discovery and Development of Spleen Tyrosine Kinase (SYK) Inhibitors, J. Med. Chem. 2012, 55, 3614-3643 incorporated in its entirety herein), fisetin (see Singh et al. Discovery and Development of Spleen Tyrosine Kinase (SYK) Inhibitors, J. Med. Chem. 2012, 55, 3614-3643 incorporated in its entirety herein), myricetin (see Singh et al. Discovery and Development of Spleen Tyrosine Kinase (SYK) Inhibitors, J. Med. Chem. 2012, 55, 3614-3643 incorporated in its entirety herein), morin (see Singh et al. Discovery and Development of Spleen Tyrosine Kinase (SYK) Inhibitors, J. Med. Chem. 2012, 55, 3614-3643 incorporated in its entirety herein).

In one embodiment, the additional therapeutically active agent is a MEK inhibitor. MEK inhibitors are well known, and include, for example, trametinib/GSK1120212 (N-(3-{3-Cyclopropyl-5-[(2-fluoro-4-iodophenyl)amino]-6,8-dimethyl-2,4,7-trioxo-3,4,6,7-tetrahydropyrido[4,3-d]pyrimidin-1(2H-yl}phenyl)acetamide), selumetinib (6-(4-bromo-2-chloroanilino)-7-fluoro-N-(2-hydroxyethoxy)-3-methylbenzimidazole-5-carboxamide), pimasertib/AS703026/MSC 1935369 ((S)—N-(2,3-dihydroxypropyl)-3-((2-fluoro-4-iodophenyl)amino)isonicotinamide), XL-518/GDC-0973 (1-({3,4-difluoro-2-[(2-fluoro-4-iodophenyl)amino]phenyl}carbonyl)-3-[(2S)-piperidin-2-yl]azetidin-3-ol), refametinib/BAY869766/RDEA1 19 (N-(3,4-difluoro-2-(2-fluoro-4-iodophenylamino)-6-methoxyphenyl)-1-(2,3-dihydroxypropyl)cyclopropane-1-sulfonamide), PD-0325901 (N-[(2R)-2,3-Dihydroxypropoxy]-3,4-difluoro-2-[(2-fluoro-4-iodophenyl)amino]-benzamide), TAK733 ((R)-3-(2,3-Dihydroxypropyl)-6-fluoro-5-(2-fluoro-4-iodophenylamino)-8-methylpyrido[2,3-d]pyrimidine-4,7(3H,8H)-dione), MEK162/ARRY438162 (5-[(4-Bromo-2-fluorophenyl)amino]-4-fluoro-N-(2-hydroxyethoxy)-1-methyl-1H-benzimidazole-6-carboxamide), R05126766 (3-[[3-Fluoro-2-(methylsulfamoylamino)-4-pyridyl]methyl]-4-methyl-7-pyrimidin-2-yloxychromen-2-one), WX-554, R04987655/CH4987655 (3,4-difluoro-2-((2-fluoro-4-iodophenyl)amino)-N-(2-hydroxyethoxy)-5-((3-oxo-1,2-oxazinan-2yl)methyl)benzamide), or AZD8330 (2-((2-fluoro-4-iodophenyl)amino)-N-(2 hydroxyethoxy)-1,5-dimethyl-6-oxo-1,6-dihydropyridine-3-carboxamide), U0126-EtOH, PD184352 (CI-1040), GDC-0623, BI-847325, cobimetinib, PD98059, BIX 02189, BIX 02188, binimetinib, SL-327, TAK-733, PD318088.

In one embodiment, the additional therapeutically active agent is a Raf inhibitor. Raf inhibitors are known and include, for example, Vemurafinib (N-[3-[[5-(4-Chlorophenyl)-1H-pyrrolo[2,3-b]pyridin-3-yl]carbonyl]-2,4-difluorophenyl]-1-propanesulfonamide), sorafenib tosylate (4-[4-[[[[4-chloro-3-(trifluoromethyl)phenyl]carbamoylamino]phenoxy]-N-methylpyridine-2-carboxamide; 4-methylbenzenesulfonate), AZ628 (3-(2-cyanopropan-2-yl)-N-(4-methyl-3-(3-methyl-4-oxo-3,4-dihydroquinazolin-6-ylamino)phenyl)benzamide), NVP-BHG712 (4-methyl-3-(1-methyl-6-(pyridin-3-yl)-1H-pyrazolo[3,4-d]pyrimidin-4-ylamino)-N-(3-(trifluoromethyl)phenyl)benzamide), RAF-265 (1-methyl-5-[2-[5-(trifluoromethyl)-1H-imidazol-2-yl]pyridin-4-yl]oxy-N-[4-(trifluoromethyl)phenyl]benzimidazol-2-amine), 2-Bromoaldisine (2-Bromo-6,7-dihydro-1H,5H-pyrrolo[2,3-c]azepine-4,8-dione), Raf Kinase Inhibitor IV (2-chloro-5-(2-phenyl-5-(pyridin-4-yl)-1H-imidazol-4-yl)phenol), Sorafenib N-Oxide (4-[4-[[[[4-Chloro-3-(trifluoroMethyl)phenyl]aMino]carbonyl]aMino]phenoxy]-N-Methyl-2pyridinecarboxaMide 1-Oxide), PLX-4720, dabrafenib (GSK2118436), GDC-0879, RAF265, AZ 628, SB590885, ZM336372, GW5074, TAK-632, CEP-32496, LY3009120, and GX818 (Encorafenib).

In one embodiment, the additional therapeutically active agent is an AKT inhibitor, including but not limited to, MK-2206, GSK690693, Perifosine, (KRX-0401), GDC-0068, Triciribine, AZD5363, Honokiol, PF-04691502, and Miltefosine, a FLT-3 inhibitor, including but not limited to, P406, Dovitinib, Quizartinib (AC220), Amuvatinib (MP-470), Tandutinib (MLN518), ENMD-2076, and KW-2449, or a combination thereof.

In one embodiment, the additional therapeutically active agent is an mTOR inhibitor. Examples of mTOR inhibitors include but are not limited to rapamycin and its analogs, everolimus (Afinitor), temsirolimus, ridaforolimus, sirolimus, and deforolimus. Examples of MEK inhibitors include but are not limited to tametinib/GSK1120212 (N-(3-{3-Cyclopropyl-5-[(2-fluoro-4-iodophenyl)amino]-6,8-dimethyl-2,4,7-trioxo-3,4,6,7-tetrahydropyrido[4,3-d]pyrimidin-1(2H-yl}phenyl)acetamide), selumetinob (6-(4-bromo-2-chloroanilino)-7-fluoro-N-(2-hydroxyethoxy)-3-methylbenzimidazole-5-carboxamide), pimasertib/AS703026/MSC1935369 ((S)—N-(2,3-dihydroxypropyl)-3-((2-fluoro-4-iodophenyl)amino)isonicotinamide), XL-518/GDC-0973 (1-({3,4-difluoro-2-[(2-fluoro-4-iodophenyl)amino]phenyl}carbonyl)-3-[(2S)-piperidin-2-yl]azetidin-3-ol) (cobimetinib), refametinib/BAY869766/RDEA119 (N-(3,4-difluoro-2-(2-fluoro-4-iodophenylamino)-6-methoxyphenyl)-1-(2,3-dihydroxypropyl)cyclopropane-1-sulfonamide), PD-0325901 (N-[(2R)-2,3-Dihydroxypropoxy]-3,4-difluoro-2-[(2-fluoro-4-iodophenyl)amino]-benzamide), TAK733 ((R)-3-(2,3-Dihydroxypropyl)-6-fluoro-5-(2-fluoro-4-iodophenylamino)-8-methylpyrido[2,3d]pyrimidine-4,7(3H,8H)-dione), MEK162/ARRY438162 (5-[(4-Bromo-2-fluorophenyl)amino]-4-fluoro-N-(2-hydroxyethoxy)-1-methyl-1H-benzimidazole-6 carboxamide), R05126766 (3-[[3-Fluoro-2-(methylsulfamoylamino)-4-pyridyl]methyl]-4-methyl-7-pyrimidin-2-yloxychromen-2-one), WX-554, R04987655/CH4987655 (3,4-difluoro-2-((2-fluoro-4-iodophenyl)amino)-N-(2-hydroxyethoxy)-5-((3-oxo-1,2-oxazinan-2 yl)methyl)benzamide), or AZD8330 (2-((2-fluoro-4-iodophenyl)amino)-N-(2-hydroxyethoxy)-1,5-dimethyl-6-oxo-1,6-dihydropyridine-3-carboxamide).

In one embodiment, the additional therapeutically active agent is a RAS inhibitor. Examples of RAS inhibitors include but are not limited to Reolysin and siG12D LODER.

In one embodiment, the additional therapeutically active agent is a HSP inhibitor. HSP inhibitors include but are not limited to Geldanamycin or 17-N-Allylamino-17-demethoxygeldanamycin (17AAG), and Radicicol.

Additional bioactive compounds include, for example, everolimus, trabectedin, abraxane, TLK 286, AV-299, DN-101, pazopanib, GSK690693, RTA 744, ON 0910.Na, AZD 6244 (ARRY-142886), AMN-107, TKI-258, GSK461364, AZD 1152, enzastaurin, vandetanib, ARQ-197, MK-0457, MLN8054, PHA-739358, R-763, AT-9263, a FLT-3 inhibitor, a VEGFR inhibitor, an aurora kinase inhibitor, a PIK-1 modulator, an HDAC inhbitor, a c-MET inhibitor, a PARP inhibitor, a Cdk inhibitor, an IGFR-TK inhibitor, an anti-HGF antibody, a focal adhesion kinase inhibitor, a Map kinase kinase (mek) inhibitor, a VEGF trap antibody, pemetrexed, panitumumab, amrubicin, oregovomab, Lep-etu, nolatrexed, azd2171, batabulin, ofatumumab, zanolimumab, edotecarin, tetrandrine, rubitecan, tesmilifene, oblimersen, ticilimumab, ipilimumab, gossypol, Bio 111, 131-I-TM-601, ALT-110, BIO 140, CC 8490, cilengitide, gimatecan, IL13-PE38QQR, INO 1001, IPdR$_1$ KRX-0402, lucanthone, LY317615, neuradiab, vitespan, Rta 744, Sdx 102, talampanel, atrasentan, Xr 311, romidepsin, ADS-100380, sunitinib, 5-fluorouracil, vorinostat, etoposide, gemcitabine, doxorubicin, liposomal doxorubicin, 5'-deoxy-5-fluorouridine, vincristine, temozolomide, ZK-304709, seliciclib; PD0325901, AZD-6244, capecitabine, L-Glutamic acid, N-[4-[2-(2-amino-4,7-dihydro-4-oxo-1H-pyrrolo[2,3-d]pyrimidin-5-yl)ethyl]benzoyl]-, disodium salt, heptahydrate, camptothecin, PEG-labeled irinotecan, tamoxifen, toremifene citrate, anastrazole, exemestane, letrozole, DES(diethylstilbestrol), estradiol, estrogen, conjugated estrogen, bevacizumab, IMC-1C11, CHIR-258); 3-[5-(methylsulfonylpiperadinemethyl)-indolyl-quinolone, vatalanib, AG-013736, AVE-0005, goserelin acetate, leuprolide acetate, triptorelin pamoate, medroxyprogesterone acetate, hydroxyprogesterone caproate, megestrol acetate, raloxifene, bicalutamide, flutamide, nilutamide, megestrol acetate, CP-724714; TAK-165, HKI-272, erlotinib, lapatanib, canertinib, ABX-EGF antibody, erbitux, EKB-569, PKI-166, GW-572016, Ionafarnib, BMS-214662, tipifarnib; amifostine, NVP-LAQ824, suberoyl analide hydroxamic acid, valproic acid, trichostatin A, FK-228, SU11248, sorafenib, KRN951, aminoglutethimide, arnsacrine, anagrelide, L-asparaginase, Bacillus Calmette-Guerin (BCG) vaccine, adriamycin, bleomycin, buserelin, busulfan, carboplatin, carmustine, chlorambucil, cisplatin, cladribine, clodronate, cyproterone, cytarabine, dacarbazine, dactinomycin, daunorubicin, diethylstilbestrol, epirubicin, fludarabine, fludrocortisone, fluoxymesterone, flutamide, gleevec, gemcitabine, hydroxyurea, idarubicin, ifosfamide, imatinib, leuprolide, levamisole, lomustine, mechlorethamine, melphalan, 6-mercaptopurine, mesna, methotrexate, mitomycin, mitotane, mitoxantrone, nilutamide, octreotide, oxaliplatin, pamidronate, pentostatin, plicamycin, porfimer, procarbazine, raltitrexed, rituximab, streptozocin, teniposide, testosterone, thalidomide, thioguanine, thiotepa, tretinoin, vindesine, 13-cis-retinoic acid, phenylalanine mustard, uracil mustard, estramustine, altretamine, floxuridine, 5-deooxyuridine, cytosine arabinoside, 6-mecaptopurine, deoxycoformycin, calcitriol, valrubicin, mithramycin, vinblastine, vinorelbine, topotecan, razoxin, marimastat, COL-3, neovastat, BMS-275291, squalamine, endostatin, SU5416, SU6668, EMD121974, interleukin-12, IM862, angiostatin, vitaxin, droloxifene, idoxyfene, spironolactone, finasteride, cimitidine, trastuzumab, denileukin diftitox, gefitinib, bortezimib, paclitaxel, cremophor-free paclitaxel, docetaxel, epithilone B, BMS-247550, BMS-310705, droloxifene, 4-hydroxytamoxifen, pipendoxifene, ERA-923, arzoxifene, fulvestrant, acolbifene, lasofoxifene, idoxifene, TSE-424, HMR-3339, ZK186619, topotecan, PTK787/ZK 222584, VX-745, PD 184352, rapamycin, 40-O-(2-hydroxyethyl)-rapamycin, temsirolimus, AP-23573, RAD001, ABT-578, BC-210, LY294002, LY292223, LY292696, LY293684, LY293646, wortmannin, ZM336372, L-779,450, PEG-filgrastim, darbepoetin, erythropoietin, granulocyte colony-stimulating factor, zolendronate, prednisone, cetuximab, granulocyte macrophage colony-stimulating factor, histrelin, pegylated interferon alfa-2a, interferon alfa-2a, pegylated interferon alfa-2b, interferon alfa-2b, azacitidine, PEG-L-asparaginase, lenalidomide, gemtuzumab, hydrocortisone, interleukin-11, dexrazoxane, alemtuzumab, all-transretinoic acid, ketoconazole, interleukin-2, megestrol, immune globulin, nitrogen mustard, methylprednisolone, ibritgumomab tiuxetan, androgens, decitabine, hexamethylmelamine, bexarotene, tositumomab, arsenic trioxide, cortisone, editronate, mitotane, cyclosporine, liposomal daunorubicin, Edwina-asparaginase, strontium 89, casopitant, netupitant, an NK-1 receptor antagonist, palonosetron, aprepitant, diphenhydramine, hydroxyzine, metoclopramide, lorazepam, alprazolam, haloperidol, droperidol, dronabinol, dexamethasone, methylprednisolone, prochlorperazine, granisetron, ondansetron, dolasetron, tropisetron, pegfilgrastim, erythropoietin, epoetin alfa, darbepoetin alfa and mixtures thereof.

In one embodiment, the additional therapeutically active agent is selected from, but are not limited to, Imatinib mesylate (Gleevac®), Dasatinib (Sprycel®), Nilotinib (Tasigna®), Bosutinib (Bosulif®), Trastuzumab (Herceptin®), trastuzumab-DM1, Pertuzumab (Perjeta™), Lapatinib (Tykerb®), Gefitinib (Iressa®), Erlotinib (Tarceva®), Cetuximab (Erbitux®), Panitumumab (Vectibix®), Vandetanib (Caprelsa®), Vemurafenib (Zelboraf®), Vorinostat (Zolinza®), Romidepsin (Istodax®), Bexarotene (Tagretin®), Alitretinoin (Panretin®), Tretinoin (Vesanoid®), Carfilizomib (Kyprolis™), Pralatrexate (Folotyn®), Bevacizumab (Avastin®), Ziv-aflibercept (Zaltrap®), Sorafenib (Nexavar®), Sunitinib (Sutent®), Pazopanib (Votrient®), Regorafenib (Stivarga®), and Cabozantinib (Cometriq™).

In certain aspects, the additional therapeutically active agent is an anti-inflammatory agent, a chemotherapeutic agent, a radiotherapeutic, an additional therapeutic agent, or an immunosuppressive agent.

Suitable chemotherapeutic additional therapeutically active agent s include, but are not limited to, a radioactive molecule, a toxin, also referred to as cytotoxin or cytotoxic agent, which includes any agent that is detrimental to the viability of cells, and liposomes or other vesicles containing chemotherapeutic compounds. General anticancer pharmaceutical agents include: Vincristine (Oncovin®) or liposomal vincristine (Marqibo®), Daunorubicin (daunomycin or Cerubidine®) or doxorubicin (Adriamycin®), Cytarabine (cytosine arabinoside, ara-C, or Cytosar®), L-asparaginase (Elspar®) or PEG-L-asparaginase (pegaspargase or Oncaspar®), Etoposide (VP-16), Teniposide (Vumon®), 6-mercaptopurine (6-MP or Purinethol®), Methotrexate, Cyclophosphamide (Cytoxan®), Prednisone, Dexamethasone (Decadron), imatinib (Gleevec®), dasatinib (Sprycel®), nilotinib (Tasigna®), bosutinib (Bosulif®), and ponatinib (Iclusig™). Examples of additional suitable chemotherapeutic agents include but are not limited to 1-dehydrotestosterone, 5-fluorouracil decarbazine, 6-mercaptopurine, 6-thioguanine, actinomycin D, adriamycin, aldesleukin, an alkylating agent, allopurinol sodium, altretamine, amifostine, anastrozole, anthramycin (AMC)), an anti-mitotic agent, cis-dichlorodiamine platinum (II) (DDP) cisplatin), diamino dichloro platinum, anthracycline, an antibiotic, an antimetabolite, asparaginase, BCG live (intravesical), betamethasone sodium phosphate and betamethasone acetate, bicalutamide, bleomycin sulfate, busulfan, calcium leucouorin, calicheamicin, capecitabine, carboplatin, lomustine (CCNU), carmustine (BSNU), Chlorambucil, Cisplatin, Cladribine, Colchicin, conjugated estrogens, Cyclophosphamide, Cyclothosphamide, Cytarabine, Cytarabine, cytochalasin B, Cytoxan, Dacarbazine, Dactinomycin, dactinomycin (formerly actinomycin), daunirubicin HCL, daunorucbicin citrate, denileukin diftitox, Dexrazoxane, Dibromomannitol, dihydroxy anthracin dione, Docetaxel, dolasetron mesylate, doxorubicin HCL, dronabinol, *E. coli* L-asparaginase, emetine, epoetin-α, *Erwinia* L-asparaginase, esterified estrogens, estradiol, estramustine phosphate sodium, ethidium bromide, ethinyl estradiol, etidronate, etoposide citrororum factor, etoposide phosphate, filgrastim, floxuridine, fluconazole, fludarabine phosphate, fluorouracil, flutamide, folinic acid, gemcitabine HCL, glucocorticoids, goserelin acetate, gramicidin D, granisetron HCL, hydroxyurea, idarubicin HCL, ifosfamide, interferon a-2b, irinotecan HCL, letrozole, leucovorin calcium, leuprolide acetate, levamisole HCL, lidocaine, lomustine, maytansinoid, mechlorethamine HCL, medroxyprogesterone acetate, megestrol acetate, melphalan HCL, mercaptipurine, mesna, methotrexate, methyltestosterone, mithramycin, mitomycin C, mitotane, mitoxantrone, nilutamide, octreotide acetate, ondansetron HCL, paclitaxel, pamidronate disodium, pentostatin, pilocarpine HCL, plimycin, polifeprosan 20 with carmustine implant, porfimer sodium, procaine, procarbazine HCL, propranolol, rituximab, sargramostim, streptozotocin, tamoxifen, taxol, teniposide, tenoposide, testolactone, tetracaine, thioepa chlorambucil, thioguanine, thiotepa, topotecan HCL, toremifene citrate, trastuzumab, tretinoin, valrubicin, vinblastine sulfate, vincristine sulfate, and vinorelbine tartrate.

Additional therapeutic agents that can be administered in combination with a Degrader disclosed herein can include bevacizumab, sutinib, sorafenib, 2-methoxyestradiol or 2ME2, finasunate, vatalanib, vandetanib, aflibercept, volociximab, etaracizumab (MEDI-522), cilengitide, erlotinib, cetuximab, panitumumab, gefitinib, trastuzumab, dovitinib, figitumumab, atacicept, rituximab, alemtuzumab, aldesleukine, atlizumab, tocilizumab, temsirolimus, everolimus, lucatumumab, dacetuzumab, HLL1, huN901-DM1, atiprimod, natalizumab, bortezomib, carfilzomib, marizomib, tanespimycin, saquinavir mesylate, ritonavir, nelfinavir mesylate, indinavir sulfate, belinostat, panobinostat, mapatumumab, lexatumumab, dulanermin, ABT-737, oblimersen, plitidepsin, talmapimod, P276-00, enzastaurin, tipifarnib, perifosine, imatinib, dasatinib, lenalidomide, thalidomide, simvastatin, celecoxib, bazedoxifene, AZD4547, rilotumumab, oxaliplatin (Eloxatin), PD0332991, ribociclib (LEE011), amebaciclib (LY2835219), HDM201, fulvestrant (Faslodex), exemestane (Aromasin), PIM447, ruxolitinib (INC424), BGJ398, necitumumab, pemetrexed (Alimta), and ramucirumab (IMC-1121B).

In one embodiment, the additional therapy is a monoclonal antibody (MAb). Some MAbs stimulate an immune response that destroys cancer cells. Similar to the antibodies produced naturally by B cells, these MAbs may "coat" the cancer cell surface, triggering its destruction by the immune system. For example, bevacizumab targets vascular endothelial growth factor(VEGF), a protein secreted by tumor cells and other cells in the tumor's microenvironment that promotes the development of tumor blood vessels. When bound to bevacizumab, VEGF cannot interact with its cellular receptor, preventing the signaling that leads to the growth of new blood vessels. Similarly, cetuximab and panitumumab target the epidermal growth factor receptor (EGFR), and trastuzumab targets the human epidermal growth factor receptor 2 (HER-2). MAbs that bind to cell surface growth factor receptors prevent the targeted receptors from sending their normal growth-promoting signals. They may also trigger apoptosis and activate the immune system to destroy tumor cells.

In one aspect of the present invention, the additional therapeutically active agent is an immunosuppressive agent. The immunosuppressive agent can be a calcineurin inhibitor, e.g. a cyclosporin or an ascomycin, e.g. Cyclosporin A (NEORAL®), FK506 (tacrolimus), pimecrolimus, a mTOR inhibitor, e.g. rapamycin or a derivative thereof, e.g. Sirolimus (RAPAMUNE®), Everolimus (Certican®), temsirolimus, zotarolimus, biolimus-7, biolimus-9, a rapalog, e.g. ridaforolimus, azathioprine, campath 1H, a SiP receptor modulator, e.g. fingolimod or an analogue thereof, an anti IL-8 antibody, mycophenolic acid or a salt thereof, e.g. sodium salt, or a prodrug thereof, e.g. Mycophenolate Mofetil (CELLCEPT®), OKT3 (ORTHOCLONE OKT3®), Prednisone, ATGAM®, THYMOGLOBULIN®, Brequinar Sodium, OKT4, T10B9.A-3A, 33B3.1, 15-deoxyspergualin, tresperimus, Leflunomide ARAVA®, CTLAI-Ig, anti-CD25, anti-IL2R, Basiliximab (SIMULECT®), Daclizumab (ZENAPAX®), mizorbine, methotrexate, dexamethasone, ISAtx-247, SDZ ASM 981 (pimecrolimus, Elidel®), CTLA4lg (Abatacept), belatacept, LFA3lg, etanercept (sold as Enbrel® by Immunex), adalimumab (Humira®), infliximab (Remicade®), an anti-LFA-1 antibody, natalizumab (Antegren®), Enlimomab, gavilimomab, antithymocyte immunoglobulin, siplizumab, Alefacept efalizumab, pentasa, mesalazine, asacol, codeine phosphate, benorylate, fenbufen, naprosyn, diclofenac, etodolac and indomethacin, aspirin and ibuprofen.

In one embodiment, the additional therapy is bendamustine. In one embodiment, the additional therapy is obinutuzmab. In one embodiment, the additional therapy is a proteasome inhibitor, for example ixazomib or oprozomib. In one embodiment, the additional therapy is a histone deacetylase inhibitor, for example ACY241. In one embodiment, the additional therapy is a BET inhibitor, for example GSK525762A, OTX015, BMS-986158, TEN-010, CPI-0610, INCB54329, BAY1238097, FT-1101, ABBV-075, BI 894999, GS-5829, GSK1210151A (I-BET-151), CPI-203, RVX-208, XD46, MS436, PFI-1, RVX2135, ZEN3365, XD14, ARV-771, MZ-1, PLX5117, 4-[2-(cyclopropylmethoxy)-5-(methanesulfonyl)phenyl]-2-methylisoquinolin-1(2H)-one, EP11313 and EP11336. In one embodiment, the additional therapy is an MCL-1 inhibitor, for example AZD5991, AMG176, MIK665, S64315, or S63845. In one embodiment, the additional therapy is an LSD-1 inhibitor, for example ORY-1001, ORY-2001, INCB-59872, IMG-7289, TAK-418, GSK-2879552, 4-[2-(4-amino-piperidin-1-yl)-5-(3-fluoro-4-methoxy-phenyl)-1-methyl-6-oxo-1,6-dihydropyrimidin-4-yl]-2-fluoro-benzonitrile or a salt thereof. In one embodiment, the additional therapy is a CS1 antibody, for example elotuzumab. In one embodiment, the additional therapy is a CD38 antibody, for example daratumumab or isatuximab. In one embodiment, the additional therapy is a BCMA antibody or antibody-conjugate, for example GSK2857916 or BI 836909.

In some embodiments, a degrader described herein is administered in combination or alternation with one or more cellular immunotherapeutics. In some embodiments, the cellular immunotherapeutic is an engineered immune cell. Engineered immune cells include, for example, but are not limited to, engineered T-cell receptor (TCR) cells and engineered chimeric antigen receptor (CAR) cells. Engineered T Cell Receptor (TCR) Therapy generally involves the introduction of an engineered T cell receptor targeting specific cancer antigens into a patient or donor derived immune effector cell, for example a T-cell or natural killer cell. Alternatively, Chimeric Antigen Receptor (CAR) Therapy generally involves the introduction of a chimeric antigen receptor targeting a specific cancer antigen into a patient or donor derived immune effector cell, for example a T-cell, natural killer cells, or macrophage. One key advantage of CARs compared to TCRs is their ability to bind to cancer cells even if their antigens aren't presented on the surface via MHC, which can render more cancer cells vulnerable to their attacks. However, CAR cells can only recognize antigens that themselves are naturally expressed on the cell surface, so the range of potential antigen targets is smaller than with TCRs.

In some embodiments, the immunotherapeutic is an engineered TCR or CAR immune cell, wherein the TCR or CAR targets one or more tumor associated antigens selected from: BCMA, an important signaling receptor found naturally on mature B cells; often expressed by lymphoma and myeloma cells; CD19, a receptor found on the surface of almost all B cells that influences their growth, development, and activity, often expressed by leukemia, lymphoma, and myeloma cells; CD22, a receptor found primarily on the surface of mature B cells; often expressed by leukemia and lymphoma cells; CD30, a receptor that is expressed on certain types of activated immune cells, often expressed by leukemia and lymphoma cells; CD33: a surface receptor found on several types of immune cells; often expressed by leukemia cells; CD56, a protein found on both neurons and natural killer immune cells; CD123 (also known as IL-3R), a receptor found on immune cells that is involved in proliferation and differentiation, and often expressed by leukemia and lymphoma cells; CEA, a protein involved in cellular adhesion normally produced only before birth, often abnormally expressed in cancer and may contribute to metastasis; EBV-related antigens, foreign viral proteins expressed by Epstein-Barr Virus (EBV)-infected cancer cells; EGFR, a pathway that controls cell growth and is often mutated in cancer; GD2, a pathway that controls cell growth, adhesion, and migration, and is often abnormally overexpressed in cancer cells; GPC3, a cell surface protein thought to be involved in regulating growth and cell division; HER2, a pathway that controls cell growth and is commonly overexpressed in some cancers, particularly breast cancer, and is associated with metastasis; HPV-related antigens, foreign viral proteins expressed by cancer cells that develop as a consequence of having been infected with Human Papilloma Virus (HPV); MAGE antigens, the genes that produce these proteins are normally turned off in adult cells, but can become reactivated in cancer cells, flagging them as abnormal to the immune system; Mesothelin, a protein that is commonly overexpressed in cancer and may aid metastasis; MUC-1, a sugar-coated protein that is commonly overexpressed in cancer; NY-ESO-1, a protein that is normally produced only before birth, but is often abnormally expressed in cancer; PSCA, a surface protein that is found on several cell types and is often overexpressed by cancer cells; PSMA, a surface protein found on prostate cells that is often overexpressed by prostate cancer cells; ROR1, a tyrosine kinase-like orphan receptor that is mostly expressed before birth rather than in adult tissues, but is often abnormally expressed in cancer and may promote cancer cell metastasis as well as prevent cancer cell death; WT1, a protein that promotes cancer progression, is abnormally expressed in patients with cancer, especially leukemia; and Claudin 18.2: a surface protein overexpressed in some esophageal cancers and involved in invasion and survival. In some embodiments, the engineered CAR therapy is Axicabtagene ciloleucel (Yescarta®): a CD19-targeting CAR T cell immunotherapy; approved for subsets of patients with lymphoma. In some embodiments, the engineered CAR therapy is Tisagenlecleucel (Kymriah®): a CD19-targeting CAR T cell immunotherapy; approved for subsets of patients with leukemia and lymphoma. In some embodiments, the engineered CAR therapy is Lisocabtagene maraleucel (Bristol-Myers Squibb Co.): a CD19-targeting CAR T cell immunotherapy which is used to treat relapsed/refractory large B-cell lymphoma, including diffuse large B-cell lymphoma (DLBCL). In some embodiments, the engineered CAR Therapy is a BCMA CAR-T therapy, for example, but not limited to JNJ-4528 (Johnson & Johnson) and KITE-585 (Gilead). In some embodiments, the engineered CAR-T therapy is a dual specific CAR-T targeting BCMA and CD38. In some embodiments, the engineered CAR therapy is a CD20/CD22 dual targeted CAR-T cell therapy. Compositions and methods for deriving CAR immune cells are described, for example, in U.S. Pat. No. 5,359,046 (Cell Genesys); U.S. Pat. No. 5,712,149 (Cell Genesys); U.S. Pat. No. 6,103,521 (Cell Genesys); U.S. Pat. No. 7,446,190 (Memorial Sloan Kettering Cancer Center); U.S. Pat. No. 7,446,179 (City of Hope); U.S. Pat. No. 7,638,325 (U. Penn); U.S. Pat. No. 8,911,993 (U. Penn); U.S. Pat. No. 8,399,645 (St. Jude's Children's Hospital); U.S. Pat. No. 8,906,682 (U. Penn); U.S. Pat. No. 8,916,381 (U. Penn); U.S. Pat. No. 8,975,071 (U. Penn); U.S. Pat. No. 9,102,760 (U. Penn); U.S. 9,4644 (U. Penn); U.S. Pat. No. 9,855,298 (Gilead); U.S. Pat. No. 10,144,770 (St. Jude Children's Hospital); U.S. Pat. No. 10,266,580 (U. Penn); U.S. Pat. No. 10,189,903 (Seattle Children's Hospital); WO 2014/011988 (U. Penn); WO 2014/145252; WO 2014/153270 (Novartis AG); US 2018/0360880 (Memorial Sloan Kettering Cancer Center); WO 2017/0243 (Dana Farber Cancer Institute); WO 2016/115177 (Juno Therapeutics, Inc.); each of which is incorporated herein by reference.

In some embodiments, the immunotherapeutic is a non-engineered adoptive cell therapy. Adoptive cell therapy is an approach used to bolster the ability of the immune system to fight diseases, such as tumor and viral infections. According to this approach, immune cells, for example T cells or NK cells, are collected from a patient or donor, stimulated in the presence of antigen presenting cells bearing tumor or viral-associated antigens, and then expanded ex vivo. In some embodiments, the adoptive cell therapy is Tumor-Infiltrating Lymphocyte (TIL) Therapy, which harvests naturally occurring T cells that have already infiltrated patients' tumors, and are then activated and expanded, Then, and re-infused into patients. In some embodiments, the non-engineered adoptive cell therapy includes autologous or allogeneic immune cells, for example αβ T-cells activated to target multiple potential antigens. One strategy used to develop targeted non-engineered T-cells involves the ex vivo expansion of T-cells by antigen-specific stimulation of patient-derived (autologous) or donor-derived (allogeneic) T cells ex vivo. These strategies generally involve the isolation of peripheral blood mononuclear cells (PBMCs) and exposure of the cells to one or more tumor associated antigens. In particular, approaches to generate multi-antigen specific T-cells have focused on priming and activating T-cells with multiple targeted antigen overlapping peptide libraries, for example multiple libraries of 15mer peptides overlapping by 11 amino acids spanning the whole amino acid sequence of several target antigens (see for example commercially available overlapping peptide library products from JPT Technologies or Miltenyi). Strategies for activating ex vivo autologous or allogenic immune effector cells for targeting tumor associated antigens are described in, for example: US2011/0182870 (Baylor College of Medicine); US 2015/0010519 (Baylor College of Medicine); US2015/0017723 (Baylor College of Medicine); WO2006026746 (United States Government, Department of Health and Human Services); US 2015/0044258 (Cell Medica/Kurr Therapeutics); WO2016/154112 (Children's National Medical Center); WO 2017/203356 (Queensland Institute of Medical Research); WO 2018/005712 (Geneius Biotechnology, Inc.); Vera et al. Accelerated Production of Antigen-Specific T Cells for Pre-clinical and Clinical Applications using Gas-permeable Rapid Expansion Cultureware (G-Rex), April 2010 Journal of Immunotherapy 33(3):305-315; Shafer et al. Antigen-specific Cytotoxic T Lymphocytes can Target Chemoresistant Side-Population Tumor Cells in Hodgkin's Lymphoma; May 2010 Leukemia Lymphoma 51(5): 870-880; Quintarelli et al. High Avidity Cytotoxic T Lymphocytes Specific for a New PRAME-derived Peptide can Target Leukemic and Leukemic-precursor cells, Mar. 24, 2011 Blood 117(12): 3353-3362; Bollard et al. Manufacture of GMP-grade Cytotoxic T Lymphocytes Specific for LMP1 and LMP2 for Patients with EBV-associated Lymphoma, May 2011 Cytotherapy 13(5): 518-522; Ramos et al. Human Papillomavirus Type 16 E6/E7-Specific Cytotoxic T Lymphocytes for Adoptive Immunotherapy of HPV-associated Malignancies, January 2013 Immunotherapy 36(1): 66-76; Weber et al. Generation of tumor antigen-specific T cell lines from pediatric patients with acute lymphoblastic leukemia—implications for immunotherapy, Clinical Cancer Research 2013 Sep. 15; 19(18): 5079-5091; Ngo et al. Complementation of antigen presenting cells to generate T lymphocytes with broad target specificity, Journal of Immunotherapy. 2014 May; 37(4): 193-203; each of which is incorporated herein by reference. In some embodiments, the non-engineered, activated immune cell administered in combination or alternation with a degrader composition described herein is selected from activated CD4+ T-cells (T-helper cells), CD8+ T-cells (Cytotoxic T-Lymphocytes), CD3+/CD56+ Natural Killer T-cells (CD3+ NKT), and 7S T-cells (γδ T-cells), or combinations thereof. In some embodiments, the adoptive cell therapy is a composition comprising CD4+ T-cells (T-helper cells). In some embodiments, the adoptive cell therapy is a composition comprising CD8+ T-cells (Cytotoxic T-Lymphocytes). In some embodiments, the adoptive cell therapy is a composition comprising CD3+/CD56+ Natural Killer T-cells (CD3+ NKT). In some embodiments, the adoptive cell therapy is a composition comprising CD4+ T-cells (T-helper cells), CD8+ T-cells (Cytotoxic T-Lymphocytes), CD3+/CD56+ Natural Killer T-cells (CD3+ NKT), and γ=T-cells (γδT-cells).

In some embodiments, the immunotherapy is a bi-specific T-cell engager (BiTE). A bi-specific T-cell engager directs T-cells to target and bind with a specific antigen on the surface of a cancer cell. For example, Blinatumomab (Amgen), a BiTE has recently been approved as a second line therapy in Philadelphia chromosome-negative relapsed or refractory acute lymphoblastic leukemia. Blinatumomab is given by continuous intravenous infusion in 4-week cycles.

In certain embodiments, the additional therapeutically active agent is an additional inhibitor of Ikaros ("IKZF1") and/or Aiolos ("IKZF3"). In another embodiment, the additional therapeutically active agent is an inhibitor of Helios ("IKZF2"). In another embodiment, the additional therapeutically active agent is an inhibitor of Eos ("IKZF4"). In another embodiment, the additional therapeutically active agent is an inhibitor of Pegasus ("IKZF5"). In another embodiment, the additional therapeutically active agent is a cereblon ligand.

Non-limiting examples of cereblon ligands that may be used in combination with a compound of the present invention include: thalidomide, lenalidomide, pomalidomide, and iberdomide.

In another embodiment the additional compound that may be used in combination with a compound of the present invention is selected from those described in WO2012/175481, WO2015/085172, WO2015/085172, WO2017/067530, WO2017/121388, WO2017/201069, WO2018/108147, WO2018/118947, WO2019/038717, WO2019/191112, WO2020/006233, WO2020/006262, WO2020/006265, or WO2020/012334.

In another embodiment the additional compound that may be used in combination with a compound of the present invention is selected from those described in WO2019/060693, WO2019/060742, WO2019/133531, WO2019/140380, WO2019/140387, WO2010/010177, WO2020/010210, or WO2020/010227.

In another embodiment the additional compound that may be used in combination with a compound of the present invention is selected from those described in WO2015/160845, WO2016/118666, WO2016/149668, WO2016/197032, WO2016/197114, WO2017/011371, WO2017/0115901, WO2017/030814, WO2017/176708, WO2018/053354, WO2018/0716060, WO2018/102067, WO2018/118598, WO2018/119357, WO2018/119441, WO2018/119448, WO2018/140809, WO2018/226542, WO2019/023553, WO2019/099926, WO2019/195201, WO2019/195609, WO2019/199816, WO2019/023851, WO2020/041331, or WO2020/051564.

In another embodiment the additional compound that may be used in combination with a compound of the present invention is selected from those described in WO2016/105518, WO2017/007612, WO2017/024317, WO2017/024318, WO2017/024319, WO2017/1 17473, WO2017/117474, WO2017/185036, WO2018/064589, WO2018/148440, WO2018/148443, WO2018/226978, WO2019/014429, WO2019/079701, WO2019/094718, WO2019/094955, WO2019/118893, WO2019/165229, WO2020/006262, WO2020/018788, WO2020/069105, WO2020/069117, or WO2020/069125.

In another embodiment the additional compound that may be used in combination with a compound of the present invention is selected from those described in WO2017/197036, WO2017/197046, WO2017/197051, WO2017/197055, WO2017/197056, WO 2017/115218, WO2018/220149, WO2018/237026, WO2019/099868, WO2019/121562, WO2019/149922, WO2019/191112, WO2019/204354, WO2019/236483, or WO2020/051235.

V. Pharmaceutical Compositions

Any of the compounds as disclosed herein can be administered as the neat chemical, but are more typically administered as a pharmaceutical composition, that includes an effective amount for a host, typically a human, in need of such treatment for any of the disorders described herein. Accordingly, the disclosure provides pharmaceutical compositions comprising an effective amount of compound or pharmaceutically acceptable salt together with at least one pharmaceutically acceptable carrier for any of the uses described herein. The pharmaceutical composition may contain a compound or salt as the only active agent, or, in an alternative embodiment, the compound and at least one additional active agent.

In certain embodiments the pharmaceutical composition is in a dosage form that contains from about 0.0005 mg to about 2000 mg, from about 0.001 mg to about 1000 mg, from about 0.001 mg to about 600 mg, or from about 0.001 mg to about 1, 5, 10, 15, 20, 25, 50, 100, 200 or 300 mg mg of the active compound. In another embodiment the pharmaceutical composition is in a dosage form that contains from about 0.01 mg to about 1, 5, 10, 15, 20, 25, 50 or 100 mg, from about 0.05 mg to about 1, 5, 10, 15, 20, 25, 50 or 100 mg, from about 0.1 mg to about 1, 5, 10, 15, 20, 25 or 50 mg, from about 0.02 mg to about 1, 5, 10, 15, 20, 25 or 50 mg of the active compound, from about 0.5 mg to about 1, 5, 10, 15, 20, 25 or 50 mg. In another embodiment the pharmaceutical composition is in a dosage form that contains from about 0.01 mg to about 10 mg, from about 0.05 mg to about 8 mg, or from about 0.05 mg to about 6 mg, or from about 0.05 mg to about 5 mg of the active compound. In another embodiment the pharmaceutical composition is in a dosage form that contains from about 0.1 mg to about 10 mg, from about 0.5 mg to about 8 mg, or from about 0.5 mg to about 6 mg, or from about 0.5 mg to about 5 mg of the active compound. Nonlimiting examples are dosage forms with at least about 0.0005, 0.001, 0.01, 0.1, 1, 2.5, 5, 10, 25, 50, 100, 200, 250, 300, 400, 500, 600, 700, or 750 mg of active compound, or its salt. Alternative nonlimiting examples are dosage forms with not greater than about 0.01, 0.1, 1, 2.5, 5, 10, 25, 50, 100, 200, 250, 300, 400, 500, 600, 700, or 750 mg of active compound, or its salt.

The pharmaceutical composition may also include a molar ratio of the active compound and an additional therapeutically active agent. In non-limiting illustrative embodiments the pharmaceutical composition may contain a molar ratio of about up to 0.5:1, about up to 1:1, about up to 2:1, about up to 3:1 or from about up to 1.5:1 to about up to 4:1 of an anti-inflammatory or immunosuppressing agent to the compound of the present invention. Compounds disclosed herein may be administered orally, topically, parenterally, by inhalation or spray, sublingually, via implant, including ocular implant, transdermally, via buccal administration, rectally, as an ophthalmic solution, injection, including ocular injection, intravenous, intra-aortal, intracranial, subdermal, intraperitoneal, subcutaneous, transnasal, sublingual, or rectal or by other means, in dosage unit formulations containing conventional pharmaceutically acceptable carriers. For ocular delivery, the compound can be administered, as desired, for example, via intravitreal, intrastromal, intracameral, sub-tenon, sub-retinal, retro-bulbar, peribulbar, suprachoroidal, conjunctival, subconjunctival, episcleral, periocular, transscleral, retrobulbar, posterior juxtascleral, circumcorneal, or tear duct injections, or through a mucus, mucin, or a mucosal barrier, in an immediate or controlled release fashion or via an ocular device.

The pharmaceutical composition may be formulated as any pharmaceutically useful form, e.g., as an aerosol, a cream, a gel, a pill, an injection or infusion solution, a capsule, a tablet, a syrup, a transdermal patch, a subcutaneous patch, a dry powder, an inhalation formulation, in a medical device, suppository, buccal, or sublingual formulation, parenteral formulation, or an ophthalmic solution. Some dosage forms, such as tablets and capsules, are subdivided into suitably sized unit doses containing appropriate quantities of the active components, e.g., an effective amount to achieve the desired purpose.

Carriers include excipients and diluents and must be of sufficiently high purity and sufficiently low toxicity to render them suitable for administration to the patient being treated. The carrier can be inert or it can possess pharmaceutical benefits of its own. The amount of carrier employed in conjunction with the compound is sufficient to provide a practical quantity of material for administration per unit dose of the compound.

Classes of carriers include, but are not limited to binders, buffering agents, coloring agents, diluents, disintegrants, emulsifiers, flavorants, glidents, lubricants, preservatives, stabilizers, surfactants, tableting agents, and wetting agents. Some carriers may be listed in more than one class, for example vegetable oil may be used as a lubricant in some formulations and a diluent in others. Pharmaceutically acceptable carriers are carriers that do not cause any severe adverse reactions in the human body when dosed in the amount that would be used in the corresponding pharmaceutical composition. Exemplary pharmaceutically acceptable carriers include sugars, starches, celluloses, powdered tragacanth, malt, gelatin; talc, and vegetable oils. Optional active agents may be included in a pharmaceutical composition, which do not substantially interfere with the activity of the compound of the present invention.

The pharmaceutical compositions/combinations can be formulated for oral administration. These compositions can contain any amount of active compound that achieves the desired result, for example between 0.1 and 99 weight % (wt. %) of the compound including for example at least about 5 wt. % of the compound. Some embodiments contain from about 25 wt. % to about 50 wt. % or from about 5 wt. % to about 75 wt. % of the compound.

Formulations suitable for rectal administration are typically presented as unit dose suppositories. These may be prepared by admixing the active compound with one or more conventional solid carriers, for example, cocoa butter, and then shaping the resulting mixture.

Formulations suitable for topical application to the skin preferably take the form of an ointment, cream, lotion, paste, gel, spray, aerosol, or oil. Carriers which may be used include petroleum jelly, lanoline, polyethylene glycols, alcohols, transdermal enhancers, and combinations of two or more thereof.

Formulations suitable for transdermal administration may be presented as discrete patches adapted to remain in intimate contact with the epidermis of the recipient for a prolonged period of time. Formulations suitable for transdermal administration may also be delivered by iontophoresis (see, for example, Pharmaceutical Research 3 (6):318 (1986)) and typically take the form of an optionally buffered aqueous solution of the active compound. In one embodiment, microneedle patches or devices are provided for delivery of drugs across or into biological tissue, particularly the skin. The microneedle patches or devices permit drug delivery at clinically relevant rates across or into skin or other tissue barriers, with minimal or no damage, pain, or irritation to the tissue.

Formulations suitable for administration to the lungs can be delivered by a wide range of passive breath driven and active power driven single/-multiple dose dry powder inhalers (DPI). The devices most commonly used for respiratory delivery include nebulizers, metered-dose inhalers, and dry powder inhalers. Several types of nebulizers are available, including jet nebulizers, ultrasonic nebulizers, and vibrating mesh nebulizers. Selection of a suitable lung delivery device depends on parameters, such as nature of the drug and its formulation, the site of action, and pathophysiology of the lung.

Many methods and devices for drug delivery are known in the art. Non-limiting examples are described in the following patents and patent applications (fully incorporated herein by reference). Examples are U.S. Pat. No. 8,192,408 titled "Ocular trocar assembly" (Psivida Us, Inc.); U.S. Pat. No. 7,585,517 titled "Transcleral delivery" (Macusight, Inc.); U.S. Pat. Nos. 5,710,182 and 5,795,913 titled "Ophthalmic composition" (Santen OY); U.S. Pat. No. 8,663,639 titled "Formulations for treating ocular diseases and conditions", U.S. Pat. No. 8,486,960 titled "Formulations and methods for vascular permeability-related diseases or conditions", U.S. Pat. Nos. 8,367,097 and 8,927,005 titled "Liquid formulations for treatment of diseases or conditions", U.S. Pat. No. 7,455,855 titled "Delivering substance and drug delivery system using the same" (Santen Pharmaceutical Co., Ltd.); WO/2011/050365 titled "Conformable Therapeutic Shield For Vision and Pain" and WO/2009/145842 titled "Therapeutic Device for Pain Management and Vision" (Forsight Labs, LLC); U.S. Pat. Nos. 9,066,779 and 8,623,395 titled "Implantable therapeutic device", WO/2014/160884 titled "Ophthalmic Implant for Delivering Therapeutic Substances", U.S. Pat. Nos. 8,399,006, 8,277, 830, 8,795,712, 8,808,727, 8,298,578, and WO/2010/088548 titled "Posterior segment drug delivery", WO/2014/152959 and US20140276482 titled "Systems for Sustained Intraocular Delivery of Low Solubility Compounds from a Port Delivery System Implant", U.S. Pat. Nos. 8,905,963 and 9,033,911 titled "Injector apparatus and method for drug delivery", WO/2015/057554 titled "Formulations and Methods for Increasing or Reducing Mucus", U.S. Pat. Nos. 8,715,712 and 8,939,948 titled "Ocular insert apparatus and methods", WO/2013/116061 titled "Insertion and Removal Methods and Apparatus for Therapeutic Devices", WO/2014/066775 titled "Ophthalmic System for Sustained Release of Drug to the Eye", WO/2015/085234 and WO/2012/019176 titled "Implantable Therapeutic Device", WO/2012/065006 titled "Methods and Apparatus to determine Porous Structures for Drug Delivery", WO/2010/141729 titled "Anterior Segment Drug Delivery", WO/2011/050327 titled "Corneal Denervation for Treatment of Ocular Pain", WO/2013/022801 titled "Small Molecule Delivery with Implantable Therapeutic Device", WO/2012/019047 titled "Subconjunctival Implant for Posterior Segment Drug Delivery", WO/2012/068549 titled "Therapeutic Agent Formulations for Implanted Devices", WO/2012/019139 titled "Combined Delivery Methods and Apparatus", WO/2013/040426 titled "Ocular Insert Apparatus and Methods", WO/2012/019136 titled "Injector Apparatus and Method for Drug Delivery", WO/2013/040247 titled "Fluid Exchange Apparatus and Methods" (ForSight Vision4, Inc.); US/2014/0352690 titled "Inhalation Device with Feedback System", U.S. Pat. No. 8,910,625 and US/2015/0165137 titled "Inhalation Device for Use in Aerosol Therapy" (Vectura GmbH); U.S. Pat. No. 6,948,496 titled "Inhalers", US/2005/0152849 titled "Powders comprising anti-adherent materials for use in dry powder inhalers", U.S. Pat. Nos. 6,582,678, 8,137, 657, US/2003/0202944, and US/2010/0330188 titled "Carrier particles for use in dry powder inhalers", U.S. Pat. No. 6,221,338 titled "Method of producing particles for use in dry powder inhalers", U.S. Pat. No. 6,989,155 titled "Powders", US/2007/0043030 titled "Pharmaceutical compositions for treating premature ejaculation by pulmonary inhalation", U.S. Pat. No. 7,845,349 titled "Inhaler", US/2012/0114709 and U.S. Pat. No. 8,101,160 titled "Formulations for Use in Inhaler Devices", US/2013/0287854 titled "Compositions and Uses", US/2014/0037737 and U.S. Pat. No. 8,580,306 titled "Particles for Use in a Pharmaceutical Composition", US/2015/0174343 titled "Mixing Channel for an Inhalation Device", U.S. Pat. No. 7,744,855 and US/2010/0285142 titled "Method of making particles for use in a pharmaceutical composition", U.S. Pat. No. 7,541, 022, US/2009/0269412, and US/2015/0050350 titled "Pharmaceutical formulations for dry powder inhalers" (Vectura Limited).

Additional non-limiting examples of how to deliver the active compounds are provided in WO/2015/085251 titled "Intracameral Implant for Treatment of an Ocular Condition" (Envisia Therapeutics, Inc.); WO/2011/008737 titled "Engineered Aerosol Particles, and Associated Methods", WO/2013/082111 titled "Geometrically Engineered Particles and Methods for Modulating Macrophage or Immune Responses", WO/2009/132265 titled "Degradable compounds and methods of use thereof, particularly with particle replication in non-wetting templates", WO/2010/099321 titled "Interventional drug delivery system and associated methods", WO/2008/100304 titled "Polymer particle composite having high fidelity order, size, and shape particles", WO/2007/024323 titled "Nanoparticle fabrication methods, systems, and materials" (Liquidia Technologies, Inc. and the University of North Carolina at Chapel Hill); WO/2010/009087 titled "Iontophoretic Delivery of a Controlled-Release Formulation in the Eye", (Liquidia Technologies, Inc. and Eyegate Pharmaceuticals, Inc.) and WO/2009/132206 titled "Compositions and Methods for Intracellular Delivery and Release of Cargo", WO/2007/133808 titled "Nanoparticles for cosmetic applications", WO/2007/056561 titled "Medical device, materials, and methods", WO/2010/065748 titled "Method for producing patterned materials", WO/2007/081876 titled "Nanostructured surfaces for biomedical/biomaterial applications and processes thereof" (Liquidia Technologies, Inc.).

Additional non-limiting examples of drug delivery devices and methods include, for example, US20090203709 titled "Pharmaceutical Dosage Form For Oral Administration Of Tyrosine Kinase Inhibitor" (Abbott Laboratories); US20050009910 titled "Delivery of an active drug to the posterior part of the eye via subconjunctival or periocular delivery of a prodrug", US 20130071349 titled "Biodegradable polymers for lowering intraocular pressure", U.S. Pat. No. 8,481,069 titled "Tyrosine kinase microspheres", U.S. Pat. No. 8,465,778 titled "Method of making tyrosine kinase microspheres", U.S. Pat. No. 8,409,607 titled "Sustained release intraocular implants containing tyrosine kinase inhibitors and related methods", U.S. Pat. No. 8,512,738 and US 2014/0031408 titled "Biodegradable intravitreal tyrosine kinase implants", US 2014/0294986 titled "Microsphere Drug Delivery System for Sustained Intraocular Release", U.S. Pat. No. 8,911,768 titled "Methods For Treating Retinopathy With Extended Therapeutic Effect" (Allergan, Inc.); U.S. Pat. No. 6,495,164 titled "Preparation of injectable suspensions having improved injectability" (Alkermes Controlled Therapeutics, Inc.); WO 2014/047439 titled "Biodegradable Microcapsules Containing Filling Material" (Akina, Inc.); WO 2010/132664 titled "Compositions And Methods For Drug Delivery" (Baxter International Inc. Baxter Healthcare SA); US20120052041 titled "Polymeric nanoparticles with enhanced drug loading and methods of use thereof" (The Brigham and Women's Hospital, Inc.); US20140178475, US20140248358, and US20140249158 titled "Therapeutic Nanoparticles Comprising a Therapeutic Agent and Methods of Making and Using Same" (BIND Therapeutics, Inc.); U.S. Pat. No. 5,869,103 titled "Polymer microparticles for drug delivery" (Danbiosyst UK Ltd.); U.S. Pat. No. 8,628,801 titled "Pegylated Nanoparticles" (Universidad de Navarra); US2014/0107025 titled "Ocular drug delivery system" (Jade Therapeutics, LLC); U.S. Pat. No. 6,287,588 titled "Agent delivering system comprised of microparticle and biodegradable gel with an improved releasing profile and methods of use thereof", U.S. Pat. No. 6,589,549 titled "Bioactive agent delivering system comprised of microparticles within a biodegradable to improve release profiles" (Macromed, Inc.); U.S. Pat. Nos. 6,007,845 and 5,578,325 titled "Nanoparticles and microparticles of non-linear hydrophilichydrophobic multiblock copolymers" (Massachusetts Institute of Technology); US20040234611, US20080305172, US20120269894, and US20130122064 titled "Ophthalmic depot formulations for periocular or subconjunctival administration (Novartis Ag); U.S. Pat. No. 6,413,539 titled "Block polymer" (Poly-Med, Inc.); US 20070071756 titled "Delivery of an agent to ameliorate inflammation" (Peyman); US 20080166411 titled "Injectable Depot Formulations And Methods For Providing Sustained Release Of Poorly Soluble Drugs Comprising Nanoparticles" (Pfizer, Inc.); U.S. Pat. No. 6,706,289 titled "Methods and compositions for enhanced delivery of bioactive molecules" (PR Pharmaceuticals, Inc.); and U.S. Pat. No. 8,663,674 titled "Microparticle containing matrices for drug delivery" (Surmodics).

VI. General Synthesis

The compounds described herein can be prepared by methods known by those skilled in the art. In one non-limiting example, the disclosed compounds can be made using the schemes below.

Compounds of the present invention with stereocenters may be drawn without stereochemistry for convenience. One skilled in the art will recognize that pure or enriched enantiomers and diastereomers can be prepared by methods known in the art. Examples of methods to obtain optically active materials include at least the following:
  i) physical separation of crystals—a technique whereby macroscopic crystals of the individual enantiomers are manually separated. This technique can be used if crystals of the separate enantiomers exist, i.e., the material is a conglomerate, and the crystals are visually distinct;
  ii) simultaneous crystallization—a technique whereby the individual enantiomers are separately crystallized from a solution of the racemate, possible only if the enantiomer is a conglomerate in the solid state;
  iii) enzymatic resolutions—a technique whereby partial or complete separation of a racemate by virtue of differing rates of reaction for the enantiomers with an enzyme;
  iv) enzymatic asymmetric synthesis—a synthetic technique whereby at least one step in the synthesis uses an enzymatic reaction to obtain an enantiomerically pure or enriched synthetic precursor of the desired enantiomer;
  v) chemical asymmetric synthesis—a synthetic technique whereby the desired enantiomer is synthesized from an achiral precursor under conditions that produce asymmetry (i.e. chirality) in the product, which may be achieved by chiral catalysts or chiral auxiliaries;
  vi) diastereomer separations—a technique whereby a racemic compound is reaction with an enantiomerically pure reagent (the chiral auxiliary) that converts the individual enantiomers to diastereomers. The resulting diastereomers are then separated by chromatography or crystallization by virtue of their now more distinct structural differences the chiral auxiliary later removed to obtain the desired enantiomer;
  vii) first- and second-order asymmetric transformations—a technique whereby diastereomers from the racemate quickly equilibrate to yield a preponderance in solution of the diastereomer from the desired enantiomer of where preferential crystallization of the diastereomer from the desired enantiomer perturbs the equilibrium such that eventually in principle all the material is converted to the crystalline diastereomer from the desired enantiomers. The desired enantiomer is then released from the diastereomer;
  viii) kinetic resolutions—this technique refers to the achievement of partial or complete resolution of a racemate (or of a further resolution of a partially resolved compound) by virtue of unequal reaction rates of the enantiomers with a chiral, non-racemic reagent or catalyst under kinetic conditions;
  ix) enantiospecific synthesis from non-racemic precursors—a synthetic technique whereby the desired enantiomer is obtained from non-chiral starting materials and where the stereochemical integrity is not or is only minimally compromised over the course of the synthesis;
  x) chiral liquid chromatography—a technique whereby the enantiomers of a racemate are separated in a liquid mobile phase by virtue of their differing interactions with a stationary phase (including vial chiral HPLC). The stationary phase can be made of chiral material or the mobile phase can contain an additional chiral material to provoke the differing interactions;
  xi) chiral gas chromatography—a technique whereby the racemate is volatilized and enantiomers are separated by virtue of their differing interactions in the gaseous mobile phase with a column containing a fixed non-racemic chiral adsorbent phase;
  xii) extraction with chiral solvents—a technique whereby the enantiomers are separated by virtue of preferential dissolution of one enantiomer into a particular chiral solvent;
  xiii) transport across chiral membranes—a technique whereby a racemate is place in contact with a thin membrane barrier. The barrier typically separates two miscible fluids, one containing the racemate, and a driving force such as concentration or pressure differential causes preferential transport across the membrane barrier. Separation occurs as a result of the non-racemic chiral nature of the membrane that allows only one enantiomer of the racemate to pass through;
  xiv) simulated moving bed chromatography is used in one embodiment. A wide variety of chiral stationary phases are commercially available.

General Synthesis Scheme 1

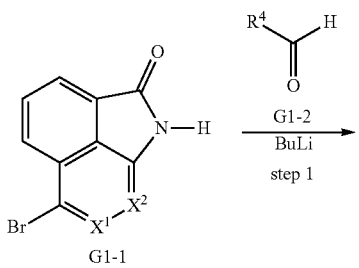

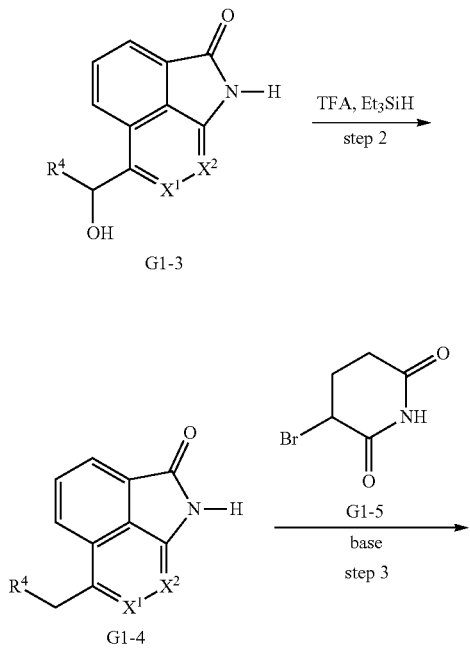

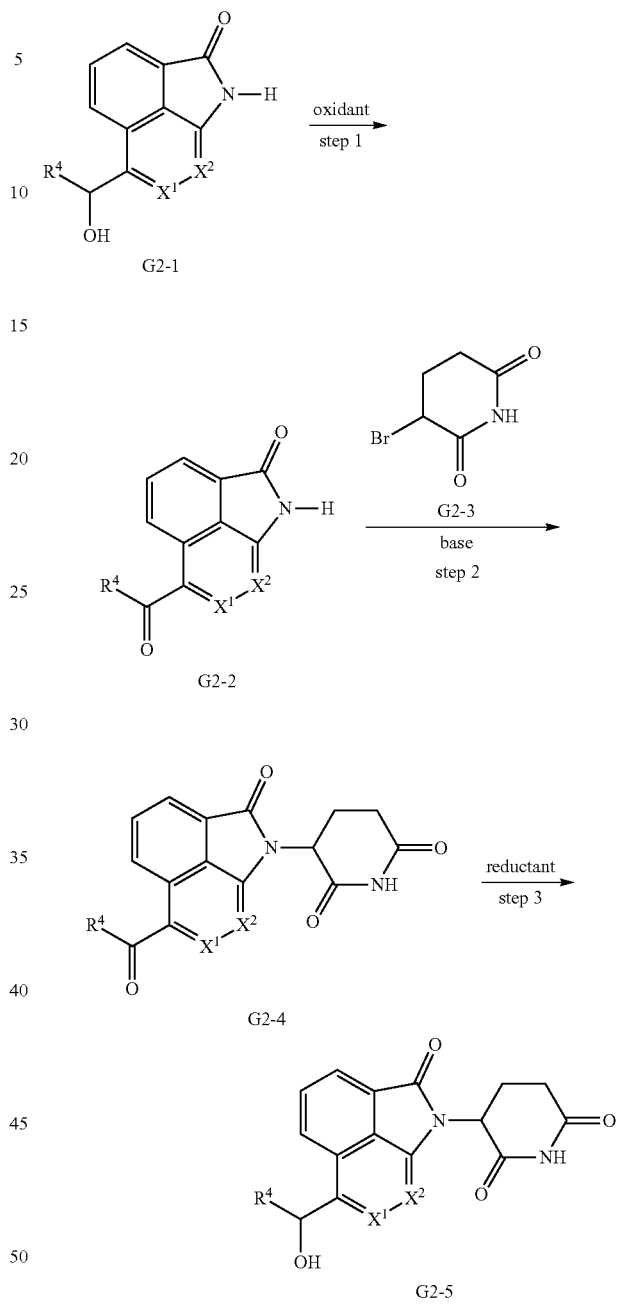

In some aspects, a compound of Formula I or Formula II can be synthesized according to the route provided in General Synthesis Scheme 1. In step 1, compound G1-1 is reacted with butyllithium (or alternatively another organo-lithium reagent such as, for example, tert-butyllithium, sec-butyllithium, phenyllithium, or methyllithium or a Grignard reagent such as, for example, isopropyl magnesium bromide or ethyl magnesium bromide) in an organic solvent (for example tetrahydrofuran or diethyl ether) at low temperature (typically −78° C. to −40° C.) followed by the addition of G1-2 to provide G1-3. In step 2, compound G1-3 with trifluoroacetic acid (or alternatively another strong oxyacid such as, for example, triflic acid) and triethylsilane (or alternatively another organosilane such as, for example, phenylsilane or an organotin hydride such as, for example, tributyltin hydride) in an organic solvent (for example 1,2-dichloroethane) with heating (for example about 60° C. or alternatively with microwave irradiation) to provide G1-4. In step 3, compound G1-4 is reacted with a base (for example sodium hydride) in an organic solvent (for example dimethylformamide or dichloromethane) followed by addition of G1-5 to provide G1-6.

In some aspects, a compound of Formula I or Formula II can be synthesized according to the route provided in General Synthesis Scheme 2. In step 1, compound G2-1 (prepared according to the procedures outlined in General Synthesis Scheme 1 for compound G1-3) is reacted with an oxidant (for example manganese dioxide or other suitable reagent for the oxidation of alcohols) in organic solvent (for example acetonitrile) to provide G2-2. In step 2, G2-2 is reacted with a base (for example sodium hydride) in an organic solvent (for example dimethylformamide or dichloromethane) followed by addition of G2-3 to provide G2-4. In step 3, G2-4 is reacted with a suitable carbonyl reductant (for example sodium cyanoborohydride) in organic solvent (for example ethanol or methanol) to provide G2-5.

General Synthesis Scheme 3

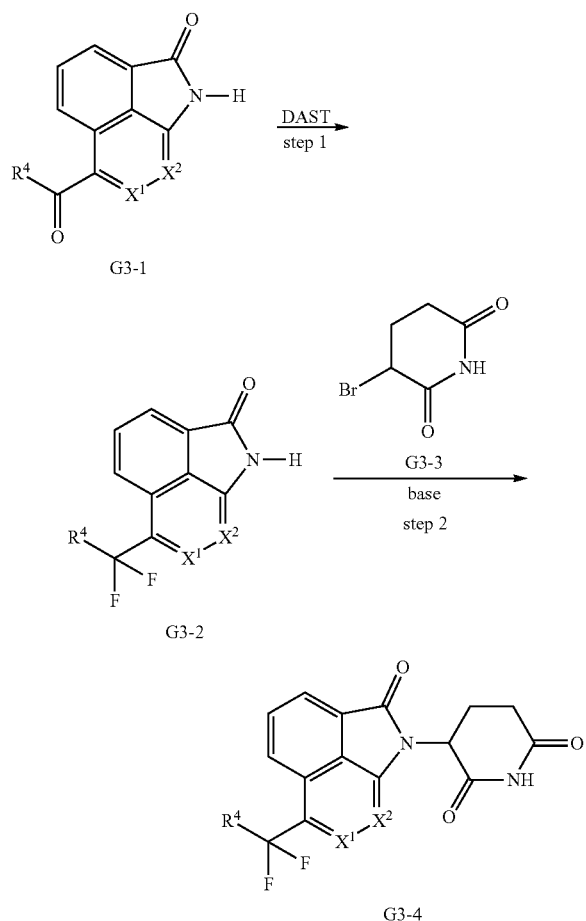

In some aspects, a compound of Formula I or Formula II can be synthesized according to the route provided in General Synthesis Scheme 3. In step 1, Compound G3-1 (prepared according to the procedures outlined in General Synthesis Scheme 2 for compound G2-2) is reacted with DAST (or other suitable nucleophilic fluorination reagent such as, for example, Deoxo-Fluor) in an organic solvent (for example dichloromethane) to provide G3-2. In step 2, compound G3-2 is reacted with a base (for example sodium hydride) in an organic solvent (for example dimethylformamide or dichloromethane) followed by addition of G3-3 to provide G3-4.

General Synthesis Scheme 4

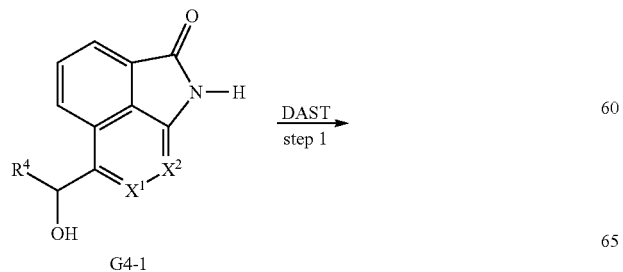

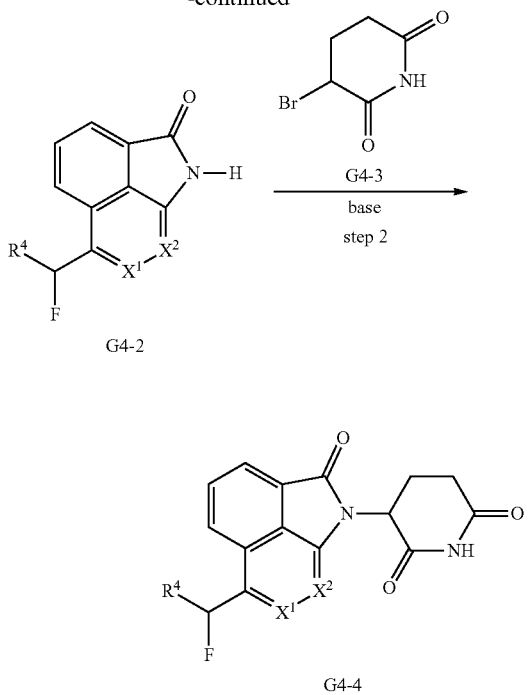

In some aspects, a compound of Formula I or Formula II can be synthesized according to the route provided in General Synthesis Scheme 4. In step 1, Compound G4-1 (prepared according to the procedures outlined in General Synthesis Scheme 1 for compound G1-3) is reacted with DAST (or other suitable nucleophilic fluorination reagent such as, for example, Deoxo-Fluor) in an organic solvent (for example dichloromethane) to provide G4-2. In step 2, compound G4-2 is reacted with a base (for example sodium hydride) in an organic solvent (for example dimethylformamide or dichloromethane) followed by addition of G4-3 to provide G4-4.

General Synthesis Scheme 5

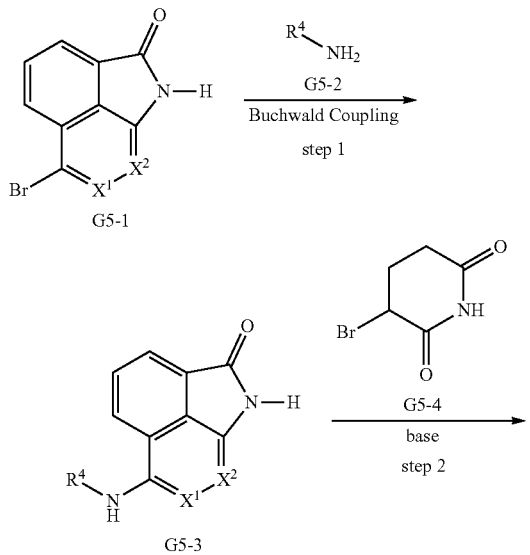

-continued

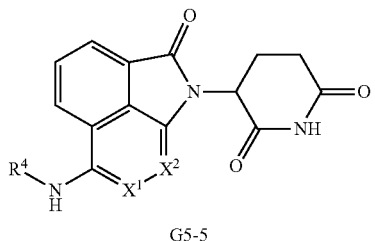

G5-5

In some aspects, a compound of Formula I or Formula II can be synthesized according to the route provided in General Synthesis Scheme 5. In step 1, compound G5-1 is reacted with G5-2 in the presence of a palladium catalyst (for example palladium(II) acetate, $Pd_2(dba)_3$, or other suitable palladium catalyst used in Buchwald-Hartwig coupling conditions), a phosphine ligand (for example BINAP, Xant-Phos, or other suitable phosphine ligand used in Buchwald-Hartwig coupling conditions), and a base (for example potassium tert-butoxide, cesium carbonate, or other suitable base used in Buchwald-Hartwig coupling conditions) in organic solvent (for example toluene, THF, dioxane, or DMF) at elevated temperature to provide G5-3. In step 2, compound G5-3 is reacted with a base (for example sodium hydride) in an organic solvent (for example dimethylformamide or dichloromethane) followed by addition of G5-4 to provide G5-5.

General Synthesis Scheme 6

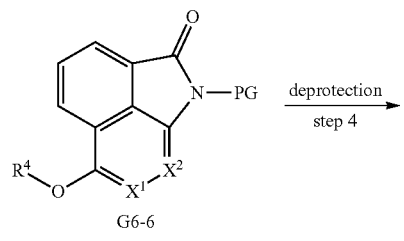

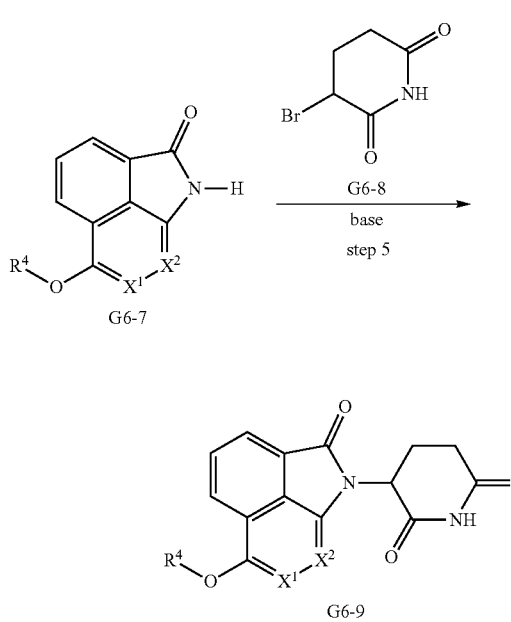

In some aspects, a compound of Formula I or Formula II can be synthesized according to the route provided in General Synthesis Scheme 6. In step 1, compound G6-1 is reacted with a metal hydroxide (for example sodium hydroxide or potassium hydroxide) in the presence of a palladium catalyst (for example $Pd_2(dba)3$) and a phosphine ligand (for example XantPhos) in an organic solvent (for example dioxane) and water to provide G6-2. In step 2, G6-2 is protected with an appropriate protecting group (for example a Boc or Cbz group) using standard conditions to provide compound G6-3. In step 3, G6-3 is reacted with G6-5 in the presence of a copper catalyst (for example copper acetate) and a base (for example pyridine or DMAP) in an organic solvent (for example 1,2-dichloroethane) at elevated temperature (for example about 80° C.) to provide compound G6-6. In step 4, the protecting group PG in G6-6 is removed using standard conditions appropriate for the specific group to provide G6-7. In step 5, compound G6-7 is reacted with a base (for example sodium hydride) in an organic solvent (for example dimethylformamide or dichloromethane) followed by addition of G6-8 to provide G6-9.

NON-LIMITING EXAMPLES OF THE PRESENT INVENTION

Where chirality is depicted in the synthetic schemes below, the designation shows the relative chirality of that stereocenter and not an absolute designation. For example,

291

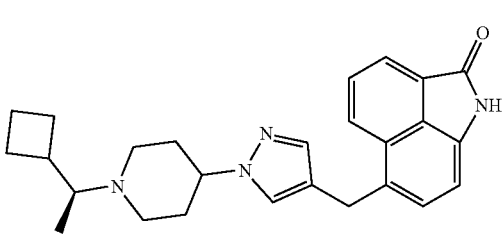

3a is depicted with a wedged bond to show that the designated chiral center was resolved by chiral chromatography. However, the absolute chirality of that stereocenter may instead be

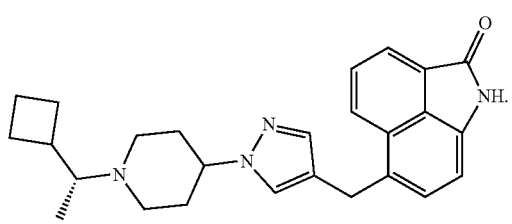

3a

Then when intermediate 3a is reacted with racemic bromoglutarimide the resulting Compound 280 can be a mixture of diastereomers.

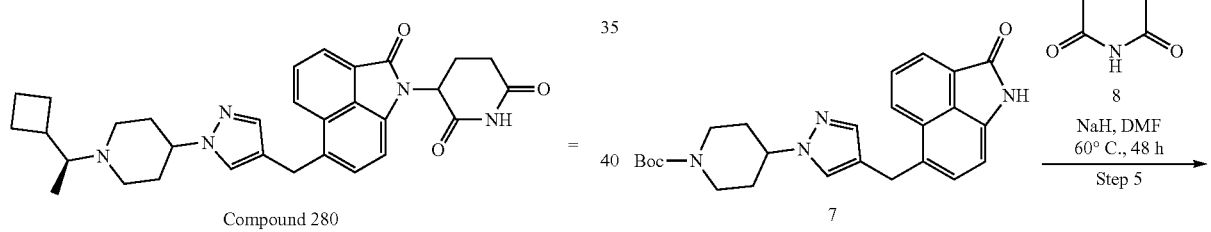

Compound 280

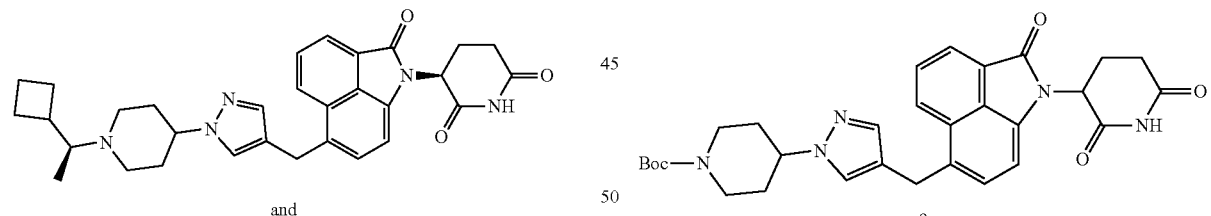

and

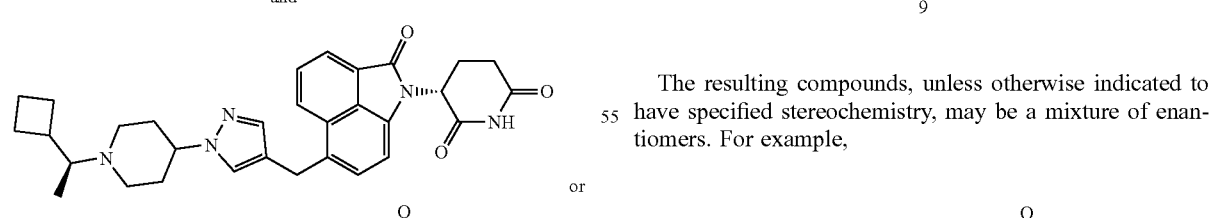

or

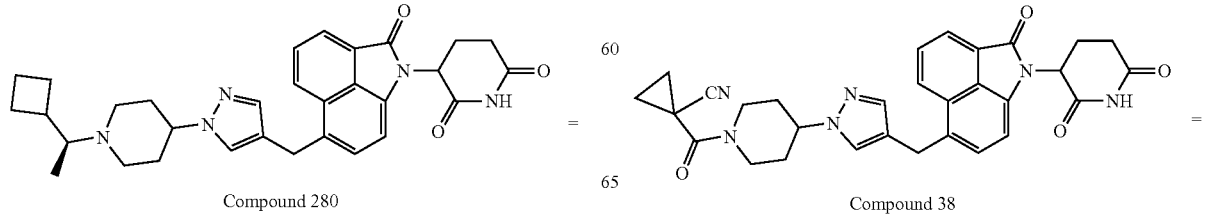

Compound 280

292
-continued

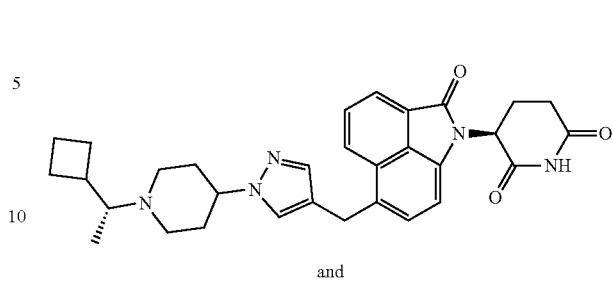

and

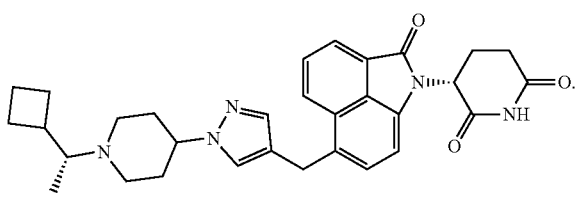

Similarly, where an achiral lactam is reacted in the experimentals below with a racemic glutarimide the resulting compound may be a mixture of enantiomers. For example, when Intermediate 7 is reacted with racemic bromoglutarimide the resulting intermediate 9 may be a mixture of enantiomers.

[Reaction scheme with compound 7, reagent 8, NaH, DMF, 60° C., 48 h, Step 5, yielding compound 9]

The resulting compounds, unless otherwise indicated to have specified stereochemistry, may be a mixture of enantiomers. For example,

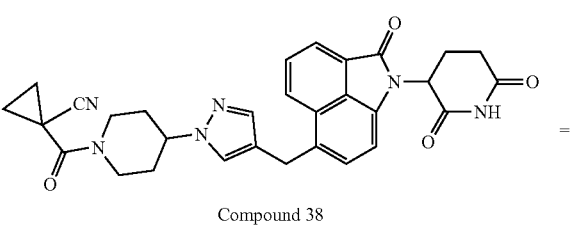

Compound 38

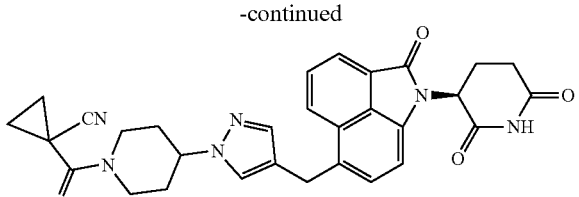

and

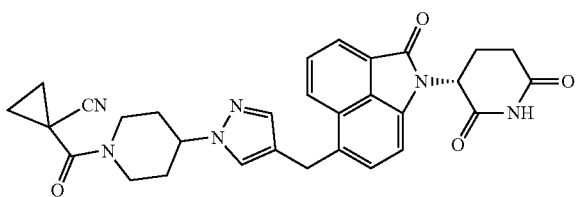

These mixtures of enantiomers can be separated by the skilled artisan using techniques known in the art including chiral chromatography, crystallization, transportation across a chiral membrane, or extraction with a chiral solvent. In fact, these techniques were employed to separate several of the compounds below. For example, intermediates 3a

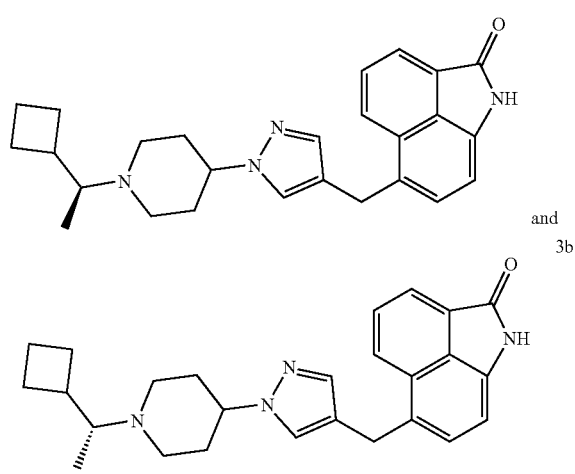

and

3b were separated by chiral chromatography using a preparative HPLC technique. Similarly, enantiomeric mixtures of glutarimides can be resolved by these techniques, including chiral chromatography. For example, a mixture of Compounds 67 and Compounds 68 was resolved by chiral chromatography using a preparative HPLC technique. The resulting separated compounds had an enantiomeric excess of 99%.

Compound 67

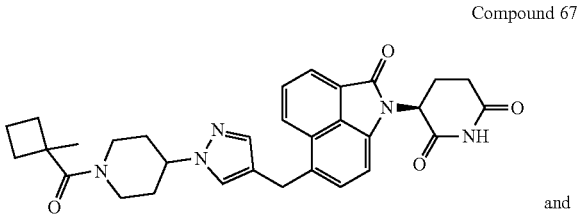

and

Compound 68

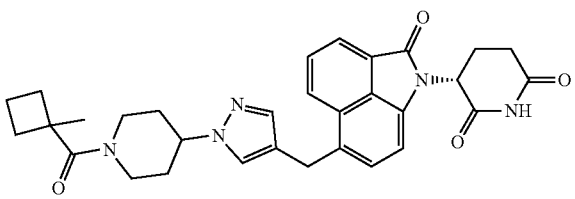

Once separated the absolute chirality may be designated by known techniques, including various forms of structural determinations of crystals. For example, X-ray diffraction may be used on crystals of compounds like Compound 67 and Compound 68 to determine if they are (R) or (S).

Mixtures of enantiomers may also be resolved during the synthetic sequence by using techniques known in the art. For example, enzymatic resolution and enzymatic asymmetric synthesis may be used to resolve chiral centers. Additionally, mixtures of enantiomers may be resolved by installing a protecting group or using a chiral salt. When chiral protecting groups or salts are utilized the mixture of enantiomers temporarily becomes a mixture of diastereomers allowing physical separation using known techniques.

Where the compounds of the present invention are a mixture of diastereomers they may also be resolved by techniques known in the art. For example, the mixture of diastereomers may be separated by chromatographic techniques, including reverse or normal phase HPLC, chromatography on silica gel, moving bed chromatography, and preparative TLC. Diastereomeric mixtures may also be separated by crystallization.

Example 1: Synthesis of 3-(2-Oxobenzo[cd]indol-1-yl)piperidine-2,6-dione (Compound 1)

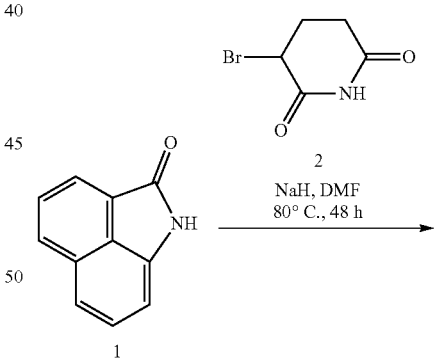

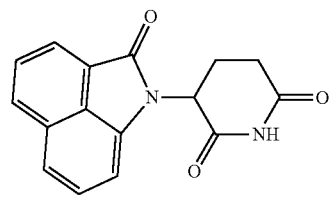

Compound 1

To a stirred solution of 1H-benzo[cd]indol-2-one 1 (100.0 mg, 591.09 μmol) in DMF (2 mL) was added sodium hydride (60% dispersion in mineral oil, 24.91 mg, 650.20 μmol, 60% purity) at 0° C., and then the reaction mixture was heated at 60° C. for 30 minutes. 3-bromopiperidine-2,6-dione 2 (113.50 mg, 591.09 μmol) was added, and the reaction mixture was heated at 60° C. for 24 hours. A new spot formed along with unreacted starting material. Additional 3-bromopiperidine-2,6-dione 2 (113.50 mg, 591.09 μmol) was added, and the reaction mixture was again heated for 24 hours. The reaction mixture was diluted with ethyl acetate, washed with water and the organic fraction was separated. The reaction mixture was then dried over anhydrous sodium sulfate and evaporated under reduced pressure to obtain the crude compound, which was purified by a preparative TLC plate (eluting with 2% MeOH-DCM) to afford 3-(2-oxobenzo[cd]indol-1-yl)piperidine-2,6-dione (Compound 1) (10 mg, 34.35 μmol, 5.81% yield, 96.28% purity) as a pale yellow solid. $^1$H NMR (d6-DMSO, 400 MHZ) δ 11.13 (s, 1H), 8.24 (d, J=8.08 Hz, 1H), 8.11 (d, J=6.92 Hz, 1H), 7.84 (t, J=7.56 Hz, 1H), 7.68 (d, J=8.4 Hz, 1H), 7.54 (t, J=7.76 Hz, 1H), 7.17 (d, J=7.12 Hz, 1H), 5.46 (dd, J=12.76, 5.08 Hz, 1H), 3.00-2.91 (m, 1H), 2.82-2.71 (m, 1H), 2.67-2.63 (m, 1H), 2.12-2.09 (m, 1H); LC MS: ES+ 281.2.

Example 2: Synthesis of tert-Butyl 4-(4-((1-(2,6-Dioxopiperidin-3-yl)-2-oxo-1,2-dihydrobenzo[cd]indol-6-yl)methyl)-1H-pyrazol-1-yl)piperidine-1-carboxylate (Compound 2)

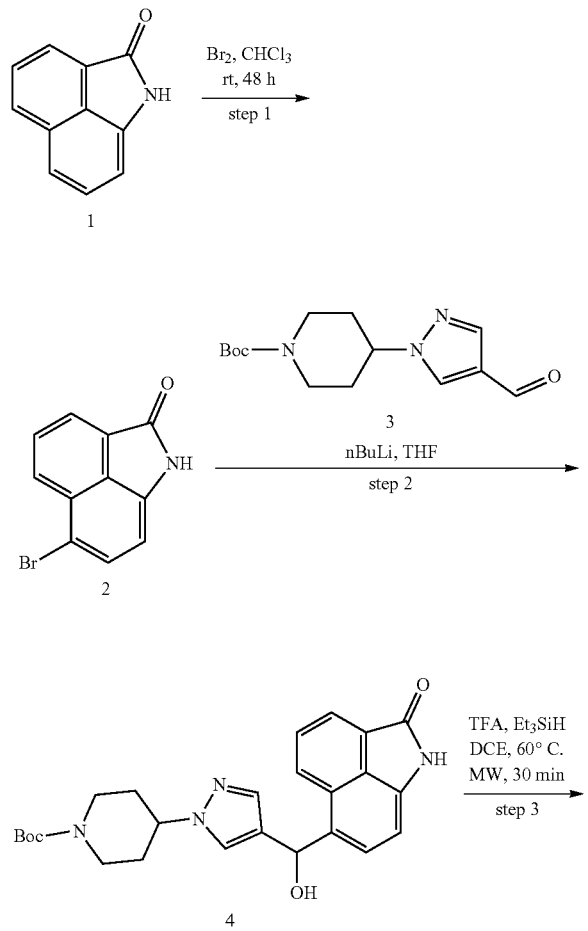

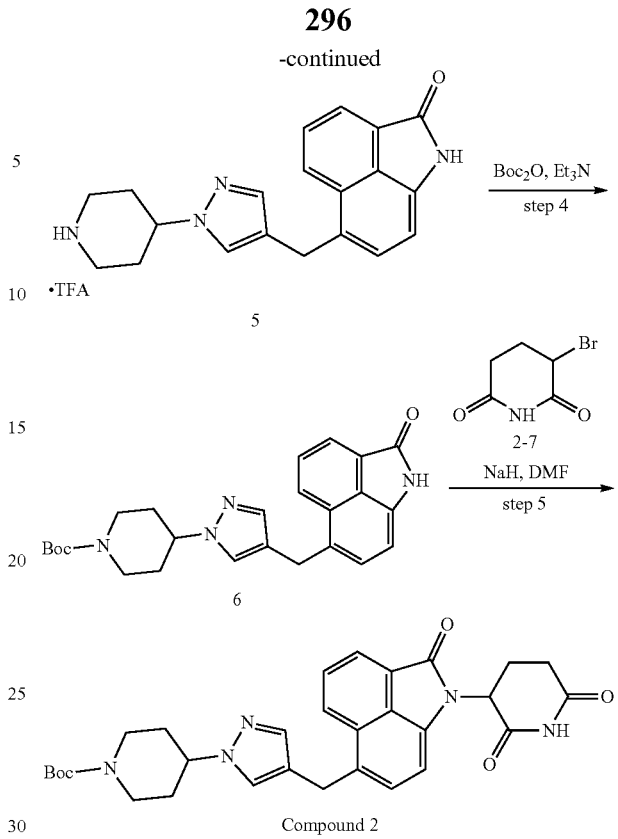

Step 1: Preparation of 6-Bromobenzo[cd]indol-2(1H)-one (2): To the stirred suspension of 1H-benzo[cd]indol-2-one 1 (3.0 g, 17.73 mmol) in CHCl₃ (50.0 mL) was added bromine (2.15 g, 26.60 mmol, 1.44 mL) with cooling drop-wise, and the reaction mixture was stirred at room temperature for 48 hours. Sodium thiosulfate solution was poured into the reaction mixture with cooling, and the yellow solid formed was filtered through sintered funnel. The solid obtained was washed with cold water and pentane, and azeotroped with toluene to afford 6-bromo-1H-benzo[cd]indol-2-one 2-2 (4 g, 16.12 mmol, 90.93% yield) as a yellow solid. LC MS: ES+ 248.1, 250.0 (bromo pattern).

Step 2: Preparation of tert-Butyl 4-(4-(Hydroxy(2-oxo-1,2-dihydrobenzo[cd]indol-6-yl)methyl)-1H-pyrazol-1-yl)piperidine-1-carboxylate (4): To the stirred solution of 6-bromo-1H-benzo[cd]indol-2-one 2-2 (1.6 g, 6.45 mmol) in THF (7 mL) was added butyllithium (2.2 M, 9.38 mL) at −78° C. After the addition was complete, the temperature was allowed to increase to −40° C., and the reaction mixture was stirred at the same temperature for 30 minutes. tert-Butyl 4-(4-formylpyrazol-1-yl)piperidine-1-carboxylate 3 (1.80 g, 6.45 mmol) in THF (7 mL) was added at −78° C., and the reaction mixture was allowed to warm to room temperature and was stirred for 16 hours. The reaction mixture was quenched with saturated aqueous ammonium chloride solution and diluted with ethyl acetate. The layers were separated, and the organic layer was washed with water. The organic layer was then dried over anhydrous sodium sulfate and evaporated under reduced pressure to obtain the crude compound which was purified by flash chromatography using 0-5% MeOH-DCM to afford tert-butyl 4-[4-[hydroxy-(2-oxo-1H-benzo[cd]indol-6-yl)methyl]pyrazol-1-yl]piperidine-1-carboxylate 4 (527 mg, 1.17 mmol, 18.22% yield) as a brown solid. 1H NMR (d6-DMSO, 400 MHZ) δ 10.70 (s, 1H), 8.34 (d, J=8.28 Hz, 1H), 7.95 (d, J=6.96 Hz, 1H), 7.72 (t, J=7.6 Hz, 1H), 7.59-7.52 (m, 2H), 7.28 (s, 1H), 6.93 (d, J=7.2 Hz, 1H), 6.22 (br s, 1H), 5.80 (br s, 1H), 4.27-4.21 (m, 1H), 4.00-3.96 (m, 2H), 2.84-2.82 (m, 2H), 1.91-1.87 (m, 2H), 1.72-1.64 (m, 2H), 1.39 (s, 9H).

Step 3: Preparation of the 2,2,2-Trifluoroacetic Acid Salt of 6-((1-(Piperidin-4-yl)-1H-pyrazol-4-yl)methyl)benzo[cd]indol-2(1H)-one (5): To a stirred solution of tert-butyl 4-[4-[hydroxy-(2-oxo-1H-benzo[cd]indol-6-yl)methyl]pyrazol-1-yl]piperidine-1-carboxylate 4 (500.0 mg, 1.11 mmol) in DCE (3 mL) was added triethylsilane (518.51 mg, 4.46 mmol, 712.24 μL) and trifluoroacetic acid (1.02 g, 8.92 mmol, 687.08 μL), and the reaction was stirred for 30 minutes under microwave irradiation at 70° C. The solvent in the reaction mixture was evaporated under reduced pressure to obtain the crude product which was washed with ether and pentane to afford 6-[(1-piperidin-1-ium-4-ylpyrazol-4-yl)methyl]-1H-benzo[cd]indol-2-one; 2,2,2-trifluoroacetate 5 (500.0 mg, 1.12 mmol, 100.47% yield) as a brown gum which was used without further purification. LC MS: ES+ 333.0.

Step 4: Preparation of tert-Butyl 4-(4-((2-Oxo-1,2-dihydrobenzo[cd]indol-6-yl)methyl)-1H-pyrazol-1-yl)piperidine-1-carboxylate (6): To a stirred solution of 6-[(1-piperidin-1-ium-4-ylpyrazol-4-yl)methyl]-1H-benzo[cd]indol-2-one; 2,2,2-trifluoroacetate 5 (500.0 mg, 1.12 mmol) in DCM (5 mL) was added triethylamine (340.00 mg, 3.36 mmol, 468.32 uL) with cooling followed by the addition of di-tert-butyl dicarbonate (366.67 mg, 1.68 mmol, 385.56 uL), and the reaction was continued at room temperature for 16 hours. The reaction mixture was diluted with ethyl acetate, washed with water and brine solution, and the organic fraction was separated. The organic layer was then dried over anhydrous sodium sulfate and evaporated under reduced pressure to obtain the crude which was purified by flash chromatography (using 0-5% MeOH-DCM) to afford tert-butyl 4-[4-[(2-oxo-1H-benzo[cd]indol-6-yl)methyl]pyrazol-1-yl]piperidine-1-carboxylate 6 (300.0 mg, 693.62 μmol, 61.93% yield) as a yellow sticky solid. LC MS: ES+ 433.0.

Step 5: Preparation of tert-Butyl 4-(4-((1-(2,6-Dioxopiperidin-3-yl)-2-oxo-1,2-dihydrobenzo[cd]indol-6-yl)methyl)-1H-pyrazol-1-yl)piperidine-1-carboxylate (Compound 2): To a stirred solution of tert-butyl 4-[4-[(2-oxo-1H-benzo[cd]indol-6-yl)methyl]pyrazol-1-yl]piperidine-1-carboxylate 6 (300.0 mg, 693.62 μmol) in DMF (1 mL) was added sodium hydride (60% dispersion in mineral oil, 53.15 mg, 1.39 mmol, 60% purity) with cooling, and the reaction mixture was heated at 60° C. for 30 minutes. 3-bromopiperidine-2,6-dione 7 (133.18 mg, 693.62 μmol) was then added, the reaction was heated at 60° C. for 4 hours followed by a further addition of 3-bromopiperidine-2,6-dione (133.18 mg, 693.62 μmol), and the reaction was further stirred for 16 hours at 60° C. The reaction mixture was diluted with ethyl acetate and washed with water, and the organic fraction was separated. The reaction mixture was then dried over anhydrous sodium sulfate and evaporated under reduced pressure to obtain the crude which was first purified by column chromatography followed by a preparative TLC plate (eluting with 60% ethyl acetate-hexane) to afford tert-butyl 4-[4-[[1-(2,6-dioxo-3-piperidyl)-2-oxo-benzo[cd]indol-6-yl]methyl]pyrazol-1-yl]piperidine-1-carboxylate (Compound 2) (20.0 mg, 33.11 μmol, 4.77% yield, 90% purity) as a pale yellow solid. $^1$H NMR (d6-DMSO, 400 MHZ) δ 11.11 (s, 1H), 8.37 (d, J=8.24 Hz, 1H), 8.08 (d, J=6.92 Hz, 1H), 7.83 (t, J=7.58 Hz, 1H), 7.59 (s, 1H), 7.35 (d, J=7.36 Hz, 1H), 7.31 (s, 1H), 7.07 (d, J=7.28 Hz, 1H), 5.43 (dd, J=12.76, 5.0 Hz, 1H), 4.24-4.23 (m, 1H), 4.17 (s, 2H), 4.00-3.96 (m, 2H), 2.96-2.66 (m, 5H), 2.09-2.06 (m, 1H), 1.91-1.88 (m, 2H), 1.72-1.66 (m, 2H), 1.39 (m, 9H); LC MS: ES+ 544.3.

Example 3. Synthesis of 3-(6-((1-(1-(Cubane-1-carbonyl)piperidin-4-yl)-1H-pyrazol-4-yl)methyl)-2-oxobenzo[cd]indol-1(2H)-yl)piperidine-2,6-dione (Compound 3)

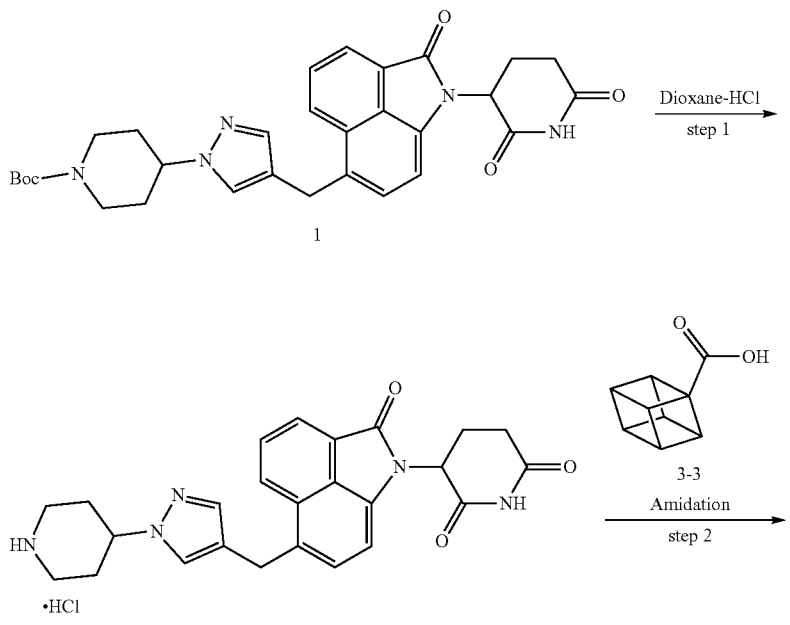

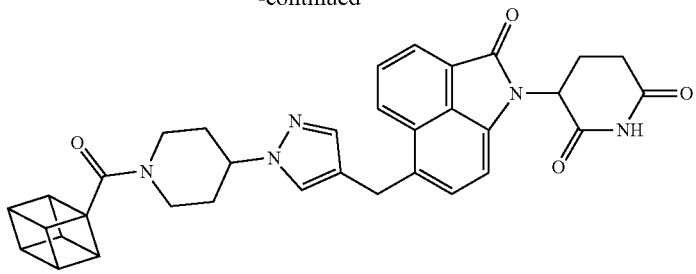

Compound 3

Step 1: Preparation of 3-(2-Oxo-6-((1-(piperidin-4-yl)-1H-pyrazol-4-yl)methyl)benzo[cd]indol-1(2H)-yl)piperidine-2,6-dione Hydrochloride (2): To the stirred solution of tert-butyl 4-[4-[[1-(2,6-dioxo-3-piperidyl)-2-oxo-benzo[cd]indol-6-yl]methyl]pyrazol-1-yl]piperidine-1-carboxylate 1 (100.0 mg, 183.95 µmol) in dioxane (1 mL) was added hydrochloric acid in dioxane (183.95 µmol, 8 mL), and the reaction was stirred at room temperature for 2 hours. TLC analysis showed complete consumption of the starting material. The solvent in the reaction mixture was evaporated under reduced pressure, and the residue was washed with ether and pentane to afford 3-[6-[[1-(1-chloro-4-piperidyl)pyrazol-4-yl]methyl]-2-oxo-benzo[cd]indol-1-yl]piperidine-2,6-dione 2 (88.0 mg, 183.35 µmol, 99.67% yield) as a yellow solid. LC MS: ES+ 444.1.

Step 2: Preparation of 3-(6-((1-(1-(Cubane-1-carbonyl)piperidin-4-yl)-1H-pyrazol-4-yl)methyl)-2-oxobenzo[cd]indol-1(2H)-yl)piperidine-2,6-dione (Compound 3): To a stirred solution of 3-[6-[[1-(1-chloro-4-piperidyl)pyrazol-4-yl]methyl]-2-oxo-benzo[cd]indol-1-yl]piperidine-2,6-dione 2 (88.0 mg, 183.35 µmol) in DMF (3.0 mL) were added cubane-1-carboxylic acid (27.16 mg, 183.35 µmol), followed by HATU (104.57 mg, 275.02 µmol) and N,N-diisopropylethylamine (71.09 mg, 550.05 µmol, 95.81 uL) at 0° C. The reaction mixture was then stirred at room temperature for 16 hours. It was diluted with ethyl acetate and water, and the layers were separated. The organic layer was washed with saturated aqueous NaHCO$_3$ solution, water, and brine, dried over sodium sulfate, and concentrated. The crude material was purified by Prepatory TLC (eluting with 3% MeOH/DCM) to get 3-[6-[[1-[1-(cubane-1-carbonyl)-4-piperidyl]pyrazol-4-yl]methyl]-2-oxo-benzo[cd]indol-1-yl]piperidine-2,6-dione (Compound 3) (55.0 mg, 94.77 µmol, 51.69% yield, 98.84% purity) as a yellow solid. $^1$H NMR (d6-DMSO, 400 MHZ) δ 11.09 (s, 1H), 8.36 (d, J=8.16 Hz, 1H), 8.08 (d, J=7.0 Hz, 1H), 7.83 (t, J=7.62 Hz, 1H), 7.60 (s, 1H), 7.35 (d, J=7.32 Hz, 1H), 7.31 (s, 1H), 7.06 (d, J=7.24 Hz, 1H), 5.42 (dd, J=12.48, 5.24 Hz, 1H), 4.33-4.31 (m, 2H), 4.18 (br s, 5H), 3.97 (br s, 4H), 3.38-3.34 (m, 1H), 3.20-3.13 (m, 1H), 2.97-2.90 (m, 1H), 2.79-2.62 (m, 3H), 2.10-2.07 (m, 1H), 2.01-1.92 (m, 2H), 1.83-1.79 (m, 1H), 1.67-1.64 (m, 1H); LC MS: ES+ 574.5.

Example 4: Synthesis of 3-(6-((1-(1-(1-Methylcyclobutane-1-carbonyl)piperidin-4-yl)-1H-pyrazol-4-yl)methyl)-2-oxobenzo[cd]indol-1(2H)-yl)piperidine-2,6-dione (Compound 4)

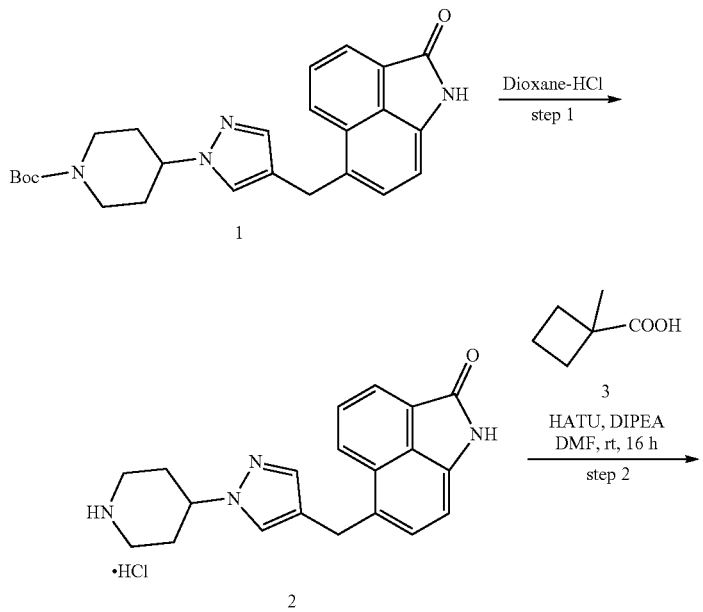

-continued

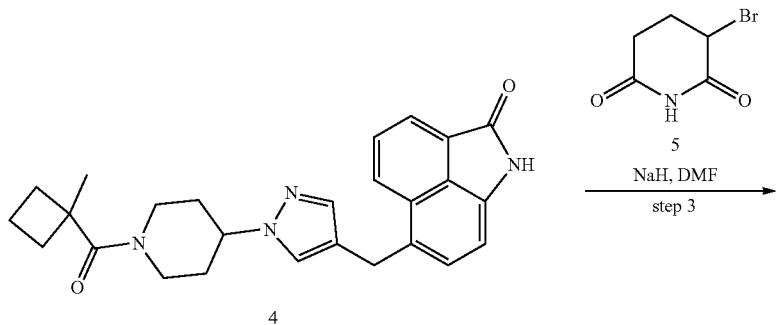

4

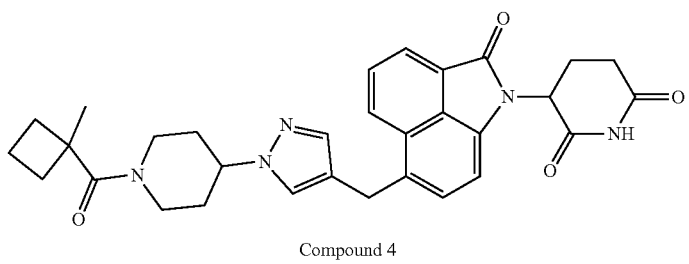

Compound 4

Step 1: Preparation of 6-((1-(Piperidin-4-yl)-1H-pyrazol-4-yl)methyl)benzo[cd]indol-2(1H)-one Hydrochloride (2): To a stirred solution of tert-butyl 4-[4-[[1-(2,6-dioxo-3-piperidyl)-2-oxo-benzo[cd]indol-6-yl]methyl]pyrazol-1-yl]piperidine-1-carboxylate 1 (100.0 mg, 183.95 µmol) in dioxane (1 mL) was added hydrochloric acid in dioxane (183.95 µmol, 8 mL), and the reaction was stirred at room temperature for 2 hours. The solvent in the reaction mixture was evaporated under reduced pressure, and the residue was washed with ether and pentane to afford 3-[6-[[1-(1-chloro-4-piperidyl)pyrazol-4-yl]methyl]-2-oxo-benzo[cd]indol-1-yl]piperidine-2,6-dione 2 (88.0 mg, 183.35 µmol, 99.67% yield) as a yellow solid. LC MS: ES+ 444.1.

Step 2: Preparation of 6-((1-(1-(1-Methylcyclobutane-1-carbonyl)piperidin-4-yl)-1H-pyrazol-4-yl)methyl)benzo[cd]indol-2(1H)-one: To a stirred solution of 6-[[1-(1-chloro-4-piperidyl)pyrazol-4-yl]methyl]-1H-benzo[cd]indol-2-one 2 (98.0 mg, 265.68 µmol) and 1-methylcyclobutanecarboxylic acid 3 (30.33 mg, 265.68 µmol) in DMF (2.0 mL) at 0° C. was added HATU (151.53 mg, 398.53 µmol) and N,N-diisopropylethylamine (171.69 mg, 1.33 mmol, 231.38 uL), and the reaction mixture was stirred at room temperature for 16 hours. The reaction mixture was then extracted with ethyl acetate, and the combined organic layer was washed with water and saturated sodium bicarbonate solution, and dried over sodium sulfate. The organic layer was then concentrated under reduced pressure to afford the crude product. The crude residue was purified by CombiFlash chromatography (eluting 1%-1.5% MeOH in DCM) to afford 6-[[1-[1-(1-methylcyclobutanecarbonyl)-4-piperidyl]pyrazol-4-yl]methyl]-1H-benzo[cd]indol-2-one 4 (66 mg, 154.02 µmol, 57.97% yield) as a pale yellow solid. LC MS: ES+ 429.3

Step 3: Preparation of 3-(6-((1-(1-(1-Methylcyclobutane-1-carbonyl)piperidin-4-yl)-1H-pyrazol-4-yl)methyl)-2-oxobenzo[cd]indol-1(2H)-yl)piperidine-2,6-dione (Compound 4): To a stirred solution of 6-[[1-[1-(1-methylcyclobutanecarbonyl)-4-piperidyl]pyrazol-4-yl]methyl]-1H-benzo[cd]indol-2-one 4 (66.0 mg, 154.02 µmol) in DMF (1 mL) was added sodium hydride (60% dispersion in mineral oil, 11.80 mg, 308.03 µmol) under cooling, and the reaction mixture was heated at 60° C. for 30 minutes. 3-bromopiperidine-2,6-dione 5 (29.57 mg, 154.02 µmol) was then added, and the reaction was heated at 60° C. for 4 hours followed by the further addition of 3-bromopiperidine-2,6-dione (29.57 mg, 154.02 µmol), and the reaction was further continued for 16 hours at 60° C. The reaction mixture was diluted with ethyl acetate and washed with water, and the organic fraction was separated. The organic layer was then dried over anhydrous sodium sulfate and evaporated under reduced pressure to obtain the crude product which was first purified by column chromatography followed by preparative TLC (developing the plate in 60% ethyl acetate-DCM) to afford 3-[6-[[1-[1-(1-methylcyclobutanecarbonyl)-4-piperidyl]pyrazol-4-yl]methyl]-2-oxo-benzo[cd]indol-1-yl]piperidine-2,6-dione (Compound 4) (15.0 mg, 27.21 µmol, 17.66% yield, 97.87% purity) as pale yellow solid. $^1$H NMR (d6-DMSO, 400 MHZ) δ 11.11 (s, 1H), 8.37 (d, J=8.44 Hz, 1H), 8.08 (d, J=6.44 Hz, 1H), 7.85-7.83 (m, 1H), 7.60 (s, 1H), 7.35 (d, J=7.12 Hz, 1H), 7.31 (s, 1H), 7.07 (d, J=6.84 Hz, 1H), 5.46-5.42 (m, 1H), 4.39-4.37 (m, 1H), 4.31-4.29 (m, 1H), 4.18 (s, 2H), 3.60-3.58 (m, 1H), 3.04-2.91 (m, 3H), 2.77-2.62 (m, 2H), 2.41-2.32 (m, 3H), 2.09-2.07 (m, 1H), 1.92-1.90 (m, 3H), 1.78-1.76 (m, 3H), 1.64-1.61 (m, 2H), 1.33 (s, 3H); LC MS: ES+ 540.4.

Example 5. Synthesis of N-(tert-Butyl)-4-(4-((1-(2,6-dioxopiperidin-3-yl)-2-oxo-1,2-dihydrobenzo[cd]indol-6-yl)methyl)-1H-pyrazol-1-yl)-N-methylpiperidine-1-carboxamide (Compound 5)

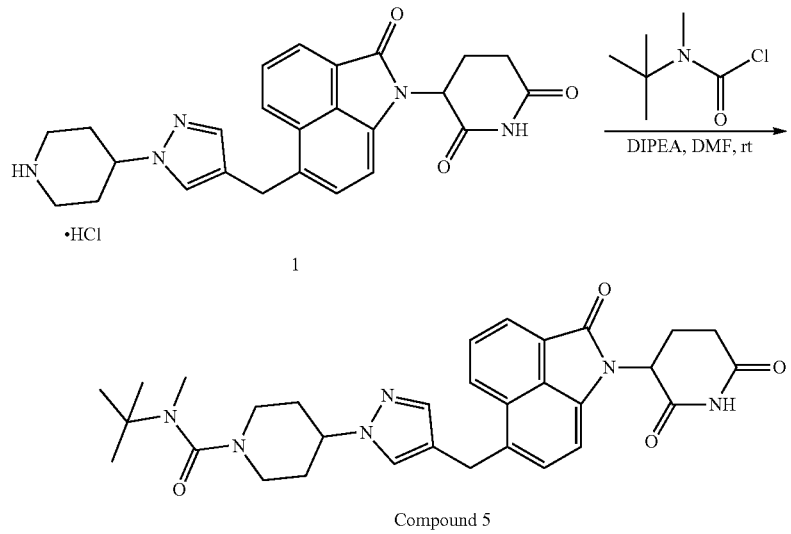

Compound 5

To an equi-molar mixture of HCl salt 1 and tert-butyl (methyl)carbamic chloride in DMF (6 mL/mmol) is added DIPEA (4.0 equiv) at 0° C. The resulting solution is stirred at ambient temperature for 16 hours. The reaction mixture is then diluted with ethyl acetate and washed with aqueous NaHCO$_3$ solution, water (x 3) and brine. The organic layer is then dried over anhydrous Na$_2$SO$_4$ and concentrated under reduced pressure. The crude mass is then purified by CombiFlash ISCO column, eluting with 2% methanol in DCM to afford N-(tert-Butyl)-4-(4-((1-(2,6-dioxopiperidin-3-yl)-2-oxo-1,2-dihydrobenzo[cd]indol-6-yl)methyl)-1H-pyrazol-1-yl)-N-methylpiperidine-1-carboxamide (Compound 5).

Example 6. Synthesis of tert-Butyl 4-(4-(1-(2,6-Dioxopiperidin-3-yl)-2-oxo-1,2-dihydrobenzo[cd]indole-6-carbonyl)-1H-pyrazol-1-yl)piperidine-1-carboxylate (Compound 6) and tert-Butyl 4-(4-((1-(2,6-Dioxopiperidin-3-yl)-2-oxo-1,2-dihydrobenzo[cd]indol-6-yl)(hydroxy)methyl)-1H-pyrazol-1-yl)piperidine-1-carboxylate (Compound 7)

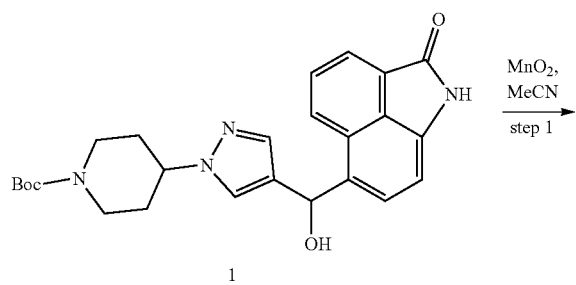

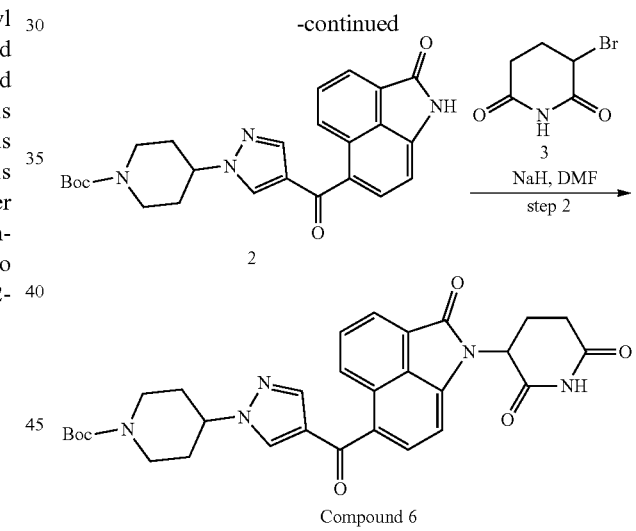

Compound 6

Step 1: Synthesis of tert-Butyl 4-(4-(2-Oxo-1,2-dihydrobenzo[cd]indole-6-carbonyl)-1H-pyrazol-1-yl)piperidine-1-carboxylate (2): To a stirred solution of tert-butyl 4-(4-(hydroxy(2-oxo-1,2-dihydrobenzo[cd]indol-6-yl)methyl)-1H-pyrazol-1-yl)piperidine-1-carboxylate 1 in acetonitrile is added manganese(IV) oxide (10 equiv.) and the reaction mixture is stirred at room temperature for 16 hr. TLC and LCMS show product formation. The reaction mixture is filtered through a celite pad, and the filtrate is concentrated under reduced pressure to get a crude mass which is purified by combiflash chromatography using 1.5% MeOH-DCM as eluent to afford desired product tert-butyl 4-(4-(2-oxo-1,2-dihydrobenzo[cd]indole-6-carbonyl)-1H-pyrazol-1-yl)piperidine-1-carboxylate 2.

Step 2: Synthesis of tert-Butyl 4-(4-(1-(2,6-Dioxopiperidin-3-yl)-2-oxo-1,2-dihydrobenzo[cd]indole-6-carbonyl)-1H-pyrazol-1-yl)piperidine-1-carboxylate (Compound 6):

To the stirred solution of compound 2 in THF is added sodium hydride (60% dispersion in mineral oil, 1 equiv.) and the reaction mixture is refluxed at 60° C. for 30 minutes. A solution of (3-bromopiperidine-2,6-dione) (0.5 equiv.) in THF is also heated at 60° C. After 30 minutes the first suspension is added to the second solution, and the heating is continued for 3 hours. The reaction mixture is diluted with ethyl acetate and washed with water and brine solution. The organic fraction is then dried over anhydrous sodium sulfate and evaporated under reduced pressure to obtain the crude compound. The crude compound is then purified by flash chromatography to obtain Compound 6.

Step 3: Synthesis of tert-Butyl 4-(4-((1-(2,6-Dioxopiperidin-3-yl)-2-oxo-1,2-dihydrobenzo[cd]indol-6-yl)(hydroxy)methyl)-1H-pyrazol-1-yl)piperidine-1-carboxylate (Compound 7): A stirred solution of Compound 6 in ethanol is cooled to 0° C., and sodium borotriacetoxyhydride (1.2 equiv.) is added to the reaction mixture. The reaction mixture is stirred at room temperature for 16 hours. It is quenched with water and extracted with ethyl acetate. The combined organic phase is dried over sodium sulfate, concentrated and purified by column chromatography using (silica, gradient, 0/6-2% Methanol in DCM) to provide Compound 7.

Example 7. Synthesis of tert-Butyl 4-(4-((1-(2,6-Dioxopiperidin-3-yl)-2-oxo-1,2-dihydrobenzo[cd]indol-6-yl)difluoromethyl)-1H-pyrazol-1-yl)piperidine-1-carboxylate (Compound 8)

mixture is stirred at the same temperature for 30 minutes and then slowly brought up to room temperature. LC-MS shows the desired product. It is quenched with water and extracted with ethyl acetate. The combined organic phase is dried over sodium sulfate, concentrated and purified by column chromatography using (silica, gradient, 0%-2% Methanol in DCM) to provide 2.

Step 2: Synthesis of tert-Butyl 4-(4-((1-(2,6-Dioxopiperidin-3-yl)-2-oxo-1,2-dihydrobenzo[cd]indol-6-yl)difluoromethyl)-1H-pyrazol-1-yl)piperidine-1-carboxylate (Compound 8): To a stirred solution of compound 2 in THF is added sodium hydride (60% dispersion in mineral oil, 1 equiv.), and the reaction mixture was refluxed at 60° C. for 30 minutes. A solution of 3-bromopiperidine-2,6-dione 3 (0.5 equiv.) in THF is also heated at 60° C. After 30 minutes the first suspension is added to the second solution with heating, and the heating is continued for 3 hours. The reaction mixture is diluted with ethyl acetate and washed with water and brine solution. The organic phase is then dried over anhydrous sodium sulfate and evaporated under reduced pressure to obtain the crude compound. The crude compound is then purified by flash chromatography to Compound 8.

Example 8: Synthesis of 3-(6-(4-(Morpholinomethyl)benzyl)-2-oxobenzo[cd]indol-1(2H)-yl)piperidine-2,6-dione (Compound 9)

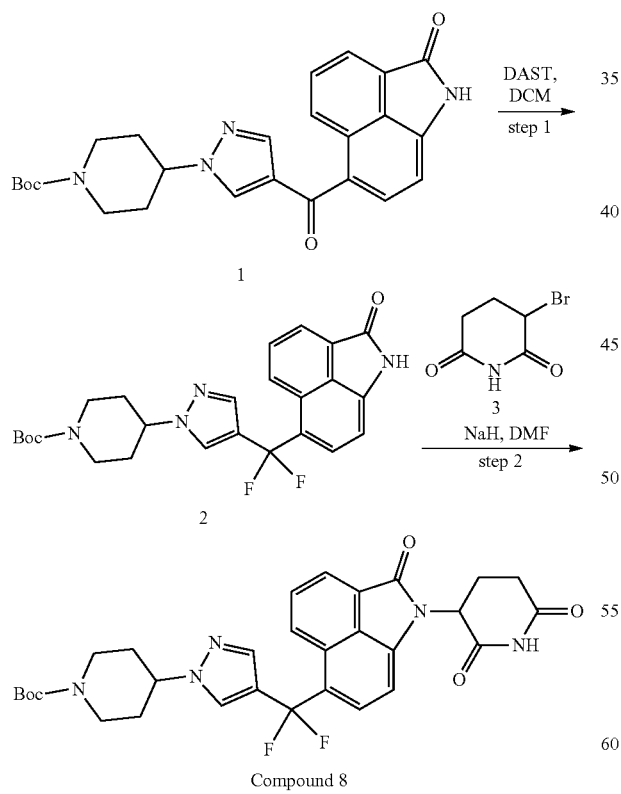

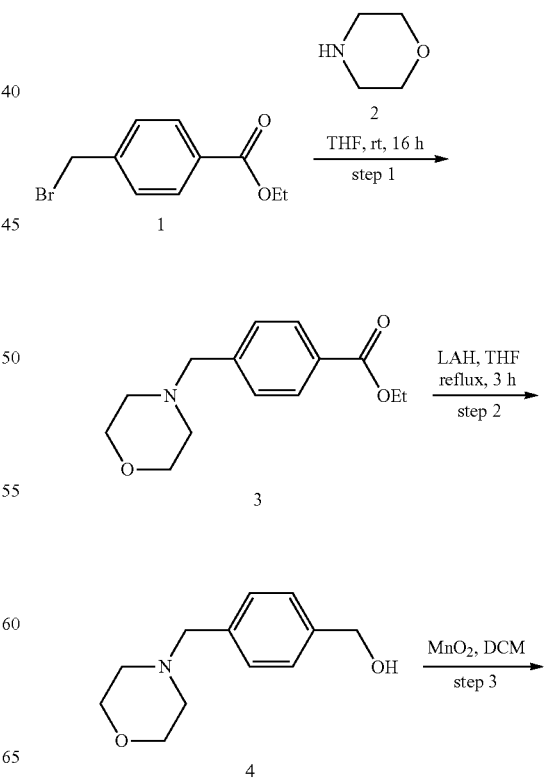

Step 1: Synthesis of tert-Butyl 4-(4-(Difluoro(2-oxo-1,2-dihydrobenzo[cd]indol-6-yl)methyl) 1H-pyrazol-1-yl)piperidine-1-carboxylate (2): To a stirred solution of 1 in DCM is added DAST (3 equiv.) at −30° C., and the reaction

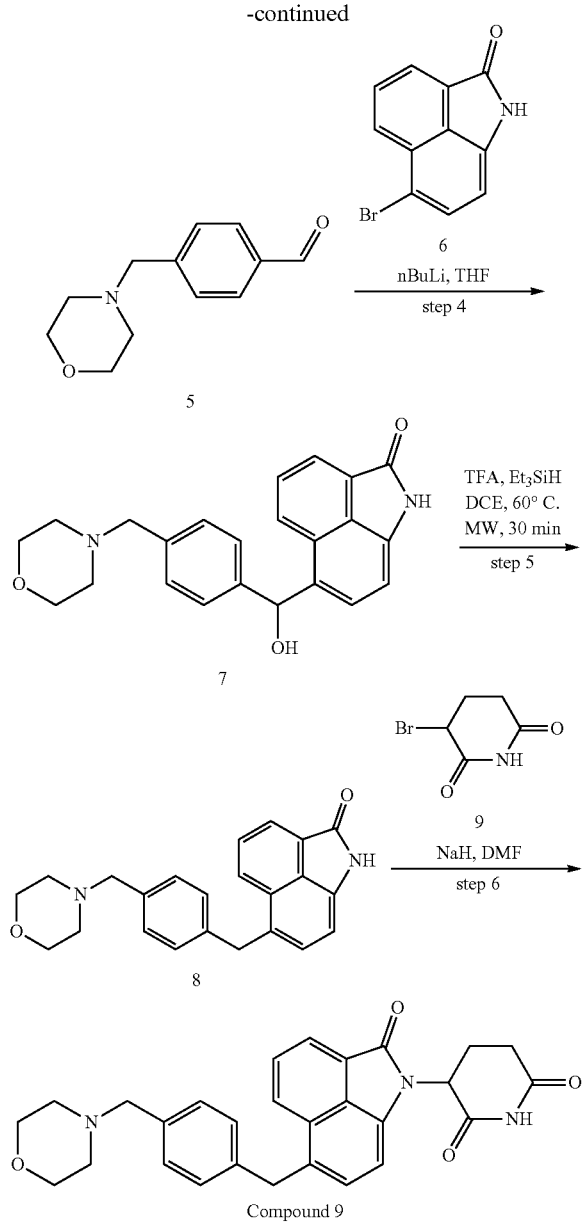

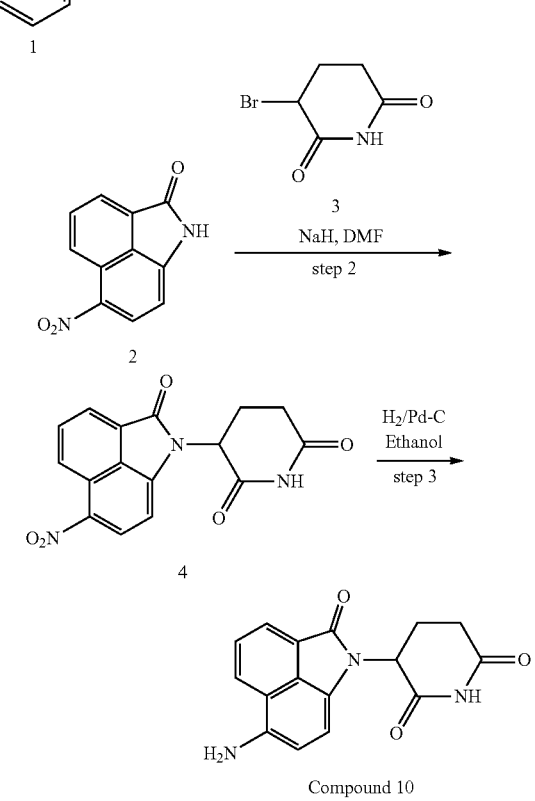

Step 5: Synthesis of 6-(4-(Morpholinomethyl)benzyl)benzo[cd]indol-2(1H)-one (8): To a stirred solution of 7 in DCE is added triethylsilane (3 equiv.) and trifluoroacetic acid (10 equiv.), and the reaction is stirred for 30 minutes under microwave irradiation at 70° C. The solvent in the reaction mixture is evaporated under reduced pressure to obtain the crude product which is washed with ether and pentane to afford 8 as a brown gum that is used without further purification.

Step 6: Synthesis of 3-(6-(4-(Morpholinomethyl)benzyl)-2-oxobenzo[cd]indol-1(2H)-yl)piperidine-2,6-dione (Compound 9): To the stirred solution of 8 in THF is added sodium hydride (60% dispersion in mineral oil, 1 equiv.), and the reaction mixture is refluxed at 60° C. for 30 minutes. A solution of 3-bromopiperidine-2,6-dione 9 (0.5 equiv.) in THF is also heated at 60° C. After 30 minutes the first suspension is added to the second solution with heating, and the heating is continued for 3 hours. The reaction mixture is diluted with ethyl acetate and washed with water and brine solution. The organic fraction is then dried over anhydrous sodium sulfate and evaporated under reduced pressure to obtain the crude compound. The crude compound is then purified by flash chromatography to obtain Compound 9.

Example 9. Synthesis of 3-(6-Amino-2-oxobenzo[cd]indol-1(2H)-yl)piperidine-2,6-dione (Compound 10)

Step 1-3: 4-(Morpholinomethyl)benzaldehyde was prepared in Steps 1-3 according to the literature procedure provided in WO 2015/086636.

Step 4: Synthesis of 6-(Hydroxy(4-(morpholinomethyl)phenyl)methyl)benzo[cd]indol-2(1H)-one (7): To a stirred solution of 6-bromo-1H-benzo[cd]indol-2-one 6 (1 equiv.) in THF is added butyllithium (2.2 equiv.) at −78° C. After the addition is complete the temperature is allowed to increase to −40° C., and the reaction mixture is stirred at the same temperature for 30 minutes. 5 (1 eq) in THF (7 mL) is added at −78° C., and then the reaction mixture is allowed to warm to room temperature and is stirred for 16 hours. The reaction mixture is quenched with saturated aqueous ammonium chloride solution and diluted with ethyl acetate. The layers are separated, and the organic phase was washed with water. The organic phase is then dried over anhydrous sodium sulfate and evaporated under reduced pressure to obtain the crude compound which is purified by flash chromatography using 0-5% MeOH-DCM to afford the desired product 7.

Step 1: Synthesis of 6-Nitrobenzo[cd]indol-2(1H)-one (2): To a stirred solution of 1 in acetic acid is added nitric acid at 0° C., and the resulting reaction mixture is stirred at room temperature for 1 hr. Progress of the reaction was monitored by TLC. After completion, the reaction mixture is added to ice-water and extracted with ethyl acetate. The combined organic layer is washed with brine solution and dried over anhydrous $Na_2SO_4$, filtered and concentrated under reduced pressure to afford the desired product 2 which is further purified by column chromatography or recrystallization.

Step 2: Synthesis of 3-(6-Nitro-2-obobenzo[cd]indol-1(2H)-yl)piperidine-2,6-dione (4): To the stirred solution of compound 2 in THF is added sodium hydride (60% dispersion in mineral oil, 1 equiv.), and the reaction mixture is refluxed at 60° C. for 30 minutes. A solution of 3-bromopiperidine-2,6-dione 3 (0.5 equiv.) in THF was also heated at 60° C. After 30 minutes the first suspension was added to the second solution with heating, and the heating was continued for 3 hours. The reaction mixture was diluted with ethyl acetate and washed with water and brine solution. The organic fraction was then dried over anhydrous sodium sulfate and evaporated under reduced pressure to obtain the crude compound. The crude compound was then purified by flash chromatography to obtain 4.

Step 3: Synthesis of 3-(6-Amino-2-oxobenzo[cd]indol-1(2H)-yl)piperidine-2,6-dione (Compound 10): A stirred solution of 4 in ethanol was degassed with argon for 10 minutes. 10% Pd/C (30 Wt %) was added to the reaction mixture, and it was subjected to hydrogenation under a hydrogen balloon for 16 hours. It was filtered through celite and concentrated under reduced pressure to obtain Compound 10 as solid.

Example 10. Synthesis of tert-Butyl 4-(4-((1-(2,6-Dioxopiperidin-3-yl)-2-oxo-1,2-dihydrobenzo[cd]indol-6-yl)amino)-1H-pyrazol-1-yl)piperidine-1-carboxylate (Compound 11) and 3-(6-((1-(1-((2r,3r,5r,6r,7r,8r)-Cubane-1-carbonyl)piperidin-4-yl)-1H-pyrazol-4-yl)amino)-2-oxobenzo[cd]indol-1(2H)-yl)piperidine-2,6-dione (Compound 12)

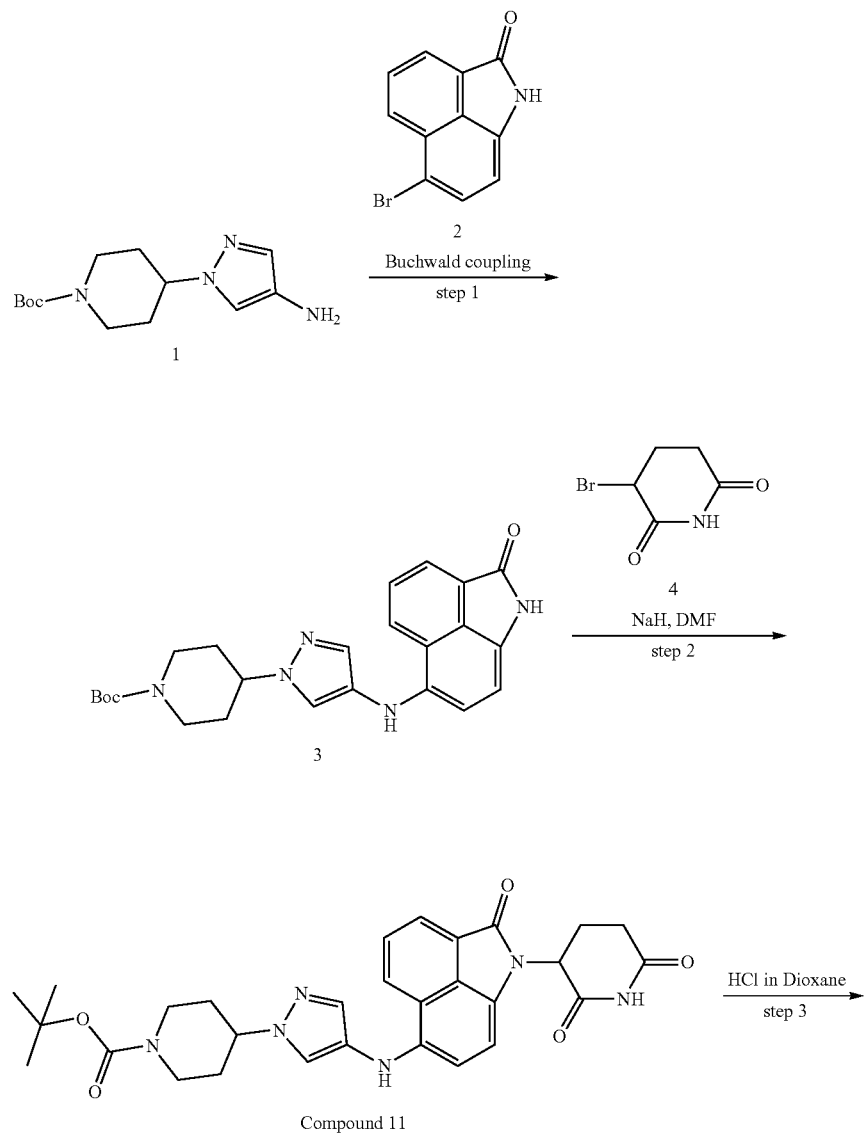

Compound 11

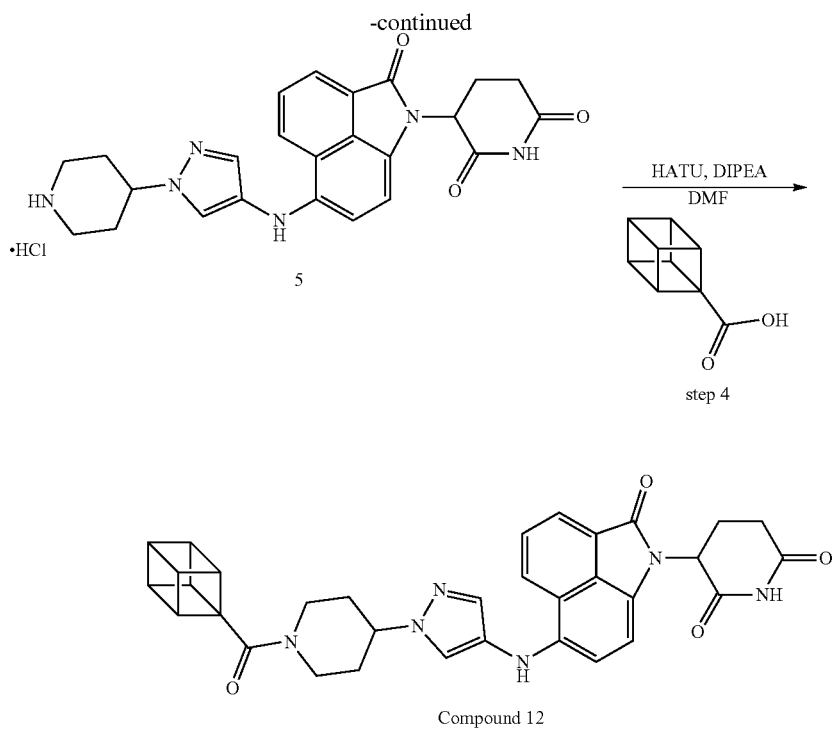

Step 1: Synthesis of tert-Butyl 4-(4-((2-Oxo-1,2-dihydrobenzo[cd]indol-6-yl)amino)-1H-pyrazol-1-yl)piperidine-1-carboxylate (3): To a stirred solution of tert-butyl 4-(4-aminopyrazol-1-yl)piperidine-1-carboxylate (20 mg, 75.09 µmol) and 6-bromo-1H-benzo[cd]indol-2-one (18.63 mg, 75.09 µmol) intoluene (5 mL) in a sealed tube was added potassium tert butoxide (25.28 mg, 225.28 µmol), and the reaction mixture was degassed for 5 min under argon atmosphere. $Pd_2(dba)_3$ (6.88 mg, 7.51 µmol) and BINAP (4.68 mg, 7.51 µmol) were added, and the reaction mixture was again purged for 2 min under argon atmosphere. The reaction mixture was heated to 90° C. for 16 hr. After consumption of SM reaction, the mixture was filtered through a celite bed and concentrated in vacuo. Purification by CombiFlash column chromatography (eluted by 15% ethyl acetate in n-hexane) provided tert-butyl 4-[4-[(2-oxo-1H-benzo[cd]indol-6-yl)amino]pyrazol-1-yl]piperidine-1-carboxylate 3 as a yellow liquid. LCMS (ES+)=249.9 [M+H]+.

Step 2: Synthesis of tert-Butyl 4-(4-((1-(2,6-Dioxopiperidin-3-yl)-2-oxo-1,2-dihydrobenzo[cd]indol-6-yl)amino)-1H-pyrazol-1-yl)piperidine-1-carboxylate (Compound 11): To a stirred solution of compound 3 in THF is added sodium hydride (60% dispersion in mineral oil, 1 equiv.), and the reaction mixture is refluxed at 60° C. for 30 minutes. A solution of 3-bromopiperidine-2,6-dione 4 (0.5 equiv.) in THF is also heated at 60° C. After 30 minutes the first suspension is added to the second solution with heating, and the heating is continued for 3 hours. The reaction mixture is diluted with ethyl acetate and washed with water and brine solution. The organic fraction is then dried over anhydrous sodium sulfate and evaporated under reduced pressure to obtain the crude compound. The crude compound is then purified by flash chromatography to obtain Compound 11.

Step 3: Synthesis of 3-(2-Oxo-6-((1-(piperidin-4-yl)-1H-pyrazol-4-yl)amino)benzo[cd]indol-1(2H)-yl)piperidine-2,6-dione (5): To a stirred solution of Compound 11 in 1,4 dioxane is added HCl in dioxane (4 M). The reaction mixture is stirred at 25° C. for 16 hr. After complete consumption of the starting material, the reaction is concentrated under reduced pressure. The resulting solid is washed with 10-20% ethyl acetate in n-hexane and dried to give the title compound 5.

Step 4: Synthesis of 3-(6-((1-(1-((2r,3r,5r,6r,7r,8r)-Cubane-1-carbonyl)piperidin-4-yl)-1H-pyrazol-4-yl)amino)-2-oxobenzo[cd]indol-1(2H)-yl)piperidine-2,6-dione (Compound 12): To a stirred solution of 5 and cubane-1-carboxylic acid (1 equiv.) in DMF (2 mL) is added HATU (1.5 equiv.) and DIPEA (3 equiv.), and the reaction mixture is stirred at 25° C. for 16 hr. Completion of the reaction is determined by LC-MS. The reaction mixture is diluted with ethyl acetate and washed with water. The organic layer is separated, dried over sodium sulfate, and concentrated under reduced pressure to give the crude. This crude is purified by preparatory TLC (using 100% ethyl acetate) to give the Compound 12 as a solid.

Example 11. Synthesis of 3-(6-(4-(Morpholinomethyl)phenoxy)-2-oxobenzo[cd]indol-1(2H)-yl)piperidine-2,6-dione (Compound 13)

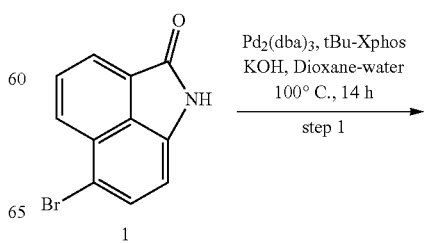

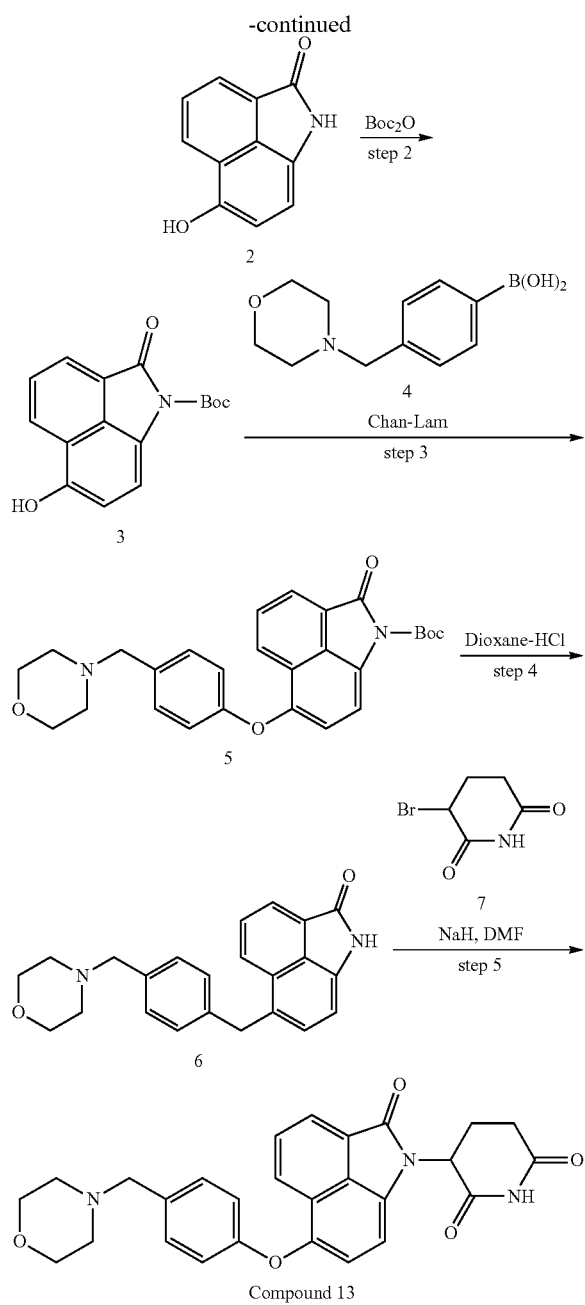

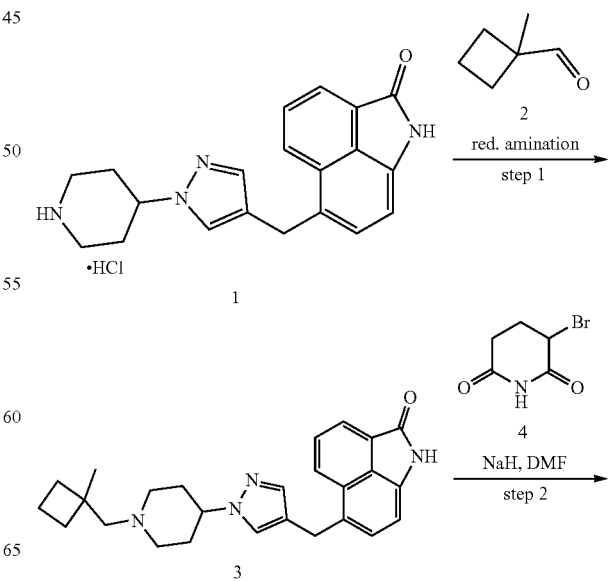

the reaction as confirmed by TLC and LC-MS, the solvent is removed. The crude is extracted with ethyl acetate and water. The organic layer is dried over with Na$_2$SO$_4$. The solvent is removed under vacuum to get the desired product 3.

Step 3: Synthesis of tert-Butyl 6-(4-(Morpholinomethyl)phenoxy)-2-oxobenzo[cd]indole-1(2H)-carboxylate (5): To a stirred solution of 3 and 4 in DCE is added pyridine (2 equiv.). The reaction mixture is degassed with oxygen followed by the addition of copper acetate (0.1 equiv.) and DMAP (0.1 equiv). The reaction mixture is heated at 80° C. for 24 hr. After completion of the reaction, the solvent is removed, and the crude is extracted with ethyl acetate and water. The organic layer is dried over with Na$_2$SO$_4$, and the solvent is removed under vacuum to get desired product 5.

Step 4: Synthesis of 6-(4-(Morpholinomethyl)phenoxy)benzo[cd]indol-2(1H)-one (6): To a stirred solution of 5 (1 equiv.) in DCM is added TFA (10.0 equiv.). The resulting solution is stirred at RT for 4 hr. The reaction is monitored by LCMS and TLC. After completion, the reaction is concentrated under reduced pressure to get crude compound 6 that is directly used in the next step without any other purification.

Step 5: Synthesis of 3-(6-(4-(Morpholinomethyl)phenoxy)-2-oxobenzo[cd]indol-1(2H)-yl)piperidine-2,6-dione (Compound 13): To the stirred solution of compound 6 in THF is added sodium hydride (60% dispersion in mineral oil, 1 equiv.), and the reaction mixture is refluxed at 60° C. for 30 minutes. A solution of 3-bromopiperidine-2,6-dione 7 (0.5 equiv.) in THF is also heated at 60° C. After 30 minutes the first suspension is added to the second solution with heating, and the heating is continued for 3 hours. The reaction mixture is diluted with ethyl acetate and washed with water and brine solution. The organic fraction is then dried over anhydrous sodium sulfate and evaporated under reduced pressure to obtain the crude compound. The crude compound is then purified by flash chromatography to obtain Compound 13.

Example 12. Synthesis of 3-(6-((1-(1-((1-Methylcyclobutyl)methyl)piperidin-4-yl)-1H-pyrazol-4-yl)methyl)-2-oxobenzo[cd]indol-1(2H)-yl)piperidine-2,6-dione (Compound 14)

Step 1: Synthesis of 6-Hydroxybenzo[cd]indol-2(1H)-one (2): To a stirred solution of 1 in dioxane (8 mL) and water (2 mL), potassium hydroxide (2 equiv) is added, and the resulting solution is degassed with N$_2$ for 15 minutes followed by the addition of (1E,4E)-1,5-diphenylpenta-1,4-dien-3-one palladium (5%) and tert-butyl Xphos (15%). The reaction mixture is heated at 100° C. in a sealed tube for 12 hr. After formation of desired pdt as evidence from LC-MS, the reaction mixture is filtered through celite bed and washed with ethyl acetate. The combined organic layer is separated and evaporated. The crude residue is purified by column chromatography to afford 2 as a solid.

Step 2: Synthesis of tert-Butyl 6-Hydroxy-2-oxobenzo[cd]indole-1(2H)-carboxylate (3): To a stirred solution of 2 in methanol (5 mL) and triethylamine (2 equiv) is slowly added di-tert-butyl dicarbonate (1.5 eq). After completion of -continued

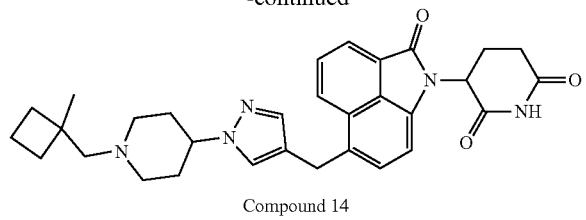

Compound 14

Step 1: Synthesis of 6-((1-(1-((1-Methylcyclobutyl)methyl)piperidin-4-yl)-1H-pyrazol-4-yl)methyl)benzo[cd]indol-2(1H)-one (3): To a stirred solution of 1 and 1-methylcyclobutane-1-carbaldehyde 2 (1 equiv.) in dry dichloroethane (3 mL) was added sodium cyanoborohydride (2 equiv.) at 0° C., and the reaction mixture was stirred at 0° C. for 2h. The reaction is warmed to rt over the period of 1 h and stirred at rt for 12h. The completion of the reaction is confirmed by TLC. The reaction mixture is quenched with water (25 mL) and extracted with DCM (2×25 mL). The combine organic layer is further washed with brine (1×25 mL), dried over anhydrous Na$_2$SO$_4$, and concentrated to get the crude product 3.

Step 2: Synthesis of 3-(6-((1-(1-((1-Methylcyclobutyl)methyl)piperidin-4-yl)-1H-pyrazol-4-yl)methyl)-2-oxobenzo[cd]indol-1(2H)-yl)piperidine-2,6-dione (Compound 14): To the stirred solution of compound 3 in THF is added sodium hydride (60% dispersion in mineral oil, 1 equiv.), and the reaction mixture is refluxed at 60° C. for 30 minutes. A solution of 3-bromopiperidine-2,6-dione 4 (0.5 equiv.) in THF is also heated at 60° C. After 30 minutes the first suspension is added to the second solution with heating, and the heating is continued for 3 hours. The reaction mixture is diluted with ethyl acetate and washed with water and brine solution. The organic fraction is then dried over anhydrous sodium sulfate and evaporated under reduced pressure to obtain the crude compound. The crude compound is then purified by flash chromatography to obtain Compound 14.

Example 13: Synthesis of 3-(6-((1-(1-(1-Methylcyclobutane-1-carbonyl)piperidin-4-yl)-1H-1,2,3-triazol-4-yl)methyl)-2-oxobenzo[cd]indol-1(2H)-yl)piperidine-2,6-dione (Compound 15)

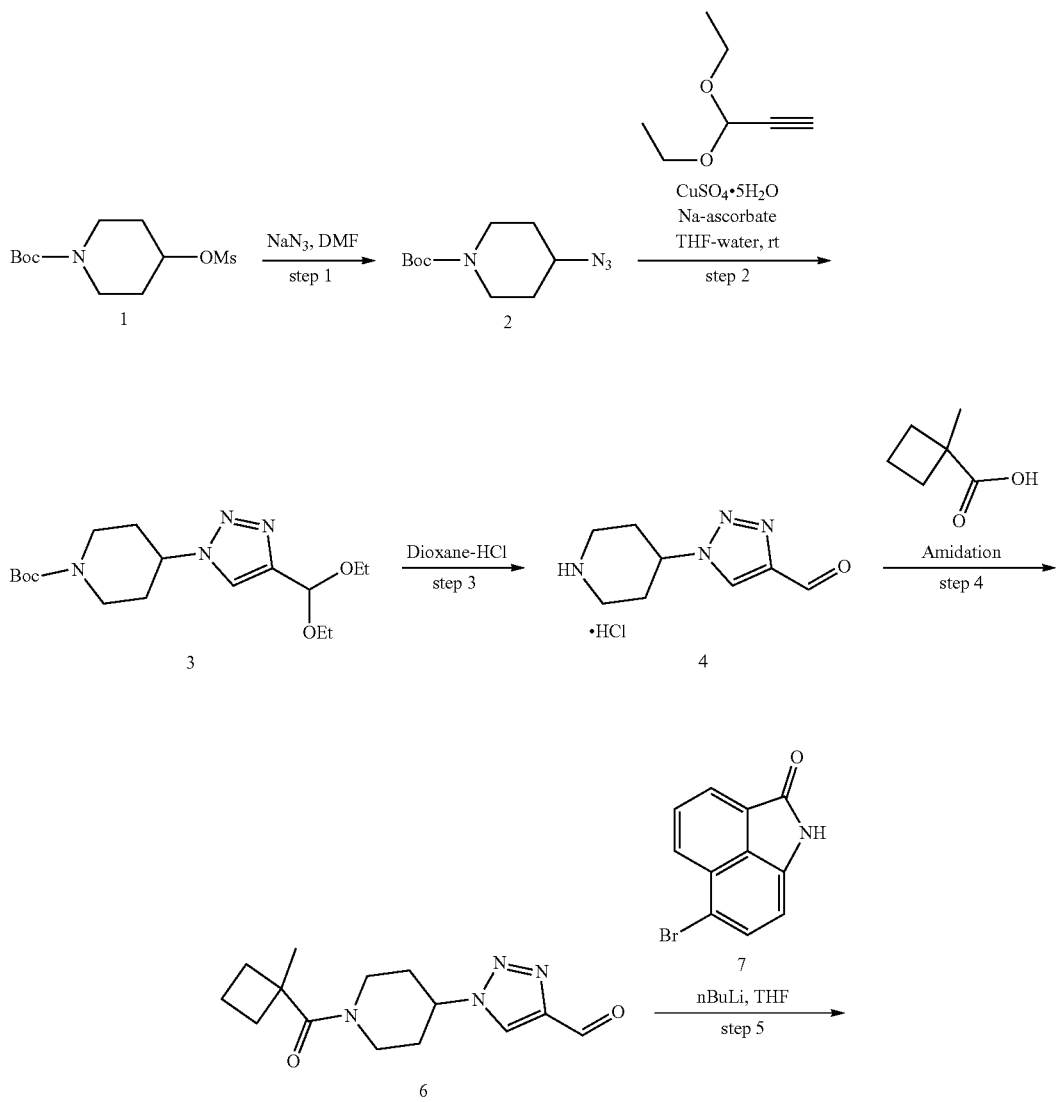

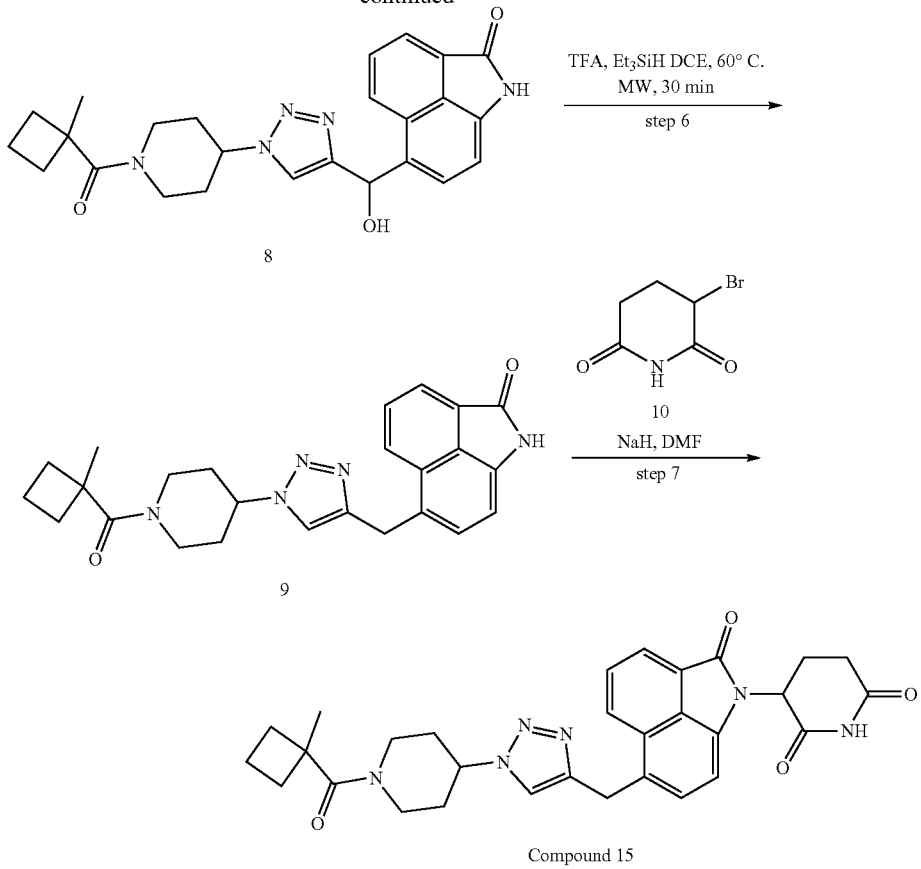

Compound 15

Step 1: Synthesis of tert-Butyl 4-Azidopiperidine-1-carboxylate (2): To a DMF solution of 1 is added sodium azide (3 equiv.), and the reaction mixture is heated under reflux at 70° C. for 2 hours. The reaction is monitored by TLC to observe consumption of starting material. The reaction is quenched with water and extracted with ethyl acetate. The ethyl acetate layer is washed with brine, dried over anhydrous $Na_2SO_4$ and evaporated to get crude compound. The crude compound is purified by silica gel column chromatography to get pure compound 2 as a white solid.

Step 2: Synthesis of tert-Butyl 4-(4-(Diethoxymethyl)-1H-1,2,3-triazol-1-yl)piperidine-1-carboxylate 3: To a stirred solution of tert-butyl 4-azidopiperidine-1-carboxylate 2 and 3,3-diethoxyprop-1-yne in Water and DMSO (1:4) is added copper sulfate (5%) at 25° C. The reaction is stirred for 5 min followed by addition of sodium ascorbate (15%). The reaction mixture is then stirred for 2 h at 25° C. The reaction is diluted with cold water and extracted with ethyl acetate (2 x). The combined organic layers are dried over anhydrous sodium sulfate and concentrated under reduced pressure to yield crude product. The crude product is purified by silica gel column chromatography to provide 3.

Step 3: Synthesis of 1-(Piperidin-4-yl)-1H-1,2,3-triazole-4-carbaldehyde 4: To a stirred solution of 3 in 1,4 dioxane is added HCl in dioxane (4 M). The reaction mixture is stirred at 25° C. for 16 hr. After complete consumption of SM, the reaction is concentrated under reduced pressure, washed with 10-20% ethyl acetate in n-hexane, and dried to give the title compound 4 as a solid.

Step 4: Synthesis of 1-(1-(1-Methylcyclobutane-1-carbonyl)piperidin-4-yl)-1H-1,2,3-triazole-4-carbaldehyde (6):

To a stirred solution of 4 and 1-methylcyclobutane-1-carboxylic acid 5 (1 equiv.) in DMF (2 mL) is added HATU (1.5 equiv.) and DIPEA (3 equiv.), and the reaction mixture is stirred at 25° C. for 16 hr. Completion of the reaction is confirmed by LC-MS, and the reaction mixture is diluted with ethyl acetate and washed with water. The organic layer is separated, dried over sodium sulfate, and concentrated under reduced pressure to give the crude. The crude is purified by silica gel column chromatography to give the title compound 6 as solid.

Step 5: Synthesis of 6-(Hydroxy(1-(1-(1-methylcyclobutane-1-carbonyl)piperidin-4-yl)-1H-1,2,3-triazol-4-yl)methyl)benzo[cd]indol-2(1H)-one (8): To the stirred solution of 6-bromo-1H-benzo[cd]indol-2-one 7 (1 equiv.) in THF is added butyllithium (2.2 equiv.) at −78° C., and the temperature is allowed to increase to −40° C. The reaction mixture is stirred at the same temperature for 30 minutes followed by the addition of 6 (1 equiv.) in THF at −78° C., and then the reaction mixture is allowed to warm to room temperature and stirred for 16 hours. The reaction mixture is quenched with saturated aqueous ammonium chloride solution and diluted with ethyl acetate. The layers are separated, and the organic phase is washed with water. The organic layer is dried over anhydrous sodium sulfate and evaporated under reduced pressure to obtain the crude compound which is purified by flash chromatography using 0-5% MeOH-DCM to afford desired product 8.

Step 6: Synthesis of 6-((1-(1-(1-Methylcyclobutane-1-carbonyl)piperidin-4-yl)-1H-1,2,3-triazol-4-yl)methyl)benzo[cd]indol-2(1H)-one (9): To a stirred solution of 8 in DCE is added triethylsilane (2 equiv.) and trifluoroacetic acid (5 equiv.), and the reaction is stirred for 30 minutes under microwave irradiation at 70° C. The solvent is evaporated under reduced pressure to obtain the crude which is washed with ether and pentane to afford 9 as a brown gum in the form of crude.

Step 7: Synthesis of 3-(6-((1-(1-(1-Methylcyclobutane-1-carbonyl)piperidin-4-yl)-1H-1,2,3-triazol-4-yl)methyl)-2-oxobenzo[cd]indol-1(2H)-yl)piperidine-2,6-dione (Compound 15): To the stirred solution of compound 9 in THF is added sodium hydride (60% dispersion in mineral oil, 1 equiv.), and the reaction mixture is refluxed at 60° C. for 30 minutes. A solution of 3-bromopiperidine-2,6-dione 10 (0.5 equiv.) in THF is also heated at 60° C. After 30 minutes the first suspension is added to the second solution with heating, and the heating is continued for 3 hours. The reaction mixture is diluted with ethyl acetate and washed with water and brine solution. The organic fraction is then dried over anhydrous sodium sulfate and evaporated under reduced pressure to obtain the crude compound. The crude compound is then purified by flash chromatography to obtain Compound 15.

Example 14. Synthesis of 3-(6-((3-Chloro-1-(1-(1-methylcyclobutane-1-carbonyl)piperidin-4-yl)-1H-pyrazol-4-yl)methyl)-2-oxobenzo[cd]indol-1(2H)-yl)piperidine-2,6-dione (Compound 16)

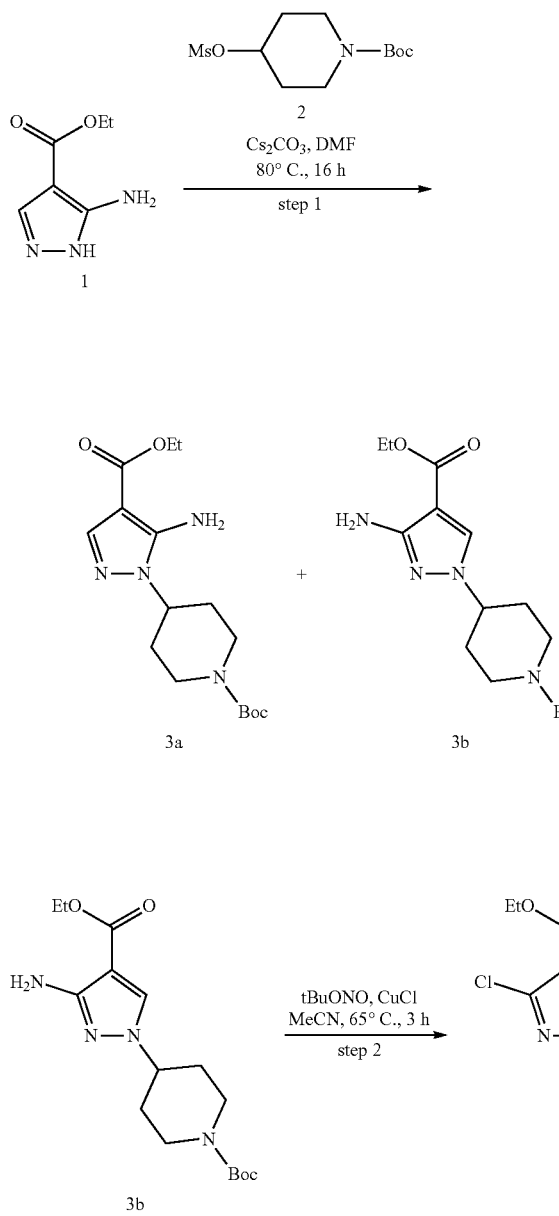

-continued
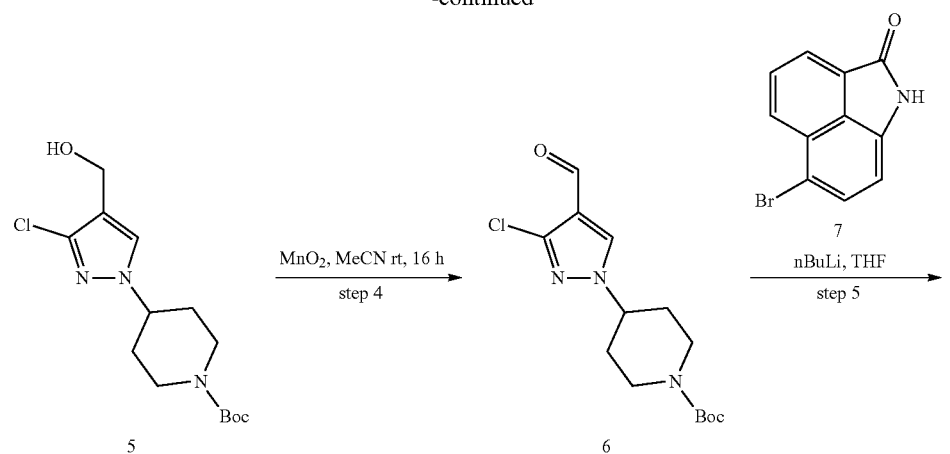
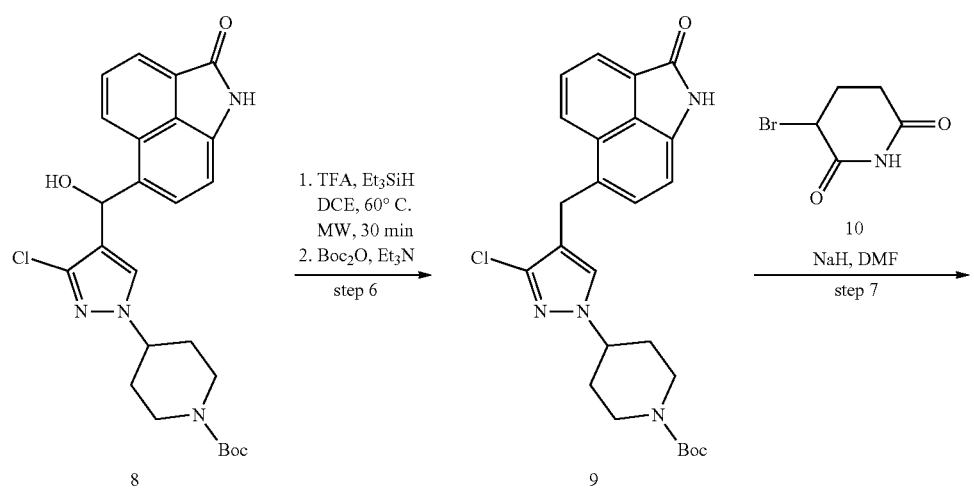
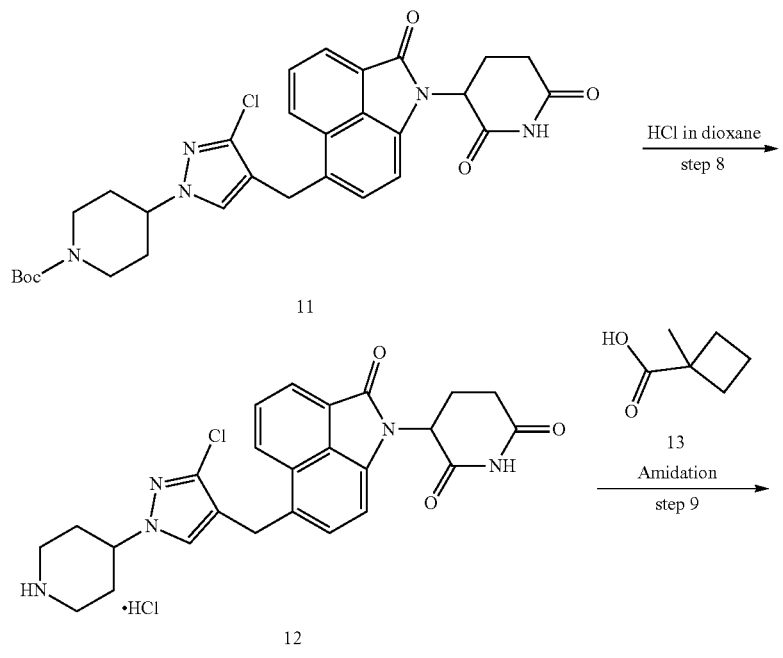

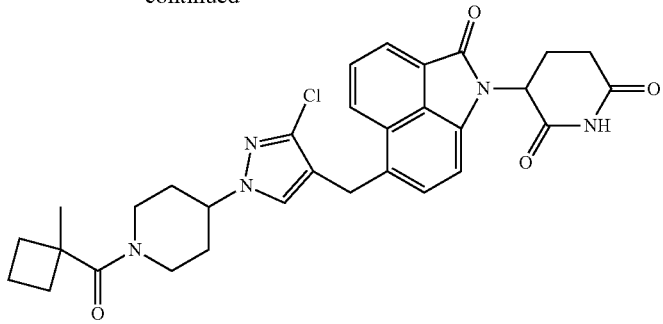

Compound 16

Step 1: Synthesis of tert-Butyl 4-(5-Amino-4-(ethoxycarbonyl)-1H-pyrazol-1-yl)piperidine-1-carboxylate (3a) and tert-butyl 4-(3-amino-4-(ethoxycarbonyl)-1H-pyrazol-1-yl) piperidine-1-carboxylate (3b): To a stirred solution of ethyl 5-amino-1H-pyrazole-4-carboxylate 1 (10.0 g, 64.45 mmol) in DMF (100 mL) was added tert-butyl 4-methylsulfonyloxypiperidine-1-carboxylate 2 (25.21 g, 90.23 mmol) and Cesium carbonate (42.00 g, 128.90 mmol), and the reaction mixture was stirred at 80° C. for 16 hours. TLC showed the formation of the two isomeric new spots and consumption of both starting materials. The reaction mixture was then cooled to room temperature, diluted with ethyl acetate, and washed with water. The organic layer was dried over sodium sulfate and concentrated under reduced pressure. The crude was then purified by column chromatography eluting 10-12% ethyl acetate in dichloromethane to afford 3a (4.5 g, 13.30 mmol, 20.63% yield) as a white solid and eluting 15-20% ethyl acetate in dichloromethane to afford 3b (4.8 g, 14.18 mmol, 22.01% yield) as a white solid.

Step 2: Synthesis of tert-Butyl 4-(3-Chloro-4-(ethoxycarbonyl)-1H-pyrazol-1-yl)piperidine-1-carboxylate (4): To a stirred solution of tert-butyl 4-(3-amino-4-ethoxycarbonyl-pyrazol-1-yl)piperidine-1-carboxylate (2.1 g, 6.21 mmol) in acetonitrile (10.0 mL) at 0° C. was added tert-Butyl nitrite (tech. 90%, 959.89 mg, 9.31 mmol, 1.11 mL) followed by CuCl (921.53 mg, 9.31 mmol), and the reaction mixture was stirred at room temperature for 1 hour. The reaction was heated at 65° C. for 2 hours. TLC showed a new non-polar spot and starting material was consumed. The reaction mixture was then cooled to room temperature, diluted with ethyl acetate, and washed with water. The organic layer was washed with saturated sodium bicarbonate solution and brine solution, dried over sodium sulfate, and concentrated under reduced pressure to afford the crude product. The crude was then purified by column chromatography eluting 1-1.5% MeOH-DCM to afford tert-butyl 4-(3-chloro-4-ethoxycarbonyl-pyrazol-1-yl)piperidine-1-carboxylate 4 (1 g, 2.79 mmol, 45.03% yield) as a gummy green liquid.

Step 3: Synthesis of tert-Butyl 4-(3-Chloro-4-(hydroxymethyl)-1H-pyrazol-1-yl)piperidine-1-carboxylate (5): To a stirred solution of 4 in THF at 0° C. under inert atmosphere is added DIBAL-H (4 equiv., 25% intoluene) drop-wise. After completion of addition, the mixture is stirred at same temperature for 1 h. Upon TLC showing starting material consumption, the mixture is quenched with water and diluted with EtOAc. The solid precipitate is filtered through a celite pad, and the filtrate is concentrated to dryness to afford 5 as crude.

Step 4: Synthesis of tert-Butyl 4-(3-Chloro-4-formyl-1H-pyrazol-1-yl)piperidine-1-carboxylate (6): To a stirred solution of 5 in DCM is added manganese dioxide (10 equiv.), and the reaction was stirred at room temperature overnight. Upon completion of the reaction, the reaction mixture is filtered, and the filtrate is evaporated under reduced pressure. The crude material is then purified by column chromatography to afford 6.

Step 5: Synthesis of tert-Butyl 4-(3-Chloro-4-(hydroxy(2-oxo-1,2-dihydrobenzo[cd]indol-6-yl)methyl)-1H-pyrazol-1-yl)piperidine-1-carboxylate (8): To a stirred solution of 6-bromo-1H-benzo[cd]indol-2-one 7 (1 equiv.) in THF is added butyllithium (2.2 equiv.) at −78° C., and after the addition is complete the temperature is allowed to increase to −40° C. and stirred for 30 minutes. 6 (1 equiv.) in THF is added at −78° C., and then the reaction mixture is allowed to warm to room temperature and is stirred for 16 hours. The reaction mixture is quenched with saturated aqueous ammonium chloride solution and diluted with ethyl acetate. The layers are separated, and the organic layer is washed with water. The organic phase is dried over anhydrous sodium sulfate and evaporated under reduced pressure to obtain the crude compound, which is purified by flash chromatography using 0-5% MeOH-DCM to afford desired product 8.

Step 6: Synthesis of tert-Butyl 4-(3-Chloro-4-((2-oxo-1,2-dihydrobenzo[cd]indol-6-yl)methyl)-1H-pyrazol-1-yl)piperidine-1-carboxylate (9): To a stirred solution of 8 in DCE is added triethylsilane (2 equiv.) and trifluoroacetic acid (5 equiv.), and the reaction is stirred for 30 minutes under microwave irradiation at 70° C. The solvent is evaporated under reduced pressure to obtain the crude which is washed with ether and pentane to afford 9 as brown gum in the form of crude.

Step 7: Synthesis of tert-Butyl 4-(3-Chloro-4-((1-(2,6-dioxopiperidin-3-yl)-2-oxo-1,2-dihydrobenzo[cd]indol-6-yl)methyl)-1H-pyrazol-1-yl)piperidine-1-carboxylate (11): To the stirred solution of compound 9 in THF is added sodium hydride (60% dispersion in mineral oil, 1 equiv.), and the reaction mixture is refluxed at 60° C. for 30 minutes. A solution of 3-bromopiperidine-2,6-dione 10 (0.5 equiv.) in THF is also heated at 60° C. After 30 minutes the first suspension is added to the second solution with heating, and the heating is continued for 3 hours. The reaction mixture is diluted with ethyl acetate and washed with water and brine solution. The organic fraction is then dried over anhydrous sodium sulfate and evaporated under reduced pressure to obtain the crude compound. The crude compound is then purified by flash chromatography to obtain 11.

Step 8: Synthesis of 3-(6-((3-Chloro-1-(piperidin-4-yl)-1H-pyrazol-4-yl)methyl)-2-oxobenzo[cd]indol-1(2H)-yl)piperidine-2,6-dione (12): To a stirred solution of 11 in dioxane is added hydrochloric acid in dioxane (10 equiv.), and the reaction is stirred at room temperature for 2 hours. TLC is checked for complete consumption of the starting material. The solvent in the reaction mixture is evaporated under reduced pressure, and the crude is washed with ether and pentane to afford 12 as a solid.

Step 9: Synthesis of 3-(6-((3-Chloro-1-(1-(1-methylcyclobutane-1-carbonyl)piperidin-4-yl)-1H-pyrazol-4-yl)methyl)-2-oxobenzo[cd]indol-1(2H)-yl)piperidine-2,6-dione (Compound 16): To a stirred solution of 12 and 1-methylcyclobutane-1-carboxylic acid 13 (1 equiv) in DMF (2 mL) is added HATU (1.5 eq) and DIPEA (3 eq), and the reaction mixture is stirred at 25° C. for 16 hr. Upon completion of the reaction as determined by LC-MS, the reaction mixture is diluted with ethyl acetate and washed with water. The organic layer is separated, dried over sodium sulfate, and concentrated under reduced pressure to give the crude. This crude is purified by silica gel column chromatography to give Compound 16 as a solid.

Example 15. Synthesis of 3-(6-((1-(1-(1-Methylcyclobutane-1-carbonyl)piperidin-4-yl)-1H-pyrrolo[2,3-c]pyridin-3-yl)methyl)-2-oxobenzo[cd]indol-1(2H)-yl)piperidine-2,6-dione (Compound 17)

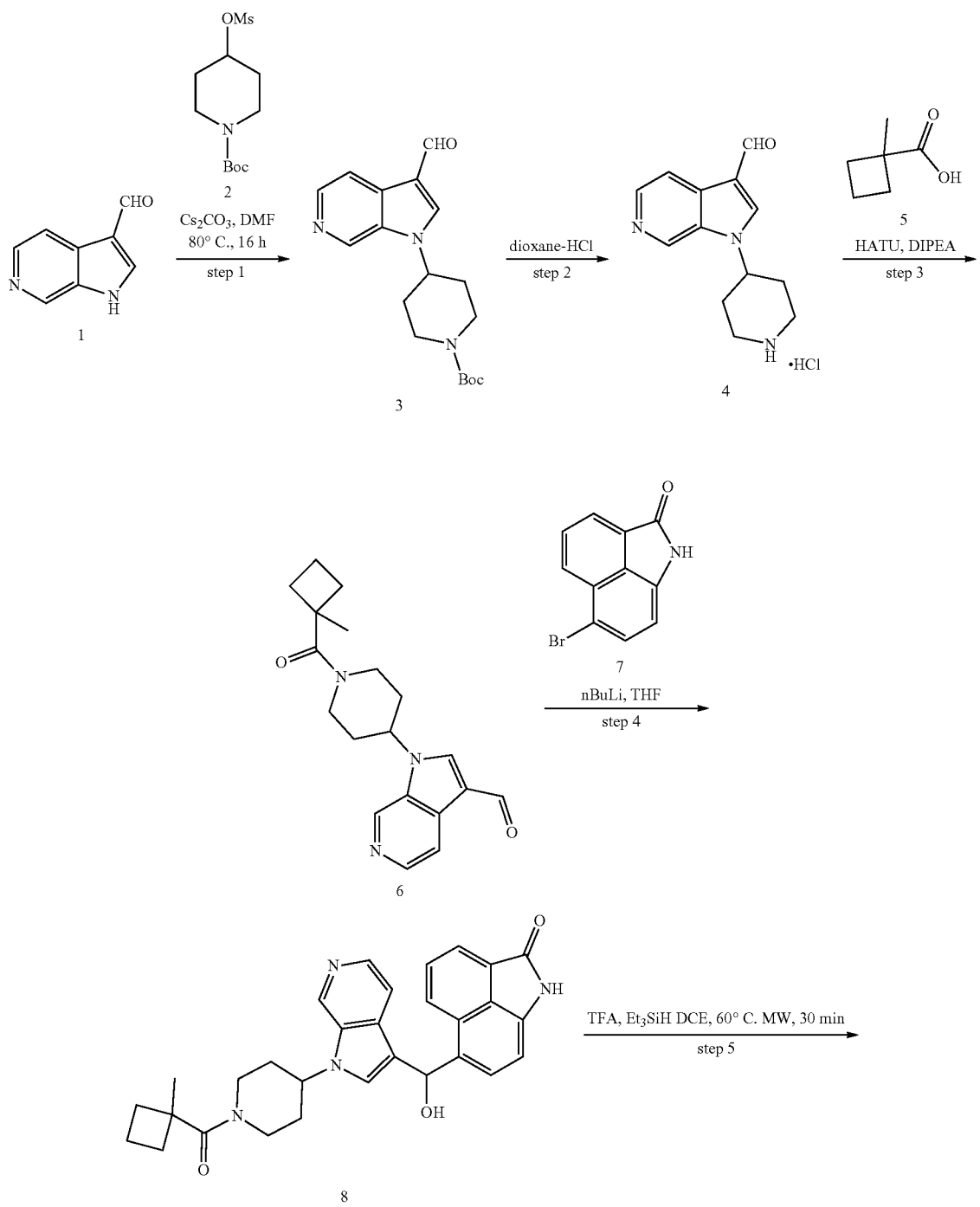

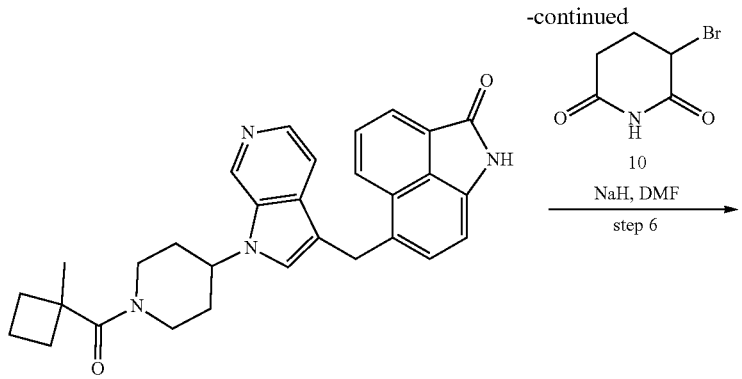

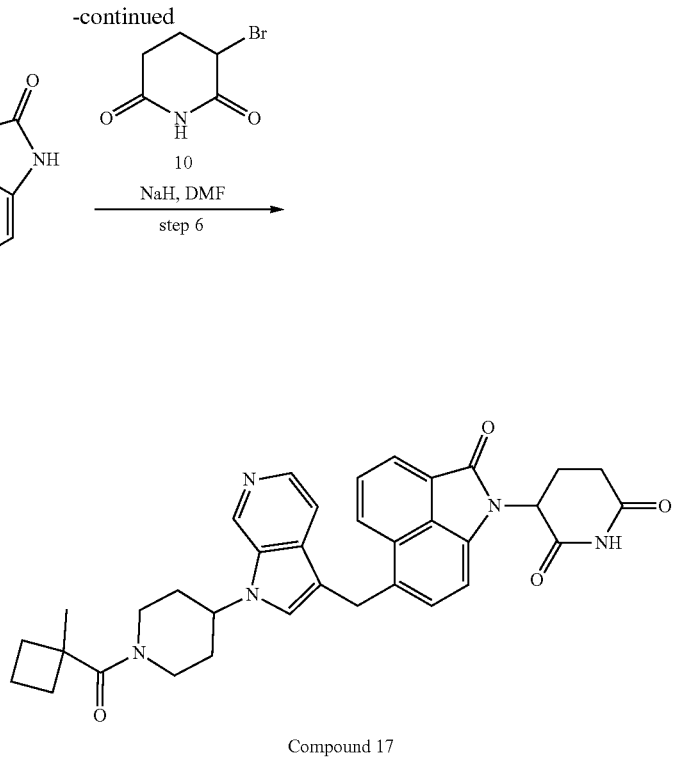

Compound 17

Step 1: Synthesis of tert-Butyl 4-(3-Formyl-1H-pyrrolo[2,3-c]pyridin-1-yl)piperidine-1-carboxylate (3): To a solution of 1H-pyrrolo[2,3-c]pyridine-3-carbaldehyde 1 (250 mg, 1.71 mmol) and tert-butyl 4-methylsulfonyloxypiperidine-1-carboxylate 2 (1 equiv.) in DMF (5 mL) was added cesium carbonate (1.11 g, 3.42 mmol), and the reaction was heated to 80° C. for 16 hr. LC-MS showed formation of product with majority SM. Another equiv of tert-butyl 4-methylsulfonyloxypiperidine-1-carboxylate was added, and the reaction was heated at 90° C. for another 16 h. LC-MS showed formation of majority product. The reaction was cooled to rt, diluted with water and extracted with EtOAc successively. The combined organic phase was washed with water and brine and dried over sodium sulfate. The crude was purified by CombiFlash eluting with 100% EtOAc to get tert-butyl 4-(3-formylpyrrolo[2,3-c]pyridin-1-yl)piperidine-1-carboxylate 3 (300 mg, 910.77 µmol, 53.24% yield) as pure product. LCMS (ES+)=330.2 [M+H]$^+$.

Step 2: Synthesis of 1-(Piperidin-4-yl)-1H-pyrrolo[2,3-c]pyridine-3-carbaldehyde (4): To a solution of tert-butyl 4-(3-formylpyrrolo[2,3-c]pyridin-1-yl)piperidine-1-carboxylate 3 (200 mg, 607.18 µmol) in dioxane (15 mL) was added dioxane-HCl (4 M, 455.38 µL), and the reaction was stirred at 25° C. for 16 h. LC-MS showed formation of product. The reaction was evaporated to dryness to provide 1-(4-piperidyl)pyrrolo[2,3-c]pyridine-3-carbaldehyde hydrochloride 4 (155 mg, 583.28 µmol, 96.06% yield) as a white solid.

Step 3: Synthesis of 1-(1-(1-Methylcyclobutane-1-carbonyl)piperidin-4-yl)-1H-pyrrolo[2,3-c]pyridine-3-carbaldehyde (6): To a solution of 1-(4-piperidyl)pyrrolo[2,3-c]pyridine-3-carbaldehyde hydrochloride 4 (780 mg, 2.94 mmol) and 1-methylcyclobutanecarboxylic acid 5 (335.03 mg, 2.94 mmol) in DMF (50 mL) was added DIPEA (1.14 g, 8.81 mmol, 1.53 mL), and the reaction was stirred for a few minutes at 25° C. HATU (1.34 g, 3.52 mmol) was added to the reaction mixture, and stirring was continued for 16 hr. LC-MS showed formation of product. Water was added, and the reaction mixture was extracted with EtOAc. The organic phase was washed with water, brine and dried over Na$_2$SO$_4$. The crude was evaporated to dryness and purified by prep TLC eluting with 3% MeOH in DCM to afford 1-[1-(1-methylcyclobutanecarbonyl)-4-piperidyl]pyrrolo[2,3-c]pyridine-3-carbaldehyde 6 (820 mg, 2.52 mmol, 85.85% yield) as a yellow solid. LCMS (ES+)=326.2 [M+H]+.

Step 4: Synthesis of 6-(Hydroxy(1-(1-(1-methylcyclobutane-1-carbonyl)piperidin-4-yl)-1H-pyrrolo[2,3-c]pyridin-3-yl)methyl)benzo[cd]indol-2(1H)-one (8): To a stirred solution of 6-bromo-1H-benzo[cd]indol-2-one 7 (1 equiv.) in THF is added butyllithium (2.2 equiv.) at −78° C. Upon addition, the temperature is allowed to increase to −40° C. and the reaction mixture is stirred at the same temperature for 30 minutes. 6 (1 equiv.) in THF is added at −78° C., and the reaction mixture is allowed to warm to room temperature and is stirred for 16 hours. The reaction mixture is quenched with saturated aqueous ammonium chloride solution and diluted with ethyl acetate. The layers are separated, and the organic phase is washed with water. The organic layer is dried over anhydrous sodium sulfate and evaporated under reduced pressure to obtain the crude compound which is purified by flash chromatography using 0-5% MeOH-DCM to afford desired product 8.

Step 5: Synthesis of 6-((1-(1-(1-Methylcyclobutane-1-carbonyl)piperidin-4-yl)-1H-pyrrolo[2,3-c]pyridin-3-yl)methyl)benzo[cd]indol-2(1H)-one (9): To a stirred solution of 8 in DCE is added triethylsilane (2 equiv.) and trifluoroacetic acid (5 equiv.), and the reaction is stirred for 30 minutes under microwave irradiation at 70° C. The solvent is evaporated under reduced pressure to obtain the crude which is washed with ether and pentane to afford 9 as brown gum in the form of crude.

Step 6: Synthesis of 3-(6-((1-(1-(1-Methylcyclobutane-1-carbonyl)piperidin-4-yl)-1H-pyrrolo[2,3-c]pyridin-3-yl)methyl)-2-oxobenzo[cd]indol-1(2H)-yl)piperidine-2,6-dione (Compound 17): To a stirred solution of compound 9 in THF is added sodium hydride (60% dispersion in mineral oil, 1 equiv.), and the reaction mixture is refluxed at 60° C. for 30 minutes. A solution of 3-bromopiperidine-2,6-dione 10 (0.5 equiv.) in THF is also heated at 60° C. After 30 minutes the first suspension is added to the second solution with heating, and the heating is continued for 3 hours. The reaction mixture is diluted with ethyl acetate and washed with water and brine solution. The organic fraction is then dried over anhydrous sodium sulfate and evaporated under reduced pressure to obtain the crude compound. The crude compound is then purified by flash chromatography to obtain Compound 17.

Example 16. Synthesis of 3-(6-((1-(1-(Cubane-1-carbonyl)-4-methylpiperidin-4-yl)-1H-pyrazol-4-yl)methyl)-2-oxobenzo[cd]indol-1(2H)-yl)piperidine-2,6-dione (Compound 18)

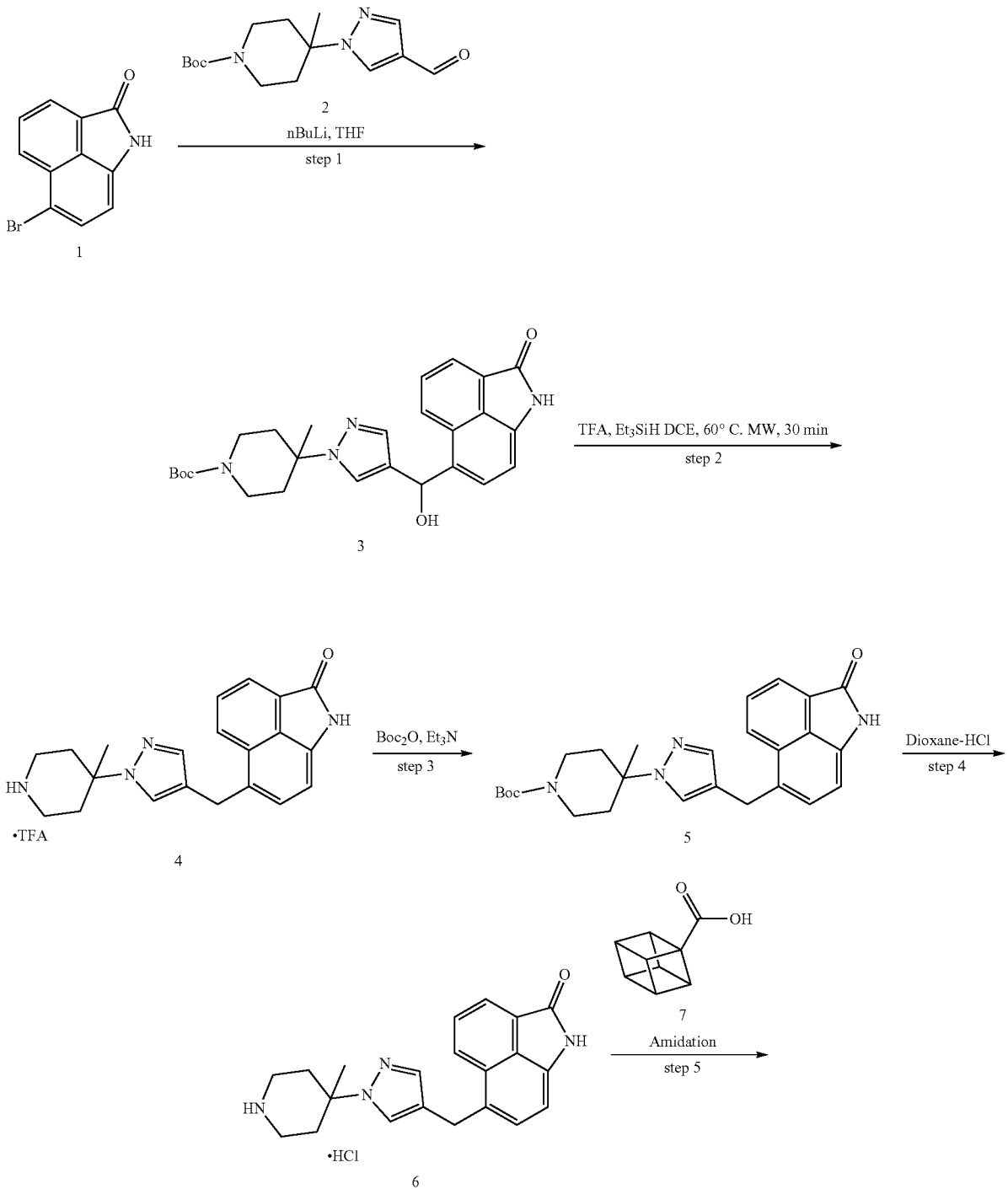

-continued

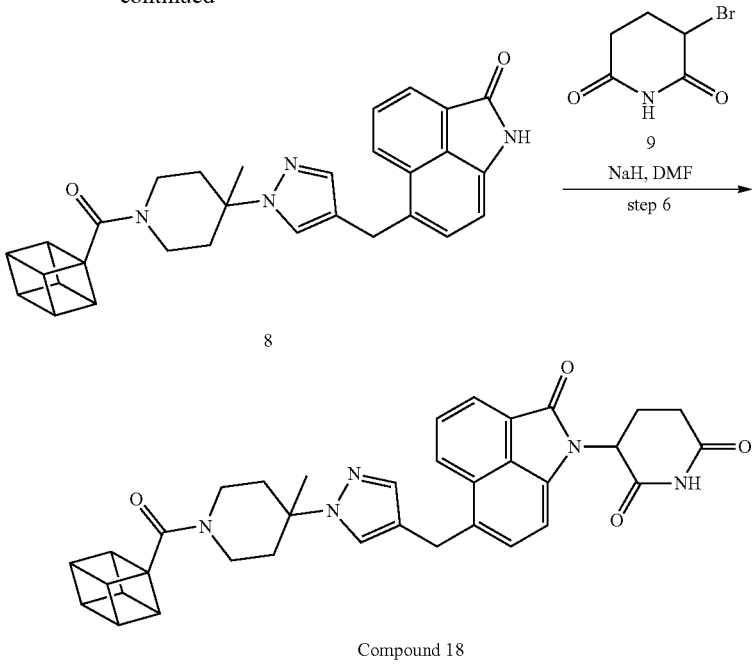

Compound 18

Step 1: Preparation of tert-Butyl 4-(4-(Hydroay(2-oxo-1, 2-dihydrobenzo[cd]indol-6-yl)methyl)-1H-pyrazol-1-yl) 4.methylpiperidine-1-carboxylate (3): To a stirred solution of 6-bromo-1H-benzo[cd]indol-2-one 1 (430.0 mg, 1.73 mmol) in THF (5 mL) was added n-butyllithium (2.36 M, 2.35 mL) at −78° C., and upon addition the temperature was increased to −40° C. and the reaction mixture was stirred 30 minutes. tert-Butyl 4-(4-formylpyrazol-1-yl)-4-methyl-piperidine-1-carboxylate 2 (508.50 mg, 1.73 mmol) in THF (5 mL) was added at −78° C., and then the reaction mixture was warmed to room temperature and stirred for 16 hours. The reaction mixture was quenched with ammonium chloride solution, diluted with ethyl acetate, and washed with water, and the organic layer was separated. The organic phase was dried over anhydrous sodium sulfate and evaporated under reduced pressure to obtain the crude compound which was purified by flash chromatography (using 0/6-5% MeOH-DCM) to afford tert-butyl 4-[4-[hydroxy-(2-oxo-1H-benzo [cd]indol-6-yl)methyl]pyrazol-1-yl]-4-methyl-piperidine-1-carboxylate 3 (75 mg, 162.15 µmol, 9.35% yield) as a brown solid. LC MS: ES+ 445.5 (−18 due to deoxygenated fragment).

Step 2: Preparation of Trifluoroacetic Acid Salt of 6-((1-(4-Methylpiperidin-4-yl)-1H-pyrazol-4-yl)methyl)benzo [cd]indol-2(1H)-one (4): To a stirred solution of 6-[[1-(4-methyl-4-piperidyl)pyrazol-4-yl]methyl]-1H-benzo[cd] indol-2-one 3 (75.0 mg, 162.15 µmol) in DCE (1 mL) was added triethylsilane (75.42 mg, 648.59 µmol, 103.59 µL) and trifluoroacetic acid (147.91 mg, 1.30 mmol, 99.94 µL), and the reaction mixture was stirred at 80° C. for 2 hours. The reaction was concentrated under reduced pressure and triturated with diethyl ether to afford [4-methyl-4-[4-[(2-oxo-1H-benzo[cd]indol-6-yl)methyl]pyrazol-1-yl]-1-piperidyl] 2,2,2-trifluoroacetate 4 (72 mg, 156.37 µmol, 96.44% yield) as a brown gummy solid. LC MS: ES+ 347.2.

Step 3: Preparation of tert-Butyl 4-Methyl-4-(4-((2-oxo-1,2-dihydrobenzo[cd]indol-6-yl)methyl)-1H-pyrazol-1-yl) piperidine-1-carboxylate (5): To a stirred solution of [4-methyl-4-[4-[(2-oxo-1H-benzo[cd]indol-6-yl)methyl] pyrazol-1-yl]-1-piperidyl]2,2,2-trifluoroacetate 4 (72.0 mg, 156.37 µmol) in DCM (6 mL) was added triethylamine (47.47 mg, 469.11 µmol, 65.38 µL) with cooling followed by di-tert-butyl dicarbonate (51.19 mg, 234.55 µmol, 53.83 µL), and the reaction was stirred at room temperature for 16 hours. The reaction mixture was diluted with ethyl acetate, washed with water and brine solution, and the organic layer was separated. The organic phase was dried over anhydrous sodium sulfate and evaporated under reduced pressure to obtain the crude which was purified by flash chromatography (using 0/6-5% MeOH-DCM to afford tert-butyl 4-methyl-4-[4-[(2-oxo-1H-benzo[cd]indol-6-yl)methyl] pyrazol-1-yl]piperidine-1-carboxylate 5 (40.0 mg, 89.58 µmol, 57.29% yield) as yellow sticky solid. LC MS: ES+ 447.4.

Step 4: Preparation of 6-((1-(4-Methylpiperidin-4-yl)-1H-pyrazol-4-yl)methyl)benzo[cd]indol-2(1H)-one hydrochloride (6): To a stirred solution of tert-butyl 4-methyl-4-[4-[(2-oxo-1H-benzo[cd]indol-6-yl)methyl]pyrazol-1-yl] piperidine-1-carboxylate 5 (40.0 mg, 89.58 µmol) in 1,4-dioxane (1 mL) was added hydrochloric acid in dioxane (89.58 µmol, 2 mL), and the reaction was stirred at room temperature for 2 hours. The solvent was evaporated under reduced pressure, and the crude was washed with ether and pentane to afford 6-[[1-(1-chloro-4-methyl-4-piperidyl) pyrazol-4-yl]methyl]-1H-benzo[cd]indol-2-one 6 (34 mg, 88.80 µmol, 99.13% yield) as yellow solid. LC MS: ES+ 347.4.

Step 5: Preparation of 6-((1-(1-(Cubane-1-carbonyl)-4-methylpiperidin-4-yl)-1H-pyrazol-4-yl)methyl)benzo[cd] indol-2(1H)-one (8): To a stirred solution of 6-[[1-(1-chloro-4-methyl-4-piperidyl)pyrazol-4-yl]methyl]-1H-benzo[cd] indol-2-one 6 (34.0 mg, 88.80 µmol) in DMF (1 mL) was added N,N-diisopropylethylamine (34.43 mg, 266.40 µmol, 46.40 µL) with cooling followed by cubane-1-carboxylic acid 7 (13.16 mg, 88.80 µmol) and HATU (50.65 mg, 133.20 µmol), and the reaction mixture was stirred at room temperature for 16 hours. The reaction mixture was diluted with ethyl acetate and washed with sodium bicarbonate solution, water and brine solution. The organic fraction was separated, dried over anhydrous sodium sulfate and evaporated under reduced pressure to obtain the crude compound, which was purified by preparative TLC plate (eluting with 3% MeOH-DCM) to afford 6-[[1-[1-(cubane-1-carbonyl)-4-methyl-4-piperidyl]pyrazol-4-yl]methyl]-1H-benzo[cd]indol-2-one 8 (20.0 mg, 41.97 μmol, 47.26% yield) as yellow solid. LC MS: ES+ 477.3.

Step 6: Preparation of 3-(6-((1-(1-(Cubane-1-carbonyl)-4methylpiperidin-4-yl)-1H-pyrazol-4-yl)methyl)-2-oxobenzo[cd]indol-1(2H)-yl)piperidine-2,6-dione (Compound 18): To a stirred solution 6-[[1-[1-(cubane-1-carbonyl)-4-methyl-4-piperidyl]pyrazol-4-yl]methyl]-1H-benzo[cd]indol-2-one 8 (20.0 mg, 41.97 μmol) in DMF (1 mL) was added sodium hydride (60% dispersion in mineral oil, 3.22 mg, 83.93 μmol) with cooling, and the reaction was heated at 60° C. for 30 minutes. 3-Bromopiperidine-2,6-dione 9 (8.06 mg, 41.97 μmol) was added with heating, and the reaction was continued for 4 hours at 60° C. TLC showed consumption of 9, so 3-bromopiperidine-2,6-dione (8.06 mg, 41.97 μmol) was further added, and the reaction mixture was heated at 60° C. for 16 hours. The reaction mixture was diluted with ethyl acetate, washed with water and the organic fraction was separated. The organic phase was then dried over anhydrous sodium sulfate and evaporated under reduced pressure to obtain the crude compound, which was purified by preparative TLC plate (eluting with 40% ethyl acetate-DCM) to afford 3-[6-[[1-[1-(cubane-1-carbonyl)-4-methyl-4-piperidyl]pyrazol-4-yl]methyl]-2-oxo-benzo[cd]indol-1-yl]piperidine-2,6-dione (Compound 18) (7 mg, 11.75 μmol, 27.99% yield, 98.62% purity) as a yellow solid. $^1$H NMR (d6-DMSO, 400 MHZ) δ 11.10 (s, 1H), 8.39 (d, J=8.28 Hz, 1H), 8.08 (d, J=6.96 Hz, 1H), 7.84 (d, J=7.52 Hz, 1H), 7.81 (s, 1H), 7.36-7.33 (m, 2H), 7.07 (d, J=7.32 Hz, 1H), 5.43 (dd, J=12.68, 5.16 Hz, 1H), 4.21 (s, 2H), 4.15 (br s, 3H), 3.96 (br s, 4H), 3.74-3.70 (m, 1H), 3.23-3.18 (m, 1H), 3.05-2.88 (m, 3H), 2.80-2.72 (m, 1H), 2.66-2.62 (m, 1H), 2.40-2.27 (m, 2H), 2.10-2.07 (m, 1H), 1.86-1.71 (m, 2H), 1.34 (s, 3H); LC MS: ES+ 588.5.

Example 17. Synthesis of 3-(6-((1-(4-Methyl-1-(1-methylcyclobutane-1-carbonyl)piperidin-4-yl)-1H-pyrazol-4-yl)methyl)-2-oxobenzo[cd]indol-1(2H)-yl)piperidine-2,6-dione (Compound 19)

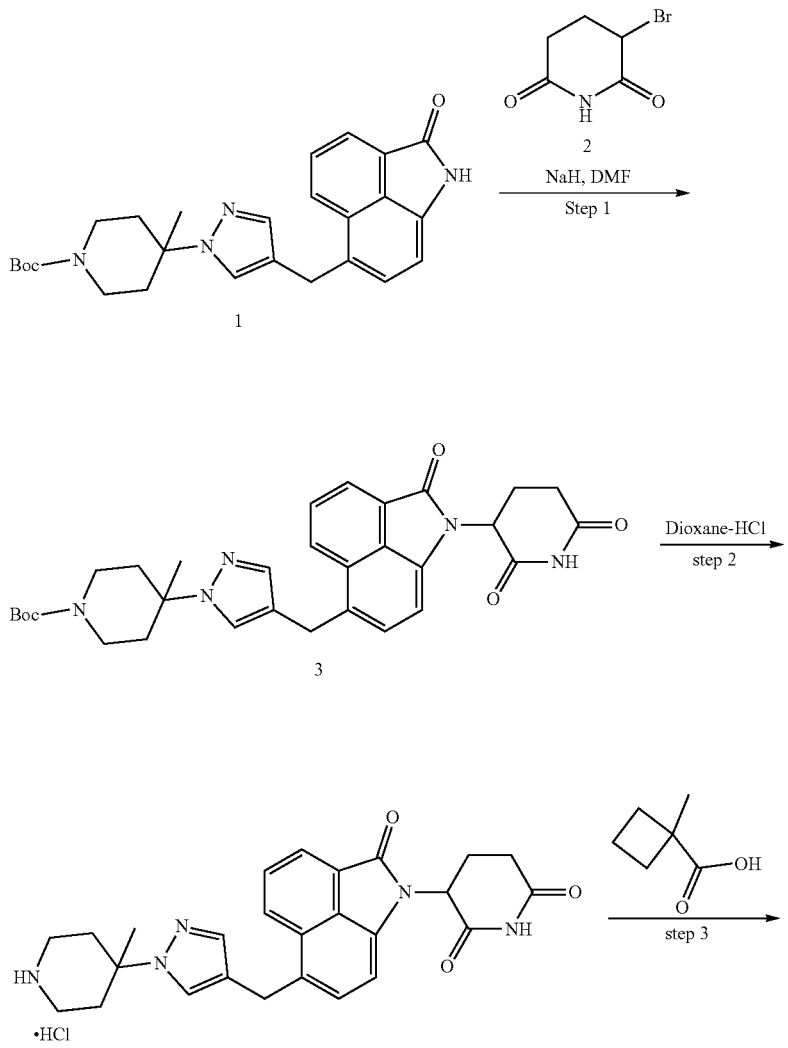

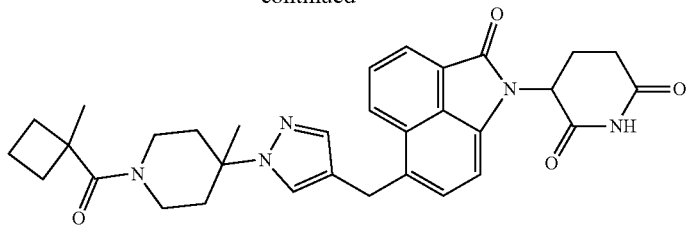

Compound 19

Step 1: Synthesis of tert-Butyl 4-(4-((1-(2,6-Dioxopiperidin-3-yl)-2-oxo-1,2-dihydrobenzo[cd]indol-6-yl)methyl)-1H-pyrazol-1-yl)4-methylpiperidine-1-carboxylate (3): To a stirred solution of 6-bromo-1H-benzo[cd]indol-2-one 2 (1 equiv.) in THF is added butyllithium (2.2 equiv.) at −78° C., and upon addition the temperature is allowed to increase to −40° C. and is stirred for 30 minutes. 1(1 equiv.) in THF is added at −78° C., and the reaction mixture is allowed to warm to room temperature and is stirred for 16 hours. The reaction mixture is quenched with saturated aqueous ammonium chloride solution and diluted with ethyl acetate. The Layers are separated, and the organic layer is washed with water. The organic phase is dried over anhydrous sodium sulfate and evaporated under reduced pressure to obtain the crude compound which is purified by flash chromatography using 0-5% MeOH-DCM to afford desired product 3.

Step 2: Synthesis of 3-(6-((1-(4-Methylpiperidin-4-yl)-1H-pyrazol-4-yl)methyl)-2-oxobenzo[cd]indol-1(2H)-yl)piperidine-2,6-dione (4): To a stirred solution of 3 in dioxane is added hydrochloric acid in dioxane (10 eq) and the reaction is stirred at room temperature for 2 hours. TLC is checked for complete consumption of the starting material. The solvent in the reaction mixture is evaporated under reduced pressure and washed with ether and pentane to afford 4 as solid.

Step 3: Synthesis of 3-(6-((1-(4-Methyl-1-(1-methylcyclobutane-1-carbonyl)piperidin-4-yl)-1H-pyrazol-4-yl)methyl)-2-oxobenzo[cd]indol-1(2H)-yl)piperidine-2,6-dione (Compound 19): To a stirred solution of 4 and 1-methylcyclobutane-1-carboxylic acid 5 (1 equiv) in DMF (2 mL) is added HATU (1.5 equiv.) and DIPEA (3 equiv.), and the reaction mixture is stirred at 25° C. for 16 hr. The reaction mixture is diluted with ethyl acetate and washed with water. The organic layer is separated, dried over sodium sulfate, and concentrated under reduced pressure to give the crude. This crude is purified by silica gel column chromatography to give Compound 19 as a solid.

Example 18. Synthesis of tert-Butyl 4-(4-((1-(2,6-Dioxopiperidin-3-yl)-2-oxo-1,2-dihydrobenzo[cd]indol-6-yl)(hydroxy)methyl)-1H-pyrazol-1-yl)-4-methylpiperidine-1-carboxylate (Compound 20)

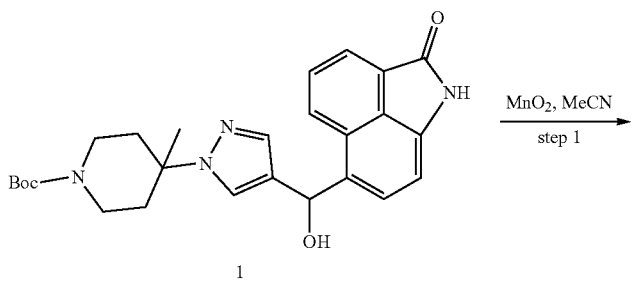

1

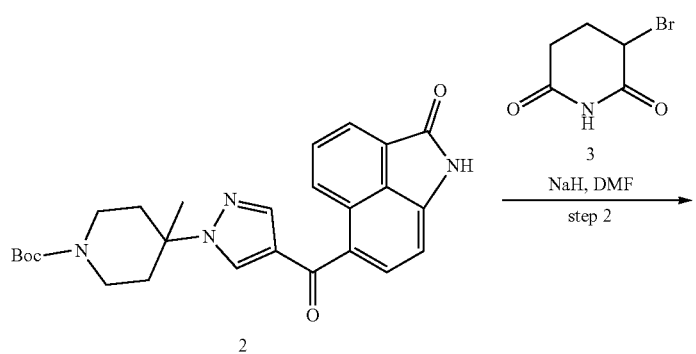

2

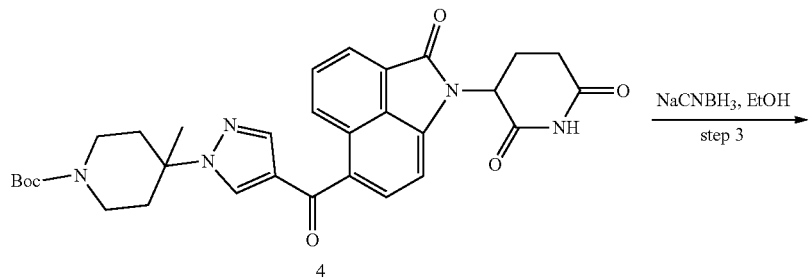

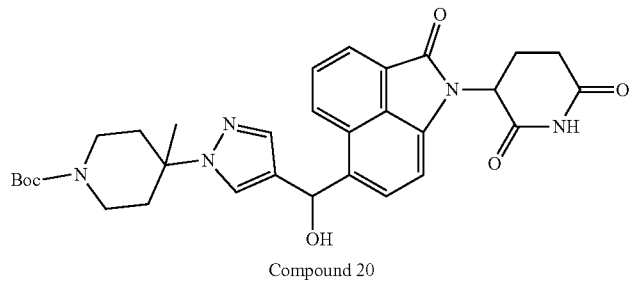

Compound 20

Step 1: Synthesis of tert-Butyl 4-Methyl-4-(4-(2-oxo-1,2-dihydrobenzo[cd]indole-6-carbonyl)-1H-pyrazol-1-yl)piperidine-1-carboxylate (2): To a stirred solution of 1 in DCM is added manganese dioxide (10 equiv.) at room temperature, and the reaction is stirred overnight. After completion, the reaction mixture is filtered, and the filtrate part is evaporated under reduced pressure. The crude material is then purified by column chromatography to afford 2.

Step 2: Synthesis of tert-Butyl 4-(4-(1-(2,6-Dioxopiperidin-3-yl)-2-oxo-1,2-dihydrobenzo[cd]indole-6-carbonyl)-1H-pyrazol-1-yl)4-methylpiperidine-1-carboxylate (4): To a stirred solution of compound 2 in THF is added sodium hydride (60% dispersion in mineral oil, 1 equiv.), and the reaction mixture is refluxed at 60° C. for 30 minutes. A solution of (3-bromopiperidine-2,6-dione) 3 (0.5 equiv.) in THF is also heated at 60° C. After 30 minutes, the first suspension is added to the second solution with heating, and the heating is continued for 3 hours. The reaction mixture is diluted with ethyl acetate and washed with water and brine solution. The organic fraction is then dried over anhydrous sodium sulfate and evaporated under reduced pressure to obtain the crude compound. The crude compound is then purified by flash chromatography to obtain 4.

Step 3: Synthesis of tert-Butyl 4-(4-((1-(2,6-Dioxopiperidin-3-yl)-2-oxo-1,2-dihydrobenzo[cd]indol-6-yl)(hydroxy)methyl)-1H-pyrazol-1-yl)-4-methylpiperidine-1-carboxylate (Compound 20): To a stirred solution of 4 in dry dichloroethane is added sodium cyanoborohydride (2 equiv.) at 0° C. and the reaction mixture is stirred at 0° C. for 2h. The reaction is warmed to rt over the period of 1 h and stirred at rt for 12h. The completion of the reaction is confirmed by TLC. The reaction mixture is quenched with water (25 mL) and extracted with DCM (2×25 mL). The combine organic layer is further washed with brine (1×25 mL), dried over anhydrous $Na_2SO_4$, concentrated to provide the crude product Compound 20.

Example 19. Synthesis of 3-(6-((1-(4-Methyl-1-((1-methylcyclobutyl)methyl)piperidin-4-yl)-1H-pyrazol-4-yl)methyl)-2-oxobenzo[cd]indol-1(2H)-yl)piperidine-2,6-dione (Compound 21)

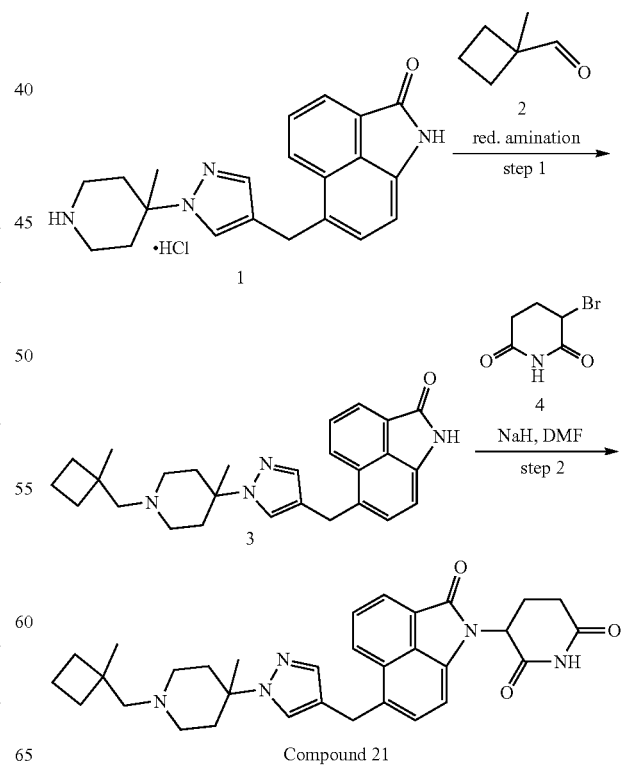

Compound 21

Step 1: Synthesis of 6-((1-(4-Methyl-1-((1-methylcyclobutyl)methyl)piperidin-4-yl)-1H-pyrazol-4-yl)methyl)benzo[cd]indol-2(1H)-one (3): To a stirred solution of 1 in THF in a microwave vial is added 1-methylcyclobutane-1-carbaldehyde 2 (1 equiv.) followed by the addition of dibutyltin dichloride (2 equiv.), and the reaction is stirred for 1 hour at rt. Phenylsilane (1 equiv) is added to the mixture, and the reaction mixture is irradiated in a microwave for 2 hr. The completion of the reaction is confirmed by TLC. The reaction mixture is quenched with water (25 mL) and extracted with DCM (2×25 mL). The combine organic layer is further washed with brine (1×25 mL), dried over anhydrous $Na_2SO_4$, and concentrated to provide the crude product 3.

Step 2: Synthesis of 3-(6-((1-(4-Methyl-1-((1-methylcyclobutyl)methyl)piperidin-4-yl)-1H-pyrazol-4-yl)methyl)-2-oxobenzo[cd]indol-1(2H)-yl)piperidine-2,6-dione (Compound 21): To a stirred solution of 3 in THF is added sodium hydride (60% dispersion in mineral oil, 1 equiv.), and the reaction mixture is refluxed at 60° C. for 30 minutes. A solution of (3-bromopiperidine-2,6-dione) (0.5 equiv.) in THF is also heated at 60° C. After 30 minutes, the first suspension is added to the second solution with heating, and the heating is continued for 3 hours. The reaction mixture is diluted with ethyl acetate and washed with water and brine solution. The organic fraction is then dried over anhydrous sodium sulfate and evaporated under reduced pressure to obtain the crude compound. The crude compound is then purified by flash chromatography to obtain Compound 21.

Example 20: Synthesis of tert-Butyl 4-(4-((1-(2,6-Dioxopiperidin-3-yl)-2-oxo-1,2-dihydropyrrolo[4,3,2-ij]isoquinolin-6-yl)methyl)-1H-pyrazol-1-yl)piperidine-1-carboxylate (Compound 22) and 3-(6-((1-(1-(Cubane-1-carbonyl)piperidin-4-yl)-1H-pyrazol-4-yl)methyl)-2-oxopyrrolo[4,3,2-ij]isoquinolin-1(2H)-yl)piperidine-2,6-dione (Compound 23)

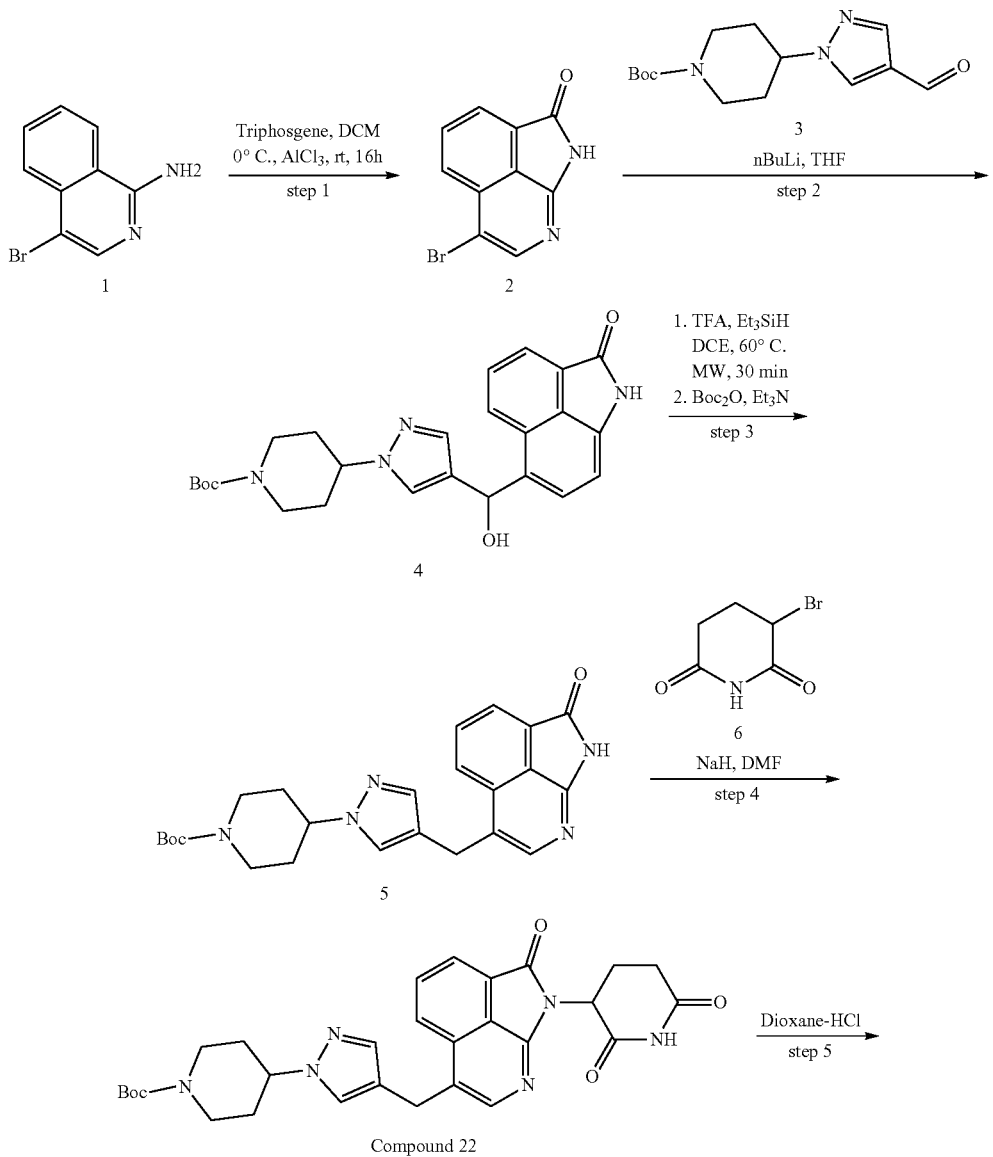

Compound 22

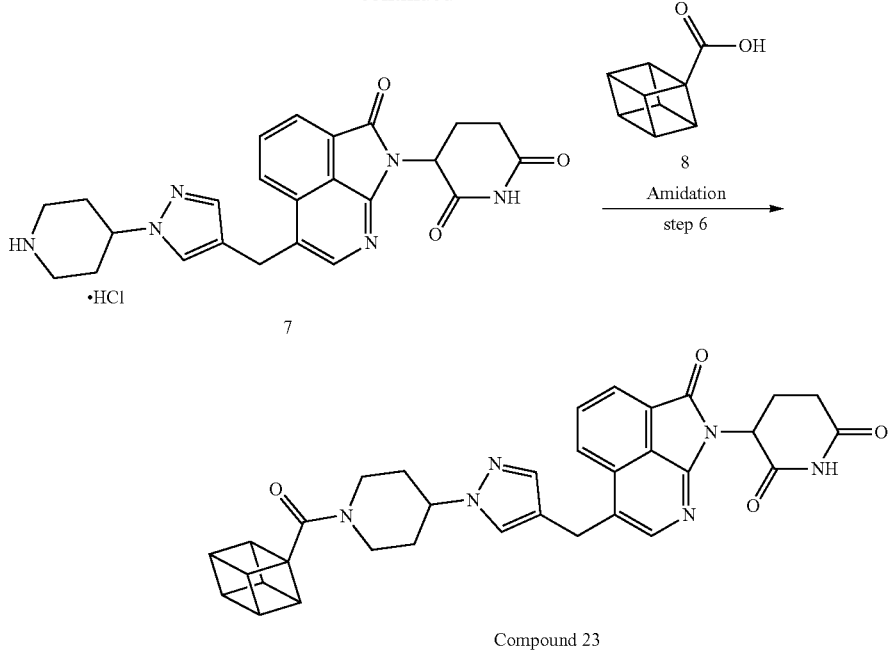

Compound 23

Step 1: Synthesis of 6-Bromopyrrolo[4,3,2-ij]isoquinolin-2(1H)-one (2): To a stirred solution of triphosgene (332.58 mg, 1.12 mmol) in DCM (10 mL) was added pyridine (620.55 mg, 7.85 mmol, 634.51 µL) at −15° C., and the reaction was stirred for 10 minutes. 4-bromoisoquinolin-1-amine 1 (500 mg, 2.24 mmol) was added at −15° C., and the reaction was gradually warmed to rt and stirred for 6h. Aluminum chloride (298.88 mg, 2.24 mmol, 122.49 µL) was added to the reaction mixture, and it was stirred at RT for 16h. It was diluted with water, extracted with ethyl acetate, and washed with water and brine. The organic layer was dried over sodium sulfate and concentrated under reduced pressure. The crude was purified by CombiFlash eluting with 25% ethyl acetate in hexane to afford 155 mg of 2.

Step 2: Synthesis of tert-Butyl 4-(4-(Hydroxy(2-oxo-1,2-dihydropyrrolo[4,3,2-ij]isoquinolin-6-yl)methyl)-1H-pyrazol-1-yl)piperidine-1-carboxylate (4): To a stirred solution of 6-bromopyrrolo[4,3,2-ij]isoquinolin-2(1H)-one 2 (1 equiv.) in THF is added butyllithium (2.2 equiv.) at −78° C. After the addition is complete the temperature is allowed to increase to −40° C., and the reaction mixture is stirred at the same temperature for 30 minutes. 3 (1 equiv.) in THF is added at −78° C., and then the reaction mixture is allowed to warm to room temperature and is stirred for 16 hours. The reaction mixture is quenched with saturated aqueous ammonium chloride solution and diluted with ethyl acetate. The layers are separated, and the organic phase is washed with water. The organic layer is then dried over anhydrous sodium sulfate and evaporated under reduced pressure to obtain the crude compound which is purified by flash chromatography using 0-5% MeOH-DCM to afford desired product 4.

Step 3: Synthesis of tert-Butyl 4-(4-((2-Oxo-1,2-dihydropyrrolo[4,3,2-ij]isoquinolin-6-yl)methyl)-1H-pyrazol-1-yl)piperidine-1-carboxylate (5): To a stirred solution of 4 in DCE is added triethylsilane (2 equiv.) and trifluoroacetic acid (5 equiv.), and the reaction is stirred for 30 minutes under microwave irradiation at 70° C. The solvent in the reaction mixture is evaporated under reduced pressure to obtain the crude which is washed with ether and pentane to afford 5.

Step 4: Synthesis of tert-Butyl 4-(4-((1-(2,6-Dioxopiperidin-3-yl)-2-oxo-1,2-dihydropyrrolo[4,3,2-ij]isoquinolin-6-yl)methyl)-1H-pyrazol-1-yl)piperidine-1-carboxylate (Compound 22): To a stirred solution of compound 5 in THF is added sodium hydride (60% dispersion in mineral oil, 1 equiv.), and the reaction mixture is refluxed at 60° C. for 30 minutes. A solution of (3-bromopiperidine-2,6-dione) 6 (0.5 equiv.) in THF is also heated at 60° C. After 30 minutes the first suspension is added to the second solution with heating, and the heating is continued for 3 hours. The reaction mixture is diluted with ethyl acetate and washed with water and brine solution. The organic fraction is then dried over anhydrous sodium sulfate and evaporated under reduced pressure to obtain the crude compound. The crude compound is then purified by flash chromatography to obtain Compound 22.

Step 5: Synthesis of 3-(2-Oxo-6-((1-(piperidin-4-yl)-1H-pyrazol-4-yl)methyl)pyrrolo[4,3,2-ij]isoquinolin-1(2H)-yl)piperidine-2,6-dione (7):

To a stirred solution of Compound 22 in dioxane is added hydrochloric acid in dioxane (10 equiv.), and the reaction is stirred at room temperature for 2 hours. Upon completion of the reaction as determined by TLC, the solvent in the reaction mixture is evaporated under reduced pressure and washed with ether and pentane to afford 7.

Step 6: Synthesis of 3-(6-((1-(1-(Cubane-1-carbonyl)piperidin-4-yl)-1H-pyrazol-4-yl)methyl)-2-oxopyrrolo[4,3,2-ij]isoquinolin-1(2H)-yl)piperidine-2,6-dione (Compound 23): To a stirred solution of 7 and cubane-1-carboxylic acid 8 (1 equiv.) in DMF (2 mL) is added HATU (1.5 equiv.) and DIPEA (3 equiv.), and the reaction mixture is stirred at 25° C. for 16 hr. When LCMS shows the desired mass, the reaction mixture is diluted with ethyl acetate and washed with water. The organic layer is separated, dried over sodium sulfate and concentrated under reduced pressure to give the crude Compound 23. This crude is purified by prep-TLC (using 100% ethyl acetate) to give Compound 23 as solid.

Example 21. Synthesis of tert-Butyl 4-(4-((1-(2,6-Dioxopiperidin-3-yl)-2-oxo-1,2-dihydropyrrolo[2,3,4-de]isoquinolin-6-yl)methyl)-1H-pyrazol-1-yl)piperidine-1-carboxylate (Compound 24) and 3-(6-((1-(1-(Cubane-1-carbonyl)piperidin-4-yl)-1H-pyrazol-4-yl)methyl)-2-oxopyrrolo[2,3,4-de]isoquinolin-1(2H)-yl)piperidine-2,6-dione (Compound 25)
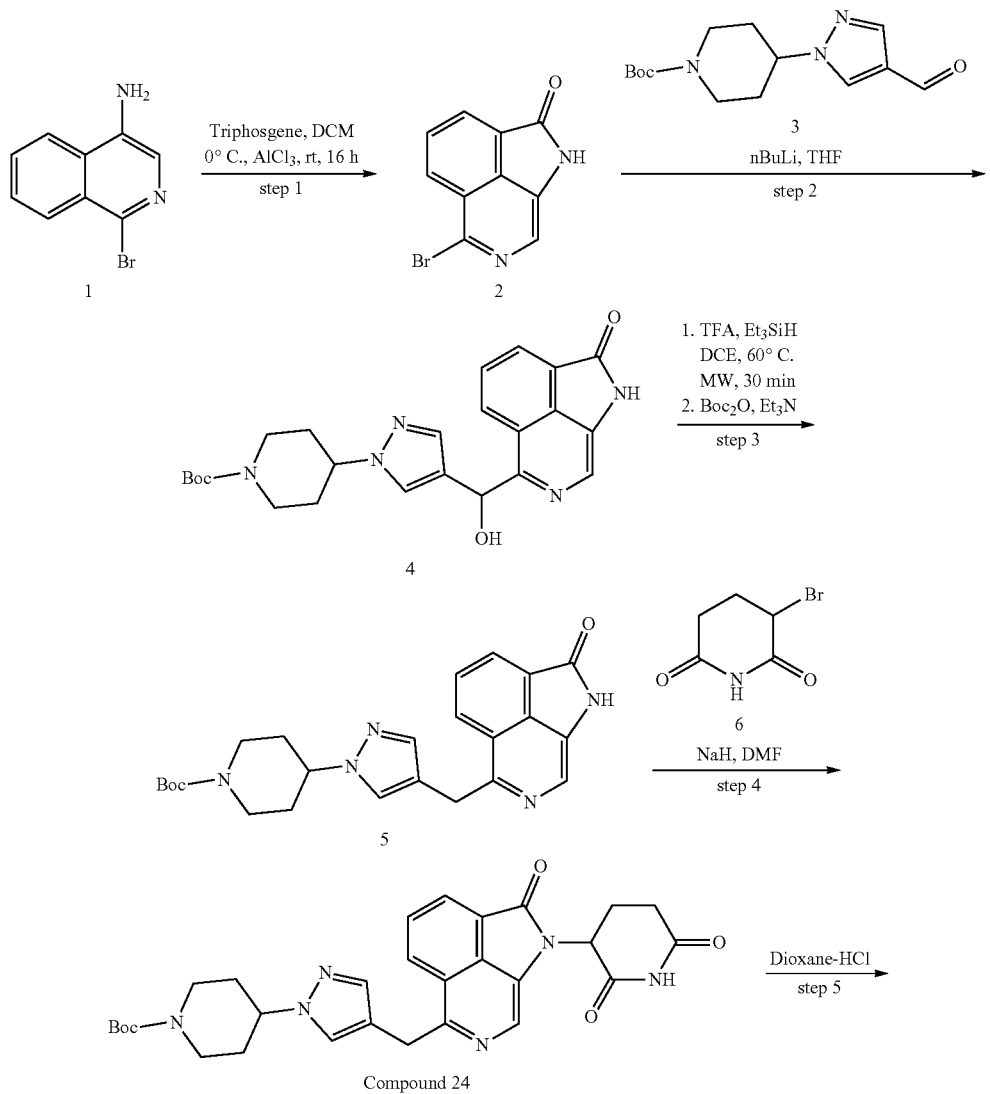
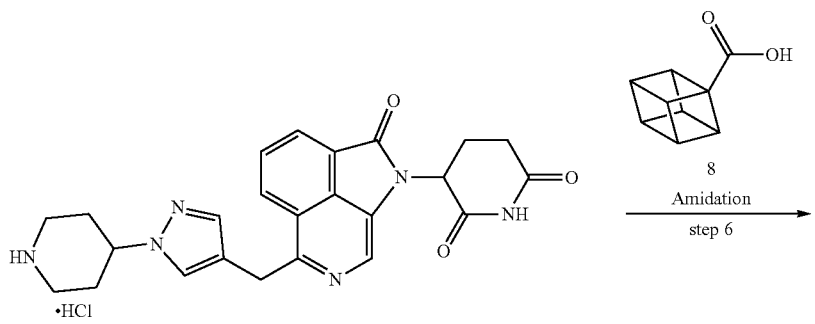

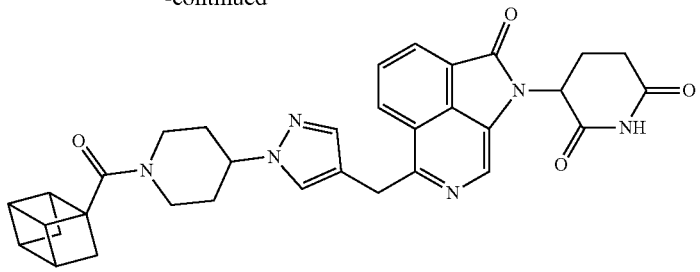

Compound 25

Step 1: Synthesis of 6-Bromopyrrolo[2,3,4-de]isoquinolin-2(1H)-one (2): To a stirred solution of triphosgene (0.5 equiv.) in DCM is added pyridine (3 equiv.) at −15° C., and the reaction is stirred for 10 minutes. 1-bromoisoquinolin-4-amine 1 (1 equiv.) is added at −15° C., and the reaction is gradually warmed to rt and stirred for 6h. Aluminum chloride (1 equiv) is added to the reaction mixture and the reaction is stirred at rt for 16h. The reaction is diluted with water, extracted with ethyl acetate, and washed with water and brine. The reaction is then dried over sodium sulfate and concentrated under reduced pressure. The crude is purified by CombiFlash eluting at 25% ethyl acetate in hexane to afford 2.

Step 2: Synthesis of tert-Butyl 4-(4-(Hydroxy(2-oxo-1,2-dihydropyrrolo[2,3,4-de]isoquinolin-6-yl)methyl)-1H-pyrazol-1-yl)piperidine-1-carboxylate (4): To a stirred solution of 6-bromopyrrolo[2,3,4-de]isoquinolin-2(1H)-one 2 (1 equiv.) in THF is added butyllithium (2.2 equiv.) at −78° C. Upon addition the temperature is allowed to increase to −40° C. and the reaction mixture is stirred at the same temperature for 30 minutes. 3 (1 equiv.) in THF is added at −78° C. and then the reaction mixture is allowed to warm to room temperature and is stirred for 16 hours. The reaction mixture is quenched with saturated aqueous ammonium chloride solution and diluted with ethyl acetate. The layers are separated, and the organic layer is washed with water. The combined organic layers are then dried over anhydrous sodium sulfate and evaporated under reduced pressure to obtain the crude compound which is purified by flash chromatography using 0-5% MeOH-DCM to afford desired product 4.

Step 3: Synthesis of tert-Butyl 4-(4-((2-Oxo-1,2-dihydropyrrolo[2,3,4-de]isoquinolin-6-yl)methyl)-1H-pyrazol-1-yl)piperidine-1-carboxylate (5): To a stirred solution of 4 in DCE is added triethylsilane (2 equiv.) and trifluoroacetic acid (5 equiv.), and the reaction is stirred for 30 minutes under microwave irradiation at 70° C. The solvent in the reaction mixture is evaporated under reduced pressure to obtain the crude which is washed with ether and pentane to afford 5.

Step 4: Synthesis of tert-Butyl 4-(4-((1-(2,6-Dioxopiperidin-3-yl)-2-oxo-1,2-dihydropyrrolo[2,3,4-de]isoquinolin-6-yl)methyl)-1H-pyrazol-1-yl)piperidine-1-carboxylate (Compound 24): To a stirred solution of compound 5 in DMF is added sodium hydride (60% dispersion in mineral oil, 1 equiv.), and the reaction mixture is refluxed at 60° C. for 30 minutes. A solution of 3-bromopiperidine-2,6-dione 6 (0.5 equiv.) in DMF is also heated at 60° C. After 30 minutes the first suspension is added to the second solution with heating, and the heating is continued for 3 hours. The reaction mixture is diluted with ethyl acetate and washed with water and brine solution. The organic fraction is then dried over anhydrous sodium sulfate and evaporated under reduced pressure to provide the crude compound. The crude compound is then purified by flash chromatography to provide Compound 24.

Step 5: Synthesis of 3-(2-Oxo-6-((1-(piperidin-4-yl)-1H-pyrazol-4-yl)methyl)pyrrolo[2,3,4-de]isoquinolin-1(2H)-yl)piperidine-2,6-dione (7): To a stirred solution of Compound 24 in dioxane is added hydrochloric acid in dioxane (10 equiv.), and the reaction is stirred at room temperature for 2 hours. Upon consumption of the SM as determined by TLC, the solvent in the reaction mixture is evaporated under reduced pressure and washed with ether and pentane to afford 7 as solid.

Step 6: Synthesis of 3-(6-((1-(1-(Cubane-1-carbonyl)piperidin-4-yl)-1H-pyrazol-4-yl)methyl)-2-oxopyrrolo[2,3,4-de]isoquinolin-1(2H)-yl)piperidine-2,6-dione (Compound 25): To a stirred solution of 7 and cubane-1-carboxylic acid 8 (1 equiv.) in DMF (2 mL) is added HATU (1.5 equiv.) and DIPEA (3 equiv.), and the reaction mixture is stirred at 25° C. for 16 hr. When LCMS shows desired mass, the reaction mixture is diluted with ethyl acetate and washed with water. The organic layer is separated, dried over sodium sulfate and concentrated under reduced pressure to give the crude. This crude is purified by prep-TLC (using 100% ethyl acetate) to give Compound 25 as solid.

Example 22. Synthesis of 3-(6-((4-(1-(1-Methylcyclobutane-1-carbonyl)piperidin-4-yl)-1H-pyrazol-1-yl)methyl)-2-oxobenzo[cd]indol-1(2H)-yl)piperidine-2,6-dione (Compound 26)

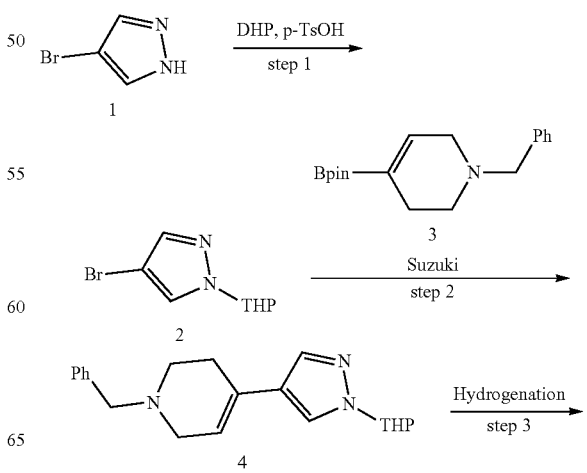

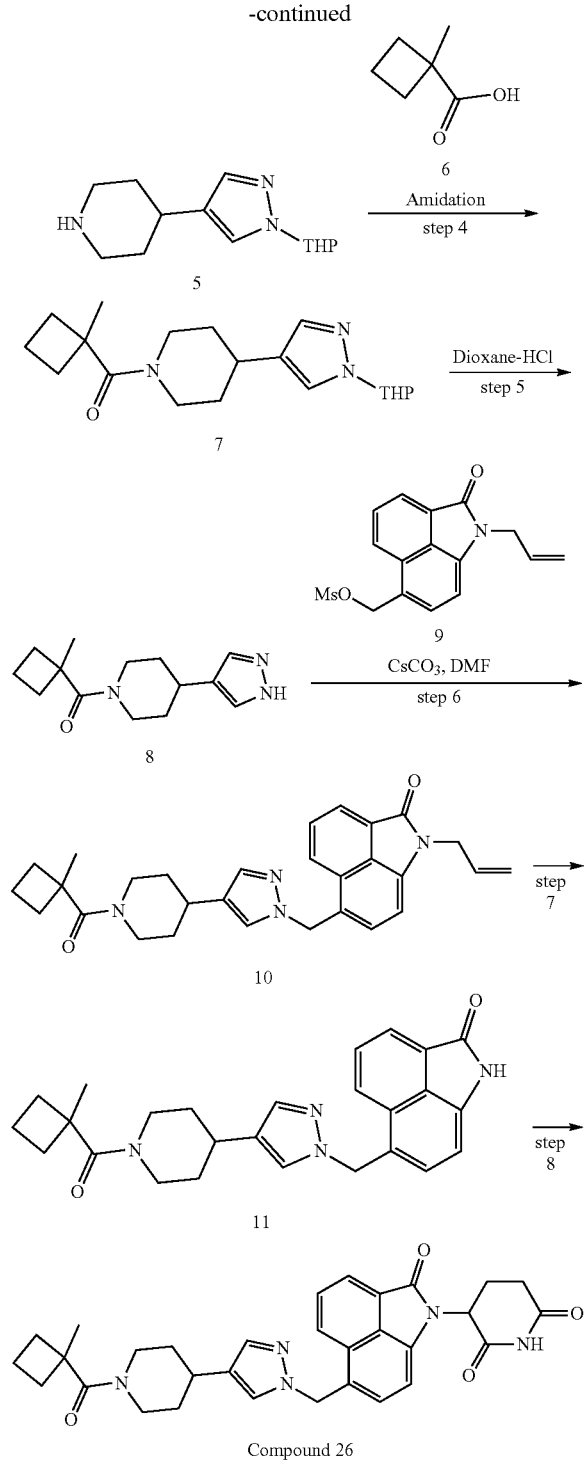

was purified by CombiFlash to get the pure compound 4-bromo-1-tetrahydropyran-2-yl-pyrazole 2 (3.44 g, 14.89 mmol, 72.93% yield).

Step 2: Synthesis of 1-Benzyl-4-(1-(tetrahydro-2H-pyran-2-yl)-1H-pyrazol-4-yl)-1,2,3,6-tetrahydropyridine (4): To a stirred solution of 4-bromo-1-tetrahydropyran-2-yl-pyrazole 2 (700 mg, 3.03 mmol) in water (4.0 mL) and DMF (16.0 mL) was added sodium carbonate (642.11 mg, 6.06 mmol, 253.80 μL) and 1-benzyl-4-(4,4,5,5-tetramethyl-1,3,2-dioxaborolan-2-yl)-3,6-dihydro-2H-pyridine 3 (1.09 g, 3.63 mmol), and the reaction mixture was degassed with argon for 10 mins. Then [1,1'-bis(diphenylphosphino)ferrocene] palladium(II) chloride dichloromethane (247.37 mg, 302.91 μmol) was added, and the reaction mixture was stirred at 100° C. overnight in a sealed tube. Upon complete consumption of SM as determined by TLC, the reaction mixture was diluted with ethyl acetate and washed with water and brine solution. The organic layer was dried over $Na_2SO_4$ and filtered. The reaction mixture was evaporated under vacuum, and the crude was purified by CombiFlash to get the pure compound 1-benzyl-4-(1-tetrahydropyran-2-ylpyrazol-4-yl)-3,6-dihydro-2H-pyridine 4 (230 mg, 711.13 μmol, 23.48% yield).

Step 3: Synthesis of 4-(1-(Tetrahydro-2H-pyran-2-yl)-1H-pyrazol-4-yl)piperidine (5): A stirred solution of 4 in ethanol is degassed with argon for 10 minutes. 10% Pd/C (30 Wt %) is added to the reaction mixture, and it is subjected to hydrogenation under a hydrogen balloon for 16 hours. The reaction mixture is filtered through celite and concentrated under reduced pressure to obtain 5 as desired product.

Step 4: Synthesis of (1-Methylcyclobutyl)(4-(1-(tetrahydro-2H-pyran-2-yl)-1H-pyrazol-4-yl)piperidin-1-yl)methanone (7): To a stirred solution of 1-methylcyclobutanecarboxylic acid 6 (194.26 mg, 1.70 mmol) in DMF (2.0 mL) was added N-ethyl-N-isopropyl-propan-2-amine 5 (439.91 mg, 3.40 mmol, 592.87 μL), and the reaction mixture was stirred at rt for 5 mins. HATU (647.12 mg, 1.70 mmol) was added, and the reaction mixture was stirred for another 5 mins. After that 4-(1-tetrahydropyran-2-ylpyrazol-4-yl)piperidine 5 (267 mg, 1.13 mmol) in DMF (2.0 mL) was added to the reaction mixture drop-wise, the reaction mixture was stirred at rt for overnight. Upon consumption of the SM as determined by TLC, the reaction mix was diluted with ethyl acetate and washed with cold $NaHCO_3$ solution. The reaction mix was dried over $Na_2SO_4$, filtered, and concentrated under reduce pressure to provide crude product which was purified by column chromatography to provide 7.

Step 5: Synthesis of (4-(1H-Pyrazol-4-yl)piperidin-1-yl)(1-methylcyclobutyl)methanone (8): To a stirred solution of (1-methylcyclobutyl)(4-(1-(tetrahydro-2H-pyran-2-yl)-1H-pyrazol-4-yl)piperidin-1-yl)methanone 7 in dioxane is added 4M HCl in dioxane (2 equiv.), and the reaction is stirred at RT for 1 h. The solution is concentrated under reduced pressure to afford (4-(1H-pyrazol-4-yl)piperidin-1-yl)(l-methylcyclobutyl)methanone 8 as solid.

Step 6: 1-Allyl-6-((4-(1-(1-methylcyclobutane-1-carbonyl)piperidin-4-yl)-1H-pyrazol-1-yl)methyl)benzo[cd]indol-2(1H)-one (10): A magnetically stirred solution of 8 (1.2 equiv.) and 9 (1 equiv.) in DMF is treated with $Cs_2CO_3$ (2.5 equiv.) and stirred at RT for 4 h. The reaction is monitored over a period of 24 h (temp 25-50° C.) via TLC and LC-MS. After consumption of SM, the reaction mixture is washed with water. The phases are separated, and the aqueous layer is further extracted with EtOAc. The organic layers are combined, dried over $MgSO_4$, and filtered. The solvents are removed under reduced pressure to give a residue, which is purified by column chromatography (eluted with 80% EA/Hex) to yield product 10 as a white solid.

Step 7: Synthesis of 6-((4-(1-(1-Methylcyclobutane-1-carbonyl)piperidin-4-yl)-1H-pyrazol-1-yl)methyl)benzo[cd]indol-2(1H)-one (11): A solution of 10 (1 equiv.) in dry DCM is added to a mixture of Pd(PPh$_3$)$_4$(10%) and 1,3 dimethyl barbituric acid (3 equiv.) under argon. The reaction mixture is stirred for 5 h at 35° C., quenched with saturated aqueous NaHCO$_3$, and extracted with CH$_2$Cl$_2$. The combined organic layers are dried over MgSO$_4$, filtered, and concentrated. The crude is purified by column chromatography in 100-200 Silica in 3-4% MeOH in DCM to afford the desired compound 11 as solid.

Step 8: Synthesis of 3-(6-((4-(1-(1-Methylcyclobutane-1-carbonyl)piperidin-4-yl)-1H-pyrazol-1-yl)methyl)-2-oxobenzo[cd]indol-1(2H)-yl)piperidine-2,6-dione (Compound 26): To the stirred solution of compound 11 in DMF is added sodium hydride (60% dispersion in mineral oil, 1 equiv.), and the reaction mixture is refluxed at 60° C. for 30 minutes. A solution of 3-bromopiperidine-2,6-dione (0.5 equiv.) in DMF is also heated at 60° C. After 30 minutes the first suspension is added to the second solution with heating, and the heating is continued for 3 hours. The reaction mixture is diluted with ethyl acetate and washed with water and brine solution. The organic fraction is then dried over anhydrous sodium sulfate and evaporated under reduced pressure to obtain the crude compound. The crude compound is then purified by flash chromatography to obtain Compound 26.

Example 23. Synthesis of 4-(4-(4-((1-(2,6-Dioxopiperidin-3-yl)-2-oxo-1,2-dihydrobenzo[cd]indol-6-yl)methyl)benzyl)piperazin-1-yl)-3-fluorobenzonitrile (Compound 27)

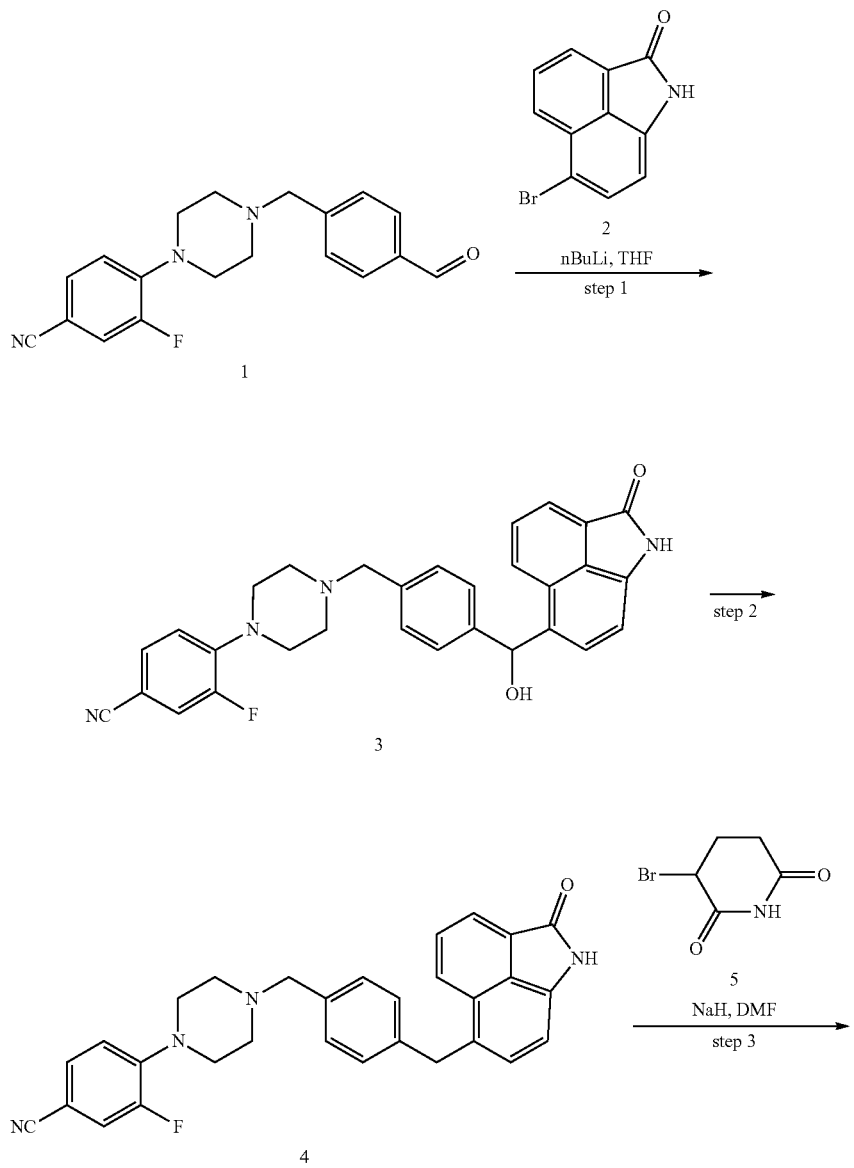

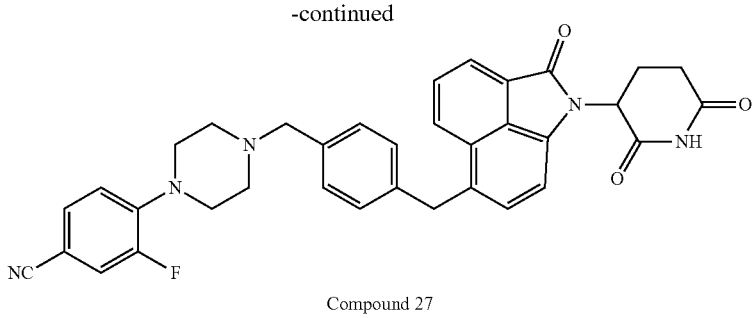

Compound 27

Step 1: Synthesis of 3-Fluoro-4-(4-(4-(hydroxy(2-oxo-1,2-dihydrobenzo[cd]indol-6-yl)methyl)benzyl)piperazin-1-yl)benzonitrile (3): To a stirred solution of 6-bromo-1H-benzo[cd]indol-2-one 2 (1 equiv.) in THF is added butyllithium (2.2 equiv.) at −78° C. Upon addition, the temperature is allowed to increase to −40° C. and the reaction mixture is stirred at the same temperature for 30 minutes. 3-fluoro-4-(4-(4-formylbenzyl)piperazin-1-yl)benzonitrile 1 (1 equiv.) in THF at −78° C., and then the reaction mixture is allowed to warm to room temperature and is stirred for 16 hours. The reaction mixture is quenched with saturated aqueous ammonium chloride solution and diluted with ethyl acetate. The layers are separated, and the organic layer is washed with water. The organics are then dried over anhydrous sodium sulfate and evaporated under reduced pressure to obtain the crude compound which is purified by flash chromatography using 0-5% MeOH-DCM to afford desired product 3.

Step 2: Synthesis of 3-Fluoro-4-(4-(4-((2-oxo-1,2-dihydrobenzo[cd]indol-6-yl)methyl)benzyl)piperazin-1-yl)benzonitrile (4): To the stirred solution of 3 in DCE is added triethylsilane (3 equiv.) and trifluoroacetic acid (10 equiv.), and the reaction is stirred for 30 minutes under microwave irradiation at 70° C. The solvent in the reaction mixture is evaporated under reduced pressure to obtain the crude which is washed with ether and pentane to afford 4 as brown gum in the form of crude.

Step 3: Synthesis of 4-(4-(4-((1-(2,6-Dioxopiperidin-3-yl)-2-oxo-1,2-dihydrobenzo[cd]indol-6-yl)methyl)benzyl)piperazin-1-yl)-3-fluorobenzonitrile (Compound 27): To a stirred solution of compound 4 in THF is added sodium hydride (60% dispersion in mineral oil, 1 equiv.), and the reaction mixture is refluxed at 60° C. for 30 minutes. A solution of (3-bromopiperidine-2,6-dione) 5 (0.5 equiv.) in THF is also heated at 60° C. After 30 minutes the first suspension is added to the second solution with heating, and the heating is continued for 3 hours. The reaction mixture is diluted with ethyl acetate and washed with water and brine solution. The organic fraction is then dried over anhydrous sodium sulfate and evaporated under reduced pressure to obtain the crude compound. The crude compound is then purified by flash chromatography to obtain Compound 27.

Example 24. Synthesis of 3-(6-((1-(1-(Cubane-1-carbonyl)piperidin-4-yl)-1H-pyrazol-4-yl)amino)-2-oxopyrrolo[2,3,4-de]isoquinolin-1(2H)-yl)piperidine-2,6-dione (Compound 28)

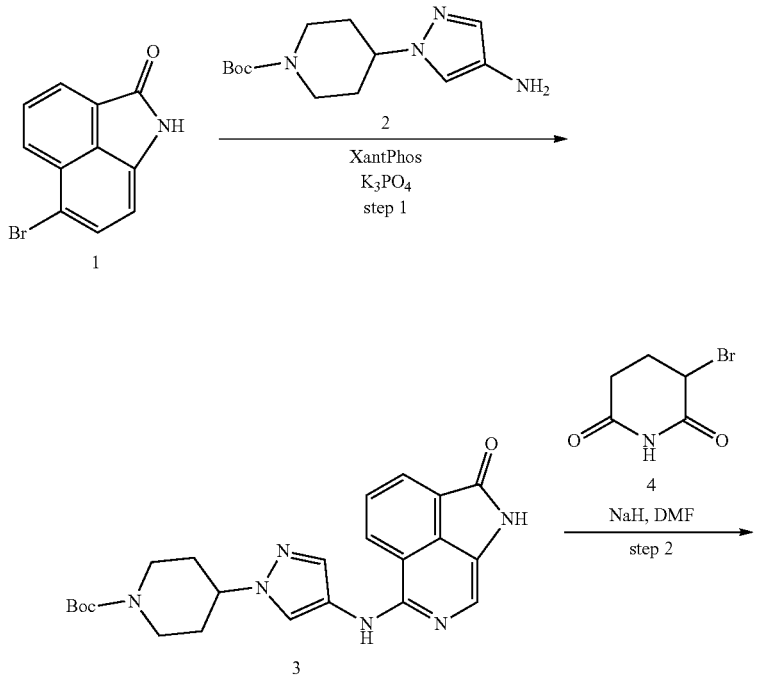

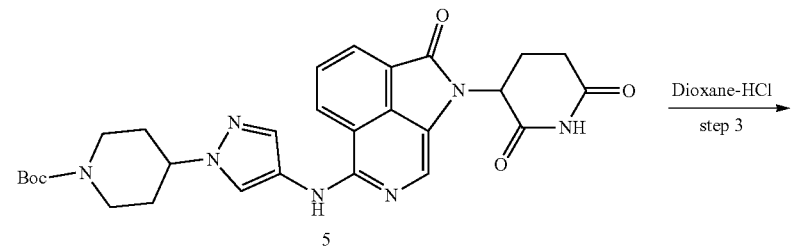

5

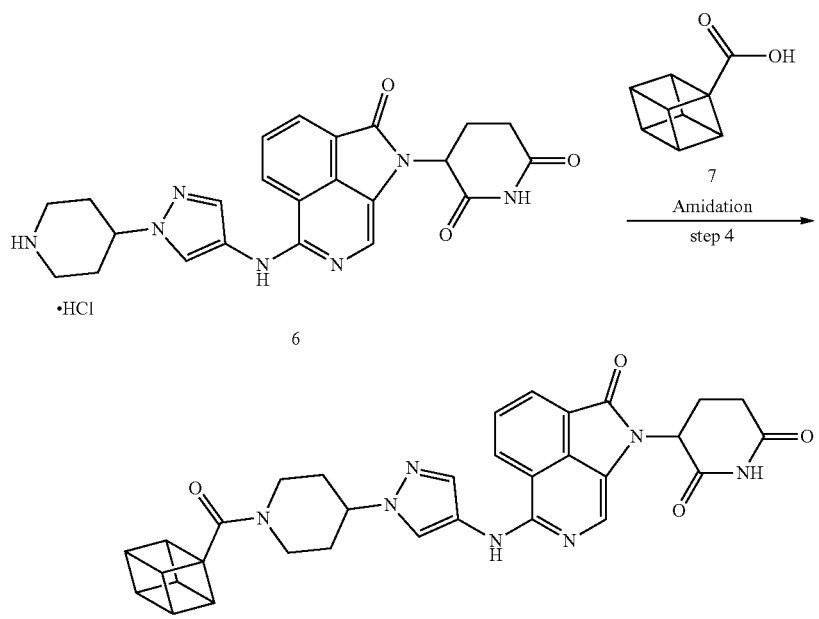

Compound 28

Step 1: Synthesis of tert-Butyl 4-(4-((2-Oxo-1,2-dihydro-pyrrolo[2,3,4-de]isoquinolin-6-yl)amino)-1H-pyrazol-1-yl)piperidine-1-carboxylate (3): To a stirred solution of tert-butyl 4-(4-aminopyrazol-1-yl)piperidine-1-carboxylate 2 (1 equiv.) and 6-bromopyrrolo[2,3,4-de]isoquinolin-2(1H)-one 1 (1 equiv.) intoluene in a sealed tube is added cesium carbonate (2.5 equiv.), and the reaction mixture is degassed for 5 min under argon atmosphere. Then pd$_2$(dba)3 (10%) and Xantphos (20%) are added, and the solution is again purged for 2 min under argon atmosphere. Thereafter, the reaction mixture is heated to 90° C. for 16 hr. After consumption of SM is noted, the reaction mixture is filtered through a celite bed and concentrated in vacuo. Purification by CombiFlash column chromatography (eluted by 15% ethyl acetate in n-hexane) gives the title compound 3.

Step 2: tert-Butyl 4-(4-((1-(2,6-Dioxopiperidin-3-yl)-2-oxo-1,2-dihydropyrrolo[2,3,4-de]isoquinolin-6-yl)amino)-1H-pyrazol-1-yl)piperidine-1-carboxylate (5): To a stirred solution of compound 3 in DMF is added Sodium hydride (60% dispersion in mineral oil, 1 equiv.), and the reaction mixture is refluxed at 60° C. for 30 minutes. A solution of (3-bromopiperidine-2,6-dione) 4 (0.5 equiv.) in DMF is also heated at 60° C. After 30 minutes the first suspension is added to the second solution with heating, and the heating is continued for 3 hours. The reaction mixture is diluted with ethyl acetate and washed with water and brine solution. The organic fraction is then dried over anhydrous sodium sulfate and evaporated under reduced pressure to obtain the crude compound. The crude compound is then purified by flash chromatography to obtain 5.

Step 3: Synthesis of 3-(2-Oxo-6-((1-(piperidin-4-yl)-1H-pyrazol-4-yl)amino)pyrrolo[2,3,4-de]isoquinolin-1(2H)-yl)piperidine-2,6-dione (6): To the stirred solution of 5 in dioxane is added hydrochloric acid in dioxane (10 equiv.), and the reaction mixture is stirred at room temperature for 2 hours. TLC is checked until complete consumption of the starting material is noted. At that point, the solvent in the reaction mixture is evaporated under reduced pressure and washed with ether and pentane to afford 6.

Step 4: Synthesis of 3-(6-((1-(1-(Cubane-1-carbonyl)piperidin-4-yl)-1H-pyrazol-4-yl)amino)-2-oxopyrrolo[2,3,4-de]isoquinolin-1(2H)-yl)piperidine-2,6-dione (Compound 28): To a stirred solution of 6 and cubane-1-carboxylic acid 7 (1 equiv.) in DMF (2 mL) is added HATU (1.5 equiv.) and DIPEA (3 equiv.), and the reaction mixture is stirred at 25° C. for 16 hr. According to LCMS, when desired mass is observed, the reaction mixture is diluted with ethyl acetate and washed with water. The organic layer is separated, dried over sodium sulfate and concentrated under reduced pressure to give the crude. This crude is purified by prep-TLC (using 100% ethyl acetate) to give Compound 28 as a solid.

Example 25. Synthesis of 3-(6-Hydroxy-2-oxobenzo[cd]indol-1(2H)-yl)piperidine-2,6-dione (Compound 29), tert-Butyl 4-(4-((1-(2,6-Dioxopiperidin-3-yl)-2-oxo-1,2-dihydrobenzo[cd]indol-6-yl)oxy)-1H-pyrazol-1-yl)piperidine-1-carboxylate (Compound 30), and 3-(6-((1-(1-((2r,3r,5r,6r,7r,8r)-Cubane-1-carbonyl)piperidin-4-yl)-1H-pyrazol-4-yl)oxy)-2-oxobenzo[cd]indol-1(2H)-yl)piperidine-2,6-dione (Compound 31)
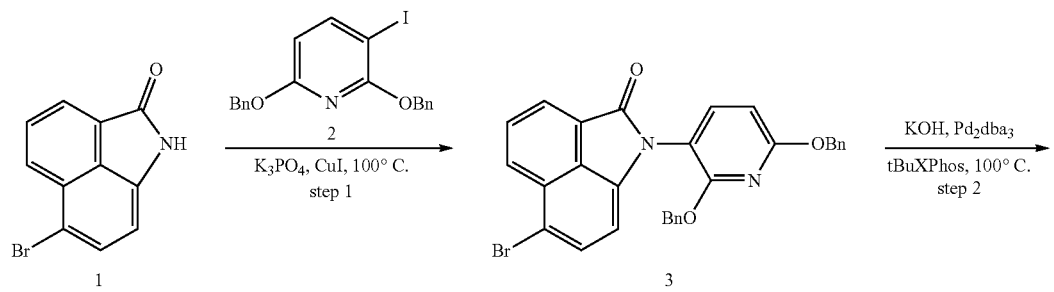
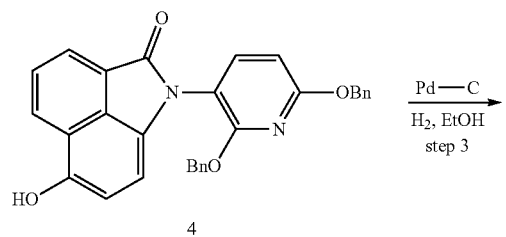
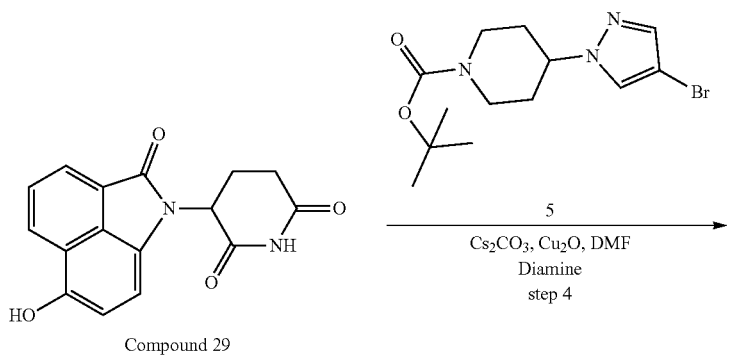
Compound 29
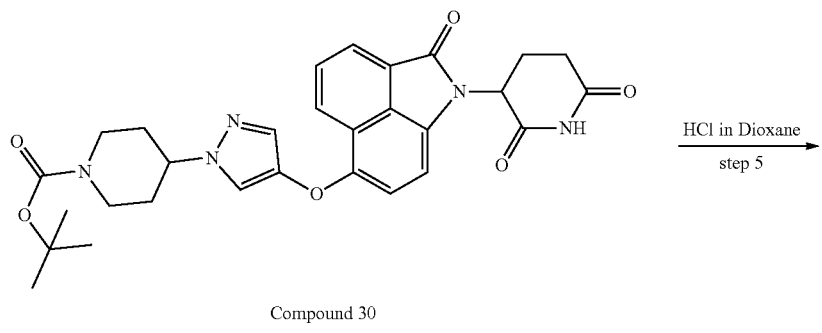
Compound 30

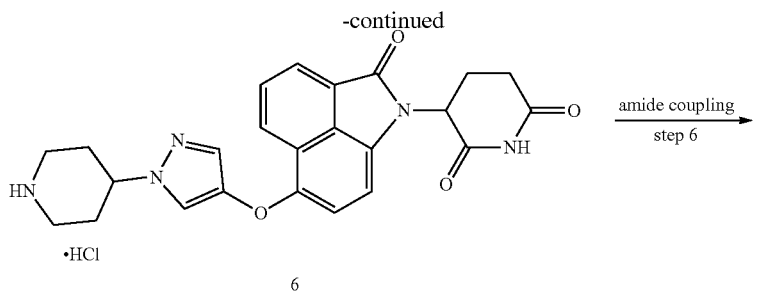

Compound 31

Step 1: Synthesis of 1-(2,6-Bis(benzyloxy)pyridin-3-yl)-6-bromobenzo[cd]indol-2(1H)-one (3): To a stirred solution of 2,6-dibenzyloxy-3-iodo-pyridine 2 (1 equiv.) and 6-bromobenzo[cd]indol-2(1H)-one 1 (1.2 equiv.) in dioxane is added tribasic potassium phosphate (1 equiv.), and the reaction mixture is degassed for 10 mins. Subsequently, (1R,2R)-(−)-1,2-diaminocyclohexane (0.1 equiv.) is added followed by copper (I) iodide (2%). and again the solution is degassed for 5 mins. The reaction mixture is then stirred at 100° C. for 16 hr. The reaction mixture is then allowed to come to RT and is extracted with ethyl acetate. The organic phase is washed with brine and dried over anhyd. $Na_2SO_4$. The solvent is evaporated and the residue is purified by column chromatography (eluted with 40% Ethylacetate in Hexane) on silica gel to furnish the desired product 1-(2,6-bis(benzyloxy)pyridin-3-yl)-6-bromobenzo[cd]indol-2(1H)-one 3 as solid.

Step 2: Synthesis of 1-(2,6-Bis(benzyloxy)pyridin-3-yl)-6-hydroxybenzo[cd]indol-2(1H)-one (4): To the stirred solution of 1-(2,6-bis(benzyloxy)pyridin-3-yl)-6-bromobenzo[cd]indol-2(1H)-one 3 in dioxane (8 mL) and water (2 mL) is added potassium Hydroxide (2 equiv.), and the resulting solution is degassed with $N_2$ for 15 minutes followed by the addition of (1E,4E)-1,5-diphenylpenta-1,4-dien-3-one; palladium (5%) and Tert-Butyl Xphos-2-Di-tert-butylphosphino-2',4',6 (15%). The reaction mixture is further heated at 100° C. in a sealed tube for 12 hr. After formation of desired pdt as evidence from LCMS, the reaction mixture is filtered through a celite bed and washed with ethyl acetate. The combined organic layers are separated and evaporated. The crude residue is purified by column chromatography to afford 1-(2,6-bis(benzyloxy)pyridin-3-yl)-6-hydroxybenzo[cd]indol-2(1H)-one 4 as solid.

Step 3: Synthesis of 3-(6-Hydroxy-2-oxobenzo[cd]indol-1(2H)-yl)piperidine-2,6-dione (Compound 29): A solution of 1-(2,6-bis(benzyloxy)pyridin-3-yl)-6-hydroxybenzo[cd]indol-2(1H)-one 4 in ethyl acetate/Ethanol (1/1) was hydrogenated using Palladium, 10% on carbon, Type 487, (10%) under balloon pressure for 12 hr at rt. After completion of reaction, the reaction mixture is filtered through a celite bed and washed with ethyl acetate several times. The filtrate is collected and concentrated under reduced pressure to afford 3-(6-hydroxy-2-oxobenzo[cd]indol-1(2H)-yl)piperidine-2,6-dione (Compound 29) as crude product.

Step 4: Synthesis of tert-Butyl 4-(4-((1-(2,6-Dioxopiperidin-3-yl)-2-oxo-1,2-dihydrobenzo[cd]indol-6-yl)oxy)-1H-pyrazol-1-yl)piperidine-1-carboxylate (Compound 30): After standard cycles of evacuation and back-filling with dry and pure nitrogen, an oven-dried Schlenk tube equipped with a magnetic stirring bar is charged with $Cu_2O$ (0.1 mmol), rel-(1R,2R)—$N^1,N^2$-Bis(2-pyridinylmethylene)-1,2-cyclohexanediamine (0.4 mmol), $Cs_2CO_3$ (4.0 mmol), activated and powdered 3 A molecular sieves (600 mg), 3-(6-hydroxy-2-oxobenzo[cd]indol-1(2H)-yl)piperidine-2,6-dione Compound 29 (2.0 mmol), and tert-butyl 4-(4-bromo-1H-pyrazol-1-yl)piperidine-1-carboxylate 5 (3.0 mmol), if a solid. The tube is evacuated, back-filled with nitrogen and capped with a rubber septum. If liquids, the phenol and the aryl halide are added under a stream of nitrogen by syringe at room temperature, followed by anhydrous and degassed acetonitrile or DMF (1.2 mL). The septum is removed, the tube is sealed under a positive pressure of nitrogen and stirred in an oil bath (preheated to 82° C. or 110° C.) for the required time period. The reaction mixture is allowed to cool to room temperature, diluted with dichloromethane and filtered through a plug of Celite®, the filter cake being further washed with dichloromethane (~20 mL). The filtrate is concentrated in vacuo to yield the crude product that is purified by silica gel chromatography to provide Compound 30.

Step 5: Synthesis of 3-(2-Oxo-6-((1-(piperidin-4-yl)-1H-pyrazol-4-yl)oxy)benzo[cd]indol-1(2H)-yl)piperidine-2,6-dione (6): To a stirred solution of Compound 30 in dioxane is added hydrochloric acid in dioxane (10 equiv.), and the reaction is stirred at room temperature for 2 hours. TLC is checked for complete consumption of the starting material. The solvent in the reaction mixture is evaporated under reduced pressure and washed with ether and pentane to afford 6 as a solid.

Step 6: Synthesis of 3-(6-((1-(1-((2r,3r,5r,6r,7r,8r)-Cubane-1-carbonyl)piperidin-4-yl)-1H-pyrazol-4-yl)oxy)-2-oxobenzo[cd]indol-1(2H)-yl)piperidine-2,6-dione (Compound 31): To a stirred solution of 6 and cubane-1-carboxylic acid (1 equiv.) in DMF (2 mL) is added HATU (1.5 equiv.) and DIPEA (3 equiv.), and the reaction mixture is stirred at 25° C. for 16 hr. According to LCMS, when the desired mass is observed, the reaction mixture is diluted with ethyl acetate and washed with water. The organic layer is separated, dried over sodium sulfate and concentrated under reduced pressure to give the crude. This crude is purified by silica gel chromatography to give Compound 31 as a solid.

Example 26. Synthesis of tert-Butyl 4-(4-((1-(2,6-Dioxopiperidin-3-yl)-2-oxo-1,2-dihydropyrrolo[2,3,4-de]isoquinolin-6-yl)oxy)-1H-pyrazol-1-yl)piperidine-1-carboxylate (Compound 32)

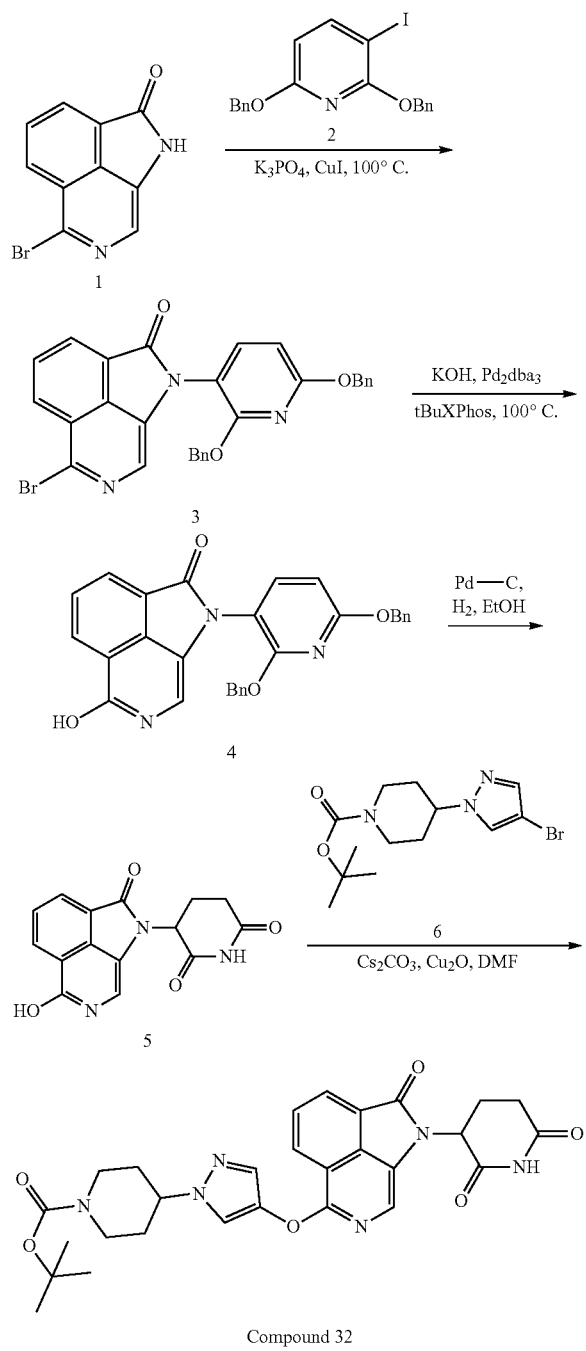

Step 1: Synthesis of 1-(2,6-Bis(benzyloxy)pyridin-3-yl)-6-bromopyrrolo[2,3,4-de]isoquinolin-2(1H)-one (3): To a stirred solution of 2,6-dibenzyloxy-3-iodo-pyridine 2 (1 equiv.) and 6-bromopyrrolo[2,3,4-de]isoquinolin-2(1H)-one 1 (1.2 equiv.) in dioxane is added tribasic potassium phosphate (1 equiv.), and the solution is degassed for 10 mins. Subsequently, (1R,2R)-(−)-1,2-diaminocyclohexane (0.1 equiv.) is added followed by copper (I) iodide (2%), and again the solution is degassed for 5 mins. The reaction mixture is then stirred at 100° C. for 16 hr. The reaction mixture is then allowed to come to RT and is extracted with ethyl acetate. The organic phase is washed with brine, and finally dried over anhyd. $Na_2SO_4$. The solvent is evaporated and the residue is purified by column chromatography (eluted with 40% Ethylacetate in Hexane) on silica gel to furnish the desired product 1-(2,6-bis(benzyloxy)pyridin-3-yl)-6-bromopyrrolo[2,3,4-de]isoquinolin-2(1H)-one 3 as solid.

Step 2: Synthesis of 1-(2,6-Bis(benzyloxy)pyridin-3-yl)-6-hydroxypyrrolo[2,3,4-de]isoquinolin-2(1H)-one (4): To a stirred solution of 1-(2,6-bis(benzyloxy)pyridin-3-yl)-6-bromopyrrolo[2,3,4-de]isoquinolin-2(1H)-one 3 in dioxane (8 mL) and water (2 mL) is added potassium hydroxide (2 equiv.), and the resulting solution is degassed with $N_2$ for 15 minutes followed by the addition of (1E,4E)-1,5-diphenylpenta-1,4-dien-3-one; palladium (5%) and Tert-Butyl Xphos-2-Di-tert-butylphosphino-2',4',6 (15%). The reaction mixture is heated at 100° C. in a sealed tube for 12 hr. After formation of desired pdt as evidence from LCMS, the reaction mixture is filtered through a celite bed and washed with ethyl acetate. The combined organic layer is separated and evaporated. The crude residue is purified by column chromatography to afford 1-(2,6-bis(benzyloxy)pyridin-3-yl)-6-hydroxypyrrolo[2,3,4-de]isoquinolin-2(1H)-one 4 as solid.

Step 3: Synthesis of 3-(6-hydroxy-2-Oxopyrrolo[2,3,4-de]isoquinolin-1(2H)-yl)piperidine-2,6-dione (5): A solution of 1-(2,6-bis(benzyloxy)pyridin-3-yl)-6-hydroxypyrrolo[2,3,4-de]isoquinolin-2(1H)-one 4 in ethyl acetate/ethanol (1/1) is hydrogenated using palladium, 10% on carbon, Type 487, (10%) under balloon pressure for 12 hr at rt. After completion of the reaction, the reaction mixture is filtered through a celite bed and washed with ethyl acetate several times. The filtrate is collected and concentrated under reduced pressure to afford 3-(6-hydroxy-2-oxopyrrolo[2,3,4-de]isoquinolin-1(2H)-yl)piperidine-2,6-dione 5 as a crude product.

Step 4: Synthesis of tert-Butyl 4-(4-((1-(2,6-Dioxopiperidin-3-yl)-2-oxo-1,2-dihydropyrrolo[2,3,4-de]isoquinolin-6-yl)oxy)-1H-pyrazol-1-yl)piperidine-1-carboxylate (Compound 32): After standard cycles of evacuation and backfilling with dry and pure nitrogen, an oven-dried Schlenk tube equipped with a magnetic stirring bar is charged with $Cu_2O$ (0.1 mmol), rel-(1R,2R)—$N^1,N^2$-Bis(2-pyridinylmethylene)-1,2-cyclohexanediamine (0.4 mmol), $Cs_2CO_3$ (4.0 mmol), activated and powdered 3 A molecular sieves (600 mg), 3-(6-hydroxy-2-oxopyrrolo[2,3,4-de]isoquinolin-1(2H)-yl)piperidine-2,6-dione (2.0 mmol) 5, and tert-butyl 4-(4-bromo-1H-pyrazol-1-yl)piperidine-1-carboxylate (3.0 mmol) 6, if a solid. The tube is evacuated, back-filled with nitrogen and capped with a rubber septum. If liquids, the phenol and the aryl halide are added under a stream of nitrogen by syringe at room temperature, followed by anhydrous and degassed acetonitrile or DMF (1.2 mL). The septum is removed, the tube sealed under a positive pressure of nitrogen and stirred in an oil bath (preheated to 82° C. or 110° C.), for the required time period. The reaction mixture is allowed to cool to room temperature, diluted with dichloromethane and filtered through a plug of Celite®, the filter cake is further washed with dichloromethane (~20 mL). The filtrate is concentrated in vacuo to yield the crude product, and is purified by silica gel chromatography to yield Compound 32.

Example 27. Synthesis of tert-Butyl 4-(4-((1-(2,6-Dioxopiperidin-3-yl)-2-oxo-1,2-dihydropyrrolo[4,3, 2-ij]isoquinolin-6-yl)amino)-1H-pyrazol-1-yl)piperidine-1-carboxylate (Compound 33)

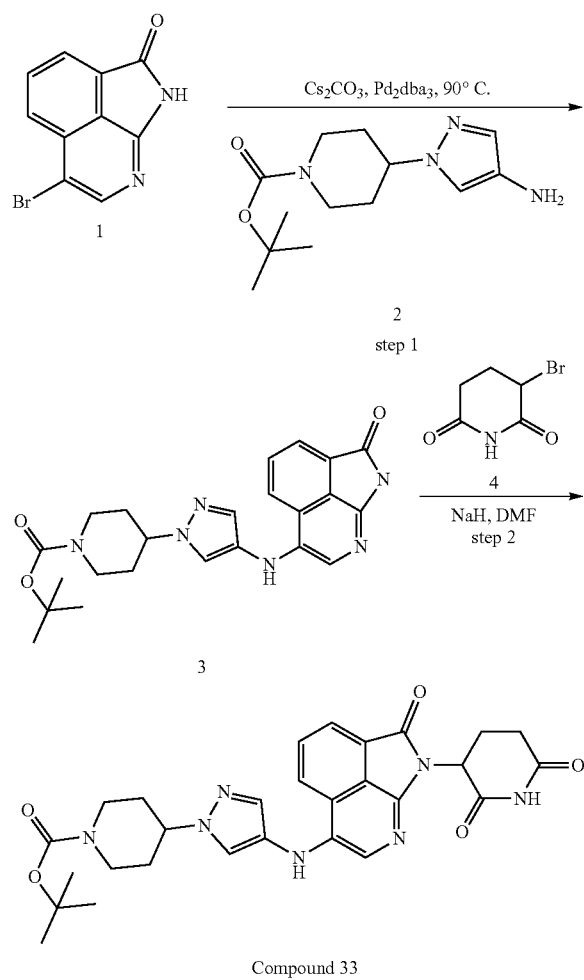

Compound 33

Step 1: Synthesis of tert-Butyl 4-(4-((2-Oxo-1,2-dihydropyrrolo[4,3,2-ij]isoquinolin-6-yl)amino-1H-pyrazol-1-carboxylate (3): In a sealed tube a stirred solution of tert-butyl 4-(4-aminopyrazol-1-yl)piperidine-1-carboxylate 2 (1 equiv.) and 3-(6-bromo-2-oxopyrrolo[4,3,2-ij]isoquinolin-1 (2H)-yl)piperidine-2,6-dione 1 (1 equiv.) intoluene is added cesium carbonate (2.5 equiv.), and then the reaction mixture is degassed for 5 min under an argon atmosphere. To the solution is added pd₂(dba)₃ (10%) and Xantphos (20%), and the solution is purged for 2 min under argon atmosphere/The reaction mixture is heated to 90° C. for 16 hr. After consumption of SM, the reaction mixture is filtered through a celite bed and concentrated in vacuo. Purification by CombiFlash column chromatography (eluted by 15% ethyl acetate in n-hexane) to provides the title compound 3.

Step 2: Synthesis of tert-Butyl 4-(4-((1-(2,6-Dioxopiperidin-3-yl)-2-oxo-1,2-dihydropyrrolo[4,3, 2-ij]isoquinolin-6-yl)amino)-1H-pyrazol-1-yl)piperidine-1-carboxylate (Compound 33): To a stirred solution of compound 3 in DMF is added sodium hydride (i60% dispersion in mineral oil, 1 equiv.), and the reaction mixture is refluxed at 60° C. for 30 minutes. A solution of (3-bromopiperidine-2,6-dione) 4 (0.5 equiv.) in DMF is also heated at 60° C. After 30 minutes the first suspension is added to the second solution with heating, and the heating is continued for 3 hours. The reaction mixture is diluted with ethyl acetate and washed with water and brine solution. The organic fraction is then dried over anhydrous sodium sulfate and evaporated under reduced pressure to obtain the crude compound. The crude compound is then purified by flash chromatography to obtain Compound 33.

Example 28: Synthesis of tert-Butyl 4-(4-((1-(2,6-Dioxopiperidin-3-yl)-2-oxo-1,2-dihydropyrrolo[4,3, 2-ij]isoquinolin-6-yl)oxy)-1H-pyrazol-1-yl)piperidine-1-carboxylate (Compound 34)

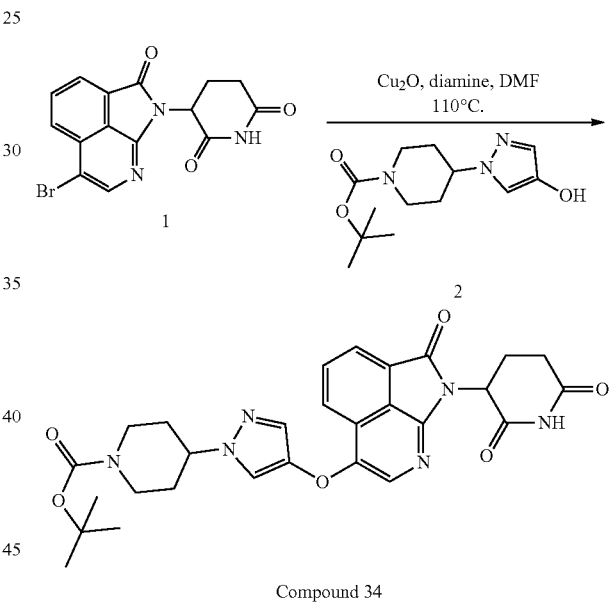

Compound 34

A Schlenk tube equipped with a magnetic stirring bar is charged with Cu₂O (0.1 mmol), rel-(1R,2R)—N¹,N²-Bis(2-pyridinylmethylene)-1,2-cyclohexanediamine (0.4 mmol), Cs₂CO₃ (4.0 mmol), activated and powdered 3 A molecular sieves (600 mg), tert-butyl 4-(4-hydroxy-1H-pyrazol-1-yl) piperidine-1-carboxylate 2 (2.0 mmol), and 3-(6-bromo-2-oxopyrrolo[4,3,2-ij]isoquinolin-1(2H)-yl)piperidine-2,6-dione 1(3.0 mmol), if a solid. The tube is evacuated, backfilled with nitrogen and capped with a rubber septum. If liquids, the phenol and the aryl halide were added under a stream of nitrogen by syringe at room temperature, followed by anhydrous and degassed acetonitrile or DMF (1.2 mL). The septum is removed, the tube sealed under a positive pressure of nitrogen and stirred in an oil bath (preheated to 110° C.), for the required time period. The reaction mixture is allowed to cool to room temperature, diluted with dichloromethane and filtered through a plug of Celite®, the filter cake being further washed with dichloromethane (~20 mL).

The filtrate is concentrated in vacuo to yield the crude product that is purified by silica gel chromatography to yield Compound 33.

Example 29. Synthesis of 6-(chloromethyl)-1-(4-methoxybenzyl)benzo[cd]indol-2(1H)-one (Compound 35)

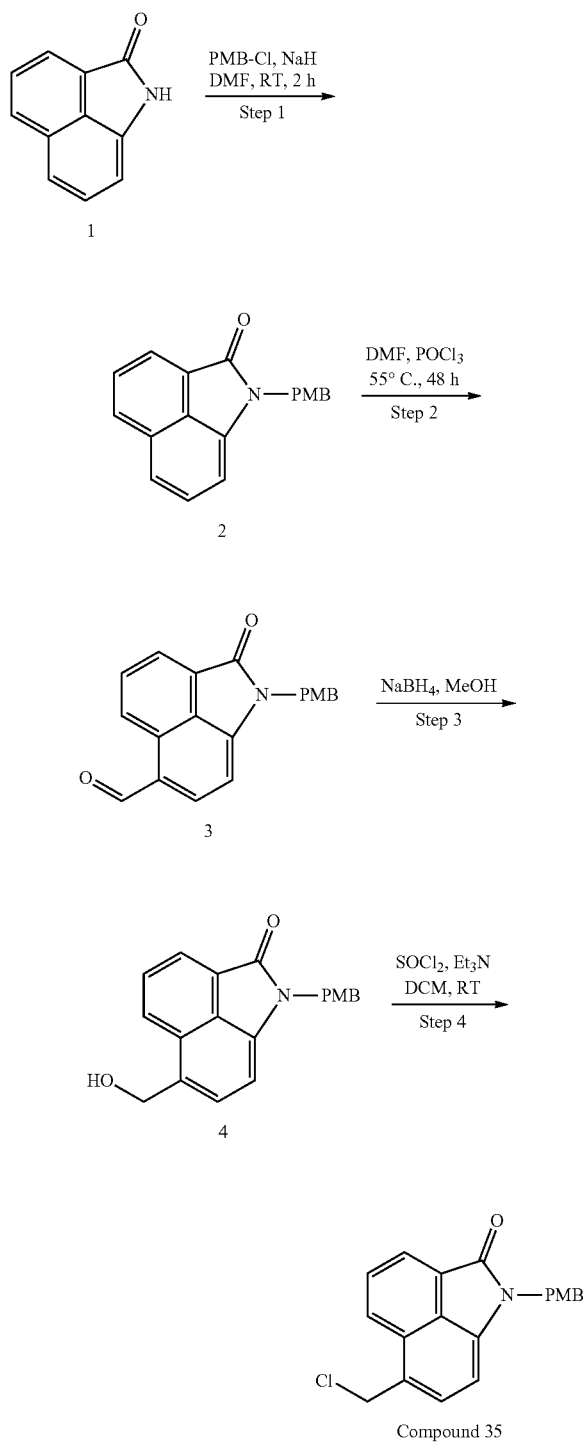

Step 1: Synthesis of 1-(4-methoxybenzyl)benzo[cd]indol-2(1H)-one: To a stirred solution of 1H-benzo[cd]indol-2-one 1 (25 g, 147.77 mmol) in DMF (500 mL) was added Sodium hydride (in oil dispersion) 60% dispersion in mineral oil (8.14 g, 203.43 mmol, 60% purity) at 0° C. portion wise and stirred for 1 hour at 0° C. After that p-Methoxy benzyl bromide (44.57 g, 221.66 mmol, 31.83 mL) was added slowly and reaction mass was stirred at 25° C. for 16 hrs. The progress of the reaction was monitored by TLC, SM was consumed in TLC. Then the reaction mass was quenched in ice-water at 0° C. and precipitate (solid) formed was filtered through sintered. The solid was then washed with water and diethyl ether and dried through rotavapor to get 1-[(4-methoxyphenyl)methyl]benzo[cd]indol-2-one 2 (40 g, 121.66 mmol, 82.33% yield, 88% purity) as pale yellow solid. LC MS: ES+ 290.4.

Step 2: Synthesis of 1-(4-methoxybenzyl)-2-oxo-1,2-dihydrobenzo[cd]indole-6-carbaldehyde: To the stirred solution of DMF (113.68 g, 1.56 mol, 120.42 mL) was added Phosphorous oxychloride (238.48 g, 1.56 mol, 145.42 mL) at 0° C. and stirred for 1 hr at RT. After that 1-[(4-methoxyphenyl)methyl]benzo[cd]indol-2-one 2 (30 g, 103.69 mmol) was added at 0° C. Then the reaction mixture was stirred at room temperature again for 1 hr. The reaction mass was then heated at 90° C. for 16 hrs. TLC matched with authentic and starting was consumed. The reaction mixture was cooled to 25° C. and quenched in ice-water, solid formed was filtered through sintered and washed with water successively. The solid was dried under reduced pressure to afford the crude product. The crude was then purified by column chromatography eluting by DCM/MeOH to afford 1-[(4-methoxyphenyl)methyl]-2-oxo-benzo[cd]indole-6-carbaldehyde 3 (15 g, 44.90 mmol, 43.31% yield, 95% purity). LC MS: ES+ 318.4.

Step 3: Synthesis of 6-(hydroxymethyl)-1-(4-methoxybenzyl)benzo[cd]indol-2(1H)-one: To a stirred suspension of 1-[(4-methoxyphenyl)methyl]-2-oxo-benzo[cd]indole-6-carbaldehyde 3 (10.2 g, 32.14 mmol) in Methanol (500 mL) was added Sodium borohydride (6.08 g, 160.71 mmol, 5.68 mL) at 0° C. and the reaction mixture was stirred at room temperature for 3 hr. TLC showed consumption of SM and formation of polar spot. The reaction mixture was quenched with cold water (5 mL) and concentrated under reduced pressure to afford yellow solid residue, which was washed with water, filtered and dried under reduced pressure to afford 6-(hydroxymethyl)-1-[(4-methoxyphenyl)methyl]benzo[cd]indol-2-one 4 (10 g, 31.31 mmol, 97.42% yield) as off Yellow solid. LC MS: ES+ 320.2.

Step 4: Synthesis of 6-(chloromethyl)-1-(4-methoxybenzyl)benzo[cd]indol-2(1H)-one: To a stirred suspension of 6-(hydroxymethyl)-1-[(4-methoxyphenyl)methyl]benzo[cd]indol-2-one 4 (10 g, 31.31 mmol) in DCM (220 mL) was added TEA (9.51 g, 93.94 mmol, 13.09 mL) and stirred at 0° C. and thionyl chloride (11.18 g, 93.94 mmol, 6.86 mL) was added drop wised. After completion of addition the reaction mixture was stirred at room temperature for overnight. The reaction mixture was concentrated under reduced pressure to get residue, which was diluted with EtOAc and neutralized with saturated solution of NaHCO₃. The layers were separated, organic layer was washed with water, brine, dried with Na₂SO₄ and concentrated under reduced pressure for dryness to afford Compound 35 (8 g, 23.68 mmol, 75.63% yield) as brown solid. LC MS: ES+338.2.

Example 30. Synthesis of 3-(2-oxo-6-((1-(piperidin-4-yl)-1H-pyrazol-4-yl)methyl)benzo[cd]indol-1(2H)-yl)piperidine-2,6-dione hydrochloride (Compound 36)

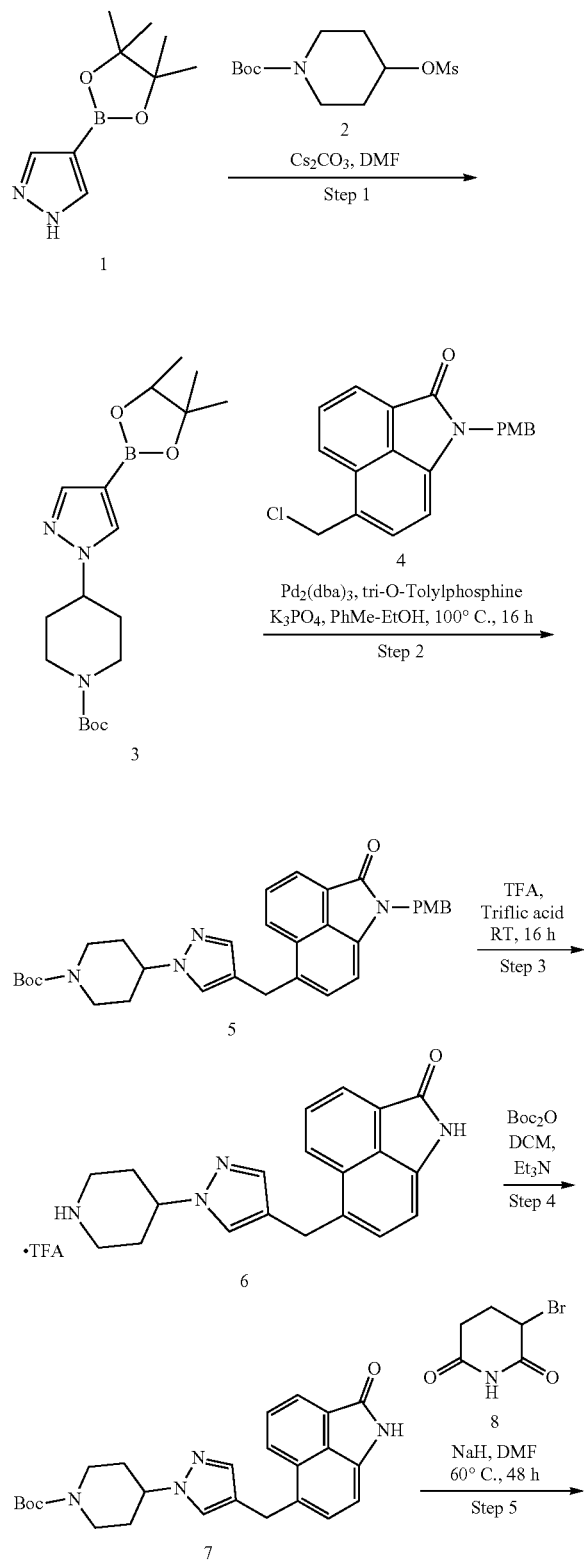

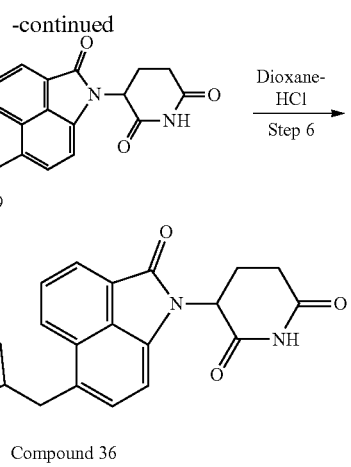

Step 1: Synthesis of tert-butyl 4-(4-(4,4,5,5-tetramethyl-1,3,2-dioxaborolan-2-yl)-1H-pyrazol-1-yl)piperidine-1-carboxylate: To the stirred solution of 4-(4,4,5,5-tetramethyl-1,3,2-dioxaborolan-2-yl)-1H-pyrazole 1 (15 g, 77.30 mmol) and tert-butyl 4-methylsulfonyloxypiperidine-1-carboxylate 2 (21.60 g, 77.30 mmol) in DMF (130.0 mL) was added Cesium carbonate (50.37 g, 154.61 mmol) and then the reaction mass was heated at 80° C. for 16 hours. The reaction mass was then cooled to room temperature and then it was extracted with ethyl acetate. The organic part was then dried over sodium sulfate and concentrated under reduced pressure to afford the crude material. The crude was then purified by column chromatography eluting 1.5-2% Methanol in DCM to afford tert-butyl 4-[4-(4,4,5,5-tetramethyl-1,3,2-dioxaborolan-2-yl)pyrazol-1-yl]piperidine-1-carboxylate 3 (10.0 g, 25.18 mmol, 32.57% yield, 95% purity) as a white solid. LC MS: ES+ 378.1.

Step 2: Synthesis of tert-butyl 4-(4-((1-(4-methoxybenzyl)-2-oxo-1,2-dihydrobenzo[cd]indol-6-yl)methyl)-1H-pyrazol-1-yl)piperidine-1-carboxylate: To the stirred solution of 6-(chloromethyl)-1-[(4-methoxyphenyl)methyl]benzo[cd]indol-2-one 4 (3800 mg, 11.25 mmol) and tert-butyl 4-[4-(4,4,5,5-tetramethyl-1,3,2-dioxaborolan-2-yl)pyrazol-1-yl]piperidine-1-carboxylate 3 (6.37 g, 16.87 mmol) in a sealed tube in Ethanol (7 mL), Toluene (14 mL) and 4 drops of water was added tripotassium; phosphate (5.97 g, 28.12 mmol). The reaction mixture was degassed with argon for 10 minutes. Then tris-o-tolylphosphane (684.78 mg, 2.25 mmol) and (1E,4E)-1,5-diphenylpenta-1,4-dien-3-one; palladium (1.03 g, 1.12 mmol) were added to the reaction mixture and it was heated at 90° C. for 16 h. Reaction mixture was cooled to RT, diluted with ethyl acetate, washed with water, brine, dried over sodium sulfate and concentrated under reduced pressure. Crude material was purified by column chromatography eluting at 40% ethyl acetate in hexane to afford tert-butyl 4-[4-[[1-[(4-methoxyphenyl)methyl]-2-oxo-benzo[cd]indol-6-yl]methyl]pyrazol-1-yl]piperidine-1-carboxylate 5 (4.6 g, 7.82 mmol, 69.55% yield, 94% purity) as yellow solid. LC MS: ES+ 553.4.

Step 3: Synthesis of Preparation of 2,2,2-trifluoroacetaldehyde compound with 6-((1-(piperidin-4-yl)-1H-pyrazol-4-yl)methyl)benzo[cd]indol-2(1H)-one (1:1): To the stirred solution of tert-butyl 4-[4-[[1-[(4-methoxyphenyl)methyl]-2-oxo-benzo[cd]indol-6-yl]methyl]pyrazol-1-yl]piperidine-1-carboxylate 5 (4.5 g, 8.14 mmol) in TFA (10 mL) was added Trifluoromethanesulfonic acid (6.11 g, 40.71 mmol, 3.57 mL) at 0° C. and the reaction mixture was stirred at RT for 16 h. Reaction mixture was concentrated under reduced pressure to afford 6-[[1-(4-piperidyl)pyrazol-4-yl]methyl]-1H-benzo[cd]indol-2-one 6 (3.63 g, 6.51 mmol, 79.89% yield, 80% purity) as brown gum. This crude material was forwarded to the next step without further purification, LC MS: ES+ 333.3.

Step 4: Synthesis of tert-butyl 4-(4-((2-oxo-1,2-dihydrobenzo[cd]indol-6-yl)methyl)-1H-pyrazol-1-yl)piperidine-1-carboxylate: To the stirred solution of 6-[[1-(4-piperidyl)pyrazol-4-yl]methyl]-1H-benzo[cd]indol-2-one 6 (3.62 g, 10.89 mmol) in DCM (10 mL) was added Triethyl amine (3.31 g, 32.67 mmol, 4.55 mL), followed by Di-tert-butyl dicarbonate (3.57 g, 16.34 mmol, 3.75 mL) at 0° C. The reaction mixture was stirred at RT for 16 h. Reaction mixture was diluted with ethyl acetate, washed with saturated sodium bicarbonate solution, brine, dried over sodium sulfate and concentrated under reduced pressure. Crude material was purified by combi flash eluting at 60% ethyl acetate in hexane to afford tert-butyl 4-[4-[(2-oxo-1H-benzo[cd]indol-6-yl)methyl]pyrazol-1-yl]piperidine-1-carboxylate 7 (3.2 g, 6.73 mmol, 61.82% yield, 91% purity) as yellow solid, LC MS: ES+ 433.4.

Step 5: Synthesis of tert-butyl 4-(4-((1-(2,6-dioxopiperidin-3-yl)-2-oxo-1,2-dihydrobenzo[cd]indol-6-yl)methyl)-1H-pyrazol-1-yl)piperidine-1-carboxylate: To the stirred solution of tert-butyl 4-[4-[(2-oxo-1H-benzo[cd]indol-6-yl)methyl]pyrazol-1-yl]piperidine-1-carboxylate 7 (1 g, 2.31 mmol) in THF (20 mL) was added Sodium hydride (in oil dispersion) 60% dispersion in mineral oil (924.74 mg, 23.12 mmol, 60% purity) at cold condition and the reaction mixture was stirred at room temperature for 10 minutes followed by the addition of 3-bromopiperidine-2,6-dione 8 (2.22 g, 11.56 mmol) portion wise. It was then stirred at room temperature for 10 minutes and heated at 70° C. for 30 minutes. TLC was checked which showed almost complete consumption of the starting material and formation of the desired spot. The reaction mixture was diluted with ethyl acetate, washed with cold water and the organic fraction was separated. It was then dried over anhydrous sodium sulphate and evaporated under reduced pressure to obtain the crude which was washed with ether and pentane to afford tert-butyl 4-[4-[[1-(2,6-dioxo-3-piperidyl)-2-oxo-benzo[cd]indol-6-yl]methyl]pyrazol-1-yl]piperidine-1-carboxylate 9 (1 g, 1.84 mmol, 79.56% yield) as yellow solid, LC MS: ES+ 544.3.

Step 6: Synthesis of 3-(2-oxo-6-((1-(piperidin-4-yl)-1H-pyrazol-4-yl)methyl)benzo[cd]indol-1(2H)-yl)piperidine-2,6-dione hydrochloride: To the stirred solution of tert-butyl 4-[4-[[1-(2,6-dioxo-3-piperidyl)-2-oxobenzo[cd]indol-6-yl]methyl]pyrazol-1-yl]piperidine-1-carboxylate 9 (380.0 mg, 699.03 umol) in Dioxane (5 mL) was added Hydrochloric acid in dioxane (699.03 umol, 15.0 mL) and the reaction mixture was stirred at room temperature for 2 hours. TLC was checked which showed complete consumption of the starting material. The solvent in the reaction mixture was evaporated under reduced pressure to obtain a yellow solid which was washed with ether and pentane to afford 3-[6-[[1-(1-chloro-4-piperidyl)pyrazol-4-yl]methyl]-2-oxo-benzo[cd]indol-1-yl]piperidine-2,6-dione Compound 36 (330.0 mg, 687.56 umol, 98.36% yield) as yellow solid. LC MS: ES+ 444.4.

Example 31. General Synthesis of Compound 37-Compound 54

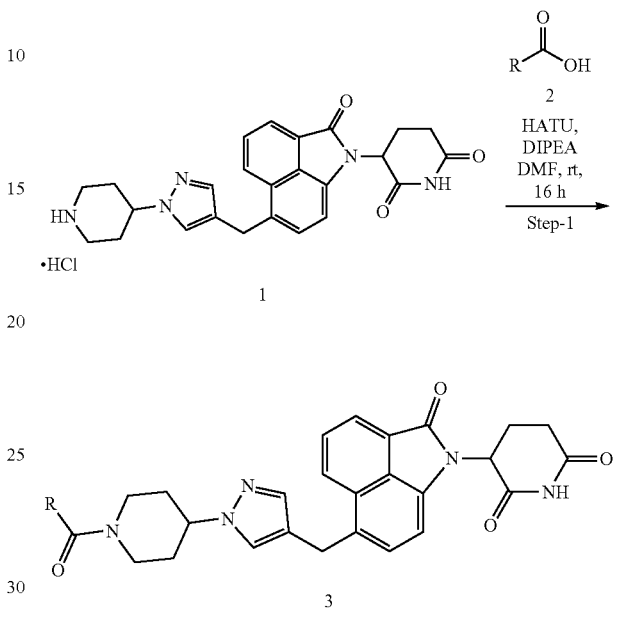

To an equi-molar mixture of Amine and Acid DMF (6 mL/mmol) were added HATU (1.5 equiv) and DIPEA (5.0 equiv) at 0° C. The resulting solution was stirred at ambient temperature for 16 hours. The reaction mixture was then diluted with Ethyl acetate and washed with aqueous NaHCO$_3$solution, water (×3) and brine. The organic layer was then dried over anhydrous Na$_2$SO$_4$ and concentrated under reduced pressure. Crude mass was then purified by CombiFlash ISCO column, eluting with 2% methanol in DCM to afford 3:

Compound 37

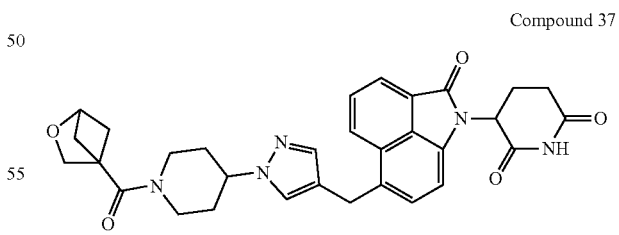

$^1$H NMR (400 MHz, DMSO-d6) δ 11.11 (s, 1H), 8.37 (d, J=8.36 Hz, 1H), 8.08 (d, J=6.8 Hz, 1H), 7.85-7.81 (m, 1H), 7.58 (s, 1H), 7.35 (d, J=7.32 Hz, 1H), 7.32 (s, 1H), 7.07 (d, J=7.56 Hz, 1H), 4.40 (s, 2H), 4.31-4.30 (m, 1H), 4.18 (s, 2H), 3.70-3.66 (m, 3H), 3.13-3.12 (m, 1H), 3.00-2.92 (m, 2H), 2.75-2.67 (m, 2H), 2.09-2.07 (m, 2H), 1.97-1.95 (m, 2H), 1.74-1.72 (m, 3H), 1.26-1.24 (m, 2H); LC MS: ES+ 554.5.

Compound 38

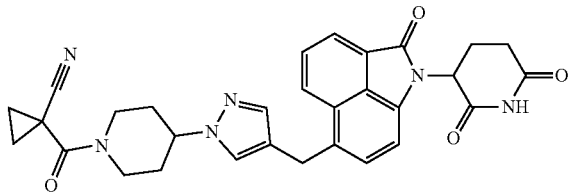

Yellow solid, 105.0 mg, 45.54% yield, 96.98% purity. $^1$H NMR (400 MHz, DMSO-d6) δ 11.10 (s, 1H), 8.37 (d, J=8.24 Hz, 1H), 8.08 (d, J=6.96 Hz, 1H), 7.83 (t, J=7.6 Hz, 1H), 7.59 (s, 1H), 7.36 (d, J=7.4 Hz, 1H), 7.33 (s, 1H), 7.07 (d, J=7.24 Hz, 1H), 5.43 (dd, J=12.44, 4.76 Hz, 1H), 4.39-4.35 (m, 1H), 4.29-4.25 (m, 2H), 4.19 (s, 2H), 2.97-2.90 (m, 1H), 2.79-2.72 (m, 1H), 2.67-2.62 (m, 1H), 2.10-2.00 (m, 5H), 1.82-1.80 (m, 2H), 1.58-1.57 (m, 2H), 1.50-1.49 (m, 2H); LC MS: ES+ 537.2.

Compound 39

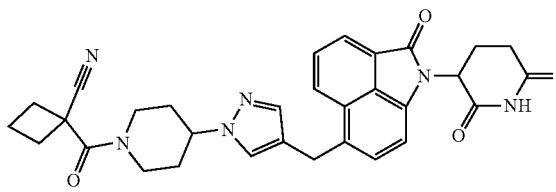

Yellow solid, 145.0 mg, 58.63% yield, 99.73% purity. $^1$H NMR (400 MHz, DMSO-d6) δ 11.10 (s, 1H), 8.37 (d, J=8.24, 1H), 8.08 (d, J=6.96 Hz, 1H), 7.83 (t, J=7.64 Hz, 1H), 7.59 (s, 1H), 7.36 (d, J=7.32 Hz, 1H), 7.33 (s, 1H), 7.07 (d, J=7.28 Hz, 1H), 5.43 (dd, J=12.8, 5.16 Hz, 1H), 4.38-4.34 (m, 2H), 4.18 (s, 2H), 3.68-3.65 (m, 1H), 3.26-3.20 (m, 1H), 2.97-2.62 (m, 6H), 2.61-2.56 (m, 2H), 2.15-2.08 (m, 2H), 1.99-1.97 (m, 2H), 1.90-1.83 (m, 2H), 1.75-1.72 (m, 1H); LC MS: ES+ 551.2.

Compound 40

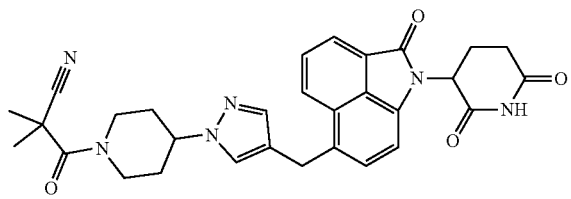

Yellow solid, 160.0 mg, 66.04% yield, 99.59% purity. $^1$H NMR (400 MHz, DMSO-d6) δ 11.11 (s, 1H), 8.37 (d, J=8.28 Hz, 1H), 7.83 (t, J=7.62 Hz, 1H), 7.60 (s, 1H), 7.36 (d, J=Hz, 1H), 7.33 (s, 1H), 7.07 (d, J=7.28 Hz, 1H), 5.43 (dd, J=12.64, 5.08 Hz, 1H), 4.40-4.31 (m, 3H), 4.18 (s, 2H), 3.11-2.90 (m, 3H), 2.77-2.72 (m, 1H), 2.66-2.62 (m, 1H), 2.09-1.99 (m, 3H), 1.83-1.81 (m, 2H), 1.52 (s, 6H); LC MS: ES+ 539.2.

Compound 41

Yellow solid, 34 mg, 44.47% yield, 99.23% purity. $^1$H NMR (400 MHz, DMSO-d6) δ 11.10 (s, 1H), 8.37 (d, J=8.72 Hz, 1H), 8.08 (d, J=6.92 Hz, 1H), 7.83 (t, J=7.28 Hz, 1H), 7.59 (s, 1H), 7.35 (d, J=7.24 Hz, 1H), 7.31 (s, 1H), 7.07 (d, J=7.2 Hz, 1H), 5.44-5.42 (m, 1H), 4.33-4.30 (m, 2H), 4.18 (s, 2H), 3.62-3.61 (m, 2H), 3.48-3.43 (m, 2H), 2.95-2.87 (m, 4H), 2.76-2.73 (m, 1H), 2.66-2.60 (m, 2H), 2.10-2.07 (m, 1H), 1.95-1.94 (m, 3H), 1.70-1.64 (m, 2H), 1.44-1.43 (m, 2H), 1.24 (s, 3H); LC MS: ES+ 570.54.

Compound 42

Yellow solid, 35 mg, 45.94% yield, 95.90% purity. $^1$H NMR (400 MHz, DMSO-d6) δ 11.11 (s, 1H), 8.65 (d, J=4.36 Hz, 2H), 8.36 (d, J=7.68 Hz, 1H), 8.08 (d, J=6.88 Hz, 1H), 7.83 (t, J=7.3 Hz, 1H), 7.59 (s, 1H), 7.40-7.33 (m, 4H), 7.07 (d, J=7.28 Hz, 1H), 5.44-5.42 (m, 1H), 4.51-4.48 (m, 1H), 4.38-4.36 (m, 1H), 4.19 (s, 2H), 3.49-3.45 (m, 1H), 3.23-3.17 (m, 1H), 2.95-2.94 (m, 2H), 2.79-2.73 (m, 1H), 2.67-2.63 (m, 1H), 2.08-2.07 (m, 2H), 1.87-1.86 (m, 3H); LC MS: ES+ 549.5.

Compound 43

Yellow solid, 44 mg, 60.00/a yield, 99.63% purity. $^1$H NMR (400 MHz, DMSO-d6) δ 11.10 (s, 1H), 8.65-8.61 (m, 2H), 8.37 (d, J=8.24 Hz, 1H), 8.08 (d, J=6.96 Hz, 1H), 7.85-7.81 (m, 2H), 7.60 (s, 1H), 7.48-7.45 (m, 1H), 7.36 (d, J=7.36 Hz, 1H), 7.33 (s, 1H), 7.07 (d, J=7.28 Hz, 1H), 5.43 (dd, J=12.76, 5.16 Hz, 1H), 4.52-4.50 (m, 1H), 4.40-4.34 (m, 1H), 4.19 (s, 2H), 3.58-3.57 (m, 1H), 2.97-2.90 (m, 2H), 2.80-2.72 (m, 1H), 2.70-2.60 (m, 2H), 2.10-2.07 (m, 2H), 1.95-1.80 (m, 3H); LC MS: ES+ 549.5.

Compound 44

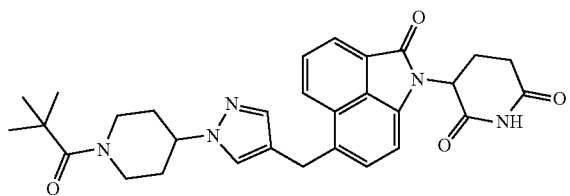

Yellow solid, 38 mg, 53.21% yield, 98.40% purity. ¹H NMR (400 MHz, DMSO-d6) δ 11.11 (s, 1H), 8.37 (d, J=7.96 Hz, 1H), 8.08 (d, J=6.92 Hz, 1H), 7.83 (t, J=7.8 Hz, 1H), 7.60 (s, 1H), 7.35 (d, J=7.32 Hz, 1H), 7.31 (s, 1H), 7.07 (d, J=7.4 Hz, 1H), 5.44-5.42 (m, 1H), 4.33-4.30 (m, 3H), 4.18 (s, 2H), 2.92-2.85 (m, 3H), 2.76-2.72 (m, 1H), 2.66-2.57 (m, 1H), 2.08-2.06 (m, 1H), 1.96-1.93 (m, 2H), 1.73-1.67 (m, 2H), 1.18 (s, 9H); LC MS: ES+ 528.51.

Compound 45

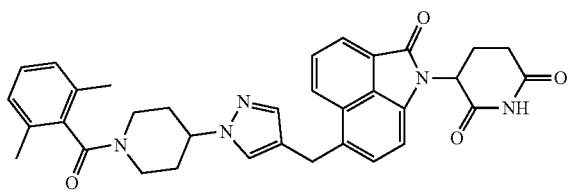

Yellow solid, 21 mg, 26.89% yield, 98.16% purity. ¹H NMR (400 MHz, DMSO-d6) δ 11.11 (s, 1H), 8.37 (d, J=8.28 Hz, 1H), 8.08 (d, J=6.96 Hz, 1H), 7.82 (t, J=7.64 Hz, 1H), 7.59 (s, 1H), 7.35 (d, J=7.36 Hz, 1H), 7.33 (s, 1H), 7.16 (t, J=7.52 Hz, 1H), 7.07-7.04 (m, 3H), 5.43 (dd, J=12.76, 5.24 Hz, 1H), 4.65-4.61 (m, 1H), 4.34-4.33 (m, 1H), 4.18 (s, 2H), 3.26-3.23 (m, 1H), 3.13-3.10 (m, 1H), 2.94-2.88 (m, 2H), 2.76-2.72 (m, 1H), 2.66-2.62 (m, 1H), 2.20 (s, 3H), 2.11 (s, 3H), 2.07-2.04 (m, 2H), 1.89-1.86 (m, 1H), 1.81-1.78 (m, 1H), 1.77-1.66 (m, 1H); LC MS: ES+ 576.49.

Compound 46

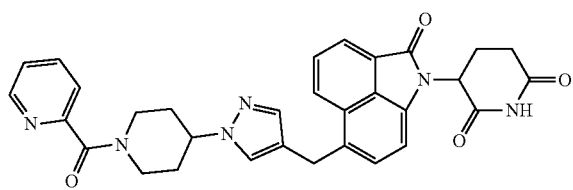

Yellow solid, 32 mg, 43.71% yield, 99.79% purity. ¹H NMR (400 MHz, DMSO-d6) δ 11.12 (s, 1H), 8.58-8.57 (m, 1H), 8.37 (d, J=8.2 Hz, 1H), 8.08 (d, J=6.96 Hz, 1H), 7.91 (t, J=7.06 Hz, 1H), 7.83 (t, J=7.62 Hz, 1H), 7.61 (s, 1H), 7.56 (d, J=7.64 Hz, 1H), 7.48-7.45 (m, 1H), 7.36 (d, J=7.2 Hz, 1H), 7.32 (s, 1H), 7.07 (d, J=7.16 Hz, 1H), 5.44-5.42 (m, 1H), 4.55-4.52 (m, 1H), 4.39-4.38 (m, 1H), 4.18 (s, 2H), 3.74-3.70 (m, 1H), 3.18-3.12 (m, 1H), 2.96-2.90 (m, 2H), 2.79-2.72 (m, 1H), 2.66-2.62 (m, 1H), 2.07-2.03 (m, 2H), 1.86-1.82 (m, 3H); LC MS: ES+ 549.5.

Compound 47

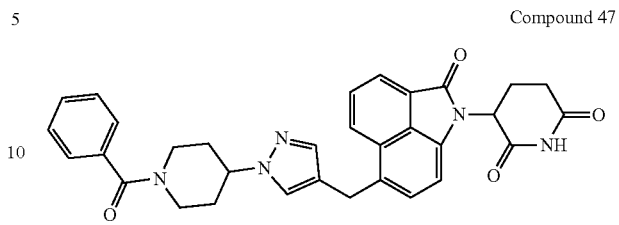

Yellow solid, 32 mg, 43.29% yield, 98.66% purity. ¹H NMR (400 MHz, DMSO-d6) δ 11.12 (s, 1H), 8.37 (d, J=8.16 Hz, 1H), 8.08 (d, J=6.92 Hz, 1H), 7.83 (t, J=7.58 Hz, 1H), 7.61 (s, 1H), 7.44-7.33 (m, 7H), 7.07 (d, J=7.28 Hz, 1H), 5.44-5.42 (m, 1H), 4.52-4.51 (m, 1H), 4.36-4.35 (m, 1H), 4.19 (s, 2H), 3.62-3.61 (m, 1H), 3.15-3.14 (m, 1H), 2.99-2.91 (m, 2H), 2.79-2.72 (m, 1H), 2.66-2.62 (m, 1H), 2.09-1.80 (m, 5H); LC MS: ES+ 548.5.

Compound 48

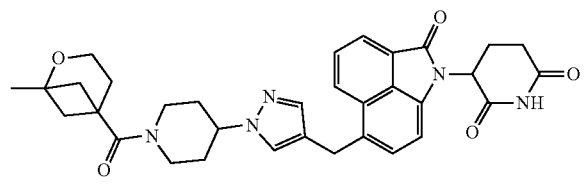

Yellow solid, 55.0 mg, 68.12% yield, 100.00% purity. ¹H NMR (400 MHz, DMSO-d6) δ 11.11 (s, 1H), 8.37 (d, J=7.96 Hz, 1H), 8.08 (d, J=6.44 Hz, 1H), 7.83 (t, J=7.34 Hz, 1H), 7.59 (s, 1H), 7.35 (d, J=7.44 Hz, 1H), 7.31 (s, 1H), 7.07 (d, J=7.0 Hz, 1H), 5.44-5.42 (m, 1H), 4.36-4.33 (m, 2H), 4.24-4.21 (m, 1H), 4.18 (s, 2H), 3.76 (s, 2H), 3.10-3.08 (m, 1H), 2.95-2.93 (m, 2H), 2.85-2.83 (m, 1H), 2.76-2.69 (m, 1H), 2.67-2.62 (m, 1H), 2.08-2.01 (m, 1H), 1.99-1.93 (m, 4H), 1.72-1.60 (m, 4H); LC MS: ES+ 554.2.

Compound 49

Yellow solid, 55.0 mg, 64.65% yield, 99.71% purity. ¹H NMR (400 MHz, DMSO-d6) δ 11.11 (s, 1H), 8.36 (d, J=7.92 Hz, 1H), 8.08 (d, J=6.68 Hz, 1H), 7.83 (t, J=7.3 Hz, 1H), 7.58 (s, 1H), 7.35 (d, J=7.2 Hz, 1H), 7.32 (s, 1H), 7.07 (d, J=6.8 Hz, 1H), 5.44-5.42 (m, 1H), 4.33-4.31 (m, 2H), 4.18 (s, 2H), 3.97-3.96 (m, 2H), 3.82-3.81 (m, 1H), 3.09-3.08 (m, 1H), 2.98-2.91 (m, 1H), 2.79-2.72 (m, 1H), 2.66-2.63 (m, 2H), 2.15-1.90 (m, 9H), 1.72-1.64 (m, 2H), 1.12 (s, 3H); LC MS: ES+ 582.3.

Compound 50

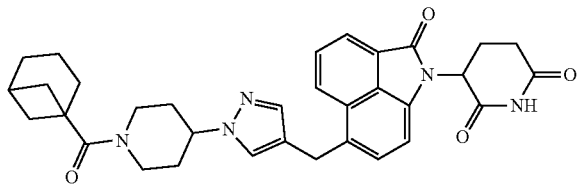

Yellow solid, 50.0 mg, 52.01% yield, 98.07% purity. $^1$H NMR (400 MHz, DMSO-d6) δ 11.11 (s, 1H), 8.37 (d, J=8.2 Hz, 1H), 8.08 (d, J=7.08 Hz, 1H), 7.83 (t, J=7.48 Hz, 1H), 7.59 (s, 1H), 7.35 (d, J=6.96 Hz, 1H), 7.31 (s, 1H), 7.07 (d, J=7.16 Hz, 1H), 5.45-5.42 (m, 1H), 4.32-4.26 (m, 2H), 4.18 (s, 2H), 3.75-3.73 (m, 1H), 3.06-2.90 (m, 2H), 2.76-2.71 (m, 1H), 2.66-2.62 (m, 3H), 2.11-2.07 (m, 4H), 1.94-1.92 (m, 2H), 1.82-1.81 (m, 4H), 1.72-1.70 (m, 2H), 1.64-1.63 (m, 3H); LC MS: ES+ 566.2.

Compound 53

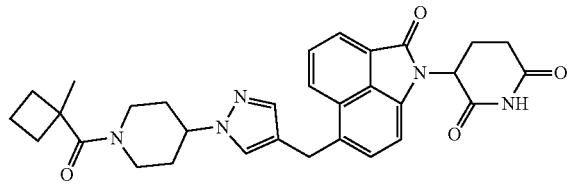

Yellow solid, 255.0 mg, 45.02% yield, 99.45% purity. $^1$H NMR (400 MHz, DMSO-d6) δ 11.11 (s, 1H), 8.37 (d, J=8.24 Hz, 1H), 8.08 (d, J=6.96 Hz, 1H), 7.83 (t, J=7.6 Hz, 1H), 7.60 (s, 1H), 7.35 (d, J=7.28 Hz, 1H), 7.31 (s, 1H), 7.07 (d, J=7.2 Hz, 1H), 5.44-5.42 (m, 1H), 4.40-4.39 (m, 1H), 4.32-4.29 (m, 1H), 4.18 (s, 2H), 3.58-3.57 (m, 1H), 3.05-2.91 (m, 2H), 2.76-2.72 (m, 1H), 2.66-2.63 (m, 2H), 2.40-2.33 (m, 2H), 2.09-2.08 (m, 1H), 1.94-1.87 (m, 3H), 1.78-1.59 (m, 5H), 1.33 (s, 3H); LC MS: ES+ 540.5.

Compound 51

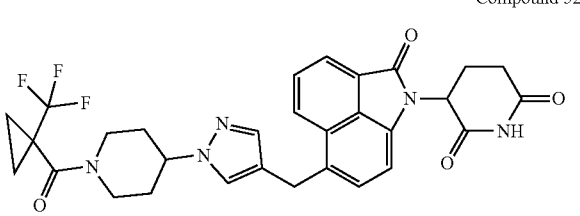

Yellow solid, 140.0 mg, 60.42% yield, 96.07% purity. $^1$H NMR (400 MHz, DMSO-d6) δ 11.10 (s, 1H), 8.37 (d, J=7.48 Hz, 1H), 8.08 (d, J=6.28 Hz, 1H), 7.83 (t, J=6.82 Hz, 1H), 7.58 (s, 1H), 7.36 (d, J=7.36 Hz, 1H), 7.32 (s, 1H), 7.07 (d, J=6.84 Hz, 1H), 5.44-5.42 (m, 1H), 4.42-4.41 (m, 1H), 4.34-4.33 (m, 1H), 4.18 (s, 2H), 3.55-3.53 (m, 1H), 3.17-3.12 (m, 1H), 2.95-2.91 (m, 1H), 2.77-2.62 (m, 5H), 2.43-2.30 (m, 2H), 2.10-2.07 (m, 1H), 1.95-1.94 (m, 3H), 1.76-1.74 (m, 3H); LC MS: ES+ 594.5.

Compound 54

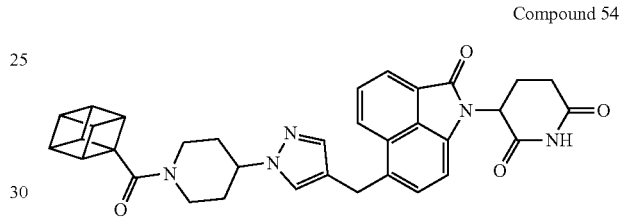

Yellow solid, 45.0 mg, 35.77% yield, 95% purity. $^1$H NMR (400 MHz, DMSO-d6) δ 11.09 (s, 1H), 8.36 (d, J=8.2 Hz, 1H), 8.08 (d, J=6.84 Hz, 1H), 7.83 (t, J=7.54 Hz, 1H), 7.60 (s, 1H), 7.35 (d, J=7.28 Hz, 1H), 7.32 (s, 1H), 7.07 (d, J=7.16 Hz, 1H), 5.43-5.40 (m, 1H), 4.33-4.31 (m, 2H), 4.18 (s, 5H), 3.98 (s, 4H), 3.34-3.31 (m, 1H), 3.20-3.14 (m, 1H), 2.98-2.91 (m, 1H), 2.75-2.63 (m, 3H), 2.10-2.07 (m, 1H), 2.01-1.92 (m, 2H), 1.83-1.80 (m, 1H), 1.67-1.64 (m, 1H); LC MS: ES+ 574.2.

Example 32. General Synthesis of Compound 55-Compound 66

Compound 52

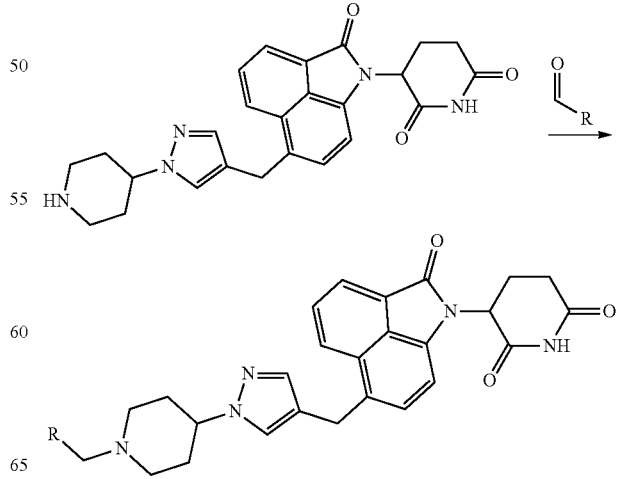

Yellow solid, 140.0 mg, 63.80% yield, 99.06% purity. $^1$H NMR (400 MHz, DMSO-d6) δ 11.11 (s, 1H), 8.36 (d, J=7.84 Hz, 1H), 8.08 (d, J=6.48 Hz, 1H), 7.85-7.82 (m, 1H), 7.58 (s, 1H), 7.36-7.33 (m, 2H), 7.07 (d, J=6.96 Hz, 1H), 5.44-5.42 (m, 1H), 4.35-4.27 (m, 3H), 4.18 (s, 2H), 2.96-2.90 (m, 3H), 2.77-2.73 (m, 1H), 2.67-2.62 (m, 1H), 2.10-2.07 (m, 1H), 2.00-1.96 (m, 2H), 1.76-1.74 (m, 2H), 1.28-1.19 (m, 4H); LC MS: ES+ 580.2.

To a stirred solution of Amine (1.0 equiv) in THF (6 mL/mmol) was added Triethylamine (2.0 equiv) at 0° C. Then Aldehyde (1.0 equiv), Phenylsilane (1.0 equiv) and Dibutyltindichloride (1.2 equiv) were added to the reaction mixture. The resulting solution was stirred at 90° C. for 16 hours. Reaction mixture was then diluted with Ethyl acetate and washed with aqueous NaHCO₃ solution, water (×3) and brine. The organic layer was then dried over anhydrous Na₂SO₄ and concentrated under reduced pressure. Crude mass was then purified by CombiFlash ISCO column, eluting with 3% methanol in DCM to afford the final compound.

Compound 55

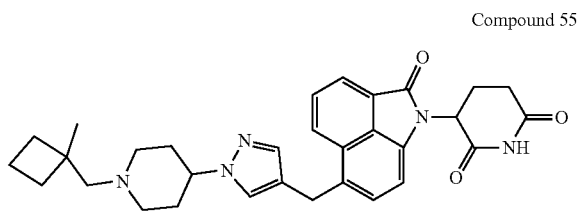 [SMILES: CC1(CN2CCC(n3cc(Cc4ccc5c6c(cccc46)C(=O)N5C4CCC(=O)NC4=O)cn3)CC2)CCC1]

Yellow solid, 3.8 g, 71.92% yield, 99.49% purity. ¹H NMR (400 MHz, DMSO-d6) δ 11.11 (s, 1H), 8.37 (d, J=8.2 Hz, 1H), 8.08 (d, J=6.96 Hz, 1H), 7.82 (t, J=7.6 Hz, 1H), 7.57 (s, 1H), 7.35 (d, J=7.24 Hz, 1H), 7.28 (s, 1H), 7.06 (d, J=7.24 Hz, 1H), 5.43 (dd, J=12.64, 4.8 Hz, 1H), 4.17 (s, 2H), 3.99-3.96 (m, 1H), 2.94-2.90 (m, 1H), 2.75-2.62 (m, 4H), 2.22 (s, 2H), 2.09-2.02 (m, 3H), 1.99-1.69 (m, 8H), 1.61-1.56 (m, 2H), 1.13 (s, 3H); LC MS: ES+ 526.4.

Compound 56

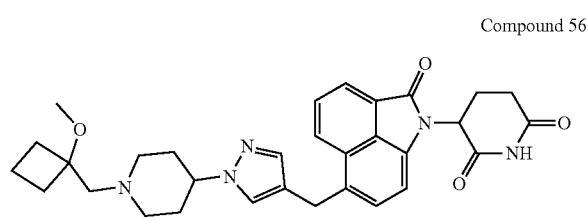 [SMILES: COC1(CN2CCC(n3cc(Cc4ccc5c6c(cccc46)C(=O)N5C4CCC(=O)NC4=O)cn3)CC2)CCC1]

Yellow solid, 95 mg, 40.71% yield, 96.71% purity. ¹H NMR (400 MHz, DMSO-d6) δ 11.12 (s, 1H), 8.37 (d, J=8.04 Hz, 1H), 8.08 (d, J=6.84 Hz, 1H), 7.82 (t, J=7.44 Hz, 1H), 7.58 (s, 1H), 7.35 (d, J=7.12 Hz, 1H), 7.28 (s, 1H), 7.06 (d, J=7.24 Hz, 1H), 5.44-5.42 (m, 1H), 4.17 (s, 2H), 3.98-3.97 (m, 1H), 3.05 (s, 3H), 2.98-2.91 (m, 3H), 2.79-2.72 (m, 1H), 2.66-2.62 (m, 1H), 2.46 (s, 2H), 2.19-2.07 (m, 3H), 1.98-1.93 (m, 2H), 1.85-1.83 (m, 6H), 1.66-1.64 (m, 1H), 1.55-1.50 (m, 1H); LC MS: ES+ 542.3.

Compound 57

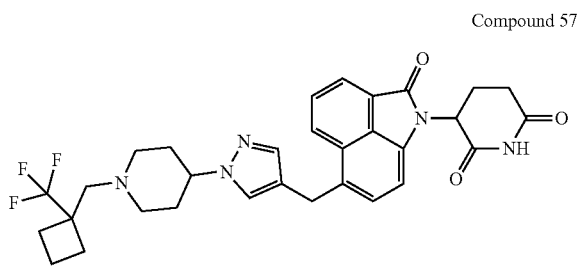 [SMILES: O=C1CCC(N2C(=O)c3cccc4c(Cc5cnn(C6CCN(CC7(C(F)(F)F)CCC7)CC6)c5)ccc2c34)C(=O)N1]

Yellow solid, 179.0 mg, 58.52% yield, 98.70% purity. ¹H NMR (400 MHz, DMSO-d6) δ 11.11 (s, 1H), 8.37 (d, J=8.2 Hz, 1H), 8.08 (d, J=6.88 Hz, 1H), 7.83 (t, J=7.62 Hz, 1H), 7.58 (s, 1H), 7.35 (d, J=7.32 Hz, 1H), 7.29 (s, 1H), 7.07 (d, J=7.24 Hz, 1H), 5.43 (dd, J=12.2, 4.72 Hz, 1H), 4.17 (s, 2H), 4.03-4.00 (m, 1H), 2.95-2.91 (m, 1H), 2.84-2.81 (m, 2H), 2.77-2.72 (m, 1H), 2.66-2.62 (m, 1H), 2.56 (s, 2H), 2.28-2.21 (m, 2H), 2.19-2.01 (m, 5H), 1.93-1.86 (m, 6H); LC MS: ES+580.5.

Compound 58

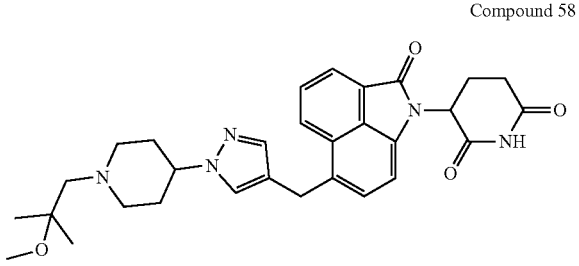 [SMILES: COC(C)(C)CN1CCC(n2cc(Cc3ccc4c5c(cccc35)C(=O)N4C3CCC(=O)NC3=O)cn2)CC1]

Yellow solid, 75.0 mg, 54.65% yield, 96.49% purity. ¹H NMR (400 MHz, DMSO-d6) δ 11.11 (s, 1H), 8.37 (d, J=8.28 Hz, 1H), 8.08 (d, J=6.6 Hz, 1H), 7.83 (t, J=7.72 Hz, 1H), 7.57 (s, 1H), 7.35 (d, J=7.24 Hz, 1H), 7.28 (s, 1H), 7.07 (d, J=7.16 Hz, 1H), 5.45-5.42 (m, 1H), 4.17 (s, 2H), 3.98-3.97 (m, 1H), 3.07 (s, 3H), 2.96-2.94 (m, 3H), 2.76-2.62 (m, 2H), 2.26 (s, 2H), 2.18-2.15 (m, 2H), 2.09-2.08 (m, 1H), 1.86-1.83 (m, 4H), 1.07 (s, 6H); LC MS: ES+ 530.3.

Compound 59

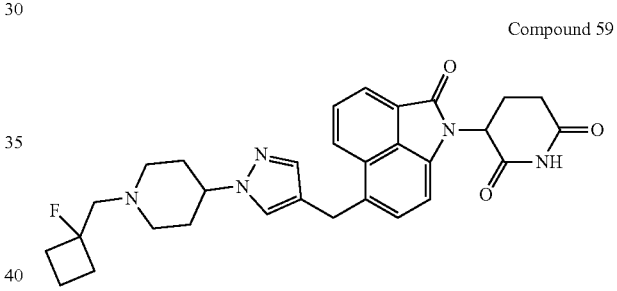

Yellow solid, 20.0 mg, 14.35% yield, 95.02% purity. ¹H NMR (400 MHz, DMSO-d6) δ 11.11 (s, 1H), 8.37 (d, J=8.2 Hz, 1H), 8.08 (d, J=6.92 Hz, 1H), 7.83 (t, J=7.62 Hz, 1H), 7.58 (s, 1H), 7.35 (d, J=7.32 Hz, 1H), 7.29 (s, 1H), 7.07 (d, J=7.28 Hz, 1H), 4.17 (s, 2H), 4.01-3.98 (m, 1H), 2.98-2.91 (m, 3H), 2.77-2.72 (m, 1H), 2.67-2.62 (m, 2H), 2.55-2.50 (m, 2H), 2.19-2.04 (m, 6H), 1.88-1.84 (m, 4H), 1.73-1.71 (m, 1H), 1.47-1.45 (m, 1H); LC MS: ES+ 530.2.

Compound 60

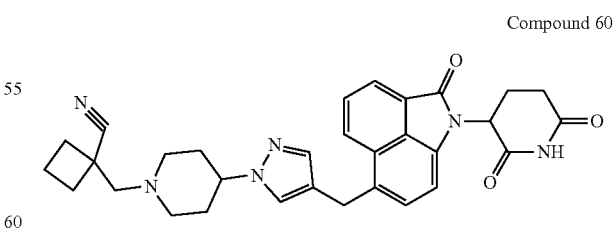

Yellow solid, 30 mg, 20.51% yield, 99.39% purity. ¹H NMR (400 MHz, DMSO-d6) δ 11.11 (s, 1H), 8.38 (d, J=8.24 Hz, 1H), 8.08 (d, J=6.96 Hz, 1H), 7.83 (t, J=7.62 Hz, 1H), 7.59 (s, 1H), 7.35 (d, J=7.32 Hz, 1H), 7.29 (s, 1H), 7.07 (d, J=7.32 Hz, 1H), 5.43 (dd, J=12.52, 4.64 Hz, 1H), 4.17 (s, 2H), 4.04-4.00 (m, 1H), 2.96-2.89 (m, 3H), 2.77-2.72 (m, 1H), 2.65-2.62 (m, 3H), 2.38-2.32 (m, 2H), 2.27-2.20 (m, 2H), 2.18-2.05 (m, 4H), 1.98-1.96 (m, 1H), 1.87-1.85 (m, 4H); LC MS: ES+ 537.6.

(m, 1H), 2.33-2.27 (m, 2H), 2.05-2.04 (m, 3H), 1.89-1.83 (m, 4H), 1.60-1.58 (m, 1H), 0.83 (s, 9H); LC MS: ES+ 514.7.

Compound 61

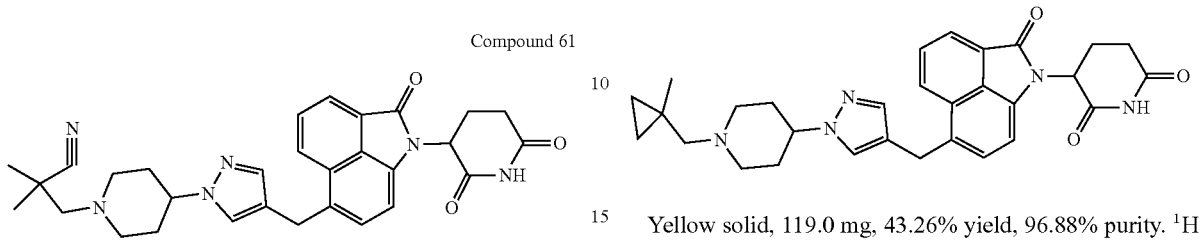

Yellow solid, 15.0 mg, 5.19% yield, 94.51% purity. $^1$H NMR (400 MHz, DMSO-d6) δ 11.11 (s, 1H), 8.38 (d, J=8.28 Hz, 1H), 8.08 (d, J=6.96 Hz, 1H), 7.83 (t, J=7.6 Hz, 1H), 7.58 (s, 1H), 7.36 (d, J=7.36 Hz, 1H), 7.30 (s, 1H), 7.07 (d, J=7.24 Hz, 1H), 5.43 (dd, J=13.04, 5.28 Hz, 1H), 4.18 (s, 2H), 4.03-4.01 (m, 1H), 2.96-2.93 (m, 3H), 2.77-2.62 (m, 2H), 2.45 (s, 2H), 2.42-2.32 (m, 2H), 2.09-2.06 (m, 1H), 1.90-1.85 (m, 4H), 1.25 (s, 6H); LC MS: ES+ 525.5.

Compound 64

Yellow solid, 119.0 mg, 43.26% yield, 96.88% purity. $^1$H NMR (400 MHz, DMSO-d6) δ 11.11 (s, 1H), 8.37 (d, J=8.16 Hz, 1H), 8.08 (d, J=6.88 Hz, 1H), 7.83 (t, J=7.64 Hz, 1H), 7.58 (s, 1H), 7.35 (d, J=7.24 Hz, 1H), 7.29 (s, 1H), 7.07 (d, J=7.24 Hz, 1H), 5.44-5.42 (m, 1H), 4.18 (s, 2H), 4.00-3.99 (m, 1H), 3.00-2.91 (m, 3H), 2.80-2.73 (m, 1H), 2.67-2.62 (m, 1H), 2.11-2.10 (m, 3H), 1.91-1.88 (m, 6H), 1.01 (s, 3H), 0.26-0.21 (m, 4H); LC MS: ES+ 512.3.

Compound 62

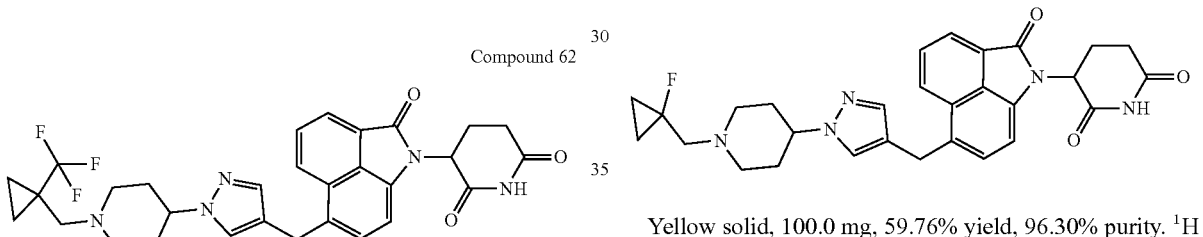

Yellow solid, 120.0 mg, 60.46% yield, 95% purity. $^1$H NMR (400 MHz, DMSO-d6) δ 11.11 (s, 1H), 8.37 (d, J=8.08 Hz, 1H), 8.08 (d, J=6.0 Hz, 1H), 7.85-7.83 (m, 1H), 7.58 (s, 1H), 7.35 (d, J=7.0 Hz, 1H), 7.29 (s, 1H), 7.07 (d, J=6.52 Hz, 1H), 5.44-5.42 (m, 1H), 4.17 (s, 2H), 4.02-4.01 (m, 1H), 2.95-2.93 (m, 3H), 2.76-2.72 (m, 1H), 2.66-2.62 (m, 1H), 2.06-1.99 (m, 3H), 1.88-1.86 (m, 4H), 0.94 (s, 2H), 0.70 (s, 2H); LC MS: ES+ 566.4.

Compound 65

Yellow solid, 100.0 mg, 59.76% yield, 96.30% purity. $^1$H NMR (400 MHz, DMSO-d6) δ 11.11 (s, 1H), 8.37 (d, J=8.24 Hz, 1H), 8.08 (d, J=6.96 Hz, 1H), 7.83 (t, J=7.6 Hz, 1H), 7.59 (s, 1H), 7.35 (d, J=7.32 Hz, 1H), 7.30 (s, 1H), 7.07 (d, J=7.28 Hz, 1H), 5.43 (dd, J=12.6, 5.0 Hz, 1H), 4.18 (s, 2H), 4.03-4.01 (m, 1H), 3.12-2.90 (m, 3H), 2.80-2.62 (m, 4H), 2.22-2.19 (m, 2H), 2.09-2.07 (m, 1H), 1.90-1.88 (m, 4H), 0.99-0.95 (m, 2H), 0.66-0.65 (m, 2H); LC MS: ES+ 516.3.

Compound 63

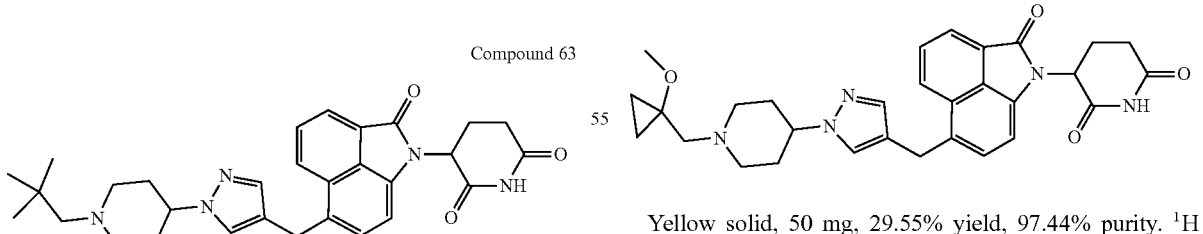

Yellow solid, 75.0 mg, 42.55% yield, 97.14% purity. $^1$H NMR (400 MHz, DMSO-d6) δ 11.12 (s, 1H), 8.38 (d, J=8.32 Hz, 1H), 8.08 (d, J=6.76 Hz, 1H), 7.83 (t, J=7.54 Hz, 1H), 7.57 (s, 1H), 7.36 (d, J=7.64 Hz, 1H), 7.29 (s, 1H), 7.07 (d, J=7.24 Hz, 1H), 5.44-5.42 (m, 1H), 4.17 (s, 2H), 3.99-3.97 (m, 1H), 2.99-2.91 (m, 1H), 2.81-2.77 (m, 2H), 2.67-2.62

Compound 66

Yellow solid, 50 mg, 29.55% yield, 97.44% purity. $^1$H NMR (400 MHz, DMSO-d6) δ 11.11 (s, 1H), 8.38 (d, J=8.24 Hz, 1H), 8.08 (d, J=6.92 Hz, 1H), 7.83 (t, J=7.66 Hz, 1H), 7.59 (s, 1H), 7.35 (d, J=7.28 Hz, 1H), 7.29 (s, 1H), 7.07 (d, J=7.28 Hz, 1H), 5.43 (dd, J=12.64, 4.88 Hz, 1H), 4.18 (s, 2H), 4.01-3.99 (m, 1H), 3.20 (s, 3H), 3.13-3.05 (m, 2H), 3.03-2.90 (m, 1H), 2.80-2.62 (m, 2H), 2.50-2.48 (m, 2H), 2.10-2.07 (m, 3H), 1.88-1.85 (m, 4H), 0.67 (s, 2H), 0.42 (s, 2H); LC MS: ES+ 528.2.

Example 33. Synthesis of-3-[6-[[1-[1-(1-methylcyclobutanecarbonyl)-4-piperidyl]pyrazol-4-yl]methyl]-2-oxo-benzo[cd]indol-1-yl]piperidine-2,6-dione (Compound 67) and 3-[6-[[1-[1-(1-methylcyclobutanecarbonyl)-4-piperidyl]pyrazol-4-yl]methyl]-2-oxo-benzo[cd]indol-1-yl]piperidine-2,6-dione (Compound 68)

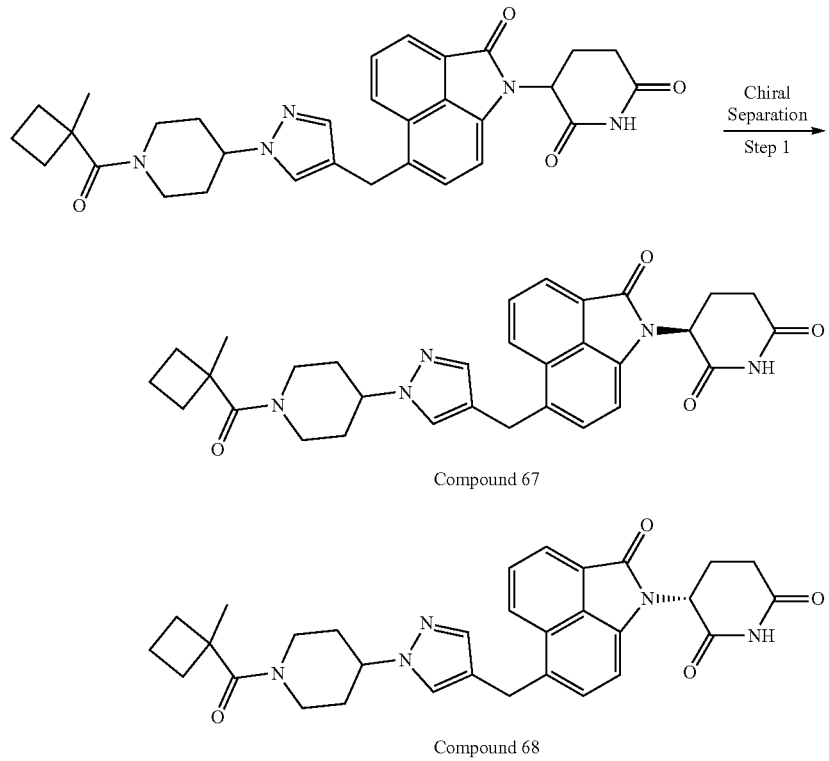

Compound 67

Compound 68

Step 1: Synthesis of 3-[6-[[1-[1-(1-methylcyclobutanecarbonyl)-4-piperidyl]pyrazol-4-yl]methyl]-2-oxo-benzo[cd]indol-1-yl]piperidine-2,6-dione and 3-[6-1[1-[1-(1-methylcyclobutanecarbonyl)-4-piperidyl]pyrazol-4-yl]methyl]-2-oxo-benzo[cd]indol-1-yl]piperidine-2,6-dione: Racemic 300 mg of 3-(6-((1-(1-(1-methylcyclobutane-1-carbonyl)piperidin-4-yl)-1H-pyrazol-4-yl)methyl)-2-oxobenzo[cd]indol-1(2H)-yl)piperidine-2,6-dione was separated to its enantiomers by Reverse phase prep HPLC to afford 3-[6-[[1-[1-(1-methylcyclobutanecarbonyl)-4-piperidyl]pyrazol-4-yl]methyl]-2-oxo-benzo[cd]indol-1-yl]piperidine-2,6-dione Compound 67 (100.0 mg, 33% yield, eluted as first fraction, % ee 99) and 3-[6-[[1-[1-(1-methylcyclobutanecarbonyl)-4-piperidyl]pyrazol-4-yl]methyl]-2-oxo-benzo[cd]indol-1-yl]piperidine-2,6-dione Compound 68 (85.0 mg, 28% yield, eluted as second fraction, % ee 99) as yellow solids. $^1$H NMR (400 MHz, DMSO-d6) δ 11.11 (s, 1H), 8.37 (d, J=8.24 Hz, 1H), 8.08 (d, J=6.96 Hz, 1H), 7.83 (t, J=7.6 Hz, 1H), 7.60 (s, 1H), 7.35 (d, J=7.28 Hz, 1H), 7.31 (s, 1H), 7.07 (d, J=7.2 Hz, 1H), 5.44-5.42 (m, 1H), 4.40-4.39 (m, 1H), 4.32-4.29 (m, 1H), 4.18 (s, 2H), 3.58-3.57 (m, 1H), 3.05-2.91 (m, 2H), 2.76-2.72 (m, 1H), 2.66-2.63 (m, 2H), 2.40-2.33 (m, 2H), 2.09-2.08 (m, 1H), 1.94-1.87 (m, 3H), 1.78-1.59 (m, 5H), 1.33 (s, 3H); LC MS: ES+ 540.5.

Example 34. Synthesis of 3-(6-((1-(4-methylpiperidin-4-yl)-1H-pyrazol-4-yl)methyl)-2-oxobenzo[cd]indol-1(2H)-yl)piperidine-2,6-dione hydrochloride (Compound 69)

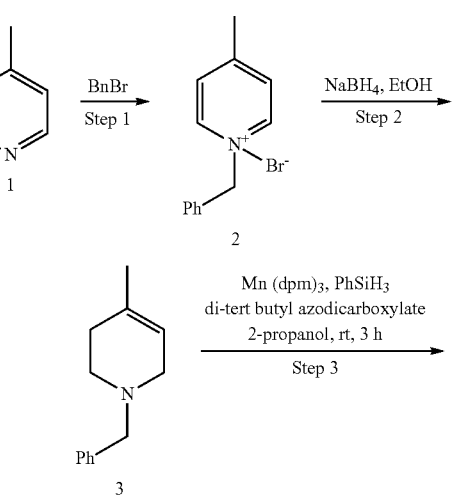

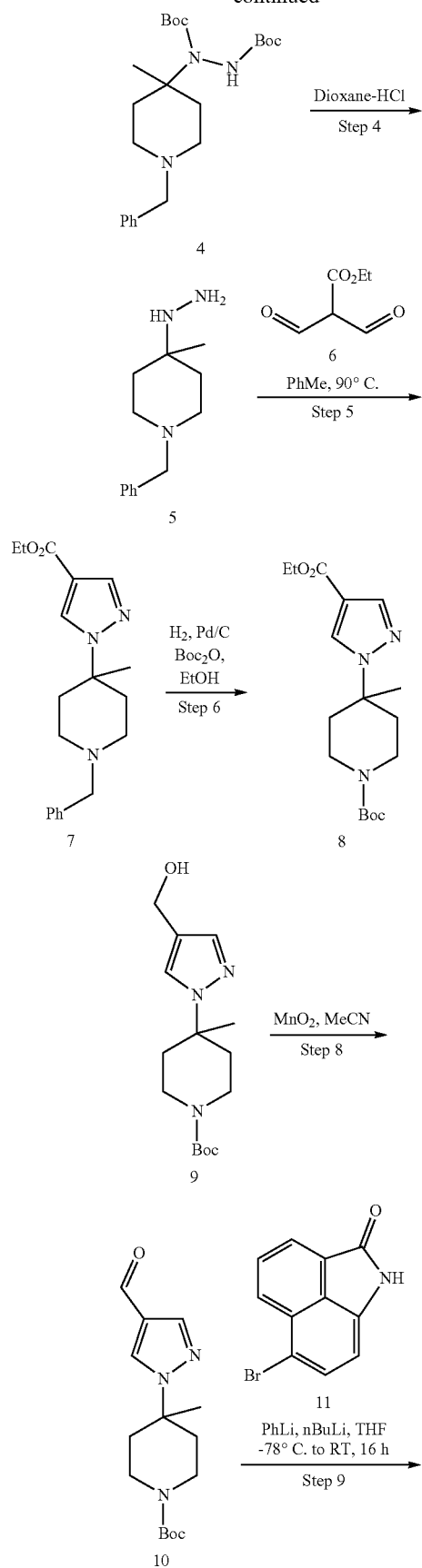
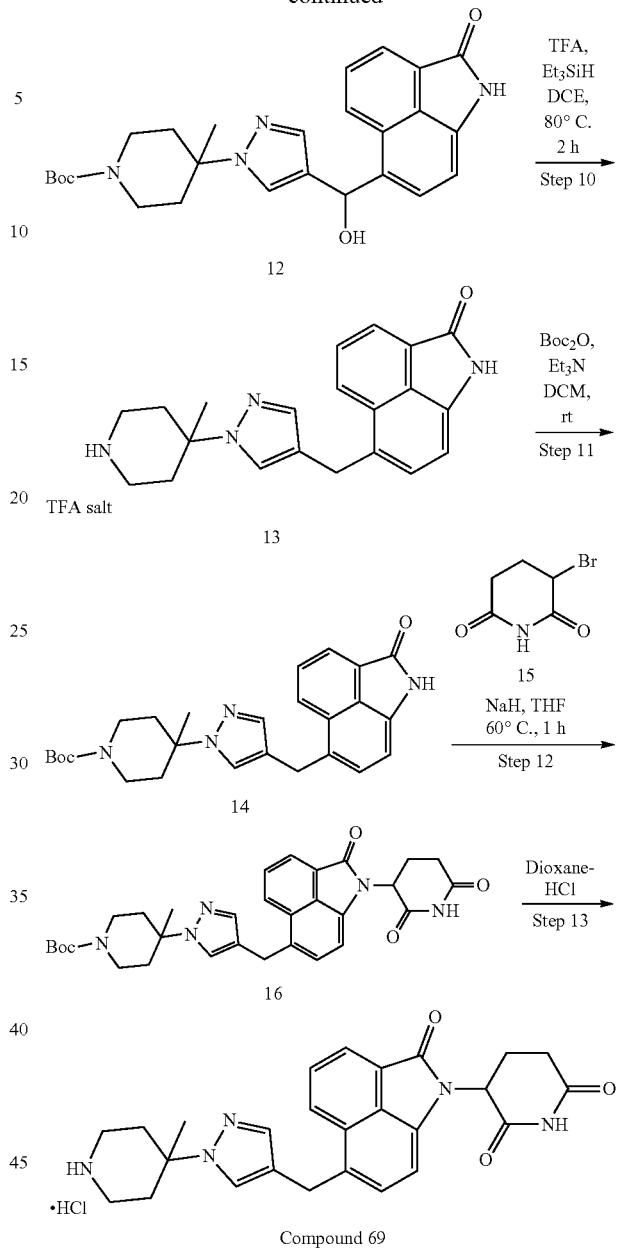

Step 1: Synthesis of 1-benzyl-1-bromo-4-methyl-pyridinium bromide (2): To the stirred solution of 4-methylpyridine (20 g, 214.76 mmol, 20.90 mL) in dry grade acetonitrile (100 mL), Benzyl bromide (44.08 g, 257.71 mmol, 30.61 mL) was added at rt and the resultant reaction mixture was heated at 100° C. for 12 hr. After completion of reaction (monitored by TLC), volatiles were removed under vacuum and the solid thus obtained was triturated with ethyl acetate and ether to obtain 1-benzyl-1-bromo-4-methyl-pyridine (2) (56 g, 211.99 mmol, 98.71% yield) as yellowish solid. LC MS: ES+ 183.9.

Step 2: Synthesis of 1-benzyl-4-methyl-3,6-dihydro-2H-pyridine (3): To the stirred solution of 1-benzyl-1-bromo-4-methyl-pyridinium bromide (2) (56.0 g, 211.99 mmol) in mixed solvent of EtOH (72 mL) and Water (8 mL), Sodium borohydride (20.05 g, 529.98 mmol, 18.74 mL) was added portion wise at 0° C. After complete addition, reaction mass was stirred for 12 hr at ambient temperature. After completion of the reaction as monitored by LC MS, the reaction mixture was quenched with addition of water (30 mL) and ethanol was removed under reduced pressure. The aqueous part was extracted with ethyl acetate (2×200 ml). The combine organic part was dried over anhydrous $Na_2SO_4$ and concentrated under vacuum. The crude residue was purified by column chromatography (100-200 silica; 2% EtOAc in Hexane) to afford 1-benzyl-4-methyl-3,6-dihydro-2H-pyridine (3) (39.3 g, 209.85 mmol, 98.99% yield) yellow oil, LC MS: ES+ 187.8.

Step 3: Synthesis of tert-butyl N-(1-benzyl-4-methyl-4-piperidyl)-N-(tert-butoxycarbonylamino) carbamate (4): To a well degassed stirred solution of 1-benzyl-4-methyl-3,6-dihydro-2H-pyridine (3) (25.0 g, 133.49 mmol) in 2-propanol (20 mL), phenylsilane (14.44 g, 133.49 mmol, 16.45 mL) and [(Z)-1-tert-butyl-3-hydroxy-4,4-dimethyl-pent-2-enylidene]oxonium; manganese (1.61 g, 2.67 mmol) was added at 0° C. followed by tert-butyl-N-tert-butoxycarbonyliminocarbamate (46.11 g, 200.23 mmol) under nitrogen atmosphere. After complete addition, reaction mixture was stirred at same temperature for 6 hr. After completion of the reaction (monitored by TLC), reaction mass was evaporated and the crude thus obtained was purified by column chromatography (100-200 silica; 30% EtOAc in Hexane) to afford tert-butyl N-(1-benzyl-4-methyl-4-piperidyl)-N-(tert-butoxycarbonylamino)carbamate (4) (15 g, 35.75 mmol, 26.78% yield) as yellow sticky solid, LC MS: ES+ 420.0.

Step 4: Synthesis of (1-benzyl-4-methyl-4-piperidyl)hydrazine (5): 4M Dioxane-HCl (30 mL) was added to tert-butyl N-(1-benzyl-4-methyl-4-piperidyl)-N-(tert-butoxycarbonylamino)carbamate (4) (15.0 g, 35.75 mmol), at 0° C. and stirred for 8 hr at rt. After completion of reaction as evidenced from LCMS, volatiles were removed under vacuum. The crude thus obtained was dissolved in 10% MeOH in DCM and neutralized with Amberlyst-A21 resin. The solid polymer was filtered off and washed with 10% MeOH in DCM several times. The combined filtrate was concentrated under reduced pressure to afford (1-benzyl-4-methyl-4-piperidyl)hydrazine (5) (7.4 g, 33.74 mmol, 94.37% yield, 90% purity) as yellow solid, LC MS: ES+ 220.0.

Step 5: Synthesis of ethyl 1-(1-benzyl-4-methyl-4-piperidyl)pyrazole-4-carboxylate (7): To a stirred solution of ethyl 2-formyl-3-oxo-propanoate (6) (4.73 g, 32.83 mmol) intoluene (15 mL) crude (1-benzyl-4-methyl-4-piperidyl)hydrazine (5) (6.0 g, 27.36 mmol) was added at 0° C. and heated for 12 hr at 90° C. After completion of the reaction (monitored by LC MS) all the volatiles were evaporated and crude thus obtained was purified by column chromatography (100-200 Silica; 30% EtOAc in Hexane as eluent) to afford ethyl 1-(1-benzyl-4-methyl-4-piperidyl)pyrazole-4-carboxylate (7) (4.36 g, 13.33 mmol, 48.72% yield) as light yellow gum, LC MS: ES+ 328.3.

Step 6: Synthesis of tert-butyl 4-(4-ethoxycarbonylpyrazol-1-yl)-4-methyl-piperidine-1-carboxylate (8): To the stirred solution of ethyl 1-(1-benzyl-4-methyl-4-piperidyl)pyrazole-4-carboxylate (7) (6.0 g, 18.33 mmol) in EtOH (20 mL), tert-butoxycarbonyl tert-butyl carbonate (10.85 g, 49.73 mmol, 11.41 mL) and Triethylamine (7.55 g, 74.59 mmol, 10.40 mL) was added. Then the reaction mixture was degassed with Argon for 15 minutes followed by the addition of 20% Palladium on Carbon (moist) (2.93 g, 27.49 mmol) and the resultant reaction mixture was stirred under hydrogen atmosphere for 16 hr at RT. After completion of the reaction (monitored by TLC and LCMS), the reaction mixture was filtered through celite. The filtrate was then concentrated and purified by column chromatography (100-200 Silica; 2% Methanol in DCM) to afford the desired compound tert-butyl 4-(4-ethoxycarbonylpyrazol-1-yl)-4-methyl-piperidine-1-carboxylate (8) (4.8 g, 14.23 mmol, 57.22% yield, 99% purity) as brown gum, LC MS: ES+ 338.3.

Step 7: Synthesis of tert-butyl 4-[4-(hydroxymethyl)pyrazol-1-yl]-4-methyl-piperidine-1-carboxylate (9): To the stirred solution of tert-butyl 4-(4-ethoxycarbonylpyrazol-1-yl)-4-methyl-piperidine-1-carboxylate (8) (4.8 g, 10.67 mmol) in THF (50 mL), Diisobutylaluminum hydride (10.12 g, 71.13 mmol, 60 mL) was added drop wise at −78° C. and stirred for 1 hr at rt under N2 atmosphere. After complete consumption, as evidenced from TLC, reaction mass was diluted with ethyl acetate (300 mL) and quenched with water (50 mL). Organic phase was separated, dried over anhydrous $Na_2SO_4$ and concentrated under reduced pressure to afford tert-butyl 4-[4-(hydroxymethyl)pyrazol-1-yl]-4-methyl-piperidine-1-carboxylate (9) (4.05 g, 13.72 mmol, 96.43% yield) as brown gum which was carried forward to the next step without any further purification, LC MS: ES+ 296.2.

Step 8: Synthesis of tert-butyl 4-(4-formylpyrazol-1-yl)-4-methyl-piperidine-1-carboxylate (10): To a stirred solution of tert-butyl 4-[4-(hydroxymethyl)pyrazol-1-yl]-4-methyl-piperidine-1-carboxylate (9) (4.0 g, 13.54 mmol) in Acetonitrile (20 mL), was added activated MnO2 (9.42 g, 108.34 mmol) and stirred at RT for 24 hr. After completion of the reaction (monitored by TLC and LC MS), reaction mass was filtered through celite and the filtrate was concentrated under reduced pressure. Crude mass was purified by column chromatography (100-200 silica; 2-3% MeOH in DCM as eluent) to afford tert-butyl 4-(4-formylpyrazol-1-yl)-4-methyl-piperidine-1-carboxylate (10) (3.0 g, 10.23 mmol, 75.52% yield) as colorless sticky soli. LC MS: ES+ 294.3.

Step 9: Synthesis of tert-butyl 4-(4-(hydroxy(2-oxo-1,2-dihydrobenzo[cd]indol-6-yl)methyl)-1H-pyrazol-1-yl)-4-methylpiperidine-1-carboxylate: To the stirred solution of 6-bromo-1H-benzo[cd]indol-2-one 11 (4.3 g, 17.33 mmol) in THF (50.0 mL) was added Phenyllithium, typically 1.9M in di-n-butyl ether (1.8 M, 9.63 mL) at −78° C. and the reaction mixture was stirred at the same temperature for 1 hour followed by the addition of Butyllithium (1.9 M, 10.04 mL) at −78° C. and after the addition was complete the temperature was allowed to increase to −40° C. and the reaction mixture was stirred at the same temperature for 30 minutes followed by the addition of tert-butyl 4-(4-formylpyrazol-1-yl)-4-methyl-piperidine-1-carboxylate 10 (5.08 g, 17.33 mmol) in THF (50.0 mL) at −78° C. and then the reaction mixture was allowed to warm to room temperature and was continued for 16 hours. Reaction mixture was quenched with ammonium chloride solution, diluted with ethyl acetate, washed with water and the organic fraction was separated. It was then dried over anhydrous sodium sulphate and evaporated under reduced pressure to obtain the crude compound which was purified by flash chromatography using 0-5% MeOH-DCM to afford tert-butyl 4-[4-[hydroxy-(2-oxo-1H-benzo[cd]indol-6-yl)methyl]pyrazol-1-yl]-4-methyl-piperidine-1-carboxylate 12 (1.5 g, 2.26 mmol, 13.02% yield, 69.6% purity) as brown solid. LC MS: ES+ 462.9.

Step 10: Synthesis of 2,2,2-trifluoroacetaldehyde compound with 6-((1-(4-methylpiperidin-4-yl)-1H-pyrazol-4-yl)methyl)benzo[cd]indol-2(1H)-one (1:1): To the stirred solution of tert-butyl 4-[4-[hydroxy-(2-oxo-1H-benzo[cd]indol-6-yl)methyl]pyrazol-1-yl]-4-methyl-piperidine-1-carboxylate 12 (1.43 g, 3.09 mmol) in DCE (6 mL) was added Triethylsilane (1.44 g, 12.37 mmol, 1.98 mL), Trifluoroacetic acid (2.82 g, 24.73 mmol, 1.91 mL) and the reaction mixture was heated at 80° C. for 2 hours in a sealed tube. The solvent in the reaction mixture was evaporated under reduced pressure and triturated with ether to obtain [4-methyl-4-[4-[(2-oxo-1H-benzo[cd]indol-6-yl)methyl]pyrazol-1-yl]-1-piperidyl] 2,2,2-trifluoroacetate 13 (1.5 g, 1.92 mmol, 62.24% yield, 73.7% purity) as crude which was used directly in the next step. LC MS: ES+ 347.2.

Step 11: Synthesis of tert-butyl 4-methyl-4-(4-((2-oxo-1,2-dihydrobenzo[cd]indol-6-yl)methyl)-1H-pyrazol-1-yl)piperidine-1-carboxylate: To a stirred solution of [4-methyl-4-[4-[(2-oxo-1H-benzo[cd]indol-6-yl)methyl]pyrazol-1-yl]-1-piperidyl] 2,2,2-trifluoroacetate 13 (1.4 g, 3.04 mmol) in DCM (10.0 mL) was added Triethylamine (923.01 mg, 9.12 mmol, 1.27 mL) at 0° C. followed by the addition of Di-tert-butyl dicarbonate (995.39 mg, 4.56 mmol, 1.05 mL) and the reaction was stirred at room temperature for 16 hours. The reaction mixture was diluted with ethyl acetate, washed with water and the organic fraction was separated. It was dried over anhydrous sodium sulphate and evaporated under reduced pressure to obtain the crude compound which was purified by flash chromatography using 0-5% MeOH-DCM to afford tert-butyl 4-methyl-4-[4-[(2-oxo-1H-benzo[cd]indol-6-yl)methyl]pyrazol-1-yl]piperidine-1-carboxylate 14 (800.0 mg, 1.67 mmol, 54.80% yield, 93% purity) as brown solid. LC MS: ES+ 447.3.

Step 12: Synthesis of tert-butyl 4-(4-((1-(2,6-dioxopiperidin-3-yl)-2-oxo-1,2-dihydrobenzo[cd]indol-6-yl)methyl)-1H-pyrazol-1-yl)-4-methylpiperidine-1-carboxylate: To the stirred solution of tert-butyl 4-methyl-4-[4-[(2-oxo-1H-benzo[cd]indol-6-yl)methyl]pyrazol-1-yl]piperidine-1-carboxylate 14 (800.0 mg, 1.79 mmol) in THF (20 mL) was added Sodium hydride (in oil dispersion) 60% dispersion in mineral oil (686.46 mg, 17.92 mmol, 60% purity) at cold condition and the reaction mixture was stirred at room temperature for 10 minutes followed by the addition of 3-bromopiperidine-2,6-dione 15 (1.72 g, 8.96 mmol) portion wise. It was then stirred at room temperature for 10 minutes and heated at 70° C. for 30 minutes. The reaction mixture was then diluted with ethyl acetate, washed with cold water and the organic fraction was separated. It was then dried over anhydrous sodium sulphate and evaporated under reduced pressure to obtain the crude which was washed with ether and pentane to afford tert-butyl 4-[4-[[1-(2,6-dioxo-3-piperidyl)-2-oxo-benzo[cd]indol-6-yl]methyl]pyrazol-1-yl]-4-methyl-piperidine-1-carboxylate 16 (780.0 mg, 1.39 mmol, 77.76% yield, 99.6% purity) as yellow solid. LC MS: ES+ 558.0.

Step 13: Synthesis of 3-(6-((1-(4-methylpiperidin-4-yl)-1H-pyrazol-4-yl)methyl)-2-oxobenzo[cd]indol-1(2H)-yl)piperidine-2,6-dione hydrochloride: To the stirred solution of tert-butyl 4-[4-[[1-(2,6-dioxo-3-piperidyl)-2-oxo-benzo[cd]indol-6-yl]methyl]pyrazol-1-yl]-4-methyl-piperidine-1-carboxylate 16 (780.0 mg, 1.40 mmol) in Dioxane (5 mL) was added Hydrochloric acid in dioxane (1.40 mmol, 10 mL) and the reaction mixture was stirred at room temperature for 2 hours. Solvent in the reaction mixture was evaporated under reduced pressure to obtain a yellow solid which was washed with ether and pentane to afford 3-[6-[[1-(1-chloro-4-methyl-4-piperidyl)pyrazol-4-yl]methyl]-2-oxo-benzo[cd]indol-1-yl]piperidine-2,6-dione Compound 69 (690.0 mg, 1.21 mmol, 86.30% yield, 92.8% purity) as yellow solid. LC MS: ES+ 458.3.

Example 35. General Synthesis of Compound 70-Compound 93

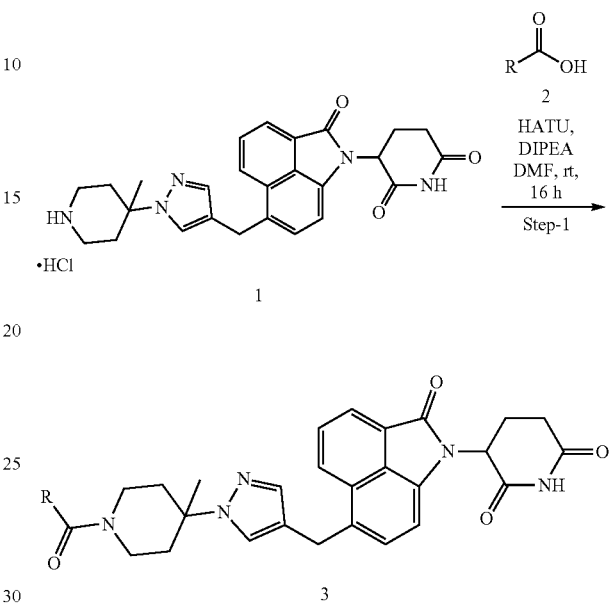

To an equi-molar mixture of Amine and Acid DMF (6 mL/mmol) were added HATU (1.5 equiv) and DIPEA (5.0 equiv) at 0° C. The resulting solution was stirred at ambient temperature for 16 hours. The reaction mixture was then diluted with Ethyl acetate and washed with aqueous NaHCO₃ solution, water (×3) and brine. The organic layer was then dried over anhydrous Na₂SO₄ and concentrated under reduced pressure. Crude mass was then purified by CombiFlash ISCO column, eluting with 2% methanol in DCM to afford 3.

Compound 70

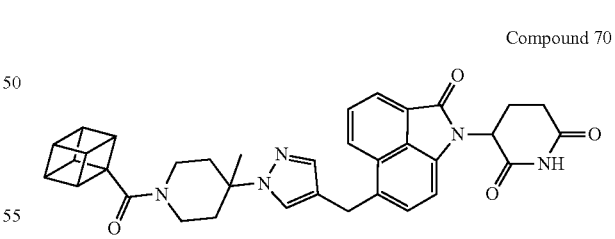

Yellow solid, 30.0 mg, 63.04% yield, 100% purity. $^1$H NMR (400 MHz, DMSO-d6) δ 11.11 (s, 1H), 8.39 (d, J=8.04 Hz, 1H), 8.08 (d, J=7.0 Hz, 1H), 7.85-7.81 (m, 2H), 7.36-7.33 (m, 2H), 7.07 (d, J=7.2 Hz, 1H), 5.45-5.42 (m, 1H), 4.20 (s, 2H), 4.15 (s, 3H), 3.96 (s, 4H), 3.74-3.70 (m, 1H), 3.22-3.18 (m, 1H), 3.05-2.91 (m, 3H), 2.77-2.72 (m, 1H), 2.67-2.62 (m, 1H), 2.41-2.27 (m, 2H), 2.08-2.07 (m, 1H), 1.83-1.82 (m, 1H), 1.72-1.71 (m, 1H), 1.34 (s, 3H); LC MS: ES+ 588.5.

Compound 71

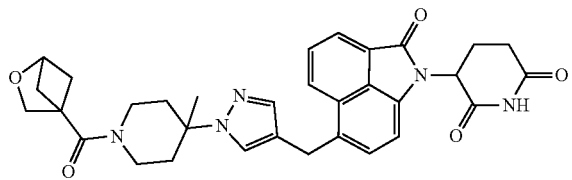

Yellow solid 40.0 mg, 57.30% yield, 98.76% purity. $^1$H NMR (400 MHz, DMSO-d6) δ 11.11 (s, 1H), 8.39 (d, J=8.24 Hz, 1H), 8.08 (d, J=6.92 Hz, 1H), 7.83 (t, J=7.64 Hz, 1H), 7.78 (s, 1H), 7.36-7.33 (m, 2H), 7.07 (d, J=7.32 Hz, 1H), 5.43 (dd, J=12.8, 5.2 Hz, 1H), 4.39 (s, 1H), 4.20 (s, 2H), 3.75-3.71 (m, 1H), 3.64 (s, 2H), 3.43-3.41 (m, 1H), 3.14-3.12 (m, 2H), 2.95-2.90 (m, 1H), 2.77-2.72 (m, 1H), 2.67-2.62 (m, 1H), 2.33-2.29 (m, 2H), 2.09-2.02 (m, 3H), 1.77-1.70 (m, 4H), 1.35 (s, 3H); LC MS: ES+ 568.5.

Compound 72

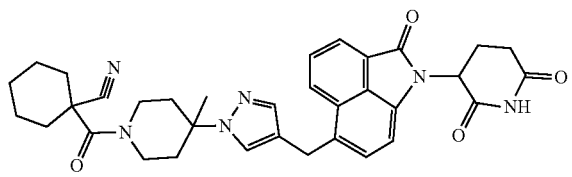

Yellow solid, 35 mg, 47.95% yield, 98.63% purity. $^1$H NMR (400 MHz, DMSO-d6) δ 11.10 (s, 1H), 8.39 (d, J=8.28 Hz, 1H), 8.08 (d, J=7.0 Hz, 1H), 7.85-7.80 (m, 2H), 7.36-7.34 (m, 2H), 7.07 (d, J=7.2 Hz, 1H), 5.43 (dd, J=12.8, 5.2 Hz, 1H), 4.21 (s, 2H), 3.80-3.78 (m, 2H), 2.95-2.88 (m, 2H), 2.76-2.72 (m, 1H), 2.67-2.62 (m, 1H), 2.36-2.34 (m, 2H), 2.09-2.07 (m, 1H), 2.02-1.98 (m, 2H), 1.82-1.80 (m, 2H), 1.76-1.62 (m, 5H), 1.54-1.50 (m, 2H), 1.38 (s, 3H), 1.24-1.18 (m, 2H); LC MS: ES+ 593.3.

Compound 73

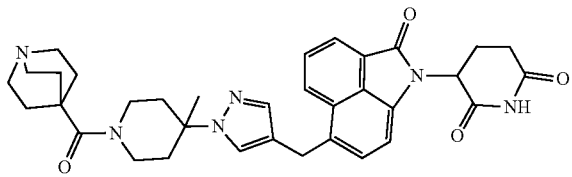

Yellow solid, 20 mg, 22.55% yield, 95% purity. $^1$H NMR (400 MHz, DMSO-d6) δ 11.11 (s, 1H), 8.39 (d, J=8.08 Hz, 1H), 8.08 (d, J=6.56 Hz, 1H), 7.83 (t, J=7.48 Hz, 1H), 7.76 (s, 1H), 7.36-7.33 (m, 2H), 7.07 (d, J=7.48 Hz, 1H), 5.45-5.42 (m, 1H), 4.20 (s, 2H), 3.76-3.74 (m, 2H), 3.54-3.52 (m, 1H), 3.27-3.25 (m, 2H), 3.14-3.01 (m, 2H), 2.86-2.84 (m, 5H), 2.32-2.25 (m, 2H), 2.10-2.07 (m, 2H), 1.77-1.75 (m, 7H), 1.36 (s, 3H); LC MS: ES+ 595.3.

Compound 74

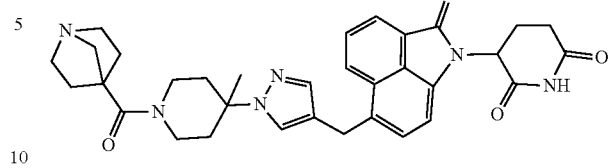

Yellow solid, 21 mg, 29.72% yield, 99.82% purity. $^1$H NMR (400 MHz, DMSO-d6) δ 11.11 (s, 1H), 8.39 (d, J=8.6 Hz, 1H), 8.08 (d, J=7.2 Hz, 1H), 7.83 (t, J=7.66 Hz, 1H), 7.78 (s, 1H), 7.36-7.34 (m, 2H), 7.07 (d, J=6.64 Hz, 1H), 5.45-5.42 (m, 1H), 4.21 (s, 2H), 3.70-3.69 (m, 2H), 3.31-3.24 (m, 3H), 3.11-3.09 (m, 2H), 2.96-2.92 (m, 1H), 2.85-2.84 (m, 4H), 2.77-2.73 (m, 1H), 2.67-2.62 (m, 1H), 2.33-2.26 (m, 2H), 2.09-2.08 (m, 1H), 1.85-1.83 (m, 3H), 1.75-1.74 (m, 2H), 1.36 (s, 3H); LC MS: ES+ 581.6.

Compound 75

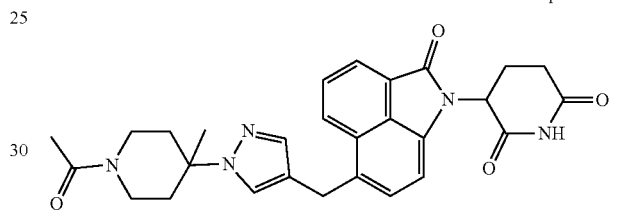

Yellow solid, 60.0 mg, 70.33% yield, 99.57% purity. $^1$H NMR (400 MHz, DMSO-d6) δ 11.09 (s, 1H), 8.36 (d, J=8.24 Hz, 1H), 8.06 (d, J=6.92 Hz, 1H), 7.80 (t, J=7.56 Hz, 1H), 7.76 (s, 1H), 7.33-7.31 (m, 2H), 7.05 (d, J=7.36 Hz, 1H), 5.44-5.39 (m, 1H), 4.18 (s, 2H), 3.68-3.64 (m, 1H), 3.47-3.45 (m, 1H), 3.17-3.12 (m, 1H), 3.07-3.02 (m, 1H), 2.94-2.89 (m, 1H), 2.74-2.70 (m, 1H), 2.65-2.59 (m, 1H), 2.31-2.29 (m, 1H), 2.23-2.20 (m, 1H), 2.07-2.05 (m, 1H), 1.94 (s, 3H), 1.79-1.73 (m, 1H), 1.69-1.63 (m, 1H), 1.32 (s, 3H); LC MS: ES+ 500.2.

Compound 76

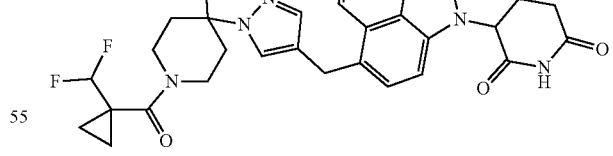

Yellow solid, 13 mg, 30.28% yield, 95% purity. $^1$H NMR (400 MHz, DMSO-d6) δ 11.11 (s, 1H), 8.39 (d, J=8.24 Hz, 1H), 8.08 (d, J=6.96 Hz, 1H), 7.85-7.80 (m, 2H), 7.36-7.34 (m, 2H), 7.07 (d, J=7.28 Hz, 1H), 6.04-5.76 (m, 1H), 5.43 (dd, J=12.68, 5.0 Hz, 1H), 4.21 (s, 2H), 3.78-3.73 (m, 2H), 3.21-3.19 (m, 2H), 2.95-2.90 (m, 1H), 2.77-2.72 (m, 1H), 2.66-2.62 (m, 1H), 2.34-2.32 (m, 2H), 2.09-2.07 (m, 1H), 1.77-1.76 (m, 2H), 1.34 (s, 3H), 1.05-0.99 (m, 4H); LC MS: ES+576.5.

Compound 77

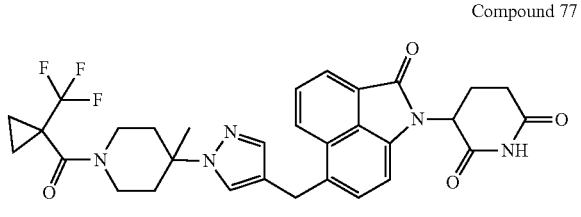 [SMILES: CC1(n2cc(Cc3ccc4c5c(cccc35)C(=O)N4C3CCC(=O)NC3=O)cn2)CCN(C(=O)C2(C(F)(F)F)CC2)CC1]

Yellow solid, 110.0 mg, 50.62% yield, 99.54% purity. $^1$H NMR (400 MHz, DMSO-d6) δ 11.11 (s, 1H), 8.39 (d, J=8.28 Hz, 1H), 8.08 (d, J=6.96 Hz, 1H), 7.82 (m, 2H), 7.36-7.34 (m, 2H), 7.07 (d, J=7.28 Hz, 1H), 5.43 (dd, J=12.72, 5.08 Hz, 1H), 4.21 (s, 2H), 3.79-3.75 (m, 2H), 3.29-3.22 (m, 2H), 2.96-2.88 (m, 1H), 2.77-2.72 (m, 1H), 2.67-2.62 (m, 1H), 2.36-2.32 (m, 2H), 2.09-2.07 (m, 1H), 1.79-1.78 (m, 2H), 1.35 (s, 3H), 1.28-1.26 (m, 2H), 1.22-1.17 (m, 2H); LC MS: ES+594.3.

Compound 78

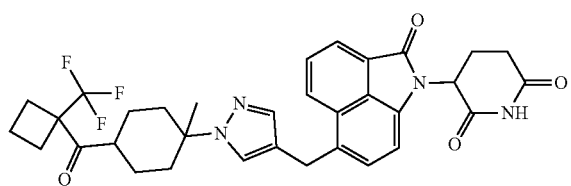

Yellow solid, 110.0 mg, 49.02% yield, 98.67% purity. $^1$H NMR (400 MHz, DMSO-d6) δ 11.11 (s, 1H), 8.39 (d, J=8.28 Hz, 1H), 8.08 (d, J=7.0 Hz, 1H), 7.82 (t, J=7.68 Hz, 1H), 7.79 (s, 1H), 7.36-7.34 (m, 2H), 7.07 (d, J=7.32 Hz, 1H), 5.43 (dd, J=12.72, 5.08 Hz, 1H), 4.21 (s, 2H), 3.79-3.78 (m, 1H), 3.13-3.06 (m, 2H), 2.95-2.88 (m, 1H), 2.77-2.72 (m, 1H), 2.69-2.61 (m, 4H), 2.41-2.39 (m, 2H), 2.33-2.31 (m, 2H), 2.10-2.07 (m, 1H), 1.94-1.91 (m, 1H), 1.77-1.76 (m, 3H), 1.35 (s, 3H); LC MS: ES+ 608.3.

Compound 79

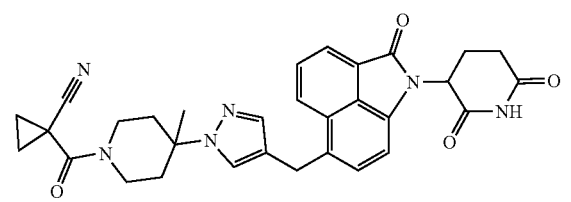

Yellow solid, 122.0 mg, 53.98% yield, 98.63% purity. $^1$H NMR (400 MHz, DMSO-d6) δ 11.11 (s, 1H), 8.39 (d, J=8.24 Hz, 1H), 8.08 (d, J=6.92 Hz, 1H), 7.86-7.82 (m, 2H), 7.36-7.31 (m, 2H), 7.07 (d, J=7.24 Hz, 1H), 5.45-5.42 (m, 1H), 4.21 (s, 2H), 3.81-3.80 (m, 2H), 3.19-3.18 (m, 1H), 2.97-2.88 (m, 1H), 2.80-2.62 (m, 1H), 2.39-2.38 (m, 2H), 2.08-2.07 (m, 2H), 1.85-1.84 (m, 2H), 1.56-1.47 (m, 4H), 1.37 (s, 3H); LC MS: ES+ 551.2.

Compound 80

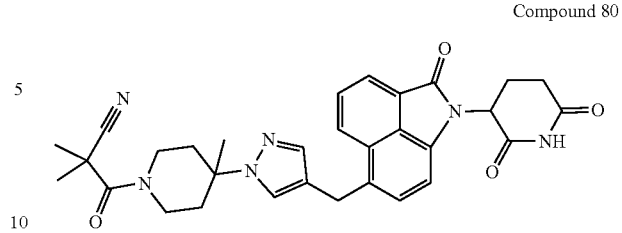

Yellow solid, 125.0 mg, 61.62% yield, 99.27% purity. $^1$H NMR (400 MHz, DMSO-d6) δ 11.11 (s, 1H), 8.39 (d, J=8.28 Hz, 1H), 8.08 (d, J=6.6 Hz, 1H), 7.85-7.82 (m, 2H), 7.36-7.35 (m, 2H), 7.07 (d, J=6.96 Hz, 1H), 5.45-5.42 (m, 1H), 4.21 (s, 2H), 3.81-3.80 (m, 2H), 3.24-3.23 (m, 2H), 2.98-2.91 (m, 1H), 2.80-2.57 (m, 2H), 2.38-2.37 (m, 2H), 2.08-2.07 (m, 1H), 1.83-1.82 (m, 2H), 1.50 (s, 6H), 1.38 (s, 3H); LC MS: ES+ 553.5.

Compound 81

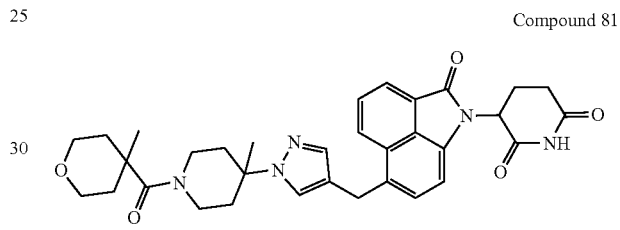

Yellow solid, 110.0 mg, 51.39% yield, 99.37% purity. $^1$H NMR (400 MHz, DMSO-d6) δ 11.11 (s, 1H), 8.39 (d, J=8.28 Hz, 1H), 7.82 (t, J=7.5 Hz, 1H), 7.77 (s, 1H), 7.36-7.33 (m, 2H), 7.07 (d, J=6.72 Hz, 1H), 5.45-5.42 (m, 1H), 4.20 (s, 2H), 3.70-3.69 (m, 2H), 3.59-3.57 (m, 2H), 3.46-3.38 (m, 2H), 3.27-3.23 (m, 2H), 2.98-2.90 (m, 1H), 2.80-2.72 (m, 1H), 2.67-2.62 (m, 1H), 2.29-2.26 (m, 2H), 2.08-2.07 (m, 1H), 2.00-1.87 (m, 2H), 1.76-1.72 (m, 2H), 1.42-1.39 (m, 2H), 1.35 (s, 3H), 1.21 (s, 3H); LC MS: ES+ 584.3.

Compound 82

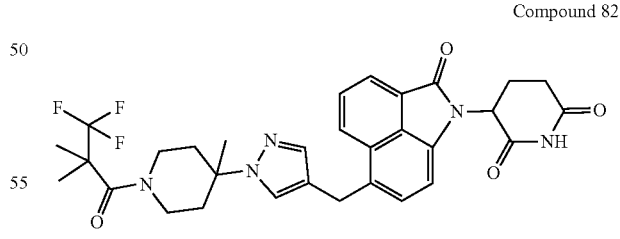

Yellow solid, 35.0 mg, 40.38% yield, 97.37% purity. $^1$H NMR (400 MHz, DMSO-d6) δ 11.08 (br s, 1H), 8.39 (d, J=8.24 Hz, 1H), 8.08 (d, J=6.96 Hz, 1H), 7.83 (t, J=7.64 Hz, 1H), 7.78 (s, 1H), 7.36-7.34 (m, 2H), 7.07 (d, J=7.32 Hz, 1H), 5.43 (dd, J=12.76, 5.2 Hz, 1H), 4.21 (s, 2H), 3.76-3.72 (m, 2H), 3.23-3.18 (m, 2H), 2.96-2.91 (m, 1H), 2.77-2.72 (m, 1H), 2.67-2.62 (m, 1H), 2.33-2.30 (m, 2H), 2.09-2.07 (m, 1H), 1.81-1.75 (m, 2H), 1.44 (s, 6H), 1.36 (s, 3H); LC MS: ES+ 596.2.

Compound 83

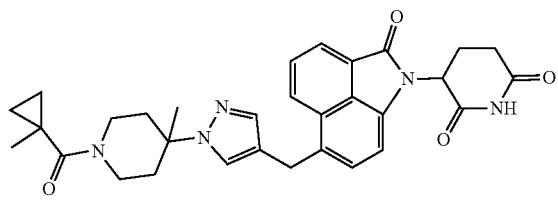

Yellow solid, 30.0 mg, 38.31% yield, 97.66% purity. $^1$H NMR (400 MHz, DMSO-d6) δ 11.10 (s, 1H), 8.39 (d, J=8.24 Hz, 1H), 8.08 (d, J=6.96 Hz, 1H), 7.83 (t, J=7.66 Hz, 1H), 7.79 (s, 1H), 7.36-7.34 (m, 2H), 7.07 (d, J=7.32 Hz, 1H), 5.43 (dd, J=12.8, 5.12 Hz, 1H), 4.21 (s, 2H), 3.74-3.70 (m, 2H), 3.23-3.21 (m, 2H), 2.95-2.90 (m, 1H), 2.77-2.72 (m, 1H), 2.67-2.62 (m, 1H), 2.32-2.28 (m, 2H), 2.09-2.07 (m, 1H), 1.78-1.73 (m, 2H), 1.35 (s, 3H), 1.18 (s, 3H), 0.77-0.75 (m, 2H), 0.51-0.49 (m, 2H); LC MS: ES+ 540.3.

Compound 84

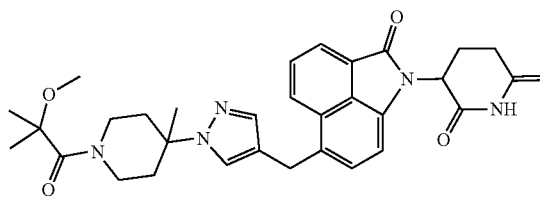

Yellow solid, 26.0 mg, 32.18% yield, 97.80% purity. $^1$H NMR (400 MHz, DMSO-d6) δ 11.09 (s, 1H), 8.39 (d, J=8.12 Hz, 1H), 8.08 (d, J=6.92 Hz, 1H), 7.85-7.80 (m, 2H), 7.37-7.34 (m, 2H), 7.07 (d, J=7.12 Hz, 1H), 5.45-5.42 (m, 1H), 4.21 (s, 2H), 4.08-4.07 (m, 1H), 3.74-3.73 (m, 1H), 3.55-3.54 (m, 1H), 3.20-3.15 (m, 1H), 3.10 (s, 3H), 2.98-2.91 (m, 1H), 2.76-2.72 (m, 1H), 2.67-2.56 (m, 1H), 2.34-2.32 (m, 2H), 2.09-2.08 (m, 1H), 1.78-1.77 (m, 2H), 1.36 (s, 3H), 1.29 (s, 6H); LC MS: ES+ 558.3.

Compound 85

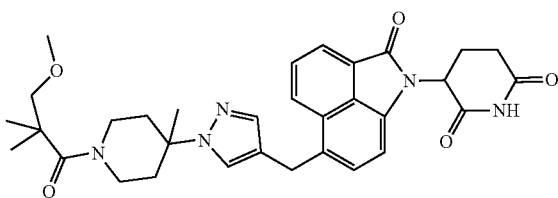

Yellow solid, 32.0 mg, 39.17% yield, 99.17% purity. $^1$H NMR (400 MHz, DMSO-d6) δ 11.11 (s, 1H), 8.39 (d, J=8.24 Hz, 1H), 8.08 (d, J=6.92 Hz, 1H), 7.82 (t, J=7.64 Hz, 1H), 7.77 (s, 1H), 7.36-7.33 (m, 2H), 7.07 (d, J=7.36 Hz, 1H), 5.45-5.42 (m, 1H), 4.20 (s, 2H), 3.72-3.67 (m, 2H), 3.33-3.29 (m, 3H), 3.22-3.18 (m, 4H), 2.96-2.94 (m, 1H), 2.80-2.72 (m, 1H), 2.66-2.62 (m, 1H), 2.29-2.25 (m, 2H), 2.09-2.07 (m, 2H), 1.74-1.69 (m, 2H), 1.35 (s, 3H), 1.15 (s, 6H); LC MS: ES+572.3.

Comound 86

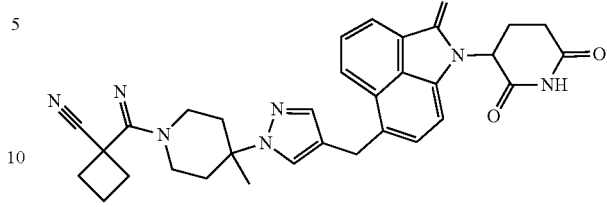

Yellow solid, 125.0 mg, 42.73% yield, 97.69% purity. $^1$H NMR (400 MHz, DMSO-d6) δ 11.11 (s, 1H), 8.39 (d, J=8.24 Hz, 1H), 8.08 (d, J=7.0 Hz, 1H), 7.85-7.80 (m, 2H), 7.36-7.34 (m, 2H), 7.07 (d, J=7.28 Hz, 1H), 5.43 (dd, J=12.84, 5.2 Hz, 1H), 4.21 (s, 2H), 3.80-3.75 (m, 1H), 3.45-3.42 (m, 1H), 3.18-3.14 (m, 2H), 2.96-2.91 (m, 1H), 2.76-2.62 (m, 4H), 2.57-2.54 (m, 2H), 2.41-2.32 (m, 2H), 2.11-2.07 (m, 2H), 1.87-1.78 (m, 3H); LC MS: ES+ 565.2.

Compound 87

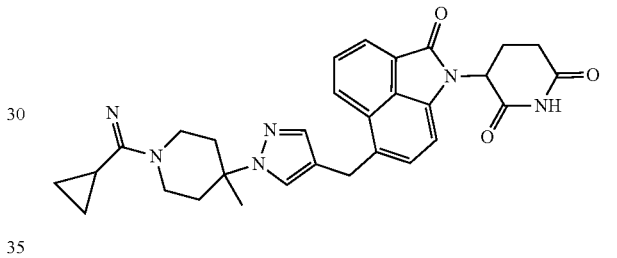

Yellow solid, 165.0 mg, 61.69% yield, 99.45% purity. $^1$H NMR (400 MHz, DMSO-d6) δ 11.11 (s, 1H), 8.39 (d, J=8.24 Hz, 1H), 8.08 (d, J=6.96 Hz, 1H), 7.83 (t, J=7.64 Hz, 1H), 7.79 (s, 1H), 7.36-7.34 (m, 2H), 7.07 (d, J=7.32 Hz, 1H), 5.43 (dd, J=12.8, 5.12 Hz, 1H), 4.18 (s, 2H), 3.80-3.68 (m, 2H), 3.39-3.38 (m, 1H), 3.14-3.12 (m, 1H), 2.99-2.90 (m, 1H), 2.80-2.72 (m, 1H), 2.69-2.62 (m, 1H), 2.34-2.32 (m, 1H), 2.25-2.23 (m, 1H), 2.09-2.07 (m, 1H), 1.97-1.92 (m, 1H), 1.81-1.67 (m, 2H), 1.36 (s, 3H), 0.680-0.66 (m, 4H); LC MS: ES+ 526.2.

Compound 88

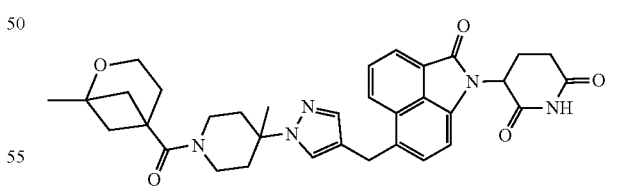

Yellow solid, 38.0 mg, 50.97% yield, 97.04% purity. $^1$H NMR (400 MHz, DMSO-d6) δ 11.11 (s, 1H), 8.39 (d, J=8.24 Hz, 1H), 8.08 (d, J=7.0 Hz, 1H), 7.82 (t, J=7.62 Hz, 1H), 7.77 (s, 1H), 7.36-7.33 (m, 2H), 7.07 (d, J=7.28 Hz, 1H), 5.43 (dd, J=12.68, 5.08 Hz, 1H), 4.20 (s, 2H), 3.95 (t, J=6.42 Hz, 2H), 3.66-3.65 (m, 1H), 3.46-3.45 (m, 1H), 3.10-3.08 (m, 2H), 2.94-2.90 (m, 1H), 2.77-2.72 (m, 1H), 2.67-2.62 (m, 1H), 2.33-2.27 (m, 2H), 2.10-1.99 (m, 7H), 1.74-1.73 (m, 2H), 1.34 (s, 3H), 1.11 (s, 3H); LC MS: ES+ 596.3.

Compound 89

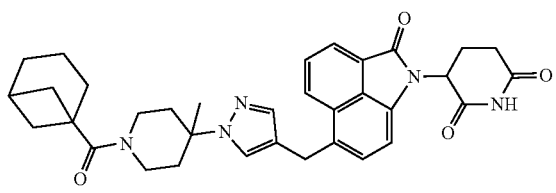

Yellow solid, 40.0 mg, 54.86% yield, 96.57% purity. $^1$H NMR (400 MHz, DMSO-d6) δ 11.11 (s, 1H), 8.39 (d, J=8.24 Hz, 1H), 8.08 (d, J=6.96 Hz, 1H), 7.82 (t, J=7.62 Hz, 1H), 7.77 (s, 1H), 7.36-7.33 (m, 2H), 7.07 (d, J=7.28 Hz, 1H), 5.43 (dd, J=12.76, 5.16 Hz, 1H), 4.20 (s, 2H), 3.64-3.62 (m, 1H), 3.40-3.39 (m, 1H), 3.09-3.07 (m, 2H), 2.99-2.90 (m, 1H), 2.81-2.72 (m, 1H), 2.69-2.62 (m, 1H), 2.34-2.26 (m, 2H), 2.09-2.07 (m, 4H), 1.79-1.60 (m, 9H), 1.34 (s, 3H); LC MS: ES+580.3.

Compound 90

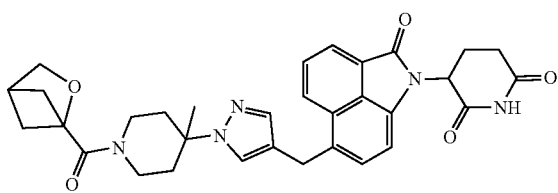

Yellow solid, 40.0 mg, 56.75% yield, 97.82% purity. $^1$H NMR (400 MHz, DMSO-d6) δ 11.11 (s, 1H), 8.39 (d, J=8.04 Hz, 1H), 8.08 (d, J=7.0 Hz, 1H), 7.83 (t, J=7.64 Hz, 1H), 7.78 (s, 1H), 7.35-7.33 (m, 2H), 7.07 (d, J=7.28 Hz, 1H), 5.45-5.42 (m, 1H), 4.20 (s, 2H), 3.75-3.67 (m, 4H), 3.14-3.09 (m, 1H), 2.95-2.91 (m, 1H), 2.83-2.79 (m, 1H), 2.76-2.72 (m, 1H), 2.67-2.62 (m, 1H), 2.49-2.47 (m, 1H), 2.33-2.29 (m, 2H), 2.08-2.07 (m, 1H), 1.98-1.96 (m, 2H), 1.76-1.72 (m, 2H), 1.60-1.57 (m, 2H), 1.35 (s, 3H); LC MS: ES+ 568.3.

Compound 91

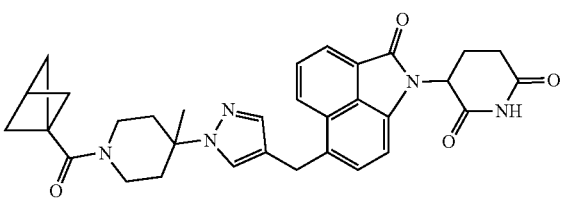

Yellow solid, 40.0 mg, 58.47% yield, 97.94% purity. $^1$H NMR (400 MHz, DMSO-d6) δ 11.11 (s, 1H), 8.39 (d, J=8.12 Hz, 1H), 8.08 (d, J=6.96 Hz, 1H), 7.83 (t, J=7.64 Hz, 1H), 7.77 (s, 1H), 7.36-7.33 (m, 2H), 7.07 (d, J=7.2 Hz, 1H), 5.45-5.42 (m, 1H), 4.20 (s, 2H), 3.69-3.63 (m, 2H), 3.09-3.06 (m, 1H), 2.98-2.90 (m, 1H), 2.79-2.72 (m, 1H), 2.67-2.62 (m, 1H), 2.43 (s, 2H), 2.33-2.22 (m, 2H), 2.06-2.00 (m, 7H), 1.75-1.72 (m, 2H), 1.35 (s, 3H); LC MS: ES+ 552.3.

Compound 92

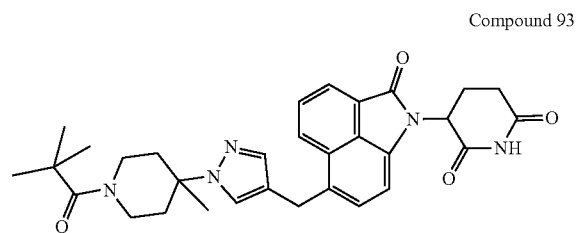 [SMILES: CC(C)(C)C(=O)N1CCC(C)(n2cc(Cc3ccc4c5c(cccc35)C(=O)N4C3CCC(=O)NC3=O)cn2)CC1]

Yellow solid, 110 mg, 48.55% yield, 98.94% purity. $^1$H NMR (400 MHz, DMSO-d6) δ 11.11 (s, 1H), 8.39 (d, J=Hz, 1H), 8.08 (d, J=Hz, 1H), 7.82 (t, J=Hz, 1H), 7.78 (s, 1H), 7.36-7.33 (m, 2H), 7.07 (d, J=Hz, 1H), 5.43 (dd, J=Hz, 1H), 4.20 (s, 2H), 3.69-3.67 (m, 1H), 3.29-3.28 (m, 1H), 3.07-3.05 (m, 2H), 2.99-2.90 (m, 1H), 2.80-2.69 (m, 1H), 2.67-2.62 (m, 1H), 2.39-2.28 (m, 4H), 2.09-2.07 (m, 1H), 1.94-1.83 (m, 1H), 1.78-1.74 (m, 4H), 1.62-1.55 (m, 1H), 1.34 (s, 3H), 1.31 (s, 3H); LC MS: ES+ 554.2.

Compound 93

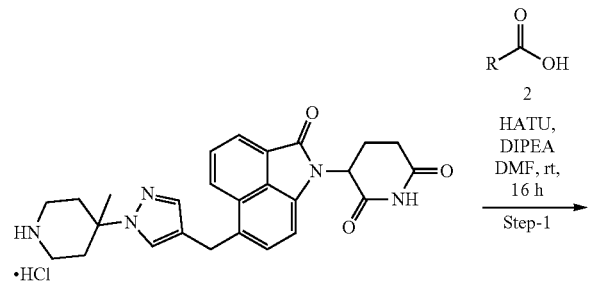

Yellow solid, 120 mg, 43.48% yield, 99.32% purity. $^1$H NMR (400 MHz, DMSO-d6) δ 11.11 (s, 1H), 8.39 (d, J=8.2 Hz, 1H), 8.08 (d, J=6.92 Hz, 1H), 7.83 (t, J=7.58 Hz, 1H), 7.78 (s, 1H), 7.35-7.33 (m, 1H), 7.07 (d, J=7.08 Hz, 1H), 5.44-5.42 (m, 1H), 4.21 (s, 2H), 3.70-3.68 (m, 2H), 3.25-3.22 (m, 2H), 2.98-2.91 (m, 1H), 2.76-2.72 (m, 1H), 2.67-2.62 (m, 1H), 2.27-2.26 (m, 2H), 2.09-2.08 (m, 1H), 1.76-1.71 (m, 2H), 1.35 (s, 3H), 1.16 (s, 9H); LC MS: ES+ 542.2.

Example 36. General Synthesis of Compound 94-Compound 98

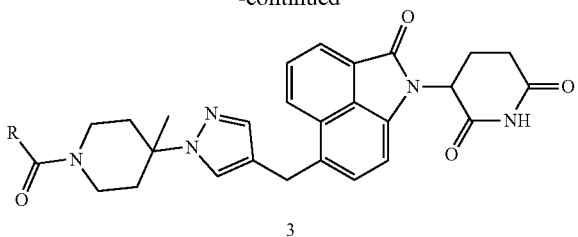

Compound 96

To an equi-molar mixture of Amine and Acid DMF (2 ml) were added HATU (1.5 equiv) and DIPEA (5.0 equiv) at 0° C. The resulting solution was stirred at ambient temperature for 16 hours. The reaction mixture was then diluted with Ethyl acetate and washed with aqueous NaHCO3 solution, water (×3) and brine. The organic layer was then dried over anhydrous Na$_2$SO$_4$ and concentrated under reduced pressure. Crude mass was then purified by Combi-Flash (eluting with 2% methanol in DCM) followed by Prep-TLC to afford 3.

Yellow solid 32 mg, 47% yield, 98.2% Purity. $^1$H NMR (400 MHz, DMSO-d6): δ 11.12 (s, 1H), 8.40 (d, J=8.2 Hz, 1H), 8.08 (d, J=6.9 Hz, 1H), 7.85-7.81 (m, 2H), 7.34 (m, 2H), 7.08 (d, J=7.2 Hz, 1H), 5.44-5.43 (m, 1H), 4.21 (s, 2H), 4.21 (m, 2H), 3.29 (m, 1H), 3.18 (m, 1H), 2.95-2.91 (m, 1H), 2.76-2.62 (m, 2H), 2.33 (m, 2H), 2.08 (m, 1H), 1.78 (m, 2H), 1.55-1.49 (m, 3H), 1.37 (s, 9H). LCMS (ES+)=546.2 [M+H]+.

Compound 94

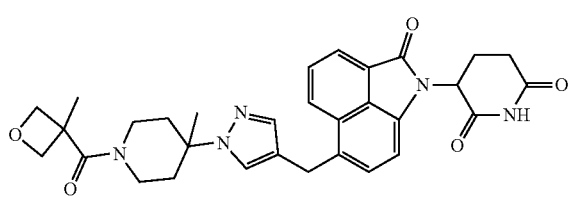

Compound 97

Yellow solid 28 mg, 41.41% yield, 99.07% Purity. $^1$H NMR (400 MHz, DMSO-d6): δ 11.10 (s, 1H), 8.39 (d, J=8.0 Hz, 1H), 8.09 (d, J=7.0 Hz, 1H), 7.85-7.81 (m, 1H), 7.79 (s, 1H), 7.36-7.34 (m, 2H), 7.07 (d, J=7.2 Hz, 1H), 5.46-5.41 (m, 1H), 4.78-4.74 (m, 2H), 4.24-4.21 (m, 4H), 3.75 (m, 1H), 3.07 (m, 1H), 2.98-2.86 (m, 3H), 2.76-2.62 (m, 2H), 2.32-2.31 (m, 2H), 2.09-2.08 (m, 1H), 1.78-1.75 (m, 2H), 1.50 (s, 3H), 1.35 (s, 3H). LCMS: (ES+)=556.4 [M+H]+.

Yellow solid 36 mg, 51.71% yield, 98.93% Purity. $^1$H NMR (400 MHz, DMSO-d6): δ 11.11 (s, 1H), 8.40 (d, J=8.3 Hz, 1H), 8.08 (d, J=7.0 Hz, 1H), 7.85-7.81 (m, 2H), 7.36-7.34 (m, 2H), 7.07 (d, J=7.2 Hz, 1H), 5.44-5.42 (m, 1H), 4.20 (s, 2H), 3.86 (m, 2H), 2.98-2.91 (m, 1H), 2.79-2.73 (m, 1H), 2.69-2.62 (m, 2H), 2.33 (m, 2H), 2.08 (m, 1H), 1.80 (m, 3H), 1.73 (s, 6H), 1.38 (s, 3H). LCMS (ES+)=562.4 [M+H]+.

Compound 95

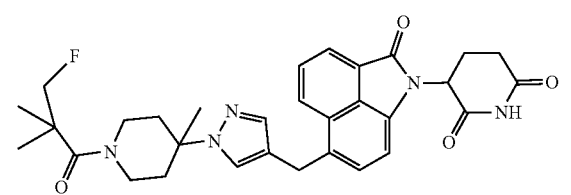

Compound 98

Yellow solid 40 mg, 56.44% yield, 98.61% Purity. $^1$H NMR (400 MHz, DMSO-d6): δ 11.11 (s, 1H), 8.39 (d, J=8.2 Hz, 1H), 8.08 (d, J=7.0 Hz, 1H), 7.85-7.81 (m, 1H), 7.78 (s, 1H), 7.36-7.34 (m, 2H), 7.07 (d, J=7.3 Hz, 1H), 5.46-5.41 (m, 1H), 4.42 (m, 1H), 4.29 (m, 1H), 4.21 (m, 2H), 3.73-3.69 (m, 1H), 3.24-3.19 (m, 2H), 2.96-2.90 (m, 1H), 2.77-2.73 (m, 1H), 2.69-2.63 (m, 2H), 2.32-2.28 (m, 2H), 2.09-2.07 (m, 1H), 1.78-1.73 (m, 2H), 1.36 (s, 3H), 1.22-1.21 (m, 6H). LCMS (ES+)=560.3 [M+H]+.

Yellow solid 15 mg, 18.59% yield, 99.44% Purity. $^1$H NMR (400 MHz, DMSO-d6): δ 11.1 (s, 1H), 8.39 (d, J=8.0 Hz, 1H), 8.08 (d, J=7.0 Hz, 1H), 7.83 (t, J=7.6 Hz, 1H), 7.78 (s, 1H), 7.36-7.34 (m, 2H), 7.07 (d, J=7.2 Hz, 1H), 5.46-5.42 (m, 1H), 4.52-4.49 (m, 1H), 4.21 (s, 2H), 3.73-3.70 (m, 2H), 3.39-3.38 (m, 2H), 3.23-3.18 (m, 2H), 2.95-2.92 (m, 1H), 2.76-2.73 (m, 1H), 2.67-2.63 (m, 1H), 2.31-2.28 (m, 2H), 2.09-2.06 (m, 1H), 1.77-1.72 (m, 2H), 1.35 (s, 3H), 1.13 (s, 6H). LCMS (ES+)=558.6[M+H]+.

Example 37. General Synthesis of Compound 99-Compound 106

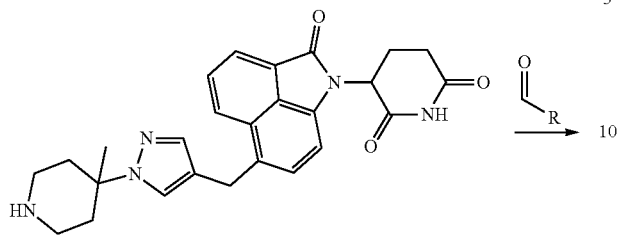

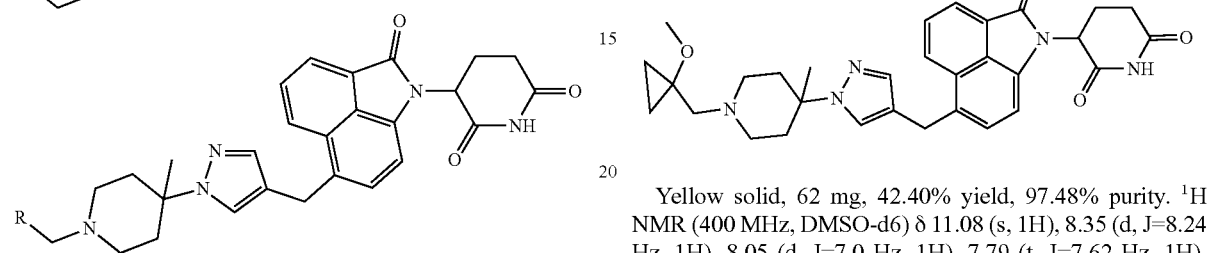

To a stirred solution of Amine (1.0 equiv) in THF (6 mL/mmol) was added Triethylamine (2.0 equiv) at 0° C. Then Aldehyde (1.0 equiv), Phenylsilane (1.0 equiv) and Dibutyltindichloride (1.2 equiv) were added to the reaction mixture. The resulting solution was stirred at 90° C. for 16 hours. Reaction mixture was then diluted with Ethyl acetate and washed with aqueous NaHCO$_3$ solution, water (×3) and brine. The organic layer was then dried over anhydrous Na$_2$SO$_4$ and concentrated under reduced pressure. Crude mass was then purified by CombiFlash ISCO column, eluting with 3% methanol in DCM to afford 3.

Compound 99

Yellow solid, 125.0 mg, 45.53% yield, 99.48% purity. $^1$H NMR (400 MHz, DMSO-d6) δ 11.10 (s, 1H), 8.38 (d, J=8.32 Hz, 1H), 8.08 (d, J=6.88 Hz, 1H), 7.82 (t, J=7.6 Hz, 1H), 7.70 (s, 1H), 7.36-7.30 (m, 2H), 7.07 (d, J=7.08 Hz, 1H), 5.44-5.42 (m, 1H), 4.20 (s, 2H), 2.95-2.91 (m, 1H), 2.77-2.73 (m, 1H), 2.68-2.62 (m, 1H), 2.50-2.49 (m, 2H), 2.37-2.26 (m, 4H), 2.14-2.10 (m, 4H), 1.90-1.88 (m, 1H), 1.76-1.74 (m, 4H), 1.57-1.55 (m, 2H), 1.28 (s, 3H), 1.11 (s, 3H); LC MS: ES+540.3.

Compound 100

Yellow solid, 130.0 mg, 60.22% yield, 98.59% purity. $^1$H NMR (400 MHz, DMSO-d6) δ 11.11 (s, 1H), 8.38 (d, J=8.24 Hz, 1H), 8.08 (d, J=6.88 Hz, 1H), 7.81 (t, J=7.58 Hz, 1H), 7.71 (s, 1H), 7.37-7.31 (m, 2H), 7.07 (d, J=7.24 Hz, 1H), 5.43 (dd, J=12.64, 4.8 Hz, 1H), 4.20 (s, 2H), 2.99-2.90 (m, 1H), 2.80-2.69 (m, 1H), 2.66-2.62 (m, 1H), 2.50-2.49 (m, 3H), 2.34-2.32 (m, 2H), 2.15-1.92 (m, 4H), 1.82-1.78 (m, 2H), 1.29 (s, 3H), 1.00 (s, 3H); LC MS: ES+ 526.6.

Compound 101

Yellow solid, 62 mg, 42.40% yield, 97.48% purity. $^1$H NMR (400 MHz, DMSO-d6) δ 11.08 (s, 1H), 8.35 (d, J=8.24 Hz, 1H), 8.05 (d, J=7.0 Hz, 1H), 7.79 (t, J=7.62 Hz, 1H), 7.69 (s, 1H), 7.32 (d, J=6.96 Hz, 1H), 7.27 (s, 1H), 7.04 (d, J=7.28 Hz, 1H), 5.40 (dd, J=12.76, 5.08 Hz, 1H), 4.17 (s, 2H), 3.14 (s, 3H), 2.93-2.89 (m, 1H), 2.74-2.69 (m, 1H), 2.64-2.53 (m, 2H), 2.46-2.05 (m, 7H), 2.07-2.04 (m, 1H), 1.76-1.74 (m, 2H), 1.26 (s, 3H), 0.61 (s, 2H), 0.35 (s, 2H); LC MS: ES+ 541.7.

Compound 102

Yellow solid, 70 mg, 41.94% yield, 97.62% purity. $^1$H NMR (400 MHz, DMSO-d6) δ 11.11 (s, 1H), 8.38 (d, J=8.2 Hz, 1H), 8.08 (d, J=6.92 Hz, 1H), 7.82 (t, J=7.58 Hz, 1H), 7.73 (s, 1H), 7.35-7.30 (m, 2H), 7.07 (d, J=7.24 Hz, 1H), 5.43 (dd, J=12.56, 4.88 Hz, 1H), 4.20 (s, 2H), 2.98-2.90 (m, 1H), 2.79-2.72 (m, 1H), 2.69-2.59 (m, 3H), 2.41-2.30 (m, 4H), 2.22-2.18 (m, 2H), 2.09-2.07 (m, 1H), 1.83-1.79 (m, 2H), 1.29 (s, 3H), 1.20 (s, 2H), 0.85 (s, 2H); LC MS: Es+ 537.3.

Compound 103

Yellow solid, 59 mg, 34.51% yield, 98.70% purity. $^1$H NMR (400 MHz, DMSO-d6) δ 11.11 (s, 1H), 8.38 (d, J=8.28 Hz, 1H), 8.08 (d, J=6.96 Hz, 1H), 7.82 (t, J=7.62 Hz, 1H), 7.71 (s, 1H), 7.35 (d, J=7.28 Hz, 1H), 7.30 (s, 1H), 7.07 (d, J=7.28 Hz, 1H), 5.43 (dd, J=12.6, 5.04 Hz, 1H), 4.20 (s, 2H), 3.02 (s, 3H), 2.94-2.90 (m, 1H), 2.78-2.72 (m, 1H), 2.67-2.62 (m, 1H), 2.51-2.50 (m, 2H), 2.36 (s, 2H), 2.33-2.22 (m, 4H), 2.10-2.07 (m, 1H), 1.99-1.90 (m, 2H), 1.88-1.82 (m, 2H), 1.78-1.74 (m, 2H), 1.66-1.61 (m, 1H), 1.53-1.49 (m, 1H), 1.28 (s, 3H); LC MS: ES+ 556.7.

104

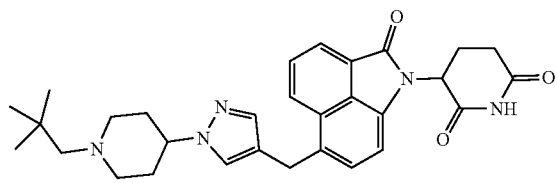

Yellow solid, 130.0 mg, 57.40% yield, 94.32% purity. ¹H NMR (400 MHz, DMSO-d6) δ 11.10 (s, 1H), 8.39 (d, J=8.24 Hz, 1H), 8.08 (d, J=6.96 Hz, 1H), 7.82 (t, J=7.62 Hz, 1H), 7.70 (s, 1H), 7.34 (d, J=7.24 Hz, 1H), 7.30 (s, 1H), 7.07 (d, J=7.24 Hz, 1H), 5.43 (dd, J=12.64, 4.88 Hz, 1H), 4.20 (s, 2H), 2.97-2.90 (m, 1H), 2.77-2.72 (m, 1H), 2.67-2.62 (m, 1H), 2.50-2.49 (m, 2H), 2.33-2.29 (m, 4H), 2.09-2.07 (m, 1H), 1.96 (s, 2H), 1.79-1.75 (m, 2H), 1.29 (s, 3H), 0.81 (s, 9H); LC MS: ES+ 528.5.

Compound 105

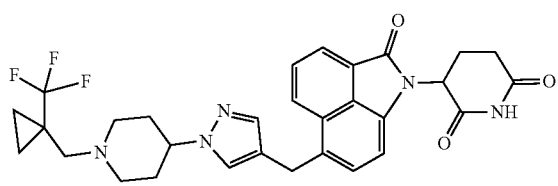

Yellow solid, 90.0 mg, 57.17% yield, 96.90% purity. ¹H NMR (400 MHz, DMSO-d6) δ 11.11 (s, 1H), 8.39-8.37 (m, 1H), 8.09-8.07 (m, 1H), 7.83-7.81 (m, 1H), 7.71 (s, 1H), 7.36-7.30 (m, 2H), 7.09-7.06 (m, 1H), 5.44-5.42 (m, 1H), 4.19 (s, 2H), 3.03-2.91 (m, 1H), 2.77-2.73 (m, 1H), 2.67-2.62 (m, 1H), 2.40 (s, 2H), 2.30-2.28 (m, 2H), 2.16-2.15 (m, 2H), 2.08-2.07 (m, 1H), 1.78-1.77 (m, 2H), 1.28 (s, 3H), 0.92 (s, 2H), 0.66 (s, 2H); LC MS: ES+ 580.3.

Compound 106

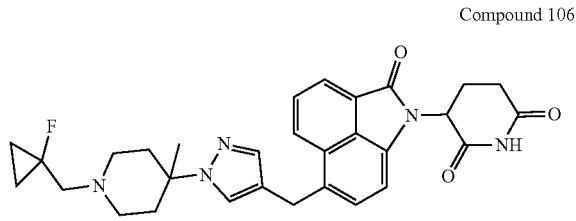 [SMILES: CC1(n2cc(Cc3ccc4c5c(cccc35)C(=O)N4C3CCC(=O)NC3=O)cn2)CCN(CC2(F)CC2)CC1]

Yellow solid, 100.0 mg, 70.18% yield, 97.81% purity. ¹H NMR (400 MHz, DMSO-d6) δ 11.10 (s, 1H), 8.38 (d, J=8.24 Hz, 1H), 8.08 (d, J=6.92 Hz, 1H), 7.82 (t, J=7.62 Hz, 1H), 7.73 (s, 1H), 7.34 (d, J=7.32 Hz, 1H), 7.30 (s, 1H), 7.07 (d, J=7.28 Hz, 1H), 5.43 (dd, J=12.84, 5.24 Hz, 1H), 4.20 (s, 2H), 2.95-2.90 (m, 1H), 2.78-2.72 (m, 1H), 2.67-2.57 (m, 5H), 2.33-2.29 (m, 4H), 2.09-2.07 (m, 1H), 1.83-1.78 (m, 2H), 1.29 (s, 3H), 0.97-0.87 (m, 2H), 0.62-0.60 (m, 2H); LC MS: ES+ 530.2.

Example 38. Synthesis of tert-butyl 4-(4-((1-(2,6-dioxopiperidin-3-yl)-2-oxo-1,2-dihydrobenzo[cd]indol-6-yl)methyl)benzyl)piperazine-1-carboxylate (Compound 107)

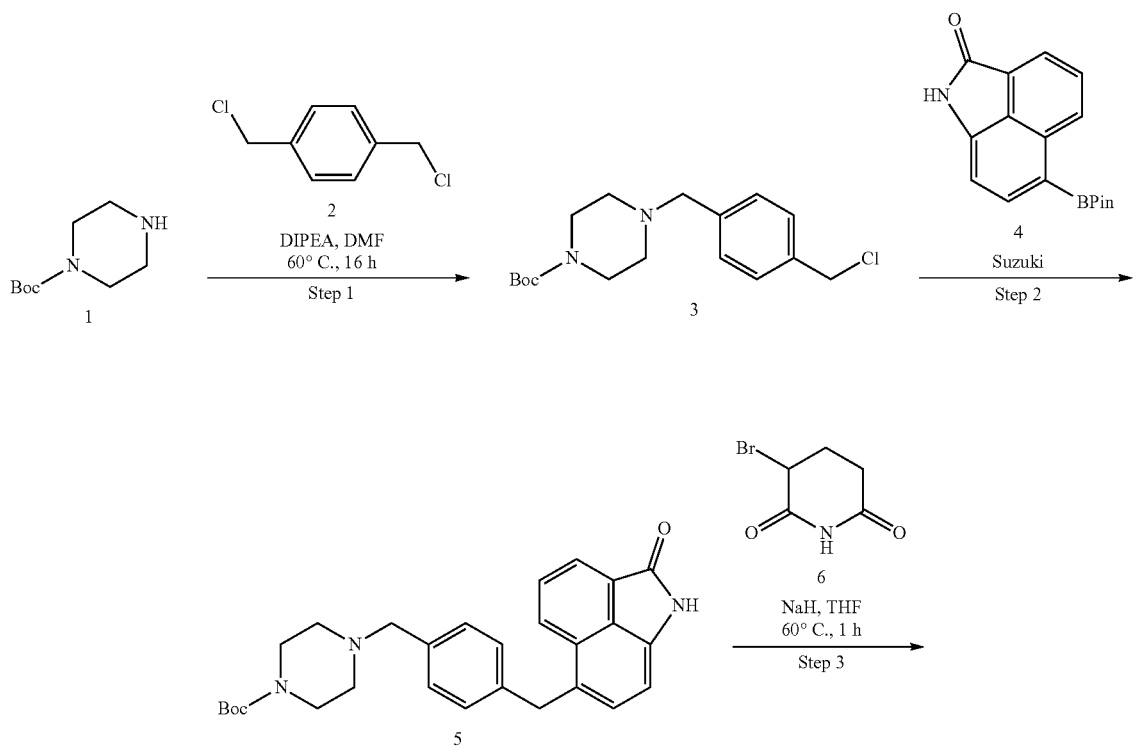

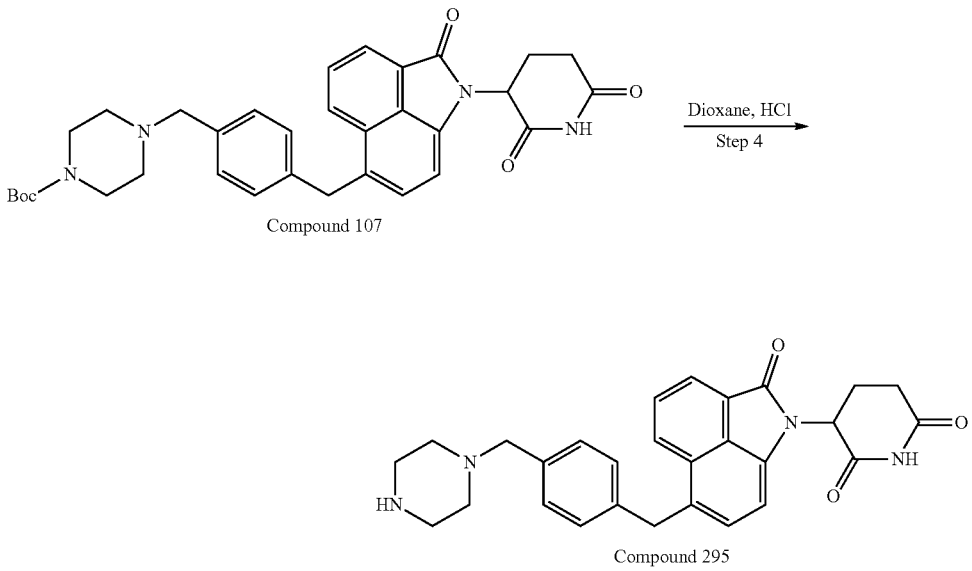

Compound 107

Compound 295

Step 1: Synthesis of tert-butyl 4-(4-(chloromethyl)benzyl)piperazine-1-carboxylate: To a stirred solution of tert-butyl piperazine-1-carboxylate 1 (10 g, 53.69 mmol) in DMF (100 mL) was added DIPEA (20.82 g, 161.07 mmol, 28.06 mL) and stirred for 5 min. Then 1,4-bis(chloromethyl)benzene 2 (9.40 g, 53.69 mmol, 6.62 mL) was added and the reaction was heated at 60° C. for 16 hours. After completion of the reaction (monitored by TLC), the reaction mixture was diluted with ethyl acetate and washed with water and brine, dried over sodium sulfate and concentrated. Crude material was purified by column chromatography (100-200 silica, 25-30% EtOAc in hexane) to afford tert-butyl 4-[[4-(chloromethyl)phenyl]methyl]piperazine-1-carboxylate 3 (7 g, 19.39 mmol, 36.12% yield, 90% purity) as off white solid. LC MS: ES+ 324.9.

Step 2: Synthesis of tert-butyl 4-(4-((2-oxo-1,2-dihydrobenzo[cd]indol-6-yl)methyl)benzyl)piperazine-1-carboxylate: To a stirred solution of tert-butyl 4-[[4-(chloromethyl)phenyl]methyl]piperazine-1-carboxylate 3 (4 g, 12.31 mmol) and 6-(4,4,5,5-tetramethyl-1,3,2-dioxaborolan-2-yl)-1H-benzo[cd]indol-2-one 4 (7.27 g, 24.63 mmol) in ethanol (20 mL) and Toluene (40 mL) was added Potassium phosphate tribasic anhydrous (7.84 g, 36.94 mmol) and the reaction mass was degassed under nitrogen atmosphere over 10 minutes. Tri-o-Tolyl phosphine (749.58 mg, 2.46 mmol) and (1E,4E)-1,5-diphenylpenta-1,4-dien-3-one; palladium (1.13 g, 1.23 mmol) was then added to this reaction mass and it was heated at 90° C. over night. Then the reaction mixture was filtered through sintered funnel using celite bed. Filtrate was diluted with ethyl acetate and washed with water. The organic part was dried over $Na_2SO_4$ and evaporated under reduced pressure. Crude thus obtained was purified by combi-flash chromatography (eluted at 0-30% EA/DCM) to get the pure compound tert-butyl 4-[[4-[(2-oxo-1H-benzo[cd]indol-6-yl)methyl]phenyl]methyl]piperazine-1-carboxylate 5 (3.2 g, 6.29 mmol, 51.12% yield, 90% purity) as yellow solid. LC MS: ES+ 458.4.

Step 3: Synthesis of tert-butyl 4-(4-((1-(2,6-dioxopiperidin-3-yl)-2-oxo-1,2-dihydrobenzo[cd]indol-6-yl)methyl)benzyl)piperazine-1-carboxylate: To a stirred solution of tert-butyl 4-[[4-[(2-oxo-1H-benzo[cd]indol-6-yl)methyl]phenyl]methyl]piperazine-1-carboxylate 5 (3.1 g, 6.78 mmol) in dry THF (80 mL) was added Sodium hydride (in oil dispersion) 60% dispersion in mineral oil (2.34 g, 101.63 mmol) at 0° C. and stirred for 15 minutes followed by the addition of 3-bromopiperidine-2,6-dione 6 (6.50 g, 33.88 mmol). Resulting reaction mixture was stirred at 70° C. for 1 hour. After complete conversion, reaction mixture was quenched with ice water and extracted with ethyl acetate (2×100 mL). Combined organic layer was separated, dried over sodium sulfate and concentrated. Crude reaction mass was purified by combiflash column chromatography (0-30% Ethyl acetate in DCM as eluent) to afford tert-butyl 4-[[4-[[1-(2,6-dioxo-3-piperidyl)-2-oxo-benzo[cd]indol-6-yl]methyl]phenyl]methyl]piperazine-1-carboxylate Compound 107 (2.3 g, 3.85 mmol, 56.83% yield, 95.20% purity) as yellow solid.

$^1$H NMR (400 MHz, DMSO-d6) δ 11.12 (s, 1H), 8.32 (d, J=8.12 Hz, 1H), 8.07 (d, J=6.88 Hz, 1H), 7.80 (t, J=7.58 Hz, 1H), 7.40 (d, J=7.2 Hz, 1H), 7.25-7.09 (m, 5H), 5.44 (dd, J=12.64, 4.76 Hz, 1H), 4.37 (s, 2H), 3.38 (s, 2H), 3.25 (s, 4H), 2.98-2.90 (m, 1H), 2.79-2.69 (m, 1H), 2.66-2.62 (m, 1H), 2.24 (s, 4H), 2.10-2.07 (m, 1H), 1.36 (s, 9H); LC MS: ES+ 569.3.

Step 4: Synthesis of 3-(2-oxo-6-(4-(piperazin-1-ylmethyl)benzyl)benzo[cd]indol-1(2H)-yl)piperidine-2,6-dione hydrochloride: To a stirred solution of tert-butyl 4-[[4-[[1-(2,6-dioxo-3-piperidyl)-2-oxo-benzo[cd]indol-6-yl]methyl]phenyl]methyl]piperazine-1-carboxylate 7 (2.3 g, 4.04 mmol) in 1,4-DIOXANE (20 mL) was added DIOXANE-HCL (50 mL) at 0° C. and stirred the reaction mass was stirred at room temperature 4 hours. Reaction mass was concentrated under reduced pressure, crude was triturated with ether-pentane to afford desired compound 3-[2-oxo-6-[[4-(piperazin-1-ylmethyl)phenyl]methyl]benzo[cd]indol-1-yl]piperidine-2,6-dione; hydrochloride Compound 295 (2 g, 3.51 mmol, 86.76% yield, 95% purity) as light yellow solid. LC MS: ES+ 469.4.

Example 39. General Synthesis of Compound 108-Compound 112

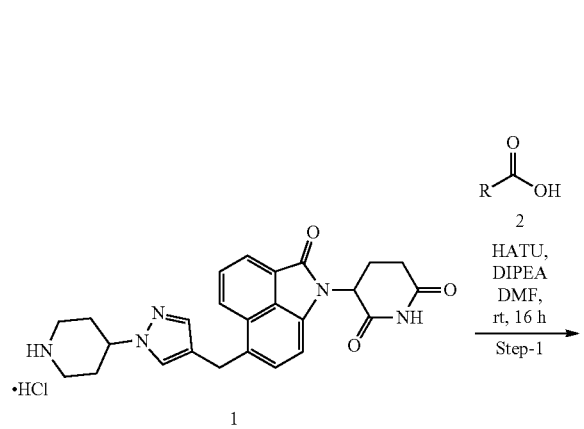

1

2

HATU,
DIPEA
DMF,
rt, 16 h
Step-1

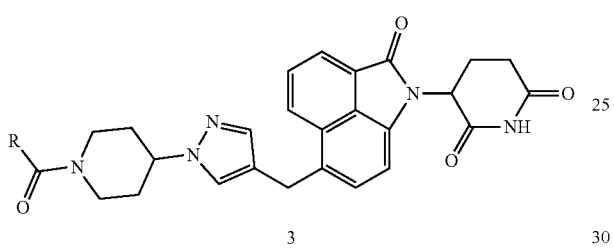

3

To an equi-molar mixture of Amine and Acid DMF (6 mL/mmol) were added HATU (1.5 equiv) and DIPEA (5.0 equiv) at 0° C. The resulting solution was stirred at ambient temperature for 16 hours. The reaction mixture was then diluted with Ethyl acetate and washed with aqueous NaHCO$_3$ solution, water (×3) and brine. The organic layer was then dried over anhydrous Na$_2$SO$_4$ and concentrated under reduced pressure. Crude mass was then purified by CombiFlash ISCO column, eluting with 2% methanol in DCM to afford 3.

Compound 108

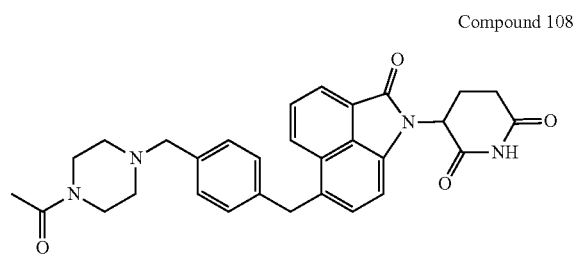 [SMILES: CC(=O)N1CCN(Cc2ccc(Cc3ccc4c5c(cccc35)C(=O)N4C3CCC(=O)NC3=O)cc2)CC1]

Yellow solid, 23.0 mg, 21.09% yield, 92.73% purity. 1H NMR (400 MHz, DMSO-d6) δ 11.12 (s, 1H), 8.33 (d, J=8.32 Hz, 1H), 8.07 (d, J=6.96 Hz, 1H), 7.81 (t, J=7.6 Hz, 1H), 7.40 (d, J=7.44 Hz, 1H), 7.25-7.23 (m, 2H), 7.20-7.18 (m, 2H), 7.10 (d, J=7.32 Hz, 1H), 5.44 (dd, J=13.52, 5.4 Hz, 1H), 4.38 (s, 2H), 3.40-3.36 (m, 6H), 2.95-2.92 (m, 1H), 2.76-2.73 (m, 1H), 2.66-2.63 (m, 1H), 2.32-2.28 (m, 2H), 2.25-2.21 (m, 2H), 2.10-2.07 (m, 1H), 1.94 (s, 3H); LC MS:511.2.

Compound 109

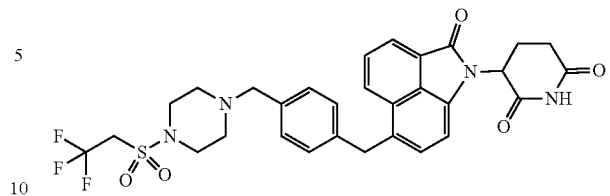

Yellow solid, 45.0 mg, 36.97% yield, 100% purity. 1H NMR (400 MHz, DMSO-d6) δ 11.12 (s, 1H), 8.33 (d, J=8.36 Hz, 1H), 8.07 (d, J=6.96 Hz, 1H), 7.81 (t, J=7.60 Hz, 1H), 7.41 (d, J=7.4 Hz, 1H), 7.26-7.18 (m, 4H), 7.10 (d, J=7.08 Hz, 1H), 5.44-5.43 (m, 1H), 4.47 (q, J=10.28 Hz, 2H), 4.38 (s, 2H), 3.44 (s, 2H), 3.19 (brs, 4H), 2.96-2.92 (m, 1H), 2.76-2.73 (m, 1H), 2.67-2.62 (m, 1H), 2.39 (brs, 4H), 2.09-2.07 (m, 1H); LC MS: ES+ 615.2.

Compound 110

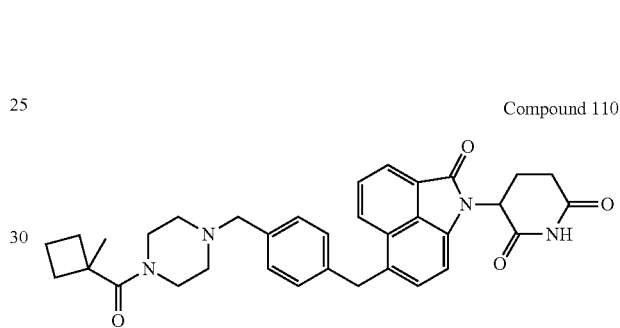

Yellow solid, 40.0 mg, 33.04% yield, 92.36% purity. $^1$H NMR (400 MHz, DMSO-d6) δ 11.12 (s, 1H), 8.32 (d, J=8.24 Hz, 1H), 8.07 (d, J=7.0 Hz, 1H), 7.80 (t, J=7.66 Hz, 1H), 7.40 (d, J=7.32 Hz, 1H), 7.25-7.11 (m, 5H), 5.44 (dd, J=12, 4.44 Hz, 1H), 4.37 (s, 2H), 3.39-3.32 (m, 4H), 3.20-3.18 (m, 2H), 2.94-2.90 (m, 1H), 2.76-2.73 (m, 1H), 2.66-2.62 (m, 1H), 2.35-2.30 (m, 2H), 2.30-2.25 (m, 4H), 2.10-2.08 (m, 1H), 1.91-1.84 (m, 1H), 1.76-1.72 (m, 2H), 1.59-1.56 (m, 1H), 1.29 (s, 3H); LC MS: ES+ 565.6.

Compound 111

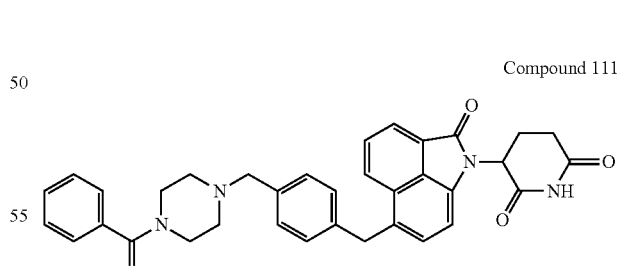

Yellow solid, 70.0 mg, 60.98% yield, 98.78% purity. 1H NMR (400 MHz, DMSO-d6) δ 11.11 (s, 1H), 8.32 (d, J=8.28 Hz, 1H), 8.07 (d, J=6.96 Hz, 1H), 7.81 (t, J=7.56 Hz, 1H), 7.43-7.39 (m, 4H), 7.36-7.33 (m, 2H), 7.25-7.18 (m, 4H), 7.10 (d, J=7.28 Hz, 1H), 5.43 (dd, J=12.8, 5.28 Hz, 1H), 4.38 (s, 2H), 3.57 (brs, 2H), 3.42 (s, 2H), 2.94-2.90 (m, 1H), 2.76-2.73 (m, 1H), 2.66-2.62 (m, 1H), 2.34-2.32 (m, 4H), 2.11-2.07 (m, 1H); LC MS: ES+ 573.3.

Compound 112

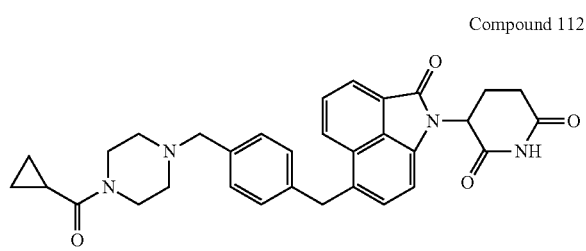 [SMILES: O=C1CCC(N2C(=O)c3cccc4c(Cc5ccc(CN6CCN(C(=O)C7CC7)CC6)cc5)ccc2c34)C(=O)N1]

Yellow solid, 55.0 mg, 49.51% yield, 95.65% purity. 1H NMR (400 MHz, DMSO-d6) δ 11.11 (s, 1H), 8.32 (d, J=8.24 Hz, 1H), 8.07 (d, J=6.96 Hz, 1H), 7.80 (t, J=7.68 Hz, 1H), 7.41 (d, J=7.32 Hz, 1H), 7.26-7.19 (m, 4H), 7.10 (d, J=7.28 Hz, 1H), 5.44 (dd, J=12.72, 5.08 Hz, 1H), 4.38 (s, 2H), 3.61 (brs, 2H), 3.41 (s, 4H), 2.96-2.92 (m, 1H), 2.77-2.73 (m, 1H), 2.67-2.63 (m, 1H), 2.33-2.25 (m, 4H), 2.10-2.07 (m, 1H), 1.92-1.89 (m, 1H), 0.69-0.65 (m, 4H); LC MS: ES+ 537.2.

Example 40. General Synthesis of (Compound 113)

Compound 113

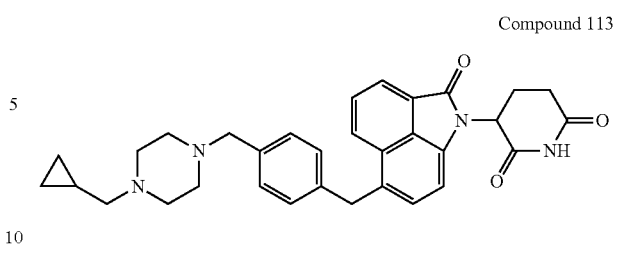

Yellow solid, 75.0 mg, 54.68% yield, 98.08% purity. 1H NMR (400 MHz, DMSO-d6) δ 11.11 (s, 1H), 8.32 (d, J=8.20 Hz, 1H), 8.07 (d, J=6.96 Hz, 1H), 7.80 (t, J=7.76 Hz, 1H), 7.40 (d, J=7.28 Hz, 1H), 7.22-7.16 (m, 4H), 7.10 (d, J=7.08 Hz, 1H), 5.45-5.41 (m, 1H), 4.37 (s, 2H), 3.37 (s, 2H), 2.95-2.92 (m, 1H), 2.76-2.73 (m, 1H), 2.67-2.63 (m, 1H), 2.63-2.50 (m, 1H), 2.40-2.32 (m, 7H), 2.12-2.09 (m, 3H), 0.77 (brm, 1H), 0.42 (brs, 2H), 0.03 (brs, 2H); LC MS: ES+ 523.2.

Example 41. General Synthesis of Compound 114-Compound 123

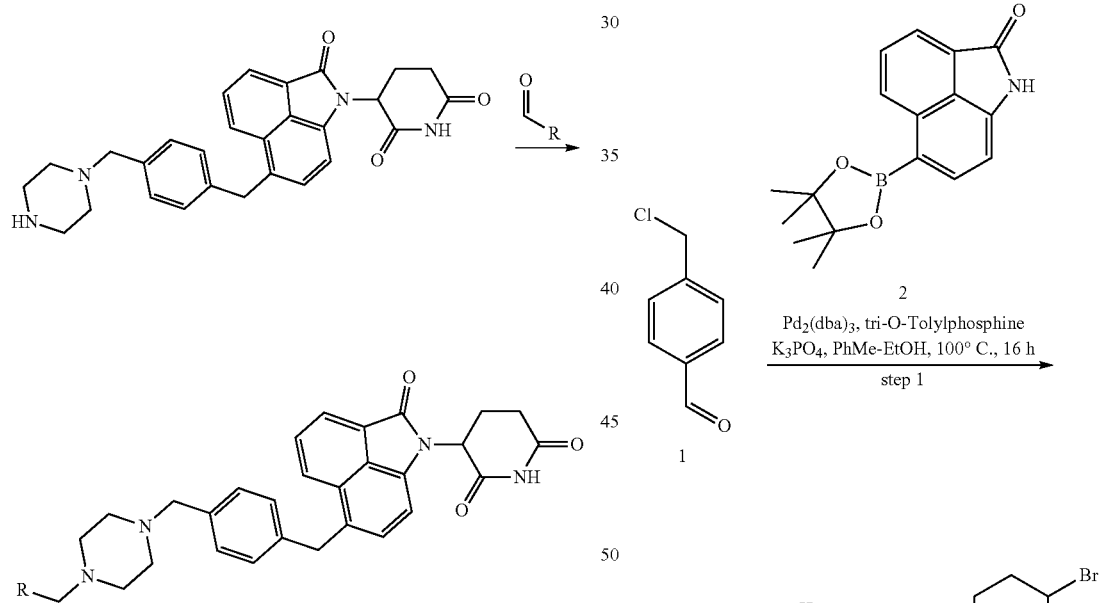

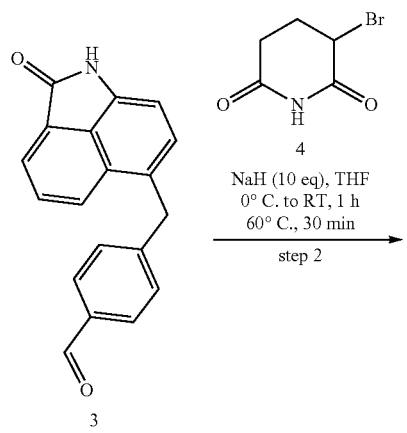

To a stirred solution of Amine (1.0 equiv) in THF (6 mL/mmol) was added Triethylamine (2.0 equiv) at 0° C. Then Aldehyde (1.0 equiv), Phenylsilane (1.0 equiv) and Dibutyltindichloride (1.2 equiv) were added to the reaction mixture. The resulting solution was stirred at 90° C. for 16 hours. Reaction mixture was then diluted with Ethyl acetate and washed with aqueous NaHCO$_3$ solution, water (×3) and brine. The organic layer was then dried over anhydrous Na$_2$SO$_4$ and concentrated under reduced pressure. Crude mass was then purified by CombiFlash ISCO column, eluting with 2-3% methanol in DCM to afford the final compound.

-continued

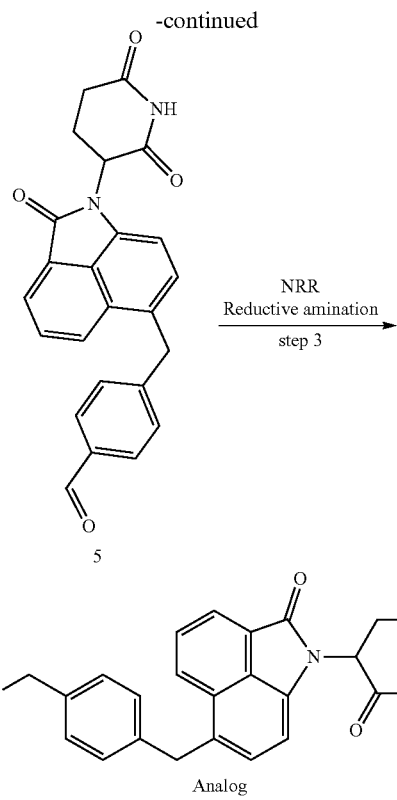

Step 1: Synthesis of 4-((2-obo-1,2-dihydrobenzo[cd]indol-6-yl)methyl)benzaldehyde: To a stirred solution of 4-(chloromethyl)benzaldehyde 1 (9.5 g, 61.45 mmol) and 6-(4,4,5,5-tetramethyl-1,3,2-dioxaborolan-2-yl)-1H-benzo[cd]indol-2-one 2 (36.27 g, 122.90 mmol) in ethanol (30 mL) and Toluene (60.0 mL) was added Potassium phosphate tribasic anhydrous (39.13 g, 184.35 mmol) and the reaction mass was degassed under nitrogen atmosphere over 10 minutes. Tri-o-Tolyl phosphine (3.74 g, 12.29 mmol) and (1E,4E)-1,5-diphenylpenta-1,4-dien-3-one; palladium (5.63 g, 6.15 mmol) were added to this reaction mass and resultant reaction mixture heated at 90° C. over night. Reaction mixture was filtered through sintered funnel using celite bed and filtrate was diluted with ethyl acetate. Organic part was separated and washed with water. It was dried over Na$_2$SO$_4$ and evaporated under reduced pressure. Crude material was purified by combi-flash chromatography to get the desired compound 4-[(2-oxo-1H-benzo[cd]indol-6-yl)methyl]benzaldehyde 3 (5.5 g, 7.27 mmol, 11.84% yield, 38% purity) as yellow solid. LC MS: ES+ 288.0.

Step 2: Synthesis of 4-((1-(2,6-dioxopiperidin-3-yl)-2-oxo-1,2-dihydrobenzo[cd]indol-6-yl)methyl)benzaldehyde: To a stirred solution of 4-[(2-oxo-1H-benzo[cd]indol-6-yl)methyl]benzaldehyde 3 (3.0 g, 10.44 mmol) in dry THF (30.0 mL), Sodium hydride (in oil dispersion) 60% dispersion in mineral oil (4.00 g, 100.02 mmol, 60% purity) was added at 0° C. and stirred for 15 minutes followed by the addition of 3-bromopiperidine-2,6-dione 4 (10.02 g, 52.21 mmol). Resulting reaction mixture was stirred at 70° C. for 1.5 hour. Reaction mixture was heated to reflux for 2 hours. After complete conversion as evidenced from LCMS, reaction mixture was quenched with water and extracted with ethyl acetate (2×20 mL). Combined organic layer was separated, dried over sodium sulfate and concentrated. Crude reaction mass was purified by combi-flash (2.5% MeOH in DCM as eluent) to afford 4-[[1-(2,6-dioxo-3-piperidyl)-2-oxo-benzo[cd]indol-6-yl]methyl]benzaldehyde 5 (1.4 g, 2.81 mmol, 26.92% yield, 80% purity) as yellow solid. LC MS: ES+ 399.2.

Step 3: Synthesis of analogs: To a stirred solution of Amine (1.0 equiv) in THF (6 mL/mmol) was added Triethylamine (2.0 equiv) at 0° C. (when amine is hydrochloride salt). Then Aldehyde (1.0 equiv), Phenylsilane (1.0 equiv) and Dibutyltindichloride (1.2 equiv) were added to the reaction mixture. The resulting solution was stirred at 90° C. for 16 hours. Reaction mixture was then diluted with Ethyl acetate and washed with aqueous NaHCO$_3$ solution, water (×3) and brine. The organic layer was then dried over anhydrous Na$_2$SO$_4$ and concentrated under reduced pressure. Crude mass was then purified by CombiFlash ISCO column, eluting with 2-3% methanol in DCM to afford the analog.

Compound 114

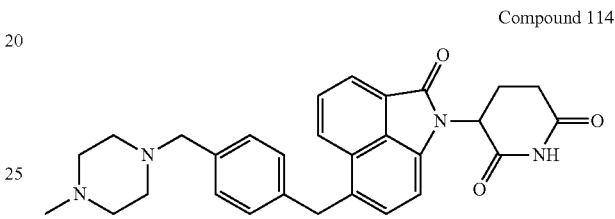

Yellow solid, 46.0 mg, 8.25% yield, 95.00% purity. $^1$H NMR (400 MHz, DMSO-d6) δ 11.12 (s, 1H), 8.32 (d, J=8.0 Hz, 1H), 8.07 (d, J=7.0 Hz, 1H), 7.80 (t, J=7.92 Hz, 1H), 7.40 (d, J=7.36 Hz, 1H), 7.24-7.16 (m, 4H), 7.10 (d, J=7.20 Hz, 1H), 5.45-5.42 (m, 1H), 4.37 (s, 2H), 3.38 (s, 2H), 3.32 (s, 3H), 2.95-2.90 (m, 1H), 2.76-2.73 (m, 1H), 2.70-2.65 (m, 1H), 2.65-2.62 (m, 1H), 2.40-2.30 (m, 5H), 2.17-2.10 (m, 2H), 2.10-2.07 (m, 1H); LC MS: ES- 481.2.

Compound 115

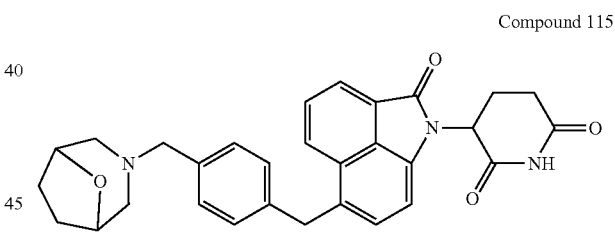

Yellow solid, 70.0 mg, 10.99% yield, 98.76% purity. $^1$H NMR (400 MHz, DMSO-d6) δ 11.12 (s, 1H), 8.32 (d, J=8.24 Hz, 1H), 8.07 (d, J=6.92 Hz, 1H), 7.81 (t, J=7.44 Hz, 1H), 7.39 (d, J=7.4 Hz, 1H), 7.24-7.16 (m, 4H), 7.10 (d, J=7.24 Hz, 1H), 5.44 (dd, J=12.72, 4.96 Hz, 1H), 4.37 (s, 2H), 4.15 (s, 2H), 3.35 (s, 2H), 2.98-2.90 (m, 1H), 2.79-2.73 (m, 1H), 2.69-2.62 (m, 1H), 2.50-2.42 (m, 2H), 2.14-2.07 (m, 3H), 1.82-1.75 (m, 2H), 1.68-1.67 (m, 2H); LC MS: ES+ 496.2.

Compound 116

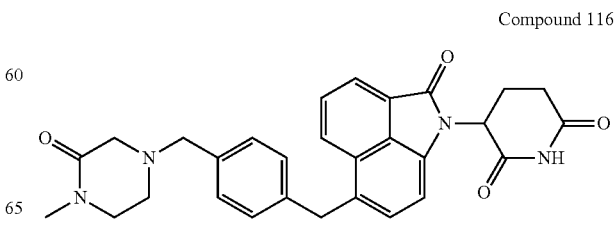

7.39-7.32 (m, 3H), 7.24-7.18 (m, 4H), 7.14-7.09 (m, 3H), 5.46-5.43 (m, 1H), 4.47-4.44 (m, 1H), 4.37 (s, 2H), 3.88-3.86 (m, 1H), 3.64-3.58 (m, 1H), 3.47-3.38 (m, 2H), 2.99-2.91 (m, 1H), 2.79-2.73 (m, 2H), 2.69-2.64 (m, 2H), 2.09-2.07 (m, 2H), 1.93-1.87 (m, 1H); LC MS: ES+ 564.2.

Yellow solid, 76.0 mg, 12.35% yield, 99.00% purity. ¹H NMR (400 MHz, DMSO-d6) δ 11.12 (s, 1H), 8.32 (d, J=8.16 Hz, 1H), 8.07 (d, J=6.88 Hz, 1H), 7.80 (t, J=7.6 Hz, 1H), 7.40 (d, J=7.24 Hz, 1H), 7.26-7.19 (m, 4H), 7.10 (d, J=7.24 Hz, 1H), 5.45-5.41 (m, 1H), 4.38 (s, 2H), 3.44 (s, 2H), 3.20-2.16 (m, 2H), 2.89 (s, 3H), 2.78 (s, 4H), 2.74-2.69 (m, 1H), 2.66-2.62 (m, 2H), 2.10-2.07 (m, 1H); LC MS: ES+ 497.2.

Compound 120

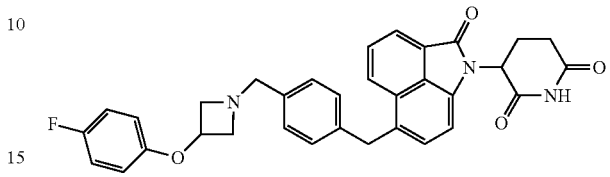

Compound 117

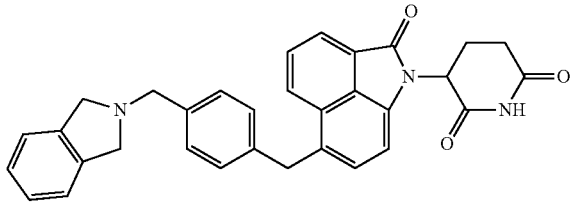

Yellow solid, 32.0 mg, 7.58% yield, 97.99% purity. ¹H NMR (400 MHz, DMSO-d6) δ 11.12 (s, 1H), 8.31 (d, J=8.24 Hz, 1H), 8.07 (d, J=6.96 Hz, 1H), 7.80 (t, J=7.52 Hz, 1H), 7.40 (d, J=7.36 Hz, 1H), 7.23-7.15 (m, 4H), 7.11-7.05 (m, 3H), 6.83-6.79 (m, 2H), 5.44-5.41 (m, 1H), 4.73-4.70 (m, 1H), 4.37 (s, 2H), 3.65 (t, J=6.64 Hz, 2H), 3.54 (s, 2H), 2.97-2.92 (m, 3H), 2.76-2.73 (m, 1H), 2.67-2.62 (m, 1H), 2.10-2.07 (m, 1H); LC MS: ES+ 550.3.

Yellow solid, 42.0 mg, 7.03% yield, 95.09% purity. ¹H NMR (400 MHz, DMSO-d6) δ 11.12 (s, 1H), 8.34 (d, J=8.24 Hz, 1H), 8.08 (d, J=6.88 Hz, 1H), 7.82 (t, J=7.2 Hz, 1H), 7.42 (d, J=6.68 Hz, 1H), 7.31-7.26 (m, 4H), 7.17-7.10 (m, 5H), 5.45-5.43 (m, 1H), 4.39 (s, 2H), 3.78 (s, 6H), 3.05-2.95 (m, 1H), 2.92-2.87 (m, 1H), 2.76-2.66 (m, 1H), 2.10-2.07 (m, 1H); LC MS: ES+ 502.2.

Compound 121

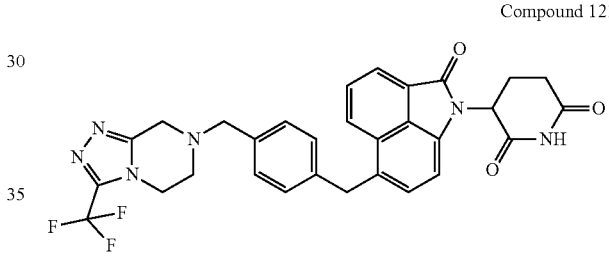

Compound 118

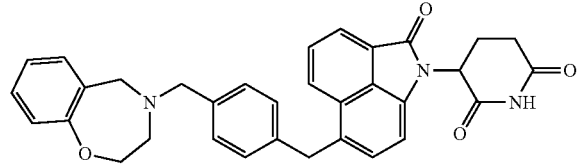

Yellow solid, 65.0 mg, 17.10% yield, 94.39% purity. ¹H NMR (400 MHz, DMSO-d6) δ 11.12 (s, 1H), 8.33 (d, J=8.24 Hz, 1H), 8.07 (d, J=7.0 Hz, 1H), 7.81 (t, J=7.6 Hz, 1H), 7.41 (d, J=7.32 Hz, 1H), 7.29-7.24 (m, 4H), 7.10 (d, J=7.32 Hz, 1H), 5.47-5.43 (m, 1H), 4.39 (s, 2H), 4.10 (t, J=5.08 Hz, 2H), 3.78 (s, 2H), 3.69 (s, 2H), 2.99-2.90 (m, 1H), 2.86 (t, J=5.24 Hz, 1H), 2.78-2.72 (m, 1H), 2.67-2.62 (m, 1H), 2.08-2.07 (m, 1H); LC MS: ES+ 575.6.

Yellow solid, 50.0 mg, 14.70/a yield, 98.09% purity. ¹H NMR (400 MHz, DMSO-d6) δ 11.12 (s, 1H), 8.32 (d, J=8.16 Hz, 1H), 8.07 (d, J=6.8 Hz, 1H), 7.80 (t, J=7.56 Hz, 1H), 7.41 (dd, J=7.28 Hz, 1H), 7.26-7.09 (m, 6H), 6.99-6.94 (m, 3H), 5.45-5.42 (m, 1H), 4.38 (s, 2H), 3.96 (br s, 2H), 3.69 (s, 2H), 3.53 (s, 2H), 2.96-2.90 (m, 3H), 2.76-2.62 (m, 2H), 2.08-2.07 (m, 1H); LC MS: ES+ 532.2.

Compound 122

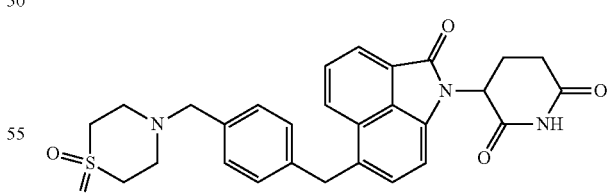

Compound 119

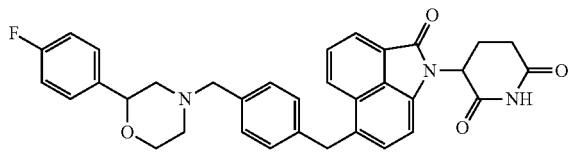

Yellow solid, 45.0 mg, 17.16% yield, 99.09% purity. ¹H NMR (400 MHz, DMSO-d6) δ 11.12 (s, 1H), 8.33 (d, J=8.28 Hz, 1H), 8.07 (dd, J=6.96 Hz, 1H), 7.80 (t, J=7.62 Hz, 1H), 7.41 (d, J=7.32 Hz, 1H), 7.26-7.20 (m, 4H), 7.10 (d, J=7.28 Hz, 1H), 5.44 (dd, J=12.24, 4.8 Hz, 1H), 4.38 (s, 2H), 3.58 (s, 2H), 3.05 (br s, 4H), 2.95-2.90 (m, 1H), 2.81-2.79 (m, 5H), 2.73-2.62 (m, 1H), 2.10-2.07 (m, 1H); LC MS: ES– 516.2.

Yellow solid, 50.0 mg, 23.20% yield, 98.45% purity. ¹H NMR (400 MHz, DMSO-d6) δ 11.12 (s, 1H), 8.30 (d, J=8.2 Hz, 1H), 8.07 (d, J=6.96 Hz, 1H), 7.79-7.77 (m, 1H), Compound 123

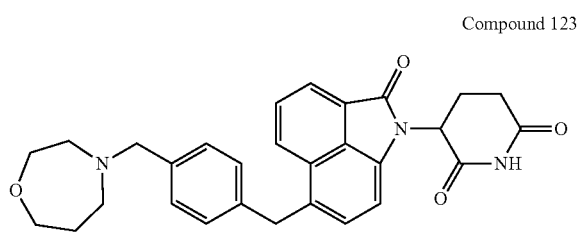 [SMILES: O=C1CCC(N2C(=O)c3cccc4c(Cc5ccc(CN6CCCOCC6)cc5)ccc2c34)C(=O)N1]

Yellow solid, 30.0 mg, 9.30% yield, 94.10% purity. $^1$H NMR (400 MHz, DMSO-d6) δ 11.12 (s, 1H), 8.32 (d, J=8.2 Hz, 1H), 8.07 (d, J=6.92 Hz, 1H), 7.80 (t, J=7.56 Hz, 1H), 7.40 (d, J=7.0 Hz, 1H), 7.24-7.21 (m, 4H), 7.10 (d, J=7.24 Hz, 1H), 5.44 (dd, J=12.4, 5.12 Hz, 1H), 4.37 (s, 2H), 3.65 (t, J=5.92 Hz, 1H), 3.54-3.52 (m, 4H), 2.95-2.91 (m, 1H), 2.77-2.73 (m, 1H), 2.66-2.62 (m, 1H), 2.52-2.43 (m, 4H), 2.10-2.07 (m, 2H); LC MS: ES+ 484.5.

Example 42. Synthesis of Synthesis of methyl 1-(2,6-dioxo-3-piperidyl)-2-oxo-benzo[cd]indole-6-carboxylate (Compound 124)

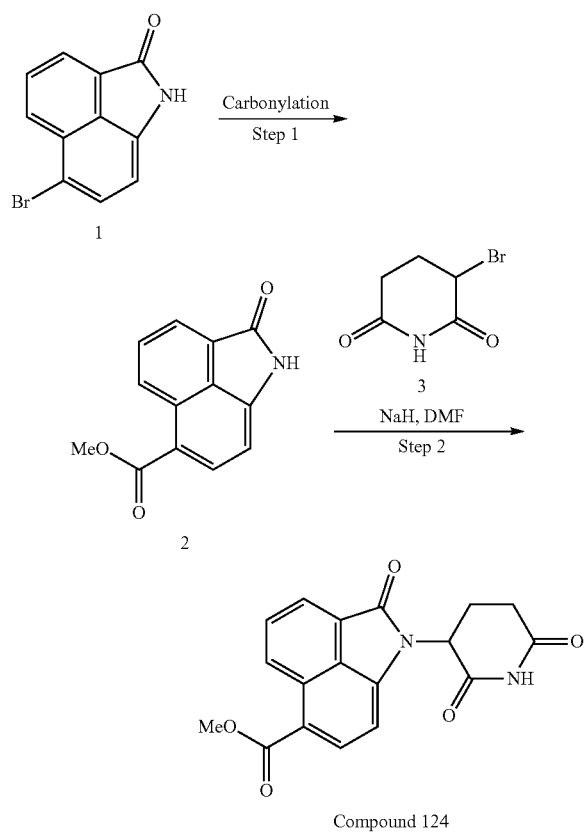

Step 1: Synthesis of 2-oxo-1H-benzo[cd]indole-6-carboxylate (2): A stirred solution of 6-bromo-1H-benzo[cd]indol-2-one (1) (1 g, 4.03 mol) and DPPP (332.51 mg, 806.21 umol) in Methanol (30 mL) in a PARR autoclave vessel was degassed with Argon for 5 minutes, followed by addition of TEA (1.63 g, 16.12 mmol, 2.25 mL) and Palladium (II) acetate (90.50 mg, 403.10 umol). The resultant reaction mixture was heated at 100° C. and for 16 hr under 70 psi of Carbon monoxide atmosphere in par auto clave. After completion of the reaction mixture TLC showed new spot, the reaction mixture was filtered through celite pad and filtrate was concentrated to get crude mass which was purified by combiflash chromatography using 10% EtOAc-Hexane as eluent to afford methyl 2-oxo-1H-benzo[cd]indole-6-carboxylate (2) (800 mg, 69.88% yield) as yellow solid. LC MS: ES+ 228.3.

Step 2: Synthesis of methyl 1-(2,6-dioxo-3-piperidyl)-2-oxo-benzo[cd]indole-6-carboxylate (4): To a stirred solution of methyl 2-oxo-1H-benzo[cd]indole-6-carboxylate (2) (100 mg, 440.11 umol) in DMF (3 mL) was added Sodium hydride (60% dispersion in mineral oil) (33.73 mg, 880.22 umol) and stirred at 70° C. for 30 min. Then 3-bromopiperidine-2,6-dione (3) (84.51 mg, 440.11 umol) was added and the reaction mixture was allowed to stir at that temp for 16h. TLC showed formation of a new polar spot along with un-reacted SM. The reaction mixture was quenched with water and extracted with ethyl acetate. The organic part was dried over sodium sulphate and concentrated. The crude thus obtained was purified by Prep TLC plate in 2% MeOH in DCM to afford methyl 1-(2,6-dioxo-3-piperidyl)-2-oxo-benzo[cd]indole-6-carboxylate Compound 124 (13 mg, 7.86% yield) as yellow solid. $^1$H NMR (400 MHz, DMSO-d6) δ 11.15 (s, 1H), 8.98 (d, J=Hz, 1H), 8.31 (d, J=Hz, 1H), 8.16 (d, J=Hz, 1H), 7.95 (t, J=Hz, 1H), 7.26 (d, J=Hz, 1H), 5.50-5.47 (m, 1H), 3.92 (s, 3H), 3.04-2.82 (m, 1H), 2.77-2.71 (m, 1H), 2.66-2.64 (m, 1H), 2.12-2.10 (m, 1H); LC MS: ES+ 339.1.

Example 43. Synthesis of 3-[6-[[4-[1-(1-methylcyclobutanecarbonyl)-4-piperidyl]triazol-1-yl]methyl]-2-oxo-benzo[cd]indol-1-yl]piperidine-2,6-dione (Compound 125)

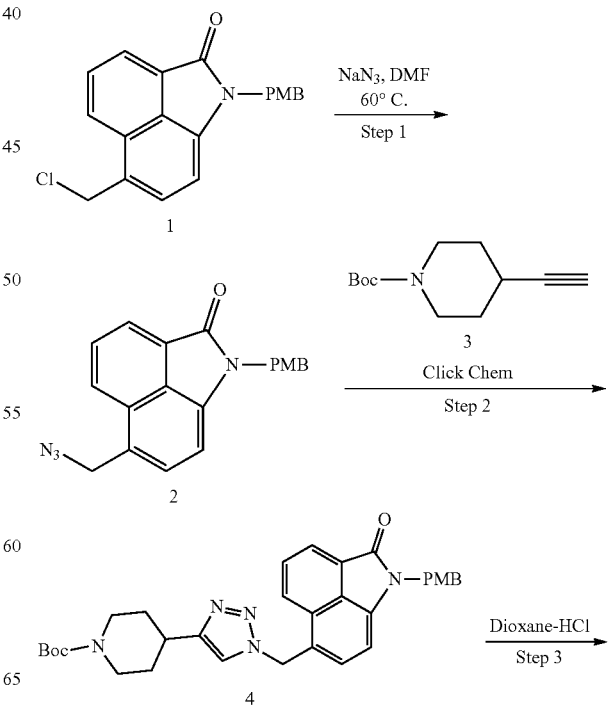

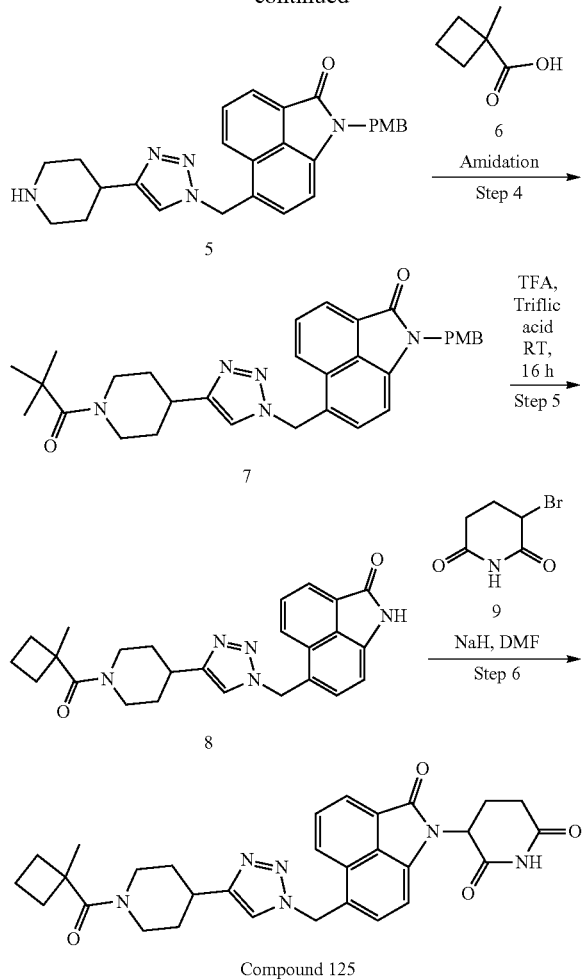

Compound 125

Step 1: Synthesis of 6-(azidomethyl)-1-[(4-methoxyphenyl)methyl]benzo[cd]indol-2-one (2): To a stirred solution of 6-(chloromethyl)-1-[(4-methoxyphenyl)methyl]benzo[cd]indol-2-one (1) (600 mg, 1.78 mmol) in DMF (10 mL) was added Sodium azide (346.41 mg, 5.33 mmol) under cooling condition and the resultant reaction mixture was stirred at room temperature for 16 hr. After completion (monitored by TLC) the reaction mixture was diluted with EtOAc and washed with water and brine, dried over sodium sulphate and concentrated under reduced pressure to afford 6-(azidomethyl)-1-[(4-methoxyphenyl)methyl]benzo[cd]indol-2-one (2) (500 mg, 72.75% yield) as sticky solid. LC MS: ES+ 345.3.

Step 2: Synthesis of tert-butyl 4-[1-[[1-[(4-methoxyphenyl)methyl]-2-oxo-benzo[cd]indol-6-yl]methyl]triazol-4-yl]piperidine-1-carboxylate (4): To a stirred solution of 6-(azidomethyl)-1-[(4-methoxyphenyl)methyl]benzo[cd]indol-2-one (2) (500 mg, 1.45 mmol) and tert-butyl 4-ethynylpiperidine-1-carboxylate (3) (303.87 mg, 1.45 mmol) in THF (12 mL) a solution of copper; sulfate; pentahydrate (36.25 mg, 145.19 umol) in water (3 mL) was added and stirred for 15 minutes followed by the addition of sodium;(2R)-2-[1,2-dihydroxyethyl]-4-hydroxy-5-oxo-2H-furan-3-olate (115.06 mg, 580.78 umol). The resultant reaction mixture was stirred at RT for 16 hours. After completion (monitored by TLC) the reaction mixture was filtered through celite bed and the filtrate was concentrated under reduced pressure. The crude thus obtained was purified by column chromatography (Silica, Gradient 0-3% MeOH in DCM) to afford tert-butyl 4-[1-[[1-[(4-methoxyphenyl)methyl]-2-oxo-benzo[cd]indol-6-yl]methyl]triazol-4-yl]piperidine-1-carboxylate (4) (500 mg, 61.15% yield) as light yellow solid. LC MS: ES+ 554.6.

Step 3: Synthesis of 1-[(4-methoxyphenyl)methyl]-6-[[4-(4-piperidyl)triazol-1-yl]methyl]benzo[cd]indol-2-one; hydrochloride (5): To a stirred solution of tert-butyl 4-[1-[[1-[(4-methoxyphenyl)methyl]-2-oxo-benzo[cd]indol-6-yl]methyl]triazol-4-yl]piperidine-1-carboxylate (4) (150 mg, 270.93 umol) in Dioxane (2 mL) was added Dioxane-HCl (4M) (4 mL) under cooling condition and the resultant reaction mixture was stirred at RT for 4 hours. After completion (monitored by TLC) the reaction mixture was concentrated under reduced pressure. The crude was triturated with Ether-Pentane to afford 1-[(4-methoxyphenyl)methyl]-6-[[4-(4-piperidyl)triazol-1-yl]methyl]benzo[cd]indol-2-one; hydrochloride (5) (110 mg, 69.4% Yield) as light yellow solid. LC MS: ES+ 454.5.

Step 4: Synthesis of 1-[(4-methoxyphenyl)methyl]-6-[[4-[1-(1-methylcyclobutanecarbonyl)-4-piperidyl]triazol-1-yl]methyl]benzo[cd]indol-2-one (7): To the stirred solution of 1-[(4-methoxyphenyl)methyl]-6-[[4-(4-piperidyl)triazol-1-yl]methyl]benzo[cd]indol-2-one; hydrochloride (5) (600 mg, 1.22 mmol) and 1-methylcyclobutanecarboxylic acid (6) (139.77 mg, 1.22 mmol) in DMF (10 mL) was added DIPEA (791.27 mg, 6.12 mmol, 1.07 mL) and stirred for 15 minutes followed by the addition of HATU (558.71 mg, 1.47 mmol) and was allowed to stir for 16 hr at RT. After completion (monitored by LCMS), the reaction mixture was diluted with Ethyl acetate and washed with cold water, brine, dried over sodium sulfate and concentrated under reduced pressure. The crude thus obtained was purified by column chromatography (silica, gradient: 0-3% MeOH in DCM) to afford 1-[(4-methoxyphenyl)methyl]-6-[[4-[1-(1-methylcyclobutanecarbonyl)-4-piperidyl]triazol-1-yl]methyl]benzo[cd]indol-2-one (7) (400 mg, 53.4% yield) as gummy solid. LC MS: ES+ 550.3.

Step 5: Synthesis of 6-[[4-[1-(1-methylcyclobutanecarbonyl)-4-piperidyl]triazol-1-yl]methyl]-1H-benzo[cd]indol-2-one (8): To a stirred solution of compound 1-[(4-methoxyphenyl)methyl]-6-[[4-[1-(1-methylcyclobutanecarbonyl)-4-piperidyl]triazol-1-yl]methyl]benzo[cd]indol-2-one (7) (400 mg, 727.72 umol) in TFA (4.0 mL) was added Trifluoromethanesulfonic acid (546.08 mg, 3.64 mmol, 319.35 uL) under cooling condition and the resultant reaction mixture was stirred at RT for 16 hr. After completion (monitored by TLC) the reaction mixture was concentrated under reduced pressure and crude mass was basified with saturated sodium bicarbonate solution and extracted with ethyl acetate. The layers were separated and the organic part was dried over sodium sulphate and concentrated under reduced pressure. Crude thus obtained was purified by Combiflash column (Gradient 0-3% MeOH in DCM) to afford 6-[[4-[1-(1-methylcyclobutanecarbonyl)-4-piperidyl]triazol-1-yl]methyl]-1H-benzo[cd]indol-2-one (8) (300 mg, 91.18% yield) as light yellow solid. LC MS: ES+ 430.4.

Step 6: Synthesis of 3-[6-[[4-[1-(1-methylcyclobutanecarbonyl)-4-piperidyl]triazol-1-yl]methyl]-2-oxo-benzo[cd]indol-1-yl]piperidine-2,6-dione: To a stirred solution of 6-[[4-[1-(1-methylcyclobutanecarbonyl)-4-piperidyl]triazol-1-yl]methyl]-1H-benzo[cd]indol-2-one (8) (140 mg, 325.95 umol) in THF (5 mL) was added Sodium hydride 60% dispersion in mineral oil (22.48 mg, 977.85 umol) at 0° C. and stirred for 5 min. Then 3-bromopiperidine-2,6-dione (9) (125.17 mg, 651.90 umol) was added under cooling condition and the reaction mixture was stirred at 70° C. for 60 min. After completion (monitored by TLC) the reaction mixture was quenched in ice and extracted with ethyl acetate. The organic part was further washed with water and brine, dried over sodium sulfate and concentrated. The crude was purified by Prep TCL Plate in 2.5% MeOH in DCM to afford 3-[6-[[4-[1-(1-methylcyclobutanecarbonyl)-4-piperidyl]triazol-1-yl]methyl]-2-oxo-benzo[cd]indol-1-yl]piperidine-2,6-dione Compound 125 (30 mg, 17% yield) as yellow solid. ¹H NMR (400 MHz, DMSO-d6) δ 11.13 (s, 1H), 8.43 (d, J=8.28 Hz, 1H), 8.12 (d, J=7.0 Hz, 1H), 7.96 (s, 1H), 7.88 (t, J=7.66 Hz, 1H), 7.58 (d, J=7.44 Hz, 1H), 7.17 (d, J=7.36 Hz, 1H), 5.46 (dd, J=12.64, 4.84 Hz, 1H), 4.30-4.28 (m, 1H), 3.51-3.49 (m, 1H), 3.03-2.63 (m, 6H), 2.49-2.32 (m, 2H), 2.09-2.07 (m, 1H), 1.93-1.85 (m, 3H), 1.79-1.73 (m, 2H), 1.61-1.57 (m, 1H), 1.42-1.39 (m, 2H), 1.31 (s, 3H); LC MS: ES+ 542.3.

Example 44. Synthesis of 3-[6-[[1-[1-(3-fluoro-2-pyridyl)-4-methyl-4-piperidyl]pyrazol-4-yl]methyl]-2-oxo-benzo[cd]indol-1-yl]piperidine-2,6-dione (Compound 126)

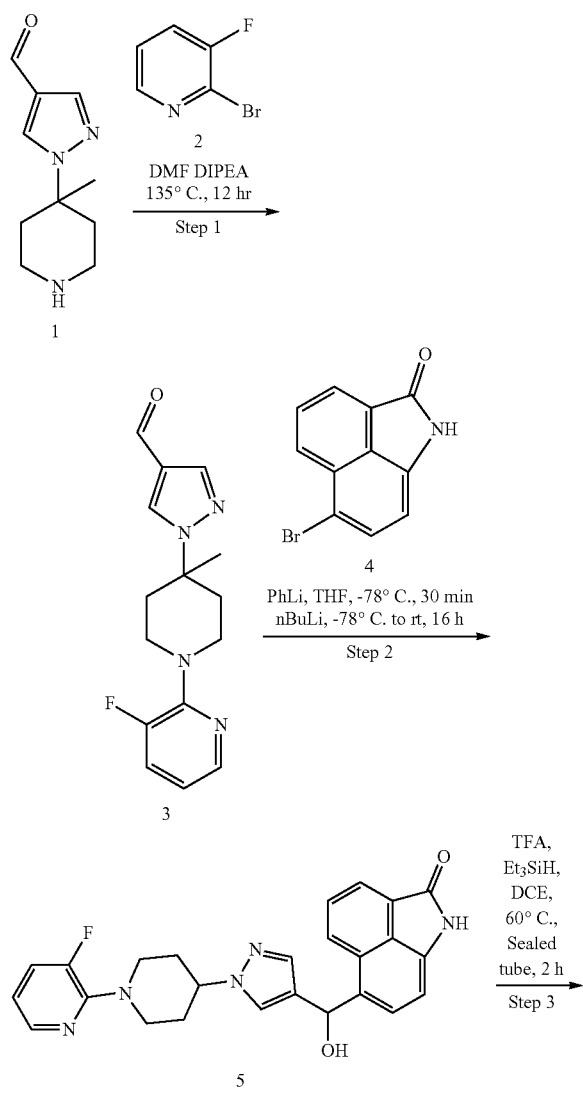

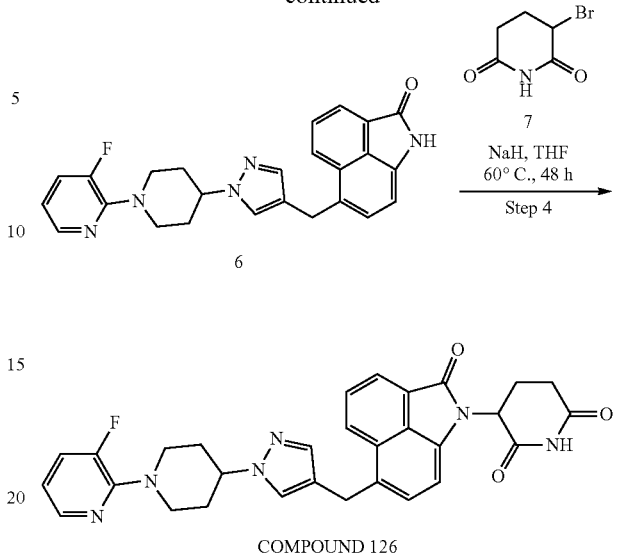

COMPOUND 126

Step 1: Synthesis 1-[1-(3-fluoro-2-pyridyl)-4-methyl-4-piperidyl]pyrazole-4-carbaldehyde (3): To the stirred solution of 1-(4-methyl-4-piperidyl)pyrazole-4-carbaldehyde (1) (325 mg, 1.68 mmol) in NMP (2.0 mL) was added N,N-Diisopropylethylamine (652.08 mg, 5.05 mmol, 878.82 uL) drop wise followed by the addition of 2,3-difluoropyridine (2) (193.54 mg, 1.68 mmol) and resulting solution was heated at 135° C. in a sealed tube for 12 hours. After completion of reaction (evidenced from LC MS), reaction mix was diluted with ethyl acetate (30 mL) and washed with cold water (2×15 mL). Organic phase was separated, dried over anhydrous sodium sulfate and evaporated under vacuum. Crude thus obtained was purified by flash chromatography (silica, gradient: 0 to 70% EtOAc in Hexane) to afford 1-[1-(3-fluoro-2-pyridyl)-4-methyl-4-piperidyl]pyrazole-4-carbaldehyde (3) (300 mg, 1.03 mmol, 61.25% yield, 99% purity). LC MS: ES+ 289.4.

Step 2: Synthesis of 6-[[1-[1-(3-fluoro-2-pyridyl)-4-methyl-4-piperidyl]pyrazol-4-yl]-hydroxy-methyl]-1H-benzo[cd]indol-2-one (5): To the stirred solution of 6-bromo-1H-benzo[cd]indol-2-one (4) (270 mg, 1.09 mmol) in dry grade THF (5.0 mL), was added Phenyllithium, 1.9M in di-n-butyl ether (91.47 mg, 1.09 mmol, 112.93 uL) at −78° C. under N2 atmosphere and the reaction was stirred at the same temperature for 30 minutes followed by the addition of n-Butyllithium (76.69 mg, 1.20 mmol) same temperature. After complete addition, the temperature was allowed to increase to −40° C. and the reaction mixture was stirred at the same temperature for 30 minutes. After getting the dess-bormo spot in TLC (30% ethyl acetate in Hexane) solution of 1-[1-(3-fluoro-2-pyridyl)-4-methyl-4-piperidyl]pyrazole-4-carbaldehyde (3) (260.45 mg, 903.36 umol) in dry THF (5.0 mL) was added at −78° C. and stirring was continued for 16 hr at room temperature. After completion of reaction (evidenced from TLC and LC MS), the reaction mixture was quenched with saturated ammonium chloride solution and extracted with ethyl acetate (2×40 mL). Organic phase was washed with water (2×20 mL) and separated, dried over anhydrous sodium sulphate and evaporated under reduced pressure to obtain the crude compound which was purified by flash chromatography (silica, gradient: 0-5% MeOH in DCM) to afford 6-[[1-[1-(3-fluoro-2-pyridyl)-4-methyl-4-piperidyl]pyrazol-4-yl]-hydroxymethyl]-1H-benzo[cd]indol-2-one (5) (88 mg, 190.43 umol, 17.50% yield) as brown solid and stored at ambient temperature in a round bottomed flask. LC MS: ES+ 458.5.

Step 3: Synthesis of 6-[[1-[1-(3-fluoro-2-pyridyl)-4methyl-4-piperidyl]pyrazol-4-yl]methyl]-1H-benzo[cd]indol-2-one (6): To the stirred solution of 6-[[1-[1-(3-fluoro-2-pyridyl)-4-methyl-4-piperidyl]pyrazol-4-yl]-hydroxymethyl]-1H-benzo[cd]indol-2-one (5) (86 mg, 187.98 umol) in DCE (2.0 mL) was added triethylsilane (87.43 mg, 751.92 umol, 120.10 uL) and Trifluoroacetic acid, 99% (171.47 mg, 1.50 mmol, 115.86 uL). Resulting solution heated at 70° C. under microwave condition for 30 mins. After completion of reaction (evidenced from TLC and LC MS), volatiles were removed. Solid residue was re dissolved in ethyl acetate (50 mL) and washed with saturated bicarbonate solution. Organic phase was separated, died over anhydrous sodium sulfate and concentrated. Crude reaction mass was purified by flash chromatography (silica, gradient: 0-5% MeOH in DCM) to afford 6-[[1-[1-(3-fluoro-2-pyridyl)-4-methyl-4-piperidyl]pyrazol-4-yl]methyl]-1H-benzo[cd]indol-2-one (6) (56 mg, 120.50 umol, 64.10% yield) as yellow solid which was kept at ambient temperature in a round bottomed flask. LC MS: ES+442.2.

Step 4: Synthesis of 3-[6-[[1-[1-(3-fluoro-2-pyridyl)-4methyl-4-piperidyl]pyrazol-4-yl]methyl]-2-oxo-benzo[cd]indol-1-yl]piperidine-2,6-dione: To a ice cooled solution of 6-[[1-[1-(3-fluoro-2-pyridyl)-4-methyl-4-piperidyl]pyrazol-4-yl]methyl]-1H-benzo[cd]indol-2-one (55.00 mg, 124.58 umol) (6) in dry THF (3 mL), Sodium hydride (60% dispersion in mineral oil) (28.64 mg, 1.25 mmol) was added portion wise, maintaining the temp <5 C. Once the addition is over, the resultant mixture was stirred for 15 minutes at RT. Then the reaction mixture was again cooled to 0° C. and 3-bromopiperidine-2,6-dione (7) (119.60 mg, 622.88 umol) was added to it portion wise. After complete addition, resulting solution was heated at 70° C. for 2 hour. After completion (evidenced from TLC), the reaction mixture was again cooled to 0° C. and quenched with ice cooled water (10 mL). Aqueous part was extracted with ethyl acetate (2×20 mL).

Combined extracts was dried over anhydrous sodium sulfate and concentrated under reduced pressure. Crude mass was purified by Preparative TLC (gradient: 2.5% MeOH in DCM) to 3-[6-[[1-[1-(3-fluoro-2-pyridyl)-4-methyl-4-piperidyl]pyrazol-4-yl]methyl]-2-oxo-benzo[cd]indol-1-yl]piperidine-2,6-dione Compound 126 (30 mg, 54.02 umol, 43.37% yield) as yellow solid which was stored in a round bottomed flask at 5° C. inside a refrigerator. $^1$H NMR (400 MHz, DMSO-d6) δ 11.11 (s, 1H), 8.40 (d, J=8.24 Hz, 1H), 8.08 (d, J=7.08 Hz, 1H), 7.98 (d, J=4.6 Hz, 1H), 7.84-7.81 (m, 2H), 7.50-7.45 (m, 1H), 7.35-7.33 (m, 2H), 7.07 (d, J=7.32 Hz, 1H), 6.86-6.83 (m, 1H), 5.43 (dd, J=12.68, 4.96 Hz, 1H), 4.21 (s, 2H), 3.51 (m, 2H), 3.21-3.16 (m, 2H), 2.94 (m, 1H), 2.75-2.61 (m, 3H), 2.42-2.40 (m, 2H), 2.09-2.07 (m, 1H), 1.92-1.88 (m, 2H), 1.38 (s, 3H); LC MS: ES+ 553.3.

Example 45. Synthesis of 3-[6-[[4-[4-methyl-1-[1-(trifluoromethyl)cyclopropanecarbonyl]-4-piperidyl]triazol-1-yl]methyl]-2-oxo-benzo[cd]indol-1-yl]piperidine-2,6-dione (Compound 127)

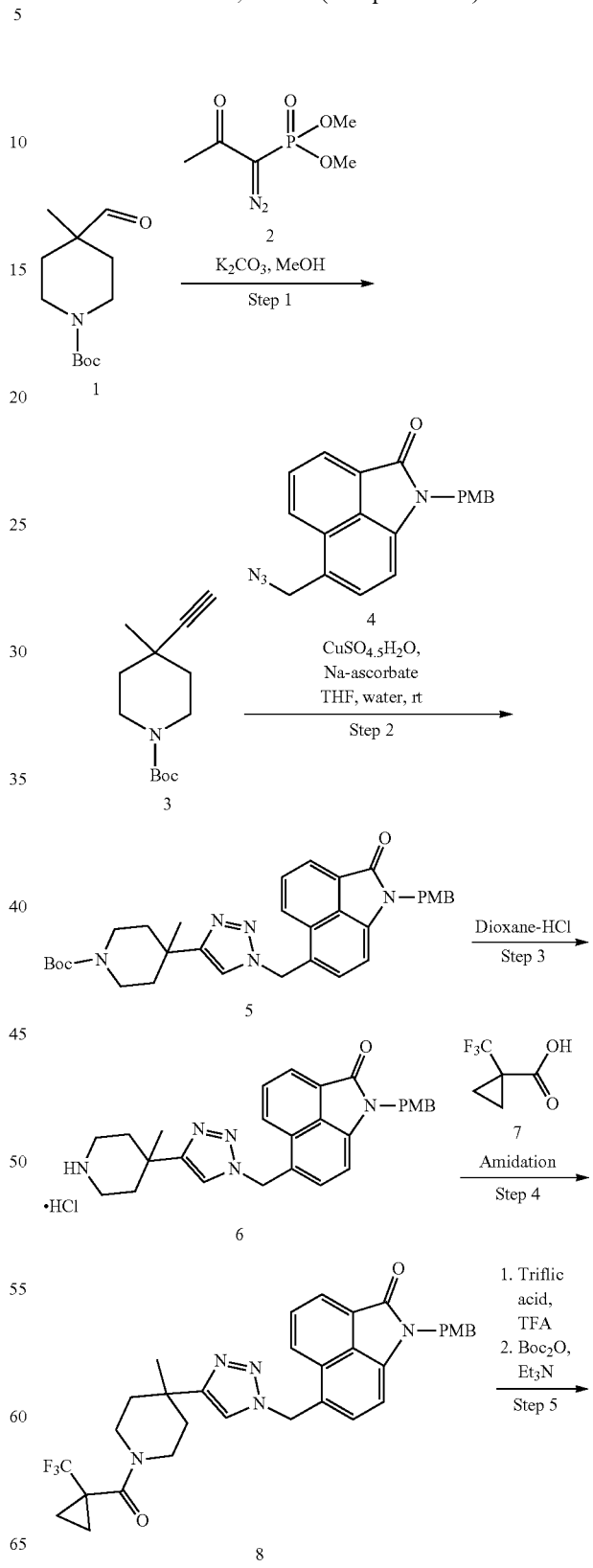

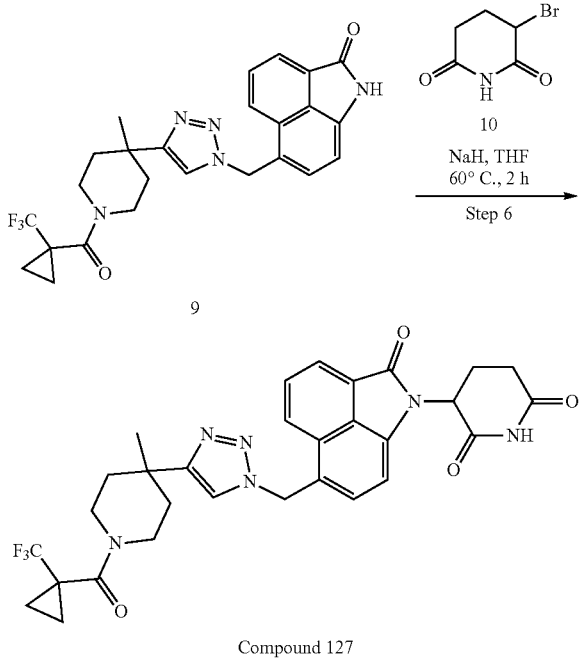

Compound 127

Step 1: Synthesis of tert-butyl 4-ethynyl-4-methyl-piperidine-1-carboxylate (3): To the stirred solution of tert-butyl 4-formyl-4-methyl-piperidine-1-carboxylate 1 (2.0 g, 8.80 mmol) in anhydrous Methanol (10.0 mL) was added Potassium carbonate, anhydrous, 99% (2.43 g, 17.60 mmol, 1.06 mL) and stirred the at room temperature for 30 mins. Dimethyl (1-diazo-2-oxopropyl)phosphonate 2 (2.03 g, 10.56 mmol) was added drop wise to the reaction mix and stirred the reaction mix at rt for overnight. After completion of reaction (evidenced from TLC), volatiles were removed under vacuum. Solid thus obtained was dissolved in ethyl acetate (100 mL) and washed with saturated NaHCO$_3$solution. Organic portion was separated, dried over anhydrous Na$_2$SO$_4$ and evaporated under vacuum to afford the crude compound tert-butyl 4-ethynyl-4-methyl-piperidine-1-carboxylate 3 (1.95 g, 7.86 mmol, 89.32% yield) which is used for the next step without any purification. LC MS: ES+ 224.2.

Step 2: Synthesis of tert-butyl 4-[1-[[1-[(4-methoxyphenyl)methyl]-2-oxo-benzo[cd]indol-6-yl]methyl]triazol-4-yl]-4-methyl-piperidine-1-carboxylate (5): To the stirred solution of tert-butyl 4-ethynyl-4-methyl-piperidine-1-carboxylate 3 (800 mg, 3.58 mmol) in THF (15.0 mL) was added 6-(azidomethyl)-1-[(4-methoxyphenyl)methyl]benzo[cd]indol-2-one 4 (616.84 mg, 1.79 mmol) at room temperature. After that, solution of copper; sulfate; pentahydrate (111.81 mg, 447.81 umol) in Water (5.0 mL) was added drop wise added to the reaction mix followed by sodium;(2R)-2-[(1S)-1,2-dihydroxyethyl]-4-hydroxy-5-oxo-2H-furan-3-olate (141.94 mg, 716.49 umol) and stirring was continued for 4 hours at same temperature. After completion of reaction, then the reaction mix was diluted with ethyl acetate (40 mL) and filtered through bed of celite. Filtrate was collected and evaporated under vacuum. Crude thus obtained purified by flash chromatography (100-200 silica; 0-60% Ethyl acetate in Hexane) to afford tert-butyl 4-[1-[[1-[(4-methoxyphenyl)methyl]-2-oxo-benzo[cd]indol-6-yl]methyl]triazol-4-yl]-4-methyl-piperidine-1-carboxylate 5 (900 mg, 1.49 mmol) as yellow solid and stored in a round bottomed flask at ambient temperature. LC MS: ES+ 568.2.

Step 3: Synthesis of 1-[(4-methoxyphenyl)methyl]-6-[[4-(4-methyl-4-piperidyl)triazol-1-yl]methyl]benzo[cd]indol-2-one; hydrochloride (6): To the cold solution of tert-butyl 4-[1-[[1-[(4-methoxyphenyl)methyl]-2-oxo-benzo[cd]indol-6-yl]methyl]triazol-4-yl]-4-methyl-piperidine-1-carboxylate 5 (900 mg, 1.59 mmol) in dioxane (5 mL) 4.0 M in Dioxane-HCl (1.59 mmol, 10.0 mL) was added drop wise and stirred the reaction at rt for 4 hours. After completion of reaction (evidenced from LCMS) volatiles were evaporated under reduced pressure. Solid material thus obtained was washed with diethyl ether (50 mL) and dried under reduced pressure to afford 1-[(4-methoxyphenyl)methyl]-6-[[4-(4-methyl-4-piperidyl)triazol-1-yl]methyl]benzo[cd]indol-2 one; hydrochloride 6 (830 mg, 1.49 mmol, 93.96% yield) as yellow solid and stored in round bottom flask at 5° C. in refrigerator. LC MS: ES+ 468.4.

Step 4: Synthesis of 1-[(4-methoxyphenyl)methyl]-6-[[4-[4-methyl-1-[1-(trifluoromethyl)cyclopropanecarbonyl]-4-piperidyl]triazol-1-yl]methyl]benzo[cd]indol-2-one (8): To the stirred solution of 1-(trifluoromethyl)cyclopropanecarboxylic acid 7 (100.89 mg, 654.73 umol) in dry grade DMF (5.0 mL) was added HATU (339.48 mg, 892.82 umol) and stirred for 15 minutes at room temperature under N2 atmosphere. Solution of 1-[(4-methoxyphenyl)methyl]-6-[[4-(4-methyl-4-piperidyl)triazol-1-yl]methyl]benzo[cd]indol-2-one; hydrochloride 6 (300 mg, 595.21 umol) and N-ethyl-N-isopropyl-propan-2-amine (384.63 mg, 2.98 mmol, 518.38 uL) in dry grade DMF (3.0 mL) was added to the resulting solution at 0° C. and stirred for another 12 hours at room temperature. After completion of reaction (evidenced from LCMS), ice cooled water (5 mL) was added to the reaction mixture and extracted with ethyl acetate (3×30 mL). Organic portion was separated, dried over anhydrous sodium sulfate and concentrated. Crude thus obtained washed with diethyl ether to get the pure compound 1-[(4-methoxyphenyl)methyl]-6-[[4-[4-methyl-1-[1-(trifluoromethyl)cyclopropanecarbonyl]-4-piperidyl]triazol-1-yl]methyl]benzo[cd]indol-2-one 8 (320 mg, 519.52 umol, 87.28% yield) as yellow solid which stored in a round bottomed flask at ambient temperature. LC MS: ES+ 604.3.

Step 5: Synthesis of 6-[[4-[4-methyl-1-[1-(trifluoromethyl)cyclopropanecarbonyl]-4-piperidyl]triazol-1-yl]methyl]-1H-benzo[cd]indol-2-one (9): To the stirred solution of 1-[(4-methoxyphenyl)methyl]-6-[[4-[4-methyl-1-[1-(trifluoromethyl)cyclopropanecarbonyl]-4-piperidyl]triazol-1-yl]methyl]benzo[cd]indol-2-one 8 (320 mg, 530.12 umol) in TFA (2.0 mL), trifluoromethanesulfonic acid (477.36 mg, 3.18 mmol, 279.16 uL) was added at room temperature and stirred for 12 hours at same temp. After complete consumption of starting material (evidenced from TLC), RM was quenched with saturated sodium bicarbonate solution (maintain pH-8) and extracted with ethyl acetate (40 mL). Organic portion was separated, dried over sodium sulfate and concentrated under reduced pressure. The crude thus obtained was purified by flash chromatography (100-200 silica; 0-100% Ethyl acetate in Hexane) to afford 6-[[4-[4-methyl-1-[1-(trifluoromethyl)cyclopropanecarbonyl]-4-piperidyl]triazol-1-yl]methyl]-1H-benzo[cd]indol-2-one 9 (234 mg, 479.15 umol, 90.38% yield) which kept in a round bottomed flask at ambient temperature. LC MS: ES+ 484.3.

Step 6: Synthesis of 3-[6-[[4-[4-methyl-1-[1-(trifluoromethyl)cyclopropanecarbonyl]-4-piperidyl]triazol-1-yl]methyl]-2-oxo-benzo[cd]indol-1-yl]piperidine-2,6-dione:
To a ice cooled solution of 6-[[4-[4-methyl-1-[1-(trifluoromethyl)cyclopropanecarbonyl]-4-piperidyl]triazol-1-yl]

methyl]-1H-benzo[cd]indol-2-one 9 (122 mg, 252.33 umol) in dry THF (10.0 mL) Sodium hydride 60% dispersion in mineral oil (55.57 mg, 2.42 mmol) portion wise, maintaining the temp <5° C. Once the addition is over, the resultant mixture was stirred for 15 minutes at RT. Then the reaction mixture was again cooled to 0° C. and 3-bromopiperidine-2,6-dione 10 (242.25 mg, 1.26 mmol) was added to it portion wise. After complete addition, resulting solution was heated at 70° C. for 1 hour. After completion (evidenced from TLC), the reaction mixture was again cooled to 0° C. and quenched with ice cooled water (40 mL). Aqueous part was extracted with ethyl acetate (3×50 mL). Combined extracts was dried over anhydrous sodium sulfate and concentrated under reduced pressure. Crude mass was purified by flash chromatography (silica, gradient: 2.5% MeOH in DCM) to afford 3-[6-[[4-[4-methyl-1-[1-(trifluoromethyl)cyclopropanecarbonyl]-4-piperidyl]triazol-1-yl]methyl]-2-oxo-benzo[cd]indol-1-yl]piperidine-2,6-dione Compound 127 (48.0 mg, 80.01 umol, 31.71% yield, 99.11% purity) as yellow solid which was stored in a round bottomed flask at 5° C. inside a refrigerator.

$^1$H NMR (400 MHz, DMSO-d6) δ 11.13 (s, 1H), 8.42 (d, J=8.2 Hz, 1H), 8.13 (d, J=7.12 Hz, 1H), 8.06 (s, 1H), 7.89 (t, J=7.12 Hz, 1H), 7.56 (d, J=7.08 Hz, 1H), 7.17 (d, J=7.4 Hz, 1H), 5.99 (s, 2H), 5.47-5.45 (m, 1H), 3.76-3.73 (m, 2H), 2.98-2.92 (m, 1H), 2.76-2.50 (m, 4H), 2.10-1.99 (m, 3H), 1.53 (br m, 2H), 1.25-1.14 (m, 7H); LC MS: ES+ 593.4.

Example 46. Synthesis of 4-[4-[[1-[[1-(2,6-dioxo-3-piperidyl)-2-oxo-benzo[cd]indol-6-yl]methyl]pyrazol-4-yl]methyl]piperazin-1-yl]-3-fluoro-benzonitrile (Compound 128)

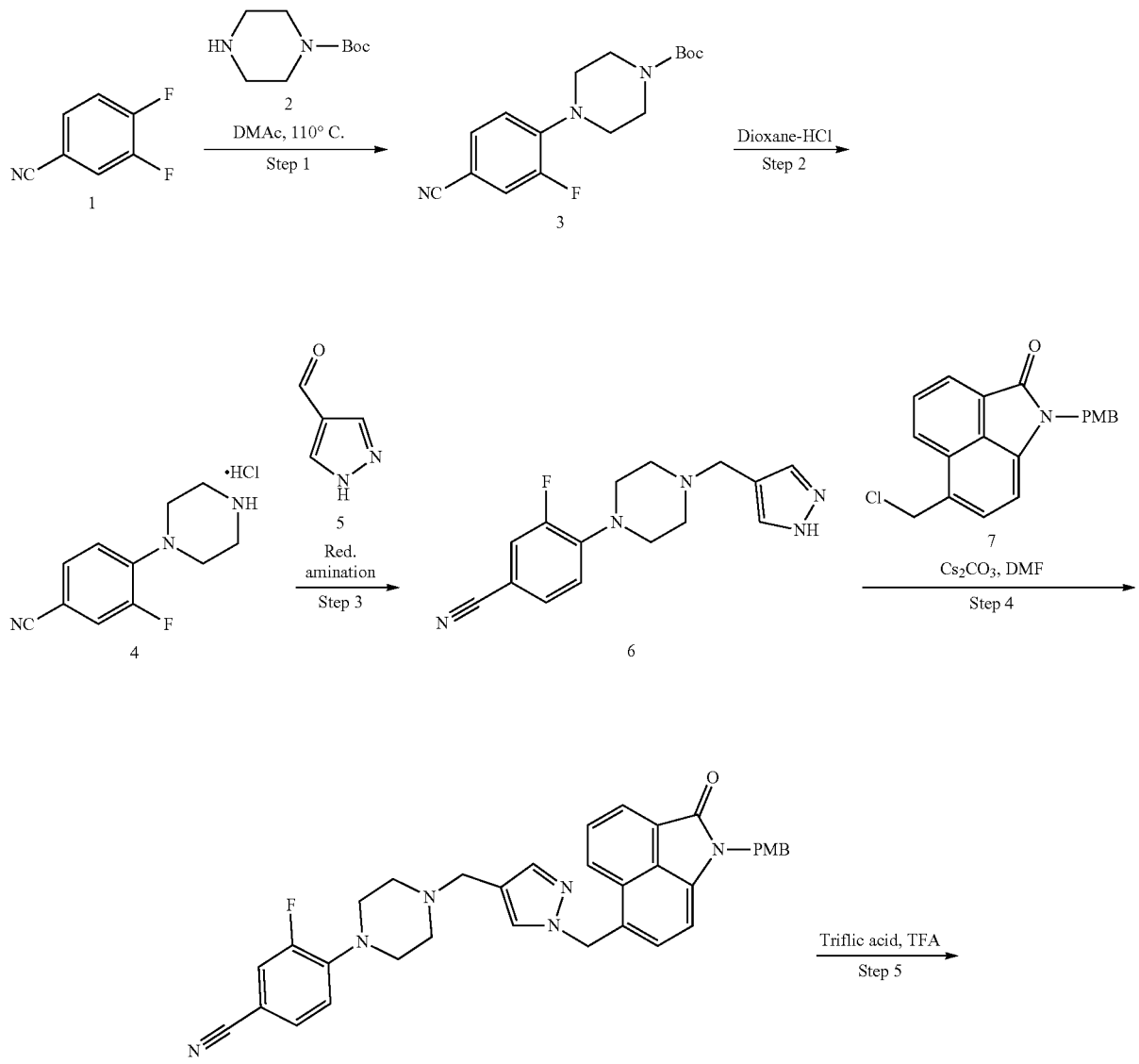

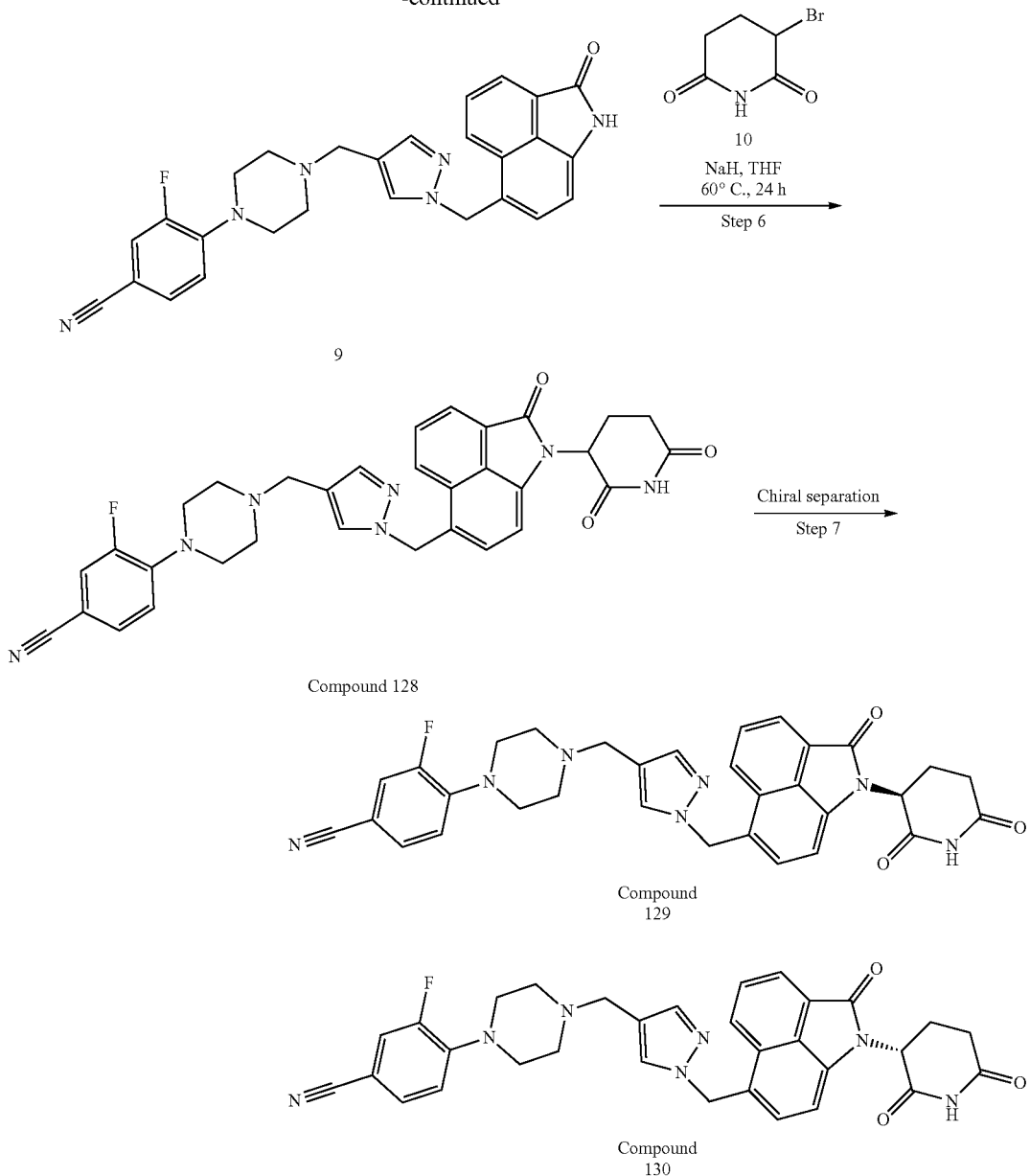

Step 1: Synthesis of tert-butyl 4-(4-cyano-2-fluoro-phenyl)piperazine-1-carboxylate (3): To a stirred solution of 3,4-difluorobenzonitrile (1) (13 g, 93.46 mmol) in DMSO (80 mL), Potassium carbonate (19.37 g, 140.18 mmol, 8.46 mL) and tert-butyl piperazine-1-carboxylate (2) (19.15 g, 102.80 mmol) were added and the resultant reaction mixture was heated at 100° C. for 16 hours. After completion (monitored by TLC), the reaction mixture was allowed to cool and water (500 ml) was added to it. The solid that formed was filtered off, washed with water, and dried under vacuum to obtain tert-butyl 4-(4-cyano-2-fluoro-phenyl)piperazine-1-carboxylate (3) (20 g, 66% yield) as a white solid. LC MS: ES+ 306.2.

Step 2: Synthesis of 3-fluoro-4-piperazin-1-yl-benzonitrile Hydrochloride salt (4): To a stirred solution of tert-butyl 4-(4-cyano-2-fluoro-phenyl)piperazine-1-carboxylate (3) (20 g, 65.50 mmol) in Dioxane (15 mL) was added Dioxane-HCl (65.50 mmol, 50 mL) and the reaction mixture was stirred at RT for 3 hours. All the volatiles were removed under reduced pressure. The solid obtained was triturated with ether to afford 3-fluoro-4-piperazin-1-yl-benzonitrile; hydrochloride (4) (17 g, 88% yield) as a white solid. LC MS: ES+ 206.4.

Step 3: Synthesis of 3-fluoro-4-[4-(1H-pyrazol-4-ylmethyl)piperazin-1-yl]benzonitrile (6): To a stirred solution of 3-fluoro-4-piperazin-1-yl-benzonitrile; hydrochloride (4) (2 g, 8.27 mmol) in Methanol (20 mL) was added Acetic acid (496.93 mg, 8.27 mmol, 473.27 uL) and the reaction was stirred at RT for 10 min. Then 1H-pyrazole-4-carbaldehyde (5) (1.19 g, 12.41 mmol) followed by Sodium cyanoborohydride (780.03 mg, 12.41 mmol) and Triethyl amine (1.26 g, 12.41 mmol, 1.73 mL) were added and the reaction mixture was stirred at RT for 16 hr. After completion of the reaction (monitored by TLC) the reaction mixture was diluted with DCM and washed with water, sodium bicarbonate and brine, dried over sodium sulfate and concentrated under reduced pressure. The crude was purified by combiflash column (Gradient 0-3% MeOH in DCM) to afford 3-fluoro-4-[4-(1H-pyrazol-4-ylmethyl)piperazin-1-yl]benzonitrile (6) (1 g, 40.66% yield) as yellow gum. LC MS: ES+ 286.3.

Step 4: Synthesis of 3-fluoro-4-[4-[[1-[[1-[(4-methoxyphenyl)methyl]-2-oxo-benzo[cd]indol-6-yl]methyl]pyrazol-3-yl]methyl]piperazin-1-yl]benzonitrile (8): To a stirred solution of 3-fluoro-4-(1H-pyrazol-4-ylmethyl)piperazin-1-yl]benzonitrile (6) (2 g, 7.01 mmol) in DMF (40 mL) were added Cesium carbonate (5.71 g, 17.52 mmol) and 6-(chloromethyl)-1-[(4-methoxyphenyl)methyl]benzo[cd]indol-2-one (7) (3.55 g, 10.51 mmol) and the resultant reaction mixture was heated at 90° C. for 16h. After completion of the reaction (monitored by TLC) the reaction mixture was diluted with cooled water extracted with ethyl acetate (Twice). The combined organic layer was further washed with water and saturated brine solution, dried over sodium sulphate and concentrated under reduced pressure. The crud thus obtained was purified by combiflash Column (Gradient 0-1% MeOH in DCM) to afford 3-fluoro-4-[4-[[1-[[1-[(4-methoxyphenyl)methyl]-2-oxo-benzo[cd]indol-6-yl]methyl]pyrazol-3-yl]methyl]piperazin-1-yl]benzonitrile (8) (2.6 g, 56.90% yield) as light yellow solid. LC MS ES+ 587.4.

Step 5: Synthesis of 3-fluoro-4-[4-[1-[(2-oxo-1H-benzo[cd]indol-5-yl)methyl]pyrazol-4-yl]piperazin-1-yl]benzonitrile (9): To a stirred solution of 3-fluoro-4-[4-[1-[[1-[(4-methoxyphenyl)methyl]-2-oxo-benzo[cd]indol-5-yl]methyl]pyrazol-4-yl]piperazin-1-yl]benzonitrile (8) (2.5 g, 4.37 mmol) in TFA (20 mL) was added trifluoromethanesulfonic acid (6.55 g, 43.66 mmol, 3.83 mL) and the resultant reaction mixture was stirred at room temperature for 16h. After completion of the reaction (monitored by TLC) the reaction mass was concentrated under reduced pressure. The crude was then basified with saturated bicarbonate solution and extracted with ethyl acetate. The organic layer was further washed with water and brine, dried over sodium sulphate and concentrated under reduced pressure. The crude thus obtained was purified by combiflash column (3% MeOH in DCM) to afford 3-fluoro-4-[4-[1-[(2-oxo-1H-benzo[cd]indol-5-yl)methyl]pyrazol-4-yl]piperazin-1-yl]benzonitrile (9) (1.4 g, 67.33% yield) as light yellow solid. LC MS ES+ 467.3.

Step 6: Synthesis of 4-[4-[[1-[[1-(2,6-dioxo-3-piperidyl)-2-oxo-benzo[cd]indol-6-yl]methyl]pyrazol-4-yl]methyl]piperazin-1-yl]-3-fluoro-benzonitrile: To a cooled solution of 3-fluoro-4-[4-[[1-[(2-oxo-1H-benzo[cd]indol-6-yl)methyl]pyrazol-4-yl]methyl]piperazin-1-yl]benzonitrile (9) (800 mg, 1.71 mmol) in dry THF (7 mL), Sodium hydride (60% dispersion in mineral oil) (394.25 mg, 17.15 mmol) was added portion wise, maintaining the temp <5° C. Once the addition is over, the resultant mixture was stirred for 15 minutes at RT. Then the reaction mixture was again cooled to 0° C. and 3-bromopiperidine-2,6-dione (10) (1.65 g, 8.57 mmol) was added to it portion wise. After complete addition, resulting solution was heated at 70° C. 1 hour. After completion (evidenced from TLC), the reaction mixture was cooled to 0° C. and quenched with the addition of ice cooled water. Aqueous part was extracted with ethyl acetate (Twice). Combined organics was separated, dried over sodium sulphate and concentrated under reduced pressure. Crude mass was purified by column chromatography (silica, gradient: 30-100% EtOAc in DCM) to afford 4-[4-[[1-[[1-(2,6-dioxo-3-piperidyl)-2-oxo-benzo[cd]indol-6-yl]methyl]pyrazol-4-yl]methyl]piperazin-1-yl]-3-fluoro-benzonitrile Compound 128 (600 mg, 60.5% yield) as yellow solid. $^1$H NMR (400 MHz, DMSO-d6) δ 11.12 (s, 1H), 8.40 (d, J=8.16 Hz, 1H), 8.10 (d, J=6.88 Hz, 1H), 7.85 (t, J=7.66 Hz, 1H), 7.75 (s, 1H), 7.67 (m, 1H), 7.54 (d, J=8.36 Hz, 1H), 7.48 (d, J=9.32 Hz, 1H), 7.35 (s, 1H), 7.14-7.08 (m, 2H), 5.72 (s, 2H), 5.47-5.44 (m, 1H), 3.36 (s, 2H), 3.13 (br s, 4H), 2.98-2.91 (m, 1H), 2.80-2.73 (m, 1H), 2.67-2.63 (m, 1H), 2.45 (br s, 4H), 2.09-2.07 (m, 1H); LC MS: ES+ 578.2.

Step 7: Chiral separation: Synthesis of 4-[4-[[1-[[1-[-2,6-dioxo-3-piperidyl]-2-oxo-benzo[cd]indol-6-yl]methyl]pyrazol-4-yl]methyl]piperazin-1-yl]-3-fluoro-benzonitrile (Compound 129) and 4-[4-[[1-[[1-[2,6-dioxo-3-piperidyl]-2-oxo-benzo[cd]indol-6-yl]methyl]pyrazol-4-yl]methyl]piperazin-1-yl]-3-fluoro-benzonitrile (Compound 130): Using a C-Amylose A (250×30 mm) 5p column passing through a mobile phase of 45% $CO_2$+55% isopropyl alcohol at a flow rate of 30 mL/min, a temperature of 35 C and ABPR of 120 bar to afford 4-[4-[[1-[[1-(2,6-dioxo-3-piperidyl)-2-oxo-benzo[cd]indol-6-yl]methyl]pyrazol-4-yl]methyl]piperazin-1-yl]-3-fluoro-benzonitrile (11) (600 mg, 1.04 mmol) was separated into enantiomers by chiral SFC method to afford 4-[4-[[1-[[1-[2,6-dioxo-3-piperidyl]-2-oxo-benzo[cd]indol-6-yl]methyl]pyrazol-4-yl]methyl]piperazin-1-yl]-3-fluoro-benzonitrile Compound 129) (220 mg, % ee 98.1)) as first eluting peak from column $^1$H NMR (400 MHz, DMSO-d6) δ 11.12 (s, 1H), 8.40 (d, J=8.16 Hz, 1H), 8.10 (d, J=6.88 Hz, 1H), 7.85 (t, J=7.66 Hz, 1H), 7.75 (s, 1H), 7.67 (m, 1H), 7.54 (d, J=8.36 Hz, 1H), 7.48 (d, J=9.32 Hz, 1H), 7.35 (s, 1H), 7.14-7.08 (m, 2H), 5.72 (s, 2H), 5.45 (dd, J=12.8, 5.12 Hz, 1H), 3.35 (s, 2H), 3.13 (br s, 4H), 2.98-2.91 (m, 1H), 2.80-2.73 (m, 1H), 2.67-2.63 (m, 1H), 2.45 (br s, 4H), 2.09-2.07 (m, 1H); LC MS: ES+ 578.6; and 4-[4-[[1-[[1-[2,6-dioxo-3-piperidyl]-2-oxo-benzo[cd]indol-6-yl]methyl]pyrazol-4-yl]methyl]piperazin-1-yl]-3-fluoro-benzonitrile Compound 130 (215 mg, % ee 100) as second eluting peak from column as yellow solids, $^1$H NMR (400 MHz, DMSO-d6) δ 11.12 (s, 1H), 8.40 (d, J=8.16 Hz, 1H), 8.10 (d, J=6.88 Hz, 1H), 7.85 (t, J=7.66 Hz, 1H), 7.75 (s, 1H), 7.67 (m, 1H), 7.54 (d, J=8.36 Hz, 1H), 7.48 (d, J=9.32 Hz, 1H), 7.35 (s, 1H), 7.14-7.08 (m, 2H), 5.72 (s, 2H), 5.45 (dd, J=12.8, 5.12 Hz, 1H), 3.35 (s, 2H), 3.13 (br s, 4H), 2.98-2.91 (m, 1H), 2.80-2.73 (m, 1H), 2.67-2.63 (m, 1H), 2.45 (br s, 4H), 2.09-2.07 (m, 1H); LC MS: ES+ 578.6.

Example 47. Synthesis of 4-[4-[[4-[[1-(2,6-dioxo-3-piperidyl)-2-oxo-benzo[cd]indol-6-yl]methyl]phenyl]methyl]-4,7-diazaspiro[2.5]octan-7-yl]-3-fluoro-benzonitrile (Compound 131)

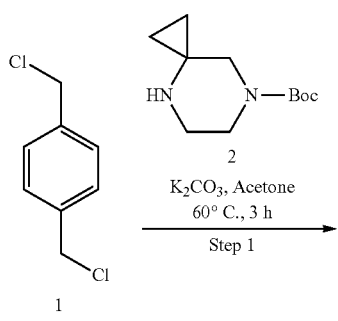

427
-continued

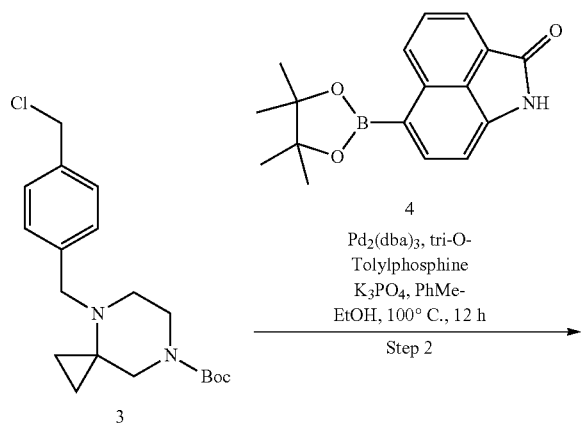

428
-continued

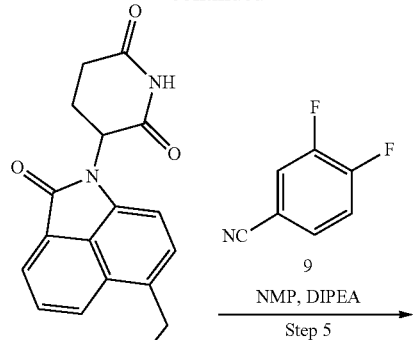

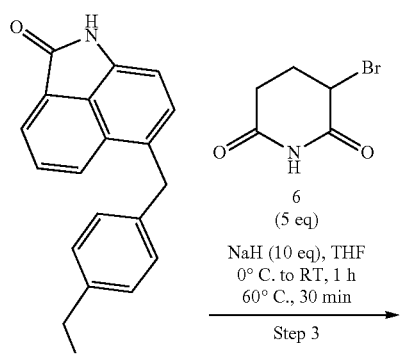

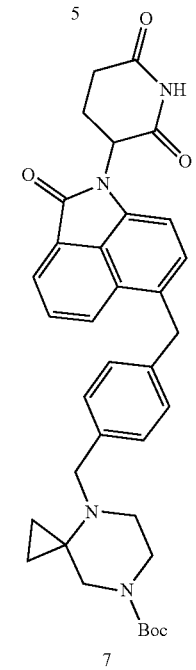

Compound 131

Step 1: Synthesis of tert-butyl 4-[[4-(chloromethyl)phenyl]methyl]-4,7-diazaspiro[2.5]octane-7-carboxylate (3): To a stirred solution of tert-butyl 4,7-diazaspiro[2.5]octane-7-carboxylate 1 (550 mg, 2.59 mmol) in dry grade acetone (5.0 mL) was added Potassium carbonate, anhydrous, 99% (1.07 g, 7.77 mmol, 469.09 uL) at RT and the resultant reaction mixture was heated at 50° C. for 20 minutes. 1,4-bis(chloromethyl)benzene 2 (453.53 mg, 2.59 mmol, 319.39 uL) was then added to the reaction mixture and heating was continued for 3 hours. After completion of reaction (monitored by TLC and LCMS), volatiles were removed under vacuum and the solid thus obtained was taken in Ethyl acetate (50 mL), washed with water (3×20 ml), Brine (2×15 mL), dried over anhydrous sodium sulfate and concentrated under reduced pressure. Crude mass was purified by column chromatography (silica, gradient: 10-50% Ethyl acetate in Hexane) to afford tert-butyl 4-[[4-(chloromethyl)phenyl]methyl]-4,7-diazaspiro[2.5]octane-7-carboxylate 3 (300 mg, 795.14 umol, 30.69% yield) as colorless sticky solid which was stored in a round bottomed flask at 5° C. inside a refrigerator. LC MS: ES+ 351.4.

Step 2: Synthesis of tert-butyl 4-[[4-[(2-oxo-1H-benzo[cd]indol-6-yl)methyl]phenyl]methyl]-4,7-diazaspiro[2.5]octane-7-carboxylate (5): To a well degassed solution of -butyl 4-[[4-(chloromethyl)phenyl]methyl]-4,7-diazaspiro[2.5]octane-7-carboxylate 3 (700 mg, 1.99 mmol) and 6-(4,4,5,5-tetramethyl-1,3,2-dioxaborolan-2-yl)-1H-benzo[cd]indol-2-one 4 (1.18 g, 3.99 mmol) in Ethanol (2 mL)-Toluene (4 mL), Potassium phosphate tribasic, anhydrous, (1.27 g, 5.98 mmol) was added followed by the addition of Tri-o-Tolyl phosphine (121.44 mg, 398.99 umol) and Pd$_2$(dba)$_3$ (182.68 mg, 199.50 umol). The resulting mixture was then heated at 90° C. for 12 hours. After completion of reaction (as monitored by LCMS), the reaction mixture was filtered through a bed of celite, washed with ethyl acetate (30 mL). The combined filtrate was then washed with water (3×20 mL) and brine (2×15 mL), dried over anhydrous sodium sulfate and concentrated under reduced pressure. Crude mass was purified by column chromatography (silica, gradient: 0-20% Ethyl acetate in DCM) to obtain tert-butyl 4-[[4-[(2-oxo-1H-benzo[cd]indol-6-yl)methyl]phenyl]methyl]-4,7-diazaspiro[2.5]octane-7-carboxylate 5 (450 mg, 809.55 umol, 40.58% yield, 87% purity) as yellow solid which was stored in a Tarson plastic bottle at ambient temperature. LC MS: ES+ 484.4.

Step 3: Synthesis tert-butyl 4-[[4-[[1-(2,6-dioxo-3-piperidyl)-2-oxo-benzo[cd]indol-6-yl]methyl]phenyl]methyl]-4,7-diazaspiro[2.5]octane-7-carboxylate (7): To a ice cooled solution tert-butyl 4-[[4-[(2-oxo-1H-benzo[cd]indol-6-yl)methyl]phenyl]methyl]-4,7-diazaspiro[2.5]octane-7-carboxylate 5 (425 mg, 878.83 umol) in dry THF (10 mL), Sodium hydride (60% dispersion in mineral oil) (202.04 mg, 8.42 mmol) was added portion wise, maintaining the temp <5° C. Once the addition is over, the resultant mixture was stirred for 15 minutes at RT. Then the reaction mixture was again cooled to 0° C. and 3-bromopiperidine-2,6-dione 6 (843.72 mg, 4.39 mmol) was added to it portion wise. After complete addition, resulting solution was heated at 70° C. for 1 hour. After completion (evidenced from TLC), the reaction mixture was again cooled to 0° C. and quenched with ice cooled water (40 mL). Aqueous part was extracted with ethyl acetate (3×50 mL). Combined extracts was dried over anhydrous sodium sulfate and concentrated under reduced pressure. Crude mass was purified by PREP-TLC (50% ethyl acetate in DCM as eluent) to afford tert-butyl 4-[[4-[[1-(2,6-dioxo-3-piperidyl)-2-oxo-benzo[cd]indol-6-yl]methyl]phenyl]methyl]-4,7-diazaspiro[2.5]octane-7-carboxylate 7 (320 mg, 414.33 umol, 47.15% yield) as yellow solid which was stored in a round bottomed flask at 5° C. inside a refrigerator. LC MS: ES+ 595.7.

Step 4: Synthesis of 3-[6-[[4-(4,7-diazaspiro[2.5]octan-4-ylmethyl)phenyl]methyl]-2-oxo-benzo[cd]indol-1-yl]piperidine-2,6-dione; hydrochloride (8): To the stirred solution of tert-butyl 4-[[4-[[1-(2,6-dioxo-3-piperidyl)-2-oxo-benzo[cd]indol-6-yl]methyl]phenyl]methyl]-4,7-diazaspiro[2.5]octane-7-carboxylate 7 (200 mg, 336.30 umol) in dry Dioxane (5.0 mL), Dioxane-HCl (336.30 umol, 5.0 mL) was added at 0° C. and stirred for 2 at rt. After completion of reaction (evidenced from LC MS), volatiles were removed under reduced pressure to afford crude 3-[6-[[4-(4,7-diazaspiro[2.5]octan-4-ylmethyl)phenyl]methyl]-2-oxo-benzo[cd]indol-1-yl]piperidine-2,6-dione; hydrochloride 8 (150 mg, 198.24 umol, 58.95% yield, 75% purity) as yellow solid. LC MS: ES+ 495.4.

Step 5: Synthesis of 4-[4-[[4-[[1-(2,6-dioxo-3-piperidyl)-2-oxo-benzo[cd]indol-6-yl]methyl]phenyl]methyl]-4,7-diazaspiro[2.5]octan-7-yl]-3-fluoro-benzonitrile: To the well degassed solution of 3-[6-[[4-(4,7-diazaspiro[2.5]octan-4-ylmethyl)phenyl]methyl]-2-oxo-benzo[cd]indol-1-yl]piperidine-2,6-dione; hydrochloride 8 (175 mg, 329.54 umol) in NMP (2.0 mL), N,N-Diisopropylethylamine (255.54 mg, 1.98 mmol, 344.39 uL) was added followed by 3,4-difluorobenzonitrile (68.76 mg, 494.31 umol). Resulting solution was then heated at 110° C. for 12 hr in sealed tube. After completion of reaction as evidenced from LC MS, reaction mixture was cooled to RT and ice cooled water (5 mL) was added to it. Aqueous part was extracted with ethyl acetate (3×30 mL). Organic phase was separated, dried over sodium sulfate and concentrated. Crude residue was purified by PREP TLC (40% Ethyl acetate in DCM) to afford 4-[4-[[4-[[1-(2,6-dioxo-3-piperidyl)-2-oxo-benzo[cd]indol-6-yl]methyl]phenyl]methyl]-4,7-diazaspiro[2.5]octan-7-yl]-3-fluoro-benzonitrile Compound 131 (40.0 mg, 64.57 umol, 19.60% yield) as yellow solid which was stored in a round bottomed flask at 5° C. inside a refrigerator. $^1$H NMR (400 MHz, DMSO-d6) δ 11.12 (s, 1H), 8.31 (d, J=8.24 Hz, 1H), 8.07 (d, J=6.96 Hz, 1H), 7.80 (t, J=7.36 Hz, 1H), 7.65 (d, J=12.88 Hz, 1H), 7.54 (d, J=7.48 Hz, 1H), 7.39 (d, J=7.48 Hz, 1H), 7.23-7.16 (m, 4H), 7.12-7.08 (m, 2H), 5.44-5.42 (m, 1H), 4.36 (s, 2H), 3.76 (s, 2H), 3.18 (m, 2H), 3.07 (s, 2H), 2.98-2.91 (m, 1H), 2.77-2.74 (m, 3H), 2.66-2.62 (m, 1H), 2.07 (br m, 1H), 0.64 (m, 2H), 0.54 (m, 2H); LC MS: ES+ 614.2.

Example 48. Synthesis of N-tert-butyl-4-[4-[[1-(2,6-dioxo-3-piperidyl)-2-oxo-benzo[cd]indol-6-yl]methyl]pyrazol-1-yl]-N-methyl-piperidine-1-carboxamide (Compound 132)

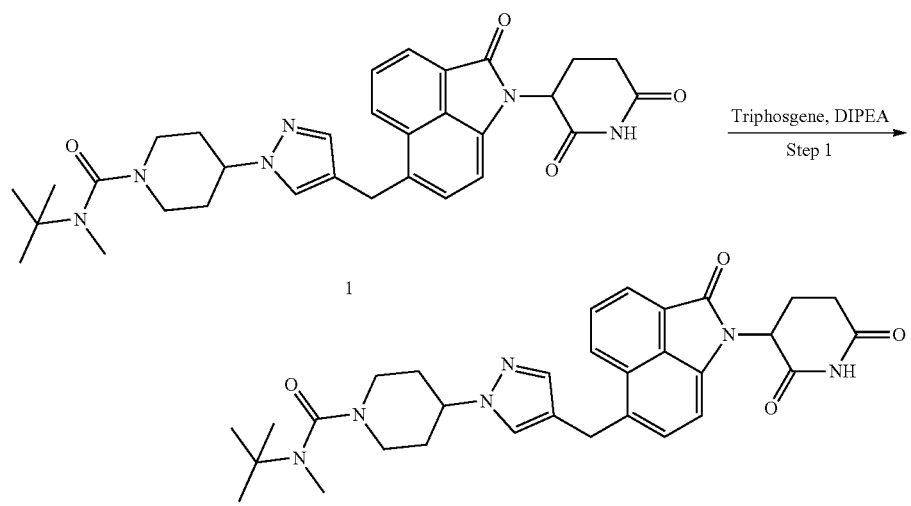

Compound 132

Step 1: Synthesis of N-tert-butyl-4-[4-[[1-(2,6-dioxo-3-piperidyl)-2-oxo-benzo[cd]indol-6-yl]methyl]pyrazol-1-yl]-N-methyl-piperidine-1-carboxamide: To the stirred solution of bis(trichloromethyl) carbonate (75.07 mg, 252.97 umol) in dry grade DCM (20 mL), solution of 3-[2-oxo-6-[[1-(4-piperidyl)pyrazol-4-yl]methyl]benzo[cd]indol-1-yl]piperidine-2,6-dione 1 (249.32 mg, 562.16 umol) in dry DCM (20 mL) was added drop wise at 0° C. followed by the addition of solution of N,N Di isopropyl ethyl amine (163.48 mg, 1.26 mmol, 220.32 uL) in DCM (5 mL) under inert atmosphere. After complete addition, reaction mixture was kept on stirring at rt for 30 minutes at rt. Then solution of N,2-dimethylpropan-2-amine (49 mg, 562.16 umol, 67.40 uL) in DCM (20 mL) was added to the reaction mixture at rt and stirred further for 12 hours at same temperature. After completion of reaction (evidenced from LC MS), reaction mixture was washed with water (2×20 mL)/brine (20 mL). Organic part was separated, dried over anhydrous sodium sulfate and concentrated under reduced pressure. Crude thus obtained was purified by Preparative TLC Plate (eluting with 60% Ethyl acetate in DCM) to afford N-tert-butyl-4-[4-[[1-(2,6-dioxo-3-piperidyl)-2-oxo-benzo[cd]indol-6-yl]methyl]pyrazol-1-yl]-N-methyl-piperidine-1-carboxamide Compound 132 (20 mg, 34.13 umol, 6.07% yield, 95% purity) as yellow solid. $^1$H NMR (400 MHz, DMSO-d6) δ 11.11 (s, 1H), 8.37 (d, J=8.28 Hz, 1H), 8.08 (d, J=6.8 Hz, 1H), 7.82 (t, J=7.28 Hz, 1H), 7.35 (d, J=7.2 Hz, 1H), 7.31 (s, 1H), 7.07 (d, J=7.28 Hz, 1H), 5.43 (dd, J=7.16 Hz, 1H), 4.18 (br s, 3H), 3.67 (m, 2H), 2.94-2.90 (m, 1H), 2.80-2.77 (m, 3H), 2.62 (br s, 4H), 1.90-1.87 (m, 1H), 1.74-1.66 (m, 4H), 1.22 (s, 9H); LC MS: ES+ 557.3.

Example 49. Synthesis of tert-butyl 4-[[4-[[1-(2,6-dioxo-3-piperidyl)-2-oxo-benzo[cd]indol-6-yl]methyl]phenyl]methyl]-4,7-diazaspiro[2.5]octane-7-carboxylate (Compound 133)

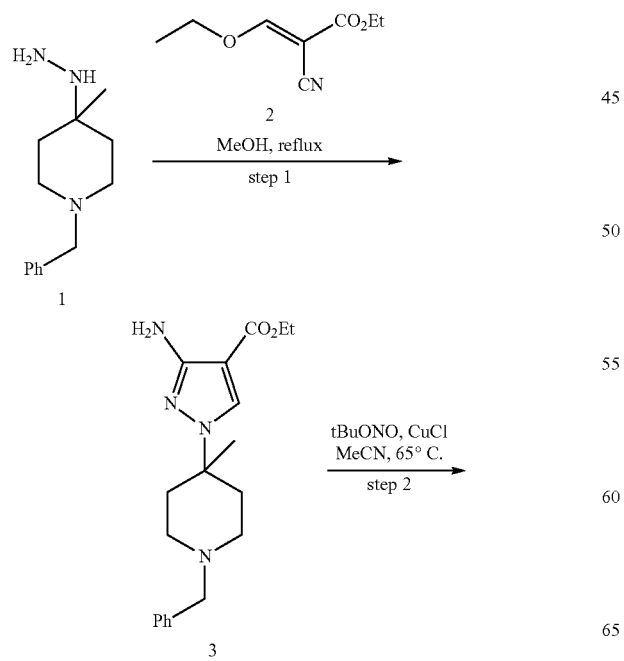

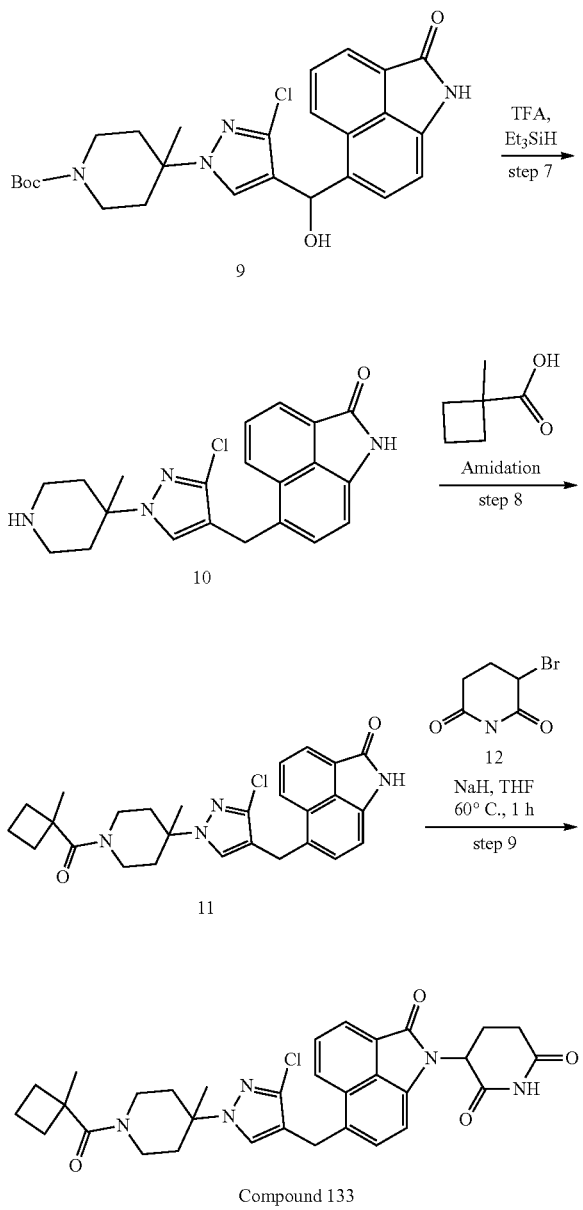

Step 1: Synthesis of 3-amino-1-(1-benzyl-4-methyl-4-piperidyl)pyrazole-4-carboxylate (3): Mixture solution of (1-benzyl-4-methyl-4-piperidyl)hydrazine 1 (2 g, 9.12 mmol) and Ethyl (ethoxymethylene)cyanoacetate 2 (1.54 g, 9.12 mmol) in Methanol (20 mL) was heated at 80° C. for 12 hours. After completion of reaction (evidenced from TLC), solvent was evaporated and crude thus obtained was purified by column chromatography (silica, gradient: 0-5% DCM in MeOH) to afford ethyl 3-amino-1-(1-benzyl-4-methyl-4-piperidyl)pyrazole-4-carboxylate 3 (1.5 g, 3.94 mmol, 43.23% yield, 90% purity) as yellow gummy solid which was stored in a round bottomed flask at 5° C. inside a refrigerator. LC MS: ES+ 343.0.

Step 2: Synthesis of 1-(1-benzyl-4-methyl-4-piperidyl)-3-chloro-pyrazole-4-carboxylate (4): To dry grade Acetonitrile (20 mL) was added tert-Butyl nitrite, tech. 90% (677.56 mg, 6.57 mmol, 781.50 uL) followed by CuCl (650.49 mg, 6.57 mmol) and the reaction mixture was then slowly heated up to 65° C. under N2 atmosphere. At this temperature, ethyl 3-amino-1-(1-benzyl-4-methyl-4-piperidyl)pyrazole-4-carboxylate 3 (1.5 g, 4.38 mmol) dissolved in dry Acetonitrile (20 mL) was slowly added to the reaction mixture. The reaction mixture was stirred at this temperature for 0.5 hour. Reaction mixture was then cooled to room temperature, water (15 mL) was added and extracted with EtOAc (2×35 mL). The organic part was then washed with saturated sodium bicarbonate solution/brine solution (30 mL), separated, dried over anhydrous sodium sulfate and concentrated under reduced pressure. Crude thus obtained was then purified by column chromatography eluting (silica, gradient: 0-10% EtOAc in Hexane) to afford ethyl 1-(1-benzyl-4-methyl-4-piperidyl)-3-chloro-pyrazole-4-carboxylate 4 (650 mg, 1.62 mmol, 36.91% yield) as brown gummy solid. LC MS: ES+ 362.0.

Step 3: Synthesis of tert-butyl 4-(3-chloro-4-ethoxycarbonyl-pyrazol-1-yl)-4-methyl-piperidine-1-carboxylate (5): To the stirred solution of ethyl 1-(1-benzyl-4-methyl-4-piperidyl)-3-chloro-pyrazole-4-carboxylate 4 (1.3 g, 3.59 mmol) in DCM (20 mL), 1-Chloroethyl chloroformate (513.62 mg, 3.59 mmol, 392.07 uL) was added at 0° C. and resulting solution was heated at 100° C. for 90 minutes. After complete conversion as monitored by TLC, solvent was evaporated and re dissolved in MeOH (20 mL). RM was then further heated at 100° C. for 1 hour.

After complete consumption of intermediate as evidenced from TLC, Methanol was evaporated and crude was re-dissolved in DCM (20 mL). To this solution, triethylamine (363.52 mg, 3.59 mmol, 500.72 uL) was added at 0° C. to maintain the pH~8, followed by the addition of tert-butoxycarbonyl tert-butyl carbonate (784.05 mg, 3.59 mmol, 824.45 uL). Resulting reaction mixture was stirred at room temperature for further 16 hours. After completion of reaction (monitored by TLC), reaction mixture was diluted with ethyl acetate (80 mL) and washed with water (25 mL). Combined organic layer was separated, dried over anhydrous sodium sulfate and concentrated. Crude residue was purified by column chromatography (silica, gradient: 0-10% EtOAc in Hexane) to afford tert-butyl 4-(3-chloro-4-ethoxycarbonyl-pyrazol-1-yl)-4-methyl-piperidine-1-carboxylate 5 (750 mg, 1.82 mmol, 50.53% yield) as light brown sticky solid which was stored in a round bottomed flask at ambient temperature. LC MS: ES+ 372.33.

Step 4: Synthesis of tert-butyl 4-[3-chloro-4-(hydroxymethyl)pyrazol-1-yl]-4-methyl-piperidine-1-carboxylate (6): To the stirred solution of tert-butyl 4-(3-chloro-4-ethoxycarbonyl-pyrazol-1-yl)-4-methyl-piperidine-1-carboxylate 5 (750 mg, 2.02 mmol) in THF (20.0 mL), Di-iso Butyl Aluminium Hydride(25% intoluene) (1.43 g, 10.08 mmol, 1.80 mL) (60.0 ml) was added drop wise at −78° C. for 1.5 hour under N2 atmosphere. After complete consumption, as evidenced from TLC, reaction mass was diluted with ethyl acetate (60 mL) and quenched with water (30 mL). Organic phase was separated, dried over anhydrous $Na_2SO_4$ and concentrated under reduced pressure to afford tert-butyl 4-[3-chloro-4-(hydroxymethyl)pyrazol-1-yl]-4-methyl-piperidine-1-carboxylate 6 (560 mg, 1.53 mmol, 75.76% yield, 90% purity). The crude was directly used for next step without any purification. LC MS: ES+ 330.3.

Step 5: Synthesis of tert-butyl 4-(3-chloro-4-formyl-pyrazol-1-yl)-4-methyl-piperidine-1-carboxylate (7): To a stirred solution of tert-butyl 4-[3-chloro-4-(hydroxymethyl)pyrazol-1-yl]-4-methyl-piperidine-1-carboxylate 6 (550 mg, 1.67 mmol) in Acetonitrile (5 mL), was added activated MnO2 (724.89 mg, 8.34 mmol and stirred at room temperature for 24 hours. After completion of the reaction (monitored by TLC and LC MS), reaction mass was filtered through bed of celite and the filtrate was concentrated under reduced pressure. Crude mass was purified by flash chromatography (0-50% EtOAc in Hexane as eluent) to get the pure compound tert-butyl 4-(3-chloro-4-formyl-pyrazol-1-yl)-4-methyl-piperidine-1-carboxylate 7 (360 mg, 988.39 umol, 59.27% yield, 90% purity) as light yellow sticky solid and stored in a round bottomed flask at 5° C. inside a refrigerator. LC MS: ES+(M-100) 228.2 (M-100).

Step 6: Synthesis of tert-butyl 4-[3-chloro-4-[hydroxy-(2-oxo-1H-benzo[cd]indol-6-yl)methyl]pyrazol-1-yl]-4-methyl-piperidine-1-carboxylate (9): To the stirred solution of 6-bromo-1H-benzo[cd]indol-2-one 8 (270 mg, 1.09 mmol) in dry grade THF (5.0 mL), was added Phenyllithium, 1.8M in di-n-butyl ether (91.47 mg, 1.09 mmol, 112.93 uL) at −78° C. under N2 atmosphere and the reaction was stirred at the same temperature for 30 minutes followed by the addition of butyllithium (76.69 mg, 1.20 mmol) at −78° C. and after the addition was complete, the temperature was allowed to increase to −40° C. and stirred at the same temperature for 30 minutes. After getting the dessbormo spot in TLC (30% ethyl acetate in Hexane) solution of tert-butyl 4-(3-chloro-4-formyl-pyrazol-1-yl)-4-methyl-piperidine-1-carboxylate 7 (356.78 mg, 1.09 mmol) in dry THF (5.0 mL) was added at −78° C. and resulting solution was allowed to warm to room temperature and stirring was continued for 16 hours. After completion of reaction (evidenced from TLC and LC MS), the reaction mixture was quenched with saturated ammonium chloride solution and extracted with ethyl acetate (2×40 mL). Organic phase was washed with water (2×20 mL) and separated, dried over anhydrous sodium sulphate and evaporated under reduced pressure to obtain the crude compound which was purified by flash chromatography (silica, gradient: 0-5% MeOH in DCM) to afford tert-butyl 4-[3-chloro-4-[hydroxy-(2-oxo-1H-benzo[cd]indol-6-yl)methyl]pyrazol-1-yl]-4-methyl-piperidine-1-carboxylate 9 (123 mg, 197.99 umol, 18.19% yield, 80% purity) as brown solid. LC MS: ES+ 479.4 (m-16).

Step 7: Synthesis of [4-[3-chloro-4-[(2-oxo-1H-benzo[cd]indol-6-yl)methyl]pyrazol-1-yl]-4-methyl-1-piperidyl] 2,2,2-trifluoroacetate (10): To the stirred solution of tert-butyl 4-[3-chloro-4-[hydroxy-(2-oxo-1H-benzo[cd]indol-6-yl)methyl]pyrazol-1-yl]-4-methyl-piperidine-1-carboxylate 9 (123 mg, 247.49 umol) in DCE (2.0 mL) was added triethylsilane (115.11 mg, 989.97 umol, 158.12 uL) and Trifluoroacetic acid, 99% (225.75 mg, 1.98 mmol, 152.54 uL) at rt. Resulting reaction mixture was heated at 70° C. under microwave condition for 30 mins. After completion of reaction (monitored by TLC and LCMS), volatiles were removed to afford crude [4-[3-chloro-4-[(2-oxo-1H-benzo[cd]indol-6-yl)methyl]pyrazol-1-yl]-4-methyl-1-piperidyl] 2,2,2-trifluoroacetate 10 (110 mg, 122.25 umol, 49.39% yield) which was used in the next step without purification. LCMS: ES+ 381.2.

Step 8: Synthesis of 6-[[3-chloro-1-[4-methyl-1-(1-methylcyclobutanecarbonyl)-4-piperidyl]pyrazol-4-yl]methyl]-1H-benzo[cd]indol-2-one (11): To the stirred solution of 6-[[3-chloro-1-(4-methyl-4-piperidyl)pyrazol-4-yl]methyl]-1H-benzo[cd]indol-2-one 10 (120 mg, 315.07 umol) in DMF (5.0 mL), HATU (179.70 mg, 472.60 umol) was added at 0° C. followed by the mixture solution of 1-methylcyclobutanecarboxylic acid (89.91 mg, 787.67 umol) and N,N-Diisopropylethylamine (203.60 mg, 1.58 mmol, 274.39 uL) under N2 atmosphere. Resulting solution was stirred for 12 hours at same temperature. After completion of reaction (monitored by LC MS, crude LC MS showed di amidation mass), RM was quenched with the addition of ice cooled water (5 mL). Aqueous part was extracted with ethyl acetate (3×30 mL). Organic portion was separated, dried over anhydrous sodium sulfate and concentrated. Crude residue was then re-dissolved in Methanol (10 mL) and stirred for 30 minutes in presence of LiOH (1.5 eq). After complete consumption of Diamide, solvent was evaporated and re-dissolved in ethyl acetate (30 ml). Organic portion was washed with 1 N HCl (20 Ml) and separated, dried over sodium sulfate, concentrated under reduced pressure to obtain crude 6-[[3-chloro-1-[4-methyl-1-(1-methylcyclobutanecarbonyl)-4-piperidyl]pyrazol-4-yl]methyl]-1H benzo[cd]indol-2-one 11 (90 mg, 177.36 umol, 56.29% yield) as brown gummy solid which was sufficiently pure to use in the next step. LC MS: ES+ 477.39

Step 9: Synthesis of tert-butyl 4-[[4-[[1-(2,6-dioxo-3-piperidyl)-2-oxo-benzo[cd]indol-6-yl]methyl]phenyl]methyl]-4,7-diazaspiro[2.5]octane-7-carboxylate: To a ice cooled solution 6-[[3-chloro-1-[4-methyl-1-(1-methylcyclobutanecarbonyl)-4-piperidyl]pyrazol-4-yl]methyl]-1H-benzo[cd]indol-2-one 11 (90 mg, 188.68 umol) in dry THF (5 mL), Sodium hydride (60% dispersion in mineral oil) (43.38 mg, 1.89 mmol) was added portion wise, maintaining the temp <5° C. Once the addition is over, the resultant mixture was stirred for 15 minutes at room temperature. Then the reaction mixture was again cooled to 0° C. and 3-bromopiperidine-2,6-dione 12 (181.14 mg, 943.40 umol) was added to it portion wise. After complete addition, resulting solution was heated at 70° C. for 2 hour. After completion (evidenced from TLC), the reaction mixture was again cooled to 0° C. and quenched with ice cooled water (40 mL). Aqueous part was extracted with ethyl acetate (2×20 mL). Combined extracts was dried over anhydrous sodium sulfate and concentrated under reduced pressure. Crude mass was purified by Preparative TLC plate (2.5% MeOH in DCM as eluent) to afford tert-butyl 4-[[4-[[1-(2,6-dioxo-3-piperidyl)-2-oxo-benzo[cd]indol-6-yl]methyl]phenyl]methyl]-4,7-diazaspiro[2.5]octane-7-carboxylate Compound 133 (320 mg, 414.33 umol, 47.15% yield) as yellow solid which was stored in a round bottomed flask at 5° C. inside a refrigerator. 1H NMR (400 MHz, DMSO-d6) δ 11.11 (s, 1H), 8.37 (d, J=8.24 Hz, 1H), 8.10 (d, J=7.0 Hz, 1H), 7.86 (t, J=7.48 Hz, 1H), 7.45 (s, 1H), 7.25 (d, J=7.28 Hz, 1H), 7.07 (d, J=7.16 Hz, 1H), 5.44 (dd, J=12.52, 5.4 Hz, 1H), 4.16 (s, 2H), 3.80 (br m, 1H), 3.33 (br m, 2H), 3.15-3.06 (m, 2H), 2.98-2.91 (m, 1H), 2.78-2.62 (m, 4H), 2.37 (br, 2H), 2.10-2.07 (br m, 1H), 1.90-1.77 (m, 4H), 1.60 (m, 1H), 1.52 (s, 3H), 1.31 (s, 3H); LC MS: ES+588.2.

Example 50. Synthesis of 3-[6-[[4-[4-(2-fluorophenyl)piperazine-1-carbonyl]phenyl]methyl]-2-oxo benzo[cd]indol-1-yl]piperidine-2,6-dione (Compound 134)

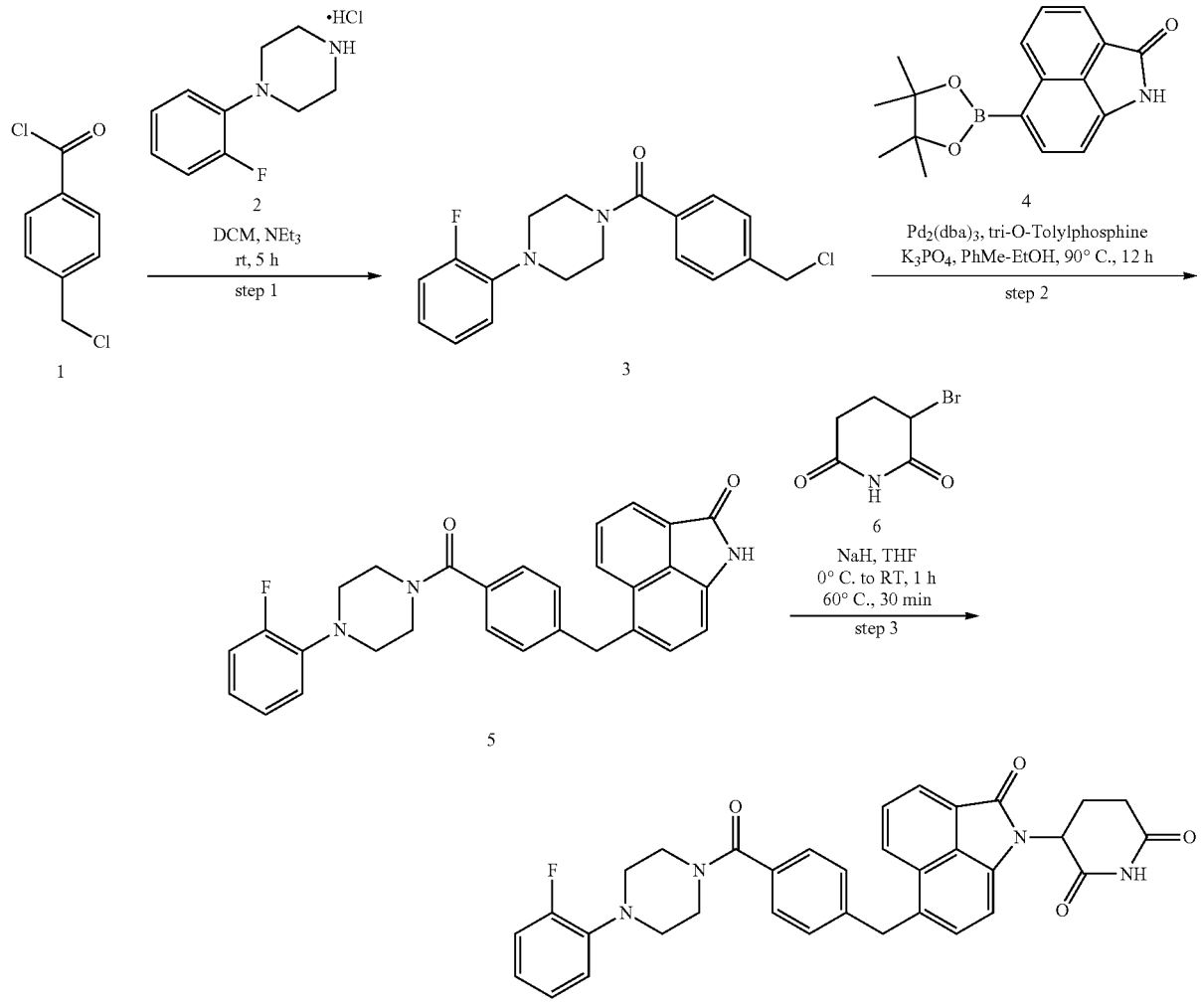

Step 1: Synthesis of [4-(chloromethyl)phenyl]-[4-(2-fluorophenyl)piperazin-1-yl]methanone (3): To the stirred solution of 1-(2-fluorophenyl)piperazine 2 (1.0 g, 5.55 mmol) in dry grade DCM (20 mL), Triethylamine, 99% (1.68 g, 16.65 mmol, 2.32 mL) was added at 0° C. followed by drop wise addition of 4-(chloromethyl)benzoyl chloride 1 (1.26 g, 6.66 mmol). After complete addition, reaction mixture was stirred for 5 hours at room temperature. Reaction mixture was diluted with DCM (30 mL) and quenched with saturated sodium bicarbonate solution. Organic phase was washed with water (20 mL)/brine (20 mL) and separated, dried over anhydrous sodium sulfate and concentrated. Crude thus obtained was purified by column chromatography (silica, gradient: 0-30% Ethyl acetate in Hexane) to afford [4-(chloromethyl)phenyl]-[4-(2-fluorophenyl)piperazin-1-yl] methanone 3 (671 mg, 1.63 mmol, 29.43% yield, 81% purity) as a white solid. LC MS: ES+ 333.3.

Step 2: Synthesis of 6-[[4-[4-(2-fluorophenyl)piperazine-1-carbonyl]phenyl]methyl]-1H-benzo[cd]indol-2-one (5): To a well degassed solution of [4-(chloromethyl)phenyl]-[4-(2-fluorophenyl)piperazin-1-yl]methanone 3 (650 mg, 1.95 mmol) and 6-(4,4,5,5-tetramethyl-1,3,2-dioxaborolan-2-yl)-1H-benzo[cd]indol-2-one 4 (1.44 g, 4.88 mmol) in Ethanol (4 mL)-Toluene (8 mL), Potassium phosphate tribasic, anhydrous, (1.24 g, 5.86 mmol) was added followed by the addition of Tri-o-Tolyl phosphine (118.89 mg, 390.63 umol) and Pd₂(dba)₃ (178.85 mg, 195.31 umol). The resulting mixture was then heated at 90° C. for 12 hours. After completion of reaction (as monitored by LCMS), the reaction mixture was filtered through a bed of celite, washed with Ethyl acetate (30 mL). The combined filtrate was then washed with water (3×30 mL) and brine (2×20 mL), dried over anhydrous sodium sulfate and concentrated under reduced pressure. Crude mass was purified by flash chromatography (gradient: 0-20% Ethyl acetate in DCM) to obtain 6-[[4-[4-(2-fluorophenyl)piperazine-1-carbonyl]phenyl]methyl]-1H-benzo[cd]indol-2-one 5 (500 mg, 966.67 umol, 49.49% yield) as yellow solid which was stored in a Tarson plastic bottle at ambient temperature. LC MS: ES+ 466.2.

Step 3: Synthesis of 3-[6-[[4-[4-(2-fluorophenyl)piperazine-1-carbonyl]phenyl]methyl]-2-oxo benzo[cd]indol-1-yl]piperidine-2,6-dione: To a ice cooled solution 6-[[4-[4-(2-fluorophenyl)piperazine-1-carbonyl]phenyl]methyl]-1H-benzo[cd]indol-2-one (130 mg, 279.26 umol) 5 in dry THF (8 mL), Sodium hydride (60% dispersion in mineral oil) (64.20 mg, 2.79 mmol) was added portion wise, maintaining the temp <5° C. Once the addition is over, the resultant mixture was stirred for 15 minutes at room temperature. Then the reaction mixture was again cooled to 0° C. and 3-bromopiperidine-2,6-dione 6 (268.10 mg, 1.40 mmol) was added to it portion wise. After complete addition, resulting solution was heated at 70° C. for 1.5 hour. After completion (evidenced from TLC), the reaction mixture was again cooled to 0° C. and quenched with ice cooled water (20 mL). Aqueous part was extracted with ethyl acetate (2×20 mL). Combined extracts was dried over anhydrous sodium sulfate and concentrated under reduced pressure. Crude mass was then purified by Preparative TLC plate (2.5% MeOH in DCM as eluent) to afford 3-[6-[[4-[4-(2-fluorophenyl)piperazine-1-carbonyl]phenyl]methyl]-2-oxo-benzo[cd]indol-1-yl]piperidine-2,6-dione Compound 134 (42 mg, 70.24 umol, 25.15% yield) as yellow solid which was stored in a round bottomed flask at 5° C. inside a refrigerator. $^1$H NMR (400 MHz, DMSO-d6) δ 11.12 (s, 1H), 8.35 (d, J=8.04 Hz, 1H), 8.08 (d, J=6.92 Hz, 1H), 7.82 (t, J=7.36 Hz, 1H), 7.45 (d, J=7.28 Hz, 1H), 7.36-7.35 (m, 4H), 7.13-7.07 (m, 3H), 7.04-7.0 (m, 2H), 5.44 (dd, J=12.84 Hz, 1H), 4.45 (s, 2H), 3.71 (br m, 2H), 3.46 (br m, 2H), 2.96 (br m, 5H), 2.76-2.63 (m, 2H), 2.08 (m, 1H); LC MS: ES+ 577.2.

Example 51. Synthesis of 3-[6-[[4-[[7-(2-fluorophenyl)-4,7-diazaspiro[2.5]octan-4-yl]methyl]phenyl]methyl]-2-oxo-benzo[cd]indol-1-yl]piperidine-2,6-dione (Compound 135)

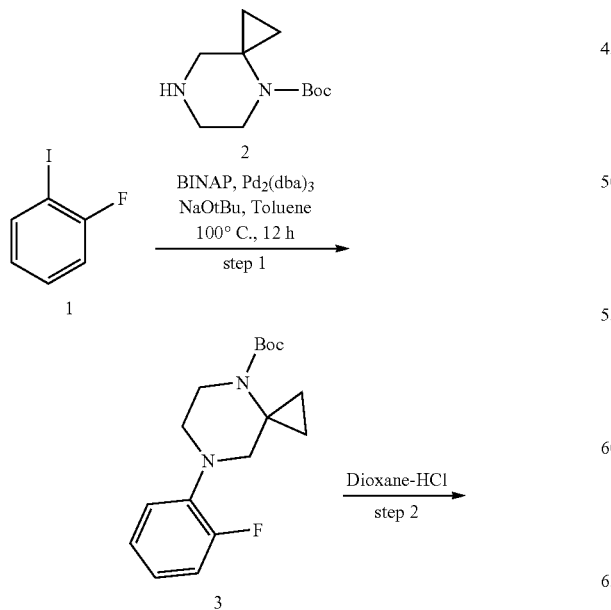

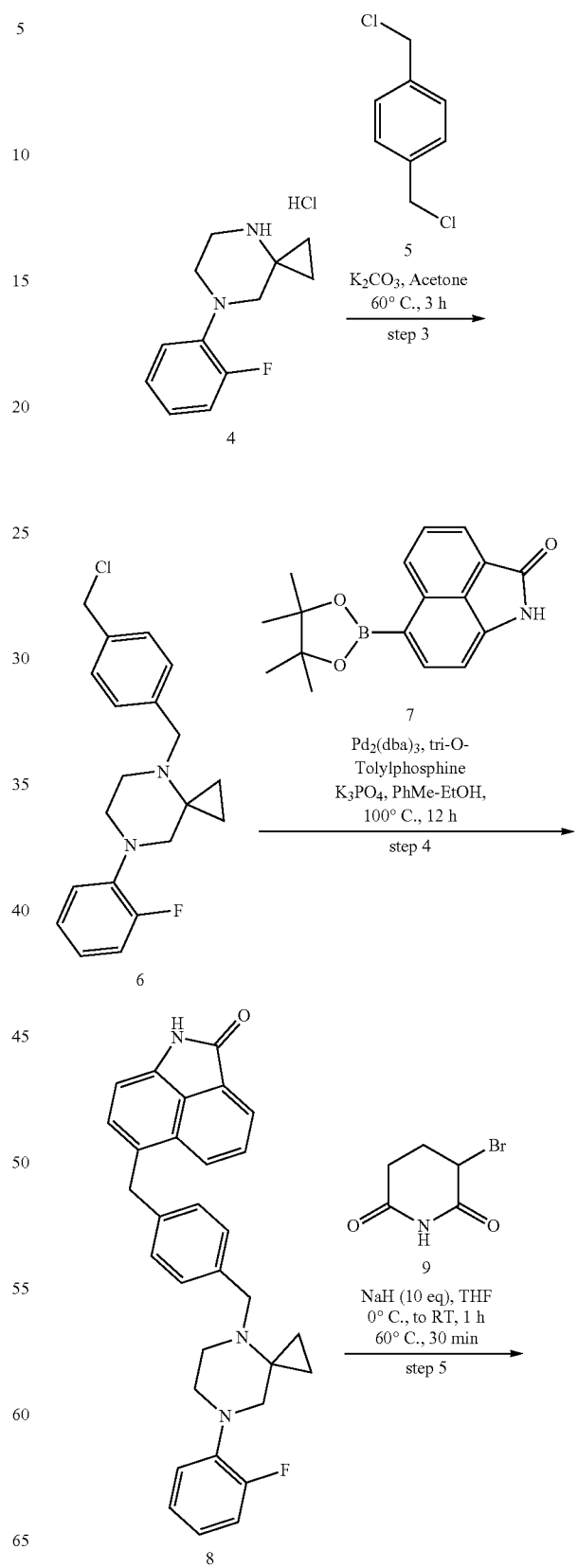

-continued

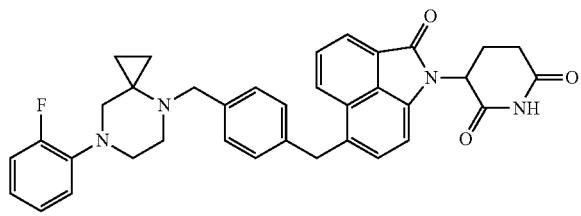

Compound 135

Step 1: Synthesis of tert-butyl 7-(2-fluorophenyl)-4,7-diazaspiro[2.5]octane-4-carboxylate (3): To a well degassed solution of 1-fluoro-2-iodo-benzene 1 (2.09 g, 9.42 mmol, 1.10 mL) intoluene (60 mL), tert-butyl 4,7-diazaspiro[2.5]octane-4-carboxylate 2 (2.0 g, 9.42 mmol) and sodium tert-butoxide (1.81 g, 18.84 mmol) were added followed by the addition of Pd$_2$(dba)$_3$ (172.54 mg, 188.42 umol), 2,2'-Bis(diphenylphosphino)-1,1'-binaphthalene (586.63 mg, 942.12 umol). The resulting mixture was then heated at 100° C. for 12 hours. After completion of reaction (as monitored by LCMS), the reaction mixture was filtered through a bed of celite, washed with ethyl acetate (30 mL). The combined filtrate was then washed with water (3×50 mL) and brine (20 mL), dried over anhydrous sodium sulfate and concentrated under reduced pressure. Crude mass was purified by flash chromatography (gradient: 0-10% Ethyl acetate in Hexane) to afford tert-butyl 7-(2-fluorophenyl)-4,7-diazaspiro[2.5]octane-4-carboxylate 3 (810 mg, 2.56 mmol, 27.22% yield) as yellow solid which was stored in a Tarson plastic bottle at ambient temperature. LC MS: ES+ 307.16.

Step 2: Synthesis of 7-(2-fluorophenyl)-4,7-diazaspiro[2.5]octane; hydrochloride (4): To a stirred solution of tert-butyl 7-(2-fluorophenyl)-4,7-diazaspiro[2.5]octane-4-carboxylate 3 (805 mg, 2.63 mmol) in Dioxane (10 mL), Dioxane-HCl (2.63 mmol, 10.0 mL) was added drop wise at 0° C. and stirred the reaction at room temperature for 16 hours. After completion of reaction (evidenced from LC MS), volatiles were removed. Solid reaction mass was triturated with diethyl ether to afford 7-(2-fluorophenyl)-4,7-diazaspiro[2.5]octane; hydrochloride 4 (630 mg, 2.17 mmol, 82.58% yield) and the crude was directly used for the next step without any further purification.

Step 3: Synthesis of 4-[[4-(chloromethyl)phenyl]methyl]-7-(2-fluorophenyl)-4,7-diazaspiro[2.5]octane (6): To a stirred solution 7-(2-fluorophenyl)-4,7-diazaspiro[2.5]octane; hydrochloride 4 (630 mg, 2.60 mmol) in dry grade acetone (5.0 mL) was added DIPEA (335.45 mg, 2.60 mmol, 452.09 uL) was added followed by Potassium carbonate, anhydrous, 99% (1.08 g, 7.79 mmol, 469.96 uL) at RT and the resultant reaction mixture was heated at 60° C. for 20 minutes. 1,4-bis(chloromethyl)benzene 5 (454.37 mg, 2.60 mmol, 319.98 uL) was then added to the reaction mixture and heating was continued for 3 hours. After completion of reaction (monitored by TLC and LCMS), volatiles were removed under vacuum and the solid thus obtained was taken in Ethyl acetate (50 mL), washed with water (3×25 ml) and Brine (2×15 mL), dried over anhydrous sodium sulfate and concentrated under reduced pressure. Crude mass was purified by column chromatography (silica, gradient: 10-30% Ethyl acetate in Hexane) to afford 4-[[4-(chloromethyl)phenyl]methyl]-7-(2-fluorophenyl)-4,7-diazaspiro[2.5]octane 6 (480 mg, 1.36 mmol, 52.55% yield) as brown sticky solid which was stored in a round bottomed flask at 5° C. inside a refrigerator. LC MS: ES+ 345.32.

Step 4: Synthesis of 6-[[4-[[7-(2-fluorophenyl)-4,7-diazaspiro[2.5]octan-4-yl]methyl]phenyl]methyl]-1H-benzo[cd]indol-2-one: To a well degassed solution of 4-[[4-(chloromethyl)phenyl]methyl]morpholine 6 (8 g, 35.44 mmol) and 6-(4,4,5,5-tetramethyl-1,3,2-dioxaborolan-2-yl)-1H-benzo[cd]indol-2-one 7 (20.92 g, 70.89 mmol) in Ethanol (4 mL)-Toluene (8 mL), Potassium phosphate tribasic, anhydrous, (886.38 mg, 4.18 mmol) was added followed by the addition of Tri-o-Tolyl phosphine (84.73 mg, 278.38 umol) and Pd$_2$(dba)$_3$ (127.46 mg, 139.19 umol). The resulting mixture was then heated at 90° C. for 12 hours. After completion of reaction (as monitored by LCMS), the reaction mixture was filtered through a bed of celite, washed with Ethyl acetate (200 mL). The combined filtrate was then washed with water (3×70 mL) and brine (2×50 mL), dried over anhydrous sodium sulfate and concentrated under reduced pressure. Crude mass was purified by flash chromatography (, gradient: 0-50% Ethyl acetate in Hexane) to afford 6-[[4-[[7-(2-fluorophenyl)-4,7-diazaspiro[2.5]octan-4-yl]methyl]phenyl]methyl]-1H-benzo[cd]indol-2-one 8 (272 mg, 552.46 umol, 39.69% yield) as yellow solid which was stored in a Tarson plastic bottle at ambient temperature. LC MS: ES+478.2.

Step 5: Synthesis of 3-[6-[[4-[[7-(2-fluorophenyl)-4,7-diazaspiro[2.5]octan-4-yl]methyl]phenyl]methyl]-2-oxo-benzo[cd]indol-1-yl]piperidine-2,6-dione: To a ice cooled solution of 6-[[4-[[7-(2-fluorophenyl)-4,7-diazaspiro[2.5]octan-4-yl]methyl]phenyl]methyl]-1H-benzo[cd]indol-2-one 8 (150 mg, 314.09 umol) in dry THF (5 mL), Sodium hydride (60% dispersion in mineral oil) (120.35 mg, 3.01 mmol) was added portion wise, maintaining the temp <5° C. Once the addition is over, the resultant mixture was stirred for 15 minutes at room temperature. Then the reaction mixture was again cooled to 0° C. and 3-bromopiperidine-2,6-dione 9 (301.54 mg, 1.57 mmol) was added to it portion wise. After complete addition, resulting solution was heated at 70° C. for 1 hour. After completion (evidenced from TLC), the reaction mixture was again cooled to 0° C. and quenched with ice cooled water (15 mL). Aqueous part was extracted with ethyl acetate (2×20 mL). Combined extracts was dried over anhydrous sodium sulfate and concentrated under reduced pressure. Crude mass was purified by Preparative TLC Plate (2.5% MeOH in DCM as eluent) to afford 3-[6-[[4-[[7-(2-fluorophenyl)-4,7-diazaspiro[2.5]octan-4-yl]methyl]phenyl]methyl]-2-oxo-benzo[cd]indol-1-yl]piperidine-2,6-dione Compound 135 (62 mg, 105.08 umol, 33.46% yield) as yellow solid which was stored in a round bottomed flask at 5° C. inside a refrigerator. 1H NMR (400 MHz, DMSO-d6) δ 11.11 (s, 1H), 8.31 (d, J=8.24 Hz, 1H), 8.07 (d, J=6.96 Hz, 1H), 7.80 (t, J=7.56 Hz, 1H), 7.38 (d, J=7.28 Hz, 1H), 7.23-7.17 (m, 4H), 7.10-7.01 (m, 4H), 6.95-6.93 (m, 1H), 5.44 (dd, J=12.68, 4.96 Hz, 1H), 4.36 (m, 2H), 3.75 (s, 2H), 2.99-2.98 (m, 2H), 2.94-2.87 (m, 3H), 2.79-2.62 (m, 4H), 2.10-2.07 (m, 1H), 0.65 (br s, 2H), 0.54 (br s, 2H); LC MS: ES+ 589.6.

Example 52. Synthesis of 3-[2-oxo-6-(prop-2-ynylamino)benzo[cd]indol-1-yl]piperidine-2,6-dione (Compound 136)

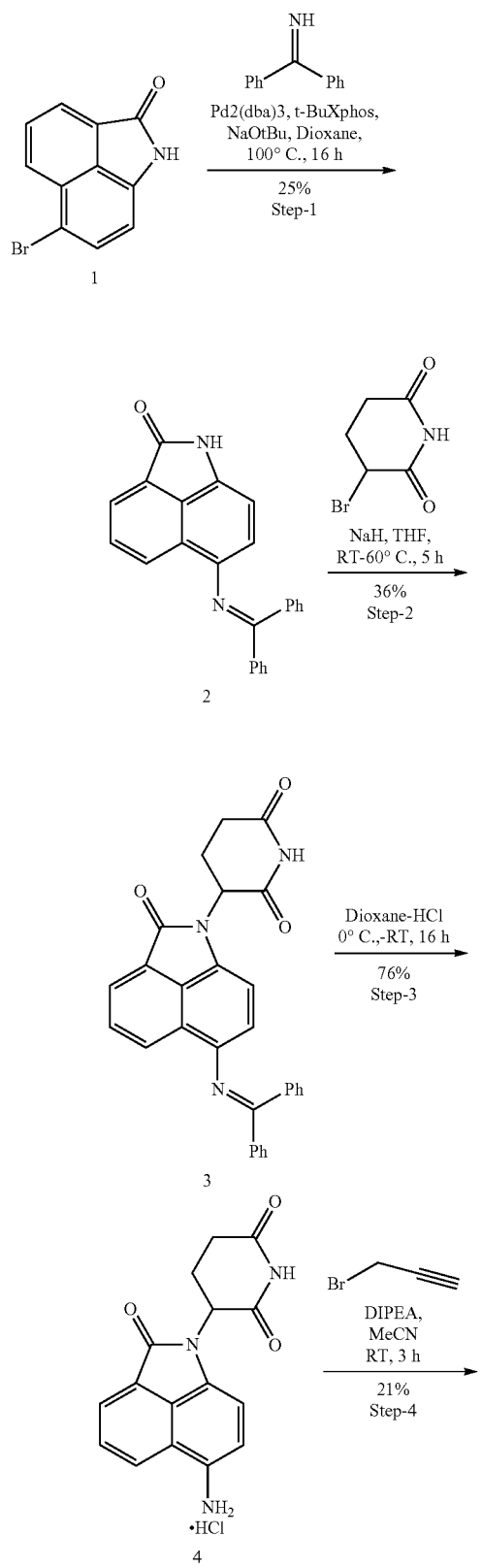

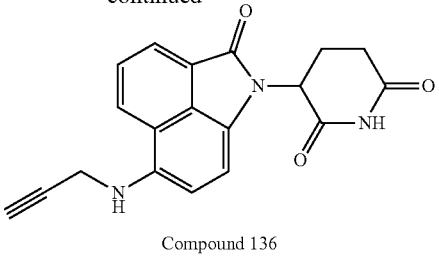

Compound 136

Step 1: Synthesis of 6-(benzhydrylideneamino)-1H-benzo[cd]indol-2-one: To a stirred solution of 6-bromo-1H-benzo[cd]indol-2-one (1 g, 4.03 mmol) and diphenylmethanimine (1.10 g, 6.05 mmol) in dioxane (15 mL), sodium tert-butoxide (1.16 g, 12.09 mmol) was added. Resulting mixture was degassed with argon and tBuXPhos (342.35 mg, 806.21 umol) and Pd2(dba)3 (738.27 mg, 806.21 umol) were added under inert atmosphere. Resulting mixture was heated at 100° C. for 16 h. After completion, reaction mixture was diluted with ethyl acetate, filtered through a short pad of celite and washed with ethyl acetate. Combined organic part was washed with water, brine, dried over anhydrous sodium sulphate, filtered and concentrated under reduced pressure. Crude mass was purified by column chromatography (30% ethyl acetate-hexane) to afford 6-(benzhydrylideneamino)-1H-benzo[cd]indol-2-one (350 mg, 1.00 mmol, 25% yield) as yellow solid. LCMS: m/z 349 [M+H]+.

Step 2: Synthesis of 3-(6-((diphenylmethylene)amino)-2-oxobenzo[cd]indol-1(2H)-yl)piperidine-2,6-dione: 3-(6-((diphenylmethylene)amino)-2-oxobenzo[cd]indol-1(2H)-yl)piperidine-2,6-dione was synthesized following same procedure as described in scheme-4, step-4 above in 36% yield. LCMS: m/z 460 [M+H]+.

Step-3: Synthesis of 3-(6-amino-2-oxo-benzo[cd]indol-1-yl)piperidine-2,6-dione hydrochloride salt: Dioxane-HCl (4M, 2 mL, 8 mmol) was added 3-[6-(benzhydrylideneamino)-2-oxo-benzo[cd]indol-1-yl]piperidine-2,6-dione (200 mg, 435.26 umol) at 0° C. Resulting mixture was warmed to ambient temperature and stirred for 16h. After completion, reaction mixture was concentrated under reduced pressure, triturated with ether and lyophilized to afford 3-(6-amino-2-oxo-benzo[cd]indol-1-yl)piperidine-2,6-dione (110 mg, 331.57 umol, 76% yield, HCl salt) LCMS: m/z 296 [M+H]+.

Step 4: Synthesis of 3-[2-oxo-6-(prop-2-ynylamino)benzo[cd]indol-1-yl]piperidine-2,6-dione: To a stirred solution of 3-(6-amino-2-oxo-benzo[cd]indol-1-yl)piperidine-2,6-dione (100 mg, 338.65 umol) in MeCN (10 mL) was added DIPEA (235.94 uL 1.35 mmol) at 0° C. and allowed to stir at RT for 30 min. 3-bromoprop-1-yne (60.43 mg, 507.97 umol, 4.81 uL) was added at RT and resulting mixture was stirred at RT for 3 h. After completion, reaction mixture was concentrated under reduced pressure, diluted with ethyl acetate and separated. Organic portion was washed with water, brine, dried over anhydrous sodium sulphate, filtered and concentrated under reduced pressure. Crude mass was purified by combiflash chromatography (15-20% ethylacetate-dichloromethane) to afford 3-[2-oxo-6-(prop-2-ynylamino)benzo[cd]indol-1-yl]piperidine-2,6-dione Compound 136 (25 mg, 70.15 umol, 21% yield) LCMS: m/z 334 [M+H]+. 1H NMR (400 MHz, DMSO-d6) δ 11.07 (bs, 1H), 8.42 (d, J=8.2 Hz, 1H), 8.05 (d, J=7.0 Hz, 1H), 7.75 (t, J=7.5 Hz, 1H), 6.98 (d, J=7.7 Hz, 1H), 6.84 (t, J=5.9 Hz, 1H), 6.45 (d, J=7.8 Hz, 1H), 5.40-5.36 (m, 1H), 4.06-4.04 (m, 2H), 3.09 (s, 1H), 2.97-2.90 (m, 1H), 2.76-2.61 (m, 2H), 2.07-2.05 (m, 1H).

Example 53. Synthesis of 3-(2-oxo-6-prop-2-ynoxy-benzo[cd]indol-1-yl)piperidine-2,6-dione (Compound 137)

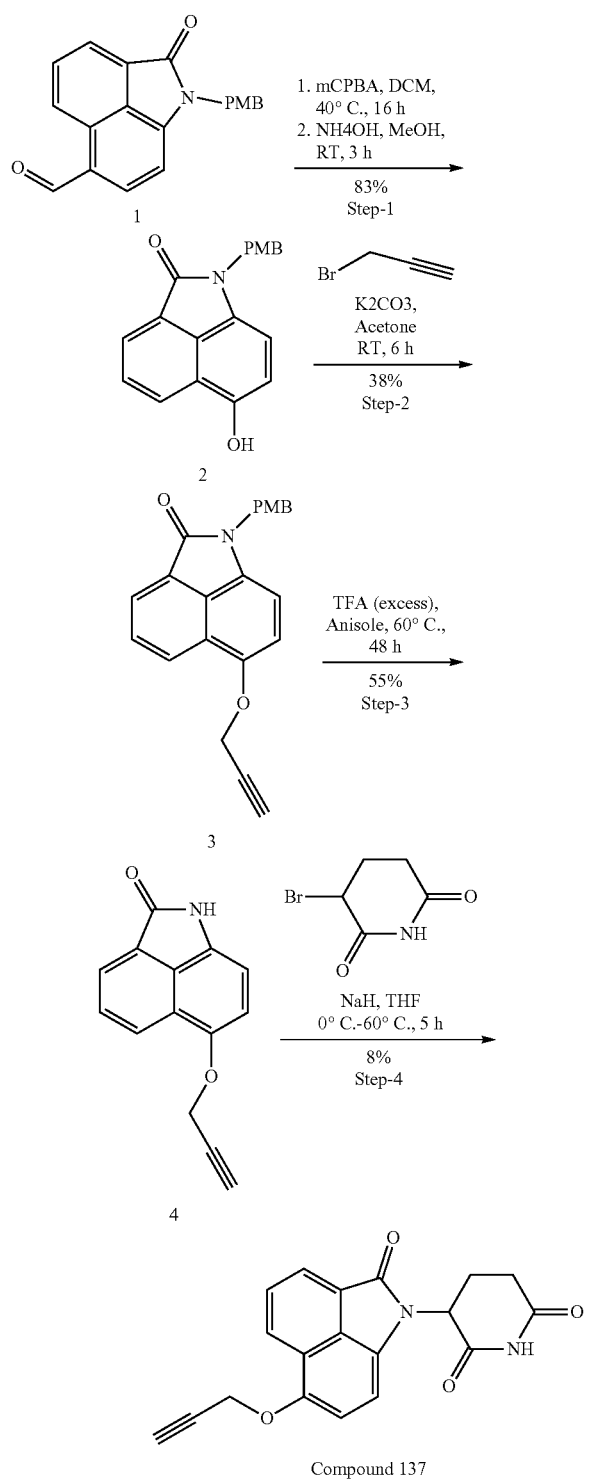

Step 1: Synthesis of 6-hydroxy-1-[(4-methoxyphenyl)methyl]benzo[cd]indol-2-one: To a stirred solution of 1-[(4-methoxyphenyl)methyl]-2-oxo-benzo[cd]indole-6-carbaldehyde (1 g, 3.15 mmol) in DCM (15 mL) was added mCPBA (60% pure, 906.32 mg, 3.15 mmol). Resulting mixture was stirred at 40° C. for 16h. After completion, reaction mixture was cooled to 0° C. and methanolic ammonia (2M) was added drop wise till red wine color persisted. The reaction mixture was again stirred at 0° C. for 3h. Reaction mixture was neutralized with NaHCO$_3$ and extracted with DCM. Combined organic part was washed with water, brine, dried over anhydrous sodium sulphate, filtered and concentrated under reduced pressure. Crude mass was triturated with n-pentane to afford 6-hydroxy-1-[(4-methoxyphenyl)methyl]benzo[cd]indol-2-one (900 mg, 2.63 mmol, 83% yield). LCMS: m/z 306 [M+H]$^+$.

Step 2: Synthesis of 1-1(4-methoxyphenyl) methyl]-6-prop-2-ynoxy-benzo [cd] indol-2-one: To a stirred solution of 6-hydroxy-1-[(4-methoxyphenyl)methyl]benzo[cd]indol-2-one (700 mg, 2.29 mmol) in acetone (10 mL) was added potassium carbonate (950.56 mg, 6.88 mmol) at RT and allowed to stir for 30 min. Propargyl bromide (246.07 uL, 2.75 mmol) was added and resulting reaction mixture was stirred at RT for 6h. After completion, reaction mixture was poured into water, neutralized with 0.1 M HCl and extracted with ethyl acetate. Combined organic layer was washed with water, brine, dried over anhydrous sodium sulphate, filtered and concentrated under reduced pressure. Crude mass was triturated with n-pentane to afford 1-[(4-methoxyphenyl) methyl]-6-prop-2-ynoxy-benzo [cd] indol-2-one (300 mg, 873.68 umol, 38% yield) LCMS: m/z 344 [M+H]$^+$.

Step 3: Synthesis of 6-prop-2-ynoxy-1H-benzo[cd]indol-2-one: To a stirred solution of 1-[(4-methoxyphenyl)methyl]-6-prop-2-ynoxy-benzo[cd]indol-2-one (250 mg, 728.07 umol) in TFA (1.25 mL, 16.22 mmol) was added anisole (158.41 uL, 1.46 mmol). Resulting solution was heated at 60° C. for 24 h. Reaction mixture was cooled to RT and TFA (1.25 mL, 16.22 mmol) and anisole (158.41 uL, 1.46 mmol) were again added and continued heating at 60° C. for additional 24 h. After completion, reaction mixture was cooled to RT, concentrated under reduced pressure, diluted with DCM and neutralized with Et3N. It was washed with water, brine, dried over anhydrous sodium sulphate, filtered and concentrated under reduced pressure. Crude mass was purified by combiflash column chromatography (30% ethyl acetate-hexane) to afford 6-prop-2-ynoxy-1H-benzo[cd]indol-2-one (90 mg, 385.08 umol, 55% yield) as a gum. LCMS: m/z 224 [M+H]$^+$.

Step 4: Synthesis of 3-(2-oxo-6-prop-2-ynoxy-benzo[cd] indol-1-yl)piperidine-2,6-dione: To a stirred solution of 6-prop-2-ynoxy-1H-benzo[cd]indol-2-one (100 mg, 447.98 umol) in THF (3 mL) was added sodium hydride (60% in mineral oil, 102.99 mg, 4.48 mmol) slowly portion wise at 0° C. Resulting mixture was stirred at RT for 30 min. 3-bromopiperidine-2,6-dione (430.08 mg, 2.24 mmol) was added in portions at RT. Resulting mixture was heated at 60° C. for 5 h. After completion, reaction mixture was quenched with crushed ice and extracted with ethyl acetate. Combined organic part was washed with water, brine, dried over anhydrous sodium sulphate, filtered and concentrated under reduced pressure. Crude mass was purified by column chromatography (70-80% ethylacetate-hexane) to afford 3-(2-oxo-6-prop-2-ynoxy-benzo[cd]indol-1-yl)piperidine-2,6-dione Compound 137 (11 mg, 32.61 umol, 8% yield). LCMS: m/z 335 [M+H] *, 1H NMR (400 MHz, DMSO-d6) δ 11.10 (bs, 1H), 8.27 (d, J=8.1 Hz, 1H), 8.13 (d, J=7.0 Hz, 1H), 7.84 (t, J=7.6 Hz, 1H), 7.07 (d, J=7.8 Hz, 1H), 6.99 (d, J=7.8 Hz, 1H), 5.45-5.40 (m, 1H), 5.01 (s, 2H), 3.63 (s, 1H), 2.98-2.90 (m, 1H), 2.78-2.62 (m, 2H), 2.10-2.07 (m, 1H).

Example 54. Synthesis of 3-(6-bromo-2-oxo-benzo[cd]indol-1-yl)piperidine-2,6-dione, (Compound 138)

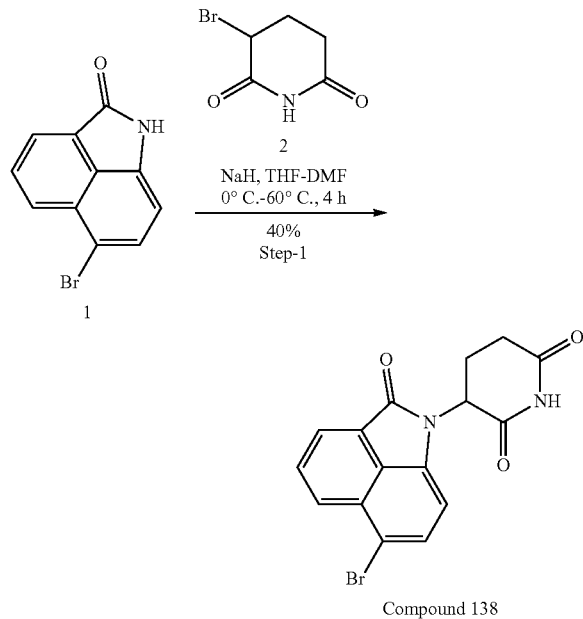

Compound 138

Step 1: Synthesis of 3-(6-bromo-2-oxo-benzo[cd]indol-1-yl)piperidine-2,6-dione: To a stirred solution of 6-bromo-1H-benzo[cd]indol-2-one (4 g, 16.12 mmol) in THF (250 mL) and DMF (25 mL) was added Sodium hydride (60% dispersion in mineral oil) (6.18 g, 161.24 mmol, 60% purity) slowly portion wise at 0° C. Resultant mixture was stirred the reaction for 30 min at RT. 3-bromopiperidine-2,6-dione (15.48 g, 80.62 mmol) was then added to it portion wise at RT and reaction mixture was heated to 70° C. and continued for 3h. After completion, reaction was quenched with crushed ice extracted with ethyl acetate. Combined organic part was washed with water and brine. Organic layer was dried with anhydrous sodium sulphate, filtered and concentrated under reduced pressure. Crude mass was purified by column chromatography (70% EA-hexane) to afford 3-(6-bromo-2-oxo-benzo[cd]indol-1-yl)piperidine-2,6-dione Compound 138 (2.6 g, 6.28 mmol, 40% yield) as yellow solid. $^1$H NMR (400 MHz, DMSO-d6) δ 11.14 (s, 1H), 8.20 (d, J=7.0 Hz, 2H), 7.98 (t, J=7.7 Hz, 1H), 7.83 (d, J=7.5 Hz, 1H), 7.12 (d, J=7.6 Hz, 1H), 2.97-2.90 (m, 2H), 2.79-2.57 (m, 2H), 2.12-2.10 (m, 1H).

Example 55. Synthesis of 3-(2-oxobenzo[cd]indol-1(2H)-yl)piperidine-2,6-dione (Compound 139)

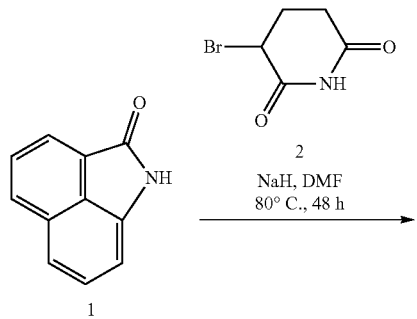

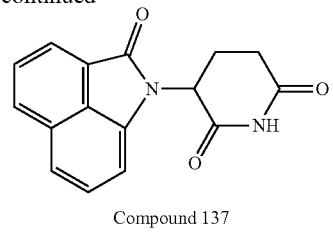

Compound 137

Step 1: Synthesis of 3-(2-oxobenzo[cd]indol-1(2H)-yl)piperidine-2,6-dione: To the stirred solution of 1H-benzo[cd]indol-2-one 1 (100.0 mg, 591.09 umol) in DMF (2 mL) was added Sodium hydride (in oil dispersion) 60% dispersion in mineral oil (24.91 mg, 650.20 umol, 60% purity) at 0° C. and then the reaction mixture was heated at 60° C. for 30 minutes followed by the addition of 3-bromopiperidine-2,6-dione 2 (113.50 mg, 591.09 umol) and the reaction mixture was heated at 60° C. for 24 hours. New spot formed along with unreacted SM. 3-bromopiperidine-2,6-dione 2 (113.50 mg, 591.09 umol) was topped up and the reaction mixture was again heated for 24 hours. Reaction mixture was diluted with ethyl acetate, washed with water and the organic fraction was separated. It was then dried over anhydrous sodium sulphate and evaporated under reduced pressure to obtain the crude compound which was purified by preparative TLC plate (eluting with 2% MeOH-DCM) to afford 3-(2-oxobenzo[cd]indol-1-yl)piperidine-2,6-dione Compound 139 (10 mg, 34.35 umol, 5.81% yield, 96.28% purity) as pale yellow solid. $^1$H NMR (d6-DMSO, 400 MHZ) δ 11.13 (s, 1H), 8.24 (d, J=8.08 Hz, 1H), 8.11 (d, J=6.92 Hz, 1H), 7.84 (t, J=7.56 Hz, 1H), 7.68 (d, J=8.4 Hz, 1H), 7.54 (t, J=7.76 Hz, 1H), 7.17 (d, J=7.12 Hz, 1H), 5.46 (dd, J=12.76, 5.08 Hz, 1H), 3.00-2.91 (m, 1H), 2.82-2.71 (m, 1H), 2.67-2.63 (m, 1H), 2.12-2.09 (m, 1H); LC MS: ES+ 281.2.

Example 56. Synthesis of tert-butyl 4-(4-((1-(2,6-dioxopiperidin-3-yl)-2-oxo-1,2-dihydrobenzo[cd]indol-6-yl)methyl)-1H-pyrazol-1-yl)piperidine-1-carboxylate (Compound 140)

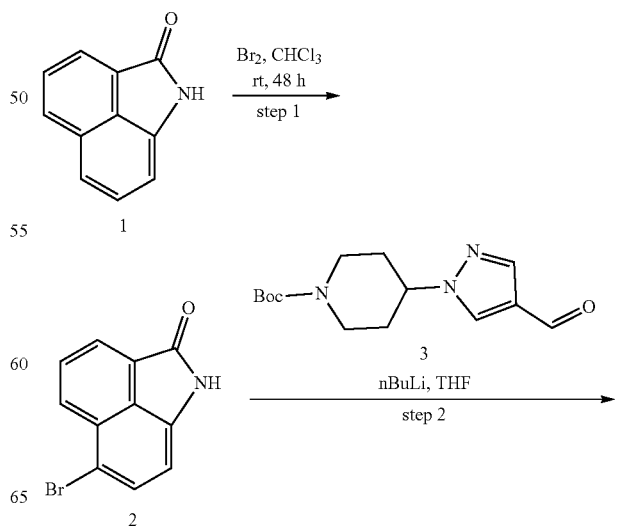

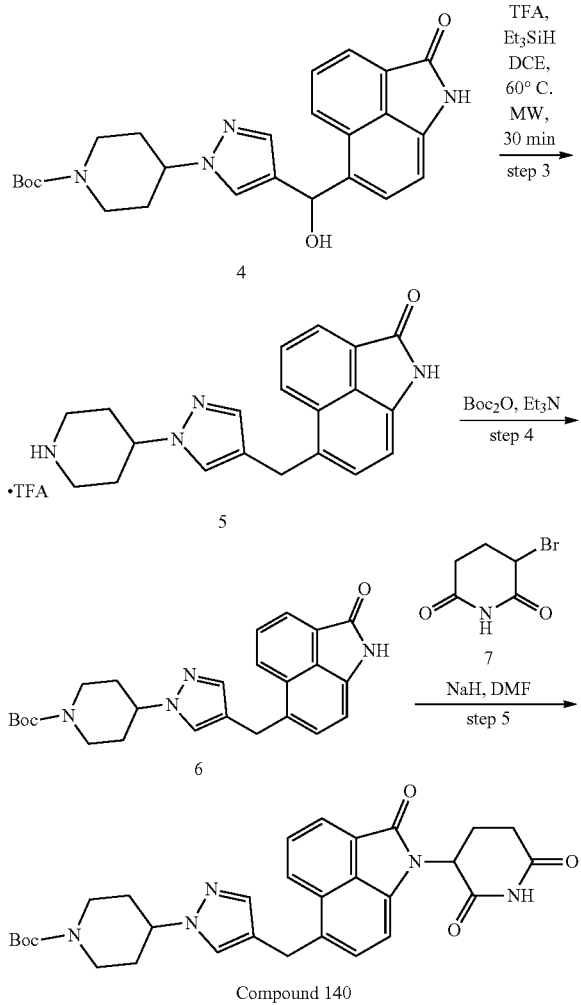

Compound 140

Step 1: Synthesis of 6-bromobenzo[cd]indol-2(1H)-one: To the stirred suspension of 1H-benzo[cd]indol-2-one 1 (3.0 g, 17.73 mmol) in CHCl3 (50.0 mL) was added Bromine (2.15 g, 26.60 mmol, 1.44 mL) at cold condition drop wise and the reaction mixture was continued at room temperature for 48 hours. Sodium thiosulphate solution was poured into the reaction mixture in cold condition and the yellow solid formed was filtered through cintered funnel. Solid obtained was washed with cold water, pentane and azeotroped with toluene to afford 6-bromo-1H-benzo[cd]indol-2-one 2 (4 g, 16.12 mmol, 90.93% yield) as yellow solid. LC MS: ES+ 248.1, 250.0 (Bromo pattern).

Step 2: Synthesis of tert-butyl 4-(4-(hydroxy(2-oxo-1,2-dihydrobenzo[cd]indol-6-yl)methyl)-1H-pyrazol-1-yl)piperidine-1-carboxylate: To the stirred solution of 6-bromo-1H-benzo[cd]indol-2-one 2 (1.6 g, 6.45 mmol) in THF (7 mL) was added Butyllithium (2.2 M, 9.38 mL) at −78° C. and after the addition was complete the temperature was allowed to increase to −40° C. and the reaction mixture was stirred at the same temperature for 30 minutes followed by the addition of tert-butyl 4-(4-formylpyrazol-1-yl)piperidine-1-carboxylate 3 (1.80 g, 6.45 mmol) in THF (7 mL) at −78° C. and then the reaction mixture was allowed to warm to room temperature and was continued for 16 hours. Reaction mixture was quenched with saturated aqueous ammonium chloride solution, diluted with ethyl acetate. Layers were separated and organic part was washed with water. It was then dried over anhydrous sodium sulphate and evaporated under reduced pressure to obtain the crude compound which was purified by flash chromatography using 0-5% MeOH-DCM to afford tert-butyl 4-[4-[hydroxy-(2-oxo-1H-benzo[cd]indol-6-yl)methyl]pyrazol-1-yl]piperidine-1-carboxylate 4 (527 mg, 1.17 mmol, 18.22% yield) as brown solid. 1H NMR (d6-DMSO, 400 MHZ) S 10.70 (s, 1H), 8.34 (d, J=8.28 Hz, 1H), 7.95 (d, J=6.96 Hz, 1H), 7.72 (t, J=7.6 Hz, 1H), 7.59-7.52 (m, 2H), 7.28 (s, 1H), 6.93 (d, J=7.2 Hz, 1H), 6.22 (br s, 1H), 5.80 (br s, 1H), 4.27-4.21 (m, 1H), 4.00-3.96 (m, 2H), 2.84-2.82 (m, 2H), 1.91-1.87 (m, 2H), 1.72-1.64 (m, 2H), 1.39 (s, 9H).

Step 3: Synthesis of 2,2,2-trifluoroacetaldehyde compound with 6-((1-(piperidin-4-yl)-1H-pyrazol-4-yl)methyl)benzo[cd]indol-2(1H)-one (1:1): To the stirred solution of tert-butyl 4-[4-[hydroxy-(2-oxo-1H-benzo[cd]indol-6-yl)methyl]pyrazol-1-yl]piperidine-1-carboxylate 4 (500.0 mg, 1.11 mmol) in DCE (3 mL) was added Triethylsilane (518.51 mg, 4.46 mmol, 712.24 uL) and Trifluoroacetic acid (1.02 g, 8.92 mmol, 687.08 uL) and the reaction was continued for 30 minutes under microwave condition at 70° C. The solvent in the reaction mixture was evaporated under reduced pressure to obtain the crude which was washed with ether and pentane to afford 6-[(1-piperidin-1-ium-4-ylpyrazol-4-yl)methyl]-1H-benzo[cd]indol-2-one; 2,2,2-trifluoroacetate 5 (500.0 mg, 1.12 mmol, 100.47% yield) as brown gum in the form of crude. LC MS: ES+ 333.0.

Step 4: Synthesis of tert-butyl 4-(4-((2-oxo-1,2-dihydrobenzo[cd]indol-6-yl)methyl)-1H-pyrazol-1-yl)piperidine-1-carboxylate: To the stirred solution of 6-[(1-piperidin-1-ium-4-ylpyrazol-4-yl)methyl]-1H-benzo[cd]indol-2-one; 2,2,2-trifluoroacetate 5 (500.0 mg, 1.12 mmol) in DCM (5 mL) was added Triethylamine (340.00 mg, 3.36 mmol, 468.32 uL) at cold condition followed by the addition of Di-tert-butyl dicarbonate (366.67 mg, 1.68 mmol, 385.56 uL) and the reaction was continued at room temperature for 16 hours. Reaction mixture was diluted with ethyl acetate, washed with water, brine solution and the organic fraction was separated. It was then dried over anhydrous sodium sulphate and evaporated under reduced pressure to obtain the crude which was purified by flash chromatography (using 0-5% MeOH-DCM) to afford tert-butyl 4-[4-[(2-oxo-1H-benzo[cd]indol-6-yl)methyl]pyrazol-1-yl]piperidine-1-carboxylate 6 (300.0 mg, 693.62 umol, 61.93% yield) as yellow sticky solid. LC MS: ES+ 433.0.

Step 5: Synthesis of tert-butyl 4-(4-((1-(2,6-dioxopiperidin-3-yl)-2-oxo-1,2-dihydrobenzo[cd]indol-6-yl)methyl)-1H-pyrazol-1-yl)piperidine-1-carboxylate: To the stirred solution of tert-butyl 4-[4-[(2-oxo-1H-benzo[cd]indol-6-yl)methyl]pyrazol-1-yl]piperidine-1-carboxylate 6 (300.0 mg, 693.62 umol) in DMF (1 mL) was added Sodium hydride (in oil dispersion) 60% dispersion in mineral oil (53.15 mg, 1.39 mmol, 60% purity) in cold condition and the reaction mixture was heated at 60° C. for 30 minutes. Then to it was added 3-bromopiperidine-2,6-dione 7 (133.18 mg, 693.62 umol) and the reaction was heated at 60° C. for 4 hours followed by the further addition of 3-bromopiperidine-2,6-dione (133.18 mg, 693.62 umol) and the reaction was further continued for 16 hours at 60° C. Reaction mixture was diluted with ethyl acetate, washed with water and the organic fraction was separated. It was then dried over anhydrous sodium sulphate and evaporated under reduced pressure to obtain the crude which was first purified by column chromatography followed by the preparative TLC plate purification (eluting with 60% ethyl acetate-hexane) to afford tert-butyl 4-[4-[[1-(2,6-dioxo-3-piperidyl)-2-oxobenzo[cd]indol-6-yl]methyl]pyrazol-1-yl]piperidine-1-carboxylate Compound 140 (20.0 mg, 33.11 umol, 4.77% yield, 90% purity) as pale yellow solid. ¹H NMR (d6-DMSO, 400 MHZ) δ 11.11 (s, 1H), 8.37 (d, J=8.24 Hz, 1H), 8.08 (d, J=6.92 Hz, 1H), 7.83 (t, J=7.58 Hz, 1H), 7.59 (s, 1H), 7.35 (d, J=7.36 Hz, 1H), 7.31 (s, 1H), 7.07 (d, J=7.28 Hz, 1H), 5.43 (dd, J=12.76, 5.0 Hz, 1H), 4.24-4.23 (m, 1H), 4.17 (s, 2H), 4.00-3.96 (m, 2H), 2.96-2.66 (m, 5H), 2.09-2.06 (m, 1H), 1.91-1.88 (m, 2H), 1.72-1.66 (m, 2H), 1.39 (m, 9H); LC MS: ES+ 544.3.

Example 57. Synthesis of tert-butyl 4-[4-[[1-[2,6-dioxo-3-piperidyl]-2-oxo-benzo[cd]indol-6-yl]methyl]pyrazol-1-yl]piperidine-1-carboxylate (Compound 141) and tert-butyl 4-[4-[[1-[2,6-dioxo-3-piperidyl]-2-oxo-benzo[cd]indol-6-yl]methyl]pyrazol-1-yl]piperidine-1-carboxylate (Compound 142)

Example 58. Synthesis of tert-butyl 4-(4-(1-(2,6-dioxopiperidin-3-yl)-2-oxo-1,2-dihydrobenzo[cd]indole-6-carbonyl)-1H-pyrazol-1-yl)piperidine-1-carboxylate (Compound 143)

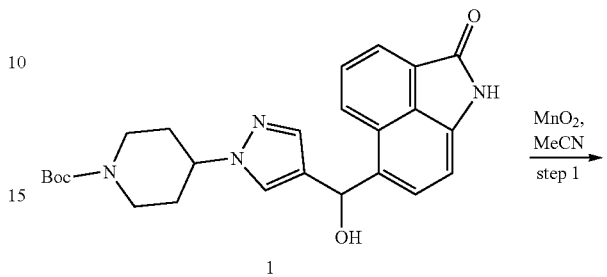

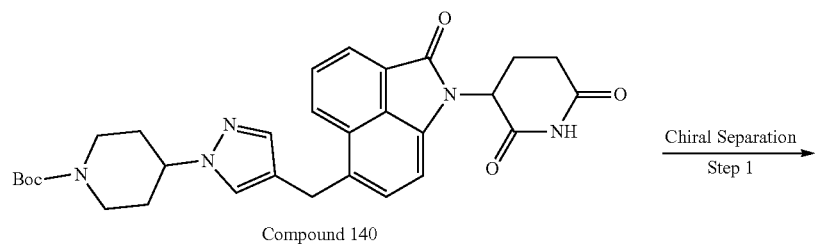

Compound 140

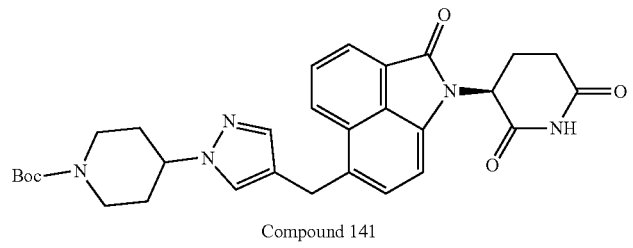

Compound 141

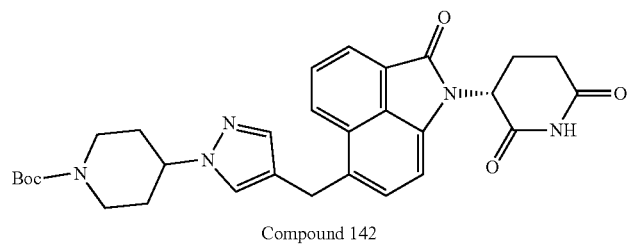

Compound 142

Step 1: Chiral separation: 150 mg of the racemate Compound 140 was submitted to Chiral Prep HPLC purification. The isomers were separated and isolated by reverse phase chiral HPLC to afford tert-butyl 4-[4-[[1-[2,6-dioxo-3-piperidyl]-2-oxo-benzo[cd]indol-6-yl]methyl]pyrazol-1-yl]piperidine-1-carboxylate Compound 141 (27.0 mg, 49.22 umol, 2.66% yield, 99.1% purity) and tert-butyl 4-[4-[[1-[2,6-dioxo-3-piperidyl]-2-oxo-benzo[cd]indol-6-yl]methyl]pyrazol-1-yl]piperidine-1-carboxylate Compound 142 (26.0 mg, 47.83 umol, 2.59% yield, 100% purity) both as yellow solid.

-continued

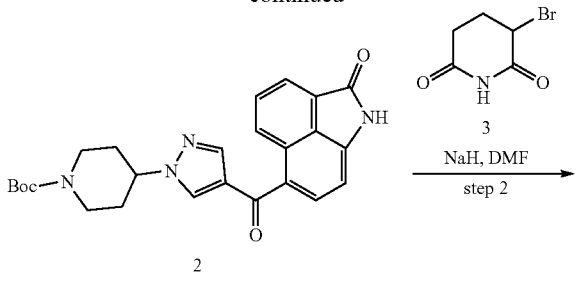

453

-continued

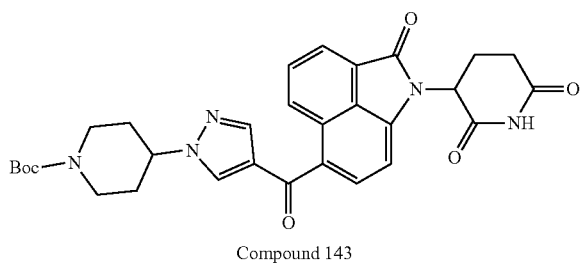

Compound 143

Step 1: Synthesis of tert-butyl 4-(4-(2-oxo-1,2-dihydrobenzo[cd]indole-6-carbonyl)-1H-pyrazol-1-yl)piperidine-1-carboxylate: To the stirred solution of tert-butyl 4-[4-[hydroxy-(2-oxo-1H-benzo[cd]indol-6-yl)methyl]pyrazol-1-yl]piperidine-1-carboxylate 1 (500 mg, 1.11 mmol) in DCM (15.0 mL) was added dioxomanganese (969.17 mg, 11.15 mmol) at 0° C. and the reaction mixture was stirred at room temperature for 16 hours. Reaction mixture was then filtered through celite bed and filtrate was then concentrated under reduced pressure to afford the crude material. The crude was then purified by column chromatography by (eluting 1.5%-2% MeOH in DCM) to afford tert-butyl 4-[4-(2-oxo-1H-benzo[cd]indole-6-carbonyl)pyrazol-1-yl]piperidine-1-carboxylate 2 (220 mg, 492.72 umol, 44.20% yield) as green solid. LC MS: ES+ 447.4.

Step 2: Synthesis of tert-butyl 4-(4-(1-(2,6-dioxopiperidin-3-yl)-2-oxo-1,2-dihydrobenzo[cd]indole-6-carbonyl)-1H-pyrazol-1-yl)piperidine-1-carboxylate: In a round bottomed flask under nitrogen atmosphere tert-butyl 4-[4-(2-oxo-1H-benzo[cd]indole-6-carbonyl)pyrazol-1-yl]piperidine-1-carboxylate 2 (220 mg, 492.72 umol) was taken in DMF (3.0 mL) and then at 0° C. Sodium hydride (in oil dispersion) 60% dispersion in mineral oil (22.66 mg, 985.45 umol) was added portion wise into the reaction mixture. It was then heated at 60° C. for 30 minutes and then 3-bromopiperidine-2,6-dione (94.61 mg, 492.72 umol) was added into the reaction mixture. It was stirred for 16 hours at room temperature. Again 3-bromopiperidine-2,6-dione (94.61 mg, 492.72 umol) was added and then it was heated at 60° C. for 16 hours. Reaction mixture was cooled to room temperature and extracted with ethyl acetate. Organic layer was separated, dried over sodium sulfate and concentrated under reduced pressure to afford the crude compound. Crude material was the purified by Preparative TLC Plate (eluting with 50% ethyl acetate in dichloromethane) to afford tert-butyl 4-[4-[1-(2,6-dioxo-3-piperidyl)-2-oxo-benzo[cd]indole-6-carbonyl]pyrazol-1-yl]piperidine-1-carboxylate Compound 143 (15 mg, 26.90 umol, 5.46% yield) as a white solid. $^1$H NMR (D6-DMSO, 400 MHZ) δ 11.17 (s, 1H), 8.58 (d, J=8.32 Hz, 1H), 8.46 (s, 1H), 8.18 (d, J=6.96 Hz, 1H), 8.04 (d, J=7.6 Hz, 1H), 7.99 (s, 1H), 7.92 (t, J=7.7 Hz, 1H), 7.25 (d, J=7.56 Hz, 1H), 5.53 (dd, J=12.8, 5.28 Hz, 1H), 4.49-4.44 (m, 1H), 4.07-4.03 (m, 2H), 3.01-2.66 (m, 5H), 2.18-2.14 (m, 1H), 2.06-2.02 (m, 2H), 1.88-1.80 (m, 2H), 1.41 (s, 9H); LC MS: ES+ 558.5.

454

Example 59. Synthesis of 3-(6-Amino-2-oxo-2H-benzo[cd]indol-1-yl)-piperidine-2,6-dione hydrochloride (Compound 144)

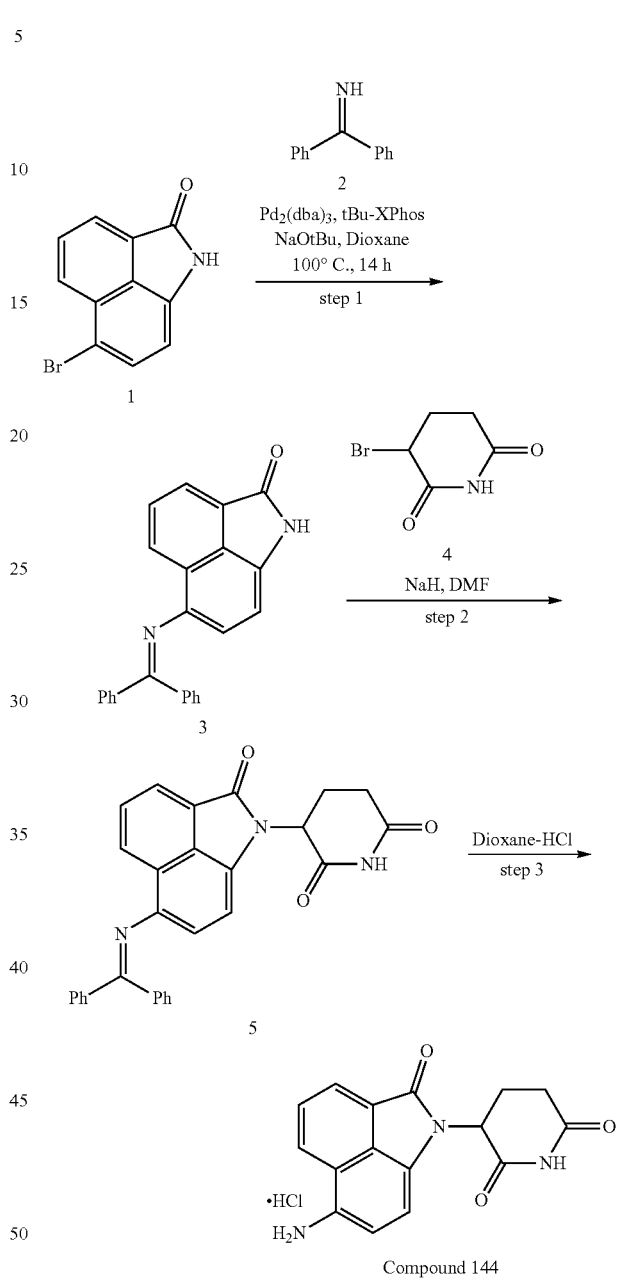

Compound 144

Step 1: Synthesis of 6-(Benzhydrylidene-amino)-1H-benzo[cd]indol-2-one: To a well degassed stirred solution of 6-bromo-1H-benzo[cd]indol-2-one 1 (1.0 g, 4.03 mmol) and diphenylmethanimine 2 (1.10 g, 6.05 mmol, 1.01 mL) in dry grade Toluene (5.0 mL), sodium; 2-methylpropan-2-olate (1.16 g, 12.09 mmol), (5-diphenylphosphanyl-9,9-dimethylxanthen-4-yl)-diphenyl-phosphane (466.49 mg, 806.21 umol) and (1E,4E)-1,5-diphenylpenta-1,4-dien-3-one; palladium (369.13 mg, 403.10 umol) were added. After complete addition, reaction mixture was heated at 80° C. in a sealed tube for 12 hours. Reaction mass was filtered through celite and the filtrate was concentrated under reduced pressure. The crude thus obtained was purified by combi-flash to get the pure compound 6-(benzhydrylideneamino)-1H-benzo

[cd]indol-2-one 3 (565 mg, 1.62 mmol, 40.23% yield) as light brown solid. LC MS: ES+ 349.2.

Step 2: Synthesis of 3-[6-(Benzhydrylidene-amino)-2-oxo-2H-benzo[cd]indol-1-yl]-piperidine-2,6-dione: To the stirred solution of 6-(benzhydrylideneamino)-1H-benzo[cd]indol-2-one 3 (293 mg, 841.00 umol) in dry DMF (3.0 mL), Sodium hydride (in oil dispersion) 60% dispersion in mineral oil (100.92 mg, 4.20 mmol) was added at 0° C. and resultant solution was heated at 70° C. for 1 hour. After that, 3-bromopiperidine-2,6-dione 4 (322.96 mg, 1.68 mmol) was added to the reaction mixture and heating was continued for 12 hours. Reaction was monitored by TLC which showed incomplete consumption of the 6-(benzhydrylideneamino)-1H-benzo[cd]indol-2-one 3 along with desired spot as confirmed from LCMS. For complete completion of reaction further 3-bromopiperidine-2,6-dione (322.96 mg, 1.68 mmol) was added to the reaction mixture and heating was continued for further 6 hours. After almost completion of reaction (~65% as confirmed by LC MS), reaction mixture was quenched with saturated ammonium chloride solution and extracted with ethyl acetate. Organic phase was separated, dried over sodium sulfate and concentrated under vacuum. Crude residual part was purified combi-flash (30% DCM in ethyl acetate) to afford 3-[6-(benzhydrylideneamino)-2-oxo-benzo[cd]indol-1-yl]piperidine-2,6-dione 5 (70 mg, 152.34 umol, 18.11% yield) as light yellow solid. LC MS: ES+460.3.

Step 3: Synthesis of 3-(6-Amino-2-oxo-2H-benzo[cd]indol-1-yl)-piperidine-2,6-dione hydrochloride: 4.0 M dioxane-HCl(2.0 mL) was added to the 3-[6-(benzhydrylideneamino)-2-oxo-benzo[cd]indol-1-yl]piperidine-2,6-dione 5 (60 mg, 130.58 umol) followed by 0.2 ml of water at 0° C. and stirred for 3 hours at room temperature. Volatiles were removed under reduced pressure. Crude solid material was washed with DCM and ether several times. Solid material was lyophilized to afford HCl salt of 3-(6-amino-2-oxo-benzo[cd]indol-1-yl)piperidine-2,6-dione Compound 144 (45.0 mg, 122.08 umol, 93.49% yield, 90% purity, 021) as brown solid. $^1$H NMR (d$_6$ DMSO, 400 MHz) δ 11.06 (s, 1H); 8.40 (d, J=8.04 Hz, 1H), 8.05-8.03 (m, 1H), 7.72 (m, 1H), 6.91-6.89 (m, 1H), 6.62-6.59 (m, 1H), 5.37-5.35 (m, 1H), 2.92-2.88 (m, 1H), 2.71-2.59 (m, 2H), 2.06-2.04 (m, 1H); LC MS: ES+ 296.3.

Example 60. Synthesis of 1-(2,6-dioxopiperidin-3-yl)-2-oxo-1,2-dihydrobenzo[cd]indole-6-carbonitrile (Compound 145)

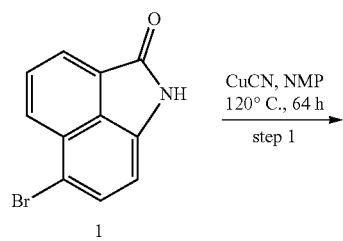

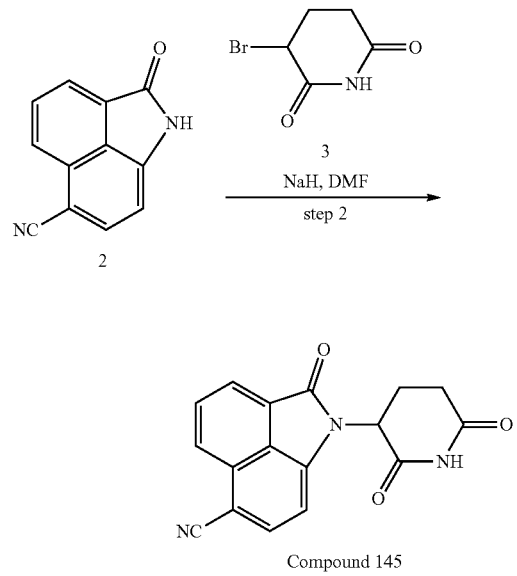

Compound 145

Step 1: Synthesis of 2-oxo-1,2-dihydrobenzo[cd]indole-6-carbonitrile: To a stirred solution of 6-bromo-1H-benzo[cd]indol-2-one 1 (5 g, 20.16 mmol) in NMP (25 mL) was added cuprous; cyanide (3.61 g, 40.31 mmol, 1.24 mL) and the reaction was stirred at 120° C. for 16 h. LCMS showed ~15% product formation along with unreacted SM. Again cuprous; cyanide (3.61 g, 40.31 mmol, 1.24 mL) was added and the reaction was continued for 48 h. LCMS showed formation of desired compound. The reaction mixture was diluted with ethyl acetate and washed with water and brine, dried over sodium sulphate and concentrated. The crude was purified by column chromatography in 100-200 silica to afford 2-oxo-1H-benzo[cd]indole-6-carbonitrile 2 (1.5 g, 6.18 mmol, 30.66% yield, 80% purity) as yellow solid. LC MS: ES+ 195.4.

Step 2: Synthesis of 1-(2,6-dioxopiperidin-3-yl)-2-oxo-1,2-dihydrobenzo[cd]indole-6-carbonitrile: To the stirred solution of 2-oxo-1H-benzo[cd]indole-6-carbonitrile 2 (250 mg, 1.29 mmol) in DMF (4.0 mL) was added Sodium hydride (in oil dispersion)60% dispersion in mineral oil (98.66 mg, 2.57 mmol, 60% purity) and then it was heated at 70° C. for 1 hour. After that to it 3-bromopiperidine-2,6-dione 3 (247.20 mg, 1.29 mmol) was added under room temperature and then it was stirred at 70° C. for 16 hours. TLC was checked which shows that the starting material was present a polar new spot was formed. Again, into the reaction mixture 3-bromopiperidine-2,6-dione 3 (247.20 mg, 1.29 mmol) was added and then it was stirred at 70° C. for 16 hours. The reaction mixture was then cooled to room temperature and it was then extracted with ethyl acetate. The organic part was then dried over sodium sulfate to afford the crude material. The crude was then purified by Preparative TLC method by eluting (40% ethyl acetate in dichloromethane) to afford 1-(2,6-dioxo-3-piperidyl)-2-oxo-benzo[cd]indole-6-carbonitrile Compound 145 (8 mg, 26.01 umol, 2.02% yield, 99.26% purity) as a white solid. $^1$H NMR (d$_6$ DMSO, 400 MHz) δ 11.19 (s, 1H), 8.31-8.22 (m, 3H), 8.07-8.06 (m, 1H), 7.36 (d, J=7.28 Hz, 1H), 5.53-5.51 (m, 1H), 2.95-2.90 (m, 1H), 2.77-2.62 (m, 2H), 2.14-2.12 (m, 1H); LC MS: ES− 304.1.

Example 61. Synthesis of 3-[6-[[4-(3-oxa-6-azabicyclo[3.1.1]heptan-6-ylmethyl)phenyl]methyl]-2-oxo-benzo[cd]indol-1-yl]piperidine-2,6-dione (Compound 146)

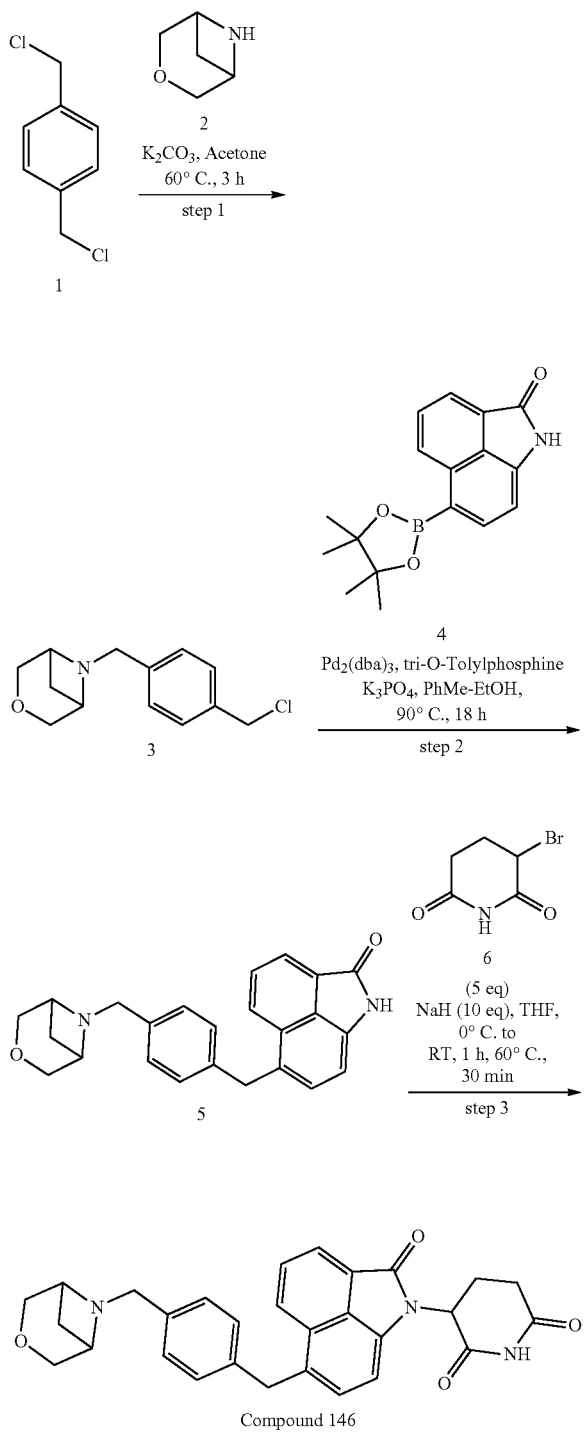

Step 1: Synthesis of 6-[[4-(chloromethyl)phenyl]methyl]-3-oxa-6-azabicyclo[3.1.1]heptane: To a stirred solution of 3-oxa-6-azabicyclo[3.1.1]heptane; hydrochloride (2) (800 mg, 5.90 mmol, 1.00 mL) in Acetone (15 mL), Potassium carbonate, anhydrous, 99% (1.22 g, 8.85 mmol, 534.14 uL) was added and the resultant reaction mixture was stirred at 50° C. for 20 minutes followed by the addition of 1,4-bis(chloromethyl)benzene (1) (1.03 g, 5.90 mmol, 727.35 uL). Resulting solution was further heated at same temperature for 3 hours. After completion (monitored by TLC and LCMS), all the volatiles were removed under reduced pressure and re-dissolved in ethyl acetate. Organic portion was washed with water and brine, dried over sodium sulfate and concentrated. The crude thus obtained was purified by column chromatography in (gradient: 0-30% EtOAc in DCM) to afford 6-[[4-(chloromethyl)phenyl]methyl]-3-oxa-6-azabicyclo[3.1.1]heptane 3 (800 mg, 51.33% yield) as yellow gum. LC MS: ES+ 238.2.

Step 2: Synthesis of 6-[[4-(3-oxa-6-azabicyclo[3.1.1]heptan-6-ylmethyl)phenyl]methyl]-1H-benzo[cd]indol-2-one: To a stirred solution of 6-[[4-(chloromethyl)phenyl]methyl]-3-oxa-6-azabicyclo[3.1.1]heptane (3) (600 mg, 2.52 mmol) and 6-(4,4,5,5-tetramethyl-1,3,2-dioxaborolan-2-yl)-1H-benzo[cd]indol-2-one (4) (1.49 g, 5.05 mmol) in ethanol (5 mL) and Toluene (10 mL) was added Potassium phosphate tribasic anhydrous (1.61 g, 7.57 mmol) and the reaction mass was degassed under nitrogen atmosphere over 10 minutes. Then Tri-o-Tolyl phosphine (153.64 mg, 504.79 umol) and (1E,4E)-1,5-diphenylpenta-1,4-dien-3-one; palladium (231.12 mg, 252.39 umol) was added to this reaction mass and at 90° C. for 18 hours. After completion (monitored by TLC) the reaction mixture was passed through celite bed and washed with EtOAc. The filtrate was further washed with water and brine, dried over sodium sulphate and concentrated. The crude thus obtained was purified by combiflash chromatography in (gradient: 0-30% EtOAc in DCM) to afford the desired compound 6-[[4-(3-oxa-6-azabicyclo[3.1.1]heptan-6-ylmethyl)phenyl]methyl]-1H-benzo[cd]indol-2-one (5) (300 mg, 24.39% yield). LC MS: ES+ 371.3.

Step 3: Synthesis of 3-[6-[[4-(3-oxa-6-azabicyclo[3.1.1]heptan-6-ylmethyl)phenyl]methyl]-2-oxo-benzo[cd]indol-1-yl]piperidine-2,6-dione: To a stirred solution of 6-[[4-(3-oxa-6-azabicyclo[3.1.1]heptan-6-ylmethyl)phenyl]methyl]-1H-benzo[cd]indol-2-one (5) (150 mg, 404.92 umol) in dry THF (10 mL) Sodium hydride 60% dispersion in mineral oil (93.09 mg, 4.05 mmol) was added at 0° C. and stirred for 15 minutes followed by the addition of 3-bromopiperidine-2,6-dione (6) (388.75 mg, 2.02 mmol). The resulting reaction mixture was stirred at 70° C. for 1 hr. After completion (monitored by TLC and LCMS), the reaction mixture was quenched in ice and extracted with ethyl acetate. Organic layer was further washed with water and brine, dried over sodium sulfate and concentrated. The crude thus obtained was purified by PREP-TLC (10% MeOH in EtOAc as eluent) to afford 3-[6-[[4-(3-oxa-6-azabicyclo[3.1.1]heptan-6-ylmethyl)phenyl]methyl]-2-oxo-benzo[cd]indol-1-yl]piperidine-2,6-dione Compound 146 (90.0 mg, 41.54% yield) as yellow solid. $^1$H NMR (DMSO-d$_6$, 400 MHz) δ 11.11 (s, 1H), 8.32 (d, J=8.24 Hz, 1H), 8.07 (d, J=6.96 Hz, 1H), 7.80 (t, J=7.8 Hz, 1H), 7.40 (d, J=7.32 Hz, 1H), 7.26-7.20 (m, 4H), 7.09 (d, J=7.24 Hz, 1H), 5.46-5.41 (m, 1H), 4.36 (s, 2H), 4.10 (d, J=10.68 Hz, 1H), 3.69 (s, 2H), 3.57 (d, J=10.68 Hz, 1H), 3.39-3.33 (m, 2H), 2.97-2.90 (m, 1H), 2.79-2.73 (m, 1H), 2.70-2.63 (m, 1H), 2.10-2.07 (m, 2H), 1.87-1.85 (m, 2H), 1.71-1.67 (m, 1H); LC MS: ES+482.2.

Example 62. Synthesis of tert-butyl 4-(4-(1-(1-(2,6-dioxopiperidin-3-yl)-2-oxo-1,2-dihydrobenzo[cd]indol-6-yl)ethyl)-1H-pyrazol-1-yl)piperidine-1-carboxylate (Compound 147)

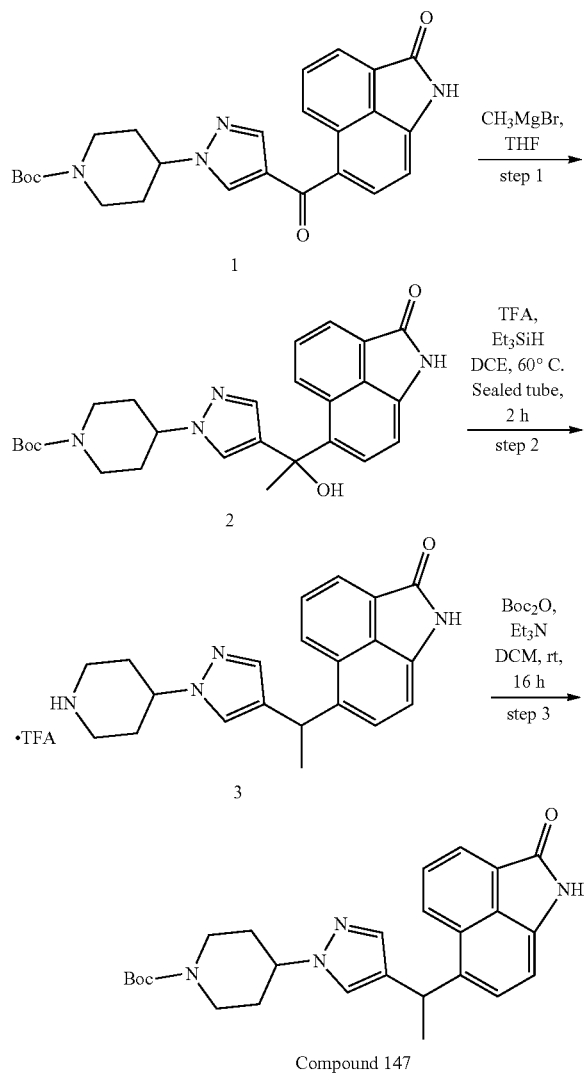

Step 1: Synthesis of tert-butyl 4-(4-(1-hydroxy-1-(2-oxo-1,2-dihydrobenzo[cd]indol-6-yl)ethyl)-1H-pyrazol-1-yl)piperidine-1-carboxylate: To the stirred solution of tert-butyl 4-[4-(2-oxo-1H-benzo[cd]indole-6-carbonyl)pyrazol-1-yl] piperidine-1-carboxylate 1 (400.0 mg, 895.86 umol) in THF (10 mL) was added Methylmagnesium bromide, 3M in ether (3 M, 1.49 mL) at −50° C. After completion of addition the reaction mixture was allowed to warm to room temperature and continued at room temperature for 16 hours. The reaction mixture was quenched with ammonium chloride solution, diluted with ethyl acetate, washed with water and the organic fraction was separated. It was dried over anhydrous sodium sulphate and evaporated under reduced pressure to obtain the crude compound which was purified by flash chromatography using 0-5% MeOH-DCM to afford tert-butyl 4-[4-[1-hydroxy-1-(2-oxo-1H-benzo[cd]indol-6-yl)ethyl]pyrazol-1-yl]piperidine-1-carboxylate 2 (285.0 mg, 611.23 umol, 68.23% yield, 99.2% purity) as brown solid. LC MS: ES− 461.2.

Step 2: Synthesis of 2,2,2-trifluoroacetaldehyde compound with 6-(1-(1-(piperidin-4-yl)-1H-pyrazol-4-yl)ethyl)benzo[cd]indol-2(1H)-one (1:1): To the stirred solution of tert-butyl 4-[4-[1-hydroxy-1-(2-oxo-1H-benzo[cd]indol-6-yl)ethyl]pyrazol-1-yl]piperidine-1-carboxylate 2 (284.0 mg, 614.00 umol) in DCE (2 mL) was added Triethylsilane (285.58 mg, 2.46 mmol, 392.29 uL), Trifluoroacetic acid (560.07 mg, 4.91 mmol, 378.42 uL) and the reaction was heated at 80° C. in a sealed tube for 2 hours. The solvent in the reaction mixture was evaporated under reduced pressure to obtain the crude compound which was triturated with ether to afford [4-[4-[1-(2-oxo-1H-benzo[cd]indol-6-yl)ethyl]pyrazol-1-yl]-1-piperidyl] 2,2,2-trifluoroacetate 3 (280.0 mg, 462.55 umol, 75.33% yield, 94.9% purity) as brown gum which was used directly in the next step. LC MS: ES+ 347.2.

Step 3: Synthesis of tert-butyl 4-(4-(1-(2-oxo-1,2-dihydrobenzo[cd]indol-6-yl)ethyl)-1H-pyrazol-1-yl)piperidine-1-carboxylate: To the stirred solution of [4-[4-[1-(2-oxo-1H-benzo[cd]indol-6-yl)ethyl]pyrazol-1-yl]-1-piperidyl] 2,2,2-trifluoroacetate 3 (280.0 mg, 608.10 umol) in DCM (5 mL) was added Triethylamine (184.60 mg, 1.82 mmol, 254.27 uL) at 0° C. followed by the addition of Di-tert-butyl dicarbonate (199.08 mg, 912.16 umol, 209.33 uL) and the reaction was continued at room temperature for 16 hours. TLC was checked which showed complete consumption of the starting material along with the formation of the desired spot. The reaction mixture was diluted with ethyl acetate, washed with water, the organic fraction was separated, dried over anhydrous sodium sulphate and evaporated under reduced pressure to obtain the crude compound which was purified by flash chromatography using 0-5% MeOH-DCM to afford tert-butyl 4-[4-[1-(2-oxo-1H-benzo[cd]indol-6-yl)ethyl]pyrazol-1-yl]piperidine-1-carboxylate 4 (190.0 mg, 414.01 umol, 68.08% yield, 97.3% purity) as brown solid. LC MS: ES+447.3.

Step 4: Synthesis of tert-butyl 4-(4-(1-(1-(2,6-dioxopiperidin-3-yl)-2-oxo-1,2-dihydrobenzo[cd]indol-6-yl)ethyl)-1H-pyrazol-1-yl)piperidine-1-carboxylate: To the stirred solution of tert-butyl 4-[4-[1-(2-oxo-1H-benzo[cd]indol-6-yl)ethyl]pyrazol-1-yl]piperidine-1-carboxylate 4 (190.0 mg, 425.49 umol) in DMF (2 mL) was added Sodium hydride (in oil dispersion) 60% dispersion in mineral oil (81.52 mg, 2.04 mmol, 60% purity) in cold condition and the reaction mixture was heated at 60° C. for 1 hour followed by the addition of 3-bromopiperidine-2,6-dione 5 (163.40 mg, 850.99 umol) and the reaction was continued for 4 hours at 60° C. with further top up of 3-bromopiperidine-2,6-dione 5 (163.40 mg, 850.99 umol) and the reaction was continued for 16 hours at 60° C. The reaction mixture was added to a solution of citric acid (pH 5) and the extracted with ethyl acetate. The organic fraction was separated, dried over anhydrous sodium sulphate and evaporated under reduced pressure to obtain the crude which was first purified by flash chromatography using (0-60% ethyl acetate-DCM) followed by further purification by preparative TLC plate method developing the plate in (45% ethyl acetate-DCM) to afford tert-butyl 4-[4-[1-[1-(2,6-dioxo-3-piperidyl)-2-oxo-benzo[cd]indol-6-yl]ethyl]pyrazol-1-yl]piperidine-1-carboxylate Compound 147 (20.0 mg, 35.87 umol, 8.43% yield, 100% purity) as yellow solid. $^1$H NMR (400 MHz, DMSO-d6): 11.11 (s, 1H), 8.40 (d, J=8.2 Hz, 1H), 8.08 (d, J=6.92 Hz, 1H), 7.81 (t, J=7.68 Hz, 1H), 7.62 (d, J=4.72 Hz, 1H), 7.35-7.29 (m, 2H), 7.07 (d, J=7.44 Hz, 1H), 5.44-5.42 (m, 1H), 4.78-4.76 (m, 1H), 4.25-4.24 (m, 1H), 3.98-3.97 (m, 2H), 2.95-2.72 (m, 4H), 2.67-2.62 (m, 1H), 2.09-2.08 (m, 1H), 1.93-1.90 (m, 2H), 1.73-1.63 (m, 5H), 1.39 (s, 9H); LC MS: ES− 556.2.

Example 63. Synthesis of Synthesis of 3-(6-(1-(1-(1-(1-methylcyclobutane-1-carbonyl)piperidin-4-yl)-1H-pyrazol-4-yl)ethyl)-2-oxobenzo[cd]indol-1(2H)-yl)piperidine-2,6-dione (Compound 148) and 3-(6-(1-(1-(1-(1-methylcyclobutane-1-carbonyl)piperidin-4-yl)-1H-pyrazol-4-yl)ethyl)-2-oxobenzo[cd]indol-1(2H)-yl)piperidine-2,6-dione (Compound 149)
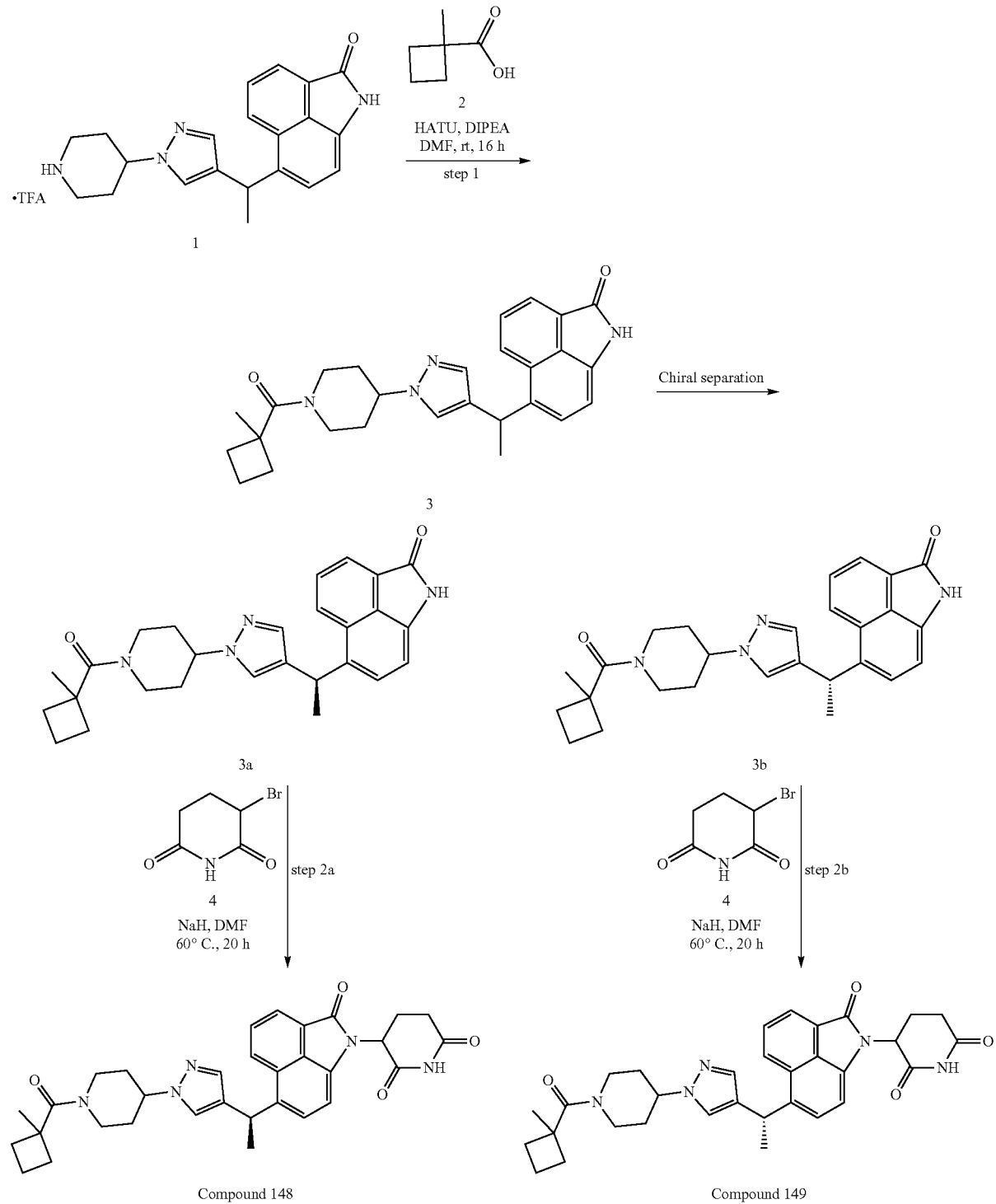

Step 1: Synthesis of 6-(1-(1-(1-(1-methylcyclobutane-1-carbonyl)piperidin-4-yl)-1H-pyrazol-4-yl)ethyl)benzo[cd]indol-2(1H)-one: To the stirred solution of 6-[1-[1-(4-piperidyl)pyrazol-4-yl]ethyl]-1H-benzo[cd]indol-2-one; 2,2,2-trifluoroacetic acid 1 (589.26 mg, 1.28 mmol) in DMF (2 mL) was added HATU (729.90 mg, 1.92 mmol) in cold condition followed by the addition 1-methylcyclobutanecarboxylic acid 2 (160.68 mg, 1.41 mmol, 143.47 uL) and the reaction was continued at room temperature for 16 hours. The reaction mixture was diluted with ethyl acetate, washed with sodium bicarbonate solution, water and the organic fraction was separated. It was dried over anhydrous sodium sulphate and evaporated under reduced pressure to obtain the crude which was purified by flash chromatography using 0-5% MeOH-DCM to afford the desired compound as racemic mixture (350.0 mg) which was submitted for normal phase prep HPLC for the separation of the chiral isomers to afford 6-[1-[1-[1-(1-methylcyclobutanecarbonyl)-4-piperidyl]pyrazol-4-yl]ethyl]-1H-benzo[cd]indol-2-one 3a (145.0 mg, 325.58 umol, 25.44% yield, 99.37% purity) and 6-[1-[1-[1-(1-methylcyclobutanecarbonyl)-4-piperidyl]pyrazol-4-yl]ethyl]-1H-benzo[cd]indol-2-one 3b (115.0 mg, 259.86 umol, 20.31% yield, 100% purity) both as yellow solid. LC MS: ES+ 443.4.

Step 2a: Synthesis of 3-(6-(1-(1-(1-(1-methylcyclobutane-1-carbonyl)piperidin-4-yl)-1H-pyrazol-4-yl)ethyl)-2-oxobenzo[cd]indol-1(2H)-yl)piperidine-2,6-dione: To the stirred solution of 6-[1-[1-[1-(1-methylcyclobutanecarbonyl)-4-piperidyl]pyrazol-4-yl]ethyl]-1H-benzo[cd]indol-2-one 3a (145.0 mg, 327.65 umol) in THF (6.0 mL) was added Sodium hydride (in oil dispersion) 60% dispersion in mineral oil (125.54 mg, 3.28 mmol, 60% purity) in cold condition and the reaction mixture was stirred at room temperature for 10 minutes followed by the addition of 3-bromopiperidine-2,6-dione 4 (314.56 mg, 1.64 mmol) portion wise. It was then stirred at room temperature for 10 minutes and heated at 70° C. for 30 minutes. TLC was checked which showed formation of the desired spot. The reaction mixture was diluted with ethyl acetate, washed with cold water and the organic fraction was separated. It was then dried over anhydrous sodium sulphate and evaporated under reduced pressure to obtain the crude which was purified by preparative TLC plate method eluting the plate in 55% ethyl acetate-DCM to afford 3-[6-[1-[1-[1-(1-methylcyclobutanecarbonyl)-4-piperidyl]pyrazol-4-yl]ethyl]-2-oxo-benzo[cd]indol-1-yl]piperidine-2,6-dione Compound 148 (70.0 mg, 125.90 umol, 38.43% yield, 99.58% purity) as yellow solid. $^1$H NMR (400 MHz, DMSO-d6): 11.11 (s, 1H), 8.40 (d, J=8.2 Hz, 1H), 8.08 (d, J=7.0 Hz, 1H), 7.81 (t, J=7.54 Hz, 1H), 7.64-7.63 (m, 1H), 7.35-7.29 (m, 2H), 7.07 (d, J=7.4 Hz, 1H), 5.44-5.42 (m, 1H), 4.78-4.76 (m, 1H), 4.40-4.29 (m, 2H), 3.59-3.58 (m, 1H), 3.06-3.01 (m, 1H), 2.98-2.91 (m, 1H), 2.78-2.62 (m, 3H), 2.41-2.32 (m, 3H), 2.08-2.07 (m, 1H), 1.97-1.85 (m, 3H), 1.80-1.78 (m, 3H), 1.65-1.63 (m, 4H), 1.34 (s, 3H); LC MS: ES+ 554.5.

Step 2b: Synthesis of 3-(6-(1-(1-(1-(1-methylcyclobutane-1-carbonyl)piperidin-4-yl)-1H-pyrazol-4-yl)ethyl)-2-oxobenzo[cd]indol-1(2H)-yl)piperidine-2,6-dione: To the stirred solution of 6-[1-[1-[1-(1-methylcyclobutanecarbonyl)-4-piperidyl]pyrazol-4-yl]ethyl]-1H-benzo[cd]indol-2-one 3b (115.0 mg, 259.86 umol) in THF (5 mL) was added Sodium hydride (in oil dispersion) 60% dispersion in mineral oil (99.57 mg, 2.60 mmol, 60% purity) in cold condition and the reaction mixture was stirred at room temperature for 10 minutes followed by the addition of 3-bromopiperidine-2,6-dione 4 (249.48 mg, 1.30 mmol) portion wise. It was then stirred at room temperature for 10 minutes and heated at 70° C. for 30 minutes. TLC was checked which showed formation of the desired spot. The reaction mixture was diluted with ethyl acetate, washed with cold water and the organic fraction was separated. It was then dried over anhydrous sodium sulphate and evaporated under reduced pressure to obtain the crude which was purified by preparative TLC plate method eluting the plate in 55% ethyl acetate-DCM to afford 3-[6-[1-[1-[1-(1-methylcyclobutanecarbonyl)-4-piperidyl]pyrazol-4-yl]ethyl]-2-oxo-benzo[cd]indol-1-yl]piperidine-2,6-dione Compound 149 (45.0 mg, 81.28 umol, 31.28% yield, 100% purity) as yellow solid. $^1$H NMR (400 MHz, DMSO-d6): 11.10 (s, 1H), 8.40 (d, J=8.16 Hz, 1H), 8.08 (d, J=6.72 Hz, 1H), 7.81 (t, J=7.38 Hz, 1H), 7.64-7.63 (m, 1H), 7.35-7.29 (m, 2H), 7.07 (d, J=7.2 Hz, 1H), 5.44-5.42 (m, 1H), 4.78-4.76 (m, 1H), 4.40-4.29 (m, 2H), 3.59-3.58 (m, 1H), 3.06-3.01 (m, 1H), 2.98-2.91 (m, 1H), 2.78-2.62 (m, 3H), 2.41-2.32 (m, 3H), 2.08-2.07 (m, 1H), 1.97-1.85 (m, 3H), 1.80-1.78 (m, 3H), 1.65-1.63 (m, 4H), 1.34 (s, 3H); LC MS: ES+ 554.5.

Example 64. Synthesis of 3-(6-(4-((1-(1-methylcyclobutane-1-carbonyl)piperidin-4-yl)methyl)benzyl)-2-oxobenzo[cd]indol-1(2H)-yl)piperidine-2,6-dione (Compound 150)

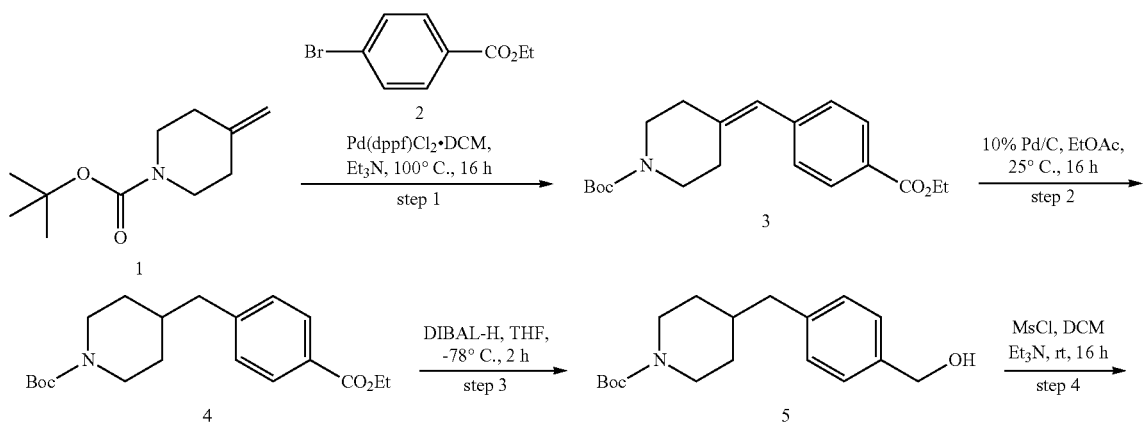

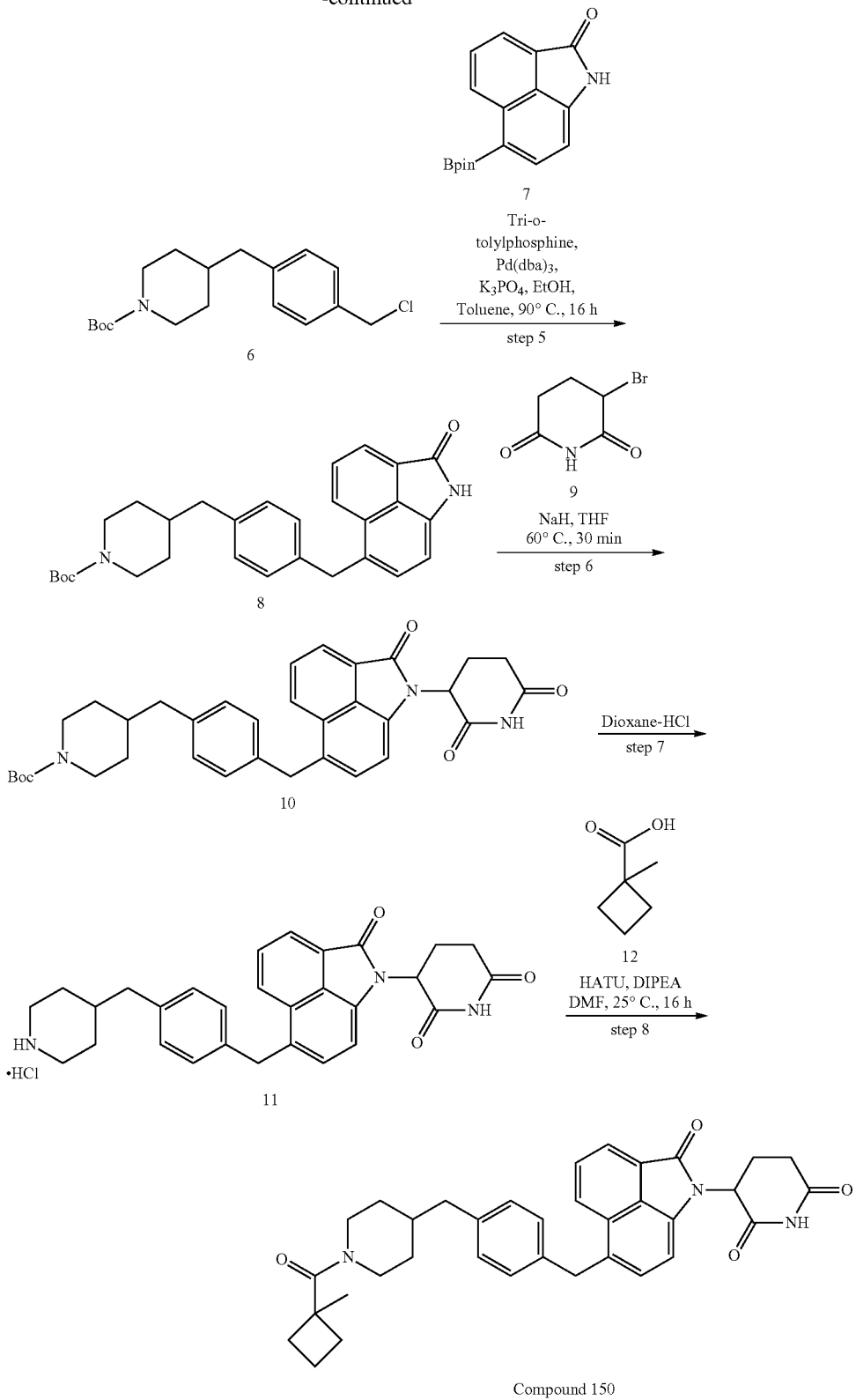

Compound 150

Step 1: Synthesis of tert-butyl 4-(4-(ethoxycarbonyl)benzylidene)piperidine-1-carboxylate: To the stirred solution of ethyl 4-bromobenzoate 2 (7 g, 30.56 mmol, 5.00 mL) in DMF (20 mL) was added tert-butyl 4-methylenepiperidine-1-carboxylate 1 (18.09 g, 91.67 mmol). It was degassed with argon for 10 minutes. Triethylamine (15.46 g, 152.79 mmol, 21.30 mL) and cyclopentyl (diphenyl) phosphane; dichloromethane; dichloropalladium; iron (2.50 g, 3.06 mmol)

were added to the reaction mixture. It was heated at 100° C. for 16 hours. It was cooled to RT, filtered through celite and washed with ethyl acetate. The organic part was washed with water, brine dried over sodium sulfate and concentrated under reduced pressure. It was purified by combiflash eluting at 10% ethyl acetate in hexane to afford tert-butyl 4-[(4-ethoxycarbonylphenyl)methylene]piperidine-1-carboxylate 3 (8.2 g, 22.84 mmol, 74.73% yield, 96.2% purity) as colourless gum. LC MS: ES+ 346.2.

Step 2: Synthesis of tert-butyl 4-(4-(ethoxycarbonyl)benzyl)piperidine-1-carboxylate: tert-butyl 4-[(4-ethoxycarbonylphenyl)methylene]piperidine-1-carboxylate 3 (8.1 g, 23.45 mmol, 6.09 mL) was taken in Ethyl acetate (75 mL). It was degassed with argon for 10 minutes. Palladium on carbon 10% (2.50 g, 2.34 mmol, 0.1 purity) was added to the reaction mixture. It was stirred at RT for 16 hours. It was filtered through celite, concentrated under reduced pressure to afford tert-butyl 4-[(4-ethoxycarbonylphenyl)methyl]piperidine-1-carboxylate 4 (8 g, 22.22 mmol, 94.78% yield, 96.52% purity) as colourless gum. LC MS: ES+ 348.4.

Step 3: Synthesis of tert-butyl 4-(4-(hydroxymethyl)benzyl)piperidine-1-carboxylate: To a stirred solution of tert-butyl 4-[(4-ethoxycarbonylphenyl)methyl]piperidine-1-carboxylate 4 (7.9 g, 22.74 mmol) in THF (100 mL) was added Diisobutylaluminum hydride, 1M solution in hexane (64.67 g, 113.69 mmol, 92.26 mL, 0.25 purity) at −78° C. drop wise. It was stirred at −78° C. for 2 h. It was quenched with sodium potassium tartrate solution, extracted with ethyl acetate, washed with brine, dried over sodium sulfate and concentrated under reduced pressure. It was purified by combiflash eluting at 15% ethyl acetate in hexane to afford tert-butyl 4-[[4-(hydroxymethyl)phenyl]methyl]piperidine-1-carboxylate 5 (4.5 g, 13.26 mmol, 58.32% yield, 90% purity) as colourless gum. LC MS: ES+ 306.2.

Step 4: Synthesis of tert-butyl 4-(4-(chloromethyl)benzyl) piperidine-1-carboxylate: To a stirred solution of tert-butyl 4-[[4-(hydroxymethyl)phenyl]methyl]piperidine-1-carboxylate 5 (4.4 g, 14.41 mmol) in DCM (40 mL) was added Triethylamine (8.75 g, 86.44 mmol, 12.05 mL) drop wise at 0° C. Thionyl Chloride (5.14 g, 43.22 mmol) was added to the reaction mixture very slowly and stirred at RT for 16 hours. It was diluted with ethyl acetate, washed with water, brine, dried over sodium sulfate and concentrated under reduced pressure. It was purified by combiflash eluting at 15% ethyl acetate in hexane to afford tert-butyl 4-[[4-(chloromethyl)phenyl]methyl]piperidine-1-carboxylate 6 (3.9 g, 11.44 mmol, 79.41% yield, 95% purity) as off white solid. $^1$H NMR (400 MHz, DMSO-d6): δ 7.33 (d, J=7.8 Hz, 2H), 7.17 (d, J=7.76 Hz, 2H), 4.72 (s, 2H), 3.90-3.87 (m, 2H), 2.71-2.63 (m, 2H), 1.65-1.63 (m, 1H), 1.53-1.50 (m, 2H), 1.37 (s, 9H), 1.04-0.92 (m, 2H).

Step 5: Synthesis of tert-butyl 4-(4-((2-oxo-1,2-dihydrobenzo[cd]indol-6-yl)methyl)benzyl)piperidine-1-carboxylate: To the stirred solution of tert-butyl 4-[[4-(chloromethyl)phenyl]methyl]piperidine-1-carboxylate 6 (780 mg, 2.41 mmol) and 6-(4,4,5,5-tetramethyl-1,3,2-dioxaborolan-2-yl)-1H-benzo[cd]indol-2-one 7 (1.07 g, 3.61 mmol) in a sealed tube in Ethanol (6 mL) and Toluene (12 mL) were added tripotassium; phosphate (1.28 g, 6.02 mmol). It was degassed with argon for 10 minutes. tris-o-tolylphosphane (146.61 mg, 481.69 umol) and (1E,4E)-1,5-diphenylpenta-1,4-dien-3-one; palladium (220.55 mg, 240.85 umol) were added to the reaction mixture. It was heated at 90° C. for 16 hours. It was cooled to RT, filtered through celite, concentrated under reduced pressure. It was purified by combiflash eluting at 30% ethyl acetate in hexane to afford tert-butyl 4-[[4-[(2-oxo-1H-benzo[cd]indol-6-yl)methyl]phenyl]methyl]piperidine-1-carboxylate 8 (680 mg, 1.34 mmol, 55.65% yield, 90% purity) as yellow solid. LC MS: ES+ 457.3.

Step 6: Synthesis of tert-butyl 4-(4-((1-(2,6-dioxopiperidin-3-yl)-2-oxo-1,2-dihydrobenzo[cd]indol-6-yl)methyl) benzyl)piperidine-1-carboxylate: To a stirred solution of tert-butyl 4-[[4-[(2-oxo-1H-benzo[cd]indol-6-yl)methyl] phenyl]methyl]piperidine-1-carboxylate 8 (680 mg, 1.49 mmol) in THF (10 mL) was added Sodium hydride (in oil dispersion)60% dispersion in mineral oil (570.67 mg, 14.89 mmol, 0.6 purity) portion wise at 0° C. It was stirred at RT for 10 minutes. tert-butyl 4-[[4-[(2-oxo-1H-benzo[cd]indol-6-yl)methyl]phenyl]methyl]piperidine-1-carboxylate 9 (680 mg, 1.49 mmol) was added to the reaction mixture at RT portion wise. It was heated at 70° C. for 1 hour. It was cooled to RT, diluted with ethyl acetate, poured to ice cold water, separated organic part, washed with water, brine and dried over sodium sulfate. It was evaporated under reduced pressure. It was purified by preparative TLC (20% ethyl acetate in DCM) to afford tert-butyl 4-[[4-[[1-(2,6-dioxo-3-piperidyl)-2-oxo-benzo[cd]indol-6-yl]methyl]phenyl]methyl] piperidine-1-carboxylate 10 (690 mg, 1.17 mmol, 78.82% yield, 96.58% purity) as yellow solid. LC MS: ES+ 568.6.

Step 7: Synthesis of 3-(2-oxo-6-(4-(piperidin-4-ylmethyl) benzyl)benzo[cd]indol-1(2H)-yl)piperidine-2,6-dione hydrochloride: To a stirred solution of tert-butyl 4-[[4-[[1-(2,6-dioxo-3-piperidyl)-2-oxo-benzo[cd]indol-6-yl]methyl] phenyl]methyl]piperidine-1-carboxylate 10 (685 mg, 1.21 mmol) in Dioxane (5 mL) was added 4M Dioxane-HCl (1.21 mmol, 10 mL) at 0° C. It was stirred at RT for 3 hours. It was concentrated under reduced pressure to afford 3-[2-oxo-6-[[4-(4-piperidylmethyl) phenyl]methyl]benzo[cd]indol-1-yl]piperidine-2,6-dione, hydrochloride 11 (650 mg, 1.01 mmol, 84.06% yield, 90.76% purity) as yellow solid. LC MS: ES+ 468.1.

Step 8: Synthesis of 3-(6-(4-((1-(1-methylcyclobutane-1-carbonyl)piperidin-4-yl)methyl)benzyl)-2-oxobenzo[cd]indol-1(2H)-yl)piperidine-2,6-dione: To a stirred solution of 3-[6-[[4-[(1-chloro-4-piperidyl)methyl]phenyl]methyl]-2-oxo-benzo[cd]indol-1-yl]piperidine-2,6-dione,hydrochloride 11 (100 mg, 198.41 umol) in DMF (5 mL) was added DIPEA (128.21 mg, 992.03 umol, 172.79 uL) at 0° C. It was stirred at RT for 10 minutes. 1-methylcyclobutanecarboxylic acid 12 (22.65 mg, 198.41 umol) and followed by HATU (90.53 mg, 238.09 umol) were added to the reaction mixture. It was stirred at RT for 16 h. It was diluted with ethyl acetate, washed with saturated bicarbonate solution, brine and dried over sodium sulfate. It was purified combiflash eluting at 20% ethyl acetate in dichloromethane to afford 3-[6-[[4-[[1-(1-methylcyclobutanecarbonyl)-4-piperidyl]methyl]phenyl] methyl]-2-oxo-benzo[cd]indol-1-yl]piperidine-2,6-dione Compound 150 (40.0 mg, 68.61 umol, 34.58% yield, 96.68% purity) as yellow solid. $^1$H NMR (400 MHz, DMSO-d6) δ 11.12 (s, 1H), 8.32 (d, J=8.2 Hz 1H), 8.07 (d, J=6.92 Hz 1H), 7.80 (t, J=7.6 Hz, 1H), 7.39 (d, J=7.24 Hz, 1H), 7.19 (d, J=7.84 Hz, 2H), 7.10-7.04 (m, 3H), 5.45-5.43 (m, 1H), 4.35 (s, 2H), 4.35-4.21 (m, 1H), 3.5-3.4 (m, 1H), 2.94-2.30 (m, 1H), 2.84-2.70 (m, 2H), 2.70-2.62 (m, 1H), 2.44-2.41 (m, 2H), 2.37-2.39 (m, 2H), 2.10-2.07 (m 1H), 1.88-1.86 (m, 1H), 1.38-1.52 (m, 6H), 1.28 (s, 3H), 0.98-0.92 (m, 3H); LC MS: ES+ 564.2.

Example 65. Synthesis of 4-(4-(4-((1-(2,6-dioxopiperidin-3-yl)-2-oxo-1,2-dihydrobenzo[cd]indol-6-yl)methyl)benzyl)piperidin-1-yl)-3-fluorobenzonitrile (Compound 151)

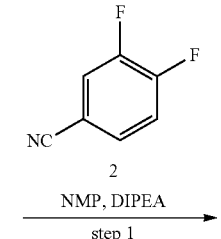

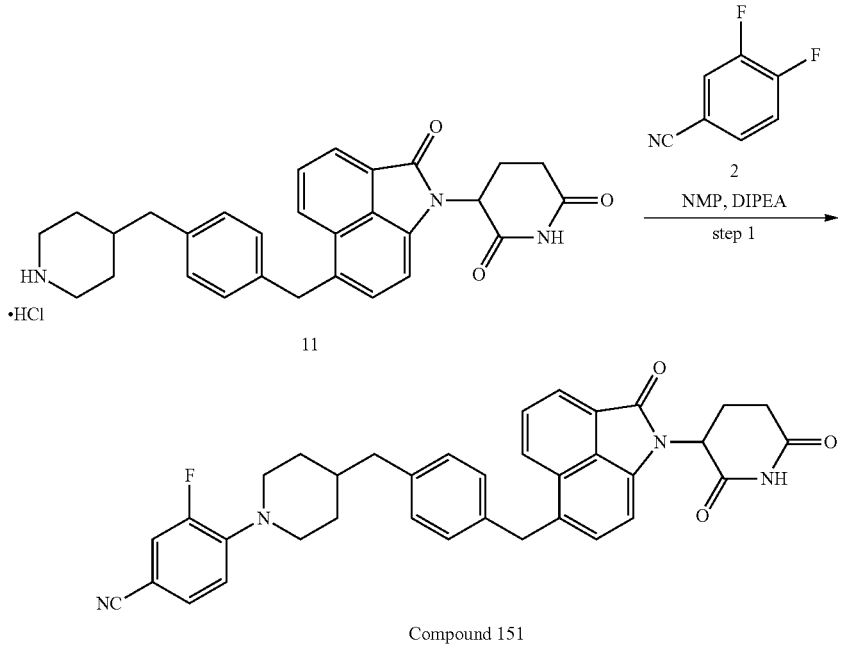

Compound 151

Step 1: Synthesis of 4-(4-(4-((1-(2,6-dioxopiperidin-3-yl)-2-oxo-1,2-dihydrobenzo[cd]indol-6-yl)methyl)benzyl) piperidin-1-yl)-3-fluorobenzonitrile: To a stirred solution of 3-[2-oxo-6-[[4-(4-piperidylmethyl)phenyl]methyl]benzo[cd]indol-1-yl]piperidine-2,6-dione; hydrochloride 1 (150 mg, 297.61 umol) in 1-methylpyrrolidin-2-one (1.55 g, 15.59 mmol, 1.5 mL), N-ethyl-N-isopropyl-propan-2-amine (230.78 mg, 1.79 mmol, 311.03 uL) was added to it under inert atmosphere in a seal tube. 3,4-difluorobenzonitrile 2 (49.68 mg, 357.13 umol) was added to the reaction mixture and the combined reaction mixture was placed on a preheated oil bath (70° C.) and reaction was continued at the same temperature for 16 hours. The reaction progression was monitored through TLC. After completion of the reaction ethyl acetate was added to the reaction mixture and the organic layer was washed with water and saturated bicarbonate solution. The ethyl acetate layer was dried over sodium sulfate and concentrated under reduced pressure. the crude product was purified through flash chromatography using 2% methanol DCM to afford 4-[4-[[4-[[1-(2,6-dioxo-3-piperidyl)-2-oxo-benzo[cd]indol-6-yl]methyl]phenyl]methyl]-1-piperidyl]-3-fluoro-benzonitrile Compound 151 (40.0 mg, 67.50 umol, 22.68% yield, 99% purity) as yellow solid. $^1$H NMR (400 MHz, DMSO-d6) δ 11.11 (s, 1H), 8.33 (d, J=8.28 Hz, 1H), 8.07 (d, J=6.96 Hz, 1H), 7.80 (t, J=7.64 Hz, 1H), 7.63 (d, J=6.74 Hz, 1H), 7.51 (d, J=8.32 Hz, 1H), 7.40 (d, J=7.32 Hz, 1H), 7.20 (d, J=7.8 Hz, 2H), 7.11-7.04 (m, 4H), 5.44 (dd, J=12.76, 5.0 Hz, 1H), 4.36 (s, 2H), 3.51-3.48 (m, 2H), 2.30-2.92 (m, 1H), 2.77-2.62 (m, 4H), 2.50-2.41 (m, 2H), 2.10-2.07 (m, 1H), 1.62-1.59 (m, 3H), 1.27-1.25 (m, 2H); LC MS: ES+ 587.2.

Example 66. Synthesis of 3-(6-(4-((1-benzylpiperidin-4-yl)methyl)benzyl)-2-oxobenzo[cd]indol-1(2H)-yl)piperidine-2,6-dione (Compound 152)

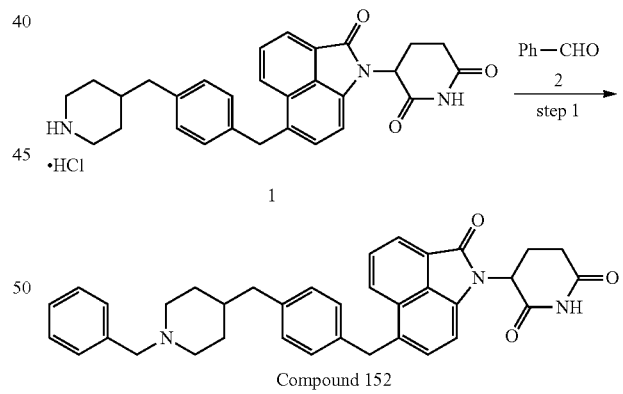

Compound 152

Step 1: Synthesis of 3-(6-(4-((1-benzylpiperidin-4-yl)methyl)benzyl)-2-oxobenzo[cd]indol-1(2H)-yl)piperidine-2,6-dione: To a stirred solution of 3-[2-oxo-6-[[4-(4-piperidylmethyl)phenyl]methyl]benzo[cd]indol-1-yl]piperidine-2,6-dione; hydrochloride 1 (150 mg, 297.61 umol) in THF (7 mL), N-ethyl-N-isopropyl-propan-2-amine (38.46 mg, 297.61 umol, 51.84 uL) was added and the combined reaction mixture was stirred for 5 mins under nitrogen atmosphere at 0° C. in a sealed tube. After that benzaldehyde 2 (31.58 mg, 297.61 umol, 30.37 uL),dibutyltin(2+); dichloride (108.51 mg, 357.13 umol, 79.79 uL), phenylsilane (32.21 mg, 297.61 umol, 36.68 uL) were added to the reaction mixture. The combined reaction mixture was placed in a preheated oil bath (90° C.). The reaction was continued at the same temperature for 16 hours. The reaction progression was monitored through TLC. After completion of the reaction THF part was concentrated under reduced pressure and ethyl acetate was added to the crude reaction mixture. The ethyl acetate layer was washed with water and saturated sodium bicarbonate solution and the organic layer was dried over sodium sulfate. The organic layer was concentrated under reduced pressure and the crude product was purified through flash chromatography using 1.5%-2% methanol DCM to afford 3-[6-[[4-[(1-benzyl-4-piperidyl)methyl]phenyl]methyl]-2-oxo-benzo[cd]indol-1-yl]piperidine-2,6-dione Compound 152 (90.0 mg, 154.09 umol, 51.78% yield, 95.48% purity) as yellow solid. 1H NMR (400 MHz, DMSO-d6) δ 11.11 (s, 1H), 8.31 (d, J=8.24 Hz, 1H), 8.06 (d, J=6.92 Hz, 1H), 7.79 (t, J=7.62 Hz, 1H), 7.38 (d, J=7.32 Hz, 1H), 7.31-7.18 (m, 7H), 7.09 (d, J=7.28 Hz, 1H), 7.03 (d, J=7.80 Hz, 2H), 5.43 (dd, J=12.72, 5.0 Hz, 1H), 4.34 (s, 2H), 3.38 (s, 2H), 2.94-2.91 (m, 1H), 280-2.62 (m, 4H), 2.42-2.40 (m, 2H), 2.09-2.07 (m, 1H), 1.82-1.77 (m, 2H), 1.48-1.41 (m, 3H), 1.17-1.09 (m, 2H); LC MS: ES+ 558.35.

Example 67. Synthesis of 3-(6-(amino(1-(1-(1-methylcyclobutane-1-carbonyl)piperidin-4-yl)-1H-pyrazol-4-yl)methyl)-2-oxobenzo[cd]indol-1(2H)-yl)piperidine-2,6-dione (Compound 153)

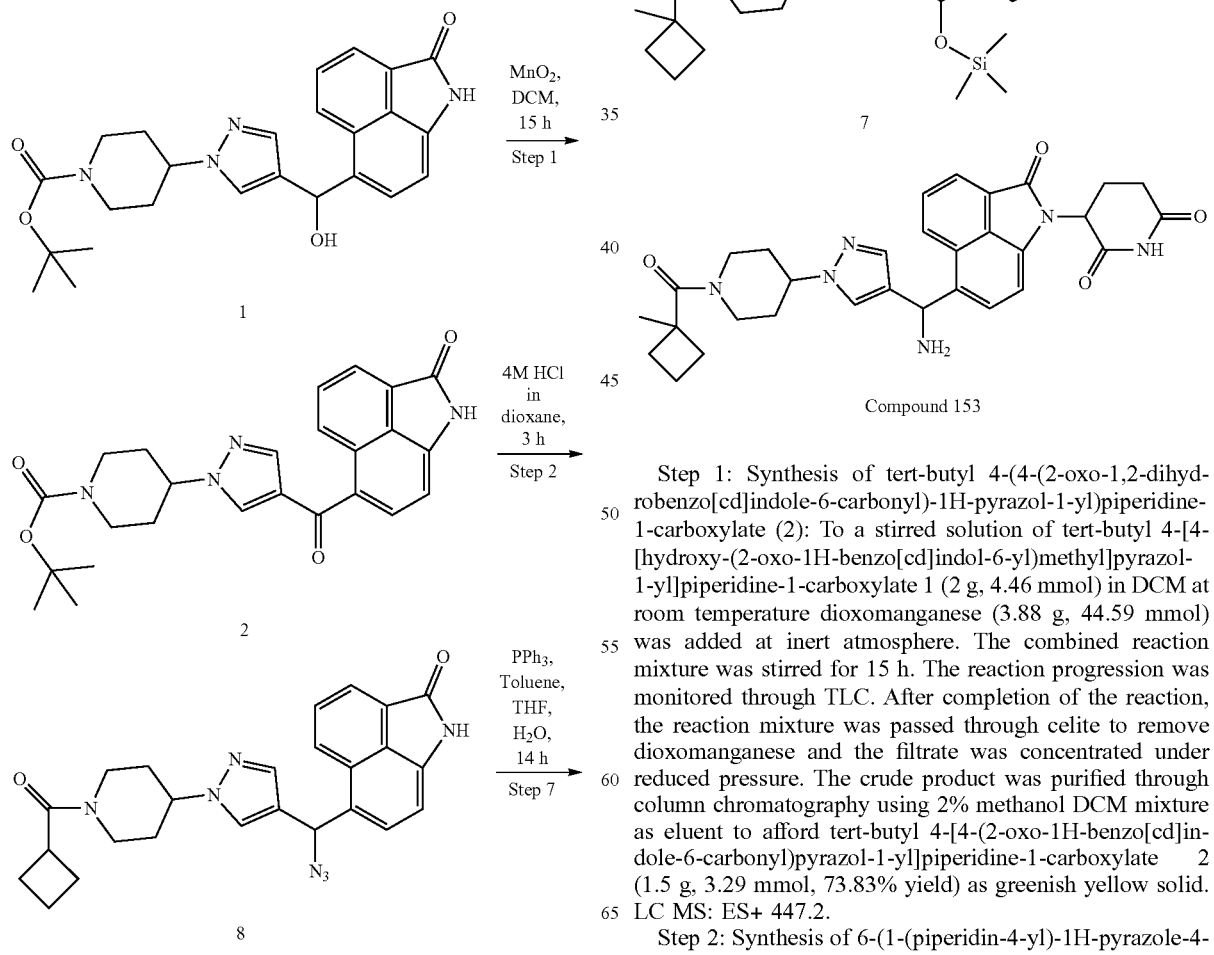

Compound 153

Step 1: Synthesis of tert-butyl 4-(4-(2-oxo-1,2-dihydrobenzo[cd]indole-6-carbonyl)-1H-pyrazol-1-yl)piperidine-1-carboxylate (2): To a stirred solution of tert-butyl 4-[4-[hydroxy-(2-oxo-1H-benzo[cd]indol-6-yl)methyl]pyrazol-1-yl]piperidine-1-carboxylate 1 (2 g, 4.46 mmol) in DCM at room temperature dioxomanganese (3.88 g, 44.59 mmol) was added at inert atmosphere. The combined reaction mixture was stirred for 15 h. The reaction progression was monitored through TLC. After completion of the reaction, the reaction mixture was passed through celite to remove dioxomanganese and the filtrate was concentrated under reduced pressure. The crude product was purified through column chromatography using 2% methanol DCM mixture as eluent to afford tert-butyl 4-[4-(2-oxo-1H-benzo[cd]indole-6-carbonyl)pyrazol-1-yl]piperidine-1-carboxylate 2 (1.5 g, 3.29 mmol, 73.83% yield) as greenish yellow solid. LC MS: ES+ 447.2.

Step 2: Synthesis of 6-(1-(piperidin-4-yl)-1H-pyrazole-4-carbonyl)benzo[cd]indol-2-one; hydrochloride (3): Dioxane (5 mL) was added to tert-butyl 4-[4-(2-oxo-1H-benzo[cd]indol-6-carbonyl)pyrazol-1-yl]piperidine-1-carboxylate 2 (1.5 g, 3.36 mmol) in a single neck 100 mL round bottom flask to make a colloidal suspension. 4 M HCl in Dioxane (10 mL) was added to the suspension and stirred for 3 h at room temperature under inert atmosphere. The reaction progression was monitored through TLC. After completion of the reaction dioxane was evaporated under reduced pressure and the crude compound was washed with diethyl ether to remove the non polar impurities. The combined compound and ether part was kept for some time to allow the complete precipitation process. The supernatant ether part was transferred to another conical flask and the settled pure compound was dried under reduced pressure to afford 6-[1-(4-piperidyl)pyrazole-4-carbonyl]-1H-benzo[cd]indol-2-one; hydrochloride 3 (1.30 g, 3.04 mmol, 90.44% yield) as greenish solid. LC MS: ES+ 347.3.

Step 3: Synthesis of 6-(1-(1-(1-methylcyclobutane-1-carbonyl)piperidin-4-yl)-1H-pyrazole-4-carbonyl)benzo[cd]indol-2-one (5): To a stirred solution of 6-[1-(4-piperidyl)pyrazole-4-carbonyl]-1H-benzo[cd]indol-2-one; hydrochloride 3 (1.2 g, 3.13 mmol) in DMF (10 mL), N-ethyl-N-isopropyl-propan-2-amine (1.62 g, 12.54 mmol, 2.18 mL) was added under nitrogen atmosphere and at 0° C. The combined reaction mixture was stirred for 5 mins at the same temperature. 1-methylcyclobutanecarboxylic acid 4 (393.55 mg, 3.45 mmol) and HATU (1.79 g, 4.70 mmol) were added to the reaction mixture. The combined reaction mixture was stirred for 16 hours at room temperature. The reaction progression was monitored through TLC. After completion of the reaction ethyl acetate was added to the reaction mixture. The organic layer was washed with cold water and brine solution to remove DMF. The ethyl acetate layer was dried over sodium sulfate, filtered and concentrated under reduced pressure. The crude product was purified through column chromatography using 100-200 mesh silica gel and 3% methanol DCM as eluent to afford 6-[1-[1-(1-methylcyclobutanecarbonyl)-4-piperidyl]pyrazole-4-carbonyl]-1H-benzo[cd]indol-2-one 5 (1 g, 2.21 mmol, 70.66% yield) as yellowish solid. LC MS: ES+ 443.3.

Step 4: Synthesis of 6-(hydroxy(1-(1-(1-methylcyclobutane-1-carbonyl)piperidin-4-yl)-1H-pyrazol-4-yl)methyl)benzo[cd]indol-2-one (6): To a stirred solution of 6-[1-[1-(1-methylcyclobutanecarbonyl)-4-piperidyl]pyrazole-4-carbonyl]-1H-benzo[cd]indol-2-one 5 (1 g, 2.26 mmol) in solvent mixture (Methanol (10 mL) and THF (10 mL)) at 0° C., Sodium borohydride (384.73 mg, 10.17 mmol, 359.56 uL) was added portion wise in the reaction mixture. The reaction mixture was stirred for 16 h at room temperature. The reaction progression was monitored through TLC. After completion of the reaction the solvent mixture was concentrated under reduced pressure. Ethyl acetate was added to the reaction mixture and washed with water. The organic layer was dried over sodium sulfate, filtered and concentrated under reduced pressure. The crude product was purified through column chromatography using 3% methanol DCM as eluent and 100-200 mesh silica gel as stationary phase to afford 6-[hydroxy-[1-[1-(1-methylcyclobutanecarbonyl)-4-piperidyl]pyrazol-4-yl]methyl]-1H-benzo[cd]indol-2-one 6 (1 g, 2.20 mmol, 97.56% yield) as yellow solid. LCMS: ES+[M-OH]: 427.3.

Step 5: Synthesis of 6-((1-(1-(1-methylcyclobutane-1-carbonyl)piperidin-4-yl)-1H-pyrazol-4-yl)(trimethylsilyl)oxy)methyl)benzo[cd]indol-2-one (7): To a stirred solution of 6-[hydroxy-[1-[1-(1-methylcyclobutanecarbonyl)-4-piperidyl]pyrazol-4-yl]methyl]-1H-benzo[cd]indol-2-one 6 (1 g, 2.25 mmol) in DMF (7 mL), Imidazole (459.44 mg, 6.75 mmol) was added at inert condition. The reaction mixture was stirred at room temperature for 5 mins. Chlorotrimethylsilane, 98+% (488.80 mg, 4.50 mmol, 571.03 uL) was added drop wise in the reaction mixture at room temperature. The reaction mixture was stirred at the same temperature for 1 h. Reaction progression was monitored through TLC. After completion of the reaction ethyl acetate was added to the reaction mixture. The combined organic layer was washed with cold water and brine to remove DMF. the ethyl acetate part was dried over sodium sulfate and concentrated under reduced pressure. The crude product was purified through column chromatography using 100-200 mesh silica gel and 2% methanol DCM mixture as eluent to afford 6-[[1-[1-(1-methylcyclobutanecarbonyl)-4-piperidyl]pyrazol-4-yl]-trimethylsilyloxy-methyl]-1H-benzo[cd]indol-2-one 7 (705 mg, 1.34 mmol, 59.44% yield) as yellow solid. LC MS: ES+[M-OTMS]: 427.4.

Step 6: Synthesis of 6-[azido-[1-[1-(1-methylcyclobutanecarbonyl)-4-piperidyl]pyrazol-4-yl]methyl]-1H-benzo[cd]indol-2-one (8): To a stirred solution of 6-[[1-[1-(1-methylcyclobutanecarbonyl)-4-piperidyl]pyrazol-4-yl]-trimethylsilyloxy-methyl]-1H-benzo[cd]indol-2-one 7 (700 mg, 1.35 mmol) in DCM (7 mL), Trimethylsilyl azide, 94% (171.69 mg, 1.49 mmol, 196.89 uL) was added under argon atmosphere. After that, trichloroiron (10.99 mg, 67.74 umol) was added to the reaction mixture. The combined reaction mixture was stirred for 2 h. The reaction progression was monitored through TLC. After completion of the reaction ethyl acetate was added to the reaction mixture. The organic layer was washed with water. The organic layer was dried over sodium sulfate and concentrated under reduced pressure to afford 6-[azido-[1-[1-(1-methylcyclobutanecarbonyl)-4-piperidyl]pyrazol-4-yl]methyl]-1H-benzo[cd]indol-2-one 8 (600 mg, 1.25 mmol, 92.44% yield, 98% purity) as yellow solid. LCMS: ES+[M-N$_3$]: 427.4.

Step 7: Synthesis of 6-(amino(1-(1-(1-methylcyclobutane-1-carbonyl)piperidin-4-yl)-1H-pyrazol-4-yl)methyl)benzo[cd]indol-2-one (9): 6-[azido-[1-[1-(1-methylcyclobutanecarbonyl)-4-piperidyl]pyrazol-4-yl]methyl]-1H-benzo[cd]indol-2-one 8 (450 mg, 958.39 umol) and Triphenylphosphine (377.06 mg, 1.44 mmol) was dissolved intoluene, THF mixture (1:1) and Water (0.5 mL) was added to it. The combine reaction mixture was placed on a pre-heated oil bath (80° C.) for 14 h. After completion of the reaction the crude reaction mixture was concentrated under vacuum and ethyl acetate was added to it. The ethyl acetate layer was washed with water and the organic layer was dried over sodium sulfate and filtered. The organic layer was concentrated under reduced pressure. The crude product was washed with 20% ethyl acetate hexane to eliminate triphenylphosphine oxide and other impurities to get the desired 6-[amino-[1-[1-(1-methylcyclobutanecarbonyl)-4-piperidyl]pyrazol-4-yl]methyl]-1H-benzo[cd]indol-2-one 9 (350 mg, 773.32 umol, 80.69%) as yellow solid. LCMS: ES+[M-NH$_2$]: 427.5.

Step 8: Synthesis of 3-(6-(amino(1-(1-(1-methylcyclobutane-1-carbonyl)piperidin-4-yl)-1H-pyrazol-4-yl)methyl)-2-oxobenzo[cd]indol-1(2H)-yl)piperidine-2,6-dione: To a stirred solution of 6-[amino-[1-[1-(1-methylcyclobutanecarbonyl)-4-piperidyl]pyrazol-4-yl]methyl]-1H-benzo[cd]indol-2-one 9 (100 mg, 225.46 umol) in THF (6 mL) Sodium hydride (in oil dispersion) 60% dispersion in mineral oil (86.39 mg, 2.25 mmol, 60% purity) was added at 0° C. under inert atmosphere the reaction mixture was stirred for 10 mins at 0° C. Further the reaction mixture was stirred for 10 mins at room temperature. Portion wise 3-bromopiperidine-2,6-dione 10 (216.45 mg, 1.13 mmol) was added to the reaction mixture and after addition the reaction was stirred for another 10 mins at room temperature. The combined reaction mixture was placed in a preheated oil bath (80° C.) and reflux for 1 h. After 1 h ethyl acetate was added to the reaction mixture and the combined reaction mixture was washed with water. The organic layer was dried over sodium sulfate and concentrated under reduced pressure. The crude product was purified through reverse phase HPLC to afford 3-[6-[amino-[1-[1-(1-methylcyclobutanecarbonyl)-4-piperidyl]pyrazol-4-yl]methyl]-2-oxo-benzo[cd]indol-1-yl]piperidine-2,6-dione Compound 153 (15.0 mg, 26.25 umol, 11.64% yield) as yellow solid. $^1$H NMR (400 MHz, DMSO-d6): δ 11.08 (s, 1H), 8.46-8.42 (m, 1H), 8.02 (d, J=6.6 Hz, 1H), 7.75 (t, J=7.8 Hz, 1H), 7.62-7.56 (m, 2H), 7.31 (s, 1H), 7.08 (d, J=7.12, 1H), 5.68 (s, 1H), 5.42-5.40 (m, 1H), 4.35 (brs, 1H), 4.27-4.26 (m, 1H), 3.58-3.57 (m, 1H), 3.02-2.89 (m, 2H), 2.75-2.60 (m, 2H), 2.38-2.29 (m, 2H), 2.06-2.04 (m, 1H), 1.91-1.86 (m, 4H), 1.75-1.59 (m, 5H), 1.31 (s, 3H), LC MS: ES– [M–H]: 553.2.

Example 68. Synthesis of tert-butyl 4-(4-(amino(1-(2,6-dioxopiperidin-3-yl)-2-oxo-1,2-dihydrobenzo[cd]indol-6-yl)methyl)-1H-pyrazol-1-yl)piperidine-1-carboxylate (Compound 154)

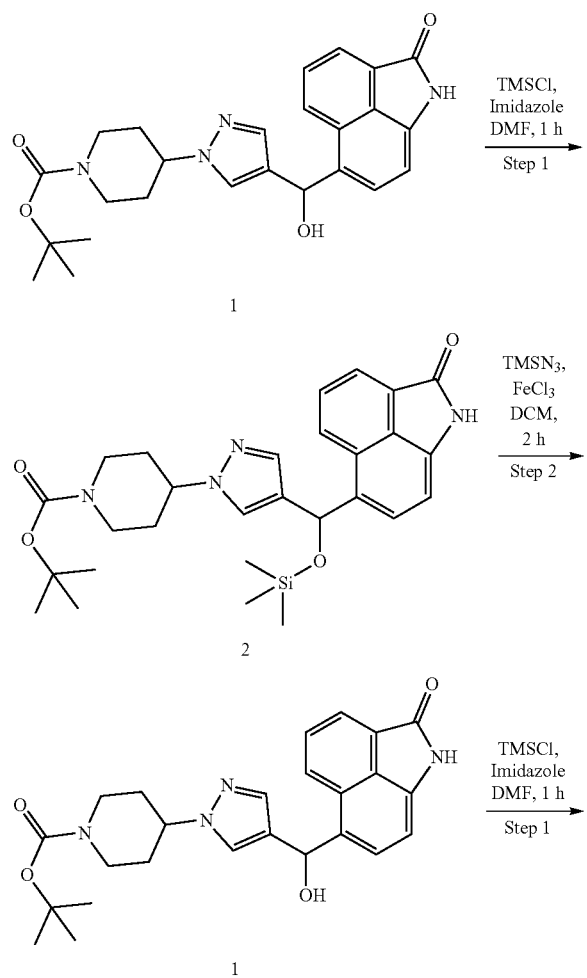

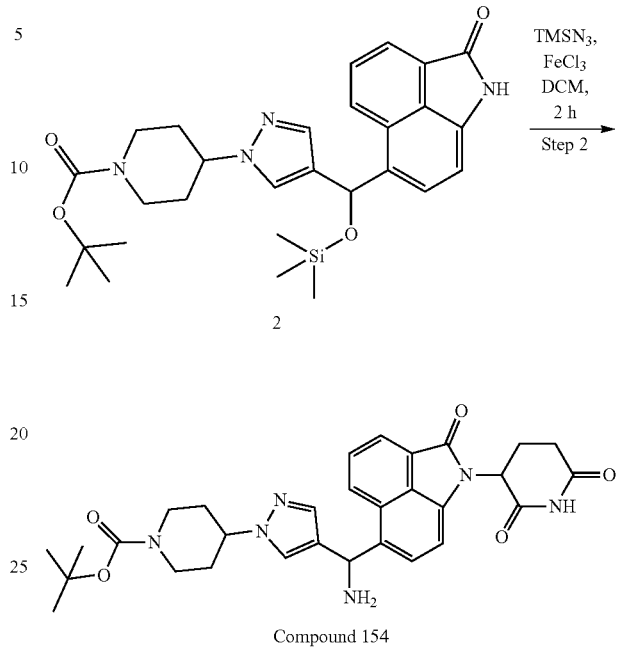

Step 1: Synthesis of tert-butyl 4-(4-((2-oxo-1,2-dihydrobenzo[cd]indol-6-yl)((trimethylsilyl)oxy)methyl)-1H-pyrazol-1-yl)piperidine-1-carboxylate (2): To a stirred solution tert-butyl 4-[4-[hydroxy-(2-oxo-1H-benzo[cd]indol-6-yl)methyl]pyrazol-1-yl]piperidine-1-carboxylate 1 (1.8 g, 4.01 mmol) in DMF, Imidazole (819.64 mg, 12.04 mmol) was added. The combined reaction mixture was stirred for 5 minutes under nitrogen atmosphere at room temperature. Chlorotrimethylsilane, 98+% (872.02 mg, 8.03 mmol, 1.02 mL) was added drop wise to the reaction mixture at room temperature. After addition, the combined reaction mixture was stirred for 1 h. The reaction progression was monitored through TLC. The reaction was quenched with water and ethyl acetate. The organic layer was washed with ice cold water followed by brine solution to remove DMF. The organic layer was dried over sodium sulfate and filtered. The organic layer was concentrated under reduced pressure. The crude product was purified with 40%6-50% ethyl acetate and hexane to afford tert-butyl 4-[4-[(2-oxo-1H-benzo[cd]indol-6-yl)-trimethylsilyloxy-methyl]pyrazol-1-yl]piperidine-1-carboxylate 2 (1 g, 1.82 mmol, 45.46% yield) as yellow solid. LCMS: ES+[M-OTMS]: 431.5.

Step 2: Synthesis of tert-butyl 4-(4-(azido(2-oxo-1,2-dihydrobenzo[cd]indol-6-yl)methyl)-1H-pyrazol-1-yl)piperidine-1-carboxylate (3): tert-butyl-4-[4-[(2-oxo-1H-benzo[cd]indol-6-yl)-trimethylsilyloxy-methyl]pyrazol-1-yl]piperidine-1 carboxylate 2 (1 g, 1.92 mmol) and Trimethylsilyl azide, 94% (243.39 mg, 2.11 mmol, 279.12 uL) were dissolved in DCM under argon atmosphere. Ferric Chloride (15.58 mg, 96.03 umol) was added to the reaction mixture and stirred for 2 h at room temperature. After completion of the reaction, ethyl acetate was added to the reaction mixture and washed with water. The organic layer was dried over sodium sulfate, filtered and concentrated under reduced pressure. The crude product was purified through column chromatography using 25% ethyl acetate and DCM mixture to afford tert-butyl 4-[4-[azido-(2-oxo-1H-benzo[cd]indol-6-yl)methyl]pyrazol-1-yl]piperidine-1-carboxylate 3 (700 mg, 1.40 mmol, 73.12% yield) as yellow solid. LCMS: ES+[M-OTMS]: 431.3.

Step 3: Synthesis of tert-butyl 4-(4-(amino(2-oxo-1,2-dihydrobenzo[cd]indol-6-yl)methyl)-1H-pyrazol-1-yl)piperidine-1-carboxylate (4): tert-butyl-4-[4-[azido-(2-oxo-1H-benzo[cd]indol-6-yl)methyl]pyrazol-1-yl]piperidine-1-carboxylate 3 (300 mg, 633.55 umol) was dissolved in THF (3 mL) Toluene (3 mL) mixture (1:1) in a two neck 50 mL round bottom flask. Triphenylphosphine (249.26 mg, 950.32 umol) was added to the reaction mixture. After that few drops of Water (0.200 mL) was added to it. The combined reaction mixture was placed on a preheated oil bath (80° C.) with a reflux condenser. The reaction mixture was heated at the same temperature for 12 h. After completion of the reaction the reaction mixture was concentrated under reduced pressure and diluted with ethyl acetate. Ethyl acetate layer was washed with water. The organic layer was dried over sodium sulfate and filtered. The ethyl acetate part was concentrated under reduced pressure to get the crude product. The crude product was washed with 20% ethyl acetate hexane mixture to remove excess triphenylphophine and triphenylphosphine oxide to afford tert-butyl 4-[4-[amino-(2-oxo-1H-benzo[cd]indol-6-yl)methyl]pyrazol-1-yl]piperidine-1-carboxylate 4 (250 mg, 335.17 umol, 52.90% yield) as yellow solid. LC MS: ES+[M-N$_3$]: 431.2.

Step 4: Synthesis of tert-butyl 4-(4-(amino(1-(2,6-dioxopiperidin-3-yl)-2-oxo-1,2-dihydrobenzo[cd]indol-6-yl)methyl)-1H-pyrazol-1-yl)piperidine-1-carboxylate: To a stirred solution of tert-butyl 4-[4-[amino-(2-oxo-1H-benzo[cd]indol-6-yl)methyl]pyrazol-1-yl]piperidine-1-carboxylate 4 (200 mg, 446.90 umol) in THF (6 mL) Sodium hydride (in oil dispersion) 60% dispersion in mineral oil (171.24 mg, 4.47 mmol, 60% purity) was added at 0° C. under inert atmosphere. The reaction mixture was stirred for 10 mins at 0° C. Further the reaction mixture was stirred for 10 mins at room temperature. Portion wise 3-bromopiperidine-2,6-dione 5 (429.05 mg, 2.23 mmol) was added to the reaction mixture and after addition the reaction mixture was stirred for another 10 mins at room temperature. The combined reaction mixture was placed in a preheated oil bath (80° C.) and reflux for 1 h. After 1 h, ethyl acetate was added to the reaction mixture and the combined reaction mixture was washed with water. The organic layer was dried over sodium sulfate and concentrated under reduced pressure. The crude product was purified with reverse phase HPLC to afford tert-butyl 4-[4-[amino-[1-(2,6-dioxo-3-piperidyl)-2-oxo-benzo[cd]indol-6-yl]methyl]pyrazol-1-yl]piperidine-1-carboxylate Compound 154 (22 mg, 38.91 umol, 8.71% yield). $^1$H NMR (400 MHz, DMSO-d6): δ 11.11 (s, 1H), 8.48-8.46 (m, 1H), 8.05 (d, J=6.88 Hz, 1H), 7.78 (t, J=7.56 Hz, 1H), 7.63 (d, J=7.28 Hz, 1H), 7.58 (d, J=4.80 Hz, 1H), 7.32 (s, 1H), 7.10 (d, J=7.16 Hz, 1H), 5.70 (s, 1H), 5.45-5.43 (m, 1H), 4.23-4.20 (m, 1H), 3.96-3.95 (m, 2H), 2.98-2.74 (m, 4H), 2.67-2.63 (m, 1H), 2.09-2.07 (m, 1H), 1.89-1.88 (m, 2H), 1.69-1.66 (m, 2H), 1.39 (s, 9H); LC MS: ES-[M-NH$_2$]: 542.2.

Example 69. Synthesis of 3-[6-[[4-(3,4-dihydro-1H-isoquinolin-2-ylmethyl)phenyl]methyl]-2-oxo-benzo[cd]indol-1-yl]piperidine-2,6-dione (Compound 155)

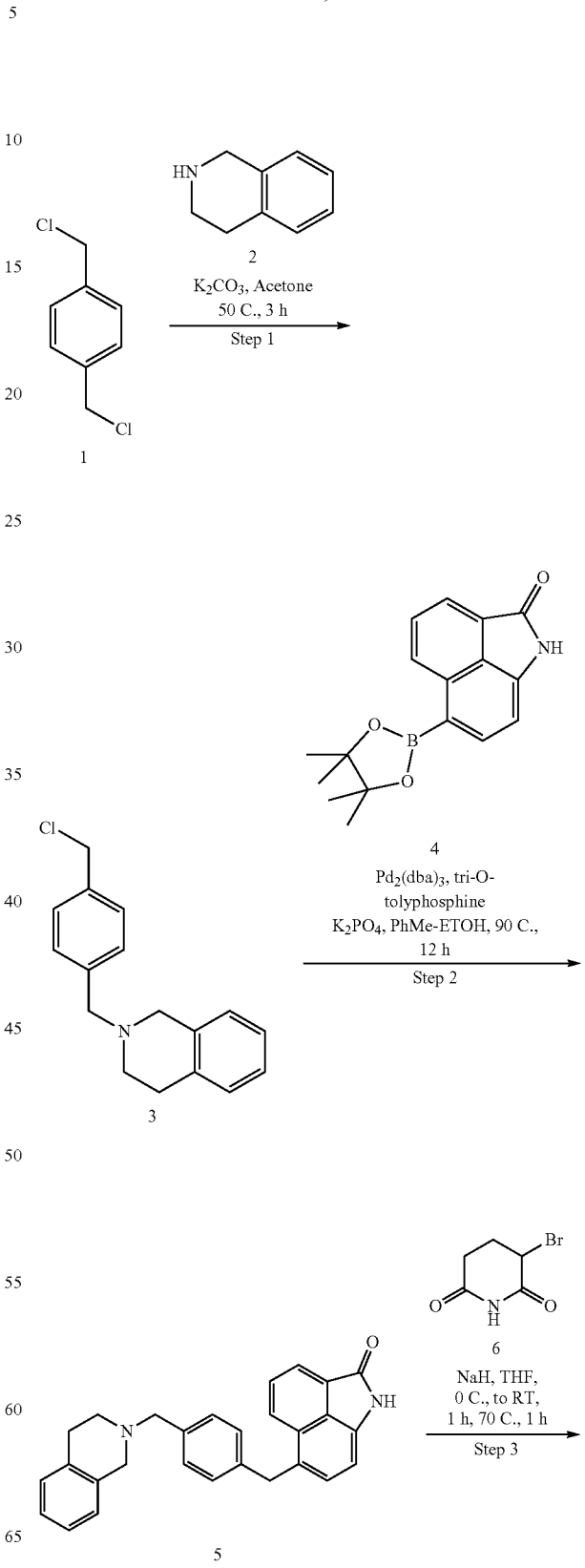

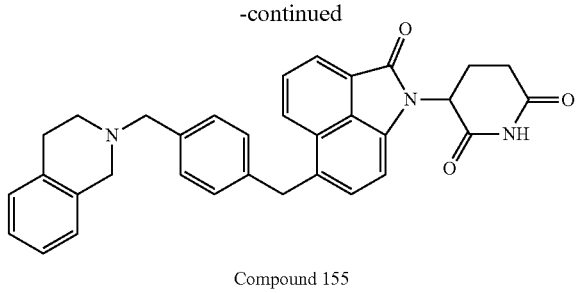

Compound 155

Step 1: Synthesis of 2-[[4-(chloromethyl)phenyl]methyl]-3,4-dihydro-1H-isoquinoline: To the stirred solution of 1,2,3,4-tetrahydroisoquinoline 2 (1 g, 7.51 mmol, 1.00 mL) in Acetone (10 mL) Potassium carbonate, anhydrous, 99% (1.04 g, 7.51 mmol, 453.14 uL) was added and stirred at 50° C. for 20 minutes followed by the addition of 1,4-bis(chloromethyl)benzene 1 (1.31 g, 7.51 mmol, 925.58 uL). Resulting solution was further heated at same temperature for 16 hr. After formation of desired product, as evidenced from LCMS, volatiles were removed and redissolved in ethyl acetate. Organic portion was washed with water/brine and separated, dried over sodium sulfate and concentrated. Crude Residue was purified by column chromatography using 30% EtOAc-Hexane to afford 2-[[4-(chloromethyl)phenyl]methyl]-3,4-dihydro-1H-isoquinoline 3 (750 mg, 2.65 mmol, 35.28% yield, 96% purity) white gum. LC MS: ES+ 272.2.

Step 2: Synthesis of 6-[[4-(3,4-dihydro-1H-isoquinolin-2-ylmethyl)phenyl]methyl]-1H-benzo[cd]indol-2-one: To a stirred solution of 2-[[4-(chloromethyl)phenyl]methyl]-3,4-dihydro-1H-isoquinoline 3 (400 mg, 1.47 mmol) and 6-(4,4,5,5-tetramethyl-1,3,2-dioxaborolan-2-yl)-1H-benzo[cd]indol-2-one 4 (868.75 mg, 2.94 mmol) in ethanol (2.5 mL) and Toluene (5 mL) was added Potassium phosphate tribasic anhydrous (937.23 mg, 4.42 mmol) and the reaction mass was degaussed under Argon atmosphere over 10 minutes. Then Tri-o-Tolyl phosphine (89.59 mg, 294.35 umol) and (1E,4E)-1,5-diphenylpenta-1,4-dien-3-one; palladium (134.77 mg, 147.18 umol) was added to this reaction mass and heated the resultant reaction mixture 90° C. over night. TLC shows consumption of starting material. Then the reaction mixture was filtered through sintered funnel using celite bed and the reaction mixture was diluted with ethyl acetate and washed with water. The organic part was dried over $Na_2SO_4$ and filtered. The reaction mix was evaporated under reduced pressure, the crude was purified by combi-flash to get the pure compound 6-[[4-(3,4-dihydro-1H-isoquinolin-2-ylmethyl)phenyl]methyl]-1H-benzo[cd]indol-2-one 5 (160 mg, 375.77 umol, 25.53% yield, 95% purity) as light yellow solid. LC MS: ES+ 405.4.

Step 3: Synthesis of 3-[6-[[4-(3,4-dihydro-1H-isoquinolin-2-ylmethyl)phenyl]methyl]-2-oxo-benzo[cd]indol-1-yl]piperidine-2,6-dione: To the stirred solution of 6-[[4-(3,4-dihydro-1H-isoquinolin-2-ylmethyl)phenyl]methyl]-1H-benzo[cd]indol-2-one 5 (159.21 mg, 393.59 umol) in THF (3 mL) was added Sodium hydride (in oil dispersion) 60% dispersion in mineral oil (150.81 mg, 3.94 mmol, 60% purity) at cold condition and the reaction mixture was stirred at room temperature for 10 minutes followed by the addition of 3-bromopiperidine-2,6-dione 6 (377.86 mg, 1.97 mmol) portion wise. It was then stirred at room temperature for 10 minutes and heated at 70° C. for 30 minutes. TLC was checked which showed almost complete consumption of the starting material and formation of the desired spot. The reaction mixture was diluted with ethyl acetate, washed with cold water and the organic fraction was separated. It was then dried over anhydrous sodium sulphate and evaporated under reduced pressure to obtain the crude which was washed with ether and pentane to afford 3-[6-[[4-(3,4-dihydro-1H-isoquinolin-2-ylmethyl)phenyl]methyl]-2-oxo-benzo[cd]indol-1-yl]piperidine-2,6-dione Compound 155 (125.0 mg, 234.56 umol, 59.59% yield, 96.75% purity) as yellow solid. $^1$H NMR (400 MHz, DMSO-d6): δ 11.12 (s, 1H), 8.33 (d, J=8.24 Hz, 1H), 8.07 (d, J=6.84 Hz, 1H), 7.80 (t, J=7.54 Hz, 1H), 7.41 (d, J=7.32 Hz, 1H), 7.25 (s, 4H), 7.12-7.07 (m, 4H), 6.98-6.95 (m, 1H), 5.44 (dd, J=12.36, 4.36 Hz, 1H), 4.38 (s, 2H), 3.56 (s, 2H), 3.48 (s, 2H), 2.95-2.90 (m, 1H), 2.78-2.76 (m, 3H), 2.70-2.61 (m, 3H), 2.10-2.07 (m, 1H)LC MS: ES+ 516.5.

Example 70. Synthesis of 3-[6-[[4-(3-oxa-8-azabicyclo[3.2.1]octan-8-ylmethyl)phenyl]methyl]-2-oxo-benzo[cd]indol-1-yl]piperidine-2,6-dione (Compound 156)

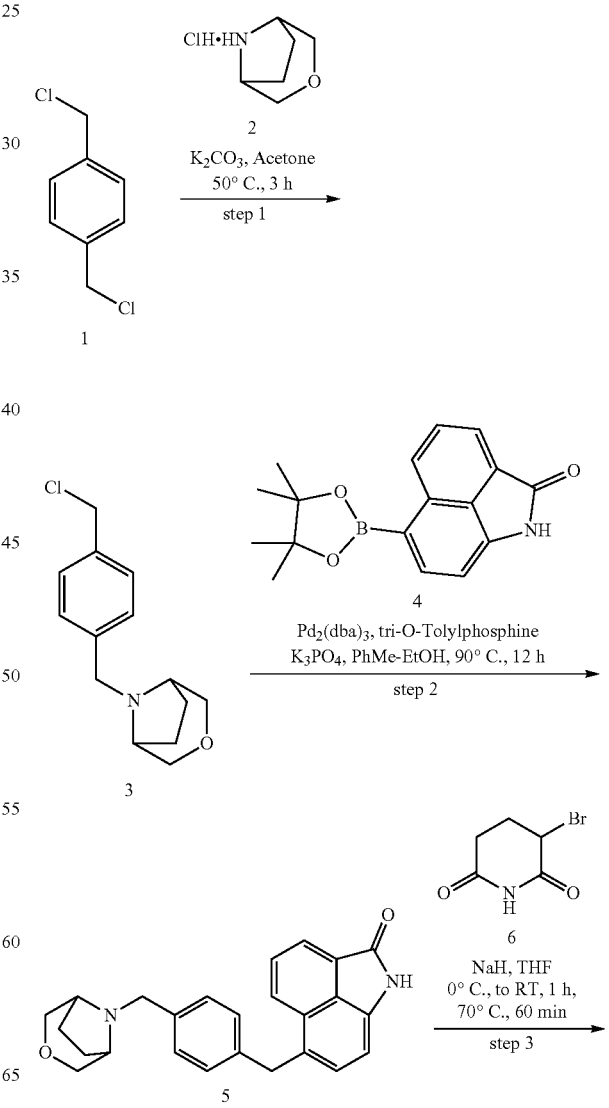

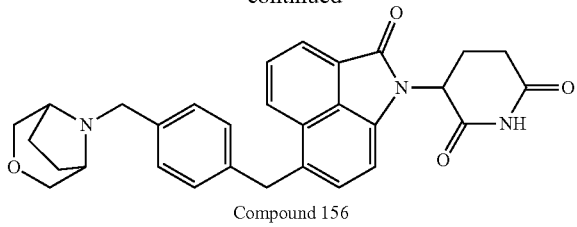

Compound 156

Step 1: Synthesis of 8-[[4-(chloromethyl)phenyl]methyl]-3-oxa-8-azabicyclo[3.2.1]octane: To the stirred solution of 3-oxa-8-azabicyclo[3.2.1]octane; hydrochloride 2 (1.00 g, 6.68 mmol, 1.00 mL) in Acetone (10 mL) added DIPEA (863.82 mg, 6.68 mmol, 1.16 mL) to basified, then Potassium carbonate, anhydrous, 99% (923.75 mg, 6.68 mmol, 403.39 uL) was added and stirred at 50° C. for 20 minutes followed by the addition of 1,4-bis(chloromethyl)benzene 1 (1.17 g, 6.68 mmol, 823.95 uL). Resulting solution was further heated at same temperature for 16 hours. After formation of desired product, as evidenced from LCMS, volatiles were removed and redissolved in ethyl acetate. Organic portion was washed with water/brine and separated, dried over sodium sulfate and concentrated under reduced pressure. Crude mass was purified by column chromatography using 1-2% MeOH-DCM as eluent to afford 8-[[4-(chloromethyl)phenyl]methyl]-3-oxa-8-azabicyclo[3.2.1]octane 3 (750 mg, 2.83 mmol, 42.34% yield, 95% purity) as a white gum. LC MS: ES+ 251.8

Step 2: Synthesis of 6-[[4-(3-oxa-8-azabicyclo[3.2.1]octan-8-ylmethyl)phenyl]methyl]-1H-benzo[cd]indol-2-one: To a stirred solution of 8-[[4-(chloromethyl)phenyl]methyl]-3-oxa-8-azabicyclo[3.2.1]octane 3 (400.00 mg, 1.59 mmol) and 6-(4,4,5,5-tetramethyl-1,3,2-dioxaborolan-2-yl)-1H-benzo[cd]indol-2-one 4 (937.88 mg, 3.18 mmol) in ethanol (2.5 mL) and Toluene (5 mL) was added Potassium phosphate tribasic anhydrous (1.01 g, 4.77 mmol) and the reaction mass was degassed under argon atmosphere over 10 minutes. Then Tri-o-Tolyl phosphine (96.72 mg, 317.77 umol) and (1E,4E)-1,5-diphenylpenta-1,4-dien-3-one; palladium (145.50 mg, 158.89 umol) was added to this reaction mass and heated the resultant reaction mixture 90° C. over night. Check TLC shows consumption of SM. Then the reaction mix was filtered through sintered funnel using celite bed and the reaction mix was diluted with ethyl acetate and washed with water. The organic part was dried over $Na_2SO_4$ and filtered. The reaction mix was evaporated under reduced pressure, the crude was purified by combi-flash to get the pure compound 6-[[4-(3-oxa-8-azabicyclo[3.2.1]octan-8-ylmethyl)phenyl]methyl]-1H-benzo[cd]indol-2-one 5 (250 mg, 637.24 umol, 40.11% yield, 98% purity) as light yellow solid. LC MS: ES+ 385.3.

Step 3: Synthesis of 3-[6-[[4-(3-oxa-8-azabicyclo[3.2.1]octan-8-ylmethyl)phenyl]methyl]-2-oxo-benzo[cd]indol-1-yl]piperidine-2,6-dione: To the stirred solution of 6-[[4-(3-oxa-8-azabicyclo[3.2.1]octan-8-ylmethyl)phenyl]methyl]-1H-benzo[cd]indol-2-one 5 (250 mg, 650.25 umol) in THF (3 mL) was added Sodium hydride (in oil dispersion) 60% dispersion in mineral oil (249.15 mg, 6.50 mmol, 60% purity) at cold condition and the reaction mixture was stirred at room temperature for 10 minutes followed by the addition of 3-bromopiperidine-2,6-dione 6 (624.27 mg, 3.25 mmol) portion wise. It was then stirred at room temperature for 10 minutes and heated at 70° C. for 30 minutes. TLC was checked which showed almost complete consumption of the starting material and formation of the desired spot. The reaction mixture was diluted with ethyl acetate, washed with cold water and the organic fraction was separated. It was then dried over anhydrous sodium sulphate and evaporated under reduced pressure to obtain the crude which was washed with ether and pentane to afford 3-[6-[[4-(3-oxa-8-azabicyclo[3.2.1]octan-8-ylmethyl)phenyl]methyl]-2-oxo-benzo[cd]indol-1-yl]piperidine-2,6-dione Compound 156 (145.0 mg, 287.91 umol, 44.28% yield, 98.40% purity) as yellow solid. $^1$H NMR (400 MHz, DMSO-d6): δ 11.12 (s, 1H), 8.33 (d, J=8.2 Hz, 1H), 8.07 (d, J=6.96 Hz, 1H), 7.80 (t, J=7.6 Hz, 1H), 7.40 (d, J=7.24 Hz, 1H), 7.25-7.21 (m, 4H), 7.10 (d, J=7.24 Hz, 1H), 5.44 (dd, J=12.52, 5.0 Hz, 1H), 4.36 (s, 2H), 3.49-3.46 (m, 2H), 3.37-3.29 (m, 4H), 2.99-2.90 (m, 3H), 2.80-2.62 (m, 2H), 2.10-2.07 (m, 1H), 1.91-1.88 (m, 2H), 1.71-1.69 (m, 2H) LC MS: ES+ 496.5.

Example 71. Synthesis of 3-[6-[[4-[[4-[(4-fluorophenyl)methyl]-1-piperidyl]methyl]phenyl]methyl]-2-oxo-benzo[cd]indol-1-yl]piperidine-2,6-dione (Compound 157)

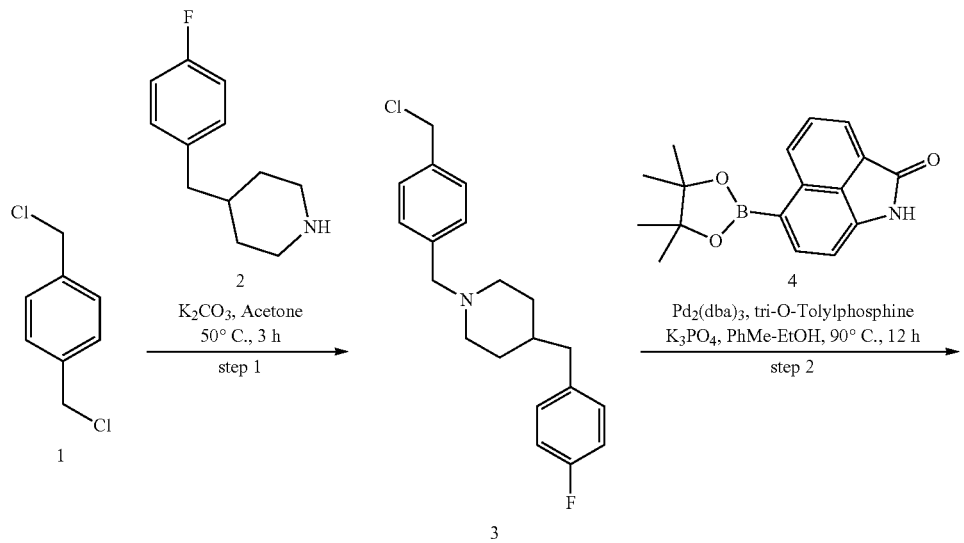

-continued

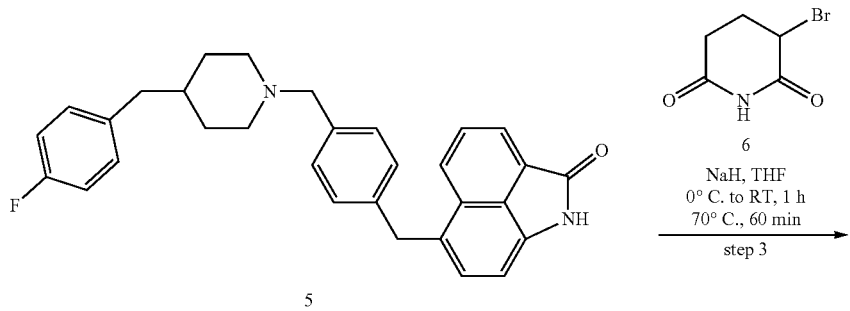

5

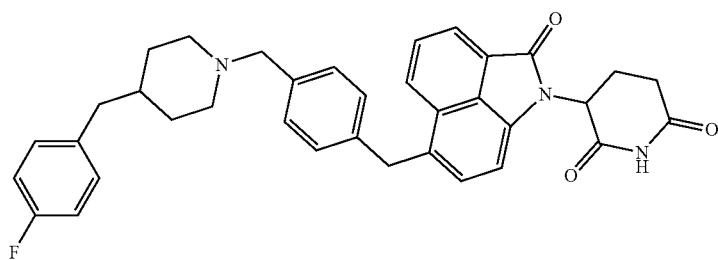

Compound 157

Step 1: Synthesis of 1-[[4-(chloromethyl)phenyl]methyl]-4-[(4-fluorophenyl)methyl]piperidine: To a stirred solution of 4-[(4-fluorophenyl)methyl]piperidine 2 (550 mg, 2.85 mmol) in DMF (5 mL) was added N,N-Diisopropylethylamine (1.10 g, 8.54 mmol, 1.49 mL) and stirred for 5 min. Then 1,4-bis(chloromethyl)benzene 1 (498.19 mg, 2.85 mmol) was added and the reaction was heated at 60° C. for 16 hours. After completion of the reaction (monitored by TLC), the reaction mixture was diluted with ethyl acetate and washed with water and brine, dried over sodium sulfate and concentrated. Crude material was purified by column chromatography (100-200 silica, 25-30% EtOAc in hexane) to afford 1-[[4-(chloromethyl)phenyl]methyl]-4-[(4-fluorophenyl)methyl]piperidine 3 (120 mg, 343.52 umol, 12.07% yield, 95% purity) as light yellow oil. LC MS: ES+ 332.18.

Step 2: Synthesis of 6-[[4-[[4-[(4-fluorophenyl)methyl]-1-piperidyl]methyl]phenyl]methyl]-1H-benzo[cd]indol-2-one: To a stirred solution of 1-[[4-(chloromethyl)phenyl]methyl]-4-[(4-fluorophenyl)methyl]piperidine 3 (150 mg, 452.01 umol) and 6-(4,4,5,5-tetramethyl-1,3,2-dioxaborolan-2-yl)-1H-benzo[cd]indol-2-one 4 (266.81 mg, 904.01 umol) in ethanol (2 mL) and Toluene (4 mL) was added Potassium phosphate tribasic anhydrous (287.84 mg, 1.36 mmol) and the reaction mass was degassed under argon atmosphere over 10 minutes. Then Tri-o-Tolyl phosphine (27.52 mg, 90.40 umol) and (1E,4E)-1,5-diphenylpenta-1,4-dien-3-one; palladium (41.39 mg, 45.20 umol) was added to this reaction mass and heated the resultant reaction mixture 90° C. over night. Then the reaction mixture was filtered through sintered funnel using celite bed and the reaction mix was diluted with ethyl acetate and washed with water. The organic part was dried over $Na_2SO_4$ and evaporated under reduced pressure. Crude material was purified by combi-flash to get the pure compound 6-[[4-[[4-[(4-fluorophenyl)methyl]-1-piperidyl]methyl]phenyl]methyl]-1H-benzo[cd]indol-2-one 5 (160 mg, 327.18 umol, 72.38% yield, 95% purity) as light yellow solid. LC MS: ES+ 465.3.

Step 3: Synthesis of 3-[6-[[4-[[4-[(4-fluorophenyl)methyl]-1-piperidyl]methyl]phenyl]methyl]-2-oxo-benzo[cd]indol-1-yl]piperidine-2,6-dione: To the stirred solution of 6-[[4-[[4-[(4-fluorophenyl)methyl]-1-piperidyl]methyl]phenyl]methyl]-1H-benzo[cd]indol-2-one 5 (180 mg, 387.45 umol) in THF (5 mL) was added Sodium hydride (in oil dispersion) 60% dispersion in mineral oil (148.46 mg, 3.87 mmol, 60% purity) at cold condition and the reaction mixture was stirred at room temperature for 10 minutes followed by the addition of 3-bromopiperidine-2,6-dione 6 (371.98 mg, 1.94 mmol) portion wise. It was then stirred at room temperature for 10 minutes and heated at 70° C. for 30 minutes. TLC was checked which showed almost complete consumption of the starting material and formation of the desired spot. The reaction mixture was diluted with ethyl acetate, washed with cold water and the organic fraction was separated. It was then dried over anhydrous sodium sulphate and evaporated under reduced pressure to obtain the crude mass which was purified by Prep TLC using 60% EtOAc-DCM as eluent to afford 3-[6-[[4-[[4-[(4-fluorophenyl)methyl]-1-piperidyl]methyl]phenyl]methyl]-2-oxo-benzo[cd]indol-1-yl]piperidine-2,6-dione Compound 157 (25.0 mg, 42.76 umol, 11.04% yield, 98.47% purity) as yellow solid. $^1$H NMR (400 MHz, DMSO-d6): δ 11.12 (s, 1H), 8.32 (d, J=8.24 Hz, 1H), 8.07 (d, J=6.96 Hz, 1H), 7.80 (t, J=7.56 Hz, 1H), 7.39 (d, J=7.36 Hz, 1H), 7.21-7.04 (m, 9H), 5.47-5.40 (m, 1H), 4.37 (s, 2H), 3.29 (s, 2H), 2.90-2.80 (m, 1H), 2.76-2.67 (m, 4H), 2.46-2.44 (m, 2H), 2.09-2.07 (m, 1H), 1.80-1.70 (m, 2H), 1.47-1.45 (m, 3H), 1.14-1.11 (m, 2H); LC MS: ES+ 476.5.

Example 72. Synthesis of 3-[6-[[4-[(4-tert-butyl-1-piperidyl)methyl]phenyl]methyl]-2-oxo-benzo[cd]indol-1-yl]piperidine-2,6-dione (Compound 158)

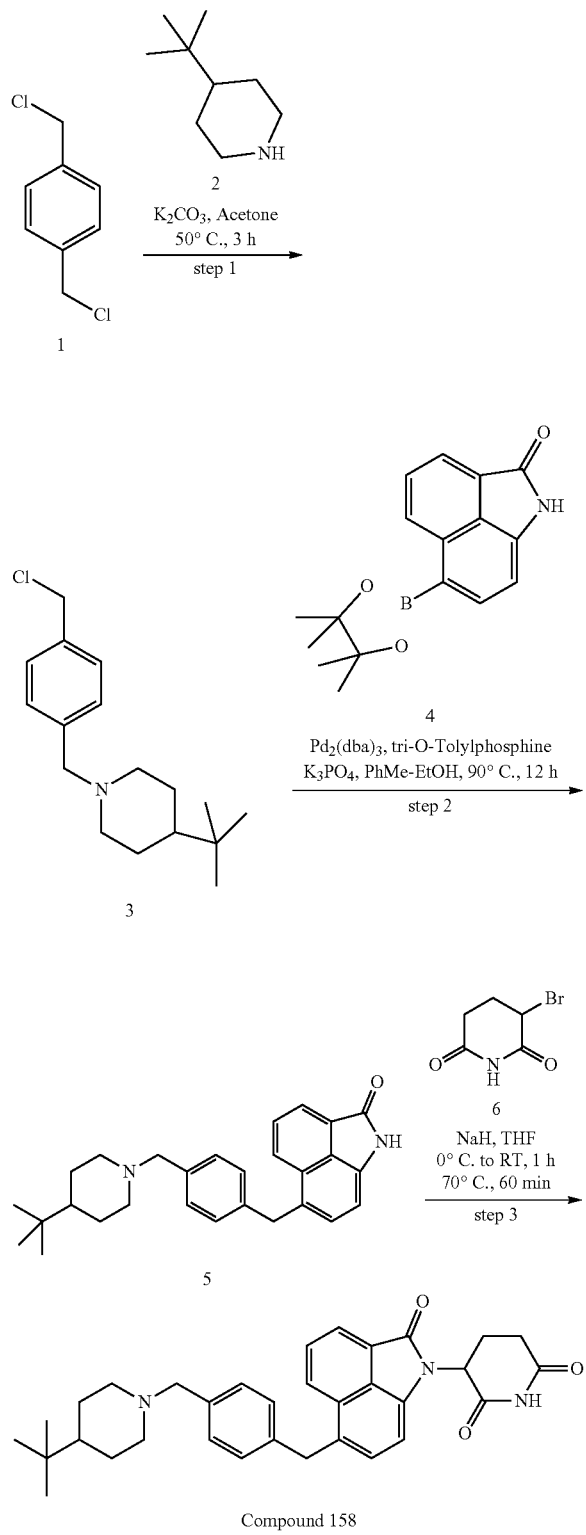

Step 1: Synthesis of 4-tert-butyl-1-[[4-(chloromethyl)phenyl]methyl]piperidine: To a stirred solution of 4-tert-butylpiperidine 2 (550 mg, 3.89 mmol) in DMF (5 mL) was added N,N-Diisopropylethylamine (1.51 g, 11.68 mmol, 2.03 mL) and stirred for 5 min. Then 1,4-bis(chloromethyl)benzene 1 (681.61 mg, 3.89 mmol) was added and the reaction was heated at 60° C. for 16 hours. After completion of the reaction (monitored by TLC), the reaction mixture was diluted with ethyl acetate and washed with water and brine, dried over sodium sulfate and concentrated. The crude was purified by column chromatography (100-200 silica, 25-30% EtOAc in hexane) to afford 4-tert-butyl-1-[[4-(chloromethyl)phenyl]methyl]piperidine 3 (170 mg, 577.10 umol, 14.82% yield, 95% purity) as yellow oil. LC MS: ES+ 280.2.

Step 2: Synthesis of 6-[[4-[(4-tert-butyl-1-piperidyl)methyl]phenyl]methyl]-1H-benzo[cd]indol-2-one: To a stirred solution of 4-tert-butyl-1-[[4-(chloromethyl)phenyl]methyl]piperidine 3 (170 mg, 607.47 umol) and 6-(4,4,5,5-tetramethyl-1,3,2-dioxaborolan-2-yl)-1H-benzo[cd]indol-2-one 4 (358.58 mg, 1.21 mmol) in ethanol (2 mL) and Toluene (4 mL) was added Potassium phosphate tribasic anhydrous (386.85 mg, 1.82 mmol) and the reaction mass was degassed under argon atmosphere over 10 minutes. Then Tri-o-Tolyl phosphine (36.98 mg, 121.49 umol) and (1E,4E)-1,5-diphenylpenta-1,4-dien-3-one; palladium (55.63 mg, 60.75 umol) was added to this reaction mass and heated the resultant reaction mixture 90° C. over night. Check TLC shows consumption of SM. Then the reaction mix was filtered through sintered funnel using celite bed and the reaction mix was diluted with ethyl acetate and washed with water. The organic part was dried over $Na_2SO_4$ and filtered. The reaction mix was evaporated under reduced pressure, the crude was purified by combi-flash to get the pure compound 6-[[4-[(4-tert-butyl-1-piperidyl)methyl]phenyl]methyl]-1H-benzo[cd]indol-2-one 5 (100 mg, 230.27 umol, 37.91% yield, 95% purity) as light yellow solid. LC MS; ES+ 413.0.

Step 3: Synthesis of 3-[6-[[4-[(4-tert-butyl-1-piperidyl)methyl]phenyl]methyl]-2-oxo-benzo[cd]indol-1-yl]piperidine-2,6-dione: To the stirred solution of 6-[[4-[(4-tert-butyl-1-piperidyl)methyl]phenyl]methyl]-1H-benzo[cd]indol-2-one 5 (100 mg, 242.39 umol) in THF (5 mL) was added Sodium hydride (in oil dispersion) 60% dispersion in mineral oil (92.87 mg, 2.42 mmol, 60% purity) at cold condition and the reaction mixture was stirred at room temperature for 10 minutes followed by the addition of 3-bromopiperidine-2,6-dione 6 (232.70 mg, 1.21 mmol) portion wise. It was then stirred at room temperature for 10 minutes and heated at 70° C. for 30 minutes. The reaction mixture was diluted with ethyl acetate, washed with cold water and the organic fraction was separated. It was then dried over anhydrous sodium sulphate and evaporated under reduced pressure to obtain the crude mass which was purified by Prep TLC using 60% EtOAc-DCM as eluent to afford 3-[6-[[4-[(4-tert-butyl-1-piperidyl)methyl]phenyl]methyl]-2-oxo-benzo[cd]indol-1-yl]piperidine-2,6-dione Compound 158 (45.0 mg, 81.64 umol, 33.68% yield, 95% purity) as yellow solid. $^1$H NMR (400 MHz, DMSO-d6): δ 11.12 (s, 1H), 8.32 (d, J=8.20 Hz, 1H), 8.07 (d, J=6.96 Hz, 1H), 7.80 (t, J=7.56 Hz, 1H), 7.40 (d, J=7.32 Hz, 1H), 7.23-7.17 (m, 4H), 7.10 (d, J=7.32 Hz, 1H), 5.46-5.41 (m, 1H), 4.37 (s, 2H), 3.29 (s, 2H), 2.95-2.90 (m, 1H), 2.80-2.73 (m, 2H), 2.66-2.62 (m, 2H), 2.10-2.07 (m, 1H), 1.80-1.70 (m, 2H), 1.55-1.52 (m, 2H), 1.17-1.14 (m, 2H), 0.95-0.85 (m, 1H), 0.79 (s, 9H); LC MS: ES+ 524.6.

Example 73. Synthesis of Chiral Separation of 3-(2-Oxo-6-{4-[4-(2,2,2-trifluoro-ethanesulfonyl)-piperazin-1-ylmethyl]-benzyl}-2H-benzo[cd]indol-1-yl)-piperidine-2,6-dione (Compound 159) and 3-(2-Oxo-6-{4-[4-(2,2,2-trifluoro-ethanesulfonyl)-piperazin-1-ylmethyl]-benzyl}-2H-benzo[cd]indol-1-yl)-piperidine-2,6-dione (Compound 160)

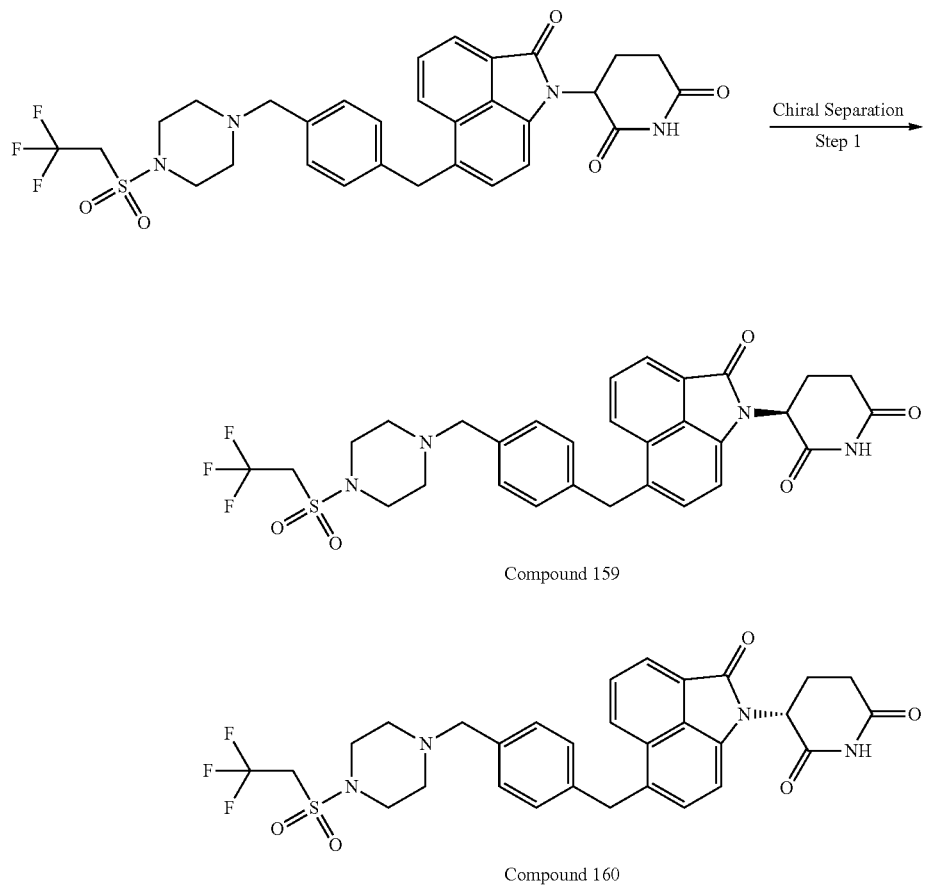

Step 1: Chiral Separation: 550 mg of Compound 109 was separated by normal phase preparative Chiral-HPLC method to afford 3-[2-oxo-6-[[4-[[4-(2,2,2-trifluoroethylsulfonyl)piperazin-1yl]methyl]phenyl]methyl]benzo[cd] indol-1-yl]piperidine-2,6-dione Compound 159(160.0 mg, 257.92 umol, 28.82% yield, 99.08% purity, % ee10) and 3-[2-oxo-6-[[4-[[4-(2,2,2-trifluoroethylsulfonyl)piperazin-1yl]methyl]phenyl]methyl] benzo[cd]indol-1-yl]piperidine-2,6-dione Compound 160 (165.0 mg, 266.17 umol, 29.74% yield, 99.15% purity, % ee-100) both as yellow solid. $^1$H NMR (d6-DMSO, 400 MHZ) d 11.12 (s, 1H), 8.32 (d, J=8.36, 1H), 8.07 (d, J=6.96, 1H), 7.80 (t, J=7.6, 1H), 7.40 (d, J=7.4, 1H), 7.25 (d, J=7.84, 2H), 7.19 (d, J=7.84, 2H), 7.10 (d, J=7.08, 1H), 5.44-5.43 (dd, J=12.8, 5.2 Hz, 1H), 4.50-4.43 (m, 2H), 4.37 (s, 2H), 3.44 (s, 2H), 3.18 (br s, 4H), 2.94 (m, 1H), 2.76-2.73 (m, 1H), 2.66-2.62 (m, 1H), 2.39 (br s, 4H), 2.09-2.08 (m, 1H); LC MS: ES+ 615.1.

Example 74. Synthesis of 3-(2-Oxo-6-{4-[4-(2,2,2-trifluoro-ethyl)-piperazin-1-ylmethyl]-benzyl}-2H-benzo[cd]indol-1-yl)-piperidine-2,6-dione (Compound 161)

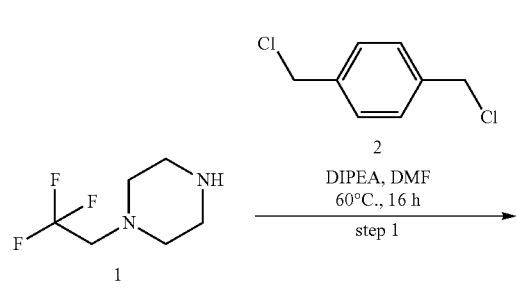

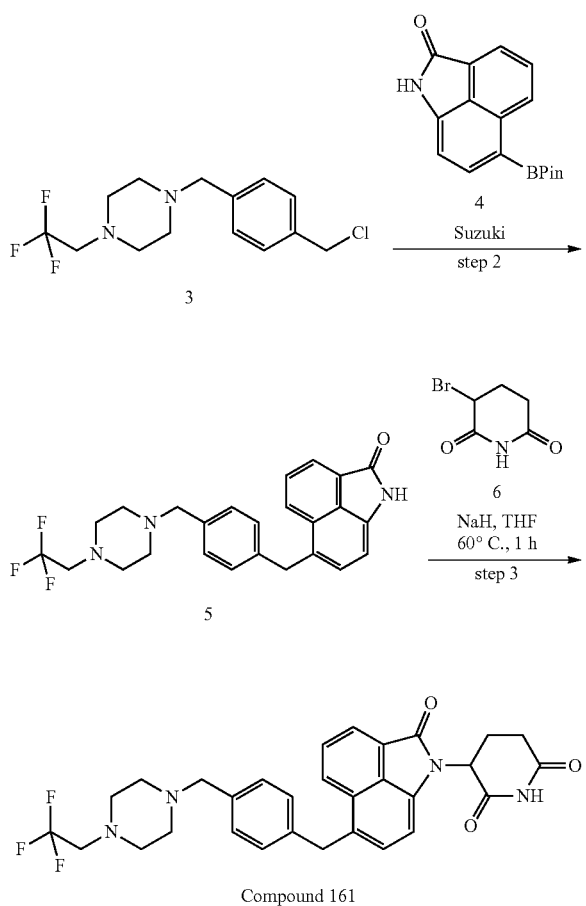

Compound 161

Step 1: Synthesis of 1-(4-Chloromethyl-benzyl)-4-(2,2,2-trifluoro-ethyl)-piperazine: To a stirred solution of 1-(2,2,2-trifluoroethyl)piperazine 1 (500.00 mg, 2.97 mmol) in DMF (5 mL) was added N,N-Diisopropylethylamine (1.15 g, 8.92 mmol, 1.55 mL) and stirred for 5 minutes. Then 1,4-bis(chloromethyl)benzene 2 (520.50 mg, 2.97 mmol) was added and the reaction was heated at 60° C. for 16 hours. After completion of the reaction (monitored by TLC), the reaction mixture was diluted with ethyl acetate and washed with water and brine, dried over sodium sulfate and concentrated. The crude was purified by flash chromatography (0-5% MeOH in DCM) to afford 1-[[4-(chloromethyl)phenyl]methyl]-4-(2,2,2-trifluoroethyl)piperidine 3 (300.0 mg, 902.65 umol, 30.36% yield, 92% purity) as yellow liquid. LC MS: ES+ 306.8.

Step 2: Synthesis of 6-{4-[4-(2,2,2-Trifluoro-ethyl)-piperazin-1-ylmethyl]-benzyl}-1H-benzo[cd]indol-2-one: To a stirred solution of 1-[[4-(chloromethyl)phenyl]methyl]-4-(2,2,2-trifluoroethyl)piperazine 3 (300.0 mg, 977.98 umol) and 6-(4,4,5,5-tetramethyl-1,3,2-dioxaborolan-2-yl)-1H-benzo[cd]indol-2-one 4 (577.28 mg, 1.96 mmol) in Ethanol (2 mL) and Toluene (4 mL) was added Potassium phosphate tribasic anhydrous (622.79 mg, 2.93 mmol) and the reaction mass was degassed under argon atmosphere for 10 minutes. Then Tri-o-Tolyl phosphine (59.53 mg, 195.60 umol) and (1E,4E)-1,5-diphenylpenta-1,4-dien-3-one; palladium (89.56 mg, 97.80 umol) was added to this reaction mass and heated at 90° C. 16 hours. The reaction mixture was filtered through sintered funnel using celite bed and the filtrate was evaporated under reduced pressure which was purified by flash chromatography using 0-5% MeOH-DCM to afford 6-[[4-[[4-(2,2,2-trifluoroethyl)piperazin-1-yl]methyl]phenyl]methyl]-1H-benzo[cd]indol-2-one 5 (177.0 mg, 397.12 umol, 40.61% yield, 98.6% purity) as yellow solid. LC MS: ES+ 440.5.

Step 3: Synthesis of 3-(2-Oxo-6-{4-[4-(2,2,2-trifluoro-ethyl)-piperazin-1-ylmethyl]-benzyl}-2H-benzo[cd]indol-1-yl)-piperidine-2,6-dione: To the stirred solution of 6-[[4-[[4-(2,2,2-trifluoroethyl)piperazin-1-yl]methyl]phenyl]methyl]-1H-benzo[cd]indol-2-one 5 (177.0 mg, 402.76 umol) in THF (10 mL) was added Sodium hydride (in oil dispersion) 60% dispersion in mineral oil (185.19 mg, 4.83 mmol, 60% purity) at cold condition and the reaction mixture was stirred at room temperature for 10 minutes followed by the addition of 3-bromopiperidine-2,6-dione 6 (386.67 mg, 2.01 mmol) portion wise. It was then stirred at room temperature for 10 minutes and heated at 70° C. for 30 minutes. After completion of reaction (monitored by TLC) the reaction mixture was diluted with ethyl acetate, washed with cold water and the organic fraction was separated. It was then dried over anhydrous sodium sulphate and evaporated under reduced pressure to obtain the crude which was washed with ether and pentane to afford 3-[2-oxo-6-[[4-[[4-(2,2,2-trifluoroethyl)piperazin-1-yl]methyl]phenyl]methyl]benzo[cd]indol-1-yl]piperidine-2,6-dione Compound 161 (120.0 mg, 217.96 umol, 54.12% yield, 100.00% purity) as yellow solid. $^1$H NMR (d6-DMSO, 400 MHZ) d 11.12 (s, 1H), 8.32 (d, J=8.16, 1H), 8.07 (d, J=6.92, 1H), 7.80 (t, J=7.62, 1H), 7.39 (d, J=7.16, 1H), 7.22 (d, J=7.72, 2H), 7.16 (d, J=7.72, 2H), 7.10 (d, J=7.24, 1H), 5.46-5.43 (m, 1H), 4.37 (s, 2H), 3.36 (s, 2H), 3.14-3.06 (m, 2H), 2.98-2.90 (m, 1H), 2.79-2.73 (m, 1H), 2.66-2.62 (m, 1H), 2.56-2.49 (br s, 4H), 2.31 (br s, 4H), 2.10-2.07 (m, 1H); LC MS: ES+ 551.5.

Example 75. Synthesis of 3-[6-[(1-cyclohexylpyrazol-4-yl)methyl]-2-oxo-benzo[cd]indol-1-yl]piperidine-2,6-dione (Compound 162)

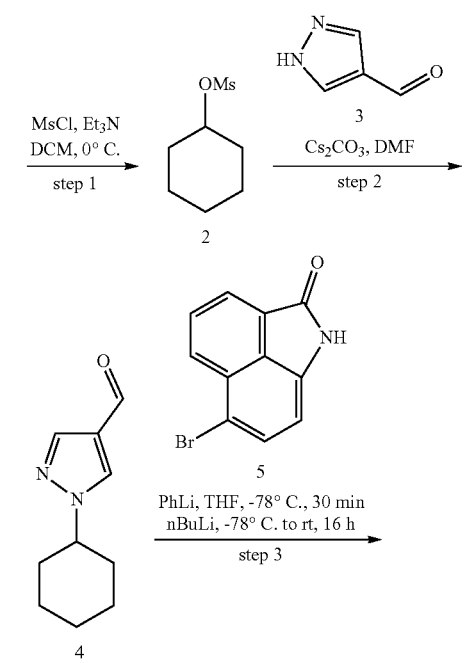

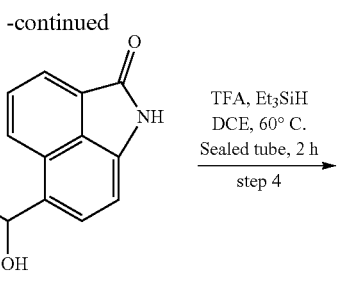

Step 1: Synthesis of cyclohexyl methanesulfonate: To a stirred solution of cyclohexanol 1 (2 g, 19.97 mmol, 2.08 mL) in DCM (20 mL), was added Triethylamine (4.45 g, 43.93 mmol, 6.12 mL), cooled the reaction mixture to 0° C. followed by drop wise addition of Methanesulfonyl chloride (2.74 g, 23.96 mmol, 1.85 mL) then reaction mixture was heated to 25° C. for 2 hours. After completion of SM, reaction mass was diluted with water and extracted with DCM, washed with saturated solution of NaHCO3, brine, dried over anhydrous sodium sulphate and evaporate under reduced pressure to give the crude compound cyclohexyl methanesulfonate 2 (3.5 g, 19.64 mmol, 98.33% yield, 100% purity) as orange liquid, which was used in next step without further purification. $^1$H NMR (400 MHz, CDCl3) δ 4.72-4.65 (m, 1H), 2.99 (s, 3H), 1.96-1.95 (m, 2H), 1.78-1.75 (m, 2H), 1.67-1.59 (m, 2H), 1.55-1.50 (m, 1H), 1.42-1.41 (m, 2H), 1.34-1.32 (m, 1H);

Step 2: Synthesis of 1-cyclohexylpyrazole-4-carbaldehyde: To the stirred solution of 1H-pyrazole-4-carbaldehyde 3 (2 g, 20.81 mmol) and cyclohexyl methanesulfonate 2 (3.71 g, 20.81 mmol) in DMF (20 mL) was added Cesium carbonate (13.56 g, 41.63 mmol) and the reaction mixture was heated at 80° C. for 16 hours. TLC was checked which showed complete consumption of the starting material along with the formation of the desired spot. The reaction mixture was diluted with ethyl acetate, washed with water and the organic fraction was separated. It was then dried over anhydrous sodium sulphate and evaporated under reduced pressure to obtain the crude which was purified by flash chromatography using 0-20% ethyl acetate-hexane to afford 1-cyclohexylpyrazole-4-carbaldehyde 4 (1.5 g, 8.33 mmol, 40.03% yield, 99% purity) as a white semisolid. LC MS: ES+ 179.0.

Step 3: Synthesis of 6-[(1-cyclohexylpyrazol-4-yl)-hydroxy-methyl]-1H-benzo[cd]indol-2-one: To the stirred solution of 6-bromo-1H-benzo[cd]indol-2-one 5 (1.39 g, 5.61 mmol) in THF (20 mL) was added Phenyl lithium, typically 1.9M in di-n-butyl ether (1.8 M, 3.12 mL) at −78° C. and the reaction was stirred at the same temperature for 30 minutes followed by the addition of Butyl lithium (2.00 M, 3.09 mL) at −78° C. and after the addition was complete the temperature was allowed to increase to −40° C. and the reaction mixture was stirred at the same temperature for 30 minutes followed by the addition of 1-cyclohexylpyrazole-4-carbaldehyde 4 (1 g, 5.61 mmol) in THF (10 mL) at −78° C. and then the reaction mixture was allowed to warm to room temperature and was continued for 16 hours. It was quenched with saturated ammonium chloride solution, extracted with ethyl acetate, washed with water, brine, dried over sodium sulphate and was concentrated under reduced pressure. It was purified by comb flash eluting at 1% methanol in dichloromethane to afford 6-[(1-cyclohexylpyrazol-4-yl)-hydroxy-methyl]-1H-benzo[cd]indol-2-one 6 (280 mg, 773.40 umol, 13.78% yield, 95.96% purity) as brown solid. LC MS: ES+ 348.3.

Step 3: Synthesis of 6-[(1-cyclohexylpyrazol-4-yl)methyl]-1H-benzo[cd]indol-2-one: To the stirred solution of 6-[(1-cyclohexylpyrazol-4-yl)-hydroxy-methyl]-1H-benzo[cd]indol-2-one 6 (280 mg, 805.97 umol) in DCE (5 mL) was added Triethylsilane (374.87 mg, 3.22 mmol, 514.93 uL), Trifluoroacetic acid (735.17 mg, 6.45 mmol, 496.74 uL) and the reaction mixture was heated at 80° C. for 2 hours. The reaction mixture was evaporated under reduced pressure to obtain the crude compound which was purified by flash chromatography using 0-3% MeOH-DCM to afford 6-[(1-cyclohexylpyrazol-4-yl)methyl]-1H-benzo[cd]indol-2-one 7 (160 mg, 458.65 umol, 56.91% yield, 95% purity) as yellow solid. LC MS: ES+ 332.4.

Step 4: Synthesis of 3-[6-[(1-cyclohexylpyrazol-4-yl)methyl]-2-oxo-benzo[cd]indol-1-yl]piperidine-2,6-dione: To the stirred solution of 6-[(1-cyclohexylpyrazol-4-yl)methyl]-1H-benzo[cd]indol-2-one 7 (60 mg, 181.04 umol) in DMF (2 mL) was added Sodium hydride (in oil dispersion) 60% dispersion in mineral oil (13.87 mg, 362.09 umol, 60% purity) in cold condition and the reaction mixture was heated at 60° C. for 1 hour followed by the addition of 3-bromopiperidine-2,6-dione 8 (34.76 mg, 181.04 umol) and the reaction was continued at 60° C. for 4 hours with further addition of 3-bromopiperidine-2,6-dione 8 (34.76 mg, 181.04 umol) and the reaction was continued for 16 hours at 70° C. The reaction mixture was quenched with cold water and EtOAc was added, layers were separated. The organic layer was washed with water, brine, dried over Na$_2$SO$_4$ and concentrated under reduced pressure to get crude mass which was purified by Prep TLC using 25% EtOAc-DCM as eluent to afford 3-[6-[(1-cyclohexylpyrazol-4-yl)methyl]-2-oxo-benzo[cd]indol-1-yl]piperidine-2,6-dione Compound 162 (8 mg, 18.08 umol, 9.99% yield, 100% purity) as yellow solid. $^1$H NMR (d6-DMSO, 400 MHZ) d 11.11 (S, 1H), 8.37 (d, J=Hz, 1H), 8.08 (d, J=8.08 Hz, 1H), 7.83 (t, J=7.38 Hz, 1H), 7.52 (s, 1H), 7.35 (d, J=7.28 Hz, 1H), 7.27 (s, 1H), 7.07 (d, J=7.24 Hz, 1H), 5.44-5.42 (m, 1H), 4.17 (s, 2H), 4.01-3.99 (m, 1H), 2.98-2.90 (m, 1H), 2.79-2.72 (m, 1H), 2.66-2.62 (m, 1H), 2.08-2.07 (m, 1H), 1.92-1.89 (m, 2H), 1.76-1.73 (m, 2H), 1.62-1.59 (m, 3H), 1.37-1.30 (m, 2H), 1.25-1.20 (m, 1H); LC MS: ES+443.5.

Example 76. Synthesis of 3-[6-[1-[1-[1-(1-methyl-cyclobutanecarbonyl)-4-piperidyl]pyrazol-4-yl]cyclopropyl]-2-oxo-benzo[cd]indol-1-yl]piperidine-2,6-dione (Compound 163) and 3-[6-[1-[1-[1-[(1-methylcyclobutyl)methyl]-4-piperidyl]pyrazol-4-yl]cyclopropyl]-2-oxo-benzo[cd]indol-1-yl]piperidine-2,6-dione (Compound 164)
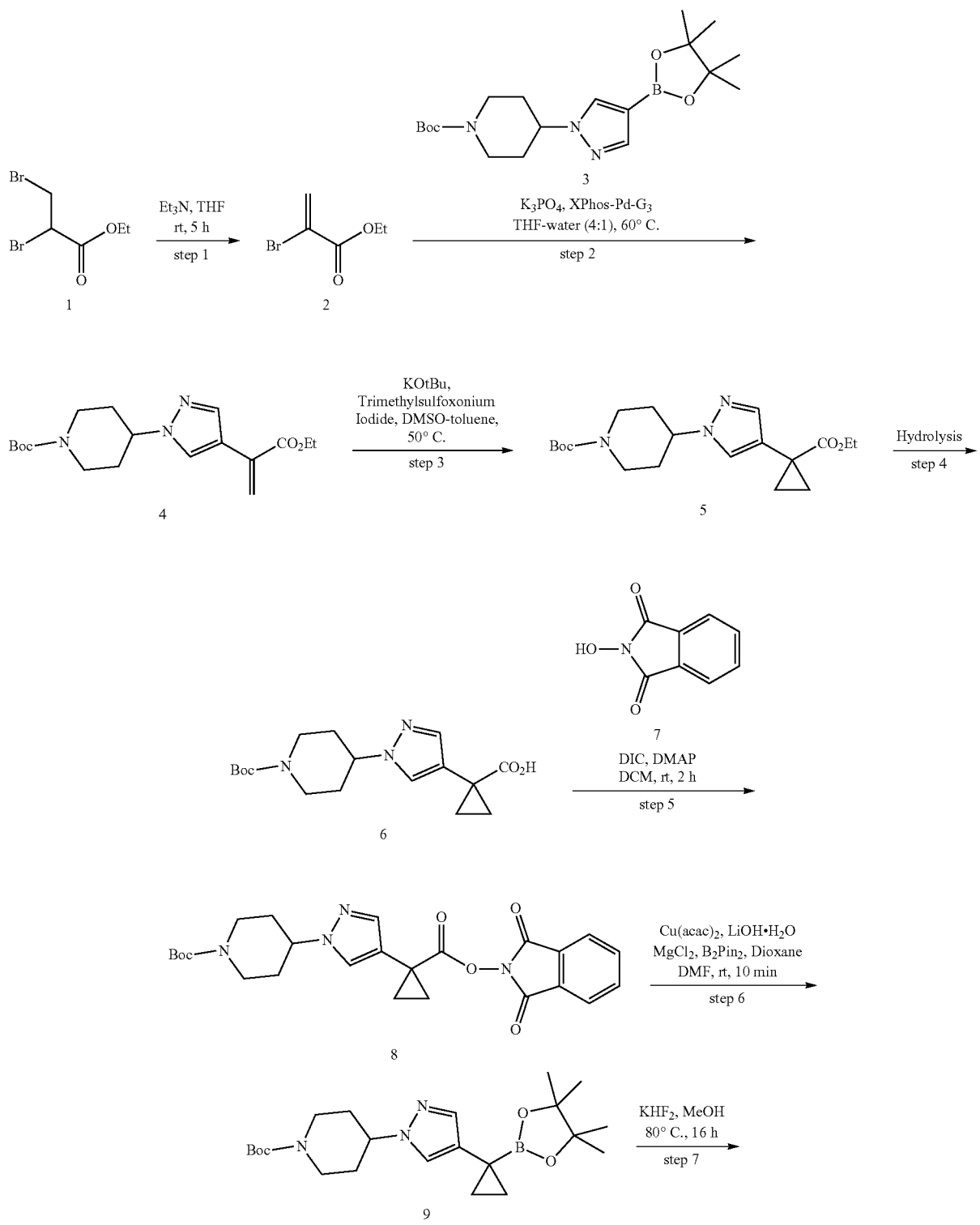

-continued
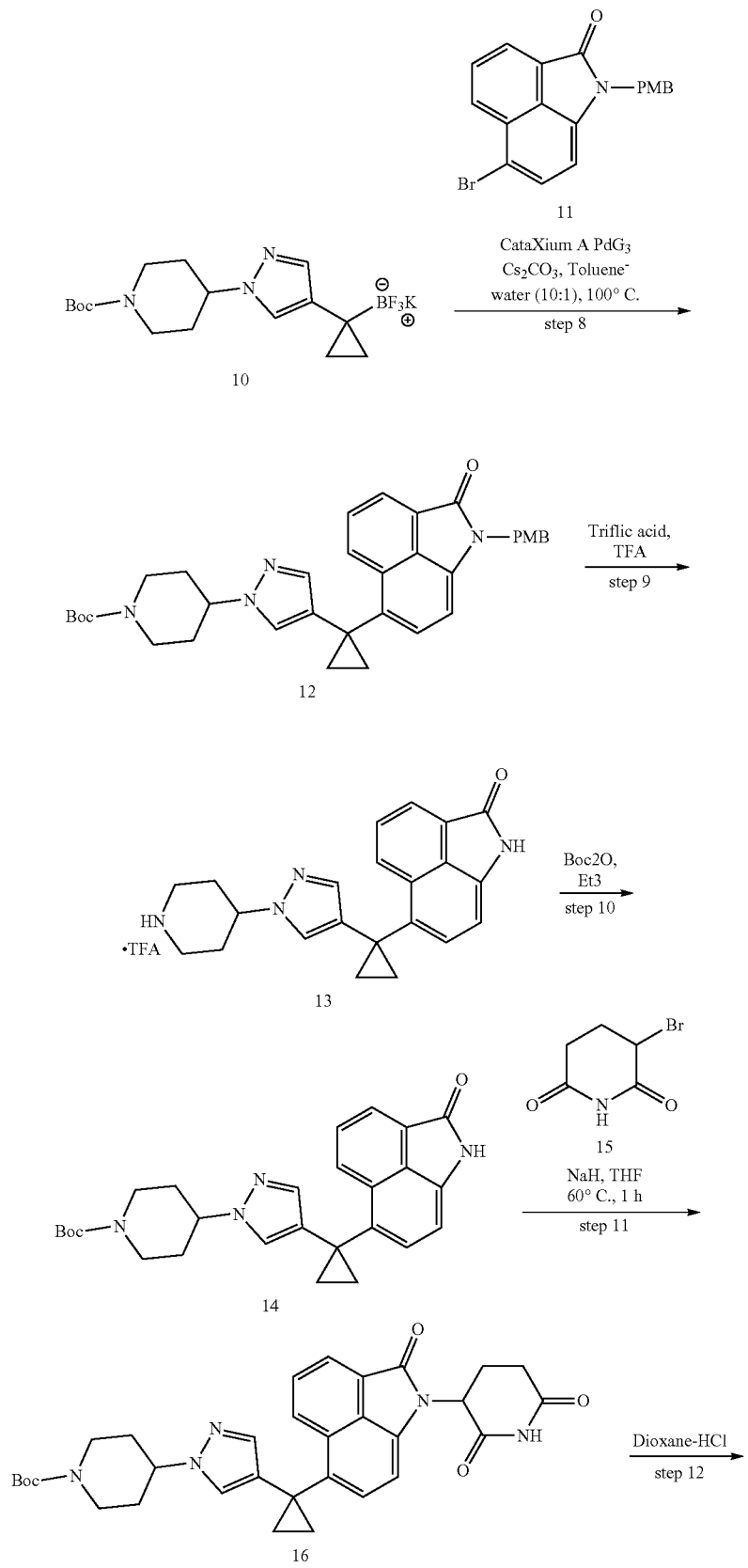

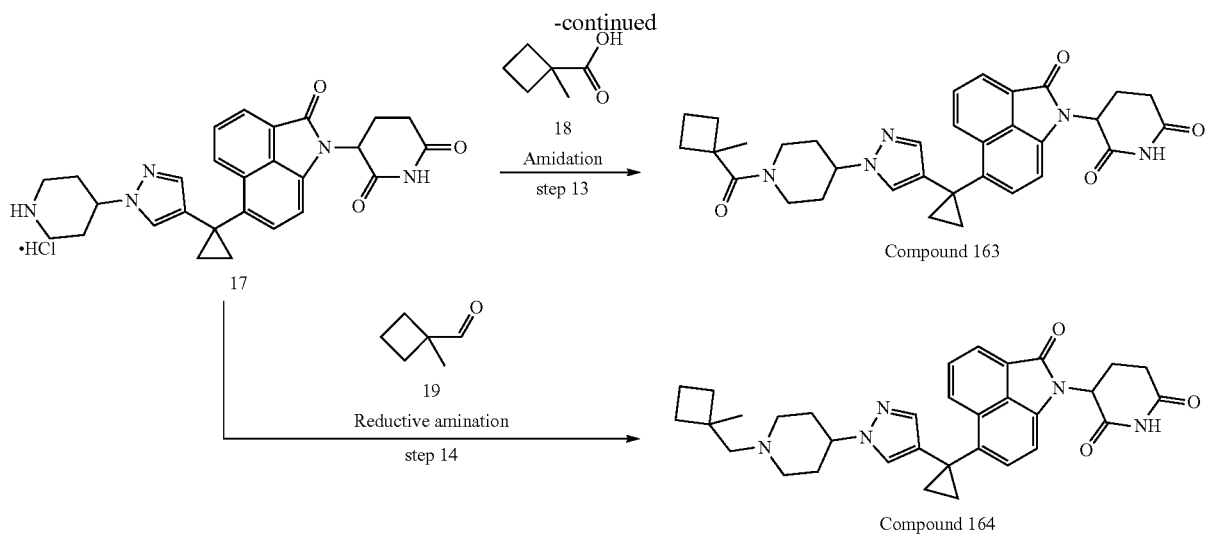

Compound 163

Compound 164

Step 1: Synthesis of ethyl 2-bromoprop-2-enoate: To a stirred solution of ethyl 2,3-dibromopropanoate 1 (9.9 g, 38.09 mmol, 5.53 mL) in THF (40 mL) was cooled to 0° C. followed by drop wise addition of Triethylamine (3.85 g, 38.09 mmol, 5.31 mL), the reaction mixture was stirred for 8 hours at room temperature. After completion of the reaction, The reaction mixture was quenched water and EtOAc, layers were separated, the organic layer was washed with saturated solution of $NaHCO_3$, brine, dried over $Na_2SO_4$ and concentrated under vacuum pump to afford ethyl 2-bromoprop-2-enoate 2 (5 g, 27.65 mmol, 72.60% yield, 99% purity) as colourless liquid, which was used in next step without further purification. 1H NMR (400 MHz, CDCl3) δ 6.94 (s, 1H), 6.25 (s, 1H), 4.27 (q, J=7.01 Hz, 2H), 1.32 (t, J=7.1 Hz, 3H).

Step 2: Synthesis of tert-butyl 4-[4-(1-ethoxycarbonylvinyl)pyrazol-1-yl]piperidine-1-carboxylate: To stirred a solution of ethyl 2-bromoprop-2-enoate 2 (3.8 g, 21.23 mmol) in THF/H2O (5 ml, 8:2), were added tert-butyl 4-[4-(4,4,5,5-tetramethyl-1,3,2-dioxaborolan-2-yl)pyrazol-1-yl]piperidine-1-carboxylate 3 (11.21 g, 29.72 mmol) and Potassium phosphate tribasic anhydrous (22.53 g, 106.14 mmol) under nitrogen atmosphere. Reaction mixture was degassed for 10 minutes using argon and was added Xphos palladacycle Gen 3 (1.80 g, 2.12 mmol). Reaction mixture was heated to 60° C. for 16 hours. After completion of reaction, quenched with water and extracted with ethyl acetate (3×10 ml), organic layer concentrated under reduced pressure to afford tert-butyl 4-[4-(1-ethoxycarbonylvinyl)pyrazol-1-yl]piperidine-1-carboxylate 4 (7 g, 17.63 mmol, 83.05% yield, 88% purity) as gummy liquid which was used in next step (immediately) without further purification. LC MS: ES+ 350.4.

Step 3: Synthesis of tert-butyl 4-[4-(1-ethoxycarbonylcyclopropyl)pyrazol-1-yl]piperidine-1-carboxylate: To a stirred solution of (Me3SOI)BLAHmethane; iodide (5.59 g, 25.41 mmol) in DMSO (40 mL) was added Potassium tert-butoxide (2.38 g, 21.18 mmol) at room temperature and stirred for 45 min at ambient temperature. Then a solution of tert-butyl 4-[4-(1-ethoxycarbonylvinyl)pyrazol-1-yl]piperidine-1-carboxylate 4 (7.4 g, 21.18 mmol) intoluene (20 ml) and DMSO (20 ml) was added over 3 min. The reaction mixture was heated at 50° C. for 16 hours. Reaction mixture cooled to RT washed by cold water. Aqueous layer was extracted with ethyl acetate. Organic layer was dried over sodium sulphate, concentrated under reduced pressure. Crude material was purified by combiflash chromatography at 10% EA/Hexane to afford tert-butyl 4-[4-(1-ethoxycarbonylcyclopropyl)pyrazol-1-yl]piperidine-1-carboxylate 5 (3.8 g, 10.35 mmol, 48.88% yield, 99% purity) as gummy liquid. LC MS: ES+ 364.1.

Step 4: Synthesis of 1-[1-(1-tert-butoxycarbonyl-4-piperidyl)pyrazol-4-yl]cyclopropanecarboxylic acid: To a stirred solution of tert-butyl 4-[4-(1-ethoxycarbonylcyclopropyl)pyrazol-1-yl]piperidine-1-carboxylate 5 (3.8 g, 10.46 mmol) in THF (15 mL) (1:1) mixture was added Lithium hydroxide, monohydrate (658.06 mg, 15.68 mmol, 435.80 uL) and stirred the reaction mixture for 16 hours in 60° C. TLC showed un-reacted starting material. A small pinch of KOH was added and the reaction mixture was further heated at 60° C. for 16 hours. The reaction mixture was diluted with water and extracted with ethyl acetate; the aqueous layer was acidified with 2 (N) HCl to pH-5-6 and extracted with 20% IPA-DCM. The organic layer was washed with brine solution, dried over sodium sulfate and concentrated to afford 1-[1-(1-tert-butoxycarbonyl-4-piperidyl)pyrazol-4-yl]cyclopropanecarboxylic acid 6 (2.2 g, 6.49 mmol, 62.11% yield, 99% purity) as a white solid. LC MS: ES+ 336.2.

Step 5: Synthesis of tert-butyl 4-[4-[1-(1,3-dioxoisoindolin-2-yl)oxycarbonylcyclopropyl]pyrazol-1-yl]piperidine-1-carboxylate: A round-bottom flask equipped with a stir bar was charged with 1-[1-(1-tert-butoxycarbonyl-4-piperidyl)pyrazol-4-yl]cyclopropanecarboxylic acid 6 (1.27 g, 3.79 mmol), 2-hydroxyisoindoline-1,3-dione 7 (679.47 mg, 4.17 mmol) and DMAP (46.26 mg, 378.66 umol). DCM (15 mL) was added (0.1-0.5 M) followed by N,N'-diisopropylmethanediimine (525.65 mg, 4.17 mmol, 648.95 uL), and the mixture was allowed to stir vigorously for 2 hours. The mixture was filtered over Celite and rinsed with additional DCM. The solvent was removed under reduced pressure, and purification by column chromatography using (20-25% EtOAc-Hexane) as eluent afforded tert-butyl 4-[4-[1-(1,3-dioxoisoindolin-2-yl)oxycarbonylcyclopropyl]pyrazol-1-yl]piperidine-1-carboxylate 8 (1.8 g, 3.30 mmol, 87.06% yield, 88% purity) as sticky red. LC MS: ES+ 481.1.

Step 6: Synthesis of tert-butyl 4[-4-[1-(4,4,5,5-tetramethyl-1,3,2-dioxaborolan-2-yl)cyclopropyl]pyrazol-1-yl]piperidine-1-carboxylate: To a culture tube equipped with a stir bar were added tert-butyl 4-[4-[1-(1,3-dioxoisoindolin-2-yl)oxycarbonylcyclopropyl]pyrazol-1-yl]piperidine-1-carboxylate 8 (2.5 g, 5.20 mmol), 4,4,5,5-tetramethyl-2-(4,4,5,5-tetramethyl-1,3,2-dioxaborolan-2-yl)-1,3,2-dioxaborolane (3.96 g, 15.61 mmol), Lithium hydroxide, monohydrate (3.27 g, 78.04 mmol, 2.17 mL), dichloromagnesium (743.04 mg, 7.80 mmol) and copper;(Z)-4-oxopent-2-en-2-olate (408.57 mg, 1.56 mmol). The tube was evacuated and backfilled with argon for 3 times. Degassed Dioxane (14 mL) and DMF (6.5 mL) in 1:2 ratio was added and the resulting mixture was stirred under 1000 rpm at RT until dark brown colour was observed (typical reaction time <10 min). The reaction mixture was diluted with EtOAc and saturated solution of ammonium chloride, and the resulting mixture was shaken vigorously until getting a clear biphasic solution. The organic phase was collected and dried over anhydrous Na$_2$SO$_4$. It was evaporated and purified by silica gel chromatography using 15%-20% EtOAc-Hexane as eluent to afford tert-butyl 4-[4-[1-(4,4,5,5-tetramethyl-1,3,2-dioxaborolan-2-yl)cyclopropyl]pyrazol-1-yl]piperidine-1-carboxylate 9 (1.2 g, 2.73 mmol, 52.50% yield, 95% purity) as light yellow liquid. LC MS: ES+ 418.0.

Step 7: Synthesis of [1-[1-(1-tert-butoxycarbonyl-4-piperidyl)pyrazol-4-yl]cyclopropyl]-trifluoro-potassio-boron: To a stirred solution of tert-butyl 4-[4-[1-(4,4,5,5-tetramethyl-1,3,2-dioxaborolan-2-yl)cyclopropyl]pyrazol-1-yl]piperidine-1-carboxylate 9 (1.4 g, 3.35 mmol) in Methanol (10 mL) was added potassium; fluoride; hydrofluoride (2.10 g, 26.84 mmol) and stirred the reaction mixture at 80° C. for 16 hours. The reaction mixture was cooled to room temperature and concentrated. Resulting residue was triturated with 50% ether in heptane (50 mL) for 10 min. The precipitate was collected by filtration, and rinsed with 100% ether (The filtrate contained pinacol). The precipitate was dissolved in hot acetonitrile (100 mL) and filtered to remove KHF$_2$. The filtrate was collected and lyophilized to afford [1-[1-(1-tert-butoxycarbonyl-4-piperidyl)pyrazol-4-yl]cyclopropyl]-trifluoro-potassio-boron 10 (800 mg, 1.99 mmol, 59.43% yield, 99% purity) as floppy white solid. $^1$H NMR (400 MHz, DMSO-d6) δ 7.19 (s, 1H), 7.02 (s, 1H), 4.14 (m, 1H), 4.00-3.97 (m, 2H), 2.85-2.82 (m, 2H), 1.91-1.88 (m, 2H), 1.70-1.63 (m, 2H), 1.40 (s, 9H), 0.47 (s, 2H), 0.05 (s, 2H); LC MS: ES+ 339 (difluoro).

Step 8: Synthesis of tert-butyl 4-[4-[1-[1-[(4-methoxyphenyl)methyl]-2-oxo-benzo[cd]indol-6-yl]cyclopropyl]pyrazol-1-yl]piperidine-1-carboxylate: In a screw cap sealed tube fitted with a septum was added 6-bromo-1-[(4-methoxyphenyl)methyl]benzo[cd]indol-2-one 11 (1.48 g, 4.03 mmol) and [1-[1-(1-tert-butoxycarbonyl-4-piperidyl)pyrazol-4-yl]cyclopropyl]-trifluoro-potassio-boron 10 (800 mg, 2.01 mmol) in toluene (15.30 mL) and Water (1.70 mL) was added Cesium carbonate (1.97 g, 6.04 mmol). The resulting mixture was degassed by bubbling Argon for 10 minutes, cataCXium® A Palladacycle Gen. 3 (73.32 mg, 100.68 umol) was added to the reaction mixture. The reaction was then heated to 95° C. for 16 hours. Upon cooling to room temperature, the reaction solution was filtered through celite, eluting with EtOAc, and concentrated to get crude mass which was purified by Prep TLC using 30% EtOAc-Hexane as eluent to afford tert-butyl 4-[4-[1-[1-[(4-methoxyphenyl)methyl]-2-oxo-benzo[cd]indol-6-yl]cyclopropyl]pyrazol-1-yl]piperidine-1-carboxylate 12 (300 mg, 513.22 umol, 25.49% yield, 99% purity) as yellow solid. LC MS: ES+ 579.6.

Step 9: Synthesis of 6-[1-[1-(4-piperidyl)pyrazol-4-yl]cyclopropyl]-1H-benzo[cd]indol-2-one: To a stirred solution of tert-butyl 4-[4-[1-[1-[(4-methoxyphenyl)methyl]-2-oxo-benzo[cd]indol-6-yl]cyclopropyl]pyrazol-1-yl]piperidine-1-carboxylate 12 (300 mg, 518.40 umol) in TFA (4 mL) was added trifluoromethanesulfonic acid (778.02 mg, 5.18 mmol, 454.98 uL) at room temperature then reaction mixture was stirred at RT for over night. LCMS showed product mass response then reaction mixture was concentrated under reduced pressured to get 6-[1-[1-(4-piperidyl)pyrazol-4-yl]cyclopropyl]-1H-benzo[cd]indol-2-one 13 (180 mg, 354.32 umol, 68.35% yield, 93% purity) which was used in next step as crude mass of TFA salt. LC MS: ES+ 359.3.

Step 10: Synthesis of tert-butyl 4-[4-[1-(2-oxo-1H-benzo[cd]indol-6-yl)cyclopropyl]pyrazol-1-yl]piperidine-1-carboxylate: To a stirred solution of 6-[1-[1-(4-piperidyl)pyrazol-4-yl]cyclopropyl]-1H-benzo[cd]indol-2-one; 2,2,2-trifluoroacetic acid 13 (180 mg, 380.99 umol) in DCM (5 mL) was added Triethyl amine (115.66 mg, 1.14 mmol, 159.31 uL), followed by Di-tert-butyl dicarbonate (83.15 mg, 380.99 umol, 87.43 uL). It was stirred at room temperature for 16 hours. Reaction mixture was concentrated under reduced pressure, diluted with water, extracted with ethyl acetate, the organic layer was washed with saturated sodium bicarbonate solution, brine, dried over sodium sulfate and concentrated under reduced pressure. Crude material was purified by combi-flash eluting at 50% ethyl acetate in hexane to afford tert-butyl 4-[4-[1-(2-oxo-1H-benzo[cd]indol-6-yl)cyclopropyl]pyrazol-1-yl]piperidine-1-carboxylate 14 (160 mg, 345.44 umol, 90.67% yield, 99% purity) as yellow solid. LC MS: ES+459.4.

Step 11: Synthesis of tert-butyl 4-[4-[1-[1-(2,6-dioxo-3-piperidyl)-2-oxo-benzo[cd]indol-6-yl]cyclopropyl]pyrazol-1-yl]piperidine-1-carboxylate: To the stirred solution of tert-butyl 4-[4-[1-(2-oxo-1H-benzo[cd]indol-6-yl)cyclopropyl]pyrazol-1-yl]piperidine-1-carboxylate 14 (160 mg, 348.93 umol) in THF (5 mL) was added Sodium hydride (in oil dispersion) 60% dispersion in mineral oil (133.70 mg, 3.49 mmol, 60% purity) at cold condition and the reaction mixture was stirred at room temperature for 10 minutes followed by the addition of 3-bromopiperidine-2,6-dione 15 (334.99 mg, 1.74 mmol) portion wise. It was then stirred at room temperature for 10 minutes and heated at 70° C. for 30 minutes. The reaction mixture was diluted with ethyl acetate, washed with cold water and the organic fraction was separated. It was then dried over anhydrous sodium sulphate and evaporated under reduced pressure to obtain the crude which was washed with ether and pentane to afford tert-butyl 4-[4-[1-[1-(2,6-dioxo-3-piperidyl)-2-oxo-benzo[cd]indol-6-yl]cyclopropyl]pyrazol-1-yl]piperidine-1-carboxylate 16 (150 mg, 260.69 umol, 74.71% yield, 99% purity) as yellow solid. LC MS: ES+ 570.6.

Step 12: Synthesis of 3-[2-oxo-6-[1-[1-(4-piperidyl)pyrazol-4-yl]cyclopropyl]benzo[cd]indol-1-yl]piperidine-2,6-dione: To a stirred solution of tert-butyl 4-[4-[1-[1-(2,6-dioxo-3-piperidyl)-2-oxo-benzo[cd]indol-6-yl]cyclopropyl]pyrazol-1-yl]piperidine-1-carboxylate 16 (150 mg, 263.32 umol) in Dioxane (1 mL) and cooled the reaction mixture to 0° C. followed by drop wised addition of 4M HCl in Dioxane (4 mL), stirred the reaction mixture for 3 hours at RT. Reaction mixture was concentrated under reduced pressure and triturated with ether, dried to afford 3-[2-oxo-6-[1-[1-(4-piperidyl)pyrazol-4-yl]cyclopropyl]benzo[cd]indol-1-yl]piperidine-2,6-dione 17 (120 mg, 234.78 umol, 89.16% yield, 99% purity) as yellow solid. LC MS: ES+ 470.4.

Step 13: Synthesis of 3-[6-[1-[1-[1-(1-methylcyclobutanecarbonyl)-4-piperidyl]pyrazol-4-yl]cyclopropyl]-2-oxo-benzo[cd]indol-1-yl]piperidine-2,6-dione: To a stirred solution of 3-[6-[1-[1-(1-chloro-4-piperidyl)pyrazol-4-yl]cyclopropyl]-2-oxo-benzo[cd]indol-1-yl]piperidine-2,6- dione 17 (65 mg, 128.46 umol) in DMF (1 mL) was added 1-methylcyclobutanecarboxylic acid 18 (14.66 mg, 128.46 umol, 13.09 uL) followed by HATU (73.27 mg, 192.69 umol) and the reaction mixture was cooled to 0° C. was added DIPEA (83.01 mg, 642.30 umol, 111.87 uL), the reaction mixture was allowed to stirred at room temperature for overnight. Reaction mixture was diluted with water and was extracted with ethyl acetate, organic layer was washed with saturated sodium bicarbonate solution(3×) followed by water and brine, dried over sodium sulphate and concentrated under reduced pressure to get the crude product. The crude product thus obtained was purified by Prep TLC using 2% of MeOH in DCM as eluent to afford 3-[6-[1-[1-[1-(1-methylcyclobutanecarbonyl)-4-piperidyl]pyrazol-4-yl]cyclopropyl]-2-oxo-benzo[cd]indol-1-yl]piperidine-2,6-dione Compound 163 (55 mg, 92.37 umol, 71.91% yield, 95% purity) as light yellow solid. $^1$H NMR (400 MHz, DMSO-d6) δ 11.12 (s, 1H), 8.35 (d, J=8.24 Hz, 1H), 8.07 (d, J=6.96 Hz, 1H), 7.81 (t, J=7.62 Hz, 1H), 7.53 (d, J=7.32 Hz, 1H), 7.39 (s, 1H), 7.10-7.07 (m, 2H), 5.44 (dd, J=12.8, 5.16 Hz, 1H), 4.35-4.25 (m, 1H), 4.22-4.19 (m, 1H), 3.57-3.56 (m, 1H), 2.99-2.91 (m, 2H), 2.77-2.73 (m, 1H), 2.67-2.63 (m, 2H), 2.39-2.34 (m, 2H), 2.10-2.07 (m, 1H), 1.93-1.86 (m, 3H), 1.78-1.75 (m, 1H), 1.64-1.58 (m, 2H), 1.32 (br s, 5H), 1.23 (br s, 2H); LC MS: ES+ 566.5.

Step 14: Synthesis of 3-[6-[1-[1-[1-[(1-methylcyclobutyl)methyl]-4-piperidyl]pyrazol-4-yl]cyclopropyl]-2-oxo-benzo[cd]indol-1-yl]piperidine-2,6-dione: To the stirred solution of 3-[6-[1-[1-(1-chloro-4-piperidyl)pyrazol-4-yl]cyclopropyl]-2-oxo-benzo[cd]indol-1-yl]piperidine-2,6-dione 17 (40 mg, 79.05 umol) in THF (2 mL) was added Triethylamine (16.00 mg, 158.10 umol, 22.04 uL) followed by the addition of 1-methylcyclobutanecarbaldehyde 19 (7.76 mg, 79.05 umol, 7.68 uL), Dibutyltindichloride (28.82 mg, 94.86 umol, 21.19 uL) and Phenylsilane (8.55 mg, 79.05 umol, 9.74 uL). The reaction mixture was then stirred at 90° C. for 16 hours. The reaction mixture was diluted with ethyl acetate, washed with sodium bicarbonate solution, water and brine solution. The organic fraction was separated. It was dried over anhydrous sodium sulphate, evaporated under reduced pressure to obtain the crude compound which was purified by flash chromatography using 0-5% MeOH-DCM to afford 3-[6-[1-[1-[1-[(1-methylcyclobutyl)methyl]-4-piperidyl]pyrazol-4-yl]cyclopropyl]-2-oxo-benzo[cd]indol-1-yl]piperidine-2,6-dione Compound 164 (20 mg, 35.88 umol, 45.39% yield, 98.97% purity) as yellow solid. $^1$H NMR (400 MHz, DMSO-d6) δ 11.11 (s, 1H), 8.35 (d, J=8.32 Hz, 1H), 8.06 (d, J=6.48 Hz, 1H), 7.80 (t, J=7.72 Hz, 1H), 7.53 (d, J=7.56 Hz, 1H), 7.34 (s, 1H), 7.08-7.07 (m, 1H), 5.45-5.43 (m, 1H), 3.91-3.89 (m, 1H), 2.96-2.92 (m, 1H), 2.80-2.59 (m, 3H), 2.20 (s, 2H), 2.08-2.07 (m, 1H), 1.99-1.97 (m, 2H), 1.92-1.87 (m, 1H), 1.79-1.77 (m, 6H), 1.58-1.56 (m, 2H), 1.31-1.29 (m, 2H), 1.24-1.23 (m, 2H), 1.11 (s, 3H); LC MS: ES+ 552.3.

Example 77. Synthesis of 4-[4-[4-[[1-(2,6-dioxo-3-piperidyl)-2-oxo-benzo[cd]indol-6-yl]methyl]-N-methyl-anilino]-1-piperidyl]-3-fluoro-benzonitrile (Compound 165)

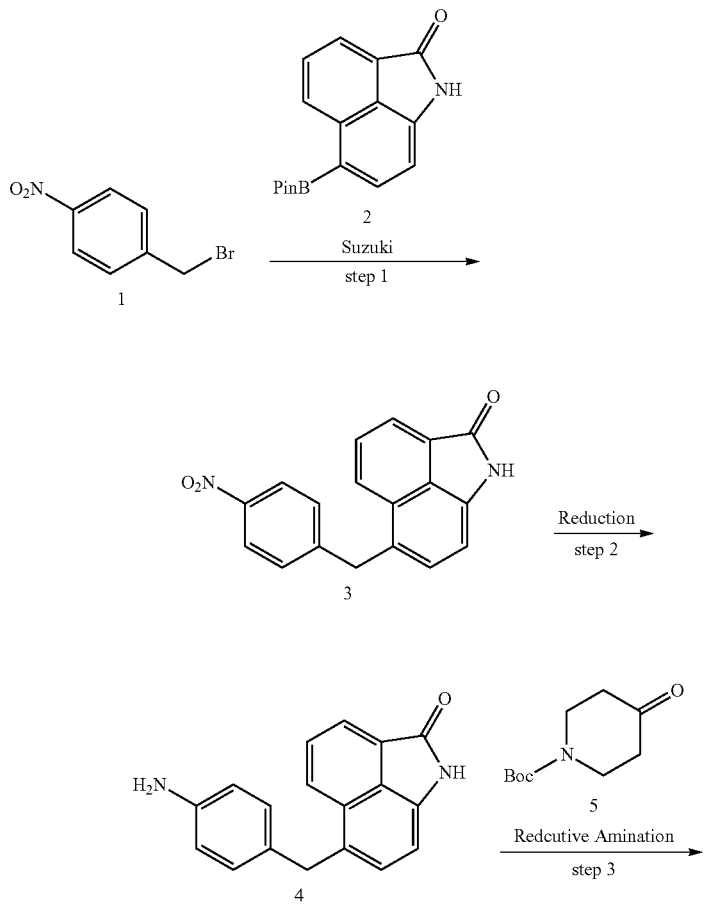

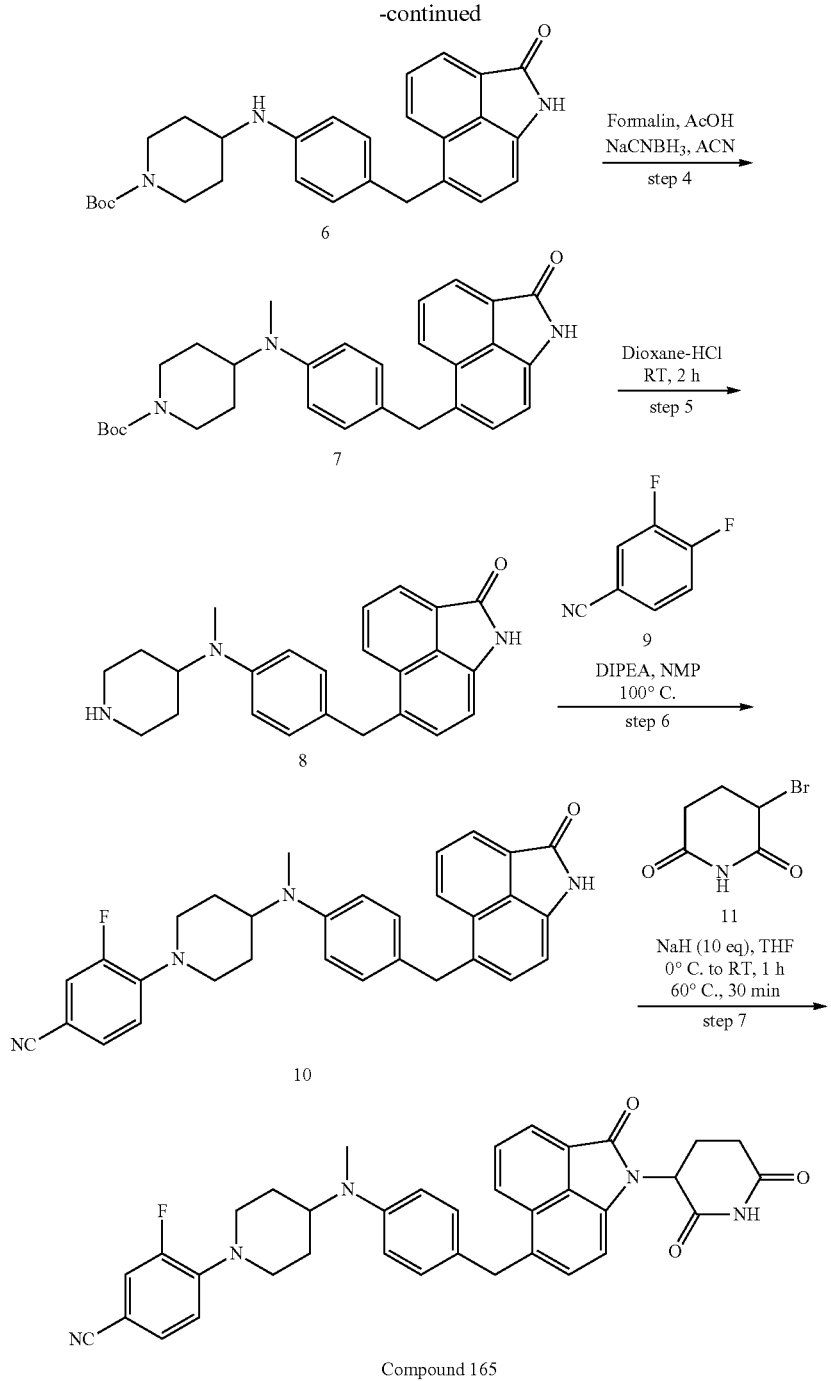

Compound 165

Step 1: Synthesis of 6-[(4-nitrophenyl)methyl]-1H-benzo[cd]indol-2-one: To a stirred solution of 1-(bromomethyl)-4-nitro-benzene (1) (10 g, 46.29 mmol) in toluene (60 mL) and Ethanol (30 mL) was added 6-(4,4,5,5-tetramethyl-1,3,2-dioxaborolan-2-yl)-1H-benzo[cd]indol-2-one (2) (20.49 g, 69.43 mmol) and Potassium phosphate tribasic anhydrous (29.48 g, 138.87 mmol). The resultant reaction mixture was degassed with Argon for 10 min then Pd2(dba)3 (4.24 g, 4.63 mmol) and Tri-o-Tolyl phosphine (2.82 g, 9.26 mmol) were added and the reaction was heated at 100° C. for 16 hr. After completion of the reaction (monitored by TLC) the reaction mixture was diluted with ethyl acetate and washed with water and brine, dried over sodium sulphate and concentrated. The crude was purified by column chromatography in 100-200 silica in 40-50% EtOAc in hexane to afford 6-[(4-nitrophenyl)methyl]-1H-benzo[cd]indol-2-one (3) (5 g, 28.40% yield) as brown solid. LC MS: ES+ 305.21.

Step 2: Synthesis of 6-[(4-aminophenyl)methyl]-1H-benzo[cd]indol-2-one: To a stirred solution of 6-[(4-nitrophenyl)methyl]-1H-benzo[cd]indol-2-one (3) (5 g, 16.43 mmol) in Methanol (50 mL) Argon gas was purged for 10 min then Pd-C (2.99 g, 24.65 mmol) was added and the reaction was stirred under Hydrogen atmosphere (Balloon) for 16 hours at RT. The reaction mixture was filtered through celite and washed with 10% MeOH in DCM. The filtrate thus obtained was concentrated under reduced pressure to afford 6-[(4-aminophenyl)methyl]-1H-benzo[cd]indol-2-one (4) (3.5 g, 63.67% yield) as brown solid. LC MS: ES+ 275.15.

Step 3: Synthesis of tert-butyl 4-[4-[(2-oxo-1H-benzo[cd]indol-6-yl)methyl]anilino]piperidine-1-carboxylate: To a stirred solution of 6-[(4-aminophenyl)methyl]-1H-benzo[cd]indol-2-one (4) (1.75 g, 6.38 mmol) in THF (30 mL) was added tert-butyl 4-oxopiperidine-1-carboxylate (5) (1.40 g, 7.02 mmol) followed by the addition of Dibutyltindichloride (2.33 g, 7.66 mmol, 1.71 mL) and Phenylsilane (690.33 mg, 6.38 mmol, 786.25 uL). The reaction mixture was then stirred at 90° C. for 16 hours in a sealed tube. The reaction mixture was diluted with ethyl acetate, washed with sodium bicarbonate solution, water and brine solution. The organic fraction was separated. It was dried over anhydrous sodium sulphate, evaporated under reduced pressure to obtain the crude compound which was purified by combiflash chromatography using 30-40% EtOAc in DCM to afford tert-butyl 4-[4-[(2-oxo-1H-benzo[cd]indol-6-yl)methyl]anilino]piperidine-1-carboxylate (6) (1.3 g, 39.64% yield) as yellow solid. LC MS: ES+ 458.4.

Step 4: Synthesis of tert-butyl 4-[N-methyl-4-[(2-oxo-1H-benzo[cd]indol-6-yl)methyl]anilino] piperidine-1-carboxylate: To a stirred solution of tert-butyl 4-[4-[(2-oxo-1H-benzo[cd]indol-6-yl)methyl]anilino]piperidine-1-carboxylate (6) (550 mg, 1.20 mmol) in Acetonitrile (7 mL) was added Formaldehyde, 37% w/w aq. soln., (360.61 mg, 12.02 mmol, 1 mL) and Acetic acid (1.01 g, 16.83 mmol, 962.42 uL) at 0° C. and the reaction mixture was stirred at that temperature for 1 hour. Then to it was added Sodium cyanoborohydride (196.39 mg, 3.13 mmol) at that temperature and the reaction was slowly warmed to RT and continued for 16 hours. After completion of the reaction (monitored by TLC) the reaction mixture was diluted with ethyl acetate, washed with water and brine solution. The organic fraction was dried over anhydrous sodium sulphate and evaporated under reduced pressure to obtain the crude which was purified by combiflash column (Gradient 15% EtOAc in DCM) to afford tert-butyl 4-[N-methyl-4-[(2-oxo-1H-benzo[cd]indol-6-yl)methyl]anilino]piperidine-1-carboxylate (7) (350 mg, 55.57% yield) as greenish yellow solid. LC MS: ES+ 472.4.

Step 5: Synthesis of 6-[[4-[methyl(4-piperidyl)amino]phenyl]methyl]-1H-benzo[cd]indol-2-one; hydrochloride salt: To a stirred solution of tert-butyl 4-[N-methyl-4-[(2-oxo-1H-benzo[cd]indol-6-yl)methyl]anilino]piperidine-1-carboxylate (7) (350 mg, 742.17 umol) in Dioxane (5 mL) was added Dioxane-HCl (742.17 umol, 15 mL) and the reaction was stirred at RT for 3 hours. After completion of the reaction (monitored by TLC) The reaction mixture was concentrated to dryness and triturated with ether to afford 6-[[4-[methyl(4-piperidyl)amino]phenyl]methyl]-1H-benzo[cd]indol-2-one; hydrochloride (8) (300 mg, 79.27% yield) as yellow solid. LC MS: ES+ 372.2.

Step 6: Synthesis of 3-fluoro-4-[4-[N-methyl-4-[(2-oxo-1H-benzo[cd]indol-6-yl)methyl]anilino]-1-piperidyl]benzonitrile: To a stirred solution of 6-[[4-[methyl(4-piperidyl)amino]phenyl]methyl]-1H-benzo[cd]indol-2-one; hydrochloride (8) (300 mg, 735.41 umol) in NMP (4 mL) was added DIPEA (475.22 mg, 3.68 mmol, 640.46 uL) followed by 3,4-difluorobenzonitrile (9) (102.30 mg, 735.41 umol) and the resulting reaction mixture was stirred at 90° C. for 16 hours. After completion (monitored by TLC) the reaction mixture was diluted with ethyl acetate and washed with water and brine, dried over sodium sulphate and concentrated. The crude was purified by combiflash column in 30% EtOAc in DCM to afford 3-fluoro-4-[4-[N-methyl-4-[(2-oxo-1H-benzo[cd]indol-6-yl)methyl]anilino]-1-piperidyl]benzonitrile (10) (100 mg, 20.51% yield) as yellow gum. LC MS: ES+ 491.4.

Step 7: Synthesis of 4-[4-[4-[[1-(2,6-dioxo-3-piperidyl)-2-oxo-benzo[cd]indol-6-yl]methyl]-N-methyl-anilino]-1-piperidyl]-3-fluoro-benzonitrile: To a stirred solution of 3-fluoro-4-[4-[N-methyl-4-[(2-oxo-1H-benzo[cd]indol-6-yl)methyl]anilino]-1-piperidyl]benzonitrile (10) (100 mg, 203.84 umol) in THF (5 mL) was added Sodium hydride (in oil dispersion) 60% dispersion in mineral oil (46.86 mg, 2.04 mmol) at 0° C. and stirred for 5 min. Then 3-bromopiperidine-2,6-dione (11) (195.70 mg, 1.02 mmol) was added under cooling condition and the reaction mixture was stirred at 70° C. for 30 min. After completion (monitored by TLC) the reaction mixture was quenched in ice and extracted with ethyl acetate. The organic part was further washed with water and brine, dried over sodium sulfate and concentrated. The crude was purified by Prep TLC Plate in 20% EtOAc in DCM to afford 4-[4-[4-[[1-(2,6-dioxo-3-piperidyl)-2-oxo-benzo[cd]indol-6-yl]methyl]-N-methyl-anilino]-1-piperidyl]-3-fluoro-benzonitrile Compound 165 (35 mg, 28.18% yield) as yellow solid. $^1$H NMR (400 MHz, DMSO-d6) δ 11.11 (s, 1H), 8.33 (d, J=8.24 Hz, 1H), 8.06 (d, J=6.96 Hz, 1H), 7.80 (t, J=7.58 Hz, 1H), 7.68-7.65 (m, 1H), 7.54 (d, J=8.44 Hz, 1H), 7.36 (d, J=7.24 Hz, 1H), 7.15-7.07 (m, 4H), 6.75 (d, J=8.52 Hz, 2H), 5.43 (dd, J=12.24, 5.08 Hz, 1H), 4.26 (s, 2H), 3.78-3.76 (m, 1H), 3.63-3.60 (m, 2H), 2.96-2.90 (m, 3H), 2.77-2.73 (m, 1H), 2.66-2.62 (m, 4H), 2.08-2.07 (m, 1H), 1.80-1.74 (m, 2H), 1.68-1.65 (m, 2H); LC MS: ES+602.2.

Example 78. Synthesis of 4-[4-[4-[[1-(2,6-dioxo-3-piperidyl)-2-oxo-benzo[cd]indol-6-yl]methyl]anilino]-1-piperidyl]-3-fluoro-benzonitrile (Compound 166)

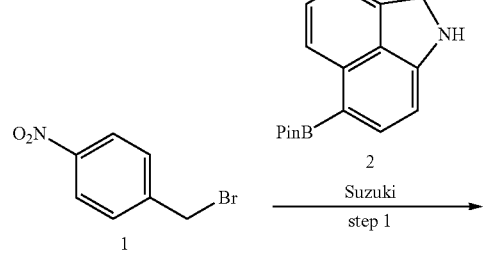

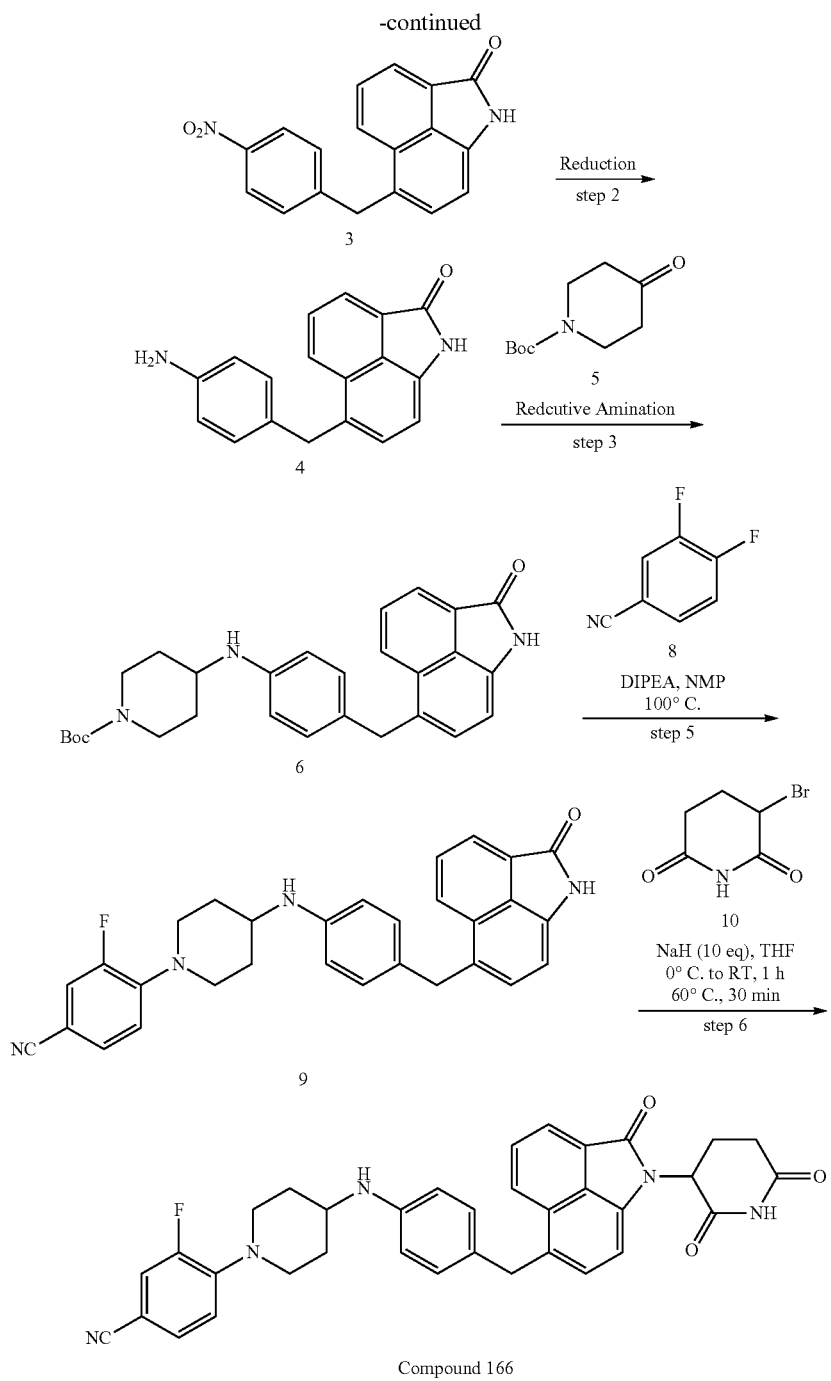

Compound 166

Step 1: Synthesis of 6-[(4-nitrophenyl)methyl]-1H-benzo[cd]indol-2-one: To a stirred solution of 1-(bromomethyl)-4-nitro-benzene (1) (10 g, 46.29 mmol) in toluene (60 mL) and Ethanol (30 mL) was added 6-(4,4,5,5-tetramethyl-1,3,2-dioxaborolan-2-yl)-1H-benzo[cd]indol-2-one (2) (20.49 g, 69.43 mmol) and Potassium phosphate tribasic anhydrous (29.48 g, 138.87 mmol). The resultant reaction mixture was degassed with Argon for 10 min then Pd2(dba)3 (4.24 g, 4.63 mmol) and Tri-o-Tolyl phosphine (2.82 g, 9.26 mmol) were added and the reaction was heated at 100° C. for 16 hours. After completion of the reaction (monitored by TLC) the reaction mixture was diluted with ethyl acetate and washed with water and brine, dried over sodium sulphate and concentrated. The crude was purified by column chromatography (silica, gradient: 40-50% EtOAc in Hexane) to afford 6-[(4-nitrophenyl)methyl]-1H-benzo[cd]indol-2-one (3) (5 g, 28.40% yield) as brown solid. LC MS: ES+ 305.21.

Step 2: Synthesis of 6-[(4-aminophenyl)methyl]-1H-benzo[cd]indol-2-one: To a stirred solution of 6-[(4-nitrophenyl)methyl]-1H-benzo[cd]indol-2-one (3) (5 g, 16.43 mmol) in Methanol (50 mL) Argon gas was purged for 10 min then Pd-C (2.99 g, 24.65 mmol) was added and the reaction was stirred under Hydrogen atmosphere (Balloon) for 16 hours at RT. The reaction mixture was filtered through celite and washed with 10% MeOH in DCM. The filtrate thus obtained was concentrated under reduced pressure to afford 6-[(4-aminophenyl)methyl]-1H-benzo[cd]indol-2-one (4) (3.5 g, 63.67% yield) as brown solid. LC MS: ES+ 275.15.

Step 3: Synthesis of tert-butyl 4-[4-[(2-oxo-1H-benzo[cd]indol-6-yl)methyl]anilino]piperidine-1-carboxylate: To a stirred solution of 6-[(4-aminophenyl)methyl]-1H-benzo[cd]indol-2-one (4) (1.75 g, 6.38 mmol) in THF (30 mL) was added tert-butyl 4-oxopiperidine-1-carboxylate (5) (1.40 g, 7.02 mmol) followed by the addition of Dibutyltindichloride (2.33 g, 7.66 mmol, 1.71 mL) and Phenylsilane (690.33 mg, 6.38 mmol, 786.25 uL). The reaction mixture was then stirred at 90° C. for 16 hours in a sealed tube. After completion of the reaction (monitored by TLC) the reaction mixture was diluted with ethyl acetate, washed with sodium bicarbonate solution, water and brine solution. The organic fraction was separated. It was dried over anhydrous sodium sulphate, evaporated under reduced pressure to obtain the crude compound which was purified by combiflash chromatography using 30-40% EtOAc in DCM to afford tert-butyl 4-[4-[(2-oxo-1H-benzo[cd]indol-6-yl)methyl]anilino]piperidine-1-carboxylate (6) (1.3 g, 39.64% yield) as yellow solid. LC MS: ES+458.4.

Step 4: Synthesis of 6-[[4-(4-piperidylamino)phenyl]methyl]-1H-benzo[cd]indol-2-one; hydrochloride salt: To a stirred solution of tert-butyl 4-[4-[(2-oxo-1H-benzo[cd]indol-6-yl)methyl]anilino]piperidine-1-carboxylate (6) (500 mg, 1.09 mmol) in Dioxane HCl (5 mL) was added Dioxan-HCl (15 mL) and the reaction mixture was stirred at RT for 3 hours. After completion of the reaction (monitored by TLC) The reaction mixture was concentrated to dryness and triturated with ether to afford 6-[[4-(4-piperidylamino)phenyl]methyl]-1H-benzo[cd]indol-2-one; hydrochloride (7) (350 mg, 81.31% yield) as yellow solid. LC MS: ES+ 357.1.

Step 5: Synthesis of 3-fluoro-4-[4-[4-[(2-oxo-1H-benzo[cd]indol-6-yl)methyl]anilino]-1-piperidyl]benzonitrile: To a stirred solution of 6-[[4-(4-piperidylamino)phenyl]methyl]-1H-benzo[cd]indol-2-one; hydrochloride (7) (350 mg, 888.53 umol) in DMF (4 mL) was added DIPEA (574.18 mg, 4.44 mmol, 773.83 uL) followed by 3,4-difluorobenzonitrile (8) (123.60 mg, 888.53 umol) and the resulting reaction mixture was stirred at 90° C. for 16 hours. After completion of the reaction (monitored by TLC) the reaction mixture was diluted with ethyl acetate and washed with water and brine, dried over sodium sulphate and concentrated. The crude was purified by combiflash column in 30% EtOAc in DCM to afford 3-fluoro-4-[4-[4-[(2-oxo-1H-benzo[cd]indol-6-yl)methyl]anilino]-1-piperidyl]benzonitrile (9) (200 mg, 33.06% yield) as yellow gum. LC MS: ES+ 477.3.

Step 6: Synthesis of 4-[4-[4-[[1-(2,6-dioxo-3-piperidyl)-2-oxo-benzo[cd]indol-6-yl]methyl]anilino]-1-piperidyl]-3-fluoro-benzonitrile: To a stirred solution of 3-fluoro-4-[4-[4-[(2-oxo-1H-benzo[cd]indol-6-yl)methyl]anilino]-1-piperidyl]benzonitrile (9) (70 mg, 146.89 umol) in THF (5 mL) was added Sodium hydride (in oil dispersion) 60% dispersion in mineral oil (56.28 mg, 1.47 mmol, 60% purity) at 0° C. and stirred for 5 min. Then 3-bromopiperidine-2,6-dione (10) (141.02 mg, 734.46 umol) was added under cooling condition and the reaction was stirred at 70° C. for 30 min. After completion of the reaction (monitored by TLC) the reaction mixture was quenched in ice and extracted with ethyl acetate. The organic part was further washed with water and brine, dried over sodium sulfate and concentrated. The crude was purified by Prep TCL Plate in 20% EtOAc in DCM to afford 4-[4-[4-[[1-(2,6-dioxo-3-piperidyl)-2-oxo-benzo[cd]indol-6-yl]methyl]anilino]-1-piperidyl]-3-fluoro-benzonitrile Compound 166 (30 mg, 34.21% yield) as yellow solid. ¹H NMR (400 MHz, DMSO-d6) δ 11.11 (s, 1H), 8.32 (d, J=8.44 Hz, 1H), 8.06 (d, J=6.88 Hz, 1H), 7.80 (t, J=7.76 Hz, 1H), 7.67-7.64 (m, 1H), 7.54 (d, J=8.36 Hz, 1H), 7.34 (d, J=7.0 Hz, 1H), 7.14-7.06 (m, 2H), 6.99 (d, J=8.12 Hz, 2H), 6.52 (d, J=Hz, 2H), 5.45-5.42 (m, 1H), 5.35 (d, J=8.52 Hz, 1H), 4.21 (s, 2H), 3.54-3.51 (m, 2H), 2.98-2.92 (m, 4H), 2.76-2.73 (m, 1H), 2.66-2.63 (m, 1H), 2.09-2.07 (m, 1H), 1.98-1.94 (m, 2H), 1.46-1.43 (m, 2H)LC MS: ES+ 588.2.

Example 79. Synthesis of 3-[6-[[4-[4-(1-methylcyclobutanecarbonyl)piperazin-1-yl]phenyl]methyl]-2-oxo-benzo[cd]indol-1-yl]piperidine-2,6-dione (Compound 167)

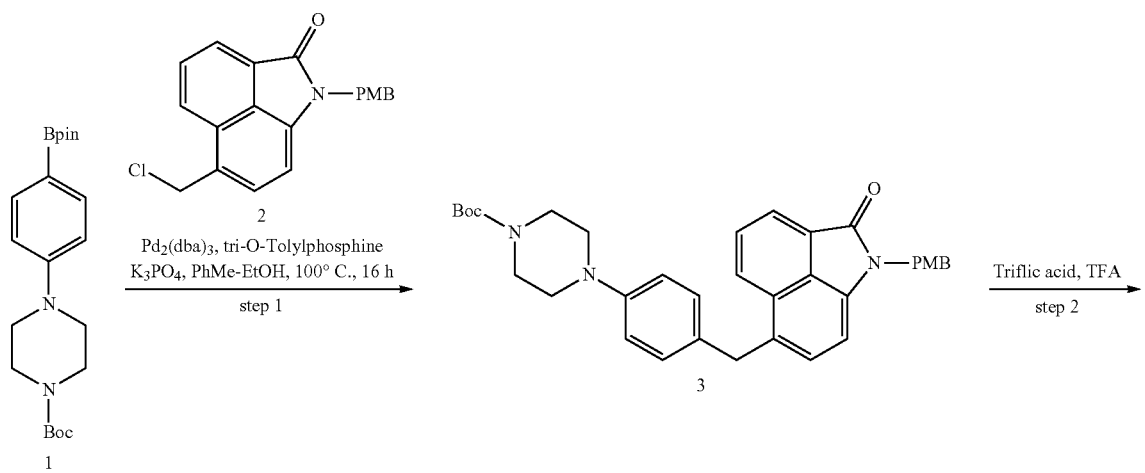

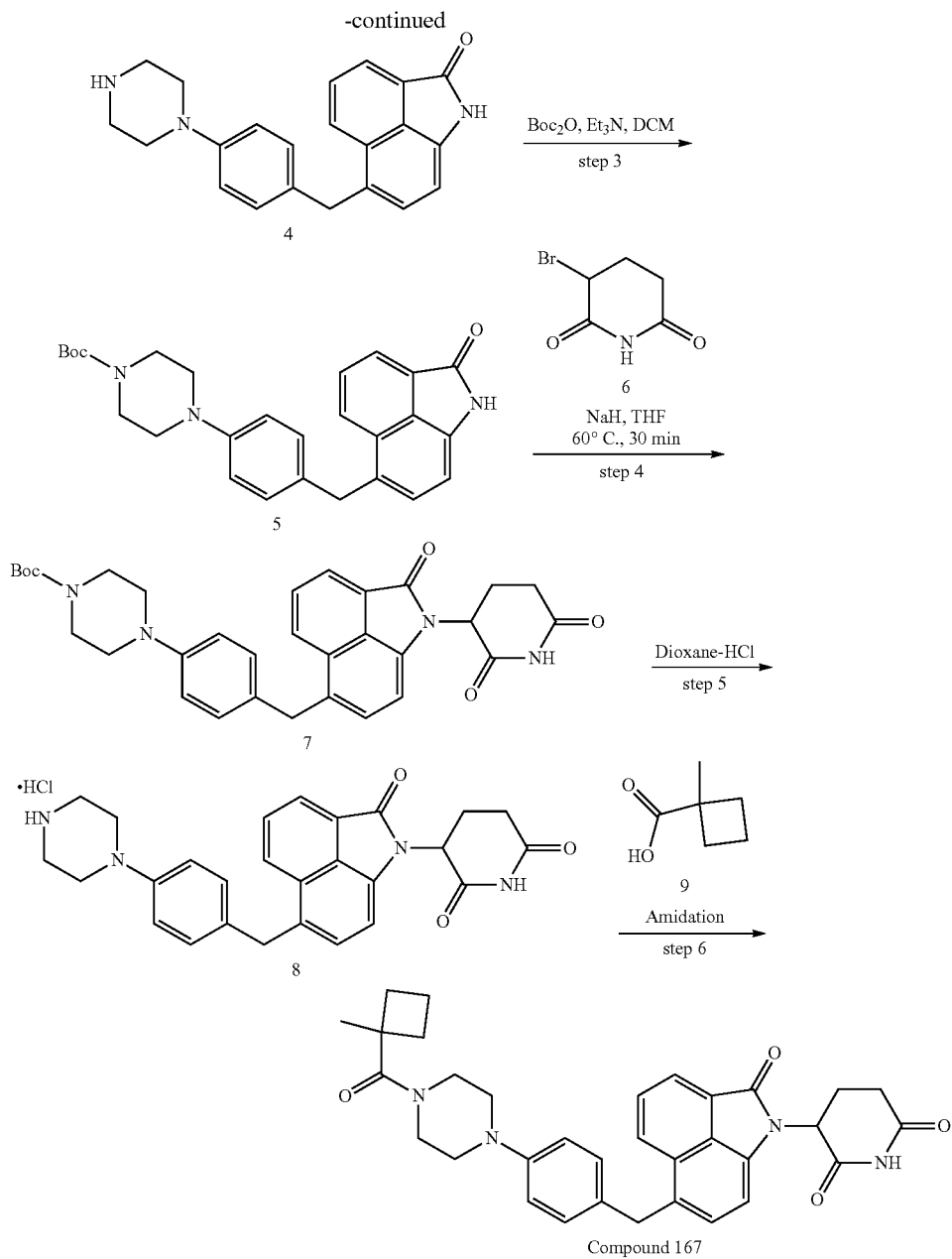

Step 1: Synthesis of tert-butyl 4-[4-[[1-[(4-methoxyphenyl)methyl]-2-oxo-benzo[cd]indol-6-yl]methyl]phenyl]piperazine-1-carboxylate: To a stirred solution of tert-butyl 4-[4-(4,4,5,5-tetramethyl-1,3,2-dioxaborolan-2-yl)phenyl]piperazine-1-carboxylate (1) (1.4 g, 3.61 mmol) and 6-(chloromethyl)-1-[(4-methoxyphenyl)methyl]benzo[cd]indol-2-one (2) (2.44 g, 7.21 mmol) intoluene (30 mL) and Ethanol (10 mL) was added Potassium phosphate tribasic anhydrous (2.30 g, 10.82 mmol) and the reaction mass was degassed with nitrogen for 10 minutes. Then Tri-o-Tolyl phosphine (219.47 mg, 721.08 umol) and (1E,4E)-1,5-diphenylpenta-1,4-dien-3-one; palladium (330.15 mg, 360.54 umol) were added and it was heated at 90° C. for 16 hours. After completion (monitored by TLC) the reaction mixture was passed through celite bed and washed with EtOAc. The filtrate was then washed with water and brine, dried over sodium sulphate and concentrated. The crude thus obtained was purified by combiflash column in (gradient: 0-30% EtOAc in DCM) to afford the desired compound tert-butyl 4-[4-[[1-[(4-methoxyphenyl)methyl]-2-oxo-benzo[cd]indol-6-yl]methyl]phenyl]piperazine-1-carboxylate (3) (1.4 g, 41.33% yield) as brown gum. LC MS: ES+ 564.2.

Step 2: Synthesis of 6-[(4-piperazin-1-ylphenyl)methyl]-1H-benzo[cd]indol-2-one: To a stirred solution of tert-butyl 4-[4-[[1-[(4-methoxyphenyl)methyl]-2-oxo-benzo[cd]indol-6-yl]methyl]phenyl]piperazine-1-carboxylate (3) (2.2 g, 3.90 mmol) in TFA (10 mL) was added trifluoromethanesulfonic acid (5.86 g, 39.03 mmol, 3.43 mL) under cooling condition. Then the reaction mixture was stirred at room temperature for 16 hr. After completion (monitored by TLC and LCMS) the reaction mass was quenched with saturated bicarbonate solution and extracted with ethyl acetate (twice). The combined organic part was dried over Sodium sulphate and concentrated under reduced pressure to afford 6-[(4-piperazin-1-ylphenyl)methyl]-1H-benzo[cd]indol-2-one (4) (1.3 g, 67.89% yield) as brown gum. LC MS: ES+ 344.1.

Step 3: Synthesis of tert-butyl 4-[4-[(2-oxo-1H-benzo[cd] indol-6-yl)methyl]phenyl]piperazine-1-carboxylate: To a stirred solution of 6-[(4-piperazin-1-ylphenyl)methyl]-1H-benzo[cd]indol-2-one (4) (1.3 g, 3.79 mmol) in DCM (20 mL) was added Triethyl Amine (1.15 g, 11.36 mmol, 1.58 mL) under cooling condition. Then Di-tert-butyl dicarbonate (991.41 mg, 4.54 mmol, 1.04 mL) was added and the resultant reaction mixture was stirred at room temperature for 16 h. After completion (monitored by TLC) the reaction mixture was diluted with DCM and washed with water and brine, dried over $Na_2SO_4$ and concentrated under reduced pressure. The crude thus obtained was purified by combi-flash column (gradient: 0-30% EtOAc in DCM) to afford pure compound tert-butyl 4-[4-[(2-oxo-1H-benzo[cd]indol-6-yl)methyl]phenyl]piperazine-1-carboxylate (5) (730 mg, 42.10% yield) as yellow solid. LC MS: ES+ 444.5.

Step 4: Synthesis of tert-butyl 4-[4-[[1-(2,6-dioxo-3-piperidyl)-2-oxo-benzo[cd]indol-6-yl]methyl] phenyl]piperazine-1-carboxylate: To a stirred solution of tert-butyl 4-[4-[(2-oxo-1H-benzo[cd]indol-6-yl)methyl]phenyl]piperazine-1-carboxylate (5) (700 mg, 1.58 mmol) in dry THF (15 mL) was added Sodium hydride 60% dispersion in mineral oil (604.72 mg, 15.78 mmol) at 0° C. and stirred for 15 minutes followed by the addition of 3-bromopiperidine-2,6-dione (6) (1.97 g, 10.26 mmol). After completion (monitored by TLC) the reaction mixture was quenched in ice and extracted with ethyl acetate. The organic part was further washed with water and brine, dried over sodium sulfate and concentrated. The crude was purified by Combiflash column (30% EtOAc in DCM) to afford tert-butyl 4-[4-[[1-(2,6-dioxo-3-piperidyl)-2-oxo-benzo[cd]indol-6-yl]methyl]phenyl]piperazine-1-carboxylate (7) (700 mg, 70.37% yield) as yellow solid. LC MS: ES+ 555.3.

Step 5: Synthesis of 3-[2-oxo-6-[(4-piperazin-1-ylphenyl) methyl]benzo[cd]indol-1-yl]piperidine-2,6-dione; Hydrochloride salt: To a stirred solution of tert-butyl 4-[4-[[1-(2, 6-dioxo-3-piperidyl)-2-oxo-benzo[cd]indol-6-yl]methyl] phenyl]piperazine-1-carboxylate (7) (700 mg, 1.26 mmol) in Dioxane (3 mL) was added Dioxane-HCl (15 mL) at 0° C. and the resulting reaction mixture was stirred at room temperature for 3 hours. After completion (monitored by TLC) the reaction mixture was concentrated under reduced pressure. The crude was triturated with ether to afford the desired compound 3-[2-oxo-6-[(4-piperazin-1-ylphenyl) methyl]benzo[cd]indol-1-yl]piperidine-2,6-dione; Hydrochloride salt (8) (550 mg, 86.19% yield) as yellow solid. LC MS: ES+ 455.5.

Step 6: Synthesis of 3-[6-[[4-[4-(1-methylcyclobutanecarbonyl)piperazin-1-yl]phenyl]methyl]-2-oxo-benzo[cd]indol-1-yl]piperidine-2,6-dione: To a stirred solution of 1-methylcyclobutanecarboxylic acid (9) (50.23 mg, 440.03 umol) in DMF (5 mL) were added DIPEA (284.34 mg, 2.20 mmol, 383.21 uL) and HATU (200.77 mg, 528.03 umol). The resultant reaction mixture was then stirred at RT for 15 minutes followed by the addition of 3-[2-oxo-6-[(4-piperazin-1-ylphenyl)methyl]benzo[cd]indol-1-yl]piperidine-2, 6-dione (8) (200 mg, 440.03 umol) and stirred at RT for 16 hours. After completion (monitored by LCMS), the reaction mixture was diluted with Ethyl acetate and washed with cold water, brine, dried over sodium sulphate and concentrated under reduced pressure. The crude thus obtained was purified by Prep TLC Plate (50% ethyl acetate in DCM) to afford the desired compound 3-[6-[[4-[4-(1-methylcyclobutanecarbonyl)piperazin-1-yl]phenyl]methyl]-2-oxo-benzo[cd]indol-1-yl]piperidine-2,6-dione Compound 167 (84.0 mg, 34.04% yield) as light yellow solid. $^1$H NMR (400 MHz, DMSO-d6) δ 11.09 (s, 1H), 8.28 (d, J=8.28 Hz, 1H), 8.03 (d, J=6.92 Hz, 1H), 7.76 (t, J=7.62 Hz, 1H), 7.34 (d, J=7.32 Hz, 1H), 7.13-7.05 (m, 3H), 6.82 (d, J=8.44 Hz, 2H), 5.40 (dd, J=12.88, 5.44 Hz, 1H), 4.26 (s, 2H), 3.52-3.50 (m, 2H), 3.30-3.29 (m, 2H), 2.98 (br s, 4H), 2.92-2.86 (m, 1H), 2.75-2.70 (m, 1H), 2.64-2.60 (m, 1H), 2.47-2.33 (m, 2H), 2.07-2.04 (m, 1H), 1.90-1.85 (m, 1H), 1.78-1.73 (m, 2H), 1.59-1.56 (m, 1H), 1.31 (s, 3H); LC MS: ES+ 551.2.

Example 80. Synthesis of 3-[6-[[4-[4-[(1-methylcyclobutyl)methyl]piperazin-1-yl]phenyl]methyl]-2-oxo-benzo[cd]indol-1-yl]piperidine-2,6-dione (Compound 168)

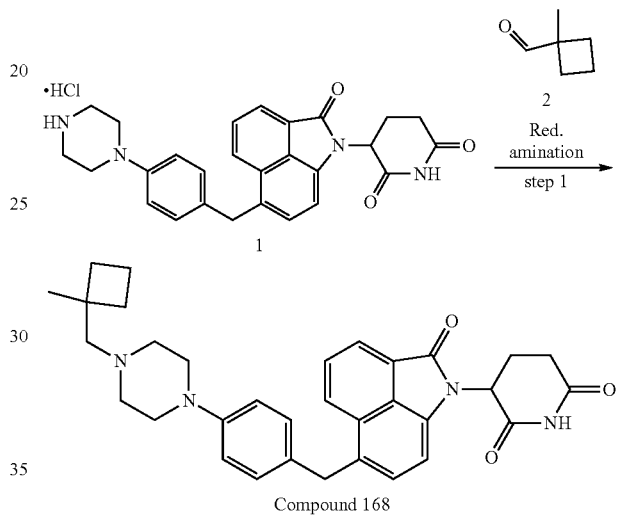

Compound 168

Step-1: Synthesis of 3-[6-[[4-[4-[(1-methylcyclobutyl) methyl]piperazin-1-yl]phenyl]methyl]-2-oxo-benzo[cd]indol-1-yl]piperidine-2,6-dione: To a stirred solution of 3-[6-[[4-(4-chloropiperazin-1-yl)phenyl]methyl]-2-oxo-benzo [cd]indol-1-yl]piperidine-2,6-dione (1) (200.0 mg, 407.35 umol) in THF (6 mL) was added Triethylamine (82.44 mg, 814.70 umol, 113.55 uL) followed by the addition of 1-methylcyclobutanecarbaldehyde (2) (39.98 mg, 407.35 umol, 39.19 uL), Dibutyltindichloride (148.53 mg, 488.82 umol, 109.21 uL) and Phenylsilane (44.08 mg, 407.35 umol, 50.20 uL). The reaction mixture was then stirred at 90° C. for 16 hours. After completion (monitored by TLC and LCMS) the reaction mass was quenched with saturated bicarbonate solution and extracted with ethyl acetate. The organic layer was separated and washed with brine, dried over sodium sulphate and concentrated under reduced pressure. The crude this obtained was purified by combiflash chromatography (gradient: 0-1% MeOH in DCM) to afford the desired compound 3-[6-[[4-[4-[(1-methylcyclobutyl) methyl]piperazin-1-yl]phenyl]methyl]-2-oxo-benzo[cd]indol-1-yl]piperidine-2,6-dione Compound 168 (70 mg, 30.42% yield) as light yellow solid. $^1$H NMR (400 MHz, DMSO-d6) δ 11.11 (s, 1H), 8.31 (d, J=8.24 Hz, 1H), 8.06 (d, J=6.96 Hz, 1H), 7.79 (t, J=7.62 Hz, 1H), 7.36 (d, J=7.32 Hz, 1H), 7.11-7.07 (m, 3H), 6.80 (d, J=8.44 Hz, 2H), 5.43 (dd, J=12.76, 5.04 Hz, 1H), 4.27 (s, 2H), 3.00-2.99 (m, 4H), 2.94-2.90 (m, 1H), 2.77-2.72 (m, 1H), 2.66-2.62 (m, 1H), 2.40 (br s, 4H), 2.24 (s, 2H), 2.10-2.07 (m, 1H), 1.94-1.90 (m, 1H), 1.86-1.82 (m, 2H), 1.79-1.71 (m, 1H), 1.62-1.58 (m, 2H), 1.15 (s, 3H); LC MS: ES+536.9.

Example 81. Synthesis of 3-[6-[[4-[1-(1-methylcyclobutanecarbonyl)-4-piperidyl]phenyl]methyl]-2-oxo-benzo[cd]indol-1-yl]piperidine-2,6-dione (Compound 169)
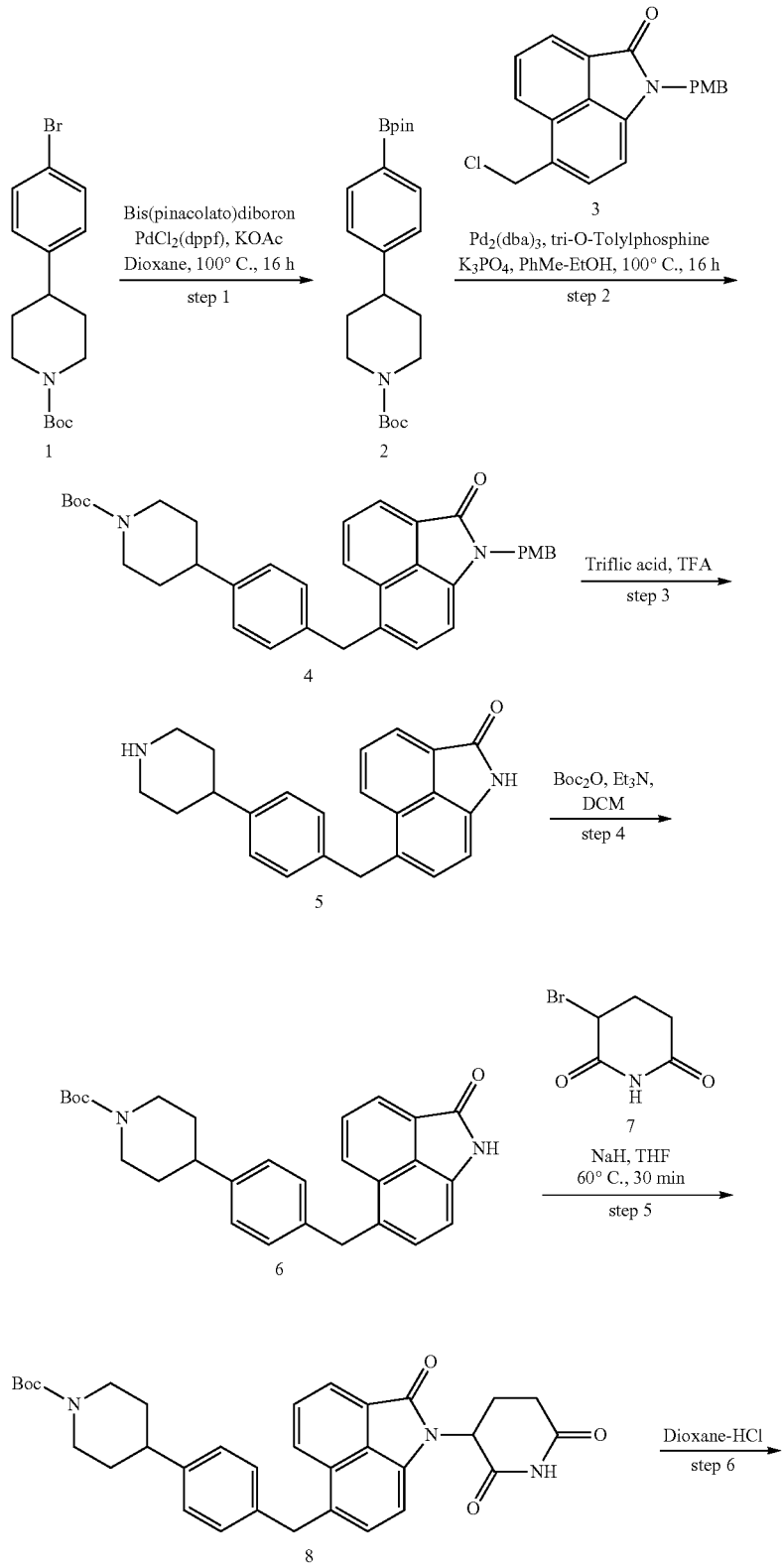

-continued

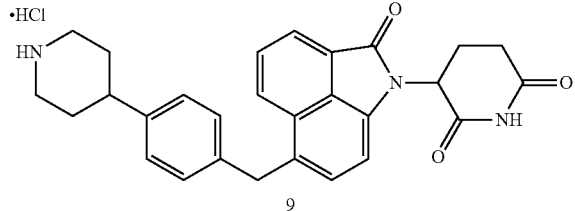

9

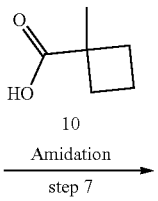

10

Amidation
step 7

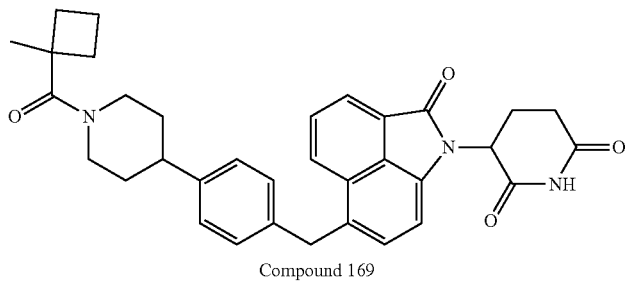 [SMILES: CC1(C(=O)N2CCC(c3ccc(Cc4ccc5c6c(cccc46)C(=O)N5C4CCC(=O)NC4=O)cc3)CC2)CCC1]

Compound 169

Step 1: Synthesis of tert-butyl 4-[4-(4,4,5,5-tetramethyl-1,3,2-dioxaborolan-2-yl)phenyl]piperidine-1-carboxylate:
To a stirred solution of tert-butyl 4-(4-bromophenyl)piperidine-1-carboxylate (1) (2 g, 5.88 mmol) in 1,4-dioxane (40 mL) was added Bis(pinacolato)Diboron (2.24 g, 8.82 mmol) and potassiumn;acetate (1.73 g, 17.63 mmol). Then Nitrogen gas was purged for 15 minutes. Followed by the addition of cyclopentyl(diphenyl)phosphane; dichloromethane; dichloropalladium; iron (480.02 mg, 587.80 umol). The resultant reaction mixture was then stirred at 90° C. for 16 hours. After completion (monitored by TLC and LCMS) the reaction mixture was filtered through celite pad and washed with ethyl acetate. The filtrate was then washed with water and brine, dried over sodium sulphate and concentrated to afford tert-butyl 4-[4-(4,4,5,5-tetramethyl-1,3,2-dioxaborolan-2-yl)phenyl]piperidine-1-carboxylate (2) (2.2 g, 96.63% yield). LC MS: ES+ 388.5.

Step 2: Synthesis of tert-butyl 4-[4-[[1-[(4-methoxyphenyl)methyl]-2-oxo-benzo[cd]indol-6-yl]methyl]phenyl]piperidine-1-carboxylate: To a stirred solution of 4-[4-(4,4,5,5-tetramethyl-1,3,2-dioxaborolan-2-yl)phenyl]piperidine-1-carboxylate (2) (2.06 g, 5.33 mmol) and 6-(chloromethyl)-1-[(4-methoxyphenyl)methyl]benzo[cd]indol-2-one (3) (1.5 g, 4.44 mmol) intoluene (32 mL) and Ethanol (16 mL) was added Potassium phosphate tribasic anhydrous (2.83 g, 13.32 mmol) and the reaction mass was degassed with nitrogen for 10 minutes. Then Tri-o-Tolyl phosphine (270.31 mg, 888.10 umol) and (1E,4E)-1,5-diphenylpenta-1,4-dien-3-one; palladium (406.63 mg, 444.05 umol) were added and it was heated at 90° C. for 16 h. After completion (monitored by TLC) the reaction mixture was passed through celite bed and washed with EtOAc. The filtrate was then washed with water and brine, dried over sodium sulphate and concentrated. The crude thus obtained was purified by combiflash column in (gradient: 0-20% EtOAc in Hexane) to afford the desired compound tert-butyl 4-[4-[[1-[(4-methoxyphenyl) methyl]-2-oxo-benzo[cd]indol-6-yl]methyl]phenyl]piperidine-1-carboxylate (4) (1.5 g, 57.03% yield) as off white solid. LC MS: ES+ 563.06.

Step 3: Synthesis of 6-[[4-(4-piperidyl)phenyl]methyl]-1H-benzo[cd]indol-2-one: To a stirred solution of tert-butyl 4-[4-[[1-[(4-methoxyphenyl)methyl]-2-oxo-benzo[cd]indol-6-yl]methyl]phenyl]piperidine-1-carboxylate (4) (1.8 g, 3.20 mmol) in TFA (5 mL) was added trifluoromethanesulfonic acid (4.80 g, 31.99 mmol, 2.81 mL) under cooling condition. Then the reaction mixture was stirred at room temperature for 16 hours. After completion (monitored by TLC and LCMS) the reaction mass was quenched with saturated bicarbonate solution and extracted with ethyl acetate (twice). The combined organic part was dried over Sodium sulphate and concentrated under reduced pressure to afford 6-[[4-(4-piperidyl)phenyl]methyl]-1H-benzo[cd]indol-2-one (5) (800 mg, 65.73% yield) as brown gum. LC MS: ES+ 343.1.

Step 4: Synthesis of tert-butyl-4-[4-[(2-oxo-1H-benzo[cd] indol-6-yl)methyl]phenyl]piperidine-1-carboxylate: To a stirred solution of 6-[[4-(4-piperidyl)phenyl]methyl]-1H-benzo[cd]indol-2-one (5) (800 mg, 2.34 mmol) in DCM (20 mL) was added Triethyl Amine (709.21 mg, 7.01 mmol, 976.87 uL) under cooling condition. Then Di-tert-butyl dicarbonate (611.85 mg, 2.80 mmol, 643.37 uL) was added and the resultant reaction mixture was stirred at room temperature for 16 h. After completion (monitored by TLC) the reaction mixture was diluted with DCM and washed with water and brine, dried over $Na_2SO_4$ and concentrated under reduced pressure. The crude thus obtained was purified by combi-flash column (gradient: 0-20% EtOAc in DCM) to afford pure compound tert-butyl 4-[4-[(2-oxo-1H-benzo[cd] indol-6-yl)methyl]phenyl]piperidine-1-carboxylate (6) (400 mg, 36.75% yield) as yellow solid. LC MS: ES+ 387.6, (M-56 Present).

Step 5: Synthesis of 4-[4-[[1-(2,6-dioxo-3-piperidyl)-2-oxo-benzo[cd]indol-6-yl]methyl]phenyl]piperidine-1-carboxylate: To a stirred solution of tert-butyl 1-[4-[(2-oxo-1H-benzo[cd]indol-6-yl)methyl]phenyl]piperidine-4-carboxylate (6) (400 mg, 903.86 umol) in dry THF (10 mL) was added Sodium hydride 60% dispersion in mineral oil (519.49 mg, 13.56 mmol) at 0° C. and stirred for 15 minutes followed by the addition of 3-bromopiperidine-2,6-dione (7) (867.75 mg, 4.52 mmol). After completion (monitored by TLC) the reaction mixture was quenched in ice and extracted with ethyl acetate. The organic part was further washed with water and brine, dried over sodium sulfate and concentrated. The crude was purified by Combiflash column (30% EtOAC in DCM) to afford 4-[4-[[1-(2,6-dioxo-3-piperidyl)-2-oxo-benzo[cd]indol-6-yl]methyl]phenyl]piperidine-1-carboxylate (8) (300 mg, 53.95% yield) as yellow solid. LC MS: ES+ 454.5, (M+H)-100 present).

Step 6: Synthesis of 3-[2-oxo-6-[[4-(4-piperidyl)phenyl]methyl]benzo[cd]indol-1-yl]piperidine-2,6-dione; Hydrochloride salt: To a stirred solution of tert-butyl tert-butyl 1-[4-[[1-(2,6-dioxo-3-piperidyl)-2-oxo-benzo[cd]indol-6-yl]methyl]phenyl]piperidine-4-carboxylate (8) (300 mg, 541.86 umol) in Dioxane (3 mL) was added Dioxane-HCl (10 mL) at 0° C. and the resulting reaction mixture was stirred at room temperature for 3 hours. After completion (monitored by TLC) the reaction mixture was concentrated under reduced pressure. The crude was triturated with Ether-Pentane to afford the desired compound 3-[2-oxo-6-[[4-(4-piperidyl)phenyl]methyl]benzo[cd]indol-1-yl]piperidine-2,6-dione (9) (260 mg, 97.03% yield) as yellow solid. LC MS: ES+ 454.38.

Step 7: Synthesis of 3-[6-[[4-[1-(1-methylcyclobutanecarbonyl)-4-piperidyl]phenyl]methyl]-2-oxo-benzo[cd]indol-1-yl]piperidine-2,6-dione: To the stirred solution of 3-[2-oxo-6-[[4-(4-piperidyl)phenyl]methyl]benzo[cd]indol-1-yl]piperidine-2,6-dione (9) (110 mg, 242.54 umol) and 1-methylcyclobutanecarboxylic acid (10) (27.68 mg, 242.54 umol) in DMF (50 mL) was added DIPEA (156.73 mg, 1.21 mmol, 211.23 uL) and stirred for 15 minutes followed by the addition of HATU (110.67 mg, 291.05 umol) and was allowed to stir for 16 hours at RT. After completion (monitored by LCMS), the reaction mixture was diluted with Ethyl acetate and washed with cold water, brine, dried over sodium sulphate and concentrated under reduced pressure. The crude thus obtained was purified by column chromatography (silica, gradient: 0-2% MeOH in DCM) to afford 3-[6-[[4-[1-(1-methylcyclobutanecarbonyl)-4-piperidyl]phenyl]methyl]-2-oxo-benzo[cd]indol-1-yl]piperidine-2,6-dione Compound 169 (72.0 mg, 53.75% yield) as light yellow solid. $^1$H NMR (400 MHz, DMSO-d6) δ 11.11 (s, 1H), 8.33 (d, J=8.2 Hz, 1H), 8.06 (d, J=6.92 Hz, 1H), 7.80 (t, J=7.58 Hz, 1H), 7.40 (d, J=7.2 Hz, 1H), 7.22-7.19 (m, 2H), 7.15-7.07 (m, 3H), 5.43 (dd, J=12.52, 5.0 Hz, 1H), 4.47-4.45 (m, 1H), 4.34 (s, 2H), 3.58-3.57 (m, 1H), 2.99-2.88 (m, 2H), 2.80-2.56 (m, 4H), 2.41-2.39 (m, 2H), 2.10-2.07 (m, 1H), 1.93-1.84 (m, 1H), 1.77-1.70 (m, 4H), 1.63-1.61 (m, 1H), 1.58-1.40 (m, 2H), 1.33 (s, 3H); LC MS: ES+ 550.3.

Example 82. Synthesis of 3-[6-[[4-[1-[(1-methylcyclobutyl)methyl]-4-piperidyl]phenyl]methyl]-2-oxo-benzo[cd]indol-1-yl]piperidine-2,6-dione (Compound 170)

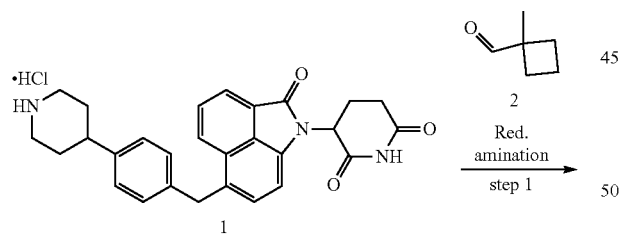

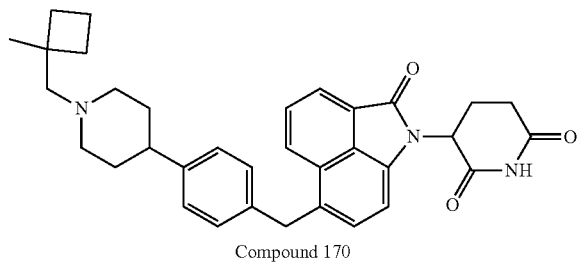

Compound 170

Step 1: Synthesis of 3-[6-[[4-[1-[(1-methylcyclobutyl)methyl]-4-piperidyl]phenyl]methyl]-2-oxo-benzo[cd]indol-1-yl]piperidine-2,6-dione: To a stirred solution of 3-[6-[[4-(1-chloro-4-piperidyl)phenyl]methyl]-2-oxo-benzo[cd]indol-1-yl]piperidine-2,6-dione (1) (200 mg, 408.17 umol) in THF (6 mL) was added Triethylamine (82.44 mg, 814.70 umol, 113.55 uL) followed by the addition of 1-methylcyclobutanecarbaldehyde (2) (40.06 mg, 408.17 umol, 39.27 uL), Dibutyltindichloride (148.83 mg, 489.80 umol, 109.43 uL) and Phenylsilane (44.17 mg, 408.17 umol, 50.31 uL). The reaction mixture was then stirred at 90° C. for 48 hours in a sealed tube. After completion (monitored by TLC and LCMS) the reaction mass was quenched with saturated bicarbonate solution and extracted with ethyl acetate. The organic layer was separated and washed with brine, dried over sodium sulphate and concentrated under reduced pressure. The crude this obtained was purified by combiflash chromatography (gradient: 0-1% MeOH in DCM) to afford the desired compound 3-[6-[[4-[1-[(1-methylcyclobutyl)methyl]-4-piperidyl]phenyl]methyl]-2-oxo-benzo[cd]indol-1-yl]piperidine-2,6-dione Compound 170 (50 mg, 22.87% yield) as light yellow solid. $^1$H NMR (400 MHz, DMSO-d6) δ 11.11 (s, 1H), 8.33 (d, J=8.24 Hz, 1H), 8.07 (d, J=6.96 Hz, 1H), 7.80 (t, J=7.62 Hz, 1H), 7.42-7.40 (m, 1H), 7.25-7.18 (m, 2H), 7.13-7.09 (m, 3H), 5.46-5.43 (m, 1H), 4.34 (s, 2H), 3.33-3.31 (m, 1H), 3.13-3.10 (m, 1H), 2.96-2.92 (m, 1H), 2.78-2.74 (m, 2H), 2.70-2.62 (m, 1H), 2.33-2.31 (m, 1H), 2.21 (s, 1H), 2.10-2.07 (m, 1H), 1.99-1.72 (m, 6H), 1.62-1.60 (m, 4H), 1.31-1.30 (m, 1H), 1.14 (s, 2H); LC MS: ES+536.3.

Example 83. Synthesis of 4-[4-[4-[[1-(2,6-dioxo-3-piperidyl)-2-oxo-benzo[cd]indol-6-yl]methyl]phenoxy]-1-piperidyl]-3-fluoro-benzonitrile (Compound 171)

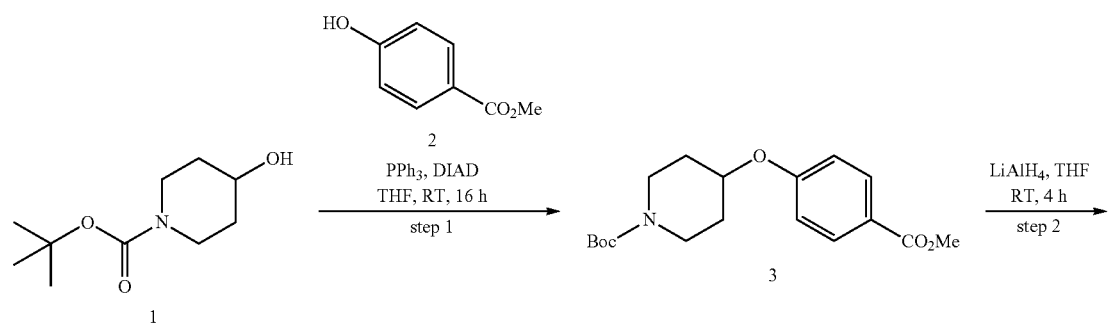

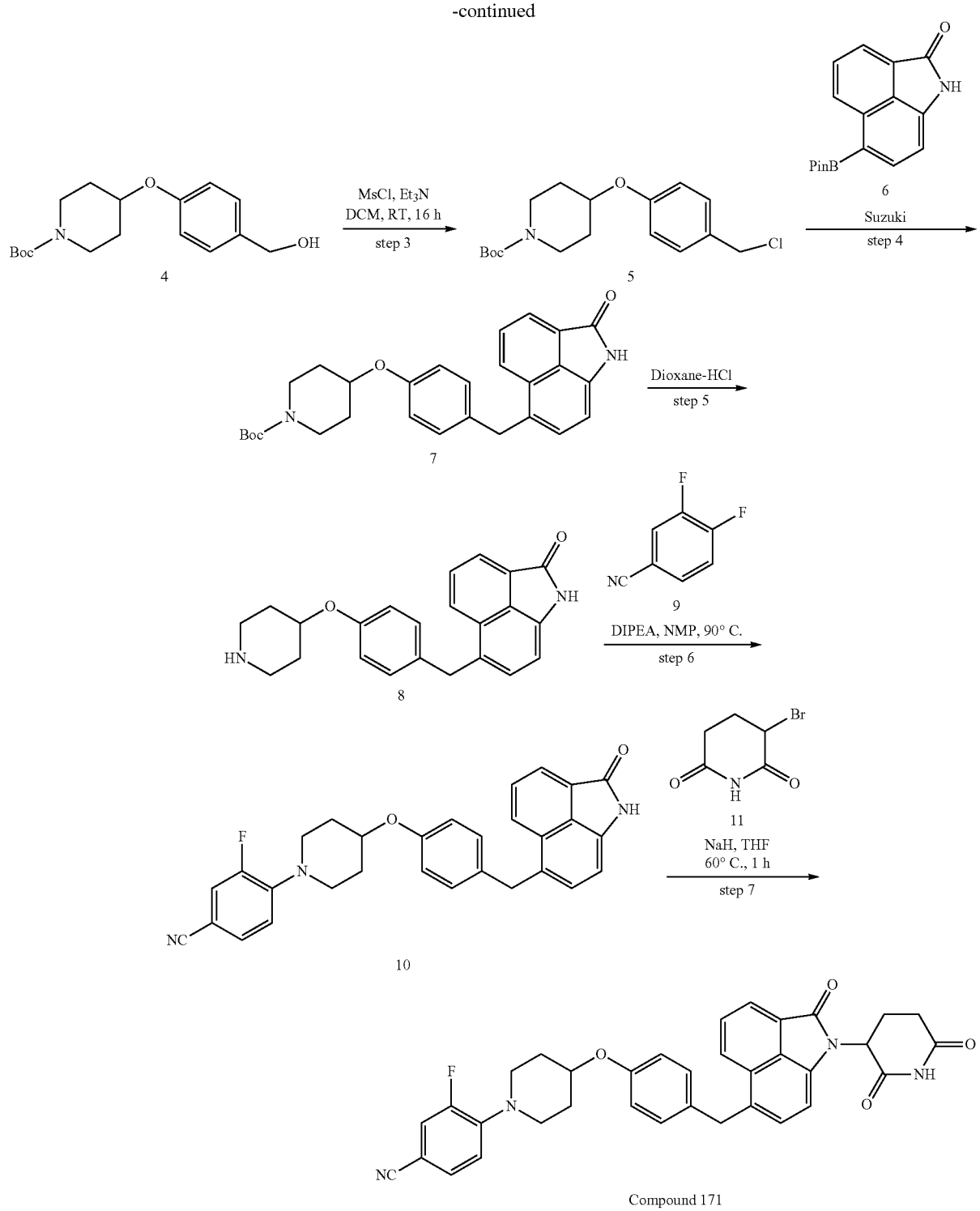

Compound 171

Step 1: Synthesis of tert-butyl 4-(4-methoxycarbonylphenoxy)piperidine-1-carboxylate: To a stirred solution of Triphenylphosphine (3.91 g, 14.91 mmol) in THF (20 mL) was added Diisopropyl azodicarboxylate (3.01 g, 14.91 mmol, 2.93 mL) at 0° C. and it was stirred at room temperature for 15 minutes when the solution became turbid, to it was added methyl 4-hydroxybenzoate (1) (2 g, 13.15 mmol) followed by the addition of tert-butyl 4-hydroxypiperidine-1-carboxylate (2) (2 g, 9.94 mmol) and the reaction was continued at room temperature for 16 hours. After completion of the reaction (monitored by TLC) the reaction mixture was evaporated under reduced pressure and purified by column chromatography (Silica; gradient 10-15% EtOAc in Hexane) to afford tert-butyl 4-(4-methoxycarbonylphenoxy) piperidine-1-carboxylate (3) (1.8 g, 53.25% yield) as a white solid. LC MS: ES+(M-100) 236.2.

Step 2: Synthesis of tert-butyl 4-[4-(hydroxymethyl)phenoxy]piperidine-1-carboxylate: To a stirred solution of tert-butyl 4-(4-methoxycarbonylphenoxy)piperidine-1-carboxylate (3) (1.8 g, 5.37 mmol) in THF (20 mL) was added Lithium aluminium hydride (728.22 mg, 21.47 mmol) (portion wise) under cooling condition and the reaction was stirred at RT for 16 h. After completion of the reaction (monitored by TLC) the reaction mixture was diluted with THF and cooled to 0° C. and to it was added Water (0.8 mL) followed by 15% aqueous NaOH (0.8 mL) and Water (2.4 mL) and then the reaction mixture was warmed to RT and stirred for 15 min. Then it was filtered off and the filtrate was dried under reduced pressure. The crude was again diluted with ethyl acetate and washed with water and brine, dried over sodium sulfate and concentrated to afford tert-butyl 4-[4-(hydroxymethyl)phenoxy]piperidine-1-carboxylate (4) (1.2 g, 63.29% yield) as a white solid. LC MS: ES+(M-100) 208.

Step 3: Synthesis of tert-butyl 4-[4-(chloromethyl)phenoxy]piperidine-1-carboxylate: To a stirred solution of tert-butyl 4-[4-(hydroxymethyl)phenoxy]piperidine-1-carboxylate (4) (800 mg, 2.60 mmol) in DCM (15 mL) was added Triethylamine (1.32 g, 13.01 mmol, 1.81 mL) under cooling condition and the reaction was stirred for 5 min. Then Mesyl Chloride (1.19 g, 10.41 mmol, 805.76 uL) was added and the reaction was allowed to warm to RT and stirred for 16 hours. After completion of the reaction (monitored by TLC) the reaction mixture was diluted with DCM and washed with sat sodium bicarbonate and brine, dried over sodium sulphate and concentrated to afford tert-butyl 4-[4-(chloromethyl)phenoxy]piperidine-1-carboxylate (5) (800 mg, 75.47% yield) as yellow sticky gum.

Step 4: Synthesis of tert-butyl 4-[4-[(2-oxo-1H-benzo[cd]indol-6-yl)methyl]phenoxy]piperidine-1-carboxylate: To a stirred solution of tert-butyl 4-[4-(chloromethyl)phenoxy]piperidine-1-carboxylate (5) (800 mg, 2.46 mmol) in toluene (12 mL) and Ethanol (6 mL) was added 6-(4,4,5,5-tetramethyl-1,3,2-dioxaborolan-2-yl)-1H-benzo[cd]indol-2-one (6) (1.09 g, 3.68 mmol) and Potassium phosphate tribasic anhydrous (1.56 g, 7.37 mmol). The resultant reaction mixture was degassed with Argon for 10 min then Pd2(dba)3 (224.68 mg, 245.53 umol) and Tri-o-Tolyl phosphine (149.46 mg, 491.05 umol) were added and the reaction was heated at 100° C. for 16 hr. After completion (monitored by TLC), the reaction mixture was diluted with ethyl acetate and washed with water and brine, dried over sodium sulphate and concentrated. The crude thus obtained was purified by combiflash column (Gradient 20-30% EtOAc in DCM) to afford tert-butyl 4-[4-[(2-oxo-1H-benzo[cd]indol-6-yl)methyl]phenoxy]piperidine-1-carboxylate (7) (400 mg, 31.98% yield) as yellow solid. LC MS: ES+ 459.5.

Step 5: Synthesis of 6-[[4-(4-piperidyloxy)phenyl]methyl]-1H-benzo[cd]indol-2-one; hydrochloride: Dioxane-HCl (5 mL) was added to tert-butyl 4-[4-[(2-oxo-1H-benzo[cd]indol-6-yl)methyl]phenoxy]piperidine-1-carboxylate (7) (400 mg, 872.32 umol) and the resultant reaction mixture was stirred at RT for 2 hours. After completion of the reaction (monitored by TLC), the reaction mixture was evaporated to dryness and triturated with ether to afford 6-[[4-(4-piperidyloxy)phenyl]methyl]-1H-benzo[cd]indol-2-one; hydrochloride (8) (340 mg, 72.29% yield) as yellow solid. LC MS: ES+ 359.3.

Step 6: Synthesis of 3-fluoro-4-[4-[4-[(2-oxo-1H-benzo[cd]indol-6-yl)methyl]phenoxy]-1-piperidyl]benzonitrile: To a stirred solution of 6-[[4-(4-piperidyloxy)phenyl]methyl]-1H-benzo[cd]indol-2-one; hydrochloride (8) (340 mg, 860.99 umol) in NMP (5 mL) was added DIPEA (556.39 mg, 4.30 mmol, 749.85 uL) followed by 3,4-difluorobenzonitrile (9) (119.77 mg, 860.99 umol) and the resulting reaction mixture was stirred at 90° C. for 16 hours. After completion of the reaction (monitored by TLC), the reaction mixture was diluted with ethyl acetate and washed with water and brine, dried over sodium sulphate and concentrated. The crude was purified by combiflash column (gradient 0-30% EtOAc in DCM) to afford 3-fluoro-4-[4-[4-[(2-oxo-1H-benzo[cd]indol-6-yl)methyl]phenoxy]-1-piperidyl]benzonitrile (10) (120 mg, 27.14% yield) as yellow gum. LC MS: ES+ 478.3.

Step 7: Synthesis of 4-[4-[4-[[1-(2,6-dioxo-3-piperidyl)-2-oxo-benzo[cd]indol-6-yl]methyl]phenoxy]-1-piperidyl]-3-fluoro-benzonitrile: To a stirred solution of 3-fluoro-4-[4-[4-[(2-oxo-1H-benzo[cd]indol-6-yl)methyl]phenoxy]-1-piperidyl]benzonitrile (10) (120 mg, 251.29 umol) in THF (5 mL) was added Sodium hydride 60% dispersion in mineral oil (57.77 mg, 2.51 mmol) at 0° C. and stirred for 5 min. Then 3-bromopiperidine-2,6-dione (11) (241.26 mg, 1.26 mmol) was added under cooling condition and the reaction was stirred at 70° C. for 30 min. After completion of the reaction (monitored by TLC) the reaction mixture was quenched in ice and extracted with ethyl acetate. The organic part was further washed with water and brine, dried over sodium sulphate and concentrated. The crude was purified by Prep TCL Plate in 20% EtOAc in DCM to afford 4-[4-[4-[[1-(2,6-dioxo-3-piperidyl)-2-oxo-benzo[cd]indol-6-yl]methyl]phenoxy]-1-piperidyl]-3-fluoro-benzonitrile Compound 171 (85 mg, 55.19% yield) as yellow solid. $^1$H NMR (400 MHz, DMSO-d6) δ 11.11 (s, 1H), 8.33 (d, J=8.24 Hz, 1H), 8.07 (d, J=6.72 Hz, 1H), 7.81 (t, J=7.62 Hz, 1H), 7.69-7.65 (m, 1H), 7.54 (d, J=7.2 Hz, 1H), 7.39 (d, J=7.28 Hz, 1H), 7.21-7.08 (m, 4H), 6.89 (d, J=8.44 Hz, 1H), 5.45-5.41 (m, 1H), 4.52-4.51 (m, 1H), 4.32 (s, 2H), 3.41-3.35 (m, 2H), 3.11-3.07 (m, 2H), 2.96-2.90 (m, 1H), 2.77-2.73 (m, 1H), 2.66-2.62 (m, 1H), 2.09-2.07 (m, 1H), 2.01-2.00 (m, 2H), 1.73-1.72 (m, 2H) LC MS: ES+ 589.3.

Example 84. Synthesis of 4-[4-[[4-[[1-(2,6-dioxo-3-piperidyl)-2-oxo-benzo[cd]indol-6 yl]methyl]phenyl]methyl]-3-oxo-piperazin-1-yl]-3-fluoro-benzonitrile (Compound 172)

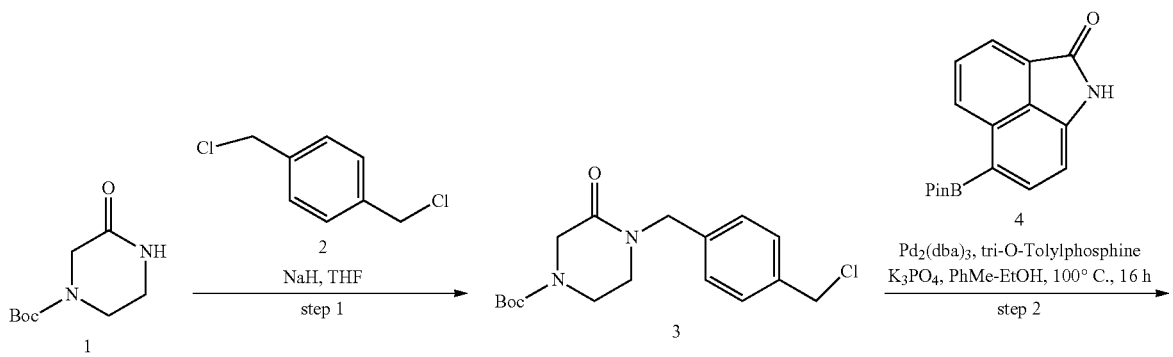

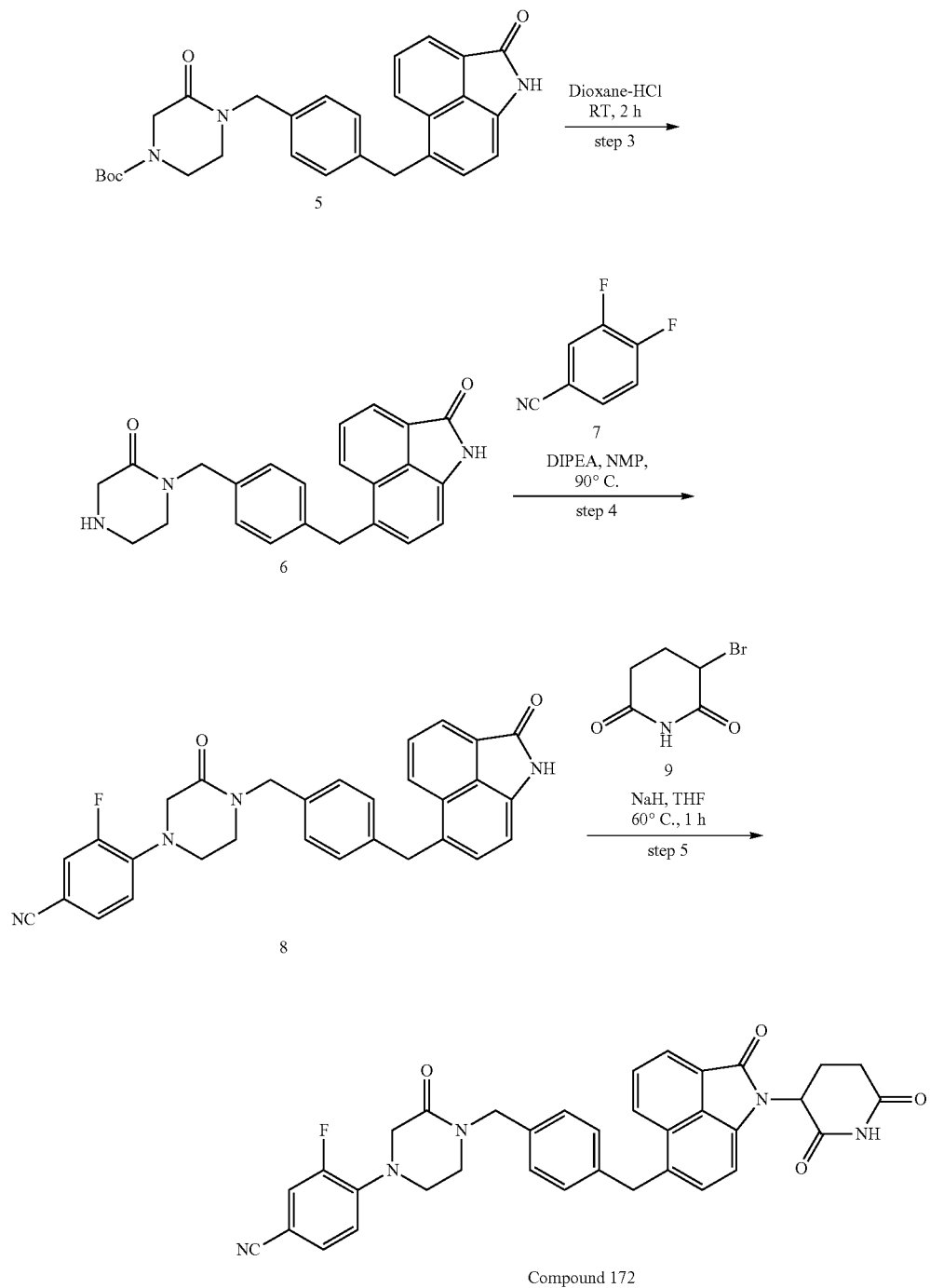

Compound 172

Step 1: Synthesis of tert-butyl 4-[[4-(chloromethyl)phenyl]methyl]-3-oxo-piperazine-1-carboxylate: To a stirred solution of tert-butyl 3-oxopiperazine-1-carboxylate (1) (2 g, 9.99 mmol) in DMF (20 mL) Sodium hydride 60% dispersion in mineral oil (275.56 mg, 11.99 mmol) was added under cooling condition and the reaction was stirred for 20 min. Then 1,4-bis(chloromethyl)benzene (2) (1.75 g, 9.99 mmol, 1.23 mL) was added and the reaction was allowed to stir at RT for 16 h. The reaction mixture was quenched with ice and extracted with ethyl acetate. The organic part was dried over sodium sulfate and concentrated. The crude was purified by column chromatography in (100-200 silica; gradient 20-30% EtOAc in hexane) to afford tert-butyl 4-[[4-(chloromethyl)phenyl]methyl]-3-oxo-piperazine-1-carboxylate (3) (1.5 g, 39.89% yield). LC MS: ES+ 339.0.

Step 2: Synthesis of 3-oxo-4-[[4-[(2-oxo-1H-benzo[cd]indol-6-yl)methyl]phenyl]methyl]-3-oxo-piperazine-1-carboxylate: To a stirred solution of tert-butyl 4-[[4-(chloromethyl)phenyl]methyl]-3-oxo-piperazine-1-carboxylate (3) (1 g, 2.95 mmol) and 6-(4,4,5,5-tetramethyl-1,3,2-dioxaborolan-2-yl)-1H-benzo[cd]indol-2-one (4) (1.05 g, 3.54 mmol) in ethanol (5 mL) and Toluene (10 mL) was added Potassium phosphate tribasic anhydrous (1.88 g, 8.85 mmol) and the reaction mass was purged with Nitrogen for 15 min, then Tri-o-Tolyl phosphine (179.66 mg, 590.27 umol) and (1E, 4E)-1,5-diphenylpenta-1,4-dien-3-one; palladium (270.26 mg, 295.13 umol) were added and the reaction was heated at 90° C. for 16 hr. After completion (monitored by TLC) the reaction mixture was passed through celite bed and washed with EtOAc. The filtrate was then washed with water and brine, dried over sodium sulphate and concentrated. The crude thus obtained was purified by combiflash column in (gradient: 0-30% EtOAc in DCM) to afford tert-butyl 3-oxo-4-[[4-[(2-oxo-1H-benzo[cd]indol-6-yl)methyl]phenyl] methyl]piperazine-1-carboxylate (5) (500 mg, 23.71% yield). LC MS: ES+472.6.

Step 3: Synthesis of 6-[[4-[(2-oxopiperazin-1-yl)methyl] phenyl]methyl]-1H-benzo[cd]indol-2-one; hydrochloride: Dioxane-HCl (10 mL) was added to tert-butyl 3-oxo-4-[[4-[(2-oxo-1H-benzo[cd]indol-6-yl)methyl]phenyl]methyl] piperazine-1-carboxylate (5) (500 mg, 1.06 mmol) and stirred at rt for 3 hours. After completion of the reaction (monitored by TLC) the reaction mixture was concentrated to dryness and triturated with ether to afford 6-[[4-[(2-oxopiperazin-1-yl)methyl]phenyl]methyl]-1H-benzo[cd]indol-2-one; hydrochloride (6) (400 mg, 71% yield). LC MS: ES+ 372.4.

Step 4: Synthesis of 3-methyl-4-[3-oxo-4-[[4-[(2-oxo-1H-benzo[cd]indol-6-yl)methyl]phenyl]methyl]piperazin-1-yl]benzonitrile: To a stirred solution of 6-[[4-[(2-oxopiperazin-1-yl)methyl]phenyl]methyl]-1H-benzo[cd]indol-2-one; hydrochloride (6) (400 mg, 980.65 umol) and 3,4-difluorobenzonitrile (7) (136.41 mg, 980.65 umol) in NMP (7 mL) was added DIPEA (633.71 mg, 4.90 mmol, 854.06 uL) and the reaction was stirred at 80° C. for 16 hours. After completion of the reaction (monitored by TLC) the reaction mixture was diluted with ethyl acetate and washed with water and brine, dried over sodium sulfate and concentrated. The crude was purified by combiflash column (Gradient 50-100% EtOAc in hexane) to afford 3-methyl-4-[3-oxo-4-[[4-[(2-oxo-1H-benzo[cd]indol-6-yl)methyl]phenyl]methyl] piperazin-1-yl]benzonitrile (8) (150 mg, 29.86% yield) as yellow solid. LC MS: ES+ 491.01.

Step 5: Synthesis of 4-[4-[[4-[[1-(2,6-dioxo-3-piperidyl)-2-oxo-benzo[cd]indol-6 yl] methyl]phenyl] methyl]-3-oxo-piperazin-1-yl]-3-fluoro-benzonitrile: To a stirred solution of 3-fluoro-4-[3-oxo-4-[[4-[(2-oxo-1H-benzo[cd]indol-6-yl)methyl]phenyl]methyl]piperazin-1-yl]benzonitrile (8) (150 mg, 305.79 umol) in THF (10 mL) was added Sodium hydride 60% dispersion in mineral oil (70.30 mg, 3.06 mmol) portion wise at 0° C. and stirred for 10 min at RT.

The reaction mixture was again cooled to 0° C. and 3-bromopiperidine-2,6-dione (9) (293.58 mg, 1.53 mmol) was added and the reaction was stirred at 70° C. for 30 min. After completion of the reaction (monitored by TLC) the reaction mixture was quenched in ice and extracted with ethyl acetate. The organic part was further washed with water and brine, dried over sodium sulfate and concentrated. The crude thus obtained was purified by Prep TLC Palte in 30% EtOAc in DCM to afford 4-[4-[[4-[[1-(2,6-dioxo-3-piperidyl)-2-oxo-benzo[cd]indol-6-yl]methyl]phenyl] methyl]-3-oxo-piperazin-1-yl]-3-fluoro-benzonitrile Compound 172 (85 mg, 46.05% yield) as yellow solid.

¹H NMR (400 MHz, DMSO-d6) δ 11.11 (s, 1H), 8.33 (d, J=8.28 Hz, 1H), 8.07 (d, J=6.96 Hz, 1H), 7.80 (t, J=7.64 Hz, 1H), 7.74-7.70 (m, 1H), 7.56 (d, J=8.36 Hz, 1H), 7.40 (d, J=7.36 Hz, 1H), 7.27 (d, J=7.96 Hz, 1H), 7.16 (d, J=7.96 Hz, 1H), 7.13-7.09 (m, 2H), 5.43 (dd, J=12.84, 4.92 Hz, 1H), 4.50 (s, 2H), 4.38 (s, 2H), 3.91 (s, 2H), 3.49-3.46 (m, 2H), 2.97-2.90 (m, 1H), 2.78-2.72 (m, 1H), 2.69-2.62 (m, 1H), 2.10-2.09 (m, 1H) LC MS: ES+ 602.01.

Example 85. Synthesis of [4-[4-[[1-[1-(1-methylcyclobutanecarbonyl)-4-piperidyl]pyrazol-4-yl]disulfanyl]pyrazol-1-yl]-1-piperidyl]-(1-methylcyclobutyl) methanone (Compound 173)

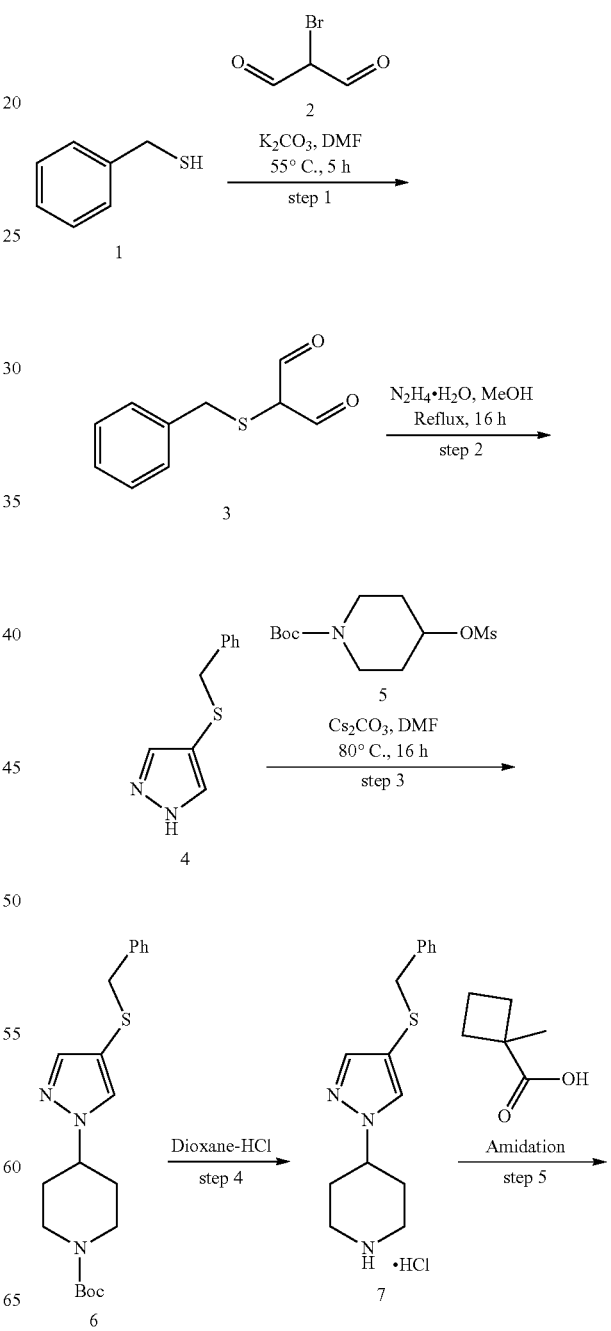

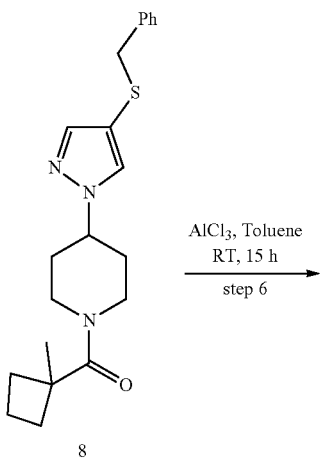

Compound 173

Step 1: Synthesis of 2-benzylsulfanylpropanedial: To a stirred solution of of phenylmethanethiol (1) (10 g, 80.51 mmol), 2-bromopropanedial (2) (12.76 g, 84.54 mmol) in DMF (80 mL) was added Potassium carbonate (12.24 g, 88.56 mmol) and the resultant reaction mixture was stirred at 55° C. for 5 hour. After completion (monitored by TLC) the reaction mixture was diluted with ethyl acetate and washed with water and brine, dried over sodium sulphate and concentrated under reduced pressure to afford 2-benzylsulfanylpropanedial (3) (9 g, 51.79% yield) as brown solid. LC MS: ES– 192.8.

Step 2: Synthesis of 4-benzylsulfanyl-1H-pyrazole: To a stirred solution of [benzyl(formyl)-$l^{4}$-sulfanyl]formaldehyde (3) (9 g, 49.39 mmol) in Methanol (90 mL) was added hydrazine; hydrate (2.47 g, 49.39 mmol, 2.40 mL) and the resultant reaction mixture was heated at 90° C. for 16 h. After completion of the reaction (monitored by TLC) the reaction mixture was concentrated under reduced pressure. The crude was then diluted with EtOAc and washed with water and brine, dried over sodium sulphate and concentrated under reduced pressure. Crude thus obtained was purified by Combiflash column (0-20% EtOAc in Hexane) to afford 4-benzylsulfanyl-1H-pyrazole (4) (7 g, 73.01% yield) as gummy solid. LC MS: ES+ 191.1.

Step 3: Synthesis of tert-butyl 4-(4-benzylsulfanylpyrazol-1-yl)piperidine-1-carboxylate: To a stirred solution of compound 4-benzylsulfanyl-1H-pyrazole (4) (3.5 g, 18.40 mmol) and tert-butyl 4-methylsulfonyloxypiperidine-1-carboxylate (5) (5.14 g, 18.40 mmol) in DMF (20 mL) was added Cesium carbonate (17.98 g, 55.19 mmol) and the resultant reaction mixture was heated at 90° C. for 16 hours. After completion (monitored by TLC) the reaction mixture was diluted with EtOAc and washed with water and brine, dried over sodium sulphate and concentrated under reduced pressure. The crude thus obtained Organic layer was dried over sodium sulphate concentrated under reduced pressure. Crude thus obtained was purified by Combi-flash column (Gradient: 0-15% EtOAc in Hexane) afforded desired compound tert-butyl 4-(4-benzylsulfanylpyrazol-1-yl)piperidine-1-carboxylate (6) (4.5 g, 62.22% yield) as light yellow solid. LC MS: ES+ 374.2.

Step 4: Synthesis of 4-(4-benzylsulfanylpyrazol-1-yl)piperidine; Hydrochloride salt: To a stirred solution of compound tert-butyl 4-(4-benzylsulfanylpyrazol-1-yl)piperidine-1-carboxylate (6) (7 g, 18.74 mmol) in Dioxane (15 mL) was added Dioxane-HCl (4M; 50 mL) and the resultant reaction mixture was stirred at room temperature for 5 hour. After completion of the reaction (monitored by TLC) the reaction mass was concentrated under reduced pressure and triturated with ether to afford 4-(4-benzylsulfanylpyrazol-1-yl)piperidine; Hydrochloride salt (7) (4.5 g, 79.92% yield) as off white solid. LC MS: ES+ 274.4.

Step 5: Synthesis of [4-(4-benzylsulfanylpyrazol-1-yl)-1-piperidyl]-(1-methylcyclobutyl)methanone: To a stirred solution of 4-(4-benzylsulfanylpyrazol-1-yl)piperidine; hydrochloride (7) (4.5 g, 14.52 mmol) and 1-methylcyclobutanecarboxylic acid (1.66 g, 14.52 mmol) in DMF (50 mL) was added DIPEA (9.38 g, 72.61 mmol, 12.6 5 mL) and stirred for 15 minutes at RT followed by the addition of HATU (6.63 g, 17.43 mmol). The resultant reaction mixture was then allowed to stir at RT for 16 h. After completion of the reaction (monitored by TLC and LC MS) the reaction mixture was diluted with ethyl acetate and washed with water and brine, dried over sodium sulphate and concentrated under reduced pressure. The crude thus obtained was purified by column chromatography (Silica; gradient 0-2% MeOH in DCM) to afford [4-(4-benzylsulfanylpyrazol-1-yl)-1-piperidyl]-(1-methylcyclobutyl)methanone (8) (5 g, 91.31% yield) as light yellow solid. LC MS: ES+ 370.0.

Step 6: Synthesis of [4-[4-[[1-[1-(1-methylcyclobutanecarbonyl)-4-piperidyl]pyrazol-4-yl]disulfanyl]pyrazol-1-yl]-1-piperidyl]-(1-methylcyclobutyl)methanone: To a stirred solution of [4-(4-benzylsulfanylpyrazol-1-yl)-1-piperidyl]-(1-methylcyclobutyl)methanone (8) (3 g, 8.12 mmol) intoluene (50 mL) was added Aluminum chloride, Anhydrous (3.25 g, 24.36 mmol, 1.33 mL) and the resultant reaction mixture was stirred at RT for 16 hours. TLC showed some unreacted SM being present the reaction mixture was heated at 80° C. for another 4 hours. After completion (monitored by TLC) the reaction mixture was diluted with cold water and extracted with EtOAc (Twice). The combined organic layer was washed with brine, dried over sodium sulphate and concentrated under reduced pressure. The crude thus obtained was purified by column chromatography (Gradient 0-2% MeOH in DCM) to afford [4-[4-[[1-[1-(1-methylcyclobutanecarbonyl)-4-piperidyl]pyrazol-4-yl]disulfanyl]pyrazol-1-yl]-1-piperidyl]-(1-methylcyclobutyl)methanone Compound 173 (1.3 g, 25.88% yield) as off white solid. LC MS: ES+ 557.2.

Example 86. Synthesis of 3-[6-[1-[1-(1-methylcyclobutanecarbonyl)-4-piperidyl]pyrazol-4-yl]sulfanyl-2-oxo-benzo[cd]indol-1-yl]piperidine-2,6-dione (Compound 174)

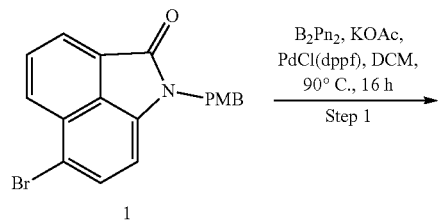

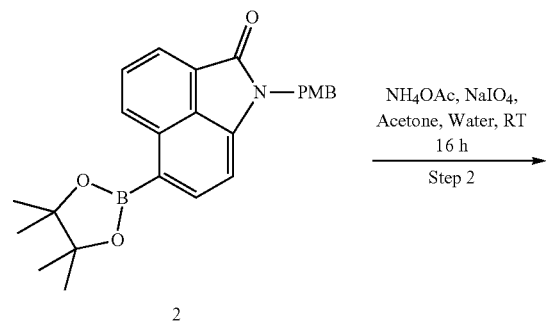

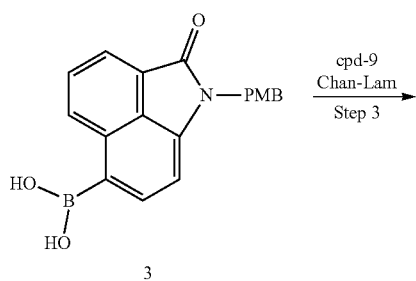

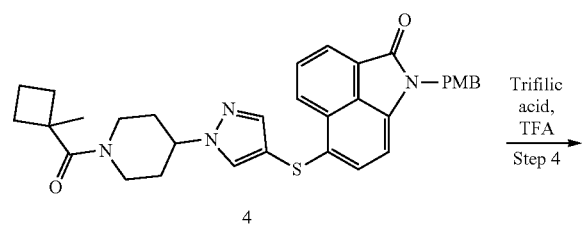

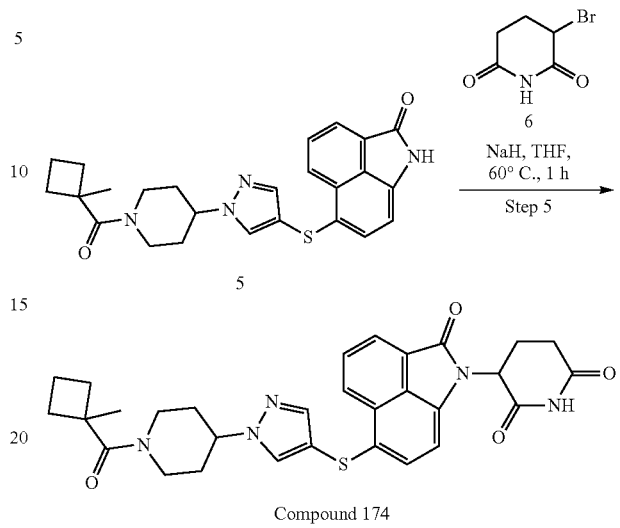

Compound 174

Step 1: Synthesis of 1-[(4-methoxyphenyl)methyl]-6-(4,4,5,5-tetramethyl-1,3,2-dioxaborolan-2-yl)benzo[cd]indol-2-one: To a stirred solution of 6-bromo-1-[(4-methoxyphenyl)methyl]benzo[cd]indol-2-one (1) (10 g, 27.16 mmol) in 1,4 dioxane (200 mL) was added Bis(pinacolato)diboron (10.34 g, 40.74 mmol) followed by well dried Potassium Acetate (8.00 g, 81.47 mmol). The resultant reaction mass was degassed well with argon for 15 minutes. PdCl2(dppf).DCM (2.22 g, 2.72 mmol) was added and the reaction mass was heated at 100° C. for 16 hours. After completion of the reaction (monitored by TLC), the reaction mixture was cooled to RT, filtered through a pad of celite, washed with more Ethyl acetate. The combined filtrate was washed with cold water, dried over sodium sulphate and concentrated under reduced pressure. The crude thus obtained was purified by Combiflash column (gradient 0-15% EtOAc in Hexane) to afford 1-[(4-methoxyphenyl)methyl]-6-(4,4,5,5-tetramethyl-1,3,2-dioxaborolan-2-yl)benzo[cd]indol-2-one (2) (10 g, 78% yield) as yellow solid. LC MS: ES+ 416.1.

Step 2: Synthesis of [1-[(4-methoxyphenyl)methyl]-2-oxo-benzo[cd]indol-6-yl]boronic acid: To the stirred solution of 1-[(4-methoxyphenyl)methyl]-6-(4,4,5,5-tetramethyl-1,3,2-dioxaborolan-2-yl)benzo[cd]indol-2-one (2) (4 g, 9.63 mmol) in Acetone (40 mL) was added a solution of Ammonium acetate (2.23 g, 28.90 mmol) in Water (20 mL) followed by sodium; periodate (8.24 g, 38.53 mmol). The resultant reaction mixture was the stirred at 70° C. for 18 hours. After completion (monitored by TLC and LCMS) the reaction mass was diluted with cold water and extracted with EtOAc (twice). The combine organic layer was then washed with brine, dried over sodium sulphate and concentrated under reduced pressure. The crude thus obtained was purified by combiflash column (Gradient 0-3% MeOH in DCM) to afford [1-[(4-methoxyphenyl)methyl]-2-oxo-benzo[cd]indol-6-yl]boronic acid (3) (2 g, 57.65% yield) as yellow solid. LC MS: ES+ 334.2.

Step 3: Synthesis of 1-[(4-methoxyphenyl)methyl]-6-[1-[1-(1-methylcyclobutanecarbonyl)-4-piperidyl]pyrazol-4-yl]sulfanyl-benzo[cd]indol-2-one: To a stirred solution of [1-[(4-methoxyphenyl)methyl]-2-oxo-benzo[cd]indol-6-yl] boronic acid (3) (299.17 mg, 898.01 umol) and [4-[4-[[1-[1-(1-methylcyclobutanecarbonyl)-4-piperidyl]pyrazol-4- yl]disulfanyl]pyrazol-1-yl]-1-piperidyl]-(1-methylcyclobutyl)methanone (9_scheme-1) (500 mg, 898.01 umol) in Ethanol (10 mL) was added tetrabutylammonium; hydroxide (2.91 g, 4.49 mmol, 3.20 mL, 40% purity). The resultant reaction mixture was degassed with oxygen for 10 minute then copper sulphate (28.67 mg, 179.60 umol, 7.96 uL) and 1,10-phenanthroline (32.37 mg, 179.60 umol) were added to the reaction mixture was stirred at RT for 16 h. After completion (monitored by TLC) the reaction mixture was filtered through celite pad and washed with ethanol and ethyl acetate. The filtrate was concentrated and again diluted with ethyl acetate and washed with water and brine, dried over sodium sulphate and concentrated under reduced pressure. Crude thus obtained was purified by Combiflash column (Gradient 0-1% MeOH in DCM) to afford 1-[(4-methoxyphenyl)methyl]-6-[1-[1-(1-methylcyclobutanecarbonyl)-4-piperidyl]pyrazol-4-yl]sulfanyl-benzo[cd]indol-2-one (4) (500 mg, 93.34% yield) as light yellow solid. LC MS: ES+567.4.

Step 4: Synthesis of 6-[1-[1-(1-methylcyclobutanecarbonyl)-4-piperidyl]pyrazol-4-yl]sulfanyl-1H-benzo[cd]indol-2-one: To the stirred solution of 1-[(4-methoxyphenyl)methyl]-6-[1-[1-(1-methylcyclobutanecarbonyl)-4-piperidyl]pyrazol-4-yl]sulfanyl-benzo[cd]indol-2-one (4) (500 mg, 882.28 umol) in TFA (4 mL) was added trifluoromethanesulfonic acid (662.05 mg, 4.41 mmol, 387.16 uL) and the resultant reaction mixture was stirred at RT for 16 hours. After completion of the reaction (monitored by TLC) the reaction mass was quenched with saturated bicarbonate solution and extracted with ethyl acetate (twice). The combined organic layer was washed with brine, dried over sodium sulphate concentrated under reduced pressure. Crude thus obtained was purified by combiflash column (Gradient 0-3% MeOH in DCM) to afford 6-[1-[1-(1-methylcyclobutanecarbonyl)-4-piperidyl]pyrazol-4-yl]sulfanyl-1H-benzo[cd]indol-2-one (5) (300 mg, 75.38% yield) as light yellow solid. LC MS: ES+ 447.1.

Step 5: Synthesis of 3-[6-[1-[1-(1-methylcyclobutanecarbonyl)-4-piperidyl]pyrazol-4-yl]sulfanyl-2-oxo-benzo[cd]indol-1-yl]piperidine-2,6-dione: To a cooled solution of 6-[1-[1-(1-methylcyclobutanecarbonyl)-4-piperidyl]pyrazol-4-yl]sulfanyl-1H-benzo[cd]indol-2-one (5) (200 mg, 417.92 umol) in dry THF (3 mL), Sodium hydride (60% dispersion in mineral oil) (15.44 mg, 671.80 umol) was added portion wise, maintaining the temp <5° C. Once the addition is over, the resultant mixture was stirred for 15 minutes at RT. Then the reaction mixture was again cooled to 0° C. and 3-bromopiperidine-2,6-dione (6) (64.50 mg, 335.90 umol) was added to it portion wise.

After complete addition, resulting solution was heated at 60° C. for 30 min. After completion (evidenced from TLC), the reaction mixture was cooled to 0° C. and quenched with the addition of ice cooled water. Aqueous part was extracted with ethyl acetate (3×100 mL). Combined organics was separated, dried over sodium sulfate and concentrated under reduced pressure. Crude mass was purified by Prep TLC Plate (30% EtOAc in DCM) to afford 3-[6-[1-[1-(1-methylcyclobutanecarbonyl)-4-piperidyl]pyrazol-4-yl]sulfanyl-2-oxo-benzo[cd]indol-1-yl]piperidine-2,6-dione Compound 174 (15 mg, 38% yield) as light yellow solid. ¹H NMR (400 MHz, DMSO-d6) δ 11.10 (s, 1H), 8.48 (d, J=8.28 Hz, 1H), 8.20 (s, 1H), 8.15 (d, J=7.0 Hz, 1H), 7.91 (t, J=7.64 Hz, 1H), 7.65 (s, 1H), 7.33 (d, J=7.48 Hz, 1H), 7.08 (d, J=7.56 Hz, 1H), 5.42 (dd, J=12.48, 4.92 Hz, 1H), 4.45-4.39 (m, 2H), 3.63-3.62 (m, 1H), 3.11-3.10 (m, 1H), 2.93-2.89 (m, 1H), 2.72-2.61 (m, 3H), 2.43-2.40 (m, 2H), 2.10-2.00 (m, 3H), 1.95-1.78 (m, 5H), 1.62-1.59 (m, 1H), 1.35 (s, 3H); LC MS: ES+ 558.4.

Example 87. Synthesis of 3-[6-[1-[1-(1-methylcyclobutanecarbonyl)-4-piperidyl]pyrazol-4-yl]sulfonyl-2-oxo-benzo[cd]indol-1-yl]piperidine-2,6-dione, (Compound 175)

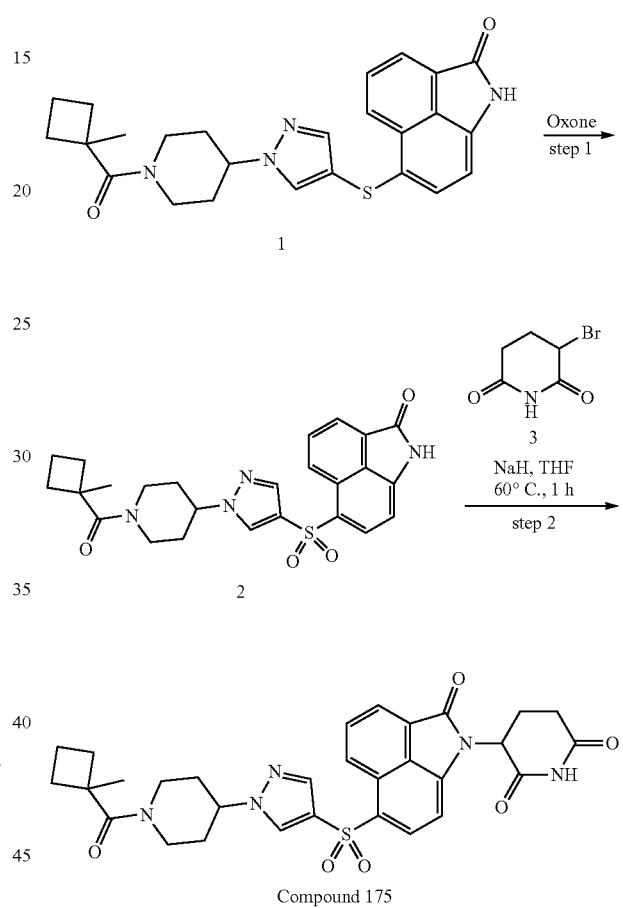

Compound 175

Step 1: Synthesis of 6-[1-[1-(1-methylcyclobutanecarbonyl)-4-piperidyl]pyrazol-4-yl]sulfonyl-1H-benzo[cd]indol-2-one: To a stirred solution of 6-[1-[1-(1-methylcyclobutanecarbonyl)-4-piperidyl]pyrazol-4-yl]sulfanyl-1H-benzo[cd]indol-2-one (1) (300 mg, 671.80 umol) in Water (1 mL) and Methanol (2 mL) was added Oxone (1.24 g, 2.02 mmol) and the resultant reaction mixture was stirred at RT for 16 hours. After completion of the reaction (monitored by TLC) the reaction mixture was passed through celite pad and washed with EtOAc. The filtrate was then washed with cold water and brine. The organic part was dried over sodium sulphate and concentrated under reduced pressure. The crude thus obtained was purified by combiflash column (Gradient 0-2% MeOH in DCM) to afford 6-[1-[1-(1-methylcyclobutanecarbonyl)-4-piperidyl]pyrazol-4-yl]sulfonyl-1H-benzo[cd]indol-2-one (2) (200 mg, 61.40% yield) as light yellow solid. LC MS ES+ 479.1.

Step 2: Synthesis of 3-[6-[1-[1-(1-methylcyclobutanecarbonyl)-4-piperidyl]pyrazol-4-yl]sulfonyl-2-oxo-benzo[cd]

indol-1-yl]piperidine-2,6-dione: To a cooled solution of 6-[1-[1-(1-methylcyclobutanecarbonyl)-4-piperidyl]pyrazol-4-yl]sulfonyl-1H-benzo[cd]indol-2-one (2) (200 mg, 417.92 umol) in dry THF (10 mL), Sodium hydride (60% dispersion in mineral oil) (96.08 mg, 4.18 mmol) was added portion wise, maintaining the temp <5° C. Once the addition is over, the resultant mixture was stirred for 15 minutes at RT. Then the reaction mixture was again cooled to 0° C. and 3-bromopiperidine-2,6-dione (3) (401.22 mg, 2.09 mmol) was added to it portion wise. After complete addition, resulting solution was heated at 60° C. for 30 min. After completion (evidenced from TLC), the reaction mixture was cooled to 0° C. and quenched with the addition of ice cooled water. Aqueous part was extracted with ethyl acetate (3×100 mL). Combined organics was separated, dried over sodium sulphate and concentrated under reduced pressure. Crude mass was purified by Prep TLC Plate (30% EtOAc in DCM) to afford 3-[6-[1-[1-(1-methylcyclobutanecarbonyl)-4-piperidyl]pyrazol-4-yl]sulfonyl-2-oxo-benzo[cd]indol-1-yl]piperidine-2,6-dione Compound 175 (50 mg, 19.2% yield) as light yellow solid. ¹H NMR (400 MHz, DMSO-d6) δ 11.18 (s, 1H), 8.79 (d, J=8.32 Hz, 1H), 8.70 (s, 1H), 8.29 (d, J=7.8 Hz, 1H), 8.21 (d, J=6.84 Hz, 1H), 8.06 (s, 1H), 7.99 (t, J=7.6 Hz, 1H), 7.34 (d, J=7.8 Hz, 1H), 5.52-5.49 (m, 1H), 4.43-4.41 (m, 1H), 3.58-3.57 (m, 1H), 3.07-3.06 (m, 1H), 2.94-2.90 (m, 1H), 2.78-2.64 (m, 3H), 2.41-2.38 (m, 2H), 2.14-2.12 (m, 1H), 1.98-1.87 (m, 3H), 1.78-1.76 (m, 4H), 1.69-1.59 (m, 1H), 1.33 (s, 3H); LC MS: ES+ 590.5.

Example 88. Synthesis of 4-[4-[[4-[[1-(2,6-dioxo-3-piperidyl)-2-oxo-benzo[cd]indol-6-yl]methyl]phenyl] methyl]piperazin-1-yl]-3-fluoro-benzonitrile (Compound 176)

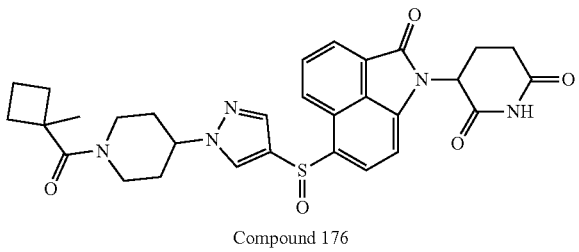

Compound 176

Step 1: Synthesis of 6-[1-[1-(1-methylcyclobutanecarbonyl)-4-piperidyl]pyrazol-4-yl]sulfinyl-1H-benzo[cd]indol-2-one: To a stirred solution of 6-[1-[1-(1-methylcyclobutanecarbonyl)-4-piperidyl]pyrazol-4-yl]sulfanyl-1H-benzo[cd]indol-2-one (1) (300 mg, 671.80 umol) in DCM (20 mL) was added 3-chlorobenzenecarboperoxoic acid (69.56 mg, 403.08 umol) and the resultant reaction mixture was stirred at RT for 16 hours. After completion (monitored by TLC) the reaction mixture was diluted with cold water and extracted with dicholomethane (Twice). The combined organic layer was dried over sodium sulphate and concentrated under reduced pressure. The crude thus obtained was purified by combiflash Column (Gradient 0-1% MeOH in DCM) to afford 6-[1-[1-(1-methylcyclobutanecarbonyl)-4-piperidyl]pyrazol-4-yl]sulfinyl-1H-benzo[cd]indol-2-one (2) (200 mg, 63.55% yield) as light yellow solid. LC MS ES+ 463.3.

Step 2: Synthesis of 4-[4-[[4-[[1-(2,6-dioxo-3-piperidyl)-2-oxo-benzo[cd]indol-6-yl]methyl]phenyl] methyl]piperazin-1-yl]-3-fluoro-benzonitrile: To an ice cooled solution of 6-[1-[1-(1-methylcyclobutanecarbonyl)-4-piperidyl]pyrazol-4-yl]sulfinyl-1H-benzo[cd]indol-2-one (2) (170 mg, 367.52 umol) in dry THF (10 mL), Sodium hydride (60% dispersion in mineral oil) (211.23 mg, 9.19 mmol) was added portion wise, maintaining the temp <5° C. Once the addition is over, the resultant mixture was stirred for 15 minutes at RT. Then the reaction mixture was again cooled to 0° C. and 3-bromopiperidine-2,6-dione (3) (352.84 mg, 1.84 mmol) was added to it portion wise. After complete addition, resulting solution was heated at 60° C. for 30 min. After completion (evidenced from TLC), the reaction mixture was cooled to 0° C. and quenched with the addition of ice cooled water. Aqueous part was extracted with ethyl acetate (3×100 mL). Combined organics was separated, dried over sodium sulphate and concentrated under reduced pressure. Crude mass was purified by Prep TLC Plate (30% EtOAc in DCM) to afford 4-[4-[[4-[[1-(2,6-dioxo-3-piperidyl)-2-oxo-benzo[cd]indol-6-yl]methyl]phenyl]methyl]piperazin-1-yl]-3-fluoro-benzonitrile Compound 176 (35 mg, 16.6% yield) light yellow solid. ¹H NMR (400 MHz, DMSO-d6) δ 11.10 (br, 1H), 8.40-8.39 (m, 1H), 8.26-8.20 (m, 1H), 8.16 (d, J=6.96 Hz, 1H), 8.09 (d, J=6.84 Hz, 1H), 7.87-7.85 (m, 1H), 7.67 (s, 1H), 7.39-7.37 (m, 1H), 5.52-5.50 (m, 1H), 4.43-4.42 (m, 2H), 3.58-3.57 (m, 1H), 3.05-2.92 (m, 3H), 2.78-2.75 (m, 1H), 2.69-2.63 (m, 2H), 2.44-2.38 (m, 2H), 2.13-2.12 (m, 1H), 1.94-1.89 (m, 3H), 1.79-1.77 (m, 3H), 1.61-1.59 (m, 1H), 1.33 (s, 3H); LC MS: ES+ 574.2.

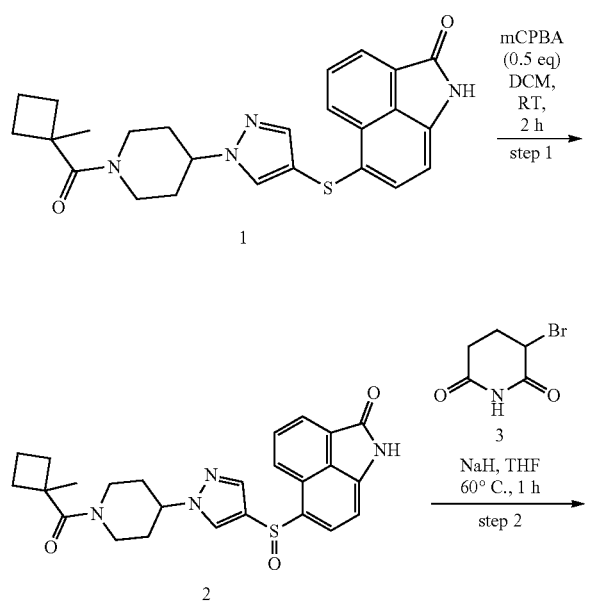

Example 89. Synthesis of 3-[6-[[1-(3-benzyloxycyclobutyl)pyrazol-4-yl]methyl]-2-oxo-benzo[cd]indol-1-yl]piperidine-2,6-dione (Compound 177)

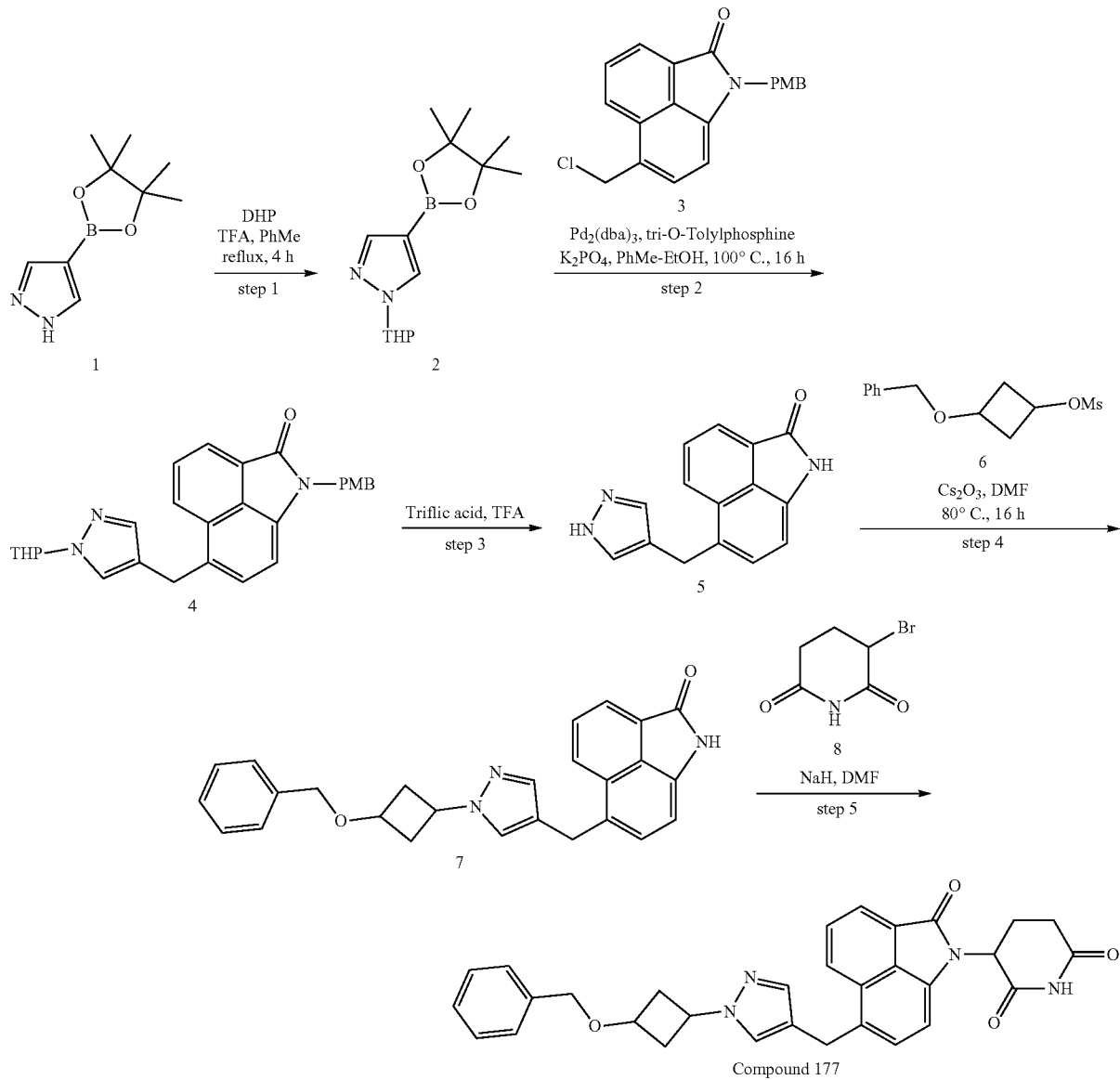

Step 1: Synthesis of 1-tetrahydropyran-2-yl-4-(4,4,5,5-tetramethyl-1,3,2-dioxaborolan-2-yl)pyrazole: To a stirred solution of 4-(4,4,5,5-tetramethyl-1,3,2-dioxaborolan-2-yl)-1H-pyrazole 1 (5.00 g, 25.78 mmol) intoluene (60 mL) and 3,4-dihydro-2H-pyran (4.55 g, 54.13 mmol, 4.92 mL) under nitrogen condition. To the reaction mixture, 2,2,2-trifluoroacetic acid (88.17 mg, 773.30 umol, 59.58 uL) was added and heated at 80° C. for 4 hours. Reaction mixture was quenched with saturated solution of Sodium bicarbonate and extracted with ethyl acetate. Separated organic layer, dried over sodium sulphate. Filtered and concentrated under reduced pressure. Crude mass was purified by column chromatography to afford 1-tetrahydropyran-2-yl-4-(4,4,5,5-tetramethyl-1,3,2-dioxaborolan-2-yl)pyrazole 2 (7.1 g, 24.25 mmol, 94.07% yield, 95% purity) as yellow oil. LCMS: ES+ 279.1.

Step 2: Synthesis of 1-[(4-methoxyphenyl)methyl]-6-[(1-tetrahydropyran-2-ylpyrazol-4-yl)methyl]benzo[cd]indol-2-one: To the stirred solution of 6-(chloromethyl)-1-[(4-methoxyphenyl)methyl]benzo[cd]indol-2-one 3 (1 g, 2.96 mmol) and 1-tetrahydropyran-2-yl-4-(4,4,5,5-tetramethyl-1,3,2-dioxaborolan-2-yl)pyrazole 2 (1.32 g, 4.74 mmol) in a sealed tube intoluene (4 mL) and Ethanol (2 mL) and 4 drops water were added tripotassium; phosphate (1.57 g, 7.40 mmol). It was degassed with argon for 10 minutes. tris-o-tolylphosphane (180.21 mg, 592.07 umol) and (1E,4E)-1,5-diphenylpenta-1,4-dien-3-one; palladium (271.08 mg, 296.03 umol) were added to the reaction mixture. It was heated at 90° C. for 16 hours. Reaction mixture was cooled to room temperature, diluted with ethyl acetate and water, and layers were separated. The organic layer was washed with water, brine, dried over sodium sulphate and concen trated under reduced pressure. It was purified by column chromatography eluting at 40% ethyl acetate in hexane to afford 1-[(4-methoxyphenyl)methyl]-6-[(1-tetrahydropyran-2-ylpyrazol-4-yl)methyl]benzo[cd]indol-2-one 4 (550 mg, 1.15 mmol, 38.92% yield, 95% purity) as yellow solid. LC MS: ES+ 454.1.

Step 3: Synthesis of 6-(1H-pyrazol-4-ylmethyl)-1H-benzo[cd]indol-2-one: To a stirred solution of 1-[(4-methoxyphenyl)methyl]-6-[(1-tetrahydropyran-2-ylpyrazol-4-yl)methyl]benzo[cd]indol-2-one 4 (550 mg, 1.21 mmol) in TFA (4 mL) was added trifluoromethanesulfonic acid (1.46 g, 9.70 mmol, 851.48 uL) at room temperature then reaction mixture was stirred at room temperature for over night. After checked TLC (Rf=0.2 in 5% MeOH/DMF) it showed one polar spot was formed and starting material was consumed then reaction mixture was concentrated under reduced pressured to get crude mass which diluted with EtOAc and saturated solution of NaHCO3, layers were separated. Combined organic layer was washed with saturated brine solution and dried under vacuum pump to afford 6-(1H-pyrazol-4-ylmethyl)-1H-benzo[cd]indol-2-one 5 (280 mg, 1.11 mmol, 91.70% yield, 99% purity) as yellow solid. LCMS: ES+ 250.3.

Synthesis of (3-benzyloxycyclobutyl) methanesulfonate: To a stirred solution of 3-benzyloxycyclobutanol (100 mg, 561.08 umol) in DCM (5 mL) was added Triethylamine (113.55 mg, 1.12 mmol, 156.41 uL), cooled the reaction mixture to 0° C. followed by drop wise addition of Methane sulfonyl chloride (77.13 mg, 673.30 umol, 52.11 uL) then reaction mixture was stirred at room temperature for 4 hours. After completion of SM, reaction mass was diluted with water and extracted with DCM, washed with saturated solution of NaHCO3, brine, dried over anhydrous sodium sulphate and evaporate under reduced pressure to give the crude compound (3-benzyloxycyclobutyl) methanesulfonate 6 (100 mg, 370.63 umol, 66.06% yield, 95% purity) as orange liquid, which was used in next step without further purification. LCMS: ES+ 257.2.

Step 4: Synthesis of 6-[[1-(3-benzyloxycyclobutyl)pyrazol-4-yl]methyl]-1H-benzo[cd]indol-2-one: To a stirred solution of 6-(1H-pyrazol-4-ylmethyl)-1H-benzo[cd]indol-2-one 5 (115 mg, 461.35 umol) and (3-benzyloxycyclobutyl) methanesulfonate 6 (130.08 mg, 507.49 umol) in DMF (10 mL) was added Cesium carbonate (450.95 mg, 1.38 mmol) at room temperature then reaction mixture was heated 80° C. over night. After completion of starting material then reaction mixture was diluted with cooled water extracted with ethyl acetate. Combined organic layer was washed with saturated brine solution and dried under reduced pressure to get crude which was purified by combiflash chromatography using 30-40% EtOAc-Hexane as eluent to afford 6-[[1-(3-benzyloxycyclobutyl)pyrazol-4-yl]methyl]-1H-benzo[cd]indol-2-one 7 (18 mg, 40.44 umol, 8.77% yield, 92% purity) as light yellow solid. LC MS: ES+ 410.2.

Step 5: Preparation of 3-[6-[[1-(3-benzyloxycyclobutyl)pyrazol-4-yl]methyl]-2-oxo-benzo[cd]indol-1-yl]piperidine-2,6-dione: To the stirred solution of 6-[[1-(3-benzyloxycyclobutyl)pyrazol-4-yl]methyl]-1H-benzo[cd]indol-2-one 7 (40.00 mg, 97.69 umol) in THF (3 mL) was added Sodium hydride (in oil dispersion) 60% dispersion in mineral oil (37.43 mg, 976.85 umol, 60% purity) at cold condition and the reaction mixture was stirred at RT for 10 minutes followed by portion wised addition of 3-bromopiperidine-2,6-dione 8 (93.78 mg, 488.43 umol) and the reaction was heated at 70° C. for 1 hours. After completion of reaction (by TLC), the reaction mixture was diluted with ethyl acetate and washed with water, organic fraction separated. It was dried over anhydrous sodium sulphate and evaporated under reduced pressure to obtain the crude which was purified by Prep TLC using 20% EtOAc-DCM as eluent to afford 3-[6-[[1-(3-benzyloxycyclobutyl)pyrazol-4-yl]methyl]-2-oxo-benzo[cd]indol-1-yl]piperidine-2,6-dione Compound 177 (14.0 mg, 25.42 umol, 26.03% yield, 94.54% purity) as light yellow solid.

¹H NMR (d6-DMSO, 400 MHZ) d 10.98 (s, 1H), 8.20 (d, J=8.20 Hz, 1H), 8.02 (d, J=6.92 Hz, 1H), 7.80 (t, J=7.68 Hz, 1H), 7.55 (s, 1H), 7.39-7.29 (m, 8H), 5.27-5.23 (m, 1H), 5.19-5.15 (m, 1H), 4.47 (s, 2H), 4.46-4.43 (m, 1H), 4.21 (s, 2H), 3.04-2.97 (m, 2H), 2.75-2.72 (m, 1H), 2.70-2.61 (m, 3H), 2.45-2.41 (m, 1H), 2.15-2.14 (m, 1H); LC MS: ES+ 521.2.

Example 90. Synthesis of 3-[2-oxo-6-[[1-[1-[spiro[3.4]octan-8-yl]-4-piperidyl]pyrazol-4-yl]methyl]benzo[cd]indol-1-yl]piperidine-2,6-dione (Compound 178) & 3-[2-oxo-6-[[1-[1-[spiro[3.4]octan-8-yl]-4-piperidyl]pyrazol-4-yl]methyl]benzo[cd]indol-1-yl]piperidine-2,6-dione (Compound 179)

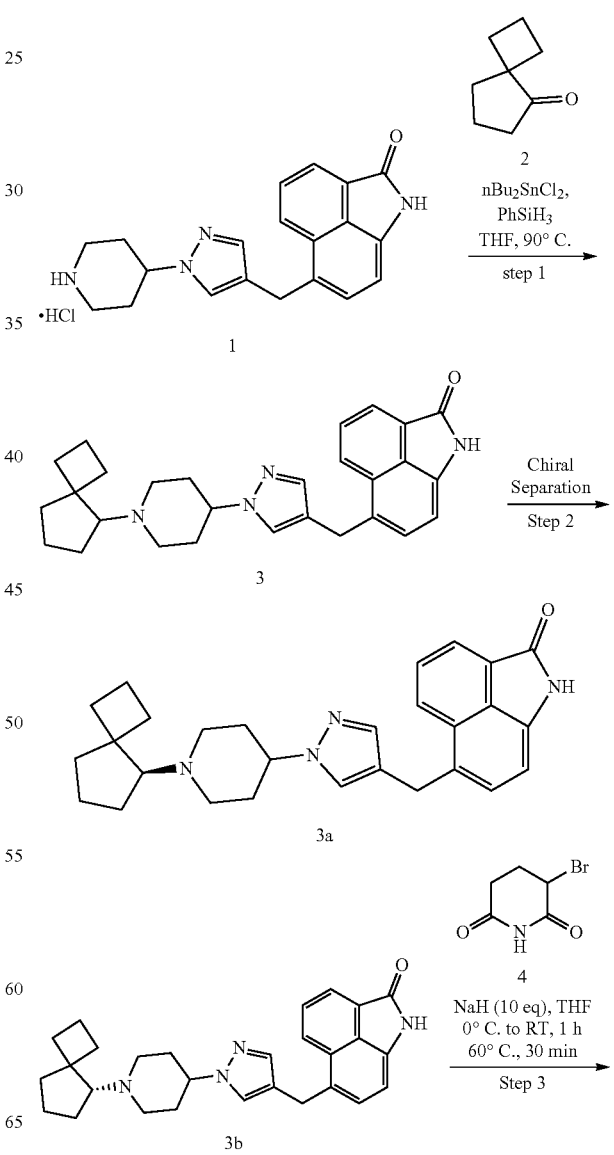

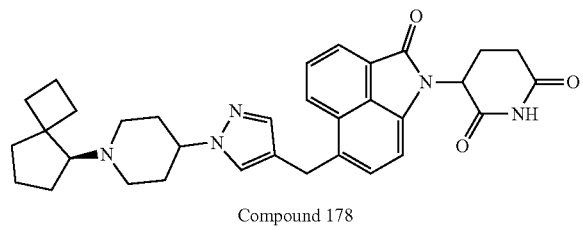

Compound 178

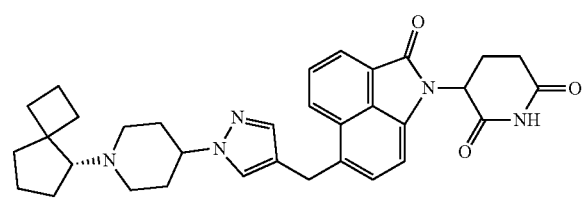

Compound 179

Step 1: Preparation of 6-[[1-(1-spiro[3.4]octan-8-yl-4-piperidyl)pyrazol-4-yl]methyl]-1H-benzo[cd]indol-2-one] (3): To the stirred solution of 6-[[1-(4-piperidyl)pyrazol-4-yl]methyl]-1H-benzo[cd]indol-2-one (1) (500 mg, 1.50 mmol) in dry grade THF (12 mL) was added Triethylamine (304.42 mg, 3.01 mmol, 419.32 uL) followed by the addition of spiro[3.4]octan-8-one 2 (186.79 mg, 1.50 mmol), Dibutyltindichloride (548.47 mg, 1.81 mmol, 403.29 uL) and Phenylsilane (162.77 mg, 1.50 mmol, 185.39 uL). After complete the reaction mixture was heated at 90° C. for 16 hours in sealed tube. After completion of reaction (monitored by LC MS), the he reaction mixture was cooled to rt and diluted with ethyl acetate (30 mL). Combined organic phase was washed with sodium bicarbonate solution, water (2×20 mL) and brine (30 ml). The organic fraction was separated, dried over anhydrous sodium sulphate and evaporated under reduced pressure to obtain the crude compound which was purified by flash chromatography (silica, gradient: 0-5% MeOH in DCM) to afford 6-[[1-(1-spiro[3.4]octan-8-yl-4-piperidyl)pyrazol-4-yl]methyl]-1H-benzo[cd]indol-2-one (3) (26 mg, 56.06 umol, 3.73% yield, 95% purity) as yellow solid. LC MS: ES+ 441.6.

Step 2: Chiral separation: Preparation 6-[[1-(1-spiro[3.4]octan-8-yl-4-piperidyl)pyrazol-4-yl]methyl]-1H-benzo[cd]indol-2-one (3a) and 6-[[1-(1-spiro[3.4]octan-8-yl-4-piperidyl)pyrazol-4-yl]methyl]-1H-benzo[cd]indol-2-one (3b): 80 mg of 6-[[1-(1-spiro[3.4]octan-8-yl-4-piperidyl)pyrazol-4-yl]methyl]-1H-benzo[cd]indol-2-one (3) was separated into enantiomers by chiral normal phase Preparative HPLC method. Prep fractions were first evaporated separately under reduced pressure to obtain solid mass. The solid was then suspended in a mixture of Acetonitrile and Water (2:3) and it was kept in a Dry-ice/Acetone bath until the Acetonitrile-Water mixture solidified. The frozen mixture was then freeze dried under lyophilizer for 20 hours to afford 6-[[1-(1-spiro[3.4]octan-8-yl-4-piperidyl)pyrazol-4-yl]methyl]-1H-benzo[cd]indol-2-one (3a) (first eluted peak, RT=5.31 min, assigned tentatively as 'S' ABS) (26 mg, % ee 96.46) and 6-[[1-(1-spiro[3.4]octan-8-yl-4-piperidyl)pyrazol-4-yl]methyl]-1H-benzo[cd]indol-2-one (3b) (second eluted peak, RT=6.32 min, assigned tentatively as 'R' ABS) (25 mg, % ee 96.86) as yellow solids which were stored in a round bottomed flask at ambient temperature. LC MS: ES+ 441.6.

Step 3: Synthesis of 3-[2-oxo-6-[[1-[1-[spiro[3.4]octan-8-yl]-4-piperidyl]pyrazol-4-yl]methyl]benzo[cd]indol-1-yl]piperidine-2,6-dione & 3-[2-oxo-6-[[1-[1-[spiro[3.4]octan-s-yl]-4-piperidyl]pyrazol-4-yl]methyl]benzo[cd]indol-1-yl]piperidine-2,6-dione: To a cooled solution of 6-[[1-[1-[spiro[3.4]octan-8-yl]-4-piperidyl]pyrazol-4-yl]methyl]-1H-benzo[cd]indol-2-one (3a) (25.00 mg, 56.74 umol) in dry THF (4 mL), Sodium hydride 60% dispersion in mineral oil (13.05 mg, 567.44 umol) was added portion wise, maintaining the temp <5° C. Once the addition is over, the resultant mixture was stirred for 15 minutes at RT. Then the reaction mixture was again cooled to 0° C. and 3-bromopiperidine-2,6-dione (4) (54.48 mg, 283.72 umol) was added to it portion wise. After complete addition, resulting solution was heated at 70° C. 1 hr. After completion (evidenced from TLC), the reaction mixture was cooled to 0° C. and quenched with the addition of ice cooled water. Aqueous part was extracted with ethyl acetate (3×50 mL). Combined organics was separated, dried over sodium sulfate and concentrated under reduced pressure. Crude mass was purified by PREP-TLC (gradient: 5% MeOH in DCM) to afford 3-[2-oxo-6-[[1-[1-[spiro[3.4]octan-8-yl]-4-piperidyl]pyrazol-4-yl]methyl]benzo[cd]indol-1-yl]piperidine-2,6-dione Compound 178 (17.0 mg, 28.21 umol, 49.71% yield, 91.54% purity) as yellow solid. $^1$H NMR (400 MHz, DMSO-d6) S 1H NMR (400 MHz, DMSO-d6) δ 11.11 (s, 1H), 8.37 (d, J=8.24 Hz, 1H), 8.08 (d, J=6.96 Hz, 1H), 7.83 (t, J=7.52 Hz, 1H), 7.58 (s, 1H), 7.35 (d, J=7.24 Hz, 1H), 7.29 (s, 1H), 7.07 (d, J=7.28 Hz, 1H), 5.44 (dd, J=11.92, 4.48 Hz, 1H), 4.36 (s, 2H), 3.96 (m, 1H), 2.94-2.91 (m, 1H), 2.84-2.82 (m, 2H), 2.66-2.63 (m, 2H), 2.49-2.30 (m, 4H), 2.09-2.07 (m, 2H), 1.88-1.74 (m, 8H), 1.60-1.52 (m, 5H), 1.32-1.30 (m, 1H); LC MS: ES+ 552.3. To a cooled solution of 6-[[1-[1-[spiro[3.4]octan-8-yl]-4-piperidyl]pyrazol-4-yl]methyl]-1H-benzo[cd]indol-2-one (3b) (25.00 mg, 56.74 umol) in dry THF (4 mL), Sodium hydride 60% dispersion in mineral oil (13.05 mg, 567.44 umol) was added portion wise, maintaining the temp <5° C. Once the addition is over, the resultant mixture was stirred for 15 minutes at RT. Then the reaction mixture was again cooled to 0° C. and 3-bromopiperidine-2,6-dione (4) (54.48 mg, 283.72 umol) was added to it portion wise. After complete addition, resulting solution was heated at 70° C. 1 hour. After completion (evidenced from TLC), the reaction mixture was cooled to 0° C. and quenched with the addition of ice cooled water. Aqueous part was extracted with ethyl acetate (3×50 mL). Combined organics was separated, dried over sodium sulfate and concentrated under reduced pressure. Crude mass was purified by PREP-TLC (gradient: 5% MeOH in DCM) to afford 3-[2-oxo-6-[[1-[1-[spiro[3.4]octan-8-yl]-4-piperidyl]pyrazol-4-yl]methyl]benzo[cd]indol-1-yl]piperidine-2,6-dione Compound 179 (18.0 mg, 30.76 umol, 54.22% yield, 94.29% purity) as yellow solid. $^1$H NMR (400 MHz, DMSO-d6) δ 11.11 (s, 1H), 8.37 (d, J=8.0 Hz, 1H), 8.08 (d, J=6.96 Hz, 1H), 7.83 (t, J=7.44 Hz, 1H), 7.58 (s, 1H), 7.35 (d, J=7.36 Hz, 1H), 7.29 (s, 1H), 7.07 (d, J=7.28 Hz, 1H), 5.44 (dd, J=12.84, 5.08 Hz, 1H), 4.36 (s, 2H), 3.96 (m, 1H), 2.94-2.91 (m, 1H), 2.83-2.72 (m, 2H), 2.66-2.63 (m, 2H), 2.49-2.30 (m, 4H), 2.09-2.06 (m, 2H), 1.88-1.67 (m, 8H), 1.56-1.52 (m, 5H), 1.32-1.30 (m, 1H); LC MS: ES+ 552.3.

Example 91. Synthesis of 3-[6-[[3-[1-(1-methylcyclobutanecarbonyl)-4-piperidyl]pyrazol-1-yl]methyl]-2-oxo-benzo[cd]indol-1-yl]piperidine-2,6-dione (Compound 180)

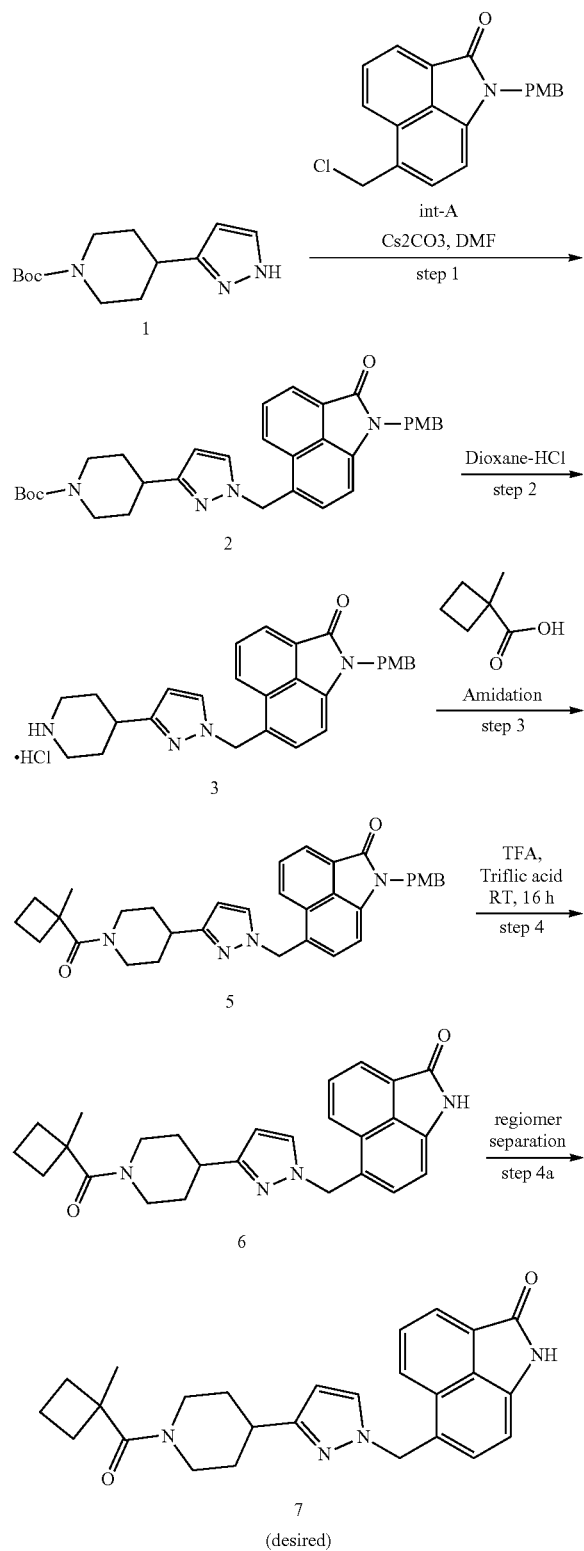

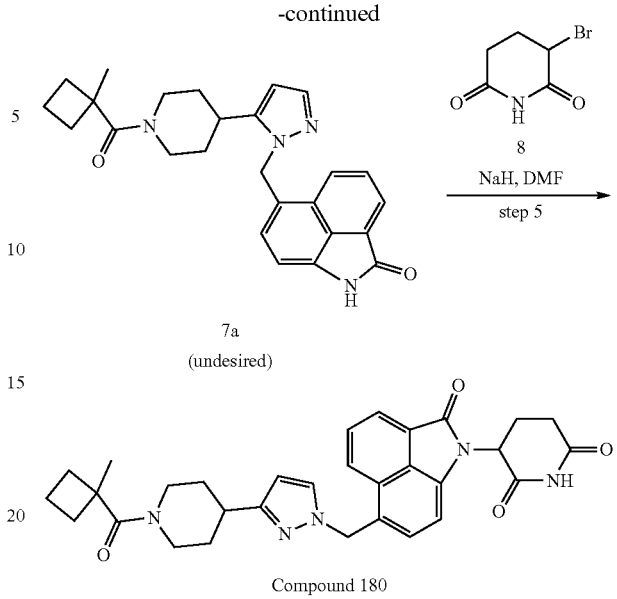

Compound 180

Step 1: Synthesis of tert-butyl 4-[1-[[1-[(4-methoxyphenyl)methyl]-2-oxo-benzo[cd]indol-6-yl]methyl]pyrazol-3-yl]piperidine-1-carboxylate: To a stirred solution of 6-(chloromethyl)-1-[(4-methoxyphenyl)methyl]benzo[cd]indol-2-one (int-A) (500.00 mg, 1.48 mmol) and tert-butyl 4-(1H-pyrazol-3-yl)piperidine-1-carboxylate (1) (372 mg, 1.48 mmol) in DMF (5 mL) was added Cesium carbonate (1.21 g, 3.70 mmol) at room temperature and the resultant reaction mixture was heated at 90° C. for 16 h. After completion (monitored by TLC) the reaction mixture was diluted with ethyl acetate and washed with water and brine, dried over sodium sulphate and concentrated under reduced pressure. The crude thus obtained was purified by combiflash Column (Gradient 20-30% EtOAc in Hexane) to afford tert-butyl 4-[1-[[1-[(4-methoxyphenyl)methyl]-2-oxo-benzo[cd]indol-6-yl]methyl]pyrazol-3-yl]piperidine-1-carboxylate (2) (400 mg, 43.03% yield) as light yellow solid. LC MS: ES+ 553.5.

Step 2: Synthesis of 1-[(4-methoxyphenyl)methyl]-6-[[3-(4-piperidyl)pyrazol-1-yl]methyl]benzo[cd]indol-2-one; hydrochloride: To a stirred solution of tert-butyl 4-[1-[[1-[(4-methoxyphenyl)methyl]-2-oxo-benzo[cd]indol-6-yl]methyl]pyrazol-3-yl]piperidine-1-carboxylate (2) (400 mg, 723.77 umol) in Dioxane (5 mL) was added Dioxane-HCl (4M) (10 mL) under cooling condition and the resultant reaction mixture was stirred at RT for 4 hours. After completion (monitored by TLC) the reaction mixture was concentrated under reduced pressure. The crude was triturated with Ether-Pentane to afford 1-[(4-methoxyphenyl)methyl]-6-[[3-(4-piperidyl)pyrazol-1-yl]methyl]benzo[cd]indol-2-one; hydrochloride (3) (300 mg, 70.9% Yield) as light yellow solid. LC MS: ES+ 453.4.

Step 3: Synthesis of 1-[(4-methoxyphenyl)methyl]-6-[[3-[1-(1-methylcyclobutanecarbonyl)-4-piperidyl]pyrazol-1-yl]methyl]benzo[cd]indol-2-one: To the stirred solution of 1-[(4-methoxyphenyl)methyl]-6-[[3-(4-piperidyl)pyrazol-1-yl]methyl]benzo[cd]indol-2-one; hydrochloride (3) (300 mg, 613.49 umol) and 1-methylcyclobutanecarboxylic acid (4) (70.02 mg, 613.49 umol) in DMF (10 mL) was added DIPEA (396.44 mg, 3.07 mmol, 534.28 uL) and stirred for 15 minutes followed by the addition of HATU (279.92 mg, 736.19 umol) and was allowed to stir for 16 hr at RT. After completion (monitored by LCMS), the reaction mixture was diluted with Ethyl acetate and washed with cold water, brine, dried over sodium sulfate and concentrated under reduced pressure. The crude thus obtained was purified by column chromatography (silica, gradient: 0-3% MeOH in DCM) to afford 1-[(4-methoxyphenyl)methyl]-6-[[3-[1-(1-methylcyclobutanecarbonyl)-4-piperidyl]pyrazol-1-yl]methyl]benzo[cd]indol-2-one (5) (300 mg, 84.6% yield) as gummy solid. LC MS: ES+ 549.5.

Step 4 and 4a: Synthesis of 6-[[3-[1-(1-methylcyclobutanecarbonyl)-4-piperidyl]pyrazol-1-yl]methyl]-1H-benzo[cd]indol-2-one & 6-[[5-[1-(1-methylcyclobutanecarbonyl)-4-piperidyl]pyrazol-1-yl]methyl]-1H-benzo[cd]indol-2-one: To a stirred solution of compound 1-[(4-methoxyphenyl)methyl]-6-[[3-[1-(1-methylcyclobutanecarbonyl)-4-piperidyl]pyrazol-1-yl]methyl]benzo[cd]indol-2-one (5) (250 mg, 455.64 umol) in TFA (3 mL) was added Trifluoromethanesulfonic acid (341.91 mg, 2.28 mmol, 199.95 uL) under cooling condition and the resultant reaction mixture was stirred at RT for 16 hours. After completion (monitored by TLC) the reaction mixture was concentrated under reduced pressure and crude mass was basified with saturated sodium bicarbonate solution and extracted with ethyl acetate. The layers were separated and the organic part was dried over sodium sulphate and concentrated under reduced pressure. Crude thus obtained was purified by Combiflash column (Gradient 0-3% MeOH in DCM) to afford compound (6) (150 mg) as regiomeric mixture. This regiomeric mixture was separated by Preparative HPLC which was done on Waters auto purification instrument. Column name: Kinetex Evo C18 (250×20 mm, 5µ) operating at ambient temperature and flow rate of 16 mL/min. Mobile phase: A=10 mM Ammonium Acetate in water, B=Acetonitrile; Gradient Profile: Mobile phase initial composition of 90% A and 10% B, then 65% A and 35% B in 3 min, then to 50% A and 50% B in 25 min., then to 100% B in 25.5 min., held this composition up to 27.5 min. for column washing, then returned to initial composition in 28 min. and held till 30 min to afford desired compound 6-[[3-[1-(1-methylcyclobutanecarbonyl)-4-piperidyl]pyrazol-1-yl]methyl]-1H-benzo[cd]indol-2-one (7) (55 mg, 27.04% yield) as yellow solid and 6-[[5-[1-(1-methylcyclobutanecarbonyl)-4-piperidyl]pyrazol-1-yl]methyl]-1H-benzo[cd]indol-2-one (7a) (30 mg, 15.06% yield) as yellow solid. LC MS: ES+ 429.4.

Step 5: Synthesis of 3-[6-[[3-[1-(1-methylcyclobutanecarbonyl)-4-piperidyl]pyrazol-1-yl]methyl]-2-oxo-benzo[cd]indol-1-yl]piperidine-2,6-dione: To a stirred solution of 6-[[3-[1-(1-methylcyclobutanecarbonyl)-4-piperidyl]pyrazol-1-yl]methyl]-1H-benzo[cd]indol-2-one (7) (50 mg, 116.68 umol) in THF (5 mL) was added Sodium hydride 60% dispersion in mineral oil (8.05 mg, 350.04 umol) at 0° C. and stirred for 5 min. Then 3-bromopiperidine-2,6-dione (8) (44.81 mg, 233.36 umol) was added under cooling condition and the reaction mixture was stirred at 70° C. for 60 min. After completion (monitored by TLC) the reaction mixture was quenched in ice and extracted with ethyl acetate. The organic part was further washed with water and brine, dried over sodium sulfate and concentrated. The crude was purified by Prep TCL Plate in 30% Acetone in DCM to afford 3-[6-[[3-[1-(1-methylcyclobutanecarbonyl)-4-piperidyl]pyrazol-1-yl]methyl]-2-oxo-benzo[cd]indol-1-yl]piperidine-2,6-dione Compound 180 (17 mg, 26.4% yield) as yellow solid. $^1$H NMR (400 MHz, DMSO-d6) δ 11.13 (s, 1H), 8.42 (d, J=8.28 Hz, 1H), 8.10 (d, J=6.96 Hz, 1H), 7.85 (t, J=7.56 Hz, 1H), 7.72 (s, 1H), 7.41 (d, J=7.20 Hz, 1H), 7.13 (d, J=7.28 Hz, 1H), 6.09 (s, 1H), 5.86 (s, 2H), 5.47-5.44 (m, 1H), 4.32-4.28 (m, 1H), 3.54-3.50 (m, 1H), 3.02-2.91 (m, 2H), 2.80-2.73 (m, 2H), 2.66-2.63 (m, 2H), 2.42-2.34 (m, 2H), 2.09-2.07 (m, 2H), 1.91-1.77 (m, 5H), 1.61-1.58 (m, 1H), 1.42-1.38 (m, 1H), 1.32 (s, 3H).LC MS: ES+ 540.5.

Example 92. Synthesis of 3-[6-[[3-[1-(1-methylcyclobutanecarbonyl)-4-piperidyl]-2-oxo-imidazolidin-1-yl]methyl]-2-oxo-benzo[cd]indol-1-yl]piperidine-2,6-dione (Compound 181)

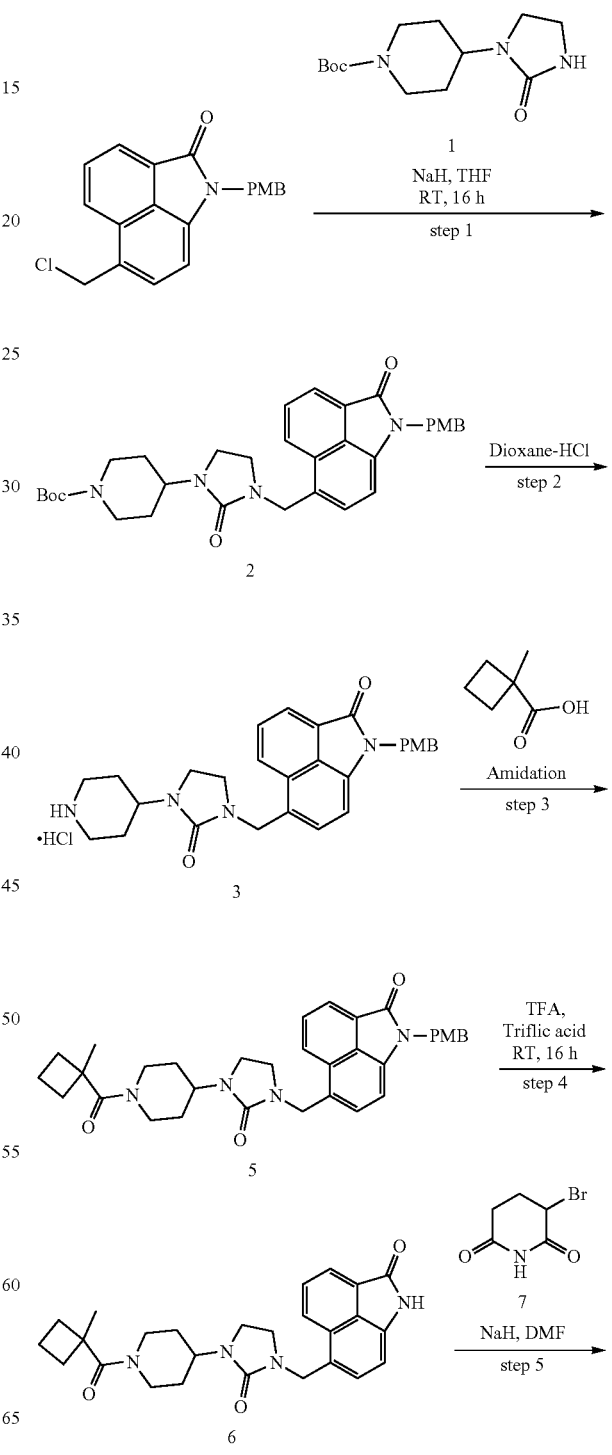

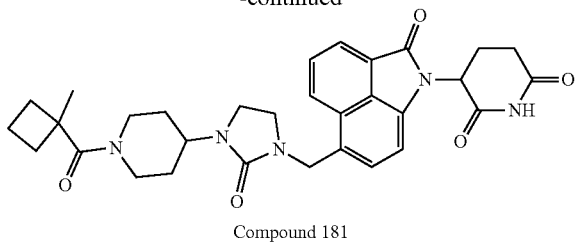

Compound 181

Step-1: Synthesis of tert-butyl 4-[3-[[1-[(4-methoxyphenyl)methyl]-2-oxo-benzo[cd]indol-6-yl]methyl]-2-oxo-imidazolidin-1-yl]piperidine-1-carboxylate: To a stirred solution of tert-butyl 4-(2-oxoimidazolidin-1-yl)piperidine-1-carboxylate (1) (318.93 mg, 1.18 mmol) in THF (10 mL) was added Sodium hydride 60% dispersion in mineral oil (54.45 mg, 2.37 mmol) at room temperature and the resultant reaction mixture was stirred at RT for 30 minutes. Then 6-(chloromethyl)-1-[(4-methoxyphenyl)methyl]benzo[cd]indol-2-one (int-A) (400 mg, 1.18 mmol) was added and the reaction mixture was allowed to stir at RT for 16 h. After completion (monitored by TLC) the reaction mixture was quenched with crushed ice and was extracted with EtOAc (Twice). The combined organic layer was further washed with water and brine, dried over sodium sulphate and concentrated under reduced pressure. The crude thus obtained was purified by combiflash column (Gradient 0-3% MeOH in DCM) to afford tert-butyl 4-[3-[[1-[(4-methoxyphenyl)methyl]-2-oxo-benzo[cd]indol-6-yl]methyl]-2-oxo-imidazolidin-1-yl]piperidine-1-carboxylate (2) (320 mg, 28.41% yield) as light yellow solid. LC MS ES+ 571.6.

Step-2: Synthesis of 1-[(4-methoxyphenyl)methyl]-6-[[2-oxo-3-(4-piperidyl)imidazolidin-1-yl]methyl]benzo[cd]indol-2-one; hydrochloride: To a stirred solution of tert-butyl 4-[3-[[1-[(4-methoxyphenyl)methyl]-2-oxo-benzo[cd]indol-6-yl]methyl]-2-oxo-imidazolidin-1-yl]piperidine-1-carboxylate (2) (300 mg, 525.69 umol) in Dioxane (5 mL) was added Dioxane-HCl (4M) (10 mL) under cooling condition and the resultant reaction mixture was stirred at RT for 4 hours. After completion (monitored by TLC) the reaction mixture was concentrated under reduced pressure. The crude was triturated with Ether-Pentane to afford 1-[(4-methoxyphenyl)methyl]-6-[[2-oxo-3-(4-piperidyl)imidazolidin-1-yl]methyl]benzo[cd]indol-2-one; hydrochloride (3) (250 mg, 83.13% Yield) as off white solid. LC MS: ES+ 471.1.

Step-3: Synthesis of 1-[(4-methoxyphenyl)methyl]-6-[[3-[1-(1-methylcyclobutanecarbonyl)-4-piperidyl]-2-oxo-imidazolidin-1-yl]methyl]benzo[cd]indol-2-one: To the stirred solution of 1-[(4-methoxyphenyl)methyl]-6-[[2-oxo-3-(4-piperidyl)imidazolidin-1-yl]methyl]benzo[cd]indol-2-one; hydrochloride (3) (250 mg, 493.07 umol) and 1-methylcyclobutanecarboxylic acid (4) (56.28 mg, 493.07 umol) in DMF (2 mL) was added DIPEA (318.62 mg, 2.47 mmol, 429.41 uL) and stirred for 15 minutes followed by the addition of HATU (224.98 mg, 591.69 umol) and was allowed to stir for 16 hr at RT. After completion (monitored by LCMS), the reaction mixture was diluted with Ethyl acetate and washed with cold water, brine, dried over sodium sulfate and concentrated under reduced pressure. The crude thus obtained was purified by column chromatography (silica, gradient: 0-3% MeOH in DCM) to afford 1-[(4-methoxyphenyl)methyl]-6-[[3-[1-(1-methylcyclobutanecarbonyl)-4-piperidyl]-2-oxo-imidazolidin-1-yl]methyl]benzo[cd]indol-2-one (5) (220 mg, 72.81% yield) as light yellow solid. LC MS: ES+ 567.6.

Step-4: Synthesis of 6-[[3-[1-(1-methylcyclobutanecarbonyl)-4-piperidyl]-2-oxo-imidazolidin-1-yl]methyl]-1H-benzo[cd]indol-2-one: To a stirred solution of 1-[(4-methoxyphenyl)methyl]-6-[[3-[1-(1-methylcyclobutanecarbonyl)-4-piperidyl]-2-oxo-imidazolidin-1-yl]methyl]benzo[cd]indol-2-one (5) (200 mg, 352.93 umol) in TFA (3 mL) was added trifluoromethanesulfonic acid (264.84 mg, 1.76 mmol, 154.88 uL) under cooling condition. Then the reaction mixture was stirred at room temperature for 16 hr. After completion (monitored by TLC and LCMS) the reaction mass was quenched with saturated bicarbonate solution and extracted with ethyl acetate (twice). The combined organic part was dried over Sodium sulphate and concentrated under reduced pressure. The crude thus obtained was purified by combiflash Column (Gradient 0-3% MeOH in DCM) to afford 6-[[3-[1-(1-methylcyclobutanecarbonyl)-4-piperidyl]-2-oxo-imidazolidin-1-yl]methyl]-1H-benzo[cd]indol-2-one (6) (100 mg, 57.11% yield) as light yellow solid. LC MS: ES+ 447.2.

Step-5: Synthesis of 3-[6-[[3-[1-(1-methylcyclobutanecarbonyl)-4-piperidyl]-2-oxo-imidazolidin-1-yl]methyl]-2-oxo-benzo[cd]indol-1-yl]piperidine-2,6-dione: To a stirred solution of 6-[[3-[1-(1-methylcyclobutanecarbonyl)-4-piperidyl]-2-oxo-imidazolidin-1-yl]methyl]-1H-benzo[cd]indol-2-one (6) (90 mg, 201.55 umol) in THF (5 mL) was added Sodium hydride 60% dispersion in mineral oil (13.90 mg, 604.65 umol) at 0° C. and stirred for 5 min. Then 3-bromopiperidine-2,6-dione (7) (77.40 mg, 403.10 umol) was added under cooling condition and the reaction mixture was stirred at 70° C. for 30 min. After completion (monitored by TLC) the reaction mixture was quenched in ice and extracted with ethyl acetate. The organic part was further washed with water and brine, dried over sodium sulfate and concentrated. The crude was purified by Prep TCL Plate in 30% Acetone in DCM to afford 3-[6-[[3-[1-(1-methylcyclobutanecarbonyl)-4-piperidyl]-2-oxo-imidazolidin-1-yl]methyl]-2-oxo-benzo[cd]indol-1-yl]piperidine-2,6-dione Compound 181 (17 mg, 13.9% yield) as yellow solid.

$^1$H NMR (400 MHz, DMSO-d6) δ 11.12 (s, 1H), 8.45 (d, J=8.36 Hz, 1H), 8.10 (d, J=6.84 Hz, 1H), 7.86 (t, J=7.36 Hz, 1H), 7.43 (d, J=7.28 Hz, 1H), 7.11 (d, J=7.32 Hz, 1H), 5.46-5.43 (m, 1H), 4.67 (s, 2H), 4.50-4.46 (m, 1H), 3.89-3.70 (m, 1H), 3.60-3.50 (m, 1H), 3.16-2.10 (m, 4H), 3.02-2.92 (m, 2H), 2.77-2.73 (m, 1H), 2.67-2.63 (m, 2H), 2.39-2.34 (m, 2H), 2.11-2.08 (m, 1H), 1.90-1.80 (m, 1H), 1.80-1.70 (m, 2H), 1.65-1.55 (m, 3H), 1.55-1.45 (m, 2H), 1.32 (s, 3H). LC MS: ES+ 558.3.

Example 93. Synthesis of 6-(4,4,5,5-tetramethyl-1,3,2-dioxaborolan-2-yl)-1H-benzo[cd]indol-2-one (Compound 182)

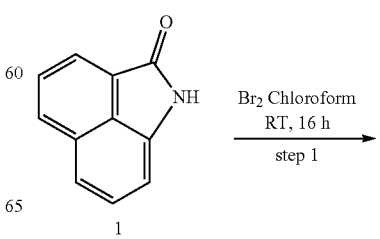

1

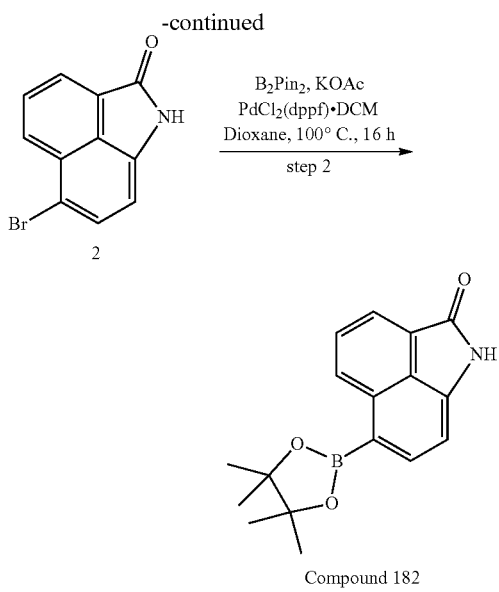

Step-1: Synthesis of 6-bromo-1H-benzo[cd]indol-2-one (2): To a stirred suspension of 1H-benzo[cd]indol-2-one (1) (250 g, 1.48 mol) in Chloroform (2.5 L), a solution of molecular bromine (354.23 g, 2.22 mol, 113.53 mL) in Chloroform (500 mL) was added drop wise at 0° C. and the reaction mixture was stirred at room temperature for 16 hours. After completion of the reaction (monitored by TLC), the reaction mass was poured into saturated aqs. solution of Sodium thiosulphate. The yellow solid formed was filtered through sintered funnel, washed with water, pentane and stripped with toluene to afford 6-bromo-1H-benzo[cd]indol-2-one (2) (350 g, 90% yield) as yellow solid. LC MS: ES+ 2 (248.2 and 250.2).

Step-2: Synthesis of 6-(4,4,5,5-tetramethyl-1,3,2-dioxaborolan-2-yl)-1H-benzo[cd]indol-2-one: To a stirred solution of 6-bromo-1H-benzo[cd]indol-2-one (2) (100 g, 403.10 mmol) in 1,4 dioxane (1 L) was added Bis(pinacolato)diboron (153.55 g, 604.66 mmol) followed by well dried Potassium Acetate (118.68 g, 1.21 mol, 75.60 mL). The resultant reaction mass was degassed well with argon for 15 minutes. PdCl2(dppf).DCM (32.92 g, 40.31 mmol) was added and the reaction mass was heated at 100° C. for 16 hours. After completion of the reaction (monitored by TLC), the reaction mixture was cooled to RT, filtered through a pad of celite, washed with more Ethyl acetate. The combined filtrate was washed with cold water, dried over sodium sulphate and concentrated under reduced pressure to afford 6-(4,4,5,5-tetramethyl-1,3,2-dioxaborolan-2-yl)-1H-benzo[cd]indol-2-one Compound 182 (110 g, 64% yield) as brown gum. LC MS: ES+ 295.7.

Example 94. Synthesis of 4-[4-[[4-[[1-(2,6-dioxo-3-piperidyl)-2-oxo-benzo[cd]indol-6 yl]methyl] phenyl] methyl] piperazin-1-yl]-3-fluoro-benzonitrile (Compound 183, Compound 184, and (Compound 185)

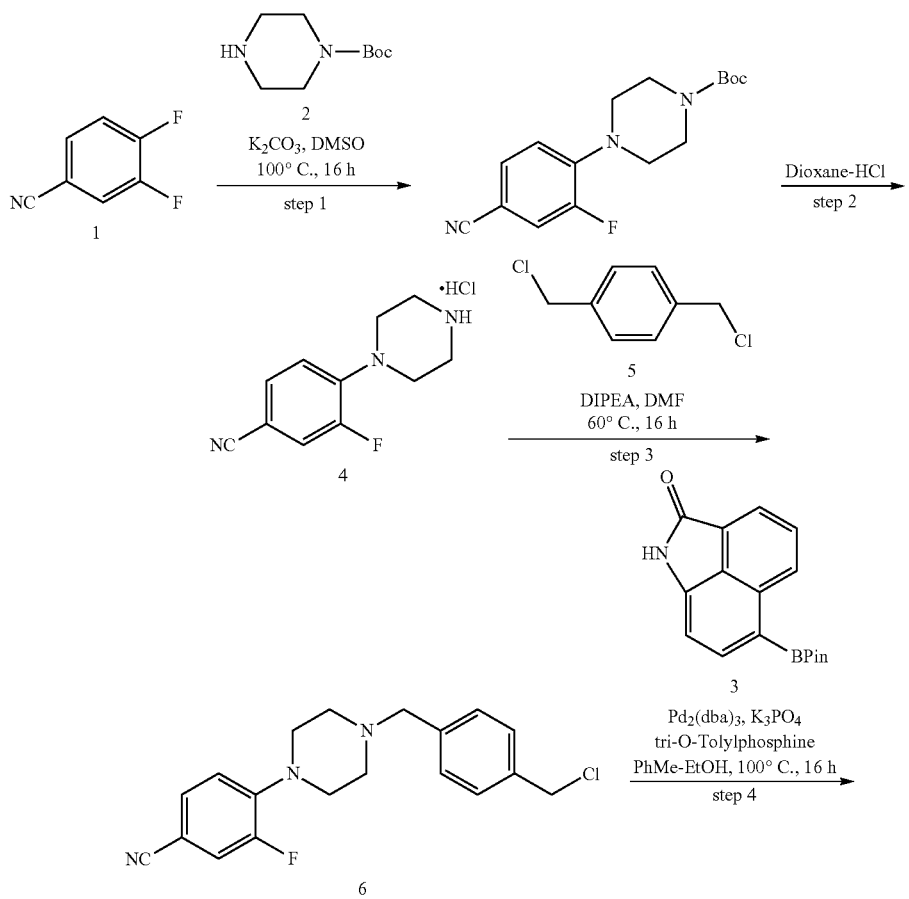

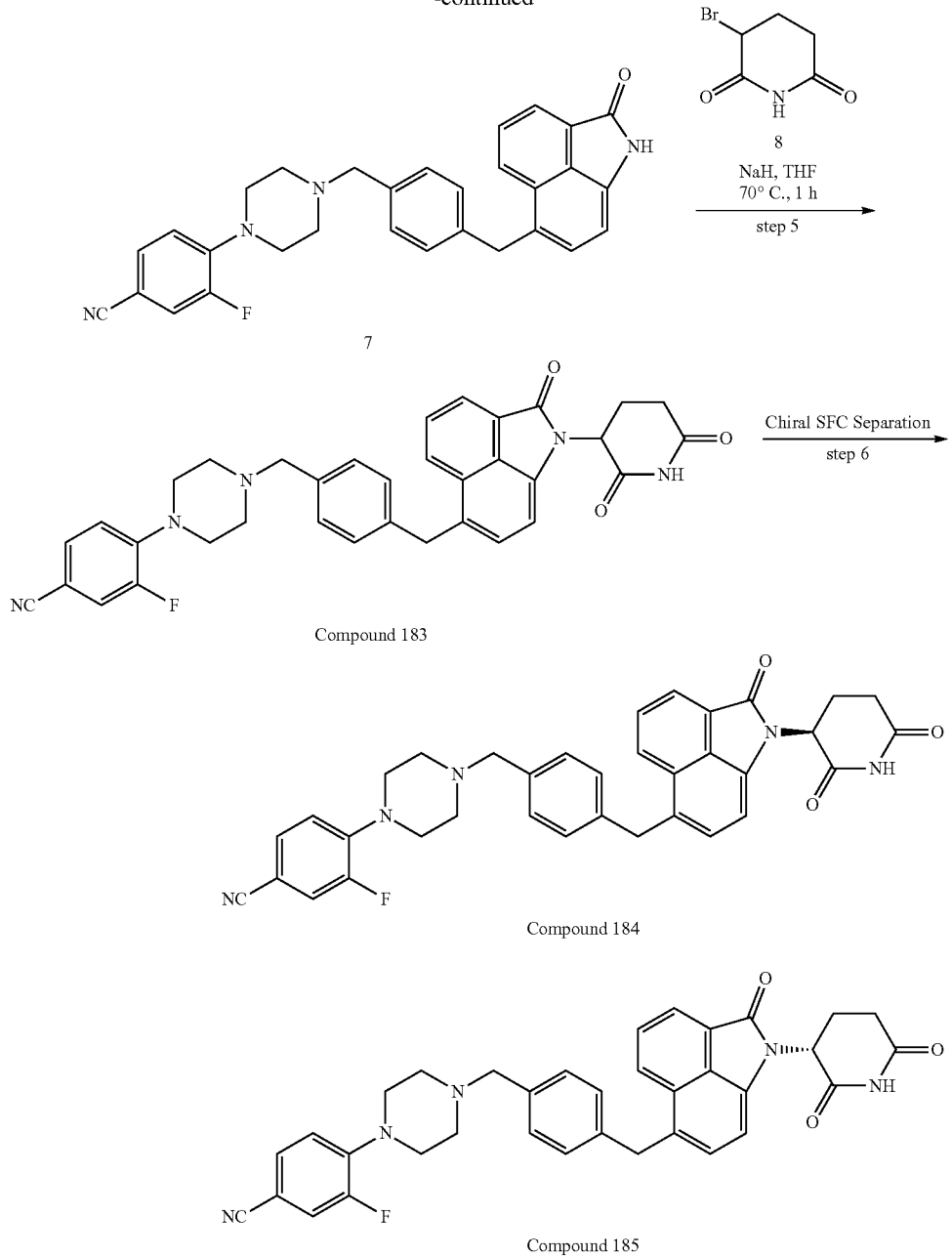

Compound 183

Compound 184

Compound 185

Step-1: Synthesis of tert-butyl 4-(4-cyano-2-fluoro-phenyl)piperazine-1-carboxylate (3): To a stirred solution of 3,4-difluorobenzonitrile (1) (13 g, 93.46 mmol) in DMSO (80 mL), Potassium carbonate (19.37 g, 140.18 mmol, 8.46 mL) and tert-butyl piperazine-1-carboxylate (2) (19.15 g, 102.80 mmol) were added and the resultant reaction mixture was heated at 100° C. for 16 hours. After completion (monitored by TLC), the reaction mixture was allowed to cool and water (500 ml) was added to it. The solid that formed was filtered off, washed with water, and dried under vacuum to obtain tert-butyl 4-(4-cyano-2-fluoro-phenyl)piperazine-1-carboxylate (3) (20 g, 66% yield) as a white solid. LC MS: ES+ 306.2.

Step-2: Synthesis of 3-fluoro-4-piperazin-1-yl-benzonitrile Hydrochloride salt (4): To a stirred solution of tert-butyl 4-(4-cyano-2-fluoro-phenyl)piperazine-1-carboxylate (3) (20 g, 65.50 mmol) in Dioxane (15 mL) was added Dioxane-HCl (65.50 mmol, 50 mL) and the reaction mixture was stirred at RT for 3 hours. All the volatiles were removed under reduced pressure. The solid obtained was triturated with ether to afford 3-fluoro-4-piperazin-1-yl-benzonitrile; hydrochloride (4) (17 g, 88% yield) as a white solid. LC MS: ES+ 206.4.

Step-3: Synthesis of 4-[4-[[4-(chloromethyl)phenyl]methyl]piperazin-1-yl]-3-fluoro-benzonitrile (6): To a stirred solution of 3-fluoro-4-piperazin-1-yl-benzonitrile; hydrochloride (4) (15 g, 62.06 mmol) in DMF (75 mL) was added DIPEA (24.06 g, 186.19 mmol, 32.43 mL) and the reaction mixture was stirred for 5 minutes. Then 1,4-bis (chloromethyl)benzene (5) (10.86 g, 62.06 mmol, 7.65 mL)

was added in one portion and the reaction was heated at 60° C. for 16 hours. After completion (monitored by TLC), the reaction mixture was diluted with ethyl acetate and washed with water and brine, dried over sodium sulfate and concentrated. The crude thus obtained was purified by column chromatography (silica, gradient: 10-30% EtOAc in Hexane) to afford 4-[4-[[4-(chloromethyl)phenyl]methyl] piperazin-1-yl]-3-fluoro-benzonitrile (6) (7 g, 32% yield) as a white solid. LC MS: (Es, ES+ 2) 344.2, 346.4.

Step-4: Synthesis of 3-fluoro-4-[4-[[4-[(2-oxo-1H-benzo [cd]indol-6-yl)methyl]phenyl]methyl]piperazin-1-yl]benzonitrile (7): To a well degassed solution of 4-[4-[[4-(chloromethyl)phenyl]methyl]piperazin-1-yl]-3-fluoro-benzonitrile (6) (7 g, 20.36 mmol) and 6-(4,4,5,5-tetramethyl-1,3-dioxolan-2-yl)-1H-benzo[cd]indol-2-one (3) (9.08 g, 30.54 mmol) in ethanol (30 mL) and Toluene (60 mL), Potassium phosphate tribasic, anhydrous, (10.80 g, 50.90 mmol) was added followed by the addition of Tri-o-Tolyl phosphine (1.24 g, 4.07 mmol) and Pd2(dba)3 (1.86 g, 2.04 mmol). The resulting mixture was then heated at 100° C. for 16 hours. After completion of reaction (as monitored by LCMS), the reaction mixture was filtered through a bed of celite, washed with Ethyl acetate. The combined filtrate was washed with water and brine, dried over sodium sulfate and concentrated under reduced pressure. Crude mass was purified by column chromatography (silica, gradient: 0-40% Ethyl acetate in Hexane) to obtain 3-fluoro-4-[4-[[4-[(2-oxo-1H-benzo[cd]indol-6-yl) methyl]phenyl]methyl]piperazin-1-yl]benzonitrile (7) (5.5 g, 52% yield,) as yellow solid. LC MS: ES+ 477.4.

Step-5: Synthesis of 4-[4-[[4-[[1-(2,6-dioxo-3-piperidyl)-2-oxo-benzo[cd]indol-6 yl ] methyl]phenyl] methyl] piperazin-1-yl]-3-fluoro-benzonitrile: To a cooled solution of fluoro-4-[4-[[4-[(2-oxo-1H-benzo[cd]indol-6-yl)methyl] phenyl]methyl]piperazin-1-yl]benzonitrile (7) (5.5 g, 11.54 mmol) in dry THF (30 mL), Sodium hydride (60% dispersion in mineral oil) (2.65 g, 115.41 mmol) was added portion wise, maintaining the temp <5° C. Once the addition is over, the resultant mixture was stirred for 15 minutes at RT. Then the reaction mixture was again cooled to 0° C. and 3-bromopiperidine-2,6-dione (8) (11.08 g, 57.71 mmol) was added to it portion wise. After complete addition, resulting solution was heated at 70° C. 1 hour. After completion (evidenced from TLC), the reaction mixture was cooled to 0° C. and quenched with the addition of ice cooled water. Aqueous part was extracted with ethyl acetate (3×100 mL). Combined organics was separated, dried over sodium sulfate and concentrated under reduced pressure. Crude mass was purified by column chromatography (silica, gradient: 30-100% EtOAc in DCM) to afford 4-[4-[[4-[[1-(2,6-dioxo-3-piperidyl)-2-oxo-benzo[cd]indol-6-yl]methyl]phenyl] methyl]piperazin-1-yl]-3-fluoro-benzonitrile Compound 183 (4.4 g, 63% yield) as yellow solid. $^1$H NMR (400 MHz, DMSO-d6) δ 11.12 (s, 1H), 8.32 (d, J=8.28 Hz, 1H), 8.07 (d, J=6.92 Hz, 1H), 7.80 (t, J=7.66 Hz, 1H), 7.66 (d, J=12.4 Hz, 1H), 7.54 (d, J=8.36 Hz, 1H), 7.40 (d, J=7.28 Hz, 1H), 7.26-7.19 (m, 4H), 7.11-7.05 (m, 2H), 5.44 (dd, J=12.64, 4.84 Hz, 1H), 4.37 (s, 2H), 3.49 (s, 2H), 3.12 (br s, 4H), 2.98-2.90 (m, 1H), 2.79-2.73 (m, 1H), 2.70-2.62 (m, 1H), 2.45 (br s, 4H), 2.10-2.07 (m, 1H); LC MS: ES+ 588.48.

Step-6 (Chiral separation): Preparation of 4-(4-(4-((1-(2,6-dioxopiperidin-3-yl)-2-oxo-1,2-dihydrobenzo[cd]indol-6-yl)methyl)benzyl)piperazin-1-yl)-3-fluorobenzonitrile and 4-(4-(4-((1-(2,6-dioxopiperidin-3-yl)-2-oxo-1,2-dihydrobenzo[cd]indol-6-yl)methyl)benzyl)piperazin-1-yl)-3-fluorobenzonitrile: 4.4 g of 4-[4-[[4-[[1-(2,6-dioxo-3-piperidyl)-2-oxo-benzo[cd]indol-6-yl]methyl]phenyl]methyl] piperazin-1-yl]-3-fluoro-benzonitrile Compound 183 was separated into enantiomers by chiral SFC method to afford 4-(4-(4-((1-(2,6-dioxopiperidin-3-yl)-2-oxo-1,2-dihydrobenzo[cd]indol-6-yl)methyl)benzyl)piperazin-1-yl)-3-fluorobenzonitrile Compound 184 (1.5 g, % ee 100) and 4-(4-(4-((1-(2,6-dioxopiperidin-3-yl)-2-oxo-1,2-dihydrobenzo[cd]indol-6-yl)methyl)benzyl)piperazin-1-yl)-3-fluorobenzonitrile Compound 185 (1.55 g, % ee 100) as yellow solids.

Example 95. Synthesis of -(6-((1-(3,3-difluoro-1-((1-methylcyclobutyl)methyl)piperidin-4-yl)-1H-pyrazol-4-yl)methyl)-2-oxobenzo[cd]indol-1(2H)-yl) piperidine-2,6-dione (Compound 186) and 3-(6-((1-(3,3-difluoro-1-((1-methylcyclobutyl)methyl) piperidin-4-yl)-1H-pyrazol-4-yl)methyl)-2-oxobenzo [cd]indol-1(2H)-yl)piperidine-2,6-dione (Compound 187)

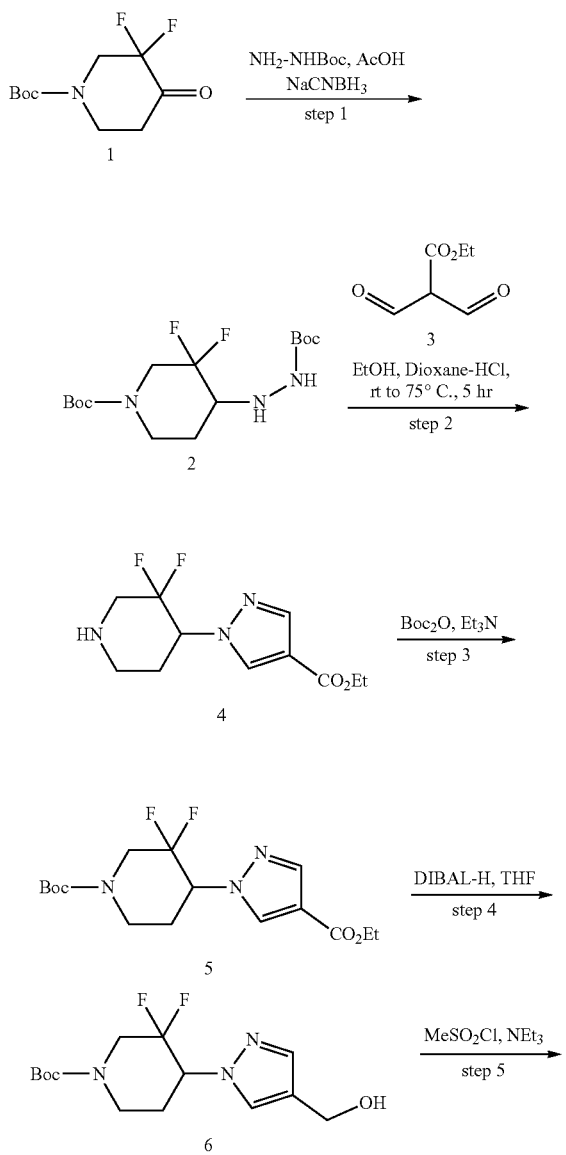

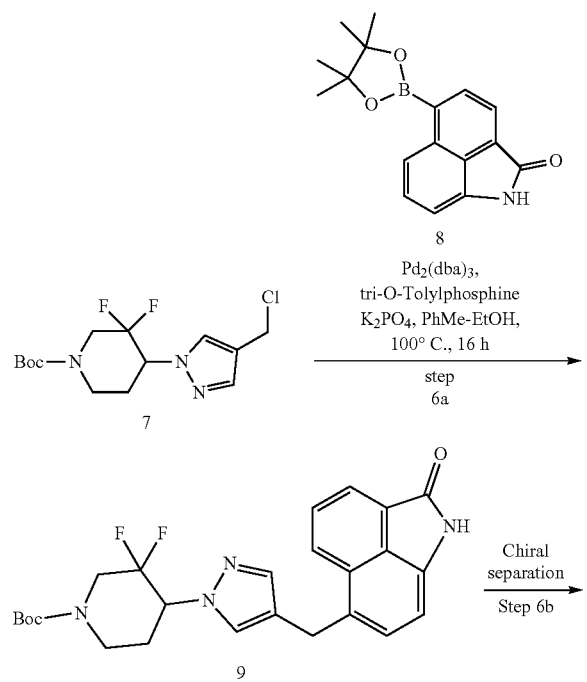
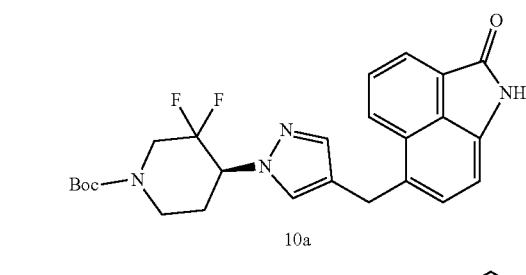
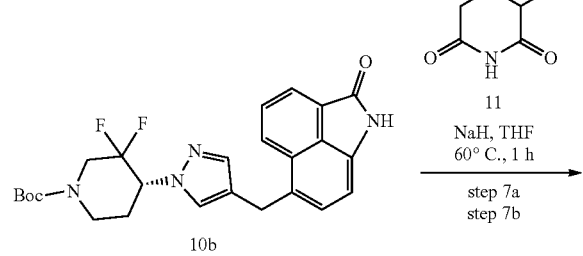
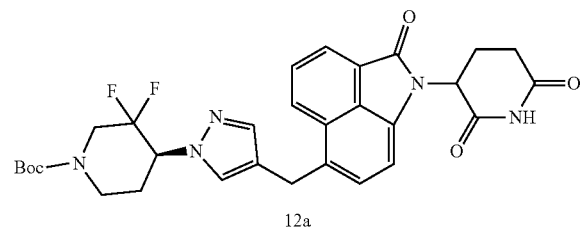
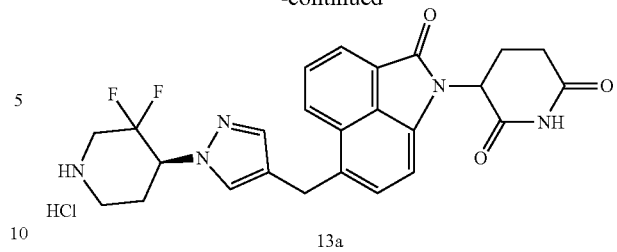
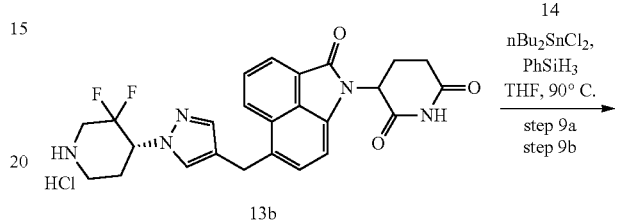
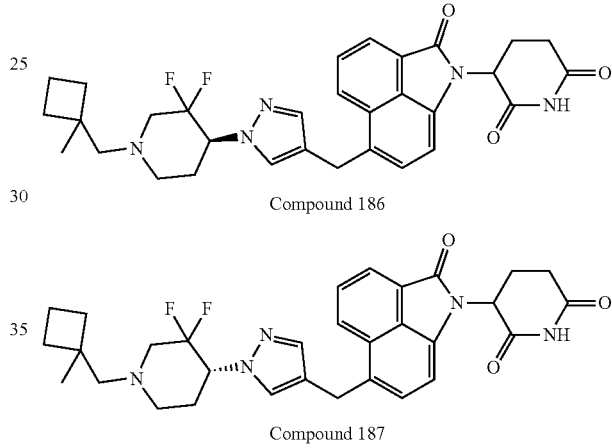

Step 1: Synthesis of obtain tert-butyl 4-(2-tert-butoxycarbonylhydrazino)-3,3-difluoro-piperidine-1-carboxylate (2): Mixture solution of tert-butyl 3,3-difluoro-4-oxo-piperidine-1-carboxylate (1) (3.0 g, 12.75 mmol) and tert-butyl N-aminocarbamate (1.69 g, 12.75 mmol) in Acetic acid (13 mL) was stirred at rt for 2 hours. After that, Sodium cyanoborohydride (1.04 g, 16.58 mmol) was added to the reaction mixture and stirring was continued for 12 hours at room temperature. After completion of reaction (evidenced from TLC), volatiles were removed under reduced pressure. Resulting Sticky solid was then quenched with 5 N NaOH to maintain pH-9. Aqueous part was extracted with DCM (2×50 mL), separated, dried over anhydrous sodium sulfate and concentrated under reduced pressure to obtain crude tert-butyl 4-(2-tert-butoxycarbonylhydrazino)-3,3-difluoropiperidine-1-carboxylate (2) (4.11 g, 9.36 mmol, 73.37% yield). LC MS: ES+ 352.1.

Step-2: Synthesis of ethyl 1-(3,3-difluoro-4-piperidyl) pyrazole-4-carboxylate; hydrochloride (4): To the mixture solution of tert-butyl 4-(2-tert-butoxycarbonylhydrazino)-3,3-difluoro-piperidine-1-carboxylate (2) (4.11 g, 11.70 mmol) and ethyl 2-formyl-3-oxo-propanoate (3) (1.69 g, 11.70 mmol) in Ethanol (72 mL), 4M dioxane-HCl (38 mL) was added drop wise at rt. After complete addition, RM was heated at 75° C. for 5 hours. After completion of reaction (evidenced from LC MS), volatiles were removed under reduced pressure. Resulting brown gummy solid was quenched with saturated sodium bicarbonate solution. Aqueous part was extracted with ethyl acetate (2×50 mL), separated, dried over anhydrous sodium sulfate and concentrated to afford ethyl 1-(3,3-difluoro-4-piperidyl)pyrazole-4-carboxylate; hydrochloride (4) (3.0 g, 7.23 mmol, 61.77% yield) which was directly used in the next step without any purification. LC MS: ES+ 260.4.

Step-3: Synthesis of tert-butyl 4-(4-ethoxycarbonylpyrazol-1-yl)-3,3-difluoro-piperidine-1-carboxylate (5): To the stirred solution of ethyl 1-(3,3-difluoro-4-piperidyl)pyrazole-4-carboxylate; hydrochloride (4) (3.0 g, 10.14 mmol) in dry grade THF (10.0 mL) was added Triethylamine, 99% (2.05 g, 20.29 mmol, 2.83 mL) and Di-tert-butyl dicarbonate (6.64 g, 30.43 mmol, 6.98 mL) at 0° C. and after complete addition the reaction mix was stirred at rt for 12 hours. After completion of reaction (monitored by LC MS), volatiles were removed and resulting reaction mass was redissolved in ethyl acetate (50 mL). Organic phase was washed with water (40 mL)/brine (30 mL), separated, dried over anhydrous sodium sulfate and concentrated. Crude thus obtained was purified by column chromatography (silica, gradient: 0-40% Ethyl acetate in Hexane) to afford tert-butyl 4-(4-ethoxycarbonylpyrazol-1-yl)-3,3-difluoro-piperidine-1-carboxylate (5) (2.6 g, 7.16 mmol, 70.60% yield) as sticky solid which was stored in a round bottomed flask at 5° C. inside a refrigerator. LC MS: ES+ 304.2 (M-56).

Step 4: Synthesis of tert-butyl 3,3-difluoro-4-[4-(hydroxymethyl)pyrazol-1-yl]piperidine-1-carboxylate (6): To the stirred solution of tert-butyl 4-(4-ethoxycarbonylpyrazol-1-yl)-3,3-difluoro-piperidine-1-carboxylate (5) (1.0 g, 2.78 mmol) in dry grade THF (10.0 mL), Diisobutylaluminum hydride (7.91 g, 13.91 mmol, 9.22 mL) was added drop wise at −78° C. and stirred for 4 hours at same temperature under N2 atmosphere. After complete consumption, as evidenced from TLC, reaction mass was diluted with ethyl acetate (30 mL) and quenched with water (20 mL). Organic phase was separated, dried over anhydrous Na$_2$SO$_4$ and concentrated under reduced pressure to afford tert-butyl 3,3-difluoro-4-[4-(hydroxymethyl)pyrazol-1-yl]piperidine-1-carboxylate (6) (857 mg, 2.62 mmol, 94.14% yield) as yellow gum which was carried forward to the next step without any further purification. LC MS: ES+ 318.1.

Step-5: Synthesis of tert-butyl 4-[4-(chloromethyl)pyrazol-1-yl]-3,3-difluoro-piperidine-1-carboxylate (7): N,N-Diisopropylethylamine (2.61 g, 20.17 mmol, 3.51 mL) neat was added by syringe to a stirred solution of tert-butyl 3,3-difluoro-4-[4-(hydroxymethyl)pyrazol-1-yl]piperidine-1-carboxylate (6) (1.6 g, 5.04 mmol) in dry grade DCM (17 mL) at 0° C. under nitrogen atmosphere, followed by Methanesulfonyl chloride, 98% (1.44 g, 12.61 mmol, 975.63 uL) neat by syringe and stirred the reaction mix at rt for 16 hours. After completion of reaction (evidenced from TLC), the reaction was diluted to 50 ml DCM and washed with 2N HCl (10 mL). Organic phase was further washed with saturated sodium bicarbonate solution and separated, dried over anhydrous sodium sulfate and concentrated to afford tert-butyl 4-[4-(chloromethyl)pyrazol-1-yl]-3,3-difluoro-piperidine-1-carboxylate (7) (1.65 g, 3.93 mmol, 77.97% yield, 80% purity) as brown gummy solid which was carried forward to the next step without any further purification. LC MS: ES+ 280.1 (M-56).

Step 6a: Synthesis of tert-butyl 3,3-difluoro-4-[4-[(2-oxo-1H-benzo[cd]indol-6-yl)methyl]pyrazol-1-yl]piperidine-1-carboxylate (9): To a well degassed solution of tert-butyl 4-[4-(chloromethyl)pyrazol-1-yl]-3,3-difluoro-piperidine-1-carboxylate (7) (1.74 g, 5.18 mmol and 6-(4,4,5,5-tetramethyl-1,3,2-dioxaborolan-2-yl)-1H-benzo[cd]indol-2-one (8) (20.92 g, 70.89 mmol) in Ethanol (4 mL)-Toluene (8 mL), Potassium phosphate tribasic, anhydrous, ((3.30 g, 15.55 mmol) was added followed by the addition of Tri-o-Tolyl phosphine (315.45 mg, 1.04 mmol) and Pd2(dba)$_3$ (474.53 mg, 518.20 umol). The resulting mixture was then heated at 90° C. for 12 hours. After completion of reaction (as monitored by LCMS), the reaction mixture was filtered through a bed of celite, washed with Ethyl acetate (200 mL). The combined filtrate was then washed with water (3×50 mL) and brine (2×40 mL), dried over anhydrous sodium sulfate and concentrated under reduced pressure. Crude mass was purified by column chromatography (silica, gradient: 0-20% Ethyl acetate in DCM) to obtain tert-butyl 3,3-difluoro-4-[4-[(2-oxo-1H-benzo[cd]indol-6-yl)methyl]pyrazol-1-yl]piperidine-1-carboxylate (9) (225 mg, 256.14 umol, 4.94% yield) as yellow solid which was stored in a Tarson plastic bottle at ambient temperature. LC MS: ES+ 469.2.

Step 6b: Chiral separation: Compound was separated by normal phase Chiral HPLC using following method to afford 4-[4-[[1-(2,6-dioxo-3-piperidyl)-2-oxo-benzo[cd]indol-6-yl]methyl]pyrazol-1-yl]-3,3-difluoro-piperidine-1-carboxylate cpd-10a (100 mg) and 4-[4-[[1-(2,6-dioxo-3-piperidyl)-2-oxo-benzo[cd]indol-6-yl]methyl]pyrazol-1-yl]-3,3-difluoro-piperidine-1-carboxylate 10b (100 mg).

Step-7a: Synthesis of tert-butyl 4-[4-[[1-(2,6-dioxo-3-piperidyl)-2-oxo-benzo[cd]indol-6-yl]methyl]pyrazol-1-yl]-3,3-difluoro-piperidine-1-carboxylate (12a): To a ice cooled solution of 3,3-difluoro-4-[4-[(2-oxo-1H-benzo[cd]indol-6-yl)methyl]pyrazol-1-yl]piperidine-1-carboxylate (100.00 mg, 213.45 umol) (10a) in dry THF (5 mL), Sodium hydride (60% dispersion in mineral oil) (85.38 mg, 2.13 mmol, 60/a purity) was added portion wise, maintaining the temp <5° C. Once the addition is over, the resultant mixture was stirred for 15 minutes at RT. Then the reaction mixture was again cooled to 0° C. and 3-bromopiperidine-2,6-dione (11) (204.92 mg, 1.07 mmol) was added to it portion wise. After complete addition, resulting solution was heated at 70° C. for 1 hour. After completion (evidenced from TLC), the reaction mixture was again cooled to 0° C. and quenched with ice cooled water (10 mL). Aqueous part was extracted with ethyl acetate (2×20 mL). Combined extracts was dried over anhydrous sodium sulfate and concentrated under reduced pressure. Crude mass was purified by flash chromatography (silica, gradient: 2.5% MeOH in DCM) to tert-butyl 4-[4-[[1-(2,6-dioxo-3-piperidyl)-2-oxo-benzo[cd]indol-6-yl]methyl]pyrazol-1-yl]-3,3-difluoro-piperidine-1-carboxylate (12a) (100 mg, 167.36 umol, 78.41% yield, 97% purity) as yellow solid as yellow solid which was stored in a round bottomed flask at 5° C. inside a refrigerator; LC MS: ES+ 580.4.

Step-7b: Synthesis of tert-butyl 4-[4-[[1-(2,6-dioxo-3-piperidyl)-2-oxo-benzo[cd]indol-6-yl]methyl]pyrazol-1-yl]-3,3-difluoro-piperidine-1-carboxylate (12b): To a stirred solution of tert-butyl 3,3-difluoro-4-[4-[(2-oxo-1H-benzo[cd]indol-6-yl)methyl]pyrazol-1-yl]piperidine-1-carboxylate (10b) (100.00 mg, 213.45 umol) in dry THF (5.0 mL), Sodium hydride (in oil dispersion) 60% dispersion in mineral oil (85.38 mg, 2.13 mmol, 60% purity) was added at 0° C. and stirred for 15 minutes followed by the addition of 3-bromopiperidine-2,6-dione 11 (204.92 mg, 1.07 mmol). Resulting reaction mixture was stirred at 70° C. for 1.5 hour. As most of the SM was remain un-reactive as evidenced from TLC and LCMS, reaction mixture was heated to reflux for 2 hours. After complete conversion of SM as evidenced from LCMS, reaction mixture was quenched with water and extracted with ethyl acetate (2×20 mL). Combined organic layer was separated, dried over sodium sulfate and concentrated. Crude reaction mass was purified by PREP-TLC (2.5% MeOH in DCM as eluent) to afford tert-butyl 4-[4-[[1-(2,6-dioxo-3-piperidyl)-2-oxo-benzo[cd]indol-6-yl]methyl]pyrazol-1-yl]-3,3-difluoro-piperidine-1-carboxylate (12b) (100 mg, 155.28 umol, 72.75% yield, 90% purity) as yellow solid; LC MS: ES+ 580.4.

Step-8a: Synthesis of 3-(6-((1-(3,3-difluoropiperidin-4-yl)-1H-pyrazol-4-yl)methyl)-2-oxobenzo[cd]indol-1(2H)-yl)piperidine-2,6-dione (13a): To a stirred solution of tert-butyl 4-[4-[[1-(2,6-dioxo-3-piperidyl)-2-oxo-benzo[cd]indol-6-yl]methyl]pyrazol-1-yl]-3,3-difluoro-piperidine-1-carboxylate 12a (100 mg, 172.53 umol) in dry dioxane (2.0 mL), dioxane/HCl (172.53 umol, 1.0 mL) was added at 0° C. Resulting reaction mixture was stirred at rt for 4 hours. After complete conversion of SM as evidenced from LCMS, reaction mixture was quenched with sodium bicarbonate solution and extracted with ethyl acetate (2×20 mL). Combined organic layer was separated, dried over sodium sulfate and concentrated. Crude reaction mass was washed with diethyl ether to afford 3-[6-[[1-[3,3-difluoro-4-piperidyl]pyrazol-4-yl]methyl]-2-oxo-benzo[cd]indol-1-yl]piperidine-2,6-dione 13a (82 mg, 157.34 umol, 91.19% yield, 92% purity) as yellow solid.

Step 8b: Synthesis of 3-(6-((1-(3,3-difluoropiperidin-4-yl)-1H-pyrazol-4-yl)methyl)-2-oxobenzo[cd]indol-1(2H)-yl)piperidine-2,6-dione (13b): To a stirred solution of tert-butyl (4-[4-[[1-(2,6-dioxo-3-piperidyl)-2-oxo-benzo[cd]indol-6-yl]methyl]pyrazol-1-yl]-3,3-difluoro-piperidine-1-carboxylate (100 mg, 172.53 umol) in dry dioxane (2.0 mL), dioxane/HCl (172.53 umol, 1.0 mL) was added at 0° C. Resulting reaction mixture was stirred at rt for 4 hours. After complete conversion of SM as evidenced from LCMS, reaction mixture was quenched with sodium bicarbonate solution and extracted with ethyl acetate (2×20 mL). Combined organic layer was separated, dried over sodium sulfate and concentrated. Crude reaction mass was washed with diethyl ether to afford 3-[6-[[1-[3,3-difluoro-4-piperidyl]pyrazol-4-yl]methyl]-2-oxo-benzo[cd]indol-1-yl]piperidine-2,6-dione 13b (60 mg, 120.13 umol, 69.63% yield, 96% purity) as yellow solid.

Step 9a: Synthesis of 3-(6-((1-(3,3-difluoro-1-((1-methylcyclobutyl)methyl)piperidin-4-yl)-1H-pyrazol-4-yl)methyl)-2-oxobenzo[cd]indol-1(2H)-yl)piperidine-2,6-dione: To the stirred solution of 3-[6-[[1-[3,3-difluoro-4-piperidyl]pyrazol-4-yl]methyl]-2-oxo-benzo[cd]indol-1-yl]piperidine-2,6-dione 13a (82.0 mg, 171.02 umol) in THF (12.0 mL) was added 1-methylcyclobutanecarbaldehyde 14 (20.14 mg, 205.22 umol), followed by the addition of Dibutyltindichloride (62.36 mg, 205.22 umol, 45.85 uL) and Phenylsilane (18.51 mg, 171.02 umol). The reaction mixture was then stirred at 90° C. for 16 hours. Reaction mixture was diluted with ethyl acetate, washed with sodium bicarbonate solution, water and brine solution. The organic fraction was separated. It was dried over anhydrous sodium sulphate, evaporated under reduced pressure to obtain the crude compound which was purified by flash chromatography using 0-5% MeOH-DCM to afford 3-[6-[[1-[3,3-difluoro-1-[(1-methylcyclobutyl)methyl]-4-piperidyl]pyrazol-4-yl]methyl]-2-oxo-benzo[cd]indol-1-yl]piperidine-2,6-dione Compound 186 (25.0 mg, 43.68 umol, 25.54% yield, 98.13% purity) as yellow solid. $^1$H NMR (400 MHz, DMSO-d6) δ 11.11 (s, 1H), 8.39 (d, J=8.28 Hz, 1H), 8.08 (d, J=6.96 Hz, 1H), 7.82 (t, J=7.58 Hz, 1H), 7.61 (s, 1H), 7.39-7.36 (m, 2H), 7.08 (d, J=7.16 Hz, 1H), 5.44-5.42 (m, 1H), 4.65-4.60 (m, 1H), 4.20 (s, 2H), 2.97-2.91 (m, 2H), 2.81-2.62 (m, 3H), 2.42-2.27 (m, 5H), 2.10-2.08 (m, 1H), 1.95-1.74 (m, 5H), 1.62-1.60 (m, 2H), 1.14 (s, 3H); LC MS: ES+ 562.2.

Step-9b: Synthesis of 3-(6-((1-(3,3-difluoro-1-((1-methylcyclobutyl)methyl)piperidin-4-yl)-1H-pyrazol-4-yl)methyl)-2-oxobenzo[cd]indol-1(2H)-yl)piperidine-2,6-dione: To the stirred solution of 3-[6-[[1-[3,3-difluoro-4-piperidyl]pyrazol-4-yl]methyl]-2-oxo-benzo[cd]indol-1-yl]piperidine-2,6-dione 13b (60.0 mg, 125.14 umol) in THF (12.0 mL) was added followed by the addition of 1-methylcyclobutanecarbaldehyde 14 (14.74 mg, 150.16 umol), dibutyltindichloride (45.63 mg, 150.16 umol, 33.55 uL) and Phenylsilane (13.54 mg, 125.14 umol). The reaction mixture was then stirred at 90° C. for 16 hours. Reaction mixture was diluted with ethyl acetate, washed with sodium bicarbonate solution, water and brine solution. The organic fraction was separated. It was dried over anhydrous sodium sulphate, evaporated under reduced pressure to obtain the crude compound which was purified by flash chromatography using 0-5% MeOH-DCM to afford 3-[6-[[1-[3,3-difluoro-1-[(1-methylcyclobutyl)methyl]-4-piperidyl]pyrazol-4-yl]methyl]-2-oxo-benzo[cd]indol-1-yl]piperidine-2,6-dione Compound 187 (5.0 mg, 8.42 umol, 6.73% yield, 94.61% purity) as yellow solid. $^1$H NMR (400 MHz, DMSO-d6) δ 11.11 (s, 1H), 8.39 (d, J=8.6 Hz, 1H), 8.08 (d, J=7.52 Hz, 1H), 7.85-7.82 (m, 1H), 7.61 (s, 1H), 7.38-7.36 (m, 2H), 7.08 (d, J=7.32 Hz, 1H), 5.45-5.42 (m, 1H), 4.63-4.62 (m, 1H), 4.20 (s, 2H), 2.94-2.73 (m, 4H), 2.66-2.62 (m, 1H), 2.36-2.27 (m, 3H), 2.08-2.06 (m, 1H), 1.95-1.74 (m, 3H), 1.62-1.60 (m, 2H), 1.53-1.52 (m, 1H), 1.14 (s, 3H), 0.92-0.85 (m, 2H); LC MS: ES+ 562.3.

Example 96. Synthesis of 3-[6-[[4-[[4-(2-fluorophenyl)piperazin-1-yl]methyl]phenyl]methyl]-2-oxo-benzo[cd]indol-1-yl]piperidine-2,6-dione (Compound 18), Compound 189, and Compound 190)

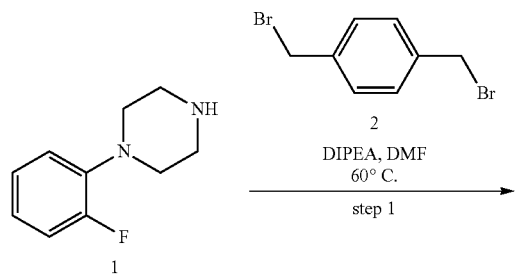

-continued
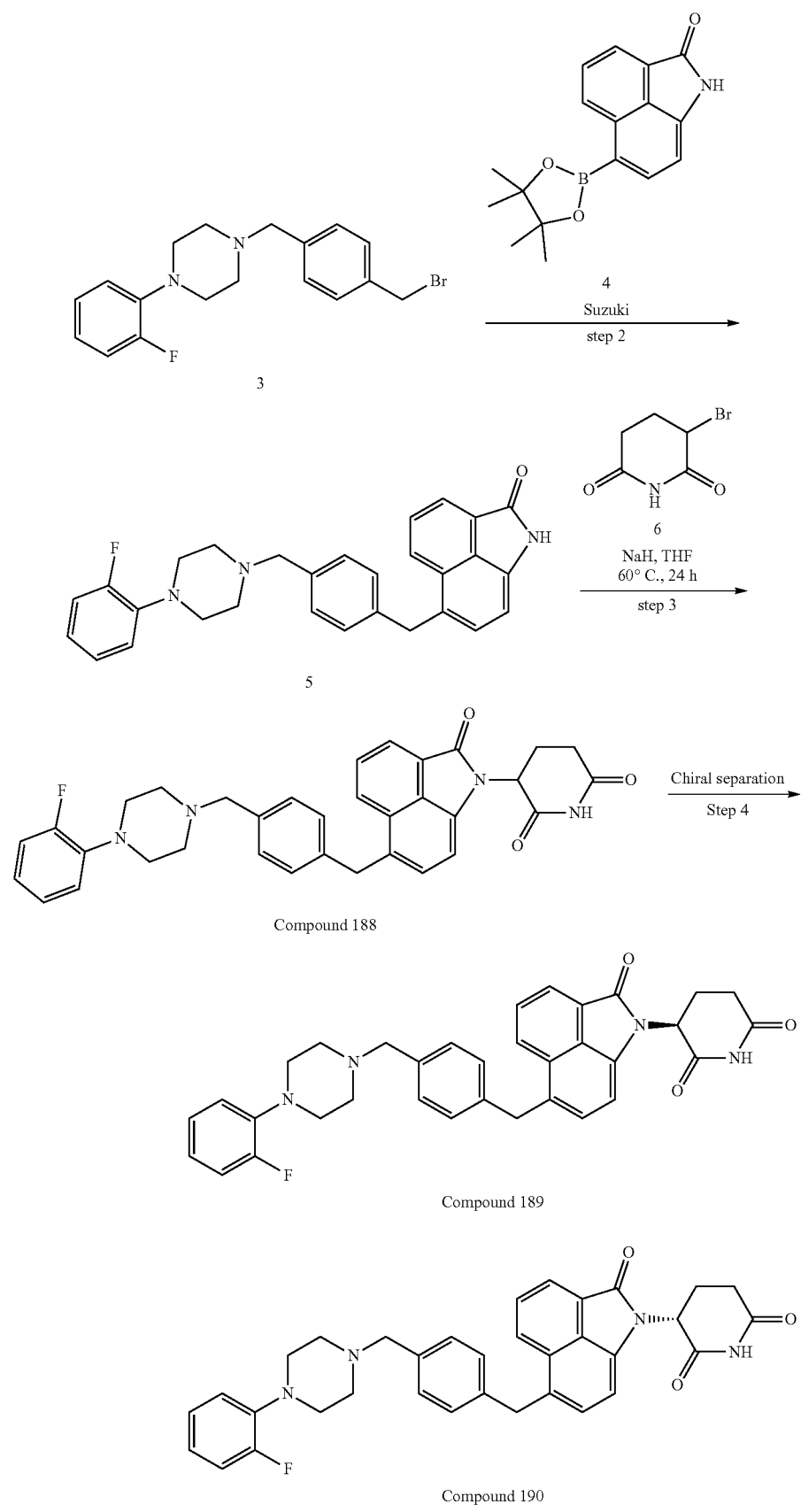
Compound 188
Compound 189
Compound 190

Step 1: Synthesis of 1-[[4-(chloromethyl)phenyl]methyl]-4-(2-fluorophenyl)piperazine (3): To a stirred solution of 1-(2-fluorophenyl)piperazine (1) (2 g, 11.10 mmol) in dry grade DMF (5 mL), DIPEA (4.30 g, 33.29 mmol, 5.80 mL) was added followed by 1,4-bis(chloromethyl)benzene (2) (3.89 g, 22.19 mmol, 2.74 mL). Resulting reaction mixture was heated at 60° C. for 12 hours. After completion of reaction (evidenced from LC MS), ice cooled water (25 ml) was added to RM and extracted with ethyl acetate (3×30 mL). Organic portion was separated, dried over anhydrous sodium sulfate and concentrated under reduced pressure. Crude reaction mass was purified by column chromatography (silica, gradient: 0-40% Ethyl acetate in Hexane) to afford 1-[[4-(chloromethyl)phenyl]methyl]-4-(2-fluorophenyl)piperazine (3) (3 g, 8.47 mmol, 76.31% yield, 90% purity) as yellow solid; LC MS: ES+ 319.4.

Step 2: Synthesis of 6-[[4-[[4-(2-fluorophenyl)piperazin-1-yl]methyl]phenyl]methyl]-1H-benzo[cd]indol-2-one (5): To the stirred solution of 6-(4,4,5,5-tetramethyl-1,3-dioxolan-2-yl)-1H-benzo[cd]indol-2-one (4) (500 mg, 1.68 mmol) and 1-[[4-(chloromethyl)phenyl]methyl]-4-(2-fluorophenyl)piperazine (536.10 mg, 1.68 mmol) (3) in Ethanol (1 mL) and Toluene (2 mL) was added tripotassium; phosphate (892.33 mg, 4.20 mmol) followed by 0.5 ml water and the reaction mass was degassed under nitrogen atmosphere over 10 minutes. Then tris-o-tolylphosphane (102.36 mg, 336.31 umol) and (1E,4E)-1,5-diphenylpenta-1,4-dien-3-one; palladium (153.98 mg, 168.15 umol) were added to this reaction mass and heated the resultant reaction mixture 90° C. for overnight. After completion of reaction, RM was filtered through celite bed, washed with Ethyl acetate (50 mL). Filtrate was collected and washed with water (2×20 mL)/brine (20 mL). Combined organic layer was separated, dried over sodium sulfate and concentrated under vacuum. Crude was purified by column chromatography (silica, gradient: 0-40% Ethylacetate in Hexane) to afford 6-[[4-[[4-(2-fluorophenyl)piperazin-1-yl]methyl]phenyl]methyl]-1H-benzo[cd]indol-2-one (5) (280 mg, 539.49 umol, 32.08% yield, 87% purity) as yellow solid; LC MS: 452.4.

Step 3: Preparation of 3-[6-[[4-[[4-(2-fluorophenyl)piperazin-1-yl]methyl]phenyl]methyl]-2-oxo-benzo[cd]indol-1-yl]piperidine-2,6-dione: To a ice cooled solution of 6-[[4-[[4-(2-fluorophenyl)piperazin-1-yl]methyl]phenyl]methyl]-1H-benzo[cd]indol-2-one 5 (80 mg, 177.17 umol) in dry THF (8 mL), Sodium hydride (in oil dispersion) 60% dispersion in mineral oil (67.89 mg, 1.77 mmol, 60% purity) was added portion wise, maintaining the temp <5° C. Once the addition is over, the resultant mixture was stirred for 15 minutes at RT. Then the reaction mixture was again cooled to 0° C. and 3-bromopiperidine-2,6-dione 6 (170.10 mg, 885.87 umol) was added to it portion wise. After complete addition, resulting solution was heated at 70° C. for 1 hour. After completion (evidenced from TLC), the reaction mixture was again cooled to 0° C. and quenched with ice cooled water (40 mL). Aqueous part was extracted with ethyl acetate (3×50 mL). Combined extracts were dried over anhydrous sodium sulfate and concentrated under reduced pressure. Crude mass was purified by flash chromatography (silica, gradient: 3% MeOH in DCM) to afford 3-[6-[[4-[[4-(2-fluorophenyl)piperazin-1-yl]methyl]phenyl]methyl]-2-oxo-benzo[cd]indol-1-yl]piperidine-2,6-dione Compound 188 (20 mg, 34.69 umol, 19.58% yield, 97.59% purity). 1H NMR (400 MHz, DMSO-d6) δ 11.12 (s, 1H), 8.32 (d, J=8.16 Hz, 1H), 8.07 (d, J=6.92 Hz, 1H), 7.81 (t, J=7.92 Hz, 1H), 7.41 (d, J=7.24 Hz, 1H), 7.26-7.20 (m, 4H), 7.11-7.05 (m, 3H), 7.0-6.93 (br m, 2H), 5.43 (dd, J=12.64, 4.76 Hz, 1H), 4.38 (s, 2H), 3.45 (s, 2H), 2.96 (br s, 5H), 2.76-2.73 (m, 1H), 2.66-2.62 (m, 1H), 2.50 (br s, 4H), 2.10-2.09 (m, 1H); LC MS: ES+ 563.5.

Step 4: Chiral separation: (Compound 189 and Compound 190): 550 mg of 3-[6-[[4-[[4-(2-fluorophenyl)piperazin-1-yl]methyl]phenyl]methyl]-2-oxo-benzo[cd]indol-1-yl]piperidine-2,6-dione Compound 188 was separated into enantiomers by SFC method. Prep fractions were first evaporated separately under reduced pressure to obtain solid mass. The solid was then suspended in a mixture of Acetonitrile and Water (2:3) and it was kept in a Dry-ice/Acetone bath until the Acetonitrile-Water mixture solidified. The frozen mixture was then freeze dried under lyophilizer for 20 hours to afford 3-[6-[[4-[[4-(2-fluorophenyl)piperazin-1-yl]methyl]phenyl]methyl]-2-oxo-benzo[cd]indol-1-yl]piperidine-2,6-dione Compound 189 (96 mg, 165.66 umol, 16.95% yield, 97.09% purity) (first eluted peak, RT=8.38 min, assigned tentatively as 'S' ABS) (96 mg, % ee 100) 3-[6-[[4-[[4-(2-fluorophenyl)piperazin-1-yl]methyl]phenyl]methyl]-2-oxo-benzo[cd]indol-1-yl]piperidine-2,6-dione (100 mg, 164.78 umol, 16.86% yield, 92.71% purity) Compound 190 (second eluted peak, RT=11.8 min, assigned tentatively as 'R' ABS) (100 mg, % ee 97.4) as yellow solids.

Example 97. Synthesis of 3-[6-[[1-[1-[(1-methylcyclobutyl)methyl]-4-(trifluoromethyl)-4-piperidyl]pyrazol-4-yl]methyl]-2-oxo-benzo[cd]indol-1-yl]piperidine-2,6-dione (Compound 191)

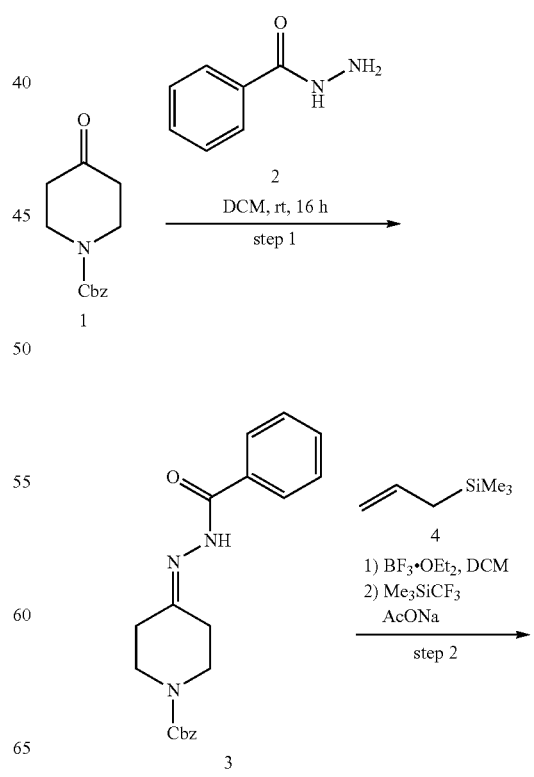

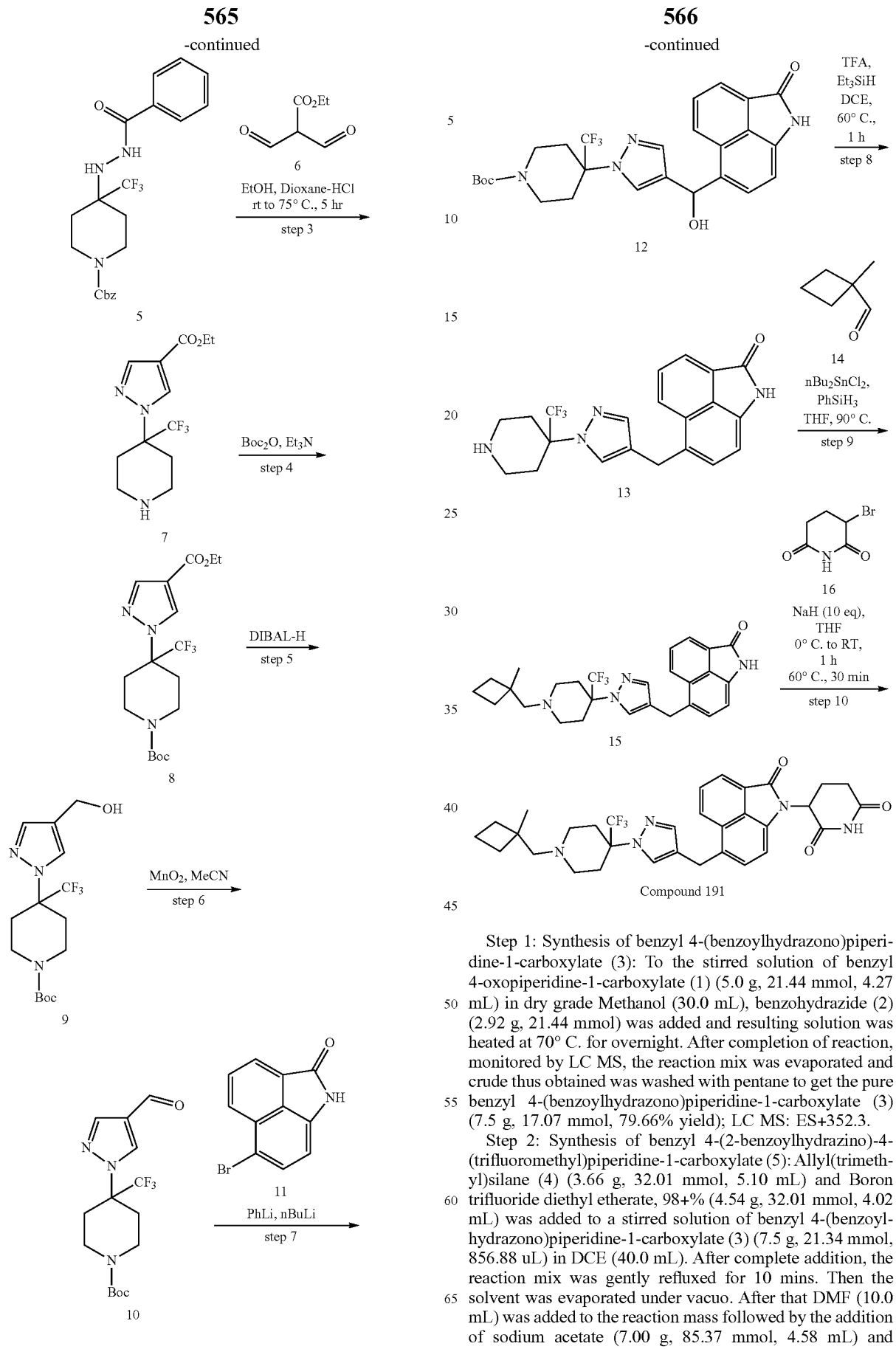

Step 1: Synthesis of benzyl 4-(benzoylhydrazono)piperidine-1-carboxylate (3): To the stirred solution of benzyl 4-oxopiperidine-1-carboxylate (1) (5.0 g, 21.44 mmol, 4.27 mL) in dry grade Methanol (30.0 mL), benzohydrazide (2) (2.92 g, 21.44 mmol) was added and resulting solution was heated at 70° C. for overnight. After completion of reaction, monitored by LC MS, the reaction mix was evaporated and crude thus obtained was washed with pentane to get the pure benzyl 4-(benzoylhydrazono)piperidine-1-carboxylate (3) (7.5 g, 17.07 mmol, 79.66% yield); LC MS: ES+352.3.

Step 2: Synthesis of benzyl 4-(2-benzoylhydrazino)-4-(trifluoromethyl)piperidine-1-carboxylate (5): Allyl(trimethyl)silane (4) (3.66 g, 32.01 mmol, 5.10 mL) and Boron trifluoride diethyl etherate, 98+% (4.54 g, 32.01 mmol, 4.02 mL) was added to a stirred solution of benzyl 4-(benzoylhydrazono)piperidine-1-carboxylate (3) (7.5 g, 21.34 mmol, 856.88 uL) in DCE (40.0 mL). After complete addition, the reaction mix was gently refluxed for 10 mins. Then the solvent was evaporated under vacuo. After that DMF (10.0 mL) was added to the reaction mass followed by the addition of sodium acetate (7.00 g, 85.37 mmol, 4.58 mL) and trifluoromethyl trimethyl silane (6.07 g, 42.69 mmol, 6.31 mL) and stirred the reaction mix at room temperature for overnight. After completion of reaction (evidenced from TLC), ice cooled water (20 mL) was added to the reaction mix and the reaction mix was extracted with ethyl acetate (3×50 mL) and washed with brine solution (2×40 ml). Organic part was separated, dried over anhydrous $Na_2SO_4$ and concentrated under vacuum. Resulting crude reaction mass was purified by flash chromatography (gradient: 0-40% Ethyl acetate in Hexane) to afford benzyl 4-(2-benzoylhydrazino)-4-(trifluoromethyl)piperidine-1-carboxylate (5) (5.94 g, 14.10 mmol, 66.04% yield) as colorless solid and stored in a round bottomed flask at ambient temperature; LC MS: ES+422.1.

Step 3: Synthesis of ethyl 1-[4-(trifluoromethyl)-4-piperidyl]pyrazole-4-carboxylate (7): Solution of benzyl 4-(2-benzoylhydrazino)-4-(trifluoromethyl)piperidine-1-carboxylate (5) (5.94 g, 14.08 mmol) and ethyl 2-formyl-3-oxo-propanoate (6) (2.03 g, 14.08 mmol) in Ethanol (87 mL), 4(M) dioxane-HCl (46 mL) was added drop wise fashion. After complete addition, reaction mixture is heated at 75° C. for 16 hours. After completion of reaction, monitored by LC MS, volatiles were removed vacuum. Solid reaction mass was partitioned between sat $NaHCO_3$(pH:7-8) and EtOAc (100 mL). Organic layer is washed water (50 mL) and brine (50 mL), separated, dried over $MgSO_4$ and concentrated under reduced pressure to afford ethyl 1-[4-(trifluoromethyl)-4-piperidyl]pyrazole-4-carboxylate (7) (4.0 g, 10.30 mmol, 73.13% yield) as brown sticky solid which was stored in a round bottomed flask at ambient temperature; LC MS: ES+ 292.0.

Step 4: Synthesis of tert-butyl 4-(4-ethoxycarbonylpyrazol-1-yl)-4-(trifluoromethyl)piperidine-1-carboxylate (8): To the stirred solution of ethyl 1-[4-(trifluoromethyl)-4-piperidyl]pyrazole-4-carboxylate (7) (4.22 g, 14.49 mmol) in THF (10.0 mL), was added Triethylamine, 99% (7.33 g, 72.44 mmol, 10.10 mL) followed by Di-tert-butyl dicarbonate (9.49 g, 43.46 mmol, 9.98 mL) at 0° C. Resulting solution was stirred at rt for 12 hours. Reaction mix was evaporated and the crude compound was dissolved in ethyl acetate (100 mL). Organic phase was washed with water (2×40 mL) and brine (50 mL). After separation of organic phase, dried over $Na_2SO_4$ and evaporated. Crude reaction mass was purified by flash chromatography (gradient: 0-30% Ethyl acetate in Hexane) to afford tert-butyl 4-(4-ethoxycarbonylpyrazol-1-yl)-4-(trifluoromethyl)piperidine-1-carboxylate (8) (2.6 g, 6.24 mmol, 43.10% yield) as yellow sticky solid which was stored in a round bottomed flask at ambient temperature; LC MS: ES– 390.25.

Step 5: Synthesis of tert-butyl 4-[4-(hydroxymethyl)pyrazol-1-yl]-4-(trifluoromethyl)piperidine-1-carboxylate (9): To the stirred solution of tert-butyl 4-(4-ethoxycarbonylpyrazol-1-yl)-4-(trifluoromethyl)piperidine-1-carboxylate (8) (1.0 g, 2.56 mmol) in THF (10 mL), Diisobutylaluminum hydride (7.27 g, 12.78 mmol, 10.37 mL, 25% purity) was added drop wise at –78° C. and stirred for 4 hours at rt under N2 atmosphere. After complete consumption, as evidenced from TLC, reaction mass was diluted with ethyl acetate (50 mL) and quenched with aqueous solution of Sodium Potassium tartarate (20 mL). Organic phase was separated, dried over anhydrous $Na_2SO_4$ and concentrated under reduced pressure to afford tert-butyl 4-[4-(hydroxymethyl)pyrazol-1-yl]-4-(trifluoromethyl)piperidine-1-carboxylate (9) (890 mg, 2.42 mmol, 94.72% yield) as brown gum which was carried forward to the next step without any further purification; LC MS: ES+ 294.2 (M-56).

Step 6: Synthesis of tert-butyl 4-(4-formylpyrazol-1-yl)-4-(trifluoromethyl)piperidine-1-carboxylate (10): To a stirred solution of tert-butyl 4-[4-(hydroxymethyl)pyrazol-1-yl]-4-(trifluoromethyl)piperidine-1-carboxylate (9) (900 mg, 2.58 mmol) in Acetonitrile (20 mL), was added activated $MnO2$ (2.24 g, 25.76 mmol) and stirred at RT for 24 hours. After completion of the reaction (monitored by TLC and LC MS), reaction mass was filtered through celite and the filtrate was concentrated under reduced pressure. Crude mass was purified by flash chromatography (gradient: 0-30% Ethyl acetate in Hexane) to afford tert-butyl 4-(4-formylpyrazol-1-yl)-4-(trifluoromethyl)piperidine-1-carboxylate 10 (630 mg, 1.72 mmol, 66.89% yield) as colorless gummy solid; LC MS: ES+ 292.1 (M-56).

Step 7: Synthesis of tert-butyl 4[-4-[hydroxy-(2-oxo-1H-benzo[cd]indol-6-yl)methyl]pyrazol-1-yl]-4-(trifluoromethyl)piperidine-1-carboxylate (12): To the stirred solution of 6-bromo-1H-benzo[cd]indol-2-one (11) (450 mg, 1.81 mmol) in dry grade THF (20.0 mL), was added Phenyl-lithium, typically 1.8M in di-n-butyl ether (152.45 mg, 1.81 mmol, 188.20 uL) at –78° C. and the reaction was stirred at the same temperature for 30 minutes followed by the addition of n-Butyllithium (127.82 mg, 2.00 mmol) at same temperature under N2 atmosphere. After complete addition, the temperature of reaction mixture was allowed to increase to –40° C. and stirred at the same temperature for 30 minutes. After getting the des-bromo spot in TLC (30% ethyl acetate in Hexane), solution of tert-butyl 4-(4-formylpyrazol-1-yl)-4-(trifluoromethyl)piperidine-1-carboxylate (10) (630.05 mg, 1.81 mmol) in dry THF (20.0 mL) was added at –78° C. stirring was continued for 16 hours at room temperature. Reaction mixture was quenched with saturated ammonium chloride solution and extracted with ethyl acetate (2×40 mL). Organic phase was washed with water (2×20 mL) and separated, dried over anhydrous sodium sulphate and evaporated under reduced pressure to obtain the crude compound which was purified by flash chromatography (silica, gradient: 0-5% MeOH in DCM) to afford tert-butyl 4-[4-[hydroxy-(2-oxo-1H-benzo[cd]indol-6-yl) methyl]pyrazol-1-yl]-4-(trifluoromethyl)piperidine-1-carboxylate (12) (225 mg, 370.27 umol, 20.41% yield) as brown solid which was stored in a round bottomed flask at ambient temperature; LC MS: ES+ 517.5.

Step 8: Synthesis of 2,2,2-trifluoroacetate; 6-[[1-[4-(trifluoromethyl)-4-piperidyl]pyrazol-4-yl]methyl]-1H-benzo[cd]indol-2-one (13): To the stirred solution of tert-butyl 4-[4-[hydroxy-(2-oxo-1H-benzo[cd]indol-6-yl)methyl] pyrazol-1-yl]-4-(trifluoromethyl)piperidine-1-carboxylate (12) (223 mg, 431.74 umol) in DCE (2.0 mL) was added triethylsilane (200.81 mg, 1.73 mmol, 275.84 uL) and Trifluoroacetic acid, 99% (393.82 mg, 3.45 mmol, 266.09 uL). Resulting solution heated at 70° C. under microwave condition for 30 mins. After completion of reaction (evidenced from TLC and LC MS), volatiles were removed. Solid residue was re dissolved in ethyl acetate (30 mL) and washed with saturated bicarbonate solution. Organic phase was separated, died over anhydrous sodium sulfate and concentrated. Crude reaction mass was purified by flash chromatography (gradient: 0-5% MeOH in DCM) to afford 2,2,2-trifluoroacetate; 6-[[1-[4-(trifluoromethyl)-4-piperidyl]pyrazol-4-yl]methyl]-1H-benzo[cd]indol-2-one (13) (140 mg, 178.50 umol, 41.35% yield) as yellow solid which was kept at ambient temperature in a round bottomed flask; LC MS: ES+ 401.3.

Step 9: Synthesis of 6-[[1-[1-[(1-methylcyclobutyl) methyl]-4-(trifluoromethyl)-4-piperidyl]pyrazol-4-yl] methyl]-1H-benzo[cd]indol-2-one (15): To the stirred solution of 6-[[1-[4-(trifluoromethyl)-4-piperidyl]pyrazol-4-yl]methyl]-1H-benzo[cd]indol-2-one (13) (140 mg, 349.65 umol) in THF (12 mL), 1-methylcyclobutanecarbaldehyde (14) (37.75 mg, 384.62 umol) was added followed by the addition of Dibutyltindichloride (127.49 mg, 419.58 umol, 93.74 uL) and Phenylsilane (37.84 mg, 349.65 umol, 43.09 uL). Resulting reaction mixture was then heated at 90° C. in a sealed tube for 16 hours. After completion of reaction (evidenced from TLC), the reaction mixture was diluted with ethyl acetate (20 mL), washed with sodium bicarbonate solution, water (10 mL) and brine (10 mL) solution. The organic portion was separated, dried over anhydrous sodium sulphate and evaporated under reduced pressure to obtain the crude compound which was purified by flash chromatography using (gradient: 0-5% MeOH in DCM) to afford 6-[[1-[1-[(1-methylcyclobutyl)methyl]-4-(trifluoromethyl)-4-piperidyl]pyrazol-4-yl]methyl]-1H-benzo[cd]indol-2-one (15) (45 mg, 74.61 umol, 21.34% yield, 80% purity) as yellow solid which was stored at ambient temperature in a round bottomed flask; LC MS: ES+483.4.

Step 10: Synthesis of 3-[6-[[1-[1-[(1-methylcyclobutyl)methyl]-4-(trifluoromethyl)-4 piperidyl]pyrazol-4-yl]methyl]-2-oxo-benzo[cd]indol-1-yl]piperidine-2,6-dione:
To a ice cooled solution of 6-[[1-[1-[(1-methylcyclobutyl)methyl]-4-(trifluoromethyl)-4-piperidyl]pyrazol-4-yl]methyl]-1H-benzo[cd]indol-2-one (15) (42 mg, 87.04 umol) in dry THF (5 mL), Sodium hydride (60% dispersion in mineral oil) ((33.35 mg, 870.40 umol) was added portion wise, maintaining the temp <5° C. Once the addition is over, the resultant mixture was stirred for 15 minutes at RT. Then the reaction mixture was again cooled to 0° C. and 3-bromopiperidine-2,6-dione (16) (83.56 mg, 435.20 umol) was added to it portion wise. After complete addition, resulting solution was heated at 70° C. for 1 hour. After completion (evidenced from TLC), the reaction mixture was again cooled to 0° C. and quenched with ice cooled water (10 mL). Aqueous part was extracted with ethyl acetate (2×20 mL). Combined extracts was dried over anhydrous sodium sulfate and concentrated under reduced pressure. Crude mass was purified by PREP-TLC (2.5% MeOH in DCM as eluent) to afford 3-[6-[[1-[1-[(1-methylcyclobutyl)methyl]-4-(trifluoromethyl)-4-piperidyl]pyrazol-4-yl]methyl]-2-oxo-benzo[cd]indol-1-yl]piperidine-2,6-dione Compound 191 (22 mg, 36.88 umol, 42.37% yield) as yellow solid which was stored in a round bottomed flask at 5° C. inside a refrigerator. 1H NMR (400 MHz, DMSO-d6) δ 11.12 (s, 1H), 8.36 (d, J=8.24 Hz, 1H), 8.09 (d, J=7.0 Hz, 1H), 8.02 (s, 1H), 7.81 (t, J=7.76 Hz, 1H), 7.47 (s, 1H), 7.34 (d, J=7.24 Hz, 1H), 7.10 (d, J=7.28 Hz, 1H), 5.43 (dd, J=12.6, 4.76 Hz, 1H), 4.25 (s, 2H), 2.97-2.91 (m, 1H), 2.8-2.67 (br m, 6H), 2.06 (s, 3H), 2.0-1.89 (m, 3H), 1.74-1.68 (m, 7H), 0.85 (s, 3H); LC MS: ES+ 594.7.

Example 98. Synthesis of 3-[6-[[1-[1-(1-methylcyclobutanecarbonyl)-4-piperidyl]triazol-4-yl]methyl]-2-oxo-benzo[cd]indol-1-yl]piperidine-2,6-dione (Compound 192)

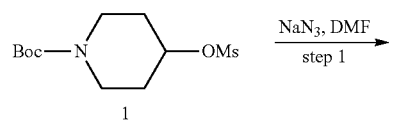

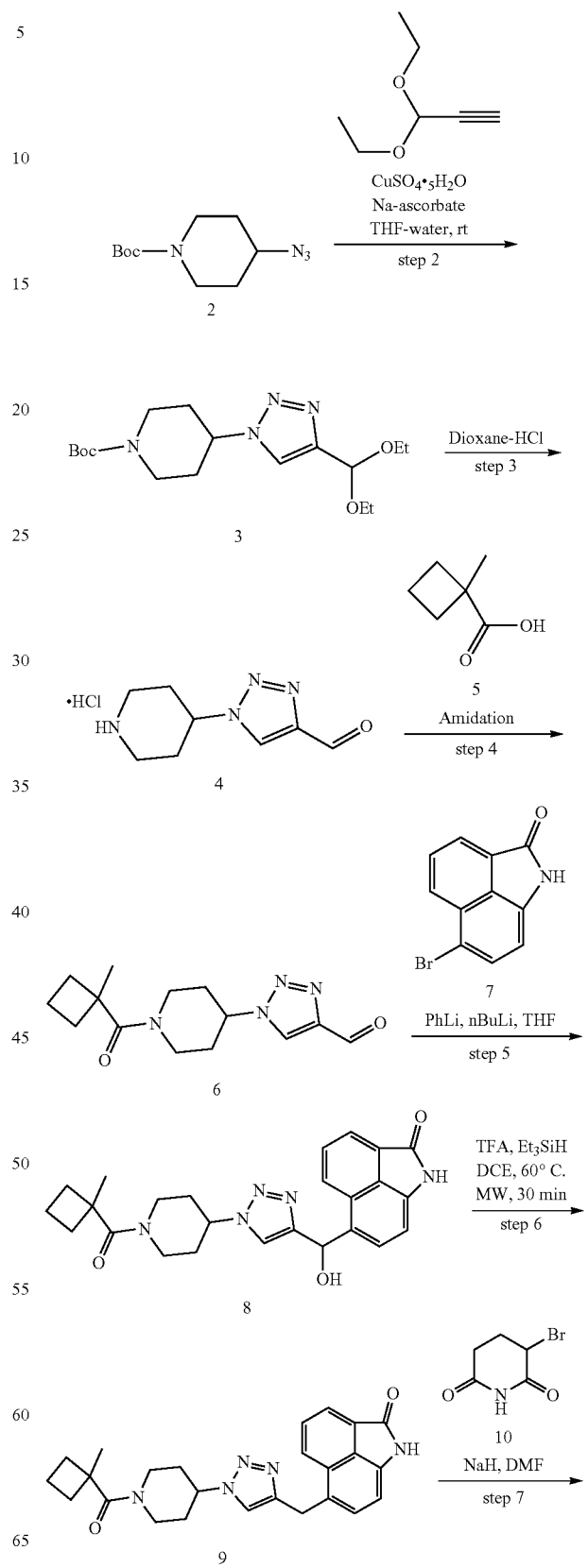

-continued

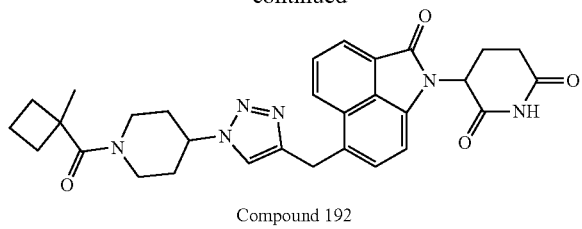

Compound 192

Step 1: Synthesis of tert-butyl 4-azidopiperidine-1-carboxylate (2): To the stirred solution of tert-butyl 4-methylsulfonyloxypiperidine-1-carboxylate (1) (10 g, 35.80 mmol) in dry grade DMF (50.0 mL), was added Sodium azide (9.31 g, 143.19 mmol, 5.03 mL) and resulting solution was refluxed at 100° C. for 2 hours. After completion of reaction (evidenced from TLC), the reaction mix was poured into crushed ice and extracted with Ethyl acetate (2×200 mL). Organic phase was separated, dried over anhydrous sodium sulfate and concentrated to afford crude tert-butyl 4-azidopiperidine-1-carboxylate (2) (8 g, 33.59 mmol, 93.83% yield, 95% purity) which was directly used for the next step without any further purification; LC MS: ES+ 227.2.

Step 2: Synthesis of tert-butyl 4-[4-(diethoxymethyl)triazol-1-yl]piperidine-1-carboxylate (3): To the stirred solution of 3,3-diethoxyprop-1-yne (4.5 g, 35.11 mmol) in THF (50 mL), was added tert-butyl 4-azidopiperidine-1-carboxylate (2) (7.94 g, 35.11 mmol) followed by aqueous solution (10 mL) of coppersulfate pentahydrate (876.64 mg, 3.51 mmol) and resulting solution was rt for 15 mins. After that sodium; (2R)-2-[1,2-dihydroxyethyl]-4-hydroxy-5-oxo-2H-furan-3-olate (2.78 g, 14.04 mmol) was added to the reaction mixture and stirring was continued for further 12 hours at same temperature. After complete consumption of SM (Monitored by TLC), then the reaction mix was diluted with ethyl acetate (100 mL) and filtered through bed of celite. Filtrate was collected and evaporated under vacuum. Crude thus obtained was purified by flash chromatography (silica, gradient: 0-5% MeOH in DCM) to obtain tert-butyl 4-[4-(diethoxymethyl)triazol-1-yl]piperidine-1-carboxylate (3) (11.54 g, 29.30 mmol, 83.46% yield) which was stored in round bottomed flask at 5° C. in a refrigerator; LC MS: ES+ 355.3.

Step 3: Synthesis of 1-(4-piperidyl)triazole-4-carbaldehyde; hydrochloride (4): To the stirred solution of tert-butyl 4-[4-(diethoxymethyl)triazol-1-yl]piperidine-1-carboxylate (3) (9.5 g, 26.80 mmol) in Dioxane (10 mL) 4.0 M in dioxane Hydrogen chloride solution (977.22 mg, 26.80 mmol, 40.0 mL) was added drop wise at 0° C. and stirred the reaction mix for overnight at rt. After completion of reaction (evidenced from LC MS), volatiles were removed under reduced pressure. Solid thus obtained was triturated with diethyl ether to afford 1-(4-piperidyl)triazole-4-carbaldehyde; hydrochloride (4) (5.6 g, 20.80 mmol, 77.59% yield, 94% purity); LC MS: ES+181.2.

Step 4: Synthesis of 1-[1-(1-methylcyclobutanecarbonyl)-4-piperidyl]triazole-4-carbaldehyde (6): To the stirred solution of 1-methylcyclobutanecarboxylic acid (5) (3.06 g, 26.77 mmol) in dry grade DMF (10.0 mL), was added HATU (339.48 mg, 892.82 umol) and stirred for 15 minutes at rt under N2 atmosphere. Solution of 1-(4-piperidyl)triazole-4-carbaldehyde; hydrochloride (4) (5.8 g, 26.77 mmol) and N-ethyl-N-isopropyl-propan-2-amine (17.30 g, 133.85 mmol, 23.31 mL) in dry grade DMF (3.0 mL) was added to the resulting solution at 0° C. and stirred for another 12 hr at rt. After completion of reaction (evidenced from LCMS), ice cooled water (5 mL) was added to the reaction mixture and extracted with ethyl acetate (3×70 mL). Organic portion was separated, dried over anhydrous sodium sulfate and concentrated. Crude thus obtained was purified by flash chromatography (silica, gradient: 0-5% MeOH in DCM) to obtain 1-[1-(1-methylcyclobutanecarbonyl)-4-piperidyl]triazole-4-carbaldehyde 6 (4.32 g, 14.23 mmol, 53.14% yield) as yellow solid; LC MS: ES+ 277.3.

Step 5: Synthesis of afford 6-[hydroxy-[1-[1-(1-methylcyclobutanecarbonyl)-4-piperidyl]triazol-4-yl]methyl]-1H-benzo[cd]indol-2-one (8): To the stirred solution of 6-bromo-1H-benzo[cd]indol-2-one (7) (1.65 g, 6.65 mmol) in dry grade THF (20.0 mL), was added Phenyllithium, 1.9M in di-n-butyl ether (559.00 mg, 6.65 mmol, 690.12 uL) at −78° C. under N2 atmosphere and the reaction was stirred at the same temperature for 30 minutes followed by the addition of n-Butyllithium (468.65 mg, 7.32 mmol) same temperature. After complete addition, the temperature was allowed to increase to −40° C. and the reaction mixture was stirred at the same temperature for 30 minutes. After getting the des-bromo spot in TLC (30% ethyl acetate in Hexane) solution of 1-[1-(1-methylcyclobutanecarbonyl)-4-piperidyl]triazole-4-carbaldehyde (6) (1.84 g, 6.65 mmol) in dry THF (20.0 mL) was added at −78° C. and stirring was continued for 16 hours at room temperature. Reaction mixture was quenched with saturated ammonium chloride solution and extracted with ethyl acetate (2×50 mL). Organic phase was washed with water (2×30 mL) and separated, dried over anhydrous sodium sulphate and evaporated under reduced pressure to obtain the crude compound which was purified by flash chromatography (silica, gradient: 0-5% MeOH in DCM) to afford 6-[hydroxy-[1-[1-(1-methylcyclobutanecarbonyl)-4-piperidyl]triazol-4-yl]methyl]-1H-benzo[cd]indol-2-one (8) (281 mg, 523.51 umol, 7.87% yield, 83% purity) as brown solid and stored at ambient temperature in a round bottomed flask; LC MS: ES+ 446.4.

Step 6: Synthesis of 6-[[1-[1-(1-methylcyclobutanecarbonyl)-4-piperidyl]triazol-4-yl]methyl]-1H-benzo[cd]indol-2-one (9): To the stirred solution of 6-[hydroxy-[1-[1-(1-methylcyclobutanecarbonyl)-4-piperidyl]triazol-4-yl]methyl]-1H-benzo[cd]indol-2-one (8) (280 mg, 628.49 umol) in DCE (2.0 mL) was added triethylsilane (292.32 mg, 2.51 mmol, 401.54 uL) and Trifluoroacetic acid, 99% (573.28 mg, 5.03 mmol, 387.35 uL). Resulting solution heated at 70° C. under microwave condition for 30 mins. After completion of reaction (evidenced from TLC and LC MS), volatiles were removed. Solid residue was re dissolved in ethyl acetate (50 mL) and washed with saturated bicarbonate solution. Organic phase was separated, died over anhydrous sodium sulfate and concentrated. Crude reaction mass was purified by flash chromatography (silica, gradient: 0-5% MeOH in DCM) to afford 6-[[1-[1-(1-methylcyclobutanecarbonyl)-4-piperidyl]triazol-4-yl]methyl]-1H-benzo[cd]indol-2-one (9) (190 mg, 402.55 umol, 64.05% yield) as yellow solid which was kept at ambient temperature in a round bottomed flask. LC MS: ES+430.4.

Step 7: Synthesis of 3-[6-[[1-[1-(1-methylcyclobutanecarbonyl)-4-piperidyl]triazol-4-yl]methyl]-2-oxo-benzo[cd]indol-1-yl]piperidine-2,6-dione: To a ice cooled solution of -[[1-[1-(1-methylcyclobutanecarbonyl)-4-piperidyl]triazol-4-yl]methyl]-1H-benzo[cd]indol-2-one (105 mg, 244.46 umol) (9) in dry THF (10 mL), Sodium hydride (60% dispersion in mineral oil) (56.20 mg, 2.44 mmol) was added portion wise, maintaining the temp <5° C. Once the addition is over, the resultant mixture was stirred for 15 minutes at RT. Then the reaction mixture was again cooled to 0° C. and 3-bromopiperidine-2,6-dione (10) (187.76 mg, 977.85 umol) was added to it portion wise. After complete addition, resulting solution was heated at 70° C. for 2 hours. After completion (evidenced from TLC), the reaction mixture was again cooled to 0° C. and quenched with ice cooled water (10 mL). Aqueous part was extracted with ethyl acetate (3×30 mL). Combined extracts was dried over anhydrous sodium sulfate and concentrated under reduced pressure. Crude mass was purified by flash chromatography (silica, gradient: 2.5% MeOH in DCM) to afford i3-[6-[[1-[1-(1-methylcyclobutanecarbonyl)-4-piperidyl]triazol-4-yl]methyl]-2-oxo-benzo[cd]indol-1-yl]piperidine-2,6-dione Compound 192 (42 mg, 74.95 umol, 30.66% yield) as yellow solid which was stored in a round bottomed flask at 5° C. inside a refrigerator. H NMR (400 MHz, DMSO-d6) δ 11.12 (s, 1H), 8.39 (d, J=8.24 Hz, 1H), 8.09 (d, J=6.96 Hz, 1H), 7.96 (s, 1H) 7.84 (t, J=7.16 Hz, 1H), 7.39 (d, J=7.4 Hz, 1H), 7.09 (d, J=7.16 Hz, 1H), 5.43 (dd, J=13.0, 5.24 Hz, 1H), 4.67-4.66 (m 1H), 4.41 (br s, 3H), 3.59 (m, 1H), 3.32-3.1 (m, 1H), 2.95-2.91 (m, 1H), 2.77-2.62 (m, 3H), 2.41-2.39 (m, 3H), 2.32-2.01 (m, 2H), 1.98-1.77 (m, 5H), 1.61-1.58 (m, 1H), 1.33 (s, 3H); LC MS: ES+ 541.5.

Example 99. Synthesis of -[4-[[1-(2,6-dioxo-3-piperidyl)-2-oxo-benzo[cd]indol-6-yl]methyl]pyrazol-1-yl]-1-[(1-methylcyclobutyl)methyl]piperidine-4-carbonitrile (Compound 193)

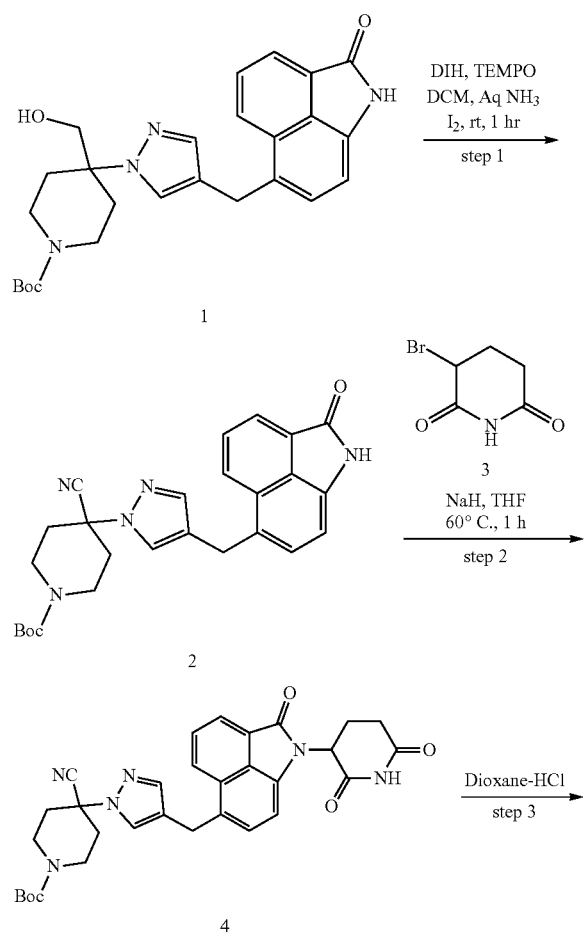

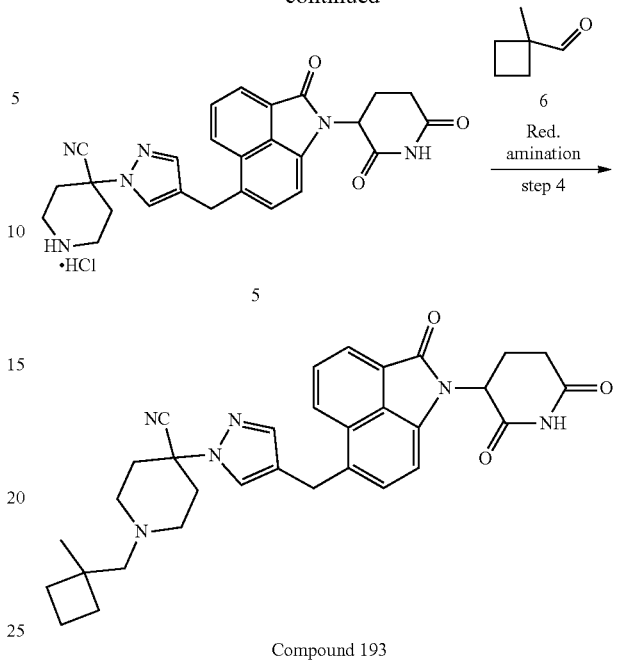

Compound 193

Step 1: Synthesis of tert-butyl 4-cyano-4-[4-[(2-oxo-1H-benzo[cd]indol-6-yl)methyl]pyrazol-1-yl]piperidine-1-carboxylate (2): 1,3-Diiodo-5,5-dimethylhydantoin (180.70 mg, 475.63 umol) was added to a mixture of tert-butyl 4-(hydroxymethyl)-4-[4-[(2-oxo-1H-benzo[cd]indol-6-yl)methyl]pyrazol-1-yl]piperidine-1-carboxylate (1) (200 mg, 432.40 umol) and TEMPO (3.38 mg, 21.62 umol) in DCM (5.0 mL) at r.t. under argon, and the mixture was stirred at room temperature until the alcohol was consumed (1 h). Molecular iodine (164.62 mg, 648.59 umol) and 28-30% aq. NH3 (432.40 umol, 1.0 mL) were added to the reaction mixture at r.t. and the resulting mixture was stirred at same temperature for 2 h. After completion of reaction (monitored by TLC) the reaction mixture was poured into sat. aq Na2SO3 (20 mL) and extracted with DCM (3×20 mL). The organic layer was dried over anhydrous sodium sulfate and concentrated under reduced pressure to afford tert-butyl 4-cyano-4-[4-[(2-oxo-1H-benzo[cd]indol-6-yl)methyl]pyrazol-1-yl]piperidine-1-carboxylate (2) (45 mg, 96.39 umol, 22.29% yield) which was sufficiently pure and used in the next step; LC MS: ES+ 458.5.

Step 2: Synthesis of tert-butyl 4-cyano-4-[4-[[1-(2,6-dioxo-3-piperidyl)-2-oxo-benzo[cd]indol-6-yl]methyl]pyrazol-1-yl]piperidine-1-carboxylate (4): To the stirred solution tert-butyl 4-cyano-4-[4-[(2-oxo-1H-benzo[cd]indol-6-yl)methyl]pyrazol-1-yl]piperidine-1-carboxylate (2) (160 mg, 349.71 umol) in dry grade THF (5 mL), Sodium hydride (60% dispersion in mineral oil (134.00 mg, 3.50 mmol, 60% purity) added portion wise, maintaining the temp <5° C. Once the addition is over, the resultant mixture was stirred for 15 minutes at room temperature. Then the reaction mixture was again cooled to 0° C. and 3-bromopiperidine-2,6-dione (3) (335.74 mg, 1.75 mmol) was added to it portion wise. After complete addition, resulting solution was heated at 70° C. for 1 hour. After completion (evidenced from TLC), the reaction mixture was again cooled to 0° C. and quenched with ice cooled water (20 mL). Aqueous part was extracted with ethyl acetate (3×50 mL). Combined extracts was dried over anhydrous sodium sulfate and concentrated under reduced pressure. Crude mass was purified by preparative TLC (2.5% MeOH in DCM) to afford tert-butyl 4-cyano-4-[4-[[1-(2,6-dioxo-3-piperidyl)-2-oxo-benzo[cd]indol-6-yl]methyl]pyrazol-1-yl]piperidine-1-carboxylate (4) (90 mg, 147.20 umol, 42.09% yield) as yellow solid; LC MS: ES+ 569.4.

Step 3: Synthesis of 4-[4-[[1-(2,6-dioxo-3-piperidyl)-2-oxo-benzo[cd]indol-6-yl]methyl]pyrazol-1-yl]piperidine-4-carbonitrile hydrochloride (5): 4 M dioxane-HCL (3 mL) was added to the cooled solution of tert-butyl 4-cyano-4-[4-[[1-(2,6-dioxo-3-piperidyl)-2-oxo-benzo[cd]indol-6-yl]methyl]pyrazol-1-yl]piperidine-1-carboxylate (4) (90 mg, 158.28 umol) and stirred for 2 hours at room temperature. After completion of reaction (monitored by LC MS) volatiles were removed to afford 4-[4-[[1-(2,6-dioxo-3-piperidyl)-2-oxo-benzo[cd]indol-6-yl]methyl]pyrazol-1-yl]piperidine-4-carbonitrile hydrochloride (5) (78 mg, 125.12 umol, 79.05% yield, 81% purity) as yellow solid; LC MS: ES+ 469.39.

Step 4: Synthesis of 4-[4-[[1-(2,6-dioxo-3-piperidyl)-2-oxo-benzo[cd]indol-6-yl]methyl]pyrazol-1-yl]-1-[(1-methylcyclobutyl)methyl]piperidine-4-carbonitrile: To the stirred solution of 1-chloro-4-[4-[[1-(2,4-dioxocyclohexyl)-2-oxo-benzo[cd]indol-6-yl]methyl]pyrazol-1-yl]piperidine-4-carbonitrile (5) (70 mg, 138.89 umol) in dry grade THF (12 mL) was added triethyl amine (28.11 mg, 277.79 umol, 38.72 uL) followed by the addition of 1-methylcyclobutanecarbaldehyde (6) (20.45 mg, 208.34 umol), Dibutyltindichloride (50.64 mg, 166.67 umol, 37.24 uL) and Phenylsilane (15.03 mg, 138.89 umol, 17.12 uL). After complete addition, the reaction mixture was then stirred at 90° C. for 16 hours. Reaction mixture was diluted with ethyl acetate (40 mL), and washed with sodium bicarbonate solution, water (2×20 mL) and brine (25 ml). The organic fraction was separated, dried over anhydrous sodium sulphate and evaporated under reduced pressure to obtain the crude compound which was purified by flash chromatography (silica, gradient: 0-5% MeOH in DCM) to afford 4-[4-[[1-(2,6-dioxo-3-piperidyl)-2-oxo-benzo[cd]indol-6-yl]methyl]pyrazol-1-yl]-1-[(1-methylcyclobutyl)methyl]piperidine-4-carbonitrile Compound 193 (38 mg, 68.69 umol, 49.46% yield, 99.54% purity) as yellow solid stored under Nitrogen Desiccators ("Terra Universal") at approximately 22° C. $^1$H NMR (400 MHz, DMSO-d6) δ 11.12 (s, 1H), 8.39 (d, J=8.2 Hz, 1H), 8.09 (d, J=6.96 Hz, 1H), 7.92 (s, 1H), 7.83 (t, J=7.56 Hz, 1H), 7.51 (s, 1H), 7.37 (d, J=7.32 Hz, 1H), 7.08 (d, J=7.24 Hz, 1H), 5.43 (dd, J=12.76, 5.08 Hz, 1H), 4.22 (s, 1H), 2.94-2.62 (m, 6H), 2.44-2.07 (m, 9H), 1.93-1.91 (m, 1H), 1.85-1.70 (m, 3H), 1.61-1.56 (m, 2H), 1.12 (s, 3H); LC MS: ES+ 551.3.

Example 100. Synthesis of -[6-[[1-[4-(aminomethyl)-1-[1-(trifluoromethyl)cyclopropanecarbonyl]-4-piperidyl]pyrazol-4-yl]methyl]-2-oxo-benzo[cd]indol-1-yl]piperidine-2,6-dione (Compound 194)

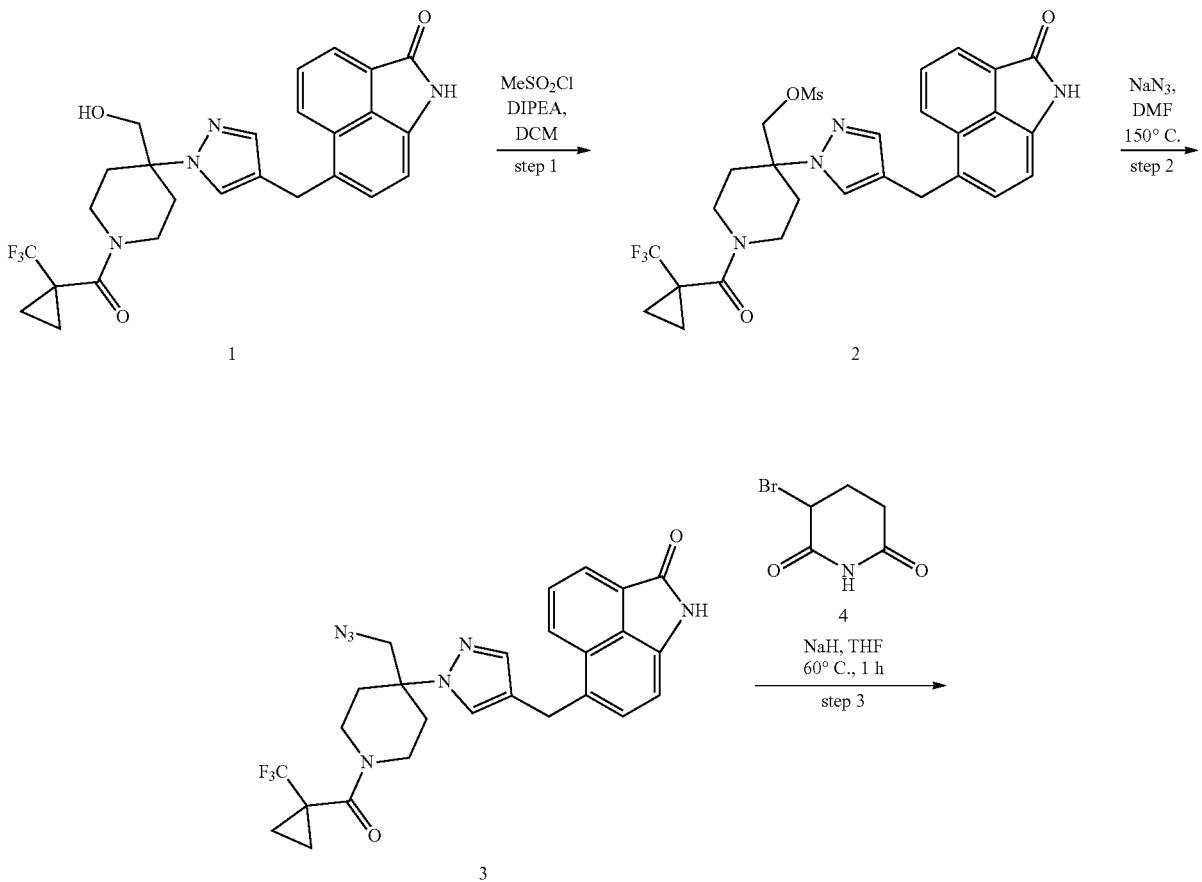

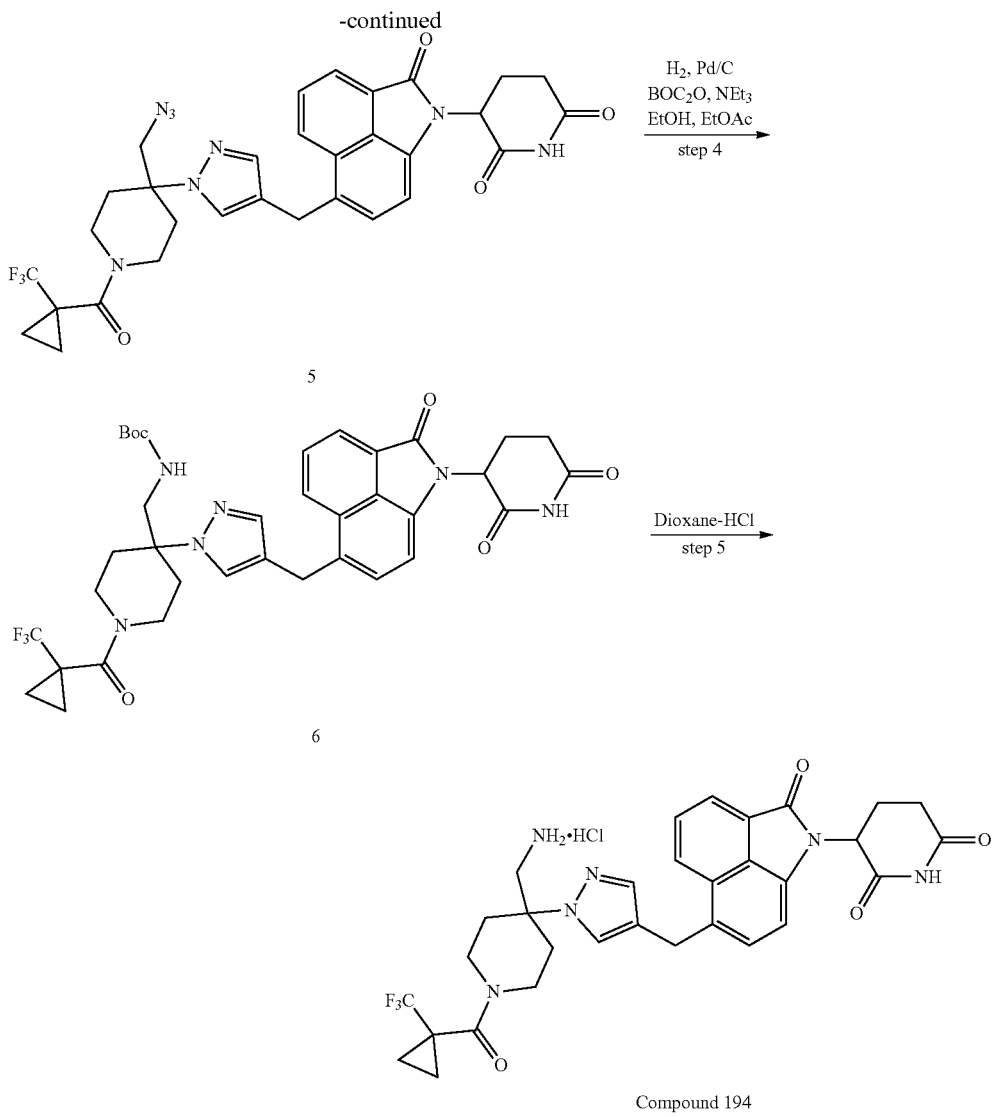

Compound 194

Step 1: Synthesis of [4-[4-[(2-oxo-1H-benzo[cd]indol-6-yl)methyl]pyrazol-1-yl]-1-[1-(trifluoromethyl)cyclopropanecarbonyl]-4-piperidyl]methyl methanesulfonate (2): To a cooled solution of 6-[[1-[4-(hydroxymethyl)-1-[1-(trifluoromethyl)cyclopropanecarbonyl]-4-piperidyl]pyrazol-4-yl]methyl]-1H-benzo[cd]indol-2-one (1) (200 mg, 401.21 umol) in dry grade DCM (5.0 mL), N,N-Diisopropylethylamine (259.27 mg, 2.01 mmol, 349.41 uL) was added drop wise and stirred the reaction mix for 10 mins. Methane sulfonyl chloride, 98% (91.92 mg, 802.41 umol, 62.11 uL) was added to the reaction at 0° C. It was then stirred at rt for 1 hour. After completion of reaction (Evidenced from TLC) the reaction mix was diluted with DCM (25 ml) and quenched with NaHCO$_3$ solution. Organic portion was washed with brine (30 mL) and separated, dried over anhydrous sodium sulfate, evaporated under reduced pressure to afford crude [4-[4-[(2-oxo-1H-benzo[cd]indol-6-yl)methyl]pyrazol-1-yl]-1-[1(trifluoromethyl)cyclopropanecarbonyl]-4-piperidyl]methyl methanesulfonate (2) (230 mg, 378.95 umol, 94.45% yield, 95% purity) which was directly used in the next step without any purification (LC MS not responding).

Step 2: Synthesis of afford diazonio-[[4-[4-[(2-oxo-1H-benzo[cd]indol-6-yl)methyl]pyrazol-1-yl]-1-[1-(trifluoromethyl)cyclopropanecarbonyl]-4-piperidyl]methyl]azanide (3): To the stirred solution of 6-[[1-[4-(hydroxymethyl)-1-[1-(trifluoromethyl)cyclopropanecarbonyl]-4-piperidyl]pyrazol-4-yl]methyl]-1H-benzo[cd]indol-2-one (2) (80 mg, 160.48 umol) in dry grade DMF (4 mL), Sodium azide (52.16 mg, 802.41 umol, 28.20 uL) was added and resulting solution was heated at 150° C. for 4 hours. After completion of reaction as evidenced from TLC, reaction mixture was cooled at rt and ice cooled water (10 mL) was added to it. Aqueous part was extracted with ethyl acetate (3×30 mL). Organic phase was washed with brine (30 mL), separated, dried over anhydrous sodium sulfate and concentrated under reduced pressure to afford crude diazonio-[[4-[4-[(2-oxo-1H-benzo[cd]indol-6-yl)methyl]pyrazol-1-yl]-1-[1-(trifluoromethyl)cyclopropanecarbonyl]-4-piperidyl]methyl]azanide (3) (40 mg, 57.31 umol, 35.71% yield, 75% purity) which was directly in the next step without further purification; LC MS: ES+ 524.4.

Step 3: Synthesis of diazonio-[[4-[4-[[1-(2,6-dioxo-3-piperidyl)-2-oxo-benzo[cd]indol-6-yl]methyl]pyrazol-1-yl]-

1-[1-(trifluoromethyl)cyclopropanecarbonyl]-4-piperidyl]methyl]azanide (5): To the stirred solution of crude diazonio-[[4-[4-[(2-oxo-1H-benzo[cd]indol-6-yl)methyl]pyrazol-1-yl]-1-[1-(trifluoromethyl)cyclopropanecarbonyl]-4-piperidyl]methyl]azanide (3) (80 g, 152.82 mmol) in dry grade THF (4 mL), was added Sodium hydride 60% dispersion in mineral oil (58.55 g, 1.53 mol, 60% purity) was added portion wise, maintaining the temp <5° C. Once the addition is over, the resultant mixture was stirred for 15 minutes at RT. Then the reaction mixture was again cooled to 0° C. and 3-bromopiperidine-2,6-dione (4) (146.71 g, 764.08 mmol) was added to it portion wise. After complete addition, resulting solution was heated at 70° C. for 1 hour. After completion (evidenced from TLC), the reaction mixture was again cooled to 0° C. and quenched with ice cooled water (40 mL). Aqueous part was extracted with ethyl acetate (3×50 mL). Combined extracts was dried over anhydrous sodium sulfate and concentrated under reduced pressure. Resulting crude solid was washed with ether and pentane to afford diazonio-[[4-[4-[[1-(2,6-dioxo-3-piperidyl)-2-oxo-benzo[cd]indol-6-yl]methyl]pyrazol-1-yl]-1-[1-(trifluoromethyl)cyclopropanecarbonyl]-4-piperidyl]methyl]azanide (5) (60 mg, 71.86 umol, 47.02% yield) as yellow solid; LC MS: ES+635.6.

Step 4: Synthesis of tert-butyl N-[[4-[4-[[1-(2,6-dioxo-3-piperidyl)-2-oxo-benzo[cd]indol-6-yl]methyl]pyrazol-1-yl]-1-[1-(trifluoromethyl)cyclopropanecarbonyl]-4-piperidyl]methyl]carbamate (6): To the stirred solution of diazonio-[[4-[4-[[1-(2,6-dioxo-3-piperidyl)-2-oxo-benzo[cd]indol-6-yl]methyl]pyrazol-1-yl]-1-[1-(trifluoromethyl)cyclopropanecarbonyl]-4-piperidyl]methyl]azanide (5) (60 mg, 94.55 umol) in Ethanol (4 mL)-ethyl acetate (4 mL), Triethylamine (19.13 mg, 189.09 umol, 26.36 uL) and tert-butoxycarbonyl tert-butyl carbonate (30.95 mg, 141.82 umol, 32.55 uL) were added followed by 10 mol % Palladium (40.25 mg, 378.19 umol). Resulting solution was evacuated and hydrogenated under balloon pressure for 12 hours. After completion of reaction (evidenced from LC MS), reaction mixture was filtered through bed of celite and washed with ethyl acetate (50 mL). Filtrate was collected and evaporated. Crude residue was purified by PREP-TLC (40% Ethyl acetate in Hexane) to afford tert-butyl N-[[4-[4-[[1-(2,6-dioxo-3-piperidyl)-2-oxo-benzo[cd]indol-6-yl]methyl]pyrazol-1-yl]-1-[1-(trifluoromethyl)cyclopropanecarbonyl]-4-piperidyl]methyl]carbamate (6) (35 mg, 42.96 umol, 45.44% yield, 87% purity) as yellow solid and stored in round bottomed flask at ambient temperature; LC MS: ES+ 709.65.

Step 5: Synthesis of 3-[6-[[1-[4-(aminomethyl)-1-[1-(trifluoromethyl)cyclopropanecarbonyl]-4-piperidyl]pyrazol-4-yl]methyl]-2-oxo-benzo[cd]indol-1-yl]piperidine-2,6-dione: 4M Dioxane-HCl (2 mL) was added to tert-butyl N-[[4-[4-[[1-(2,6-dioxo-3-piperidyl)-2-oxo-benzo[cd]indol-6-yl]methyl]pyrazol-1-yl]-1-[1-(trifluoromethyl)cyclopropanecarbonyl]-4-piperidyl]methyl]carbamate (6) (35 mg, 49.38 umol) at 0° C. and stirred for 3 hours. After completion of reaction, as evidenced from LCMS, volatiles were removed and resulting solid was triturated with diethyl ether and lyophilised to obtain 3-[6-[[1-[4-(aminomethyl)-1-[1-(trifluoromethyl)cyclopropanecarbonyl]-4-piperidyl]pyrazol-4-yl]methyl]-2-oxo-benzo[cd]indol-1-yl]piperidine-2,6-dione Compound 194 (22.0 mg, 32.87 umol, 66.55% yield) as yellow solid and stored under Nitrogen Desiccators ("Terra Universal") at approximately 22° C. $^1$H NMR (400 MHz, DMSO-d6) δ 11.12 (s, 1H), 8.41 (d, J=8.24 Hz, 1H), 8.10 (d, J=6.88 Hz, 1H), 7.92 (s, 1H), 7.85-7.83 (br m, 3H), 7.50 (s, 1H), 7.39 (d, J=7.32 Hz, 1H), 7.07 (d, J=7.2 Hz, 1H), 5.46-5.44 (m, 1H), 4.24 (s, 1H), 3.95-3.92 (m, 2H), 3.7-3.66 (m, 1H), 3.48-3.47 (m, 1H), 3.16 (s, 2H), 2.95 (t, 12.3 Hz, 2H), 2.83-2.50 (br m, 2H), 2.50 (m, 2H), 2.09-2.08 (m, 2H), 1.90 (m, 2H), 1.28-1.18 (m, 5H); LC MS: ES+ 609.5.

Example 101. Synthesis of 3-[6-[[1-[4-(hydroxymethyl)-1-[1-(trifluoromethyl)cyclopropanecarbonyl]-4-piperidyl]pyrazol-4-yl]methyl]-2-oxo-benzo[cd]indol-1-yl]piperidine-2,6-dione (Compound 195)

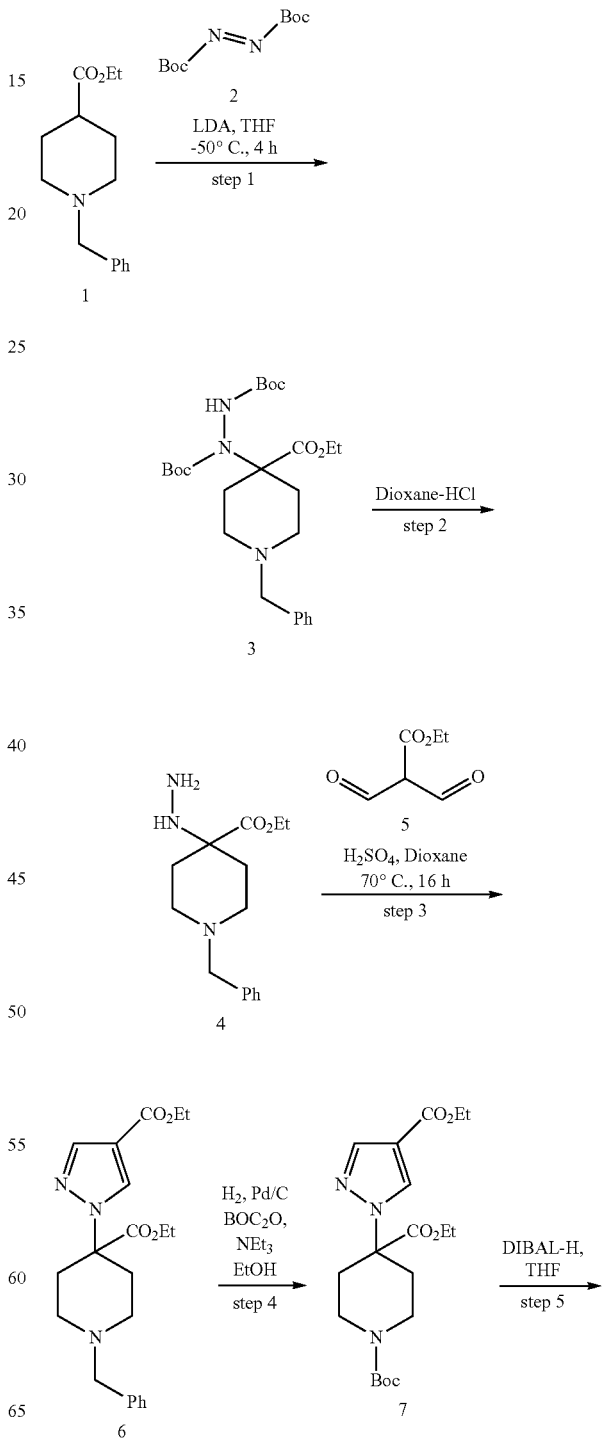

581
-continued

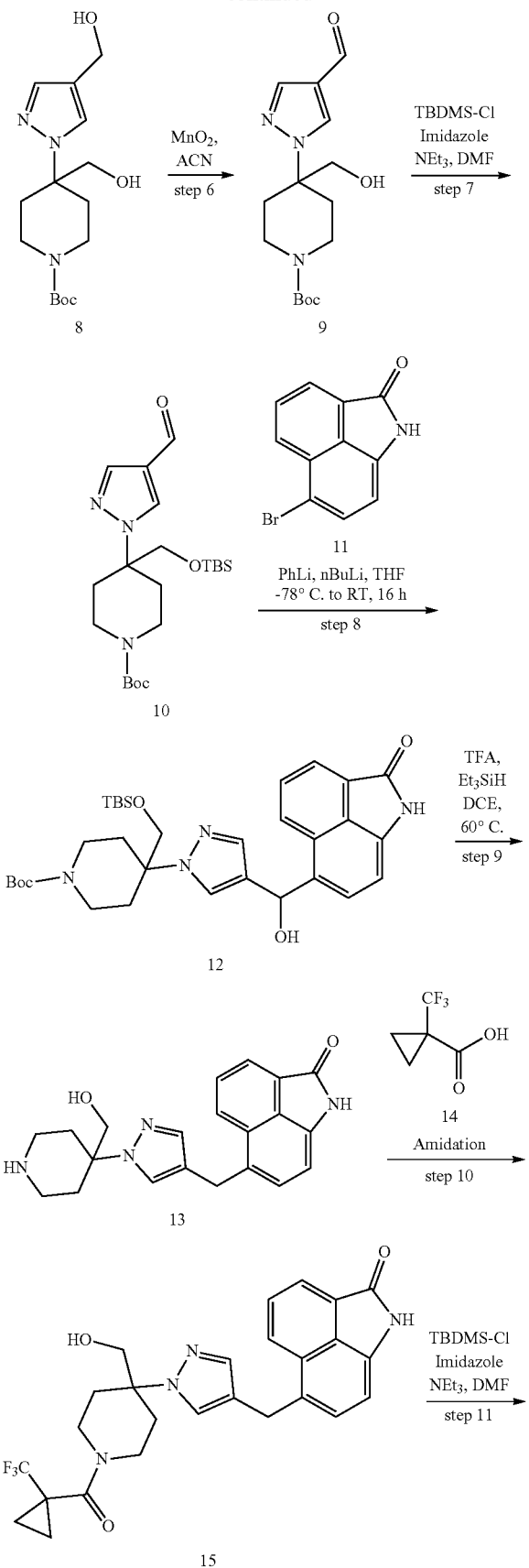

582
-continued

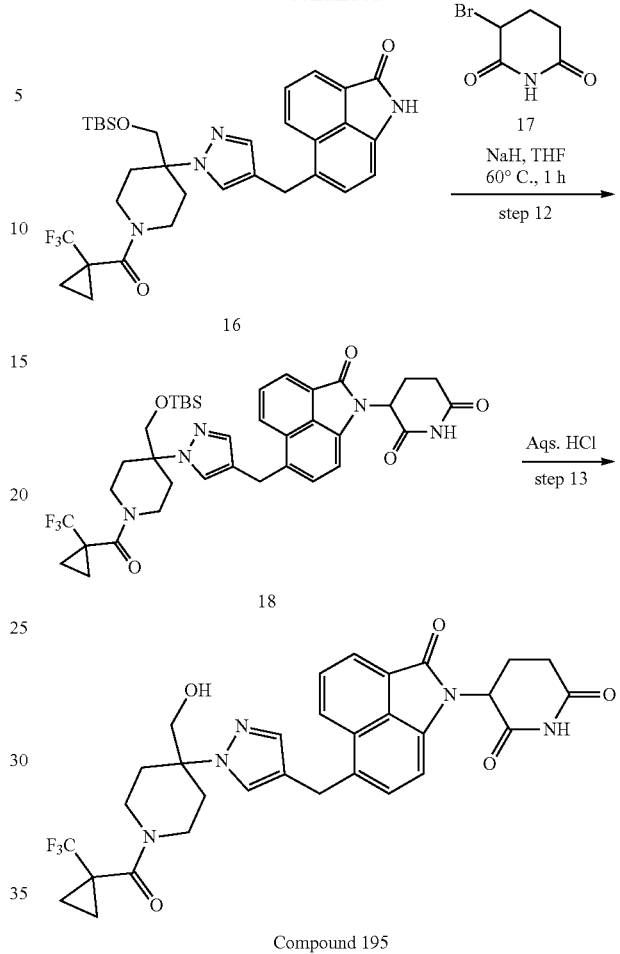

Compound 195

Step 1: Synthesis of ethyl 1-benzyl-4-[tert-butoxycarbonyl-(tert-butoxycarbonylamino)amino]piperidine-4-carboxylate (3): To the solution of Diisopropylamine, 99+% (5.81 g, 57.39 mmol, 8.09 mL) in dry grade THF (50.0 mL) was added n-Butyllithium, 1.67M in hexane (2.45 g, 38.26 mmol, 22.56 mL) at −78° C. under argon atmosphere and stirred the reaction mix at −78° C. for 1 hour. Then propyl 1-benzylpiperidine-4-carboxylate (1) (10.0 g, 38.26 mmol) was added drop wise to the reaction mix at −78° C. and stirred the reaction mix at the same temperature. After 1 hour, tert-butyl (NE)-N-tert-butoxycarbonyliminocarbamate (10.20 g, 44.30 mmol) was added and stirred the reaction at rt for overnight. After completion of reaction (evidenced from TLC), the reaction mix was diluted with ethylacetate (100 mL) and quenched with saturated ammonium chloride solution. Organic portion was washed with brine and separated, dried over anhydrous sodium sulfate and evaporated under reduced pressure. Resulting crude reaction mass was purified by column chromatography (silica, gradient: 10-30% Ethyl acetate in Hexane) to get the pure compound ethyl 1-benzyl-4-[tert-butoxycarbonyl-(tert-butoxycarbonylamino)amino]piperidine-4-carboxylate (3) (10.0 g, 18.84 mmol, 49.25% yield); LC MS: ES+ 478.2.

Step 2: Synthesis of ethyl 1-benzyl-4-hydrazino-piperidine-4-carboxylate (4): To a stirred cooled solution of ethyl 1-benzyl-4-[tert-butoxycarbonyl-(tert-butoxycarbonylamino)amino]piperidine-4-carboxylate (3) (30.0 g, 62.82 mmol) in dioxane (100 mL), Dioxane/HCl (62.82 mmol, 70 mL) was added drop wise and stirred the reaction mixture at room temperature for 16 hours. After completion of reaction (Monitored by LCMS), volatiles were removed under reduced pressure. Resulting solid material was dissolved in (200 mL of 5% MeOH in DCM) and neutralized with the addition of amberlite 21. After neutralization (pH~8) it was filtered and solid resin was washed with (10% MeOH in DCM) several time. Filtrate was evaporated to afford the crude ethyl 1-benzyl-4-hydrazino-piperidine-4-carboxylate (4) (17 g, 56.39 mmol, 89.77% yield) as light brown gummy solid which was stored in a round bottomed glass at 5° C. in refrigerator. The crude was directly used for the next step without any furthered purification; LC MS: ES+ 278.0.

Step 3: Synthesis of ethyl 1-benzyl-4-(4-ethoxycarbonylpyrazol-1-yl)piperidine-4-carboxylate (6): To a stirred solution of ethyl 1-benzyl-4-hydrazino-piperidine-4-carboxylate (4) (2.0 g, 7.21 mmol) intoluene (15 mL) was added Ethyl-2-formyl-3-oxopropionate (5) (1.25 g, 8.65 mmol) at 0° C. and heated at 100° C. for 6 hours. After completion of reaction (monitored by LC MS) solvent was evaporated and resulting gummy solid was re dissolved in ethyl acetate (50 mL). Organic portion was washed with water (2×30 mL) and brine (40 mL). After separation of organic phase, it was dried over anhydrous sodium sulfate and concentrated and crude thus obtained was purified by column chromatography (silica, gradient: 10-30% Ethyl acetate in Hexane) to get the compound ethyl 1-benzyl-4-(4-ethoxycarbonylpyrazol-1-yl)piperidine-4-carboxylate (6) (2.0 g, 4.51 mmol, 62.60% yield, 87% purity) as colourless sticky solid (2.0 g, 4.51 mmol, 62.60% yield) which stored in round bottomed flask at ambient temperature; LC MS: ES+ 385.9.

Step 4: Synthesis of 01-tert-butyl 04-ethyl 4-(4-ethoxycarbonylpyrazol-1-yl)piperidine-1,4-dicarboxylate (7): To the stirred solution of ethyl 1-benzyl-4-(4-ethoxycarbonylpyrazol-1-yl)piperidine-4-carboxylate (6) (2.0 g, 5.19 mmol) in EtOH (50 mL)-ethyl acetate (50 mL), tert-butoxycarbonyl tert-butyl carbonate (2.26 g, 10.38 mmol, 2.38 mL) and Triethylamine, 99% (1.58 g, 15.57 mmol, 2.17 mL) was added. Then the reaction mixture was degassed with Argon for 15 minutes followed by the addition of 20% Palladium on Carbon (1.06 g, 9.98 mmol) and the resultant reaction mixture was stirred under hydrogen atmosphere for 16 hours at room temperature. After completion of the reaction (monitored by TLC and LCMS), the reaction mixture was filtered through a bed of celite, washed with ethyl acetate (100 mL). The combined filtrate was then washed with water (3×50 mL) and brine (2×40 mL), dried over anhydrous sodium sulfate and concentrated under reduced pressure. Crude mass was purified by column chromatography (silica, gradient: 0-30% Ethyl acetate in Hexane) to obtain desired compound O1-tert-butyl 04-ethyl 4-(4-ethoxycarbonylpyrazol-1-yl)piperidine-1,4-dicarboxylate (7) (1.24 g, 3.07 mmol, 59.22% yield) as light brown sticky solid which stored in round bottomed glass at ambient temperature; LC MS: ES+ 396.5.

Step 5: Synthesis of tert-butyl 4-(hydroxymethyl)-4-[4-(hydroxymethyl)pyrazol-1-yl]piperidine-1-carboxylate (8): To the cooled solution of 01-tert-butyl 04-ethyl 4-(4-ethoxycarbonylpyrazol-1-yl)piperidine-1,4-dicarboxylate (7) (4.43 g, 11.20 mmol) in dry grade THF (50.0 mL), Lithium borohydride (2.68 g, 123.23 mmol) was added and stirred the solution at room temperature for 16 hours under N2 atmosphere. After complete consumption, as evidenced from TLC, reaction mass was diluted with ethyl acetate (100 mL) and quenched with water (50 mL). Organic phase was separated, dried over anhydrous Na$_2$SO$_4$ and concentrated under reduced pressure to afford tert-butyl 4-(hydroxymethyl)-4-[4-(hydroxymethyl)pyrazol-1-yl]piperidine-1-carboxylate (8) (3.2 g, 9.76 mmol, 87.15% yield) as colourless sticky solid, stored at ambient temperature in around bottomed flask. LC MS: ES+ 312.3. The crude was directly used for next step without any purification.

Step 6: Synthesis of tert-butyl 4-(4-formylpyrazol-1-yl)-4-(hydroxymethyl)piperidine-1-carboxylate (9): To a stirred solution of tert-butyl 4-(hydroxymethyl)-4-[4-(hydroxymethyl)pyrazol-1-yl]piperidine-1-carboxylate (8) (1.7 g, 5.46 mmol) in HPLC grade Acetonitrile (10 mL) was added activated dioxomanganese (2.37 g, 27.30 mmol) at rt and the reaction mix was stirred at rt for 12 hours. After completion of the reaction (monitored by TLC and LC MS), reaction mass was filtered through bed of celite, washed with ethyl acetate (100 mL). Filtrate was concentrated under reduced pressure and thus crude was obtained purified by column chromatography (100-200 silica; Ethyl acetate in Hexane) to afford tert-butyl 4-(4-formylpyrazol-1-yl)-4-(hydroxymethyl)piperidine-1-carboxylate (9) (1.5 g, 4.80 mmol, 87.92% yield) as colourless sticky solid which was stored in round bottomed flask at 5° C. in refrigerator; LC MS: ES+ 310.4.

Step 7: Synthesis of 4-[[tert-butyl(dimethyl)silyl]oxymethyl]-4-(4-formylpyrazol-1-yl)piperidine-1-carboxylate (10): To the stirred solution of tert-butyl 4-(4-formylpyrazol-1-yl)-4-(hydroxymethyl)piperidine-1-carboxylate (9) (180 mg, 581.85 umol) in dry DMF (2 mL), Imidazole (79.22 mg, 1.16 mmol) and Triethylamine 176.63 mg, 1.75 mmol, 243.29 uL) were added followed by tert-butyl-chloro-dimethyl-silane (105.24 mg, 698.22 umol, 129.92 uL) at 0° C. Resultant reaction mixture was heated at 50° C. for 3 hours. After complete consumption of SM, as evidenced from TLC, ice cooled water (5 mL) was added to the reaction mixture and extracted with ethyl acetate (3×20 mL). Organic part was separated, dried over anhydrous sodium sulfate and evaporated under crude pressure. Crude thus obtained was purified by column chromatography (100-200 silica; 0-25% Ethyl acetate in Hexane) to afford tert-butyl 4-[[tert-butyl (dimethyl)silyl]oxymethyl]-4-(4-formylpyrazol-1-yl)piperidine-1-carboxylate (10) (150 mg, 318.68 umol, 54.77% yield) as colorless sticky solid which was stored in a round bottomed flask at 5° C. in refrigerator; LC MS: ES+ 424.4.

Step 8: Synthesis of tert-butyl 4[-4-[hydroxy-(2-oxo-1H-benzo[cd]indol-6-yl)methyl]pyrazol-1-yl]-4-(trimethylsilyloxymethyl)piperidine-1-carboxylate (12): To the stirred solution of 6-bromo-1H-benzo[cd]indol-2-one (750 mg, 3.02 mmol) (11) in super dry THF (5.0 mL) was added Phenyllithium, typically 1.9M in di-n-butyl ether (254.09 mg, 3.02 mmol, 313.69 uL) through oven dried syringe at −78° C. under N2 atmosphere and the reaction was stirred at the same temperature for 30 minutes. After that, n-Butyllithium, 2.2M in hexane (213.04 mg, 3.33 mmol) was added to it at −78° C. After complete addition, temperature was allowed to increase to −40° C. and the reaction mixture was stirred at the same temperature for 30 minutes. After getting the des-bromo [evidenced from TLC (30% ethyl acetate in Hexane)] solution of tert-butyl 4-[[tert-butyl(dimethyl)silyl]oxymethyl]-4-(4-formylpyrazol-1-yl)piperidine-1-carboxylate (10) (1.28 g, 3.02 mmol) in dry THF (5.0 mL) was added at −78° C. and then the reaction mixture was allowed to warm to room temperature and was continued for 16 hours. After completion reaction mixture [evidenced from TLC], reaction mixture was quenched with saturated ammonium chloride solution and diluted with ethyl acetate (50 mL). Organic portion was washed with water (2×30 mL), separated, dried over anhydrous sodium sulphate and evaporated under reduced pressure to obtain the crude compound which was purified by flash chromatography (silica, gradient: 0-5% MeOH-DCM) to afford tert-butyl 4-[4-[hydroxy-(2-oxo-1H-benzo[cd]indol-6-yl)methyl]pyrazol-1-yl]-4-(trimethylsilyloxymethyl)piperidine-1-carboxylate (12) (639 mg, 1.02 mmol, 33.87% yield) as brown solid which stored in round bottomed flask at ambient temperature; LC MS: ES+ 593.4.

Step 9: Synthesis of [4-(hydroxymethyl)-4-[4-[(2-oxo-1H-benzo[cd]indol-6-yl)methyl]pyrazol-1-yl]-1-piperidyl] (13): To a stirred solution of tert-butyl 4-[[tert-butyl(dimethyl)silyl]oxymethyl]-4-[4-[hydroxy-(2-oxo-1H-benzo[cd]indol-6-yl)methyl]pyrazol-1-yl]piperidine-1-carboxylate (12) (639 mg, 1.08 mmol) in DCE (2.0 mL) was added triethylsilane (501.37 mg, 4.31 mmol, 688.69 uL) and Trifluoroacetic acid, 99% (983.25 mg, 8.62 mmol, 664.36 uL). Resulting reaction mix was heated at 70° C. under microwave condition for 30 mins. After completion of reaction (evidenced from LC MS and TLC), volatiles were removed under reduced pressure to afford [4-(hydroxymethyl)-4-[4-[(2-oxo-1H-benzo[cd]indol-6-yl)methyl]pyrazol-1-yl]-1-piperidyl] (630 mg, 906.90 umol, 84.13% yield) as yellow solid and stored in a round bottomed flask at ambient temperature (13); LC MS: ES+ 477.5.

Step 10: Synthesis of 6-[[1-[4-(hydroxymethyl)-1-[1-(trifluoromethyl)cyclopropanecarbonyl]-4-piperidyl]pyrazol-4-yl]methyl]-1H-benzo[cd]indol-2-one (15): To the stirred solution of 1-(1,1-difluoroethyl)cyclopropanecarboxylic acid (14) (323.09 mg, 2.15 mmol) in dry grade DMF (5.0 mL), HATU (613.74 mg, 1.61 mmol) was added at 0° C. followed by the mixture solution of 6-[[1-[4-(hydroxymethyl)-4-piperidyl]pyrazol-4-yl]methyl]-1H-benzo[cd]indol-2-one (13) and N,N-Diisopropylethylamine (695.38 mg, 5.38 mmol, 937.17 uL) under N2 atmosphere. After complete addition, reaction mixture was stirred for 16 h at room temperature. After completion of reaction (evidenced from LCMS; Crude LCMS showed desired mass along with di amidation mass peak), ice cooled water (5 mL) was added to the reaction mixture and extracted with ethyl acetate (3×30 mL). Organic portion was separated, dried over anhydrous sodium sulfate and concentrated. Crude thus obtained was then re-dissolved in Methanol (10 mL) and stirred with LiOH (1.5 eq) at rt for 30 minutes. After complete consumption of intermediate, solvent was evaporated and re-dissolved in ethyl acetate (50 mL). Organic portion was washed with water (2×30 mL) and separated, dried over anhydrous sodium sulfate and concentrated under reduced pressure to obtain 6-[[1-[4-(hydroxymethyl)-1-[1-(trifluoromethyl)cyclopropanecarbonyl]-4-piperidyl]pyrazol-4-yl]methyl]-1H-benzo[cd]indol-2-one (15) (500 mg, 822.47 umol, 76.43% yield, 82% purity) as brown gummy solid which was sufficiently pure to use in the next step; LC MS: ES+ 499.4.

Step 11: Synthesis of 6-[[1-[4-[[tert-butyl(dimethyl)silyl]oxymethyl]-1-[1-(trifluoromethyl)cyclopropanecarbonyl]-4-piperidyl]pyrazol-4-yl]methyl]-1H-benzo[cd]indol-2-one (16): To the stirred solution of 6-[[1-[4-(hydroxymethyl)-1-[1-(trifluoromethyl)cyclopropanecarbonyl]-4-piperidyl]pyrazol-4-yl]methyl]-1H-benzo[cd]indol-2-one (15) (1.0 g, 2.01 mmol) in dry grade DMF (5.0 mL), Triethylamine, 99% (608.97 mg, 6.02 mmol, 838.80 uL) was added at 0° C. followed by the addition of tert-Butyldimethylsilyl chloride (453.52 mg, 3.01 mmol, 559.91 uL). After complete addition, resulting mixture was heated at 60° C. for 1 hr. After completion of reaction [monitored by LCMS, Crude LCMS showed desired mass peak along with di-TBDMS protected mass), reaction mixture was quenched with the addition of ice cooled water (5 mL). Aqueous part was extracted with ethyl acetate (3×50 mL) and washed with brine (2×40 mL). Organic portion was separated, dried over anhydrous sodium sulfate and concentrated. Thus crude was obtained purified by column chromatography to afford di TBDMS protected product. The crude material was then re-dissolved in Ethanol (10 ml) and stirred in presence of K2CO3 (4 eq) for 30 minutes at rt. After complete consumption of intermediate, solvent was evaporated and re-dissolved in ethyl acetate (100 mL). Organic part was washed with water (2×30 mL0 and separated, dried over anhydrous sodium sulfate and concentrated to afford 6-[[1-[4-[[tert-butyl(dimethyl)silyl]oxymethyl]-1-[1-(trifluoromethyl)cyclopropanecarbonyl]-4-piperidyl]pyrazol-4-yl]methyl]-1H-benzo[cd]indol-2-one (16) (1.0 g, 1.57 mmol, 78.10% yield) which was sufficiently pure and used in the next step; LC MS: ES+ 613.2.

Step 12: Synthesis of 3-[6-[[1-[4-[[tert-butyl(dimethyl)silyl]oxymethyl]-1-[1-(trifluoromethyl)cyclopropanecarbonyl]-4-piperidyl]pyrazol-4-yl]methyl]-2-oxo-benzo[cd]indol-1-yl]piperidine-2,6-dione (18): To a stirred solution of 6-[[1-[4-[[tert-butyl(dimethyl)silyl]oxymethyl]-1-[1-(trifluoromethyl)cyclopropanecarbonyl]-4-piperidyl]pyrazol-4-yl]methyl]-1H-benzo[cd]indol-2-one (16) (200 mg, 326.39 umol) in dry THF (10.0 mL), Sodium hydride 60% dispersion in mineral oil (78.33 mg, 3.26 mmol) was added at 0° C. Once the addition is over, the resultant mixture was stirred for 15 minutes at RT. Then the reaction mixture was again cooled to 0° C. and 3-bromopiperidine-2,6-dione (17) (313.36 mg, 1.63 mmol) was added to it portion wise. After complete addition, resulting solution was heated at 70° C. for 1 hour. After completion (evidenced from TLC), the reaction mixture was again cooled to 0° C. and quenched with ice cooled water (20 mL). Aqueous part was extracted with ethyl acetate (2×20 mL). Combined extracts was dried over anhydrous sodium sulfate and concentrated under reduced pressure. Crude mass was purified by PREP-TLC (2.5% MeOH in DCM as eluent) to afford 3-[6-[[1-[4-[[tert-butyl(dimethyl)silyl]oxymethyl]-1-[1-(trifluoromethyl)cyclopropanecarbonyl]-4-piperidyl]pyrazol-4-yl]methyl]-2-oxo-benzo[cd]indol-1-yl]piperidine-2,6-dione (18) (120 mg, 149.20 umol, 45.71% yield, 90% purity) as yellow solid; LC MS: ES+ 610.2.

Step 13: Synthesis of 3-[6-[[1-[4-(hydroxymethyl)-1-[1-(trifluoromethyl)cyclopropanecarbonyl]-4-piperidyl]pyrazol-4-yl]methyl]-2-oxo-benzo[cd]indol-1-yl]piperidine-2,6-dione: 4M Dioxane-HCl (2 mL) was added to 3-[6-[[1-[4-[[tert-butyl(dimethyl)silyl]oxymethyl]-1-[1-(trifluoromethyl)cyclopropanecarbonyl]-4-piperidyl]pyrazol-4-yl]methyl]-2-oxo-benzo[cd]indol-1-yl]piperidine-2,6-dione (18) (60 mg, 82.89 umol) at 0° C. and stirred for 16 hr at rt. After completion of reaction as evidenced from LC MS, volatiles were removed. Crude was re dissolved in ethyl acetate (15 mL) and quenched with saturated sodium bicarbonate solution (maintaining pH-8). Organic part was separated, dried over sodium sulfate and concentrated under vacuum. Crude was purified by PREP-TLC (5% MeOH in DCM) to afford 3-[6-[[1-[4-(hydroxymethyl)-1-[1-(trifluoromethyl)cyclopropanecarbonyl]-4-piperidyl]pyrazol-4-yl]methyl]-2-oxo-benzo[cd]indol-1-yl]piperidine-2,6-dione Compound 195 (30 mg, 47.97 umol, 57.88% yield) as yellow solid and stored under Nitrogen Desiccators ("Terra Universal") at approximately 22° C. $^1$H NMR (400 MHz, DMSO-d6) δ 11.11 (s, 1H), 8.40 (d, J=8.12 Hz, 1H), 8.08 (d, J=6.8 Hz, 1H), 7.84-7.87 (m, 2H), 7.35 (br s, 2H), 7.06 (d, J=7.12 Hz, 1H), 5.44 (dd, J=12.52, 4.76 Hz, 1H), 4.94 (s, 1H), 4.21 (s, 2H), 4.0-3.98 (br m, 2H), 3.39 (s, 2H), 2.94-2.91 (m, 2H), 2.76-2.73 (m, 1H), 2.66-2.62 (m, 1H), 2.38-2.34 (m, 2H), 2.08 (br m, 1H), 1.82-1.80 (m, 1H), 1.26-1.25 (m, 2H), 1.51-1.50 (m, 2H); LC MS: ES+ 610.2.

Example 102. Synthesis of 4-[4-[4-[[1-(2,6-dioxo-3-piperidyl)-2-oxo-benzo[cd]indol-6-yl]methyl]benzoyl]piperazin-1-yl]-3-fluoro-benzonitrile (Compound 196)
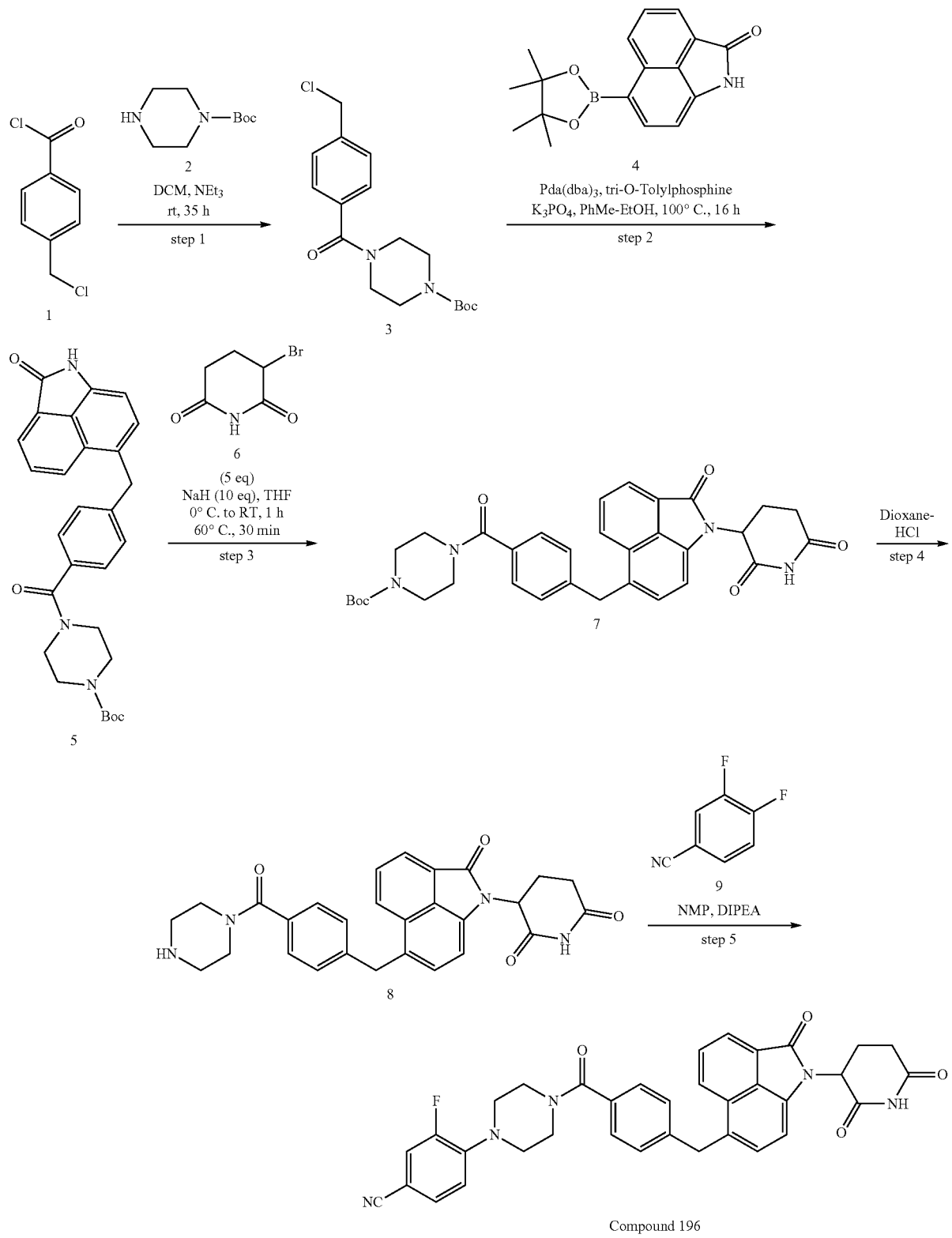
Compound 196

Step 1: Synthesis of tert-butyl 4-[4-(chloromethyl)benzoyl]piperazine-1-carboxylate (3): To the stirred solution of tert-butyl piperazine-1-carboxylate (2) (2.0 g, 10.74 mmol) in dry grade DCM (10.0 mL), Triethylamine, 99% (3.26 g, 32.21 mmol, 4.49 mL) was added at 0° C. followed by drop wise addition of 4-(chloromethyl)benzoyl chloride (1) (2.44 g, 12.89 mmol). After complete addition, reaction mixture was stirred for 5 hours at room temperature. After formation of desired pdt (evidenced from LCMS), RM was diluted with DCM (30 mL) and quenched with saturated sodium bicarbonate solution. Organic phase was washed with water (2×15 ml)/brine (20 mL) and separated, dried over sodium sulfate and concentrated. Crude was purified by column chromatography ((silica, gradient: 0-30% Ethyl acetate in Hexane) to afford tert-butyl 4-[4-(chloromethyl)benzoyl] piperazine-1-carboxylate (3) (2.2 g, 6.10 mmol, 56.84% yield, 94% purity) as a white solid which kept at ambient temperature in a round bottomed flask. LC MS: ES+ 339.4.

Step 2: Synthesis of tert-butyl 4-[4-[(2-oxo-1H-benzo[cd] indol-6-yl)methyl]benzoyl]piperazine-1-carboxylate (5): To a well degassed solution of tert-butyl 4-[4-(chloromethyl) benzoyl]piperazine-1-carboxylate (3) (600 mg, 1.77 mmol) and 6-(4,4,5,5-tetramethyl-1,3,2-dioxaborolan-2-yl)-1H-benzo[cd]indol-2-one (4) (1.05 g, 3.54 mmol) in Ethanol (2 mL)-Toluene (4 mL), Potassium phosphate tribasic, anhydrous, (1.13 g, 5.31 mmol) was added followed by the addition of Tri-o-Tolyl phosphine (107.80 mg, 354.16 umol) and Pd2(dba)₃ (162.16 mg, 177.08 umol). The resulting mixture was then heated at 90° C. for 12 hours. After completion of reaction (as monitored by LCMS), the reaction mixture was filtered through a bed of celite, washed with ethyl acetate (30 mL). The combined filtrate was then washed with water (3×15 mL) and brine (2×15 mL), dried over anhydrous sodium sulfate and concentrated under reduced pressure. Crude mass was purified by column chromatography (silica, gradient: 0-20% Ethyl acetate in DCM) to obtain tert-butyl 4-[4-[(2-oxo-1H-benzo[cd]indol-6-yl)methyl]benzoyl]piperazine-1-carboxylate (5) (350 mg, 526.99 umol, 29.76% yield) as yellow solid which was stored in a Tarson plastic bottle at ambient temperature; LC MS: ES+ 472.3.

Step 3: Synthesis of tert-butyl 4-[4-[[1-(2,6-dioxo-3-piperidyl)-2-oxo-benzo[cd]indol-6yl]methyl]benzoyl]piperazine-1-carboxylate (7): To a ice cooled solution of tert-butyl 4-[4-[(2-oxo-1H-benzo[cd]indol-6-yl)methyl]benzoyl]piperazine-1-carboxylate (5) (680 mg, 1.44 mmol) in dry THF (10 mL), Sodium hydride (60% dispersion in mineral oil) (346.10 mg, 14.42 mmol) was added portion wise, maintaining the temp <5° C. Once the addition is over, the resultant mixture was stirred for 15 minutes at RT. Then the reaction mixture was again cooled to 0° C. and 3-bromopiperidine-2,6-dione (6) (1.38 g, 7.21 mmol) was added to it portion wise. After complete addition, resulting solution was heated at 70° C. for 1 hour. After completion (evidenced from TLC), the reaction mixture was again cooled to 0° C. and quenched with ice cooled water (10 mL). Aqueous part was extracted with ethyl acetate (2×20 mL). Combined extracts was dried over anhydrous sodium sulfate and concentrated under reduced pressure. Crude mass was purified by Preparative TLC (gradient: 50% EtOAc in DCM) to afford tert-butyl 4-[4-[[1-(2,6-dioxo-3-piperidyl)-2-oxo-benzo[cd]indol-6-yl]methyl]benzoyl]piperazine-1-carboxylate (7) (500 mg, 532.06 umol, 36.90% yield) as yellow solid which was Tarson plastic bottle at ambient temperature; LC MS: ES+ 583.4.

Step 4: Synthesis of tert 3-[2-oxo-6-[[4-(piperazine-1-carbonyl)phenyl]methyl]benzo[cd]indol-1-yl]piperidine-2,6-dione; hydrochloride (8): To the stirred solution of tert-butyl 4-[4-[[1-(2,6-dioxo-3-piperidyl)-2-oxo-benzo[cd] indol-6-yl]methyl]benzoyl]piperazine-1-carboxylate (7) (500 mg, 858.16 umol) in dry Dioxane (5.0 mL), Dioxane/HCl (858.16 umol, 7.0 mL) was added at 0° C. and stirred for 5 hr at rt. After completion of reaction (evidenced from LC MS) volatiles were removed under reduced pressure.

Solid material thus obtained was triturated with Diethyl ether to afford 3-[2-oxo-6-[[4-(piperazine-1-carbonyl)phenyl]methyl]benzo[cd]indol-1-yl]piperidine-2,6-dione; hydrochloride (8) (450 mg, 615.72 umol, 71.75% yield) as yellow solid; LC MS: ES+ 483.4.

Step 5: Synthesis of 4-[4-[4-[[1-(2,6-dioxo-3-piperidyl)-2-oxo-benzo[cd]indol-6-yl]methyl]benzoyl]piperazin-1-yl]-3-fluoro-benzonitrile: To the well degassed solution of 3-[2-oxo-6-[[4-(piperazine-1-carbonyl)phenyl]methyl]benzo[cd]indol-1-yl]piperidine-2,6-dione; hydrochloride (8) (200 mg, 385.36 umol) in NMP (2.0 mL), N,N-Diisopropylethylamine (298.83 mg, 2.31 mmol, 402.73 uL) was added followed by 3,4-difluorobenzonitrile (9) (80.41 mg, 578.05 umol). Resulting solution was then heated at 110° C. for 12 hr. After completion of reaction (evidenced from LC MS), RM was cooled to RT and ice cooled water (5 mL) was added to it. Aqueous part was extracted with ethyl acetate (3×30 mL). Organic phase was separated, dried over sodium sulfate and concentrated. Crude residue was purified by Preparative TLC (gradient: 40% EtOAc in DCM) to afford 4-[4-[4-[[1-(2,6-dioxo-3-piperidyl)-2-oxo-benzo[cd]indol-6-yl]methyl]benzoyl]piperazin-1-yl]-3-fluoro-benzonitrile Compound 196 (31.0 mg, 50.25 umol, 13.04% yield) as yellow solid which was stored in a round bottomed flask at 5° C. inside a refrigerator. 1H NMR (400 MHz, DMSO-d6) δ 11.12 (s, 1H), 8.35 (d, J=8.16 Hz, 1H), 8.08 (d, J=6.8 Hz, 1H), 7.82 (t, J=7.36 Hz, 1H), 7.72 (d, J=13.28 Hz, 1H), 7.57 (d, J=8.44 Hz, 1H), 7.46 (d, J=7.24 Hz, 1H), 7.38-7.35 (m, 4H), 7.13-7.09 (m, 2H), 5.45-5.43 (m, 1H), 4.45 (s, 2H), 3.81 (br, 2H), 3.58 (br, 2H), 3.18 (br, 4H), 2.95-2.92 (m, 1H), 2.80-2.62 (m, 2H), 2.07 (m, 1H); LC MS: ES+ 600.2.

Example 103. Synthesis of 3-[2-oxo-6-[[4-[(3-oxo-morpholin-4-yl)methyl]phenyl]methyl]benzo[cd] indol-1-yl]piperidine-2,6-dione (Compound 197)

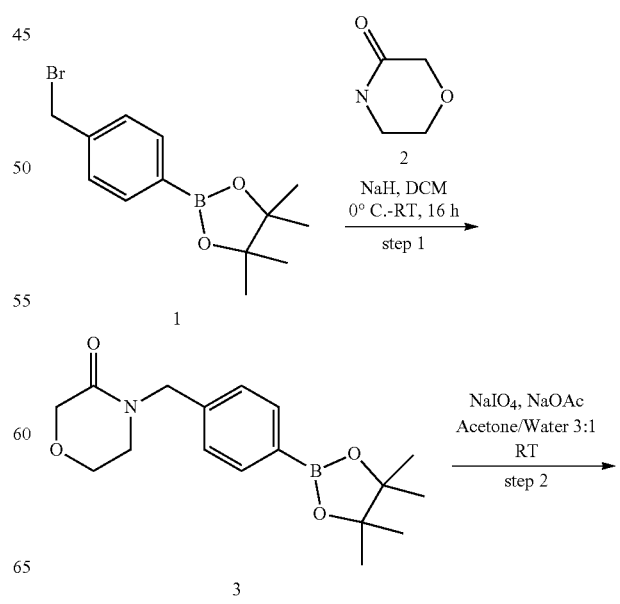

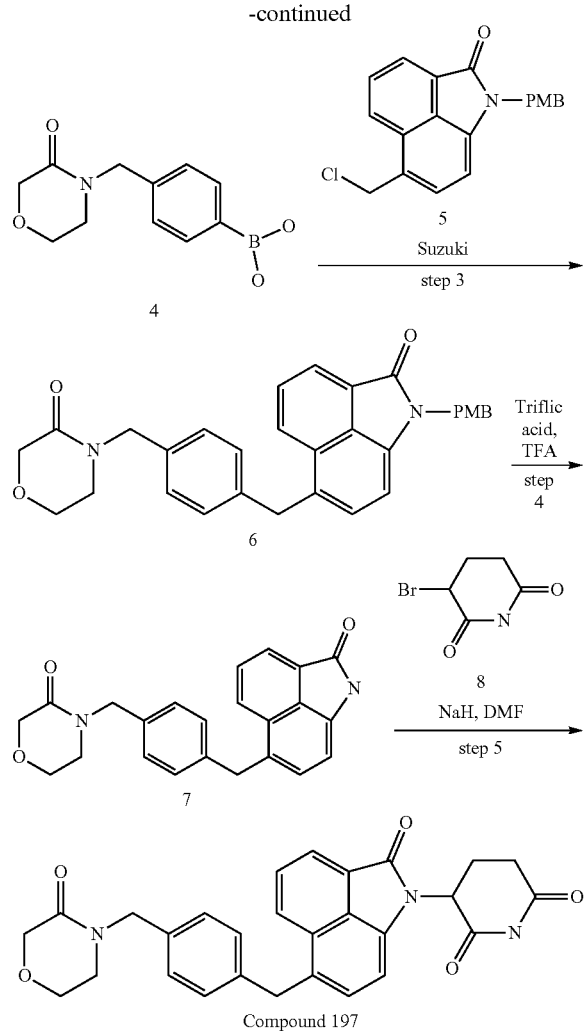

Step-1: Synthesis of 4-[[4-(4,4,5,5-tetramethyl-1,3,2-dioxaborolan-2-yl)phenyl]methyl]morpholin-3-one 3: To a stirred solution of morpholin-3-one 2 (3 g, 29.67 mmol) in DCM (100.0 mL), cooled to 0° C., was added sodium hydride (60/a dispersion in mineral oil; 3.56 g, 89.03 mmol, 60% purity) and stirred the reaction mix at the same temperature for 30 mins. 2-[4-(bromomethyl)phenyl]-4,4,5,5-tetramethyl-1,3,2-dioxaborolane 1 (10.58 g, 35.61 mmol) was then added and stirred the reaction at rt for 16 h. TLC/LC shows complete consumption of SM. The reaction mix was then taken under ice-cooled condition, and excess NaH was quenched with ice. The organic phase was then washed with water, followed by brine, and finally dried over anhyd. Na$_2$SO$_4$. The solvent was evaporated and the residue was purified by column chromatography on silica gel (50% EA/Hex) to furnish the desired product 4-[[4-(4,4,5,5-tetramethyl-1,3,2-dioxaborolan-2-yl)phenyl]methyl]morpholin-3-one 3 (1.8 g, 5.11 mmol, 17.21% yield, 90% purity) as yellow solid; LCMS (ES+)=318.2 [M+H]$^+$.

Step-2: Synthesis of [4-[(3-oxomorpholin-4-yl)methyl]phenyl]boronic acid 4: To the stirred solution of 4-[[4-(4,4,5,5-tetramethyl-1,3,2-dioxaborolan-2-yl)phenyl]methyl]morpholin-3-one 3 (1.8 g, 5.67 mmol) in Acetone (45 mL)-Water (15 mL), sodium periodate (6.07 g, 28.37 mmol) and ammonium acetate (2.19 g, 28.37 mmol) were added at rt and stirred for 16 hr at same temp. After completion of reaction as monitored by LC MS, DCM was added and washed with water. Organic phase was separated, dried over sodium sulfate and concentrated to afford [4-[(3-oxomorpholin-4-yl)methyl]phenyl]boronic acid 4 (820 mg, 3.14 mmol, 55.33% yield, 90% purity) as colorless solid which was used in next step without further purification.

Step-3: Synthesis of 4-[[4-[[1-[(4-methoxyphenyl)methyl]-2-oxo-benzo[cd]indol-6-yl]methyl]phenyl]methyl]morpholin-3-one 6: To a stirred solution of 6-(chloromethyl)-1-[(4-methoxyphenyl)methyl]benzo[cd]indol-2-one 5 (1.44 g, 3.40 mmol) and [4-[(3-oxomorpholin-4-yl)methyl]phenyl]boronic acid 4 (1.2 g, 5.11 mmol) intoluene (25 mL) in a sealed tube was added tripotassium phosphate (1.81 g, 8.51 mmol) and degassed for 10 min. Subsequently, Tetrakis(triphenylphosphine)palladium(0) (393.31 mg, 340.36 umol) was added and degassed at argon atmosphere for 10 min. The reaction mixture was heated at 100° C. for 18 h. The reaction mixture was then allowed to come to RT, filtered over Celite and was washed thoroughly with ethyl acetate. The solvent was evaporated and the residue was purified by column chromatography on silica gel (eluting 90% EA/Hex-100% EA) to furnish the desired product 4-[[4-[[1-[(4-methoxyphenyl)methyl]-2-oxo-benzo[cd]indol-6-yl]methyl]phenyl]methyl]morpholin-3-one 6 (350 mg, 639.51 umol, 18.79/a yield, 90% purity) as yellow viscous liquid; LCMS (ES+)=493.3 [M+H]+.

Step-4: Synthesis of 4-[[4-[(2-oxo-1H-benzo[cd]indol-6-yl)methyl]phenyl]methyl]morpholin-3-one 7: To 4-[[4-[[1-[(4-methoxyphenyl)methyl]-2-oxo-benzo[cd]indol-6-yl]methyl]phenyl]methyl] morpholin-3-one 6 (300 mg, 609.06 umol) (300 mg, 609.06 umol) in TFA (2 mL) was added Trifluoromethanesulfonic acid (365.63 mg, 2.44 mmol, 213.82 uL) at rt and stirred for 16 hr at same temp. After complete consumption of SM, reaction mixture was evaporated to remove the excess reagents. It was dissolved in DCM, and washed with satd. NaHCO3. Organic portion was separated, dried over sodium sulfate and concentrated under reduced pressure to get the residue which was purified by column chromatography on silica gel (eluting 3% MeOH/DCM) to furnish the desired product 4-[[4-[(2-oxo-1H-benzo[cd]indol-6-yl)methyl]phenyl]methyl]morpholin-3-one 7 (150 mg, 362.50 umol, 59.52% yield, 90% purity) as brown viscous liquid; LCMS (ES+)=373.2 [M+H]+.

Step-5: Synthesis of 3-[2-oxo-6-[[4-[(3-oxomorpholin-4-yl)methyl]phenyl]methyl]benzo[cd]indol-1-yl]piperidine-2,6-dione: To a stirred solution of 4-[[4-[(2-oxo-1H-benzo[cd]indol-6-yl)methyl]phenyl]methyl]morpholin-3-one 7 (250 mg, 671.29 umol) in DMF (5 mL), was added Sodium hydride (in oil dispersion) 60% dispersion in mineral oil (77.17 mg, 2.01 mmol, 60% purity) at 0° C. Then reaction mixture was then heated to 0-60° C. for 1 h. 3-bromopiperidine-2,6-dione (154.67 mg, 805.55 umol) was then added to the reaction mixture (twice within a gap of 1 h), and the heating was continued for 16 hr. Due to non-completion of SM, further 3-bromopiperidine-2,6-dione (154.67 mg, 805.55 umol) was added and reaction was continued at 60° C. for further 16 h. After that reaction was quenched with cold water and extracted with ethyl acetate, dried over sodium sulphate, and concentrated under reduced pressure to give the crude. This crude was purified by first Combi-Flash Column Chromatography followed by PREP-HPLC to eventually afford the title compound 3-[2-oxo-6-[[4-[(3-oxomorpholin-4-yl)methyl]phenyl]methyl]benzo[cd]indol-1-yl]piperidine-2,6-dione Compound 197 (30 mg, 61.64 umol, 9.18% yield, 99.34% purity as yellow solid. LCMS (ES+)=484.2 [M+H]+. 1H NMR (400 MHz, DMSO-d6): δ 11.12 (s, 1H, D20 Exchangeable), 8.33 (d, J=8 Hz, 1H), 8.07

(d, J=6.8 Hz, 1H), 7.83-7.79 (m, 1H), 7.41 (d, J=6.9 Hz, 1H), 7.29-7.27 (m, 2H), 7.16-7.09 (m, 3H), 5.45-5.43 (m, 1H), 4.47 (s, 2H), 4.38 (s, 2H), 4.07 (s, 2H), 3.76 (m, 2H), 3.19 (m, 2H), 2.95-2.92 (m, 1H), 2.79-2.73 (m, 1H), 2.69-2.63 (m, 1H), 2.07 (m, 1H).

Example 104. Synthesis of 3-[6-[-[1-(1-methylcyclohexyl)pyrazol-4-yl]methyl]-2-oxo-benzo[cd]indol-1-yl]piperidine-2,6-dione (Compound 198)

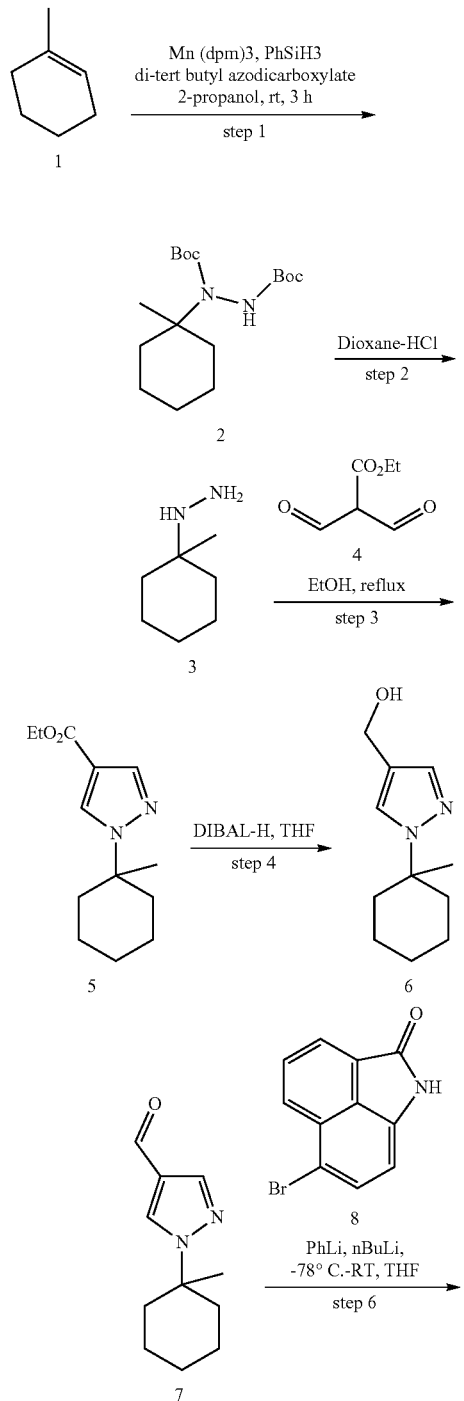

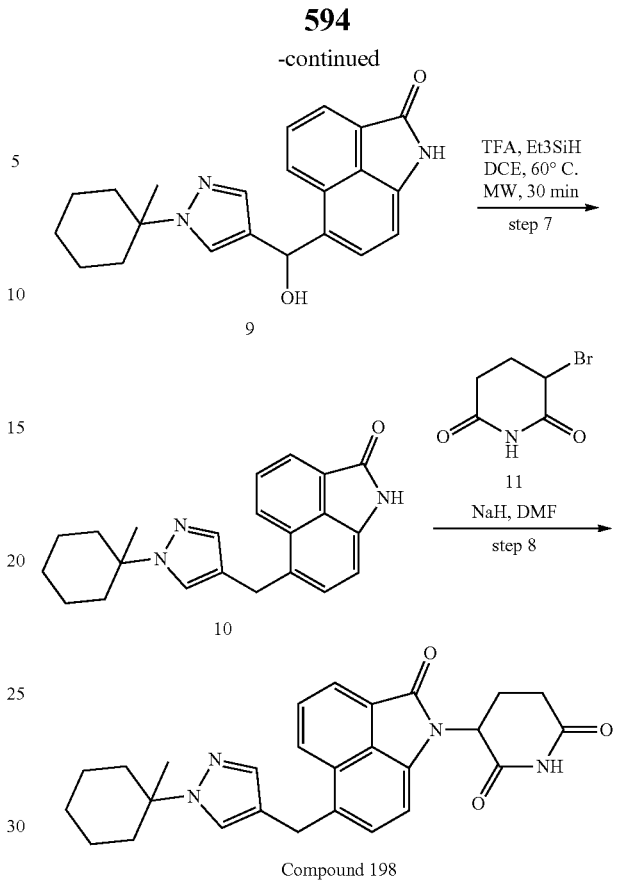

Compound 198

Step-1: Synthesis of tert-butyl N-(tert-butoxycarbonylamino)-N-(1-methylcyclohexyl)carbamate 2: To the well stirred solution of 1-methylcyclohexene 1 (2.5 g, 26.00 mmol, 3.09 mL) in 2-Propanol (50 mL) at 0° C. was added Di-tert-butyl azodicarboxylate (8.98 g, 38.99 mmol) and Tris(2,2,6,6-tetramethyl-3,5-heptanedionato)manganese (III) (314.41 mg, 519.91 umol) and finally phenylsilane (3.38 g, 31.19 mmol, 3.84 mL). The reaction mixture was allowed to come to RT and stirred at this temp. for 16 h. After complete consumption of SM, reaction mass was evaporated and the crude residue was purified by column chromatography (1-5% EA/Hex) to afford tert-butyl N-(tert-butoxycarbonylamino)-N-(1-methylcyclohexyl)carbamate 2 (1.5 g, 3.65 mmol, 14.05% yield, 80% purity).

Step-2: Synthesis of (1-methylcyclohexyl)hydrazine 3: To a stirred solution of tert-butyl N-(tert-butoxycarbonylamino)-N-(1-methylcyclohexyl)carbamate 2 (12.5 g, 38.06 mmol) in Dioxane (100 mL) was added Dioxane-HCl (4 M, 190.29 mL) drop wise at 0° C. It was then allowed to come to RT and stirred for 16 h. Crude LCMS showed complete consumption of starting material and formation of product. The reaction mass was evaporated to dryness and subsequently washed thoroughly with pentane eventually to afford (1-methylcyclohexyl)hydrazine 3 (5 g, 11.44 mmol, 30.05% yield, 60% purity) as a white solid; LCMS (ES+)=128.3 [M+H]+.

Step-3: Synthesis of ethyl 1-(1-methylcyclohexyl)pyrazole-4-carboxylate 5: To a stirred solution of (1-methylcyclohexyl)hydrazine 3 (7.5 g, 46.80 mmol) intoluene (100 mL) was added Ethyl-2-formyl-3-oxopropionate 4 (8.09 g, 56.16 mmol) and stirred the reaction mix at 100° C. for 16 hr. The reaction mix was then evaporated under vacuum to remove the volatiles and the crude residue thus obtained was purified by column chromatography (2-3% EA/Hex) to afford ethyl 1-(1-methylcyclohexyl)pyrazole-4-carboxylate 5 (4 g, 13.54 mmol, 28.94% yield, 80% purity) as a yellowish oil; LCMS (ES+)=237.4 [M+H]+.

Step-4: Synthesis of [1-(1-methylcyclohexyl)pyrazol-4-yl]methanol 6: To a stirred solution of ethyl 1-(1-methylcyclohexyl)pyrazole-4-carboxylate 5 (1.4 g, 5.92 mmol) in THF (10.0 mL) was added DIBAL-H (1.6 M, 18.51 mL) at −78° C. and stirred at this temp. for 1 h. The reaction mixture was slowly allowed to come to RT and stirred for 6h. The progress of the reaction was monitored via TLC/LC-MS. The reaction mixture was then again cooled to −−78° C., quenched with satd. NH4Cl soln., slowly allowed to come to RT and stirred for some time. The solid residue settled down, the liquid portion was filtered via celite, and thoroughly washed with DCM. The organic layer was washed with water, brine and dried over anhyd. Na$_2$SO$_4$. Evaporation of the organic layer gave [1-(1-methylcyclohexyl)pyrazol-4-yl]methanol 6 (700 mg, 3.24 mmol, 54.74% yield, 90% purity) as a viscous liquid; LCMS (ES+)=195.3 [M+H]+.

Step-5: Synthesis of 1-(1-methylcyclohexyl)pyrazole-4-carbaldehyde 7: To a stirred solution of [1-(1-methylcyclohexyl)pyrazol-4-yl]methanol 6 (1.83 g, 9.42 mmol) in Acetonitrile (50 mL) was added Dioxomanganese (8.19 g, 94.20 mmol) at rt and stirred the reaction mixture for 16 h. The progress of the reaction was monitored via TLC/LC-MS, which showed formation of aldehyde as well as presence of un-reacted SM. The reaction mixture was then filtered via celite, thoroughly washed with EtOAc. and evaporated under vacuum to obtain a crude which was purified by column chromatography (eluted with 8-9% EA/Hex) to yield 1-(1-methylcyclohexyl)pyrazole-4-carbaldehyde 7 (740 mg, 3.46 mmol, 36.78% yield, 90% purity) as colorless viscous liquid; LCMS (ES+)=193.2 [M+H]+.

Step-6: Synthesis of 6-[hydroxy-[1-(1-methylcyclohexyl)pyrazol-4-yl]methyl]-1H-benzo[cd]indol-2-one 9: To the stirred solution of 1-(1-methylcyclohexyl)pyrazole-4-carbaldehyde 7 (0.5 g, 2.60 mmol) in THF (25 mL) was added Phenyllithium, typically 1.9 M in di-n-butyl ether (1.8 M, 1.59 mL) at −78° C. and the reaction was stirred at the same temperature for 30 minutes followed by the addition of Butyllithium, typically 2.5 M in n-Hexane (1.7 M, 1.68 mL) at −78° C. and after the addition was complete the temperature was allowed to increase to −40° C. and the reaction mixture was stirred at the same temperature for 30 minutes followed by the addition of 6-bromo-1H-benzo[cd]indol-2-one 8 (645.17 mg, 2.60 mmol) in THF (25 mL) at −78° C. and then the reaction mixture was allowed to warm to room temperature and was continued for 16 hours. It was quenched with saturated ammonium chloride solution, extracted with ethyl acetate, washed with water, brine, dried over sodium sulfate and was concentrated under reduced pressure. It was purified by Comb flash (eluting with 75-80% EA/Hex) to afford 6-[hydroxy-[1-(1-methylcyclohexyl)pyrazol-4-yl]methyl]-1H-benzo[cd]indol-2-one 9 (220 mg, 547.81 umol, 21.06% yield, 90% purity) as yellowish solid; LCMS (ES+)=362.2 [M+H]+.

Step-7: Synthesis of 6-[[1-(1-methylcyclohexyl)pyrazol-4-yl]methyl]-1H-benzo[cd]indol-2-one 10: To a stirred solution of 6-[hydroxy-[1-(1-methylcyclohexyl)pyrazol-4-yl]methyl]-1H-benzo[cd]indol-2-one 9 (125 mg, 345.84 umol) in DCE (5 mL) was added Triethylsilane (160.86 mg, 1.38 mmol, 220.96 uL) and Trifluoroacetic acid (315.46 mg, 2.77 mmol, 213.15 uL) in a sealed tube. It was heated at 70° C. for 2h. The progress of the reaction was monitored via TLC/LC-MS. The volatiles were removed under vacuum to obtain a crude mass which was dissolved in DCM, washed thoroughly with satd. NaHCO3soln. and finally dried over anhyd. Na$_2$SO$_4$. The solvent was evaporated to furnish the crude desired product 6-[[1-(1-methylcyclohexyl)pyrazol-4-yl]methyl]-1H-benzo[cd]indol-2-one 10 (105 mg, 273.57 umol, 79.10% yield, 90% purity) as brownish floppy solid. It would be used in the next step without further purification; LCMS (ES+)=346.2 [M+H]+.

Step-8: Synthesis of 3-[6-[[1-(1-methylcyclohexyl)pyrazol-4-yl]methyl]-2-oxo-benzo[cd]indol-1-yl]piperidine-2,6-dione: To a stirred solution of 6-[[1-(1-methylcyclohexyl)pyrazol-4-yl]methyl]-1H-benzo[cd]indol-2-one 10 (200 mg, 578.98 umol) in THF (5 mL) was added Sodium hydride (60% dispersion in mineral oil; 221.84 mg, 5.79 mmol, 60% purity) at 0° C. and the reaction mixture was stirred at this temperature for 5 min. Ice-bath was then removed and the reaction mixture was stirred for another 10 min before 3-bromopiperidine-2,6-dione 11 (555.85 mg, 2.89 mmol) was added to it at once and the reaction mixture was stirred at this temperature for another 10 min. Subsequently, the reaction mixture was heated at 70° C. for 18 hr. After that reaction was quenched with cold water and extracted with ethyl acetate, dried over sodium sulphate, and concentrated under reduced pressure to give the crude. This crude was purified by Combi-Flash Column Chromatography (eluting with 60% EA/Hex) to eventually afford the title compound 3-[6-[[1-(1-methylcyclohexyl)pyrazol-4-yl]methyl]-2-oxo-benzo[cd]indol-1-yl]piperidine-2,6-dione 12 (65 mg, 140.43 umol, 24.25% yield, 98.63% purity) Compound 198 as a yellow solid (obtained after lyophilization). LCMS (ES+)=457.2 [M+H]+. 1H NMR (400 MHz, DMSO-d6): δ 11.12 (s, 1H, D20 Exchangeable), 8.40 (d, J=8.2 Hz, 1H), 8.09 (d, J=6.7 Hz, 1H), 7.85-7.81 (m, 1H), 7.69 (s, 1H), 7.35 (d, J=7.2 Hz, 1H), 7.29 (s, 1H), 7.08 (d, J=7.2 Hz, 1H), 5.46-5.41 (m, 1H), 4.20 (s, 2H), 2.98-2.90 (m, 1H), 2.79-2.73 (m, 1H), 2.69-2.62 (m, 1H), 2.18 (m, 2H), 2.09-2.07 (m, 1H), 1.65-1.63 (m, 2H), 1.46 (m, 2H), 1.46 (m, 4H), 1.35 (m, 3H).

Example 105. Synthesis of 1-[[4-[4-[[1-(2,6-dioxo-3-piperidyl)-2-oxo-benzo[cd]indol-6-yl]methyl]pyrazol-1-yl]-1-piperidyl]methyl]cyclopropanecarbonitrile (Compound 199)

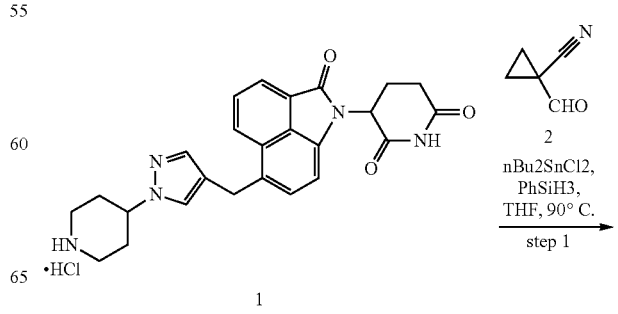

-continued

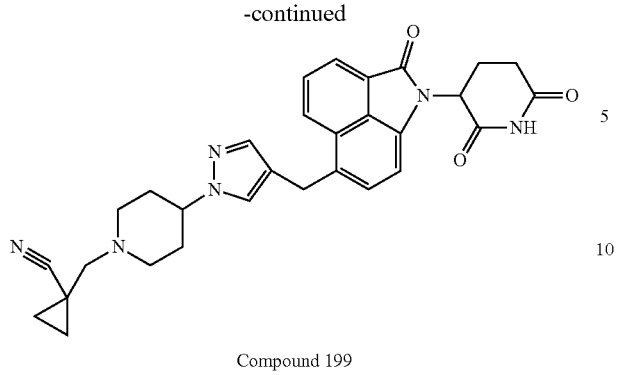

Compound 199

Step-1: Synthesis of 1-[[4-[4-[[1-(2,6-dioxo-3-piperidyl)-2-oxo-benzo[cd]indol-6-yl]methyl]pyrazol-1-yl]-1-piperidyl]methyl]cyclopropanecarbonitrile: To a stirred solution of 3-[2-oxo-6-[[1-(4-piperidyl)pyrazol-4-yl]methyl]benzo[cd]indol-1-yl]piperidine-2,6-dione 1 (300 mg, 676.44 umol) in THF (5 mL) in a sealed tube was added Triethylamine (136.90 mg, 1.35 mmol, 188.57 uL) and stirred for 5 minutes. To it was subsequently added 1-formylcyclopropanecarbonitrile 2 (83.63 mg, 879.38 umol) followed by Dibutyltindichloride (246.64 mg, 811.73 umol, 181.36 uL) and Phenylsilane (73.20 mg, 676.44 umol, 83.37 uL) and the reaction mixture was stirred at 90° C. for 14 h. The reaction was monitored via TLC and LC. TLC showed the appearance of new spot. The reaction mixture was then diluted with EtOAc, washed with satd. NaHCO3soln. and extracted with EtOAc. The organic layer was separated, dried over anhydrous sodium sulphate, and evaporated under reduced pressure to obtain a crude which was subjected to Combi-Flash column chromatography (eluted with 0-5% MeOH/DCM; 2% McOH/DCM) to yield 1-[[4-[4-[[1-(2,6-dioxo-3-piperidyl)-2-oxo-benzo[cd]indol-6-yl]methyl]pyrazol-1-yl]-1-piperidyl]methyl]cyclopropanecarbonitrile Compound 199 (55 mg, 102.80 umol, 15.20% yield, 97.68% purity as a yellowish solid. LCMS (ES+)=523.3 [M+H]+. 1H NMR (400 MHz, DMSO-d6): δ 11.13 (s, 1H, D20 Exchangeable), 8.39 (d, J=8.2 Hz, 1H), 8.09 (d, J=6.9 Hz, 1H), 7.84 (t, J=7.5 Hz, 1H), 7.61 (s, 1H), 7.36 (d, J=7 Hz, 1H), 7.31 (s, 1H), 7.07 (d, J=7.5 Hz, 1H), 5.86 (s, 1H), 5.45-5.43 (m, 1H), 4.18 (s, 2H), 4.04 (m, 1H), 3.31 (m, 2H), 3.04-3.01 (m, 2H), 2.95 (m, 1H), 2.67 (s, 1H), 2.62 (m, 1H), 2.41 (m, 2H), 2.11 (m, 2H), 1.89 (m, 3H), 1.23 (m, 4H).

Example 106. Synthesis of 3-[6-[[3-chloro-1-[1-[(1-methylcyclobutyl)methyl]-4-piperidyl]pyrazol-4-yl]methyl]-2-oxo-benzo[cd]indol-1-yl]piperidine-2,6-dione (Compound 200)

-continued

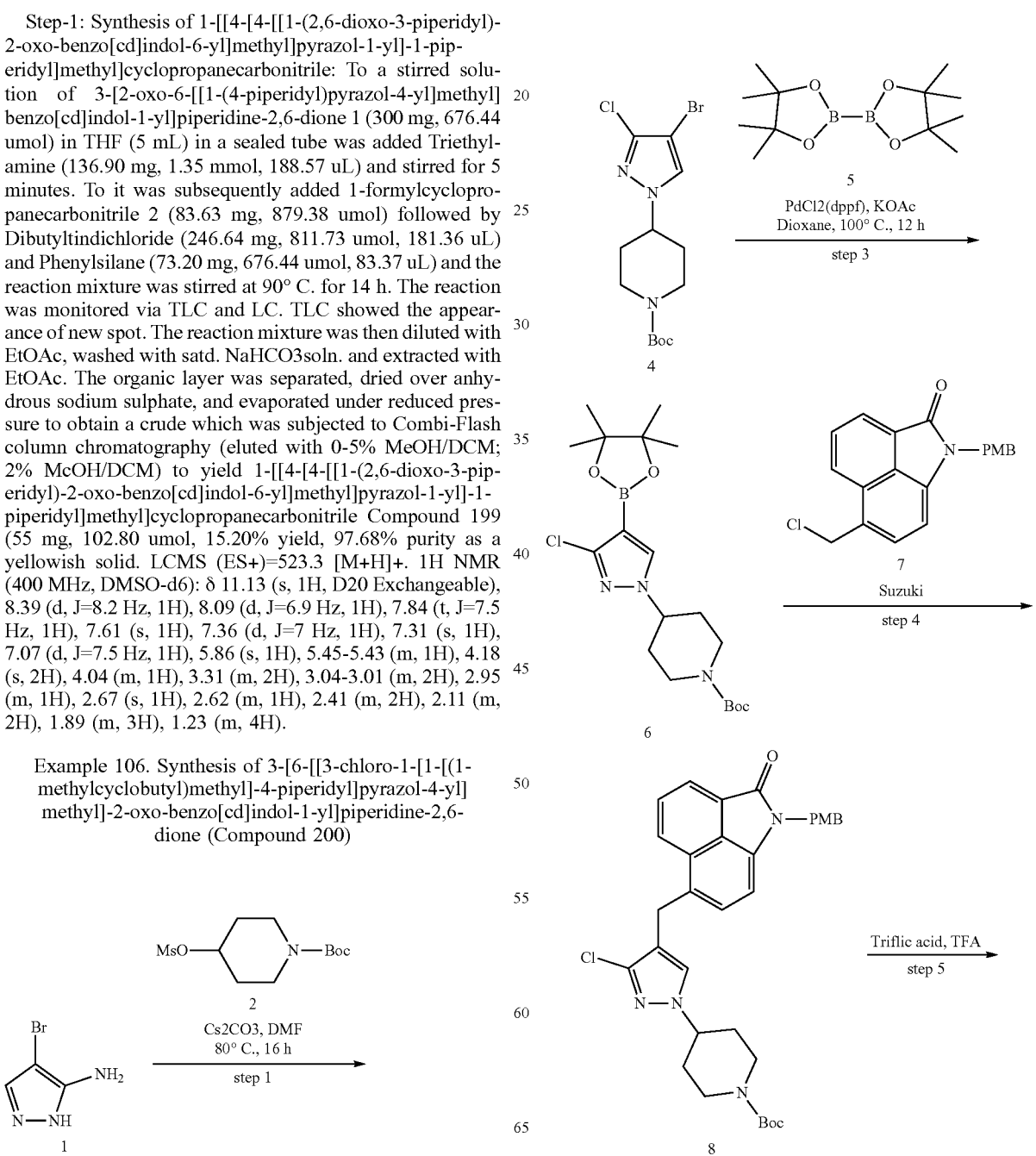

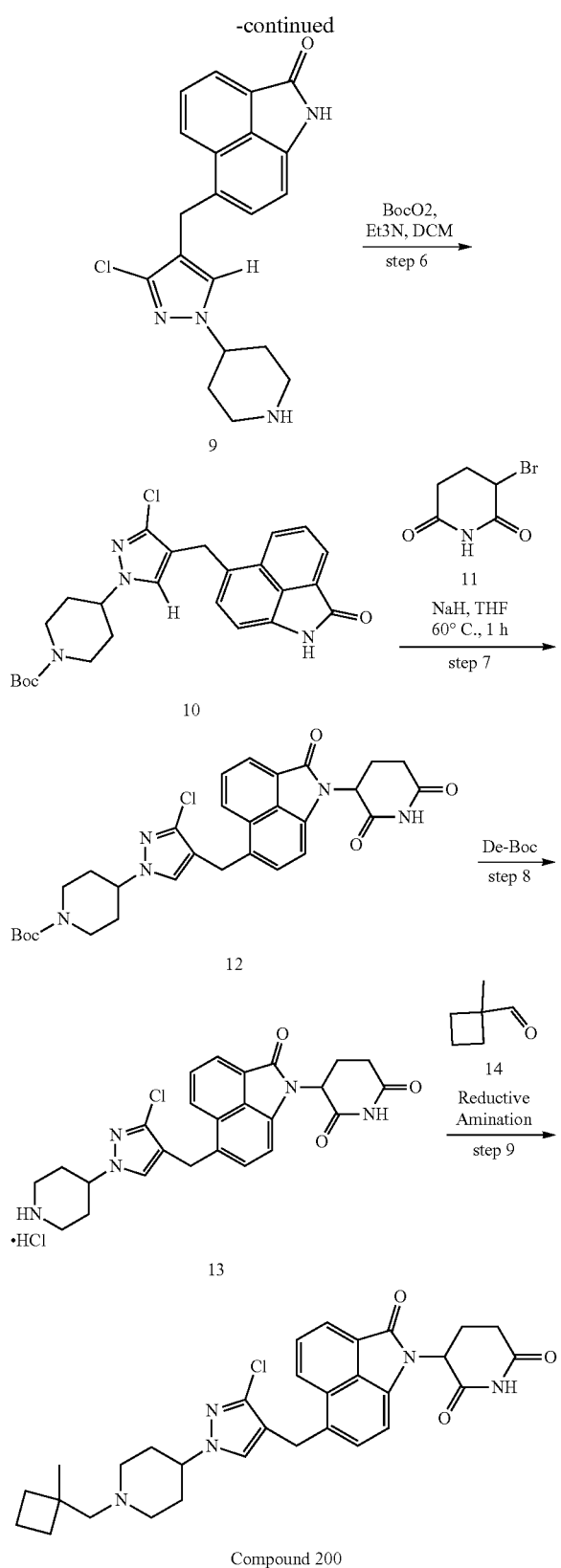

dine-1-carboxylate 2 (20.69 g, 74.08 mmol) followed by Cesium carbonate (40.23 g, 123.47 mmol) and the reaction mixture was stirred in a seal tube at 90° C. for 16 hr. SM was consumed in TLC. The reaction mixture was then diluted with ethyl acetate and washed with chilled water followed by brine. The combined organic layer was dried over anhydrous sodium sulfate and concentrated under reduced pressure to get the crude which was purified by column chromatography on silica gel (eluting with 45% ethyl acetate in Hexane to get the desired product tert-butyl 4-(3-amino-4-bromo-pyrazol-1-yl)piperidine-1-carboxylate 3 (6 g, 13.90 mmol, 22.52% yield, 80% purity) as dark green color semi liquid; LC-MS (ES+)=347.3 [M+H]+.

Step-2: Synthesis of tert-butyl 4-(4-bromo-3-chloro-pyrazol-1-yl)piperidine-1-carboxylate 4: To a acetonitrile (20 mL) was added tert-Butyl nitrite, tech. 90% (1.49 g, 13.03 mmol, 1.72 mL, 90% purity) followed by CuCl (1.29 g, 13.03 mmol) and the reaction mixture was then slowly heated up to 65° C. At this point, tert-butyl 4-(3-amino-4-bromo-pyrazol-1-yl)piperidine-1-carboxylate 3 (3 g, 8.69 mmol) dissolved in Acetonitrile (10 mL) was slowly added to the reaction mixture. The reaction mixture was stirred at this temperature for 0.5 h. TLC shows a new non polar spot and starting was consumed. Water was then added. The reaction mixture was then cooled to room temperature; water was added and extracted with EtOAc. The organic part was then washed with saturated sodium bicarbonate solution and brine solution and then it was dried over sodium sulfate and the organic part was concentrated under reduced pressure to afford the crude product. The crude was then purified by column chromatography eluting 10% of ethyl acetate in Hexane to afford tert-butyl 4-(4-bromo-3-chloro-pyrazol-1-yl)piperidine-1-carboxylate 4 (1 g, 2.47 mmol, 28.40% yield, 90% purity) as a white solid.

Step-3: Synthesis of tert-butyl 4-[3-chloro-4-(4,4,5,5-tetramethyl-1,3,2-dioxaborolan-2-yl)pyrazol-1-yl]piperidine-1-carboxylate 6: A stirred solution of tert-butyl 4-(4-bromo-3-chloro-pyrazol-1-yl)piperidine-1-carboxylate 4 (2 g, 5.48 mmol) and 4,4,5,5-tetramethyl-2-(4,4,5,5-tetramethyl-1,3,2-dioxaborolan-2-yl)-1,3,2-dioxaborolane 5 (2.09 g, 8.23 mmol) in 1,4 dioxane (20 mL) was degassed with argon, and to this soln was sequentially added Potassium Acetate (1.61 g, 16.45 mmol, 1.03 mL) and finally Pd(dppf)Cl2.DCM (447.88 mg, 548.45 umol) and again degassed for 5 minutes before the reaction mixture was heated at 100° C. for 16 h. TLC was checked and LC-MS was analyzed which showed the desired mass of the Boronate ester derivative. The reaction mixture was diluted with EtOAc, layers were separated. The organic layer was washed with water, brine dried over NaSO4 and concentrated under reduced pressure to afford tert-butyl 4-[3-chloro-4-(4,4,5,5-tetramethyl-1,3,2-dioxaborolan-2-yl)pyrazol-1-yl]piperidine-1-carboxylate 6 (1.6 g, 1.17 mmol, 21.26% yield, 30% purity) as brown sticky solid which was used in next step without further purification; LCMS (ES+)=412.2 [M+H]+.

Step-4: Synthesis of tert-butyl 4-[3-chloro-4-[[1-[(4-methoxyphenyl)methyl]-2-oxo-benzo[cd]indol-6-yl]methyl]pyrazol-1-yl]piperidine-1-carboxylate 8: To a stirred solution of 6-(chloromethyl)-1-[(4-methoxyphenyl)methyl]benzo[cd]indol-2-one 7 (2.1 g, 4.97 mmol) and tert-butyl 4-[3-chloro-4-(4,4,5,5-tetramethyl-1,3,2-dioxaborolan-2-yl)pyrazol-1-yl]piperidine-1-carboxylate 6 (7.68 g, 7.46 mmol) in a sealed tube intoluene (20 mL) was added Tripotassium phosphate (3.69 g, 17.41 mmol). It was degassed with argon for 10 minutes. Tetrakis(triphenylphosphine)palladium(0) (862.05 mg, 746.01 umol) was then added to the reaction mixture, and degassed for another 5 min. It was then heated Step-1: Synthesis of tert-butyl 4-(3-amino-4-bromo-pyrazol-1-yl)piperidine-1-carboxylate 3: To a stirred solution of 4-bromo-1H-pyrazol-3-amine 1(10 g, 61.73 mmol) in DMF (150 mL) was added tert-butyl 4-methylsulfonyloxypiperiat 90° C. for 16 h. The reaction mixture was cooled to RT, diluted with ethyl acetate, filtered over celite, and concentrated under reduced pressure to get crude mass which was purified by Combi-flash Column Chromatography using 35% EtOAc-Hex as eluent to afford tert-butyl 4-[3-chloro-4-[[1-[(4-methoxyphenyl)methyl]-2-oxo-benzo[cd]indol-6-yl]methyl]pyrazol-1-yl]piperidine-1-carboxylate 8 (800 mg, 1.09 mmol, 21.92% yield, 80% purity) as yellow viscous liquid; LCMS (ES+)=587.1 [M+H]+.

Step-5: Synthesis of 6-[[3-chloro-1-(4-piperidyl)pyrazol-4-yl]methyl]-1H-benzo[cd]indol-2-one 9: To tert-butyl 4-[3-chloro-4-[[1-[(4-methoxyphenyl)methyl]-2-oxo-benzo[cd]indol-6-yl]methyl]pyrazol-1-yl]piperidine-1-carboxylate 8 (500 mg, 851.63 umol) in Trifluoroacetic acid (10 mL) was added Trifluoromethanesulfonic Acid (2.56 g, 17.03 mmol, 1.49 mL) at 0° C. The reaction mixture was allowed to come to RT and stirred for 16 hr at same temp. After complete consumption of SM, reaction mixture was evaporated to remove the excess reagents. It was dissolved in DCM, and washed with satd. NaHCO₃. Organic portion was separated, dried over sodium sulfate and concentrated under reduced pressure to furnish the desired product 6-[[3-chloro-1-(4-piperidyl)pyrazol-4-yl]methyl]-1H-benzo[cd]indol-2-one 9 (200 mg, 381.63 umol, 44.81% yield, 70% purity) as brown viscous liquid, which was used in the next step without further purification; LCMS (ES+)=367.1 [M+H]+.

Step-6: Synthesis of tert-butyl 4-[3-chloro-4-[(2-oxo-1H-benzo[cd]indol-6-yl)methyl]pyrazol-1-yl]piperidine-1-carboxylate 10: To a stirred solution of 6-[[3-chloro-1-(4-piperidyl)pyrazol-4-yl]methyl]-1H-benzo[cd]indol-2-one 9 (300 mg, 817.79 umol) in DCM (10 mL) was added Triethylamine (248.26 mg, 2.45 mmol, 341.95 uL) at 0° C. followed by Triethylamine (248.26 mg, 2.45 mmol, 341.95 uL) and the reaction was stirred at room temperature for 16 hours. TLC was checked which showed complete consumption of the starting material along with the formation of the desired spot. The reaction mixture was diluted with ethyl acetate, washed with water and the organic fraction was separated. It was dried over anhydrous sodium sulphate and evaporated under reduced pressure to obtain the crude compound which was purified by flash chromatography using 70-75% EA-Hex to afford tert-butyl 4-[3-chloro-4-[(2-oxo-1H-benzo[cd]indol-6-yl)methyl]pyrazol-1-yl]piperidine-1-carboxylate 10 (160 mg, 308.38 umol, 37.71% yield, 90% purity) as brown solid; LCMS (ES+)=467.1 [M+H]+.

Step-7: Synthesis of tert-butyl 4-[3-chloro-4-[[1-(2,6-dioxo-3-piperidyl)-2-oxo-benzo[cd]indol-6-yl]methyl]pyrazol-1-yl]piperidine-1-carboxylate 12: To a stirred solution of tert-butyl 4-[3-chloro-4-[(2-oxo-1H-benzo[cd]indol-6-yl)methyl]pyrazol-1-yl]piperidine-1-carboxylate 10 (220 mg, 471.13 umol) in THF (5 mL), was added Sodium hydride (376.87 mg, 9.42 mmol, 60% purity) at 0° C. portion wise and the reaction mixture was stirred at this temperature for 3-5 min. Ice-bath was then removed and the reaction mixture was stirred for another 3-5 min before 3-bromopiperidine-2,6-dione 11 (452.31 mg, 2.36 mmol) was added to it at 0° C. portion wise and the reaction mixture was stirred at this temperature for another 1-2 min. Subsequently, the reaction mixture was heated at 70° C. for 1 hr. After that reaction was quenched with ice and cold water and extracted with ethyl acetate, dried over sodium sulphate, and concentrated under reduced pressure to give the crude. This crude was purified by repetitive washing with Diethyl ether to eventually afford the title compound tert-butyl 4-[3-chloro-4-[[1-(2,6-dioxo-3-piperidyl)-2-oxo-benzo[cd]indol-6-yl]methyl]pyrazol-1-yl]piperidine-1-carboxylate 12 (180 mg, 280.25 umol, 59.48% yield, 90% purity) as yellow solid (obtained after lyophilization); LCMS (ES+)=578.3 [M+H]+.

Step-8: Synthesis of 3-[6-[[3-chloro-1-(4-piperidyl)pyrazol-4-yl]methyl]-2-oxo-benzo[cd]indol-1-yl]piperidine-2,6-dione; hydrochloride 13: To a stirred solution of tert-butyl 4-[3-chloro-4-[[1-(2,6-dioxo-3-piperidyl)-2-oxo-benzo[cd]indol-6-yl]methyl]pyrazol-1-yl]piperidine-1-carboxylate 12 (170.00 mg, 294.09 umol) in Dioxane (10 mL) was added Dioxane-HCl (4 M, 1.47 mL) drop wise at 0° C. It was then allowed to come to RT and stirred for 16 h. Crude LCMS showed complete consumption of starting material and formation of product. The reaction mass was evaporated to dryness eventually to afford 3-[6-[[3-chloro-1-(4-piperidyl)pyrazol-4-yl]methyl]-2-oxo-benzo[cd]indol-1-yl]piperidine-2,6-dione; hydrochloride 13 (100 mg, 184.68 umol, 62.80% yield, 95% purity) as yellowish solid; LCMS (ES+)=478.3 [M+H]+.

Step-9: Synthesis of 3-[6-[[3-chloro-1-[1-[(1-methylcyclobutyl)methyl]-4-piperidyl]pyrazol-4-yl]methyl]-2-oxo-benzo[cd]indol-1-yl]piperidine-2,6-dione: To a stirred solution of 3-[6-[[3-chloro-1-(4-piperidyl)pyrazol-4-yl]methyl]-2-oxo-benzo[cd]indol-1-yl]piperidine-2,6-dione 13 (as HCl salt; 150 mg, 313.85 umol) in THF (6 mL) in a sealed tube was added Triethylamine (79.40 mg, 784.61 umol, 109.36 uL) and stirred for 5 minutes. To it was subsequently added 1-methylcyclobutanecarbaldehyde 14 (36.96 mg, 376.61 umol, 36.24 uL) followed by Dibutyltindichloride (114.43 mg, 376.61 umol, 84.14 uL) and Phenylsilane (33.96 mg, 313.85 umol, 38.68 uL) and the reaction mixture was stirred at 90° C. for 14 h. The reaction was monitored via TLC and LC. TLC showed the appearance of new spot. The reaction mixture was then diluted with EtOAc, washed with satd. NaHCO3soln. and extracted with EtOAc. The organic layer was separated, dried over anhydrous sodium sulphate, and evaporated under reduced pressure to obtain a crude which was subjected to Combi-Flash column chromatography (eluted with 0-5% MeOH/DCM; 2% MeOH/DCM) to yield 3-[6-[[3-chloro-1-[1-[(1-methylcyclobutyl)methyl]-4-piperidyl]pyrazol-4-yl]methyl]-2-oxo-benzo[cd]indol-1-yl]piperidine-2,6-dione Compound 200 (65 mg, 109.50 umol, 34.89% yield, 94.35% purity as a light yellow solid; LCMS (ES+)=560.2 [M+H]⁺. 1H NMR (400 MHz, DMSO-d6): δ 11.12 (s, 1H, D20 Exchangeable), 8.38 (d, J=8.2 Hz, 1H), 8.10 (d, J=7 Hz, 1H), 7.85 (t, J=7.8 Hz, 1H), 7.69 (s, 1H), 7.30 (d, J=7.4 Hz, 1H), 7.07 (d, J=7.4 Hz, 1H), 5.43 (dd, J=5.1, 12.8 Hz, 1H), 4.13 (s, 2H), 3.99 (m, 1H), 2.95 (m, 1H), 2.75-2.50 (m, 4H), 2.22 (m, 2H), 2.09-1.99 (m, 3H), 1.93-1.89 (m, 1H), 1.82-1.74 (m, 5H), 1.72-1.69 (m, 1H), 1.61-1.56 (m, 3H), 1.13 (s, 3H).

Example 107. Synthesis of tert-butyl 4-[(4-ethoxycarbonylphenyl)methylene]piperidine-1-carboxylate (Compound 201)

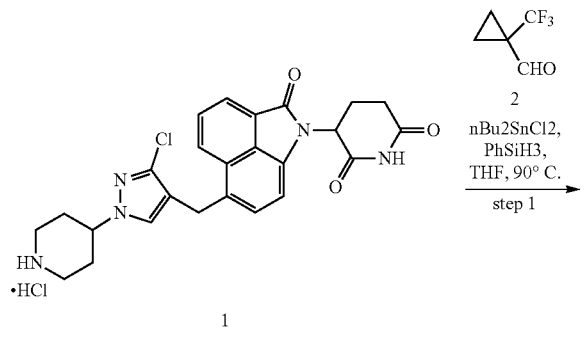

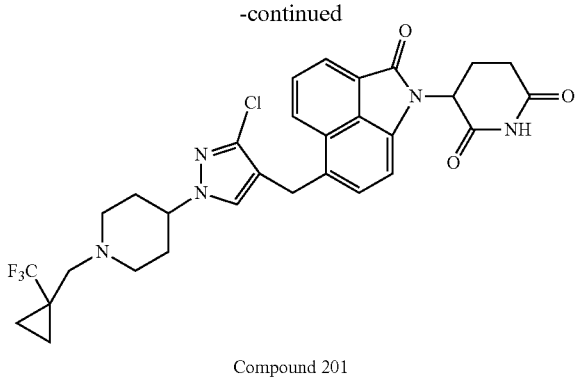

Compound 201

Step-1: Synthesis of tert-butyl 4-[(4-ethoxycarbonylphenyl)methylene]piperidine-1-carboxylate: To a stirred solution of 3-[6-[[3-chloro-1-(4-piperidyl)pyrazol-4-yl]methyl]-2-oxo-benzo[cd]indol-1-yl]piperidine-2,6-dione 1 (as HCl salt; 150 mg, 313.85 umol) in THF (5 mL) in a sealed tube was added Triethylamine (79.40 mg, 784.61 umol, 109.36 uL) and stirred for 5 minutes. To it was subsequently added 1-(trifluoromethyl)cyclopropanecarbaldehyde 2 (65.01 mg, 470.77 umol, 35.56 uL) followed by Dibutyltindichloride (114.43 mg, 376.61 umol, 84.14 uL) and Phenylsilane (40.75 mg, 376.61 umol, 46.42 uL) and the reaction mixture was stirred at 90° C. for 14 h. The reaction was monitored via TLC and LC. TLC showed the appearance of new spot. The reaction mixture was then diluted with EtOAc, washed with satd. NaHCO$_3$soln. and extracted with EtOAc. The organic layer was separated, dried over anhydrous sodium sulphate, and evaporated under reduced pressure to obtain a crude which was subjected to Combi-Flash column chromatography (eluted with 0-5% MeOH/DCM; 0.5% MeOH/DCM) to yield 3-[6-[[3-chloro-1-[[1-(trifluoromethyl)cyclopropyl]methyl]-4-piperidyl]pyrazol-4-yl]methyl]-2-oxo-benzo[cd]indol-1-yl]piperidine-2,6-dione Compound 201 (57 mg, 90.69 umol, 28.90% yield, 95.47% purity as a light-yellow solid. LCMS (ES+)=600.5 [M+H]$^+$. 1H NMR (400 MHz, DMSO-d6): δ 11.12 (s, 1H, D20 Exchangeable), 8.37 (d, J=8.2 Hz, 1H), 8.10 (d, J=6.9 Hz, 1H), 7.85 (t, J=7.6 Hz, 1H), 7.69 (s, 1H), 7.30 (d, J=7.6 Hz, 1H), 7.08 (d, J=7.2 Hz, 1H), 5.45-5.43 (m, 1H), 4.13 (s, 2H), 4.04-4.02 (m, 1H), 2.95-2.92 (m, 3H), 2.67-2.72 (s, 1H), 2.67-2.62 (m, 1H), 2.49 (m, 2H), 2.09-2.08 (m, 1H), 2.04-1.98 (m, 2H), 1.85-1.81 (m, 4H), 0.94 (m, 2H), 0.71 (m, 2H).

Example 108. Synthesis of 3-[6-[[4-[[4-(4-fluorophenyl)sulfonylpiperazin-1-yl]methyl]phenyl]methyl]-2-oxo-benzo[cd]indol-1-yl]piperidine-2,6-dione (Compound 202)

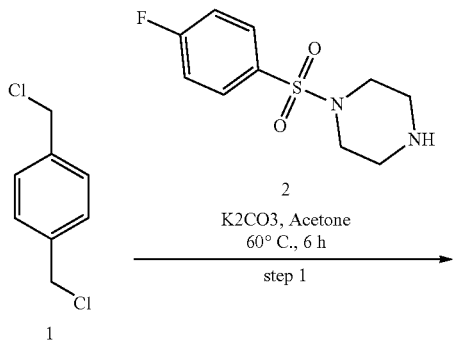

1

K2CO3, Acetone
60° C., 6 h
step 1

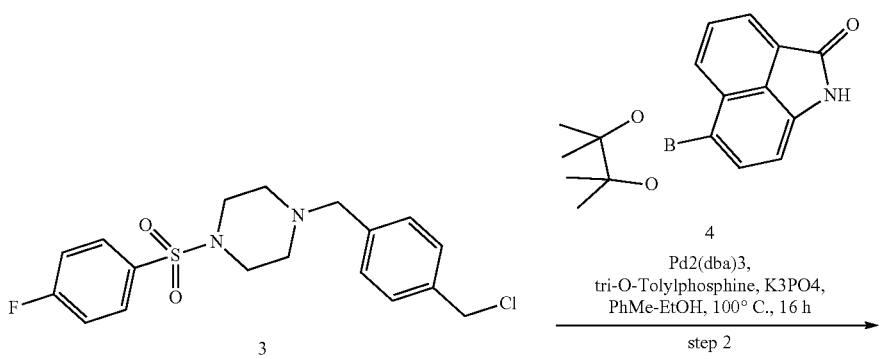

3

Pd2(dba)3,
tri-O-Tolylphosphine, K3PO4,
PhMe-EtOH, 100° C., 16 h step 2

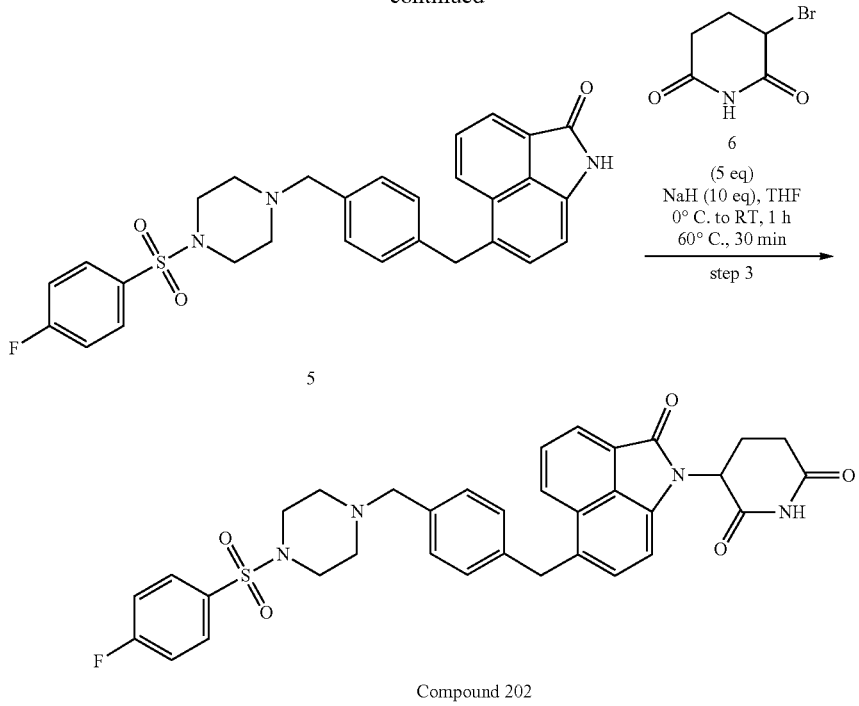

Compound 202

Step-1: Synthesis of 1-[[4-(chloromethyl)phenyl]methyl]-4-(4-fluorophenyl)sulfonyl-piperazine 3: To a stirred solution of 1-(4-fluorophenyl)sulfonylpiperazine 2 (1.00 g, 4.11 mmol, 1.00 mL) in Acetone (15 mL) was added Potassium carbonate, anhydrous, 99% (568.07 mg, 4.11 mmol, 248.07 uL) and stirred at 50° C. for 20 minutes. Subsequently to it was added 1,4-bis(chloromethyl)benzene 1 (719.51 mg, 4.11 mmol, 506.70 uL) and the reaction mixture was heated for another 6 h. The reaction mixture was cooled to RT, evaporated to remove the volatiles, water was added and extracted with ethyl acetate. The combined organic layers were washed with brine, dried over sodium sulphate, and concentrated under reduced pressure to give the crude. This crude was purified by Combi-Flash column chromatography to afford 1-[[4-(chloromethyl)phenyl]methyl]-4-(4-fluorophenyl)sulfonyl-piperazine 3 (700 mg, 1.74 mmol, 42.26% yield, 95% purity) as a viscous liquid.

Step-2: Synthesis of 6-[[4-[[4-(4-fluorophenyl)sulfonylpiperazin-1-yl]methyl]phenyl]methyl]-1H-benzo[cd]indol-2-one 5: To a stirred solution of 1-[[4-(chloromethyl)phenyl]methyl]-4-(4-fluorophenyl)sulfonyl-piperazine 3 (700 mg, 1.83 mmol) and 6-(4,4,5,5-tetramethyl-1,3,2-dioxaborolan-2-yl)-1H-benzo[cd]indol-2-one 4 (1.08 g, 3.66 mmol) in ethanol (5 mL) and Toluene (10 mL) was added Potassium phosphate tribasic anhydrous (1.16 g, 5.48 mmol) and the reaction mass was degassed under nitrogen atmosphere over 5 minutes. Then Tri-o-Tolyl phosphine (111.29 mg, 365.65 umol) and (1E,4E)-1,5-diphenylpenta-1,4-dien-3-one; palladium (167.42 mg, 182.83 umol) were added to this reaction mass, and degassed for another 5 min. It was then heated at 90° C. for 16 h. The reaction mixture was cooled to RT, diluted with ethyl acetate, filtered over celite, and concentrated under reduced pressure to get crude mass which was purified by Combi-flash Column Chromatography using 20% EtOAc-Hex as eluent to afford 6-[[4-[[4-(4-fluorophenyl)sulfonylpiperazin-1-yl]methyl]phenyl] methyl]-1H-benzo[cd]indol-2-one 5 (450 mg, 829.14 umol, 45.35% yield, 95% purity) as yellow solid; LCMS (ES+)=516.3 [M+H]+.

Step-3: Synthesis 3-[6-[[4-[[4-(4-fluorophenyl)sulfonylpiperazin-1-yl]methyl]phenyl]methyl]-2-oxo-benzo[cd]indol-1-yl]piperidine-2,6-dione: To a stirred solution of 6-[[4-[[4-(4-fluorophenyl)sulfonylpiperazin-1-yl]methyl]phenyl]methyl]-1H-benzo[cd]indol-2-one 5 (100 mg, 193.95 umol) in THF (10 mL), was added Sodium hydride (168.15 mg, 4.20 mmol, 60% purity) at 0° C. portion wise and the reaction mixture was stirred at this temperature for 3-5 min. Ice-bath was then removed and the reaction mixture was stirred for another 3-5 min before 3-bromopiperidine-2,6-dione (186.20 mg, 969.75 umol) was added to it at 0° C. portion wise and the reaction mixture was stirred at this temperature for another 1-2 min. Subsequently, the reaction mixture was heated at 70° C. for 1 hr. After that reaction was quenched with ice and cold water and extracted with ethyl acetate, dried over sodium sulphate, and concentrated under reduced pressure to give the crude. This crude was purified by Combi-flash Column Chromatography to afford the title compound 3-[6-[[4-[[4-(4-fluorophenyl)sulfonylpiperazin-1-yl]methyl]phenyl]methyl]-2-oxo-benzo[cd]indol-1-yl]piperidine-2,6-dione Compound 202 (65 mg, 94.11 umol, 48.53% yield, 90.74% purity as yellow solid (obtained after lyophilization); LCMS (ES+)=627.6 [M+H]+. 1H NMR (400 MHz, DMSO-d6): δ 11.09 (s, 1H, D2O Exchangeable), 8.28 (d, J=8.3 Hz, 1H), 8.04 (d, J=7.0 Hz, 1H), 7.79-7.73 (m, 3H), 7.45 (t, J=7.7 Hz, 2H), 7.36 (d, J=7.4 Hz, 1H), 7.19-7.17 (m, 2H), 7.10-7.06 (m, 3H), 5.44-5.39 (m, 1H), 4.33 (s, 2H), 3.36 (s, 2H), 2.95-2.89 (m, 1H), 2.83 (m, 4H), 2.75-2.71 (m, 1H), 2.67-2.60 (m, 1H), 2.34 (m, 4H), 2.08-2.05 (m, 1H).

Example 109. Synthesis of 3-[6-[[4-[[1-(4-fluorophenyl)-4-piperidyl]methyl]phenyl]methyl]-2-oxo-benzo[cd]indol-1-yl]piperidine-2,6-dione (Compound 203)
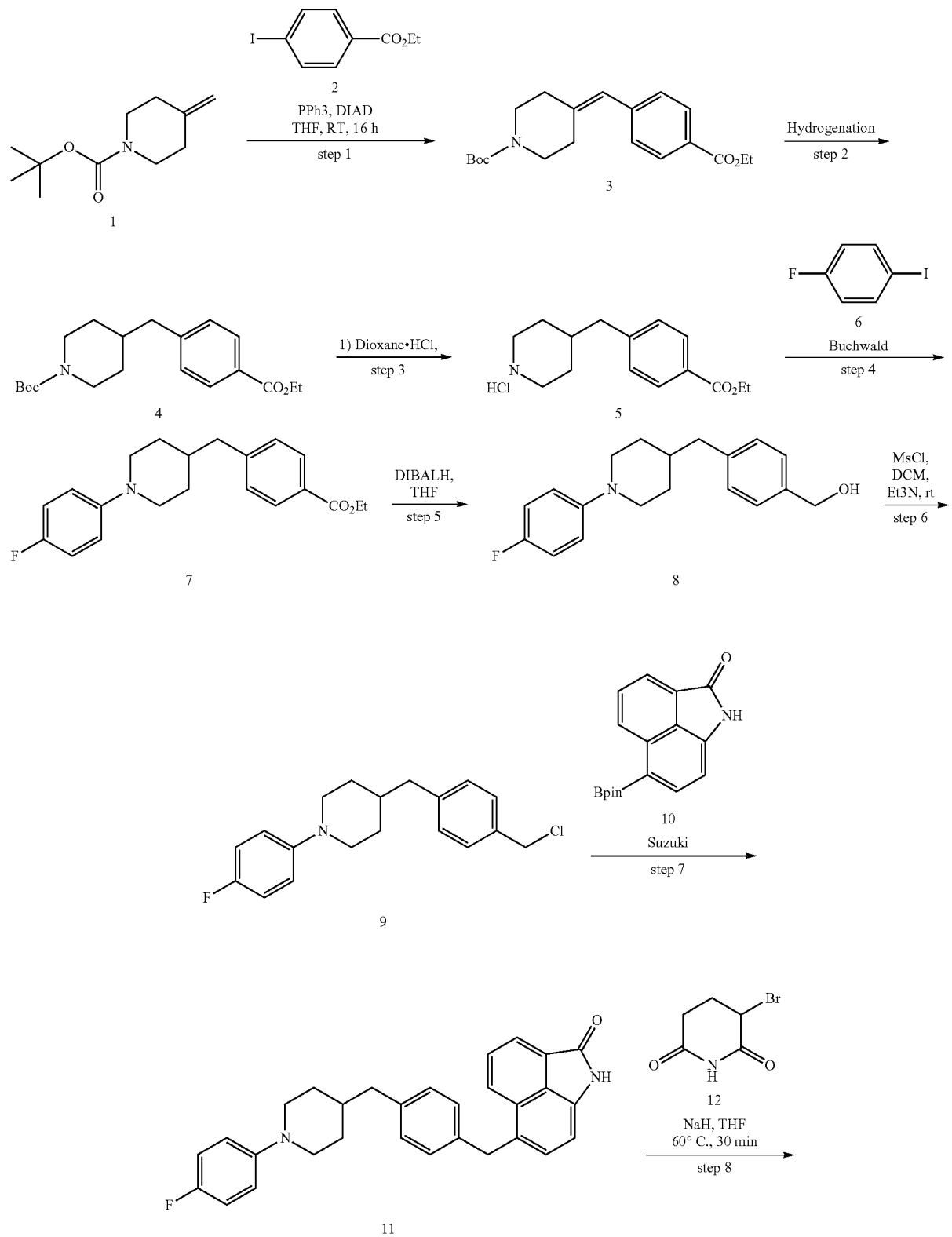

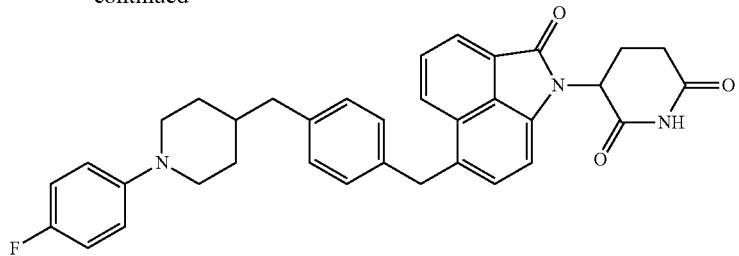

Compound 203

Step-1: Synthesis of tert-butyl 4-[(4-ethoxycarbonylphenyl)methylene]piperidine-1-carboxylate 3: To a stirred solution of ethyl 4-iodoethylbenzoate 1 (5 g, 21.39 mmol, 3.57 mL) in DMF (15 mL) in a sealed tube was added tert-butyl 4-methylenepiperidine-1-carboxylate 2 (12.66 g, 64.17 mmol) and resulting solution was degassed with argon for 5 minutes followed the addition of Triethyl amine (10.82 g, 106.95 mmol, 14.91 mL) and cyclopentyl(diphenyl)phosphane; dichloromethane; dichloropalladium; iron (1.75 g, 2.14 mmol). It was heated at 100° C. for 16 h. After complete consumption of SM as evidenced from TLC (20% ethyl acetate in hexane), RM was filtered through celite bed, washed with EtOAc and ice cooled water was added to the filtrate. Aqueous part was extracted with ethyl acetate. The organic layer was washed with water, brine and dried over NaSO4 and concentrated under reduced pressure to afford a crude which was purified by Combi-flash Column Chromatography (eluting at 5% ethyl acetate in hexane) to afford mixture of isomers of tert-butyl 4-[(4-ethoxycarbonylphenyl)methylene]piperidine-1-carboxylate 3 (4 g, 10.42 mmol, 48.72% yield, 90% purity) as colorless gum.

Step-2: Synthesis of tert-butyl 4-[(4-ethoxycarbonylphenyl)methyl]piperidine-1-carboxylate 4: To a stirred soln of tert-butyl 4-[(4-ethoxycarbonylphenyl)methylene]piperidine-1-carboxylate 3 (2 g, 5.79 mmol) in EtOAc (100 mL) was added Pd-Charcoal (2 g). A H2 balloon was attached to it, and hydrogenated applying vacuum. It was then stirred at RT. After the reaction was over, it was filtered over Celite, evaporated and the crude mass was subjected to Combiflash chromatography over silica to obtain the pure tert-butyl 4-[(4-ethoxycarbonylphenyl)methyl]piperidine-1-carboxylate 4 (1.5 g, 4.10 mmol, 70.84% yield, 95% purity) as colorless viscous liquid; LCMS (ES+)=348.4 [M+H]+.

Step-3: Synthesis ethyl 4-(4-piperidylmethyl)benzoate; hydrochloride 5: To a stirred solution of tert-butyl 4-[(4-ethoxycarbonylphenyl)methyl]piperidine-1-carboxylate 4 (4 g, 11.51 mmol) in Dioxane (20 mL) was added Dioxane-HCl (4 M, 57.56 mL) drop wise at 0° C. It was then allowed to come to RT and stirred for 16 h. Crude LCMS showed complete consumption of starting material and formation of product. The reaction mass was evaporated to dryness eventually to afford ethyl 4-(4-piperidylmethyl)benzoate; hydrochloride 5 (4 g, 9.09 mmol, 78.99% yield, 95% purity) as a colorless solid; LCMS (ES+)=248.2 [M+H]+.

Step-4: Synthesis of ethyl 4-[[1-(4-fluorophenyl)-4-piperidyl]methyl]benzoate 7: To a stirred solution of ethyl 4-(4-piperidylmethyl)benzoate; hydrochloride 5 (2 g, 7.05 mmol) in tert-Butanol (40 mL) was added Caesium carbonate (9.18 g, 28.19 mmol) under argon in a sealed tube and degassed for 10 minutes. It was stirred for another 20 min under this condition. 1-fluoro-4-iodo-benzene 6 (4.69 g, 21.14 mmol, 2.43 mL) was then added and was degassed with argon for 5 minutes. Subsequently RuPhos (328.85 mg, 704.74 umol) was added to the reaction mixture followed by Tris(dibenzylideneacetone)dipalladium(0) (214.50 mg, 704.74 umol), and degassed for another 5 min. It was then heated at 90° C. for 16 h. The reaction mixture was cooled to RT, diluted with ethyl acetate, washed with satd. NaHCO3soln, and extracted with Ethyl acetate. The organic layer was washed with water, brine and dried over NaSO4 and concentrated under reduced pressure to afford a crude which was purified by Combi-flash Column Chromatography using 3.5% EtOAc-Hex as eluent to obtain ethyl 4-[[1-(4-fluorophenyl)-4-piperidyl]methyl]benzoate 7 (550 mg, 1.53 mmol, 21.72% yield, 95% purity) as a brown sticky liquid; LCMS (ES+)=341.9 [M+H]+.

Step-5: Synthesis of [4-[[1-(4-fluorophenyl)-4-piperidyl]methyl]phenyl]methanol 8: To a stirred solution of ethyl 4-[[1-(4-fluorophenyl)-4-piperidyl]methyl]benzoate 7 (1.3 g, 3.81 mmol) in THF (5.0 mL) was added DIBAL-H (1.6 M, 9.52 mL) at −78° C. and stirred within the temperature range of −78−−50° C. for 2h. The progress of the reaction was monitored via TLC. After completion of SM (4 h), the reaction mixture was then quenched with satd. Rochelle salt soln., slowly allowed to come to RT and stirred for some time. The solid residue settled down, the liquid portion was filtered via celite, and thoroughly washed with DCM. The organic layer was washed with water, brine and dried over anhyd. $Na_2SO_4$. and concentrated under reduced pressure to afford a crude which was purified by Combi-flash Column Chromatography using 20% EtOAc-Hex as eluent to obtain [4-[[1-(4-fluorophenyl)-4-piperidyl]methyl]phenyl]methanol 8 (700 mg, 2.22 mmol, 58.34% yield, 95% purity) as a white solid. LCMS (ES+)=300.3 [M+H]+.

Step-6: Synthesis of 4-[[4-(chloromethyl)phenyl]methyl]-1-(4-fluorophenyl)piperidine 9: To a stirred suspension of [4-[[1-(4-fluorophenyl)-4-piperidyl]methyl]phenyl]methanol 8 (450 mg, 1.50 mmol) in DCM (10 mL) was added Triethylamine (760.49 mg, 7.52 mmol, 1.05 mL) at 0° C. and stirred under cold condition for 30 minutes. Subsequently, Mesyl chloride (688.73 mg, 6.01 mmol, 465.36 uL) was added drop wise at 0° C. and the reaction mixture was allowed to come to RT and stirred at that temperature for 16 h. The volatiles were removed to obtain a crude mass which was dissolved in DCM, washed thoroughly with satd. NaHCO3soln. and finally dried over anhyd. $Na_2SO_4$. The solvent was evaporated to furnish the desired product 4-[[4-(chloromethyl)phenyl]methyl]-1-(4-fluorophenyl)piperidine 9 (250 mg, 471.95 umol, 31.40% yield, 60% purity) as a viscous liquid (crude). On scratching with diethyl ether and pentane, the product solidified; LCMS (ES+)=318.2 [M+H]+.

Step-7: Synthesis of 6-[[4-[[1-(4-fluorophenyl)-4-piperidyl]methyl]phenyl]methyl]-1H-benzo[cd]indol-2-one 11:

To a stirred solution of 4-[[4-(chloromethyl)phenyl]methyl]-1-(4-fluorophenyl)piperidine 9 (450 mg, 1.42 mmol) and 6-(4,4,5,5-tetramethyl-1,3,2-dioxaborolan-2-yl)-1H-benzo[cd]indol-2-one 10 (626.82 mg, 2.12 mmol) in Ethanol (5 mL) and Toluene (10 mL) was added Potassium phosphate tribasic anhydrous (901.64 mg, 4.25 mmol) and the reaction mass was degassed under nitrogen atmosphere over 5 minutes. Then Tri-o-Tolyl phosphine (86.19 mg, 283.17 umol) and (1E,4E)-1,5-diphenylpenta-1,4-dien-3-one; palladium (129.65 mg, 141.59 umol) were added to this reaction mass, and degassed for another 5 min. It was then heated at 90° C. for 16 h. The reaction mixture was cooled to RT, diluted with ethyl acetate, filtered over celite, and thoroughly with Ethyl acetate. The organic layer was washed with water, brine and dried over NaSO4 and concentrated under reduced pressure to afford a crude which was purified by Combi-flash Column Chromatography using 18-20% EtOAc-Hex as eluent to obtain 6-[[4-[[1-(4-fluorophenyl)-4-piperidyl]methyl]phenyl]methyl]-1H-benzo[cd]indol-2-one 11 (200 mg, 399.52 umol, 28.22% yield, 90% purity) as a yellow solid; LCMS (ES+)=451.1 [M+H]+.

Step-8: Synthesis of 3-[6-[[4-[[1-(4-fluorophenyl)-4-piperidyl]methyl]phenyl]methyl]-2-oxo-benzo[cd]indol-1-yl]piperidine-2,6-dione: To a stirred solution of 6-[[4-[[1-(4-fluorophenyl)-4-piperidyl]methyl]phenyl]methyl]-1H-benzo[cd]indol-2-one 11 (350 mg, 776.84 umol) in THF (10 mL), was added Sodium hydride (621.41 mg, 15.54 mmol, 60% purity) at 0° C. portion wise and the reaction mixture was stirred at this temperature for 3-5 min. Ice-bath was then removed and the reaction mixture was stirred for another 3-5 min before 3-bromopiperidine-2,6-dione 12 (745.80 mg, 3.88 mmol) was added to it at 0° C. portion wise and the reaction mixture was stirred at this temperature for another 1-2 min. Subsequently, the reaction mixture was heated at 70° C. for 1 hr. After that reaction was quenched with ice and cold water and extracted with ethyl acetate, dried over sodium sulphate, and concentrated under reduced pressure to give a crude which was purified by Combi-flash Column Chromatography using 40% EtOAc-Hex as eluent to obtain 3-[6-[[4-[[1-(4-fluorophenyl)-4-piperidyl]methyl]phenyl]methyl]-2-oxo-benzo[cd]indol-1-yl]piperidine-2,6-dione Compound 203 (90 mg, 104.69 umol, 13.48% yield, 98% purity as yellow solid (obtained after lyophilization); LCMS (ES+)=562.5 [M+H]+. 1H NMR (400 MHz, DMSO-d6): δ 11.12 (s, 1H, D20 Exchangeable), 8.33 (d, J=8.3 Hz, 1H), 8.07 (d, J=6.9 Hz, 1H), 7.82 (t, J=7.6 Hz, 1H), 7.39 (d, J=7.3 Hz, 1H), 7.20 (d, J=7.8 Hz, 2H), 7.11-7.07 (m, 3H), 6.98 (t, J=8.8 Hz, 2H), 6.89-6.87 (m, 2H), 5.46-5.42 (m, 1H), 4.36 (s, 2H), 3.52 (d, J=12.0 Hz, 2H), 2.95-2.91 (m, 1H), 2.78-2.73 (m, 1H), 2.67-2.63 (m, 1H), 2.49-2.46 (m, 3H), 2.10-2.07 (m, 1H), 1.61-1.58 (m, 3H), 1.28-1.23 (m, 3H).

Example 110. Synthesis of 3-[6-[[1-[1-[1-[(dimethylamino)methyl]cyclobutanecarbonyl]-4-piperidyl]pyrazol-4-yl]methyl]-2-oxo-benzo[cd]indol-1-yl]piperidine-2,6-dione (Compound 204) and 3-[6-[[1-[1-[1-(hydroxymethyl)cyclobutanecarbonyl]-4-piperidyl]pyrazol-4-yl]methyl]-2-oxo-benzo[cd]indol-1-yl]piperidine-2,6-dione (Compound 205)

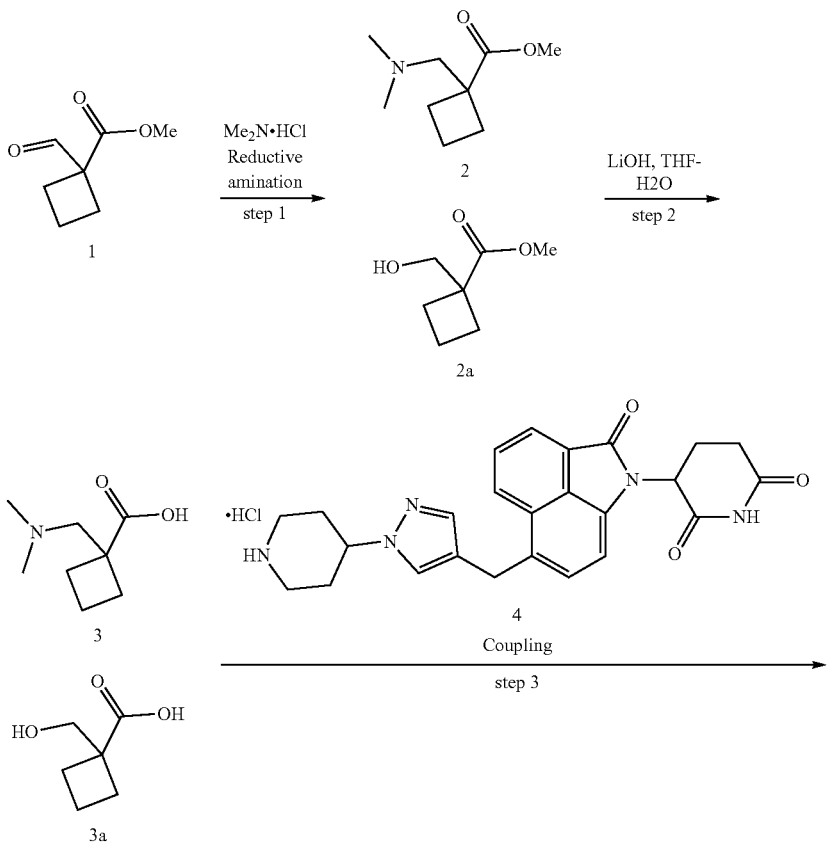

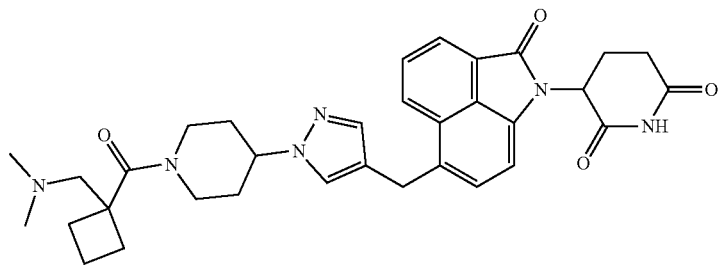

Compound 204

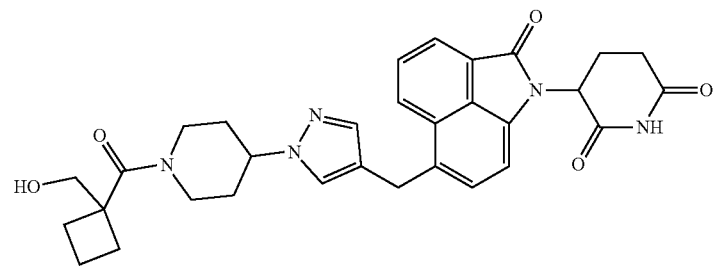

Compound 205

Step-1: Synthesis of methyl 1-[(dimethylamino)methyl] cyclobutanecarboxylate 2: To a stirred solution of methyl 1-formylcyclobutanecarboxylate 1 (100 mg, 703.47 umol) in THF (5 mL) in a sealed tube was added Triethylamine (177.96 mg, 1.76 mmol, 245.13 uL) and stirred for 5 minutes. To it was subsequently added N-methylmethanamine; hydrochloride (86.05 mg, 1.06 mmol) followed by Dibutyltindichloride (256.50 mg, 844.17 umol, 188.60 uL) and Phenylsilane (91.35 mg, 844.17 umol, 104.04 uL) and the reaction mixture was stirred at 90° C. for 14 h. The reaction mixture was then diluted with EtOAc, washed with satd. NaHCO$_3$ soln. and extracted with EtOAc. The organic layer was separated, dried over anhydrous sodium sulphate, and evaporated under reduced pressure to obtain methyl 1-[(dimethylamino)methyl]cyclobutanecarboxylate 2 (40 mg, 116.80 umol, 16.60% yield, 50% purity) (crude). [NMR and GC-MS support the formation].

Step-2: Synthesis of 1-[(dimethylamino)methyl]cyclobutanecarboxylic acid 3: To a stirred solution of methyl 1-[(dimethylamino)methyl]cyclobutanecarboxylate 2 (100.00 mg, 116.80 umol) in THF (2.5 mL) was added LiOH.H2O (5.88 mg, 140.16 umol, 247.34 uL) at 0° C. and the reaction mixture was allowed to come to RT and continued stirring at RT for 16 h. The reaction mixture was evaporated to obtain a crude mass which was acidified with HCl in Dioxane (4 M stock solution) to pH~1. The combined reaction mass was then lyophilized (using CH3CN/Water mixture) to obtain 1-[(dimethylamino)methyl]cyclobutanecarboxylic acid 3 (60 mg, 76.33 umol, 65.35% yield, 20% purity) as colorless solid, used for the next step without further purification. N.B. Aqueous work-up could not be performed as the desired acid compound was found to have the tendency to mix up with the aqueous portion, hence the obtained mass consists of the desired 1-[(dimethylamino) methyl]cyclobutanecarboxylic acid 3 (60 mg, 76.33 umol, 65.35% yield, 20/a purity) along with NaCl. It was planned to be utilized in the next step without further purification.

Step-3: Synthesis 3-[6-[[1-[1-[1-[(dimethylamino) methyl]cyclobutanecarbonyl]-4-piperidyl]pyrazol-4-yl] methyl]-2-oxo-benzo[cd]indol-1-yl]piperidine-2,6-dione:
To a stirred solution of 3-[2-oxo-6-[[1-(4-piperidyl)pyrazol-4-yl]methyl]benzo[cd]indol-1-yl]piperidine-2,6-dione; hydrochloride 4 (30.53 mg, 63.61 umol) was added DIPEA (32.88 mg, 254.44 umol, 44.32 uL) followed by 1-[(dimethylamino)methyl]cyclobutanecarboxylic acid 3 (60 mg, 76.33 umol) and HATU (36.28 mg, 95.41 umol) and reaction mixture was stirred at 25° C. for 16 hr. The progress of the reaction was monitored via TLC and LC-MS. Water was then added to the reaction mixture, and the aqueous layer was extracted with EtOAc. The organic layers were combined, dried over anhyd. Na$_2$SO$_4$, and filtered, and the solvents were removed under reduced pressure to give a residue, which was purified by column chromatography (eluted with 3% MeOH/DCM) to yield a mixture of products. It was further repurified in PREP-HPLC eventually to obtain 3-[6-[[1-[1-[1-[(dimethylamino)methyl]cyclobutanecarbonyl]-4-piperidyl]pyrazol-4-yl]methyl]-2-oxo-benzo [cd]indol-1-yl]piperidine-2,6-dione Compound 204 (3 mg, 9.78 umol, 15.38% yield, 95% purity) as a yellow solid (after lyophilization). LCMS (ES+)=583.7 [M+H]+. Apart from this, one by-product 5a was also formed, probably, while attempting to prepare the actual starting material 3 (via 2), presumably it was not formed, or formed in traces, rather 3a (via 2a) was formed which eventually gave the undesired coupled product 3-[6-[[1-[1-[1-(hydroxymethyl) cyclobutanecarbonyl]-4-piperidyl]pyrazol-4-yl]methyl]-2-oxo-benzo[cd]indol-1-yl]piperidine-2,6-dione Compound 205 (12 mg, 20.81 umol, 19.63% yield, 96.35% purity) as a yellow solid. LCMS (ES+)=556.6 [M+H]+.

615

Example 111. Synthesis of 3-[6-[[5-chloro-2-[1-[(1-methylcyclobutyl)methyl]-4-piperidyl]pyrazol-3-yl]methyl]-2-oxo-benzo[cd]indol-1-yl]piperidine-2,6-dione (Compound 206)

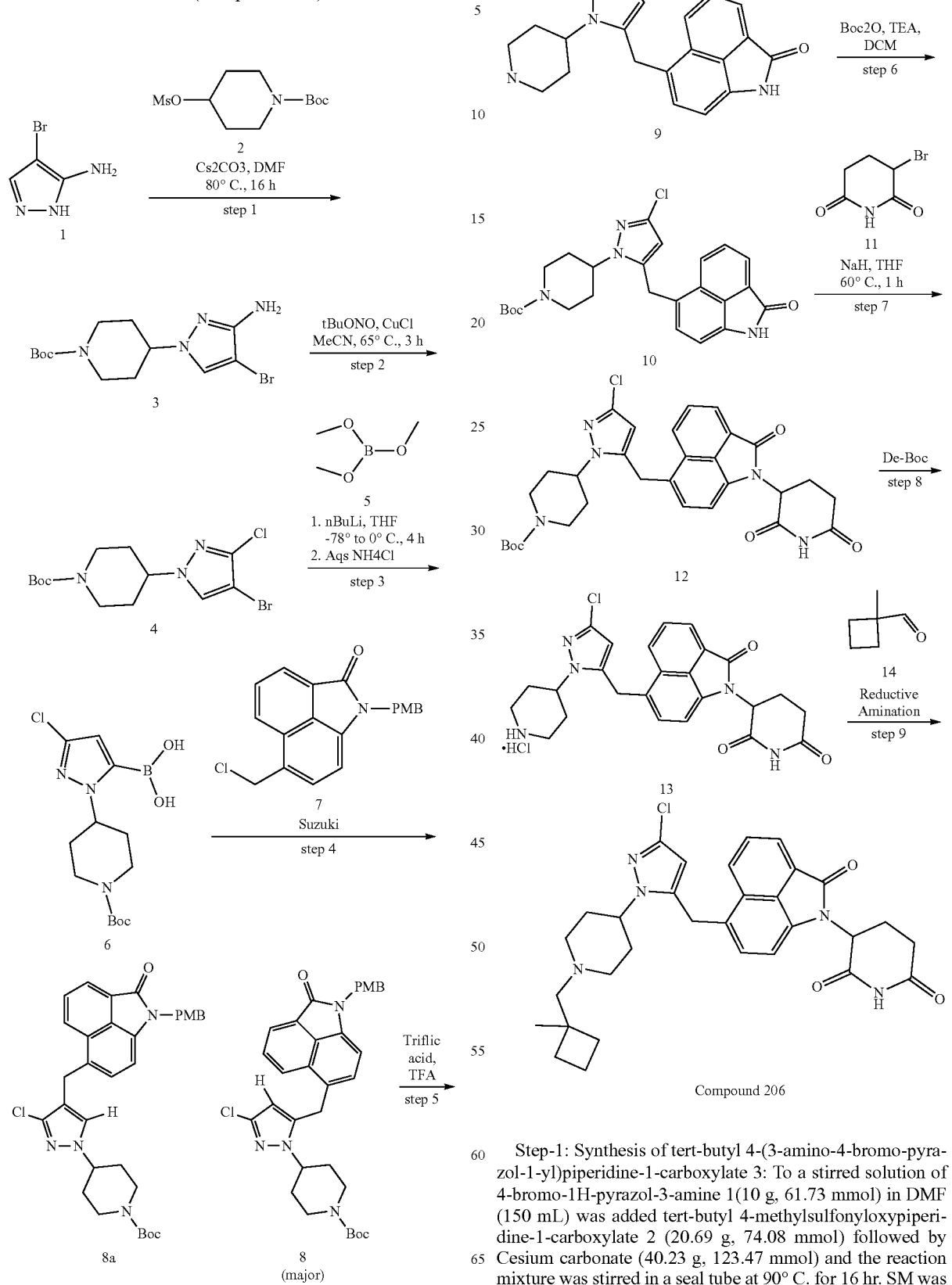

Step-1: Synthesis of tert-butyl 4-(3-amino-4-bromo-pyrazol-1-yl)piperidine-1-carboxylate 3: To a stirred solution of 4-bromo-1H-pyrazol-3-amine 1(10 g, 61.73 mmol) in DMF (150 mL) was added tert-butyl 4-methylsulfonyloxypiperidine-1-carboxylate 2 (20.69 g, 74.08 mmol) followed by Cesium carbonate (40.23 g, 123.47 mmol) and the reaction mixture was stirred in a seal tube at 90° C. for 16 hr. SM was consumed in TLC. The reaction mixture was then diluted with ethyl acetate and washed with chilled water followed by brine. The combined organic layer was dried over anhydrous sodium sulfate and concentrated under reduced pressure to get the crude which was purified by column chromatography on silica gel (eluting with 45% ethyl acetate in Hexane to get the desired product tert-butyl 4-(3-amino-4-bromo-pyrazol-1-yl)piperidine-1-carboxylate 3 (6 g, 13.90 mmol, 22.52% yield, 80% purity) as dark green color semi liquid. LC-MS (ES+)=347.3 [M+H]+.

Step-2: Synthesis of tert-butyl 4-(4-bromo-3-chloro-pyrazol-1-yl)piperidine-1-carboxylate 4: To a acetonitrile (20 mL) was added tert-Butyl nitrite, tech. 90% (1.49 g, 13.03 mmol, 1.72 mL, 90% purity) followed by CuCl (1.29 g, 13.03 mmol) and the reaction mixture was then slowly heated up to 65° C. At this point, tert-butyl 4-(3-amino-4-bromo-pyrazol-1-yl)piperidine-1-carboxylate 3 (3 g, 8.69 mmol) dissolved in Acetonitrile (10 mL) was slowly added to the reaction mixture. The reaction mixture was stirred at this temperature for 0.5 h. TLC shows a new non polar spot and starting was consumed. Water was then added. The reaction mixture was then cooled to room temperature; water was added and extracted with EtOAc. The organic part was then washed with saturated sodium bicarbonate solution and brine solution and then it was dried over sodium sulfate and the organic part was concentrated under reduced pressure to afford the crude product. The crude was then purified by column chromatography eluting 10% of ethyl acetate in Hexane to afford tert-butyl 4-(4-bromo-3-chloro-pyrazol-1-yl)piperidine-1-carboxylate 4 (1 g, 2.47 mmol, 28.40% yield, 90% purity) as a white solid.

Step-3: Synthesis of [2-(1-tert-butoxycarbonyl-4-piperidyl)-5-chloro-pyrazol-3-yl]boronic acid 6: To a stirred solution in tert-butyl 4-(4-bromo-3-chloro-pyrazol-1-yl)piperidine-1-carboxylate 4 (2 g, 5.48 mmol) in dry THF (7 mL) under inert atmosphere at −78° C. was added n-Butyl-lithium (1.6 M, 3.43 mL) in a drop-wise fashion. After completion of addition the reaction mixture was stirred for 1 h at same temperature, and checked TLC. As some SM seemed to be present along with desired corresponding des-Bromo variant, additional 0.5 mL of Butyllithium was added. After 30 min, trimethyl borate 5 (854.86 mg, 8.23 mmol, 934.27 uL) was added drop wise to the reaction mixture, and stirred for 2 hr without adding further dry ice (thereby allowing the reaction temperature to gradually increase). After another 1 h, TLC was checked and LC-MS was analyzed which showed the desired mass of the Boronic acid derivative. The reaction mixture was quenched with sat. solution of NH4Cl and diluted with EtOAc, layers were separated. The organic layer was washed with water, brine dried over NaSO4 and concentrated under reduced pressure to afford [2-(1-tert-butoxycarbonyl-4-piperidyl)-5-chloro-pyrazol-3-yl]boronic acid 6 (1.4 g, 3.40 mmol, 61.96% yield, 80/a purity) as brown sticky solid which was used in next step without further purification; LCMS (ES+)=330.3 [M+H]+.

Step-4: Synthesis of tert-butyl 4-[3-chloro-5-[[1-[(4-methoxyphenyl)methyl]-2-oxo-benzo[cd]indol-6-yl]methyl]pyrazol-1-yl]piperidine-1-carboxylate 8: To a stirred solution of 6-(chloromethyl)-1-[(4-methoxyphenyl)methyl]benzo[cd]indol-2-one 7 (1.23 g, 3.64 mmol) and [2-(1-tert-butoxycarbonyl-4-piperidyl)-5-chloro-pyrazol-3-yl]boronic acid 6 (1.80 g, 4.37 mmol) in a sealed tube intoluene (6 mL) and Ethanol (3 mL) and 5 drops of water were added tripotassium phosphate (1.93 g, 9.10 mmol). It was degassed with argon for 10 minutes. tris-o-tolylphosphane (221.64 mg, 728.18 umol) and Pd2dba3 (333.41 mg, 364.09 umol) were then added to the reaction mixture, and degassed for another 5 min. It was then heated at 90° C. for 16 h. The reaction mixture was cooled to RT, diluted with ethyl acetate, filtered over celite, washed with EtOAc and concentrated under reduced pressure to get crude mass which was purified by Combi-flash Column Chromatography using 35% EtOAc-Hex as eluent to afford tert-butyl 4-[3-chloro-5-[[1-[(4-methoxyphenyl)methyl]-2-oxo-benzo[cd]indol-6-yl]methyl]pyrazol-1-yl]piperidine-1-carboxylate 8 (750 mg, 1.15 mmol, 31.58% yield, 90% purity) as yellow solid; LCMS (ES+)=587.2 [M+H]+.

Step-5: Synthesis of 6-[[5-chloro-2-(4-piperidyl)pyrazol-3-yl]methyl]-1H-benzo[cd]indol-2-one 9: To tert-butyl 4-[3-chloro-5-[[1-[(4-methoxyphenyl)methyl]-2-oxo-benzo[cd]indol-6-yl]methyl]pyrazol-1-yl]piperidine-1-carboxylate 8 (460.00 mg, 783.50 umol) in Trifluoroacetic acid (10 mL) was added Trifluoromethanesulfonic Acid (2.35 g, 15.67 mmol, 1.38 mL) at 0° C. The reaction mixture was allowed to come to RT and stirred for 16 hr at same temp. After complete consumption of SM, reaction mixture was evaporated to remove the excess reagents. It was dissolved in DCM, and washed with satd. NaHCO₃. Organic portion was separated, dried over sodium sulfate and concentrated under reduced pressure to furnish the desired product 6-[[5-chloro-2-(4-piperidyl)pyrazol-3-yl]methyl]-1H-benzo[cd]indol-2-one 9 (300 mg, 654.23 umol, 83.50% yield, 80% purity) as brown viscous liquid, which was used in the next step without further purification; LCMS (ES+)=367.1 [M+H]+.

Step-6: Synthesis of tert-butyl 4-[3-chloro-5-[(2-oxo-1H-benzo[cd]indol-6-yl)methyl]pyrazol-1-yl]piperidine-1-carboxylate 10: To a stirred solution of 6-[[5-chloro-2-(4-piperidyl)pyrazol-3-yl]methyl]-1H-benzo[cd]indol-2-one 9 (550 mg, 1.50 mmol) in DCM (10 mL) was added Triethylamine (455.14 mg, 4.50 mmol, 626.91 uL) at 0° C. followed by Di-tert-butyl dicarbonate (392.66 mg, 1.80 mmol, 412.89 uL) and the reaction was stirred at room temperature for 6 hours. TLC was checked which showed complete consumption of the starting material along with the formation of the desired spot. The reaction mixture was diluted with ethyl acetate, washed with water and the organic fraction was separated. It was dried over anhydrous sodium sulphate and evaporated under reduced pressure to obtain the crude compound which was purified by flash chromatography using 70-75% EA-Hex to afford tert-butyl 4-[3-chloro-5-[(2-oxo-1H-benzo[cd]indol-6-yl)methyl]pyrazol-1-yl]piperidine-1-carboxylate 10 (350 mg, 674.58 umol, 44.99% yield, 90% purity) as brown solid; LCMS (ES+)=467.2 [M+H]+.

Step-7: Synthesis of tert-butyl 4-[3-chloro-5-[[1-(2,6-dioxo-3-piperidyl)-2-oxo-benzo[cd]indol-6-yl]methyl]pyrazol-1-yl]piperidine-1-carboxylate 12: To a stirred solution of tert-butyl 4-[3-chloro-5-[(2-oxo-1H-benzo[cd]indol-6-yl)methyl]pyrazol-1-yl]piperidine-1-carboxylate 10 (320.00 mg, 685.29 umol) in THF (5 mL), was added Sodium hydride (548.18 mg, 13.71 mmol, 60% purity) at 0° C. portion wise and the reaction mixture was stirred at this temperature for 3-5 min. Ice-bath was then removed and the reaction mixture was stirred for another 3-5 min before 3-bromopiperidine-2,6-dione 11 (657.91 mg, 3.43 mmol) was added to it at 0° C. portion wise and the reaction mixture was stirred at this temperature for another 1-2 min. Subsequently, the reaction mixture was heated at 70° C. for 1 hr. After that reaction was quenched with ice and cold water and extracted with ethyl acetate, dried over sodium sulphate, and concentrated under reduced pressure to give the crude. This crude was purified by repetitive washing with Diethyl ether to eventually afford the title compound tert-butyl 4-[3-chloro-5-[[1-(2,6-dioxo-3-piperidyl)-2-oxo-benzo[cd]indol- 6-yl]methyl]pyrazol-1-yl]piperidine-1-carboxylate 12 (350 mg, 544.93 umol, 79.52% yield, 90% purity) as yellow solid (obtained after lyophilization); LCMS (ES+)=578.2 [M+H]+.

Step-8: Synthesis of 3-[6-[[5-chloro-2-(1-chloro-4-piperidyl)pyrazol-3-yl]methyl]-2-oxo-benzo[cd]indol-1-yl]piperidine-2,6-dione; hydrochloride 13: To a stirred solution of tert-butyl 4-[3-chloro-5-[[1-(2,6-dioxo-3-piperidyl)-2-oxo-benzo[cd]indol-6-yl]methyl]pyrazol-1-yl]piperidine-1-carboxylate 12 (350.00 mg, 605.48 umol) in Dioxane (10 mL) was added Dioxane-HCl (4 M, 3.03 mL) drop wise at 0° C. It was then allowed to come to RT and stirred for 16 h. Crude LCMS showed complete consumption of starting material and formation of product. The reaction mass was evaporated to dryness eventually to afford 3-[6-[[5-chloro-2-(1-chloro-4-piperidyl)pyrazol-3-yl]methyl]-2-oxo-benzo[cd]indol-1-yl]piperidine-2,6-dione; hydrochloride 13 (200 mg, 349.92 umol, 57.79% yield, 90% purity) as yellowish solid; LCMS (ES+)=478.2 [M+H]+.

Step-9: Synthesis of 3-[6-[[5-chloro-2-[1-[(1-methylcyclobutyl)methyl]-4-piperidyl]pyrazol-3-yl]methyl]-2-oxo-benzo[cd]indol-1-yl]piperidine-2,6-dione: To a stirred solution of 3-[6-[[5-chloro-2-(4-piperidyl)pyrazol-3-yl]methyl]-2-oxo-benzo[cd]indol-1-yl]piperidine-2,6-dione 13 (as HCl salt; 250 mg, 523.08 umol) in THF (8 mL) in a sealed tube was added Triethylamine (105.86 mg, 1.05 mmol, 145.81 uL) and stirred for 5 minutes. To it was subsequently added 1-methylcyclobutanecarbaldehyde 14 (61.60 mg, 627.69 umol) followed by Dibutyltindichloride (190.72 mg, 627.69 umol, 140.24 uL) and Phenylsilane (56.60 mg, 523.08 umol, 64.47 uL) and the reaction mixture was stirred at 90° C. for 14 h. The reaction was monitored via TLC and LC. TLC showed the appearance of new spot. The reaction mixture was then diluted with EtOAc, washed with satd. NaHCO3soln. and extracted with EtOAc. The organic layer was separated, dried over anhydrous sodium sulphate, and evaporated under reduced pressure to obtain a crude which was subjected to Combi-Flash column chromatography (eluted with 0-5% DCM/MeOH) to yield 3-[6-[[5-chloro-2-[1-[(1-methylcyclobutyl)methyl]-4-piperidyl]pyrazol-3-yl]methyl]-2-oxo-benzo[cd]indol-1-yl]piperidine-2,6-dione Compound 206 (70 mg, 118.98 umol, 22.75% yield, 95.2% purity as a light yellow solid; LCMS (ES+)=560.2 [M+H]+. 1H NMR (400 MHz, DMSO-d6): δ 11.13 (s, 1H, D20 Exchangeable), 8.36 (d, J=8.3 Hz, 1H), 8.12 (d, J=7 Hz, 1H), 7.87 (t, J=7.6 Hz, 1H), 7.31 (d, J=7.4 Hz, 1H), 7.11 (d, J=7.3 Hz, 1H), 5.86 (s, 1H), 5.45 (dd, J=5.1, 12.8 Hz, 1H), 4.51 (s, 2H), 4.22 (m, 1H), 2.95 (m, 1H), 2.72-2.63 (m, 4H), 2.22 (s, 2H), 2.11-2.02 (m, 1H), 1.99-1.84 (m, 5H), 1.89-1.82 (m, 2H), 1.79-1.78 (m, 1H), 1.75-1.70 (m, 4H), 1.14 (s, 3H).

Example 112. Synthesis of 3-(6-((1-(1-(1-methylcyclobutane-1-carbonyl)piperidin-4-yl)-1H-pyrazol-4-yl)oxy)-2-oxobenzo[cd]indol-1(2H)-yl)piperidine-2,6-dione (Compound 207)

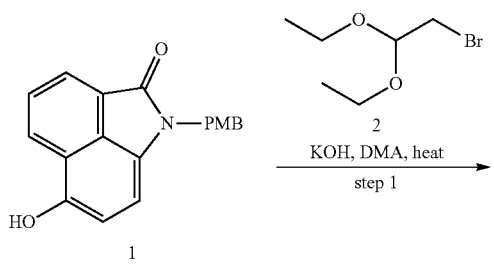

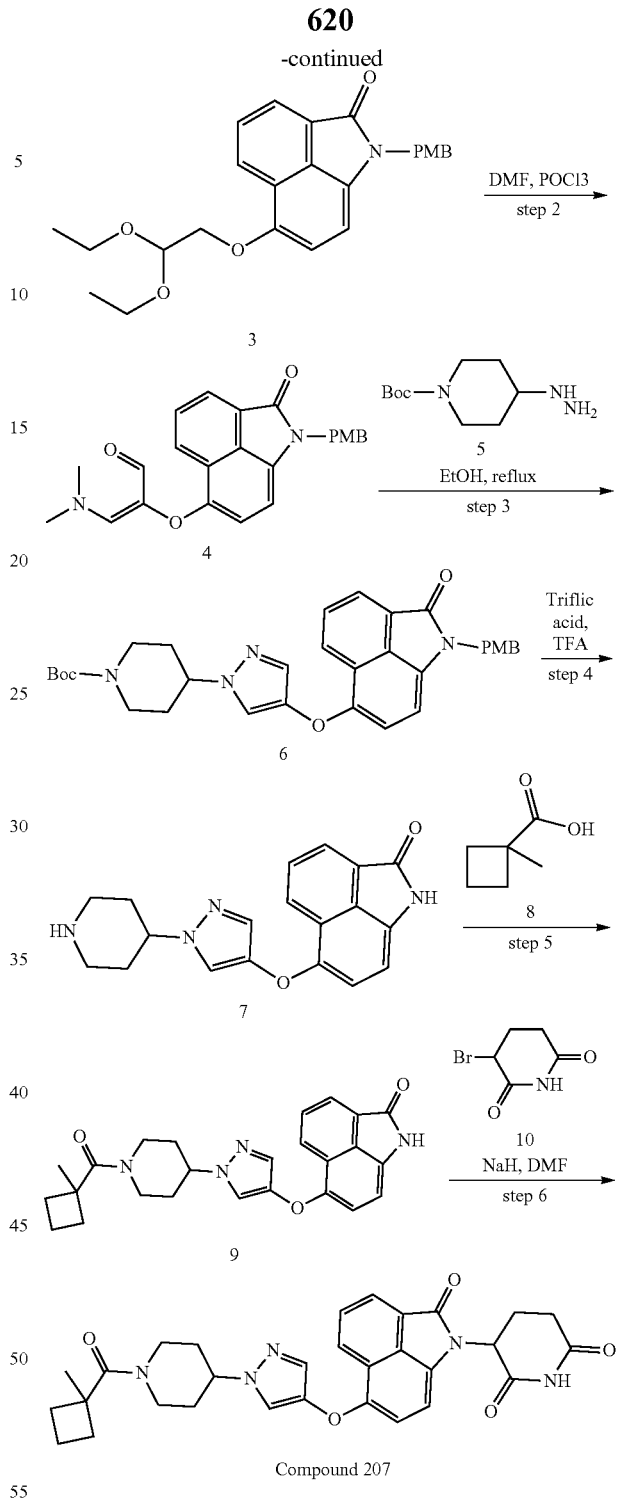

Step-1: Synthesis of 4-(4-Formyl-pyrazol-1-yl)-piperidine-1-carboxylic acid tert-butyl ester: To a solution of 1H-pyrazole-4-carbaldehyde (4.7 g, 48.91 mmol) and tert-butyl 4-methoxysulfonyloxy-piperidine-1-carboxylate (17.34 g, 58.70 mmol) in DMF (50 mL) was added cesium carbonate (39.84 g, 122.28 mmol) and heated to 90° C. in a sealed tube for 16 h. Crude LCMS showed formation of product. The reaction mass was cooled and added to water. The organics was extracted with EtOAc. Combined organics was washed with water, brine and dried over $Na_2SO_4$. Combined solvents was evaporated to dryness and purified by combiflash with eluting solvent 20-80% EtOAc in hexane to afford tert-butyl 4-(4-formylpyrazol-1-yl)piperidine-1-carboxylate (4 g, 11.46 mmol, 23.42% yield, 80% purity) as brown solid; LCMS (ES+)=280.4 [M+H]+.

Step-2: Synthesis of (E)-3-(dimethylamino)-2-((1-(4-methoxybenzyl)-2-oxo-1,2-dihydrobenzo[cd]indol-6-yl)oxy)acrylaldehyde: Phosphorous oxychloride (3.64 g, 23.73 mmol, 2.22 mL) was added in dimethyl formamide (1.73 g, 23.73 mmol, 1.84 mL) at 0° C. and stirred for 15 mins. Compound 6-(2,2-diethoxyethoxy)-1-[(4-methoxyphenyl)methyl]benzo[cd]indol-2-one (1 g, 2.37 mmol) was added at RT. Then the reaction mixture was heated at 80° C. for 3 hr. TLC showed a new spot and starting was consumed. The reaction mixture was cooled to 0° C. and quenched with ice-water and extracted with EtOAc. The organic part was washed with water and brine solution and then it was dried over sodium sulfate and the organic part was concentrated under reduced pressure to afford (Z)-3-(dimethylamino)-2-[1-[(4-methoxyphenyl)methyl]-2-oxo-benzo[cd]indol-6-yl]oxy-prop-2-enal (800 mg, 1.69 mmol, 71.22% yield, 85% purity) as crude product; LCMS (ES+)=403.4 [M+H]+.

Step-3: Synthesis of tert-butyl 4-(4-((1-(4-methoxybenzyl)-2-oxo-1,2-dihydrobenzo[cd]indol-6-yl)oxy)-1H-pyrazol-1-yl)piperidine-1-carboxylate: The (Z)-3-(dimethylamino)-2-[1-[(4-methoxyphenyl)methyl]-2-oxo-benzo[cd]indol-6-yl]oxy-prop-2-enal (1.3 g, 3.23 mmol) was dissolved in a mixture of Methanol (20 mL) and Water (6 mL).Tert-butyl 4-(5,6-dioxo-1,4,2,3-dioxadiazinan-2-yl)piperidine-1-carboxylate (973.27 mg, 3.23 mmol) was then added, and the reaction mixture was stirred at 90° C. for 16 hr. It was then concentrated under reduced pressure, and the residue was purified by combiflash with eluting solvent EtOAc:hexane to provide the title compound tert-butyl 4-[4-[1-[(4-methoxyphenyl)methyl]-2-oxo-benzo[cd]indol-6-yl]oxypyrazol-1-yl]piperidi-ne-1-carboxyla-te (800 mg, 1.15 mmol, 35.72% yield, 80% purity) as a pale yellow solid; LCMS (ES+)=555.6 [M+H]+.

Step-4: Synthesis of 6-((1-(piperidin-4-yl)-1H-pyrazol-4-yl)oxy)benzo[cd]indol-2(1H)-one: To an ice cold solution of tert-butyl 4-[4-[1-[(4-methoxyphenyl)methyl]-2-oxo-benzo[cd]indol-6-yl]-oxy-py-razol-1-yl]piperidine-1-carboxylate (180 mg, 324.54 umol) in TFA (6 mL) was added trifluoromethane sulphonic acid (146.12 mg, 973.61 umol, 85.95 uL). The reaction was continued at 25° C. for 16 hr. The reaction mass was evaporated to dryness and added to saturated sodium bicarbonate solution and extracted with EtOAc. The organics was dried over sodium sulphate and evaporated to dryness to get 6-[1-(4-piperidyl)pyrazol-4-yl]oxy-1H-benzo[cd]indol-2-one (100 mg, 209.35 umol, 64.51% yield, 70% purity) as crude; LCMS (ES+)=335.3 [M+H]+.

Step-5: Synthesis of 6-((1-(1-(1-methylcyclobutane-1-carbonyl)piperidin-4-yl)-1H-pyrazol-4-yl)oxy)benzo-[cd]indol-2(1H)-one: To a solution of 6-[1-(4-piperidyl)pyrazol-4-yl]oxy-1H-benzo[cd]indol-2-one (200 mg, 598.14 umol) and 1-methylcyclobutanecarboxylic acid (68.27 mg, 598.14 umol) in DMF (5 mL) was added DIPEA (231.92 mg, 1.79 mmol, 312.55 uL) and followed by HATU (250.17 mg, 657.95 umol) and stirred at 25° C. for 16 hr. Crude LCMS showed formation of product. The reaction was diluted with water and extracted with EtOAc. The combined organics was washed with water and brine and dried over sodium sulphate. The crude was purified by combiflash with eluting solvent EtOAc: hexane to get 6-[1-[1-(1-methylcyclobutanecarbonyl)-4-piperidyl]pyrazol-4-yl]oxy-1H-benzo[cd]indol-2-one (70 mg, 157.72 umol, 26.37% yield, 97% purity) as dark brown solid; LCMS (ES+)=431.3 [M+H]+.

Step-6: Synthesis of 3-(6-((1-(1-(1-methylcyclobutane-1-carbonyl)piperidin-4-yl)-1H-pyrazol-4-yl)oxy)-2-oxobenzo[cd]indol-1(2H)-yl)piperidine-2,6-dione: To an ice cold solution of 6-[1-[1-(1-methylcyclobutanecarbonyl)-4-piperidyl]pyrazol-4-yl]oxy-1H-benzo-[cd]indol-2-one (70 mg, 162.60 umol) in THF (5 mL) was added Sodium hydride (in oil dispersion) 60% dispersion in mineral oil (65.03 mg, 1.63 mmol, 60% purity) stirred at 25° C. for 10 mins. Compound 3-bromopiperidine-2,6-dione (156.11 mg, 813.01 umol) was added at a time and again stirred for 10 mins at 25° C. The reaction was then heated to 70° C. for 0.5 hr. Crude LCMS showed formation of product. The reaction was cooled to RT and diluted with water and extracted with EtOAc. The combined organics was washed with water and brine and dried over sodium sulphate. Crude was evaporated to dryness and purified by Prep HPLC to get 3-[6-[1-[1-(1-methylcyclobutanecarbonyl)-4-piperidyl]pyrazol-4-yl]oxy-2-oxo-benzo[cd]indol-1-yl]piperidine-2,6-dione Compound 207 (45 mg, 80.03 umol, 49.22% yield, 96.32% purity) as yellow solid. 1H NMR (400 MHz, DMSO-d6): δ 11.10 (bs, 1H), 8.36 (d, J=8 Hz, 1H) 8.18 (d, J=8 Hz, 1H), 7.96 (s, 1H), 7.91 (t, J=8 Hz, 1H), 7.49 (s, 1H), 7.03 (d, J=8 Hz, 1H) 6.92 (d, J=8 Hz, 1H), 5.45-5.41 (m, 1H), 4.40-4.34 (m, 2H), 3.61 (m, 1H), 3.12 (m, 1H), 2.97-2.90 (m, 1H), 2.76-2.62 (m, 3H), 2.43-2.40 (m, 2H), 2.10-2.03 (m, 3H), 1.95-1.90 (m, 1H), 1.88-1.79 (m, 4H), 1.62 (m, 1H), 1.36 (s, 3H); LCMS (ES+)=542.2 [M+H]+.

Example 113. Synthesis of 4-(4-((1-((1-(2,6-dioxopiperidin-3-yl)-2-oxo-1,2-dihydrobenzo[cd]indol-6-yl)methyl)-1-H-pyrazol-3-yl)methyl)piperazin-1-yl)-3-fluorobenzonitrile (Compound 208) and 4-(4-((1-((1-(2,6-dioxopiperidin-3-yl)-2-oxo-1,2-dihydrobenzo[cd]indol-6-yl)methyl)-1-H-pyrazol-5-yl)methyl)piperazin-1-yl)-3-fluorobenzonitrile (Compound 209)

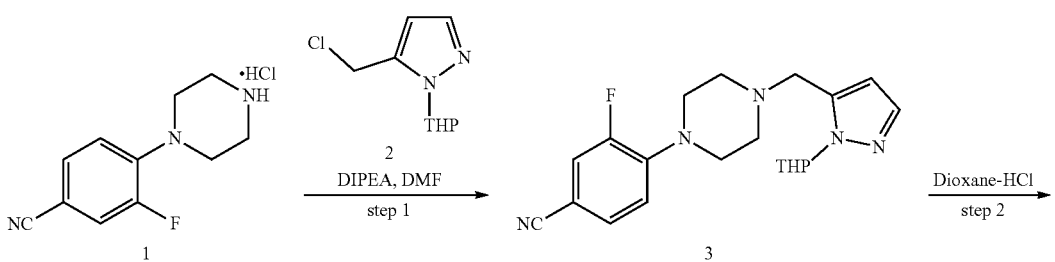

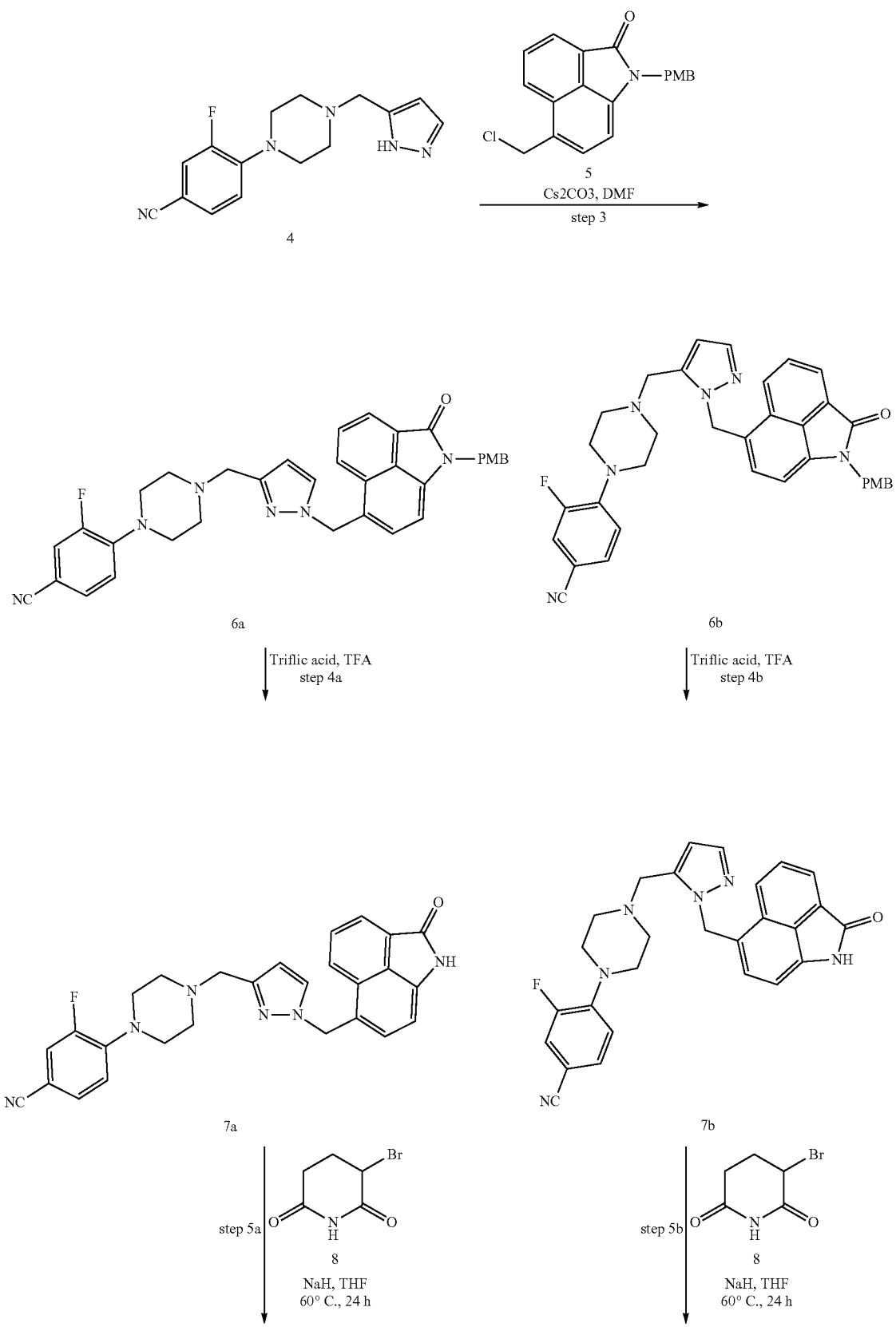

-continued

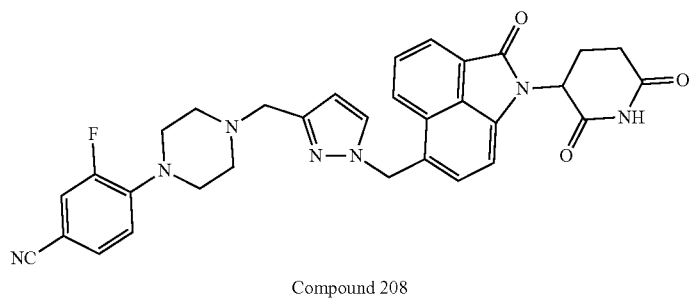

Compound 208

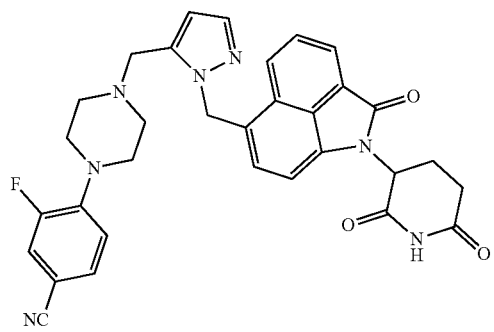

Compound 209

Step-1: Synthesis of 3-fluoro-4-(4-((1-(tetrahydro-2H-pyran-2-yl)-1H-pyrazol-5-yl)methyl)piperazin-1-yl)be-nzonitrile: To a solution of 3-fluoro-4-piperazin-1-yl-benzonitrile; hydrochloride (3.61 g, 14.95 mmol) in DMF (25 mL) was added DIPEA (5.80 g, 44.85 mmol, 7.81 mL) and stirred at RT for 10 mins. Compound 5-(chlo-romethyl)-1-tetrahydropyran-2-yl-pyrazole (5 g, 14.95 mmol) was added to the reaction and stirred at ambient tempr for 18 h. Crude LCMS showed formation of product. The reaction was cooled, added to water and extracted with EtOAc. The combined organics was washed with water, brine and dried over sodium sulphate. The crude was purified by combiflash with eluting solvent MeOH/DCM to get 3-fluoro-4-[4-[(2-tetrahydropyran-2-ylpyrazol-3-yl)methyl]piperazin-1-yl]benzonitrile (3.6 g, 9.26 mmol, 61.92% yield, 95% purity) as sticky gel; LCMS (ES+)=370.2 [M+H]+.

Step-2: Synthesis of 4-(4-((1H-pyrazol-5-yl)methyl)piperazin-1-yl)-3-fluorobenzonitrile: To a solution of 3-fluoro-4-[4-[(2-tetrahydropyran-2-ylpyrazol-3-yl)methyl]piperazin-1-yl]benzonitrile (4.2 g, 11.37 mmol) in Ethanol (30 mL) was added HCl (34.54 mg, 34.11 mmol, 43.18 uL, 36 purity) and stirred at 25° C. for 16 h. Completion of reaction was confirmed by TLC. The reaction mass was evaporated to dryness. The crude mass was dissolved in EtOAc and washed by bicarbonate solution and brine and dried over sodium sulphate and evaporated crude was purified by combiflash with MeOH in DCM to get 3-fluoro-4-[4-(1H-pyrazol-5-ylmethyl)piperazin-1-yl]benzonitrile (2.8 g, 8.54 mmol, 75.10% yield, 87% purity) as sticky solid; LCMS (ES+)=286.8 [M+H]+.

Step-3: Synthesis of 3-fluoro-4-(4-((1-((1-(4-methoxybenzyl)-2-oxo-1,2-dihydrobenzo[cd]indol-6-yl)methyl)-1H-pyrazol-3-yl)methyl)piperazin-1-yl)benzonitrile and 3-fluoro-4-(4-((1-((1-(4-methoxybenzyl)-2-oxo-1,2-dihydrobenzo[cd]indol-6-yl)methyl)-1H-pyrazol-5-yl)methyl)piperazin-1-yl)benzonitrile: To the stirred solution of 3-fluoro-4-[4-(1H-pyrazol-5-ylmethyl)piperazin-1-yl]benzonitrile (1.5 g, 5.26 mmol) and 6-(chloromethyl)-1-[(4-methoxyphenyl)methyl]benzo[cd]indol-2-one (1.78 g, 5.26 mmol) in DMF (25 mL) was added Cesium carbonate (5.14 g, 15.77 mmol). It was heated at 90° C. for 16 hr. It was cooled to RT, diluted with EtOAc, washed with water, brine, dried over sodium sulfate and concentrated under reduced pressure, Crude was purified by combiflash with eluting solvent EtOAc/hexane and 5% MeOH in DCM to afford 3-fluoro-4-[4-[[2-[[1-[(4-methoxyphenyl)methyl]-2-oxo-benzo[cd]indol-6-yl]methyl]-pyrazol-3-yl]methyl]piperazin-1-yl]benzonitrile (260 mg, 416.60 umol, 7.92% yield, 94% purity) as brown solid and polar spot was again purified by Prep HPLC to get 3-fluoro-4-[4-[[2-[[1-[(4-methoxyphenyl)methyl]-2-oxo-benzo[cd]indol-6-yl]methyl]pyrazol-3-yl]methyl]piperazin-1-yl]benzonitrile (260 mg, 416.60 umol, 7.92% yield, 94% purity) as yellow solid; LCMS (ES+)=587.2 [M+H]+.

Step-4a: Synthesis of 3-fluoro-4-(4-((1-((2-oxo-1,2-dihydrobenzo[cd]indol-6-yl)methyl)-1H-pyrazol-3-yl)me-thyl)piperazin-1-yl)benzonitrile: To an ice cold solution of 3-fluoro-4-[4-[[1-[[1-[(4-methoxyphenyl)methyl]-2-oxo-benzo[cd]indol-6-yl]meth-yl]pyrazol-3-yl]methyl]piperazin-1-yl]benzonitrile (350.00 mg, 596.60 umol) in TFA (15 mL) was added Trifluoromethanesulfonic acid, 98+% (268.61 mg, 1.79 mmol, 157.08 uL). The reaction was continued at 25° C. for 16 hr. The reaction mass was evaporated to dryness and added to saturated sodium bicarbonate solution and extracted with EtOAc. The organics was dried over sodium sulphate and evaporated to dryness to get 3-fluoro-4-[4-[[1-[(2-oxo-1H-benzo[cd]indol-6-yl)methyl]pyrazol-3-yl]methyl]-piperazin-1-yl]benzonitrile (270 mg, 463.01 umol, 77.61% yield, 80% purity) as crude; LCMS (ES+)=467.3 [M+H]+.

Step-4b: Synthesis of 3-fluoro-4-(4-((1-((2-oxo-1,2-dihydrobenzo[cd]indol-6-yl)methyl)-1H-pyrazol-5-yl)me-thyl)piperazin-1-yl)benzonitrile: To an ice cold solution of 3-fluoro-4-[4-[[2-[[1-[(4-methoxyphenyl)methyl]-2-oxo-benzo[cd]indol-6-yl]meth-yl]pyrazol-3-yl]methyl]piperazin-1-yl]benzonitrile (250 mg, 426.14 umol) in TFA (5 mL) was added Trifluoromethanesulfonic acid, 98+% (191.87 mg, 1.28 mmol, 112.20 uL). The reaction was continued at 25° C. for 16 hr. The reaction mass was evaporated to dryness and added to saturated sodium bi-carbonate solution and extracted with EtOAc. The organics was dried over sodium sulphate and evapo-rated to dryness to get 3-fluoro-4-[4-[[2-[(2-oxo-1H-benzo[cd]indol-6-yl)methyl]pyrazol-3-yl]methyl]pipera-zin-1-yl]benzonitrile (192 mg, 370.41 umol, 86.92% yield, 90% purity) as crude; LCMS (ES+)=467.3 [M+H]+.

Step-5a: Synthesis of 4-(4-((1-((1-(2,6-dioxopiperidin-3-yl)-2-oxo-1,2-dihydrobenzo[cd]indol-6-yl)methyl)-1-H-pyrazol-3-yl)methyl)piperazin-1-yl)-3-fluorobenzonitrile:
To an ice cold solution of 3-fluoro-4-[4-[[1-[(2-oxo-1H-benzo[cd]indol-6-yl)methyl]pyrazol-3-yl]methyl]-piperazin-1-yl]benzonitrile (100.00 mg, 214.36 umol) in THF (30 mL) was added Sodium hydride (in oil dispersion) 60% dispersion in mineral oil (82.13 mg, 2.14 mmol, 60% purity) stirred at 25° C. for 10 mins. Compound 3-bromopiperidine-2,6-dione (205.80 mg, 1.07 mmol) was added at a time and again stirred for 10 mins at 25° C. The reaction was then heated to 70° C. for 0.5 hr. Crude LCMS showed formation of product. The reaction was cooled to RT and diluted with water and extracted with EtOAc. The combined organics was washed with water and brine and dried over sodium sulphate. Crude was evaporated to dryness and purified by Prep HPLC to get 4-[4-[[1-[[1-(2,6-dioxo-3-piperidyl)-2-oxo-benzo[cd]indol-6-yl]methyl]pyrazol-3-yl]methyl]piperazin-1-yl]-3-fluoro-benzonitrile Compound 208 (16 mg, 27.51 umol, 12.83% yield, 99.3% purity) as yellow solid. 1H NMR (400 MHz, DMSO-d6): δ 11.12 (bs, 1H), 8.41 (d, J=8 Hz, 1H) 8.10 (d, J=8 Hz, 1H), 7.85 (t, J=8 Hz, 1H), 7.78 (s, 1H), 7.68 (d, J=12 Hz, 1H), 7.55 (d, J=8 Hz, 1H), 7.45 (d, J=8 Hz, 1H), 7.14-7.06 (m, 2H), 6.16 (s, 1H), 5.72 (s, 2H), 5.46-5.44 (m, 1H), 3.46 (s, 2H), 3.13 (bs, 4H), 2.94-2.92 (m, 1H), 2.79-2.73 (m, 1H), 2.67-2.63 (m, 1H), 2.43 (bs, 4H), 2.08-2.01 (m, 1H). LCMS (ES+)=578.2 [M+H]+.

Step-5b: Synthesis of 4-(4-((1-((1-(2,6-dioxopiperidin-3-yl)-2-oxo-1,2-dihydrobenzo[cd]indol-6-yl)methyl)-1-H-pyrazol-5-yl)methyl)piperazin-1-yl)-3-fluorobenzonitrile:

To an ice cold solution of 3-fluoro-4-[4-[[2-[(2-oxo-1H-benzo[cd]indol-6-yl)methyl]pyrazol-3-yl]methyl]piperazin-1-yl]benzonitrile (200 mg, 428.72 umol) in THF (10 mL) was added sodium hydride (185.85 mg, 4.29 mmol, 60% purity) stirred at 25° C. for 10 mins. Compound 3-bromopiperidine-2,6-dione (411.59 mg, 2.14 mmol) was added at a time and again stirred for 10 mins at 25° C. The reaction was then heated to 70° C. for 0.5 hr. Crude LCMS showed formation of product. The reaction was cooled to RT and diluted with water and extracted with EtOAc. The combined organics was washed with water and brine and dried over sodium sulphate.

Crude was evaporated to dryness and purified by Prep HPLC to get 4-[4-[[2-[[1-(2,6-dioxo-3-piperidyl)-2-oxo-benzo[cd]indol-6-yl]methyl]pyrazol-3-yl]methyl]piperazin-1-yl]-3-fluoro-benzonitrile Compound 209 (31 mg, 53.32 umol, 12.44% yield, 99.34% purity) as yellow solid. 1H NMR (400 MHz, DMSO-d6): δ 11.10 (bs, 1H), 8.47 (d, J=8 Hz, 1H) 8.09 (d, J=8 Hz, 1H), 7.86 (t, J=8 Hz, 1H), 7.67 (dd, J=12 Hz, J1=1.6 Hz, 1H),7.53 (dd, J=8 Hz, J1=1.6 Hz, 1H), 7.43 (s, 1H), 7.22 (d, J=4 Hz, 1H), 7.09 (d, J=8 Hz, 1H), 7.01 (t, J=8 Hz, 1H), 6.24 (s, 1H), 5.83 (s, 2H), 5.45-5.41 (m, 1H), 3.56 (s, 2H), 2.96-2.89 (m, 1H), 2.85 (bs, 4H), 2.76-2.61 (m, 2H), 2.42 (bs, 4H), 2.07-2.01 (m, 1H). LCMS (ES+)=578.2 [M+H]+.

Example 114. Synthesis of 3-(2-oxo-6-(4-((4-phenylpiperazin-1-yl)methyl)benzyl)benzo[cd]indol-1(2H)-yl)piperi-dine-2,6-dione (Compound 210)

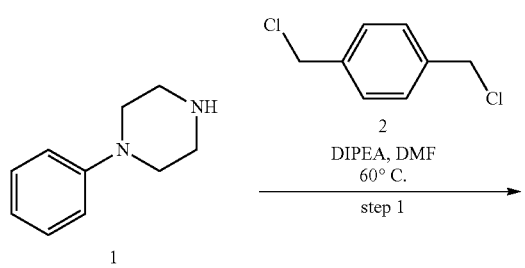

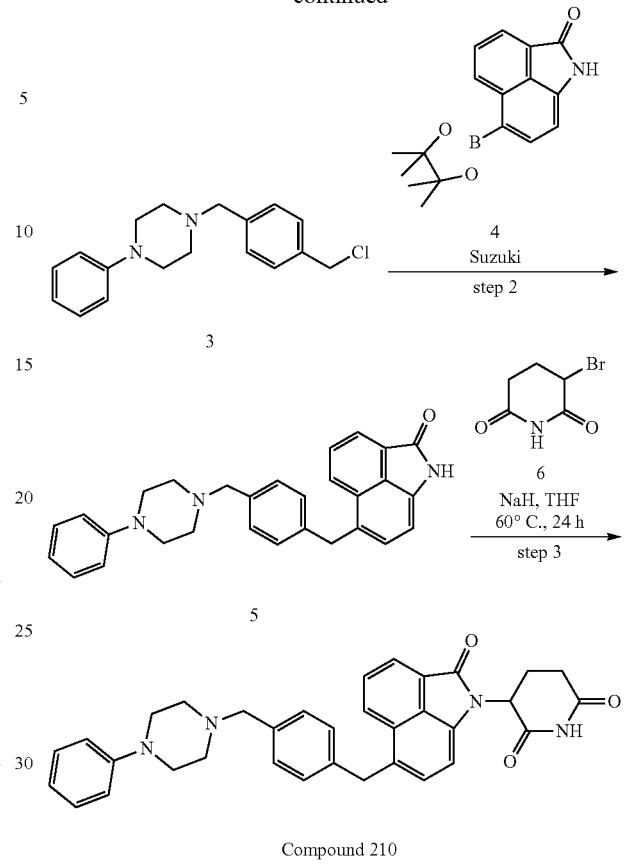

Compound 210

Step-1: Synthesis of 1-(4-(chloromethyl)benzyl)-4-phenylpiperazine: To the stirred solution of 1-phenylpiperazine (2 g, 12.33 mmol) in DMF (20 mL), DIPEA (4.78 g, 36.98 mmol, 6.44 mL) was added followed by 1,4-bis(chloromethyl)benzene (4.32 g, 24.66 mmol, 3.04 mL). The resulting reaction mixture was heated at 60° C. for 12 hr. After completion of reaction, ice cooled water was added to RM and extracted with EtOAc. Organic portion was separated, dried over sodium sulfate and concentrated. Crude LCMS showed formation of product. Crude mass was evaporated and purified by combiflash with eluting solvent 10-30% EtOAc in hexane to afford 1-[[4-(chloromethyl)phenyl]methyl]-4-phenyl-piperazine (1.6 g, 4.79 mmol, 38.83% yield, 90% purity) as off white solid; LCMS (ES+)=301.4 [M+H]+.

Step-2: Synthesis of 6-(4-((4-phenylpiperazin-1-yl)methyl)benzyl)benzo[cd]indol-2(1H)-one: To a stirred solution of 6-(4,4,5,5-tetramethyl-1,3,2-dioxaborolan-2-yl)-1H-benzo[cd]indol-2-one (735.83 mg, 2.49 mmol) and 1-[[4-(chloromethyl)phenyl]methyl]-4-phenyl-piperazine (500 mg, 1.66 mmol) in Ethanol (2 mL) and Toluene (7 mL) was added tri potassium; phosphate (882.02 mg, 4.16 mmol) and degassed under nitrogen atmosphere over 10 minutes. Then tris-o-tolylphosphane (101.18 mg, 332.42 umol) and (1E, 4E)-1,5-diphenylpenta-1,4-dien-3-one; palladium (152.20 mg, 166.21 umol) was added to the reaction mass and heated the resultant reaction mixture 90° C. for 16 hr. After completion of reaction, reaction mass was filtered through celite bed. Filtrate was collected and diluted with EtOAc and washed with water and brine. Combined organic solvent was separated, dried over sodium sulfate and concen-trated under vacuum. Crude was purified by combiflash with eluting solvent 10-50% EtOAc in hexane to afford 6-[[4-[(4-phenylpiperazin-1-yl)methyl]phenyl]methyl]-1H-benzo[cd]indol-2-one (370 mg, 768.09 umol, 46.21% yield, 90% purity) as brown gel.

Step-3: Synthesis of 3-(2-oxo-6-(4-((4-phenylpiperazin-1-yl)methyl)benzyl)benzo[cd]indol-1(2H)-yl)piperi-dine-2,6-dione: To an ice cold solution of 6-[[4-[(4-phenylpiperazin-1-yl)methyl]phenyl]methyl]-1H-benzo[cd]indol-2-one (100.00 mg, 230.66 umol) in THF (30 mL) was added Sodium hydride (in oil dispersion) 60% dispersion in mineral oil (8.84 mg, 220.97 umol, 60% purity) stirred at 25° C. for 10 mins. Compound 3-bromopiperidine-2,6-dione (221.44 mg, 1.15 mmol) was added at a time and again stirred for 10 mins at 25° C. The reaction was then heated to 70° C. for 0.5 hr. Crude LCMS showed formation of product. The reaction was cooled to RT and diluted with water and extracted with EtOAc. The combined organics was washed with water and brine and dried over sodium sulphate. Crude was evaporated to dryness and purified by Prep HPLC to get 3-[2-oxo-6-[[4-[(4-phenylpiperazin-1-yl)methyl]phenyl]methyl]benzo[cd]indol-1-yl]piperidine-2,6-dione Compound 210 (46 mg, 84.30 umol, 36.55% yield, 99.81% purity) as yellow solid. 1H NMR (400 MHz, DMSO-d6): δ 11.11 (bs, 1H), 8.34 (d, J=8 Hz, 1H), 8.08 (d, J=8 Hz, 1H), 7.83 (t, J=8 Hz, 1H), 7.42 (d, J=8 Hz, 1H), 7.26 (m, 6H), 7.11 (d, J=8 Hz, 1H), 6.89 (d, J=8 Hz, 2H), 6.76 (t, J=8 Hz, 1H), 5.45-5.43 (m, 1H), 4.38 (s, 2H), 3.44 (s, 2H), 3.08 (bs, 4H), 2.98-2.90 (m, 1H), 2.80-2.73 (m, 1H), 2.70-2.57 (m, 1H), 2.45 (bs, 4H), 2.10 (m, 1H); LCMS (ES+)=545.3 [M+H]+.

Example 115. Synthesis of 3-(6-((1-(4-methyl-1-(1-(trifluoromethyl)cyclopropane-1-carbonyl)piperidin-4-yl)-1H-1,2,3-triazol-4-yl)methyl)-2-oxobenzo[cd]indol-1(2H)-yl)piperidine-2,6-dione (Compound 211)

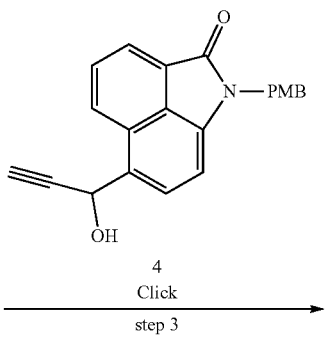

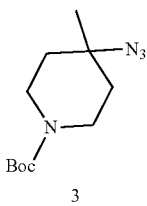

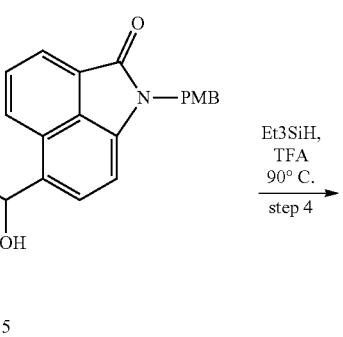

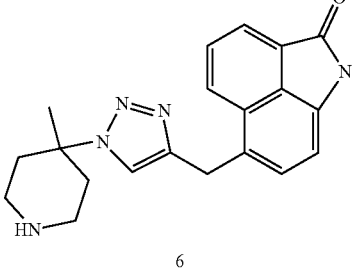

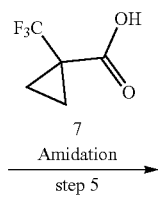

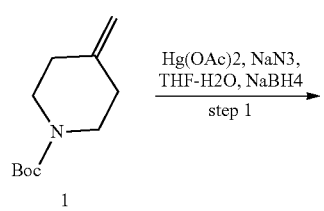

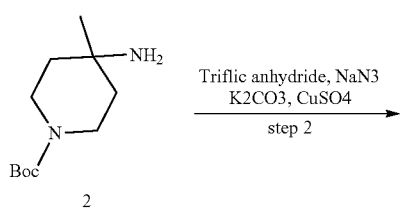

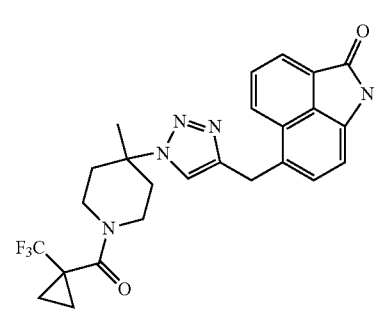

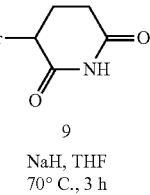

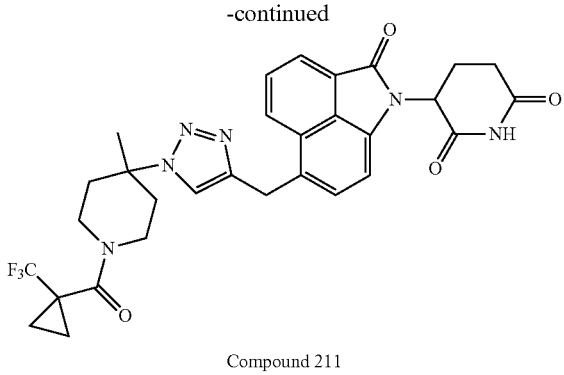

Compound 211

Step-1: Synthesis of tert-butyl 4-amino-4-methylpiperidine-1-carboxylate: To 50 ml of a 50% tetrahydrofuran aqueous solution of Mercury(II) acetate, 98+% (1.78 g, 5.58 mmol, 541.75 uL), Sodium azide (988.62 mg, 15.21 mmol, 534.39 uL) and tert-butyl 4-methylenepiperidine-1-carboxylate (1 g, 5.07 mmol) were added, followed by stirring for 17 hours under heating at 900 C. After cooling to room temperature, 0.71 ml of a 15% potassium hydroxide aqueous solution, and further a suspension of Sodium Borohydride (143.83 mg, 3.80 mmol, 134.42 uL) in 0.71 ml of a 15% potassium hydroxide aqueous solution, were added, followed by stirring for 30 minutes at room temperature. The reaction mixture was diluted with diethyl ether, washed with water and brine, and dried over anhydrous sodium sulfate, followed by distilling off the solvent under reduced pressure to give tert-butyl 4-amino-4-methylpiperidine-1-carboxylate (1.1 g, 2.75 mmol, 54.18% yield, 60% purity) as title compound.

Step-2: Synthesis of tert-butyl 4-azido-4-methylpiperidine-1-carboxylate: Trifluoromethanesulfonic anhydride (1.32 g, 4.67 mmol, 783.65 uL) was added to a mixture of sodium azide (758.38 mg, 11.67 mmol, 409.94 uL), H2O (14 mL), and DCM (25 mL) at 0 C. The mixture was stirred at 0° C. for 2h, then the layers are separated. The aqueous layer was extracted with CH2Cl2 (2×10 mL). The combined extracts were washed with saturated aqueous Na2CO3, then added to a stirring mixture of tert-butyl 4-amino-4-methylpiperidine-1-carboxylate (500 mg, 2.33 mmol), Potassium carbo-nate-granular (483.68 mg, 3.50 mmol, 211.21 uL), copper sulphate (37.24 mg, 233.31 umol, 10.34 uL), $H_2O$ (27 mL), and Methanol (45 mL). The resulting mixture was stirred for 16 h, then evaporated, and diluted with H2O (50 mL) and extracted with DCM. Combined organics was washed with water and dried over sodium sulphate. Organics was evaporated to dryness to get tert-butyl 4-azido-4-methylpiperidine-1-carboxylate as crude; LCMS (ES+)=241.4 [M+H]+.

Step-3: Synthesis of tert-butyl 4-(4-(hydroxy(1-(4-methoxybenzyl)-2-oxo-1,2-dihydrobenzo[cd]indol-6-yl) methyl)-1H-1,2,3-triazol-1-yl)-4-methylpiperidine-1-carboxylate: To the stirred solution of tert-butyl 4-azido-4-methyl-piperidine-1-carboxylate (200 mg, 832.29 umol) and 6-(1-hydroxyprop-2-ynyl)-1-[(4-methoxyphenyl)methyl] benzo[cd]indol-2-one (285.79 mg, 832.29 umol) in THF (5 mL), solution of copper sulphate.5H₂O (20.78 mg, 83.23 umol, 5.77 uL) in Water (1 mL) was added and stirred for 15 minutes followed by the addition of sodium; (2R)-2-[1,2-dihydroxyethyl]-4-hydroxy-5-oxo-2H-furan-3-olate (65.95 mg, 332.92 umol). The reaction mass was kept on stirring for further 24 h at 25° C. After complete consumption of SM, reaction mass was filtered through celite bed dried over sodium sulphate. Filtrate was evaporated and the crude residue was purified by combiflash with eluting solvent 30-100% EtOAc in hexane to afford tert-butyl 4-[4-[hydroxy-[1-[(4-methoxyphenyl) methyl]-2-oxo-benzo[cd]indol-6-yl]methyl]triazol-1-yl]-4-methyl-piperidine-1-carboxylate (97 mg, 113.01 umol, 13.58% yield, 68% purity) as sticky gel; LCMS (ES+)=584.4 [M+H]+.

Step-4: Synthesis of 6-((1-(4-methylpiperidin-4-yl)-1H-1,2,3-triazol-4-yl)methyl)benzo[cd]indol-2(1H)-one: To solution of tert-butyl 4-[4-[hydroxy-[1-[(4-methoxyphenyl) methyl]-2-oxo-benzo[cd]indol-6-yl]methyl]-triazol-1-yl]-4-methyl-piperidine-1-carboxylate (50 mg, 85.66 umol) in TFA (78.14 mg, 685.31 umol, 52.80 uL) was added triethyl silane (39.84 mg, 342.66 umol, 54.73 uL) in a sealed tube. The reaction was heated to 90° C. for 2 hr. Crude LCMS showed formation of product. The reaction was evaporated to dryness and neutralized by sodium bicarbonate solution and extracted by EtOAc. Combined organics was dried over sodium sulphate and evaporated to dryness and triturated with pentane to get 6-[[1-(4-methyl-4-piperidyl)triazol-4-yl] methyl]-1H-benzo[cd]indol-2-one (22 mg, 50.66 umol, 59.14% yield, 80% purity) as brown solid; LCMS (ES+)=348.4 [M+H]+.

Step-5: Synthesis of 6-((1-(4-methyl-1-(1-(trifluoromethyl)cyclopropane-1-carbonyl)piperidin-4-yl)-1H-1,2, 3-triazol-4-yl)methyl)benzo[cd]indol-2(1H)-one: To a solution of 6-[[1-(4-methyl-4-piperidyl)triazol-4-yl]methyl]-1H-benzo[cd]indol-2-one (300 mg, 863.53 umol) in DMF (10 mL) was added 1-(trifluoromethyl)cyclopropanecarboxylic acid (146.36 mg, 949.88 umol) and DIPEA (334.81 mg, 2.59 mmol, 451.23 uL) followed by HATU (492.51 mg, 1.30 mmol) and stirred at 25° C. for 16 h. Crude LCMS showed formation of product. The reaction mass was added to water and extracted with EtOAc. The combined organics was washed with water, brine and dried over sodium sulphate. Crude was evaporated to dryness and purified by combiflash with eluting solvent EtOAc in hexane to get 6-[[1-[4-methyl-1-[1-(trifluoromethyl)cyclopropanecarbonyl]-4-piperidyl]triazol-4-yl]methyl]-1H-benzo[cd]indol-2-one (130 mg, 241.99 umol, 28.02% yield, 90% purity) as dark brown gel; LCMS (ES+)=484.1 [M+H]+.

Step-6: Synthesis of 3-(6-((1-(4-methyl-1-(1-(trifluoromethyl)cyclopropane-1-carbonyl)piperidin-4-yl)-1H-1,2,3-triazol-4-yl)methyl)-2-oxobenzo[cd]indol-1(2H)-yl)piperidine-2,6-dione: To an ice cold solution of 6-[[1-[4-methyl-1-[1-(trifluoromethyl)cyclopropanecarbonyl]-4-piperidyl] triazol-4-yl]methyl]-1H-benzo[cd]indol-2-one (130 mg, 268.88 umol) in DMF (10 mL) was added Sodium hydride (in oil dispersion) 60% dispersion in mineral oil (103.03 mg, 2.69 mmol, 60% purity) stirred at 25° C. for 10 mins. Compound 3-bromopiperidine-2,6-dione (258.14 mg, 1.34 mmol) was added at a time and again stirred for 10 mins at 25° C. The reaction was then heated to 70° C. for 0.5 hr. Crude LCMS showed formation of product. The reaction was cooled to RT and diluted with water and extracted with EtOAc. The combined organics was washed with water and brine and dried over sodium sulphate. Crude was evaporated to dryness and purified by Prep HPLC to get 3-[6-[[1-[4-methyl-1-[1-(trifluoromethyl) cyclopro-panecarbonyl]-4-piperidyl]triazol-4-yl]methyl]-2-oxo-benzo[cd]indol-1-yl]piperidine-2,6-dione Compound 211 (20 mg, 33.55 umol, 12.48% yield, 99.74% purity) as yellow solid. 1H NMR (400 MHz, DMSO-d6): δ 11.12 (bs, 1H), 8.42 (d, J=12 Hz, 1H), 8.10-8.08 (d, J=8 Hz, 2H), 7.85 (t, J=8 Hz, 1H), 7.39 (d, J=8 Hz, 1H), 7.10 (d, J=8 Hz, 1H), 5.45-5.43 (m, 1H), 4.43 (s, 2H), 3.77 (m, 2H), 2.94-2.92 (m, 1H), 2.76-2.72 (m, 1H), 2.67-2.62 (m, 1H), 2.37 (bs, 2H), 2.09 (bs, 1H), 1.90 (bs, 2H), 1.45 (s, 3H), 1.26 (bs, 2H), 1.17 (bs, 2H); LCMS (ES+)=595.3 [M+H]+.

Example 116. Synthesis of 3-[6-[[1-(4-tert-butoxy-cyclohexyl)pyrazol-4-yl]methyl]-2-oxo-benzo[cd]indol-1-yl]piperidine-2,6-dione (Compound 212) and 3-[6-[[1-(4-tert-butoxycyclohexyl)pyrazol-4-yl]methyl]-2-oxo-benzo[cd]indol-1-yl]piperidine-2,6-dione (Compound 213)

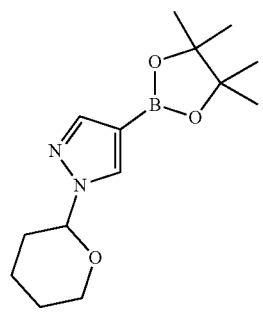

1

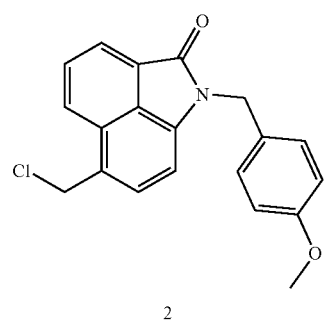

2

$\xrightarrow{\text{K}_3\text{PO}_4\text{, tri o-toluene}}_{\text{Tol:EtOH(5:1)}}$ Step 1

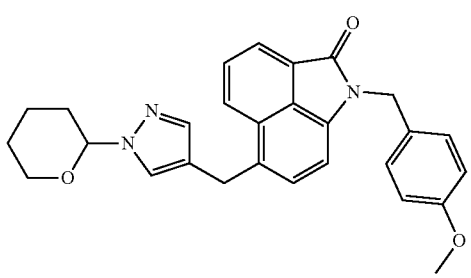

3

$\xrightarrow[\text{25° C., 16 h}]{\text{HCl in dioxane}}$ Step 2

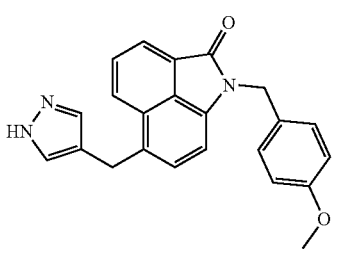

4

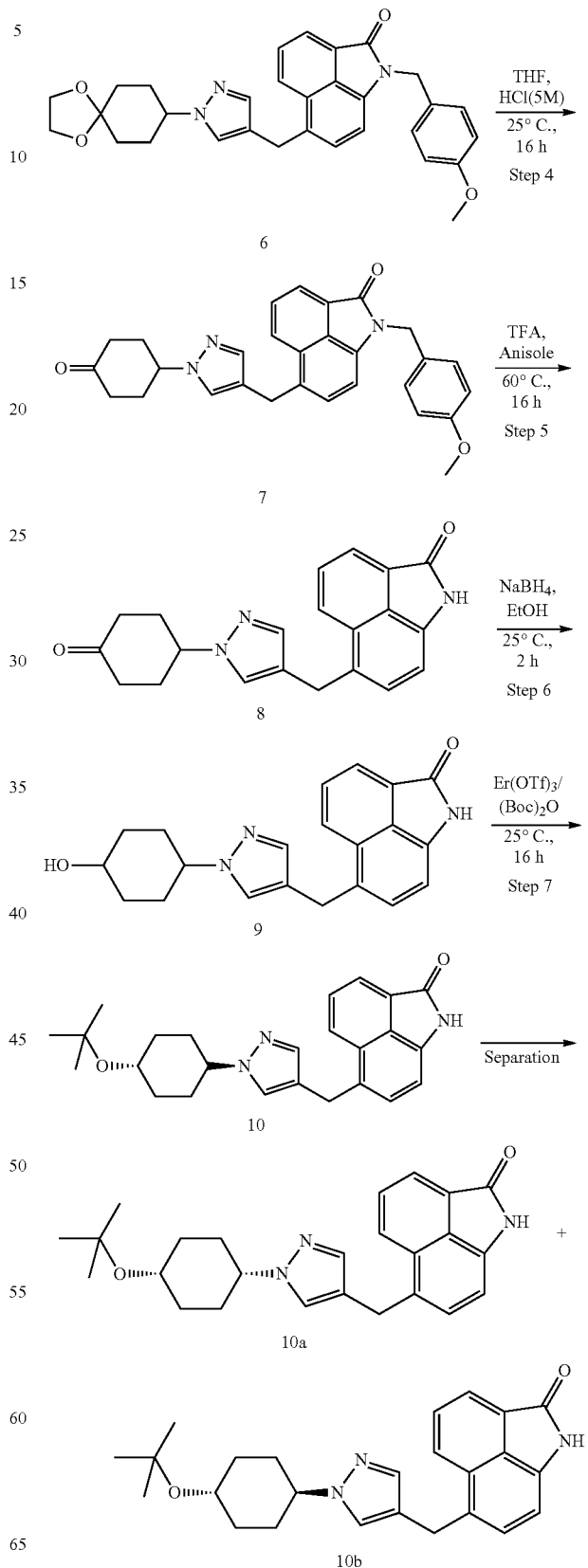

-continued

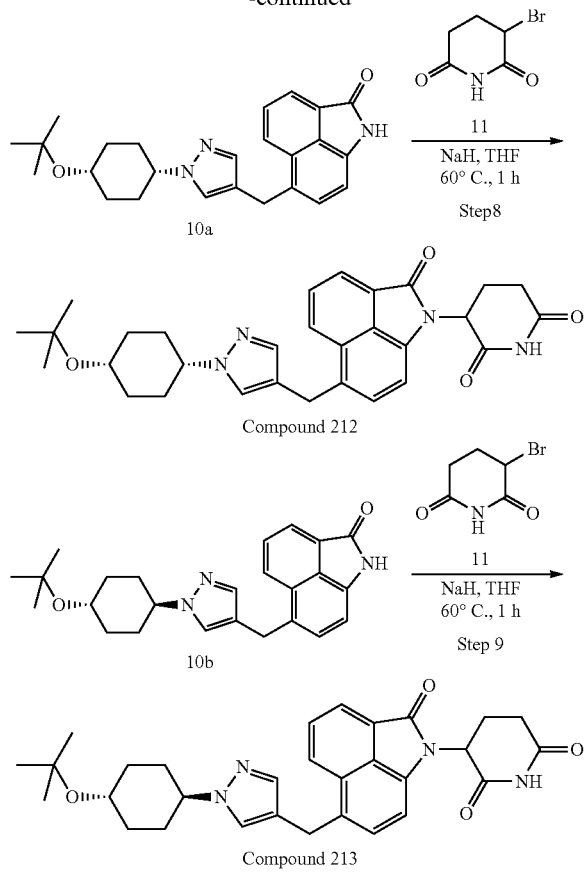

Step-1: Synthesis of 1-[(4-methoxyphenyl)methyl]-6-[(1-tetrahydropyran-2-ylpyrazol-4-yl)methyl]benzo[cd]indol-2-one: In a sealed tube a stirred solution of 1-tetrahydropyran-2-yl-4-(4,4,5,5-tetramethyl-1,3,2-dioxaborolan-2-yl) pyrazole (4.12 g, 14.80 mmol) and 6-(chloromethyl)-1-[(4-methoxyphenyl)methyl]benzo[cd]indol-2-one (5 g, 14.80 mmol) in the mixture of solvent Toluene (100 mL) and Ethanol (50 mL), was added Potassium phosphate tribasic anhydrous (7.85 g, 37.00 mmol), reaction was degassed under argon atmosphere for 10 mins. Then added Tris (dibenzylideneacetone)dipalladium(0) (1.36 g, 1.48 mmol) and Tris(o-tolyl)phosphine (901.04 mg, 2.96 mmol), again degassed for 5 mins. Then tube was closed and heated to 110° C. for 16 hr. After completion of SM, reaction was filtered through celite bed and concentrated under reduced pressure to give the crude. It was purified by combiflash column chromatography (using 30% EA in hexane) to give the title compound 1-[(4-methoxyphenyl)methyl]-6-[(1-tetrahydropyran-2-ylpyrazol-4-yl)methyl]benzo[cd]indol-2-one (4.7 g, 9.33 mmol, 63.01% yield, 90% purity) as yellow solid; LC-MS: (ES+)=454.4 [M+H]+.

Step-2: Synthesis of 1-Piperidin-4-yl-1H-pyrrolo[2,3-b]pyridine-3-carbaldehyde: To a stirred solution of tert-butyl 4-(3-formylpyrrolo[2,3-b]pyridin-1-yl)piperidine-1-carboxylate 3 (525 mg, 1.59 mmol) in 1,4 dioxane (10 mL) was added HCl in dioxane (4 M, 11.95 mL). The reaction mixture was stirred at 25° C. for 16 hr. After completion of SM, the reaction was concentrated under reduced pressure and then washed with 10-20% ethyl acetate in n-hexane and finally dried to give the title compound 1-(4-piperidyl) pyrrolo[2,3-b]pyridine-3-carbaldehyde (350 mg, 1.53 mmol, 95.78% yield) as off-white solid; LCMS (ES+)=230.0 [M+H]+.

Step-3: Synthesis of 6-[[1-(1,4-dioxaspiro[4.5]decan-8-yl)pyrazol-4-yl]methyl]-1-[(4-methoxyphenyl)methyl] benzo[cd]indol-2-one: To a stirred solution of 1-[(4-methoxyphenyl)methyl]-6-(1H-pyrazol-4-ylmethyl)benzo [cd]indol-2-one (2.7 g, 7.31 mmol) and 1,4-dioxaspiro[4.5] decan-8-yl methanesulfonate (3.45 g, 14.62 mmol) in DMF (20 mL), was added Cesium carbonate (4.76 g, 14.62 mmol), reaction mixture was heated to 90° C. for 16 hr. After completion of SM, reaction mixture was quenched with water and extracted with ethyl acetate, dried over sodium sulphate, concentrated under reduced pressure to give the crude. It was purified by combiflash column chromatography (50% ethyl acetate in hexane) to give the title compound 6-[[1-(1,4-dioxaspiro[4.5]decan-8-yl)pyrazol-4-yl]methyl]-1-[(4-methoxyphenyl)methyl]benzo[cd]indol-2-one (1.5 g, 2.65 mmol, 36.25% yield, 90% purity) as yellow solid; LCMS (ES+)=510.3 [M+H]+.

Step-4: Synthesis of 1-[(4-methoxyphenyl)methyl]-6-[[1-(4-oxocyclohexyl)pyrazol-4-yl]methyl]benzo[cd]indol-2-one: To a stirred solution of 6-[[1-(1,4-dioxaspiro[4.5]decan-8-yl)pyrazol-4-yl]methyl]-1-[(4-methoxyphenyl) methyl]benzo[cd]indol-2-one (1.5 g, 2.94 mmol) in THF (10 mL), was added HCl (5 M, 2.94 mL) and the reaction mixture was stirred at 25° C. for 20 hr. After completion of SM, solvent was concentrated under reduced pressure and neutralized by sodium bicarbonate and extracted with ethyl acetate, dried over sodium sulphate, concentrated under reduced pressure to give the title compound 1-[(4-methoxyphenyl)methyl]-6-[[1-(4-oxocyclohexyl)pyrazol-4-yl] methyl]benzo[cd]indol-2-one (1 g, 1.93 mmol, 65.68% yield, 90% purity) as yellow solid; LCMS (ES+)=466.5 [M+H]+.

Step-5: Synthesis of 6-[[1-(4-oxocyclohexyl)pyrazol-4-yl]methyl]-1H-benzo[cd]indol-2-one: To a stirred solution of 1-[(4-methoxyphenyl)methyl]-6-[[1-(4-oxocyclohexyl) pyrazol-4-yl]methyl]benzo[cd]indol-2-one (300 mg, 644.41 umol) in Trifluoroacetic acid (7 mL), was added Anisole (696.87 mg, 6.44 mmol, 701.07 uL), reaction mixture was stirred at 60° C. for 16 hr. After completion of SM, TFA was removed and dissolved in ice cooled water and neutralized by saturated solution of sodium bicarbonate and extracted with ethyl acetate; separate the organic layer, dried over sodium sulphate, concentrated under reduced pressure, to give the crude. It was purified by combiflash column chromatography (using ethyl acetate) to give the title compound 6-[[1-(4-oxocyclohexyl)pyrazol-4-yl]methyl]-1H-benzo[cd] indol-2-one (80 mg, 208.46 umol, 32.35% yield, 90% purity) as yellow solid; LCMS (ES+)=346.2 [M+H]+.

Step-6: Synthesis of 6-[[1-(4-hydroxycyclohexyl)pyrazol-4-yl]methyl]-1H-benzo[cd]indol-2-one: To a stirred solution of 6-[[1-(4-oxocyclohexyl)pyrazol-4-yl]methyl]-1H-benzo[cd]indol-2-one (100.00 mg, 289.52 umol) in Ethanol (10 mL), reaction mixture was cooled to 0° C., sodium borohydride (21.91 mg, 579.05 umol, 20.47 uL) was added to it and stirred at 25° C. for 2 hr. After completion of SM, reaction was quenched with ice cold water and then solvent was removed under reduced pressure, then dissolved in water and extracted with ethyl acetate, separate the organic layer, dried over sodium sulphate, concentrated under reduced pressure, to give the crude. It was purified by combiflash column chromatography (using ethyl acetate) to give the title compound 6-[[1-(4-hydroxycyclohexyl)pyrazol-4-yl]methyl]-1H-benzo[cd]indol-2-one (75 mg, 194.30 umol, 67.11% yield, 90% purity) as yellow sticky liquid; LCMS (ES+)=348.2 [M+H]+.

Step-7: Synthesis of 6-[[1-(4-tert-butoxycyclohexyl)pyrazol-4-yl]methyl]-1-[(4-methoxyphenyl)methyl]benzo[cd]

indol-2-one: To a stirred solution of 6-[[1-(4-hydroxycyclohexyl)pyrazol-4-yl]methyl]-1-[(4-methoxyphenyl)methyl]benzo[cd]indol-2-one (750 mg, 1.60 mmol) was dissolved in Di-tert-butyl dicarbonate (805.21 mg, 3.69 mmol, 846.70 uL) under mild heating (less than 40° C.). Then Erbium(III) trifluoromethanesulfonate (98.57 mg, 160.41 umol) was added to the mixture under N2 atmosphere and the mixture was stirred at 25° C. for 16 hr. The reaction was monitored by TLC. After that the mixture was diluted with Et2O and the Et2O layer was washed with H$_2$O. The organic phase was dried over Na$_2$SO$_4$, filtered, and then evaporated under vacuum to give the crude. This crude was purified by combi-flash column chromatography 6-[[1-(4-tert-butoxycyclohexyl)pyrazol-4-yl]methyl]-1-[(4-methoxyphenyl)methyl]benzo[cd]indol-2-one (200 mg, 351.37 umol, 21.90% yield, 92% purity) as yellow solid. LCMS (ES+)=524.5 [M+H]+. NOTE: Separated the isomer by Prep-HPLC purification and individually proceeded for the next step.

Step-8: Synthesis of 3-[6-[[1-(4-tert-butoxycyclohexyl)pyrazol-4-yl]methyl]-2-oxo-benzo[cd]indol-1-yl]piperidine-2,6-dione: To a stirred solution of 6-[[1-(4-tert-butoxycyclohexyl)pyrazol-4-yl]methyl]-1H-benzo[cd]indol-2-one (50.00 mg, 123.91 umol) in THF (10 mL), reaction mixture was cooled to 0° C., then slowly added Sodium hydride (in oil dispersion) 60% dispersion in mineral oil (142.44 mg, 3.72 mmol, 60% purity). Then reaction was stirred for 5 mins to 0° C., then added 3-bromopiperidine-2,6-dione (118.96 mg, 619.55 umol) portion wise, again stirred for 5 mins. Then reaction mixture was heated to 60° C. for 1 hr. After that reaction was quenched by ice cold water and extracted with ethyl acetate, separate the organic layer, dried over sodium sulphate, concentrated under reduced pressure to give the crude. This crude was purified by prep-TLC plate (using 80% EA in Hexane) to give the title compound 3-[6-[[1-(4-tert-butoxycyclohexyl)pyrazol-4-yl]methyl]-2-oxo-benzo[cd]indol-1-yl]piperidine-2,6-dione Compound 212 (15 mg, 27.70 umol, 22.36% yield, 95.04% purity) as yellow solid; LCMS (ES+)=515.3 [M+H]+. 1H NMR (400 MHz, DMSO-d6): δ 11.11 (s, 1H), 8.36-8.34 (d, 1H), 8.09-8.07 (d, 1H), 7.82 (t, 1H), 7.48 (s, 1H), 7.35-7.34 (d, 1H), 7.27 (s, 1H), 7.07-7.06 (d, 1H), 5.45-5.41 (m, 1H), 4.17 (s, 2H), 3.98 (brs, 1H), 3.45 (brs, 1H), 2.94 (m, 1H), 2.75-2.72 (m, 1H), 2.66-2.62 (m, 1H), 2.09-2.06 (m, 1H), 1.88-1.86 (m, 2H), 1.78-1.73 (m, 4H), 1.34-1.23 (m, 3H), 1.11 (s, 9H).

Step-9: Synthesis of 3-[6-[[1-(4-tert-butoxycyclohexyl)pyrazol-4-yl]methyl]-2-oxo-benzo[cd]indol-1-yl]piperidine-2,6-dione: To a stirred solution of 6-[[1-(4-tert-butoxycyclohexyl)pyrazol-4-yl]methyl]-1H-benzo[cd]indol-2-one (50.00 mg, 123.91 umol) in THF (10 mL), reaction mixture was cooled to 0° C., then slowly added Sodium hydride (in oil dispersion) 60% dispersion in mineral oil (142.44 mg, 3.72 mmol, 60% purity). Then reaction was stirred for 5 mins to 0° C., then added 3-bromopiperidine-2,6-dione (118.96 mg, 619.55 umol) portion wise, again stirred for 5 mins. Then reaction mixture was heated to 60° C. for 1 hr. After that reaction was quenched by ice cold water and extracted with ethyl acetate, separate the organic layer, dried over sodium sulphate, concentrated under reduced pressure to give the crude. This crude was purified by prep-HPLC to give the title compound 3-[6-[[1-(4-tert-butoxycyclohexyl)pyrazol-4-yl]methyl]-2-oxo-benzo[cd]indol-1-yl]piperidine-2,6-dione Compound 213 (5 mg, 9.63 umol, 7.77% yield, 99.09% purity) as yellow solid. LCMS (ES+)=515.3 [M+H]+. 1H NMR (400 MHz, DMSO-d6): δ 11.10 (s, 1H), 8.39-8.37 (d, 1H), 8.09-8.07 (d, 1H), 7.83 (t, 1H), 7.53 (s, 1H), 7.36-7.34 (d, 1H), 7.27 (s, 1H), 7.08-7.06 (d, 1H), 5.45-5.40 (m, 1H), 4.18 (s, 2H), 4.08-3.98 (m, 1H), 3.73 (brs, 1H), 2.99-2.90 (m, 2H), 2.79-2.69 (m, 1H), 2.66-2.62 (m, 1H), 2.09-2.05 (m, 1H), 2.01-1.95 (m, 1H), 1.70-1.68 (m, 2H), 1.60-1.46 (m, 4H), 1.12 (s, 9H).

Example 117. Synthesis of 3-fluoro-4-[4-[[2-fluoro-4-[(2-oxo-1H-benzo[cd]indol-6-yl)methyl]phenyl]methyl]piperazin-1-yl]benzonitrile (Compound 214)

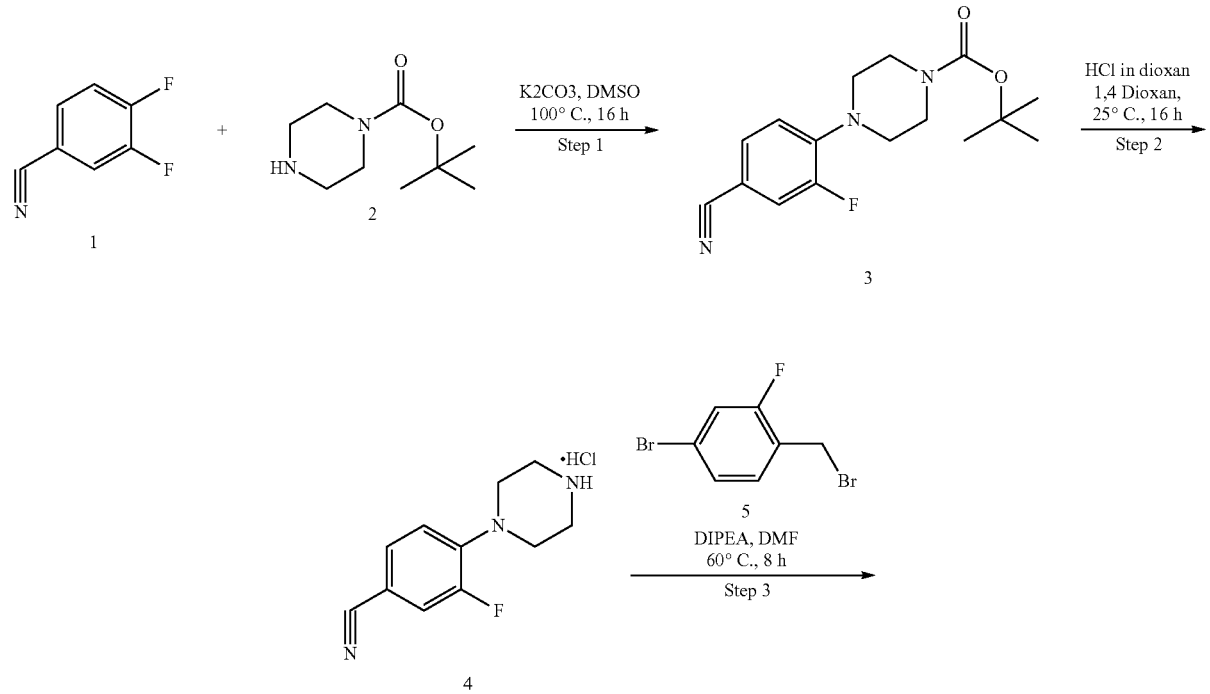

-continued
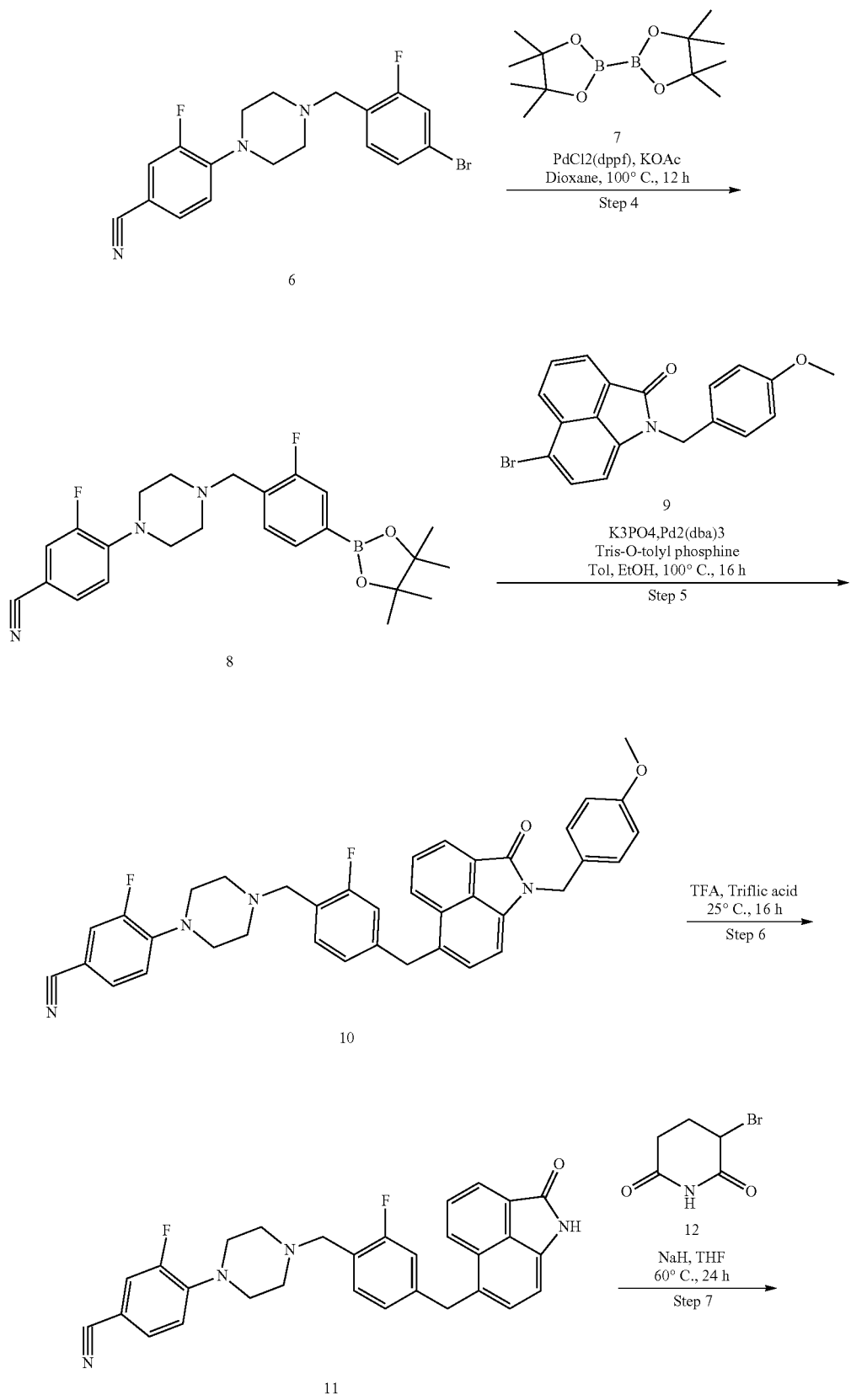

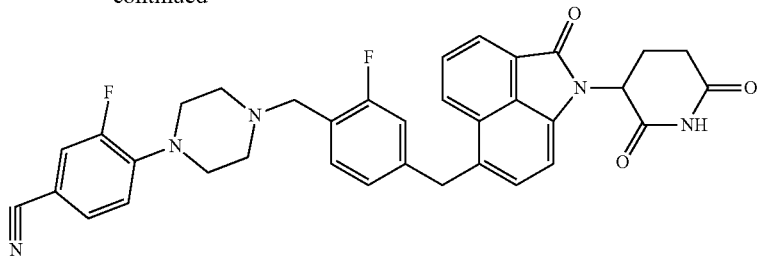

Compound 214

Step-1: Synthesis of 4-(4-Cyano-2-fluoro-phenyl)-piperazine-1-carboxylic acid tert-butyl ester: To a stirred solution of 3,4-difluorobenzonitrile (5.23 g, 37.58 mmol) in DMSO (25 mL) was added Potassium carbonate—granular (10.39 g, 75.17 mmol, 4.54 mL) and tert-butyl piperazine-1-carboxylate (7 g, 37.58 mmol) and heated at 100° C. for 16 hr. The reaction mixture was cooled and ice cold water was added, a white solid precipitate was formed. The solid precipitate was filtered through a sintered funnel and washed with water and dried in rotavpour to afford the desired compound 4-(4-Cyano-2-fluoro-phenyl)-piperazine-1-carboxylic acid tert-butyl ester as a white solid. LCMS (ES+)=306.3 [M+H]+.

Step-2: Synthesis of 3-fluoro-4-piperazin-1-yl-benzonitrile: To a stirred solution of 4-(4-tert-butoxypiperazin-1-yl)-3-fluoro-benzonitrile; methane; hydrate (3.5 g, 11.31 mmol) in Dioxan (20 mL) was added HCl in Dioxan (4 M, 28.28 mL) and stirred the reaction mixture at 25° C. for 16 hr. After completion of SM, reaction mixture was dried under reduced pressure, titrated with pentane to afford the desired compound 3-fluoro-4-piperazin-1-yl-benzonitrile (2.5 g, 10.14 mmol, 89.60% yield, 98% purity) as off-white solid.

Step-3: Synthesis of 4-[4-[(4-bromo-2-fluoro-phenyl)methyl]piperazin-1-yl]-3-fluoro-benzonitrile: To stirred solution of 3-fluoro-4-piperazin-1-yl-benzonitrile (7 g, 34.11 mmol) in DMF (70 mL) was added Potassium carbonate, anhydrous, 99% (11.79 g, 85.27 mmol, 5.15 mL) stirred for 10 minutes and then 4-bromo-1-(bromomethyl)-2-fluoro-benzene (9.14 g, 34.11 mmol) was added and stirred the reaction mixture at 60° C. for 8 hr. After completion of SM, reaction mixture was quenched with ice cold water and solid was filtered. Then Again solid was washed with water, dried under rotavaour to give the title compound 4-[4-[(4-bromo-2-fluoro-phenyl)methyl]piperazin-1-yl]-3-fluoro-benzonitrile (9 g, 21.80 mmol, 63.91% yield, 95% purity) as a white solid. LCMS (ES+)=394.1 [M+H]+.

Step-4: Synthesis of 3-fluoro-4-[4-[[2-fluoro-4-(4,4,5,5-tetramethyl-1,3,2-dioxaborolan-2-yl)phenyl]methyl]piperazin-1-yl]benzonitrile: To a stirred solution of 4-[4-[(4-bromo-2-fluoro-phenyl)methyl]piperazin-1-yl]-3-fluoro-benzonitrile (1 g, 2.55 mmol) and 4,4,5,5-tetramethyl-2-(4,4,5,5-tetramethyl-1,3,2-dioxaborolan-2-yl)-1,3,2-dioxaborolane (776.88 mg, 3.06 mmol) in 1,4-Doxane (5 mL) was added Potassium acetate (625.51 mg, 6.37 mmol, 398.41 uL) then degassed for 10 mins, later [1,1'-Bis(diphenylphosphino)ferrocene]dichloropalladium(II), complex with dichloromethane (208.04 mg, 254.95 umol) was added and again degassed for 5 mins, after degassing the tube was closed with teflon cap and stirred at 90° C. for 16 hr. The progress of the reaction was monitored by TLC, after reaction completion reaction mixture was filtered through celite bed and washed with ethyl acetate and concentrated under reduced pressure to give the title compound 3-fluoro-4-[4-[[2-fluoro-4-(4,4,5,5-tetramethyl-1,3,2-dioxaborolan-2-yl)phenyl]methyl]piperazin-1-yl]benzonitrile (1 g, 682.90 umol, 26.79% yield, 30% purity) as black sticky liquid. LC-MS: (ES+)=440.4 [M+H]+.

Step-5: Synthesis of (3-fluoro-4-[4-[[2-fluoro-4-[[1-[(4-methoxyphenyl)methyl]-2-oxo-benzo[cd]indol-6-yl]methyl]phenyl]methyl]piperazin-1-yl]benzonitrile: In a sealed tube a stirred solution of 3-fluoro-4-[4-[[2-fluoro-4-(4,4,5,5-tetramethyl-1,3,2-dioxaborolan-2-yl)phenyl]methyl]piperazin-1-yl]benzonitrile (1.30 g, 2.96 mmol) and 6-(chloromethyl)-1-[(4-methoxyphenyl)methyl]benzo[cd]indol-2-one (1 g, 2.96 mmol) in the mixture of solvent Toluene (10 mL) and Ethanol (5 mL), was added Potassium phosphate tribasic anhydrous (1.57 g, 7.40 mmol), reaction was degassed under argon atmosphere for 10 mins. Then added Tris(dibenzylideneacetone)dipalladium(0) (271.08 mg, 296.03 umol) and Tris(o-tolyl)phosphine (180.20 mg, 592.07 umol), again degassed for 5 mins. Then tube was closed and heated to 90° C. for 16 hr. After completion of SM, reaction was filtered through celite bed and concentrated under reduced pressure to give the crude. It was purified by combiflash column chromatography (using 30% EA in hexane) to give the title compound 3-fluoro-4-[4-[[2-fluoro-4-[[1-[(4-methoxyphenyl)methyl]-2-oxo-benzo[cd]indol-6-yl]methyl]phenyl]methyl]piperazin-1-yl]benzonitrile (800 mg, 1.17 mmol, 39.57% yield, 90% purity) as yellow solid. LCMS (ES+)=614.9 [M+H]+.

Step-6: Synthesis of 3-fluoro-4-[4-[[2-fluoro-4-[(2-oxo-1H-benzo[cd]indol-6-yl)methyl]phenyl]methyl]piperazin-1-yl]benzonitrile: To a stirred solution of 3-fluoro-4-[4-[[2-fluoro-4-[[1-[(4-methoxyphenyl)methyl]-2-oxo-benzo[cd]indol-6-yl]methyl]phenyl]methyl]piperazin-1-yl]benzonitrile (300 mg, 488.06 umol) in TFA (10 mL), was added Trifluoromethanesulphonic acid (366.23 mg, 2.44 mmol, 214.17 uL), reaction mixture was stirred at 25° C. for 16 hr. After completion of SM, TFA was removed and dissolved in ice cooled water and neutralised by saturated solution of sodium bicarbonate and extracted with ethyl acetate, separate the organic layer, dried over sodium sulphate, concentrated under reduced pressure, to give the crude. It was purified by combiflash column chromatography (using ethyl acetate) to give the title compound 3-fluoro-4-[4-[[2-fluoro-4-[(2-oxo-1H-benzo[cd]indol-6-yl)methyl]phenyl]methyl]piperazin-1-yl]benzonitrile (210 mg, 394.92 umol, 80.92% yield, 93% purity) as yellow solid. LCMS (ES+)=495.1 [M+H]+.

Step-7: Synthesis of 3-fluoro-4-[4-[[2-fluoro-4-[(2-oxo-1H-benzo[cd]indol-6-yl)methyl]phenyl]methyl]piperazin-1-yl]benzonitrile: To a stirred solution of 3-fluoro-4-[4-[[2-fluoro-4-[(2-oxo-1H-benzo[cd]indol-6-yl)methyl]phenyl]

methyl]piperazin-1-yl]benzonitrile (210 mg, 424.64 umol) in THF (20 mL), reaction mixture was cooled to 0° C., then slowly added Sodium hydride (in oil dispersion) 60% dispersion in mineral oil (488.12 mg, 12.74 mmol, 60% purity). Then reaction was stirred for 2 mins in without ice bath and then again cooled to 0° C., then added 3-bromopiperidine-2,6-dione (407.68 mg, 2.12 mmol) portion wise, again stirred for 2 mins in without ice bath. Then reaction mixture was heated to 60° C. for 1 hr. After that reaction was quenched by ice cold water and extracted with ethyl acetate, separate the organic layer, dried over sodium sulphate, concentrated under reduced pressure to give the crude. This crude was purified by combiflash column chromatography (50% EA in Hexane) to give the title compound 4-[4-[[4-[[1-(2,6-dioxo-3-piperidyl)-2-oxo-benzo[cd]indol-6-yl]methyl]-2-fluoro-phenyl]methyl]piperazin-1-yl]-3-fluoro-benzonitrile Compound 214 (48 mg, 77.74 umol, 18.31% yield, 98.09% purity) as light yellow solid. LCMS (ES+)=606.5 [M+H]+. 1H NMR (400 MHz, DMSO-d6): δ 11.13 (s, 1H), 8.36-8.34 (d, 1H), 8.09-8.07 (d, 1H), 7.82 (t, 1H), 7.69-7.65 (d, 1H), 7.55-7.53 (d, 1H), 7.45-7.44 (d, 1H), 7.30 (t, 1H), 7.14-7.09 (m, 4H), 5.45 (t, 1H), 4.40 (s, 2H), 3.50 (s, 2H), 3.12 (brs, 4H), 2.95-2.91 (m, 1H), 2.77-2.73 (m, 1H), 2.66-2.62 (m, 1H), 2.50 (brs, 4H), 2.10-2.07 (m, 1H).

Example 118. Synthesis of 3-(6-(4-((1-oxa-8-azaspiro[4.5]decan-8-yl)methyl)benzyl)-2-oxobenzo[cd]indol-1(2H)-yl)piperidine-2,6-dione (Compound 215), 3-[6-[[4-(1-oxa-8-azaspiro[4.5]decan-8-ylmethyl)phenyl]methyl]-2-oxo-benzo[cd]indol-1-yl]piperidine-2,6-dione) (Compound 216) and 3-[6-[[4-(1-oxa-8-azaspiro[4.5]decan-8-ylmethyl)phenyl]methyl]-2-oxo-benzo[cd]indol-1-yl]piperidine-2,6-dione (Compound 217)

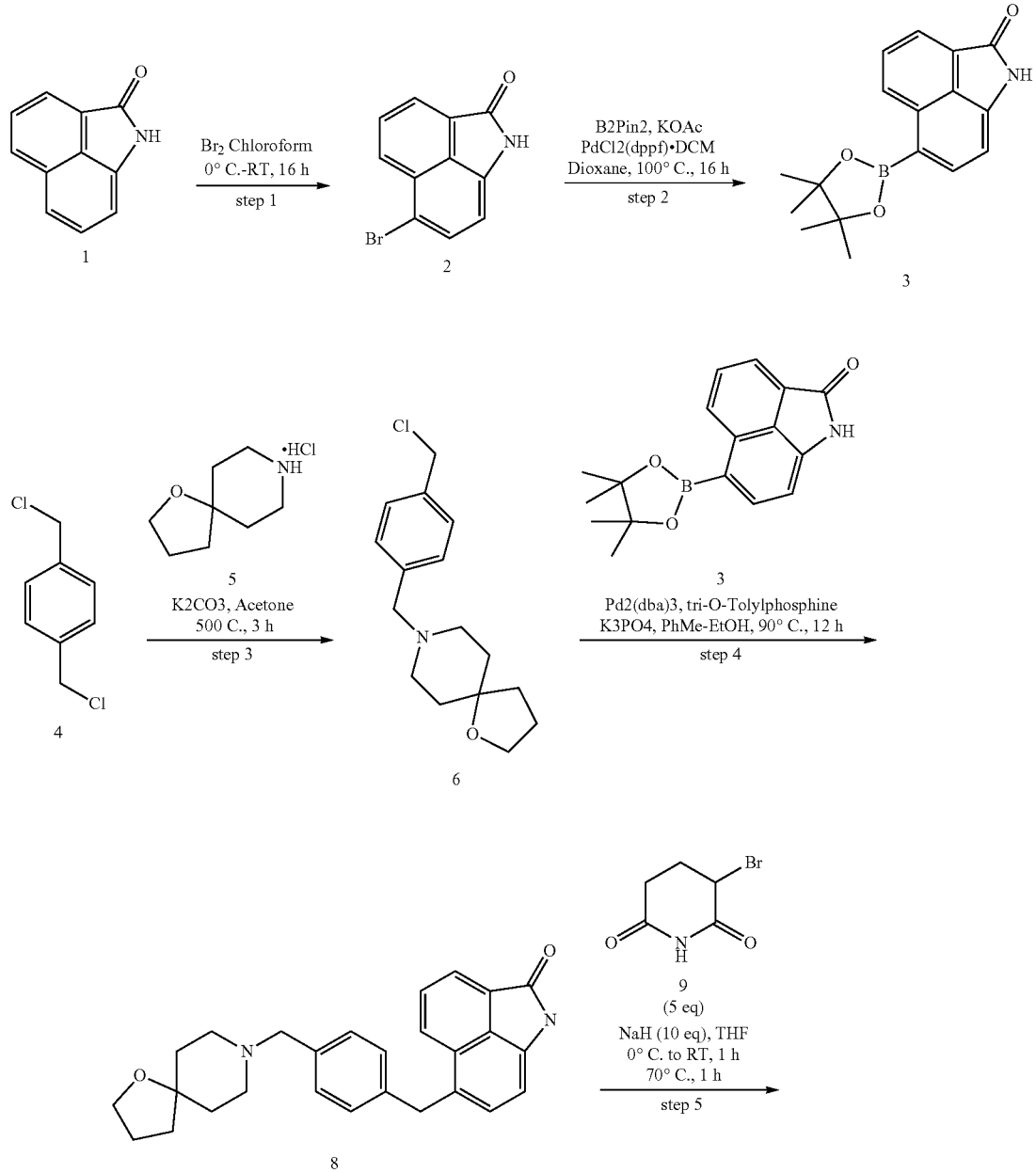

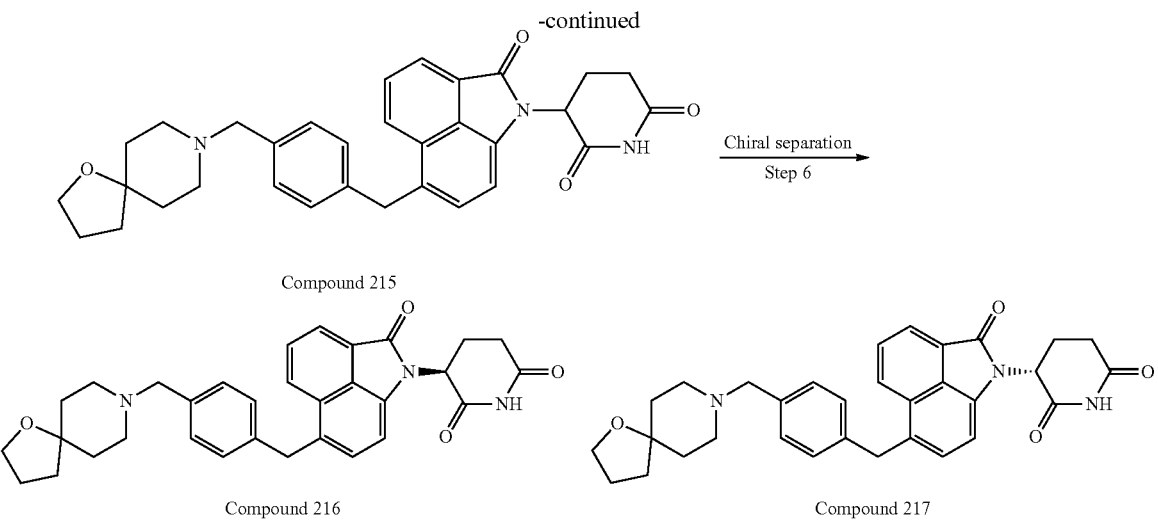

Compound 215

Compound 216

Compound 217

Step 1: Synthesis of 6-bromo-1H-benzo[cd]indol-2-one (2): To a stirred suspension of 1H-benzo[cd]indol-2-one (1) (250 g, 1.48 mol) in Chloroform (2.5 L), a solution of molecular bromine (354.23 g, 2.22 mol, 113.53 mL) in Chloroform (500 mL) was added drop wise at 0° C. and the reaction mixture was stirred at room temperature for 16 hours. After completion of the reaction (monitored by TLC), the reaction mass was poured into saturated aqs. solution of Sodium thiosulphate. The yellow solid formed was filtered through cintered funnel, washed with water, pentane and stripped with toluene to afford 6-bromo-1H-benzo[cd]indol-2-one (2) (350 g, 90% yield) as yellow solid. LC MS: ES+ 2 (248.2 and 250.2).

Step 2: Synthesis of 6-(4,4,5,5-tetramethyl-1,3,2-dioxaborolan-2-yl)-1H-benzo[cd]indol-2-one: To a stirred solution of 6-bromo-1H-benzo[cd]indol-2-one (2) (100 g, 403.10 mmol) in 1,4-Dioxane (1 L) was added Bis(pinacolato)diboron (153.55 g, 604.66 mmol) followed by well dried Potassium Acetate (118.68 g, 1.21 mol, 75.60 mL). The resultant reaction mass was degassed well with argon for 15 minutes. PdCl2(dppf).DCM (32.92 g, 40.31 mmol) was added and the reaction mass was heated at 100° C. for 16 hours. After completion of the reaction (monitored by TLC), the reaction mixture was cooled to RT, filtered through a pad of celite, washed with Ethyl acetate. The combined filtrate was then washed with cold water, dried over anhydrous sodium sulphate and concentrated under reduced pressure to afford crude 6-(4,4,5,5-tetramethyl-1,3,2-dioxaborolan-2-yl)-1H-benzo[cd]indol-2-one (3) (110 g, 64% yield) as brown gum. This was forwarded without further purification, LC MS: ES+ 295.7.

Step 3: Synthesis of 8-(4-(chloromethyl)benzyl)-1-oxa-8-azaspiro[4.5]decane (6): To a stirred solution of 1-oxa-8-azaspiro[4.5]decane; hydrochloride (5) (5 g, 28.14 mmol) in dry grade Acetone (50 mL) was added DIPEA (3.64 g, 28.14 mmol, 4.90 mL) followed by Potassium carbonate, anhydrous, 99% (11.67 g, 84.43 mmol, 5.10 mL) at RT and the resultant reaction mixture was heated at 50° C. for 20 minutes. 1,4-bis(chloromethyl)benzene (4) (9.85 g, 56.28 mmol, 6.94 mL) was then added to the reaction mixture and heating was continued for 3 hours. After completion of reaction (monitored by TLC and LCMS), volatiles were removed under vacuum and the solid thus obtained was taken in Ethyl acetate (20 mL), washed with water (×3) and Brine, dried over anhydrous sodium sulfate and concentrated under reduced pressure. Crude mass was purified by column chromatography (silica, gradient: 0-5% MeOH in DCM) to afford 8-[[4-(chloromethyl)phenyl]methyl]-1-oxa-8-azaspiro[4.5]decane (6) (4.68 g, 16.56 mmol, 58.84% yield, 99% purity) as colorless sticky solid. LC MS: ES+ 280.4.

Step 4: Synthesis of 6-(4-((1-oxa-8-azaspiro[4.5]decan-8-yl)methyl)benzyl)benzo[cd]indol-2(1H)-one (8): To a well degassed solution of 8-[[4-(chloromethyl)phenyl]methyl]-1-oxa-8-azaspiro[4.5]decane (6) (4.68 g, 16.73 mmol) and 6-(4,4,5,5-tetramethyl-1,3,2-dioxaborolan-2-yl)-1H-benzo[cd]indol-2-one (7) (9.87 g, 33.45 mmol) in ethanol (20.0 mL)-Toluene (40.0 mL), Potassium phosphate tribasic anhydrous (10.65 g, 50.18 mmol) was added followed by the addition Tri-o-Tolyl phosphine (1.02 g, 3.35 mmol) and Pd2(dba)3 (1.53 g, 1.67 mmol). The resulting mixture was then heated at 90° C. for 12 hours. After completion of reaction (as monitored by LCMS), the reaction mixture was filtered through a bed of celite, washed with Ethyl acetate. The combined filtrate was washed with water and brine, dried over anhydrous sodium sulfate and concentrated under reduced pressure. Crude mass was purified by column chromatography (silica, gradient: 0-5% MeOH in DCM) to obtain 6-[[4-(1-oxa-8-azaspiro[4.5]decan-8-ylmethyl)phenyl]methyl]-1H-benzo[cd]indol-2-one (8) (2.83 g, 6.17 mmol, 36.91% yield, 90% purity) as yellow solid. LC MS: ES+ 413.0.

Step 5: Synthesis of 3-(6-(4-((1-oxa-8-azaspiro[4.5]decan-8-yl)methyl)benzyl)-2-oxobenzo[cd]indol-1(2H)-yl)piperidine-2,6-dione: To a ice cooled solution of 6-[[4-(1-oxa-8-azaspiro[4.5]decan-8-ylmethyl)phenyl]methyl]-1H-benzo[cd]indol-2-one (8) (2.83 g, 6.86 mmol) in dry THF (20 mL), Sodium hydride (60% dispersion in mineral oil) (2.63 g, 68.60 mmol, 60% purity) was added portion wise, maintaining the temp <5° C. Once the addition is over, the resultant mixture was stirred for 15 minutes at RT. Then the reaction mixture was again cooled to 0° C. and 3-bromopiperidine-2,6-dione (9) (6.59 g, 34.30 mmol) was added to it portion wise. After complete addition, resulting solution was heated at 70° C. for 1 hour. After completion (evidenced from TLC), the reaction mixture was again cooled to 0° C. and quenched with ice cooled water. Aqueous part was extracted with ethyl acetate (3×20 mL). Combined extract was dried over anhydrous sodium sulfate and concentrated under reduced pressure. Crude mass was washed with diethyl ether/pentane to afford 3-[6-[[4-(1-oxa-8-azaspiro[4.5]decan-8-ylmethyl)phenyl]methyl]-2-oxo-benzo[cd]indol-1-yl]piperidine-2,6-dione Compound 215(2.7 g, 5.15 mmol, 75.1% yield) as yellow solid. LC MS: ES+ 524.3.

Step 6: Chiral separation: Synthesis of 3-[6-[[4-(1-oxa-8-azaspiro[4.5]decan-8-ylmethyl)phenyl]methyl]-2-oxo-benzo[cd]indol-1-yl]piperidine-2,6-dione) and 3-[6-[[4-(1-oxa-8-azaspiro[4.5]decan-8-ylmethyl)phenyl]methyl]-2-oxo-benzo[cd]indol-1-yl]piperidine-2,6-dione: 1.2 g of 3-(6-(4-((1-oxa-8-azaspiro[4.5]decan-8-yl)methyl)benzyl)-2-oxobenzo[cd]indol-1(2H)-yl)piperidine-2,6-dione Compound 215 was separated into enantiomers by chiral normal phase Preparative HPLC method. Prep fractions were first evaporated separately under reduced pressure to obtain solid mass. The solid was then suspended in a mixture of Acetonitrile and Water (2:3) and it was kept in a Dry-ice/Acetone bath until the Acetonitrile-Water mixture solidified. The frozen mixture was then freeze dried under lyophilizer for 20 hours to afford 3-[6-[[4-(1-oxa-8-azaspiro[4.5]decan-8-ylmethyl)phenyl]methyl]-2-oxo-benzo[cd]indol-1-yl]piperidine-2,6-dione Compound 216 (first eluted peak, RT=6.29 min, assigned tentatively as 'S' ABS) (420 mg, % ee 99.28) and 3-[6-[[4-(1-oxa-8-azaspiro[4.5]decan-8-ylmethyl)phenyl]methyl]-2-oxo-benzo[cd]indol-1-yl]piperidine-2,6-dione Compound 217 (second eluted peak, RT=12.34 min, assigned tentatively as 'R' ABS) (360 mg, % ee 99.04) as yellow solids.

Example 119. Synthesis of 3-(6-(4-(morpholinomethyl)benzyl)-2-oxobenzo[cd]indol-1(2H)-yl)piperidine-2,6-dione (Compound 218), enantiomer 1 3-(6-(4-(morpholinomethyl)benzyl)-2-oxobenzo[cd]indol-1(2H)-yl)piperidine-2,6-dione (Compound 219) and enantiomer 2 3-(6-(4-(morpholinomethyl)benzyl)-2-oxobenzo[cd]indol-1(2H)-yl)piperidine-2,6-dione (Compound 220)

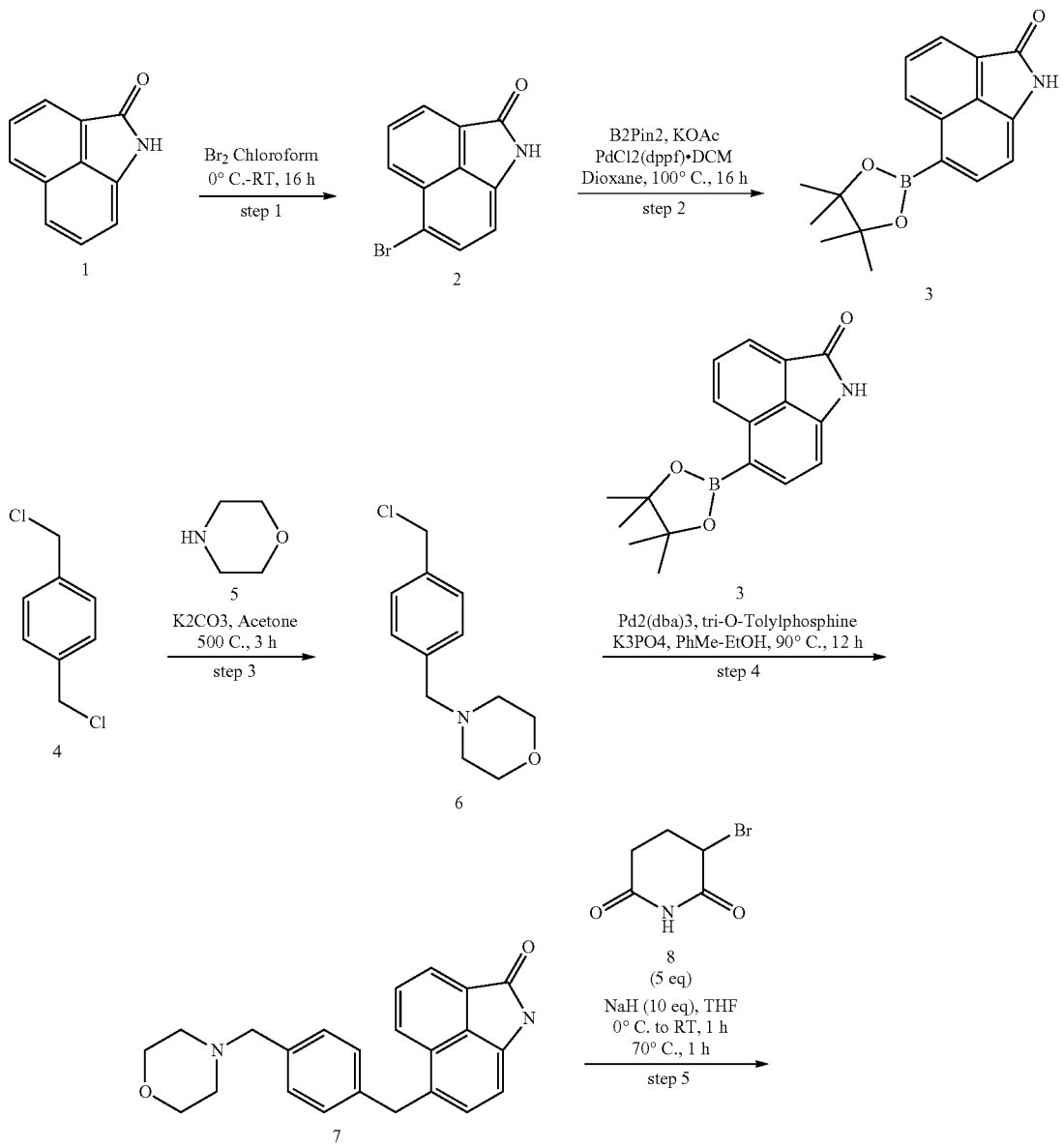

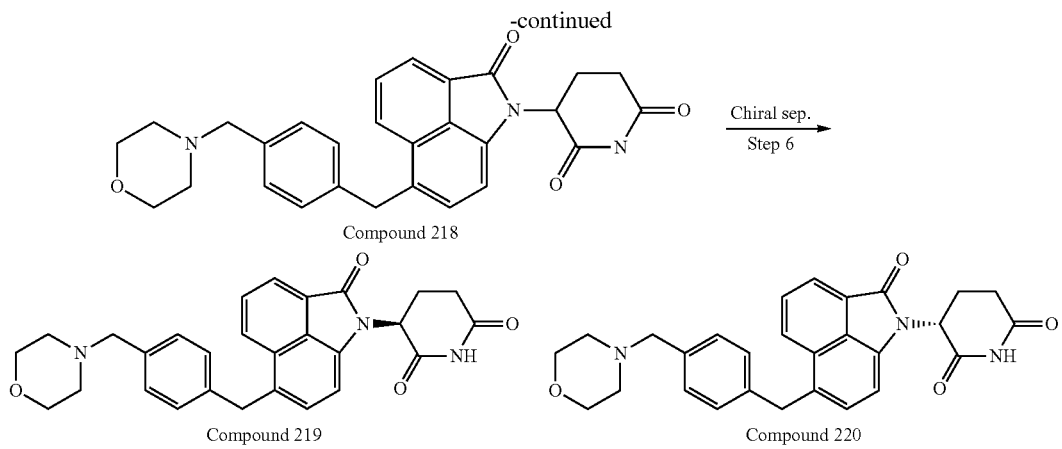

Compound 218

Compound 219

Compound 220

Step 1: Synthesis of 6-bromo-1H-benzo[cd]indol-2-one (2): To a stirred suspension of 1H-benzo[cd]indol-2-one (1) (250 g, 1.48 mol) in Chloroform (2.5 L), a solution of molecular bromine (354.23 g, 2.22 mol, 113.53 mL) in Chloroform (500 mL) was added drop wise at 0° C. and the reaction mixture was stirred at room temperature for 16 hours. After completion of the reaction (monitored by TLC), the reaction mass was poured into saturated aqs. solution of Sodium thiosulphate. The yellow solid formed was filtered through sintered funnel, washed with water, pentane and stripped with toluene to afford 6-bromo-1H-benzo[cd]indol-2-one (2) (350 g, 90% yield) as yellow solid which was stored in a Tarson plastic bottle at ambient temperature. LC MS: ES+ 2 (248.2 and 250.2).

Step 2: Synthesis of 6-(4,4,5,5-tetramethyl-1,3,2-dioxaborolan-2-yl)-1H-benzo[cd]indol-2-one (3): To a stirred solution of 6-bromo-1H-benzo[cd]indol-2-one (2) (20 g, 80.62 mmol) in 1,4 dioxane (500 mL) was added Bis (pinacolato) diboron (30.71 g, 120.93 mmol) followed by well dried potassium acetate (23.74 g, 241.86 mmol, 15.12 mL). The resultant reaction mass was degassed well with argon for 15 minutes. Pd2(dba)$_3$ (6.58 g, 8.06 mmol) was added and the reaction mass was heated at 100° C. for 16 hours. After completion of the reaction (monitored by TLC), the reaction mixture was cooled to RT, filtered through a pad of celite, washed with Ethyl acetate (1 L). The combined filtrate was then washed with cold water (3×300 mL), dried over anhydrous sodium sulphate and concentrated under reduced pressure to afford crude 6-(4,4,5,5-tetramethyl-1,3,2-dioxaborolan-2-yl)-1H-benzo[cd]indol-2-one (3) (23 g, 46.76 mmol, 58.00% yield) as brown gum which was stored in a round bottomed flask at 5° C. inside a refrigerator. This was forwarded without further purification; LC MS: ES+ 295.7.

Step 3: Synthesis of 4-(4-(chloromethyl)benzyl)morpholine (6): To a stirred solution of Morpholine (5) (8 g, 91.83 mmol, 8.03 mL) in analytical grade acetone (15 mL) was added Potassium carbonate, anhydrous, 99% (12.69 g, 91.83 mmol, 5.54 mL) at RT and the resultant reaction mixture was heated at 50° C. for 20 minutes. 1,4-bis(chloromethyl) benzene (4) (16.07 g, 91.83 mmol, 11.32 mL) was then added to the reaction mixture and heating was continued for 3 hours. After completion of reaction (monitored by TLC and LCMS), volatiles were removed under vacuum and the solid thus obtained was taken in Ethyl acetate (50 mL), washed with water (3×25 ml) and Brine (2×15 mL), dried over anhydrous sodium sulfate and concentrated under reduced pressure. Crude mass was purified by column chromatography (silica, gradient: 10-30% Ethyl acetate in Hexane) to afford 4-[[4-(chloromethyl)phenyl]methyl]morpholine (6) (10 g, 44.30 mmol, 48.25% yield) as colourless sticky solid which was stored in a round bottomed flask at 5° C. inside a refrigerator; LC MS: ES+ 226.2.

Step 4: Synthesis of 6-(4-(morpholinomethyl)benzyl) benzo[cd]indol-2(1H)-one (7): To a well degassed solution of 4-[[4-(chloromethyl)phenyl]methyl]morpholine (6) (8 g, 35.44 mmol) and 6-(4,4,5,5-tetramethyl-1,3,2-dioxaborolan-2-yl)-1H-benzo[cd]indol-2-one (3) (20.92 g, 70.89 mmol) in Ethanol (20 mL)-Toluene (40 mL), Potassium phosphate tribasic, anhydrous, (22.57 g, 106.33 mmol) was added followed by the addition of Tri-o-Tolyl phosphine (2.16 g, 7.09 mmol) and Pd2(dba)3 (3.25 g, 3.54 mmol). The resulting mixture was then heated at 90° C. for 12 hours. After completion of reaction (as monitored by LCMS), the reaction mixture was filtered through a bed of celite, washed with Ethyl acetate (200 mL). The combined filtrate was then washed with water (3×50 mL) and brine (2×40 mL), dried over anhydrous sodium sulfate and concentrated under reduced pressure. Crude mass was purified by column chromatography (silica, gradient: 0-20% Ethyl acetate in DCM) to obtain 6-[[4-(morpholinomethyl)phenyl]methyl]-1H-benzo[cd]indol-2-one (7) (6.5 g, 17.59 mmol, 49.63% yield) as yellow solid which was stored in a Tarson plastic bottle at ambient temperature. LC MS: ES+ 359.3.

Step 5: Synthesis of 3-(6-(4-(morpholinomethyl)benzyl)-2-oxobenzo[cd]indol-1(2H)-yl)piperidine-2,6-dione: To a ice cooled solution of 6-[[4-(morpholinomethyl)phenyl] methyl]-1H-benzo[cd]indol-2-one (7) (4.8 g, 13.39 mmol) in dry THF (50 mL), Sodium hydride (60% dispersion in mineral oil) (3.08 g, 133.92 mmol) was added portion wise, maintaining the temp <5° C. Once the addition is over, the resultant mixture was stirred for 15 minutes at RT. Then the reaction mixture was again cooled to 0° C. and 3-bromopiperidine-2,6-dione (8) (12.86 g, 66.96 mmol) was added to it portion wise. After complete addition, resulting solution was heated at 70° C. for 1 hour. After completion (evidenced from TLC), the reaction mixture was again cooled to 0° C. and quenched with ice cooled water (40 mL). Aqueous part was extracted with ethyl acetate (3×50 mL). Combined extracts was dried over anhydrous sodium sulfate and concentrated under reduced pressure. Crude mass was purified by flash chromatography (silica, gradient: 2.5% MeOH in DCM) to afford 3-[6-[[4-(morpholinomethyl)phenyl] methyl]-2-oxo-benzo[cd]indol-1-yl]piperidine-2,6-dione Compound 218 (4 g, 8.36 mmol, 62.44% yield) as yellow solid which was stored in a round bottomed flask at 5° C. inside a refrigerator. ¹H NMR (400 MHz, DMSO-d6) δ 11.12 (s, 1H), 8.31 (d, J=8.2 Hz, 1H), 8.06 (d, J=6.92 Hz, 1H), 7.80 (t, J=7.58 Hz, 1H), 7.39 (d, J=7.24 Hz, 1H), 7.24-7.17 (m, 4H), 7.10 (d, J=7.2 Hz, 1H), 5.44 (dd, J=12.36, 4.76 Hz, 1H), 4.36 (s, 1H), 3.51 (br s, 4H), 3.36 (s, 2H), 2.98-2.90 (m, 1H), 2.79-2.73 (m, 1H), 2.69-2.62 (m, 1H), 2.28 (br s, 4H), 2.10-2.07 (m, 1H); LC MS: ES+ 470.2.

Step 6: Chiral separation: Preparation of 3-(6-(4-(morpholinomethyl)benzyl)-2-oxobenzo[cd]indol-1(2H)-yl)piperidine-2,6-dione and 3-(6-(4-(morpholinomethyl)benzyl)-2-oxobenzo[cd]indol-1(2H)-yl)piperidine-2,6-dione: 3.8 g of 3-(6-(4-(morpholinomethyl)benzyl)-2-oxobenzo[cd]indol-1(2H)-yl)piperidine-2,6-dione Compound 218 was separated into enantiomers by chiral normal phase Preparative HPLC method. Prep fractions were first evaporated separately under reduced pressure to obtain solid mass. The solid was then suspended in a mixture of Acetonitrile and Water (2:3) and it was kept in a Dry-ice/Acetone bath until the Acetonitrile-Water mixture solidified. The frozen mixture was then freeze dried under lyophilizer for 20 hours to afford 3-(6-(4-(morpholinomethyl)benzyl)-2-oxobenzo[cd]indol-1(2H)-yl)piperidine-2,6-dione Compound 219 (first eluted peak, RT=9.33 min, assigned tentatively as 'S' ABS) (1.3 g, % ee 99.9) and 3-(6-(4-(morpholinomethyl)benzyl)-2-oxobenzo[cd]indol-1(2H)-yl)piperidine-2,6-dione Compound 220 (second eluted peak, RT=21.99 min, assigned tentatively as 'R' ABS) (1.3 g, % ee 99.76) as yellow solids which were transferred in 20 mL clear bar-coded glass vials and stored under Nitrogen Desiccators at approximately 22° C.

Example 120. Synthesis of 3[-20-[[4-(morpholinomethyl)phenyl]methyl]-25-oxo-27,30-diazatricyclododeca-(2),1(18),7(20),19(21),22(27)-pentaen-30-yl]piperidine-2,6-dione (Compound 221)

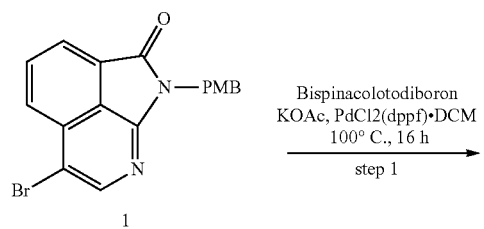

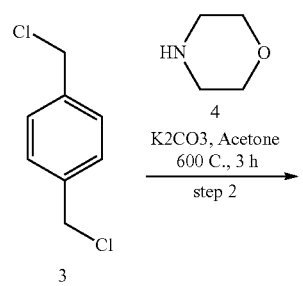

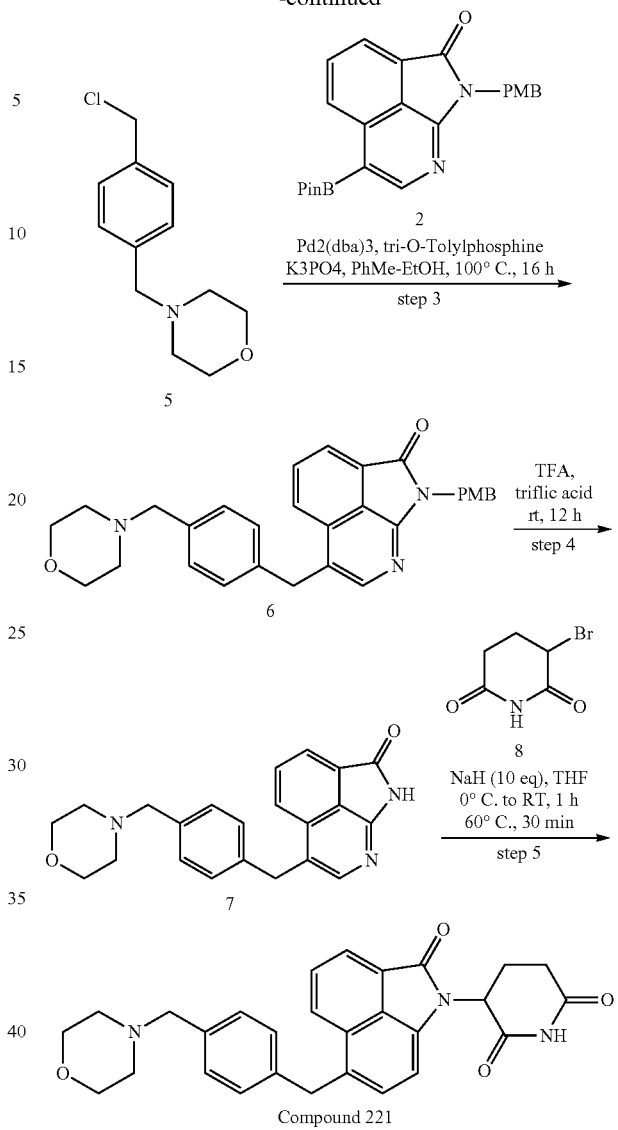

Step 1: Synthesis of 26-[(4-methoxyphenyl)methyl]-15-(4,4,5,5-tetramethyl-1,3,2-dioxaborolan-2-yl)-25,26-diazatricyclododeca-6,8(19),13(15),18(20),21(25)-pentaen-22-one (2): To a stirred solution of 14-bromo-19-[(4-methoxyphenyl)methyl]-18,19-diazatricyclododeca-1,3 (13),8(14),12(15),16(18)-pentaen-17-one (1) (1 g, 2.71 mmol) in 1,4 dioxane (20 mL) was added Bis(pinacolato) diboron (1.03 g, 4.06 mmol) followed by well dried potassium acetate (797.45 mg, 8.13 mmol, 507.93 uL). The resultant reaction mass was degassed well with argon for 15 minutes. cyclopentyl(diphenyl)phosphane; dichloromethane; dichloropalladium; iron (221.18 mg, 270.85 umol) was added and the reaction mass was heated at 100° C. for 16 hours. After completion of the reaction (monitored by TLC), the reaction mixture was cooled to RT, filtered through a pad of celite, washed with more Ethyl acetate. The combined filtrate was washed with cold water, dried over sodium sulphate and concentrated under reduced pressure to afford crude 26-[(4-methoxyphenyl)methyl]-15-(4,4,5,5-tetramethyl-1,3,2-dioxaborolan-2-yl)-25,26-diazatricyclododeca-6,8(19),13(15),18(20),21(25)-pentaen-22-one 2 (1.5 g(crude) g, 2.16 mmol, 79.82% yield, 60% purity) as brown gum. LC MS: ES+ 417.1.

Step 2: Synthesis of 4-[[4-(chloromethyl)phenyl]methyl] morpholine (3): To a stirred solution of morpholine 4 (5 g, 57.39 mmol, 5.02 mL) in dry grade ACETONE (200.0 mL) was added POTASSIUM CARBONATE (23.80 g, 172.18 mmol, 10.39 mL) at RT and the resultant reaction mixture was heated at 60° C. for 60 minutes. 1,4-bis(chloromethyl) benzene 3 (10.05 g, 57.39 mmol, 7.08 mL) was then added to the reaction mixture and heating was continued for 16 hours. After completion of reaction (monitored by TLC and LCMS), volatiles were removed under vacuum and the solid thus obtained was taken in Ethyl acetate (70 mL), washed with water (×3) and Brine, dried over anhydrous sodium sulfate and concentrated under reduced pressure. Crude mass was purified by column chromatography (silica, gradient: 10-30% Ethyl acetate in Hexane) to afford 4-[[4-(chloromethyl)phenyl]methyl]morpholine 5 (6.1 g, 25.67 mmol, 44.73% yield, 95% purity) as colourless sticky solid. LC MS: ES+ 226.09.

Step 3: Synthesis of 32-[(4-methoxyphenyl)methyl]-26-[[4-(morpholinomethyl)phenyl]methyl]-30,32-diazatricyclododeca-1(3),2(24),12(26),25(27),28(30)-pentaen-29-one: To a well degassed solution of 4-[[4-(chloromethyl)phenyl]methyl]morpholine 5 (400 mg, 1.77 mmol) and 26-[(4-methoxyphenyl)methyl]-15-(4,4,5,5-tetramethyl-1,3,2-dioxaborolan-2-yl)-25,26-diazatricyclododeca-6(8),7(18),13(15),19,21(25)-pentaen-22-one 2 (1.48 g, 3.54 mmol) in ethanol (5.0 mL)-Toluene (10 mL), Potassium phosphate tribasic anhydrous (1.13 g, 5.32 mmol) was added followed by the addition Tri-o-Tolyl phosphine (107.88 mg, 354.43 umol) and (1E,4E)-1,5-diphenylpenta-1,4-dien-3-one; palladium (162.28 mg, 177.22 umol). The resulting mixture was then heated at 90° C. for 12 hours. After completion of reaction (as monitored by LCMS), the reaction mixture was filtered through a bed of celite, washed with Ethyl acetate (100 mL). The combined filtrate was washed with water (3×20 mL) and brine (2×15 mL), dried over anhydrous sodium sulfate and concentrated under reduced pressure. Crude mass was purified by column chromatography (silica, gradient: 0-5% MeOH in DCM) to obtain 32-[(4-methoxyphenyl)methyl]-26-[[4-(morpholinomethyl)phenyl]methyl]-30,32-diazatricyclododeca-1(3),2(24),12(26),25(27),28(30)-pentaen-29-one 6 (420 mg, 788.21 umol, 44.48% yield, 90% purity) as yellow solid and stored in a round bottom glass at rt. LC MS: ES+ 480.1.

Step 4: Synthesis of 18-[[4-(morpholinomethyl)phenyl]methyl]-22,23-diazatricyclododeca-(2),1(16),7(18),17(19),20(22)-pentaen-21-one (7): To the stirred solution of 3 2-[(4-methoxyphenyl)methyl]-26-[[4-(morpholinomethyl)phenyl]methyl]-30,32-diazatricyclododeca-1(3),2(24),12(26),25(27),28(30)-pentaen-29-one 6 (420 mg, 875.79 umol) in TFA (10 mL) Triflic acid (1.97 g, 13.14 mmol, 1.15 mL) drop wise and the reaction mixture was stirred at 25° C. for 16 hours. After completion of reaction, the reaction mixture was evaporated and quenched with saturated sodium bicarbonate solution. Aqueous part was extracted with ethyl acetate (3×25 mL), washed with water followed by brine. The organic part was dried over sodium sulphate and concentrated to afford crude 18-[[4-(morpholinomethyl)phenyl]methyl]-22,23-diazatricyclododeca-(2),1(16),7(18),17(19),20(22)-pentaen-21-one 7 (230 mg, 531.13 umol, 60.65% yield, 83% purity) as brown solid. LC MS: ES+ 360.2.

Step 5: Synthesis of 3-[20-[[4-(morpholinomethyl)phenyl]methyl]-25-oxo-27,30-diazatricyclododeca-(2),1(18),7(20),19(21),22(27)-pentaen-30-yl]piperidine-2,6-dione: To a cooled solution of 18-[[4-(morpholinomethyl)phenyl]methyl]-22,23-diazatricyclododeca-(2),1(16),7(18),17(19), 20(22)-pentaen-21-one 7 (200 mg, 556.45 umol) in dry THF (20 mL), Sodium hydride (in oil dispersion) 60% dispersion in mineral oil (213.21 mg, 5.56 mmol, 60% purity) was added portion wise, maintaining the temp <5° C. Once the addition is over, the resultant mixture was stirred for 15 minutes at RT. Then the reaction mixture was again cooled to 0° C. and 3-bromopiperidine-2,6-dione 8 (534.22 mg, 2.78 mmol) was added to it portion wise. After complete addition, resulting solution was heated at 70° C. 1 hour. After completion (evidenced from TLC), the reaction mixture was cooled to 0° C. and quenched with the addition of ice cooled water. Aqueous part was extracted with ethyl acetate (3×50 mL). Combined organics was separated, dried over sodium sulphate and concentrated under reduced pressure. Crude mass was purified by flash chromatography (silica, gradient: 0-2.5% MeOH in DCM) to afford Racemic 3-[20-[[4-(morpholinomethyl)phenyl]methyl]-25-oxo-27,30-diazatricyclododeca-(2),1(18),7(20),19(21),22(27)-pentaen-30-yl]piperidine-2,6-dione Compound 221 (16 mg, 31.87 umol, 5.73% yield, 93.73% purity). $^1$H NMR (400 MHz, DMSO-d6) δ 11.11 (s, 1H), 8.24 (d, J=8.2 Hz, 1H), 8.15-8.12 (m, 2H), 7.97 (t, J=7.6 Hz, 1H), 7.27 (d, J=7.88 Hz, 2H), 7.19 (d, J=7.84 Hz, 2H), 5.40 (dd, J=12.68, 5.36 Hz, 1H), 4.29 (s, 2H), 3.52-3.51 (m, 4H), 3.40 (s, 2H), 2.97-2.83 (m, 2H), 2.67-2.63 (m, 1H), 2.32-2.28 (m, 4H), 2.14-2.11 (m, 1H); LC MS: ES+ 471.6.

Example 121. Synthesis of 3-[23-[[4-(1-oxa-8-azaspiro[4.5]decan-8-ylmethyl)phenyl]methyl]-28-oxo-31,34-diazatricyclododeca-(2),1(21),7(23),22(24),25(31)-pentaen-34-yl]piperidine-2,6-dione (Compound 222)

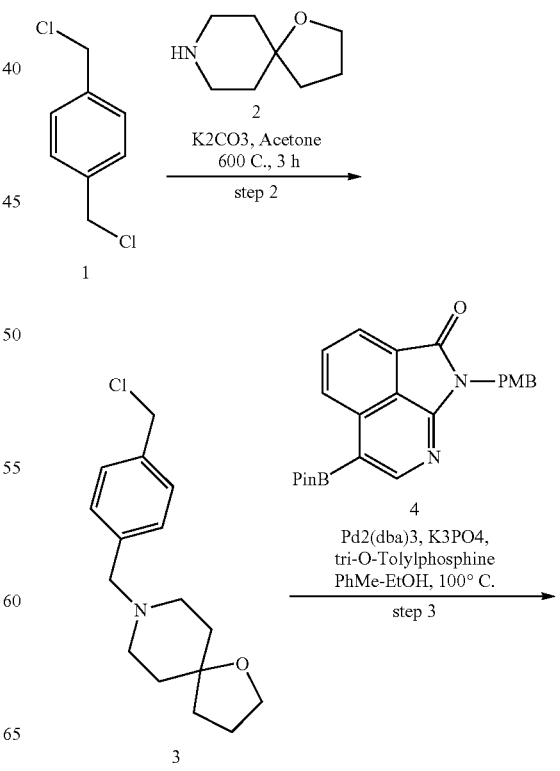

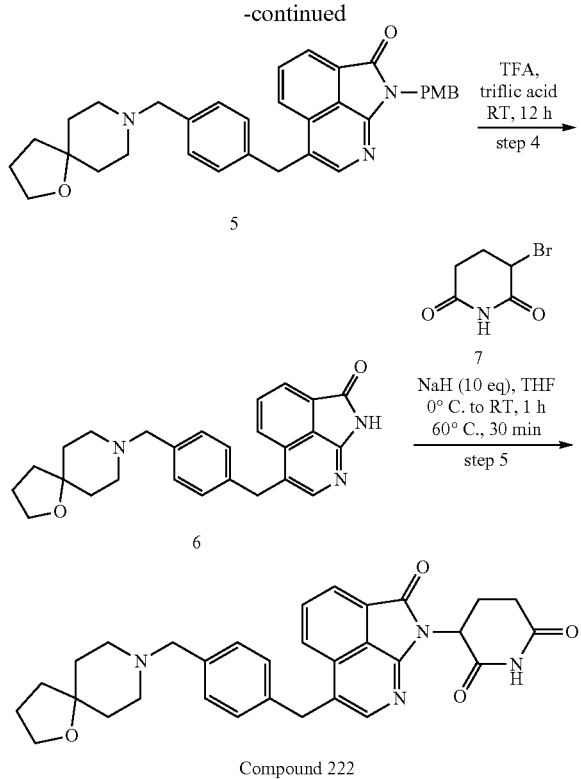

Step 1: Synthesis of 8-(4-(chloromethyl)benzyl)-1-oxa-8-azaspiro[4.5]decane: To the stirred solution of 1-oxa-8-azaspiro[4.5]decane; hydrochloride 1 (1.0 g, 5.63 mmol) in Acetone (10 mL) was added and stirred at 60° C. for 20 minutes followed by the addition of 1,4-bis(chloromethyl) benzene 2 (1.97 g, 11.26 mmol, 1.39 mL).Resulting solution was further heated at same temperature for 4 hr. After formation of desired pdt, as evidenced from LCMS, volatiles were removed and re-dissolved in ethyl acetate. Organic portion was washed with eater/brine and separated, dried over sodium sulfate and concentrated. Crude Residue was purified by column chromatography to afford 8-[[4-(chloromethyl)phenyl]methyl]-1-oxa-8-azaspiro[4.5]decane 3 (861 mg, 2.95 mmol, 52.49% yield, 96% purity) as yellow gum. $^1$H NMR (400 MHz, DMSO-d6) δ 7.36 (d, J=7.8 Hz, 2H), 7.28 (d, J=7.72 Hz, 2H), 4.73 (s, 2H), 3.67 (t, J=Hz, 2H), 3.44 (s, 2H), 2.39 (br s, 2H), 2.31 (br s, 2H), 1.85-1.78 (m, 2H), 1.62-1.59 (m, 2H), 1.53-1.51 (m, 4H);

Step 2: Synthesis of 36-[(4-methoxyphenyl)methyl]-29-[[4-(1-oxa-8-azaspiro[4.5]decan-8-ylmethyl)phenyl]methyl]-34,36-diazatricyclododeca-1(3),2(27),12(29),28(30),31(34)-pentaen-32-one: To a well degassed solution of 8-[[4-(chloromethyl)phenyl]methyl]-1-oxa-8-azaspiro[4.5]decane 3 (400 mg, 1.43 mmol) and 26-[(4-methoxyphenyl)methyl]-15-(4,4,5,5-tetramethyl-1,3,2-dioxaborolan-2-yl)-25,26-diazatricyclododeca-6(8),7(18),13(15),19,21(25)-pentaen-22-one 4 (1.19 g, 2.86 mmol) in ethanol (5.0 mL), Potassium phosphate tribasic anhydrous (910.37 mg, 4.29 mmol) was added followed by the addition Tri-o-Tolyl phosphine (87.02 mg, 285.91 umol) and (1E,4E)-1,5-diphenylpenta-1,4-dien-3-one; palladium (130.91 mg, 142.96 umol). The resulting mixture was then heated at 90° C. for 12 hours. After completion of reaction (as monitored by LCMS), the reaction mixture was filtered through a bed of celite, washed with Ethyl acetate (100 mL). The combined filtrate was washed with water (3×20 mL) and brine (2×15 mL), dried over anhydrous sodium sulfate and concentrated under reduced pressure. Crude mass was purified by column chromatography (silica, gradient:0-5% MeOH in DCM) to obtain 36-[(4-methoxyphenyl)methyl]-29-[[4-(1-oxa-8-azaspiro[4.5]decan-8-ylmethyl)phenyl]methyl]-34,36-diazatricyclododeca-1(3),2(27),12(29),28(30),31(34)-pentaen-32-one 5 (300 mg, 505.94 umol, 35.39% yield, 90% purity) as yellow solid and stored in a round bottom glass at rt. LC MS: ES+ 534.2.

Step 3: Synthesis of 21-[[4-(1-oxa-8-azaspiro[4.5]decan-8-ylmethyl)phenyl]methyl]-26,27-diazatricyclododeca-(2),1(19),7(21),20(22),23(26)-pentaen-24-one: To the stirred solution of 36-[(4-methoxyphenyl)methyl]-29-[[4-(1-oxa-8-azaspiro[4.5]decan-8-ylmethyl)phenyl]methyl]-34,36-diazatricyclododeca-1(3),2(27),12(29),28(30),31(34)-pentaen-32-one 5 (300 mg, 562.16 umol) in TFA (10 mL) Triflic acid (1.27 g, 8.43 mmol, 740.07 uL) was added drop wise. The reaction mixture was stirred at 25° C. for 16 hours. After completion of reaction, the reaction mixture was evaporated and quenched with saturated sodium bicarbonate solution and extracted with ethyl acetate (3×25 mL), washed with water followed by brine. The organic part was dried over sodium sulphate and concentrated to afford crude 21-[[4-(1-oxa-8-azaspiro[4.5]decan-8-ylmethyl)phenyl]methyl]-26,27-diazatricyclododeca-(2),1(19),7(21),20(22),23(26)-pentaen-24-one 6 (216 mg, 511.91 umol, 91.06% yield, 98% purity) as brown solid. LC MS: ES+ 414.1.

Step 4: Synthesis of 3-[23-[[4-(1-oxa-8-azaspiro[4.5]decan-8-ylmethyl)phenyl]methyl]-28-oxo-31,34-diazatricyclododeca-(2),1(21),7(23),22(24),25(31)-pentaen-34-yl]piperidine-2,6-dione: To a ice cooled solution of 21-[[4-(1-oxa-8-azaspiro[4.5]decan-8-ylmethyl)phenyl]methyl]-26,27-diazatricyclododeca-(2),1(19),7(21),20(22),23(26)-pentaen-24-one 6 (70 mg, 169.28 umol) in dry THF (3.0 mL),Sodium hydride (in oil dispersion) 60% dispersion in mineral oil (67.71 mg, 1.69 mmol, 60% purity) was added portion wise, maintaining the temp <5° C. Once the addition is over, the resultant mixture was stirred for 15 minutes at RT. Then the reaction mixture was again cooled to 0° C. and 3-bromopiperidine-2,6-dione 7 (162.52 mg, 846.41 umol) was added to it portion wise. After complete addition, resulting solution was heated at 70° C. for 1 hour. After completion (evidenced from TLC), the reaction mixture was again cooled to 0° C. and quenched with ice cooled water (20 mL). Aqueous part was extracted with ethyl acetate (3×50 mL). Combined extracts was dried over anhydrous sodium sulfate and concentrated under reduced pressure. Crude mass was purified by Prep TLC (silica, gradient: 80% Ethylacetate in DCM) to afford 3-[23-[[4-(1-oxa-8-azaspiro[4.5]decan-8-ylmethyl)phenyl]methyl]-28-oxo-31,34-diazatricyclododeca-(2),1(21),7(23),22(24),25(31)-pentaen-34-yl]piperidine-2,6-dione Compound 222 (7.0 mg, 12.44 umol, 7.35% yield, 93.24% purity) as yellow solid which was stored in a round bottomed flask at 5° C. inside a refrigerator. $^1$H NMR (400 MHz, DMSO-d6) δ 11.12 (s, 1H), 8.24 (d, J=8.08 Hz, 1H), 8.15-8.12 (m, 2H), 7.99-7.96 (m, 1H), 7.26-7.19 (m, 4H), 5.40 (dd, J=12.44, 5.36 Hz, 1H), 4.30 (s, 2H), 3.67-3.64 (m, 2H), 3.34-3.32 (m, 2H), 3.00-2.84 (m, 2H), 2.67-2.63 (m, 1H), 2.42-2.13 (m, 5H), 1.82-1.81 (m, 2H), 1.60-1.59 (m, 2H), 1.50-1.49 (m, 4H); LC MS: ES+ 525.2.

Example 122. Synthesis of 3-[6-[[1-[1-(1-cyclopropylcyclopropyl)-4-piperidyl]pyrazol-4-yl]methyl]-2-oxo-benzo[cd]indol-1-yl]piperidine-2,6-dione (Compound 223)

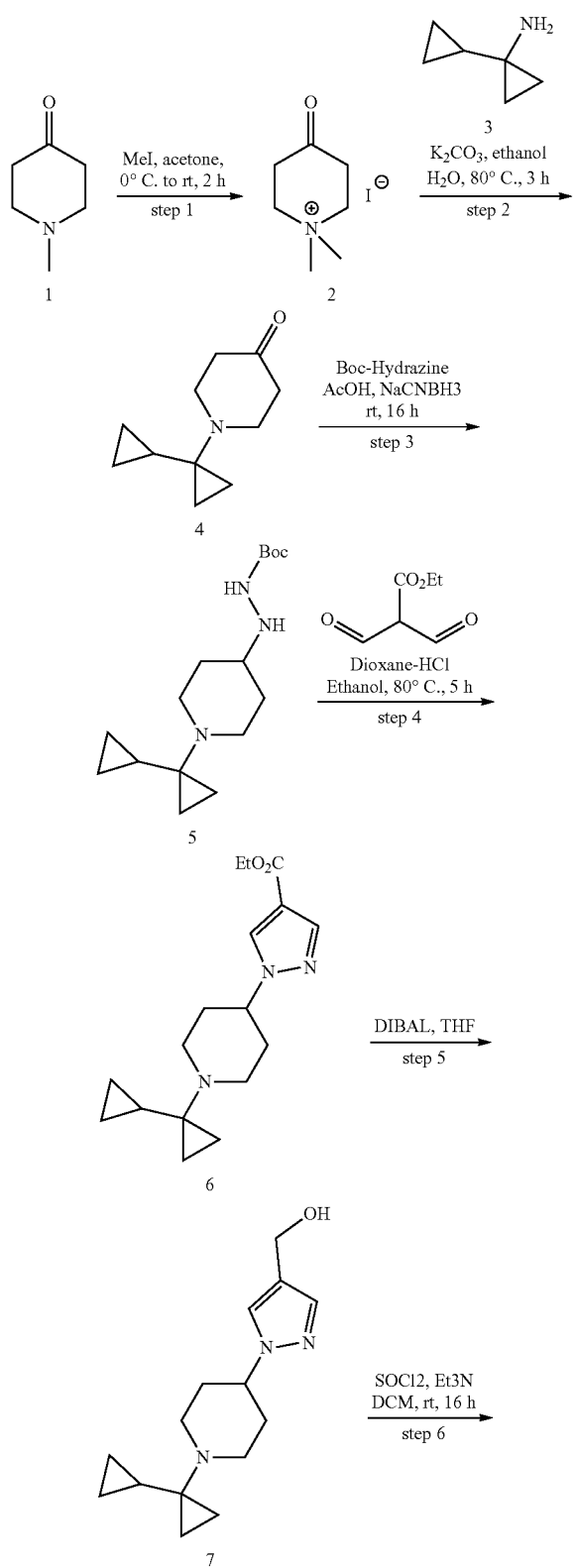

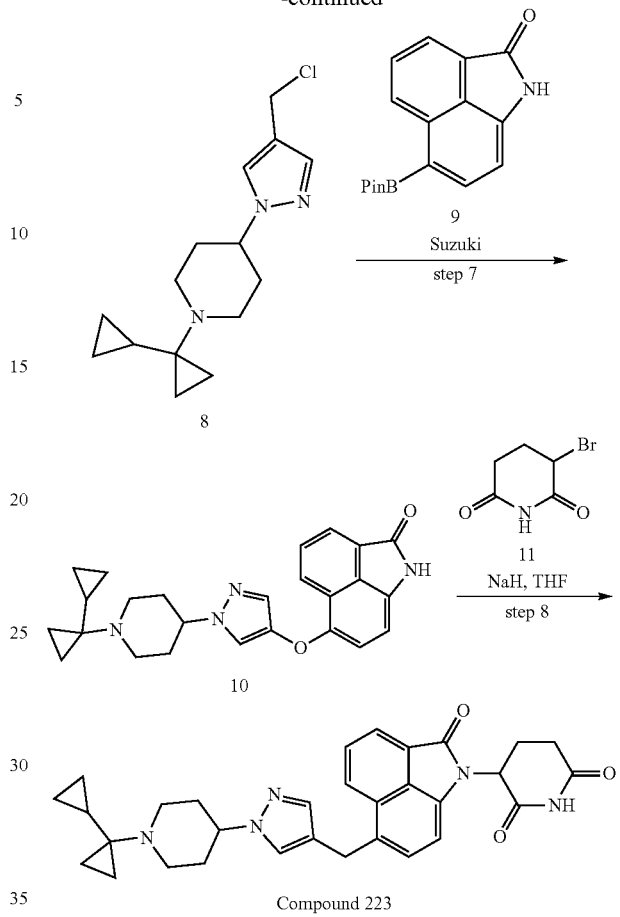

Step 1: Synthesis of 1,1-dimethyl-4-oxopiperidin-1-ium iodide: To the stirred solution of 1-methyl-piperidine-4-one 1 (2.3 g, 20.35 mmol) in 15 ml of acetone was cooled to 0° C. and add 1.3 ml of Methyl iodide slowly into the reaction mixture and then it was stirred at ambient temperature for 24 hours. The reaction mass was then concentrated and filtered through sintered and then the solid compound was dried under vacuum to afford 1,1-dimethyl-piperidine-4-one 2 (4.0 g) as brown solid.

Step 2: Synthesis of 1-(1-cyclopropylcyclopropyl)piperidin-4-one: To the stirred solution of N-chloro-1-cyclopropyl-cyclopropanamine 3 (2.0 g, 14.97 mmol) and 1-iodo-1,1-dimethyl-1$^{5}$-azinan-4-one 2 (3.82 g, 14.97 mmol) in Ethanol (50.0 mL) and Potassium carbonate—granular (2.48 g, 17.96 mmol, 1.08 mL) in solution of Water (24.0 mL) was added and the reaction mixture was then heated at 80° C. for 3 hours. Reaction mass was then cooled to room temperature and then it was diluted with ethyl acetate and the layers were separated. It was dried over sodium sulfate and concentrated under reduced pressure at a very low temperature. Then again it was extracted with dichloromethane and with a very little amount of water and then dried over sodium sulfate. The crude was then triturated with diethyl ether and then decanted part was concentrated under reduced pressure to afford 1-(1-cyclopropylcyclopropyl)piperidin-4-one 4 (2.2 g, 10.34 mmol, 69.06% yield, 84.22% purity) as brown liquid and it was used for the next step without purification. LC MS: ES+ 179.8. NOTE: All the concentration processes were done in a very low temperature.

Step 3: Synthesis of tert-butyl N-[[1-(1-cyclopropylcyclopropyl)-4 piperidyl]amino]carbamate: To the stirred solution of 1-(1-cyclopropylcyclopropyl)piperidin-4-one 4 (600.0 mg, 3.35 mmol) in Acetic Acid (7.0 mL) was added tert-butyl N-aminocarbamate (442.36 mg, 3.35 mmol) and then it was stirred at 25° C. for 2 hours. Sodium cyanoborohydride (252.41 mg, 4.02 mmol) was added in portion wise manner. After the addition process was done it was stirred at 25° C. for 16 hours. The reaction mass then concentrated under reduced pressure and then 5(N) NaOH was added just to maintain pH-8 and extracted with dichloromethane. Organic layer was separated and then it was dried over anhydrous sodium sulfate and then it was concentrated under reduced pressure to afford the crude material. The crude was then purified by column chromatography eluting 6-7% MeOH in DCM to afford tert-butyl N-[[1-(1-cyclopropylcyclopropyl)-4-piperidyl]amino]carbamate 5 (650.0 mg, 2.20 mmol, 65.74% yield, 100% purity) as brown sticky material. LC MS: ES+ 295.8.

Step 4: Synthesis of ethyl 1-[1-(1-cyclopropylcyclopropyl)-4-piperidyl]pyrazole-4-carboxylate: To the stirred solution of tert-butyl N-[[1-(1-cyclopropylcyclopropyl)-4-piperidyl]amino]carbamate 5 (620.0 mg, 2.10 mmol) in Ethanol (24 mL) was added ethyl 2-formyl-3-oxo-propanoate (302.48 mg, 2.10 mmol, 264.63 uL) and then 4M Dioxane-HCl (12 mL) at 25° C. and then the reaction mass was stirred at 75° C. for 5 hours. Reaction mass was then concentrated under reduced pressure and then it was extracted with ethyl acetate and the organic layer was washed with saturated sodium bicarbonate solution and then it was dried over anhydrous sodium sulfate and concentrated under reduced pressure to afford the crude material. The crude was then purified by column chromatography by eluting 5-7% MeOH in DCM to afford ethyl 1-[1-(1-cyclopropylcyclopropyl)-4-piperidyl]pyrazole-4-carboxylate 6 (550.0 mg, 1.60 mmol, 76.37% yield, 88.41% purity) as a white solid; LC MS: ES+ 303.9.

Step 5: Synthesis of [1-[1-(1-cyclopropylcyclopropyl)-4-piperidyl]pyrazol-4-yl]methanol: To the stirred solution of ethyl 1-[1-(1-cyclopropylcyclopropyl)-4-piperidyl]pyrazole-4-carboxylate 6 (2.2 g, 7.25 mmol) in THF (35.0 mL) was added DIBAL (20.63 g, 36.26 mmol, 29.42 mL, 25% purity) at −78° C. drop wise manner and then it was stirred at -50 to −65° C. for 1 hour. Reaction mass was then diluted with ethyl acetate and poured into a conical containing ice and then to it Rochelle salt was added. It was stirred at ambient temperature for 1 hour. Then the layers were separated and the organic fraction was dried over anhydrous sodium sulfate, concentrated under reduced pressure to afford [1-[1-(1-cyclopropylcyclopropyl)-4-piperidyl]pyrazol-4-yl]methanol 7 (1.8 g, 6.47 mmol, 89.16% yield, 93.88% purity) as brown solid. It was used for the next step without purification; LC MS: ES+ 261.9.

Step 6: Synthesis of 4-[4-(chloromethyl)pyrazol-1-yl]-1-(1-cyclopropylcyclopropyl)piperidine: N,N-Diisopropylethylamine (1.48 g, 11.48 mmol, 2.00 mL) was added by syringe to a stirred solution of [1-[1-(1-cyclopropylcyclopropyl)-4-piperidyl]pyrazol-4-yl]methanol 7 (2.0 g, 7.65 mmol) in DCM (50.0 mL) at 0° C. under nitrogen, followed by Methanesulfonyl chloride, 98% (876.56 mg, 7.65 mmol, 592.27 uL) neat by syringe and stirred the reaction mix at room temperature for overnight. The reaction was diluted with 100 ml DCM and cooled the reaction mix then the reaction mix was washed with 2(N) HCl and with saturated NaHCO3solution. The organics were isolated, dried over Na$_2$SO$_4$ and concentrated to afford the crude compound 4-[4-(chloromethyl)pyrazol-1-yl]-1-(1-cyclopropylcyclopropyl)piperidine 8 (1.7 g, 4.25 mmol, 55.58% yield, 70% purity) as light yellow gum; LC MS: ES+ 281.1.

Step 7: Synthesis of 6-[[1-[1-(1-cyclopropylcyclopropyl)-4-piperidyl]pyrazol-4-yl]methyl]-1H-benzo[cd]indol-2-one: To a stirred solution of 4-[4-(chloromethyl)pyrazol-1-yl]-1-(1-cyclopropylcyclopropyl)piperidine 8 (800 mg, 2.86 mmol) and 6-(4,4,5,5-tetramethyl-1,3,2-dioxaborolan-2-yl)-1H-benzo[cd]indol-2-one 9 (1.69 g, 5.72 mmol) in ethanol (2.0 mL) and Toluene (4.0 mL) was added Potassium phosphate tribasic anhydrous (1.82 g, 8.58 mmol) and the reaction mass was degassed under nitrogen atmosphere over 10 minutes. Then Tri-o-Tolyl phosphine (174.05 mg, 571.82 umol) and (1E,4E)-1,5-diphenylpenta-1,4-dien-3-one; palladium (261.81 mg, 285.91 umol) was added to this reaction mass and the resultant reaction mixture was heated 90° C. for overnight. Reaction mix was filtered through sintered funnel using celite bed and the filtrate was diluted with ethyl acetate, washed with water. The organic part was dried over Na$_2$SO$_4$, filtered and evaporated under reduced pressure. Crude material was purified by combi-flash chromatography to get the pure compound 6-[[1-[1-(1-cyclopropylcyclopropyl)-4-piperidyl]pyrazol-4-yl]methyl]-1H-benzo[cd]indol-2-one 10 (98 mg, 213.80 umol, 7.48% yield, 90% purity) as greenish solid. LC MS: ES+ 413.4.

Step 8: Synthesis of 3-[6-[[1-[1-(1-cyclopropylcyclopropyl)-4-piperidyl]pyrazol-4-yl]methyl]-2-oxo-benzo[cd]indol-1-yl]piperidine-2,6-dione: To a ice cooled solution of 6-[[1-[1-(1-cyclopropylcyclopropyl)-4-piperidyl]pyrazol-4-yl]methyl]-1H-benzo[cd]indol-2-one 10 (98 mg, 237.56 umol) in dry THF (5.0 mL), Sodium hydride (in oil dispersion) 60% dispersion in mineral oil (91.03 mg, 2.38 mmol, 60% purity) was added portion wise, maintaining the temp <5° C. Once the addition is over, the resultant mixture was stirred for 15 minutes at RT. Then the reaction mixture was again cooled to 0° C. and 3-bromopiperidine-2,6-dione 11(228.07 mg, 1.19 mmol) was added to it portion wise. After complete addition, resulting solution was heated at 70° C. for 1 hour. After completion (evidenced from TLC), the reaction mixture was again cooled to 0° C. and quenched with ice cooled water (20 mL). Aqueous part was extracted with ethyl acetate (3×50 mL). Combined extracts was dried over anhydrous sodium sulfate and concentrated under reduced pressure. Crude mass was purified by Prep TLC (silica, gradient: 80% Ethyl acetate in DCM) to afford 3-[6-[[1-[1-(1-cyclopropylcyclopropyl)-4-piperidyl]pyrazol-4-yl]methyl]-2-oxo-benzo[cd]indol-1-yl]piperidine-2,6-dione Compound 223 (17 mg, 30.67 umol, 12.91% yield, 94.46% purity) as yellow solid which was stored in a round bottomed flask at 5° C. inside a refrigerator. $^1$H NMR (400 MHz, DMSO-d6) δ 11.11 (s, 1H), 8.37 (d, J=8.28 Hz, 1H), 8.08 (d, J=6.96 Hz, 1H), 7.82 (t, J=7.6 Hz, 1H), 7.56 (s, 1H), 7.35 (d, J=7.32 Hz, 1H), 7.28 (s, 1H), 7.06 (d, J=7.24 Hz, 1H), 5.43 (dd, J=12.72, 5.08 Hz, 1H), 4.17 (s, 2H), 4.01-3.99 (m, 1H), 2.99-2.86 (m, 3H), 2.79-2.62 (m, 4H), 2.09-2.06 (m, 1H), 1.90-1.87 (m, 2H), 1.72-1.69 (m, 2H), 1.24-1.23 (m, 1H), 0.30 (br s, 4H), 0.23 (br s, 2H), 0.09 (br s, 2H); LC MS: ES+ 524.7.

Example 123. General Synthesis of Compound 224-Compound 231

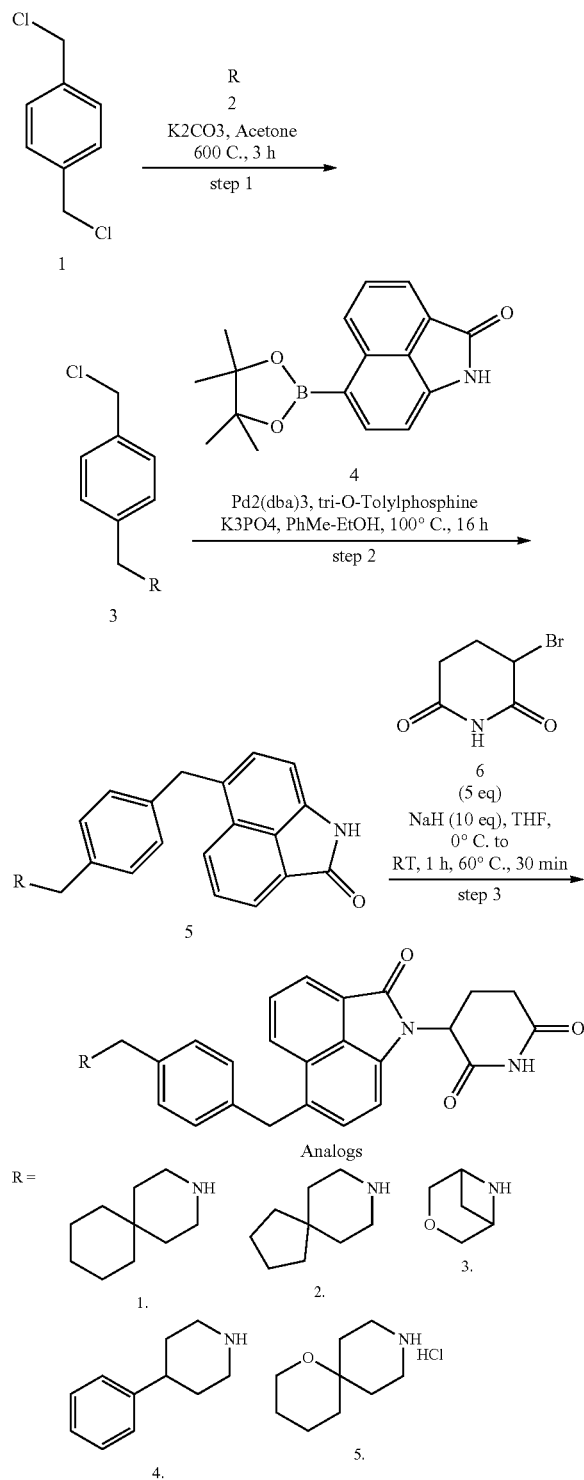

Step 1: To a stirred solution of Amine 2 (1 eq) in dry grade acetone (15 mL) was added Potassium carbonate, anhydrous, 99% (3 eq) at RT and the resultant reaction mixture was heated at 50° C. for 20 minutes. 1,4-bis(chloromethyl) benzene (1) (1 eq) was then added to the reaction mixture and heating was continued for 3 hours. After completion of reaction (monitored by TLC and LCMS), volatiles were removed under vacuum and the solid thus obtained was taken in Ethyl acetate (50 mL), washed with water (3×25 ml) and Brine (2×15 mL), dried over anhydrous sodium sulfate and concentrated under reduced pressure. Crude mass was purified by column chromatography (silica, gradient: 10-30% Ethyl acetate in Hexane) to afford (3) as colorless sticky solid which was stored in a round bottomed flask at 5° C. inside a refrigerator.

Step 2: To a well degassed solution of (3) (1 eq) and 6-(4,4,5,5-tetramethyl-1,3,2-dioxaborolan-2-yl)-1H-benzo[cd]indol-2-one (4) (2 eq) in Ethanol (2 mL)-Toluene (4 mL), Potassium phosphate tribasic, anhydrous, (3 eq) was added followed by the addition of Tri-o-Tolyl phosphine (0.2 eq) and Pd2(dba)3 (0.1 eq). The resulting mixture was then heated at 90° C. for 12 hours. After completion of reaction (as monitored by LCMS), the reaction mixture was filtered through a bed of celite, washed with Ethyl acetate. The combined filtrate was then washed with water and brine, dried over anhydrous sodium sulfate and concentrated under reduced pressure. Crude mass was purified by column chromatography (silica, gradient: 0-20% Ethyl acetate in DCM) to obtain (5) as yellow solid which was stored in a Tarson plastic bottle at ambient temperature.

Step 3: To an ice cooled solution of (5) (1 eq) in dry THF (4 mL), Sodium hydride (60% dispersion in mineral oil) (10 eq) was added portion wise, maintaining the temp <5° C. Once the addition is over, the resultant mixture was stirred for 15 minutes at RT. Then the reaction mixture was again cooled to 0° C. and 3-bromopiperidine-2,6-dione (6) (5 eq) was added to it portion wise. After complete addition, resulting solution was heated at 70° C. for 1 hour. After completion (evidenced from TLC), the reaction mixture was again cooled to 0° C. and quenched with ice cooled water. Aqueous part was extracted with ethyl acetate. Combined extracts was dried over anhydrous sodium sulfate and concentrated under reduced pressure. Crude mass was purified by flash chromatography (silica, gradient: 2.5% MeOH in DCM) to afford an analog as yellow solid which was stored in a round bottomed flask at 5° C. inside a refrigerator.

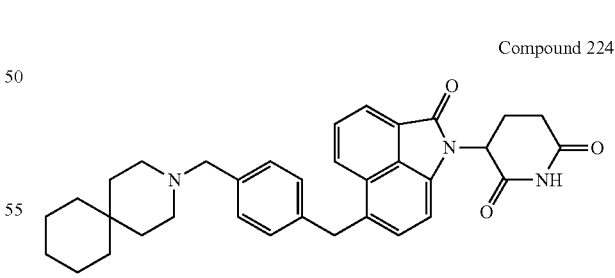

Compound 224

(55 mg, 98.74 umol, 26.53% yield, 96.17% purity) as yellow solid. $^1$H NMR (400 MHz, DMSO-d6) δ 11.12 (s, 1H), 8.28 (d, J=8.28 Hz, 1H), 8.07 (d, J=6.96 (Hz, 1H), 7.80 (t, J=7.76 Hz, 1H), 7.41 (d, J=7.28 Hz, 1H), 7.24-7.21 (m, 4H), 7.10 (d, J=7.28 Hz, 1H), 5.44 (dd, J=12.72, 5.0 Hz, 1H), 4.38 (s, 2H), 3.38 (br s, 2H), 2.99-2.90 (m, 1H), 2.8-2.62 (m, 3H), 2.49-2.32 (br m, 4H), 2.1-2.07 (m, 1H), 1.34 (br, 9H), 1.26-1.23 (br m, 4H); LC MS: ES+ 536.3.

Compound 225

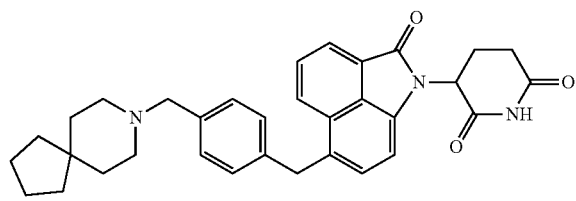

(42.0 mg, 78.75 umol, 21.55% yield, 97.81% purity) as yellow solid. $^1$H NMR (400 MHz, DMSO-d6) δ 11.13 (s, 1H), 8.31 (d, J=8.16 Hz, 1H), 8.07 (d, J=6.96 Hz, 1H), 7.80 (t, J=7.68 Hz, 1H), 7.40 (d, J=7.48 Hz, 1H), 7.22-7.17 (m, 4H), 7.10 (d, J=7.28 Hz, 1H), 5.44 (dd, J=12.72, 5.36 Hz, 1H), 4.37 (s, 2H), 3.34 (s, 2H), 2.98-2.90 (m, 1H), 2.76-2.62 (m, 2H), 2.246 (br m, 4H), 2.10-2.07 (m, 1H), 1.528 (br s, 4H), 1.34-1.32 (m, 8H); LC MS: ES+ 522.6.

Compound 226

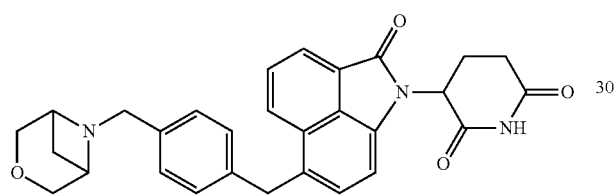

(23.0 mg, 45.78 umol, 33.92% yield, 95.85% purity) as yellow solid. $^1$H NMR (400 MHz, DMSO-d6) δ 11.11 (s, 1H), 8.33 (d, J=8.16 Hz, 1H), 8.07 (d, J=7.04 Hz, 1H), 7.80 (t, J=7.92 Hz, 1H), 7.40 (d, J=7.24 Hz, 1H), 7.23 (m, 4H), 7.10 (d, J=7.32 Hz, 1H), 5.44-5.42 (m, 1H), 4.37-4.35 (br s, 4H), 3.63 (s, 2H), 2.98-2.88 (m, 3H), 2.80-2.49 (m, 5H), 2.21 (d, J=7.4 Hz, 1H), 2.10 (br, 1H); LC MS: ES+ 482.2.

Compound 227

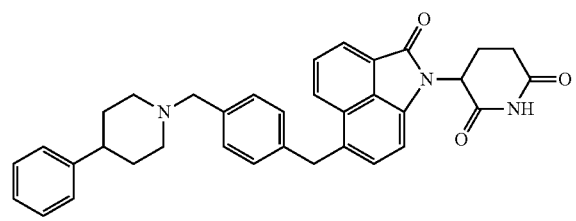

(82 mg, 144.32 umol, 31.21% yield, 95.68% purity) as yellow solid. $^1$H NMR (400 MHz, DMSO-d6) δ 11.12 (s, 1H), 8.34 (d, J=8.2 Hz, 1H), 8.07 (d, J=7.0 Hz, 1H), 7.81 (t, J=7.84 Hz, 1H), 7.42 (d, J=7.4 Hz, 1H), 7.27-7.10 (m, 10H), 5.44 (dd, J=12.6, 4.8 Hz, 1H), 4.39 (s, 2H), 3.36 (br s, 2H), 2.98-2.92 (m, 3H), 2.79-2.62 (m, 3H), 2.32-2.08 (br m, 3H), 1.90 (m, 4H), LC MS: ES+544.3.

Compound 228

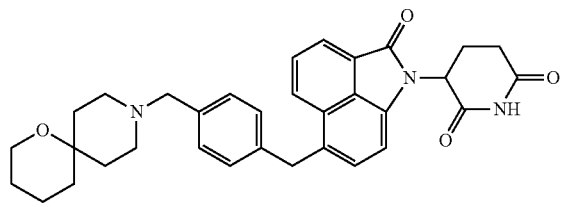

(32.0 mg, 58.15 umol, 25.84% yield, 97.70% purity) as yellow solid. $^1$H NMR (400 MHz, DMSO-d6) δ 11.12 (s, 1H), 8.32 (d, J=8.28 Hz, 1H), 8.07 (d, J=7.08 Hz, 1H), 7.80 (t, J=7.68 Hz, 1H), 7.40 (d, J=7.16 Hz, 1H), 7.21-7.18 (m, 4H), 7.10 (d, J=7.4 Hz, 1H), 5.45-5.42 (m, 1H), 4.37 (s, 2H), 3.49 (m, 2H), 3.38 (br, 2H), 2.97-2.92 (m, 1H), 2.76-2.73 (m, 1H), 2.69-2.62 (m, 1H), 2.49-2.32 (br, 2H), 2.21-2.07 (br m, 3H), 1.52 (br, 2H), 1.39 (br m, 2H), 1.33-1.23 (m, 6H); LC MS: ES+ 538.5.

Compound 229

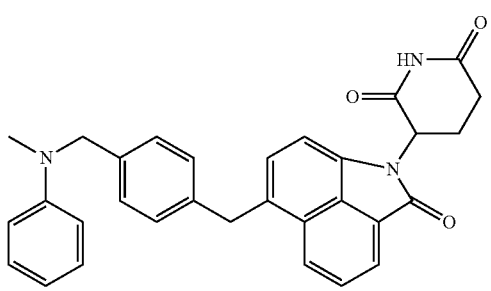

(60.0 mg, 122.03 umol, 23.09% yield, 99.57% purity) as yellow solid. $^1$H NMR (400 MHz, DMSO-d6) δ 11.11 (s, 1H), 8.31 (d, J=8.24 Hz, 1H), 8.06 (d, J=6.92 Hz, 1H), 7.79 (t, J=7.64 Hz, 1H), 7.38 (d, J=7.32 Hz, 1H), 7.22 (d, J=7.88 Hz, 2H), 7.13-7.07 (m, 5H), 6.66 (d, J=8.08 Hz, 2H), 6.57 (t, J=7.16 Hz, 1H), 5.43 (dd, J=12.72, 4.88 Hz, 1H), 4.47 (s, 2H), 4.35 (s, 2H), 2.94 (s, 3H), 2.93-2.91 (m, 1H), 2.79-2.62 (m, 2H), 2.09-2.06 (m, 1H); LC MS: ES+ 490.2.

Compound 230

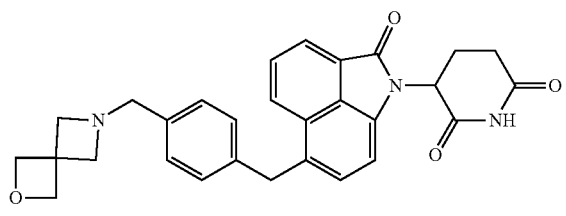

(65 mg, 133.77 umol, 38.71% yield, 99.10% purity) as yellow solid. $^1$H NMR (400 MHz, DMSO-d6) δ 11.12 (s, 1H), 8.30 (d, J=8.32 Hz, 1H), 8.07 (d, J=6.96 Hz, 1H), 7.80 (t, J=7.6 Hz, 1H), 7.39 (d, J=7.36 Hz, 1H), 7.20 (d, J=7.8 Hz, 2H), 7.13-7.09 (m, 3H), 5.44 (dd, J=12.68, 4.72 Hz, 1H), 4.55 (s, 4H), 4.36 (s, 2H), 3.39 (s, 2H), 3.20 (s, 4H), 2.98-2.90 (m, 1H), 2.79-2.62 (m, 2H), 2.10-2.07 (m, 1H); LC MS: ES+ 482.2.

Compound 231

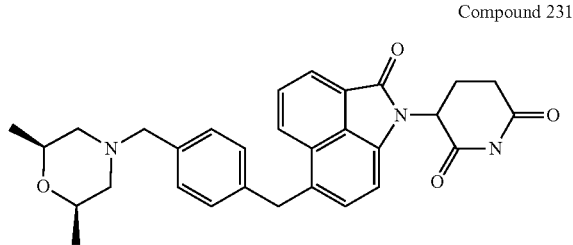 [SMILES: C[C@@H]1CN(Cc2ccc(Cc3ccc4c5c(cccc35)C(=O)N4C3CCC(=O)NC3=O)cc2)C[C@H](C)O1]

(44.0 mg, 85.60 umol, 15.04% yield, 96.80% purity) as yellow solid. ¹H NMR (400 MHz, DMSO-d6) δ 11.12 (s, 1H), 8.32 (d, J=8.16 Hz, 1H), 8.07 (d, J=6.92 Hz, 1H), 7.80 (t, J=7.62 Hz, 1H), 7.40 (d, J=7.32 Hz, 1H), 7.23 (d, J=7.88 Hz, 2H), 7.17 (d, J=7.6 Hz, 2H), 7.10 (d, J=7.2 Hz, 1H), 5.46-5.42 (m, 1H), 4.37 (s, 2H), 3.50-3.48 (m, 2H), 3.34 (s, 2H), 2.95-2.91 (m, 1H), 2.77-2.73 (m, 1H), 2.66-2.59 (m, 3H), 2.10-2.09 (m, 1H), 1.57 (t, J=10.62 Hz, 2H), 0.98 (d, J=6.16 Hz, 6H); LC MS: ES+ 498.5.

Example 124. Synthesis of 3-(6-(4-((4-(2-hydroxypropan-2-yl)piperidin-1-yl)methyl)benzyl)-2-oxobenzo[cd]indol-1(2H)-yl)piperidine-2,6-dione (Compound 232)

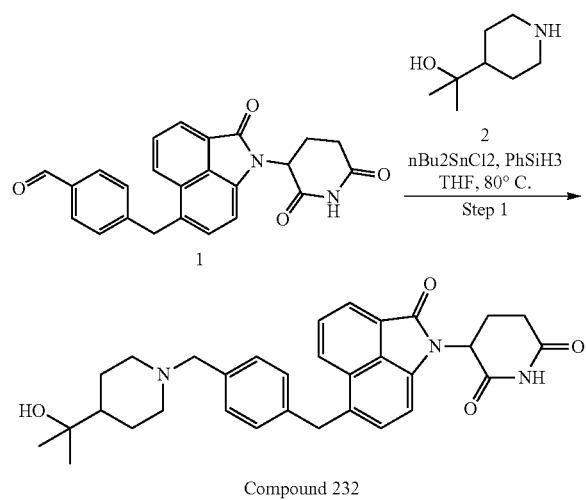

Compound 232

Step 1: Synthesis of 3-(6-(4-((4-(2-hydroxypropan-2-yl)piperidin-1-yl)methyl)benzyl)-2-oxobenzo[cd]indol-1(2H)-yl)piperidine-2,6-dione Compound 232 following general reductive amination procedure. (90.0 mg, 162.66 umol, 12.26% yield, 95.0% purity) as yellow solid. ¹H NMR (400 MHz, DMSO-d6) δ 11.11 (s, 1H), 8.32 (d, J=8.2 Hz, 1H), 8.07 (d, J=7.0 Hz, 1H), 7.80 (t, J=7.64 Hz, 1H), 7.40 (d, J=7.24 Hz, 1H), 7.25-7.17 (m, 4H), 7.10 (d, J=7.28 Hz, 1H), 5.44-5.41 (m, 1H), 4.37 (s, 2H), 4.00 (br s, 1H), 2.95-2.93 (m, 1H), 2.79-2.62 (m, 4H), 2.10-2.09 (m, 1H), 1.77-1.76 (m, 2H), 1.60-1.57 (m, 2H), 1.23-1.14 (m, 4H), 0.99 (s, 6H); LC MS: ES+526.2.

Example 125. Synthesis of 3-(6-((1-(1-((1-fluorocyclopropyl)methyl)-4-methylpiperidin-4-yl)-1H-pyrazol-4-yl)methyl)-2-oxobenzo[cd]indol-1(2H)-yl)piperidine-2,6-dione (Compound 106)

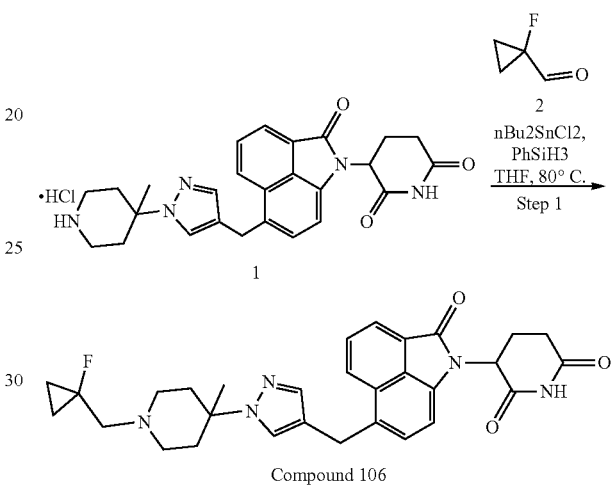

Compound 106

Step 1: Synthesis of 3-(6-((1-(1-((1-fluorocyclopropyl)methyl)-4-methylpiperidin-4-yl)-1H-pyrazol-4-yl)methyl)-2-oxobenzo[cd]indol-1(2H)-yl)piperidine-2,6-dione, Compound 106 following general reductive amination procedure. (100.0 mg, 184.69 umol, 70.18% yield, 97.81% purity) as yellow solid. ¹H NMR (400 MHz, DMSO-d6) δ 11.10 (s, 1H), 8.38 (d, J=8.24 Hz, 1H), 8.08 (d, J=6.92 Hz, 1H), 7.82 (t, J=7.62 Hz, 1H), 7.73 (s, 1H), 7.34 (d, J=7.32 Hz, 1H), 7.30 (s, 1H), 7.07 (d, J=7.28 Hz, 1H), 5.43 (dd, J=12.84, 5.24 Hz, 1H), 4.20 (s, 2H), 2.95-2.90 (m, 1H), 2.78-2.72 (m, 1H), 2.67-2.63 (m, 5H), 2.33-2.29 (m, 4H), 2.10-2.07 (m, 1H), 1.83-1.78 (m, 2H), 1.29 (s, 3H), 0.97-0.87 (m, 2H), 0.62-0.60 (m, 2H); LC MS: ES+ 530.2.

Example 126. Synthesis of 3-(6-((1-(4-methyl-1-((1-(trifluoromethyl)cyclopropyl)methyl)piperidin-4-yl)-1H-pyrazol-4-yl)methyl)-2-oxobenzo[cd]indol-1(2H)-yl)piperidine-2,6-dione (Compound 105)

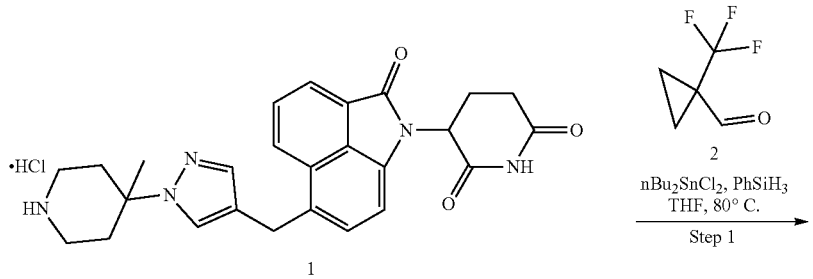

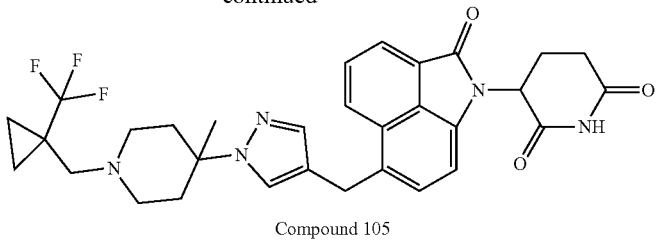

Compound 105

Step 1: Synthesis of 3-(6-((1-(4-methyl-1-((1-(trifluoromethyl)cyclopropyl)methyl)piperidin-4-yl)-1H-pyrazol-4-yl)methyl)-2-oxobenzo[cd]indol-1(2H)-yl)piperidine-2,6-dione, Compound 105 following general reductive amination procedure. (90.0 mg, 150.46 umol, 57.17% yield, 96.90% purity) as yellow solid. $^1$H NMR (400 MHz, DMSO-d6) δ 11.11 (s, 1H), 8.38 (d, J=7.68 Hz, 1H), 8.08 (d, J=6.36 Hz, 1H), 7.83-7.81 (m, 1H), 7.71 (s, 1H), 7.36-7.30 (m, 2H), 7.07 (d, J=6.04 Hz, 1H), 5.44-5.42 (m, 1H), 4.19 (s, 2H), 3.03-2.91 (m, 1H), 2.77-2.62 (m, 2H), 2.50-2.48 (m, 2H), 2.40 (s, 2H), 2.30-2.29 (m, 2H), 2.15-2.07 (m, 3H), 1.78-1.77 (m, 2H), 1.28 (s, 3H), 0.92 (br s, 2H), 0.66 (br s, 2H); LC MS: ES+ 580.3.

Example 127. Synthesis of 3-(6-((1-(4-methyl-1-((1-methylcyclobutyl)sulfonyl)piperidin-4-yl)-1H-pyrazol-4-yl)methyl)-2-oxobenzo[cd]indol-1(2H)-yl)piperidine-2,6-dione (Compound 233)

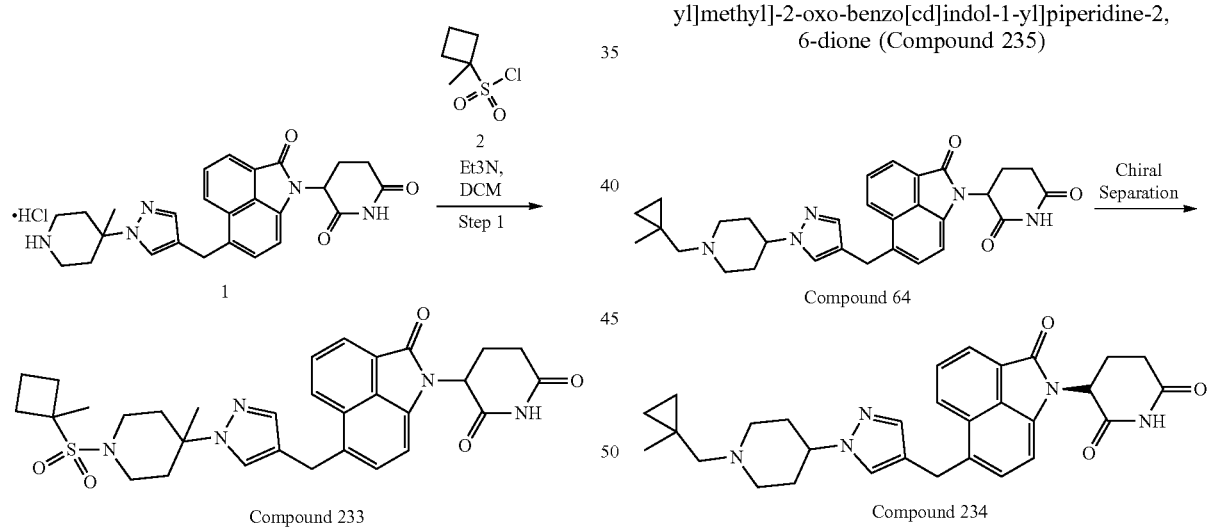

Step 1: Synthesis of 3-(6-((1-(4-methyl-1-((1-methylcyclobutyl)sulfonyl)piperidin-4-yl)-1H-pyrazol-4-yl)methyl)-2-oxobenzo[cd]indol-1(2H)-yl)piperidine-2,6-dione: To the stirred solution of 3-[6-[[1-(1-chloro-4-methyl-4-piperidyl)pyrazol-4-yl]methyl]-2-oxo-benzo[cd]indol-1-yl]piperidine-2,6-dione 1 (80.0 mg, 161.95 umol) in DCM (1 mL) was added Triethylamine (49.16 mg, 485.85 umol, 67.72 uL) in cold condition followed by the addition 1-methylcyclobutanesulfonyl chloride 2 (27.31 mg, 161.95 umol, 20.23 uL) and the reaction was continued at room temperature for 16 hours. The reaction mixture was diluted with ethyl acetate, washed with sodium bicarbonate solution, water and the organic fraction was separated. It was dried over anhydrous sodium sulphate and evaporated under reduced pressure to obtain the crude which was purified by preparative TLC plate method developing the plate in 3% MeOH-DCM to afford 3-[6-[[1-[4-methyl-1-(1-methylcyclobutyl)sulfonyl-4-piperidyl]pyrazol-4-yl]methyl]-2-oxo-benzo[cd]indol-1-yl]piperidine-2,6-dione Compound 233 (18.0 mg, 29.90 umol, 18.47% yield, 97.97% purity) as yellow solid. $^1$H NMR (400 MHz, DMSO-d6) δ 11.11 (s, 1H), 8.38 (d, J=8.08 Hz, 1H), 8.08 (d, J=6.92 Hz, 1H), 7.82 (t, J=7.74 Hz, 1H), 7.76 (s, 1H), 7.35 (s, 2H), 7.07 (d, J=7.24 Hz, 1H), 5.43-5.41 (m, 1H), 4.20 (s, 2H), 3.38-3.32 (m, 2H), 3.03-2.94 (m, 3H), 2.70-2.50 (m, 4H), 2.36-2.32 (m, 3H), 2.08-2.07 (m, 1H), 1.95-1.93 (m, 1H), 1.80-1.76 (m, 4H), 1.38 (s, 3H), 1.34 (s, 3H); LC MS: ES+ 590.5.

Example 128. Synthesis of 3-[6-[[1-[1-[(1-methylcyclopropyl)methyl]-4-piperidyl]pyrazol-4-yl]methyl]-2-oxo-benzo[cd]indol-1-yl]piperidine-2,6-dione (Compound 234) and 3-[6-[[1-[1-[(1-methylcyclopropyl)methyl]-4-piperidyl]pyrazol-4-yl]methyl]-2-oxo-benzo[cd]indol-1-yl]piperidine-2,6-dione (Compound 235)

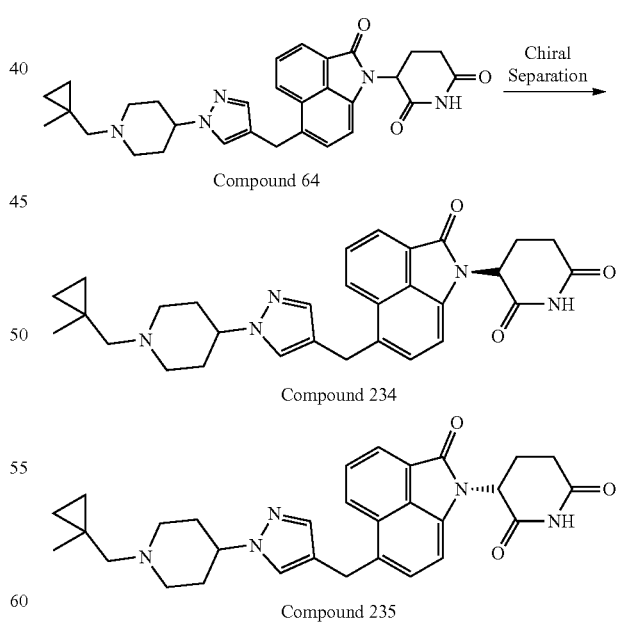

Step 1: Chiral separation of 3-[6-[[1-[1-[(1-methylcyclopropyl)methyl]-4-piperidyl]pyrazol-4-yl]methyl]-2-oxo-benzo[cd]indol-1-yl]piperidine-2,6-dione Compound 64 (1.5 g, 2.93 mmol) was separated into enantiomers by Normal phase Chiral Prep HPLC to afford 3-[6-[[1-[1-[(1- methylcyclopropyl)methyl]-4-piperidyl]pyrazol-4-yl] methyl]-2-oxo-benzo[cd]indol-1-yl]piperidine-2,6-dione Compound 234 (600.0 mg, 39.94% yield, % ee 100, first eluting fraction) as yellow solid and 3-[6-[[1-[1-[(1-methylcyclopropyl)methyl]-4-piperidyl]pyrazol-4-yl]methyl]-2-oxo-benzo[cd]indol-1-yl]piperidine-2,6-dione Compound 235 (550.0 mg, 36.53% yield, % ee 100, second eluting fraction) as yellow solid.

Example 129. Synthesis of 3-[6-[[1-[1-[(1-methyl-cyclobutyl)methyl]-4-piperidyl]pyrazol-4-yl] methyl]-2-oxo-benzo[cd]indol-1-yl]piperidine-2,6-dione (Compound 236) and 3-[6-[[1-[1-[(1-methylcyclobutyl)methyl]-4-piperidyl]pyrazol-4-yl] methyl]-2-oxo-benzo[cd]indol-1-yl]piperidine-2,6-dione (Compound 237)

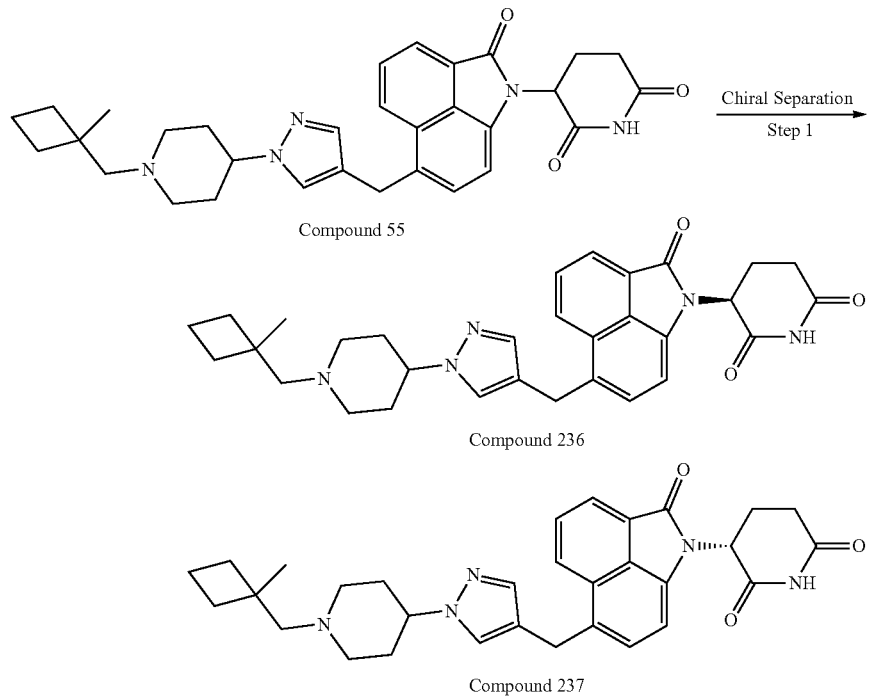

Step 1: Chiral separation of 3-[6-[[1-[1-[(1-methylcyclobutyl)methyl]-4-piperidyl]pyrazol-4-yl]methyl]-2-oxo-benzo[cd]indol-1-yl]piperidine-2,6-dione (1.8 g, 3.42 mmol) was separated to the enantiomers by Normal phase Chiral Prep HPLC to afford 3-[6-[[1-[1-[(1-methylcyclobutyl)methyl]-4-piperidyl]pyrazol-4-yl]methyl]-2-oxo-benzo[cd]indol-1-yl]piperidine-2,6-dione Compound 236 (840.0 mg, 46.51% yield, eluted as first fraction, % ee 99) and 3-[6-[[1-[1-[(1-methylcyclobutyl)methyl]-4-piperidyl] pyrazol-4-yl]methyl]-2-oxo-benzo[cd]indol-1-yl]piperidine-2,6-dione Compound 237 (650.0 mg, 35.82% yield, as second fraction, % ee 99) as yellow solids.

Example 130. Synthesis of 3-[6-[[1-[4-methyl-1-(2-oxabicyclo[2.1.1]hexane-4-carbonyl)-4-piperidyl] pyrazol-4-yl]methyl]-2-oxo-benzo[cd]indol-1-yl] piperidine-2,6-dione (Compound 238) and 3-[6-[[1-[4-methyl-1-(2-oxabicyclo[2.1.1]hexane-4-carbonyl)-4-piperidyl]pyrazol-4-yl]methyl]-2-oxo-benzo[cd]indol-1-yl]piperidine-2,6-dione (Compound 239)

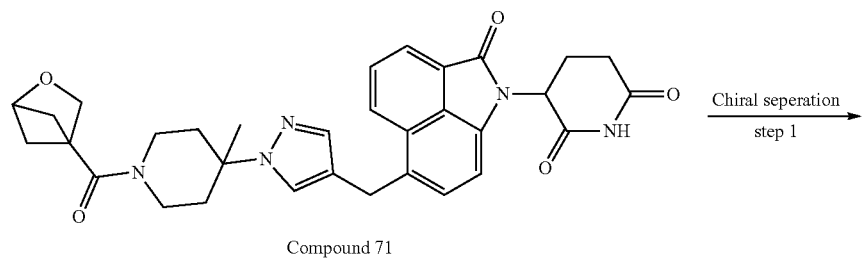

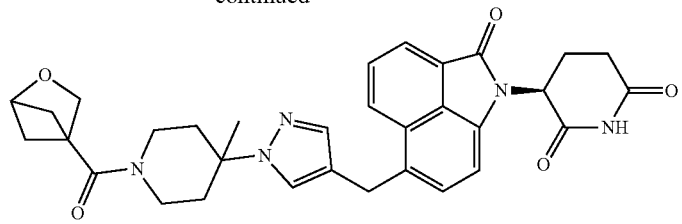

Compound 238

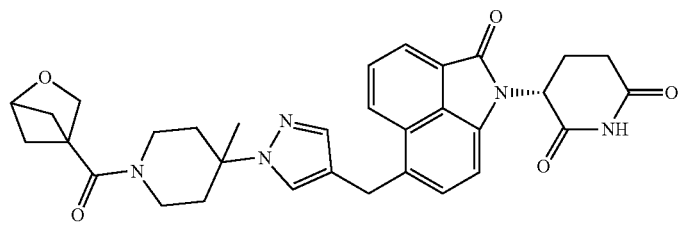

Compound 239

Step 1: Chiral separation: 250 mg of 3-(6-{1-[4-Methyl-1-(2-oxa-bicyclo[2.1.1]hexane-4-carbonyl)-piperidin-4-yl]-1H-pyrazol-4-ylmethyl}-2-oxo-2H-benzo[cd]indol-1-yl)-piperidine-2,6-dione Compound 71 was separated into enantiomers by chiral SFC method to afford 3-[6-[[1-[4-methyl-1-(2-oxabicyclo[2.1.1]hexane-4-carbonyl)-4-piperidyl]pyrazol-4-yl]methyl]-2-oxo-benzo[cd]indol-1-yl]piperidine-2,6-dione Compound 238 (85 mg, 24.47% yield, eluted as first fraction, % ee 100) and 3-[6-[[1-[4-methyl-1-(2-oxabicyclo[2.1.1]hexane-4-carbonyl)-4-piperidyl]pyrazol-4-yl]methyl]-2-oxo-benzo[cd]indol-1-yl]piperidine-2,6-dione Compound 239 (92 mg, 26.56% yield, eluted as second fraction, % ee 95) as yellow solids.

Example 131. Synthesis of 3-(2-oxo-6-((1-(1-(2,2,3,3-tetramethylcyclopropyl)piperidin-4-yl)-1H-pyrazol-4-yl)methyl)benzo[cd]indol-1(2H)-yl)piperidine-2,6-dione (Compound 240)

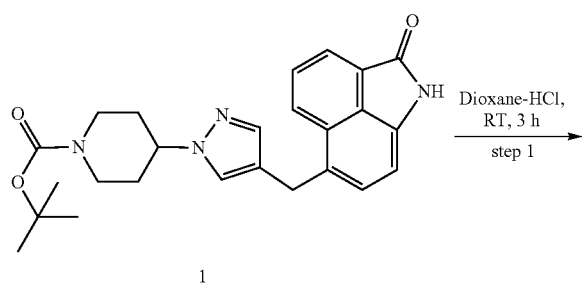

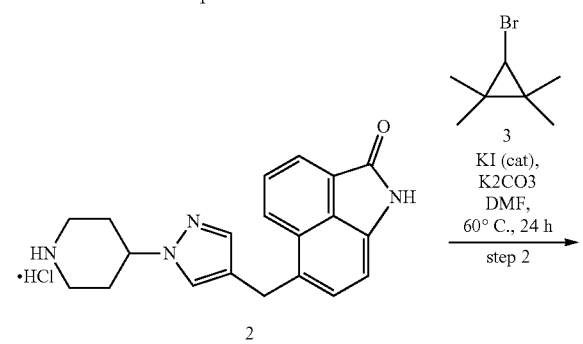

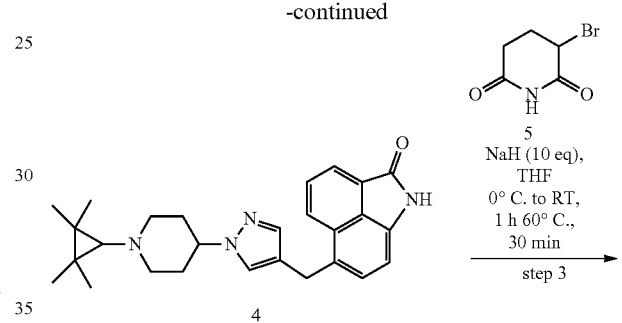

Compound 240

Step-1: Synthesis of 6-((1-(piperidin-4-yl)-1H-pyrazol-4-yl)methyl)benzo[cd]indol-2(1H)-one hydrochloride: To a stirred solution of tert-butyl 4-[4-[(2-oxo-1H-benzo[cd]indol-6-yl)methyl]pyrazol-1-yl]piperidine-1-carboxylate 1 (200 mg, 462.41 umol) in Dioxane (2 mL) was added 4M Dioxane-HCl (462.41 umol, 5 mL) at 0° C. It was stirred at RT for 2 hours. It was concentrated under reduced pressure to afford 6-[[1-(4-piperidyl)pyrazol-4-yl]methyl]-1H-benzo[cd]indol-2-one 2 (160 mg, 430.65 umol, 93.13% yield, 99.28% purity) as yellow solid; LC MS: ES+ 333.2.

Step-2: Synthesis of 6-((1-(1-(2,2,3,3-tetramethylcyclopropyl)piperidin-4-yl)-1H-pyrazol-4-yl)methyl)benzo[cd]indol-2(1H)-one: To a stirred solution of 6-[[1-(4-piperidyl)pyrazol-4-yl]methyl]-1H-benzo[cd]indol-2-one 2 (300 mg, 902.53 umol) in DMF (1 mL) was added Potassium carbonate (374.22 mg, 2.71 mmol, 163.41 uL) and followed by 3-bromo-1,1,2,2-tetramethyl-cyclopropane 3 (191.79 mg, 1.08 mmol) at 0° C. and Potassium iodide(cat.). It was heated at 60° C. for 16 hours. It was diluted with ethyl acetate, washed with water, brine, dried over sodium sulfate and concentrated under reduced pressure. It was cooled to RT, diluted with ethyl acetate, washed with ice cold water, brine, dried over sodium sulfate and concentrated under reduced pressure. It was purified by preparative TLC (1% methanol in ethyl acetate) to afford 6-[[1-[1-(2,2,3,3-tetramethylcyclopropyl)-4-piperidyl]pyrazol-4-yl]methyl]-1H-benzo[cd]indol-2-one 4 (15 mg, 28.00 umol, 3.10% yield, 80% purity) as yellow solid; LC MS: ES+ 428.3.

Step-3: Synthesis of 3-(2-oxo-6-((1-(1-(2,2,3,3-tetramethylcyclopropyl)piperidin-4-yl)-1H-pyrazol-4-yl)methyl)benzo[cd]indol-1(2H)-yl)piperidine-2,6-dione: To a stirred solution of 6-[[1-[1-(2,2,3,3-tetramethylcyclopropyl)-4-piperidyl]pyrazol-4-yl]methyl]-1H-benzo[cd]indol-2-one 4 (50 mg, 116.67 umol) in DMF (1 mL) was added Sodium hydride (in oil dispersion) 60% dispersion in mineral oil (2.68 mg, 116.67 umol) at 0° C. It was stirred at RT for 10 minutes. 3-bromopiperidine-2,6-dione (44.80 mg, 233.34 umol) was added to the reaction mixture portion wise at 0° C. After stirring at 0° C. for 5 minutes it was heated at 70° C. for 1 hour. It was cooled to RT, diluted with ice cold water, extracted with ethyl acetate, washed with brine, dried over sodium sulfate and concentrated under reduced pressure. It was purified by preparative TLC (3% methanol in dichloromethane) to afford 3-[2-oxo-6-[[1-[1-(2,2,3,3-tetramethylcyclopropyl)-4-piperidyl]pyrazol-4-yl]methyl]benzo[cd]indol-1-yl]piperidine-2,6-dione Compound 240 (18 mg, 33.00 umol, 28.29% yield, 98.94% purity) as yellow solid. $^1$H NMR (400 MHz, DMSO-d6) δ 11.11 (s, 1H), 8.37 (d, J=8.04 Hz, 1H), 8.08 (d, J=8.24 Hz, 1H), 7.83-7.81 (m, 1H), 7.55 (s, 1H), 7.35 (d, J=6.36 Hz, 1H), 7.28 (s, 1H), 7.07 (d, J=7.28 Hz, 1H), 5.45-5.42 (m, 1H), 5.02 (br s, 1H), 4.17 (s, 2H), 3.95-3.93 (m, 1H), 3.03-2.94 (m, 3H), 2.76-2.49 (m, 2H), 2.32-2.10 (m, 3H), 1.89-1.76 (m, 7H), 1.63 (s, 3H), 1.08 (s, 6H); LC MS: ES+ 540.6.

Example 132. Synthesis of 4-{4-[1-(2,6-Dioxo-piperidin-3-yl)-2-oxo-1,2-dihydro-benzo[cd]indole-6-carbonyl]-pyrazol-1-yl}-4-methyl-piperidine-1-carboxylic acid tert-butyl ester (Compound 241)

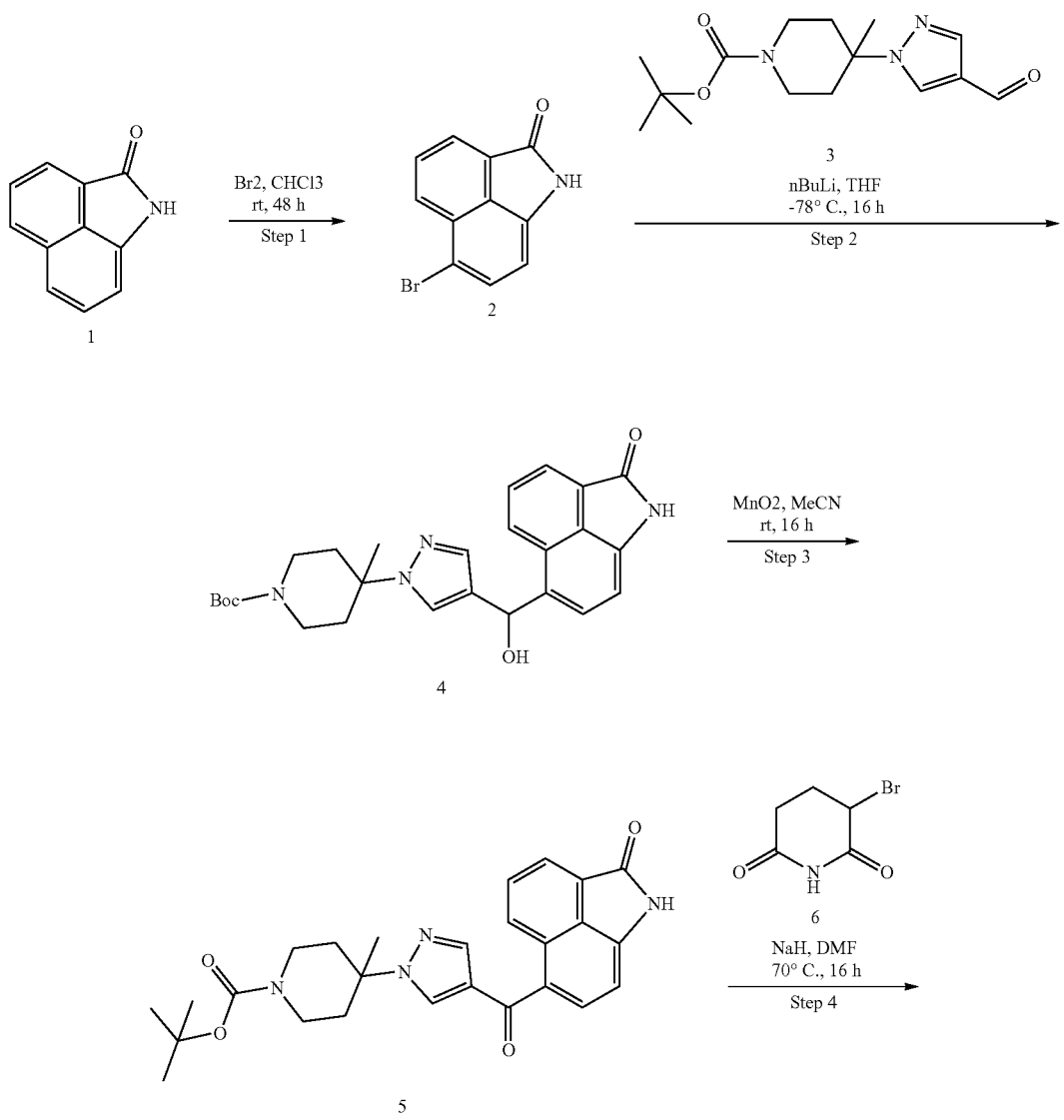

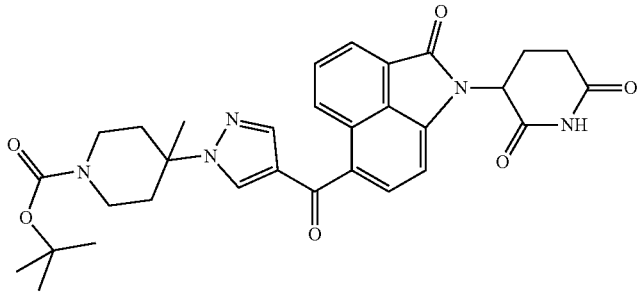

Compound 241

Step-1: Synthesis of 6-Bromo-1H-benzo[cd]indol-2-one: To the stirred suspension of 1H-benzo[cd]indol-2-one 1 (20 g, 118.22 mmol) in CHCl3 (250 mL) was added molecular bromine (28.34 g, 177.33 mmol, 9.08 mL) at cold condition drop wise and the reaction was continued at room temperature for 48 hours. After completion of the reaction (monitored by TLC and LCMS) the reaction mixture was poured into saturated aq. solution of sodium thiosulphate and the yellow solid formed was filtered through sintered funnel, washed with water, pentane and aziotroped with toluene to afford 6-bromo-1H-benzo[cd]indol-2-one 2 (23.5 g, 92.83 mmol, 78.53% yield, 98% purity) as yellow solid; LCMS: ES+ 250.1.

Step-2: Synthesis of 4-{4-[Hydroxy-(2-oxo-1,2-dihydro-benzo[cd]indol-6-yl)-methyl]-pyrazol-1-yl}-4-methyl-piperidine-1-carboxylic acid tert-butyl ester: To the stirred solution of 6-bromo-1H-benzo[cd]indol-2-one 2 (510 mg, 2.06 mmol) in THF (7 mL) was added Butyllithium (2.15 M, 2.10 mL) at −78° C. and after the addition was complete the temperature was allowed to increase to −40° C. and the reaction mixture was stirred at the same temperature for 30 minutes followed by the addition of tert-butyl 4-(4-formylpyrazol-1-yl)-4-methyl-piperidine-1-carboxylate 3 (603.10 mg, 2.06 mmol) in THF (7 mL) at −78° C. and then the reaction mixture was allowed to warm to room temperature and was continued for 16 hours. Reaction mixture was quenched with ammonium chloride solution, diluted with ethyl acetate, washed with water and the organic fraction was separated. It was then dried over anhydrous sodium sulphate and evaporated under reduced pressure to obtain the crude compound which was purified by flash chromatography using 0-5% MeOH-DCM to afford tert-butyl 4-[4-[hydroxy-(2-oxo-1H-benzo[cd]indol-6-yl)methyl]pyrazol-1-yl]-4-methyl-piperidine-1-carboxylate 4 (210.0 mg, 426.32 umol, 20.74% yield, 93.9% purity) as brown solid; LCMS: ES+ 445.1 (mass without the —OH group).

Step-3: Synthesis of 4-Methyl-4-[4-(2-oxo-1,2-dihydro-benzo[cd]indole-6-carbonyl)-pyrazol-1-yl]-piperidine-1-carboxylic acid tert-butyl ester: To the stirred solution of tert-butyl 4-[4-[hydroxy-(2-oxo-1H-benzo[cd]indol-6-yl)methyl]pyrazol-1-yl]-4-methyl-piperidine-1-carboxylate 4 (210.0 mg, 454.02 umol) in DCM (4.0 mL) was added Manganese dioxide (394.71 mg, 4.54 mmol) and the reaction mixture was stirred at room temperature for 16 hours. After completion of the reaction (monitored by TLC) the reaction mixture was filtered over celite bed, washed with ethyl acetate and the filtrate was evaporated under reduced pressure to obtain the crude compound which was purified by flash chromatography using 0-5% MeOH-DCM to afford tert-butyl 4-methyl-4-[4-(2-oxo-1H-benzo[cd]indole-6-carbonyl)pyrazol-1-yl]piperidine-1-carboxylate 5 (135.0 mg, 284.64 umol, 62.69% yield, 97.1% purity) as pale yellow solid; LCMS: ES+ 461.4.

Step-4: Synthesis of 4-{4-[1-(2,6-Dioxo-piperidin-3-yl)-2-oxo-1,2-dihydro-benzo[cd]indole-6-carbonyl]-pyrazol-1-yl}-4-methyl-piperidine-1-carboxylic acid tert-butyl ester: To the stirred solution of tert-butyl 4-methyl-4-[4-(2-oxo-1H-benzo[cd]indole-6-carbonyl)pyrazol-1-yl]piperidine-1-carboxylate 5 (135.0 mg, 293.14 umol) in DMF (1 mL) was added Sodium hydride (in oil dispersion) 60% dispersion in mineral oil (29.31 mg, 732.86 umol, 60% purity) at cold condition and the reaction mixture was heated at 70° C. for 1 hour followed by the addition of 3-bromopiperidine-2,6-dione (56.29 mg, 293.14 umol) and the reaction was heated at 70° C. for 4 hours with further top up of 3-bromopiperidine-2,6-dione 6 (56.29 mg, 293.14 umol). The reaction was continued at 70° C. for 16 hours. The reaction mixture was diluted with ethyl acetate, washed with water and the organic fraction was separated. It was then dried over anhydrous sodium sulphate and evaporated under reduced pressure to obtain the crude which was purified by preparative TLC plate method developing the plate in 40% ethyl acetate-DCM to afford tert-butyl 4-[4-[1-(2,6-dioxo-3-piperidyl)-2-oxo-benzo[cd]indole-6-carbonyl]pyrazol-1-yl]-4-methyl-piperidine-1-carboxylate Compound 241 (10.0 mg, 17.38 umol, 5.93% yield, 99.34% purity) as light yellow solid. $^1$H NMR (400 MHz, DMSO-d6) δ 11.19 (s, 1H), 8.59 (d, J=8.36 Hz, 1H), 8.51 (s, 1H), 8.18 (d, J=6.88 Hz, 1H), 8.07 (d, J=7.68 Hz, 1H), 8.03 (s, 1H), 7.92 (t, J=7.7 Hz, 1H), 7.27 (d, J=7.56 Hz, 1H), 5.53 (dd, J=12.64, 4.32 Hz, 1H), 3.52-3.48 (m, 2H), 3.20-3.19 (m, 2H), 2.97-2.93 (m, 2H), 2.83-2.76 (m, 1H), 2.70-2.67 (m, 1H), 2.40-2.27 (m, 2H), 2.16-2.15 (m, 1H), 1.87-1.84 (m, 2H), 1.47 (s, 3H), 1.39 (s, 9H); LC MS: ES+ 572.5.

Example 133. Synthesis of 3-{2-Oxo-6-[1-(1-spiro[3.4]oct-5-yl-piperidin-4-yl)-1H-pyrazol-4-ylmethyl]-2H-benzo[cd]indol-1-yl}-piperidine-2,6-dione (Compound 242) and 3-{2-Oxo-6-[1-(1-spiro[3.4]oct-5-yl-piperidin-4-yl)-1H-pyrazol-4-ylmethyl]-2H-benzo[cd]indol-1-yl}-piperidine-2,6-dione (Compound 243)
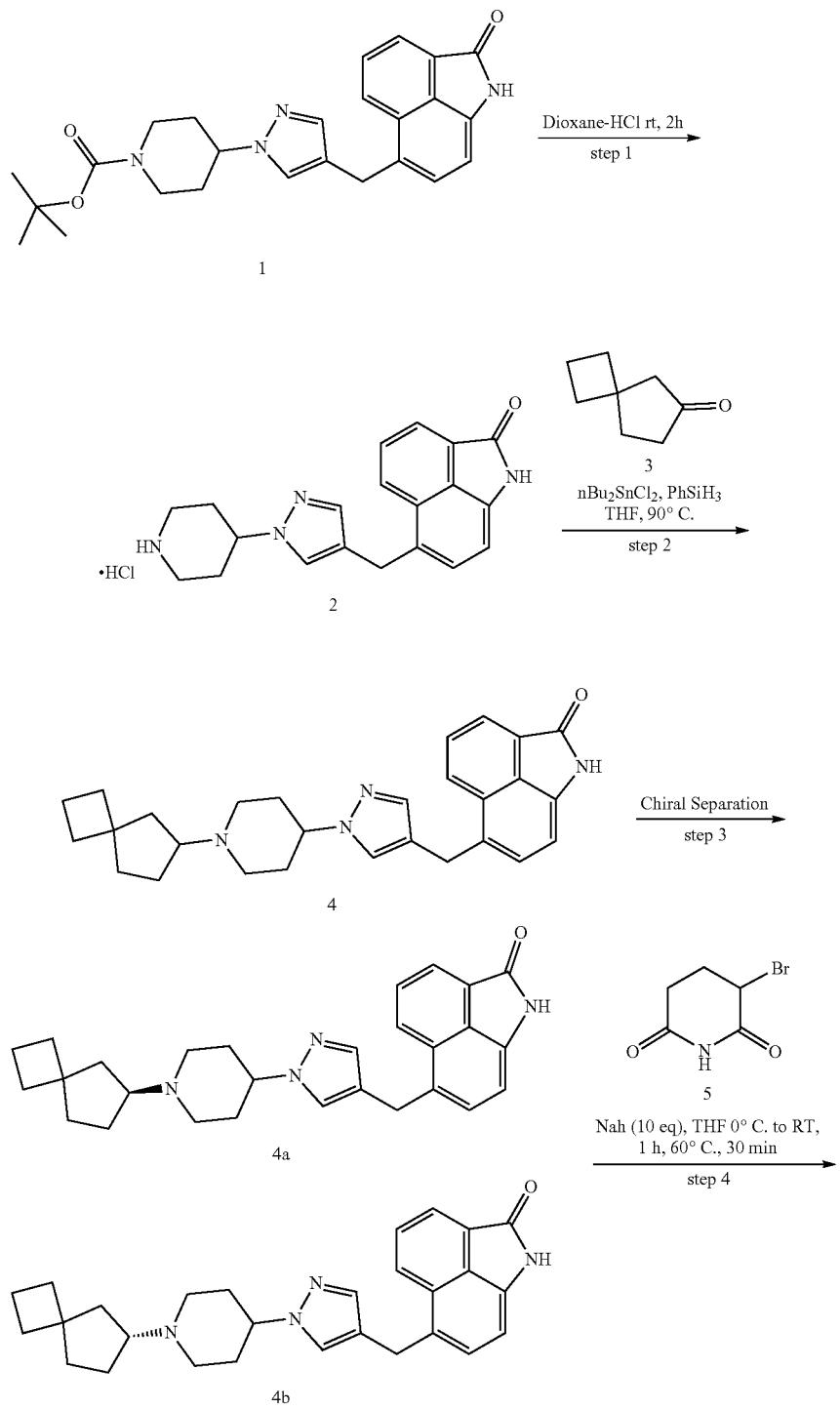

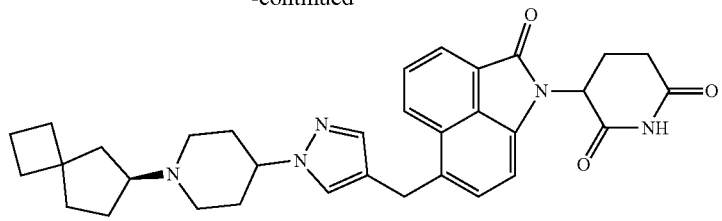

Compound 242

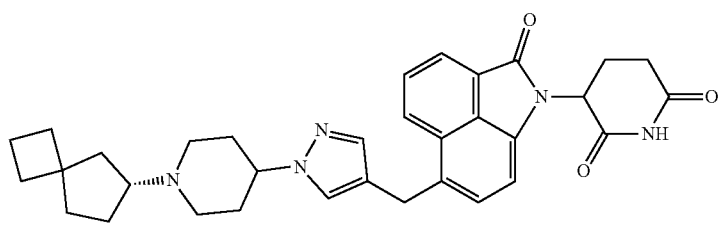

Compound 243

Step-1: Synthesis of 6-(1-Piperidin-4-yl-1H-pyrazol-4-ylmethyl)-1H-benzo[cd]indol-2-one, HCl salt: To a stirred solution of tert-butyl 4-[4-[(2-oxo-1H-benzo[cd]indol-6-yl)methyl]pyrazol-1-yl]piperidine-1-carboxylate 1 (200 mg, 462.41 umol) in Dioxane (2 mL) was added 4M Dioxane-HCl (462.41 umol, 5 mL) at 0° C. It was stirred at RT for 2 hours. It was concentrated under reduced pressure to afford 6-[[1-(4-piperidyl)pyrazol-4-yl]methyl]-1H-benzo[cd]indol-2-one 2 (160 mg, 430.65 umol, 93.13% yield, 99.28% purity) as yellow solid. LCMS: ES+ 333.2.

Step-2: Synthesis of 6-[1-(1-Spiro[3.4]oct-5-yl-piperidin-4-yl)-1H-pyrazol-4-ylmethyl]-1H-benzo[cd]indol-2-one: To a stirred solution of 6-[[1-(1-chloro-4-piperidyl)pyrazol-4-yl]methyl]-1H-benzo[cd]indol-2-one 2 (200 mg, 542.21 umol) in THF (5 mL) was added Triethylamine (109.73 mg, 1.08 mmol, 151.15 uL) followed by the addition of spiro[3.4]octan-7-one 3 (67.33 mg, 542.21 umol), Dibutyltindichloride (197.70 mg, 650.65 umol, 145.37 uL) and Phenylsilane (58.67 mg, 542.21 umol, 66.83 uL). The reaction mixture was then stirred at 90° C. for 16 hours. After completion of the reaction (monitored by LCMS) the reaction mixture was cooled to RT, diluted with ethyl acetate, washed with water, brine dried over sodium sulfate and concentrated under reduced pressure. It was purified by combi flash eluting at 1% methanol in dichloromethane to afford 6-[[1-(1-spiro[3.4]octan-7-yl-4-piperidyl)pyrazol-4-yl]methyl]-1H-benzo[cd]indol-2-one 4 (175 mg, 378.18 umol, 69.75% yield, 95.21% purity) as yellow solid. LCMS: ES+ 440.9

Step-3: Chiral separation of 6-[1-(1-Spiro[3.4]oct-5-yl-piperidin-4-yl)-1H-pyrazol-4-ylmethyl]-1H-benzo[cd]indol-2-one (4a) and 6-[1-(1-Spiro[3.4]oct-5-yl-piperidin-4-yl)-1H-pyrazol-4-ylmethyl]-1H-benzo[cd]indol-2-one (4b): 6-[[1-(1-spiro[3.4]octan-7-yl-4-piperidyl)pyrazol-4-yl]methyl]-1H-benzo[cd]indol-2-one 4 (175 mg, 397.20 umol) was submitted to SFC for chiral separation. Chiral isomers were separated by SFC to afford 6-[[1-[1-[spiro[3.4]octan-7-yl]-4-piperidyl]pyrazol-4-yl]methyl]-1H-benzo[cd]indol-2-one 4b (70 mg, 158.88 umol, 40.00% yield, 100% purity) (Peak 1) as yellow solid LCMS: ES+ 441.6 and 6-[[1-[1-[spiro[3.4]octan-7-yl]-4-piperidyl]pyrazol-4-yl]methyl]-1H-benzo[cd]indol-2-one 4a (70 mg, 155.39 umol, 39.12% yield, 97.80% purity) (Peak 2) as yellow solid. LCMS: ES+ 441.6.

Step-4: Synthesis of 3-{2-Oxo-6-[1-(1-spiro[3.4]oct-5-yl-piperidin-4-yl)-1H-pyrazol-4-ylmethyl]-2H-benzo[cd]indol-1-yl}-piperidine-2,6-dione and 3-{2-Oxo-6-[1-(1-spiro[3.4]oct-5-yl-piperidin-4-yl)-1H-pyrazol-4-ylmethyl]-2H-benzo[cd]indol-1-yl}-piperidine-2,6-dione: To a stirred solution of 6-[[1-[1-[spiro[3.4]octan-7-yl]-4-piperidyl]pyrazol-4-yl]methyl]-1H-benzo[cd]indol-2-one 4a (65.00 mg, 147.53 umol) in THF (7 mL) was added Sodium hydride (in oil dispersion) 60% dispersion in mineral oil (56.53 mg, 1.48 mmol, 60% purity) portion wise at 0° C. It was stirred at RT for 10 minutes. 3-bromopiperidine-2,6-dione 5 (141.64 mg, 737.67 umol) was added to the reaction mixture at RT portion wise. It was heated at 70° C. for 1 hour. It was cooled to RT, diluted with ethyl acetate, poured to ice cold water, separated organic part, washed with water, brine and dried over sodium sulfate. It was evaporated under reduced pressure. It was purified by preparative TLC (5% Methanol in Ethyl acetate in DCM) to afford 3-[2-oxo-6-[[1-[1-[spiro[3.4]octan-7-yl]-4-piperidyl]pyrazol-4-yl]methyl]benzo[cd]indol-1-yl]piperidine-2,6-dione Compound 242 (28.0 mg, 46.78 umol, 31.70% yield, 92.16% purity) as yellow solid. $^1$H NMR (400 MHz, DMSO-d6) δ 11.11 (s, 1H), 8.37 (d, J=8.24 Hz, 1H), 8.08 (d, J=7.00 Hz, 1H), 7.82 (t, J=7.64 Hz, 1H), 7.57 (s, 1H), 7.34 (d, J=7.28 Hz, 1H), 7.28 (s, 1H), 7.06 (d, J=7.28 Hz, 1H), 5.43 (dd, J=12.68, 5.04 Hz, 1H), 4.17 (s, 2H), 3.99-3.97 (m, 1H), 2.92-2.90 (m, 3H), 2.82-2.62 (m, 2H), 2.10-2.07 (m, 1H), 1.94-1.72 (m, 15H), 1.60-1.57 (m, 2H), 1.41-1.35 (m, 2H); LC MS: ES+ 552.72.

To a stirred solution of 6-[[1-[1-[spiro[3.4]octan-7-yl]-4-piperidyl]pyrazol-4-yl]methyl]-1H-benzo[cd]indol-2-one 4b (80.00 mg, 181.58 umol) in THF (5 mL) was added Sodium hydride (in oil dispersion) 60% dispersion in mineral oil (66.65 mg, 1.74 mmol, 0.6 purity) portion wise at 0° C. It was stirred at RT for 10 minutes. 3-bromopiperidine-2,6-dione 5 (174.33 mg, 907.90 umol) was added to the reaction mixture at RT portion wise. It was heated at 70° C. for 1 h. It was cooled to RT, diluted with ethyl acetate, poured to ice cold water, separated organic part, washed with water, brine and dried over sodium sulfate. It was evaporated under reduced pressure. It was diethyl ether to afford 3-[2-oxo-6-[[1-[1-[spiro[3.4]octan-7-yl]-4-piperidyl]pyrazol-4-yl]methyl]benzo[cd]indol-1-yl]piperidine-2,6-dione Compound 243 (21.5 mg, 37.04 umol, 20.40% yield, 95.05% purity) as light green solid. $^1$H NMR (400 MHz, DMSO-d6) δ 11.12 (s, 1H), 8.37 (d, J=8.12 Hz, 1H), 8.08 (d, J=6.92 Hz, 1H), 7.82 (t, J=7.56 Hz, 1H), 7.57 (s, 1H), 7.34 (d, J=6.52 Hz, 1H), 7.28 (s, 1H), 7.06 (d, J=7.36 Hz, 1H), 5.44-5.41 (m, 1H), 4.17 (s, 2H), 3.99-3.97 (m, 1H), 2.91-2.49 (m, 4H), 2.09-1.77 (m, 16H), 1.67-1.57 (m, 2H), 1.41-1.38 (m, 2H); LC MS: ES+ 552.3.

Example 134. Synthesis of 3-{2-Oxo-6-[1-(1-spiro[3.3]hept-1-yl-piperidin-4-yl)-1H-pyrazol-4-ylmethyl]-2H-benzo[cd]indol-1-yl}-piperidine-2,6-dione (Compound 244) and 3-{2-Oxo-6-[1-(1-spiro[3.3]hept-1-yl-piperidin-4-yl)-1H-pyrazol-4-ylmethyl]-2H-benzo[cd]indol-1-yl}-piperidine-2,6-dione (Compound 245)
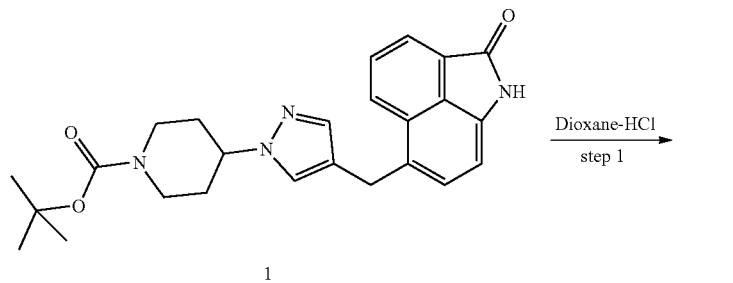
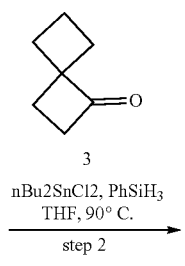
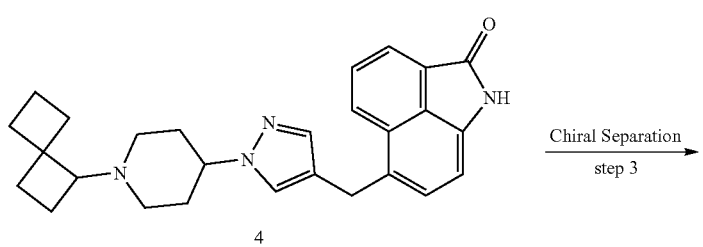
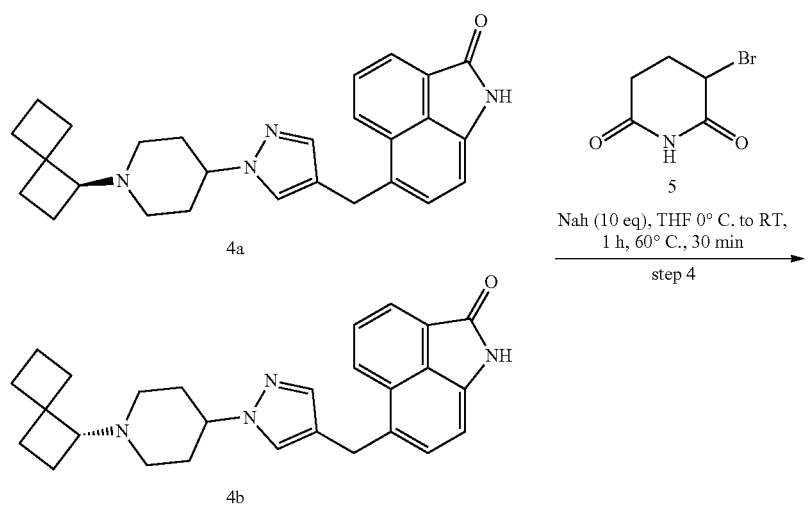

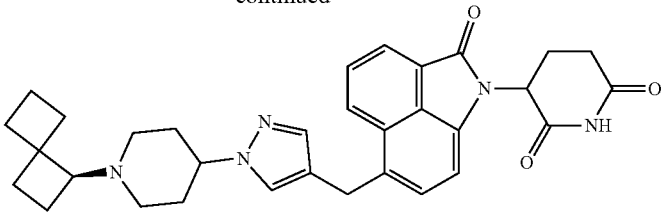

Compound 244

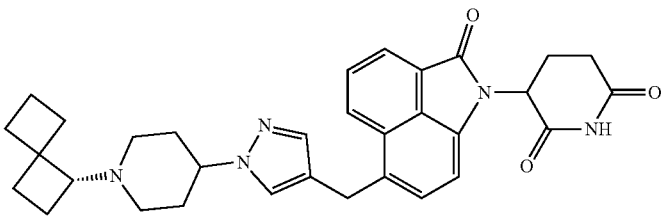

Compound 245

Step-1: Synthesis of 6-(1-Piperidin-4-yl-1H-pyrazol-4-ylmethyl)-1H-benzo[cd]indol-2-one, HCl salt: To a stirred solution of tert-butyl 4-[4-[(2-oxo-1H-benzo[cd]indol-6-yl)methyl]pyrazol-1-yl]piperidine-1-carboxylate 1 (500 mg, 1.16 mmol) in Dioxane (5 mL) was added 4M Dioxane-HCl (1.16 mmol, 5 mL) at 0° C. It was stirred at RT for 3 hours. It was concentrated under reduced pressure to afford 6-[[1-(4-piperidyl)pyrazol-4-yl]methyl]-1H-benzo[cd]indol-2-one 2 (405 mg, 1.05 mmol, 91.18% yield, 96% purity) as yellow solid. LCMS: ES+ 333.4.

Step-2: Synthesis of 6-[1-(1-Spiro[3.3]hept-1-yl-piperidin-4-yl)-1H-pyrazol-4-ylmethyl]-1H-benzo[cd]indol-2-one: To a stirred solution of 6-[[1-(1-chloro-4-piperidyl)pyrazol-4-yl]methyl]-1H-benzo[cd]indol-2-one 2 (330 mg, 894.65 umol) in THF (5 mL) was added Triethylamine (181.06 mg, 1.79 mmol, 249.39 uL) followed by the addition of spiro[3.3]heptan-3-one 3 (98.55 mg, 894.65 umol), Dibutyltindichloride (326.21 mg, 1.07 mmol, 239.86 uL) and Phenylsilane (96.81 mg, 894.65 umol, 110.26 uL). The reaction mixture was then stirred at 90° C. for 16 hours. It was cooled to RT, diluted with ethyl acetate, washed with water, brine dried over sodium sulfate and concentrated under reduced pressure. It was purified by combiflash eluting at 1% methanol in dichloromethane to afford 6-[[1-(1-spiro[3.3]heptan-3-yl-4-piperidyl)pyrazol-4-yl]methyl]-1H-benzo[cd]indol-2-one 4 (225 mg, 496.68 umol, 55.52% yield, 94.16% purity) as yellow solid, LCMS: ES+ 427.1.

Step-3: Chiral separation of 6-[1-(1-Spiro[3.3]hept-1-yl-piperidin-4-yl)-1H-pyrazol-4-ylmethyl]-1H-benzo[cd]indol-2-one (4a) and 6-[1-(1-Spiro[3.3]hept-1-yl-piperidin-4-yl)-1H-pyrazol-4-ylmethyl]-1H-benzo[cd]indol-2-one (4b): 6-[[1-(1-spiro[3.3]heptan-3-yl-4-piperidyl)pyrazol-4-yl]methyl]-1H-benzo[cd]indol-2-one 4 (225 mg, 527.49 umol) was submitted for chiral separation by SFC. Chiral isomers were separated by SFC to afford 6-[[1-[1-[spiro[3.3]heptan-3-yl]-4-piperidyl]pyrazol-4-yl]methyl]-1H-benzo[cd]indol-2-one (4b) (85 mg, 199.27 umol, 37.78% yield, 100% purity) (peak 1) as light yellow solid LCMS: ES+ 427.0 and 6-[[1-[1-[spiro[3.3]heptan-3-yl]-4-piperidyl]pyrazol-4-yl]methyl]-1H-benzo[cd]indol-2-one (4a) (105 mg, 237.35 umol, 45.00% yield, 96.42% purity) (peak 2) as light yellow solid; LCMS: ES+427.0.

Step-4: Synthesis of 3-{2-Oxo-6-[1-(1-spiro[3.3]hept-1-yl-piperidin-4-yl)-1H-pyrazol-4-ylmethyl]-2H-benzo[cd]indol-1-yl)-piperidine-2,6-dione and 3-{2-Oxo-6-[1-(1-spiro[3.3]hept-1-yl-piperidin-4-yl)-1H-pyrazol-4-ylmethyl]-2H-benzo[cd]indol-1-yl}-piperidine-2,6-dione: To the stirred solution of 6-[[1-[1-[spiro[3.3]heptan-3-yl]-4-piperidyl]pyrazol-4-yl]methyl]-1H-benzo[cd]indol-2-one 4a (80.00 mg, 187.55 umol) in THF (15 mL) was added Sodium hydride (in oil dispersion) 60% dispersion in mineral oil (75.73 mg, 1.98 mmol, 60% purity) at cold condition and the reaction mixture was stirred at room temperature for 10 minutes followed by the addition of 3-bromopiperidine-2,6-dione 5 (180.06 mg, 937.75 umol) portionwise. It was then stirred at room temperature for 10 minutes and heated at 80° C. for 30 minutes. TLC was checked which showed almost complete consumption of the starting material and formation of the desired spot. The reaction mixture was diluted with ethyl acetate, washed with cold water and the organic fraction was separated. It was then dried over anhydrous sodium sulphate and evaporated under reduced pressure to obtain the crude which was purified by preparative TLC plate method developing the plate in 95% ethyl acetate-DCM to afford 3-[2-oxo-6-[[1-[1-[spiro[3.3]heptan-3-yl]-4-piperidyl]pyrazol-4-yl]methyl]benzo[cd]indol-1-yl]piperidine-2,6-dione Compound 244 (42.0 mg, 74.21 umol, 39.57% yield, 95% purity) as yellow solid. $^{1}$H NMR (400 MHz, DMSO-d6) δ 11.11 (s, 1H), 8.38 (d, J=8.4 Hz, 1H), 8.08 (d, J=7.00 Hz, 1H), 7.83 (t, J=7.6 Hz, 1H), 7.59 (s, 1H), 7.35 (d, J=Hz, 1H), 7.29 (s, 1H), 7.07 (d, J=7.2 Hz, 1H), 5.44-5.41 (m, 1H), 4.18 (s, 2H), 4.03 (br s, 1H), 2.99-2.91 (m, 2H), 2.77-2.62 (m, 3H), 2.40-2.36 (m, 1H), 2.24-2.20 (m, 1H), 2.09-2.07 (m, 1H), 1.96-1.72 (m, 12H), 1.57-1.55 (m, 1H), 1.45-1.42 (m, 1H); LC MS: ES+ 538.3. To a stirred solution of 6-[[1-[1-[spiro[3.3]heptan-3-yl]-4-piperidyl]pyrazol-4-yl]methyl]-1H-benzo[cd]indol-2-one 4b (100.00 mg, 234.44 umol) in THF (4 mL) was added Sodium hydride (in oil dispersion) 60% dispersion in mineral oil (89.83 mg, 2.34 mmol, 0.6 purity) at 0° C. It was stirred at RT for 10 minutes. 3-bromopiperidine-2,6-dione 5 (225.07 mg, 1.17 mmol) was added portion wise. It was stirred at RT for 10 minutes. It was heated at 80° C. for 1 hour. It was cooled to RT, diluted with ethyl acetate, poured into icecold water, separated organic part, washed with brine, dried over sodium sulfate and concentrated under reduced pressure. It was purified by preparative TLC (80% ethyl acetate in dichloromethane) to afford 3-[2-oxo-6-[[1-[1-[spiro[3.3]

heptan-3-yl]-4-piperidyl]pyrazol-4-yl]methyl]benzo[cd]indol-1-yl]piperidine-2,6-dione Compound 245 (48.0 mg, 84.81 umol, 36.18% yield, 95% purity) as yellow solid. $^1$H NMR (400 MHz, DMSO-d6) δ 11.11 (s, 1H), 8.38 (d, J=8.2 Hz, 1H), 8.08 (d, J=6.96 Hz, 1H), 7.83 (t, J=7.64 Hz, 1H), 7.59 (s, 1H), 7.35 (d, J=7.32 Hz, 1H), 7.29 (s, 1H), 7.07 (d, J=7.28 Hz, 1H), 5.43 (dd, J=12.76, 5.16 Hz, 1H), 4.18 (s, 2H), 4.03-4.01 (m, 1H), 2.99-2.94 (m, 2H), 2.77-2.62 (m, 3H), 2.39-2.36 (m, 1H), 2.24-2.20 (m, 1H), 2.09-2.06 (m, 1H), 1.95-1.65 (m, 13H), 1.57-1.55 (m, 1H), 1.45-1.40 (m, 1H); LC MS: ES+538.3.
Example 135. Synthesis of 3-(6-((4-(4-(1-methylcyclobutane-1-carbonyl)piperazin-1-yl)-1H-pyrazol-1-yl)methyl)-2-oxobenzo[cd]indol-1(2H)-yl)piperidine-2,6-dione (Compound 246)
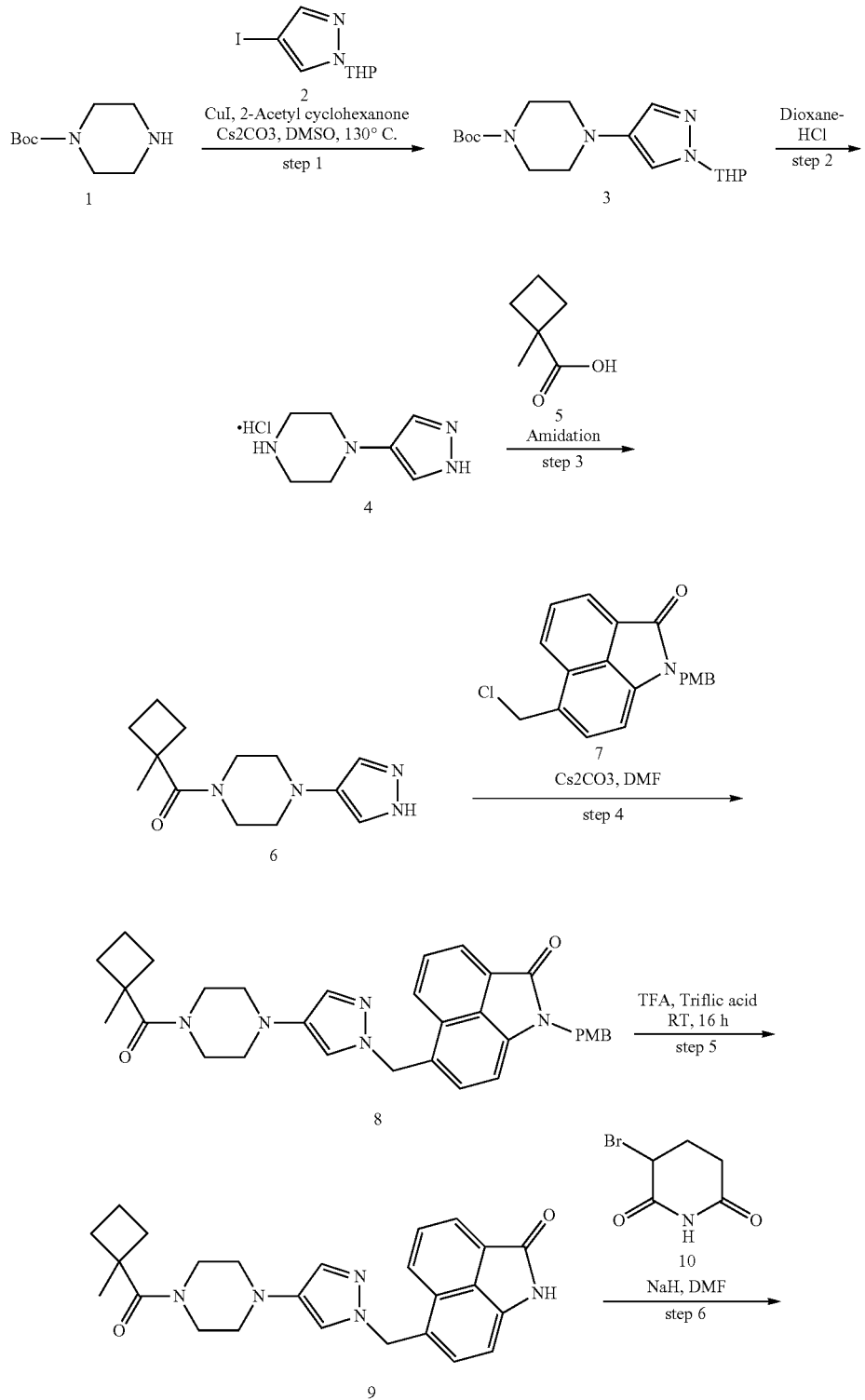

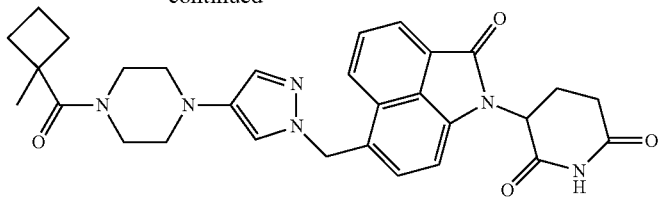

Compound 246

Step-1: Synthesis of tert-butyl 4-(1-(tetrahydro-2H-pyran-2-yl)-1H-pyrazol-4-yl)piperazine-1-carboxylate: To a stirred solution of 4-iodo-1-tetrahydropyran-2-yl-pyrazole 2 (5.3 g, 19.06 mmol) and tert-butyl piperazine-1-carboxylate 1 (3.55 g, 19.06 mmol) in DMSO (30 mL) was added Cesium carbonate (15.52 g, 47.65 mmol) Reaction mixture was degassed with argon for 10 min. To the reaction mixture, Copper (I) iodide (1.09 g, 5.72 mmol, 193.76 uL) and 2-acetylcyclohexanone (801.49 mg, 5.72 mmol, 756.12 uL) were added and again degassed for 5 min. Reaction mixture was then heated at 110° C. for 18 hours. The reaction mixture was diluted with ethyl acetate and water, layers were separated and organic layer was washed with water, brine, dried over Na$_2$SO$_4$ and concentrated under reduced pressure to get crude mass which was purified by column chromatography using 40-50% EtOAc-Hexane as eluent to afford tert-butyl 4-(1-tetrahydropyran-2-ylpyrazol-4-yl)piperazine-1-carboxylate 3 (1 g, 2.69 mmol, 14.14% yield, 90.66% purity) as light black gum. LC MS: ES+ 337.5.

Step-2: Synthesis of 1-(1H-pyrazol-4-yl)piperazine hydrochloride: To a stirred solution of tert-butyl 4-(1-tetrahydropyran-2-ylpyrazol-4-yl)piperazine-1-carboxylate 3 (1 g, 2.97 mmol) in 4M HCl in Dioxane (10 mL) and cooled the reaction mixture to 0° C. followed by drop wise addition of 4M HCl in Dioxane (10 mL), stirred the reaction mixture for 3 hour at RT. LCMS showed product mass, the reaction mixture was concentrated under reduced pressure and washed with Ether, dried to afford 1-(1H-pyrazol-4-yl)piperazine hydrochloride 4 (450 mg, 2.27 mmol, 76.23% yield, 95% purity) as a white gum. LC MS was not responded well.

Step-3: Synthesis of (4-(1H-pyrazol-4-yl)piperazin-1-yl)(1-methylcyclobutyl)methanone: To a stirred solution of 1-(1H-pyrazol-4-yl)piperazine; hydrochloride 4 (500 mg, 2.65 mmol) in DMF (8 mL) was added 1-methylcyclobutanecarboxylic acid 5 (302.51 mg, 2.65 mmol, 270.10 uL) followed by HATU (1.51 g, 3.98 mmol) and the reaction mixture was cooled to 0° C. was added DIPEA (1.37 g, 10.60 mmol, 1.85 mL), the reaction mixture was allowed to stirred at RT for overnight. Reaction mixture was diluted with water and was extracted with ethyl acetate, organic layer was washed with saturated sodium bicarbonate solution (3×) followed by water and brine, dried over sodium sulphate and concentrated under reduced pressure to get the crude product. The crude product thus obtained was purified by column chromatography eluting with 25% of EtOAc in Hexane to afford (1-methylcyclobutyl)-[4-(1H-pyrazol-4-yl)piperazin-1-yl]methanone 6 (220 mg, 841.64 umol, 31.76% yield, 95% purity) as a white semi solid. LC MS: ES+ 249.2. Note: In reaction diamide was formed, which was stirred with K2CO$_3$ (1 eq.) for 30 mins to get desired product.

Step-4: Synthesis of 1-(4-methoxybenzyl)-6-((4-(4-(1-methylcyclobutane-1-carbonyl)piperazin-1-yl)-1H-pyrazol-1-yl)methyl)benzo[cd]indol-2(1H)-one: To a stirred solution of 6-(chloromethyl)-1-[(4-methoxyphenyl)methyl]benzo[cd]indol-2-one 7 (367.29 mg, 1.09 mmol) and (1-methylcyclobutyl)-[4-(1H-pyrazol-4-yl)piperazin-1-yl]methanone 6 (270 mg, 1.09 mmol) in DMF (5 mL) was added Cesium carbonate (885.65 mg, 2.72 mmol) at room temperature then reaction mixture was heated 80° C. overnight. Reaction mixture was diluted with cooled water extracted with ethyl acetate. Combined organic layer was washed with saturated brine solution and dried under reduced pressure to get crude which was purified by combiflash chromatography using 30-40% EtOAc-Hexane as eluent to afford 1-[(4-methoxyphenyl)methyl]-6-[[4-[4-(1-methylcyclobutanecarbonyl)piperazin-1-yl]pyrazol-1-yl]methyl]benzo[cd]indol-2-one 8 (300 mg, 532.04 umol, 48.93% yield, 97.48% purity) as light yellow solid. LC MS: ES+ 550.4.

Step-5: Synthesis of 6-((4-(4-(1-methylcyclobutane-1-carbonyl)piperazin-1-yl)-1H-pyrazol-1-yl)methyl)benzo[cd]indol-2(1H)-one: To a stirred solution of 1-[(4-methoxyphenyl)methyl]-6-[[4-[4-(1-methylcyclobutanecarbonyl)piperazin-1-yl]pyrazol-1-yl]methyl]benzo[cd]indol-2-one 8 (150.00 mg, 272.90 umol) in TFA (3 mL) was added trifluoromethanesulfonic acid (327.65 mg, 2.18 mmol, 191.61 uL) at room temperature then reaction mixture was stirred at RT for over night. Reaction mixture was concentrated under reduced pressured to get crude mass which diluted with EtOAc and saturated solution of NaHCO$_3$, layers were separated. Combined organic layer was washed with saturated brine solution and dried under vacuum in rotavapour to afford 6-[[4-[4-(1-methylcyclobutanecarbonyl)piperazin-1-yl]pyrazol-1-yl]methyl]-1H-benzo[cd]indol-2-one 9 (115 mg, 238.29 umol, 87.32% yield, 89% purity) as brown gum. LC MS: ES+ 430.3.

Step-6: Synthesis of 3-(6-((4-(4-(1-methylcyclobutane-1-carbonyl)piperazin-1-yl)-1H-pyrazol-1-yl)methyl)-2-oxobenzo[cd]indol-1(2H)-yl)piperidine-2,6-dione: To the stirred solution of 6-[[4-[4-(1-methylcyclobutanecarbonyl)piperazin-1-yl]pyrazol-1-yl]methyl]-1H-benzo[cd]indol-2-one 9 (120.00 mg, 279.39 umol) in THF (5 mL) was added Sodium hydride (in oil dispersion)60% dispersion in mineral oil (107.05 mg, 2.79 mmol, 60% purity) at cold condition and the reaction mixture was stirred at RT for 10 minutes followed by portion wised addition of 3-bromopiperidine-2,6-dione 10 (268.23 mg, 1.40 mmol) and the reaction was heated at 70° C. for 1 hours. Reaction mixture was diluted with ethyl acetate and washed with water; organic fraction separated. It was dried over anhydrous sodium sulphate and evaporated under reduced pressure to obtain the crude which was purified by Prep TLC using 50% EtOAc-DCM as eluent to afford 3-[6-[[4-[4-(1-methylcyclobutanecarbonyl)piperazin-1-yl]pyrazol-1-yl]methyl]-2-oxo-benzo[cd]indol-1-yl]piperidine-2,6-dione Compound 246 (45 mg, 82.60 umol, 29.56% yield, 99.23% purity) as light yellow solid. $^1$H NMR (400 MHz, DMSO-d6) δ 11.12 (s, 1H), 8.39 (d, J=8.28 Hz, 1H), 8.10 (d, J=6.96 Hz, 1H), 7.85 (t, J=7.66 Hz, 1H), 7.44 (d, J=7.36 Hz, 1H), 7.39 (s, 1H), 7.20 (s, 1H), 7.12 (d, J=7.32

Hz, 1H), 5.62 (s, 2H), 5.44 (dd, J=12.44, 4.92 Hz, 1H), 3.49-3.48 (m, 2H), 3.33-3.31 (m, 2H), 2.95-2.93 (m, 1H), 2.77-2.76 (m, 5H), 2.66-2.62 (m, 1H), 2.41-2.34 (m, 2H), 2.09-2.07 (m, 1H), 1.91-1.89 (m, 1H), 1.79-1.74 (m, 2H), 1.61-1.58 (m, 1H), 1.32 (s, 3H) LC MS: ES+ 541.5.

Example 136. Synthesis of 3-[6-[methoxy-[1-[1-(1-methylcyclobutanecarbonyl)-4-piperidyl]pyrazol-4-yl]methyl]-2-oxo-benzo[cd]indol-1-yl]piperidine-2,6-dione (Compound 247)

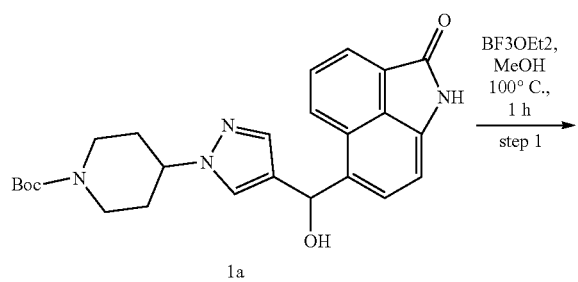

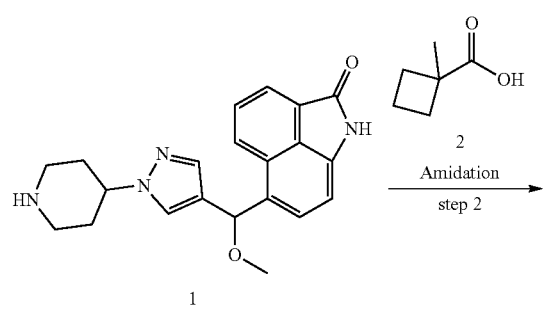

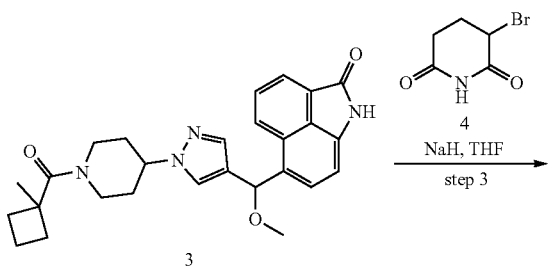

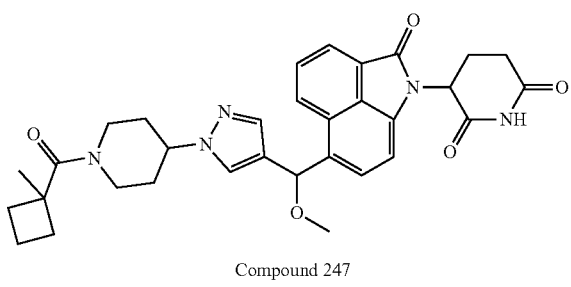

Compound 247

Step-1: Synthesis of 6-[methoxy-[1-(4-piperidyl)pyrazol-4-yl]methyl]-1H-benzo[cd]indol-2-one: To a stirred solution of tert-butyl 4-[4-[hydroxy-(2-oxo-1H-benzo[cd]indol-6-yl)methyl]pyrazol-1-yl]piperidine-1-carboxylate 1a (400 mg, 891.84 umol) in Methanol (2 mL) was added diethyloxonio(trifluoro)boranuide (12.66 mg, 89.18 umol, 11.01 uL) and the resultant reaction mixture was stirred at 100° C. for 1 hour. After completion of the reaction (monitored by TLC and LCMS) the reaction mixture was concentrated under reduced pressure and diluted with EtOAc. The organic part was then washed with water and brine, dried over sodium sulphate and concentrated. The crude thus obtained was purified by Prep TLC plate (7% MeOH in DCM) to afford 6-[methoxy-[1-(4-piperidyl)pyrazol-4-yl]methyl]-1H-benzo[cd]indol-2-one (1) (320 mg, 99% yield) as yellow solid. LC MS ES+ 363.2.

Step-2: Synthesis of 6-[methoxy-[1-[1-(1-methylcyclobutanecarbonyl)-4-piperidyl]pyrazol-4-yl]methyl]-1H-benzo[cd]indol-2-one: To the stirred solution of -[methoxy-[1-(4-piperidyl)pyrazol-4-yl]methyl]-1H-benzo[cd]indol-2-one (1) (325 mg, 896.74 umol) and 1-methylcyclobutanecarboxylic acid (2) (102.36 mg, 896.74 umol) in DMF (3 mL) was added DIPEA (579.49 mg, 4.48 mmol, 780.98 uL) and stirred for 15 minutes followed by the addition of HATU (511.45 mg, 1.35 mmol) and was allowed to stir for 16 hours at RT. After completion (monitored by LCMS), the reaction mixture was diluted with Ethyl acetate and washed with cold water, brine, dried over sodium sulfate and concentrated under reduced pressure. The crude thus obtained was purified by column chromatography (silica, gradient: 0-2.5% MeOH in DCM) to afford 6-[methoxy-[1-[1-(1-methylcyclobutanecarbonyl)-4-piperidyl]pyrazol-4-yl]methyl]-1H-benzo[cd]indol-2-one (3) (100 mg, 21.89% yield) as gummy solid. LC MS: ES+(M-31) 427.3

Step-3: Synthesis of 3-[6-[methoxy-[1-[1-(1-methylcyclobutanecarbonyl)-4-piperidyl]pyrazol-4-yl]methyl]-2-oxo-benzo[cd]indol-1-yl]piperidine-2,6-dione: To a stirred solution of 6-[methoxy-[1-[1-(1-methylcyclobutanecarbonyl)-4-piperidyl]pyrazol-4-yl]methyl]-1H-benzo[cd]indol-2-one (3) (50 mg, 109.04 umol) in THF (3 mL) was added Sodium hydride 60% dispersion in mineral oil (41.78 mg, 1.09 mmol) at 0° C. and stirred for 5 min. Then 3-bromopiperidine-2,6-dione (4) (104.68 mg, 545.20 umol) was added under cooling condition and the reaction mixture was stirred at 70° C. for 60 min. After completion (monitored by TLC) the reaction mixture was quenched in ice and extracted with ethyl acetate. The organic part was further washed with water and brine, dried over sodium sulfate and concentrated. The crude thus obtained was purified by Prep TLC Plate in 80% EtOAc in DCM to afford 3-[6-[methoxy-[1-[1-(1-methylcyclobutanecarbonyl)-4-piperidyl]pyrazol-4-yl]methyl]-2-oxo-benzo[cd]indol-1-yl]piperidine-2,6-dione Compound 247 (20 mg, 30.59% yield) as yellow solid. $^1$H NMR (400 MHz, DMSO-d6) δ 11.12 (s, 1H), 8.39 (d, J=8.32 Hz, 1H), 8.08 (d, J=6.96 Hz, 1H), 7.79 (t, J=7.64 Hz, 1H), 7.65 (s, 1H), 7.56 (d, J=7.12 Hz, 1H), 7.32 (s, 1H), 7.14 (d, J=7.36 Hz, 1H), 5.84 (s, 1H), 5.45 (dd, J=12.8, 5.2 Hz, 1H), 4.34-4.28 (m, 2H), 3.61-3.60 (m, 1H), 3.27 (s, 3H), 3.05-2.91 (m, 2H), 2.78-2.63 (m, 3H), 2.41-2.32 (m, 2H), 2.11-2.08 (m, 1H), 1.94-1.91 (m, 3H), 1.86-1.58 (m, 5H), 1.33 (s, 3H)LC MS: ES+(M-31) 538.5.

Example 137. Synthesis of tert-butyl 4-[4-[[1-(2,6-dioxo-3-piperidyl)-2-oxo-benzo[cd]indol-6-yl]amino]pyrazol-1-yl]piperidine-1-carboxylate (Compound 248) and 3-[6-[[1-[1-(1-methylcyclobutanecarbonyl)-4-piperidyl]pyrazol-4-yl]amino]-2-oxo-benzo[cd]indol-1-yl]piperidine-2,6-dione (Compound 249)
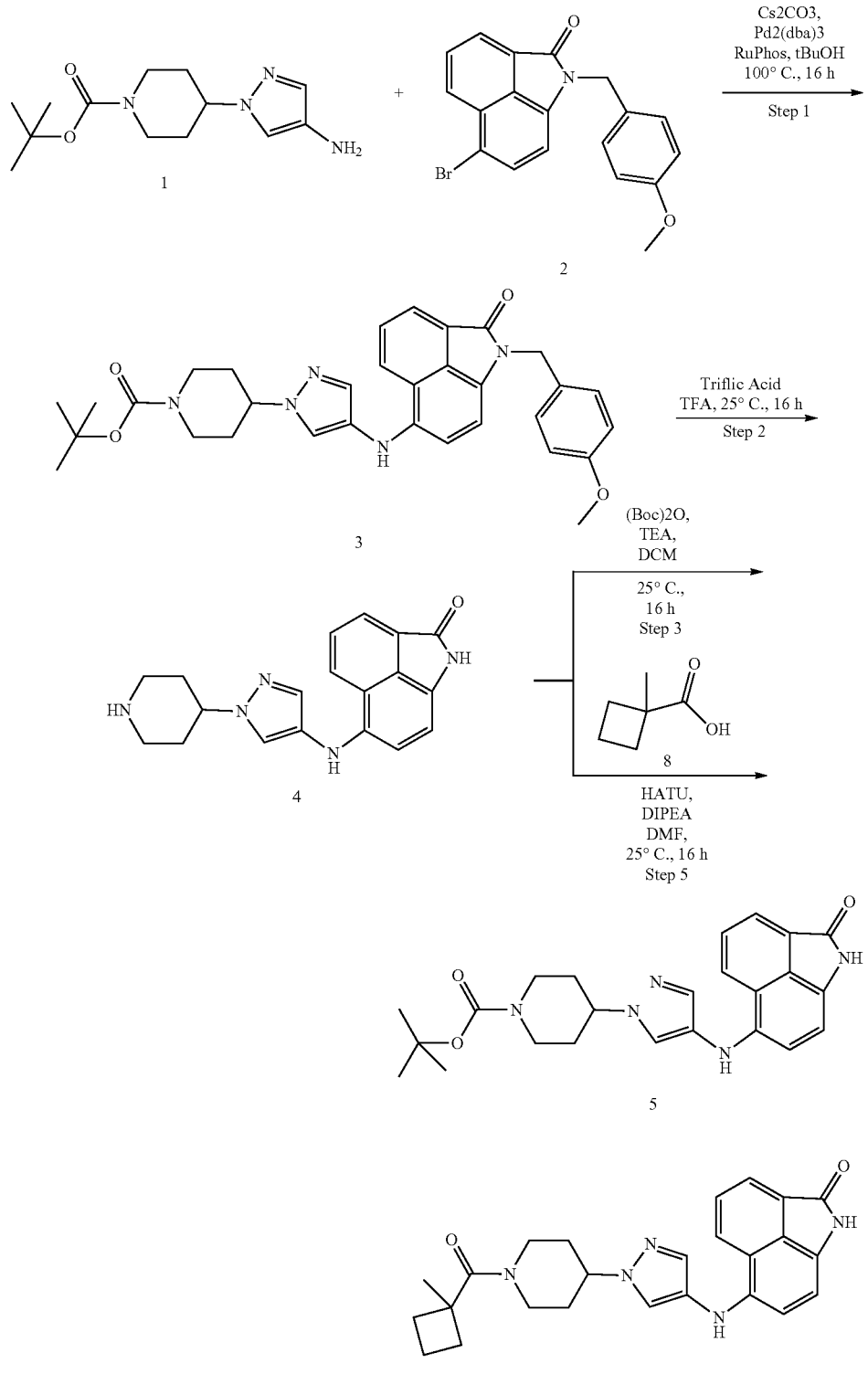

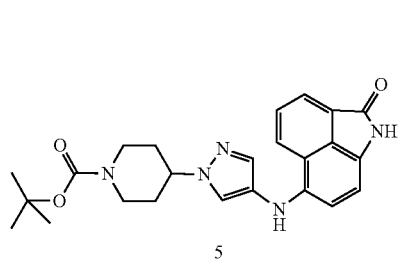
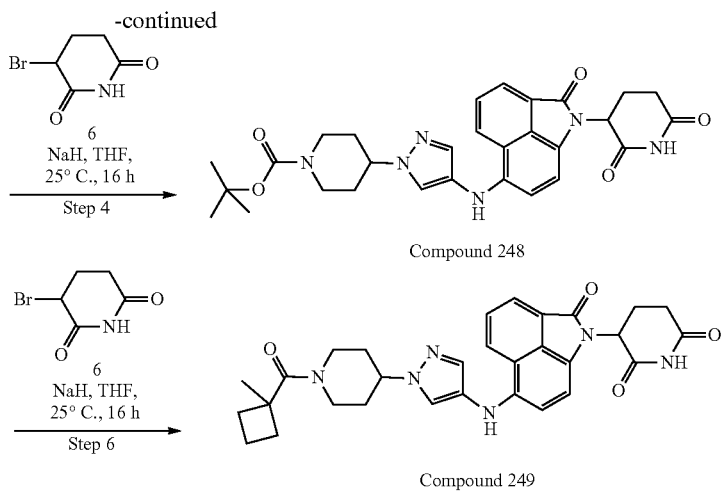
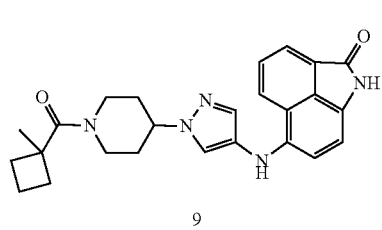

Step-1: Synthesis of tert-butyl 4-[4-[[1-[(4-methoxyphenyl)methyl]-2-oxo-benzo[cd]indol-6-yl]amino]pyrazol-1-yl]piperidine-1-carboxylate: In a sealed tube a stirred solution of tert-butyl 4-(4-aminopyrazol-1-yl)piperidine-1-carboxylate (400 mg, 1.50 mmol) and 6-bromo-1-[(4-methoxyphenyl)methyl]benzo[cd]indol-2-one (553.02 mg, 1.50 mmol) in tert butanol (2.50 mL), was added Cesium carbonate (734.00 mg, 2.25 mmol) then reaction mixture was degassed for 5 min under argon atmosphere. Then added pd₂(dba)3 (137.52 mg, 150.18 umol) and 2-Dicyclohexylphosphino-2',6'-di-I-propoxy-1,1'-biphenyl (70.08 mg, 150.18 umol) then again purged for 2 min under argon atmosphere, then the reaction mixture was heated to 100° C. for 16 hr. After completion of the reaction mass added water then extracted with ethyl acetate then organic layers was washed with brine then dried with sodium sulphate and then evaporated under reduced pressure to get the crude. This crude was purified by combiflash column chromatography (using 50% ethyl acetate in hexane) to give the title compound tert-butyl 4-[4-[[1-[(4-methoxyphenyl)methyl]-2-oxo-benzo[cd]indol-6-yl]amino]pyrazol-1-yl]piperidine-1-carboxylate (500 mg, 812.79 umol, 54.12% yield, 90% purity) as orange solid. LCMS (ES+)=554.5 [M+H]+.

Step-2: Synthesis of 6-[[1-(4-piperidyl)pyrazol-4-yl]amino]-1H-benzo[cd]indol-2-one: To a stirred solution of tert-butyl 4-[4-[[1-[(4-methoxyphenyl)methyl]-2-oxo-benzo[cd]indol-6-yl]amino]pyrazol-1-yl]piperidine-1-carboxylate (300.00 mg, 541.86 umol) in Trifluroacetic acid (10 mL), reaction mixture was cooled to 0° C., was slowly added Trifluoromethanesulfonic acid (243.97 mg, 1.63 mmol, 142.67 uL) then reaction was stirred at 25° C. for 16 hr. After completion of SM, reaction mixture was concentrated under reduced pressure, then dissolved in ice cold water and basified by solid sodium bicarbonate and extracted with ethyl acetate, dried over sodium sulphate, concentrated under reduced pressure to give the title compound 6-[[1-(4-piperidyl)pyrazol-4-yl]amino]-1H-benzo[cd]indol-2-one (150 mg, 382.44 umol, 70.58% yield, 85% purity) as orange solid. LCMS (ES+)=334.4 [M+H]+.

Step-3: Synthesis of tert-butyl 4-[4-[(2-oxo-1H-benzo[cd]indol-6-yl)amino]pyrazol-1-yl]piperidine-1-carboxylate: To a stirred solution of 6-[[1-(4-piperidyl)pyrazol-4-yl]amino]-1H-benzo[cd]indol-2-one (180 mg, 539.91 umol) in DCM (10 mL), was added Triethylamine (163.90 mg, 1.62 mmol, 225.76 uL) and followed by Di-tert-butyl dicarbonate (141.40 mg, 647.90 umol, 148.69 uL), then the reaction mixture was stirred at 25° C. for 16 hr. After completion of the reaction, added water then extracted with DCM then organic layers was washed with brine then dried with sodium sulphate and then evaporated under reduced pressure to get the crude. This crude was purified by combiflash column chromatography (using ethyl acetate) to give the title compound tert-butyl 4-[4-[(2-oxo-1H-benzo[cd]indol-6-yl)amino]pyrazol-1-yl]piperidine-1-carboxylate (200 mg, 424.45 umol, 78.61% yield, 92% purity) as orange solid. LCMS (ES+)=434.5 [M+H]+.

Step-4: Synthesis of tert-butyl 4-[4-[[1-(2,6-dioxo-3-piperidyl)-2-oxo-benzo[cd]indol-6-yl]amino]pyrazol-1-yl]piperidine-1-carboxylate: To a stirred solution of tert-butyl 4-[4-[(2-oxo-1H-benzo[cd]indol-6-yl)amino]pyrazol-1-yl]piperidine-1-carboxylate (150 mg, 346.02 umol) and 3-bromopiperidine-2,6-dione (664.39 mg, 3.46 mmol) were in THF (10 mL), reaction mixture was cooled to 0° C., then slowly drop wise added Sodium hydride (in oil dispersion) 60% dispersion in mineral oil (397.75 mg, 10.38 mmol, 60% purity). Reaction was slowly rise the temperature up to RT and then stirred for 10 mins and then heated to 65° C. for 16 hr. After that reaction was quenched by ice cold water and extracted with ethyl acetate, separate the organic layer, dried over sodium sulphate, concentrated under reduced pressure to give the crude. This crude was purified by prep-HPLC (100% acetonitrile) to give the title compound tert-butyl 4-[4-[[1-(2,6-dioxo-3-piperidyl)-2-oxo-benzo[cd]indol-6-yl]amino]pyrazol-1-yl]piperidine-1-carboxylate Compound 248 (30 mg, 53.89 umol, 15.57% yield, 97.82% purity) as orange solid. LCMS (ES+)=543.2 [M–H]+. 1H NMR (400 MHz, DMSO-d6): δ 11.07 (s, 1H), 8.59-8.57 (d, 1H), 8.08-8.06 (t, 2H), 7.86 (s, 1H), 7.80-7.76 (t, 1H), 7.49 (s, 1H), 6.90-6.88 (d, 1H), 6.66-6.64 (d, 1H), 5.39-5.37 (m, 1H), 4.36-4.30 (m, 1H), 4.06-4.03 (m, 2H), 2.93-2.90 (m, 3H), 2.71-2.61 (m, 2H), 2.07-2.00 (m, 3H), 1.85-1.75 (m, 2H), 1.41 (s, 9H).

Step-5: Synthesis of 6-[[1-[1-(1-methylcyclobutanecarbonyl)-4-piperidyl]pyrazol-4-yl]amino]-1H-benzo[cd]indol-2-one: To a stirred solution of 6-[[1-(4-piperidyl)pyrazol-4-yl]amino]-1H-benzo[cd]indol-2-one (180 mg, 539.91 umol) and 1-methylcyclobutanecarboxylic acid (73.95 mg, 647.90 umol) in DMF (10 mL), was added DIPEA (209.34 mg, 1.62 mmol, 282.12 uL) and then followed by HATU (225.82 mg, 593.91 umol), then the reaction mixture was stirred at 25° C.

for 16 hr. After completion of the reaction, added water then extracted with ethyl acetate then organic layers was washed with brine then dried with sodium sulphate and then evaporated under reduced pressure to get the crude. This crude was purified by combiflash column chromatography (using ethyl acetate) to give the title compound 6-[[1-[1-(1-methylcyclobutanecarbonyl)-4-piperidyl]pyrazol-4-yl]amino]-1H-benzo[cd]indol-2-one (105 mg, 220.02 umol, 40.75% yield, 90% purity) as orange solid. LCMS (ES+)=430.4 [M+H]+.

Step-6: Synthesis of 3-[6-[[1-[1-(1-methylcyclobutanecarbonyl)-4-piperidyl]pyrazol-4-yl]amino]-2-oxo-benzo[cd]indol-1-yl]piperidine-2,6-dione: To a stirred solution of 6-[[1-[1-(1-methylcyclobutanecarbonyl)-4-piperidyl]pyrazol-4-yl]amino]-1H-benzo[cd]indol-2-one (65 mg, 151.33 umol) and 3-bromopiperidine-2,6-dione (116.23 mg, 605.34 umol) were in THF (15 mL), reaction mixture was cooled to 0° C., then slowly drop wise added Lithium bis(trimethylsilyl)amide (1 M, 1.21 mL). Reaction was slowly rise the temperature up to RT and then stirred for 10 mins and then heated to 65° C. for 16 hr. After that reaction was quenched by ice cold water and extracted with ethyl acetate, separate the organic layer, dried over sodium sulphate, concentrated under reduced pressure to give the crude. This crude was purified by prep-TLC (using 80% ethyl acetate in DCM) to give the title compound 3-[6-[[1-[1-(1-methylcyclobutanecarbonyl)-4-piperidyl]pyrazol-4-yl]amino]-2-oxo-benzo[cd]indol-1-yl]piperidine-2,6-dione Compound 249 (10 mg, 18.19 umol, 12.02% yield, 98.36% purity) as orange solid. LCMS (ES+)=541.2 [M+H]+. 1H NMR (400 MHz, DMSO-d6): δ 11.08 (s, 1H), 8.59-8.57 (d, 1H), 8.08-8.06 (t, 2H), 7.88 (s, 1H), 7.80-7.77 (t, 1H), 7.48 (s, 1H), 6.91-6.89 (d, 1H), 6.67-6.65 (d, 1H), 5.40-5.35 (m, 1H), 4.43-4.37 (m, 2H), 3.64 (m, 1H), 3.14 (m, 1H), 2.97-2.89 (m, 1H), 2.74-2.65 (m, 2H), 2.45-2.42 (m, 3H), 2.07-2.04 (m, 3H), 1.96-1.92 (m, 2H), 1.89-1.87 (m, 4H), 1.66 (m, 2H), 1.37-1.33 (s, 3H).

Example 138. Synthesis of tert-butyl 4-[3-chloro-4-[[1-(2,6-dioxo-3-piperidyl)-2-oxo-benzo[cd]indol-6-yl]amino]pyrazol-1-yl]piperidine-1-carboxylate (Compound 250) and 3-[6-[[3-chloro-1-[1-(1-methylcyclobutanecarbonyl)-4-piperidyl]pyrazol-4-yl]amino]-2-oxo-benzo[cd]indol-1-yl]piperidine-2,6-dione (Compound 251)

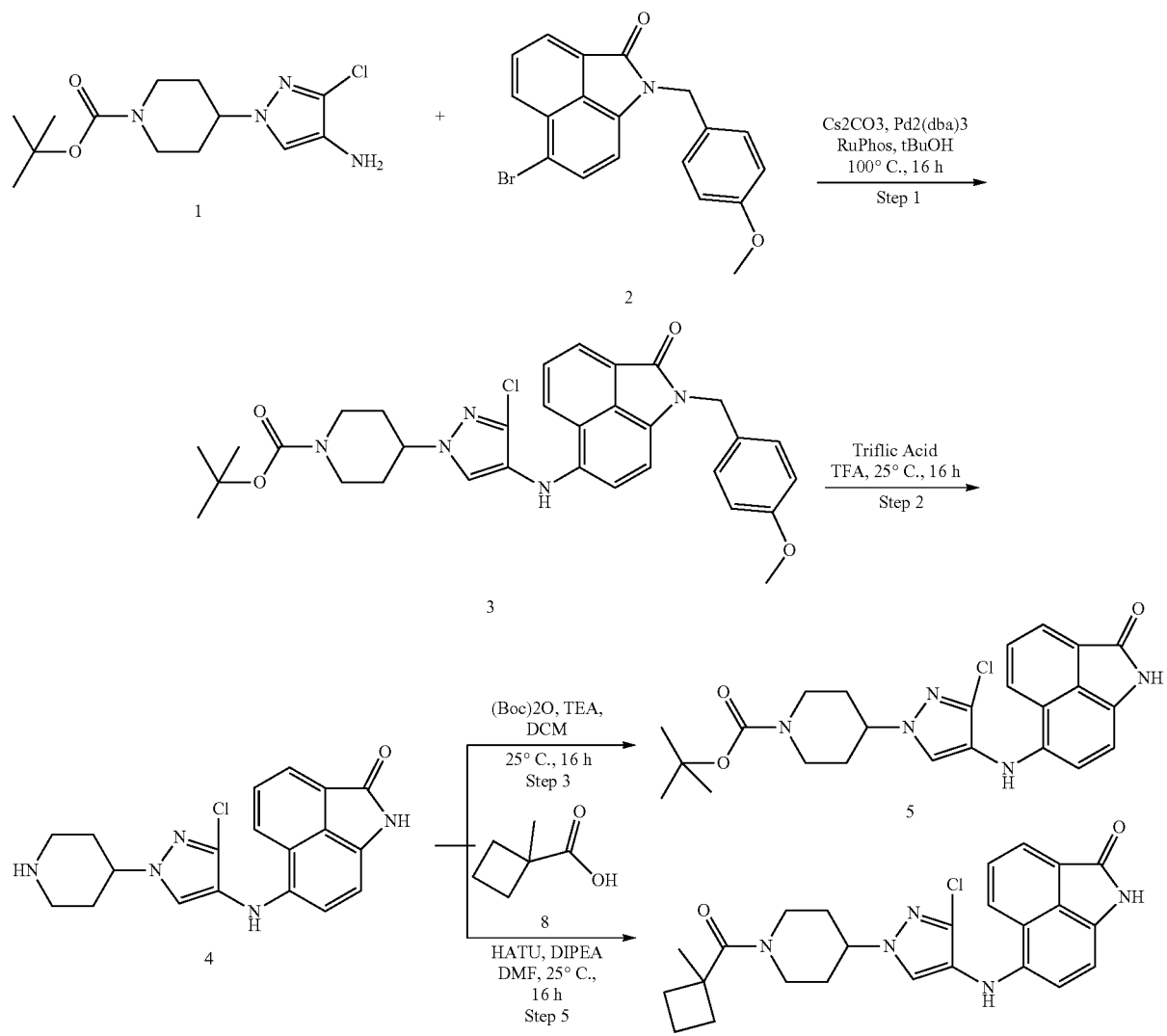

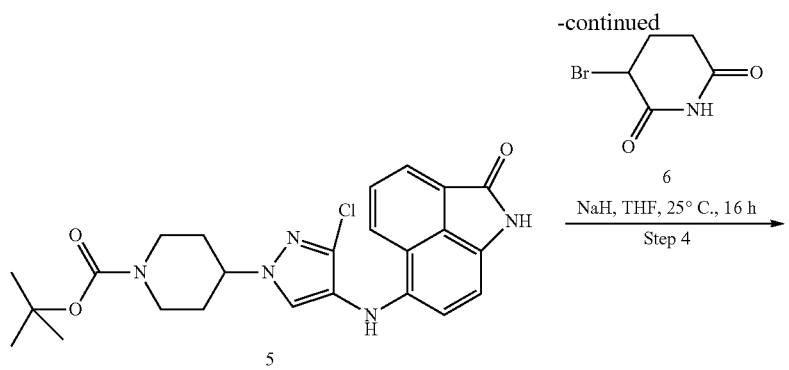

Compound 250

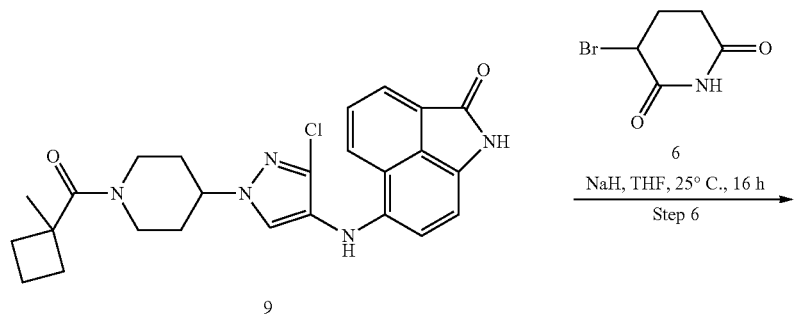

Compound 251

Step-1: Synthesis of tert-butyl 4-[3-chloro-4-[[1-[(4-methoxyphenyl)methyl]-2-oxo-benzo[cd]indol-6-yl]amino]pyrazol-1-yl]piperidine-1-carboxylate: In a sealed tube a stirred solution of tert-butyl 4-(4-amino-3-chloro-pyrazol-1-yl)piperidine-1-carboxylate (1.3 g, 4.32 mmol) and 6-bromo-1-[(4-methoxyphenyl)methyl]benzo[cd]indol-2-one (1.59 g, 4.32 mmol) in tert butanol (25 mL), was added Cesium carbonate (2.11 g, 6.48 mmol) then reaction mixture was degassed for 5 min under argon atmosphere. Then added pd$_2$(dba)3 (395.77 mg, 432.20 umol) and 2-Dicyclohexylphosphino-2',6'-di-I-propoxy-1,1'-biphenyl (201.68 mg, 432.20 umol) then again purged for 2 min under argon atmosphere, then the reaction mixture was heated to 100° C. for 16 hr. After completion of the reaction mass added water then extracted with ethyl acetate then organic layers was washed with brine then dried with sodium sulphate and then evaporated under reduced pressure to get the crude. This crude was purified by combiflash column chromatography (using 50% ethyl acetate in hexane) to give the title compound tert-butyl 4-[3-chloro-4-[[1-[(4-methoxyphenyl) methyl]-2-oxo-benzo[cd]indol-6-yl]amino]pyrazol-1-yl]piperidine-1-carboxylate (2 g, 3.23 mmol, 74.75% yield, 95% purity) as orange solid. LCMS (ES+)=588.2 [M+H]+.

Step-2: Synthesis of 6-[[3-chloro-1-(4-piperidyl)pyrazol-4-yl]amino]-1H-benzo[cd]indol-2-one: To a stirred solution of tert-butyl 4-[3-chloro-4-[[1-[(4-methoxyphenyl)methyl]-2-oxo-benzo[cd]indol-6-yl]amino]pyrazol-1-yl]piperidine-1-carboxylate (1 g, 1.70 mmol) in Trifluroacetic acid (10 mL),reaction mixture was cooled to 0° C., was slowly added Trifluoromethanesulfonic acid (765.59 mg, 5.10 mmol, 447.71 uL) then reaction was stirred at 25° C. for 16 hr. After completion of SM, reaction mixture was concentrated under reduced pressure, then dissolved in ice cold water and basified by solid sodium bicarbonate and extracted with ethyl acetate, dried over sodium sulphate, concentrated under reduced pressure to give the title compound 6-[[3-chloro-1-(4-piperidyl)pyrazol-4-yl]amino]-1H-benzo[cd]indol-2-one (600 mg, 1.55 mmol, 91.13% yield, 95% purity) as orange solid; LCMS (ES+)=368.3 [M+H]+.

Step-3: Synthesis of tert-butyl 4-[3-chloro-4-[(2-oxo-1H-benzo[cd]indol-6-yl)amino]pyrazol-1-yl]piperidine-1-carboxylate: To a stirred solution of 6-[[3-chloro-1-(4-piperidyl)pyrazol-4-yl]amino]-1H-benzo[cd]indol-2-one (150 mg, 407.80 umol) in DCM (10 mL), was added Triethylamine (123.79 mg, 1.22 mmol, 170.52 uL) and followed by Di-tert-butyl dicarbonate (106.80 mg, 489.35 umol, 112.30 uL), then the reaction mixture was stirred at 25° C. for 16 hr. After completion of the reaction, added water then extracted with DCM then organic layers was washed with brine then dried with sodium sulphate and then evaporated under reduced pressure to get the crude. This crude was purified by combiflash column chromatography (using ethyl acetate) to give the title compound tert-butyl 4-[3-chloro-4-[(2-oxo-1H-benzo[cd]indol-6-yl)amino]pyrazol-1-yl]piperidine-1-carboxylate (130 mg, 255.58 umol, 62.67% yield, 92% purity) as orange solid. LCMS (ES+)=468.1 [M+H]+.

Step-4: Synthesis of tert-butyl 4[-3-chloro-4-[[1-(2,6-dioxo-3-piperidyl)-2-oxo-benzo[cd]indol-6-yl]amino]pyrazol-1-yl]piperidine-1-carboxylate: To a stirred solution of tert-butyl 4-[3-chloro-4-[(2-oxo-1H-benzo[cd]indol-6-yl)amino]pyrazol-1-yl]piperidine-1-carboxylate (30 mg, 64.11 umol) in THF (5 mL), reaction mixture was cooled to 0° C., then portion wise added Sodium hydride (in oil dispersion) 60% dispersion in mineral oil (24.56 mg, 641.10 umol, 60% purity). Reaction was slowly rise the temperature up to RT and then stirred for 10 mins. After that 3-bromopiperidine-2,6-dione (61.55 mg, 320.55 umol) was added slowly at RT, then again stirred for 10 mins and then heated to 65° C. for 1 hr. After completion of SM, reaction was quenched by ice cold water and extracted with ethyl acetate, separate the organic layer, dried over sodium sulphate, concentrated under reduced pressure to give the crude. This crude was purified by prep-TLC (using 70% ethyl acetate in DCM) to give the title compound tert-butyl 4-[3-chloro-4-[[1-(2,6-dioxo-3-piperidyl)-2-oxo-benzo[cd]indol-6-yl]amino]pyrazol-1-yl]piperidine-1-carboxylate Compound 250 (2 mg, 3.36 umol, 5.24% yield, 97.28% purity) as orange solid. LCMS (ES+)=577.2 [M−H]+. 1H NMR (400 MHz, DMSO-d6): δ 11.07 (s, 1H), 8.60-8.57 (d, 1H), 8.09-8.08 (d, 1H), 8.03 (s, 1H), 7.85 (s, 1H), 7.82-7.78 (t, 1H), 6.88-6.86 (d, 1H), 6.22-6.20 (d, 1H), 4.43-4.33 (m, 1H), 4.03 (m, 2H), 2.92-2.89 (m, 2H), 2.70-2.60 (m, 2H), 2.05-2.02 (m, 3H), 1.80-1.77 (m, 2H), 1.41 (m, 9H).

Step-5: Synthesis of 6-[[3-chloro-1-[1-(1-methylcyclobutanecarbonyl)-4-piperidyl]pyrazol-4-yl]amino]-1H-benzo[cd]indol-2-one: To a stirred solution of 6-[[3-chloro-1-(4-piperidyl)pyrazol-4-yl]amino]-1H-benzo[cd]indol-2-one (300 mg, 815.59 umol) and 1-methylcyclobutanecarboxylic acid (111.71 mg, 978.71 umol) in DMF (15 mL), was added DIPEA (316.22 mg, 2.45 mmol, 426.17 uL) and then followed by HATU (341.12 mg, 897.15 umol), then the reaction mixture was stirred at 25° C. for 16 hr. After completion of the reaction, added water then extracted with ethyl acetate then organic layers was washed with brine then dried with sodium sulphate and then evaporated under reduced pressure to get the crude. This crude was purified by combiflash column chromatography (using ethyl acetate) to give the title compound 6-[[3-chloro-1-[1-(1-methylcyclobutanecarbonyl)-4-piperidyl]pyrazol-4-yl]amino]-1H-benzo[cd]indol-2-one (120 mg, 237.95 umol, 29.18% yield, 92% purity) as orange solid. LCMS (ES+)=464.4 [M+H]+.

Step-6: Synthesis of 3-[6-[[3-chloro-1-[1-(1-methylcyclobutanecarbonyl)-4-piperidyl]pyrazol-4-yl]amino]-2-oxo-benzo[cd]indol-1-yl]piperidine-2,6-dione: To a stirred solution of 6-[[3-chloro-1-[1-(1-methylcyclobutanecarbonyl)-4-piperidyl]pyrazol-4-yl]amino]-1H-benzo[cd]indol-2-one (64 mg, 137.94 umol) and 3-bromopiperidine-2,6-dione (79.46 mg, 413.83 umol) were in THF (10 mL), reaction mixture was cooled to 0° C., then slowly drop wise added Lithium bis(trimethylsilyl)amide (1 M, 689.72 uL). Reaction was slowly rise the temperature up to RT and then stirred for 10 mins and then heated to 65° C. for 16 hr. After that reaction was quenched by ice cold water and extracted with ethyl acetate, separate the organic layer, dried over sodium sulphate, concentrated under reduced pressure to give the crude. This crude was purified by prep-TLC (using 80% ethyl acetate in DCM) to give the title compound 3-[6-[[3-chloro-1-[1-(1-methylcyclobutanecarbonyl)-4-piperidyl]pyrazol-4-yl]amino]-2-oxo-benzo[cd]indol-1-yl]piperidine-2,6-dione Compound 251 (12 mg, 19.89 umol, 14.42% yield, 95.31% purity) as orange solid. LCMS (ES+)=575.2 [M+H]+. 1H NMR (400 MHz, DMSO-d6): δ 11.08 (s, 1H), 8.60-8.58 (d, 1H), 8.10-8.08 (d, 1H), 8.05 (s, 1H), 7.86 (s, 1H), 7.82-7.78 (t, 1H), 6.89-6.87 (d, 1H), 6.22-6.21 (d, 1H), 5.38-5.35 (m, 1H), 4.41 (m, 3H), 3.63 (m, 1H), 3.13 (m, 1H), 2.93-2.89 (m, 2H), 2.71-2.67 (m, 3H), 2.05-1.98 (m, 3H), 1.94-1.92 (m, 2H), 1.87-1.80 (m, 4H), 1.63-1.61 (m, 1H), 1.37 (s, 3H).

Example 139. Synthesis of tert-butyl 4-[4-[[1-(2,6-dioxo-3-piperidyl)-2-oxo-benzo[cd]indol-6-yl]-methyl-amino]pyrazol-1-yl]piperidine-1-carboxylate (Compound 252)

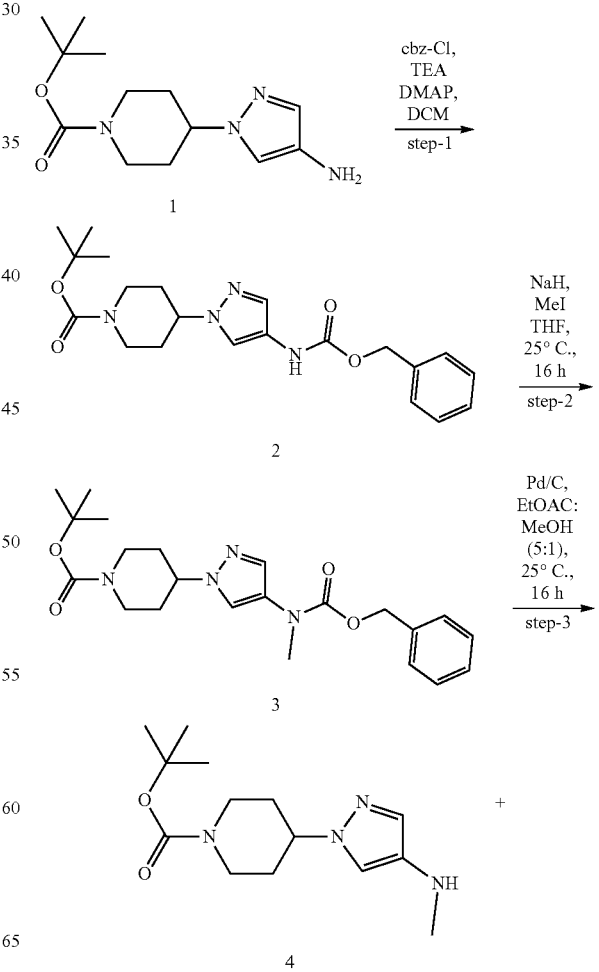

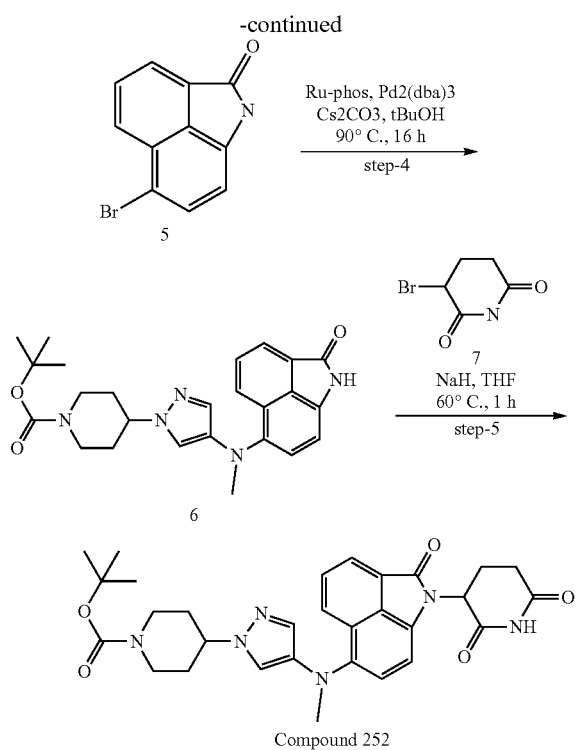

Step-1: Synthesis of tert-butyl 4-[4-(benzyloxycarbonylamino)pyrazol-1-yl]piperidine-1-carboxylate: To a stirred solution of tert-butyl 4-(4-aminopyrazol-1-yl)piperidine-1-carboxylate (1.5 g, 5.63 mmol) in DCM (20 mL), reaction was cooled to 0° C. then added Triethylamine (1.14 g, 11.26 mmol, 1.57 mL) and the catalytic amount of DMAP (68.80 mg, 563.19 umol) followed by drop wise added benzyl carbonochloridate (960.77 mg, 5.63 mmol, 800.64 uL). Then reaction mixture was stirred at 25° C. for 2 hr. After completion of SM, reaction mixture was quenched by saturated solution of sodium bicarbonate, extracted with DCM, dried over sodium sulphate, concentrated under reduced pressure to give the crude. It was purified by combiflash column chromatography (eluted by 40% ethyl acetate in n-hexane) to give the title compound tert-butyl 4-[4-(benzyloxycarbonylamino)pyrazol-1-yl]piperidine-1l-carboxylate (1.6 g, 3.92 mmol, 69.52% yield, 98% purity) as brown sticky liquid. LCMS (ES+)=401.1 [M+H]+.

Step-2: Synthesis of tert-butyl 4-[4-[benzyloxycarbonyl(methyl)amino]pyrazol-1-yl]piperidine-1-carboxylate: To a stirred solution of tert-butyl 4-[4-(benzyloxycarbonylamino)pyrazol-1-yl]piperidine-1-carboxylate (1.7 g, 4.25 mmol) in THF (35 mL), reaction was cooled to 0° C., then Sodium hydride (in oil dispersion) 60% dispersion in mineral oil (2.55 mg, 6.37 mmol, 60 purity) was added portion wise. Then reaction mixture was stirred at 0° C. for 40 mins. After that Methyl iodide (D3) stored over Copper (1.21 g, 8.49 mmol, 528.53 uL) was added slowly drop wise into the reaction mixture, then temp was rise up to RT, and reaction was stirred at RT for 16 hr. After completion of SM, reaction mixture was quenched by ice cold water, extracted with ethyl acetate, dried over sodium sulphate, concentrated under reduced pressure to give the crude. It was purified by combiflash column chromatography (eluted by 40% ethyl acetate in n-hexane) to give the title compound tert-butyl 4-[4-[benzyloxycarbonyl(methyl)amino]pyrazol-1-yl]piperidine-1-carboxylate (1.5 g, 3.51 mmol, 82.69% yield, 97% purity) as brown sticky liquid. LCMS (ES+)=415.1 [M+H]+.

Step-3: Synthesis of tert-butyl 4-[4-(methylamino)pyrazol-1-yl]piperidine-1-carboxylate: To a stirred solution of tert-butyl 4-[4-[benzyloxycarbonyl(methyl)amino]pyrazol-1-yl]piperidine-1-carboxylate (1.6 g, 3.86 mmol) in Ethyl acetate (30 mL) and Methanol (6 mL), was added Palladium (1.64 g, 15.44 mmol) then reaction mixture was stirred at 25° C. for 16 hr under hydrogen atmoshphere. After completion of SM, reaction mixture was filtered through celite bed and solution was concentrated under reduced pressure to give the title compound tert-butyl 4-[4-(methylamino)pyrazol-1-yl]piperidine-1-carboxylate (1 g, 3.39 mmol, 87.78% yield, 95% purity) as brown sticky liquid. LCMS (ES+)=281.4 [M+H]+.

Step-4: Synthesis of tert-butyl 4-[4-[methyl-(2-oxo-1H-benzo[cd]indol-6-yl)amino]pyrazol-1-yl]piperidine-1-carboxylate: In a sealed tube the stirred solution of tert-butyl 4-[4-(methylamino)pyrazol-1-yl]piperidine-1-carboxylate (500 mg, 1.78 mmol) and 6-bromo-1H-benzo[cd]indol-2-one (442.41 mg, 1.78 mmol) in tert butanol (15 mL), was added Cesium carbonate (871.60 mg, 2.68 mmol) then reaction mixture was degassed for 5 min under argon atmosphere. Then added pd$_2$(dba)3 (163.30 mg, 178.34 umol) and 2-Dicyclohexylphosphino-2',6'-di-I-propoxy-1,1'-biphenyl (166.25 mg, 356.68 umol) then again purged for 2 min under argon atmosphere, then the reaction mixture was heated to 90° C. for 16 hr. After consumption of SM reaction mixture was filtered through celite bed and concentrated in vacuo. Purification by combiflash column chromatography (eluted by 40% ethyl acetate in n-hexane) to give the title compound tert-butyl 4-[4-[methyl-(2-oxo-1H-benzo[cd]indol-6-yl)amino]pyrazol-1-yl]piperidine-1-carboxylate (280 mg, 563.09 umol, 31.57% yield, 90% purity) as yellow liquid. LCMS (ES+)=448.4 [M+H]+.

Step-5: Synthesis of tert-butyl 4-[4-[[1-(2,6-dioxo-3-piperidyl)-2-oxo-benzo[cd]indol-6-yl]-methyl-amino]pyrazol-1-yl]piperidine-1-carboxylate: To a stirred solution of tert-butyl 4-[4-[methyl-(2-oxo-1H-benzo[cd]indol-6-yl)amino]pyrazol-1-yl]piperidine-1-carboxylate (80.00 mg, 178.76 umol) in DMF (5 mL), reaction mixture was cooled to 0° C., then added Sodium hydride (in oil dispersion) 60% dispersion in mineral oil (20.55 mg, 536.28 umol, 60% purity). Then reaction was heated to 60° C. for 30 min. After that 3-bromopiperidine-2,6-dione (68.65 mg, 357.52 umol) was added to that mixture, then continue heating for 4 to 6 hr. But SM was not fully consumed, then again added 3-bromopiperidine-2,6-dione (68.65 mg, 357.52 umol) and reaction continue for 16 hr. After that reaction was diluted with water and extracted with ethyl acetate, dried over sodium sulphate, concentrated under reduced pressure to give the crude. This crude was purified by prep-TLC (using ethyl acetate) to give the title compound tert-butyl 4-[4-[[1-(2,6-dioxo-3-piperidyl)-2-oxo-benzo[cd]indol-6-yl]-methyl-amino]pyrazol-1-yl]piperidine-1-carboxylate Compound 252 (9 mg, 15.35 umol, 8.59% yield, 95.28% purity) as orange solid. LCMS (ES+)=559.6 [M+H]+. 1H NMR (400 MHz, DMSO-d6): δ 11.11 (s, 1H), 8.06-8.04 (d, 1H), 8.02-8.00 (d, 1H), 7.71 (t, 1H), 7.40 (s, 1H), 7.16-7.14 (d, 1H), 7.07-7.05 (d, 2H), 5.42 (t, 1H), 4.22-4.19 (d, 1H), 3.99-3.96 (m, 2H), 3.23 (s, 3H), 2.98-2.90 (m, 1H), 2.84-2.80 (m, 1H), 2.76-2.73 (m, 1H), 2.67-2.63 (m, 1H), 2.44-2.41 (m, 1H), 2.10-2.09 (m, 1H), 1.93-1.90 (m, 2H), 1.71-1.66 (m, 2H), 1.39 (s, 9H).

Example 140. Synthesis of 3-[6-[[1-[1-(1-methylcyclobutanecarbonyl)-4-piperidyl]pyrrolo[2,3-b]pyridin-3-yl]methyl]-2-oxo-benzo[cd]indol-1-yl]piperidine-2,6-dione (Compound 253)

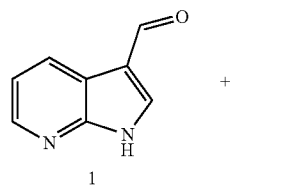

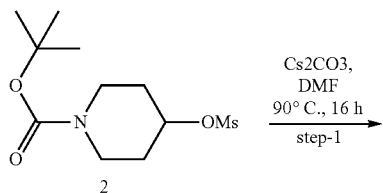

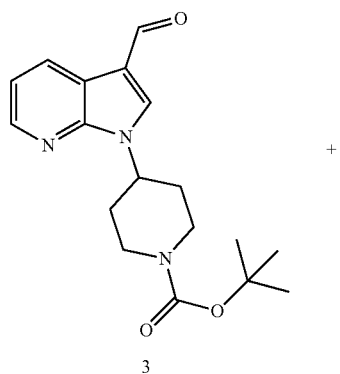

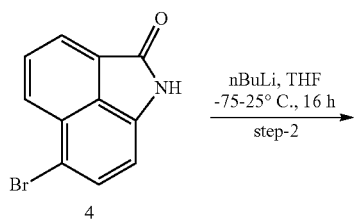

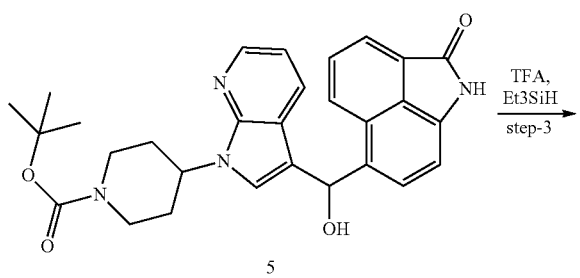

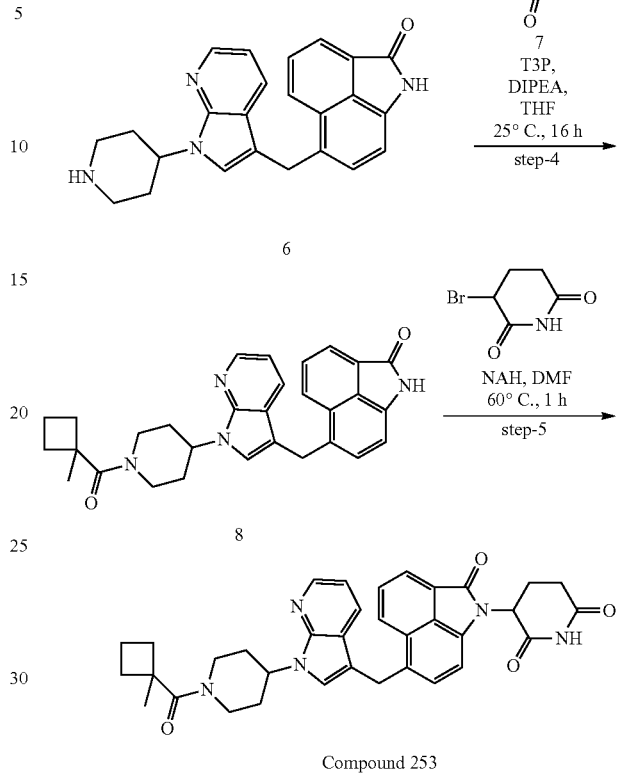

Compound 253

Step-1: Synthesis of tert-butyl 4-(3-formylpyrrolo[2,3-b]pyridin-1-yl)piperidine-1-carboxylate: To a stirred solution of 1H-pyrrolo[2,3-b]pyridine-3-carbaldehyde (2 g, 13.68 mmol) and tert-butyl 4-methylsulfonyloxypiperidine-1-carboxylate (4.21 g, 15.05 mmol) were in DMF (30 mL), was added Cesium carbonate (8.92 g, 27.37 mmol) and the reaction mixture was heated at 90° C. for 16 hr. After completion of SM, reaction mixture was diluted with ethyl acetate, washed with water, separate the organic layer, dried over sodium sulphate, concentrated under reduced pressure to give the crude. It was purified by combiflash column chromatography (15% ethyl acetate in hexane) to give the title compound tert-butyl 4-(3-formylpyrrolo[2,3-b]pyridin-1-yl)piperidine-1-carboxylate (2 g, 5.89 mmol, 43.04% yield, 97% purity) as a white solid. LCMS (ES+)=330.2 [M+H]+.

Step-2: Synthesis of tert-butyl 4-[3-[hydroxy-(2-oxo-1H-benzo[cd]indol-6-yl)methyl]pyrrolo[2,3-b]pyridin-1-yl]piperidine-1-carboxylate: To a stirred solution of 6-bromo-1H-benzo[cd]indol-2-one (100.00 mg, 403.10 umol) in THF (10 mL), reaction mixture was cooled to −78° C., then Butyl Lithium (2.2 M, 732.92 uL) was added slowly drop wise and reaction was stirred at the same temperature for 40 mins. After that tert-butyl 4-(3-formylpyrrolo[2,3-b]pyridin-1-yl)piperidine-1-carboxylate (132.78 mg, 403.10 umol) in THF (10 mL) was added slowly dropwise into the reaction mixture, and reaction was stirred at the same temperature for 40 min. After that reaction mixture was quenched by saturated solution of ammonium chloride, extracted with ethyl acetate, dried over sodium sulphate, concentrated under reduced pressure to give the crude. It was purified by combiflash column chromatography (eluted by 70% ethyl acetate in hexane) to give the title compound tert-butyl 4-[3-[hydroxy-(2-oxo-1H-benzo[cd]indol-6-yl)methyl]pyrrolo[2,3-b]pyridin-1-yl]piperidine-1-carboxylate (40 mg, 72.21 umol, 17.91% yield, 90% purity) as brown solid. LCMS (ES+)=281.4 [M+H]+.

Step-3: Synthesis of 6-[[1-(4-piperidyl)pyrrolo[2,3-b]pyridin-3-yl]methyl]-1H-benzo[cd]indol-2-one: In a microwave a stirred solution of tert-butyl 4-[3-[hydroxy-(2-oxo-1H-benzo[cd]indol-6-yl)methyl]pyrrolo[2,3-b]pyridin-1-yl]piperidine-1-carboxylate (50 mg, 100.29 umol) in DCE (2 mL), was added Trifluoroacetic acid (91.48 mg, 802.29 umol, 61.81 uL) and Triethylsilane (46.65 mg, 401.15 umol, 64.07 uL), then reaction mixture was heated to 70° C. for 0.5 hr. Crude LCMS showed the product mass. Reaction mixture was concentrated in vacuo to give the title compound 6-[[1-(4-piperidyl)pyrrolo[2,3-b]pyridin-3-yl]methyl]-1H-benzo[cd]indol-2-one (45 mg, 83.39 umol, 83.15% yield, 92% purity) as brown sticky liquid. LCMS (ES+)=383.3 [M+H]+.

Step-4: Synthesis of 6-[[1-[1-(1-methylcyclobutanecarbonyl)-4-piperidyl]pyrrolo[2,3-b]pyridin-3-yl]methyl]-1H-benzo[cd]indol-2-one: To a stirred solution of 6-[[1-(4-piperidyl)pyrrolo[2,3-b]pyridin-3-yl]methyl]-1H-benzo[cd]indol-2-one (250 mg, 653.67 umol) and 1-methylcyclobutanecarboxylic acid (82.07 mg, 719.04 umol) in THF (10 mL) was added DIPEA (253.45 mg, 1.96 mmol, 341.57 uL) and 1-Propanephosphonic acid cyclic anhydride (311.98 mg, 980.50 umol, 291.57 uL) reaction mixture was stirred at 25° C. for 16 hr. According to LCMS there was shown the desired mass and the reaction mixture was diluted with ethyl acetate and washed with water, organic layer separated, dried over sodium sulphate and concentrated under reduced pressure to give the crude. This crude was purified by column chromatography (using 10% methanol in DCM) to give the title compound 6-[[1-[1-(1-methylcyclobutanecarbonyl)-4-piperidyl]pyrrolo[2,3-b]pyridin-3-yl]methyl]-1H-benzo[cd]indol-2-one (120 mg, 225.67 umol, 34.52% yield, 90% purity) as brown solid. LCMS (ES+)=479.3 [M+H]+.

Step-6: Synthesis of 3-[6-[[1-[1-(1-methylcyclobutanecarbonyl)-4-piperidyl]pyrrolo[2,3-b]pyridin-3-yl]methyl]-2-oxo-benzo[cd]indol-1-yl]piperidine-2,6-dione: To a stirred solution of 6-[[1-[1-(1-methylcyclobutanecarbonyl)-4-piperidyl]pyrrolo[2,3-b]pyridin-3-yl]methyl]-1H-benzo[cd]indol-2-one (40.00 mg, 83.58 umol) in DMF (5 mL), reaction mixture was cooled to 0° C., then added Sodium hydride (in oil dispersion)60% dispersion in mineral oil (5.76 mg, 250.74 umol). Then reaction was heated to 60° C. for 30 min. After that 3-bromopiperidine-2,6-dione (32.10 mg, 167.16 umol) was added to that mixture, then continue heating for 4 to 6 hr. But SM was not fully consumed, then again added 3-bromopiperidine-2,6-dione (32.10 mg, 167.16 umol) and reaction continue for 16 hr. After that reaction was diluted with water and extracted with ethyl acetate, dried over sodium sulphate, concentrated under reduced pressure to give the crude. This crude was purified by prep-TLC (using ethyl acetate) to give the title compound 3-[6-[[1-[1-(1-methylcyclobutanecarbonyl)-4-piperidyl]pyrrolo[2,3-b]pyridin-3-yl]methyl]-2-oxo-benzo[cd]indol-1-yl]piperidine-2,6-dione Compound 253 (6 mg, 9.30 umol, 11.13% yield, 91.39% purity) as light yellow solid. LCMS (ES+)=590.3 [M+H]+. 1H NMR (400 MHz, DMSO-d6): δ 11.10 (s, 1H), 8.50-8.48 (d, 1H), 8.19-8.18 (d, 1H), 8.07-8.06 (d, 1H), 7.93-7.91 (d, 1H), 7.82 (t, 1H), 7.64 (s, 1H), 7.45-7.44 (d, 1H), 7.06-7.00 (m, 2H), 5.44-5.41 (m, 1H), 4.89 (brs, 1H), 4.48 (s, 3H), 3.65 (m, 1H), 3.17 (brs, 1H), 2.96-2.90 (m, 2H), 2.74-2.71 (m, 2H), 2.61 (m, 1H), 2.08-2.07 (m, 1H), 1.92-1.80 (m, 7H), 1.65 (m, 1H).

Example 141. Synthesis of 3-[6-[[4-[[4-(4-chloro-2-fluoro-phenyl)piperazin-1-yl]methyl]phenyl]methyl]-2-oxo-benzo[cd]indol-1-yl]-piperidine-2,6-dione (Compound 254) and 3-[6-[[4-[[4-(4-chloro-2-fluoro-phenyl)piperazin-1-yl]methyl]phenyl]methyl]-2-oxo-benzo[cd]indol-1-yl]piperidine-2,6-dione (Compound 255)

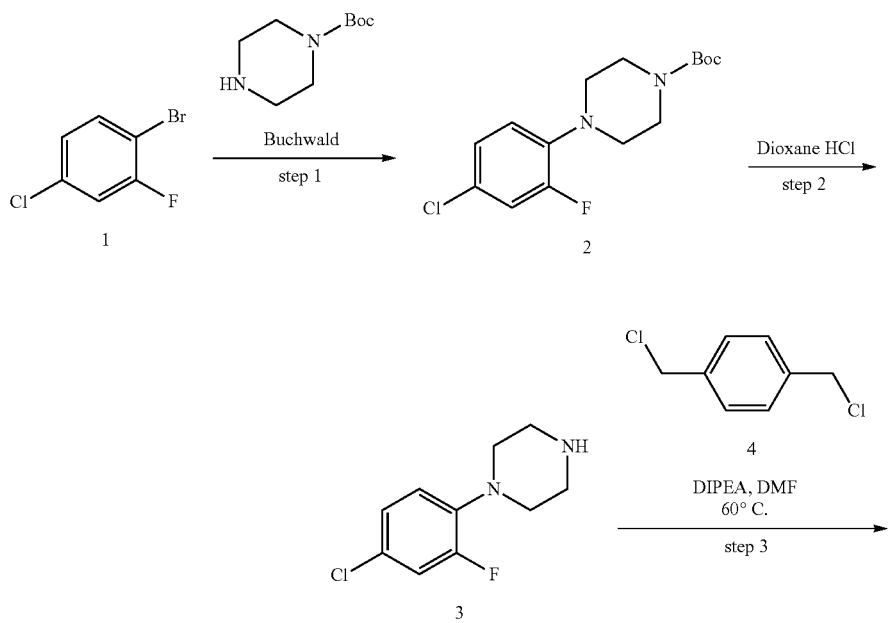

-continued
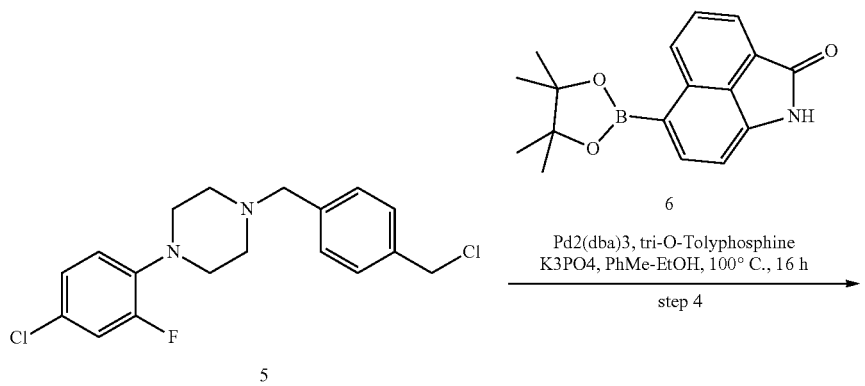
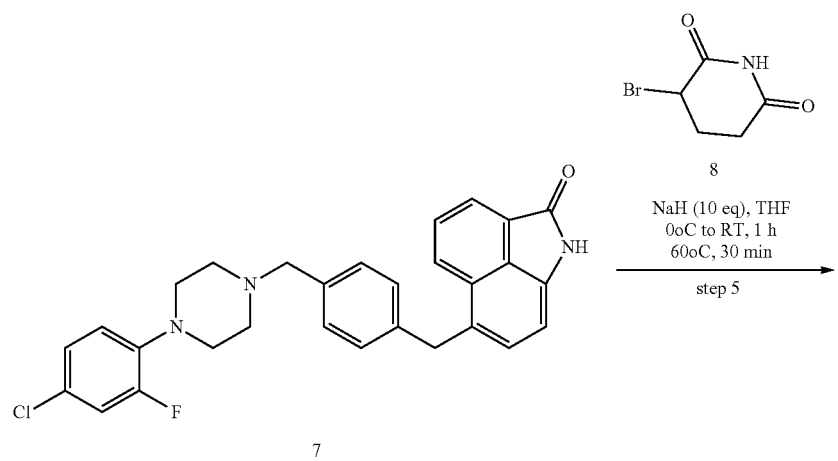
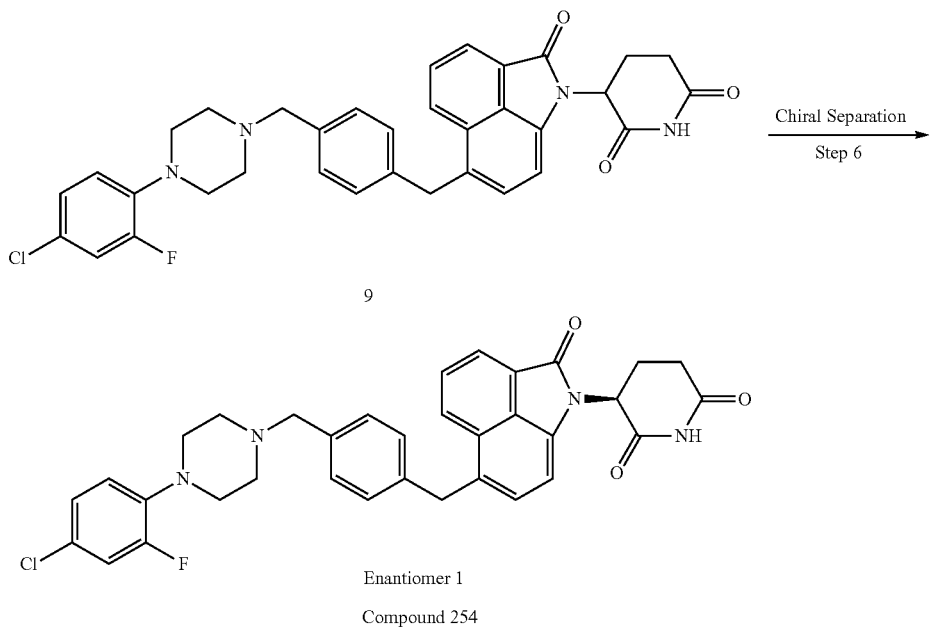
Enantiomer 1
Compound 254

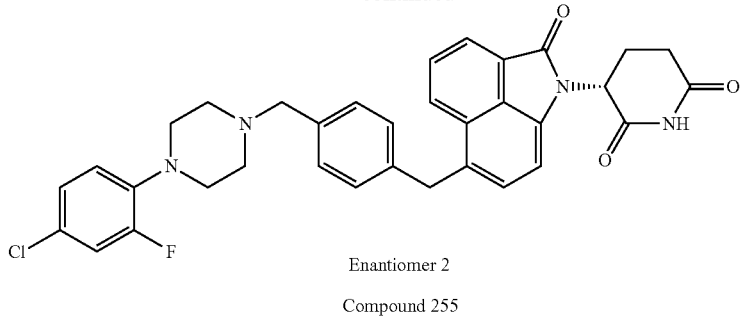

Enantiomer 2

Compound 255

Step-1: Synthesis of tert-butyl 4-(4-chloro-2-fluorophenyl)piperazine-1-carboxylate: In a sealed tube a stirred solution of 1-bromo-4-chloro-2-fluoro-benzene (300 mg, 1.43 mmol, 178.57 uL) and tert-butyl piperazine-1-carboxylate (213.42 mg, 1.15 mmol) intoluene (20 mL), was added benzyl-[1-[2-[benzyl(phenyl)phosphanyl]-1-naphthyl]-2-naphthyl]-phenyl-phosphane (18.64 mg, 28.65 umol) and sodium; 2-methylpropan-2-olate (344.14 mg, 3.58 mmol) then reaction mixture was degassed for 5 min under argon atmosphere. Then added Tris(dibenzylideneacetone)dipalladium(0) (26.23 mg, 28.65 umol) then again purged for 2 min under argon atmosphere, then the reaction mixture was heated to 110° C. for 0.5 hr. After completion of the reaction, the mass was added to water and extracted with EtOAc. Combined organics was washed with water and brine and dried over sodium sulphate. Crude was purified by combiflash with eluting solvent Hex-EtOAc to get tert-butyl 4-(4-chloro-2-fluoro-phenyl)piperazine-1-carboxylate (220 mg, 629.01 umol, 43.91% yield, 90% purity) as yellow solid.

Step-2: Synthesis of 1-(4-chloro-2-fluorophenyl)piperazine: To an ice cold solution of tert-butyl 4-(4-chloro-2-fluorophenyl)piperazine-1-carboxylate (1.3 g, 4.36 mmol) in dioxane (20 mL) was added dioxane-HCl (4 M, 21.79 mL) and stirred at 25° C. for 16 h. Crude LCMS showed complete consumption of SM and formation of product. The reaction mass was evaporated to dryness to get pure compound as HCl salt. LCMS (ES+)=215.2 [M+H]+.

Step-3: Synthesis of 1-(4-chloro-2-fluorophenyl)-4-(4-(chloromethyl) benzyl) piperazine: To a stirred solution of 1-(4-chloro-2-fluoro-phenyl)piperazine; hydrochloride (2 g, 7.96 mmol) in DMF (15 mL) was added DIPEA (3.09 g, 23.89 mmol, 4.16 mL) and stirred for 5 min. Then 1,4-bis(chloromethyl)-benzene (1.67 g, 9.56 mmol, 1.18 mL) was added and the reaction was heated at 60° C. for 16 h. After completion of the reaction (monitored by TLC), the reaction mixture was diluted with EtOAc and washed with water and brine, dried over sodium sulfate and concentrated. The crude was purified by column chromatography (100-200 silica, 25-30% EtOAc in hexane) to afford 1-(4-chloro-2-fluoro-phenyl)-4-[[4-(chloromethyl)phenyl]methyl]piperazine (1.3 g, 3.31 mmol, 41.59% yield, 90% purity) as a white solid. LCMS (ES+)=354.4 [M+H]+.

Step-4: Synthesis of 6-(4-((4-(4-chloro-2-fluorophenyl) piperazin-1-yl)methyl)benzyl)benzo[cd]indol-2(1H)-one: To a stirred solution of 1-(4-chloro-2-fluoro-phenyl)-4-[[4-(chloromethyl)phenyl]methyl]piperazine (700 mg, 1.98 mmol) and 6-(4,4,5,5-tetramethyl-1,3,2-dioxaborolan-2-yl)-1H-benzo[cd]indol-2-one (643.31 mg, 2.18 mmol) in Ethanol (2 mL) and Toluene (4 mL) was added Potassium phosphate tribasic anhydrous (1.26 g, 5.94 mmol) and the reaction mass was degassed under nitrogen atmosphere over 5 minutes. Then Tri-o-Tolyl phosphine (120.62 mg, 396.31 umol) and (1E,4E)-1,5-diphenylpenta-1,4-dien-3-one; palladium (181.45 mg, 198.15 umol) were added to reaction mass, and degassed for another 5 min. It was then heated at 90° C. for 16 h. The reaction mixture was cooled to RT, diluted with EtOAc, filtered over celite, and concentrated under reduced pressure to get crude mass which was purified by Combi-flash Column Chromatography using 20-80% EtOAc-Hex as eluent to afford 6-[[4-[[4-(4-chloro-2-fluorophenyl) piperazin-1-yl]methyl]phenyl]methyl]-1H-benzo[cd]indol-2-one as yellow viscous liquid. LCMS (ES+)=486.3 [M+H]+.

Step-5: Synthesis of 3-(6-(4-((4-(4-chloro-2-fluorophenyl)piperazin-1-yl)methyl)benzyl)-2-oxobenzo[cd]in-dol-1 (2H)-yl)piperidine-2,6-dione: To an ice cold solution of 6-[[4-[[4-(4-chloro-2-fluoro-phenyl)piperazin-1-yl]methyl]phenyl]methyl]-1H-ben-zo[cd]indol-2-one (280 mg, 576.16 umol) in THF (15 mL) was added Sodium hydride (in oil dispersion) 60% dispersion in mineral oil (240.83 mg, 5.76 mmol, 55% purity) stirred at 25° C. for 10 mins. Compound 3-bromopiperidine-2,6-dione (553.14 mg, 2.88 mmol) was added at a time and again stirred for 10 mins at 25° C. The reaction was then heated to 70° C. for 0.5 hr. Crude LCMS showed formation of product. The reaction was cooled to RT and diluted with water and extracted with EtOAc. The combined organics was washed with water and brine and dried over sodium sulphate. Crude was evaporated to dryness and purified by combiflash with eluting solvent EtOAc in DCM to get 3-[6-[[4-[[4-(4-chloro-2-fluo-ro-phenyl)piperazin-1-yl]methyl]phenyl]methyl]-2-oxo-benzo[cd]indol-1-yl]piperidine-2,6-dione (190 mg, 295.94 umol, 51.36% yield, 93% purity) as yellow solid. LCMS (ES+)=597.6 [M+H]+.

Step-6: Chiral separation: Compound 3-[6-[[4-[[4-(4-chloro-2-fluoro-phenyl)piperazin-1-yl]methyl]phenyl]methyl]-2-oxo-benzo[cd]in-dol-1-yl]piperidine-2,6-dione (166.59 mg, 279.01 umol) has been purified by following method Column: Column name: Chiralpak IC (21×250 mm),5µ Mobile Phase:DCM/Isopropanol: 60/40,Flow rate: 21.0 ml/min, Run time: 25 min. Wave length: 254 nm Solubility: IPA & DCM to afford 3-[6-[[4-[[4-(4-chloro-2-fluoro-phenyl)piperazin-1-yl]methyl]phenyl]methyl]-2-oxo-benzo[cd]indol-1-yl]-piperidine-2,6-dione Compound 254 (50 mg, 80.12 umol, 28.71% yield, 95.67% purity) and 3-[6-[[4-[[4-(4-chloro-2-fluoro-phenyl)piperazin-1-yl]methyl]phenyl]methyl]-2-oxo-benzo[cd]indol-1-yl]piperidine-2,6-dione Compound 255 (52 mg, 81.23 umol, 29.11% yield, 93.27% purity) as yellow solid. Compound 254: 1H NMR (400 MHz, MeOD): δ 8.25 (d, J=8 Hz, 1H), 8.05 (d, J=8 Hz, 1H), 7.76 (t, J=8 Hz, 1H), 7.36 (d, J=8 Hz, 1H), 7.26

(q, J=8 Hz, 4H), 7.09-6.94 (m, 4H), 5.42-5.38 (m, 1H), 4.42 (s, 2H), 3.53 (s, 2H), 3.038 (m, 4H), 2.96-2.92 (m, 1H), 2.84-2.80 (m, 2H), 2.59 (m, 4H), 2.25-2.22 (m, 1H).LCMS (ES+)=597.2 [M+H]+. Compound 255: 1H NMR (400 MHz, DMSO-d6): δ 11.11 (s, 1H) 8.34 (d, J=8 Hz, 1H), 8.08 (d, J=8 Hz, 1H), 7.82 (t, J=8 Hz, 1H), 7.42 (d, J=8 Hz, 1H), 7.31-7.20 (m, 4H), 7.16-7.09 (m, 2H), 7.01 (t, J=8 Hz, 1H), 5.46-5.41 (m, 1H), 4.38 (s, 2H), 3.44 (s, 2H), 2.95 (m, 4H), 2.77-2.73 (m, 1H), 2.66-2.62 (m, 2H), 2.10-2.07 (m, 2H). LCMS (ES+)=597.2 [M+H]+.
Example 142. Synthesis of 3-(6-(4-((4-(2,4-difluorophenyl)piperazin-1-yl)methyl)benzyl)-2-oxobenzo[cd]indol-1(2H)-yl)piperidine-2,6-dione (Compound 256) and 3-(6-(4-((4-(2,4-difluorophenyl)piperazin-1-yl)methyl)benzyl)-2-oxobenzo[cd]indol-1(2H)-yl)piperidine-2,6-dione (Compound 257)
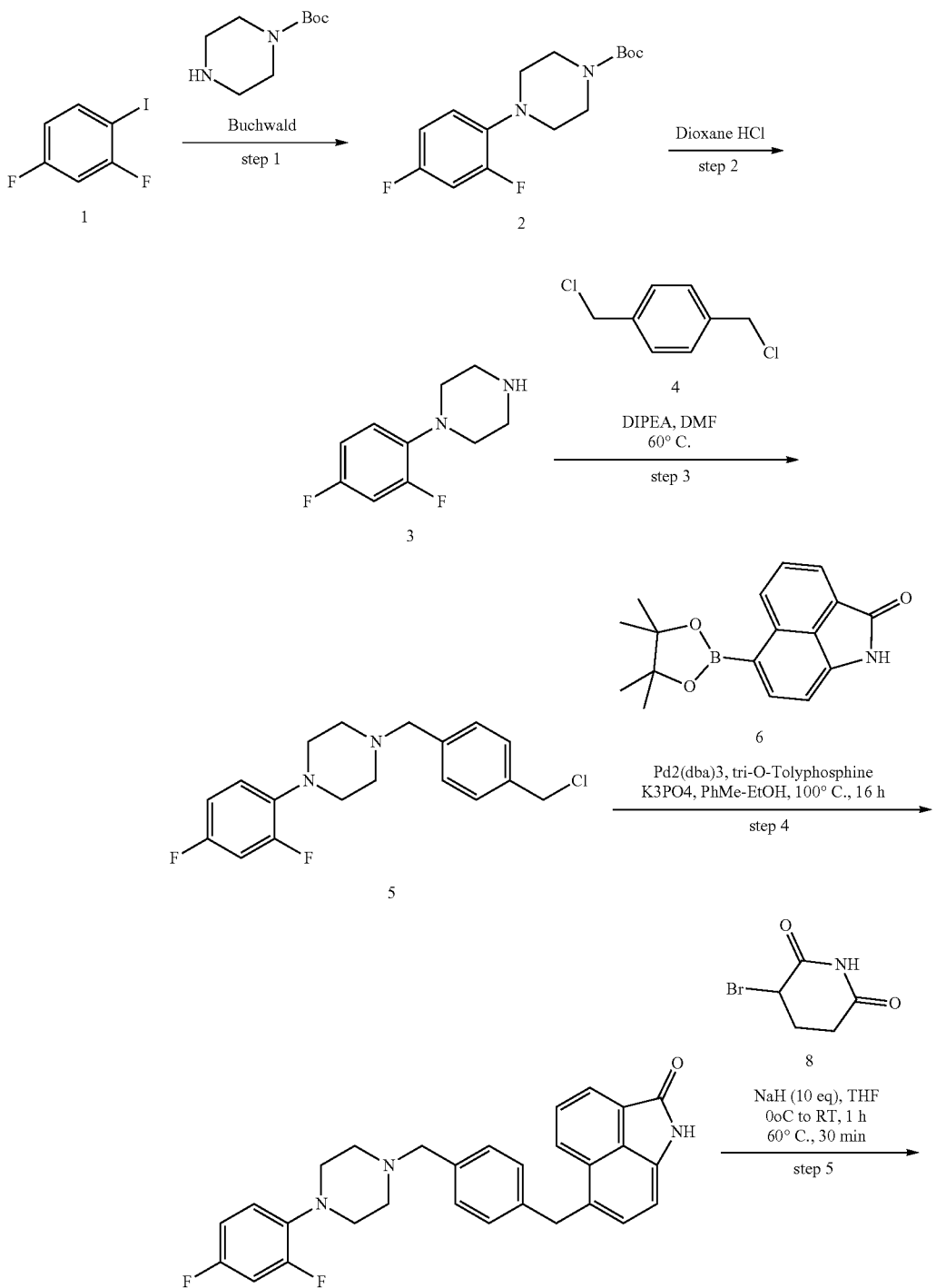

-continued

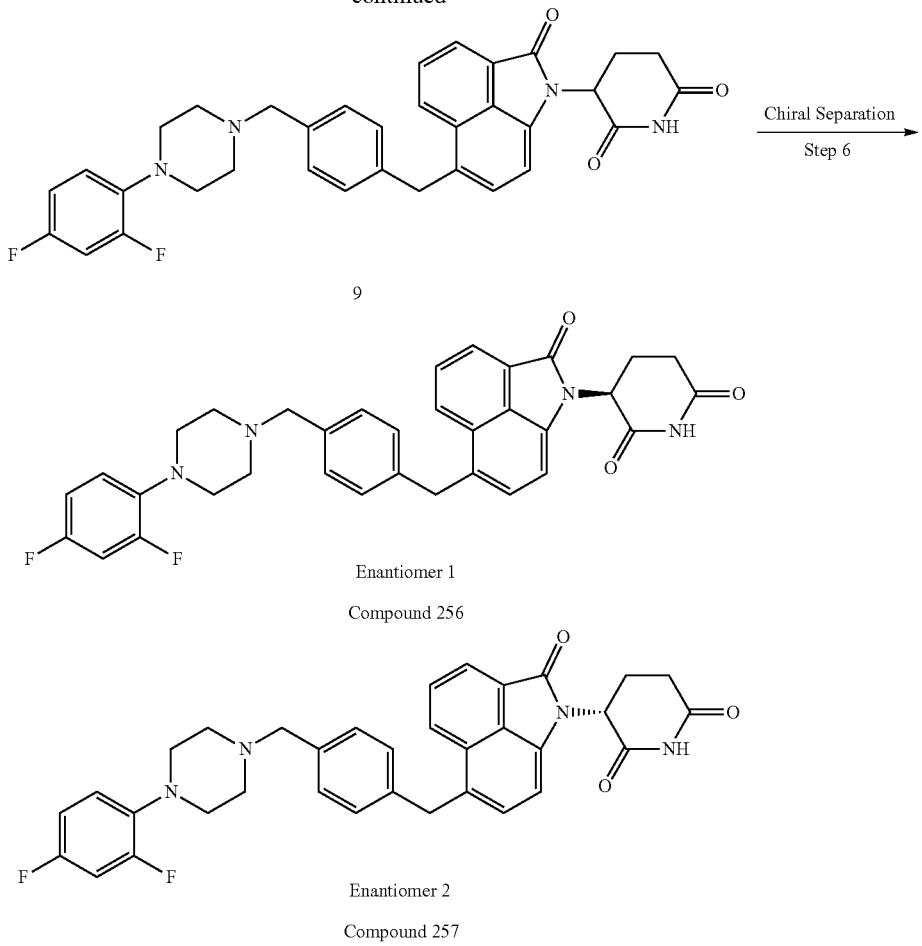

9

Enantiomer 1
Compound 256

Enantiomer 2
Compound 257

Step-1: Synthesis of tert-butyl 4-(2,4-difluorophenyl)piperazine-1-carboxylate: In a sealed tube a stirred solution of 2,4-difluoro-1-iodo-benzene (2 g, 8.33 mmol, 995.02 uL) and tert-butyl piperazine-1-carboxylate (2.33 g, 12.50 mmol) in dioxane (20 mL), was added sodium; 2-methyl-propan-2-olate(2.00 g, 20.83 mmol) and dicyclohexyl-[2-(2, 6-dimethoxyphenyl)phenyl]phosphane (342.12 mg, 833.37 umol) then reaction mixture was degassed for 5 min under argon atmosphere. Then added (1E,4E)-1,5-diphenylpenta-1,4-dien-3-one; palladium (763.13 mg, 833.37 umol) then again purged for 2 min under argon atmosphere, then the reaction mixture was heated to 100° C. for 16 hr. After completion of the reaction mass added to water then extracted with EtOAc. Organic layer was washed with water, brine and dried over sodium sulphate. The evaporated crude was purified by combiflash column chromatography (using 50% EtOAc in hexane) to get the title compound tert-butyl 4-(2,4-difluoro-phenyl)piperazine-1-carboxylate (1.3 g, 3.09 mmol, 37.13% yield, 71% purity) as off white solid. LCMS (ES+)=299.5 [M+H]+.

Step-2: Synthesis of 1-(2,4-difluorophenyl)piperazine: To an ice cold solution of tert-butyl 4-(2,4-difluorophenyl)piperazine-1-carboxylate (1.3 g, 4.36 mmol) in dioxane (20 mL) was added dioxane-HCl (4 M, 21.79 mL) and stirred at 25° C. for 16 h. Crude LCMS showed complete consumption of SM and formation of product. The reaction mass was evaporated to dryness to get pure compound as HCl salt. LCMS (ES+)=199.2 [M+H]+.

Step-3: Synthesis of 1-(4-(chloromethyl)benzyl)-4-(2,4-difluorophenyl)piperazine: To a stirred solution of 1-(2,4-difluorophenyl)piperazine; hydrochloride (1 g, 4.26 mmol) in DMF (30 mL) was added DIPEA (1.65 g, 12.78 mmol, 2.23 mL) and stirred for 5 min. Then 1,4-bis(chloromethyl)-benzene (745.95 mg, 4.26 mmol, 525.32 uL) was added and the reaction was heated at 60° C. for 16 h. After completion of the reaction (monitored by TLC), the reaction mixture was diluted with EtOAc and washed with water and brine, dried over sodium sulfate and concentrated. The crude was purified by column chromatography (100-200 silica, 25-30% EtOAc in hexane) to afford 1-[[4-(chloromethyl)phenyl] methyl]-4-(2,4-difluorophenyl)piperazine (400 mg, 1.16 mmol, 27.31% yield, 98% purity) as a white solid.

Step-4: Synthesis of 6-(4-((4-(2,4-difluorophenyl)piperazin-1-yl)methyl)benzyl)benzo[cd]indol-2(1H)-one: To a stirred solution of 1-[[4-(chloromethyl)phenyl]methyl]-4-(2, 4-difluorophenyl)piperazine (400 mg, 1.19 mmol) and 6-(4, 4,5,5-tetramethyl-1,3,2-dioxaborolan-2-yl)-1H-benzo[cd] indol-2-one (701.03 mg, 2.38 mmol) in Ethanol (2 mL) and Toluene (4 mL) was added Potassium phosphate tribasic anhydrous (756.29 mg, 3.56 mmol) and Tri-o-Tolyl phosphine (72.30 mg, 237.53 umol) and the reaction was degassed under argon atmosphere over 5 minutes. Then (1E,4E)-1,5-diphenylpenta-1,4-dien-3-one; palladium (108.75 mg, 118.76 umol) was added to this reaction mass, and degassed for another 5 min. It was then heated at 100° C. for 16 hr. Product was formed according to LCMS. The reaction mixture was cooled to RT, diluted with EtOAc and water, filtered over celite, organics was separated, washed with water followed by brine and dried over sodium sulphate and concentrated under reduced pressure to get crude mass, which was purified by Combi-flash Column Chromatography using 20-80% EtOAc-Hex as eluent to afford 6-[[4-[[4-(2,4-difluorophenyl)piperazin-1-yl]methyl]phenyl]methyl]-1H-benzo[cd]indol-2-one (250 mg, 431.29 umol, 36.32% yield, 81% purity) as off white solid. LCMS (ES+)=470.3 [M+H]+.

Step-5: Synthesis of 3-(6-(4-((4-(2,4-difluorophenyl)piperazin-1-yl)methyl)benzyl)-2-oxobenzo[cd]indol-1-(2H)yl)piperidine-2,6-dione: To an ice cold solution of 6-[[4-[[4-(2,4-difluorophenyl)piperazin-1-yl]methyl]phenyl]methyl]-1H-benzo[cd]-indol-2-one (250 mg, 532.45 umol) in THF (5 mL) was added Sodium hydride (in oil dispersion) 60% dispersion in mineral oil (127.78 mg, 5.32 mmol) stirred at 25° C. for 10 mins. Compound 3-bromopipe-ridine-2,6-dione (511.18 mg, 2.66 mmol) was added at a time and again stirred for 10 mins at 25° C. The reaction was then heated to 70° C. for 0.5 hr. Crude LCMS showed formation of product. The reaction was cooled to RT and diluted with water and extracted with EtOAc. The combined organics was washed with water and brine and dried over sodium sulphate. Crude was evaporated to dryness and purified by combi-flash with eluting solvent EtOAc in DCM to get 3-[6-[[4-[[4-(2,4-difluorophenyl)piperazin-1-yl]methyl]phenyl]methyl]-2-oxo-benzo[cd]indol-1-yl]piperidine-2,6-dione (190 mg, 317.42 umol, 59.61% yield, 97% purity) as yellow solid. LCMS (ES+)=581.6 [M+H]+.

Step-6: Chiral separation: Compound 3-[6-[[4-[[4-(2,4-difluorophenyl)piperazin-1-yl]methyl]phenyl]methyl]-2-oxo-benzo[cd]indol-1-yl]piperidine-2,6-dione (162 mg, 279.01 umol) has been purified by following method Column: Chiralpak IC (20×250 mm), 5µ Mobile Phase: DCM/IPA: 50/50, No Modifier added Flow rate: 18 ml/min, Run time: 18 min. Wave length: 224 nm Solubility: DCM only.

Isomer I Compound 256: 1H NMR (400 MHz, DMSO-d6): δ 11.12 (s, 1H) 8.34 (d, J=8 Hz, 1H), 8.08 (d, J=8 Hz, 1H), 7.83 (t, J=8 Hz, 1H), 7.42 (d, J=8 Hz, 1H), 7.26-7.18 (m, 4H), 7.05-6.98 (m, 2H), 7.05-7.01 (m, 2H), 5.46-5.42 (m, 1H), 4.38 (s, 2H), 3.44 (s, 2H), 2.91 (m, 5H), 2.80-2.62 (m, 2H), 2.50-2.46 (m, 4H), 2.10-2.07 (m, 2H). LCMS (ES+)=581.2 [M+H]+. Isomer II Compound 257: 1H NMR (400 MHz, DMSO-d6): δ 11.12 (s, 1H) 8.34 (d, J=8 Hz, 1H), 8.08 (d, J=8 Hz, 1H), 7.82 (t, J=8 Hz, 1H), 7.42 (d, J=8 Hz, 1H), 7.26-7.09 (m, 5H), 7.05-6.98 (m, 2H), 5.46-5.42 (m, 1H), 4.38 (s, 2H), 3.44 (s, 2H), 2.98-2.91 (m, 4H), 2.79-2.62 (m, 2H), 2.49 (m, 4H), 2.10-2.07 (m, 2H). LCMS (ES+)=581.2 [M+H]+.

Example 143. Synthesis of 3-(6-(4-((4-(4-fluorophenoxy)piperidin-1-yl)methyl)benzyl)-2-oxobenzo[cd]indol-1(2H)-yl)piperidine-2,6-dione (Compound 258)

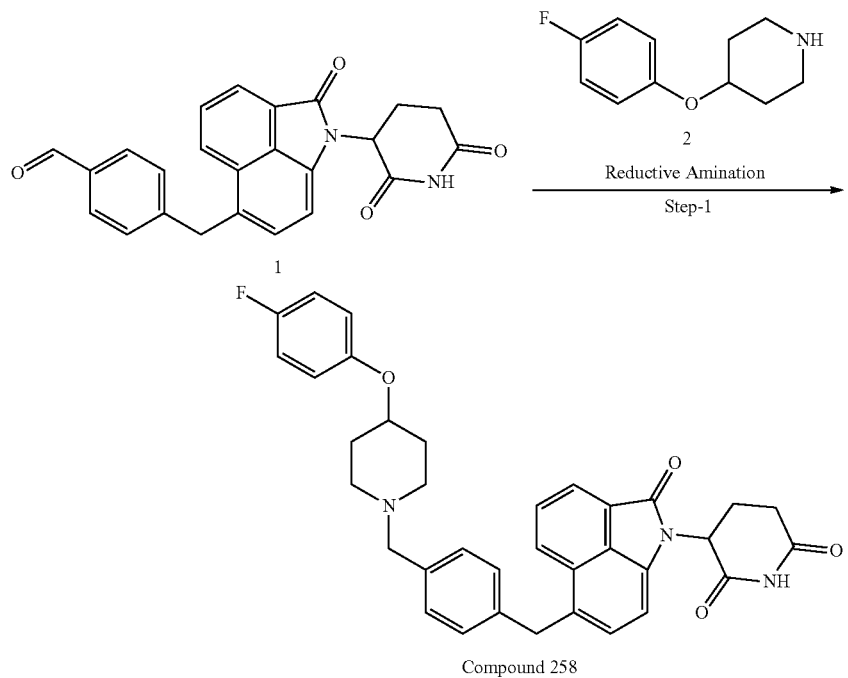

Compound 258

Step-1: Synthesis of 3-(6-(4-((4-(4-fluorophenoxy)piperidin-1-yl)methyl)benzyl)-2-oxobenzo[cd]indol-1(2H)-yl)piperidine-2,6-dione: To the stirred solution of 4-[[1-(2,6-dioxo-3-piperidyl)-2-oxo-benzo[cd]indol-6-yl]methyl]benzaldehyde (250 mg, 627.49 umol) in THF (6 mL) was added 4-(4-fluorophenoxy)piperidine (122.51 mg, 627.49 umol) followed by the addition of dibutyltin(2+); dichloride (228.79 mg, 752.99 umol, 168.23 uL) and phenylsilane (67.90 mg, 627.49 umol, 77.43 uL). The reaction mixture was then stirred at 90° C. for 16 hours in a sealed tube. TLC showed formation of new spot. The reaction mixture was diluted with ethyl acetate, washed with water and brine solution. The organic fraction was separated. It was dried over anhydrous sodium sulphate, evaporated under reduced pressure to obtain the crude compound which was purified by flash chromatography using 0-5% MeOH-DCM to afford 3-[6-[[4-[[4-(4-fluorophenoxy)-1-piperidyl]methyl]phenyl]methyl]-2-oxo-benzo[cd]indol-1-yl]piperidine-2,6-dione Compound 258 (22 mg, 37.78 umol, 6.02% yield, 99.2% purity) as yellow solid. 1H NMR (400 MHz, DMSO-d6): δ 11.09 (s, 1H), 8.31 (d, J=8 Hz, 1H), 8.05 (d, J=8 Hz, 1H), 7.80 (t, J=8 Hz, 1H), 7.39 (d, J=8 Hz, 1H), 7.21-7.15 (m, 4H), 7.08-7.02 (m, 3H), 6.90 (bs, 2H) 5.42-5.39 (m, 1H), 4.34 (s, 2H), 4.24 (s, 1H), 3.37 (s, 2H) 2.95-2.88 (m, 1H), 2.77-2.70 (m, 1H), 2.67-2.59 (m, 3H), 2.12-2.06 (m, 3H), 2.04 (m, 2H), 1.54 (m, 2H), LCMS (ES+)=578.2 [M+H]+.
Example 144. Synthesis of 3-(6-((1-((1r,4r)-4-neopentylcyclohexyl)-1H-pyrazol-4-yl)methyl)-2-oxobenzo[cd]ind-ol-1(2H)-yl)piperidine-2,6-dione (Compound 259) and 3-(6-((1-((1s, 4s)-4-neopentylcyclohexyl)-1H-pyrazol-4-yl)methyl)-2-oxobenzo[cd]ind-ol-1(2H)-yl)piperidine-2,6-dione (Compound 260)
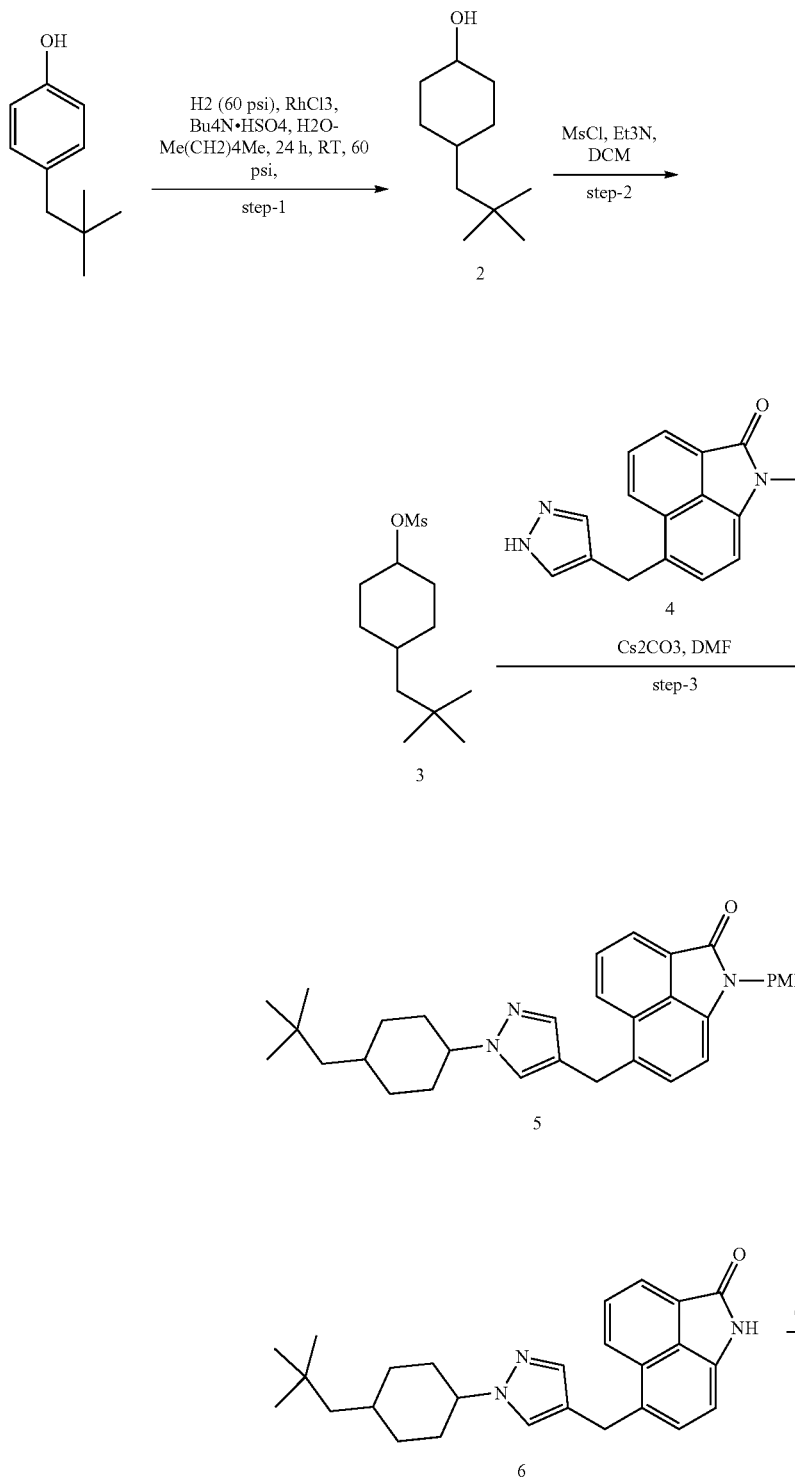

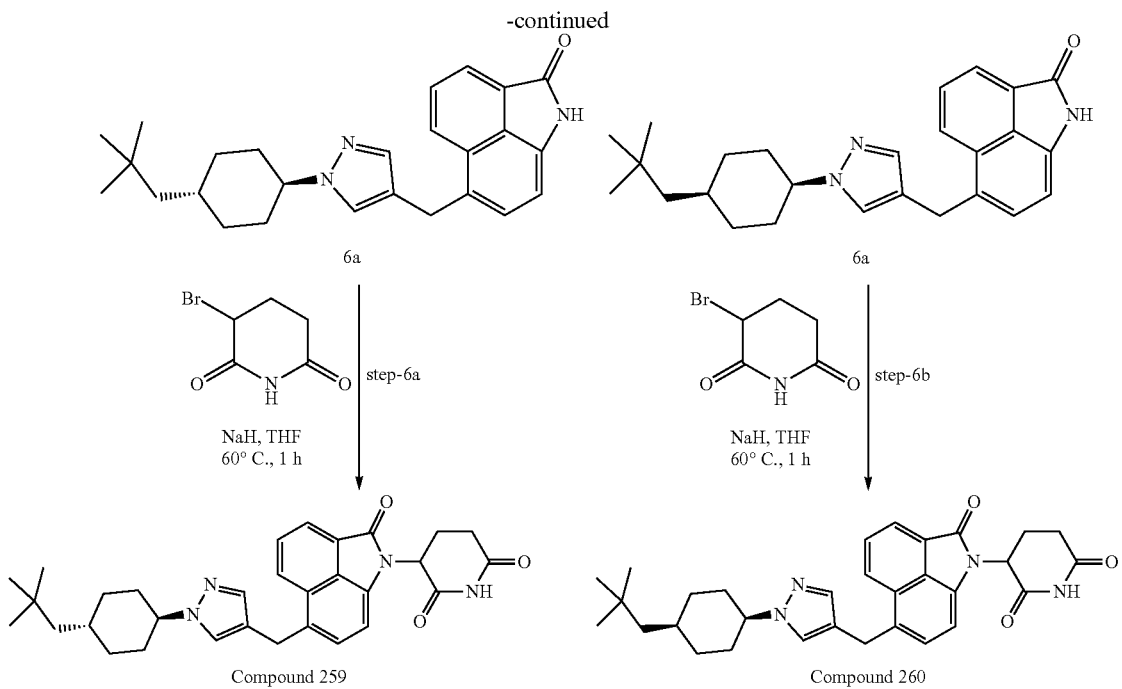

Compound 259

Compound 260

Step-1: Synthesis of 4-neopentylcyclohexan-1-ol: To a solution of 4-(2,2-dimethylpropyl)phenol (1 g, 6.09 mmol) in hexane (30 mL) was added trichlororhodium; hydrate (138.38 mg, 608.85 umol), Tetrabutylammonium hydrogen sulfate (206.73 mg, 608.85 umol) and buffer (6.09 mmol, 30 mL) (phosphate buffer of pH 7.4) reaction was stirred under hydrogen pressure 100 psi in a perr autoclave at 25° C. for 48 hr. Product was formed according to GCMS. The reaction was diluted with water and EtOAc. Organics was separated, and washed with water and brine and dried over sodium sulphate. Evaporated organics was purified by combiflash using 10-50% EtOAc in hexane to afford 4-(2,2-dimethyl-propyl)cyclohexanol (380 mg, 2.01 mmol, 32.99% yield, 90% purity) as low melting solid. Phosphate Buffer: 800 mL of distilled water was taken in a suitable container. 20.214 g of $Na_2HPO_4 \cdot 7H_2O$ and 3.394 g of $NaH_2PO_4H_2O$ was added to the solution. Adjusted solution to final desired pH using HCl or NaOH. Distilled water was added until volume is 1 L.

Step-2: Synthesis of 4-neopentylcyclohexyl methane-sulfonate: To an ice cold solution of 4-(2,2-dimethylpropyl) cyclohexanol (120 mg, 704.68 umol) in DCM (10 mL) was added triethylamine (142.61 mg, 1.41 mmol, 196.44 uL) followed by mesyl chloride (88.79 mg, 775.14 umol, 60.00 uL). The reaction was allowed to RT for 2 h. TLC showed formation of new spot. The reaction was diluted with water and DCM. The organics was separated. Combined organics was washed with water, brine and dried over sodium sulphate. The organics was evaporated to dryness to get [4-(2, 2-dimethylpropyl)cyclohexyl] methanesulfonate (170 mg, 342.22 umol, 48.56% yield, 50% purity) as crude.

Step-3: Synthesis of 1-(4-methoxybenzyl)-6-((1-(4-neo-pentylcyclohexyl)-1H-pyrazol-4-yl)methyl)benzo-[cd]in-dol-2(1H)-one: To the solution of 1-[(4-methoxyphenyl) methyl]-6-(1H-pyrazol-4-ylmethyl)benzo[cd]indol-2-one (3.47 g, 9.39 mmol) and [4-(2,2-dimethylpropyl)cyclohexyl] methanesulfonate (3.50 g, 14.09 mmol) in DMF (45 mL) in a sealed tube was added Cesium carbonate (6.12 g, 18.79 mmol) and heated to 90° C. for 16 hr. Crude LCMS showed formation of product. The reaction was cooled to RT and diluted with water, EtOAc. Organics was separated. Combined organics was washed with water, brine and dried over sodium sulphate. Crude organics was evaporated to dryness and purified by combiflash using EtOAc in hexane to afford 6-[[1-[4-(2,2-dimethylpropyl)cyclohexyl]pyrazol-4-yl] methyl]-1-[(4-methoxyphenyl)methyl]benzo-[c d]indol-2-one (2.1 g, 3.62 mmol, 38.57% yield, 90% purity) as yellow sticky gel. LCMS (ES+)=522.5 [M+H]+.

Step-4: Synthesis of 6-((1-(4-neopentylcyclohexyl)-1H-pyrazol-4-yl)methyl)benzo[cd]indol-2(1H)-one: To the stirred solution of 6-[[1-[4-(2,2-dimethylpropyl)cyclohexyl] pyrazol-4-yl]methyl]-1-[(4-methoxyphenyl) methyl]benzo [cd]indol-2-one (200 mg, 383.37 umol) in TFA (3 mL) was added triethylsilane (178.31 mg, 1.53 mmol, 244.93 uL) and the reaction mixture was heated at 90° C. for 2 hr in a sealed tube. TLC showed complete consumption of the starting material along with the formation of the desired spot. The solvent in the reaction mixture was evaporated under reduced pressure and triturated with ether to obtain 6-[[1-[4-(2,2-dimethylpropyl)cyclohexyl]pyrazol-4-yl]methyl]-1H-benzo[cd]indol-2-one (18 mg, 42.59 umol, 11.11% yield, 95% purity) as crude.

Step-5: Separation of cis/trans isomers: Crude was separated as cis/trans by SFC, using Column: Regis Reflect C-Amylose A (250×30 mm) 5µ Flow: 25 g/min Mobile Phase:50% $CO_2$+50% (0.3% Isopropylamine in MeOH) ABPR:100 bar Temperature: 35° C. Isomer I 6a (6-[[1-[4-(2,2-dimethylpropyl)cyclohexyl]pyrazol-4-yl]methyl]-1H-benzo[cd]indol-2-one (18 mg, 42.59 umol, 11.11% yield, 95% purity): 18 mg. Isomer 6b (6-[[1-[4-(2,2-dimethylpro-pyl)cyclohexyl]pyrazol-4-yl]methyl]-1H-benzo[cd]indol-2-one (40 mg, 94.64 umol, 24.69% yield, 95% purity): 40 mg.

Step-6a: Synthesis of 3-(6-((1-((1r,4r)-4-neopentylcyclo-hexyl)-1H-pyrazol-4-yl)methyl)-2-oxobenzo[cd]ind-ol-1 (2H)-yl)piperidine-2,6-dione: To an ice cold solution of 6-[[1-[4-(2,2-dimethylpropyl)cyclohexyl]pyrazol-4-yl]

methyl]-1H-benzo[cd]indol-2-one (250 mg, 622.60 umol) (Isomer II) in THF (20 mL) was added Sodium hydride (in oil dispersion) 60% dispersion in mineral oil (271.65 mg, 6.23 mmol, 55% purity) stirred at 25° C. for 10 mins. Compound 3-bromopiperidine-2,6-dione (119.55 mg, 622.60 umol) was added at a time and again stirred for 10 mins at 25° C. The reaction was then heated to 70° C. for 0.5 hr. Crude LCMS showed formation of product. The reaction was cooled to RT and diluted with water and extracted with EtOAc. The combined organics was washed with water and brine and dried over sodium sulphate. Crude was evaporated to dryness and purified by combiflash with eluting solvent EtOAc in DCM to get 3-[6-[[1-[4-(2,2-dimethylpropyl)cyclohexyl]pyrazol-4-yl]methyl]-2-oxo-benzo[cd]indol-1-yl]piperidine-2,6-dione Compound 259 (235 mg, 448.14 umol, 71.98% yield, 97.76% purity) as yellow solid. 1H NMR (400 MHz, DMSO-d6): δ 11.11 (bs, 1H), 8.37 (d, J=8 Hz, 1H), 8.09 (d, J=8 Hz, 1H), 7.84 (t, J=8 Hz, 1H), 7.51 (s, 1H), 7.35 (d, J=8 Hz, 1H), 7.27 (s, 1H), 7.07 (d, J=8 Hz, 1H), 5.45-5.41 (m, 1H), 4.17 (s, 2H), 3.99-3.93 (m, 1H), 2.94-2.90 (m, 1H), 2.75-2.72 (m, 1H), 2.66-2.62 (m, 1H), 2.09-2.06 (m, 1H), 1.90-1.87 (m, 2H), 1.77-1.62 (m, 4H), 1.35 (bs, 2H), 1.23 (bs, 2H), 1.17-1.03 (m, 4H), 0.87 (s, 9H). LCMS (ES+)=513.3 [M+H]+.

Step-6b: Synthesis of 3-(6-((1-((1s,4s)-4-neopentylcyclohexyl)-1H-pyrazol-4-yl)methyl)-2-oxobenzo[cd]ind-ol-1(2H)-yl)piperidine-2,6-dione: To an ice cold solution of 6-[[1-[4-(2,2-dimethylpropyl)cyclohexyl]pyrazol-4-yl]methyl]-1H-benzo[cd]indol-2-one (68.00 mg, 169.35 umol) (Isomer I) in THF (20 mL) was added Sodium hydride (in oil dispersion) 60% dispersion in mineral oil (73.89 mg, 1.69 mmol, 55% purity) stirred at 25° C. for 10 mins. Compound 3-bromopiperidine-2,6-dione (162.58 mg, 846.73 umol) was added at a time and again stirred for 10 mins at 25° C. The reaction was then heated to 70° C. for 0.5 hr. Crude LCMS showed formation of product. The reaction was cooled to RT and diluted with water and extracted with EtOAc. The combined organics was washed with water and brine and dried over sodium sulphate. Crude was evaporated to dryness and purified by combiflash with eluting solvent EtOAc in DCM to get 3-[6-[[1-[4-(2,2-dimethylpropyl)cyclohexyl]pyrazol-4-yl]methyl]-2-oxo-benzo[cd]indol-1-yl]piperidine-2,6-dione Compound 260 (51 mg, 97.34 umol, 57.48% yield, 97.84% purity) as yellow solid. 1H NMR (400 MHz, DMSO-d6): δ 11.11 (bs, 1H), 8.38 (d, J=8 Hz, 1H), 8.09 (d, J=8 Hz, 1H), 7.84 (t, J=8 Hz, 1H), 7.58 (s, 1H), 7.36 (d, J=8 Hz, 1H), 7.28 (s, 1H), 7.08 (d, J=8 Hz, 1H), 5.44-5.42 (m, 1H), 4.18 (s, 2H), 4.038 (m, 1H), 2.94-2.91 (m, 1H), 2.76-2.72 (m, 1H), 2.66-2.62 (m, 1H), 2.07 (m, 1H), 1.92-1.89 (m, 2H), 1.72-1.65 (m, 3H), 1.56-1.50 (bs, 2H), 1.40 (bs, 2H), 1.17-1.15 (m, 2H), 0.86 (s, 9H). LCMS (ES+)=513.3 [M+H]+.

Example 145. Synthesis of N-cyclopropyl-4-(4-((1-(2,6-dioxopiperidin-3-yl)-2-oxo-1,2-dihydrobenzo[cd]indol-6-yl)methyl)-1H-pyrazol-1-yl)-N-methylpiperidine-1-carboxamide (Compound 261)

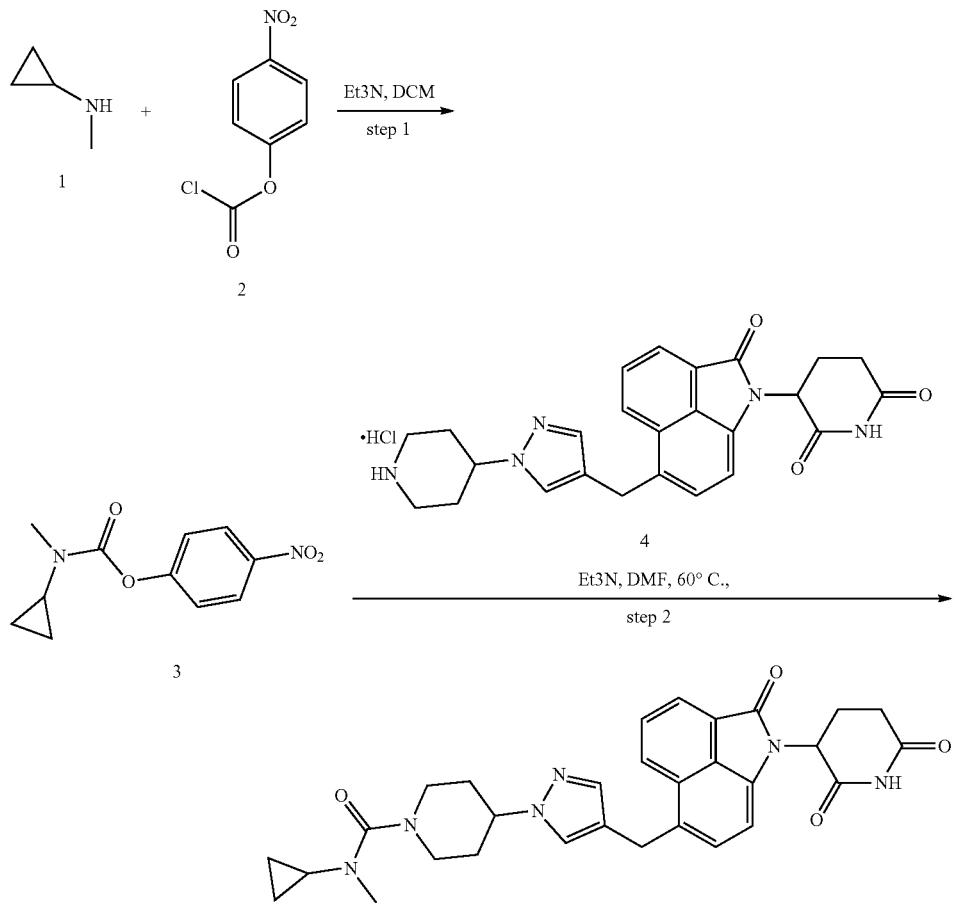

Compound 261

Step-1: Synthesis of 4-nitrophenyl cyclopropyl(methyl) carbamate: To a solution of(4-nitrophenyl) carbonochloridate (500 mg, 2.48 mmol) in DCM (10 mL) was added Triethylamine (753.04 mg, 7.44 mmol, 1.04 mL) and followed by N-methylcyclopropanamine (176.42 mg, 2.48 mmol, 297.41 uL). The reaction was stirred at rt for 3 h. Crude TLC showed complete consumption of SM and formation of new polar spot. The reaction was added to water and extracted with DCM. The combined organics was washed with water and brine and dried over sodium sulphate. Crude was evaporated to dryness to get (4-nitrophenyl)N-cyclopropyl-N-methyl-carbamate (360 mg, 761.99 umol, 30.72% yield, 50% purity) as off-white solid. LCMS (ES+)=237.2 [M+H]+.

Step-2: Synthesis of N-cyclopropyl-4-(4-((1-(2,6-dioxopiperidin-3-yl)-2-oxo-1,2-dihydrobenzo[cd]indol-6-yl) methyl)-1H-pyrazol-1-yl)-N-methylpiperidine-1-carboxamide: To a solution of 3-[2-oo-6-[[1-(4-piperidyl)pyrazol-4-yl]methyl]benzo[cd]indol-1-yl]piperidine-2,6-dione (137.41 mg, 309.83 umol, 021) and (4-nitrophenyl)N-cyclopropyl-N-methyl-carbamate (109.78 mg, 464.74 umol) in DMF (6 mL) was added triethyl amine (94.05 mg, 929.48 umol, 129.55 uL) and continued at 100° C. for 16 hr. Crude LCMS showed formation of product with some SM-2. The reaction was cooled to RT and diluted water. The whole mass was extracted with EtOAc. Combined organics was washed with water, brine and dried over sodium sulphate. Evaporated mass was purified by prep TLC with eluting solvent acetone DCM to afford N-cyclopropyl-4-[4-[[1-(2, 6-dioxo-3-piperidyl)-2-oxo-benzo-[cd]indol-6-yl]methyl] pyrazol-1-yl]-N-methyl-piperidine-1-carboxamide Compound 261 (40 mg, 71.48 umol, 23.07% yield, 96.61% purity) as yellow solid. 1H NMR (400 MHz, DMSO-d6): δ 11.11 (s, 1H), 8.38 (d, J=8 Hz, 1H) 8.09 (d, J=8 Hz, 1H), 7.85 (t, J=8 Hz, 1H), 7.58 (s, 1H), 7.36 (d, J=8 Hz, 1H), 7.31 (s, 1H), 7.08 (d, J=8 Hz, 1H), 5.45-5.42 (m, 1H), 4.21-4.18 (m, 3H), 3.76-3.72 (m, 2H), 2.94 (m, 1H), 2.82-2.73 (m, 2H), 2.71 (s, 3H), 2.66-2.62 (m, 1H), 2.57 (m, 1H), 2.09-2.08 (m, 1H), 1.90-1.87 (m, 2H), 1.79-1.74 (m, 2H), 1.23 (s, 1H), 0.63-0.62 (m, 2H), 0.47 (bs, 2H). LCMS (ES+)=541.2 [M+H]+.

Example 146. Synthesis of 4-[4-(1-{4-[1-(2,6-Dioxo-piperidin-3-yl)-2-oxo-1,2-dihydro-benzo[cd] indol-6-ylmethyl]-phenyl}-cyclopropyl)-piperazin-1-yl]-3-fluoro-benzonitrile (Compound 262)

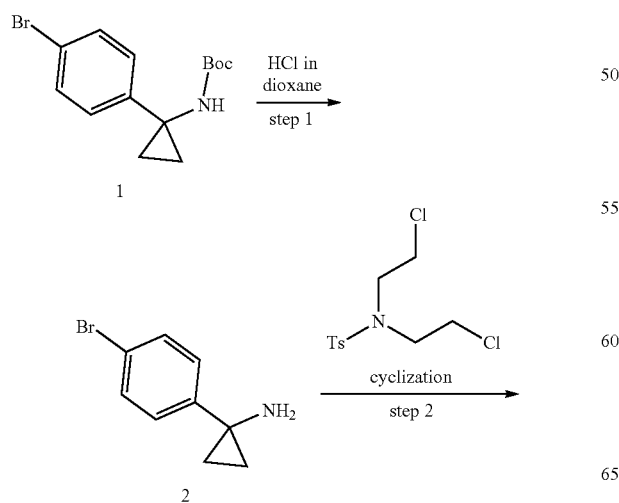

-continued

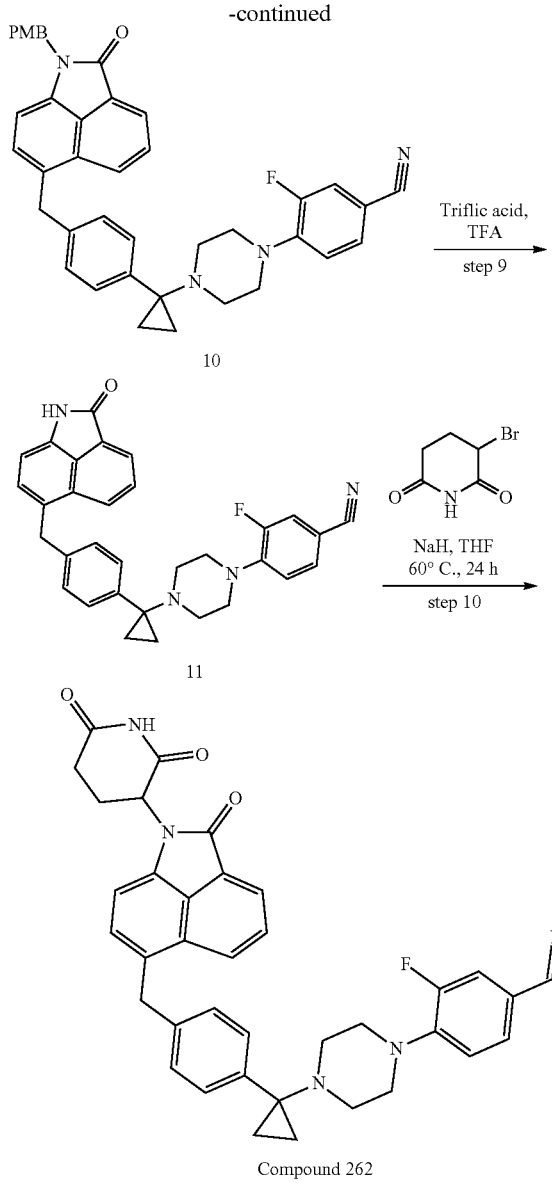

Compound 262

Step-1: Synthesis of 1-(4-Bromo-phenyl)-cyclopropylamine: To a stirred solution of tert-butyl N-[1-(4-bromophenyl)cyclopropyl]carbamate (3.0 g, 9.61 mmol) in 1,4-Dioxane (30 mL) was added Hydrogen chloride solution 4.0 M in dioxane (4.0 M, 24.02 mL) at RT and reaction mixture was stirred at RT for 16 hr. The progress of the reaction was monitored by TLC, after reaction completion reaction mixture was concentrated under reduced pressure the resultant compound was triturated with ether to get 1-(4-bromophenyl)cyclopropanamine (2.2 g, 8.41 mmol, 87.51% yield, 95% purity) as off-white solid. LC-MS: (ES+)=212.0, 214.0 [M+H]+.

Step-2: Synthesis of 1-[1-(4-Bromo-phenyl)-cyclopropyl]-4-(toluene-4-sulfonyl)-piperazine: Taken 1-(4-bromophenyl)cyclopropanamine (3.0 g, 12.07 mmol, 021) and N,N-bis(2-chloroethyl)-4-methyl-benzenesulfonamide (3.58 g, 12.07 mmol) in sealed tube and DIPEA (23.40 g, 181.05 mmol, 31.54 mL) was added and reaction mixture was stirred at 120° C. for 24 hr. The progress of the reaction was monitored by TLC, after reaction completion reaction mixture was diluted with ethyl acetate and gave water wash and brine wash separate out organic layer dried over anhydrous sodium sulfate filtered and concentrated under reduced pressure to get the crude compound and it was purified by column chromatography eluted with 0 to 20% ethyl acetate in Hexane to get 1-[1-(4-bromophenyl)cyclopropyl]-4-(p-tolylsulfonyl)piperazine (1.5 g, 3.27 mmol, 27.12% yield, 95% purity) as off-white solid. LC-MS: (ES+)=434.8, 436.8 [M+H]+.

Step-3: Synthesis of 1-[1-(4-Bromo-phenyl)-cyclopropyl]-piperazine: Hydrobromic acid, 48% (29.80 g, 368.30 mmol, 20 mL) was added to 1-[1-(4-bromophenyl)cyclopropyl]-4-(p-tolylsulfonyl)piperazine (1.0 g, 2.30 mmol) at RT and reaction mixture was stirred at RT for 24 hr. The progress of the reaction was monitored by TLC, after reaction completion reaction mixture was concentrated under reduced pressure and resultant compound was dissolved in water and adjusted pH with sodium bi carbonate and extracted with ethyl acetate and organic layer was washed with brine solution separate out organic layer dried over anhydrous sodium sulfate filtered and concentrated under reduced pressure to get 1-[1-(4-bromophenyl)cyclopropyl]piperazine (0.600 g, 2.09 mmol, 91.04% yield, 98% purity) as off-white solid. LC-MS: (ES+)=283.2 [M+H]+.

Step-4: Synthesis of 4-[1-(4-Bromo-phenyl)-cyclopropyl]-piperazine-1-carboxylic acid tert-butyl ester: To a stirred solution of 1-[1-(4-bromophenyl)cyclopropyl]piperazine (0.600 g, 2.13 mmol) in THF (10 mL) was added Triethyl amine (323.88 mg, 3.20 mmol, 446.11 uL) and followed by Di-tert-butyl dicarbonate (931.38 mg, 4.27 mmol, 979.37 uL) was added and reaction mixture was stirred at RT for 2 hr. The progress of the reaction was monitored by TLC, after reaction completion reaction mixture was concentrated and direct purified by column chromatography eluted with 0 to 20% ethyl acetate in Hexane to get tert-butyl 4-[1-(4-bromophenyl)cyclopropyl]piperazine-1-carboxylate (0.500 g, 1.25 mmol, 58.38% yield, 95% purity) as off-white solid. LC-MS: (ES+)=381.0 [M+H]+.

Step-5: Synthesis of 4-{1-[4-(4,4,5,5-Tetramethyl-[1,3,2] dioxaborolan-2-yl)-phenyl]-cyclopropyl}-piperazine-1-carboxylic acid tert-butyl ester: To a stirred solution of tert-butyl 4-[1-(4-bromophenyl)cyclopropyl]piperazine-1-carboxylate (2.0 g, 5.25 mmol) in 1,4-Dioxane (20 mL) in a sealed tube was added 4,4,5,5-tetramethyl-2-(4,4,5,5-tetramethyl-1,3,2-dioxaborolan-2-yl)-1,3,2-dioxaborolane (1.33 g, 5.25 mmol) then Potassium Acetate (1.29 g, 13.11 mmol, 819.70 uL) was added and degassed for 10 mins, later [1,1'-Bis(diphenylphosphino)ferrocene]dichloropalladium (II), complex with dichloromethane (214.17 mg, 262.26 umol) was added and again degassed for 10 mins, after degassing reaction mixture was closed with teflon cap and stirred at 90° C. for 16 hr. The progress of the reaction was monitored by TLC, after reaction completion reaction mixture was filtered and concentrated and crude was purified by column chromatography eluted with 0 to 15% ethyl acetate in Hexane to get tert-butyl 4-[1-[4-(4,4,5,5-tetramethyl-1,3,2-dioxaborolan-2-yl)phenyl]cyclopropyl]piperazine-1-carboxylate (2.0 g, 4.44 mmol, 84.56% yield, 95% purity) as off-white solid. LC-MS: (ES+)=429.0 [M+H]+.

Step-6: Synthesis of 4-(1-{4-[1-(4-Methoxy-benzyl)-2-oxo-1,2-dihydro-benzo[cd]indol-6-ylmethyl]-phenyl}-cyclopropyl)-piperazine-1-carboxylic acid tert-butyl ester: To a stirred solution of 6-(chloromethyl)-1-[(4-methoxyphenyl)methyl]benzo[cd]indol-2-one (2.0 g, 5.92 mmol) and tert-butyl 4-[1-[4-(4,4,5,5-tetramethyl-1,3,2-dioxaborolan-2-yl)phenyl]cyclopropyl]piperazine-1-carboxylate (2.54 g, 5.92 mmol) in a mixture of Toluene (12 mL) and Ethanol (6 mL)

was added Tripotassium phosphate (3.14 g, 14.80 mmol) then degassed for 10 mins, later Tris(o-tolyl)phosphine (360.41 mg, 1.18 mmol) and Tris(dibenzylideneacetone) dipalladium(0) (542.17 mg, 592.07 umol) was added and again degassed for 10 mins, after degassing reaction mixture was closed with teflon cap and stirred at 90° C. for 16 hr. The progress of the reaction was monitored by TLC, after reaction completion reaction mixture was diluted with ethyl acetate gave water wash and brine wash, separate out organic layer dried over anhydrous sodium sulfate, filtered and concentrated under reduced pressure to get the crude compound and it was purified by column chromatography eluted with 10 to 50% ethyl acetate in Hexane to get tert-butyl 4-[1-[4-[[1-[(4-methoxyphenyl)methyl]-2-oxo-benzo[cd]indol-6-yl]methyl]phenyl]cyclopropyl]piperazine-1-carboxylate (0.900 g, 1.46 mmol, 24.67% yield, 98% purity) as off-white solid. LC-MS: (ES+)=604.5 [M+H]+.

Step-7: Synthesis of 6-[4-(1-Piperazin-1-yl-cyclopropyl)-benzyl]-1H-benzo[cd]indol-2-one: To a stirred solution of tert-butyl 4-[1-[4-[[1-[(4-methoxyphenyl)methyl]-2-oxo-benzo[cd]indol-6-yl]methyl]phenyl]cyclopropyl]piperazine-1-carboxylate (0.400 g, 662.53 umol) in Trifluoro acetic acid (5 mL) was added Triflic acid (994.30 mg, 6.63 mmol, 581.46 uL) at RT 0° C. then reaction mixture was stirred at RT for 16 hr. The progress of the reaction was monitored by TLC, after reaction completion reaction mixture was concentrated under reduced pressure then crude was dissolved in water and pH was adjusted with sodium bi carbonate with 8 and extracted with ethyl acetate gave brine wash separate out organic layer dried over anhydrous sodium sulfate filtered and concentrated under reduced pressure to get the compound as yellow solid. LC-MS: (ES+)=384.3 [M+H]+.

Step-8: Synthesis of 3-Fluoro-4-(4-{1-[4-(2-oxo-1,2-dihydro-benzo[cd]indol-6-ylmethyl)-phenyl]-cyclopropyl}-piperazin-1-yl)-benzonitrile: To a stirred solution of 6-[[4-(1-piperazin-1-ylcyclopropyl)phenyl]methyl]-1H-benzo[cd]indol-2-one (0.250 g, 651.92 umol) in NMP (2 mL) was added 3,4-difluorobenzonitrile (181.37 mg, 1.30 mmol) then DIPEA (210.64 mg, 1.63 mmol, 283.88 uL) was added in a sealed tube then closed with teflon cap and stirred at 100° C. for 16 hr. The progress of the reaction was monitored by TLC, after reaction completion reaction mixture was quenched with chilled water and extracted with ethyl acetate and gave brine wash, separate out organic layer dried over anhydrous sodium sulfate filtered and concentrated under reduced pressure to get the crude compound and it was purified by column chromatography eluted with 1 to 5% MeOH in DCM to get 3-fluoro-4-[4-[1-[4-[(2-oxo-1H-benzo[cd]indol-6-yl)methyl]phenyl]cyclopropyl]piperazin-1-yl]benzonitrile (0.150 g, 283.54 umol, 43.49% yield, 95% purity) as yellow solid. LC-MS: (ES+)=503.4 [M+H]+.

Step-9: Synthesis of 4-[4-(1-{4-[1-(2,6-Dioxo-piperidin-3-yl)-2-oxo-1,2-dihydro-benzo[cd]indol-6-ylmethyl]-phenyl}-cyclopropyl)-piperazin-1-yl]-3-fluoro-benzonitrile: To a stirred solution of 3-fluoro-4-[4-[1-[4-[(2-oxo-1H-benzo[cd]indol-6-yl)methyl]phenyl]cyclopropyl]piperazin-1-yl]benzonitrile (0.150 g, 298.46 umol) in THF (5 mL) was cooled to 0° C. then Sodium hydride (in oil dispersion) 60% dispersion in mineral oil (143.25 mg, 3.58 mmol, 60% purity) was added portion wise, later reaction mixture was stirred at 0° C. for 15 mins, later 3-bromopiperidine-2,6-dione (343.84 mg, 1.79 mmol) was added and reaction mixture was stirred at RT for 30 mins, later it was stirred at 70° C. for 16 hr. The progress of the reaction was monitored by TLC after reaction completion reaction mixture was quenched with chilled water and extracted with ethyl acetate gave brine wash to the organic layer, separate out organic layer, dried over anhydrous sodium sulfate filtered and concentrated under reduced pressure to get the crude compound and it was purified by prep. HPLC to get 4-[4-[1-[4-[[1-(2,6-dioxo-3-piperidyl)-2-oxo-benzo[cd]indol-6-yl]methyl]phenyl]cyclopropyl]piperazin-1-yl]-3-fluoro-benzonitrile Compound 262 (10 mg, 16.09 umol, 5.39% yield, 98.76% purity) as yellow solid. 1HNMR (400 MHz, DMSO-d6): δ 11.11 (s, 1H), 8.35-8.33 (d, J=8 Hz, 1H), 8.07-8.05 (d, J=8 Hz, 1H), 7.82-7.78 (m, 1H), 7.64-7.60 (m, 1H), 7.51-7.49 (m, 1H), 7.41-7.39 (m, 1H), 7.26-7.24 (m, 2H), 7.19-7.17 (m, 2H), 7.11-7.09 (m, 1H), 7.04-7.00 (m, 1H), 5.44-5.42 (m, 1H), 4.38 (s, 2H), 3.16 (m, 4H), 2.97-2.91 (m, 2H), 2.79-2.72 (m, 2H), 2.66-2.62 (m, 2H), 2.08-2.07 (m, 2H), 0.85 (m, 2H), 0.71 (m, 2H), LC-MS: (ES+)=614.3 [M+H]+.

Example 147. Synthesis of 3-[6-(4-{1-[4-(1-Methyl-cyclobutanecarbonyl)-piperazin-1-yl]-cyclopropyl}-benzyl)-2-oxo-2H-benzo[cd]indol-1-yl]-piperidine-2,6-dione (Compound 263)

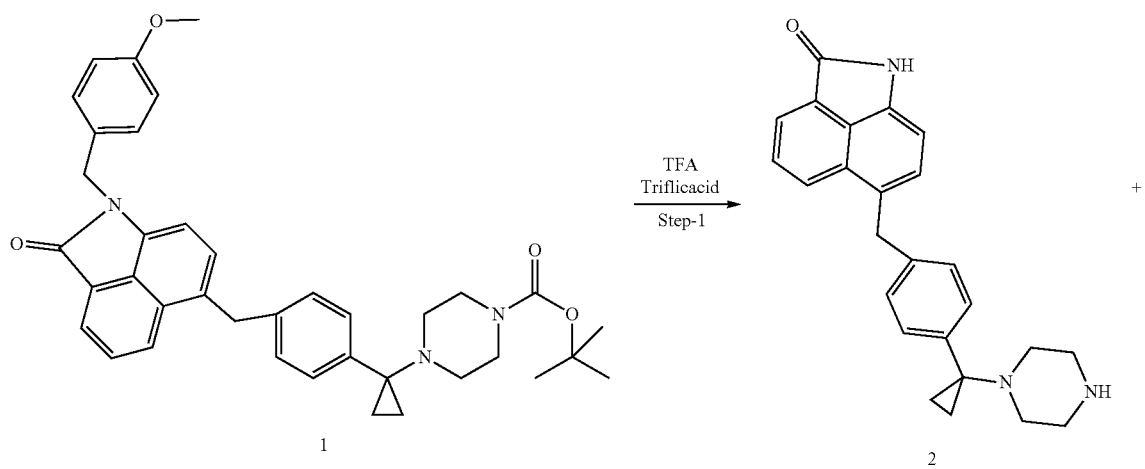

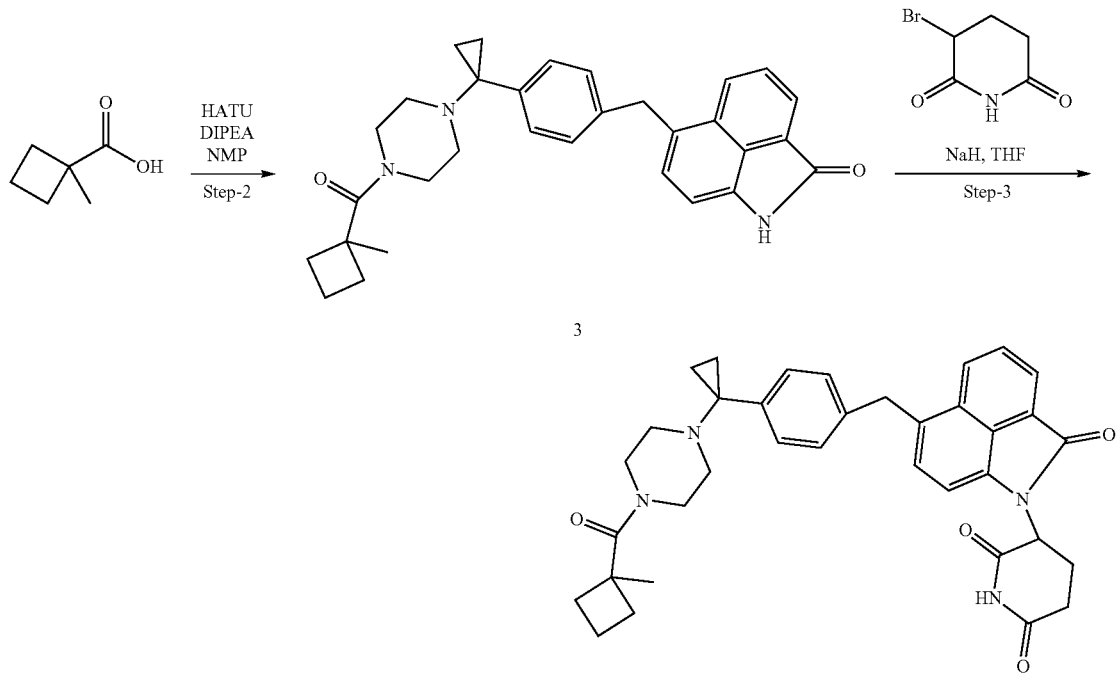

Compound 263

Step-1: Synthesis of 6-[4-(1-Piperazin-1-yl-cyclopropyl)-benzyl]-1H-benzo[cd]indol-2-one: To a stirred solution of tert-butyl 4-[1-[4-[[1-[(4-methoxyphenyl)methyl]-2-oxo-benzo[cd]indol-6-yl]methyl]phenyl]cyclopropyl]piperazine-1-carboxylate (0.400 g, 662.53 umol) in Trifluoro acetic acid (5 mL) was added Triflic acid (994.30 mg, 6.63 mmol, 581.46 uL) at RT 0° C. then reaction mixture was stirred at RT for 16 hr. The progress of the reaction was monitored by TLC, after reaction completion reaction mixture was concentrated under reduced pressure then crude was dissolved in water and pH was adjusted with sodium bi carbonate with 8 and extracted with ethyl acetate gave brine wash separate out organic layer dried over anhydrous sodium sulfate filtered and concentrated under reduced pressure to get the compound as yellow solid. LC-MS: (ES+)=384.3 [M+H]+.

Step-2: Synthesis of 6-(4-{1-[4-(1-Methyl-cyclobutanecarbonyl)-piperazin-1-yl]-cyclopropyl}-benzyl)-1H-benzo[cd]indol-2-one: To a stirred solution of 6-[[4-[1-piperazin-1-ylcyclopropyl)phenyl]methyl]-1H-benzo[cd]indol-2-one (0.100 g, 260.77 umol) in DMF (2 mL) was added 1-methylcyclobutanecarboxylic acid (59.53 mg, 521.53 umol) then N,N-Diisopropylethylamine (101.11 mg, 782.30 umol, 136.26 uL) was added and finally HATU (247.88 mg, 651.92 umol) was added and reaction mixture was stirred at RT for 16 hr. The progress of the reaction was monitored by TLC, after reaction completion reaction mixture was dissolved in ethyl acetate, gave chilled water wash and followed by brine wash separate out organic layer dried over anhydrous sodium sulfate filtered and concentrated under reduced pressure to get the crude compound and it was purified by column chromatography eluted with 1 to 5% MeOH in DCM to get 6-[[4-[1-[4-(1-methylcyclobutanecarbonyl)piperazin-1-yl]cyclopropyl]phenyl]methyl]-1H-benzo[cd]indol-2-one (0.100 g, 166.80 umol, 63.97% yield, 80% purity) as yellow solid. LC-MS: (ES+)=480.6 [M+H]+.

Step-3: Synthesis of 3-[6-(4-{1-[4-(1-Methyl-cyclobutanecarbonyl)-piperazin-1-yl]-cyclopropyl}-benzyl)-2-oxo-2H-benzo[cd]indol-1-yl]-piperidine-2,6-dione: To a stirred solution of 6-[[4-[1-[4-(1-methylcyclobutanecarbonyl)piperazin-1-yl]cyclopropyl]phenyl]methyl]-1H-benzo[cd]indol-2-one (0.100 g, 208.50 umol) in THF (5 mL) was cooled to 0° C. then Sodium hydride (in oil dispersion) 60% dispersion in mineral oil (57.52 mg, 2.40 mmol) was added as portion-wise, after addition completion reaction mixture was stirred at 0° C. for 10 mins, later 3-bromopiperidine-2,6-dione (240.21 mg, 1.25 mmol) was added and reaction mixture was stirred at RT for 10 mins, later reaction mixture was stirred at 70° C. for 16 hr. The progress of the reaction was monitored by TLC after reaction completion reaction mixture was quenched with chilled water then extracted with ethyl acetate gave brine wash to organic layer separate out organic layer dried over anhydrous sodium sulfate filtered and concentrated under reduced pressure to get the crude compound and it was purified by prep. HPLC to get 3-[6-[[4-[1-[4-(1-methylcyclobutanecarbonyl)piperazin-1-yl]cyclopropyl]phenyl]methyl]-2-oxo-benzo[cd]indol-1-yl]piperidine-2,6-dione Compound 263 (22 mg, 36.16 umol, 17.34% yield, 97.09% purity) as light yellow solid. 1HNMR (400 MHz, DMSO-d6): δ 11.12 (s, 1H), 8.32-8.30 (d, J=8 Hz, 1H), 8.07-8.05 (d, J=8 Hz, 1H), 7.80-7.76 (m, 1H), 7.41-7.39 (d, J=8 Hz, 1H), 7.24-7.22 (d, J=8 Hz, 2H), 7.14-7.08 (m, 3H), 5.45-5.41 (m, 1H), 4.37 (s, 2H), 3.29 (brs, 2H), 2.97-2.90 (m, 2H), 2.79-2.72 (m, 1H), 2.69-2.62 (m, 2H), 2.32 (m, 4H), 2.25-2.20 (m, 2H), 2.10-2.07 (m, 1H), 1.90-1.81 (m, 1H), 1.71-1.69 (m, 2H), 1.54-1.52 (m, 1H), 1.23 (s, 3H), 0.88-0.76 (m, 2H), 0.75-0.63 (m, 2H). LC-MS: (ES+)=591.3 [M+H]+.

Example 148. Synthesis of 3-[6-(4-{1-[4-(2-Fluorophenyl)-piperazin-1-yl]-cyclopropyl}-benzyl)-2-oxo-2H-benzo[cd]indol-1-yl]-piperidine-2,6-dione (Compound 264)
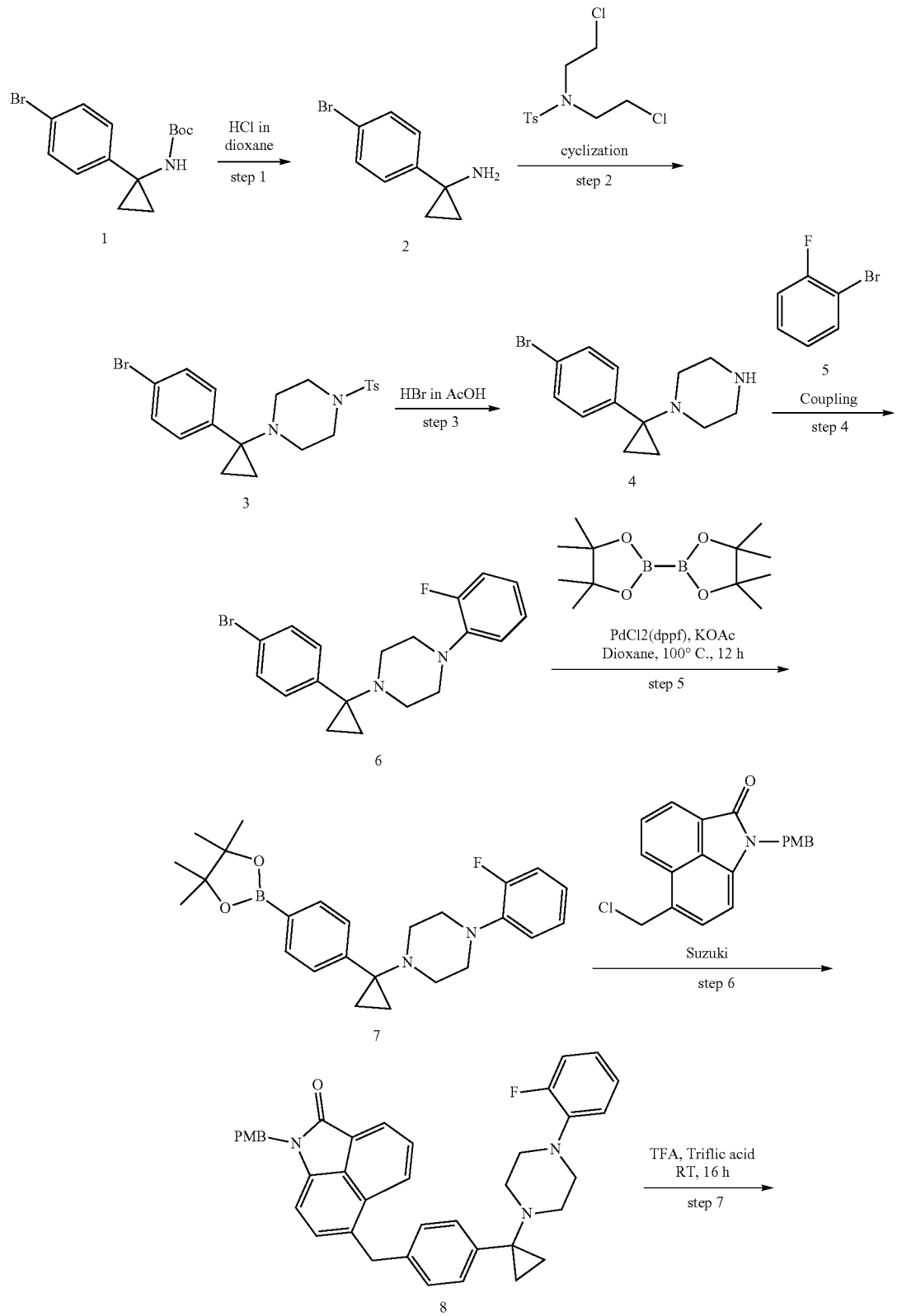

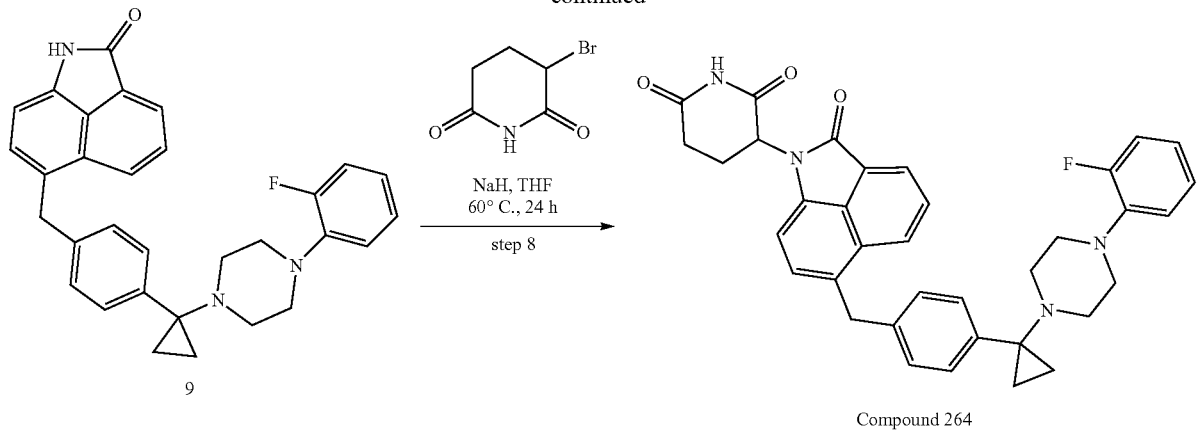

Step-1: Synthesis of 1-(4-Bromo-phenyl)-cyclopropylamine: To a stirred solution of tert-butyl N-[1-(4-bromophenyl)cyclopropyl]carbamate (3.0 g, 9.61 mmol) in 1,4-Dioxane (30 mL) was added Hydrogen chloride solution 4.0 M in dioxane (4.0 M, 24.02 mL) at RT and reaction mixture was stirred at RT for 16 hr. The progress of the reaction was monitored by TLC, after reaction completion reaction mixture was concentrated under reduced pressure the resultant compound was triturated with ether to get 1-(4-bromophenyl)cyclopropanamine (2.2 g, 8.41 mmol, 87.51% yield, 95% purity) as off-white solid. LC-MS: (ES+)=212.0, 214.0 [M+H]+.

Step-2: Synthesis of 1-[1-(4-Bromo-phenyl)-cyclopropyl]-4-(toluene-4-sulfonyl)-piperazine: Taken 1-(4-bromophenyl)cyclopropanamine (3.0 g, 12.07 mmol, 021) and N,N-bis(2-chloroethyl)-4-methyl-benzenesulfonamide (3.58 g, 12.07 mmol) in sealed tube and DIPEA (23.40 g, 181.05 mmol, 31.54 mL) was added and reaction mixture was stirred at 120° C. for 24 hr. The progress of the reaction was monitored by TLC, after reaction completion reaction mixture was diluted with ethyl acetate and gave water wash and brine wash separate out organic layer dried over anhydrous sodium sulfate filtered and concentrated under reduced pressure to get the crude compound and it was purified by column chromatography eluted with 0 to 20% ethyl acetate in Hexane to get 1-[1-(4-bromophenyl)cyclopropyl]-4-(p-tolylsulfonyl)piperazine (1.5 g, 3.27 mmol, 27.12% yield, 95% purity) as off-white solid. LC-MS: (ES+)=434.8, 436.8 [M+H]+.

Step-3: Synthesis of 1-[1-(4-Bromo-phenyl)-cyclopropyl]-piperazine: Hydrobromic acid, 48% (29.80 g, 368.30 mmol, 20 mL) was added to 1-[1-(4-bromophenyl)cyclopropyl]-4-(p-tolylsulfonyl)piperazine (1.0 g, 2.30 mmol) at RT and reaction mixture was stirred at RT for 24 hr. The progress of the reaction was monitored by TLC, after reaction completion reaction mixture was concentrated under reduced pressure and resultant compound was dissolved in water and adjusted pH with sodium bi carbonate and extracted with ethyl acetate and organic layer was washed with brine solution separate out organic layer dried over anhydrous sodium sulfate filtered and concentrated under reduced pressure to get 1-[1-(4-bromophenyl)cyclopropyl]piperazine (0.600 g, 2.09 mmol, 91.04% yield, 98% purity) as off-white solid. LC-MS: (ES+)=283.2 [M+H]+.

Step-4: Synthesis of 1-[1-(4-Bromo-phenyl)-cyclopropyl]-4-(2-fluoro-phenyl)-piperazine: To a stirred solution of 1-[1-(4-bromophenyl)cyclopropyl]piperazine (0.300 g, 1.07 mmol) and 1-bromo-2-fluoro-benzene (560.11 mg, 3.20 mmol, 350.07 uL) in Tertiary Butanol (5 mL) was added Caesium carbonate (869.03 mg, 2.67 mmol) then degassed for 10 mins, later RuPhos (49.78 mg, 106.69 umol) and Tris(dibenzylideneacetone)dipalladium(0) (97.70 mg, 106.69 umol) was added and again degassed for 10 mins, later sealed tube was closed with Teflon cap and stirred at 90° C. for 16 hrs. The progress of the reaction was monitored by TLC, after reaction completion reaction mixture was diluted with ethyl acetate and filtered through celite bed and all solvent was mixed and concentrated under reduced pressure to get the crude compound and it was purified by column chromatography eluted with 0 to 30% ethyl acetate in Hexane to get 1-[1-(4-bromophenyl)cyclopropyl]-4-(2-fluorophenyl)piperazine (0.160 g, 409.30 umol, 38.36% yield, 96% purity) as light yellow liquid. LC-MS: (ES+)=375.1, 377.2 [M+H]+.

Step-5: Synthesis of 1-(2-Fluoro-phenyl)-4-{1-[4-(4,4,5,5-tetramethyl-[1,3,2]dioxaborolan-2-yl)-phenyl]-cyclopropyl}-piperazine: To a stirred solution of 1-[1-(4-bromophenyl)cyclopropyl]-4-(2-fluorophenyl)piperazine (0.160 g, 426.35 umol) in 1,4-Dioxane (5 mL) was added 4,4,5,5-tetramethyl-2-(4,4,5,5-tetramethyl-1,3,2-dioxaborolan-2-yl)-1,3,2-dioxaborolane (129.92 mg, 511.62 umol) in a sealed tube and Potassium acetate (104.61 mg, 1.07 mmol, 66.63 uL) was added and degassed for 10 mins, later [1,1'-Bis(diphenylphosphino)ferrocene]dichloropalladium (II), complex with dichloromethane (34.82 mg, 42.64 umol) was added and again degassed for 10 mins, after degassing reaction mixture was closed with Teflon cap and reaction mixture was stirred at 90° C. for 16 hr. The progress of the reaction was monitored by TLC after reaction completion reaction mixture was diluted with ethyl acetate and filtered through celite bed and the solvent was concentrated under reduced pressure to get the crude compound and it was purified by column chromatography eluted with 0 to 30% ethyl acetate in Hexane to get 1-(2-fluorophenyl)-4-[1-[4-(4,4,5,5-tetramethyl-1,3,2-dioxaborolan-2-yl)phenyl]cyclopropyl]piperazine (0.100 g, 224.94 umol, 52.76% yield, 95% purity) as brown solid. LC-MS: (ES+)=423.4 [M+H]+.

Step-6: Synthesis of 6-(4-{1-[4-(2-Fluoro-phenyl)-piperazin-1-yl]-cyclopropyl}-benzyl)-1-(4-methoxy-benzyl)-1H-benzo[cd]indol-2-one: To a stirred solution of 6-(chloromethyl)-1-[(4-methoxyphenyl)methyl]benzo[cd]indol-2-one (0.080 g, 236.83 umol) and 1-(2-fluorophenyl)-4-[1-[4-(4,4,5,5-tetramethyl-1,3,2-dioxaborolan-2-yl)phenyl]cyclopropyl]piperazine (100.02 mg, 236.83 umol) in a mixture of Toluene (4 mL) and Ethanol (2 mL) was added Potassium phosphate (125.68 mg, 592.07 umol) in a sealed tube at RT and degassed for 10 mins, later Tri(o-tolyl)phosphine (14.42 mg, 47.37 umol) and Tris(dibenzylideneacetone)dipalladium(0) (21.69 mg, 23.68 umol) was added and again degassed for 10 mins, after degassed reaction mixture was closed with Teflon cap and stirred at 90° C. for 16 hr. The progress of the reaction was monitored by TLC after reaction completion reaction mixture was filtered through celite bed and bed was washed twice with ethyl acetate all organic solvent was mixed and concentrated under reduced pressure to get the crude compound. The crude compound was purified by column chromatography eluted with 0 to 40% ethyl acetate in hexane to get 6-(4-(1-[4-(2-Fluoro-phenyl)-piperazin-1-yl]-cyclopropyl}-benzyl)-1-(4-methoxy-benzyl)-1H-benzo[cd]indol-2-one as light yellow solid. LC-MS: (ES+)=598.1 [M+H]+.

Step-7: Synthesis of 6-(4-{1-[4-(2-Fluoro-phenyl)-piperazin-1-yl]-cyclopropyl}-benzyl)-1H-benzo[cd]indol-2-one: To a stirred solution of 6-[[4-[1-[4-(2-fluorophenyl)piperazin-1-yl]cyclopropyl]phenyl]methyl]-1-[(4-methoxyphenyl)methyl]benzo[cd]indol-2-one (0.100 g, 167.30 umol) in Trifluoroacetic acid (0.5 mL) was added Triflicacid (125.54 mg, 836.51 umol, 73.42 uL) at RT and reaction mixture was stirred at RT for 16 hr. The progress of the reaction was monitored by TLC after reaction completion reaction mixture was quenched with chilled water and extracted with ethyl acetate, separate out organic layer and the aqueous layer was basified with sodium bicarbonate and extracted with ethyl acetate, gave brine wash to the organic layer, separate out organic layer dried over anhydrous sodium sulfate filtered and concentrated under reduced pressure to get the 6-[[4-[1-[4-(2-fluorophenyl)piperazin-1-yl]cyclopropyl]phenyl]methyl]-1H-benzo[cd]indol-2-one (0.060 g, 113.07 umol, 67.59% yield, 90% purity) as yellow solid. LC-MS: (ES+)=478.3 [M+H]+.

Step-8: Synthesis of 3-[6-(4-{1-[4-(2-Fluoro-phenyl)-piperazin-1-yl]-cyclopropyl}-benzyl)-2-oxo-2H-benzo[cd]indol-1-yl]-piperidine-2,6-dione: 6-[[4-[1-[4-(2-fluorophenyl)piperazin-1-yl]cyclopropyl]phenyl]methyl]-1H-benzo[cd]indol-2-one (0.060 g, 125.64 umol) was dissolved in THF (5 mL) then cooled to 0° C., later Sodium hydride (in oil dispersion) 60% dispersion in mineral oil (50.25 mg, 1.26 mmol, 60% purity) was added portion-wise at 0° C. after addition completion reaction mixture was stirred at 0° C. for 30 mins, later 3-bromopiperidine-2,6-dione (120.62 mg, 628.18 umol) was added and reaction mixture was stirred at RT for 1 hr, later reaction mixture was stirred at 70° C. for 6 hr. The progress of the reaction was monitored by TLC after reaction completion reaction mixture was quenched carefully with chilled water and extracted with ethyl acetate gave brine wash to organic layer, separate out organic layer dried over anhydrous sodium sulfate, filtered and concentrated under reduced pressure to get the crude compound and it was purified by column chromatography eluted with 10 t0 60% ethyl acetate in Hexane to get product and further it was purified by Prep-HPLC to get 3-[6-[[4-[1-[4-(2-fluorophenyl)piperazin-1-yl]cyclopropyl]phenyl]methyl]-2-oxobenzo[cd]indol-1-yl]piperidine-2,6-dione Compound 264 (0.020 g, 32.62umol, 25.96% yield, 96% purity) as yellow solid. 1HNMR (400 MHz, MeOD-d6): δ 8.25-8.23 (d, J=8 Hz, 1H), 8.05-8.04 (d, J=4 Hz, 1H), 7.77-7.73 (m, 1H), 7.34-7.32 (d, J=8 Hz, 1H), 7.23 (m, 4H), 7.02-6.90 (m, 5H), 5.42-5.38 (m, 1H), 4.57 (s, 1H), 4.43 (m, 2H), 2.96-2.92 (m, 5H), 2.83-2.78 (m, 2H), 2.65 (m, 4H), 2.2 (m, 1H), 0.93-0.91 (m, 2H) 0.79-0.78 (m, 2H). LC-MS: (ES+)=589.2 [M+H]+.

Example 149. Synthesis of 3-(6-((1-(1-(3-methyl-3-azabicyclo[3.1.1]heptane-1-carbonyl)piperidin-4-yl)-1H-pyrazol-4-yl)methyl)-2-oxobenzo[cd]indol-1(2H)-yl)piperidine-2,6-dione (Compound 265)

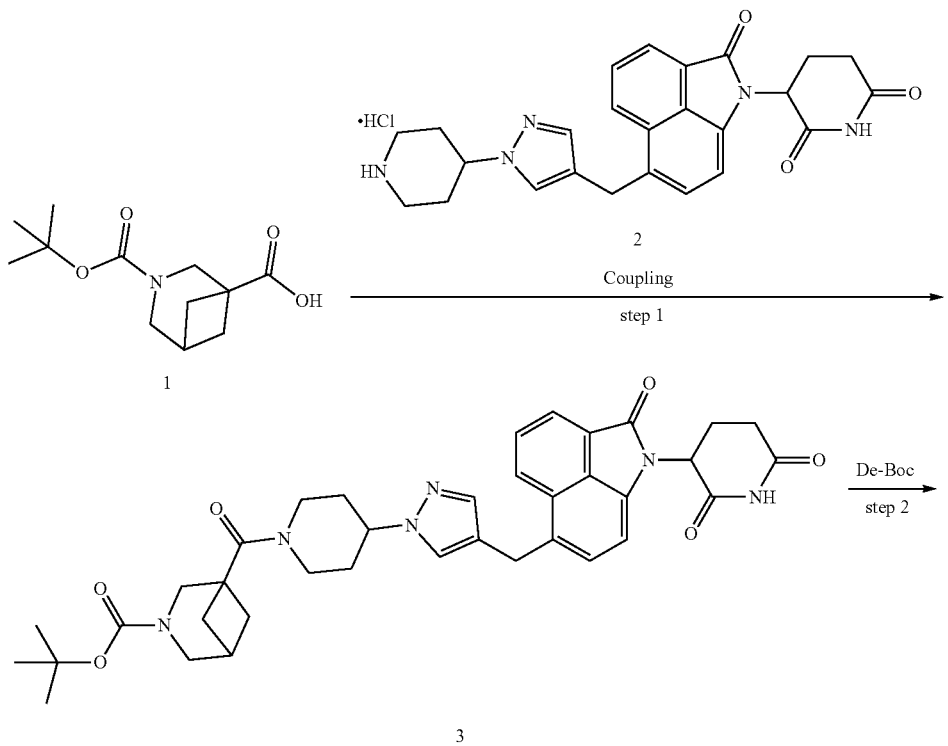

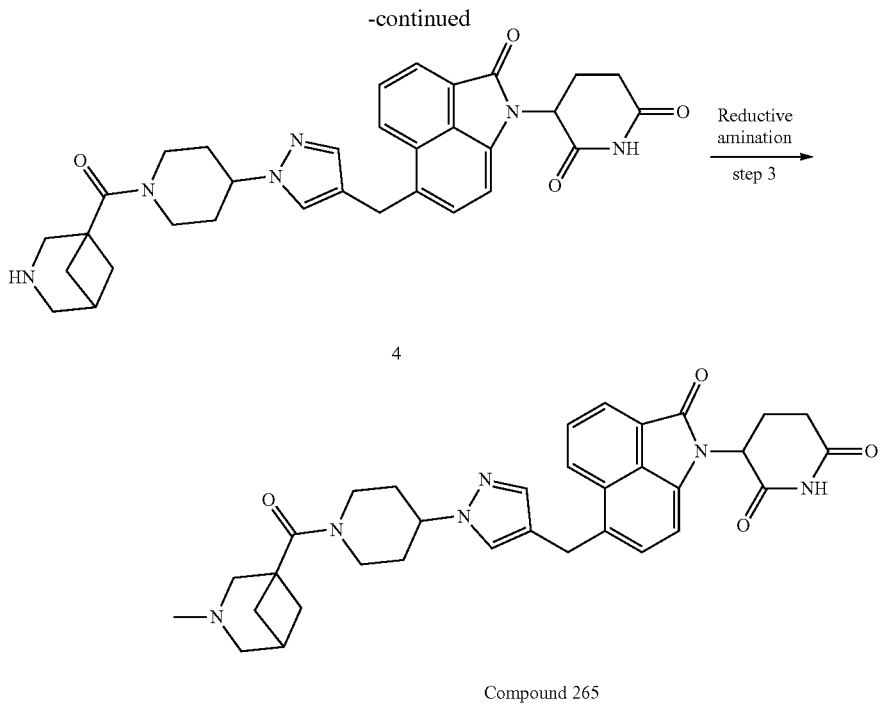

Compound 265

Step-1: Synthesis of tert-butyl 1-(4-(4-(((1-(2,6-dioxopiperidin-3-yl)-2-oxo-1,2-dihydrobenzo[cd]indol-6-yl)methyl)-1H-pyrazol-1-yl)piperidine-1-carbonyl)-3-azabicyclo[3.1.1]heptane-3-carboxylate: To a stirred solution of 3-[2-oxo-6-[[1-(4-piperidyl)pyrazol-4-yl]methyl]benzo[cd]indol-1-yl]piperidine-2,6-dione (0.120 g, 250.02 umol, 021) in DMF (2 mL) was added 3-tert-butoxycarbonyl-3-azabicyclo[3.1.1]heptane-5-carboxylic acid (60.33 mg, 250.02 umol) then HATU (285.20 mg, 750.07 umol) was added and followed by N,N-Diisopropylethylamine (161.57 mg, 1.25 mmol, 217.75 uL) N,N-Diisopropylethylamine (161.57 mg, 1.25 mmol, 217.75 uL) was added and reaction mixture was stirred at RT for 16 hr. The progress of the reaction was monitored by TLC after reaction completion reaction mixture was diluted with ethyl acetate gave water wash and followed by brine wash separate out organic layer dried over anhydrous sodium sulfate filtered and concentrated under reduced pressure to get the crude compound and it was purified by column chromatography eluting with 1 to 5% MeOH in DCM to get tert-butyl 5-[4-[4-[[1-(2,6-dioxo-3-piperidyl)-2-oxo-benzo[cd]indol-6-yl]methyl]pyrazol-1-yl]piperidine-1-carbonyl]-3-azabicyclo[3.1.1]heptane-3-carboxylate (0.040 g, 58.79 umol, 23.51% yield, 98% purity) as yellow solid. 1HNMR (400 MHz, DMSO-d6): δ 11.11 (S, 1H), 8.38-8.36 (d, J=8 Hz, 1H), 8.09-8.07 (d, J=8 Hz, 1H), 7.84-7.81 (m, 1H), 7.59-7.57 (d, J=8 Hz, 1H), 7.36-7.35 (d, J=4 Hz, 1H), 7.32 (s, 1H), 7.08-7.06 (d, J=8 Hz, 1H), 5.45-5.41 (m, 1H), 4.33-4.28 (m, 2H), 4.18 (s, 2H), 3.82 (m, 1H), 3.48-3.37 (m, 4H), 3.08 (m, 1H), 2.94-2.90 (m, 1H), 2.77-2.75 (m, 1H), 2.73-2.62 (m, 2H), 2.25-2.22 (m, 3H), 2.09-2.06 (m, 1H), 1.92 (m, 2H), 1.65 (m, 4H), 1.41 (s, 9H). LC-MS: (ES+)=667.5 [M+H]+.

Step-2: Synthesis of 3-(6-((1-(1-(3-azabicyclo[3.1.1]heptane-1-carbonyl)piperidin-4-yl)-1H-pyrazol-4-yl)methyl)-2-oxobenzo[cd]indol-1(2H)-yl)piperidine-2,6-dione: To a stirred solution of tert-butyl 5-[4-[4-[[1-(2,6-dioxo-3-piperidyl)-2-oxo-benzo[cd]indol-6-yl]methyl]pyrazol-1-yl]piperidine-1-carbonyl]-3-azabicyclo[3.1.1]heptane-3-carboxylate (0.060 g, 89.99 umol) in 1,4-Dioxane (2 mL) was added Hydrogen chloride solution 4.0 M in dioxane (4.0 M, 337.45 uL) at RT then reaction mixture was stirred at RT for 16 hr. The progress of the reaction was monitored by TLC, after reaction completion reaction mixture was concentrated under reduced pressure then resultant compound was triturated with diethyl ether to get 3-[6-[[1-[1-(3-azabicyclo[3.1.1]heptane-5-carbonyl)-4-piperidyl]pyrazol-4-yl]methyl]-2-oxo-benzo[cd]indol-1-yl]piperidine-2,6-dione (0.060 g, 78.76 umol, 87.52% yield, 95% purity) as light yellow solid. LC-MS: (ES+)=567.2 [M+H]+.

Step-3: Synthesis of 3-(6-((1-(1-(3-methyl-3-azabicyclo[3.1.1]heptane-1-carbonyl)piperidin-4-yl)-1H-pyrazol-4-yl)methyl)-2-oxobenzo[cd]indol-1(2H)-yl)piperidine-2,6-dione: To a stirred solution of 3-[6-[[1-[1-(3-azabicyclo[3.1.1]heptane-5-carbonyl)-4-piperidyl]pyrazol-4-yl]methyl]-2-oxo-benzo[cd]indol-1-yl]piperidine-2,6-dione (0.060 g, 105.89 umol) in Acetonitrile (5 mL) was added Formaldehyde, 37% w/w aq. soln., (105.89 umol, 2.0 mL) and followed by Formic Acid (2.44 g, 53.01 mmol, 2.0 mL) was added and the reaction mixture was stirred at 90° C. for 16 hr. The progress of the reaction was monitored by TLC, after reaction completion reaction mixture was concentrated under reduced pressure then resultant compound was dissolved in water and pH was adjusted to 8 with sodium bicarbonate then extracted with ethyl acetate gave brine wash, separate out organic layer dried over anhydrous sodium sulfate filtered and concentrated under reduced pressure to get the crude compound and it was purified by Prep-HPLC to get 3-[6-[[1-[1-(3-methyl-3-azabicyclo[3.1.1]heptane-5-carbonyl)-4-piperidyl]pyrazol-4-yl]methyl]-2-oxo-benzo[cd]indol-1-yl]piperidine-2,6-dione Compound 265 (20 mg, 33.75 umol, 31.88% yield, 98% purity) as yellow solid. 1HNMR (400 MHz, DMSO-d6): δ 11.12 (s, 1H), 8.38-8.36 (d, J=8 Hz, 1H), 8.09-8.07 (d, J=8 Hz, 1H), 7.84-7.81 (m, 1H), 7.59 (s, 1H), 7.59 (s, 1H), 7.36-7.34 (d, J=8 Hz, 1H), 7.31 (s, 1H), 5.45-5.41 (m, 1H), 4.32-4.26 (m, 2H), 4.18 (s, 1H), 3.77-3.74 (m, 1H), 3.06 (m, 1H), 2.97-2.94 (m, 1H), 2.76-2.73 (m, 2H), 2.72-2.63 (m, 4H), 2.28 (s, 3H), 2.12-2.05 (m, 4H), 1.93-1.88 (m, 3H), 1.80-1.65 (m, 4H). LC-MS: (ES+)=581.3 [M+H]+.

Example 150. Synthesis of tert-butyl 4-[4-[[1-(2,6-dioxo-3-piperidyl)-2-oxo-benzo[cd]indol-6-yl]-hydroxy-methyl]pyrazol-1-yl]piperidine-1-carboxylate (Compound 266)
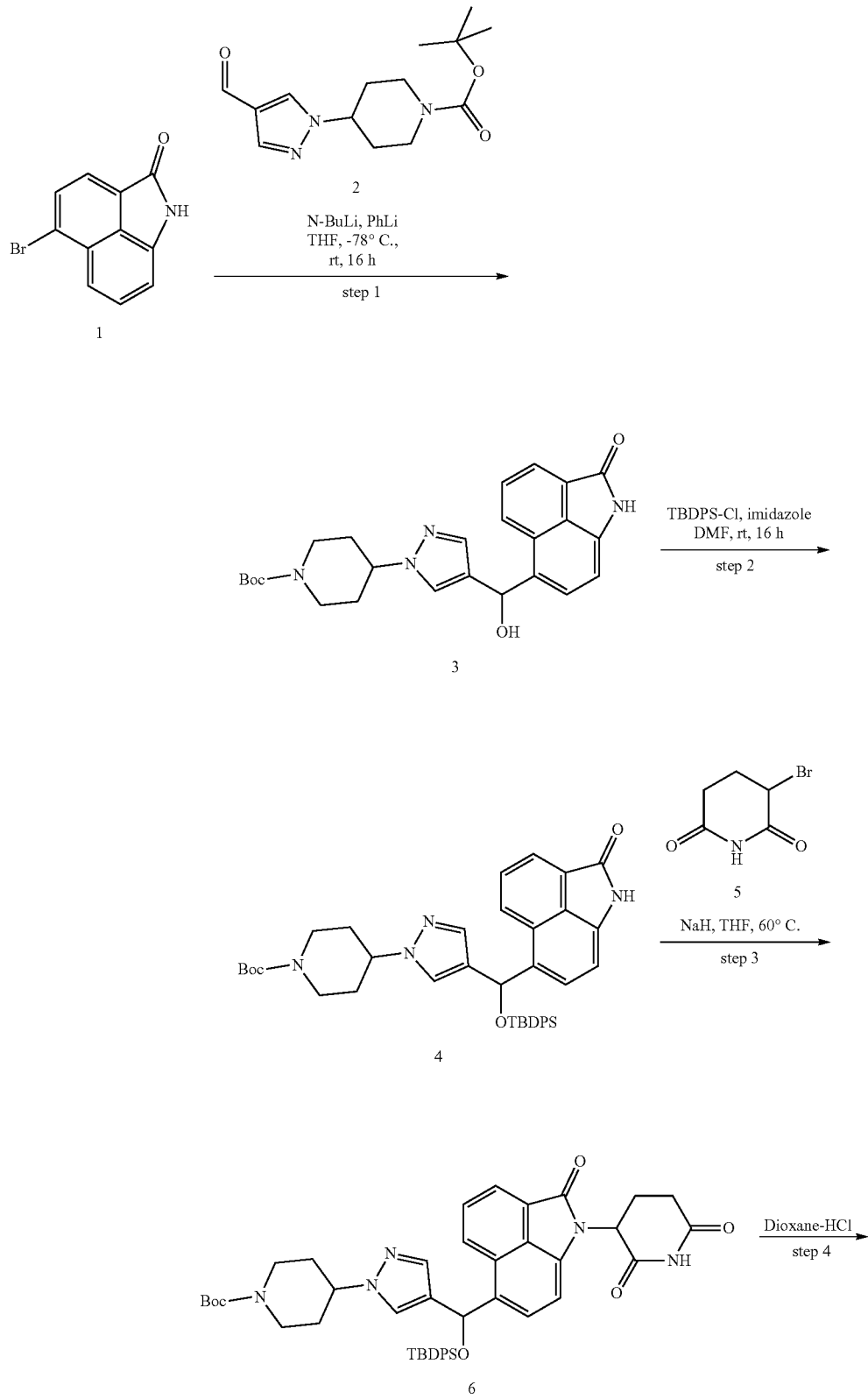

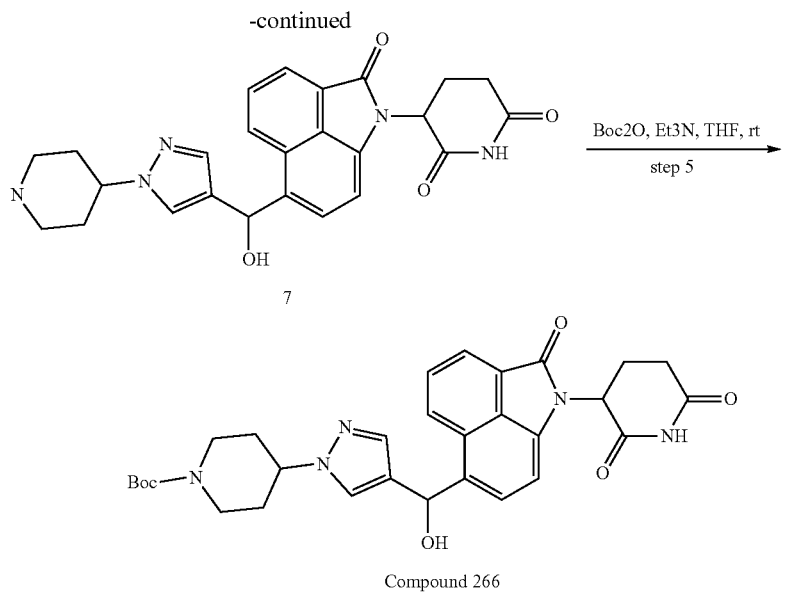

Compound 266

Step-1: Synthesis of tert-butyl 4-[4-[hydroxy-(2-oxo-1H-benzo[cd]indol-6-yl)methyl]pyrazol-1-yl]piperidine-1-carboxylate: To the stirred solution of 6-bromo-1H-benzo[cd]indol-2-one (1) (6.48 g, 26.13 mmol) in THF (100 mL) was added Phenyllithium, typically 1.9M in di-n-butyl ether (1.8 M, 14.52 mL) at −78° C. and the reaction was stirred at the same temperature for 30 minutes followed by the addition of Butyllithium (2.00 M, 14.37 mL) at −78° C. The temperature was then raised to −40° C. and was stirred at the same temperature for 30 minutes. The temperature was again lowered to −78° C. and tert-butyl 4-(4-formylpyrazol-1-yl)piperidine-1-carboxylate (2) (7.3 g, 26.13 mmol) in THF (40 mL) was added and the reaction mixture was allowed to warm to room temperature and was stirred for 16 hr. After completion of the reaction (monitored by TLC) the reaction mixture was quenched with saturated ammonium chloride solution and extracted with EtOAc. The organic part was then washed with water, brine, dried over sodium sulfate and concentrated under reduced pressure. The crude thus obtained was purified by combiflash (Gradient: 0-1% MeOH in DCM) to afford tert-butyl 4-[4-[hydroxy-(2-oxo-1H-benzo[cd]indol-6-yl)methyl]pyrazol-1-yl]piperidine-1-carboxylate (3) (6.1 g, 43.20% yield) as yellow solid; LC MS: ES+ 449.5.

Step-2: Synthesis of tert-butyl 4-[4-[[tert-butyl(diphenyl)silyl]oxy-(2-oxo-1H-benzo[cd]indol-6-yl)methyl]pyrazol-1-yl]piperidine-1-carboxylate: To a stirred solution of tert-butyl 4-[4-[hydroxy-(2-oxo-1H-benzo[cd]indol-6-yl)methyl]pyrazol-1-yl]piperidine-1-carboxylate (3) (250.0 mg, 557.40 umol) in DMF (2 mL) were added Imidazole (113.84 mg, 1.67 mmol) followed by the addition of Tert-Butylchlorodiphenylsilane (229.81 mg, 836.10 umol, 214.78 uL) at 0° C. and the reaction mixture was stirred at room temperature for 16 hours. TLC and LC MS were checked which showed unreacted SM being present along with the desired product. The reaction mixture was then diluted with EtOAc, washed with water and the organic fraction was separated. It was then dried over anhydrous sodium sulphate and concentrated under reduced pressure. Crude thus obtained was purified by flash chromatography (Gradient: 0-5% MeOH in DCM) to afford tert-butyl 4-[4-[[tert-butyl(diphenyl)silyl]oxy-(2-oxo-1H-benzo[cd]indol-6-yl)methyl]pyrazol-1-yl]piperidine-1-carboxylate (4) (140.0 mg, 36.31% yield) as yellow solid; LC MS: ES− 685.5.

Step-3: Synthesis of tert-butyl 4-[4-[[tert-butyl(diphenyl)silyl]oxy-[1-(2,6-dioxo-3-piperidyl)-2-oxo-benzo[cd]indol-6-yl]methyl]pyrazol-1-yl]piperidine-1-carboxylate: To a cooled solution of 4-[4-[[tert-butyl(diphenyl)silyl]oxy-(2-oxo-1H-benzo[cd]indol-6-yl)methyl]pyrazol-1-yl]piperidine-1-carboxylate (4) (165.0 mg, 240.21 umol) in DMF (1 mL), Sodium hydride (60% dispersion in mineral oil) (43.23 mg, 1.08 mmol) was added portion wise and the reaction mixture was heated at 70° C. for 1 hour followed by the addition of 3-bromopiperidine-2,6-dione (115.30 mg, 600.51 umol) and the reaction was continued at 70° C. for 16 hours. TLC was checked which showed incomplete consumption of the starting material along with the formation of the desired spot. The reaction mixture was diluted with ethyl acetate, washed with water and the organic fraction was separated. It was then dried over anhydrous sodium sulphate and evaporated. Crude thus obtained was purified by Prep TLC plate 30% ethyl acetate-DCM to afford tert-butyl 4-[4-[[tert-butyl(diphenyl)silyl]oxy-[1-(2,6-dioxo-3-piperidyl)-2-oxo-benzo[cd]indol-6-yl]methyl]pyrazol-1-yl]piperidine-1-carboxylate (5) (75.0 mg, 35.21% yield) as yellow solid; LC MS: ES+ 542.5.

Step-4: Synthesis of 3-[6-[[1-(1-chloro-4-piperidyl)pyrazol-4-yl]-hydroxy-methyl]-2-oxo-benzo[cd]indol-1-yl]piperidine-2,6-dione: To a stirred solution of tert-butyl 4-[4-[[tert-butyl(diphenyl)silyl]oxy-[1-(2,6-dioxo-3-piperidyl)-2-oxo-benzo[cd]indol-6-yl]methyl]pyrazol-1-yl]piperidine-1-carboxylate (5) (70.0 mg, 87.72 umol) in Dioxane (1 mL) was added Hydrochloric acid in dioxane (87.72 umol, 5 mL) and the reaction mixture was stirred at room temperature for 2 hours. After completion of the reaction (monitored by TLC) the reaction mixture was concentrated under reduced pressure and was triturated with ether and pentane to afford 3-[6-[[1-(1-chloro-4-piperidyl)pyrazol-4-yl]-hydroxy-methyl]-2-oxo-benzo[cd]indol-1-yl]piperidine-2,6-dione, Hydrochloride salt (6) (40.0 mg, 50.10% yield) as yellow solid. LC MS: ES+ 460.4.

Step-5: Synthesis of tert-butyl 4-[4-[[1-(2,6-dioxo-3-piperidyl)-2-oxo-benzo[cd]indol-6-yl]-hydroxy-methyl]pyrazol-1-yl]piperidine-1-carboxylate: To a stirred solution of 3-[6-[[1-(1-chloro-4-piperidyl)pyrazol-4-yl]-hydroxy-methyl]-2-oxo-benzo[cd]indol-1-yl]piperidine-2,6-dione (6) (40.00 mg, 80.65 umol) in DCM (6 mL) was added Triethylamine (24.48 mg, 241.96 umol, 33.72 uL) at 0° C. followed by the addition of Di-tert-butyl dicarbonate (26.40 mg, 120.98 umol, 27.76 uL) and the reaction was stirred at room temperature for 16 hours. After completion of the reaction (monitored by TLC) the reaction mixture was diluted with ethyl acetate, washed with water and the organic fraction was separated. It was then dried over anhydrous sodium sulphate and concentrated under reduced pressure. The crude thus obtained was purified by preparative TLC plate in 4% MeOH-DCM to afford tert-butyl 4-[4-[[1-(2,6-dioxo-3-piperidyl)-2-oxo-benzo[cd]indol-6-yl]-hydroxy-methyl]pyrazol-1-yl]piperidine-1-carboxylate Compound 266 (14.0 mg, 30.76% yield) as yellow solid. $^1$H NMR (400 MHz, DMSO-d6) δ 11.12 (s, 1H), 8.42-8.39 (m, 1H), 8.05 (d, J=6.92 Hz, 1H), 7.76 (t, J=7.6 Hz, 1H), 7.60-7.57 (m, 2H), 7.31 (s, 1H), 7.11 (d, J=7.28 Hz, 1H), 6.26-6.23 (m, 1H), 5.86-5.84 (m, 1H), 5.45-5.42 (m, 1H), 4.25-4.23 (m, 1H), 3.99-3.96 (m, 2H), 2.96-2.95 (m, 1H), 2.81-2.74 (m, 3H), 2.67-2.63 (m, 1H), 2.10-2.07 (m, 1H), 1.89-1.86 (m, 2H), 1.69-1.66 (m, 2H), 1.39 (s, 9H); LC MS: ES– 558.4.

Example 151. Synthesis of 3-[24-[[4-(1-oxa-8-azaspiro[4.5]decan-8-ylmethyl)phenyl]methyl]-28-oxo-31,34-diazatricyclododeca-,2(22),7(23),21(25),24(31)-pentaen-34-yl]piperidine-2,6-dione (Compound 267)

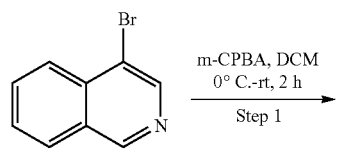

m-CPBA, DCM
0° C.-rt, 2 h
Step 1

1

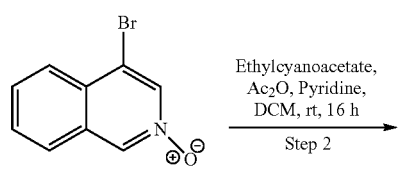

Ethylcyanoacetate,
Ac₂O, Pyridine,
DCM, rt, 16 h
Step 2

2

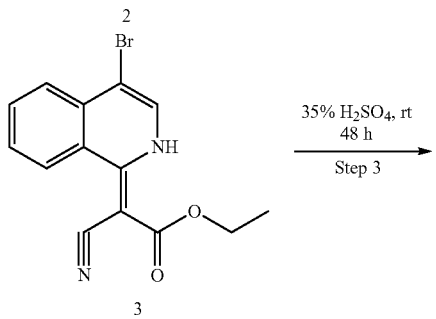

35% H₂SO₄, rt
48 h
Step 3

3

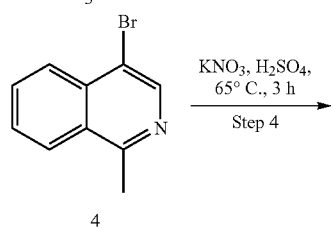

KNO₃, H₂SO₄,
65° C., 3 h
Step 4

4

-continued

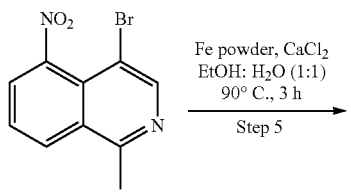

Fe powder, CaCl₂
EtOH: H₂O (1:1)
90° C., 3 h
Step 5

5

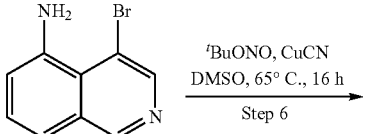

$^t$BuONO, CuCN
DMSO, 65° C., 16 h
Step 6

6

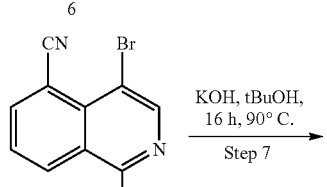

KOH, tBuOH,
16 h, 90° C.
Step 7

7

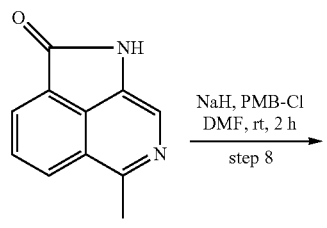

NaH, PMB-Cl
DMF, rt, 2 h
step 8

8

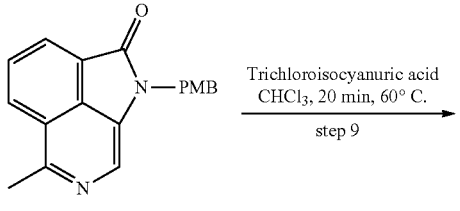

Trichloroisocyanuric acid
CHCl₃, 20 min, 60° C.
step 9

9

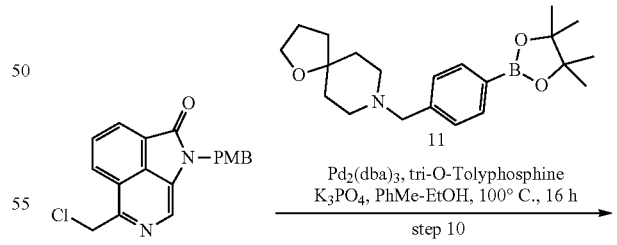

11

Pd₂(dba)₃, tri-O-Tolyphosphine
K₃PO₄, PhMe-EtOH, 100° C., 16 h
step 10

10

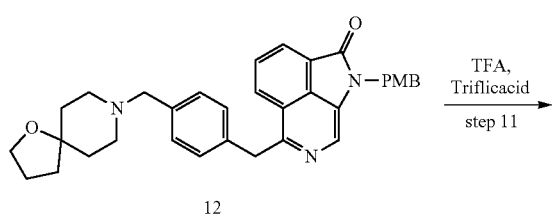

TFA,
Triflicacid
step 11

12

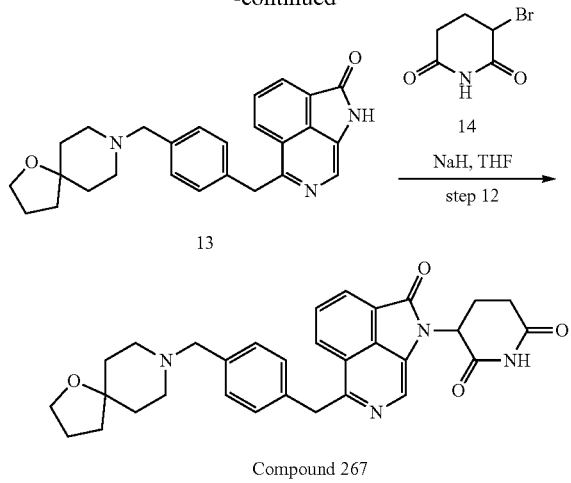

Compound 267

Step 1: Synthesis of 4-bromoisoquinoline 2-oxide (2): To a stirred solution of 4-bromoisoquinoline 1 (50 g, 240.32 mmol) in DCM (300 mL) at 0° C. portion wise 3-chlorobenzenecarboperoxoic acid (82.94 g, 480.64 mmol) was added. The combined reaction mixture was stirred 15 mins at 0° C. and then stirred for 2h at room temperature. After completion of the reaction 30% IPA DCM solution was added. 20 g Sodium Sulfite was added to quench excess MCPBA. Sodium Sulfite was filtered off through sintered flask and the filtrate (30% IPA DCM solution) was washed with saturated bicarbonate solution for 3 times followed by water. The organic layer was dried over sodium sulfate, filtered and concentrated under reduced pressure to afford 4-bromo-2-oxido-isoquinolin-2-ium 2 (46.5 g, 94.40 mmol, 78.44% yield, 90% purity) as off-white solid. LCMS: ES+ 224.31.

Step 2: Synthesis of ethyl (2Z)-2-(4-bromoisoquinolin-1 (2H)-ylidene)-2-cyanoacetate (3): To a stirred suspension of 4-bromo-2-oxido-isoquinolin-2-ium 2 (46 g, 205.31 mmol) in DCM (200 mL) ethyl 2-cyanoacetate (27.87 g, 246.37 mmol, 26.29 mL), Pyridine (19.49 g, 246.37 mmol, 19.93 mL) were added and the combined reaction mixture was cooled to 0° C. Acetic anhydride (25.15 g, 246.37 mmol, 23.29 mL) was added to the reaction mixture dropwise. The reaction mixture was stirred at 0-5° C. for 12 hours. It was then stirred at room temperature for 2 days. After completion of the reaction (monitored by LCMS), the reaction mixture was evaporated under reduced pressure, the solid was diluted with DCM, washed with water and brine solution. The organic fraction was separated, dried over anhydrous sodium sulphate, filtered and evaporated under reduced pressure to obtain the crude compound. The crude compound was purified by column chromatography using DCM to afford ethyl (2Z)-2-(4-bromo-2H-isoquinolin-1-ylidene)-2-cyano-acetate 3 (38 g, 113.11 mmol, 55.09% yield, 95% purity) as yellow solid. LC MS: ES+319.1.

Step 3: Synthesis of 4-bromo-1-methylisoquinoline (4): To ethyl (2Z)-2-(4-bromo-2H-isoquinolin-1-ylidene)-2-cyano-acetate 3 (38 g, 113.11 mmol), 35% H2SO4 solution (400 mL) was added and the combined reaction mixture was refluxed at 110° C. for 48-72 hours. After completion of the reaction (monitored by LCMS), the reaction mixture was poured into crushed ice and quenched with 20% NaOH solution, diluted with dichloromethane, washed with water, bicarbonate solution and brine. The organic fraction was separated, dried over anhydrous sodium sulphate and evaporated under reduced pressure to obtain 4-bromo-1-methyl-isoquinoline 4 (19 g, 84.70 mmol, 99% purity) as off-white solid. LC MS: ES+ 222.3.

Step 4: Synthesis of 4-bromo-1-methyl-5-nitroisoquinoline (5): To a stirred solution of 4-bromo-1-methyl-isoquinoline 4 (19 g, 85.55 mmol) in Sulfuric Acid (80 mL) portion wise Potassium nitrate, 99% (9.51 g, 94.11 mmol, 4.51 mL) was added. The combine reaction mixture was heated at 65° C. for 3 h. The reaction progression was monitored through TLC. After consumption of the starting material, the reaction mixture was poured in ice cold water and the acid solution was neutralized with potassium carbonate or 20% NaOH solution. After neutralization the aqueous layer was extracted with ethyl acetate thrice and the combined organic layer was dried over sodium sulfate and filtered. The organic layer was concentrated under reduced pressure and crude product was washed with pentane to remove nonpolar impurities. After washing, the product was dried under reduced pressure to afford 4-bromo-1-methyl-5-nitro-isoquinoline 5 (17 g, 63.02 mmol, 73.66% yield, 99% purity). LC MS: ES+ 266.9.

Step 5: Synthesis of 4-bromo-1-methylisoquinolin-5-amine (6): To a stirred solution of 4-bromo-1-methyl-5-nitro-isoquinoline 5 (17 g, 63.65 mmol) in Ethanol (50 mL) Water (50 mL), Iron powder (17.77 g, 318.26 mmol, 2.26 mL) and dichlorocalcium; dihydrate (14.04 g, 95.48 mmol) were added and the combined reaction mixture was heated at 90° C. for 3 h. The reaction progression was monitored through TLC. After completion of the reaction, the reaction mixture was passed through a whatmann filter paper to remove Fe powder and CaCl2. Ethyl acetate was added to the filtrate and the organic layer was washed with water and the organic layer was dried over sodium sulfate and filtered. The organic part was concentrated under reduced pressure. The crude product was washed with pentane to remove the non-polar impurities and dried under reduced pressure to afford 4-bromo-1-methyl-isoquinolin-5-amine 6 (14 g, 58.46 mmol, 91.84% yield, 99% purity). LC MS: ES+ 237.1.

Step 6: Synthesis of 4-bromo-1-methylisoquinoline-5-carbonitrile (7): To a stirred solution of cuprous; cyanide (5.29 g, 59.05 mmol) in tert-butyl nitrite (12.18 g, 118.09 mmol, 14.05 mL) a solution of 4-bromo-1-methyl-isoquinolin-5-amine 6 (14 g, 59.05 mmol) in DMSO (85 mL) was added drop wise. The combined reaction mixture was stirred for 16 h at 65° C. After completion of the reaction, the reaction mixture was filtered through a whatmann filter paper and the filtrate was washed with cold water and brine. The organic layer was dried over sodium sulfate and filtered. The organic layer was concentrated under reduced pressure and the crude product was purified through flash chromatography using 30% ethylacetate and hexane to afford 4-bromo-1-methyl-isoquinoline-5-carbonitrile 7 (2.5 g, 10.163 mmol, 17.21% yield, 98% purity). LC MS: ES+ 247.01.

Step 7: Synthesis of 5-methyl-11,12-diazatricyclododeca-1(3),2(6),4(8),5(11),7(9)-pentaen-10-one (8): A mixture of 4-bromo-1-methyl-isoquinoline-5-carbonitrile 7 (2.5 g, 10.12 mmol), Potassium hydroxide, flake, 85% (1.42 g, 25.29 mmol, 695.67 uL) and Tertiary Butanol (20 mL) was heated at 80° C. for 18 h in a oil bath. The progression of the reaction was monitored through TLC. After completion of the reaction, the reaction mixture was concentrated under reduced pressure. Ethyl acetate was added to the reaction mixture and the organic layer was washed with water. Organic part was dried over sodium sulfate, filtered and concentrated under reduced pressure. The crude product was purified through flash column chromatography using 3% methanol DCM as eluent to afford 5-methyl-11,12-diazatricyclododeca-1(3),2(6),4(8),5(11),7(9)-pentaen-10-one 8 (1 g, 5.32 mmol, 52.59% yield, 98% purity) as yellow solid. LC MS: ES+185.11.

Step 8: Synthesis of 1-(4-methoxybenzyl)-6-methylpyrrolo[2,3,4-de]isoquinolin-2(1H)-one (9): To a stirred solution of 5-methyl-11,12-diazatricyclododeca-1(3),2(6),4(8),5(11),7(9)-pentaen-10-one 8 (500 mg, 2.71 mmol) in DMF (4.0 mL) Sodium hydride (in oil dispersion) 60/a dispersion in mineral oil (156.02 mg, 4.07 mmol, 60% purity) was added at 0° C. The reaction mixture was stirred for 30 mins at the same temperature. 1-(chloromethyl)-4-methoxy-benzene (510.15 mg, 3.26 mmol, 425.12 uL) was added to the reaction mixture and the combined reaction mixture was stirred for 30 min at room temperature. The reaction progression was monitored through TLC. After consumption of the starting material, ethylacetate was added to the reaction mixture. The organic layer was washed with cold water followed by brine solution to remove DMF. The organic layer was dried over sodium sulfate, filtered and concentrated under reduced pressure. The crude product was purified by combi-flash to afford 20-[(4-methoxyphenyl)methyl]-11-methyl-19,20-diazatricyclododeca-2(4),3(14),9(16),11(19),15(17)-pentaen-18-one 9 (515 mg, 1.64 mmol, 60.47% yield, 97% purity) as yellowish solid. LC MS: ES+ 305.3.

Step 9: Synthesis of 6-(chloromethyl)-1-(4-methoxybenzyl)pyrrolo[2,3,4-de]isoquinolin-2(1H)-one (10): To 20-[(4-methoxyphenyl)methyl]-11-methyl-19,20-diazatricyclododeca-2,4(15),9(16),11(19),14(17)-pentaen-18-one 9 (200 mg, 657.16 umol) in Chloroform (15.0 mL) at reflux was added 1,3,5-trichloro-1,3,5-triazinane-2,4,6-trione (122.18 mg, 525.72 umol, 59.03 uL) in portions, and the mixture was heated at reflux 15 mins. After cooling, the mixture was filtered, and the filtrate was diluted with chloroform, washed with brine, dried(MgSO4), and evaporated to get the crude which was purified by prep TLC (as 5% Ethylacetate/Hexane eluent) to give 16-(chloromethyl)-20-[(4-methoxyphenyl)methyl]-19,20-diazatricyclododeca-1,3(14),8(15),13(17),16(19)-pentaen-18-one 10 (190 mg, 476.70 umol, 72.54% yield, 85% purity); LC MS: ES+ 339.3.

Step 10: Synthesis of 6-(4-((1-oxa-8-azaspiro[4.5]decan-8-yl)methyl)benzyl)-1-(4 methoxybenzyl)pyrrolo [2,3,4-de]isoquinolin-2(1H)-one (12): To a well degassed solution of 16-(chloromethyl)-20-[(4-methoxyphenyl)methyl]-19,20-diazatricyclododeca-1,3(14),8(15),13(17),16(19)-pentaen-18-one 10 (190 mg, 560.82 umol) and 8-[[4-(4,4,5,5-tetramethyl-1,3,2-dioxaborolan-2-yl)phenyl]methyl]-1-oxa-8-azaspiro[4.5]decane 11(240.45 mg, 672.99 umol) inethanol (2.0 mL)-Toluene (4.0 mL), Potassium phosphate tribasic anhydrous (238.09 mg, 1.12 mmol) was added followed by the addition Tri-o-Tolyl phosphine (27.31 mg, 89.73 umol) and (1E,4E)-1,5-diphenylpenta-1,4-dien-3-one; palladium (41.08 mg, 44.87 umol). The resulting mixture was then heated at 90° C. for 12 hours. After completion of reaction (as monitored by LCMS), the reaction mixture was filtered through a bed of celite, washed with Ethyl acetate (100 mL). The combined filtrate was washed with water (3×20 mL) and brine (2×15 mL), dried over anhydrous sodium sulfate and concentrated under reduced pressure. Crude mass was purified by column chromatography (silica, gradient: 0-5% MeOH in DCM) to obtain 36-[(4-methoxyphenyl)methyl]-30-[[4-(1-oxa-8-azaspiro[4.5]decan-8-ylmethyl)phenyl]methyl]-34,36-diazatricyclododeca-1,3(28),12(29),27(31),30(34)-pentaen-32-one 12 (40 mg, 67.46 umol, 12.03% yield, 90% purity) as yellow solid and stored in a round bottom glass at rt. LC MS: ES+ 534.5.

Step 10 a: Synthesis of 8-(4-(4,4,5,5-tetramethyl-1,3,2-dioxaborolan-2-yl)benzyl)-1-oxa-8-azaspiro[4.5]decane (11): To a stirred solution of 1-oxa-8-azaspiro[4.5]decane (1.0 g, 7.08 mmol) in ACN (15 mL), N-ethyl-N-isopropyl-propan-2-amine (1.10 g, 8.50 mmol, 1.48 mL) was added. After 10 min 2-[4-(bromomethyl)phenyl]-4,4,5,5-tetramethyl-1,3,2-dioxaborolane (2.52 g, 8.50 mmol) was added to the solution and stirred for 4 hours at room temperature. Saturated NaHCO3 solution was added and the organic part was extracted with ethyl acetate followed by brine washing. Organic solution was dried over Na2SO4,concentrated under vacuum to get a residue which was purified by column chromatography using 5% MeOH in DCM to afford 8-[[4-(4,4,5,5-tetramethyl-1,3,2-dioxaborolan-2-yl)phenyl] methyl]-1-oxa-8-azaspiro[4.5]decane 11 (0.67 g, 1.69 mmol, 23.83% yield, 90% purity).

Step 11: Synthesis of 6-(4-((1-oxa-8-azaspiro[4.5]decan-8-yl)methyl)benzyl)pyrrolo[2,3,4-de]isoquinolin-2(1H)-one (13): 36-[(4-methoxyphenyl)methyl]-30-[[4-(1-oxa-8-azaspiro[4.5]decan-8-ylmethyl)phenyl]methyl]-34,36-diazatricyclododeca-1,3(28),12(29),27(31),30(34)-pentaen-32-one 12 (50 mg, 93.69 umol) in TFA (3.0 mL), Triflic acid (211.31 mg, 1.41 mmol, 123.57 uL) dropwise. The reaction mixture was stirred at 25° C. for 16 hours. After completion of reaction, volatiles were evaporated and quenched with saturated sodium bicarbonate solution. Aqueous part was extracted with ethyl acetate (40 mL), washed with water followed by brine. The organic part was dried over sodium sulphate and concentrated to afford crude 22-[[4-(1-oxa-8-azaspiro[4.5]decan-8-ylmethyl)phenyl]methyl]-26,27-diazatricyclododeca-,2(20),7(21),19(23),22(26)-pentaen-24-one 13 (30 mg, 72.55 umol, 77.43% yield) as brown solid. Crude was carried forward in the next step. LC MS: ES+ 414.5.

Step 12: Synthesis of 3-[24-[[4-(1-oxa-8-azaspiro[4.5]decan-8-ylmethyl)phenyl]methyl]-28-oxo-31,34-diazatricyclododeca-,2(22),7(23),21(25),24(31)-pentaen-34-yl]piperidine-2,6-dione: To a cooled solution of 22-[[4-(1-oxa-8-azaspiro[4.5]decan-8-ylmethyl)phenyl]methyl]-26,27-diazatricyclododeca-,2(20),7(21),19(23),22(26)-pentaen-24-one 13 (30.00 mg, 72.55 umol) in dry THF (250 mL), Sodium hydride (in oil dispersion) 60% dispersion in mineral oil (27.80 mg, 725.50 umol, 60% purity) was added portion wise, maintaining the temp <5° C. Once the addition is over, the resultant mixture was stirred for 15 minutes at RT. Then the reaction mixture was again cooled to 0° C. and 3-bromopiperidine-2,6-dione 14 (69.65 mg, 362.75 umol) was added to it portion wise. After complete addition, resulting solution was heated at 70° C. 1 hour. After completion (evidenced from TLC), the reaction mixture was cooled to 0° C. and quenched with the addition of ice cooled water. Aqueous part was extracted with ethyl acetate (3×50 mL). Combined organics was separated, dried over sodium sulfate and concentrated under reduced pressure. Crude mass was purified by flash chromatography (silica, gradient: 0%-2.5% MeOH in DCM) to afford 3-[24-[[4-(1-oxa-8-azaspiro[4.5]decan-8-ylmethyl)phenyl]methyl]-28-oxo-31,34-diazatricyclododeca-,2(22),7(23),21(25),24(31)-pentaen-34-yl]piperidine-2,6-dione Compound 267 (10 mg, 17.87 umol, 24.63% yield, 93.75% purity) as yellow solid. $^1$H NMR (400 MHz, DMSO-d6) δ 11.14 (s, 1H), 8.56 (d, J=8.2 Hz, 1H), 8.31 (d, J=7.0 Hz, 1H), 8.21 (s, 1H), 7.94 (t, J=7.56 Hz, 1H), 7.29-7.27 (m, 2H), 7.18-7.17 (m, 2H), 5.48-5.46 (m, 1H), 4.56 (s, 2H), 3.65 (t, J=6.68 Hz, 2H), 3.35-3.31 (m, 2H), 2.98-2.92 (m, 1H), 2.82-2.78 (m, 1H), 2.67-2.63 (m, 1H), 2.36-2.27 (m, 4H), 2.13-2.10 (m, 1H), 1.82-1.78 (m, 2H), 1.60-1.56 (m, 2H), 1.50-1.45 (m, 4H); LC MS: ES+ 525.2.

749

Example 152. Synthesis of 3-[6-[[6-(1-oxa-8-azaspiro[4.5]decan-8-ylmethyl)-3-pyridyl]methyl]-2-oxo-benzo[cd]indol-1-yl]piperidine-2,6-dione (Compound 268)

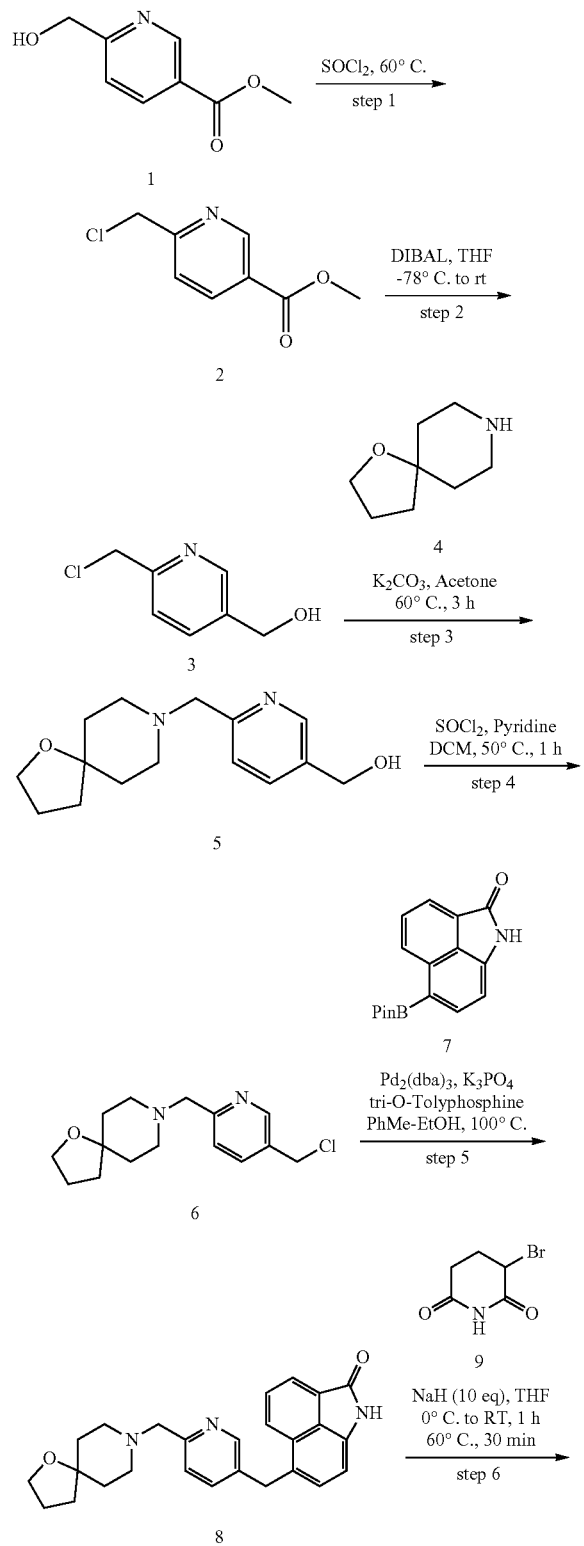

750

-continued

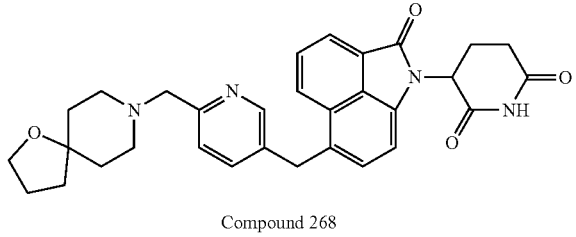

Compound 268

Step 1: Synthesis of methyl 6-(chloromethyl)pyridine-3-carboxylate (2): methyl 6-(hydroxymethyl)pyridine-3-carboxylate (1) (2.0 g, 11.96 mmol) was added portion wise to thionyl chloride (28.47 g, 239.29 mmol, 17.36 mL) in ice cold condition and stirred the reaction mixture for 30 min at rt. After completion of reaction, the reaction mixture was evaporated and quenched with sodium bicarbonate solution. Aqueous part was extracted with ethyl acetate (50 mL). The organic layer was washed with water followed by brine, dried over sodium sulphate and concentrated under reduced pressure. The crude material was purified by column chromatography by 20% ethyl acetate in hexane to afford the desired compound methyl 6-(chloromethyl)pyridine-3-carboxylate (2) (1.15 g, 5.74 mmol, 47.95% yield, 93% purity) as yellowish solid. LC MS: ES+186.16.

Step 2: Synthesis of [6-(chloromethyl)-3-pyridyl]methanol (3): To the stirred solution of -(chloromethyl)pyridine-3-carboxylate (2) (1.15 g, 6.20 mmol) in THF (20.0 mL), Diisobutylaluminum hydride (14.10 g, 24.78 mmol, 20.11 mL) was added drop wise at −78° C. and stirred for 30 minutes at rt under N2 atmosphere. After complete consumption, as evidenced from TLC, reaction mass was diluted with ethyl acetate (50 mL) and quenched 20% Sodium potassium tertrate solution. Organic phase was separated, dried over anhydrous $Na_2SO_4$ and concentrated under reduced pressure to afford [6-(chloromethyl)-3-pyridyl]methanol (3) (938 mg, 5.65 mmol, 91.26% yield, 95% purity) as reddish gummy solid which was carried forward to the next step without any further purification. LC MS: ES+ 157.9.

Step 3: Synthesis of [6-(1-oxa-8-azaspiro[4.5]decan-8-ylmethyl)-3-pyridyl]methanol (5): To a stirred solution 1-oxa-8-azaspiro[4.5]decane; hydrochloride (4) (550 mg, 3.10 mmol) in dry grade acetone (10 mL) was added Potassium carbonate, anhydrous, 99% (1.28 g, 9.29 mmol) at RT and the resultant reaction mixture was heated at 50° C. for 20 minutes. [6-(chloromethyl)-3-pyridyl]methanol (3) (975.72 mg, 6.19 mmol, 69.39 mL) was then added to the reaction mixture and heating was continued for 4 hours. After completion of reaction (monitored by TLC and LCMS), volatiles were removed under vacuum and the solid thus obtained was taken in Ethyl acetate (50 mL), washed with water (20 mL) and Brine, dried over anhydrous sodium sulfate and concentrated under reduced pressure. Crude mass was purified by column chromatography (silica, gradient: 1-5% MeOH in DCM) to afford [6-(1-oxa-8-azaspiro[4.5]decan-8-ylmethyl)-3-pyridyl]methanol (5) (600 mg, 2.06 mmol, 66.49% yield, 90% purity) as colorless sticky solid. LC MS: ES+ 263.5.

Step 4: Synthesis of 8-[[5-(chloromethyl)-2-pyridyl]methyl]-1-oxa-8-azaspiro[4.5]decane(6): To the stirred solution of [6-(1-oxa-8-azaspiro[4.5]decan-8-ylmethyl)-3-pyridyl]methanol (5) (600 mg, 2.29 mmol) in DCM (5.0 mL), thionyl chloride (544.18 mg, 4.57 mmol, 331.82 uL) was added drop wise at 0° C. and stirred for 30 minutes at rt. After completion of reaction, monitored by TLC, volatiles were removed under reduced pressure. Solid mass was redissolved in ethylacetate (30 mL) and quenched with saturated sodium bicarbonate solution. Organic phase was separated, dried over anhydrous sodium sulfate and concentrated to afford crude 8-[[5-(chloromethyl)-2-pyridyl]methyl]-1-oxa-8-azaspiro[4.5]decane (6) (550 mg, 1.86 mmol, 81.36% yield, 95% purity) as brown sticky solid which directly used in the next step without any purification. LC MS: ES+ 281.1.

Step 5: Synthesis of 6-[[6-(1-oxa-8-azaspiro[4.5]decan-8-ylmethyl)-3-pyridyl]methyl]-1H-benzo[cd]indol-2-one (8): To a well degassed solution of 8-[[5-(chloromethyl)-2-pyridyl]methyl]-1-oxa-8-azaspiro[4.5]decane (6) (450 mg, 1.60 mmol) and 6-(4,4,5,5-tetramethyl-1,3,2-dioxaborolan-2-yl)-1H-benzo[cd]indol-2-one (7) (945.99 mg, 3.21 mmol) in ethanol (2.0 mL)-Toluene (4.0 mL), Potassium phosphate tribasic anhydrous (1.02 g, 4.81 mmol) was added followed by the addition Tri-o-Tolyl phosphine (97.56 mg, 320.52 umol) and (1E,4E)-1,5-diphenylpenta-1,4-dien-3-one; palladium (146.75 mg, 160.26 umol). The resulting mixture was then heated at 90° C. for 12 hours. After completion of reaction (as monitored by LCMS), the reaction mixture was filtered through a bed of celite, washed with Ethyl acetate (100 mL). The combined filtrate was washed with water (3×20 mL) and brine (2×15 mL), dried over anhydrous sodium sulfate and concentrated under reduced pressure. Crude mass was purified by column chromatography (silica, gradient: 0-5% MeOH in DCM) to obtain 6-[[6-(1-oxa-8-azaspiro[4.5]decan-8-ylmethyl)-3-pyridyl]methyl]-1H-benzo[cd]indol-2-one (8) (90 mg, 180.65 umol, 11.27% yield, 83% purity) as yellow solid and stored in a round bottom glass at rt. LC MS: ES+ 414.3.

Step 6: Synthesis of 3-[6-[[6-(1-oxa-8-azaspiro[4.5]decan-8-ylmethyl)-3-pyridyl]methyl]-2-oxo-benzo[cd]indol-1-yl]piperidine-2,6-dione: To a cooled solution of 6-[[6-(1-oxa-8-azaspiro[4.5]decan-8-ylmethyl)-3-pyridyl]methyl]-1H-benzo[cd]indol-2-one (8) (86.00 mg, 207.98 umol) in dry THF (5.0 mL), Sodium hydride (in oil dispersion) 60% dispersion in mineral oil (79.69 mg, 2.08 mmol, 60% purity) was added portion wise, maintaining the temp <5° C. Once the addition is over, the resultant mixture was stirred for 15 minutes at RT. Then the reaction mixture was again cooled to 0° C. and 3-bromopiperidine-2,6-dione (9) (199.67 mg, 1.04 mmol) was added to it portion wise. After complete addition, resulting solution was heated at 70° C. 1 hour. After completion (evidenced from TLC), the reaction mixture was cooled to 0° C. and quenched with the addition of ice cooled water. Aqueous part was extracted with ethyl acetate (3×50 mL). Combined organics was separated, dried over sodium sulfate and concentrated under reduced pressure. Crude mass was purified by flash chromatography (silica, gradient: 0 TO 2.5% MeOH in DCM) to afford Racemic 3-[6-[[6-(1-oxa-8-azaspiro[4.5]decan-8-ylmethyl)-3-pyridyl]methyl]-2-oxo-benzo[cd]indol-1-yl]piperidine-2,6-dione Compound 268 (33 mg, 62.03 umol, 29.83% yield, 98.61% purity) as yellow solid. $^1$H NMR (400 MHz, DMSO-d6) δ 11.12 (s, 1H), 8.52 (br s, 1H), 8.37 (d, J=8.24 Hz, 1H), 8.08 (d, J=6.96 Hz, 1H), 7.82 (t, J=7.64 Hz, 1H), 7.60-7.58 (m, 1H), 7.43 (d, J=7.32 Hz, 1H), 7.30 (d, J=7.96 Hz, 1H), 7.11 (d, J=7.32 Hz, 1H), 5.44 (dd, J=12.8, 5.08 Hz, 1H), 4.40 (s, 2H), 3.66 (t, J=6.68 Hz, 2H), 3.49 (br s, 2H), 2.95-2.93 (m, 1H), 2.77-2.73 (m, 1H), 2.66-2.62 (m, 1H), 2.42-2.41 (m, 2H), 2.32 (br m, 2H), 2.10-2.07 (m, 1H), 1.82-1.77 (m, 2H), 1.61-1.57 (m, 2H), 1.50 (br s, 4H); LC MS: ES+ 525.68.

Example 153. Synthesis of 3-[6-[[6-(morpholinomethyl)-3-pyridyl]methyl]-2-oxo-benzo[cd]indol-1-yl]piperidine-2,6-dione (Compound 269)

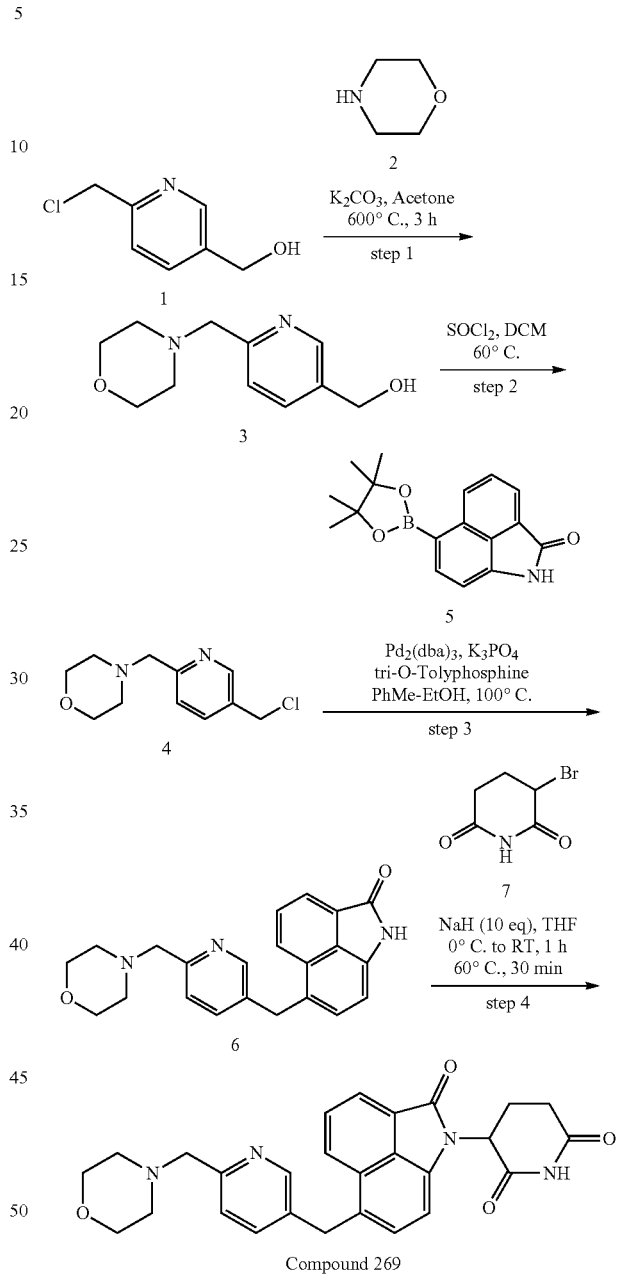

Compound 269

Step 1: Synthesis of [6-(1-oxa-8-azaspiro[4.5]decan-8-ylmethyl)-3-pyridyl]methanol (5): To a stirred solution of morpholine (2) (650 mg, 7.46 mmol, 652.61 uL) in dry grade acetone (10.0 mL) was added potassium carbonate (1.55 g, 11.19 mmol, 675.45 uL) at RT and the resultant reaction mixture was heated at 60° C. for 60 minutes. [6-(chloromethyl)-3-pyridyl]methanol (1) (587.91 mg, 3.73 mmol, 70.75 mL) was then added to the reaction mixture and heating was continued for 16 hours. After completion of reaction (monitored by TLC and LCMS), volatiles were removed under vacuum and the solid thus obtained was taken in Ethyl acetate (70 mL), washed with water (×3) and Brine, dried over anhydrous sodium sulfate and concentrated under reduced pressure. Crude mass was purified by column chromatography (silica, gradient: 10-30% Ethyl acetate in Hexane) to afford [6-(morpholinomethyl)-3-pyridyl]methanol (3) (550 mg, 2.51 mmol, 67.25% yield, 95% purity) as light yellowish solid. LC MS: ES+ 209.46.

Step 2: Synthesis of 4-[[5-(chloromethyl)-2-pyridyl]methyl]morpholine (6): To a stirred solution of [6-(morpholinomethyl)-3-pyridyl]methanol (3) (276 mg, 1.33 mmol) in DCM (5.0 mL) was cooled to 0° C. then net thionyl chloride (315.34 mg, 2.65 mmol, 192.28 uL) was added dropwise to the reaction mix and stirred the reaction mix at rt for 1 hr. Check TLC shows complete consumption of SM, then the reaction mix was evaporated under reduced pressure to remove excess thionyl chloride. After that the reaction mix was quenched with Saturated sodium carbonate solution and extracted with Ethylacetate (3×25 mL). The organic portion was washed with brine solution., dried over $Na_2SO_4$ and evaporated under rotavapour to get the crude compound 4-[[5-(chloromethyl)-2-pyridyl]methyl]morpholine (4) (288 mg, 1.26 mmol, 94.90% yield, 99% purity) as brown gum. LC MS: ES+ 227.1.

Step 3: Synthesis of 6-[[6-(morpholinomethyl)-3-pyridyl]methyl]-1H-benzo[cd]indol-2-one (8): To a well degassed solution of 4-[[5-(chloromethyl)-2-pyridyl]methyl]morpholine (4) (288 mg, 1.27 mmol) and 6-(4,4,5,5-tetramethyl-1,3,2-dioxaborolan-2-yl)-1H-benzo[cd]indol-2-one (5) (749.89 mg, 2.54 mmol) inethanol (2.0 mL)-Toluene (4.0 mL), Potassium phosphate tribasic anhydrous (809.00 mg, 3.81 mmol) was added followed by the addition Tri-o-Tolyl phosphine (77.33 mg, 254.08 umol) and (1E,4E)-1,5-diphenylpenta-1,4-dien-3-one; palladium (116.33 mg, 127.04 umol). The resulting mixture was then heated at 90° C. for 12 hours. After completion of reaction (as monitored by LCMS), the reaction mixture was filtered through a bed of celite, washed with Ethyl acetate (100 mL). The combined filtrate was washed with water (3×20 mL) and brine (2×15 mL), dried over anhydrous sodium sulfate and concentrated under reduced pressure. Crude mass was purified by column chromatography (silica, gradient: 0-5% MeOH in DCM) to obtain 6-[[6-(morpholinomethyl)-3-pyridyl]methyl]-1H-benzo[cd]indol-2-one (6) (65 mg, 126.59 umol, 9.96% yield, 70% purity) as yellow solid and stored in a round bottom glass at rt. LC MS: ES+ 360.4.

Step 4: Synthesis of afford 3-[6-[[6-(morpholinomethyl)-3-pyridyl]methyl]-2-oxo-benzo[cd]indol-1-yl]piperidine-2,6-dione: To a cooled solution of 6-[[6-(morpholinomethyl)-3-pyridyl]methyl]-1H-benzo[cd]indol-2-one (6) (50.00 mg, 139.11 umol) in dry THF (5.0 mL), Sodium hydride (in oil dispersion) 60% dispersion in mineral oil (53.30 mg, 1.39 mmol, 60% purity) was added portion wise, maintaining the temp <5° C. Once the addition is over, the resultant mixture was stirred for 15 minutes at RT. Then the reaction mixture was again cooled to 0° C. and 3-bromopiperidine-2,6-dione (7) (133.56 mg, 695.56 umol) was added to it portion wise. After complete addition, resulting solution was heated at 70° C. 1 hour. After completion (evidenced from TLC), the reaction mixture was cooled to 0° C. and quenched with the addition of ice cooled water. Aqueous part was extracted with ethyl acetate (3×50 mL). Combined organics was separated, dried over sodium sulfate and concentrated under reduced pressure. Crude mass was purified by flash chromatography (silica, gradient: 0%-2.5% MeOH in DCM) to afford 3-[6-[[6-(morpholinomethyl)-3-pyridyl]methyl]-2-oxo-benzo[cd]indol-1-yl]piperidine-2,6-dione Compound 269 (15.0 mg, 29.24 umol, 21.02% yield, 91.72% purity) as yellow solid. $^1$H NMR (400 MHz, DMSO-d6) δ 11.11 (s, 1H), 8.53 (s, 1H), 8.37 (d, J=8.28 Hz, 1H), 8.08 (d, J=6.96 Hz, 1H), 7.82 (t, J=7.64 Hz, 1H), 7.61-7.59 (m, 1H), 7.42 (d, J=7.44 Hz, 1H), 7.31 (d, J=8.0 Hz, 1H), 7.11 (d, J=7.28 Hz, 1H), 5.44 (dd, J=12.76, 5.24 Hz, 1H), 4.40 (s, 2H), 3.54-3.50 (m, 6H), 2.95-2.94 (m, 1H), 2.77-2.73 (m, 1H), 2.66-2.62 (m, 1H), 2.34 (br s, 4H), 2.10-2.07 (m, 1H); LC MS: ES+ 471.58.

Example 154. Synthesis of 3-[6-[[4-[1-(1-methylcyclobutanecarbonyl)-4-piperidyl]pyrazol-1-yl]methyl]-2-oxo-benzo[cd]indol-1-yl]piperidine-2,6-dione (Compound 270)

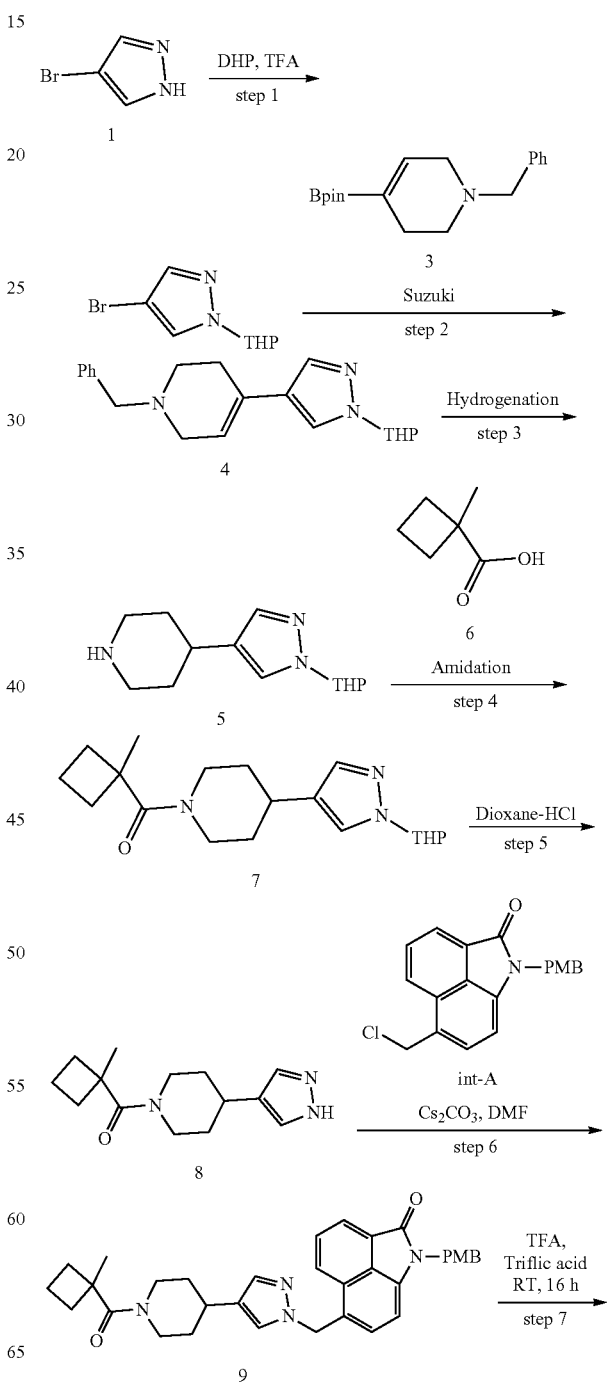

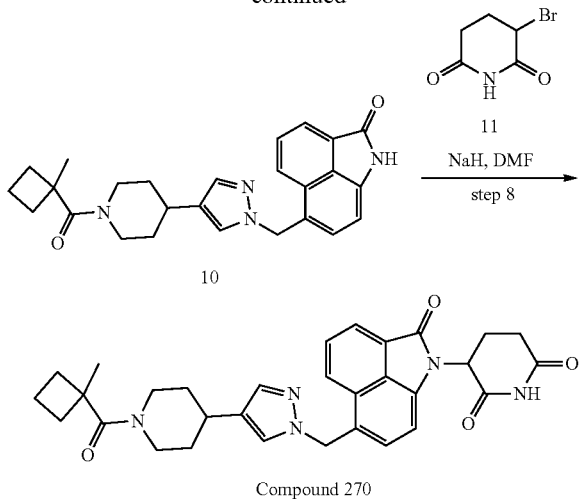

Step-1: Synthesis of 4-bromo-1-tetrahydropyran-2-yl-pyrazole: To a stirred solution of 4-bromo-1H-pyrazole (1) (10 g, 68.04 mmol) in 3,4-dihydro-2H-pyran (8.58 g, 102.06 mmol, 9.27 mL), Trifluoroacetic acid (387.90 mg, 3.40 mmol, 262.10 uL) was added drop wise under cooling condition and the resultant reaction mixture was at 80° C. for 16 h. After completion of the reaction (monitored by TLC) the reaction mixture was diluted with DCM and washed with 1(M) NaOH solution. The organic part was then dried over $Na_2SO_4$ and concentrated under reduced pressure. The crude thus obtained was purified by combi-flash column (Gradient: 0-10% EtOAc in Hexane) to afford 4-bromo-1-tetrahydro-pyran-2-yl-pyrazole (2) (14 g, 88.15% yield) as yellow gum; LC MS: ES+ 231.1.

Step-2: Synthesis of 1-benzyl-4-(1-tetrahydropyran-2-yl-pyrazol-4-yl)-3,6-dihydro-2H-pyridine: To a stirred solution of 4-bromo-1-tetrahydropyran-2-yl-pyrazole (2) (700 mg, 3.03 mmol) in Water (4.0 mL) and DMF (16.0 mL) were added Sodium carbonate (642.11 mg, 6.06 mmol), 1-benzyl-4-(4,4,5,5-tetramethyl-1,3,2-dioxaborolan-2-yl)-3,6-dihydro-2H-pyridine (3) (1.09 g, 3.63 mmol) and the resultant reaction mixture was degassed with Argon for 15 min. Then cyclopentyl(diphenyl)phosphane; dichloromethane; dichloropalladium; iron (247.37 mg, 302.91 umol) was added and stirred the reaction mixture was stirred at 100° C. for 16h in a sealed tube. After completion of the reaction (monitored by TLC) the reaction mixture was diluted with EtOAc and washed with water, brine, dried over $Na_2SO_4$ and concentrated under reduced pressure. The crude thus obtained was purified by combi-flash column (Gradient: 0-20% EtOAc in Hexane) to afford 1-benzyl-4-(1-tetrahydropyran-2-ylpyra-zol-4-yl)-3,6-dihydro-2H-pyridine (4) (230 mg, 22.07% yield) as colourless gum; LC MS: ES+ 324.4.

Step-3: Synthesis of 4-(1-tetrahydropyran-2-ylpyrazol-4-yl)piperidine: To a stirred solution of 1-benzyl-4-(1-tetrahydropyran-2-ylpyrazol-4-yl)-3,6-dihydro-2H-pyridine (4) (230 mg, 711.13 umol) in Ethylacetate (5.0 mL) and Ethanol (5.0 mL) Argon gas was purged for 10 mins. Then Palladium on carbon (20% w/w, 151.36 mg, 1.42 mmol) was added and the reaction mixture was stirred under Hydrogen atmosphere (Balloon) for 16 h. After completion of the reaction (monitored by TLC) the reaction mixture was filtered through celite pad and washed with 10/a MeOH in DCM. The collected filtrate was concentrated under reduced pressure to afford 4-(1-tetrahydropyran-2-ylpyrazol-4-yl)piperidine (5) (150 mg, 76.19% yield) as light yellow gum.

Step-4: Synthesis of (1-methylcyclobutyl)-[4-(1-tetrahydropyran-2-ylpyrazol-4-yl)-1-piperidyl] methanone: To a stirred solution of 1-methylcyclobutanecarboxylic acid (6) (194.26 mg, 1.70 mmol) in DMF (2.0 mL) was added N-ethyl-N-isopropyl-propan-2-amine (439.91 mg, 3.40 mmol, 592.87 uL) and the resultant reaction mixture was stirred at RT for 5 mins, then HATU (647.12 mg, 1.70 mmol) was added and the reaction was stirred for another 5 mins. After that a solution of 4-(1-tetrahydropyran-2-ylpyrazol-4-yl)piperidine (5) (267 mg, 1.13 mmol) in DMF (2.0 mL) was added and the reaction mixture was stirred at RT for 16 h. After completion of the reaction (monitored by TLC) the reaction mixture was diluted with EtOAc and washed with cold $NaHCO_3$, dried over $Na_2SO_4$ and concentrated under reduced pressure. The crude thus obtained was purified by combi-flash column (Gradient: 0-30% EtOAc in Hexane) to afford (1-methylcyclobutyl)-[4-(1-tetrahydropyran-2-ylpyrazol-4-yl)-1-piperidyl]methanone (7) (100 mg, 26.06% yield) as yellow sticky solid; LC MS: ES+ 332.4.

Step-5: Synthesis of (1-methylcyclobutyl)-[4-(1H-pyrazol-4-yl)-1-piperidyl]methanone; hydrochloride: To a stirred solution of (1-methylcyclobutyl)-[4-(1-tetrahydropyran-2-ylpyrazol-4-yl)-1-piperidyl]methanone (7) (100 mg, 301.70 umol) in dioxane (2 ml) was added Hydrogen chloride solution 4.0 M in dioxane (5 mL) and the resultant reaction mixture was stirred at RT for 16 h. After completion of the reaction (monitored by TLC) the reaction mixture was concentrated to dryness and triturated with ether to afford (1-methylcyclobutyl)-[4-(1H-pyrazol-4-yl)-1-piperidyl]methanone; hydrochloride (8) (90 mg, 74.52% yield) as yellow solid.

Step-6: Synthesis of 1-[(4-methoxyphenyl)methyl]-6-[[4-[1-(1-methylcyclobutanecarbonyl)-4-piperidyl]pyrazol-1-yl]methyl]benzo[cd]indol-2-one: To a stirred solution of(1-methylcyclobutyl)-[4-(1H-pyrazol-4-yl)-1-piperidyl]methanone (8) (200.00 mg, 808.62 umol) and 6-(chloromethyl)-1-[(4-methoxyphenyl)methyl]benzo[cd]indol-2-one (int-A) (273.15 mg, 808.62 umol) in DMF (2 mL) was added Cesium carbonate (526.93 mg, 1.62 mmol) and the reaction mixture was heated at 90° C. for 16 h. After completion of the reaction (monitored by TLC) the reaction mixture was diluted with EtOAc and washed with water and brine, dried over sodium sulphate and concentrated. The crude thus obtained was purified by Combiflash column (Gradient: 0-2% MeOH in DCM) to afford 1-[(4-methoxyphenyl)methyl]-6-[[4-[1-(1-methylcyclobutanecarbonyl)-4-piperidyl]pyrazol-1-yl]methyl]benzo[cd]indol-2-one (9) (300 mg, 60.86% yield) as light yellow solid. LC MS: ES+ 549.7.

Step-7: Synthesis of 6-[[4-[1-(1-methylcyclobutanecarbonyl)-4-piperidyl]pyrazol-1-yl]methyl]-1H-benzo[cd]indol-2-one: To a stirred solution of compound 1-[(4-methoxyphenyl)methyl]-6-[[4-[1-(1-methylcyclobutanecarbonyl)-4-piperidyl]pyrazol-1-yl]methyl]benzo[cd]indol-2-one (9) (500.00 mg, 911.29 umol) in TFA (4 mL) was added trifluoromethanesulfonic acid (683.83 mg, 4.56 mmol, 399.90 uL) under cooling condition and the resultant reaction mixture was stirred at room temperature for 16 h. After completion of the reaction (monitored by TLC) the reaction mixture was quenched with saturated bicarbonate solution and extracted with ethyl acetate. The organic layer was then dried over sodium sulphate and concentrated under reduced pressure. The crude thus obtained was purified by combi-flash chromatography (Gradient: 0-3% MeOH in DCM) to afford 6-[[4-[1-(1-methylcyclobutanecarbonyl)-4-piperidyl]

pyrazol-1-yl]methyl]-1H-benzo[cd]indol-2-one (10) (350 mg, 80.66% yield) as light yellow solid; LC MS: ES+ 429.4.

Step-8: Synthesis of 3-[6-[[4-[1-(1-methylcyclobutanecarbonyl)-4-piperidyl]pyrazol-1-yl]methyl]-2-oxo-benzo[cd]indol-1-yl]piperidine-2,6-dione: To a stirred solution of compound 6-[[4-[1-(1-methylcyclobutanecarbonyl)-4-piperidyl]pyrazol-1-yl]methyl]-1H-benzo[cd]indol-2-one (10) (175 mg, 408.38 umol) in DMF (3 mL) was added Sodium hydride (in oil dispersion) 60% dispersion in mineral oil (23.47 mg, 1.02 mmol) under cooling condition and then the reaction mixture was stirred at 70° C. for 1 hour. Then 3-bromopiperidine-2,6-dione (11) (78.41 mg, 408.38 umol) was added and stirred at 70° C. for another 2 hr. Again 3-bromopiperidine-2,6-dione (11) (78.41 mg, 408.38 umol) was added and the reaction was continued at 70° C. for 16 h. After completion of the reaction (monitored by TLC) the reaction mixture was quenched with ice water and extracted with EtOAc. The organic part was then dried over sodium sulphate and concentrated. The crude thus obtained was purified by Prep TLC Plate (5% MeOH in DCM) to afford 3-[6-[[4-[1-(1-methylcyclobutanecarbonyl)-4-piperidyl]pyrazol-1-yl]methyl]-2-oxo-benzo[cd]indol-1-yl]piperidine-2,6-dione Compound 270 (20 mg, 8.17% yield) as yellow solid. ¹H NMR (400 MHz, DMSO-d6) δ 11.12 (s, 1H), 8.43 (d, J=8.32 Hz, 1H), 8.10 (d, J=6.96 Hz, 1H), 7.85 (t, J=7.64 Hz, 1H), 7.67 (s, 1H), 7.45 (d, J=7.52 Hz, 1H), 7.32 (s, 1H), 7.12 (d, J=7.4 Hz, 1H), 5.67 (s, 2H), 5.47-5.42 (m, 1H), 4.35-4.31 (m, 1H), 3.52-3.48 (m, 1H), 2.99-2.90 (m, 2H), 2.76-2.72 (m, 1H), 2.66-2.63 (m, 2H), 2.41-2.34 (m, 2H), 2.09-2.07 (m, 1H), 1.92-1.82 (m, 1H), 1.82-1.76 (m, 5H), 1.60-1.57 (m, 1H), 1.40-1.42 (m, 5H); LC MS: ES– 538.5.

Example 155. Synthesis of 3-(6-((1-(4-methyl-1-(4-methyl-1-(pyridin-2-yl)piperidine-4-carbonyl)piperidin-4-yl)-1H-pyrazol-4-yl)methyl)-2-oxobenzo[cd]indol-1(2H)-yl)piperidine-2,6-dione (Compound 271)

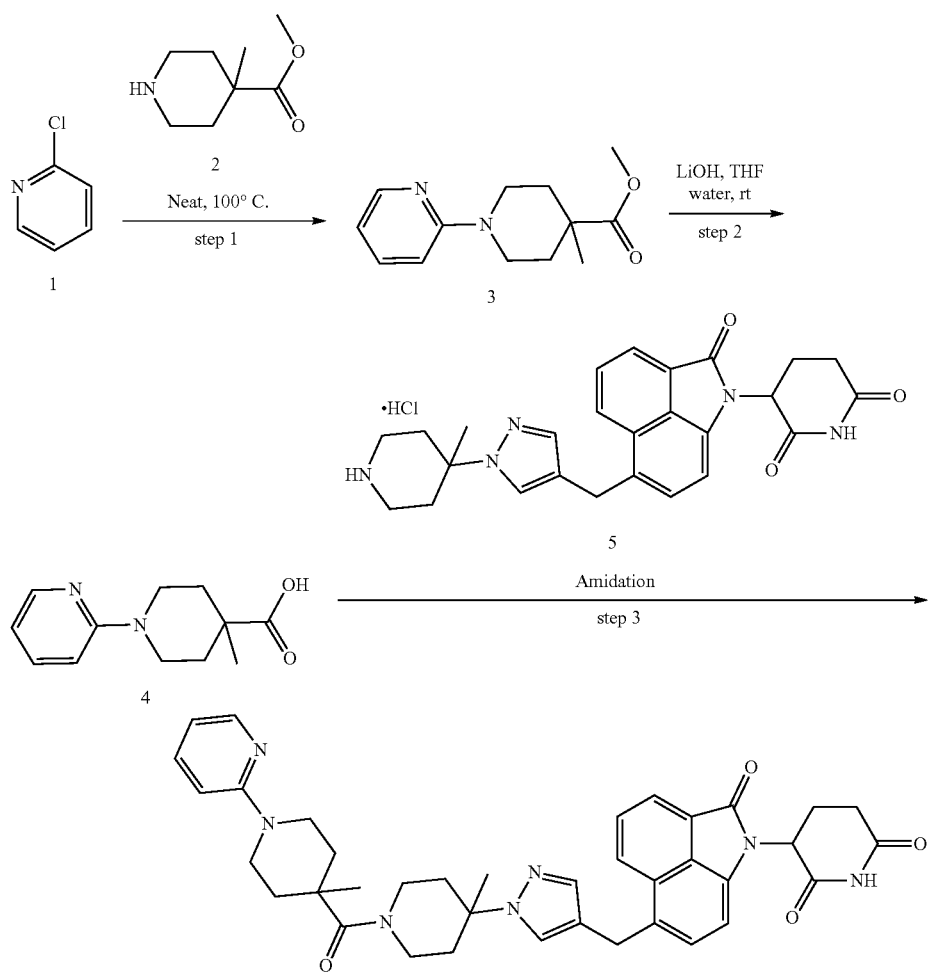

Compound 271

Step-1: Synthesis of methyl 4-methyl-1-(pyridin-2-yl)piperidine-4-carboxylate: To a stirred solution of methyl 1-chloro-4-methyl-piperidine-4-carboxylate 2 (1.15 g, 5.94 mmol, 575.47 uL) in DMF (1 mL) in a sealed tube was added Triethylamine (601.55 mg, 5.94 mmol, 828.59 uL). It was stirred at RT for 10 minutes. 2-chloropyridine 1 (450 mg, 3.96 mmol, 371.90 uL) was added to the reaction mixture. It was heated at 100° C. for 16 h. It was diluted with water, extracted with ethyl acetate, dried over sodium sulfate, concentrated under reduced pressure. It was purified by combiflash eluting at 25% ethyl acetate in hexane to afford methyl 4-methyl-1-(2-pyridyl)piperidine-4-carboxylate 3 (95 mg, 352.76 umol, 8.90% yield, 87% purity) as colourless liquid. LC MS: ES+ 235.3.

Step-2: Synthesis of 4-methyl-1-(pyridin-2-yl)piperidine-4-carboxylic acid: To the stirred solution of methyl 4-methyl-1-(2-pyridyl) piperidine-4-carboxylate 3 (85 mg, 362.79 umol) in THF (4 mL) and Water (1 mL) was added Lithium hydroxide monohydrate, 98% (30.45 mg, 725.59 umol, 20.16 uL). It was stirred at RT for 16 hours. It was quenched with 1N HCl to neutralise the solution and was extracted with ethylacetate four times. Combined organic part was washed with brine, dried over sodium sulfate, concentrated under reduced pressure to afford 4-methyl-1-(2-pyridyl)piperidine-4-carboxylic acid 4 (35 mg, 143.01 umol, 39.42% yield, 90% purity) as a white solid.

Step-3: Synthesis of 3-(6-((1-(4-methyl-1-(pyridin-2-yl)piperidine-4-carbonyl)piperidin-4-yl)-1H-pyrazol-4-yl)methyl)-2-oxobenzo[cd]indol-1(2H)-yl)piperidine-2,6-dione: To the stirred solution of 3-[6-[[1-(1-chloro-4-methyl-4-piperidyl)pyrazol-4-yl]methyl]-2-oxo-benzo[cd]indol-1-yl]piperidine-2,6-dione 5 (50.0 mg, 101.22 umol) in DMF (1 mL) was added N,N-Diisopropylethylamine (39.24 mg, 303.65 umol, 52.89 uL) in cold condition followed by the addition 4-methyl-1-(2-pyridyl)piperidine-4-carboxylic acid 4 (22.29 mg, 101.22 umol, 13.94 uL) and HATU (57.73 mg, 151.83 umol) and the reaction was continued at room temperature for 16 hours. TLC and LCMS were checked which showed formation of the desired spot. The reaction mixture was diluted with ethyl acetate, washed with sodium bicarbonate solution, water and the organic fraction was separated. It was dried over anhydrous sodium sulphate and evaporated under reduced pressure to obtain the crude which was purified by preparative TLC plate method developing the plate in 3% MeOH-DCM to afford 3-[6-[[1-[4-methyl-1-[4-methyl-1-(2-pyridyl)piperidine-4-carbonyl]-4-piperidyl]pyrazol-4-yl]methyl]-2-oxo-benzo[cd]indol-1-yl]piperidine-2,6-dione Compound 271 (11 mg, 16.54 umol, 16.34% yield, 99.22% purity) as yellow solid. 11.11 (s, 1H), 8.39 (d, J=8.28 Hz, 1H), 8.10-8.07 (m, 2H), 7.85-7.78 (m, 2H), 7.50-7.46 (m, 1H), 7.36-7.34 (m, 2H), 7.07 (d, J=7.24 Hz, 1H), 6.75 (d, J=8.64 Hz, 1H), 6.58-6.56 (m, 1H), 5.45-5.42 (m, 1H), 4.21 (s, 2H), 3.75-3.71 (m, 4H), 3.31-3.26 (m, 3H), 2.94-2.91 (m, 1H), 2.77-2.73 (m, 1H), 2.66-2.62 (m, 1H), 2.57-2.50 (m, 2H), 2.40-2.32 (m, 1H), 2.10-2.17 (m, 3H), 1.76-1.72 (m, 2H), 1.48-1.46 (m, 2H), 1.36-1.33 (m, 3H), 1.23 (s, 3H); LC MS: ES+ 660.3.

Example 156. Synthesis of 3-(6-((1-(4-methyl-1-(1-(pyridin-2-yl)piperidine-4-carbonyl)piperidin-4-yl)-1H-pyrazol-4-yl)methyl)-2-oxobenzo[cd]indol-1(2H)-yl)piperidine-2,6-dione (Compound 272)

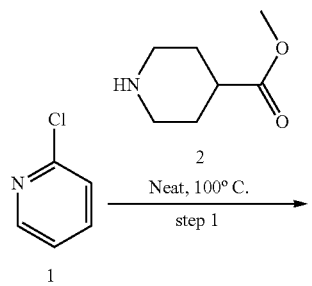

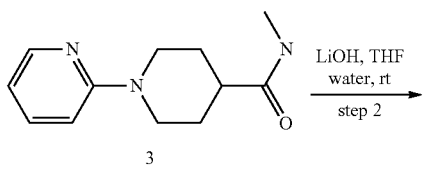

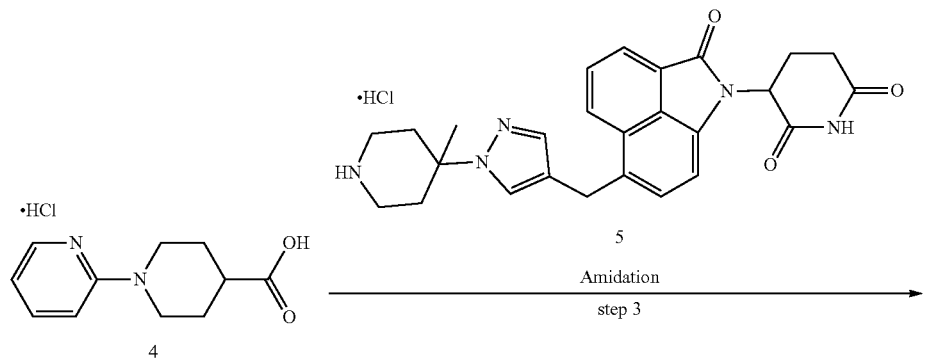

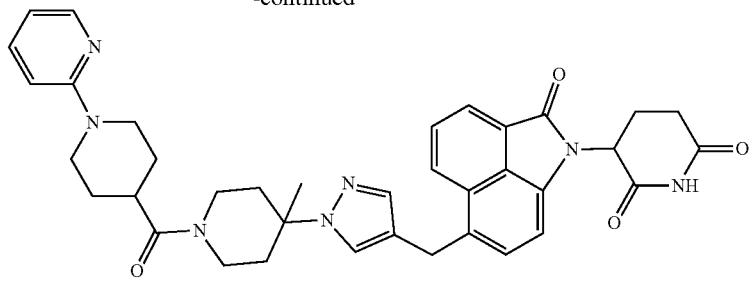

Compound 272

Step-1: Synthesis of methyl 1-(pyridin-2-yl)piperidine-4-carboxylate: To the stirred solution of 2-chloropyridine 1 (483.73 mg, 4.26 mmol, 399.78 uL) in a sealed tube was added methyl piperidine-4-carboxylate 2 (610 mg, 4.26 mmol, 575.47 uL). It was heated at 100° C. for 16 hours. It was diluted with ethyl acetate, washed with saturated sodium bicarbonate solution, dried over sodium sulfate, concentrated under reduced pressure. It was purified by combiflash eluting at 20% ethyl acetate in hexane to afford methyl 1-(2-pyridyl)piperidine-4-carboxylate 3 (210 mg, 905.72 umol, 21.26% yield, 95% purity) as colourless liquid. LC MS: ES+ 221.3.

Step-2: Synthesis of 1-(pyridin-2-yl)piperidine-4-carboxylic acid: To a stirred solution of methyl 1-(2-pyridyl)piperidine-4-carboxylate 3 (200 mg, 907.99 umol) in THF (8 mL) and Water (2 mL) was added Lithium hydroxide monohydrate, 98% (114.30 mg, 2.72 mmol, 75.69 uL). It was stirred at RT for 16 h. It was quenched with 1N HCl to neutralise the solution and was extracted with ethylacetate four times. Combined organic part was washed with brine, dried over sodium sulfate, concentrated under reduced pressure to afford 1-(2-pyridyl)piperidine-4-carboxylic acid 4 (130 mg, 598.82 umol, 65.95% yield, 95% purity) as a white solid. 12.21 (s, 1H), 8.09-8.07 (m, 1H), 7.51-7.47 (m, 1H), 6.81 (d, J=8.6 Hz, 1H), 6.60-6.57 (m, 1H), 4.18-4.15 (m, 2H), 2.94-2.87 (m, 2H), 2.46-2.45 (m, 1H), 1.86-1.82 (m, 2H), 1.55-1.45 (m, 2H).

Step-3: Synthesis of 3-(6-((1-(4-methyl-1-(1-(pyridin-2-yl)piperidine-4-carbonyl)piperidin-4-yl)-1H-pyrazol-4-yl)methyl)-2-oxobenzo[cd]indol-1(2H)-yl)piperidine-2,6-dione: To the stirred solution of 3-[6-[[1-(1-chloro-4-methyl-4-piperidyl)pyrazol-4-yl]methyl]-2-oxo-benzo[cd]indol-1-yl]piperidine-2,6-dione 5 (50.0 mg, 101.22 umol) in DMF (1 mL) was added N,N-Diisopropylethylamine (39.24 mg, 303.65 umol, 52.89 uL) in cold condition followed by the addition 1-(2-pyridyl)piperidine-4-carboxylic acid 4 (20.88 mg, 101.22 umol, 13.94 uL) and HATU (57.73 mg, 151.83 umol) and the reaction was continued at room temperature for 16 hours. TLC (5% methanol in dichloromethane) and LCMS were checked which showed formation of the desired spot. The reaction mixture was diluted with ethyl acetate, washed with sodium bicarbonate solution, water and the organic fraction was separated. It was dried over anhydrous sodium sulphate and evaporated under reduced pressure to obtain the crude which was purified by preparative TLC (3% methanol in dichloromethane) to afford 3-[6-[[1-[4-methyl-1-[1-(2-pyridyl)piperidine-4-carbonyl]-4-piperidyl]pyrazol-4-yl]methyl]-2-oxo-benzo[cd]indol-1-yl]piperidine-2,6-dione Compound 272 (27 mg, 41.59 umol, 41.09% yield, 99.46% purity) as yellow solid. 11.11 (s, 1H), 8.39 (d, J=7.84 Hz, 1H), 8.09-8.08 (m, 2H), 7.85-7.79 (m, 2H), 7.51-7.47 (m, 1H), 7.36-7.34 (m, 2H), 7.07 (d, J=7.08 Hz, 1H), 6.80 (d, J=7.92 Hz, 1H), 6.59-6.56 (m, 1H), 5.45-5.42 (m, 1H), 4.29-4.27 (m, 2H), 4.21 (s, 2H), 3.69-3.65 (m, 2H), 3.13-3.10 (m, 1H), 2.94-2.91 (m, 4H), 2.76-2.63 (m, 2H), 2.37-2.32 (m, 1H), 2.25-2.23 (m, 1H), 2.08-2.07 (m, 2H), 1.80-1.48 (m, 6H), 1.36 (s, 3H); LC MS: ES+ 646.3.

Example 157. Synthesis of 3-(6-(4-(morpholinomethyl)phenoxy)-2-oxobenzo[cd]indol-1(2H)-yl)piperidine-2,6-dione (Compound 273)

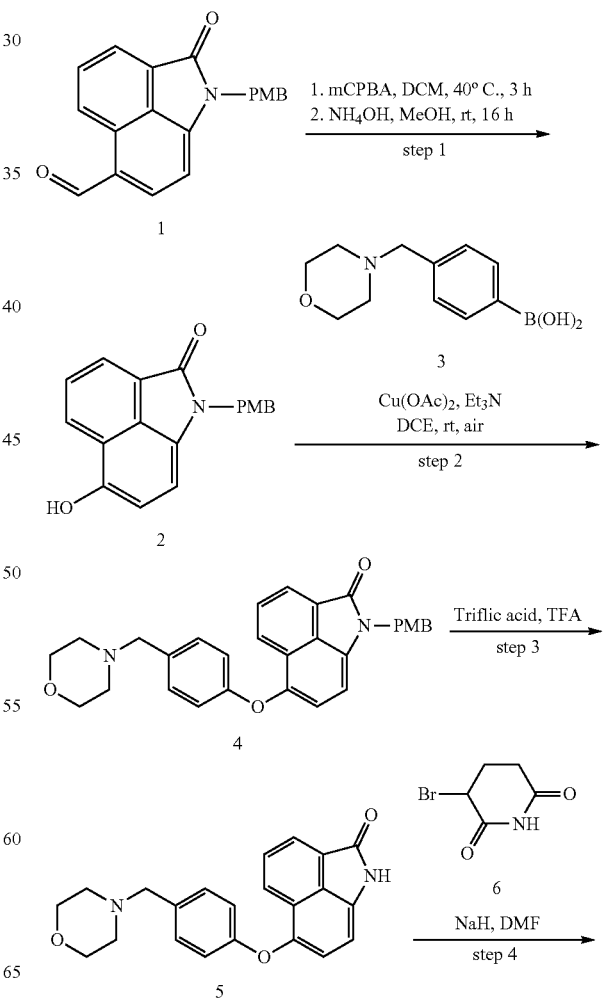

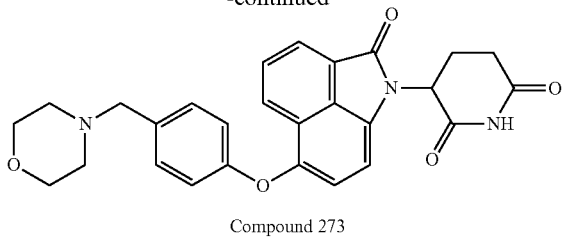

Compound 273

Step-1: Synthesis of 6-hydroxy-1-[(4-methoxyphenyl) methyl]benzo[cd]indol-2-one: To a stirred solution of 1-[(4-methoxyphenyl)methyl]-2-oxo-benzo[cd]indole-6-carbaldehyde (1) (200 mg, 630.24 umol) in DCM (10 mL), mCPBA (108.76 mg, 630.24 umol) was added at rt and the reaction mixture warmed to 40° C. and stirred for 12 hr. After completion of the reaction (monitored by TLC), the reaction mixture was cooled at 0° C. and 2 M NH3-MeOH (3.15 mmol) was added drop wise until red wine color exists and stirred for 2 hr at same temp. After that, the reaction mixture was diluted with EtOAc (20 mL) and quenched with saturated sodium bicarbonate solution and the layers were separated. The organic part was then dried over sodium sulfate and concentrated. The crude thus obtained was purified by column chromatography (100-200 silica, Gradient: 0-50% EtOAc in Hexane) to obtain sticky 6-hydroxy-1-[(4-methoxyphenyl)methyl]benzo[cd]indol-2-one (2) (145 mg, 68.57% yield) as yellow solid. LC MS: ES+ 306.

Step-2: Synthesis of 1-[(4-methoxyphenyl)methyl]-6-[4-(morpholinomethyl)phenoxy]benzo[cd]indol-2-one: To the Oxygen purged solution of 6-hydroxy-1-[(4-methoxyphenyl)methyl]benzo[cd]indol-2-one (2) (1 g, 3.28 mmol) and [4-(morpholinomethyl)phenyl]boronic acid (3) (724.01 mg, 3.28 mmol) in Methanol (5 mL) cupriosulfanylcopper (26.06 mg, 163.76 umol) and N,N,N',N'-tetramethylethane-1,2-diamine (380.61 mg, 3.28 mmol, 491.11 uL) were added and the reaction was stirred at RT for 16 h. After completion of the reaction (monitored by TLC) the reaction mixture was filtered through celite pad and washed with EtOAc. The collected filtrate was further washed with water (3 times) and brine, dried over sodium sulfate and concentrated under reduced pressure. The crude thus obtained was purified by column chromatography (100-200 Silica; Gradient: 0-30% EtOAc in DCM) to afford 1-[(4-methoxyphenyl)methyl]-6-[4-(morpholinomethyl)phenoxy]benzo[cd]indol-2-one (4) (180 mg, 10.86% yield) as yellow solid; LC MS: ES+ 481.4.

Step-3: Synthesis of 6-[4-(morpholinomethyl)phenoxy]-1H-benzo[cd]indol-2-one: To a stirred solution of 1-[(4-methoxyphenyl)methyl]-6-[4-(morpholinomethyl)phenoxy]benzo[cd]indol-2-one (4) (180 mg, 374.57 umol) in TFA (2 mL), Trifluoromethanesulfonic acid (562.15 mg, 3.75 mmol, 328.74 uL) were added and the resultant reaction mixture was stirred at RT stirred for 12 hr. After completion of the reaction (monitored by TLC) the reaction mixture was quenched with saturated sodium bicarbonate solution and extracted with ethyl acetate (Twice)). The combined organic part was then dried over sodium sulfate and concentrated under reduced pressure. The crude thus obtained was purified by column chromatography (100-200 silica; Gradient 0-2% MeOH in DCM) to afford 6-[4-(morpholinomethyl) phenoxy]-1H-benzo[cd]indol-2-one (5) (80 mg, 55.71% yield) as yellow solid; LC MS: ES+ 361.1.

Step-4: Synthesis of 3-(6-(4-(morpholinomethyl)phenoxy)-2-oxobenzo[cd]indol-1(2H)-yl)piperidine-2,6-dione: To a stirred solution of 6-[4-(morpholinomethyl)phenoxy]-1H-benzo[cd]indol-2-one (5) (80 mg, 221.97 umol) in dry DMF (2 mL), Sodium hydride (in oil dispersion) 60% dispersion in mineral oil (17.01 mg, 443.95 umol, 60% purity) was added at 0° C. and the resultant reaction mixture was heated at 70° C. for 1 hr. After that, 3-bromopiperidine-2,6-dione (6) (42.62 mg, 221.97 umol) was added and the reaction was continued for 12 hr at 70° C. Reaction was monitored by TLC and LCMS which showed unreacted SM being present. Again 3-bromopiperidine-2,6-dione (6) (42.62 mg, 221.97 umol) was added to the reaction mixture and heating was continued for another 6 hr. The reaction was then quenched with chilled water/ammonium chloride solution and extracted with ethyl acetate (3 times). The combined organic part was then dried over sodium sulfate and concentrated under reduced pressure. The crude thus obtained was purified by Prep-TLC Plate (30% EtOAc in DCM) to afford 3-[6-[4-(morpholinomethyl)phenoxy]-2-oxo-benzo[cd]indol-1-yl]piperidine-2,6-dione Compound 273 (5 mg, 4.41% yield) as yellow solid. 1H NMR (400 MHz, DMSO-d6) δ 11.15 (s, 1H), 8.17-8.13 (m, 2H), 7.87-7.83 (m, 1H), 7.30 (d, J=7.88 Hz, 2H), 7.12-7.10 (m, 1H), 7.05-7.00 (m, 3H), 5.49-5.45 (m, 1H), 3.56 (br s, 4H), 3.42 (s, 2H), 2.96-2.95 (m, 2H), 2.67-2.62 (m, 1H), 2.32 (br s, 4H), 2.10-2.07 (m, 1H); LC MS: ES+ 472.5.

Example 158. Synthesis of 3-[6-[[1-[4-[(1-methylcyclobutyl)methyl]-4-azaspiro[2.5]octan-7-yl]pyrazol-4-yl]methyl]-2-oxo-benzo[cd]indol-1-yl]piperidine-2,6-dione (Compound 274) and 3-[6-[[1-[4-[(1-methylcyclobutyl)methyl]-4-azaspiro[2.5]octan-7-yl]pyrazol-4-yl]methyl]-2-oxo-benzo[cd]indol-1-yl]piperidine-2,6-dione (Compound 275)

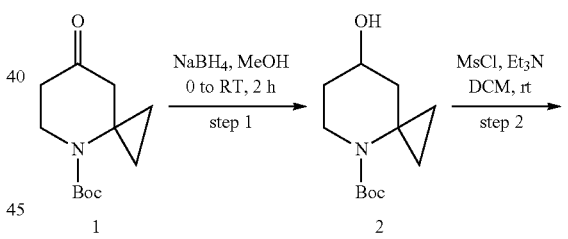

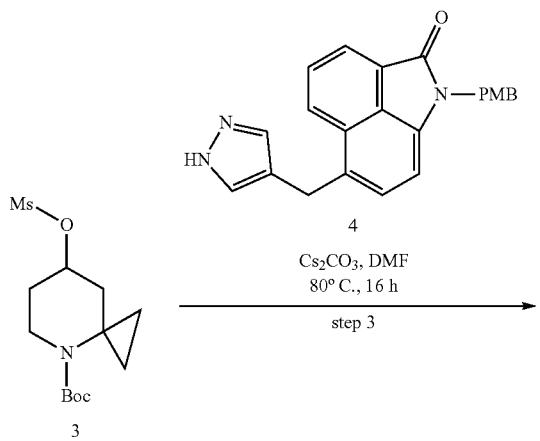

765
-continued
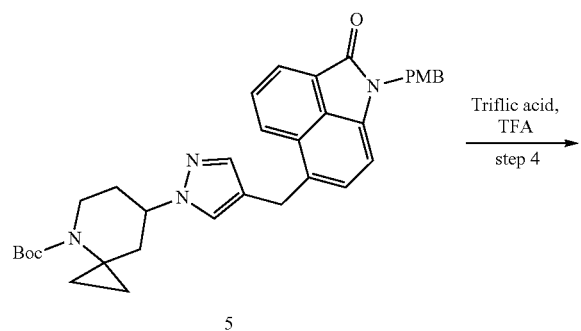
5
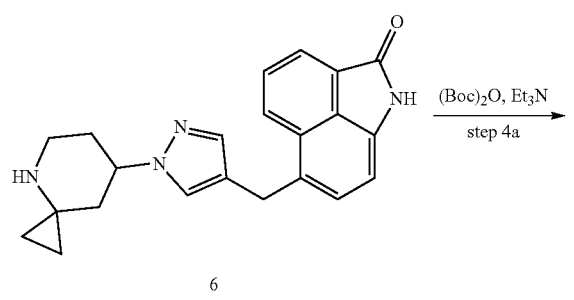
6
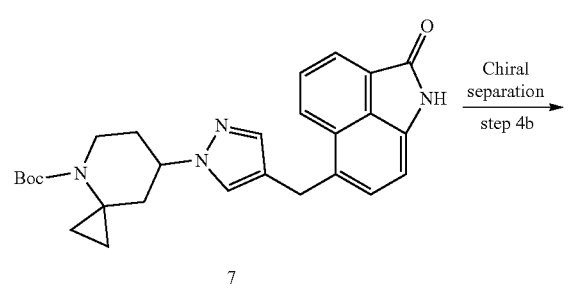
7
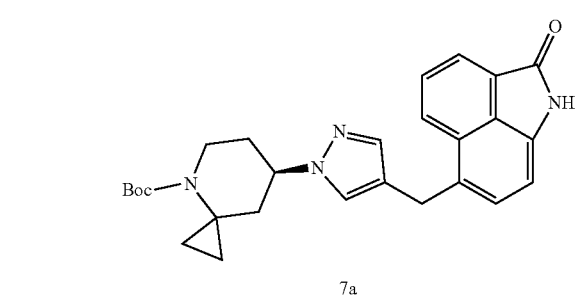
7a
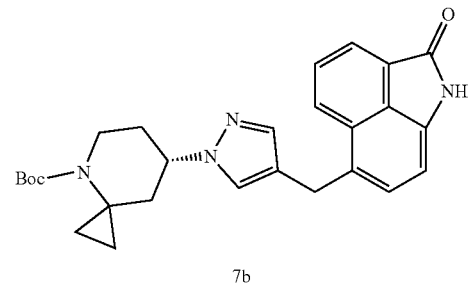
7b
766
-continued
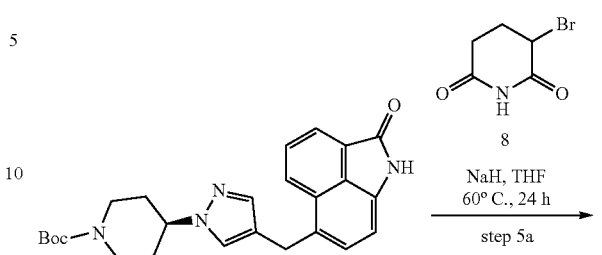
7a
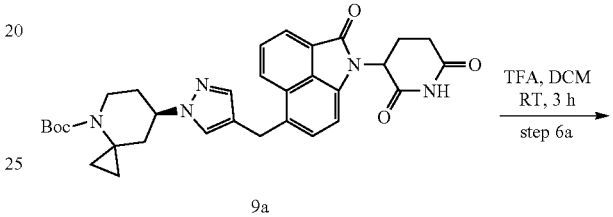
9a
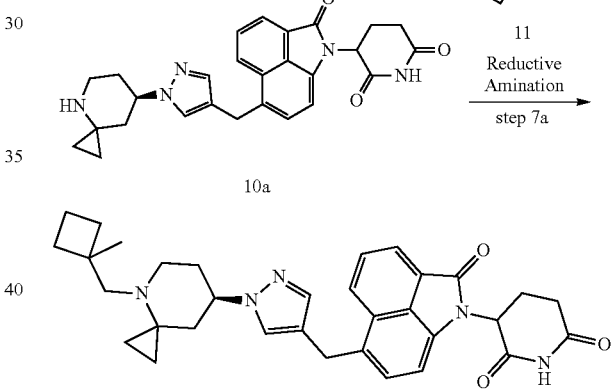 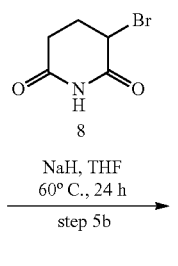
10a
Compound 274
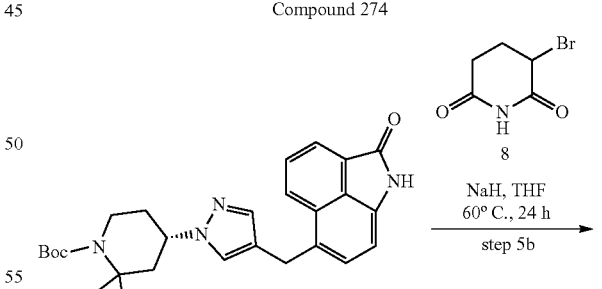
7b
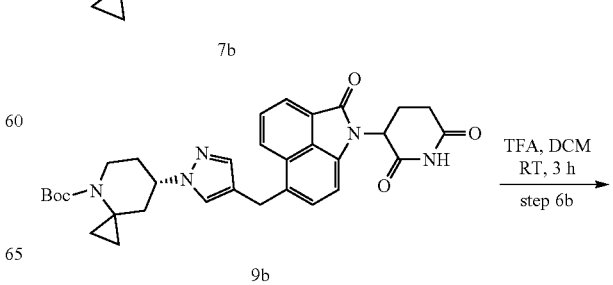
9b

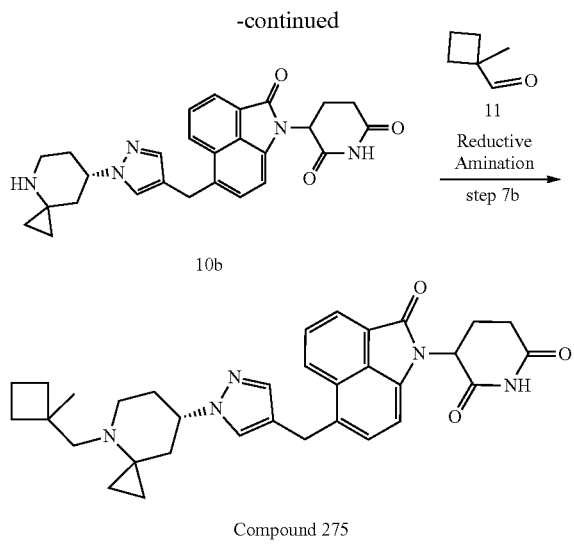

Compound 275

Step-1: Synthesis of tert-butyl 5-hydroxyspiro[2.5]octane-8-carboxylate: To a stirred solution of tert-butyl 5-oxospiro[2.5]octane-8-carboxylate (1) (1 g, 4.46 mmol) in Methanol (5 mL) was added Sodium Borohydride (202.39 mg, 5.35 mmol, 189.15 uL) under cooling condition and the reaction mass was stirred at Rt for 4h. After completion of the reaction (monitored by TLC) the reaction mass was concentrated under reduced pressure and was diluted with cold water. The aqueous part was then extracted with EtOAc and the organic layer was further washed with brine, dried over sodium sulphate and concentrated to afford tert-butyl 5-hydroxyspiro[2.5]octane-8-carboxylate (2) (1 g, 94.15% yield) as yellow solid. 1HNMR (400 MHz, DMSO-d6): 0 4.67-4.66 (d, J=4.8 Hz, 1H), 3.76-3.68 (m, 2H), 2.84-2.80 (m, 2H), 1.76-1.72 (m, 1H), 1.57-1.52 (m, 1H), 1.39 (s, 9H), 1.25-1.16 (m, 2H), 0.98-0.96 (m, 1H), 0.76-0.70 (m, 1H), 0.45-0.40 (m, 2H).

Step-2: Synthesis of tert-butyl 5-methylsulfonyloxyspiro[2.5]octane-8-carboxylate: To a stirred solution of tert-butyl 5-hydroxyspiro[2.5]octane-8-carboxylate (2) (1 g, 4.42 mmol) in DCM (20 mL) was added Triethylamine (894.26 mg, 8.84 mmol, 1.23 mL) under cooling condition and the reaction mass was stirred for 10 minutes. Then Mesyl Chloride (607.40 mg, 5.30 mmol, 410.41 uL) was added and the resultant reaction mixture was stirred at RT for 16 hours. After completion of the reaction (monitored by TLC) the reaction mixture was diluted with DCM and washed with water, saturated Sodium bicarbonate solution, brine and dried over sodium sulphate and concentrated to afford tert-butyl 5-methylsulfonyloxyspiro[2.5]octane-8-carboxylate (3) (1.2 g, 84.75% yield) as colourless gum. 1HNMR (400 MHz, DMSO-d6): 0 4.90-4.85 (m, 1H), 3.71-3.67 (m, 1H), 3.19 (s, 3H), 3.11-3.06 (m, 1H), 1.97-1.96 (m, 1H), 1.77-1.72 (m, 1H), 1.65-1.62 (m, 1H), 1.55-1.51 (m, 1H), 1.40 (s, 9H), 1.17 (t, 1H), 0.98-.095 (m, 1H), 0.82-0.76 (m, 1H), 0.65-0.60 (m, 2H).

Step-3: Synthesis of tert-butyl 7-[4-[[1-[(4-methoxyphenyl)methyl]-2-oxo-benzo[cd]indol-6-yl]methyl]pyrazol-1-yl]-4-azaspiro[2.5]octane-4-carboxylate: To a stirred solution of 1-[(4-methoxyphenyl)methyl]-7-(1H-pyrazol-4-ylmethyl)-2H-benzo[de]quinolin-3-one (4) (1.2 g, 3.13 mmol) and tert-butyl 7-methylsulfonyloxy-4-azaspiro[2.5]octane-4-carboxylate (3) (1.15 g, 3.76 mmol) in DMF (15 mL) was added Cesium carbonate (2.04 g, 6.26 mmol) and the resultant reaction mixture was stirred at 100° C. for 16 hours. After completion of the reaction (monitored by TLC) the reaction mixture was diluted with EtOAc washed with water and brine, dried over sodium sulfate and concentrated. The crude thus obtained was purified by combiflash chromatography (Gradient: 0-30% EtOAc in Hexane) to afford tert-butyl 7-[4-[[1-[(4-methoxyphenyl)methyl]-2-oxo-benzo[cd]indol-6-yl]methyl]pyrazol-1-yl]-4-azaspiro[2.5]octane-4-carboxylate (5) (1 g, 48.39% yield) as light yellow solid; LC MS: ES+ 579.8.

Step-4,4a & 4b: Synthesis of tert-butyl 7-[4-[(2-oxo-1H-benzo[cd]indol-6-yl)methyl]pyrazol-1-yl]-4-azaspiro[2.5]octane-4-carboxylate and tert-butyl 7-[4-1(2-oxo-1H-benzo[cd]indol-6-yl)methyl]pyrazol-1-yl]-4-azaspiro[2.5]octane-4-carboxylate: To a stirred solution of tert-butyl 7-[4-[[1-[(4-methoxyphenyl)methyl]-2-oxo-benzo[cd]indol-6-yl]methyl]pyrazol-1-yl]-4-azaspiro[2.5]octane-4-carboxylate (5) (1 g, 1.73 mmol) in TFA (5 mL) was added trifluoromethanesulfonic acid (2.59 g, 17.28 mmol, 1.52 mL) and the resultant reaction mixture was stirred at RT for 16 hours. After completion of the reaction (monitored by TLC and LC MS) the reaction mass was concentrated and crude thus obtained was diluted with DCM (10 mL) and TEA (874.29 mg, 8.64 mmol, 1.20 mL) was added to it under cooling condition followed by the addition of tert-butoxycarbonyl tert-butyl carbonate (565.71 mg, 2.59 mmol, 594.86 uL). The resultant reaction mixture was then stirred at Rt for 16 hours. After completion of the reaction (monitored by TLC and LC MS) the reaction mixture was diluted with DCM and washed with water, brine, dried over sodium sulphate and concentrated. The crude thus obtained was purified by combi-flash (Gradient: 0-30% EtOAc in Hexane) to afford Racemic 7-[4-(2-Oxo-1,2-dihydro-benzo[cd]indol-6-ylmethyl)-pyrazol-1-yl]-4-aza-spiro[2.5]octane-4-carboxylic acid tert-butyl ester (7) (600 mg). This Racemic was separated to its enantiomers by SFC Chiral Prep to afford tert-butyl 7-[4-[(2-oxo-1H-benzo[cd]indol-6-yl)methyl]pyrazol-1-yl]-4-azaspiro[2.5]octane-4-carboxylate (7a) (250 mg, 31.55% yield, eluted as first Fraction) and tert-butyl 7-[4-[(2-oxo-1H-benzo[cd]indol-6-yl)methyl]pyrazol-1-yl]-4-azaspiro[2.5]octane-4-carboxylate (7b) (250 mg, 31.55% yield, eluted as second fraction) as yellow solid. LC MS ES+ 459.61.

Step-5a: Synthesis of tert-butyl 7-[4-[[1-(2,6-dioxo-3-piperidyl)-2-oxo-benzo[cd]indol-6-yl]methyl]pyrazol-1-yl]-4-azaspiro[2.5]octane-4-carboxylate: To a cooled solution of tert-butyl 7-[4-[(2-oxo-1H-benzo[cd]indol-6-yl)methyl]pyrazol-1-yl]-4-azaspiro[2.5]octane-4-carboxylate (7a) (200 mg, 436.16 umol) in dry THF (10 mL), Sodium hydride (60% dispersion in mineral oil) (167.12 mg, 4.36 mmol) was added portion wise, maintaining the temp <5° C. Once the addition is over, the resultant mixture was stirred for 15 minutes at RT. Then the reaction mixture was again cooled to 0° C. and 3-bromopiperidine-2,6-dione (8) (83.75 mg, 436.16 umol) was added to it portion wise. After complete addition, resulting solution was heated at 70° C. for 1 hour. After completion (evidenced from TLC), the reaction mixture was cooled to 0° C. and quenched with the addition of ice cooled water. Aqueous part was extracted with ethyl acetate (3 times). Combined organics was separated, dried over sodium sulfate and concentrated under reduced pressure. Crude mass was purified by combiflash column (gradient: 0-30% EtOAc in DCM) to afford tert-butyl 7-[4-[[1-(2,6-dioxo-3-piperidyl)-2-oxo-benzo[cd]indol-6-yl]methyl]pyrazol-1-yl]-4-azaspiro[2.5]octane-4-carboxylate (9a) (200 mg, 75.67% yield) as yellow solid. LC MS ES+570.2.

Step-6a: Synthesis of [7-[4-[[1-(2,6-dioxo-3-piperidyl)-2-oxo-benzo[cd]indol-6-yl]methyl]pyrazol-1-yl]-4-azaspiro

[2.5]octan-4-yl] 2,2,2-trifluoroacetate: To a stirred solution of tert-butyl 7-[4-[[1-(2,6-dioxo-3-piperidyl)-2-oxo-benzo[cd]indol-6-yl]methyl]pyrazol-1-yl]-4-azaspiro[2.5]octane-4-carboxylate (9a) (200 mg, 351.09 umol) in DCM (5 mL) was added TFA (600.48 mg, 5.27 mmol, 405.73 uL) and the reaction mixture was stirred at RT for 4 hours. After completion of the reaction (monitored by TLC) the reaction mass was concentrated under reduced pressure and the crude thus obtained was triturated with Ether-Pentane to afford [7-[4-[[1-(2,6-dioxo-3-piperidyl)-2-oxo-benzo[cd]indol-6-yl]methyl]pyrazol-1-yl]-4-azaspiro[2.5]octan-4-yl]2,2,2-trifluoroacetate (10a) (200 mg, 77.58% yield) as yellow gum. LC MS ES+ 470.1.

Step-7a: Synthesis of 3-[6-[[1-[4-[(1-methylcyclobutyl)methyl]-4-azaspiro[2.5]octan-7-yl]pyrazol-4-yl]methyl]-2-oxo-benzo[cd]indol-1-yl]piperidine-2,6-dione: A solution of 3-[6-[[1-[4-azaspiro[2.5]octan-7-yl]pyrazol-4-yl]methyl]-2-oxo-benzo[cd]indol-1-yl]piperidine-2,6-dione; 2,2,2-trifluoroacetic acid (10a) (100.00 mg, 171.36 umol) in DCE (4 mL) and Triethylamine (17.34 mg, 171.36 umol, 23.88 uL) was stirred under cooling condition for 15 min. To it Acetic acid (10.29 mg, 171.36 umol, 9.80 uL) and 1-methylcyclobutanecarbaldehyde (11) (16.82 mg, 171.36 umol, 16.49 uL) were added and the reaction mixture was stirred at RT for 1 hour. Then Sodium cyanoborohydride (16.15 mg, 257.04 umol) was added and the reaction was allowed to stir at RT for 16 h. After completion of the reaction (monitored by TLC and LCMS), the reaction mixture was diluted with ethyl acetate, washed with sodium bicarbonate solution and the organic fraction was separated. It was then dried over anhydrous sodium sulphate and evaporated under reduced pressure to obtain the crude which was purified by preparative TLC plate (3% MeOH-DCM) to afford 3-[6-[[1-[4-[(1-methylcyclobutyl)methyl]-4-azaspiro[2.5]octan-7-yl]pyrazol-4-yl]methyl]-2-oxo-benzo[cd]indol-1-yl]piperidine-2,6-dione Compound 274 (25.0 mg, 26.44% yield) as yellow solid. 1HNMR (400 MHz, DMSO-d6): 0 11.11 (s, 1H), 8.36 (d, J=8.2 Hz, 1H), 8.08 (d, J=7.0 Hz, 1H), 7.83 (t, J=7.58 Hz, 1H), 7.58 (s, 1H), 7.35 (d, J=7.28 Hz, 1H), 7.31 (s, 1H), 7.07 (d, J=7.28 Hz, 1H), 5.43 (dd, J=12.64, 5.36 Hz, 1H), 4.23-4.18 (m, 3H), 2.96-2.62 (m, 6H), 2.28-2.35 (m, 2H), 2.09-2.08 (m, 2H), 1.90-1.69 (m, 4H), 1.56-1.49 (m, 3H), 1.03 (m, 4H), 0.49-0.42 (m, 3H), 0.35-0.33 (m, 1H); LC MS: ES+ 552.24.

Step-5b: Synthesis of tert-butyl 7-[4-[[1-(2,6-dioxo-3-piperidyl)-2-oxo-benzo[cd]indol-6-yl]methyl]pyrazol-1-yl]-4-azaspiro[2.5]octane-4-carboxylate: To a cooled solution of tert-butyl 7-[4-[(2-oxo-1H-benzo[cd]indol-6-yl)methyl]pyrazol-1-yl]-4-azaspiro[2.5]octane-4-carboxylate (7b) (250 mg, 545.16 umol) in dry THF (10 mL), Sodium hydride (60% dispersion in mineral oil) (208.9 mg, 5.45 mmol) was added portion wise, maintaining the temp <5° C. Once the addition is over, the resultant mixture was stirred for 15 minutes at RT. Then the reaction mixture was again cooled to 0° C. and 3-bromopiperidine-2,6-dione (8) (523 mg, 2.73 mmol) was added to it portion wise. After complete addition, resulting solution was heated at 70° C. for 1 hour. After completion (evidenced from TLC), the reaction mixture was cooled to 0° C. and quenched with the addition of ice cooled water. Aqueous part was extracted with ethyl acetate (3 times). Combined organics was separated, dried over sodium sulfate and concentrated under reduced pressure. Crude mass was purified by combiflash column (gradient: 0-30% EtOAc in DCM) to afford tert-butyl 7-[4-[[1-(2,6-dioxo-3-piperidyl)-2-oxo-benzo[cd]indol-6-yl]methyl]pyrazol-1-yl]-4-azaspiro[2.5]octane-4-carboxylate (9b) (200 mg, 61% yield) as yellow solid. LC MS ES+ 570.2.

Step-6b: Synthesis of [7-[4-[[1-(2,6-dioxo-3-piperidyl)-2-oxo-benzo[cd]indol-6-yl]methyl]pyrazol-1-yl]-4-azaspiro[2.5]octan-4-yl] 2,2,2-trifluoroacetate: To a stirred solution of tert-butyl 7-[4-[[1-(2,6-dioxo-3-piperidyl)-2-oxo-benzo[cd]indol-6-yl]methyl]pyrazol-1-yl]-4-azaspiro[2.5]octane-4-carboxylate (9b) (143.14 mg, 263.32 umol) in DCM (5 mL) was added TFA (450.36 mg, 3.95 mmol, 304.29 uL) and the reaction mixture was stirred at RT for 4 hours. After completion of the reaction (monitored by TLC) the reaction mass was concentrated under reduced pressure and the crude thus obtained was triturated with Ether-Pentane to afford [7-[4-[[1-(2,6-dioxo-3-piperidyl)-2-oxo-benzo[cd]indol-6-yl]methyl]pyrazol-1-yl]-4-azaspiro[2.5]octan-4-yl]2,2,2-trifluoroacetate (10b) (150 mg, 72.1% yield) as yellow gum. LC MS ES+ 470.1.

Step-7b: Synthesis of 3-[6-[[1-[4-[(1-methylcyclobutyl)methyl]-4-azaspiro[2.5]octan-7-yl]pyrazol-4-yl]methyl]-2-oxo-benzo[cd]indol-1-yl]piperidine-2,6-dione: A solution of 3-[6-[[1-[4-azaspiro[2.5]octan-7-yl]pyrazol-4-yl]methyl]-2-oxo-benzo[cd]indol-1-yl]piperidine-2,6-dione; 2,2,2-trifluoroacetic acid (10b) (150.00 mg, 257.04 umol) in DCE (5 mL) and Triethylamine (26.01 mg, 257.04 umol, 35.83 uL) was stirred under cooling condition for 15 min. To it Acetic acid (10.29 mg, 171.36 umol, 9.80 uL) and 1-methylcyclobutanecarbaldehyde (11) (16.82 mg, 171.36 umol, 16.49 uL) were added and the reaction mixture was stirred at RT for 1 hour. Then Sodium cyanoborohydride (16.15 mg, 257.04 umol) was added and the reaction was allowed to stir at RT for 16 h. After completion of the reaction (monitored by TLC and LCMS), the reaction mixture was diluted with ethyl acetate, washed with sodium bicarbonate solution and the organic fraction was separated. It was then dried over anhydrous sodium sulphate and evaporated under reduced pressure to obtain the crude which was purified by preparative TLC plate (3% MeOH-DCM) to afford 3-[6-[[1-[4-[(1-methylcyclobutyl)methyl]-4-azaspiro[2.5]octan-7-yl]pyrazol-4-yl]methyl]-2-oxo-benzo[cd]indol-1-yl]piperidine-2,6-dione Compound 275 (40 mg, 28.08% yield) as yellow solid. 1HNMR (400 MHz, DMSO-d6): 11.11 (s, 1H), 8.37 (d, J=8.24 Hz, 1H), 8.08 (d, J=7.0 Hz, 1H), 7.83 (t, J=7.64 Hz, 1H), 7.59 (s, 1H), 7.35 (d, J=7.36 Hz, 1H), 7.31 (s, 1H), 7.07 (d, J=7.28 Hz, 1H), 5.43 (dd, J=12.8, 5.2 Hz, 1H), 4.25-4.23 (m, 1H), 4.18 (s, 2H), 2.94-2.62 (m, 6H), 2.28-2.23 (m, 2H), 2.10-2.07 (m, 2H), 1.90-1.67 (m, 4H), 1.56-1.47 (m, 3H), 1.03 (m, 4H), 0.49-0.42 (m, 3H), 0.35-0.33 (m, 1H); LC MS: ES+ 552.24.

Example 159. Synthesis of tert-butyl 4-[1-(2,6-dioxo-3-piperidyl)-2-oxo-benzo[cd]indol-6-yl]piperidine-1-carboxylate (Compound 276)

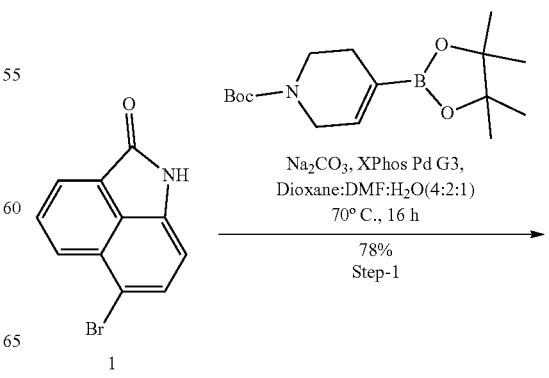

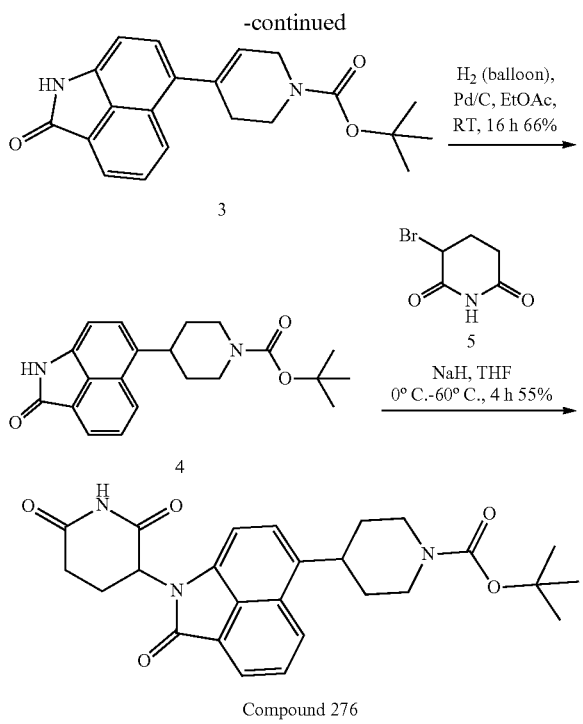

Compound 276

Step-1: Synthesis of 4-(2-oxo-1H-benzo[cd]indol-6-yl)-3,6-dihydro-2H-pyridine-1-carboxylate: To a stirred solution of 5-(-bromo-1H-benzo[cd]indol-2-one (4 g, 16.12 mmol) and tert-butyl 4-(4,4,5,5-tetramethyl-1,3,2-dioxaborolan-2-yl)-3,6-dihydro-2H-pyridine-1-carboxylate (4.99 g, 16.12 mmol) in Dioxane (15 mL), DMF (5 mL) and water (5 mL) was added sodium carbonate ((6.84 g, 64.50 mmol) and thoroughly purged with argon. Xphos pd G3 (682.41 mg, 806.21 umol) was added under inert atmosphere. Resulting mixture was heated at 90° C. for 12 h. After completion, reaction mixture was diluted with ethyl acetate, filtered through a short pad of celite and washed with ethyl acetate. Combined organic part was washed with water and brine, dried over anhydrous sodium sulphate, filtered and concentrated under reduced pressure. Crude mass was purified by column chromatography (50% ethyl acetate-hexane) to afford tert-butyl 4-(2-oxo-1H-benzo[cd]indol-6-yl)-3,6-dihydro-2H-pyridine-1-carboxylate (4.5 g, 12.84 mmol, 78% yield); LC MS: ES+ 351.2.

Step-2: Synthesis of tert-butyl 4-(2-oxo-1H-benzo[cd]indol-6-yl)piperidine-1-carboxylate: To a degassed solution of 4-(2-oxo-1H-benzo[cd]indol-6-yl)-3,6-dihydro-2H-pyridine-1-carboxylate (4.5 g, 12.84 mmol) in Ethyl acetate (30 mL) Pd/C 10% by wt (50% wet) (3.5 g, 5.50 mmol) was added. Resulting mixture was stirred at RT under hydrogen balloon pressure for 16 hours. After completion, the reaction mixture was filtered through a short pad of celite, washed with ethyl acetate and concentrated under reduced pressure. Crude mass was purified by combiflash chromatography (50% ethylacetate in hexane) to tert-butyl 4-(2-oxo-1H-benzo[cd]indol-6-yl)piperidine-1-carboxylate (2.97 g, 66%).

Step-3: Synthesis of tert-butyl 4-[1-(2,6-dioxo-3-piperidyl)-2-oxo-benzo[cd]indol-6-yl]piperidine-1-carboxylate: To a stirred solution of 6 tert-butyl 4-(2-oxo-1H-benzo[cd]indol-6-yl)piperidine-1-carboxylate (3 g, 8.51 mmol) in THF (80 mL) and DMF (20 mL) was added Sodium hydride (60% dispersion in mineral oil) (3.26 g, 85.12 mmol, 60% purity) slowly portion wise at 0° C. Resultant mixture was stirred the reaction for 30 min at RT. 3-bromopiperidine-2,6-dione (8.17 g, 42.56 mmol) was then added to it portion wise at RT and reaction mixture was heated to 70° C. and continued for 3h. After completion, reaction was quenched with crushed ice extracted with ethyl acetate. Combined organic part was washed with water and brine. Organic layer was dried with anhydrous sodium sulphate, filtered and concentrated under reduced pressure. Crude mass was purified by column chromatography (70% EA-hexane) to afford tert-butyl 4-[1-(2,6-dioxo-3-piperidyl)-2-oxo-benzo[cd]indol-6-yl]piperidine-1-carboxylate (2.22 g, 4.70 mmol, 55.22% yield) as yellow solid. 1H NMR (400 MHz, DMSO-d6) δ 11.10 (s, 1H), 8.46 (d, J=8.3 Hz, 1H), 8.10 (d, J=6.9 Hz, 1H), 7.86 (t, J=7.4 Hz, 1H), 7.37 (d, J=7.4 Hz, 1H), 7.08 (d, J=7.4 Hz, 1H), 5.46-5.41 (m, 1H), 4.12 (d, J=11.2 Hz, 2H), 3.50 (t, J=11.8 Hz, 1H), 2.99-2.90 (m, 3H), 2.80-2.62 (m, 2H), 2.09-2.07 (m, 1H), 1.85 (d, J=12.2 Hz, 2H), 1.67-1.59 (m, 2H), 1.43 (s, 9H); LC MS: ES+ 464.2.

Example 160. Synthesis of 3-(6-benzyl-2-oxo-benzo[cd]indol-1-yl)piperidine-2,6-dione (Compound 277)

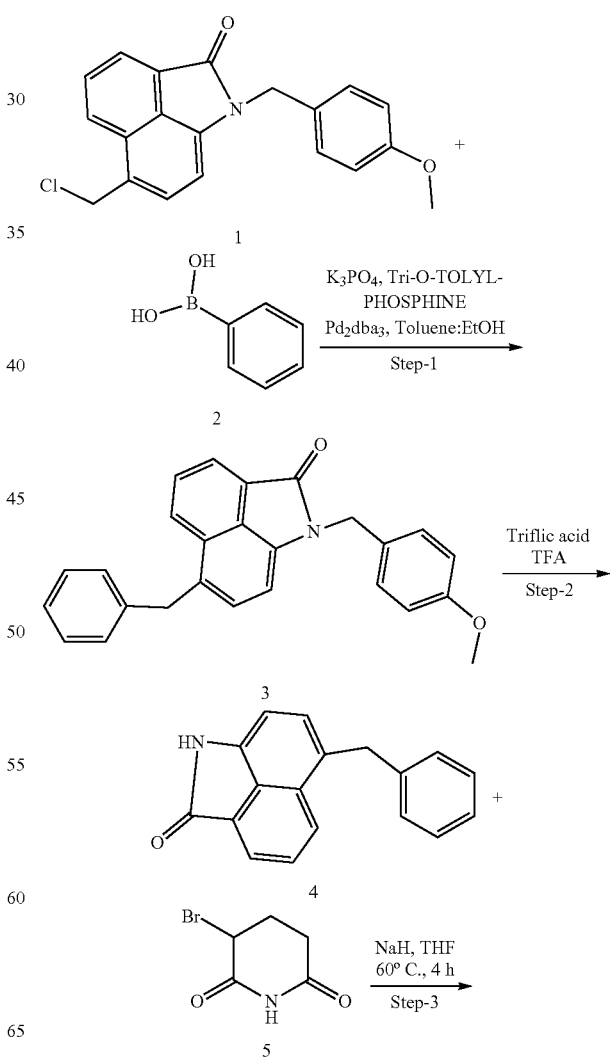

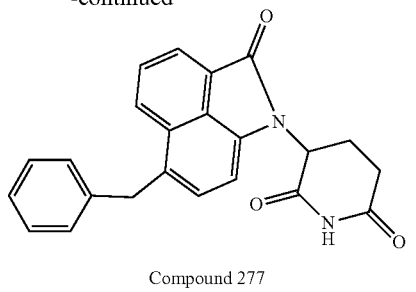

Compound 277

Step-1: Synthesis of 6-Benzyl-1-(4-methoxy-benzyl)-1H-benzo[cd]indol-2-one: To a stirred solution of 6-(chloromethyl)-1-[(4-methoxyphenyl)methyl]benzo[cd]indol-2-one (0.500 g, 1.48 mmol) and phenylboronic acid (360.95 mg, 2.96 mmol) in a mixture of Toluene (6.5 mL) and Ethanol (3.5 mL) in a sealed tube was added Potassium phosphate (785.47 mg, 3.70 mmol) then degassed for 10 mins, later Tris(o-tolyl)phosphine (90.10 mg, 296.03 umol) and Tris(dibenzylideneacetone)dipalladium(0) (135.54 mg, 148.02 umol) was added and again degassed for 10 mins, after degassing reaction mixture was closed with teflon cap and stirred at 90° C. for 16 hr. The progress of the reaction was monitored by TLC, after reaction completion reaction mixture was filtered through celite bed and bed was washed twice with ethyl acetate then collected solvent was concentrated under reduced pressure to get the crude compound and it was purified by column chromatography eluted with 10 to 30% ethyl acetate in Hexane to get 6-benzyl-1-[(4-ethoxyphenyl)methyl]benzo[cd]indol-2-one (0.300 g, 774.81 umol, 52.35% yield, 98% purity) as yellow solid. LC-MS: (ES+)=380.2 [M+H]+.

Step-2: Synthesis of 6-Benzyl-1H-benzo[cd]indol-2-one: 6-benzyl-1-[(4-methoxyphenyl)methyl]benzo[cd]indol-2-one (0.300 g, 790.62 umol) was dissolved in Trifluoroacetic acid (5 mL) and cooled to 0° C. then Triflic acid (593.27 mg, 3.95 mmol, 346.94 uL) was added and reaction mixture was stirred at RT for 16 hr. The progress of the reaction was monitored by TLC, after reaction completion reaction mixture was dissolved in water and pH was adjusted with aqueous sodium bi carbonate to 6 then extracted with ethyl acetate gave brine wash separate out organic layer dried over anhydrous sodium sulfate filtered and concentrated under reduced pressure to get the crude compound and it was purified by column chromatography eluted with 10 to 50% ethyl acetate in Hexane to get 6-benzyl-1H-benzo[cd]indol-2-one (0.190 g, 718.08 umol, 90.83% yield, 98% purity) as yellow solid. LC-MS: (ES+)=260.2 [M+H]+.

Step-3: Synthesis of 3-(6-benzyl-2-oxo-benzo[cd]indol-1-yl)piperidine-2,6-dione: 6-benzyl-1H-benzo[cd]indol-2-one (0.100 g, 385.65 umol) was dissolved in THF (10 mL) then cooled to 0° C. later Sodium hydride (in oil dispersion) 60% dispersion in mineral oil (147.77 mg, 3.86 mmol, 60% purity) was added portion wise and stirred at 0° C. for 30 mins, later 3-bromopiperidine-2,6-dione (370.25 mg, 1.93 mmol) was added and reaction mixture was stirred at RT for 30 mins, later stirred at 0° C. for 16 hr. The progress of the reaction was monitored by TLC, after reaction completion reaction mixture was quenched with chilled water then extracted with ethyl acetate gave brine wash separate out organic layer dried over dried over anhydrous sodium sulfate filtered and concentrated under reduced pressure to get the crude compound and it was purified by column chromatography eluted with 10 to 50% ethyl acetate in Hexane and followed by again purified by column chromatography eluted with 5 to 20% MeOH in DCM to get 3-(6-benzyl-2-oxo-benzo[cd]indol-1-yl)piperidine-2,6-dione Compound 277 (50 mg, 134.26 umol, 34.81% yield, 99.46% purity) yellow solid. 1HNMR (400 MHz, DMSO-d6): δ 11.11 (s, 1H), 8.33-8.30 (d, J=12 Hz, 1H), 8.07-8.06 (d, J=4 Hz, 1H), 7.82-7.78 (m, 1H), 7.41-7.39 (d, J=8 Hz, 1H), 7.29-7.24 (m, 4H), 7.17-7.15 (m, 1H) 7.11-7.09 (d, J=8 Hz, 1H), 5.46-5.41 (m, 1H), 4.39 (s, 2H), 2.98-2.90 (m, 1H), 2.79-2.70 (m, 1H), 2.66-2.62 (m, 1H), 2.10-2.09 (m, 1H). LC-MS: (ES+)=371.1 [M+H]+.

Example 161. Synthesis of 3-[6-[[3-fluoro-4-(morpholinomethyl)phenyl]methyl]-2-oxo-benzo[cd]indol-1-yl]piperidine-2,6-dione (Compound 278)

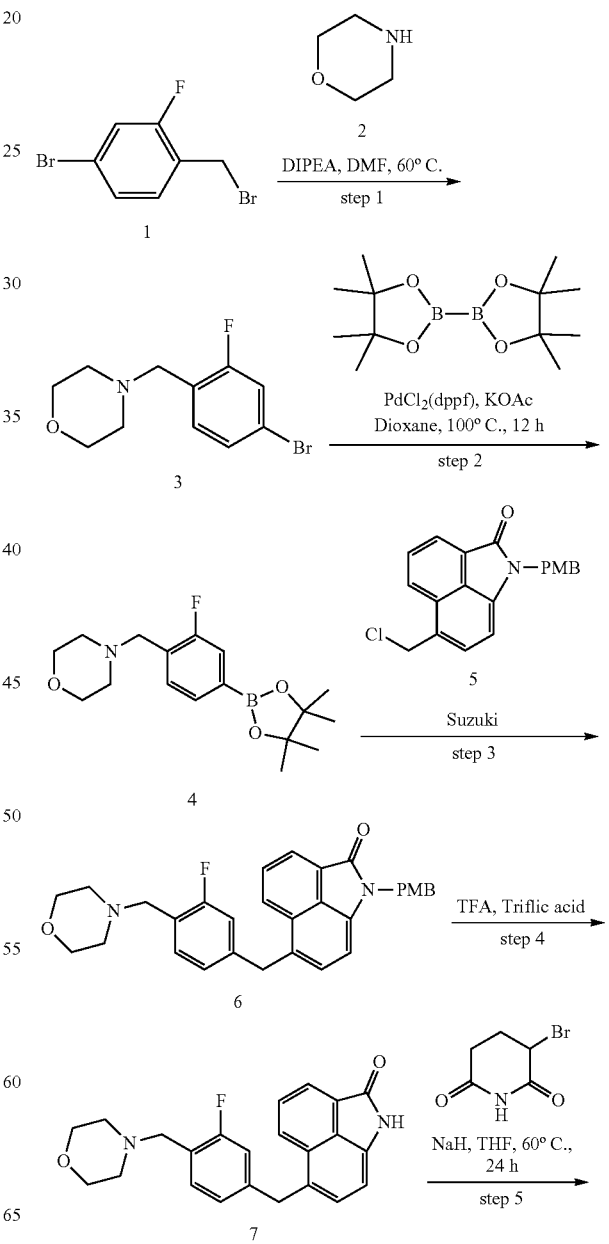

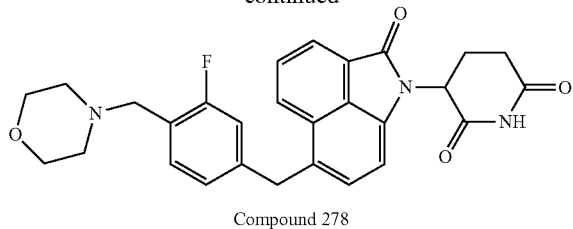

Compound 278

Step-1: Synthesis of 4-[(4-bromo-2-fluoro-phenyl)methyl]morpholine: To stirred solution of morpholine (812 mg, 9.32 mmol, 815.26 uL) in Acetone (100 mL) was added Potassium carbonate, anhydrous, 99% (3.22 g, 23.30 mmol, 1.41 mL) stirred for 10 minutes and then 4-bromo-1-(bromomethyl)-2-fluoro-benzene (3.00 g, 11.18 mmol) was added and stirred the reaction mixture at 60° C. for 8 hr. After completion of SM, reaction mixture was concentrated under reduced pressure, then diluted with ethyl acetate and washed with water, organic layer separated, dried over sodium sulphate, dried under rotavaour to give the title compound 4-[(4-bromo-2-fluoro-phenyl)methyl]morpholine (2.5 g, 92.95% yield, 95% purity) as a white solid. LC-MS: (ES+)=276.1 [M+H]+.

Step-2: Synthesis of 4-[[2-fluoro-4-(4,4,5,5-tetramethyl-1,3,2-dioxaborolan-2-yl)phenyl]methyl]morpholine: To a stirred solution of 4-[(4-bromo-2-fluoro-phenyl)methyl]morpholine (1 g, 3.65 mmol), 4,4,5,5-tetramethyl-2-(4,4,5,5-tetramethyl-1,3,2-dioxaborolan-2-yl)-1,3,2-dioxaborolan (1.20 g, 4.74 mmol) and Potassium Acetate (895.02 mg, 9.12 mmol, 570.07 uL) in 1,4-Dioxane (15 mL) was purged with Argon for 10 minutes then cyclopentyl(diphenyl)phosphane; dichloromethane; dichloropalladium; iron (297.90 mg, 364.79 umol) was added and heated the reaction mixture for 14 hr at 90° C. The reaction mixture was diluted with ethyl acetate and washed with water followed by brine. The organic layer was dried over sodium sulphate and concentrated. The crude material was purified by silica gel column chromatography by 15% ethyl acetate in hexane to afford 4-[[2-fluoro-4-(4,4,5,5-tetramethyl-1,3,2-dioxaborolan-2-yl)phenyl]methyl]morpholine (1 g, 72.54% yield, 85% Purity) as yellow sticky gum. LCMS (ES+)=322.4 [M+H]+.

Step-3: Synthesis of 6-[[3-fluoro-4-(morpholinomethyl)phenyl]methyl]-1-[(4-methoxyphenyl)methyl]benzo[cd]indol-2-one: To a stirred solution of 4-[[2-fluoro-4-(4,4,5,5-tetramethyl-1,3,2-dioxaborolan-2-yl)phenyl]methyl]morpholine 4 (350 mg, 1.09 mmol) intoluene (10 mL) and Ethanol (5 mL) was added 6-(chloromethyl)-1-[(4-methoxyphenyl)methyl]benzo[cd]indol-2-one 5 (552.14 mg, 1.63 mmol), tripotassium phosphate (578.27 mg, 2.72 mmol). The reaction mixture was degassed with argon for 15 minutes. Then tris-o-tolylphosphane (66.33 mg, 217.94 umol) and Tris(Dibenzylideneacetone)dipalladium (0) (99.78 mg, 108.97 umol) was added and again purged for 5 minutes. The reaction mixture was stirred and heated at 100° C. for 14 hr. The reaction mixture was evaporated and diluted with ethyl acetate and washed with water, followed by brine. The organic layer was dried over sodium sulphate and concentrated and the crude material was purified by silica gel column chromatography by 15-20% ethyl acetate in hexane to afford the 6-[[3-fluoro-4-(morpholinomethyl)phenyl]methyl]-1-[(4-methoxyphenyl)methyl]benzo[cd]indol-2-one (450 mg, 81.08% yield, 97.5% Purity) as yellowish solid. LCMS (ES+)=497.5 [M+H]+.

Step-4: Synthesis of 6-[[3-fluoro-4-(morpholinomethyl)phenyl]methyl]-1H-benzo[cd]indol-2-one: 6-[[3-fluoro-4-(morpholinomethyl)phenyl]methyl]-1-[(4-methoxyphenyl)methyl]benzo[cd]indol-2-one (450 mg, 906.21 umol) in TFA (10 mL) in cooled condition was added Triflic acid (2.04 g, 13.59 mmol, 1.19 mL) dropwise. The reaction mixture was stirred at 25° C. for 16 hr. The reaction mixture was evaporated and quenched with saturated sodium bicarbonate solution, extracted with ethyl acetate, washed with water followed by brine. The organic part was dried over sodium sulphate and concentrated to afford the desired compound 6-[[3-fluoro-4-(morpholinomethyl)phenyl]methyl]-1H-benzo[cd]indol-2-one (210 mg, 55.41% yield, 90% Purity) as brown solid. LCMS (ES+)=377.0 [M+H].

Step-5: Synthesis of 3-[6-[[3-fluoro-4-(morpholinomethyl)phenyl]methyl]-2-oxo-benzo[cd]indol-1-yl]piperidine-2,6-dione: To a stirred solution of 6-[[3-fluoro-4-(morpholinomethyl)phenyl]methyl]-1H-benzo[cd]indol-2-one (200 mg, 531.32 umol) in THF (15 mL) was added Sodium hydride (in oil dispersion) 60% dispersion in mineral oil (212.51 mg, 5.31 mmol, 60% purity) portionwise at 0° C. and stirred for 10 mins maintain at 0° C. After that slowly added 3-bromopiperidine-2,6-dione (510.09 mg, 2.66 mmol) then reaction mass stirred allowed to 85° C. for 1 hr. The progress of the reaction was monitored by TLC, SM was consumed in TLC. Then the reaction mass quenched with ice water and the reaction mixture was extracted with ethyl acetate and ethyl acetate part washed with water, followed by brine. The organic part was dried over sodium sulphate and concentrated under reduced pressure to give the crude. This crude was purified by Preparative HPLC to afford 3-[6-[[3-fluoro-4-(morpholinomethyl)phenyl]methyl]-2-oxo-benzo[cd]indol-1-yl]piperidine-2,6-dione (50 mg, 19.13% yield, 99.12% purity) as yellow solid. 1H NMR (400 MHz, DMSO-d6): δ 11.12 (s, 1H), 8.34 (d, J=8.2 Hz, 1H), 8.08 (d, J=6.9 Hz, 1H), 7.82 (t, J=7.6 Hz, 1H), 7.43 (d, J=7.3 Hz, 1H), 7.27 (t, J=7.8 Hz, 1H), 7.12-7.07 (m, 3H), 5.46-5.42 (m, 1H), 4.39 (s, 2H), 3.52-3.50 (m, 4H), 3.42 (s, 2H), 2.99-2.91 (m, 1H), 2.79-2.73 (m, 1H), 2.70-2.63 (m, 1H), 2.31 (m, 4H), 2.10-2.07 (m, 1H). LCMS (ES+)=488.2 [M+H]+.

Example 162. Synthesis of 4-[4-[[5-[[1-(2,6-dioxo-3-piperidyl)-2-oxo-benzo[cd]indol-6-yl]methyl]-2-pyridyl]methyl]piperazin-1-yl]-3-fluoro-benzonitrile (Compound 279)

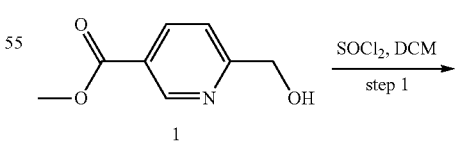

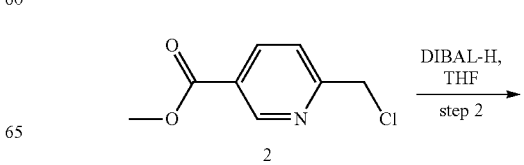

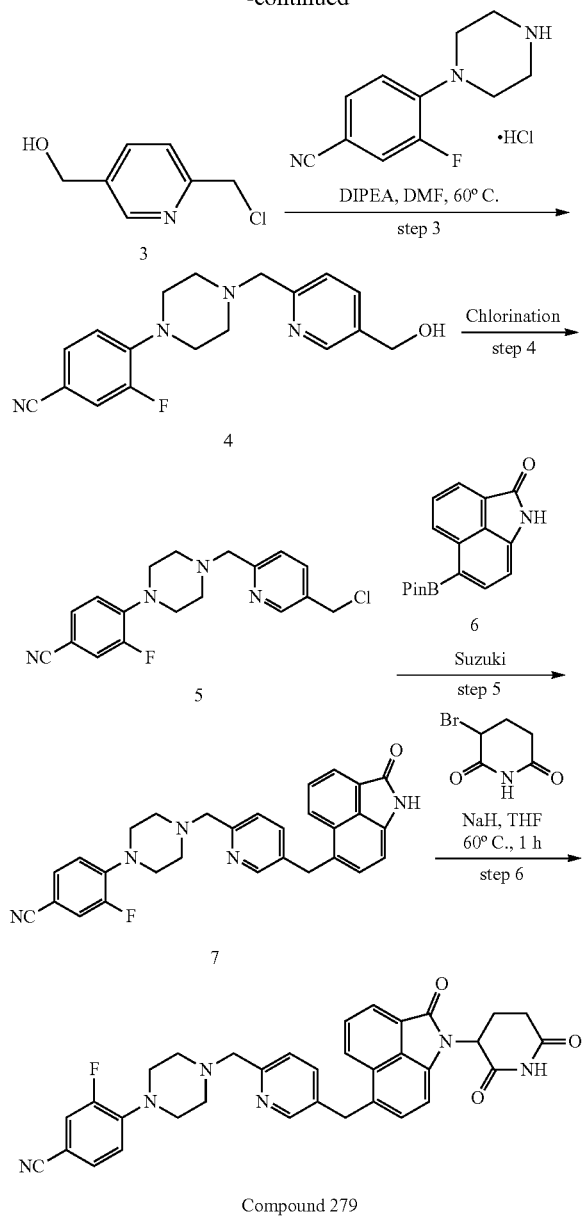

Compound 279

Step-1: Synthesis of methyl 6-(chloromethyl)pyridine-3-carboxylate: Methyl 6-(hydroxymethyl)pyridine-3-carboxylate (1 g, 5.98 mmol) was added portion wise to Thionyl chloride (14.23 g, 119.60 mmol, 8.68 mL) in ice cold condition and stirred the reaction mixture for 2 hr at 25° C. The reaction mixture was evaporated then quenched with sodium bicarbonate solution extracted with ethyl acetate. The organic layer was washed with water followed by brine and dried over sodium sulphate and concentrated. The crude material was purified by column chromatography by 20% ethyl acetate in hexane to afford methyl 6-(chloromethyl)pyridine-3-carboxylate (600 mg, 52.98% yield, 98% Purity) as yellowish solid. LCMS (ES+)=186.2 [M+H]+.

Step-2: Synthesis of [6-(chloromethyl)-3-pyridyl]methanol: To a stirred solution of methyl 6-(chloromethyl)pyridine-3-carboxylate (3.5 g, 18.86 mmol) in THF (40 mL) was cooled-40° C. and Diisobutylaluminum hydride, 25% w/w in hexane (21.45 g, 37.71 mmol, 30.61 mL, 25% purity) was added dropwise. The reaction mixture was stirred at ambient temperature for 2 hr. The reaction mixture was quenched with 20% Sodium potassium tertrate solution and extracted with ethyl acetate. The organic layer was washed with water followed by brine and dried over sodium sulphate, concentrated to afford [6-(chloromethyl)-3-pyridyl]methanol (1.9 g, 57.54% yield, 90% Purity) as deep brown gum. LCMS (ES+)=157.9 [M+H]+.

Step-3: Synthesis of 3-fluoro-4-[4-[[5-(hydroxymethyl)-2-pyridyl]methyl]piperazin-1-yl]benzonitrile: To stirred solution of 3-fluoro-4-piperazin-1-yl-benzonitrile (2 g, 8.11 mmol, 021) in DMF (20 mL) was added Potassium carbonate, anhydrous, 99% (2.80 g, 20.26 mmol, 1.22 mL) stirred for 10 minutes and then [6-(chloromethyl)-3-pyridyl]methanol (1.53 g, 9.73 mmol) was added and stirred the reaction mixture at 60° C. for 8 hr. TLC reaction mixture was filtered through a celite bed and diluted with ethyl acetate and washed with water followed by brine. The reaction mixture was dried over Sodium sulphate and concentrated. Purified by silica gel chromatography by 12-15% Ethyl acetate in hexane to afford 3-fluoro-4-[4-[[5-(hydroxymethyl)-2-pyridyl]methyl]piperazin-1-yl]benzonitrile (1.5 g, 55.84% yield, 100% Purity) as a white solid. LCMS (ES+)=327.5 [M+H]+.

Step-4: Synthesis of 4-[4-[[5-(chloromethyl)-2-pyridyl]methyl]piperazin-1-yl]-3-fluoro-benzonitrile: 3-fluoro-4-[4-[[5-(hydroxymethyl)-2-pyridyl]methyl]piperazin-1-yl]benzonitrile (1.2 g, 3.68 mmol) was added portionwise to Thionyl chloride (13.12 g, 110.31 mmol, 8.00 mL) in ice cold condition and stirred the reaction mixture for 2 hr at 25° C. The reaction mixture was evaporated then quenched with sodium bicarbonate solution extracted with ethyl acetate. The organic layer was washed with water followed by brine and dried over sodium sulphate and concentrated. The material was titrated with Pentane to afford 4-[4-[[5-(chloromethyl)-2-pyridyl]methyl]piperazin-1-yl]-3-fluoro-benzonitrile (1 g, 74.93% yield, 95% Purity) as yellowish solid. LCMS (ES+)=345.1 [M+H]+.

Step-5: Synthesis of 3-fluoro-4-[4-[[5-[(2-oxo-1H-benzo[cd]indol-6-yl)methyl]-2-pyridyl]methyl]piperazin-1-yl]benzonitrile: To a stirred solution of 4-[4-[[5-(chloromethyl)-2-pyridyl]methyl]piperazin-1-yl]-3-fluoro-benzonitrile (1 g, 2.90 mmol) intoluene (16 mL) and Ethanol (8 mL) was added 6-(4,4,5,5-tetramethyl-1,3,2-dioxaborolan-2-yl)-1H-benzo[cd]indol-2-one 6 (1.71 g, 5.80 mmol), tripotassium phosphate (1.54 g, 7.25 mmol). The reaction mixture was degassed with argon for 15 minutes. Then tris-o-tolylphosphane (176.54 mg, 580.02 umol) and Tris (Dibenzylideneacetone)dipalladium (0) (265.57 mg, 290.01 umol) was added and again purged for 5 minutes. The reaction mixture was stirred and heated at 100° C. for 14 hr. The reaction mixture was evaporated and diluted with ethyl acetate and washed with water, followed by brine. The organic layer was dried over sodium sulphate and concentrated. The crude material was purified by silica gel column chromatography by 15-20% ethyl acetate in hexane to afford 3-fluoro-4-[4-[[5-[(2-oxo-1H-benzo[cd]indol-6-yl)methyl]-2-pyridyl]methyl]piperazin-1-yl]benzonitrile (400 mg, 25.99% yield, 90% Purity) as yellowish solid. LCMS (ES+)=478.3 [M+H]+.

Step-6: Preparation of 4-[4-[[5-[[1-(2,6-dioxo-3-piperidyl)-2-oxo-benzo[cd]indol-6-yl]methyl]-2-pyridyl]methyl]piperazin-1-yl]-3-fluoro-benzonitrile: To a stirred solution of 3-fluoro-4-[4-[[5-[(2-oxo-1H-benzo[cd]indol-6-yl)methyl]-2-pyridyl]methyl]piperazin-1-yl]benzonitrile 7 (400 mg, 837.64 umol) in THF (20 mL) was added Sodium hydride (in oil dispersion) 60% dispersion in mineral oil (320.96 mg, 8.02 mmol, 60% purity) portionwise at 0° C. and stirred for 10 mins maintain at 0° C. After that slowly added 3-bromopiperidine-2,6-dione (804.18 mg, 4.19 mmol) then reaction mass stirred allowed to 85° C. for 1 hr. The progress of the reaction was monitored by TLC, SM was consumed in TLC. Then the reaction mass quenched with cool ice water and the reaction mixture was diluted with ethyl acetate and washed with water, organic layer separated, dried over sodium sulphate and concentrated under reduced pressure to give the crude. This crude was purified by Preparative HPLC to afford 4-[4-[[5-[[1-(2,6-dioxo-3-piperidyl)-2-oxo-benzo[cd]indol-6-yl]methyl]-2-pyridyl]methyl]piperazin-1-yl]-3-fluoro-benzonitrile 8 (88 mg, 17.49% yield, 97.98% purity) Compound 279 as yellow solid. LCMS (ES+)=589.2 [M+H]+. 1H NMR (400 MHz, DMSO-d6): δ 11.12 (s, 1H), 8.55 (s, 1H), 8.38 (d, J=8.3 Hz, 1H), 8.09 (d, J=7.0 Hz, 1H), 7.32 (t, J=7.7 Hz, 1H), 7.69-7.61 (m, 2H), 7.55 (d, J=8.4 Hz, 1H), 7.44 (d, J=7.4 Hz, 1H), 7.34 (d, J=8.0 Hz, 1H), 7.13-7.11 (m, 2H), 5.46-5.42 (m, 1H), 4.41 (s, 2H), 3.59 (s, 2H), 3.15 (m, 4H), 2.99-2.90 (m, 1H), 2.81-2.73 (m, 1H), 2.70-2.63 (m, 1H), 2.63-2.52 (m, 4H, merged with solvent peak), 2.10 (m, 1H).

Example 163. Synthesis of 3-[6-[[1-[1-[1-cyclobutylethyl]-4-piperidyl] pyrazol-4-yl]methyl]-2-oxo-benzo[cd]indol-1-yl]piperidine-2,6-dione (Compound 280) and 3-[6-[[1-[1-[1-cyclobutylethyl]-4-piperidyl]pyrazol-4-yl]methyl]-2-oxo-benzo[cd]indol-1-yl]piperidine-2,6-dione (Compound 281)

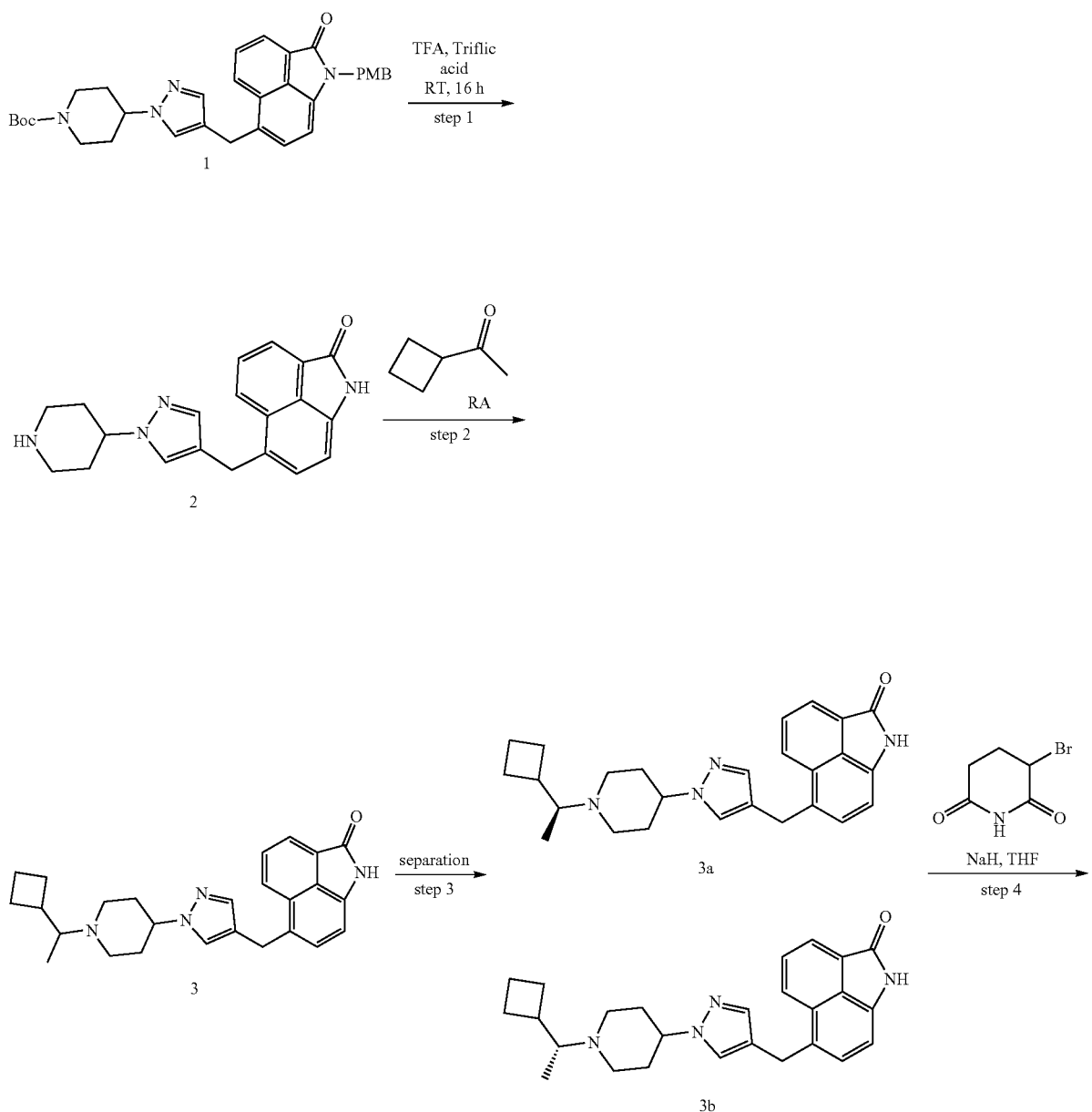

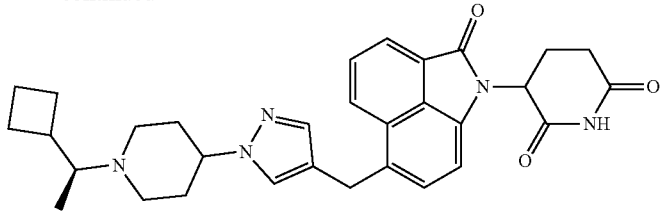

Compound 280

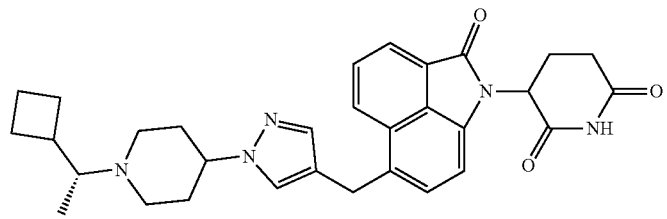

Compound 281

Step-1: Synthesis of 6-[[1-(4-piperidyl)pyrazol-4-yl] methyl]-1H-benzo[cd]indol-2-one: 32-[(4-methoxyphenyl) methyl]-23-[[1-(1-methyl-4-piperidyl)pyrazol-4-yl] methyl]-28,32-diazatri cyclododeca-2(4),3(20),10(23),21 (24),25(28)-pentaen-27-one; 2-methylpropan-2-ol; hydrate (600 mg, 1.07 mmol) in DCM (3 mL) in cooled condition was added TFA (2.44 g, 21.44 mmol, 1.65 mL) drop wise. The reaction mixture was stirred at 25° C. for 14 hr. The reaction mixture was evaporated and quenched with saturated sodium bicarbonate solution, extracted with ethyl acetate, washed with water followed by brine. The organic part was dried over sodium sulphate and concentrated and we get 6-[[1-(4-piperidyl)pyrazol-4-yl]methyl]-1H-benzo [cd]indol-2-one (390 mg, 72.19% yield, 90% purity) as solid. LCMS (ES+)=333.4 [M+H]+.

Step-2 & Step 3: Synthesis of 6-[[1-[1-(1-cyclobutyl-ethyl)-4-piperidyl]pyrazol-4-yl]methyl]-1H-benzo[cd]in-dol-2-one, 6-[[1-[1-[1-cyclobutylethyl]-4-piperidyl]pyrazol-4-yl]methyl]-1H-benzo[cd]indol-2-one and 6-[[1-[1-[1-cyclobutylethyl]-4-piperidyl]pyrazol-4-yl]methyl]-1H-benzo[cd]indol-2-one: To the stirred solution of 6-[[1-(1-chloro-4-piperidyl)pyrazol-4-yl]methyl]-1H-benzo[cd] indol-2-one (500 mg, 1.36 mmol) in THF (10 mL) was added Triethylamine (274.33 mg, 2.71 mmol, 377.87 uL) followed by the addition of 1-cyclobutylethanone (159.64 mg, 1.63 mmol, 177.38 uL), Dibutyltindichloride (494.25 mg, 1.63 mmol, 363.42 uL) and Phenylsilane (146.68 mg, 1.36 mmol, 167.06 uL). The reaction mixture was then stirred at 90° C. for 16 hours. TLC was checked which showed formation of the desired spot. The reaction mixture was diluted with ethyl acetate, washed with sodium bicarbonate solution, water and brine solution. The organic fraction was separated. It was dried over anhydrous sodium sulphate, evaporated under reduced pressure to obtain the crude compound which was purified by flash chromatography using 3-5% MeOH-DCM to afford cpd-3 6-[[1-[1-(1-cyclobutylethyl)-4-piperidyl]pyrazol-4-yl]methyl]-1H-benzo[cd]indol-2-one as enantiomeric mixture, which was further purified by chiral Prep HPLC using C Amylose A (250×30 mm) 5p, in a mobile phase of 40% CO₂+60% (0.3% Isopropylamine in MeOH, at a flow rate of 25 g/min, ABPR: 100 bar and Temperature: 35° C., to afford 3a 6-[[1-[1-[1-cyclobutylethyl]-4-piperidyl]pyrazol-4-yl] methyl]-1H-benzo[cd]indol-2-one (105 mg, 18.50% Yield, 99% Purity, ee: 100%) first eluent from the chiral column assigned as peak-1 along with 3b 6-[[1-[1-[1-cyclobutyl-ethyl]-4-piperidyl]pyrazol-4-yl]methyl]-1H-benzo[cd]in-dol-2-one (110 mg, 19.38% Yield, 99% Purity, ee: 98.10%) second eluent from the chiral column assigned as Peak-2 LC-MS: (ES+)=415.4 [M+H]+.

Step-4 Synthesis of 4a: Synthesis of 3-(6-((1-(1-(1-cy-clobutylethyl)piperidin-4-yl)-1H-pyrazol-4-yl)methyl)-2-oxobenzo[cd]indol-1(2H)-yl)piperidine-2,6-dione: To a stirred solution of 6-[[1-[1-[1-cyclobutylethyl]-4-piperidyl] pyrazol-4-yl]methyl]-1H-benzo[cd]indol-2-one (100 mg, 241.23 umol) in THF (10 mL) was added Sodium hydride (in oil dispersion) 60% dispersion in mineral oil (92.43 mg, 2.31 mmol, 60% purity) portion wise at 0° C. and stirred for 10 mins maintain at 0° C. After that slowly added 3-bromopiperidine-2, 6-dione (231.59 mg, 1.21 mmol) then reaction mass stirred allowed to 85° C. for 1 hr. The progress of the reaction was monitored by TLC and LCMS, SM was consumed in TLC. Then the reaction mass quenched with cool ice water and the reaction mixture was diluted with ethyl acetate and washed with water, organic layer separated, dried over sodium sulphate and concentrated under reduced pressure to give the crude. This crude was purified by Preparative HPLC to afford 3-[6-[[1-[1-[1-cyclobutyl-ethyl]-4-piperidyl] pyrazol-4-yl]methyl]-2-oxo-benzo[cd] indol-1-yl]piperidine-2,6-dione Compound 280 (48 mg, 36.48% yield, 96.38% purity) as yellow solid. LCMS (ES+)=526.2 [M+H]+. 1H NMR (400 MHz, DMSO-d6): δ 11.12 (s, 1H), 8.38 (d, J=8.4 Hz, 1H), 8.08 (d, J=6.9 Hz, 1H), 7.83 (t, J=7.6 Hz, 1H), 7.56 (s, 1H), 7.35 (d, J=7.3 Hz, 1H), 7.28 (s, 1H), 7.07 (d, J=7.1 Hz, 1H), 5.45-5.42 (m, 1H), 4.17 (s, 2H), 3.94 (m, 1H), 2.95-2.92 (m, 1H), 2.76-2.57 (m, 4H), 2.45 (m, 1H), 2.37-2.32 (m, 2H), 2.19-2.14 (m, 1H), 2.09-2.08 (m, 1H), 1.89-1.81 (m, 4H), 1.77-1.67 (m, 5H), 1.61-1.59 (m, 1H), 0.79 (d, J=6.4 Hz, 3H).

Step 4: Synthesis of 4b: Synthesis of 3-[6-[[1-[1-[1-cyclobutylethyl]-4-piperidyl]pyrazol-4-yl]methyl]-2-oxo-benzo[cd]indol-1-yl]piperidine-2,6-dione: To a stirred solution of 6-[[1-[1-[1-cyclobutylethyl]-4-piperidyl]pyrazol-4-yl]methyl]-1H-benzo[cd]indol-2-one (100.00 mg, 241.23 umol) in THF (10 mL) was added Sodium hydride (in oil dispersion) 60% dispersion in mineral oil (92.43 mg, 2.31 mmol, 60% purity) portion wise at 0° C. and stirred for 10 mins maintain at 0° C. After that slowly added 3-bromopiperidine-2, 6-dione (231.59 mg, 1.21 mmol) then reaction mass stirred allowed to 85° C. for 1 hr. The progress of the reaction was monitored by TLC and LCMS, SM was consumed in TLC. Then the reaction mass quenched with cool ice water and the reaction mixture was diluted with ethyl acetate and washed with water, organic layer separated, dried over sodium sulphate and concentrated under reduced pressure to give the crude. This crude was purified by Preparative HPLC to afford 3-[6-[[1-[1-[1-cyclobutylethyl]-4-piperidyl]pyrazol-4-yl]methyl]-2-oxo-benzo[cd]indol-1-yl]piperidine-2,6-dione Compound 281 (44 mg, 33.45% yield, 96.4% purity) as yellow solid. LCMS (ES+)=526.3 [M+H]+. 1H NMR (400 MHz, DMSO-d6): δ 11.12 (s, 1H), 8.38 (d, J=8.2 Hz, 1H), 8.08 (d, J=6.9 Hz, 1H), 7.83 (t, J=7.5 Hz, 1H), 7.56 (s, 1H), 7.35 (d, J=7.3 Hz, 1H), 7.28 (s, 1H), 7.07 (d, J=7.2 Hz, 1H), 5.44-5.42 (m, 1H), 4.17 (s, 2H), 3.97-3.94 (m, 1H), 2.95-2.92 (m, 1H), 2.76-2.63 (m, 5H), 2.37-2.30 (m, 2H), 2.17-2.14 (m, 1H), 2.08-2.06 (m, 1H), 1.89-1.81 (m, 4H), 1.77-1.67 (m, 5H), 1.61-1.59 (m, 1H), 0.78 (d, J=6.4 Hz, 3H).

Example 164. Synthesis of 3-(6-((1-(1-(1-cyclopropylethyl)piperidin-4-yl)-1H-pyrazol-4-yl)methyl)-2-oxobenzo[cd]indol-1(2H)-yl)piperidine-2,6-dione (Compound 282) and 3-(6-((1-(1-(1-cyclopropylethyl)piperidin-4-yl)-1H-pyrazol-4-yl)methyl)-2-oxobenzo[cd]indol-1(2H)-yl)piperidine-2,6-dione (Compound 283)

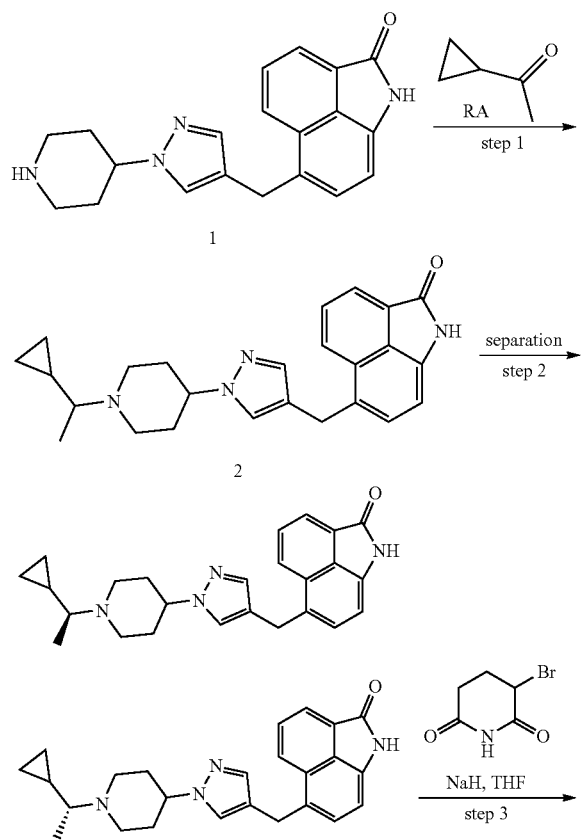

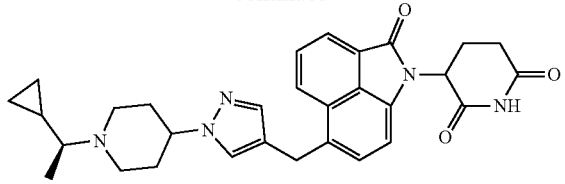

Compound 282

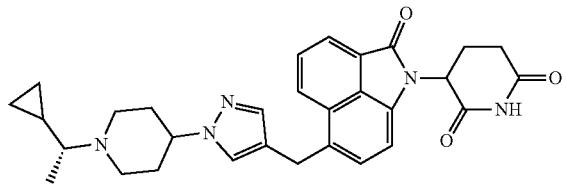

Compound 283

Step-1 & Step 2: Synthesis of 6-((1-(1-(1-cyclopropylethyl)piperidin-4-yl)-1H-pyrazol-4-yl)methyl)benzo[cd]indol-2(1H)-one, 6-[[1-[1-[1-cyclopropylethyl]-4-piperidyl]pyrazol-4-yl]methyl]-1H-benzo[cd]indol-2-one and 6-[[1-[1-[1-cyclopropylethyl]-4-piperidyl]pyrazol-4-yl]methyl]-1H-benzo[cd]indol-2-one: To the stirred solution of 6-[[1-(1-chloro-4-piperidyl)pyrazol-4-yl]methyl]-1H-benzo[cd]indol-2-one (750 mg, 2.03 mmol) in THF (12 mL) was added Triethylamine (411.50 mg, 4.07 mmol, 566.80 uL) followed by the addition of 1-cyclopropylethanone (205.24 mg, 2.44 mmol, 241.74 uL), Dibutyltindichloride (741.38 mg, 2.44 mmol, 545.13 uL) and Phenylsilane (220.02 mg, 2.03 mmol, 250.60 uL). The reaction mixture was then stirred at 90° C. for 16 hours. TLC was checked which showed formation of the desired spot. The reaction mixture was diluted with ethyl acetate, washed with sodium bicarbonate solution, water and brine solution. The organic fraction was separated. It was dried over anhydrous sodium sulphate, evaporated under reduced pressure to obtain the crude compound which was purified by flash chromatography using 3-5% MeOH-DCM to afford cpd-2 6-[[1-[1-(1-cyclopropylethyl)-4-piperidyl]pyrazol-4-yl]methyl]-1H-benzo[cd]indol-2-one as enantiomeric mixture, which was further purified by chiral Prep HPLC using Chiralpak IG (250×20 mm) 5µ with mobile phase of 55% CO$_2$+45% (0.5% Isopropylamine in Methanol, at a flow rate of 25 g/min, ABPR: 120 bar and Temperature: 35° C., to afford 2a 6-[[1-[1-[1-cyclopropylethyl]-4-piperidyl]pyrazol-4-yl]methyl]-1H-benzo[cd]indol-2-one (90 mg, 10.94% Yield, 99% Purity, ee:97.56%) first eluent from the chiral column assigned as peak-1 along with 2b 6-[[1-[1-[1-cyclopropylethyl]-4-piperidyl]pyrazol-4-yl]methyl]-1H-benzo[cd]indol-2-one (80 mg, 9.73% Yield, 99% Purity, ee: 100%) second eluent from the chiral column assigned as Peak-2 LC-MS: (ES+)=401.1 [M+H]$^+$.

Step-3 part 3a: Synthesis of 3-[6-[[1-[1-[1-cyclopropylethyl]-4-piperidyl]pyrazol-4-yl]methyl]-2-oxo-benzo[cd]indol-1-yl]piperidine-2,6-dione: To a stirred solution of 6-[[1-[1-[1-cyclopropylethyl]-4-piperidyl]pyrazol-4-yl]methyl]-1H-benzo[cd]indol-2-one (85 mg, 212.23 umol) in THF (10 mL) was added Sodium hydride (in oil dispersion) 60% dispersion in mineral oil (81.32 mg, 2.03 mmol, 60% purity) portion wise at 0° C. and stirred for 10 mins maintain at 0° C. After that slowly added 3-bromopiperidine-2, 6-dione (203.75 mg, 1.06 mmol) then reaction mass stirred allowed to 85° C. for 1 hr. The progress of the reaction was monitored by TLC and LCMS, SM was consumed in TLC.

Then the reaction mass quenched with cool ice water and the reaction mixture was diluted with ethyl acetate and washed with water, organic layer separated, dried over sodium sulphate and concentrated under reduced pressure to give the crude. This crude was purified by Preparative HPLC to afford 3-[6-[[1-[1-[1-cyclopropylethyl]-4-piperidyl]pyrazol-4-yl]methyl]-2-oxo-benzo[cd]indol-1-yl]piperidine-2,6-dione Compound 282 (50 mg, 44.41% yield, 96.43% purity) as off white solid LCMS (ES+)=512.3 [M+H]+. 1H NMR (400 MHz, DMSO-d6): δ 11.11 (s, 1H), 8.38 (d, J=8.2 Hz, 1H), 8.08 (d, J=7.0 Hz, 1H), 7.83 (t, J=7.6 Hz, 1H), 7.58 (s, 1H), 7.35 (d, J=7.3 Hz, 1H), 7.29 (s, 1H), 7.07 (d, J=7.3 Hz, 1H), 5.46-5.41 (m, 1H), 4.18 (s, 2H), 4.02-4.00 (m, 1H), 3.06 (m, 1H), 2.99-2.91 (m, 2H), 2.77-2.73 (m, 1H), 2.67-2.63 (m, 1H), 2.33 (m, 1H), 2.25 (m, 1H), 2.09-1.82 (m, 6H), 1.04 (s, 3H), 0.74 (m, 1H), 0.49 (m, 1H), 0.39 (m, 1H), 0.23 (m, 1H), 0.01 (m, 1H).

Step 3 part 3b: Synthesis of 3-[6-[[1-[1-[1-cyclopropylethyl]-4-piperidyl]pyrazol-4-yl]methyl]-2-oxo-benzo[cd]indol-1-yl]piperidine-2,6-dione: To a stirred solution of 6-[[1-[1-[1-cyclopropylethyl]-4-piperidyl]pyrazol-4-yl]methyl]-1H-benzo[cd]indol-2-one (75.00 mg, 187.26 umol) in THF (10 mL) was added Sodium hydride (in oil dispersion) 60% dispersion in mineral oil (71.75 mg, 1.79 mmol, 60% purity) portion wise at 0° C. and stirred for 10 mins maintain at 0° C. After that slowly added 3-bromopiperidine-2, 6-dione (179.78 mg, 936.29 umol) then reaction mass stirred allowed to 85° C. for 1 hr. The progress of the reaction was monitored by TLC and LCMS, SM was consumed in TLC. Then the reaction mass quenched with cool ice water and the reaction mixture was diluted with ethyl acetate and washed with water, organic layer separated, dried over sodium sulphate and concentrated under reduced pressure to give the crude. This crude was purified by Preparative HPLC to afford 3-[6-[[1-[1-[1-cyclopropylethyl]-4-piperidyl]pyrazol-4-yl]methyl]-2-oxo-benzo[cd]indol-1-yl]piperidine-2,6-dione Compound 283 (47 mg, 48.66% yield, 99.19% purity) as off white solid. LCMS (ES+)=512.5 [M+H]+. 1H NMR (400 MHz, DMSO-d6): δ 11.12 (s, 1H), 8.38 (d, J=8.2 Hz, 1H), 8.08 (d, J=7.0 Hz, 1H), 7.83 (t, J=7.6 Hz, 1H), 7.58 (s, 1H), 7.35 (d, J=7.3 Hz, 1H), 7.29 (s, 1H), 7.07 (d, J=7.3 Hz, 1H), 5.44-5.41 (m, 1H), 4.18 (s, 2H), 3.99 (m, 1H), 3.03 (m, 1H), 2.95-2.92 (m, 2H), 2.76-2.73 (m, 1H), 2.67-2.63 (m, 1H), 2.33-2.24 (m, 2H), 2.08 (m, 1H), 1.89-1.79 (m, 5H), 1.02 (d, J=6.2 Hz, 3H), 0.72-0.71 (m, 1H), 0.48 (m, 1H), 0.37 (m, 1H), 0.22 (m, 1H), -0.02 (m, 1H).

Example 165. Synthesis of 3-[6-[[4-[1-[4-(2-fluorophenyl)piperazin-1-yl]ethyl]phenyl]methyl]-2-oxo-benzo[cd]indol-1-yl]piperidine-2,6-dione (Compound 284) and 3-[6-[[4-[1-[4-(2-fluorophenyl)piperazin-1-yl]ethyl]phenyl]methyl]-2-oxo-benzo[cd]indol-1-yl]piperidine-2,6-dione (Compound 285)

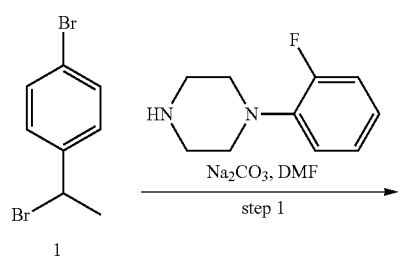

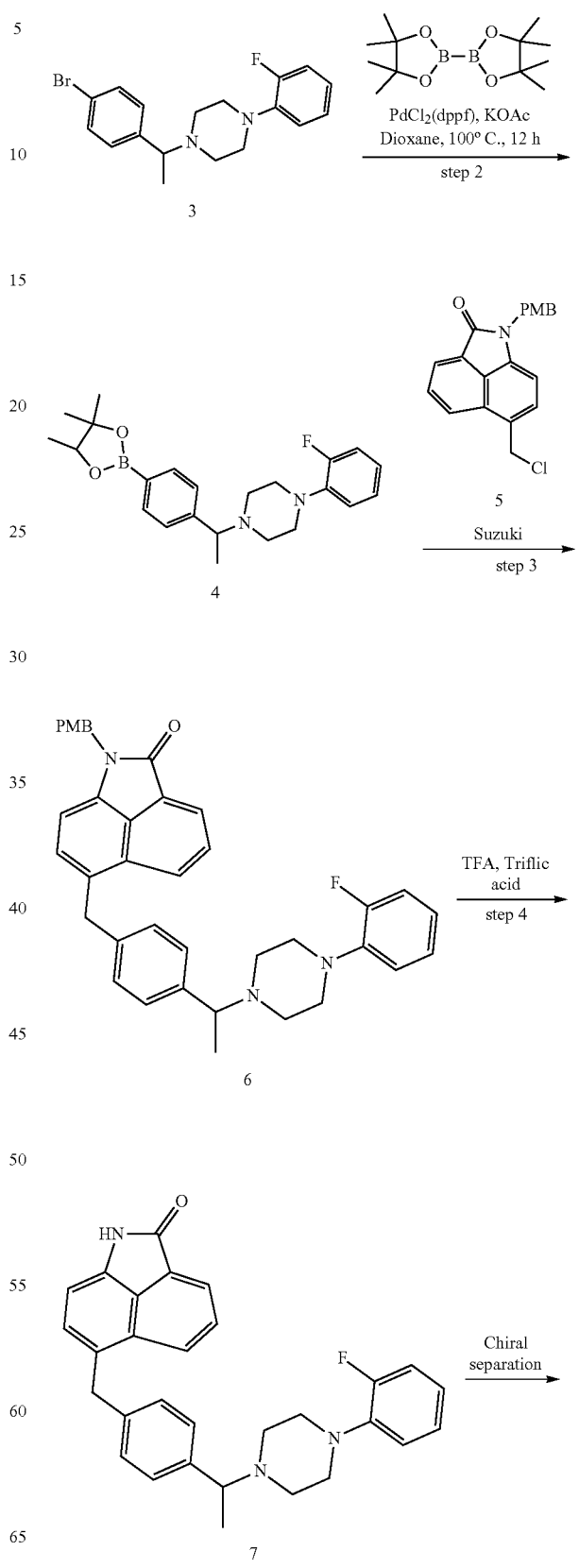

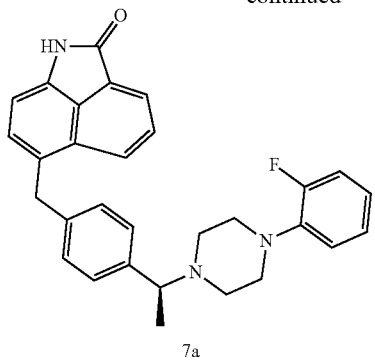

7a

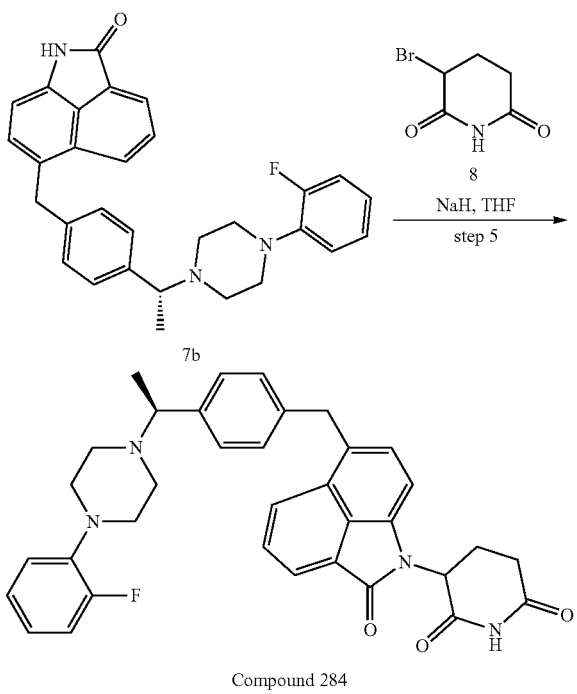

7b

Compound 284

Compound 285

Step-1: Synthesis of 1-(1-(4-bromophenyl) ethyl)-4-(2-fluorophenyl)piperazine: To a stirred solution of 1-bromo-4-(1-bromoethyl)benzene (5.0 g, 18.94 mmol) in DMF (50 mL) was added Sodium carbonate (2.01 g, 18.94 mmol, 793.56 uL) and followed by 1-(2-fluorophenyl)piperazine (3.41 g, 18.94 mmol) was added at RT and reaction mixture was stirred at RT for 16 hr. The progress of the reaction was monitored by TLC, after reaction completion reaction mixture was diluted with ethyl acetate and gave water wash and followed by brine wash separate out organic layer dried over anhydrous sodium sulfate filtered and concentrate under reduced pressure to get the crude compound and it was purified by column chromatography eluted with 0 to 30% ethyl acetate in hexane to get 1-[1-(4-bromophenyl)ethyl]-4-(2-fluorophenyl)piperazine (5.0 g, 71.21% yield) as off-white solid. LC-MS (ES+)=362.7 [M+H]+.

Step-2: Synthesis of 1-(2-fluorophenyl)-4-(1-(4-(4,4,5-trimethyl-1,3,2-dioxaborolan-2-yl)phenyl)ethyl)piperazine: To a stirred solution of 1-[1-(4-bromophenyl)ethyl]-4-(2-fluorophenyl)piperazine (5.00 g, 13.76 mmol) and 4,4,5,5-tetramethyl-2-(4,4,5,5-tetramethyl-1,3,2-dioxaborolan-2-yl)-1,3,2-dioxaborolane (3.50 g, 13.76 mmol) and Potassium acetate (3.38 g, 34.41 mmol, 2.15 mL) in a sealed tube 1,4-Dioxane (10 mL) was degassed for 10 mins, later [1,1'-Bis(diphenylphosphino)ferrocene]dichloropalladium (II), complex with dichloromethane (562.01 mg, 688.20 umol) was added again degassed for 5 mins, after degassing reaction mixture was stirred at 90° C. for 16 hr. The progress of the reaction was monitored by TLC, after reaction completion reaction mixture was filtered through celite bed and bed was washed with ethyl acetate and solvent was mixed and concentrated under reduced pressure to get the crude compound and resultant crude was purified by column chromatography eluted with 0 to 20% ethyl acetate in Hexane to get 1-(2-fluorophenyl)-4-[1-[4-(4,4,5,5-tetramethyl-1,3,2-dioxaborolan-2-yl)phenyl]ethyl]piperazine (4.0 g, 67.28% yield) as off-white solid. LC-MS: (ES+)=410.9 [M+H]+.

Step-3: Synthesis of 6-(4-(1-(4-(2-fluorophenyl) piperazin-1-yl) ethyl) benzyl)-1-(4-methoxybenzyl) benzo [cd] indol-2(1H)-one: In a sealed tube 6-(chloromethyl)-1-[(4-methoxyphenyl)methyl]benzo[cd]indol-2-one (1.0 g, 2.96 mmol),1-(2-fluorophenyl)-4-[1-[4-(4,4,5,5-tetramethyl-1,3,2-dioxaborolan-2-yl)phenyl]ethyl]piperazine (1.50 g, 3.66 mmol) and Potassium phosphate (1.57 g, 7.40 mmol) was added intoluene (24 mL) and Ethanol (12 mL) and degassed for 10 mins, later Tris(o-tolyl)phosphine (180.20 mg, 592.07 umol) and Tris(dibenzylideneacetone)dipalladium(0) (271.08 mg, 296.03 umol) was added and again degassed for 10 mins, after degassing sealed tube was closed with Teflon cap and stirred at 90° C. for 6 hr. The progress of the reaction was monitored by TLC, after reaction completion reaction mixture was filtered through celite bed and washed with ethyl acetate, solvent was mixed and concentrated under reduced pressure to get the crude compound and it was purified by column chromatography eluted with 10 to 50% ethyl acetate in Hexane to get 6-[[4-[1-[4-(2-fluorophenyl)piperazin-1-yl]ethyl]phenyl]methyl]-1-[(4-methoxyphenyl)methyl]benzo[cd]indol-2-one (0.600 g, 32.87% yield) as yellow solid. LC-MS: (ES+)=585.71 [M+H]+.

Step-4: Synthesis of 6-(4-(1-(4-(2-fluorophenyl) piperazin-1-yl) ethyl) benzyl) benzo [cd]indol-2(1H)-one, 6-[[4-[1-[4-(2-fluorophenyl)piperazin-1-yl]ethyl]phenyl]methyl]-1H-benzo[cd]indol-2-one and 6-[[4-[1-[4-(2-fluorophenyl)piperazin-1-yl]ethyl]phenyl]methyl]-1H-benzo[cd]indol-2-one: To a stirred solution of 6-[[4-[1-[4-(2-fluorophenyl)piperazin-1-yl]ethyl]phenyl]methyl]-1-[(4-methoxyphenyl)methyl]benzo[cd]indol-2-one (0.600 g, 1.02 mmol) in Trifluoroacetic acid (10 mL) was cooled to 0° C. later Triflic acid (768.71 mg, 5.12 mmol, 449.54 uL) was added then reaction mixture was stirred at RT for 16 hr. The progress of the reaction was monitored by TLC, after reaction completion reaction mixture was concentrated then resultant compound was dissolved in ethyl acetate and gave saturated solution of sodium bi carbonate and followed by brine solution, separate out organic layer dried over anhydrous sodium sulfate filtered and concentrated under reduced pressure to get the crude compound and it was purified by column chromatography eluted with 0 to 60% ethyl acetate to get cpd-7 6-[[4-[1-[4-(2 fluorophenyl)piperazin-1-yl]ethyl]phenyl]methyl]-1H-benzo[cd]indol-2-one as enantiomeric mixture. Which was further purified by chiral Prep HPLC a Column name: Chiralpak IG (21×250 mm), 5μ; Mobile Phase: Hexane/Di Chloro Methane/EtOH: 70/15/15; Flow rate: 21.0 ml/min, Run time: 20 min, Wave length: 252 nm and Solubility: MeOH to afford 7a 6-[[4-[1-[4-(2-fluorophenyl)piperazin-1-yl]ethyl]phenyl]methyl]-1H-benzo[cd]indol-2-one (0.150 g, 318.97 umol, 31.14% yield, 99% purity) first eluent from the chiral column assigned as peak-1 along with 7b 6-[[4-[1-[4-(2-fluorophenyl)piperazin-1-yl]ethyl]phenyl]methyl]-1H-benzo[cd]indol-2-one (0.150 g, 30.82% yield) second eluent from the chiral column assigned as Peak-2. LC-MS: (ES+)=466.0 [M+H]+.

Step-5: Synthesis of 3-[6-[[4-[1-[4-(2-fluorophenyl)piperazin-1-yl]ethyl]phenyl]methyl]-2-oxo-benzo[cd]indol-1-yl]piperidine-2,6-dione: To a stirred solution of 6-[[4-[1-[4-(2-fluorophenyl)piperazin-1-yl]ethyl]phenyl]methyl]-1H-benzo[cd]indol-2-one (100 mg, 214.80 umol) in THF (10 mL) was added Sodium hydride (in oil dispersion) 60% dispersion in mineral oil (98.76 mg, 2.58 mmol, 60% purity) portionwise at 0° C. and stirred for 10 mins maintain at 0° C. After that slowly added 3-bromopiperidine-2,6-dione (247.46 mg, 1.29 mmol) then reaction mass stirred allowed to 85° C. for 2 hr. The progress of the reaction was monitored by TLC, SM was consumed in TLC. Then the reaction mass quenched with cool ice water and the reaction mixture was diluted with ethyl acetate and washed with water, organic layer separated, dried over sodium sulphate and concentrated under reduced pressure to give the crude. This crude was purified by Preparative HPLC to afford 3-[6-[[4-[1-[4-(2-fluorophenyl)piperazin-1-yl]ethyl]phenyl]methyl]-2-oxo-benzo[cd]indol-1-yl]piperidine-2,6-dione Compound 284 (45 mg, 36.30% Yield) as yellow solid. LCMS (ES+)=577.3 [M+H]+. 1H NMR (400 MHz, DMSO-d6): δ 11.11 (s, 1H), 8.36 (d, J=8.2 Hz, 1H), 8.08 (d, J=−6.8 Hz, 1H), 7.82 (t, J=7.6 Hz, 1H), 7.41 (d, J=7.3 Hz, 1H), 7.26-7.20 (m, 4H), 7.11-7.05 (m, 3H), 6.99-6.97 (m, 2H), 5.46-5.42 (m, 1H), 4.38 (s, 2H), 3.39-3.37 (m, 1H), 3.29 (m, 1H), 2.95 (m, 5H), 2.79-2.70 (m, 1H), 2.67-2.63 (m, 1H), 2.42-2.41 (m, 3H), 2.11-2.08 (m, 1H), 1.26 (1, J=6.5 Hz, 3H).

Step 5: Synthesis of 3-[6-[[4-[1-[4-(2-fluorophenyl)piperazin-1-yl]ethyl]phenyl]methyl]-2-oxo-benzo[cd]indol-1-yl]piperidine-2,6-dione: To a stirred solution of 6-[[4-[1-[4-(2-fluorophenyl)piperazin-1-yl]ethyl]phenyl]methyl]-1H-benzo[cd]indol-2-one (100 mg, 214.80 umol) in THF (10 mL) was added Sodium hydride (in oil dispersion) 60% dispersion in mineral oil (98.76 mg, 2.58 mmol, 60% purity) portionwise at 0° C. and stirred for 10 mins maintain at 0° C. After that slowly added 3-bromopiperidine-2,6-dione (247.46 mg, 1.29 mmol) then reaction mass stirred allowed to 85° C. for 2 hr. The progress of the reaction was monitored by TLC, SM was consumed in TLC. Then the reaction mass quenched with cool ice water and the reaction mixture was diluted with ethyl acetate and washed with water, organic layer separated, dried over sodium sulphate and concentrated under reduced pressure to give the crude. This crude was purified by Preparative HPLC to afford 3-[6-[[4-[1-[4-(2-fluorophenyl)piperazin-1-yl]ethyl]phenyl]methyl]-2-oxo-benzo[cd]indol-1-yl]piperidine-2,6-dione Compound 285 (50 mg, 40.35% Yield) as yellow solid. LCMS (ES+)=577.3 [M+H]+. 1H NMR (400 MHz, DMSO-d6): δ 11.11 (s, 1H), 8.36 (d, J=8.2 Hz, 1H), 8.08 (d, J=7.0 Hz, 1H), 7.82 (t, J=7.6 Hz, 1H), 7.41 (d, J=7.3 Hz, 1H), 7.26-7.20 (m, 4H), 7.11-7.05 (m, 3H), 6.99-6.97 (m, 2H), 5.46-5.42 (m, 1H), 4.38 (s, 2H), 3.39-3.36 (m, 1H), 3.29 (m, 1H), 2.94 (m, 5H), 2.79-2.70 (m, 1H), 2.67-2.63 (m, 1H), 2.42-2.41 (m, 3H), 2.10-2.07 (m, 1H), 1.26 (1, J=6.5 Hz, 3H).

Example 166. Synthesis of 3-[6-[[4-[[4-(2-fluorophenyl)piperazin-1-yl]methyl]-3-methyl-phenyl]methyl]-2-oxo-benzo[cd]indol-1-yl]piperidine-2,6-dione (Compound 286)

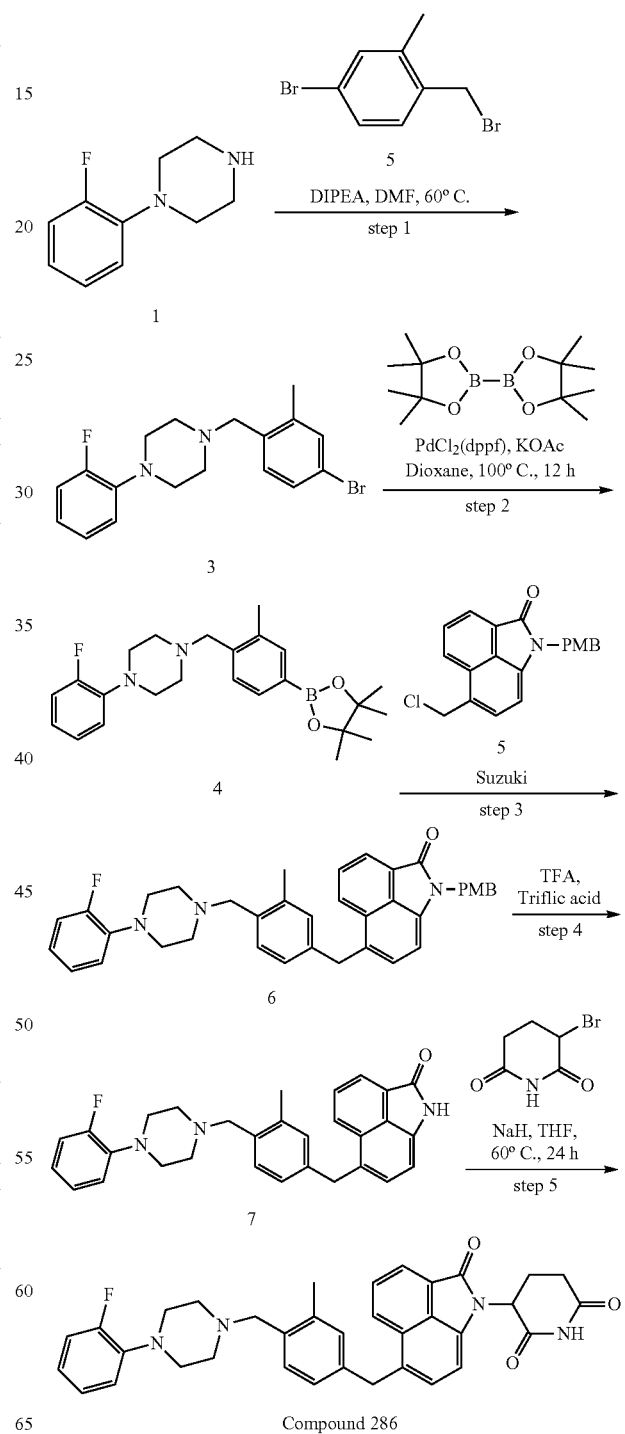

Compound 286

Step-1: Synthesis of 1-[(4-bromo-2-methyl-phenyl) methyl]-4-(2-fluorophenyl)piperazine: To stirred solution of 1-(2-fluorophenyl)piperazine (2 g, 11.10 mmol) in DMF (10 mL) was added Potassium carbonate, anhydrous, 99% (3.07 g, 22.20 mmol, 1.34 mL) stirred for 10 minutes and then 4-bromo-1-(bromomethyl)-2-methyl-benzene (3.52 g, 13.32 mmol) was added and stirred the reaction mixture at 25° C. for 16 hr. TLC reaction mixture was filtered through a celite bed and diluted with ethyl acetate and washed with water followed by brine. The reaction mixture was dried over Sodium sulphate and concentrated. Purified by silica gel chromatography by 12-15% Ethyl acetate in hexane to afford the 1-[(4-bromo-2-methyl-phenyl)methyl]-4-(2-fluorophenyl)piperazine (3.5 g, 85.06% yield, 98% purity) as a white solid; LCMS (ES+)=363.4 [M+H]+.

Step-2: Synthesis of 1-(2-fluorophenyl)-4-[[2-methyl-4-(4,4,5,5-tetramethyl-1,3,2-dioxaborolan-2-yl)phenyl] methyl]piperazine: To a stirred solution of 1-[(4-bromo-2-methyl-phenyl)methyl]-4-(2-fluorophenyl)piperazine (2 g, 5.51 mmol), 4,4,5,5-tetramethyl-2-(4,4,5,5-tetramethyl-1,3,2-dioxaborolan-2-yl)-1,3,2-dioxaborolane (1.68 g, 6.61 mmol) and Potassium Acetate (1.35 g, 13.76 mmol, 860.40 uL) in 1,4-Dioxane (25 mL) was purged with Argon for 10 minutes then cyclopentyl(diphenyl)phosphane; dichloromethane; dichloropalladium; iron (449.61 mg, 550.56 umol) was added and heated the reaction mixture for 14 hr at 90° C. The reaction mixture was diluted with ethyl acetate and washed with water followed by brine. The organic layer was dried over sodium sulphate and concentrated. The crude material was purified by silica gel column chromatography by 15% ethyl acetate in hexane to afford the 1-(2-fluorophenyl)-4-[[2-methyl-4-(4,4,5,5-tetramethyl-1,3,2-dioxaborolan-2-yl)phenyl]methyl]piperazine (1 g, 41.17% yield, 93% purity) as a white solid. LCMS (ES+)=411.6 [M+H]+.

Step-3: Synthesis of 6-[[4-[[4-(2-fluorophenyl)piperazin-1-yl]methyl]-3-methyl-phenyl]methyl]-1-[(4-methoxyphenyl)methyl]benzo[cd]indol-2-one: To a stirred solution of 1-(2-fluorophenyl)-4-[[2-methyl-4-(4,4,5,5-tetramethyl-1,3,2-dioxaborolan-2-yl)phenyl]methyl]piperazine (500 mg, 1.22 mmol) intoluene (8 mL) and Ethanol (4 mL) was added anisole; 6-(chloromethyl)-1-methyl-benzo[cd]indol-2-one (412.85 mg, 1.22 mmol), tripotassium phosphate (646.63 mg, 3.05 mmol). The reaction mixture was degassed with argon for 15 minutes. Then tris-o-tolylphosphane (74.18 mg, 243.71 umol) and Tris (Dibenzylideneacetone)dipalladium (0) (111.58 mg, 121.85 umol) was added and again purged for 5 minutes. The reaction mixture was stirred and heated at 100° C. for 14 hr. The reaction mixture was evaporated and diluted with ethyl acetate and washed with water, followed by brine. The organic layer was dried over sodium sulphate and concentrated. The crude material was purified by silica gel column chromatography by 15-20% ethyl acetate in hexane to afford the 6-[[4-[[4-(2-fluorophenyl)piperazin-1-yl]methyl]-3-methyl-phenyl]methyl]-1-[(4-methoxyphenyl)methyl]benzo[cd]indol-2-one (350 mg, 41.61% yield, 85% purity) as yellowish solid. LCMS (ES+) =586.3 [M+H]+.

Step-4: Synthesis of 6-[[4-[[4-(2-fluorophenyl)piperazin-1-yl]methyl]-3-methyl-phenyl]methyl]-1H-benzo[cd]indol-2-one: To a stirred solution of 6-[[4-[[4-(2-fluorophenyl) piperazin-1-yl]methyl]-3-methyl-phenyl]methyl]-1-[(4-methoxyphenyl)methyl]benzo[cd]indol-2-one (400 mg, 682.93 umol) in TFA (5 mL) was added Triflic acid (1.02 g, 6.83 mmol, 599.37 uL) and stirred the reaction mixture at 25° C. for 16 hr. The reaction mixture was evaporated and quenched with saturated sodium bicarbonate solution, extracted with ethyl acetate, washed with water followed by brine. The organic part was dried over sodium sulphate and concentrated and triturated with ether and pentane to afford the 6-[[4-[[4-(2-fluorophenyl)piperazin-1-yl]methyl]-3-methyl-phenyl]methyl]-1H-benzo[cd]indol-2-one (280 mg, 79.26% yield, 90% purity) as yellow solid. LCMS (ES+) =466 [M+H]+.

Step-5: Synthesis of 3-[6-[[4-[[4-(2-fluorophenyl)piperazin-1-yl]methyl]-3-methyl-phenyl]methyl]-2-oxo-benzo[cd]indol-1-yl]piperidine-2,6-dione: To a stirred solution of 6-[[4-[[4-(2-fluorophenyl)piperazin-1-yl]methyl]-3-methyl-phenyl]methyl]-1H-benzo[cd]indol-2-one (280 mg, 601.43 umol) in THF (20 mL) was added Sodium hydride (in oil dispersion) 60% dispersion in mineral oil (276.53 mg, 7.22 mmol, 60% purity) portion wise at 0° C. and stirred for 10 mins maintain at 0° C. After that slowly added 3-bromopiperidine-2,6-dione (692.88 mg, 3.61 mmol) then reaction mass stirred allowed to 85° C. for 1 hr. The progress of the reaction was monitored by TLC, SM was consumed in TLC. Then the reaction mass quenched with cool ice water and the reaction mixture was diluted with ethyl acetate and washed with water, organic layer separated, dried over sodium sulphate and concentrated under reduced pressure to give the crude. This crude was purified by Preparative HPLC to afford the 3-[6-[[4-[[4-(2-fluorophenyl)piperazin-1-yl] methyl]-3-methyl-phenyl]methyl]-2-oxo-benzo[cd]indol-1-yl]piperidine-2,6-dione Compound 286 (34 mg 9.76% yield, 99.59% purity) as yellow solid, LCMS (ES+):577.3 [M+H]+. 1H NMR (400 MHz, DMSO-d6): δ 11.12 (s, 1H), 8.34 (d, J=8.2 Hz, 1H), 8.07 (d, J=6.9 Hz, 1H), 7.81 (t, J=7.6 Hz, 1H), 7.40 (d, J=7.3 Hz, 1H), 7.14-7.04 (m, 6H), 7.00-6.91 (m, 2H), 5.46-5.42 (m, 1H), 4.37 (s, 2H), 3.41 (s, 1H), 3.3 (m, 2H, merged with solvent peak), 2.94-2.91 (m, 5H), 2.81-2.73 (m, 1H), 2.70-2.63 (m, 1H), 2.54 (m, 2H), 2.27 (s, 3H), 1.26 (m, 1H).

Example 167. Synthesis of 3-[6-[[1-[1-[1-(dimethylamino)cyclobutanecarbonyl]-4-piperidyl]pyrazol-4-yl]methyl]-2-oxo-benzo[cd]indol-1-yl]piperidine-2,6-dione (Compound 287)

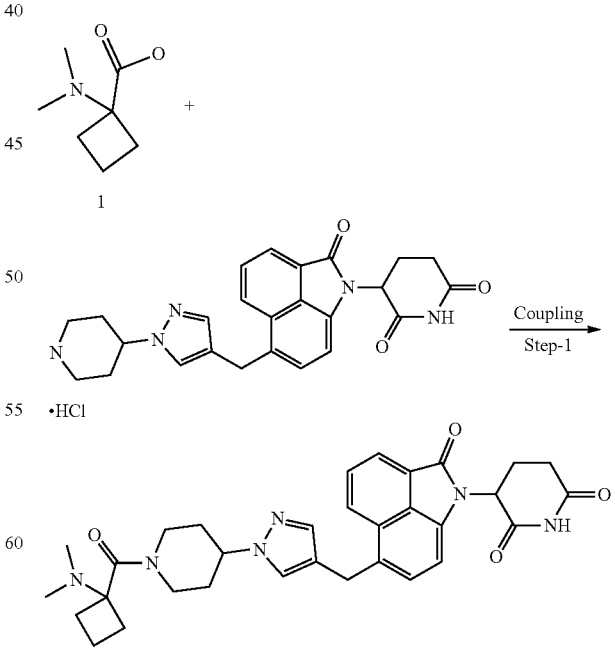

Compound 287

Step: 1: Synthesis of: 3-[6-[[1-[1-[1-(dimethylamino)cyclobutanecarbonyl]-4-piperidyl]pyrazol-4-yl]methyl]-2-oxo-benzo[cd]indol-1-yl]piperidine-2,6-dione: To a stirred solution of 1-(dimethylamino)cyclobutanecarboxylic acid (20 mg, 139.68 umol), HCl salt of 3-[2-oxo-6-[[1-(4-piperidyl)pyrazol-4-yl]methyl]benzo[cd]indol-1-yl]piperidine-2,6-dione (67.04 mg, 139.68 umol, 021) in DMF (2 mL) was added TBTU (179.40 mg, 279.36 umol, 169.59 uL, 50% purity) and Diisopropyl ethyl amine (90.26 mg, 698.41 umol, 121.65 uL) reaction mixture was stirred at 25° C. for 16 hr. LCMS showed the desired mass and the reaction mixture was diluted with ethyl acetate and washed with water, organic layer separated, dried over sodium sulphate and concentrated under reduced pressure to give the crude. This crude was purified by silica gel column chromatography (using 2% MeOH in DCM) to give the 3-[6-[[1-[1-[1-(dimethylamino)cyclobutanecarbonyl]-4-piperidyl]pyrazol-4-yl]methyl]-2-oxo-benzo[cd]indol-1-yl]piperidine-2,6-dione Compound 287 (15 mg, 18.50% yield, 97.97% purity) as yellow solid. LCMS (ES+)=569.3 [M+H]+. 1H NMR (400 MHz, DMSO-d6): δ 11.11 (s, 1H), 8.37 (d, J=8.3 Hz, 1H), 8.08 (d, J=7.0 Hz, 1H), 7.83 (t, J=7.6 Hz, 1H), 7.59 (s, 1H), 7.36 (d, J=7.3 Hz, 1H), 7.31 (s, 1H), 7.07 (d, J=7.3 Hz, 1H), 5.46-5.41 (m, 1H), 4.48-4.45 (m, 1H), 4.29-4.25 (m, 1H), 4.18 (s, 2H; merged with another 1H), 2.99-2.90 (m, 3H), 2.77-2.63 (m, 2H), 2.32 (m, 1H), 2.24-2.23 (m, 2H), 2.14 (s, 6H), 2.09-2.07 (m, 1H), 1.97-1.93 (m, 1H), 1.89-1.87 (m, 1H), 1.76-1.59 (m, 4H), 1.57-1.53 (m, 1H).

Example 168. Synthesis of 3-[2-oxo-6-[[1-(1-spiro[3.3]heptan-2-yl-4-piperidyl)pyrazol-4-yl]methyl]benzo[cd]indol-1-yl]piperidine-2,6-dione (Compound 288)

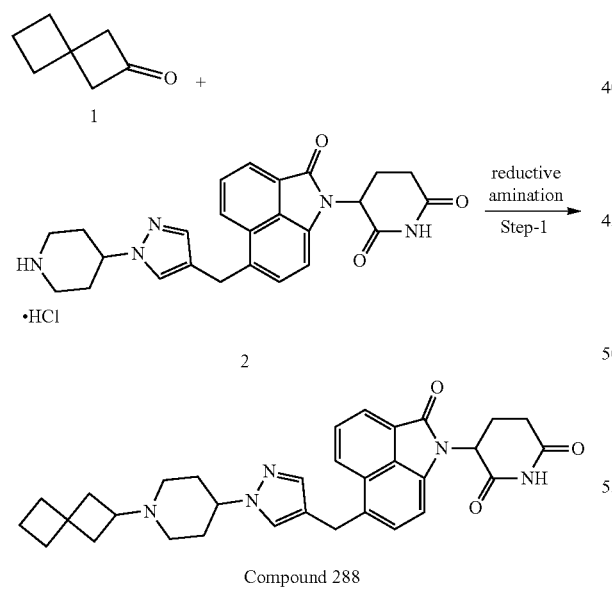

Compound 288

Step: 1: Synthesis of: 3-[2-oxo-6-[[1-(1-spiro[3.3]heptan-2-yl-4-piperidyl)pyrazol-4-yl]methyl]benzo[cd]indol-1-yl]piperidine-2,6-dione: To the stirred solution of HCl salt of 3-[2-oxo-6-[[1-(4-piperidyl)pyrazol-4-yl]methyl]benzo[cd]indol-1-yl]piperidine-2,6-dione (100 mg, 208.35 umol, 021) in THF (8 mL) was added Triethylamine, 99% (42.17 mg, 416.70 umol, 58.08 uL) followed by the addition of spiro[3.3]heptan-2-one (25.25 mg, 229.19 umol), Dibutyltindichloride (75.97 mg, 250.02 umol, 55.86 uL) and Phenylsilane (22.55 mg, 208.35 umol, 25.68 uL). The reaction mixture was then stirred at 90° C. for 16 hours. TLC was checked which showed formation of the desired spot. The reaction mixture was diluted with ethyl acetate, washed with sodium bicarbonate solution, water and brine solution. The organic fraction was separated. It was dried over anhydrous sodium sulphate, evaporated under reduced pressure to obtain the crude compound which was purified by flash chromatography using 3-4% MeOH-DCM to afford 3-[2-oxo-6-[[1-(1-spiro[3.3]heptan-2-yl-4-piperidyl)pyrazol-4-yl]methyl]benzo[cd]indol-1-yl]piperidine-2,6-dione Compound 288 (50 mg, 43.03% yield, 96.4% purity) as yellow solid LCMS (ES+)=538.3 [M+H]+. 1H NMR (400 MHz, DMSO-6): δ 11.09 (s, 1H), 8.34 (d, J=8.2 Hz, 1H), 8.05 (d, J=7.0 Hz, 1H), 7.80 (t, J=7.6 Hz, 1H), 7.54 (s, 1H), 7.32 (d, J=7.4 Hz, 1H), 7.26 (s, 1H), 7.04 (d, J=7.3 Hz, 1H), 5.43-5.38 (m, 1H), 4.15 (s, 2H), 3.97-3.95 (m, 1H), 2.96-2.88 (m, 1H), 2.75-2.69 (m, 2H), 2.67-2.64 (m, 1H), 2.48 (m, 4H, merged with solvent peak), 2.07-2.02 (m, 2H), 1.95-1.91 (m, 2H), 1.86-1.73 (m, 8H), 1.69-1.68 (m, 3H).

Example 169. Synthesis of 3-[20-[[1-[1-(1-methylcyclobutanecarbonyl)-4-piperidyl] pyrazol-4-yl]methyl]-26-oxo-30,35-diazatricyclododeca-1,3(18),5(20),17(21),22(30)-pentnen-35-yl]piperidine-2,6-dione (Compound 289)

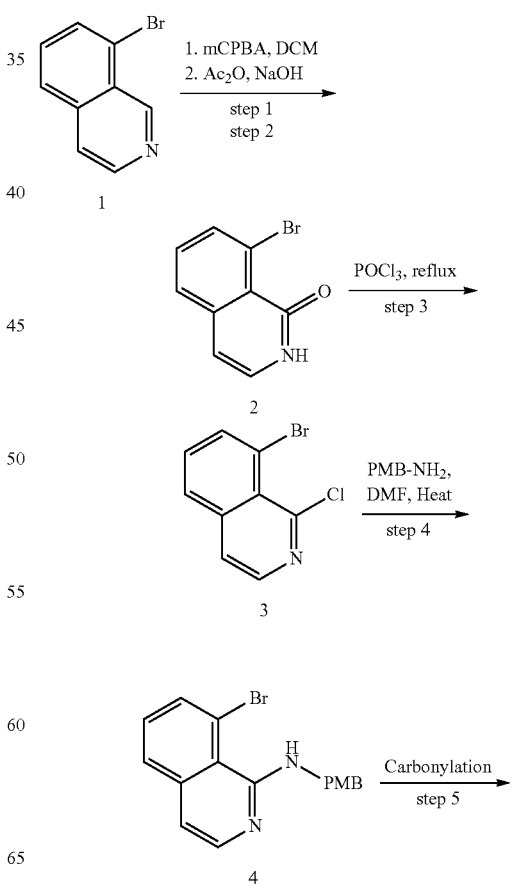

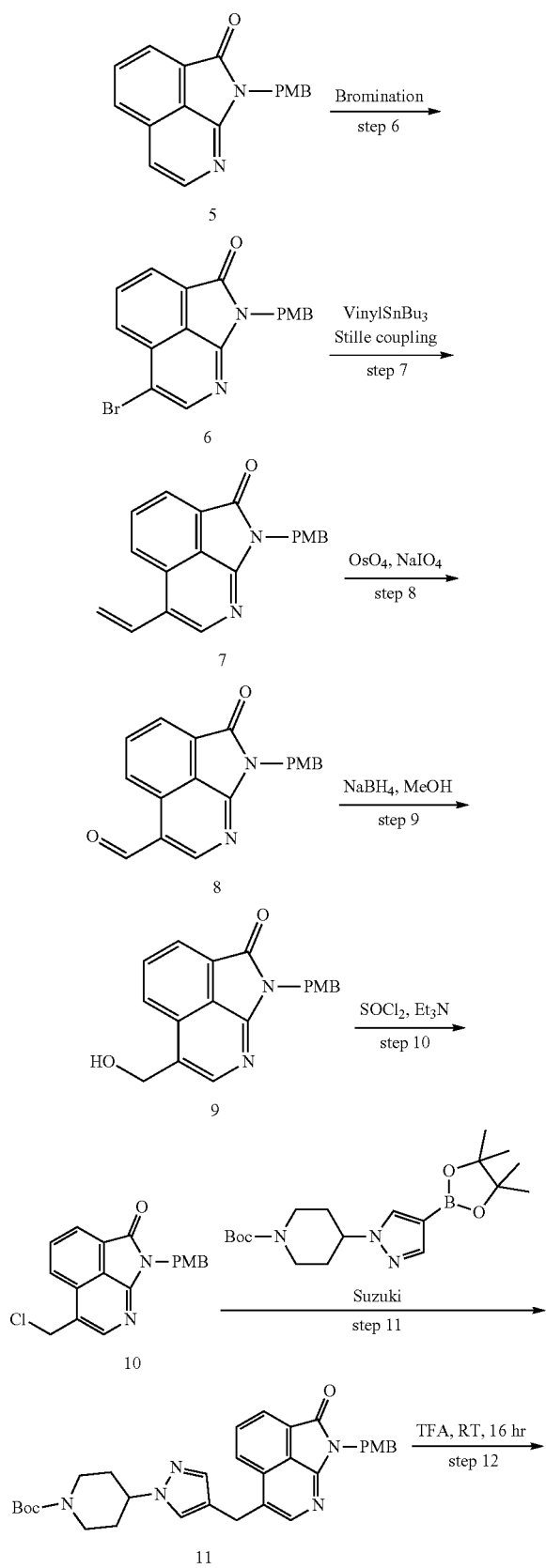

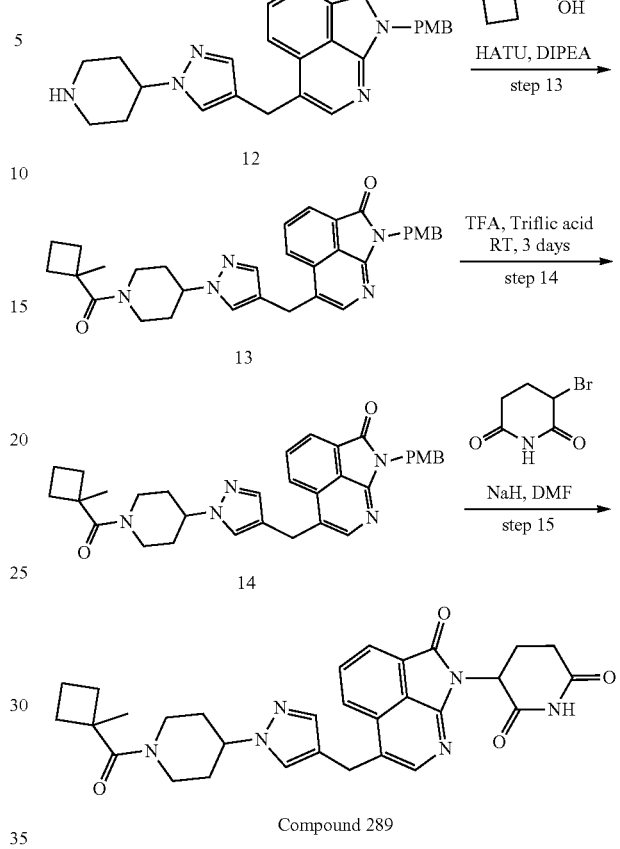

Compound 289

Step-1: Synthesis of 8-bromo-2-oxido-isoquinolin-2-ium: To a stirred solution of 8-bromoisoquinoline (100 g, 480.64 mmol) in DCM (1500 mL) was added 3-Chloroperoxybenzoic acid, 50-55%, cont. ca 10% 3-chlorobenzoic acid, balance water (161.58 g, 720.96 mmol, 77% purity) portion wise and stirred the reaction mixture at 25° C. for 3 hr. TLC showed total consumption of starting material and formation of the new polar spot. The reaction mixture was quenched with 2N NaOH solution to pH-10 and extracted with DCM. The organic layer was dried over sodium sulfate and concentrated to afford 8-bromo-2-oxido-isoquinolin-2-ium (80 g, 73.54% Yield) as off-white solid. LCMS (ES+)=223.9 [M+H]+.

Step-2: Synthesis of 8-bromo-2H-isoquinolin-1-one: The 8-bromo-2-oxido-isoquinolin-2-ium (80 g, 357.06 mmol) was suspended in acetic anhydride (729.03 g, 7.14 mmol, 675.03 mL) and the resulting mixture was heated at reflux for 3 hr then allowed to cool to room temp. The Ac2O was removed by distillation under reduced pressure to yield a solid residue that was suspended in an aqueous solution of NaOH (2 M, 600 mL). The resulting mixture was heated at 100° C. for 1 h then allowed to cool to RT. The pH of the resulting solution was adjusted to pH 6 by addition of an aqueous solution of citric acid and the mixture was extracted with ethyl acetate. The combined organic layers were dried over sodium sulphate and evaporated under reduced pressure to give the crude product 8-bromo-2H-isoquinolin-1-one (70 g, 52.50% Yield). LCMS (ES+)=224.0 [M+H]+.

Step-3: Synthesis of 8-bromo-1-chloro-isoquinoline: To a stirred solution of 8-bromo-2H-isoquinolin-1-one (40 g, 178.53 mmol) in phosphorus oxy chloride (273.74 g, 1.79 mol, 165.90 mL) was stirred at 80° C. for 3 hr. TLC showed total consumption of starting material. The reaction mixture was evaporated to dryness, basified by saturated sodium bicarbonate solution and extracted with ethyl acetate. The organic layer was dried over sodium sulphate and concentrated. The crude material was purified by column chromatography by 10-15% ethyl acetate in hexane to afford 8-bromo-1-chloro-isoquinoline (20 g, 45.73% Yield) as off-white solid. LCMS (ES+)=242.0 [M+H]+.

Step-4: Synthesis of 8-bromo-N-[(4-methoxyphenyl) methyl] isoquinolin-1-amine: 8-bromo-1-chloro-isoquinoline (22 g, 90.72 mmol) was taken in a sealed vessel in DMA (120 mL) and 4-methoxy benzyl amine (18.67 g, 136.08 mmol, 17.78 mL) was added and the reaction mixture was heated at 120° C. for 3 hr. LCMS showed the desired mass. The reaction mixture was diluted with ethyl acetate and water. The organic layer was dried over sodium sulphate and concentrated. The reaction mixture was purified by column chromatography by 5% ethyl acetate in hexane to afforded 8-bromo-N-[(4-methoxyphenyl) methyl] isoquinolin-1-amine (23 g, 62.79%) as brown sticky gum. LCMS (ES+)=344.7 [M+H]+.

Step-5: Synthesis of 19-1(4-methoxyphenyl) methyl]-18,19-diazatricyclododeca-1(3),2(12),8,14,16(18)-pentaen-17-one: 8-bromo-N-[(4-methoxyphenyl) methyl] isoquinolin-1-amine (20 g, 58.27 mmol) was taken in MeOH (500 mL), triethyl amine (23.59 g, 233.09 mmol, 32.49 mL) was added and Argon gas was purged for 10 minutes. Then DPPP (4.81 g, 11.65 mmol) and Palladium (II) acetate (1.31 g, 5.83 mmol) was added and the reaction mixture was subjected to carbonization in Parr-autoclave at 100° C. under 70Psi pressure in the atmosphere of Carbon monoxide. The reaction mixture was filtered through a celite bed and concentrated. The crude material was worked up with ethyl acetate and water followed by brine. The organic layer was dried over sodium sulphate and concentrated. The crude material was purified by column chromatography by 60% ethyl acetate in hexane to afford 19-[(4-methoxyphenyl) methyl]-18,19-diazatricyclododeca-1(3),2(12),8,14,16(18)-pentaen-17-one (9.5 g, 53.16% Yield) as off white solid. LCMS (ES+)=291.1 [M+H]+.

Step-6: Synthesis of 14-bromo-19-[(4-methoxyphenyl) methyl]-18,19-diazatricyclododeca-1(3),2(12),8(14),13(15),16(18)-pentaen-17-one: To the stirred suspension of 19-[(4-methoxyphenyl)methyl]-18,19-diazatricyclododeca-1(3),2(12),8,14,16(18)-pentaen-17-one (7 g, 24.11 mmol) in Acetonitrile (150 mL) was added N-Bromosuccinimide (4.51 g, 25.32 mmol, 2.15 mL) at cold condition drop wise and the reaction was continued at 25° C. for 14 hr hours. LCMS showed the desired mass and TLC showed new spots. The reaction mixture was evaporated and quenched with Na2S2O3 solution extracted with ethyl acetate. The organic layer was washed with water followed by brine and dried over sodium sulphate and concentrated. The crude material was purified by column chromatography to afford 14-bromo-19-[(4-methoxyphenyl) methyl]-18,19-diazatricyclododeca-1(3),2(12),8(14),13(15),16(18)-pentaen-17-one (5 g, 53.92% Yield) as yellow solid; LCMS (ES+) 369.1 [M+H]+.

Step-7: Synthesis of 21-1(4-methoxyphenyl) methyl]-16-vinyl-20,21-diazatricyclododeca-2(4),3(14),9(16),15(17),18(20)-pentaen-19-one: To a stirred solution of 14-bromo-19-[(4-methoxyphenyl)methyl]-18,19-diazatricyclododeca-1(3),2(12),8(14),13(15),16(18)-pentaen-17-one (5 g, 13.54 mmol) intoluene (100 mL) was added Tributyl vinyl tin (6.44 g, 20.31 mmol, 5.91 mL). It was degassed with argon for 10 minutes. Tri-tert-butylphosphine (2.5 M, 1.08 mL) and pd2(dba)3 (1.24 g, 1.35 mmol) was added to the reaction mixture and was further degassed with argon for 10 minutes. It was stirred at 70° C. for 16 hr. The reaction mixture was then allowed to come to RT, filtered and was extracted with ethyl acetate. The organic phase was washed with brine, and finally dried over anhyd. $Na_2SO_4$. The solvent was evaporated and the residue was purified by column chromatography on silica gel to afford 21-[(4-methoxyphenyl) methyl]-16-vinyl-20,21-diazatricyclododeca-2(4),3(14),9(16),15(17),18(20)-pentaen-19-one (1.4 g, 31.04% Yield) as yellow solid. LCMS (ES+)=317.2 [M+H]+.

Step-8: Synthesis of 20-1(4-methoxyphenyl) methyl]-18-oxo-19,20-diazatricyclododeca-1(3),2(13),8(15),14(16),17(19)-pentaene-15-carbaldehyde: To a stirred solution of 21-[(4-methoxyphenyl)methyl]-16-vinyl-20,21-diazatricyclododeca-2(4),3(14),9(16),15(17),18(20)-pentaen-19-one (2 g, 6.32 mmol) in EtOAc (30 mL) and Water (15 mL) were added sodium meta periodate (3.38 g, 15.81 mmol) and OsO4 (0.16 M, 790.26 uL) and stirred at RT for 4h. After completion of SM, reaction mixture was extracted with EtOAc. The organic phase was washed with brine, and finally dried over anhyd. $Na_2SO_4$. The solvent was evaporated to afford 20-[(4-methoxyphenyl) methyl]-18-oxo-19,20-diazatricyclododeca-1(3),2(13),8(15),14(16),17(19)-pentaene-15-carbaldehyde (1.5 g, 70.81% Yield) as a white solid. LCMS (ES+)=319.0 [M+H]+.

Step-9: Synthesis of 15-(hydroxymethyl)-20-[(4-methoxyphenyl) methyl]-19,20-diazatricyclododeca-1(3),2(13),8(15),14(16),17(19)-pentaen-18-one: To a stirred solution of 20-[(4-methoxyphenyl)methyl]-18-oxo-19,20-diazatricyclododeca-1(3),2(13),8(15),14(16),17(19)-pentaene-15-carbaldehyde (1.5 g, 4.71 mmol) in MeOH (50 mL) was cooled to zero degree then Sodium Borohydride (267.39 mg, 7.07 mmol, 249.90 uL) was added and stirred at 25° C. for 4 hr. The reaction mixture was evaporated then diluted with ethyl acetate and washed with water followed by brine. The organic layer was dried over sodium sulphate and concentrated to afford 15-(hydroxymethyl)-20-[(4-methoxyphenyl) methyl]-19,20-diazatricyclododeca-1(3),2(13),8(15),14(16),17(19)-pentaen-18-one (1.2 g, 67.57% Yield) as brown solid; LC-MS: (ES+) 321.1 [M+H]+.

Step-10: Synthesis of 15-(chloromethyl)-20-[(4-methoxyphenyl) methyl]-19,20-diazatricyclododeca-1(3),2(13),8(15),14(16),17(19)-pentaen-18-one: Thionyl Chloride (4.46 g, 37.46 mmol, 2.72 mL) in cold condition was added 15-(hydroxymethyl)-20-[(4-methoxyphenyl)methyl]-19,20-diazatricyclododeca-1(3),2(13),8(15),14(16),17(19)-pentaen-18-one (1.2 g, 3.75 mmol) and stirred at 25° C. for 3 hr. The reaction mixture was evaporated then quenched with sodium bicarbonate solution extracted with ethyl acetate. The organic layer was washed with water followed by brine and dried over sodium sulphate and concentrated. The crude material was titrated with pantane and ether to afford 15-(chloromethyl)-20-[(4-methoxyphenyl) methyl]-19,20-diazatricyclododeca-1(3),2(13),8(15),14(16),17(19)-pentaen-18-one (900 mg, 53.19% Yield) as brown solid. LCMS (ES+)=339 [M+H]+.

Step-11: Synthesis of 32-[(4-methoxyphenyl)methyl]-23-[[1-(1-methyl-4-piperidyl)pyrazol-4-yl]methyl]-28,32-diazatricyclododeca-2(4),3(20),10(23),21(24),25(28)-pentaen-27-one; 2-methylpropan-2-ol; hydrate: To a stirred solution of 15-(chloromethyl)-20-[(4-methoxyphenyl) methyl]-19,20-diazatricyclododeca-1(3),2(13),8(15),14(16),17(19)-pentaen-18-one (900 mg, 2.66 mmol) intoluene (16 mL) and Ethanol (8 mL) was added 1-hydroxy-4-[4-(4,4,5,5-tetramethyl-1,3,2-dioxaborolan-2-yl)pyrazol-1-yl]piperidine; methane; 2-methylpropan-2-ol (1.01 g, 2.66 mmol), tripotassium phosphate (1.41 g, 6.64 mmol). The reaction mixture was degassed with argon for 15 minutes. Then tris-o-tolylphosphane (161.71 mg, 531.31 umol) and Tris (Dibenzylideneacetone)dipalladium (0) (243.26 mg, 265.65 umol) was added and again purged for 10 minutes. The reaction mixture was stirred and heated at 100° C. for 14 hr. The reaction mixture was evaporated and diluted with ethyl acetate and washed with water, followed by brine. The organic layer was dried over sodium sulphate and concentrated. LCMS showed the desired mass and the reaction mixture was purified by column chromatography by 3-4% MeOH in DCM to afford 32-[(4-methoxyphenyl)methyl]-23-[[1-(1-methyl-4-piperidyl)pyrazol-4-yl]methyl]-28,32-diazatricyclo deca-2(4),3(20),10(23),21(24),25(28)-pentaen-27-one; 2-methylpropan-2-ol; hydrate (900 mg, 42.52% Yield) as yellowish solid. LCMS (ES+)=554.5 [M+H]+.

Step-12: Synthesis of 31-[(4-methoxyphenyl)methyl]-22-[[1-(4-piperidyl)pyrazol-4-yl]methyl]-27,31-diazatricyclododeca-1(3),2(19),9(22),20(23),24(27)-pentaen-26-one: 32-[(4-methoxyphenyl)methyl]-23-[[1-(1-methyl-4-piperidyl)pyrazol-4-yl]methyl]-28,32-diazatricyclododeca-2(4),3(20),10(23),21(24),25(28)-pentaen-27-one; 2-methylpropan-2-ol; hydrate (600 mg, 1.07 mmol) in DCM (3 mL) in cooled condition was added TFA (2.44 g, 21.44 mmol, 1.65 mL) dropwise. The reaction mixture was stirred at 25° C. for 14 hr. The reaction mixture was evaporated and quenched with saturated sodium bicarbonate solution, extracted with ethyl acetate, washed with water followed by brine. The organic part was dried over sodium sulphate and concentrated to afford 31-[(4-methoxyphenyl)methyl]-22-[[1-(4-piperidyl)pyrazol-4-yl]methyl]-27,31-diazatricyclododecal(3),2(19),9(22), 20(23),24(27)-pentaen-26-one (390 mg, 72.19% Yield) as yellowish solid.

Step-13: Synthesis of 37-1(4-methoxyphenyl) methyl]-26-[[1-[1-(1-methylcyclobutanecarbonyl)-4-piperidyl]pyrazol-4-yl] methyl]-33,37-diazatricyclododeca-2(4),3(23),10(26),24(27),28(33)-pentaen-30-one: To a stirred solution of 1-methylcyclobutanecarboxylic acid (47.82 mg, 418.93 umol) and 31-[(4-methoxyphenyl)methyl]-22-[[1-(4-piperidyl)pyrazol-4-yl]methyl]-27,31-diazatricyclododecal(3),2(19),9(22), 20(23),24(27)-pentaen-26-one (190 mg, 418.93 umol) in DMF (3 mL) was added DIPEA (270.71 mg, 2.09 mmol, 364.84 uL) and HATU (238.94 mg, 628.40 umol) reaction mixture was stirred at 25° C. for 16 hr. According to LCMS there was shown the desired mass and the reaction mixture was diluted with ethyl acetate and washed with water, organic layer separated, dried over sodium sulphate and concentrated under reduced pressure to give the crude. This crude was purified by column chromatography (using 3% MeOH in DCM) to of 37-[(4-methoxyphenyl) methyl]-26-[[1-[1-(1-methylcyclobutanecarbonyl)-4-piperidyl] pyrazol-4-yl] methyl]-33,37-diazatricyclododeca-2(4),3(23),10(26),24(27),28(33)-pentaen-30-one (90 mg, 38.69% Yield) as brown solid. LCMS (ES+)=550.4 [M+H]+.

Step-14: Synthesis of 18-[[1-[1-(1-methylcyclobutanecarbonyl)-4-piperidyl] pyrazol-4-yl]methyl]-25,27-diazatricyclododeca-1,3(16),5(18),15(19),20(25)-pentaen-22-one: 37-[(4-methoxyphenyl)methyl]-26-[[1-[1-(1-methylcyclobutanecarbonyl)-4-piperidyl]pyrazol-4-yl] methyl]-33,37-diazatricyclododeca-2(4),3(23),10(26),24 (27),28(33)-pentaen-30-one (90 mg, 163.74 umol) in TFA (3 mL) in cooled condition was added Triflic acid (368.61 mg, 2.46 mmol, 215.56 uL) dropwise. The reaction mixture was stirred at 25° C. for 16 hr. The reaction mixture was evaporated and quenched with saturated sodium bicarbonate solution, extracted with ethyl acetate, washed with water followed by brine. The organic part was dried over sodium sulphate and concentrated to afford 18-[[1-[1-(1-methylcyclobutanecarbonyl)-4-piperidyl] pyrazol-4-yl]methyl]-25,27-diazatricyclododeca-1,3(16),5(18),15(19),20(25)-pentaen-22-one (60 mg, 71.66% Yield) as brown solid. LCMS (ES+)=430.3[M+H].

Step-15: Synthesis of 3-[20-[[1-[1-(1-methylcyclobutanecarbonyl)-4-piperidyl] pyrazol-4-yl]methyl]-26-oxo-30,35-diazatricyclododeca-1,3(18),5(20),17(21),22(30)-pentaen-35-yl]piperidine-2,6-dione: To a stirred solution of 18-[[1-[1-(1-methylcyclobutanecarbonyl)-4-piperidyl]pyrazol-4-yl]methyl]-25,27-diazatricyclododeca-1,3(16),5(18),15 (19),20(25)-pentaen-22-one (45.00 mg, 104.77 umol) and 3-bromopiperidine-2,6-dione (60.35 mg, 314.31 umol) in THF (3 mL) in Argon atmosphere was added Lithium bis(trimethylsilyl)amide (1 M, 628.62 uL) dropwise in ice cold condition and heated the reaction mixture at 65° C. for 4 hr. LCMS showed the desired compound with unreacted starting material. The reaction mixture was quenched with ice and extracted with ethyl acetate, organic layer was washed with brine and dried over sodium sulphate and concentrated. The reaction mixture was purified by prep HPLC to afford 3-[20-[[1-[1-(1-methylcyclobutanecarbonyl)-4-piperidyl] pyrazol-4-yl] methyl]-26-oxo-30,35-diazatricyclododeca-1,3(18),5(20),17(21),22(30)-pentaen-35-yl]piperidine-2,6-dione Compound 289 (3 mg, 5.21% Yield) as off white solid. LCMS (ES+)=541.2 [M+H]+. 1H NMR (400 MHz, DMSO-d6): δ 11.09 (s, 1H), 8.31 (d, J=8.2 Hz, 1H), 8.14 (d, J=8.1 Hz, 1H), 8.09 (s, 1H), 8.00 (t, J=7.6 Hz, 1H), 7.65 (s, 1H), 7.35 (s, 1H), 5.41-5.37 (m, 1H), 4.38 (m, 1H), 4.32-4.27 (m, 1H), 4.11 (s, 2H), 3.56 (m, 1H), 3.31-2.81 (m, 3H), 2.67-2.63 (m, 2H), 2.41-2.36 (m, 2H), 2.13-2.11 (m, 1H), 1.99-1.85 (m, 3H), 1.79-1.75 (m, 3H), 1.67 (m, 1H), 1.62-1.59 (m, 1H), 1.34 (s, 3H).

Example 170. Synthesis of 3-[6-[[3-[1-(1-methylcyclobutanecarbonyl)-4-piperidyl]phenyl]methyl]-2-oxo-benzo[cd]indol-1-yl]piperidine-2,6-dione (Compound 290)

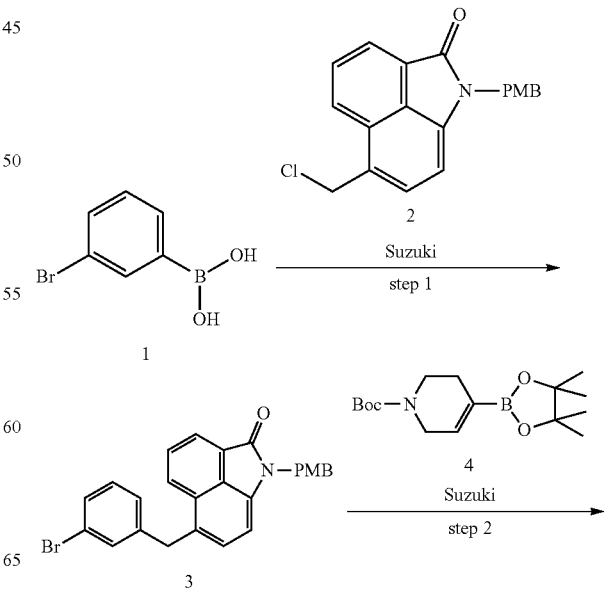

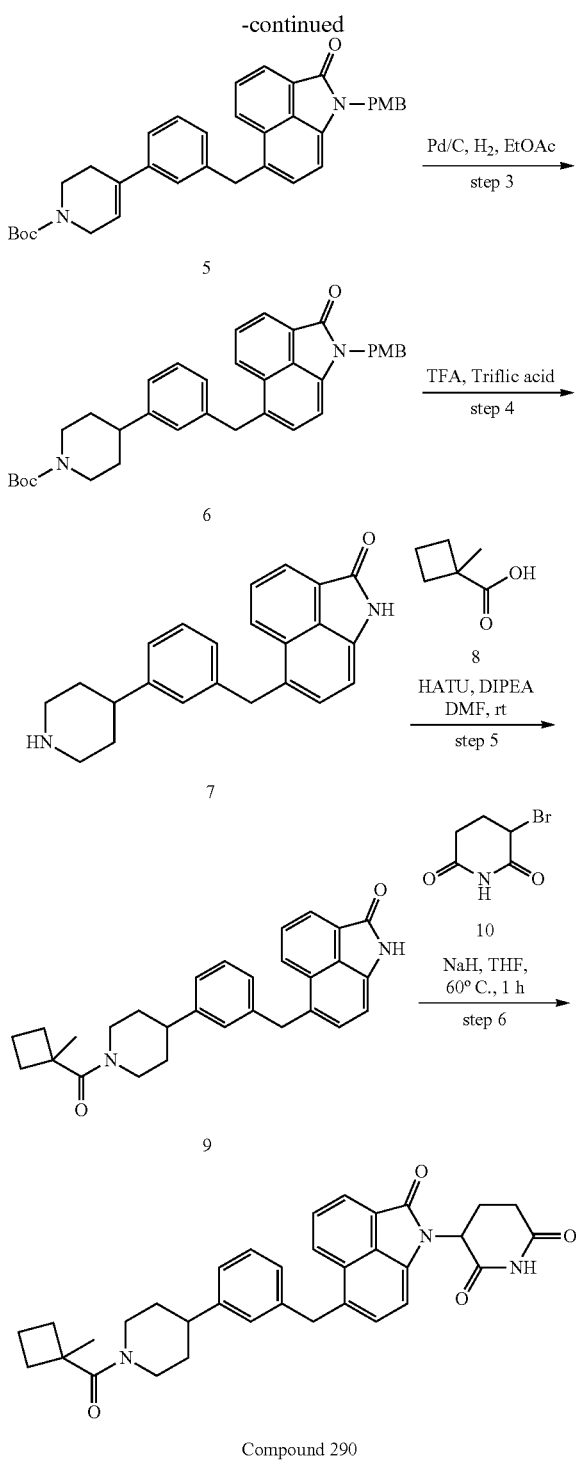

of reaction confirmed by TLC, after completion of reaction it was filtered through celite and diluted with ethyl acetate and washed with water and brine solution. The solvent was evaporated and the residue was purified by column chromatography on silica gel by 2% of ethyl acetate in pet ether to get the 6-[(3-bromophenyl)methyl]-1-[(4-methoxyphenyl) methyl]benzo[cd]indol-2-one (1.1 g, 9.92% yield, 55% purity) as yellow solid. LCMS (ES+)=460.6 [M+H]+.

Step-2: Synthesis of tert-butyl 4-[3-[[1-[(4-methoxyphenyl)methyl]-2-oxo-benzo[cd]indol-6-yl]methyl]phenyl]-3,6-dihydro-2H-pyridine-1-carboxylate: To the solution of 6-[(3-bromophenyl)methyl]-1-[(4-methoxyphenyl)methyl]benzo[cd]indol-2-one (1 g, 2.18 mmol) in Dioxane (20 mL) Dioxane (20 mL) and Water (4 mL) was added tert-butyl 4-(4,4,5,5-tetramethyl-1,3,2-dioxaborolan-2-yl)-3,6-dihydro-2H-pyridine-1-carboxylate (708.35 mg, 2.29 mmol) and Sodium carbonate (578.11 mg, 5.45 mmol, 228.50 uL) were added. The mixture was purged with argon gas for 15 min then added XPhos Pd G3 (92.34 mg, 109.09 umol) again argon gas was purged for 5 min and the mixture was stirred at 90° C. for 16 hr in a sealed tube. completion of reaction confirmed by TLC, After completion of reaction it was filtered through celite and diluted with ethyl acetate and washed with water and saturated sodium carbonate and brine solution. The solvent was evaporated and the get crude compound. And purified by column chromatography on silica gel by 20% of ethyl acetate in hexane to get the tert-butyl 4-[3-[[1-[(4-methoxyphenyl)methyl]-2-oxo-benzo[cd]indol-6-yl]methyl]phenyl]-3,6-dihydro-2H-pyridine-1-carboxylate (600 mg, yield, 29.43% Yield, 60% purity) as yellow solid. LCMS (ES+)=561 [M+H]+.

Step-3: Synthesis of tert-butyl 4-[3-[[1-[(4-methoxyphenyl)methyl]-2-oxo-benzo[cd]indol-6-yl]methyl]phenyl]piperidine-1-carboxylate: To a stirred solution of tert-butyl 4-[3-[[1-[(4-methoxyphenyl)methyl]-2-oxo-benzo[cd]indol-6-yl]methyl]phenyl]-3,6-dihydro-2H-pyridine-1-carboxylate (750 mg, 1.34 mmol) in Methanol (50 mL) was purged with Argon for 15 minutes then Palladium-carbon (10% moist) (200 mg, 1.34 mmol) was added again the reaction mixture was purged with Argon. The reaction mixture was then hydrogenated at Balloon pressure for 16 hr. LCMS showed the desired mass then the reaction mixture was filtered through a celite bed.

The filtrate was then evaporated and purified by prep-HPLC to afford the tert-butyl 4-[3-[[1-[(4-methoxyphenyl)methyl]-2-oxo-benzo[cd]indol-6-yl]methyl]phenyl]piperidine-1-carboxylate (130 mg, 17.01% yield, 98.5% purity). LCMS (ES+)=564 [M+H]+. Step-4: Synthesis of 6-[[3-(4-piperidyl)phenyl]methyl]-1H-benzo[cd]indol-2-one: Tert-butyl 4-[3-[[1-[(4-methoxyphenyl)methyl]-2-oxo-benzo[cd]indol-6-yl]methyl]phenyl]piperidine-1-carboxylate (210 mg, 373.20 umol) in TFA (3 mL) in cooled condition was added Triflic acid (280.05 mg, 1.87 mmol, 163.77 uL) drop wise. The reaction mixture was stirred at 25° C. for 16 hr. The reaction mixture was evaporated and quenched with saturated sodium bicarbonate solution, extracted with ethyl acetate, washed with water followed by brine. The organic part was dried over sodium sulphate and concentrated to afford 6-[[3-(4-piperidyl)phenyl]methyl]-1H-benzo[cd]indol-2-one (130 mg, 86.47% yield, 85% purity). LCMS (ES+)=343 [M+H]+.

Step-5: Synthesis of 6-[[3-[1-(1-methylcyclobutanecarbonyl)-4-piperidyl]phenyl]methyl]-1H-benzo[cd]indol-2-one: To a stirred solution of 6-[[3-(4-piperidyl)phenyl]methyl]-1H-benzo[cd]indol-2-one (130 mg, 379.64 umol) and 1-methylcyclobutanecarboxylic acid (43.33 mg, 379.64 umol) in DMF (3 mL) was added DIPEA (245.32 mg, 1.90

Step-1: Synthesis of 6-[(3-bromophenyl)methyl]-1-[(4-methoxyphenyl)methyl]benzo[cd]indol-2-one: To the solution of (3-bromophenyl)boronic acid (2.67 g, 13.28 mmol) intoluene (50 mL) and anisole; 6-(chloromethyl)-1-methyl-benzo[cd]indol-2-one (4.5 g, 13.28 mmol) and Potassium phosphate tribasic anhydrous (7.05 g, 33.20 mmol) were added the mixture was purged with argon gas for 15 min then added Tetrakis(triphenylphosphine)palladium(0), 99.8% (metals basis), Pd 9% min (1.53 g, 1.33 mmol) was added again argon gas was purged for 5 min and the mixture was stirred at 90° C. for 16 hr in a sealed tube. Completion mmol, 330.62 uL) and HATU (216.52 mg, 569.45 umol) reaction mixture was stirred at 25° C. for 16 hr. According to LCMS there was shown the desired mass and the reaction mixture was diluted with ethyl acetate and washed with water, organic layer separated, dried over sodium sulphate and concentrated under reduced pressure to give the crude. This crude was purified by column chromatography (using 60% Ethyl acetate in Hexane) to give the title compound 6-[[3-[1-(1-methylcyclobutanecarbonyl)-4-piperidyl]phenyl]methyl]-1H-benzo[cd]indol-2-one (100 mg, 58.86% yield, 98% purity) as a white solid. LCMS (ES+)=439.0[M+H]+.

Step-6: Synthesis of 3-[6-[[3-[1-(1-methylcyclobutanecarbonyl)-4-piperidyl]phenyl]methyl]-2-oxo-benzo[cd]indol-1-yl]piperidine-2,6-dione: To a stirred solution of 6-[[3-[1-(1-methylcyclobutanecarbonyl)-4-piperidyl]phenyl]methyl]-1H-benzo[cd]indol-2-one (100 mg, 228.02 umol) in THF (5 mL) was added Sodium hydride (in oil dispersion) 60% dispersion in mineral oil (87.37 mg, 2.28 mmol, 60% purity) portion wise at 0° C. and stirred for 10 mins maintain at 0° C. After that slowly added 3-bromopiperidine-2,6-dione (218.91 mg, 1.14 mmol) then reaction mass stirred allowed to 75° C. for 20 mins. The progress of the reaction was monitored by TLC, SM was consumed in TLC. Then the reaction mass quenched with cool ice water and the reaction mixture was diluted with ethyl acetate and washed with water, organic layer separated, dried over sodium sulphate and concentrated under reduced pressure to give the crude. This crude was purified by Preparative HPLC afford 3-[6-[[3-[1-(1-methylcyclobutanecarbonyl)-4-piperidyl]phenyl]methyl]-2-oxo-benzo[cd]indol-1-yl]piperidine-2,6-dione Compound 290 (11 mg, 8.65% yield, 98.61% purity), LCMS (ES+)=550.5 [M+H]+. 1H NMR (400 MHz, DMSO-d6): δ 11.10 (s, 1H), 8.36 (d, J=7.8 Hz, 1H), 8.07 (d, J=6.6 Hz, 1H), 7.81 (t, J=7.4 Hz, 1H), 7.40 (d, J=7.2 Hz, 1H), 7.25 (s, 1H), 7.18-7.16 (m, 1H), 7.11-7.04 (m, 3H), 5.45-5.43 (m, 1H), 4.47 (m, 1H), 4.37 (s, 2H), 3.60 (m, 1H), 2.99-2.92 (m, 2H), 2.79-2.63 (m, 3H), 2.43 (m, 2H), 2.07 (m, 2H), 1.93-1.88 (m, 1H), 1.78-1.72 (m, 4H), 1.63-1.60 (m, 1H), 1.46 (m, 2H), 1.35 (s, 3H).

Example 171. Cell Viability Assay for Table 1

Materials

RPMI 1640 medium, fetal bovine serum (FBS) and 2-mercaptoethanol were purchased from Gibco (Grand Island, N.Y., USA). CellTiter-Glo® 2.0 Assay was purchased from Promega (Madison, Wis., USA). NCIH929.1 cell line was purchased from ATCC (Manassas, Va., USA). Cell culture flasks and 384-well microplates were acquired from VWR (Radnor, Pa., USA).

Cell Viability Analysis

NCIH929.1 cell viability was determined based on quantification of ATP using CellTiter-Glo®2.0 luminescent Assay kit, which signals the presence of metabolically-active cells. Briefly, the test compound was added to 384-well plates at a top concentration of 1 µM with 10 points, half log titration in duplicates. NCIH929.1 cells were seeded into the 384-well plates in RPMI medium containing 10% FBS and 0.05 mM 2-mercaptoethanol at a cell density of 750 cells per well. Cells treated in the absence of the test compound were the negative control and cells treated in the absence of CellTiter-Glo® 2.0 were the positive control. At the same day of compound treatment, CellTiter-Glo® 2.0 was added to a plate with cells treated in the absence of the test compound to establish Cytostatic control value ($C_{T0}$). Cells treated with the test compound were incubated at 37° C. with 5% $CO_2$ for 96 hr. CellTiter-Glo reagent was then added to the cells and luminescence was acquired on EnVision™ Multilabel Reader (PerkinElmer, Santa Clara, Calif., USA).

Results

Using the above assay $IC_{50}$ data was determined for representative compounds in Table 1 below.

Example 172. Cell Viability Assay for Table 2

Materials

RPMI 1640 medium, fetal bovine serum (FBS) and 2-mercaptoethanol were purchased from Gibco (Grand Island, N.Y., USA). CellTiter-Glo® 2.0 Assay was purchased from Promega (Madison, Wis., USA). NCIH929.1 cell line was purchased from ATCC (Manassas, Va., USA). Cell culture flasks and 384-well microplates were acquired from VWR (Radnor, Pa., USA).

Cell Viability Analysis

NCIH929.1 cell viability was determined based on quantification of ATP using CellTiter-Glo® 2.0 luminescent Assay kit, which signals the presence of metabolically-active cells. Briefly, test compound was added to 384-well plates at a top concentration of 1 µM with 14 points, half log titration in duplicates. NCIH929.1 were seeded into the 384-well plates in RPMI medium containing 10% FBS and 0.05 mM 2-mercaptoethanol at a cell density of 750 cells per well. Cells treated in the absence of the test compound were the negative control, normalized to 100% viability, and cells treated in the absence of CellTiter-Glo® 2.0 were the positive control, normalized to 0% viability. Cells were incubated at 37° C. with 5% $CO_2$ for 96 hr. CellTiter-Glo reagent was then added to the cells and Luminescence was acquired on EnVision™ Multilabel Reader (PerkinElmer, Santa Clara, Calif., USA).

Results

Using the above assay $IC_{50}$ data was determined for representative compounds in Table 2 below.

Example 173 Representative Compounds

Where chirality is depicted in the tables below the designation shows the relative chirality of that stereocenter and not an absolute designation. Where a chiral center is not specified then there may be a mixture of chiralities at that chiral center for example,

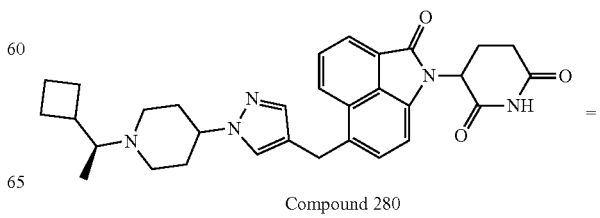

Compound 280

805
-continued
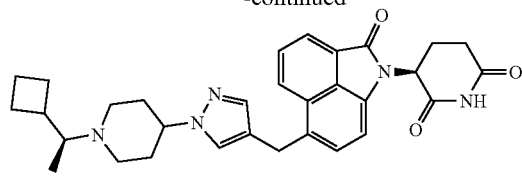
and
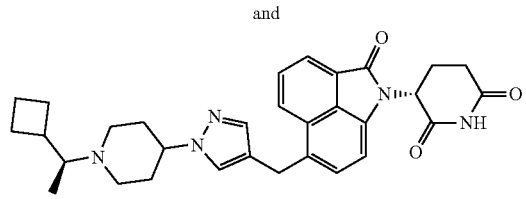
OR
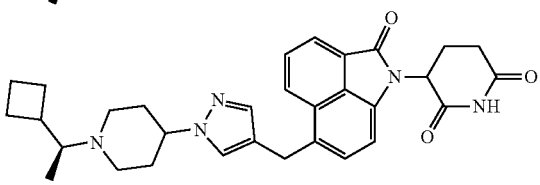
Compound 280
806
-continued
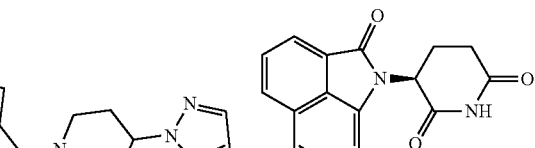
and
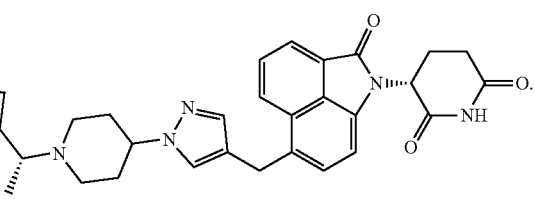
=
TABLE 1
| Compound No. | Structure | GI$_{50}$ |
|---|---|---|
| 2 | 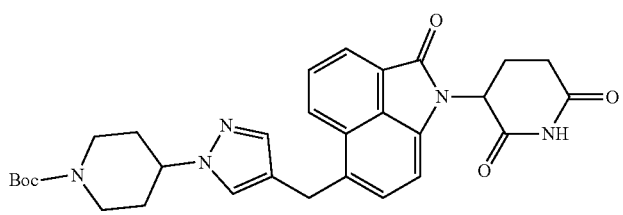 [SMILES: CC(C)(C)OC(=O)N1CCC(n2cc(Cc3ccc4c5c(cccc35)C(=O)N4C3CCC(=O)NC3=O)cn2)CC1] | ++++ |
| 3 | 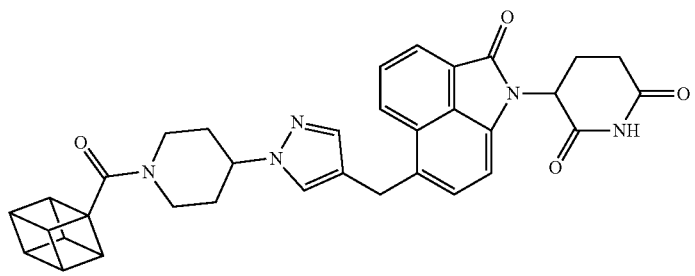 [SMILES: O=C1CCC(N2C(=O)c3cccc4c(Cc5cnn(C6CCN(C(=O)C78C9C%10C%11C9C7C%11C%108)CC6)c5)ccc2c34)C(=O)N1] | ++++ |
| 4 | 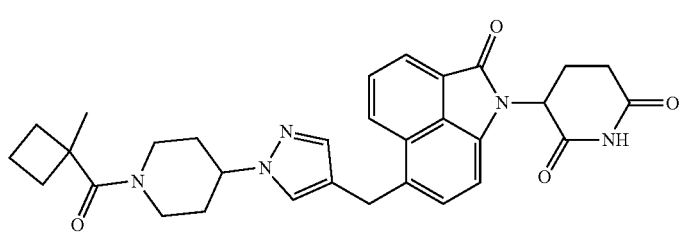 [SMILES: CC1(C(=O)N2CCC(n3cc(Cc4ccc5c6c(cccc46)C(=O)N5C4CCC(=O)NC4=O)cn3)CC2)CCC1] | ++++ |

TABLE 1-continued

| Compound No. | Structure | GI$_{50}$ |
|---|---|---|
| 18 | 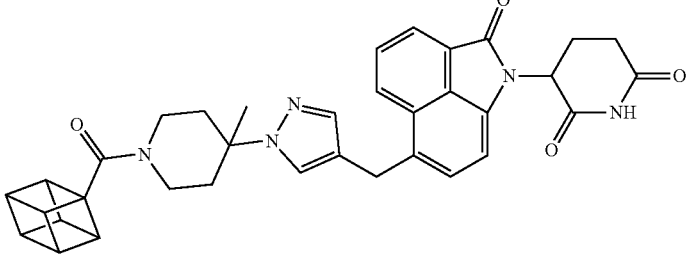 | ++++ |

In the above table: ++++ is < 1 nM; +++ is < 100 nM; ++ is < 999 nM, and + > 999 nM.

TABLE 2

| # | Structure | IC$_{50}$ (nM) |
|---|---|---|
| 36 | 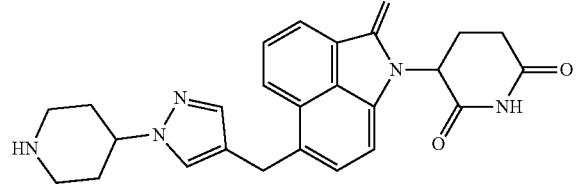<br>3-(2-oxo-6-((1-(piperidin-4-yl)-1H-pyrazol-4-yl)methyl)benzo[cd]indol-1(2H)-yl)piperidine-2,6-dione | |
| 37 | 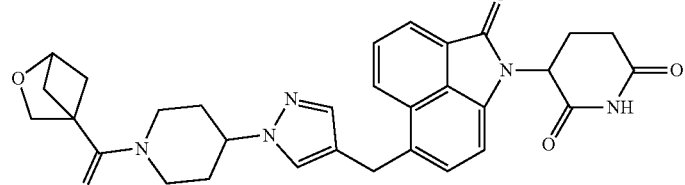<br>3-(6-((1-(1-(2-oxabicyclo[2.1.1]hexane-4-carbonyl)piperidin-4-yl)-1H-pyrazol-4-yl)methyl)-2-oxobenzo[cd]indol-1(2H)-yl)piperidine-2,6-dione | ++++ |
| 38 | 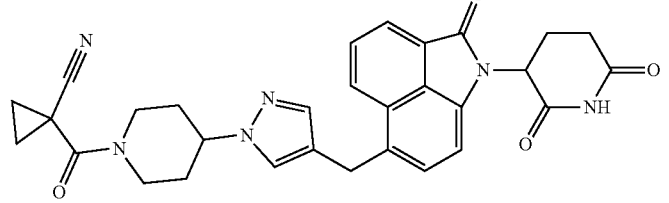<br>1-(4-(4-((1-(2,6-dioxopiperidin-3-yl)-2-oxo-1,2-dihydrobenzo[cd]indol-6-yl)methyl)-1H-pyrazol-1-yl)piperidine-1-carbonyl)cyclopropane-1-carbonitrile | ++++ |
| 39 | 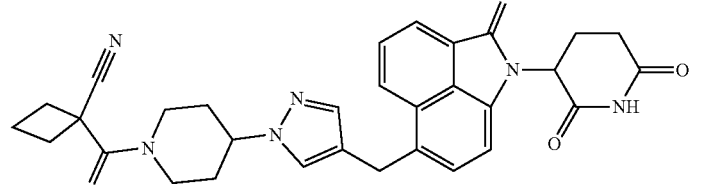<br>1-(4-(4-((1-(2,6-dioxopiperidin-3-yl)-2-oxo-1,2-dihydrobenzo[cd]indol-6-yl)methyl)-1H-pyrazol-1-yl)piperidine-1-carbonyl)cyclobutane-1-carbonitrile | ++++ |

TABLE 2-continued

| # | Structure | IC$_{50}$ (nM) |
|---|---|---|
| 40 | 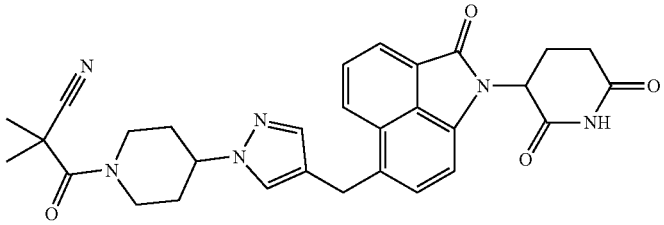 [SMILES: CC(C)(C#N)C(=O)N1CCC(n2cc(Cc3ccc4c5c(cccc35)C(=O)N4C3CCC(=O)NC3=O)cn2)CC1]<br>3-(4-(4-((1-(2,6-dioxopiperidin-3-yl)-2-oxo-1,2-dihydrobenzo[cd]indol-6-yl)methyl)-1H-pyrazol-1-yl)piperidin-1-yl)-2,2-dimethyl-3-oxopropanenitrile | ++++ |
| 41 | 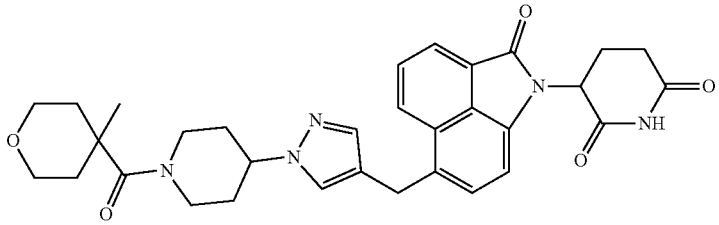 [SMILES: CC1(C(=O)N2CCC(n3cc(Cc4ccc5c6c(cccc46)C(=O)N5C4CCC(=O)NC4=O)cn3)CC2)CCOCC1]<br>3-(6-((1-(1-(4-methyltetrahydro-2H-pyran-4-carbonyl)piperidin-4-yl)-1H-pyrazol-4-yl)methyl)-2-oxobenzo[cd]indol-1(2H)-yl)piperidine-2,6-dione | ++++ |
| 42 | 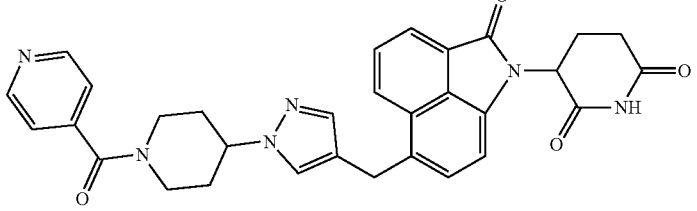<br>3-(6-((1-(1-isonicotinoylpiperidin-4-yl)-1H-pyrazol-4-yl)methyl)-2-oxobenzo[cd]indol-1(2H)-yl)piperidine-2,6-dione | ++++ |
| 43 | 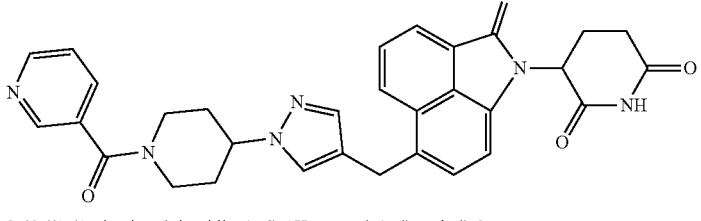<br>3-(6-((1-(1-nicotinoylpiperidin-4-yl)-1H-pyrazol-4-yl)methyl)-2-oxobenzo[cd]indol-1(2H)-yl)piperidine-2,6-dione | ++++ |
| 44 | 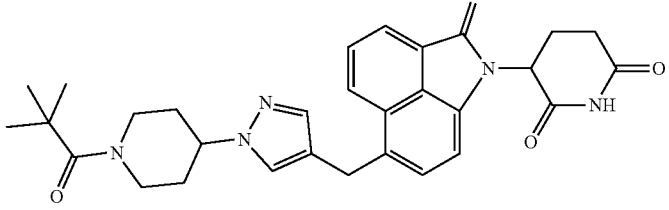<br>3-(2-oxo-6-((1-(1-pivaloylpiperidin-4-yl)-1H-pyrazol-4-yl)methyl)benzo[cd]indol-1(2H)-yl)piperidine-2,6-dione | ++++ |

TABLE 2-continued

| # | Structure | IC$_{50}$ (nM) |
|---|---|---|
| 45 | 3-(6-((1-(1-(2,6-dimethylbenzoyl)piperidin-4-yl)-1H-pyrazol-4-yl)methyl)-2-oxobenzo[cd]indol-1(2H)-yl)piperidine-2,6-dione | ++++ |
| 46 | 3-(2-oxo-6-((1-(1-picolinoylpiperidin-4-yl)-1H-pyrazol-4-yl)methyl)benzo[cd]indol-1(2H)-yl)piperidine-2,6-dione | ++++ |
| 47 | 3-(6-((1-(1-benzoylpiperidin-4-yl)-1H-pyrazol-4-yl)methyl)-2-oxobenzo[cd]indol-1(2H)-yl)piperidine-2,6-dione | ++++ |
| 48 | 3-(6-((1-(1-(2-oxabicyclo[2.1.1]hexane-1-carbonyl)piperidin-4-yl)-1H-pyrazol-4-yl)methyl)-2-oxobenzo[cd]indol-1(2H)-yl)piperidine-2,6-dione | ++++ |
| 49 | 3-(6-((1-(1-(1-methyl-2-oxabicyclo[3.1.1]heptane-5-carbonyl)piperidin-4-yl)-1H-pyrazol-4-yl)methyl)-2-oxobenzo[cd]indol-1(2H)-yl)piperidine-2,6-dione | ++++ |

TABLE 2-continued

| # | Structure | IC$_{50}$ (nM) |
|---|---|---|
| 50 | 3-(6-((1-(1-(bicyclo[3.1.1]heptane-1-carbonyl)piperidin-4-yl)-1H-pyrazol-4-yl)methyl)-2-oxobenzo[cd]indol-1(2H)-yl)piperidine-2,6-dione | ++++ |
| 51 | 3-(2-oxo-6-((1-(1-(1-(trifluoromethyl)cyclobutane-1-carbonyl)piperidin-4-yl)-1H-pyrazol-4-yl)methyl)benzo[cd]indol-1(2H)-yl)piperidine-2,6-dione | ++++ |
| 52 | 3-(2-oxo-6-((1-(1-(1-(trifluoromethyl)cyclopropane-1-carbonyl)piperidin-4-yl)-1H-pyrazol-4-yl)methyl)benzo[cd]indol-1(2H)-yl)piperidine-2,6-dione | ++++ |
| 53 | 3-(6-((1-(1-(1-methylcyclobutane-1-carbonyl)piperidin-4-yl)-1H-pyrazol-4-yl)methyl)-2-oxobenzo[cd]indol-1(2H)-yl)piperidine-2,6-dione | ++++ |
| 54 | 3-(6-((1-(1-(cubane-1-carbonyl)piperidin-4-yl)-1H-pyrazol-4-yl)methyl)-2-oxobenzo[cd]indol-1(2H)-yl)piperidine-2,6-dione | ++++ |

TABLE 2-continued

| # | Structure | IC$_{50}$ (nM) |
|---|---|---|
| 55 | 3-(6-((1-(1-((1-methylcyclobutyl)methyl)piperidin-4-yl)-1H-pyrazol-4-yl)methyl)-2-oxobenzo[cd]indol-1(2H)-yl)piperidine-2,6-dione | ++++ |
| 56 | 3-(6-((1-(1-((1-methoxycyclobutyl)methyl)piperidin-4-yl)-1H-pyrazol-4-yl)methyl)-2-oxobenzo[cd]indol-1(2H)-yl)piperidine-2,6-dione | ++++ |
| 57 | 3-(2-oxo-6-((1-(1-((1-(trifluoromethyl)cyclobutyl)methyl)piperidin-4-yl)-1H-pyrazol-4-yl)methyl)benzo[cd]indol-1(2H)-yl)piperidine-2,6-dione | ++++ |
| 58 | 3-(6-((1-(1-(2-methoxy-2-methylpropyl)piperidin-4-yl)-1H-pyrazol-4-yl)methyl)-2-oxobenzo[cd]indol-1(2H)-yl)piperidine-2,6-dione | ++++ |
| 59 | 3-(6-((1-(1-((1-fluorocyclobutyl)methyl)piperidin-4-yl)-1H-pyrazol-4-yl)methyl)-2-oxobenzo[cd]indol-1(2H)-yl)piperidine-2,6-dione | ++++ |

TABLE 2-continued

| # | Structure | IC$_{50}$ (nM) |
|---|---|---|
| 60 | 1-((4-(4-((1-(2,6-dioxopiperidin-3-yl)-2-oxo-1,2-dihydrobenzo[cd]indol-6-yl)methyl)-1H-pyrazol-1-yl)piperidin-1-yl)methyl)cyclobutane-1-carbonitrile | ++++ |
| 61 | 3-(4-(4-((1-(2,6-dioxopiperidin-3-yl)-2-oxo-1,2-dihydrobenzo[cd]indol-6-yl)methyl)-1H-pyrazol-1-yl)piperidin-1-yl)-2,2-dimethylpropanenitrile | ++++ |
| 62 | 3-(2-oxo-6-((1-(1-((1-(trifluoromethyl)cyclopropyl)methyl)piperidin-4-yl)-1H-pyrazol-4-yl)methyl)benzo[cd]indol-1(2H)-yl)piperidine-2,6-dione | ++++ |
| 63 | 3-(6-((1-(1-neopentylpiperidin-4-yl)-1H-pyrazol-4-yl)methyl)-2-oxobenzo[cd]indol-1(2H)-yl)piperidine-2,6-dione | ++++ |
| 64 | 3-(6-((1-(1-((1-methylcyclopropyl)methyl)piperidin-4-yl)-1H-pyrazol-4-yl)methyl)-2-oxobenzo[cd]indol-1(2H)-yl)piperidine-2,6-dione | ++++ |

TABLE 2-continued

| # | Structure | IC$_{50}$ (nM) |
|---|---|---|
| 65 | 3-(6-(((1-(1-((1-fluorocyclopropyl)methyl)piperidin-4-yl)-1H-pyrazol-4-yl)methyl)-2-oxobenzo[cd]indol-1(2H)-yl)piperidine-2,6-dione | ++++ |
| 66 | 3-(6-(((1-(1-((1-methoxycyclopropyl)methyl)piperidin-4-yl)-1H-pyrazol-4-yl)methyl)-2-oxobenzo[cd]indol-1(2H)-yl)piperidine-2,6-dione | ++++ |
| 67 | 3-(6-(((1-(1-(1-methylcyclobutane-1-carbonyl)piperidin-4-yl)-1H-pyrazol-4-yl)methyl)-2-oxobenzo[cd]indol-1(2H)-yl)piperidine-2,6-dione | ++++ |
| 68 | 3-(6-(((1-(1-(1-methylcyclobutane-1-carbonyl)piperidin-4-yl)-1H-pyrazol-4-yl)methyl)-2-oxobenzo[cd]indol-1(2H)-yl)piperidine-2,6-dione | ++++ |
| 69 | 3-(6-(((1-(4-methylpiperidin-4-yl)-1H-pyrazol-4-yl)methyl)-2-oxobenzo[cd]indol-1(2H)-yl)piperidine-2,6-dione | +++ |
| 70 | 3-(6-(((1-(1-(cubane-1-carbonyl)-4-methylpiperidin-4-yl)-1H-pyrazol-4-yl)methyl)-2-oxobenzo[cd]indol-1(2H)-yl)piperidine-2,6-dione | ++++ |

TABLE 2-continued

| # | Structure | IC$_{50}$ (nM) |
|---|---|---|
| 71 | 3-(6-((1-(1-(2-oxabicyclo[2.1.1]hexane-4-carbonyl)-4-methylpiperidin-4-yl)-1H-pyrazol-4-yl)methyl)-2-oxobenzo[cd]indol-1(2H)-yl)piperidine-2,6-dione | ++++ |
| 72 | 1-(4-(4-((1-(2,6-dioxopiperidin-3-yl)-2-oxo-1,2-dihydrobenzo[cd]indol-6-yl)methyl)-1H-pyrazol-1-yl)-4-methylpiperidine-1-carbonyl)cyclohexane-1-carbonitrile | ++++ |
| 73 | 3-(6-((1-(4-methyl-1-(quinuclidine-4-carbonyl)piperidin-4-yl)-1H-pyrazol-4-yl)methyl)-2-oxobenzo[cd]indol-1(2H)-yl)piperidine-2,6-dione | +++ |
| 74 | 3-(6-((1-(1-(1-azabicyclo[2.2.1]heptane-4-carbonyl)-4-methylpiperidin-4-yl)-1H-pyrazol-4-yl)methyl)-2-oxobenzo[cd]indol-1(2H)-yl)piperidine-2,6-dione | +++ |
| 75 | 3-(6-((1-(1-acetyl-4-methylpiperidin-4-yl)-1H-pyrazol-4-yl)methyl)-2-oxobenzo[cd]indol-1(2H)-yl)piperidine-2,6-dione | ++++ |

TABLE 2-continued

| # | Structure | IC$_{50}$ (nM) |
|---|---|---|
| 76 | 3-(6-(((1-(1-(1-(difluoromethyl)cyclopropane-1-carbonyl)-4-methylpiperidin-4-yl)-1H-pyrazol-4-yl)methyl)-2-oxobenzo[cd]indol-1(2H)-yl)piperidine-2,6-dione | ++++ |
| 77 | 3-(6-(((1-(4-methyl-1-(1-(trifluoromethyl)cyclopropane-1-carbonyl)piperidin-4-yl)-1H-pyrazol-4-yl)methyl)-2-oxobenzo[cd]indol-1(2H)-yl)piperidine-2,6-dione | ++++ |
| 78 | 3-(6-(((1-(4-methyl-1-(1-(trifluoromethyl)cyclobutane-1-carbonyl)piperidin-4-yl)-1H-pyrazol-4-yl)methyl)-2-oxobenzo[cd]indol-1(2H)-yl)piperidine-2,6-dione | ++++ |
| 79 | 1-(4-(4-((1-(2,6-dioxopiperidin-3-yl)-2-oxo-1,2-dihydrobenzo[cd]indol-6-yl)methyl)-1H-pyrazol-1-yl)-4-methylpiperidine-1-carbonyl)cyclopropane-1-carbonitrile | ++++ |
| 80 | 3-(4-(4-((1-(2,6-dioxopiperidin-3-yl)-2-oxo-1,2-dihydrobenzo[cd]indol-6-yl)methyl)-1H-pyrazol-1-yl)-4-methylpiperidin-1-yl)-2,2-dimethyl-3-oxopropanenitrile | ++++ |

TABLE 2-continued

| # | Structure | IC$_{50}$ (nM) |
|---|---|---|
| 81 | 3-(6-((1-(4-methyl-1-(4-methyltetrahydro-2H-pyran-4-carbonyl)piperidin-4-yl)-1H-pyrazol-4-yl)methyl)-2-oxobenzo[cd]indol-1(2H)-yl)piperidine-2,6-dione | ++++ |
| 82 | 3-(6-((1-(4-methyl-1-(3,3,3-trifluoro-2,2-dimethylpropanoyl)piperidin-4-yl)-1H-pyrazol-4-yl)methyl)-2-oxobenzo[cd]indol-1(2H)-yl)piperidine-2,6-dione | ++++ |
| 83 | 3-(6-((1-(4-methyl-1-(1-methylcyclopropane-1-carbonyl)piperidin-4-yl)-1H-pyrazol-4-yl)methyl)-2-oxobenzo[cd]indol-1(2H)-yl)piperidine-2,6-dione | ++++ |
| 84 | 3-(6-((1-(1-(2-methoxy-2-methylpropanoyl)-4-methylpiperidin-4-yl)-1H-pyrazol-4-yl)methyl)-2-oxobenzo[cd]indol-1(2H)-yl)piperidine-2,6-dione | ++++ |
| 85 | 3-(6-((1-(1-(3-methoxy-2,2-dimethylpropanoyl)-4-methylpiperidin-4-yl)-1H-pyrazol-4-yl)methyl)-2-oxobenzo[cd]indol-1(2H)-yl)piperidine-2,6-dione | ++++ |

TABLE 2-continued

| # | Structure | IC₅₀ (nM) |
|---|---|---|
| 86 | 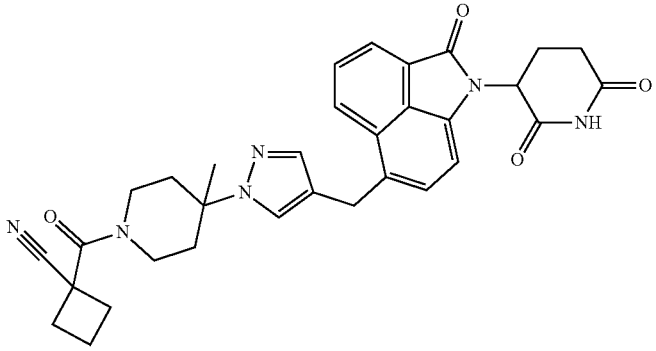 [SMILES: CC1(n2cc(Cc3ccc4c5c(cccc35)C(=O)N4C3CCC(=O)NC3=O)cn2)CCN(C(=O)C2(C#N)CCC2)CC1] 1-(4-(4-((1-(2,6-dioxopiperidin-3-yl)-2-oxo-1,2-dihydrobenzo[cd]indol-6-yl)methyl)-1H-pyrazol-1-yl)-4-methylpiperidine-1-carbonyl)cyclobutane-1-carbonitrile | ++++ |
| 87 | 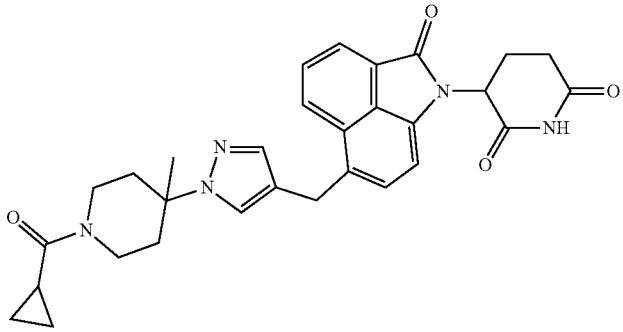 [SMILES: CC1(n2cc(Cc3ccc4c5c(cccc35)C(=O)N4C3CCC(=O)NC3=O)cn2)CCN(C(=O)C2CC2)CC1] 3-(6-((1-(1-(cyclopropanecarbonyl)-4-methylpiperidin-4-yl)-1H-pyrazol-4-yl)methyl)-2-oxobenzo[cd]indol-1(2H)-yl)piperidine-2,6-dione | |
| 88 | 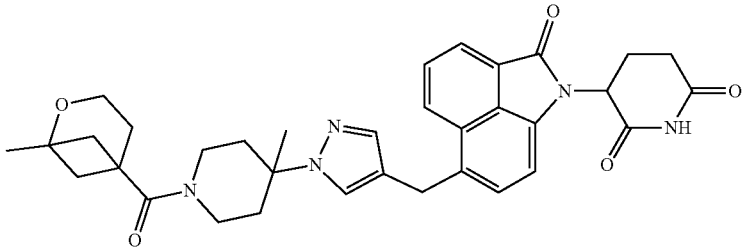 [SMILES: CC12CC(C(=O)N3CCC(C)(n4cc(Cc5ccc6c7c(cccc57)C(=O)N6C5CCC(=O)NC5=O)cn4)CC3)(CCO1)C2] 3-(6-((1-(4-methyl-1-(1-methyl-2-oxabicyclo[3.1.1]heptane-5-carbonyl)piperidin-4-yl)-1H-pyrazol-4-yl)methyl)-2-oxobenzo[cd]indol-1(2H)-yl)piperidine-2,6-dione | ++++ |
| 89 | 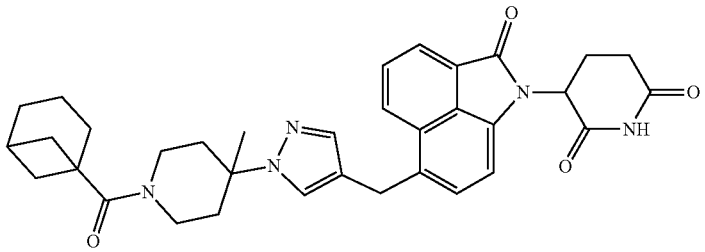 [SMILES: CC1(n2cc(Cc3ccc4c5c(cccc35)C(=O)N4C3CCC(=O)NC3=O)cn2)CCN(C(=O)C23CCCC(C2)C3)CC1] 3-(6-((1-(1-(bicyclo[3.1.1]heptane-1-carbonyl)-4-methylpiperidin-4-yl)-1H-pyrazol-4-yl)methyl)-2-oxobenzo[cd]indol-1(2H)-yl)piperidine-2,6-dione | ++++ |

TABLE 2-continued

| # | Structure | IC$_{50}$ (nM) |
|---|---|---|
| 90 | 3-(6-((1-(1-(2-oxabicyclo[2.1.1]hexane-1-carbonyl)-4-methylpiperidin-4-yl)-1H-pyrazol-4-yl)methyl)-2-oxobenzo[cd]indol-1(2H)-yl)piperidine-2,6-dione | ++++ |
| 91 | 3-(6-((1-(1-(bicyclo[1.1.1]pentane-1-carbonyl)-4-methylpiperidin-4-yl)-1H-pyrazol-4-yl)methyl)-2-oxobenzo[cd]indol-1(2H)-yl)piperidine-2,6-dione | ++++ |
| 92 | 3-(6-((1-(4-methyl-1-(1-methylcyclobutane-1-carbonyl)piperidin-4-yl)-1H-pyrazol-4-yl)methyl)-2-oxobenzo[cd]indol-1(2H)-yl)piperidine-2,6-dione | ++++ |
| 93 | 3-(6-(1-(4-methyl-1-pivaloylpiperidin-4-yl)-1H-pyrazol-4-yl)methyl)-2-oxobenzo[cd]indol-1(2H)-yl)piperidine-2,6-dione | ++++ |
| 94 | 3-(6-((1-(4-methyl-1-(3-methyloxetane-3-carbonyl)piperidin-4-yl)-1H-pyrazol-4-yl)methyl)-2-oxobenzo[cd]indol-1(2H)-yl)piperidine-2,6-dione | ++++ |

TABLE 2-continued

| # | Structure | IC$_{50}$ (nM) |
|---|---|---|
| 95 | 3-(6-((1-(1-(3-fluoro-2,2-dimethylpropanoyl)-4-methylpiperidin-4-yl)-1H-pyrazol-4-yl)methyl)-2-oxobenzo[cd]indol-1(2H)-yl)piperidine-2,6-dione | ++++ |
| 96 | 3-(6-((1-(1-(2-fluoro-2-methylpropanoyl)-4-methylpiperidin-4-yl)-1H-pyrazol-4-yl)methyl)-2-oxobenzo[cd]indol-1(2H)-yl)piperidine-2,6-dione | ++++ |
| 97 | 3-(6-((1-(1-(2-chloro-2-methylpropanoyl)-4-methylpiperidin-4-yl)-1H-pyrazol-4-yl)methyl)-2-oxobenzo[cd]indol-1(2H)-yl)piperidine-2,6-dione | ++++ |
| 98 | 3-(6-((1-(1-(3-hydroxy-2,2-dimethylpropanoyl)-4-methylpiperidin-4-yl)-1H-pyrazol-4-yl)methyl)-2-oxobenzo[cd]indol-1(2H)-yl)piperidine-2,6-dione | ++++ |
| 99 | 3-(6-((1-(4-methyl-1-((1-methylcyclobutyl)methyl)piperidin-4-yl)-1H-pyrazol-4-yl)methyl)-2-oxobenzo[cd]indol-1(2H)-yl)piperidine-2,6-dione | ++++ |

TABLE 2-continued

| # | Structure | IC$_{50}$ (nM) |
|---|---|---|
| 100 | 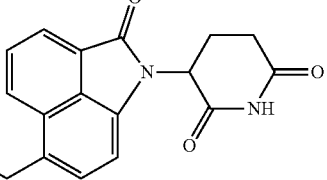<br>3-(6-((1-(4-methyl-1-((1-methylcyclopropyl)methyl)piperidin-4-yl)-1H-pyrazol-4-yl)methyl)-2-oxobenzo[cd]indol-1(2H)-yl)piperidine-2,6-dione | ++++ |
| 101 | 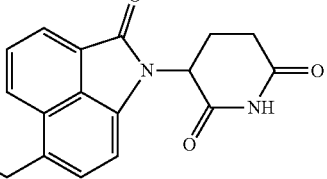<br>3-(6-((1-(1-(((1-methoxycyclopropyl)methyl)-4-methylpiperidin-4-yl)-1H-pyrazol-4-yl)methyl)-2-oxobenzo[cd]indol-1(2H)-yl)piperidine-2,6-dione | ++++ |
| 102 | 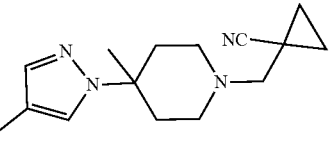<br>1-((4-(4-((1-(2,6-dioxopiperidin-3-yl)-2-oxo-1,2-dihydrobenzo[cd]indol-6-yl)methyl)-1H-pyrazol-1-yl)-4-methylpiperidin-1-yl)methyl)cyclopropane-1-carbonitrile | ++++ |
| 103 | 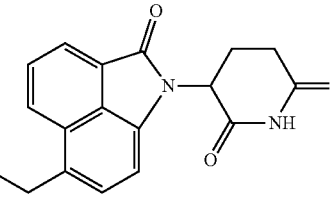<br>3-(6-((1-(1-((1-methoxycyclobutyl)methyl)-4-methylpiperidin-4-yl)-1H-pyrazol-4-yl)methyl)-2-oxobenzo[cd]indol-1(2H)-yl)piperidine-2,6-dione | ++++ |
| 104 | 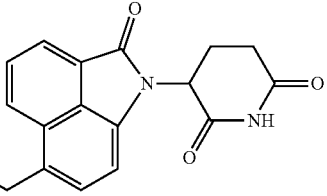<br>3-(6-((1-(4-methyl-1-neopentylpiperidin-4-yl)-1H-pyrazol-4-yl)methyl)-2-oxobenzo[cd]indol-1(2H)-yl)piperidine-2,6-dione | ++++ |
| 105 | 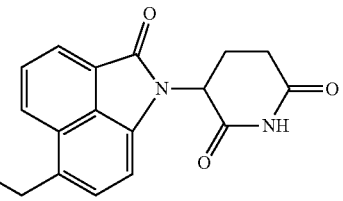<br>3-(6-((1-(4-methyl-1-((1-(trifluoromethyl)cyclopropyl)methyl)piperidin-4-yl)-1H-pyrazol-4-yl)methyl)-2-oxobenzo[cd]indol-1(2H)-yl)piperidine-2,6-dione | ++++ |

TABLE 2-continued

| # | Structure | IC$_{50}$ (nM) |
|---|---|---|
| 106 | 3-(6-((1-(1-((1-fluorocyclopropyl)methyl)-4-methylpiperidin-4-yl)-1H-pyrazol-4-yl)methyl)-2-oxobenzo[cd]indol-1(2H)-yl)piperidine-2,6-dione | ++++ |
| 107 | tert-butyl 4-(4-((1-(2,6-dioxopiperidin-3-yl)-2-oxo-1,2-dihydrobenzo[cd]indol-6-yl)methyl)benzyl)piperazine-1-carboxylate | ++++ |
| 108 | 3-(6-(4-((4-acetylpiperazin-1-yl)methyl)benzyl)-2-oxobenzo[cd]indol-1(2H)-yl)piperidine-2,6-dione | ++++ |
| 109 | 3-(2-oxo-6-(4-((4-((2,2,2-trifluoroethyl)sulfonyl)piperazin-1-yl)methyl)benzyl)benzo[cd]indol-1(2H)-yl)piperidine-2,6-dione | ++++ |
| 110 | 3-(6-(4-((4-(1-methylcyclobutane-1-carbonyl)piperazin-1-yl)methyl)benzyl)-2-oxobenzo[cd]indol-1(2H)-yl)piperidine-2,6-dione | ++++ |

TABLE 2-continued

| # | Structure | IC$_{50}$ (nM) |
|---|---|---|
| 111 | 3-(6-(4-((4-benzoylpiperazin-1-yl)methyl)benzyl)-2-oxobenzo[cd]indol-1(2H)-yl)piperidine-2,6-dione | ++++ |
| 112 | 3-(6-(4-((4-(cyclopropanecarbonyl)piperazin-1-yl)methyl)benzyl)-2-oxobenzo[cd]indol-1(2H)-yl)piperidine-2,6-dione | ++++ |
| 113 | 3-(6-(4-((4-(cyclopropylmethyl)piperazin-1-yl)methyl)benzyl)-2-oxobenzo[cd]indol-1(2H)-yl)piperidine-2,6-dione | ++++ |
| 114 | 3-(6-(4-((4-methylpiperazin-1-yl)methyl)benzyl)-2-oxobenzo[cd]indol-1(2H)-yl)piperidine-2,6-dione | ++++ |
| 115 | 3-(6-(4-((8-oxa-3-azabicyclo[3.2.1]octan-3-yl)methyl)benzyl)-2-oxobenzo[cd]indol-1(2H)-yl)piperidine-2,6-dione | ++++ |
| 116 | 3-(6-(4-((4-methyl-3-oxopiperazin-1-yl)methyl)benzyl)-2-oxobenzo[cd]indol-1(2H)-yl)piperidme-2,6-dione | ++++ |

TABLE 2-continued

| # | Structure | IC$_{50}$ (nM) |
|---|---|---|
| 117 | 3-(6-(4-(isoindolin-2-ylmethyl)benzyl)-2-oxobenzo[cd]indol-1(2H)-yl)piperidine-2,6-dione | ++++ |
| 118 | 3-(6-(4-((2,3-dihydrobenzo[f][1,4]oxazepin-4(5H)-yl)methyl)benzyl)-2-oxobenzo[cd]indol-1(2H)-yl)piperidine-2,6-dione | ++++ |
| 119 | 3-(6-(4-((2-(4-fluorophenyl)morpholino)methyl)benzyl)-2-oxobenzo[cd]indol-1(2H)-yl)piperidine-2,6-dione | ++++ |
| 120 | 3-(6-(4-((3-(4-fluorophenoxy)azetidin-1-yl)methyl)benzyl)-2-oxobenzo[cd]indol-1(2H)-yl)piperidine-2,6-dione | ++++ |
| 121 | 3-(2-oxo-6-(4-((3-(trifluoromethyl)-5,6-dihydro-[1,2,4]triazolo[4,3-a]pyrazin-7(8H)-yl)methyl)benzyl)benzo[cd]indol-1(2H)-yl)piperidine-2,6-dione | ++++ |
| 122 | 3-(6-(4-((1,4-dioxidothiomorpholino)methyl)benzyl)-2-oxobenzo[cd]indol-1(2H)-yl)piperidine-2,6-dione | ++++ |

TABLE 2-continued

| # | Structure | IC$_{50}$ (nM) |
|---|---|---|
| 123 | 3-(6-(4-((1,4-oxazepan-4-yl)methyl)benzyl)-2-oxobenzo[cd]indol-1(2H)-yl)piperidine-2,6-dione | ++++ |
| 124 | methyl 1-(2,6-dioxopiperidin-3-yl)-2-oxo-1,2-dihydrobenzo[cd]indole-6-carboxylate | |
| 125 | 3-(6-((4-(1-(1-methylcyclobutane-1-carbonyl)piperidin-4-yl)-1H-1,2,3-triazol-1-yl)methyl)-2-oxobenzo[cd]indol-1(2H)-yl)piperidine-2,6-dione | ++++ |
| 126 | 3-(6-((1-(1-(3-fluoropyridin-2-yl)piperidin-4-yl)-1H-pyrazol-4-yl)methyl)-2-oxobenzo[cd]indol-1(2H)-yl)piperidine-2,6-dione | ++++ |
| 127 | 3-(6-((4-(4-methyl-1-(1-(trifluoromethyl)cyclopropane-1-carbonyl)piperidin-4-yl)-1H-1,2,3-triazol-1-yl)methyl)-2-oxobenzo[cd]indol-1(2H)-yl)piperidine-2,6-dione | ++++ |

TABLE 2-continued

| # | Structure | IC$_{50}$ (nM) |
|---|---|---|
| 128 | 4-(4-((1-((1-(2,6-dioxopiperidin-3-yl)-2-oxo-1,2-dihydrobenzo[cd]indol-6-yl)methyl)-1H-pyrazol-4-yl)methyl)piperazin-1-yl)-3-fluorobenzonitrile | ++++ |
| 129 | 4-(4-((1-((1-(2,6-dioxopiperidin-3-yl)-2-oxo-1,2-dihydrobenzo[cd]indol-6-yl)methyl)-1H-pyrazol-4-yl)methyl)piperazin-1-yl)-3-fluorobenzonitrile | ++++ |
| 130 | 4-(4-((1-((1-(2,6-dioxopiperidin-3-yl)-2-oxo-1,2-dihydrobenzo[cd]indol-6-yl)methyl)-1H-pyrazol-4-yl)methyl)piperazin-1-yl)-3-fluorobenzonitrile | ++++ |
| 131 | 4-(4-(4-((1-(2,6-dioxopiperidin-3-yl)-2-oxo-1,2-dihydrobenzo[cd]indol-6-yl)methyl)benzyl)-4,7-diazaspiro[2.5]octan-7-yl)-3-fluorobenzonitrile | ++++ |

TABLE 2-continued

| # | Structure | IC$_{50}$ (nM) |
|---|---|---|
| 132 | 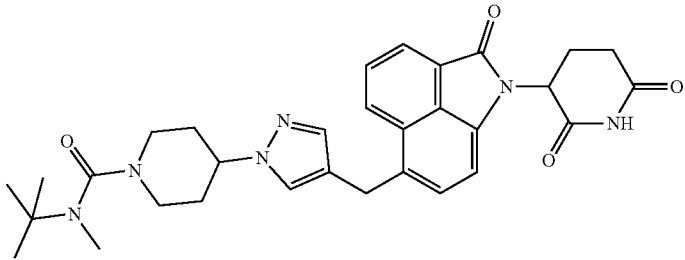 [SMILES: CN(C(=O)N1CCC(n2cc(Cc3ccc4c5c(cccc35)C(=O)N4C3CCC(=O)NC3=O)cn2)CC1)C(C)(C)C]<br>N-(tert-butyl)-4-(4-((1-(2,6-dioxopiperidin-3-yl)-2-oxo-1,2-dihydrobenzo[cd]indol-6-yl)methyl)-1H-pyrazol-1-yl)-N-methylpiperidine-1-carboxamide | ++++ |
| 133 | 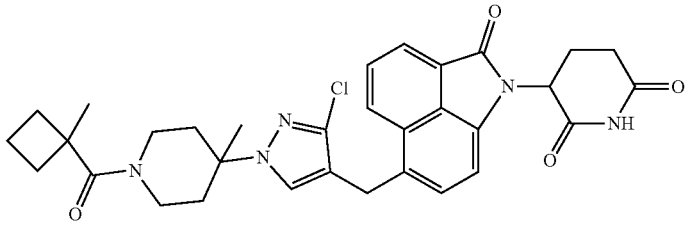 [SMILES: CC1(C(=O)N2CCC(C)(n3cc(Cc4ccc5c6c(cccc46)C(=O)N5C4CCC(=O)NC4=O)c(Cl)n3)CC2)CCC1]<br>3-(6-((3-chloro-1-(4-methyl-1-(1-methylcyclobutane-1-carbonyl)piperidin-4-yl)-1H-pyrazol-4-yl)methyl)-2-oxobenzo[cd]indol-1(2H)-yl)piperidine-2,6-dione | ++++ |
| 134 | 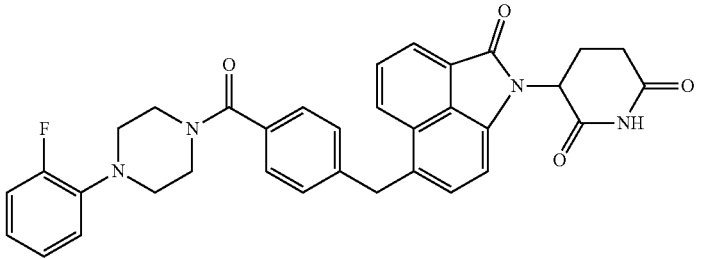 [SMILES: O=C1CCC(N2C(=O)c3cccc4c(Cc5ccc(C(=O)N6CCN(c7ccccc7F)CC6)cc5)ccc2c34)C(=O)N1]<br>3-(6-(4-(4-(2-fluorophenyl)piperazine-1-carbonyl)benzyl)-2-oxobenzo[cd]indol-1(2H)-yl)piperidine-2,6-dione | ++++ |
| 135 | 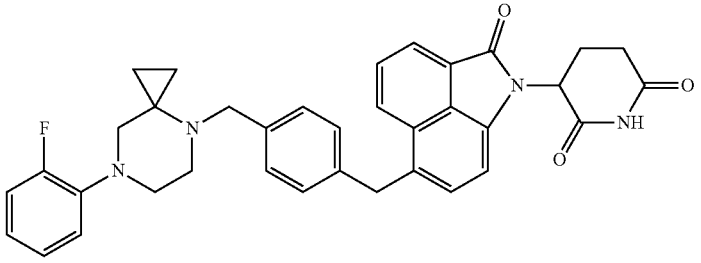 [SMILES: O=C1CCC(N2C(=O)c3cccc4c(Cc5ccc(CN6CCN(c7ccccc7F)CC67CC7)cc5)ccc2c34)C(=O)N1]<br>3-(6-(4-((7-(2-fluorophenyl)-4,7-diazaspiro[2.5]octan-4-yl)methyl)benzyl)-2-oxobenzo[cd]indol-1(2H)-yl)piperidine-2,6-dione | ++++ |
| 136 | 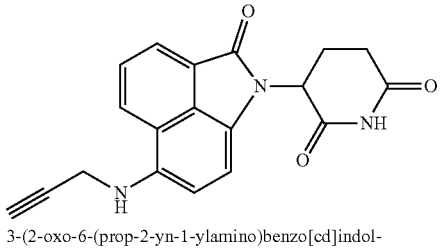<br>3-(2-oxo-6-(prop-2-yn-1-ylamino)benzo[cd]indol-1(2H)-yl)piperidine-2,6-dione | |

TABLE 2-continued

| # | Structure | IC$_{50}$ (nM) |
|---|---|---|
| 137 | 3-(2-oxo-6-(prop-2-yn-1-yloxy)benzo[cd]indol-1(2H)-yl)piperidine-2,6-dione | +++ |
| 138 | 3-(6-bromo-2-oxobenzo[cd]indol-1(2H)-yl)piperidine-2,6-dione | |
| 139 | 3-(2-oxobenzo[cd]indol-1(2H)-yl)piperidine-2,6-dione | +++ |
| 140 | tert-butyl 4-(4-((1-(2,6-dioxopiperidin-3-yl)-2-oxo-1,2-dihydrobenzo[cd]indol-6-yl)methyl)-1H-pyrazol-1-yl)piperidine-1-carboxylate | ++++ |
| 141 | tert-butyl 4-(4-((1-(2,6-dioxopiperidin-3-yl)-2-oxo-1,2-dihydrobenzo[cd]indol-6-yl)methyl)-1H-pyrazol-1-yl)piperidine-1-carboxylate | ++++ |

TABLE 2-continued

| # | Structure | IC$_{50}$ (nM) |
|---|---|---|
| 142 | 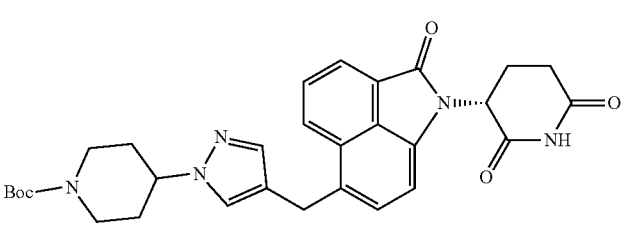 [SMILES: CC(C)(C)OC(=O)N1CCC(n2cc(Cc3ccc4c5c(cccc35)C(=O)N4[C@@H]3CCC(=O)NC3=O)cn2)CC1] tert-butyl 4-(4-((1-(2,6-dioxopiperidin-3-yl)-2-oxo-1,2-dihydrobenzo[cd]indol-6-yl)methyl)-1H-pyrazol-1-yl)piperidine-1-carboxylate | ++++ |
| 143 | 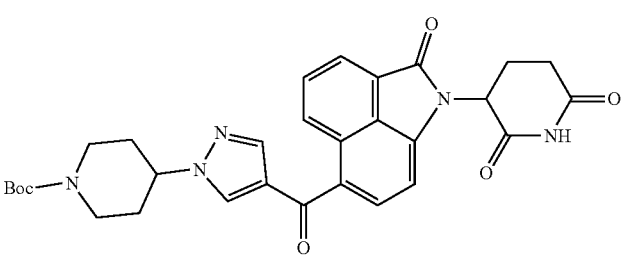 [SMILES: CC(C)(C)OC(=O)N1CCC(n2cc(C(=O)c3ccc4c5c(cccc35)C(=O)N4C3CCC(=O)NC3=O)cn2)CC1] tert-butyl 4-(4-(1-(2,6-dioxopiperidin-3-yl)-2-oxo-1,2-dihydrobenzo[cd]indole-6-carbonyl)-1H-pyrazol-1-yl)piperidine-1-carboxylate | ++ |
| 144 | 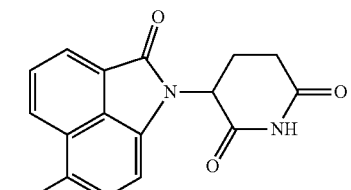 3-(6-amino-2-oxobenzo[cd]indol-1(2H)-yl)piperidine-2,6-dione | ++ |
| 145 | 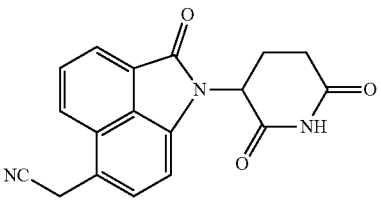 [SMILES: N#CCc1ccc2c3c(cccc13)C(=O)N2C1CCC(=O)NC1=O] 1-(2,6-dioxopiperidin-3-yl)-2-oxo-1,2-dihydrobenzo[cd]indole-6-carbonitrile | |
| 146 | 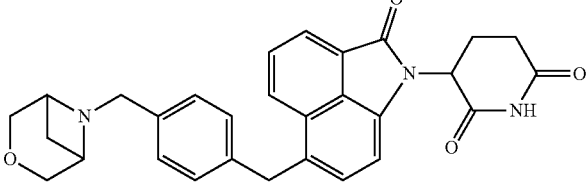 3-(6-(4-((3-oxa-6-azabicyclo[3.1.1]heptan-6-yl)methyl)benzyl)-oxobenzo[cd]indol-1(2H)-yl)piperidine-2,6-dione | ++++ |

TABLE 2-continued

| # | Structure | IC$_{50}$ (nM) |
|---|---|---|
| 147 | 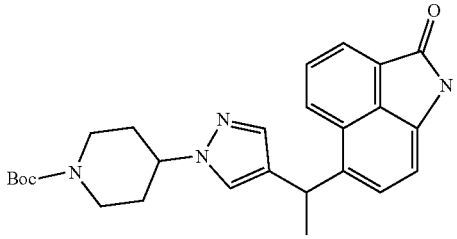 [SMILES: CC(c1cnn(C2CCN(C(=O)OC(C)(C)C)CC2)c1)c1ccc2c3c(cccc13)C(=O)N2] tert-butyl 4-(4-(1-(2-oxo-1,2-dihydrobenzo[cd]indol-6-yl)ethyl)-1H-pyrazol-1-yl)piperidine-1-carboxylate | ++++ |
| 148 | 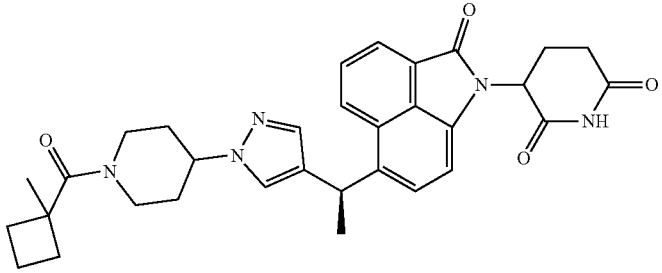 [SMILES: C[C@@H](c1cnn(C2CCN(C(=O)C3(C)CCC3)CC2)c1)c1ccc2c3c(cccc13)C(=O)N2C1CCC(=O)NC1=O] 3-(6-(1-(1-(1-(1-methylcyclobutane-1-carbonyl)piperidin-4-yl)-1H-pyrazol-4-yl)ethyl)-2-oxobenzo[cd]indol-1(2H)-yl)piperidine-2,6-dione | ++++ |
| 149 | 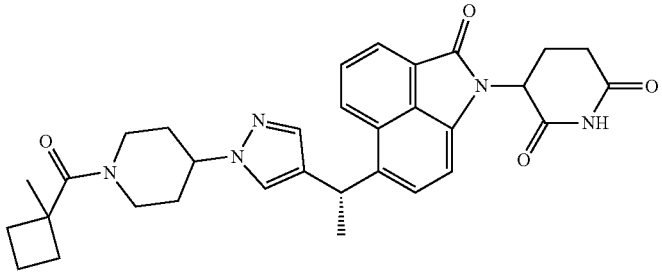 [SMILES: C[C@H](c1cnn(C2CCN(C(=O)C3(C)CCC3)CC2)c1)c1ccc2c3c(cccc13)C(=O)N2C1CCC(=O)NC1=O] 3-(6-(1-(1-(1-(1-methylcyclobutane-1-carbonyl)piperidin-4-yl)-1H-pyrazol-4-yl)ethyl)-2-oxobenzo[cd]indol-1(2H)-yl)piperidine-2,6-dione | ++++ |
| 150 | 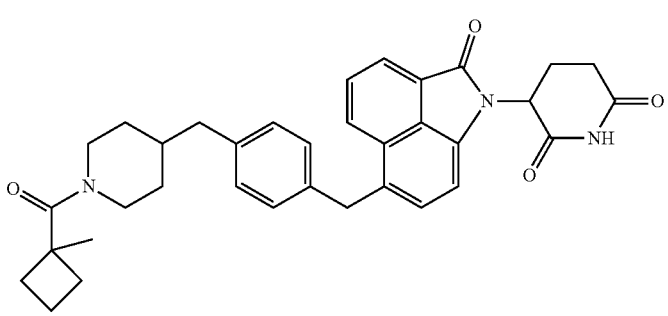 [SMILES: CC1(C(=O)N2CCC(Cc3ccc(Cc4ccc5c6c(cccc46)C(=O)N5C4CCC(=O)NC4=O)cc3)CC2)CCC1] 3-(6-(4-((1-(1-methylcyclobutane-1-carbonyl)piperidin-4-yl)methyl)benzyl)-2-oxobenzo[cd]indol-1(2H)-yl)piperidine-2,6-dione | ++++ |
| 151 | 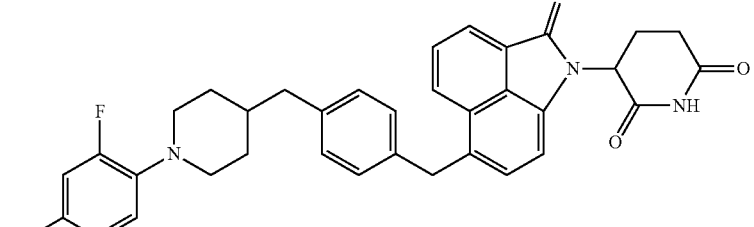 4-(4-(4-((1-(2,6-dioxopiperidin-3-yl)-2-oxo-1,2-dihydrobenzo[cd]indol-6-yl)methyl)benzyl)piperidin-1-yl)-3-fluorobenzonitrile | ++++ |

TABLE 2-continued

| # | Structure | IC$_{50}$ (nM) |
|---|---|---|
| 152 | 3-(6-(4-((1-benzylpiperidin-4-yl)methyl)benzyl)-2-oxobenzo[cd]indol-1(2H)-yl)piperidine-2,6-dione | ++++ |
| 153 | (3S)-3-(6-(amino(1-(1-(1-methylcyclobutane-1-carbonyl)piperidin-4-yl)-1H-pyrazol-4-yl)methyl)-2-oxobenzo[cd]indol-1(2H)-yl)piperidine-2,6-dione | ++++ |
| 154 | tert-butyl 4-(4-(amino(1-(2,6-dioxopiperidin-3-yl)-2-oxo-1,2-dihydrobenzo[cd]indol-6-yl)methyl)-1H-pyrazol-1-yl)piperidine-1-carboxylate | ++++ |
| 155 | 3-(6-(4-((3,4-dihydroisoquinolin-2(1H)-yl)methyl)benzyl)-2-oxobenzo[cd]indol-(2H)-yl)piperidine-2,6-dione | ++++ |
| 156 | 3-(6-(4-((3-oxa-8-azabicyclo[3.2.1]octan-8-yl)methyl)benzyl)-2-oxobenzo[cd]indol-1(2H)-yl)piperidine-2,6-dione | ++++ |

TABLE 2-continued

| # | Structure | IC$_{50}$ (nM) |
|---|---|---|
| 157 | 3-(6-(4-((4-(4-fluorobenzyl)piperidin-1-yl)methyl)benzyl)-2-oxobenzo[cd]indol-1(2H)-yl)piperidine-2,6-dione | ++++ |
| 158 | 3-(6-(4-((4-(tert-butyl)piperidin-1-yl)methyl)benzyl)-2-oxobenzo[cd]indol-1(2H)-yl)piperidine-2,6-dione | ++++ |
| 159 | 3-(2-oxo-6-(4-((4-((2,2,2-trifluoroethyl)sulfonyl)piperazin-1-yl)methyl)benzyl)benzo[cd]indol-1(2H)-yl)piperidine-2,6-dione | ++++ |
| 160 | 3-(2-oxo-6-(4-((4-((2,2,2-trifluoroethyl)sulfonyl)piperazin-1-yl)methyl)benzyl)benzo[cd]indol-1(2H)-yl)piperidine-2,6-dione | ++++ |
| 161 | 3-(2-oxo-6-(4-((4-(2,2,2-trifluoroethyl)piperazin-1-yl)methyl)benzyl)benzo[cd]indol-12H)-yl)piperidine-2,6-dione | ++++ |

TABLE 2-continued

| # | Structure | IC$_{50}$ (nM) |
|---|---|---|
| 162 | 3-(6-(((1-cyclohexyl-1H-pyrazol-4-yl)methyl)-2-oxobenzo[cd]indol-1(2H)-yl)piperidine-2,6-dione | ++++ |
| 163 | 3-(6-(1-(1-(1-(1-methylcyclobutane-1-carbonyl)piperidin-4-yl-1H-pyrazol-4-yl)cyclopropyl)-2-oxobenzo[cd]indol-1(2H)-yl)piperidine-2,6-dione | ++++ |
| 164 | 3-(6-(1-(1-(1-((1-methylcyclobutyl)methyl)piperidin-4-yl)-1H-pyrazol-4-yl)cyclopropyl)-2-oxobenzo[cd]indol-1(2H)-yl)piperidine-2,6-dione | +++ |
| 165 | 4-(4-((4-((1-(2,6-dioxopiperidin-3-yl)-2-oxo-1,2-dihydrobenzo[cd]indol-6-yl)methyl)phenyl)(methyl)amino)piperidin-1-yl)-3-fluorobenzonitrile | ++++ |
| 166 | 4-(4-((4-((1-(2,6-dioxopiperidin-3-yl)-2-oxo-1,2-dihydrobenzo[cd]indol-6-yl)methyl)phenyl)amino)piperidin-1-yl)-3-fluorobenzonitrile | ++++ |

TABLE 2-continued

| # | Structure | IC$_{50}$ (nM) |
|---|---|---|
| 167 | 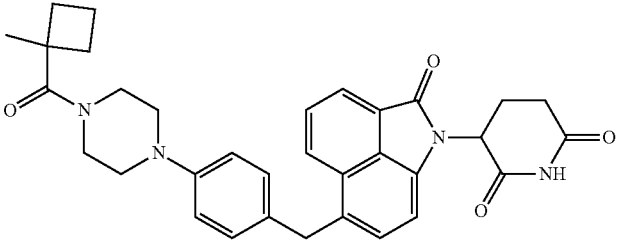 [SMILES: CC1(C(=O)N2CCN(c3ccc(Cc4ccc5c6c(cccc46)C(=O)N5C4CCC(=O)NC4=O)cc3)CC2)CCC1]<br>3-(6-(4-(4-(1-methylcyclobutane-1-carbonyl)piperazin-1-yl)benzyl)-2-oxobenzo[cd]indol-1(2H)-yl)piperidine-2,6-dione | ++++ |
| 168 | 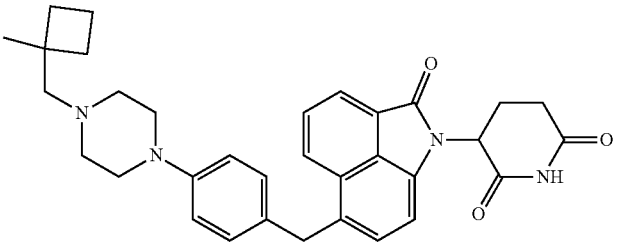 [SMILES: CC1(CN2CCN(c3ccc(Cc4ccc5c6c(cccc46)C(=O)N5C4CCC(=O)NC4=O)cc3)CC2)CCC1]<br>3-(6-(4-(4-((1-methylcyclobutyl)methyl)piperazin-1-yl)benzyl)-2-oxobenzo[cd]indol-1(2H)-yl)piperidine-2,6-dione | ++++ |
| 169 | 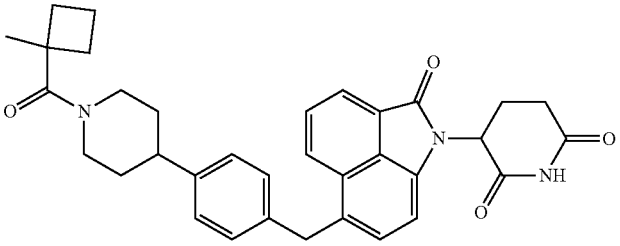 [SMILES: CC1(C(=O)N2CCC(c3ccc(Cc4ccc5c6c(cccc46)C(=O)N5C4CCC(=O)NC4=O)cc3)CC2)CCC1]<br>3-(6-(4-(1-(1-methylcyclobutane-1-carbonyl)piperidin-4-yl)benzyl)-2-oxobenzo[cd]indol-1(2H)-yl)piperidine-2,6-dione | ++++ |
| 170 | 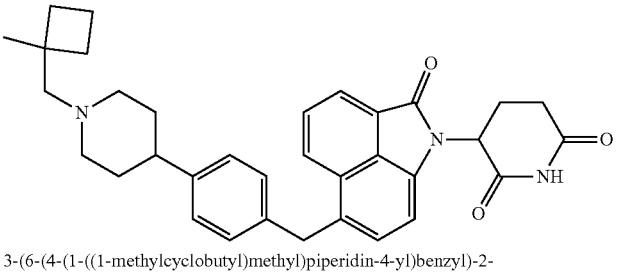<br>3-(6-(4-(1-((1-methylcyclobutyl)methyl)piperidin-4-yl)benzyl)-2-oxobenzo[cd]indol-1(2H)-yl)piperidine-2,6-dione | ++++ |
| 171 | 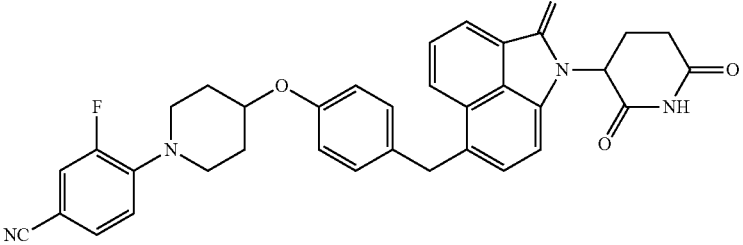<br>4-(4-(4-((1-(2,6-dioxopiperidin-3-yl)-2-oxo-1,2-dihydrobenzo[cd]indol-6-yl)methyl)phenoxy)piperidin-1-yl)-3-fluorobenzonitrile | ++++ |

TABLE 2-continued

| # | Structure | IC$_{50}$ (nM) |
|---|---|---|
| 172 | 4-(4-(4-((1-(2,6-dioxopiperidin-3-yl)-2-oxo-1,2-dihydrobenzo[cd]indol-6-yl)methyl)benzyl)-3-oxopiperazin-1-yl)-3-fluorobenzonitrile | ++++ |
| 174 | 3-(6-((1-(1-(1-methylcyclobutane-1-carbonyl)piperidin-4-yl)-1H-pyrazol-4-yl)thio)-2-oxobenzo[cd]indol-1(2H)-yl)piperidine-2,6-dione | ++++ |
| 175 | 3-(6-((1-(1-(1-methylcyclobutane-1-carbonyl)piperidin-4-yl)-1H-pyrazol-4-yl)sulfonyl)-2-oxobenzo[cd]indol-1(2H)-yl)piperidine-2,6-dione | +++ |
| 176 | 3-(6-((1-(1-(1-methylcyclobutane-1-carbonyl)piperidin-4-yl)-1H-pyrazol-4-yl)sulfinyl)-2-oxobenzo[cd]indol-1(2H)-yl)pipcridine-2,6-dione | ++++ |
| 177 | 3-(6-((1-(3-(benzyloxy)cyclobutyl)-1H-pyrazol-4-yl)methyl)-2-oxobenzo[cd]indol-1(2H)-yl)piperidine-2,6-dione | +++ |

TABLE 2-continued

| # | Structure | IC$_{50}$ (nM) |
|---|---|---|
| 178 | 3-(2-oxo-6-((1-(1-(spiro[3.4]octan-5-yl)piperidin-4-yl)-1H-pyrazol-4-yl)methyl)benzo[cd]indol-1(2H)-yl)piperidine-2,6-dione | ++++ |
| 179 | 3-(2-oxo-6-((1-(1-(spiro[3.4]octan-5-yl)piperidin-4-yl)-1H-pyrazol-4-yl)methyl)benzo[cd]indol-1(2H)-yl)pipcridinc-2,6-dione | ++++ |
| 180 | 3-(6-((3-(1-(1-methylcyclobutane-1-carbonyl)piperidin-4-yl)-1H-pyrazol-1-yl)methyl)-2-oxobenzo[cd]indol-1(2H)-yl)piperidine-2,6-dione | ++++ |
| 181 | 3-(6-((3-(1-(1-methylcyclobutane-1-carbonyl)piperidin-4-yl)-2-oxoimidazolidin-1-yl)methyl)-2-oxobenzo[cd]indol-1(2H)-yl)piperidine-2,6-dione | ++++ |
| 182 | 6-(4,4,5,5-tetramethyl-1,3,2-dioxaborolan-2-yl)benzo[cd]indol-2(1H)-one | |

TABLE 2-continued

| # | Structure | IC$_{50}$ (nM) |
|---|---|---|
| 183 | 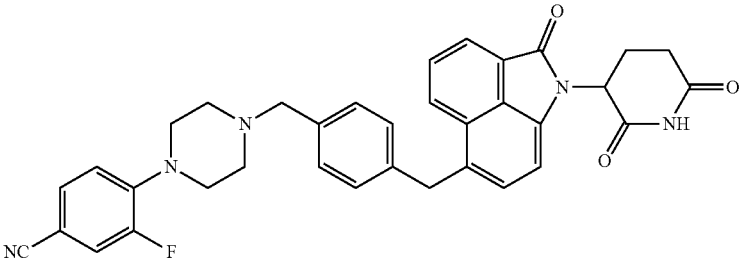 [SMILES: N#Cc1ccc(N2CCN(Cc3ccc(Cc4ccc5c6c(cccc46)C(=O)N5C4CCC(=O)NC4=O)cc3)CC2)c(F)c1]<br>4-(4-(4-((1-(2,6-dioxopiperidin-3-yl)-2-oxo-1,2-dihydrobenzo[cd]indol-6-yl)methyl)benzyl)piperazin-1-yl)-3-fluorobenzonitrile | ++++ |
| 184 | 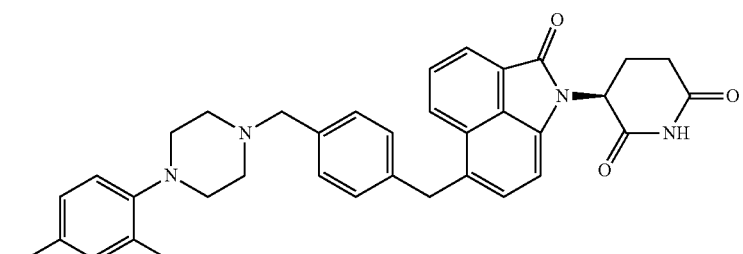<br>4-(4-(4-((1-(2,6-dioxopiperidin-3-yl)-2-oxo-1,2-dihydrobenzo[cd]indol-6-yl)methyl)benzyl)piperazin-1-yl)-3-fluorobenzonitrile | ++++ |
| 185 | 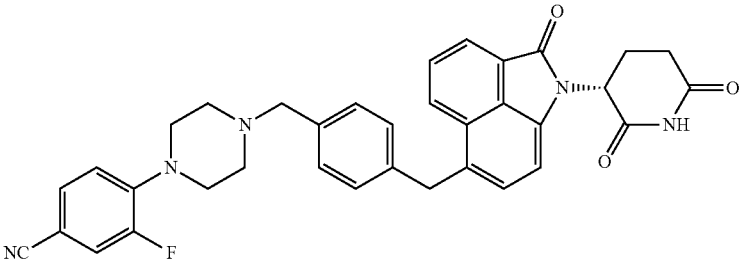 [SMILES: N#Cc1ccc(N2CCN(Cc3ccc(Cc4ccc5c6c(cccc46)C(=O)N5[C@@H]4CCC(=O)NC4=O)cc3)CC2)c(F)c1]<br>4-(4-(4-((1-(2,6-dioxopiperidin-3-yl)-2-oxo-1,2-dihydrobenzo[cd]indol-6-yl)methyl)benzyl)piperazin-1-yl)-3-fluorobenzonitrile | ++++ |
| 186 | 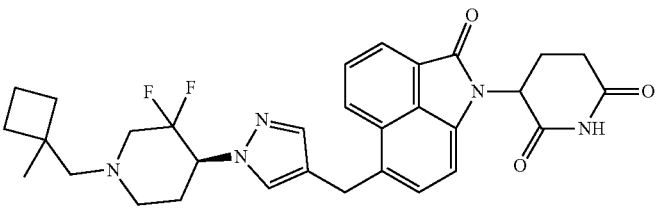 [SMILES: CC1(CN2CC[C@H](n3cc(Cc4ccc5c6c(cccc46)C(=O)N5C4CCC(=O)NC4=O)cn3)C(F)(F)C2)CCC1]<br>3-(6-((1-(3,3-difluoro-1-((1-methylcyclobutyl)methyl)piperidin-4-yl)-1H-pyrazol-4-yl)methyl)-2-oxobenzo[cd]indol-1(2H)-yl)piperidine-2,6-dione | ++++ |
| 187 | 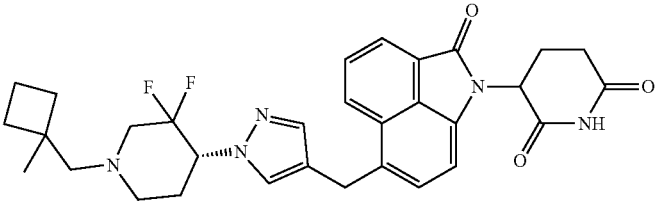 [SMILES: CC1(CN2CC[C@@H](n3cc(Cc4ccc5c6c(cccc46)C(=O)N5C4CCC(=O)NC4=O)cn3)C(F)(F)C2)CCC1]<br>3-(6-((1-(3,3-difluoro-1-((1-methylcyclobutyl)methyl)piperidin-4-yl)-1H-pyrazol-4-yl)methyl)-2-oxobenzo[cd]indol-1(2H)-yl)piperidine-2,6-dione | ++++ |

TABLE 2-continued

| # | Structure | IC$_{50}$ (nM) |
|---|---|---|
| 188 | 3-(6-(4-((4-(2-fluorophenyl)piperazin-1-yl)methyl)benzyl)-2-oxobenzo[cd]indol-1(2H)-yl)piperidine-2,6-dione | ++++ |
| 189 | 3-(6-(4-((4-(2-fluorophenyl)piperazin-1-yl)methyl)benzyl)-2-oxobenzo[cd]indol-1(2H)-yl)piperidine-2,6-dione | ++++ |
| 190 | 3-(6-(4-((4-(2-fluorophenyl)piperazin-1-yl)methyl)benzyl)-2-oxobenzo[cd]indol-1(2H)-yl)piperidine-2,6-dione | +++ |
| 191 | 3-(6-((1-(1-((1-methylcyclobutyl)methyl)-4-(trifluoromethyl)piperidin-4-yl)-1H-pyrazol-4-yl)methyl)-2-oxobenzo[cd]indol-1(2H)-yl)piperidine-2,6-dione | ++++ |
| 192 | 3-(6-((1-(1-(1-methylcyclobutane-1-carbonyl)piperidin-4-yl)-1H-1,2,3-triazol-4-yl)methyl)-2-oxobenzo[cd]indol-1(2H)-yl)piperidine-2,6-dione | ++++ |

TABLE 2-continued

| # | Structure | IC$_{50}$ (nM) |
|---|---|---|
| 193 | 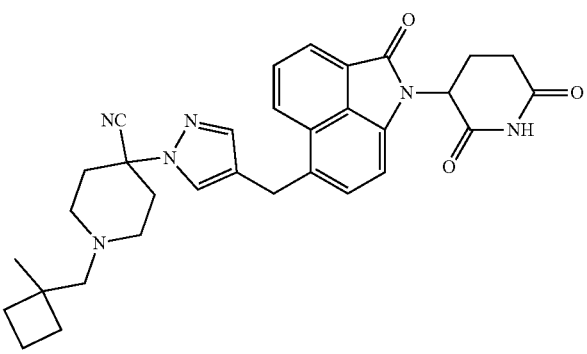 [SMILES: CC1(CN2CCC(C#N)(n3cc(Cc4ccc5c6c(cccc46)C(=O)N5C4CCC(=O)NC4=O)cn3)CC2)CCC1] 4-(4-((1-(2,6-dioxopiperidin-3-yl)-2-oxo-1,2-dihydrobenzo[cd]indol-6-yl)methyl)-1H-pyrazol-1-yl)-1-((1-methylcyclobutyl)methyl)piperidine-4-carbonitrile | ++++ |
| 194 | 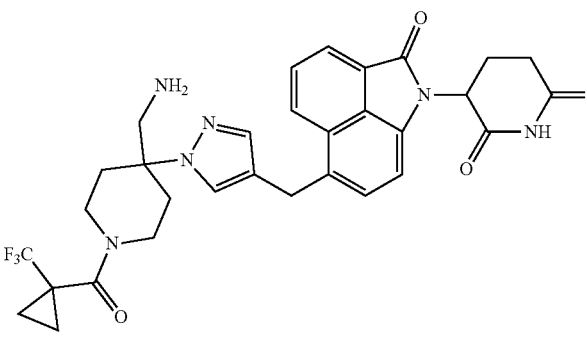 3-(6-((1-(4-(aminomethyl)-1-(1-(trifluoromethyl)cyclopropane-1-carbonyl)piperidin-4-yl)-1H-pyrazol-4-yl)methyl)-2-oxobenzo[cd]indol-1(2H)-yl)piperidine-2,6-dione hydrochloride | +++ |
| 195 | 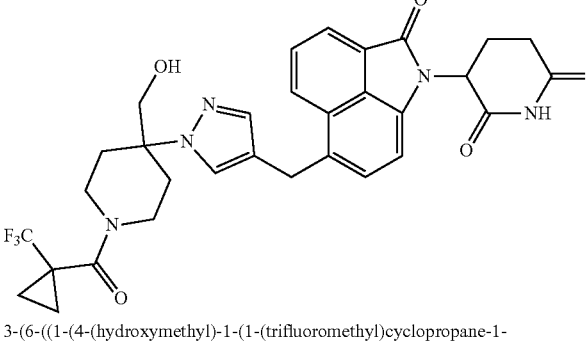 3-(6-((1-(4-(hydroxymethyl)-1-(1-(trifluoromethyl)cyclopropane-1-carbonyl)piperidin-4-yl)-1H-pyrazol-4-yl)methyl)-2-oxobenzo[cd]indol-1(2H)-yl)piperidine-2,6-dione | ++++ |
| 196 | 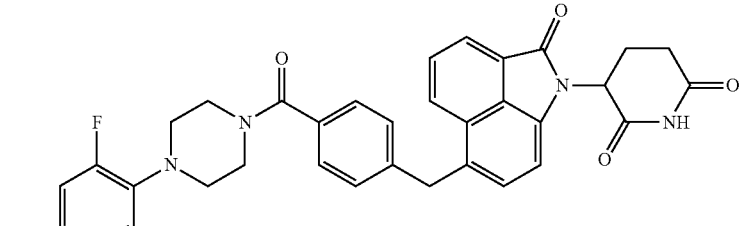 4-(4-(4-((1-(2,6-dioxopiperidin-3-yl)-2-oxo-1,2-dihydrobenzo[cd]indol-6-yl)methyl)benzoyl)piperazin-1-yl)-3-fluorobenzonitrile | ++++ |

TABLE 2-continued

| # | Structure | IC$_{50}$ (nM) |
|---|---|---|
| 197 | 3-(2-oxo-6-(4-((3-oxomorpholino)methyl)benzyl)benzo[cd]indol-1(2H)-yl)piperidine-2,6-dione | ++++ |
| 198 | 3-(6-((1-(1-methylcyclohexyl)-1H-pyrazol-4-yl)methyl)-2-oxobenzo[cd]indol-1(2H)-yl)piperidine-2,6-dione | ++++ |
| 199 | 1-((4-(4-((1-(2,6-dioxopiperidin-3-yl)-2-oxo-1,2-dihydrobenzo[cd]indol-6-yl)methyl)-1H-pyrazol-1-yl)piperidin-1-yl)methyl)cyclopropane-1-carbonitrile | ++++ |
| 200 | 3-(6-((3-chloro-1-(1-((1-methylcyclobutyl)methyl)piperidin-4-yl)-1H-pyrazol-4-yl)methyl)-2-oxobenzo[cd]indol-1(2H)-yl)piperidine-2,6-dione | ++++ |
| 201 | 3-(6-((3-chloro-1-(1-(((1-(trifluoromethyl)cyclopropyl)methyl)piperidin-4-yl)-1H-pyrazol-4-yl)methyl)-2-oxobenzo[cd]indol-1(2H)-yl)piperidine-2,6-dione | ++++ |

TABLE 2-continued

| # | Structure | IC$_{50}$ (nM) |
|---|---|---|
| 202 | 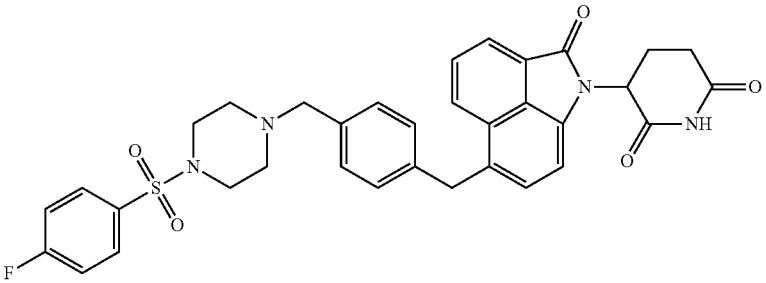 [SMILES: O=C1CCC(N2C(=O)c3cccc4c(Cc5ccc(CN6CCN(S(=O)(=O)c7ccc(F)cc7)CC6)cc5)ccc2c34)C(=O)N1]<br>3-(6-(4-((4-((4-fluorophenyl)sulfonyl)piperazin-1-yl)methyl)benzyl)-2-oxobenzo[cd]indol-1(2H)-yl)piperidine-2,6-dione | ++++ |
| 203 | 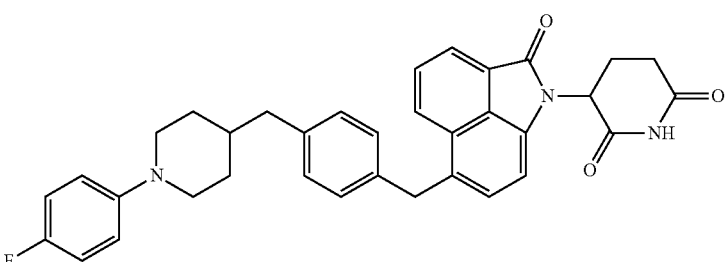<br>3-(6-(4-((1-(4-fluorophenyl)piperidin-4-yl)methyl)benzyl)-2-oxobenzo[cd]indol-1(2H)-yl)piperidine-2,6-dione | ++++ |
| 204 | 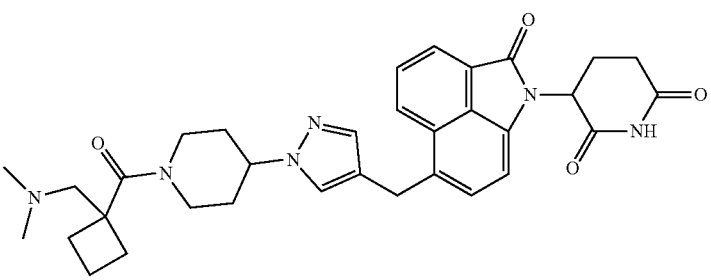 [SMILES: CN(C)CC1(C(=O)N2CCC(n3cc(Cc4ccc5c6c(cccc46)C(=O)N5C4CCC(=O)NC4=O)cn3)CC2)CCC1]<br>3-(6-((1-(1-(1-((dimethylamino)methyl)cyclobutane-1-carbonyl)piperidin-4-yl)-1H-pyrazol-4-yl)methyl)-2-oxobenzo[cd]indol-1(2H)-yl)piperidine-2,6-dione | |
| 205 | 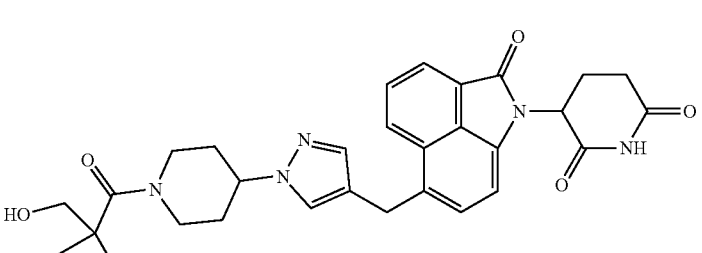<br>3-(6-((1-(1-(1-(hydroxymethyl)cyclobutane-1-carbonyl)piperidin-4-yl)-1H-pyrazol-4-yl)methyl)-2-oxobenzo[cd]indol-1(2H)-yl)piperidine-2,6-dione | ++++ |

TABLE 2-continued

| # | Structure | IC₅₀ (nM) |
|---|---|---|
| 206 | 3-(6-((3-chloro-1-(1-((1-methylcyclobutyl)methyl)piperidin-4-yl)-1H-pyrazol-5-yl)methyl)-2-oxobenzo[cd]indol-1(2H)-yl)piperidine-2,6-dione | ++++ |
| 207 | 3-(6-((1-(1-(1-methylcyclobutane-1-carbonyl)piperidin-4-yl)-1H-pyrazol-4-yl)oxy)-2-oxobenzo[cd]indol-1(2H)-yl)piperidine-2,6-dione | +++ |
| 208 | 4-(4-((1-((1-(2,6-dioxopiperidin-3-yl)-2-oxo-1,2-dihydrobenzo[cd]indol-6-yl)methyl)-1H-pyrazol-3-yl)methyl)piperazin-1-yl)-3-fluorobenzonitrile | ++++ |
| 209 | 4-(4-((1-((1-(2,6-dioxopiperidin-3-yl)-2-oxo-1,2-dihydrobenzo[cd]indol-6-yl)methyl)-1H-pyrazol-5-yl)methyl)piperazin-1-yl)-3-fluorobenzonitrile | +++ |

TABLE 2-continued

| # | Structure | IC$_{50}$ (nM) |
|---|---|---|
| 210 | 3-(2-oxo-6-(4-((4-phenylpiperazin-1-yl)methyl)benzyl)benzo[cd]indol-1(2H)-yl)piperidine-2,6-dione | ++++ |
| 211 | 3-(6-((1-(4-methyl-1-(1-(trifluoromethyl)cyclopropane-1-carbonyl)piperidin-4-yl)-1H-1,2,3-triazol-4-yl)methyl)-2-oxobenzo[cd]indol-1(2H)-yl)piperidine-2,6-dione | ++++ |
| 212 | 3-(6-((1-((1r,4r)-4-(tert-butoxy)cyclohexyl)-1H-pyrazol-4-yl)methyl)-2-oxobenzo[cd]indol-1(2H)-yl)piperidine-2,6-dione | ++++ |
| 213 | 3-(6-((1-((1s,4s)-4-(tert-butoxy)cyclohexyl)-1H-pyrazol-4-yl)methyl)-2-oxobenzo[cd]indol-1(2H)-yl)piperidine-2,6-dione | ++++ |
| 214 | 4-(4-(4-((1-(2,6-dioxopiperidin-3-yl)-2-oxo-1,2-dihydrobenzo[cd]indol-6-yl)methyl)-2-fluorobenzyl)piperazin-1-yl)-3-fluorobenzonitrile | ++++ |

TABLE 2-continued

| # | Structure | IC$_{50}$ (nM) |
|---|---|---|
| 215 | 3-(6-(4-((1-oxa-8-azaspiro[4.5]decan-8-yl)methyl)benzyl)-2-oxobenzo[cd]indol-1(2H)-yl)piperidine-2,6-dione | ++++ |
| 216 | 3-(6-(4-((1-oxa-8-azaspiro[4.5]decan-8-yl)methyl)benzyl)-2-oxobenzo[cd]indol-1(2H)-yl)piperidine-2,6-dione | ++++ |
| 217 | 3-(6-(4-((1-oxa-8-azaspiro[4.5]decan-8-yl)methyl)benzyl)-2-oxobenzo[cd]indol-1(2H)-yl)piperidine-2,6-dione | ++++ |
| 218 | 3-(6-(4-(morpholinomethyl)benzyl)-2-oxobenzo[cd]indol-1(2H)-yl)piperidine-2,6-dione | ++++ |
| 219 | 3-(6-(4-(morpholinomethyl)benzyl)-2-oxobenzo[cd]indol-1(2H)-yl)piperidine-2,6-dione | ++++ |
| 220 | 3-(6-(4-(morpholinomethyl)benzyl)-2-oxobenzo[cd]indol-1(2H)-yl)piperidine-2,6-dione | ++++ |

TABLE 2-continued

| # | Structure | IC$_{50}$ (nM) |
|---|---|---|
| 221 | 3-(6-(4-(morpholinomethyl)benzyl)-2-oxopyrrolo[4,3,2-ij]isoquinolin-1(2H)-yl)piperidine-2,6-dione | ++++ |
| 222 | 3-(6-(4-((1-oxa-8-azaspiro[4.5]decan-8-yl)methyl)benzyl)-2-oxopyrrolo[4.3.2-ij]isoquinolin-1(2H)-yl)piperidine-2,6-dione | ++++ |
| 223 | 3-(6-((1-(1-([1,1'-bi(cyclopropan)]-1-yl)piperidin-4-yl)-1H-pyrazol-4-yl)methyl)-2-oxobenzo[cd]indol-1(2H)yl)piperidine-2,6-dione | ++++ |
| 224 | 3-(6-(4-((3-azaspiro[5.5]undecan-3-yl)methyl)benzyl)-2-oxobenzo[cd]indol-1(2H)-yl)piperidine-2,6-dione | ++++ |
| 225 | 3-(6-(4-((8-azaspiro[4.5]decan-8-yl)methyl)benzyl)-2-oxobenzo[cd]indol-1(2H)-yl)piperidine-2,6-dione | ++++ |
| 226 | 3-(6-(4-((3-oxa-6-azabicyclo[3.1.1]heptan-6-yl)methyl)benzyl)-2-oxobenzo[cd]indol-1(2H)-yl)piperidine-2,6-dione | ++++ |

| # | Structure | IC$_{50}$ (nM) |
|---|---|---|
| 227 | 3-(2-oxo-6-(4-((4-phenylpiperidin-1-yl)methyl)benzyl)benzo[cd]indol-1(2H)-yl)piperidine-2,6-dione | ++++ |
| 228 | 3-(6-(4-((1-oxa-9-azaspiro[5.5]undecan-9-yl)methyl)benzyl)-2-oxobenzo[cd]indol-1(2H)-yl)piperidine-2,6-dione | ++++ |
| 229 | 3-(6-(4-((methyl(phenyl)amino)methyl)benzyl)-2-oxobenzo[cd]indol-1(2H)-yl)piperidine-2,6-dione | ++++ |
| 230 | 3-(6-(4-((2-oxa-6-azaspiro[3.3]heptan-6-yl)methyl)benzyl)-2-oxobenzo[cd]indol-1(2H)-yl)piperidine-2,6-dione | ++++ |
| 231 | 3-(6-(4-(((2R,6S)-2,6-dimethylmorpholino)methyl)benzyl)-2-oxobenzo[cd]indol-1(2H)-yl)piperidine-2,6-dione | ++++ |

TABLE 2-continued

| # | Structure | IC$_{50}$ (nM) |
|---|---|---|
| 232 | 3-(6-(4-((4-(2-hydroxypropan-2-yl)piperidin-1-yl)methyl)benzyl)-2-oxobenzo[cd]indol-1(2H)-yl)piperidine-2,6-dione | ++++ |
| 233 | 3-(6-((1-(4-methyl-1-((1-methylcyclobutyl)sulfonyl)piperidin-4-yl)-1H-pyrazol-4-yl)methyl)-2-oxobenzo[cd]indol-1(2H)-yl)piperidine-2,6-dione | ++++ |
| 234 | 3-(6-((1-(1-((1-methylcyclopropyl)methyl)piperidin-4-yl)-1H-pyrazol-4-yl)methyl)-2-oxobenzo[cd]indol-1(2H)-yl)piperidine-2,6-dione | ++++ |
| 235 | 3-(6-((1-(1-((1-methylcyclopropyl)methyl)piperidin-4-yl)-1H-pyrazol-4-yl)methyl)-2-oxobenzo[cd]indol-1(2H)-yl)piperidine-2,6-dione | ++++ |
| 236 | 3-(6-((1-(1-((1-methylcyclobutyl)methyl)piperidin-4-yl)-1H-pyrazol-4-yl)methyl)-2-oxobenzo[cd]indol-1(2H)-yl)piperidine-2,6-dione | ++++ |
| 237 | 3-(6-((1-(1-((1-methylcyclobutyl)methyl)piperidin-4-yl)-1H-pyrazol-4-yl)methyl)-2-oxobenzo[cd]indol-1(2H)-yl)piperidine-2,6-dione | ++++ |

TABLE 2-continued

| # | Structure | IC$_{50}$ (nM) |
|---|---|---|
| 238 | 3-(6-((1-(1-(2-oxabicyclo[2.1.1]hexane-4-carbonyl)-4-methylpiperidin-4-yl)-1H-pyrazol-4-yl)methyl)-2-oxobenzo[cd]indol-1(2H)-yl)piperidine-2,6-dione | ++++ |
| 239 | 3-(6-((1-(1-(2-oxabicyclo[2.1.1]hexane-4-carbonyl)-4-methylpiperidin-4-yl)-1H-pyrazol-4-yl)methyl)-2-oxobenzo[cd]indol-1(2H)-yl)piperidine-2,6-dione | ++++ |
| 240 | 3-(2-oxo-6-((1-(1-(2,2,3,3-tetramethylcyclopropyl)piperidin-4-yl)-1H-pyrazol-4-yl)methyl)benzo[cd]indol-1(2H)-yl)piperidine-2,6-dione | ++++ |
| 241 | tert-butyl 4-(4-(1-(2,6-dioxopiperidin-3-yl)-2-oxo-1,2-dihydrobenzo[cd]indole-6-carbonyl)-1H-pyrazol-1-yl)-4-methylpiperidine-1-carboxylate | +++ |
| 242 | 3-(2-oxo-6-((1-(1-(spiro[3.4]octan-5-yl)piperidin-4-yl)-1H-pyrazol-4-yl)methyl)benzo[cd]indol-1(2H)-yl)piperidine-2,6-dione | ++++ |

TABLE 2-continued

| # | Structure | IC$_{50}$ (nM) |
|---|---|---|
| 243 | 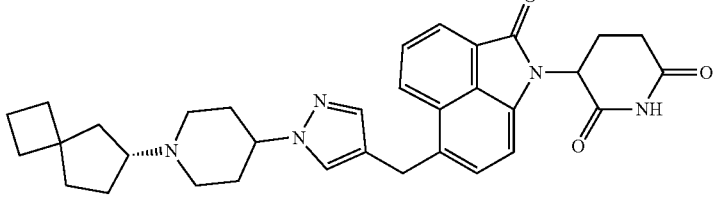<br>3-(2-oxo-6-((1-(1-(spiro[3.4]octan-5-yl)piperidin-4-yl)-1H-pyrazol-4-yl)methyl)benzo[cd]indol-1(2H)-yl)piperidine-2,6-dione | ++++ |
| 244 | 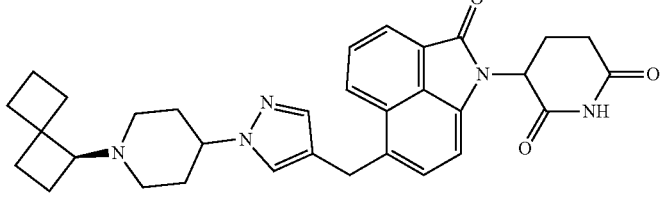<br>3-(2-oxo-6-((1-(1-(spiro[3.3]heptan-1-yl)piperidin-4-yl)-1H-pyrazol-4-yl)methyl)benzo[cd]indol-1(2H)-yl)piperidine-2,6-dione | ++++ |
| 245 | 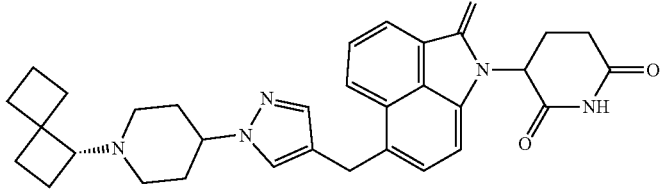<br>3-(2-oxo-6-((1-(1-(spiro[3.3]heptan-1-yl)piperidin-4-yl)-1H-pyrazol-4-yl)methyl)benzo[cd]indol-1(2H)-yl)piperidine-2,6-dione | ++++ |
| 246 | 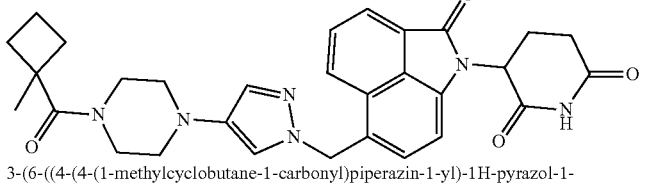<br>3-(6-((4-(4-(1-methylcyclobutane-1-carbonyl)piperazin-1-yl)-1H-pyrazol-1-yl)methyl)-2-oxobenzo[cd]indol-1(2H)-yl)piperidine-2,6-dione | ++++ |
| 247 | 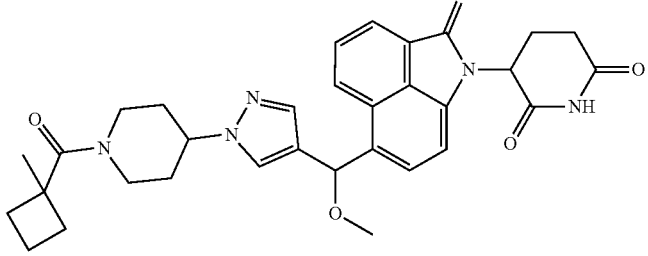<br>3-(6-(methoxy(1-(1-(1-methylcyclobutane-1-carbonyl)piperidin-4-yl)-1H-pyrazol-4-yl)methyl)-2-oxobenzo[cd]indol-1(2H)-yl)piperidine-2,6-dione | ++++ |
| 248 | 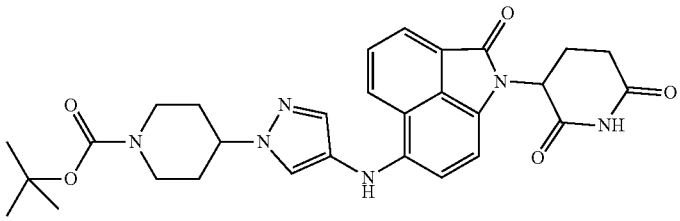 [SMILES: CC(C)(C)OC(=O)N1CCC(n2cc(Nc3ccc4c5c(cccc35)C(=O)N4C3CCC(=O)NC3=O)cn2)CC1]<br>tert-butyl 4-(4-((1-(2,6-dioxopiperidin-3-yl)-2-oxo-1,2-dihydrobenzo[cd]indol-6-yl)amino)-1H-pyrazol-1-yl)piperidine-1-carboxylate | +++ |

| # | Structure | IC$_{50}$ (nM) |
|---|---|---|
| 249 | 3-(6-((1-(1-(1-methylcyclobutane-1-carbonyl)piperidin-4-yl)-1H-pyrazol-4-yl)amino)-2-oxobenzo[cd]indol-1(2H)-yl)piperidine-2,6-dione | +++ |
| 250 | tert-butyl 4-(3-chloro-4-(((1-(2,6-dioxopiperidin-3-yl)-2-oxo-1,2-dihydrobenzo[cd]indol-6-yl)amino)-1H-pyrazol-1-yl)piperidine-1-carboxylate | +++ |
| 251 | 3-(6-((3-chloro-1-(1-(1-methylcyclobutane-1-carbonyl)piperidin-4-yl)-1H-pyrazol-4-yl)amino)-2-oxobenzo[cd]indol-1(2H)-yl)piperidine-2,6-dione | +++ |
| 252 | tert-butyl 4-(4-(((1-(2,6-dioxopiperidin-3-yl)-2-oxo-1,2-dihydrobenzo[cd]indol-6-yl)(methyl)amino)-1H-pyrazol-1-yl)piperidine-1-carboxylate | +++ |

TABLE 2-continued

| # | Structure | IC$_{50}$ (nM) |
|---|---|---|
| 253 | 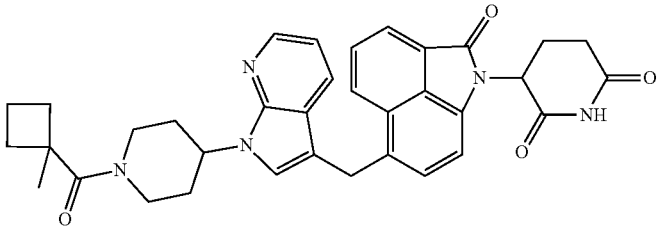 [SMILES: CC1(C(=O)N2CCC(n3cc(Cc4ccc5c6c(cccc46)C(=O)N5C4CCC(=O)NC4=O)c4cccnc43)CC2)CCC1]  3-(6-((1-(1-(1-methylcyclobutane-1-carbonyl)piperidin-4-yl)-1H-pyrrolo[2,3-b]pyridin-3-yl)methyl)-2-oxobenzo[cd]indol-1(2H)-yl)piperidine-2,6-dione | ++++ |
| 254 | 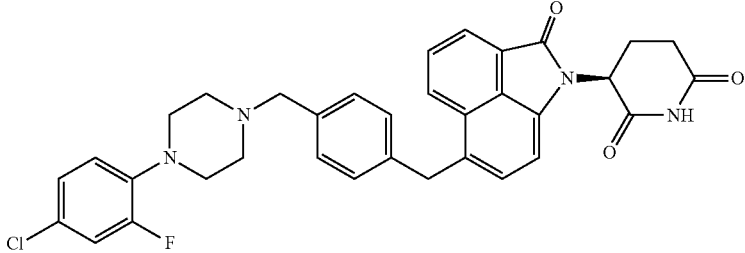 [SMILES: O=C1CC[C@H](N2C(=O)c3cccc4c(Cc5ccc(CN6CCN(c7ccc(Cl)cc7F)CC6)cc5)ccc2c34)C(=O)N1]  3-(6-(4-((4-(4-chloro-2-fluorophenyl)piperazin-1-yl)methyl)benzyl)-2-oxobenzo[cd]indol-1(2H)-yl)piperidine-2,6-dione | ++++ |
| 255 | 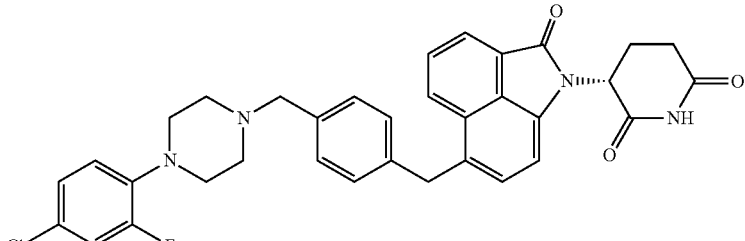  3-(6-(4-((4-(4-chloro-2-fluorophenyl)piperazin-1-yl)methyl)benzyl)-2-oxobenzo[cd]indol-1(2H)-yl)piperidine-2,6-dione | ++++ |
| 256 | 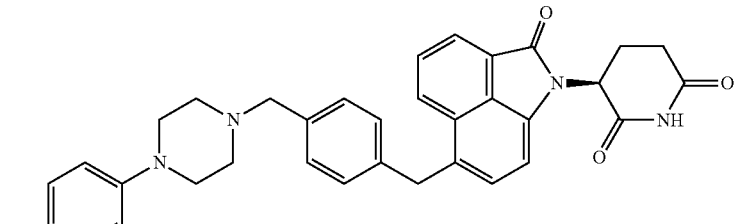  3-(6-(4-((4-(2,4-difluorophenyl)piperazin-1-yl)methyl)benzyl)-2-oxobenzo[cd]indol-1(2H)-yl)piperidine-2,6-dione | ++++ |
| 257 | 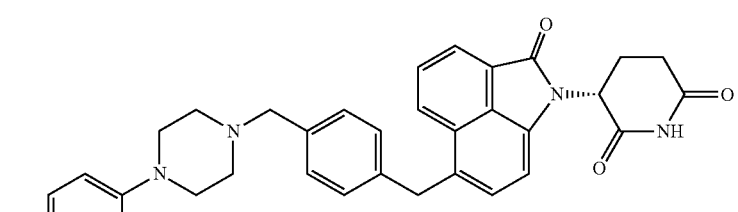  3-(6-(4-((4-(2,4-difluorophenyl)piperazin-1-yl)methyl)benzyl)-2-oxobenzo[cd]indol-1(2H)-yl)piperidine-2,6-dione | ++++ |

TABLE 2-continued

| # | Structure | IC$_{50}$ (nM) |
|---|---|---|
| 258 | 3-(6-(4-((4-(4-fluorophenoxy)piperidin-1-yl)methyl)benzyl)-2-oxobenzo[cd]indol-1(2H)-yl)piperidine-2,6-dione | ++++ |
| 259 | 3-(6-((1-((1s,4s)-4-neopentylcyclohexyl)-1H-pyrazol-4-yl)methyl)-2-oxobenzo[cd]indol-1(2H)-yl)piperidine-2,6-dione | ++++ |
| 260 | 3-(6-((1-((1r,4r)-4-neopentylcyclohexyl)-1H-pyrazol-4-yl)methyl)-2-oxobenzo[cd]indol-1(2H)-yl)piperidine-2,6-dione | ++++ |
| 261 | N-cyclopropyl-4-(4-((1-(2,6-dioxopiperidin-3-yl)-2-oxo-1,2-dihydrobenzo[cd]indol-6-yl)methyl)-1H-pyrazol-1-yl)-N-methylpiperidine-1-carboxamide | ++++ |
| 262 | 4-(4-(1-(4-((1-(2,6-dioxopiperidin-3-yl)-2-oxo-1,2-dihydrobenzo[cd]indol-6-yl)methyl)phenyl)cyclopropyl)piperazin-1-yl)-3-fluorobenzonitrile | ++++ |

TABLE 2-continued

| # | Structure | IC$_{50}$ (nM) |
|---|---|---|
| 263 | 3-(6-(4-(1-(4-(1-methylcyclobutane-1-carbonyl)piperazin-1-yl)cyclopropyl)benzyl)-2-oxobenzo[cd]indol-1(2H)-yl)piperidine-2,6-dione | ++++ |
| 264 | 3-(6-(4-(1-(4-(2-fluorophenyl)piperazin-1-yl)cyclopropyl)benzyl)-2-oxobenzo[cd]indol-1(2H)-yl)piperidine-2,6-dione | ++++ |
| 265 | 3-(6-((1-(1-(3-methyl-3-azabicyclo[3.1.1]heptane-1-carbonyl)piperidin-4-yl)-1H-pyrazol-4-yl)methyl)-2-oxobenzo[cd]indol-1(2H)-yl)piperidine-2,6-dione | ++++ |
| 266 | tert-butyl 4-(4-((1-(2,6-dioxopiperidin-3-yl)-2-oxo-1,2-dihydrobenzo[cd]indol-6-yl)(hydroxy)methyl)-1H-pyrazol-1-yl)piperidine-1-carboxylate | ++++ |

TABLE 2-continued

| # | Structure | IC$_{50}$ (nM) |
|---|---|---|
| 267 | 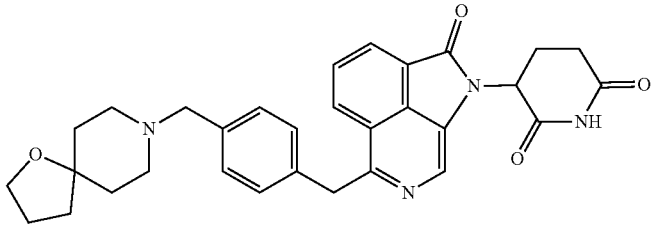 [SMILES: O=C1CCC(N2C(=O)c3cccc4c(Cc5ccc(CN6CCC7(CCCO7)CC6)cc5)ncc2c34)C(=O)N1]<br>3-(6-(4-((1-oxa-8-azaspiro[4.5]decan-8-yl)methyl)benzyl)-2-oxopyrrolo[2,3,4-de]isoquinolin-1(2H)-yl)piperidine-2,6-dione | ++++ |
| 268 | 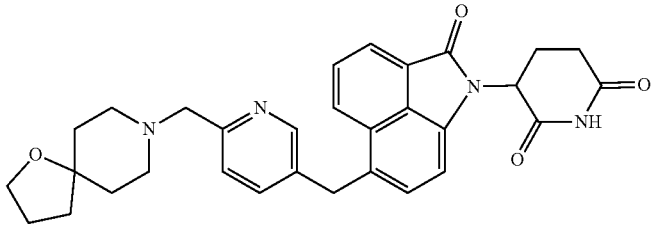 [SMILES: O=C1CCC(N2C(=O)c3cccc4c(Cc5ccc(CN6CCC7(CCCO7)CC6)nc5)ccc2c34)C(=O)N1]<br>3-(6-((6-((1-oxa-8-azaspiro[4.5]decan-8-yl)methyl)pyridin-3-yl)methyl)-2-oxobenzo[cd]indol-1(2H)-yl)piperidine-2,6-dione | ++++ |
| 269 | 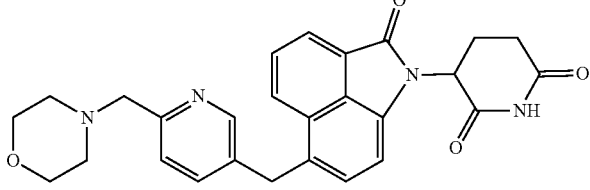<br>3-(6-((6-(morpholinomethyl)pyridin-3-yl)methyl)-2-oxobenzo[cd]indol-1(2H)-yl)piperidine-2,6-dione | ++++ |
| 270 | 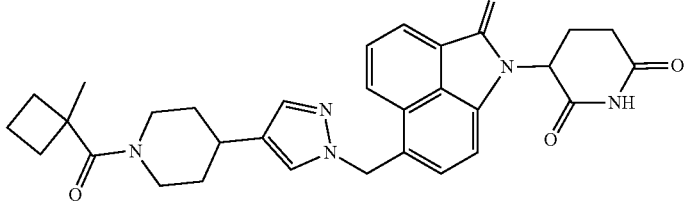<br>3-(6-((4-(1-(1-methylcyclobutane-1-carbonyl)piperidin-4-yl)-1H-pyrazol-1-yl)methyl)-2-oxobenzo[cd]indol-1(2H)-yl)piperidine-2,6-dione | ++++ |
| 271 | 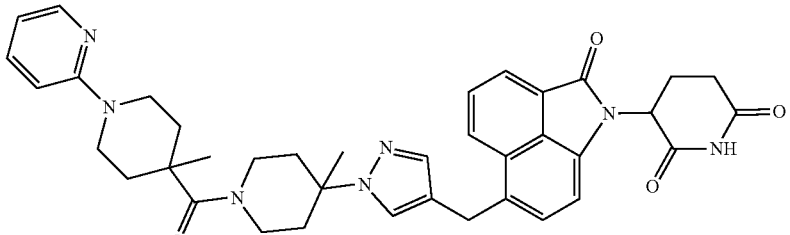<br>3-(6-((1-(4-methyl-1-(4-methyl-1-(pyridin-2-yl)piperidine-4-carbonyl)piperidin-4-yl)-1H-pyrazol-4-yl)methyl)-2-oxobenzo[cd]indol-1(2H)-yl)piperidine-2,6-dione | ++++ |

TABLE 2-continued

| # | Structure | IC$_{50}$ (nM) |
|---|---|---|
| 272 | 3-(6-((1-(4-methyl-1-(1-(pyridin-2-yl)piperidine-4-carbonyl)piperidin-4-yl)-1H-pyrazol-4-yl)methyl)-2-oxobenzo[cd]indol-1(2H)-yl)piperidine-2,6-dione | ++++ |
| 273 | 3-(6-(4-(morpholinomethyl)phenoxy)-2-oxobenzo[cd]indol-1(2H)-yl)piperidine-2,6-dione | ++++ |
| 274 | 3-(6-((1-((7R)-4-(2-methylbutyl)-4-azaspiro[2.5]octan-7-yl)-1H-pyrazol-4-yl)methyl)-2-oxobenzo[cd]indol-1(2H)-yl)piperidine-2,6-dione | ++++ |
| 275 | 3-(6-((1-(4-((1-methylcyclobutyl)methyl)-4-azaspiro[2.5]ocian-7-yl)-1H-pyrazol-4-yl)methyl)-2-oxobenzo[cd]indol-1(2H)-yl)piperidine-2,6-dione | ++++ |
| 276 | tert-butyl 4-(1-(2,6-dioxopiperidin-3-yl)-2-oxo-1,2-dihydrobenzo[cd]indol-6-yl)piperidine-1-carboxylate | |

TABLE 2-continued

| # | Structure | IC$_{50}$ (nM) |
|---|---|---|
| 277 | 3-(6-benzyl-2-oxobenzo[cd]indol-1(2H)-yl)piperidine-2,6-dione | ++++ |
| 278 | 3-(6-(3-fluoro-4-(morpholinomethyl)benzyl)-2-oxobenzo[cd]indol-1(2H)-yl)piperidine-2,6-dione | ++++ |
| 279 | 4-(4-((5-(((1-(2,6-dioxopiperidin-3-yl)-2-oxo-1,2-dihydrobenzo[cd]indol-6-yl)methyl)pyridin-2-yl)methyl)piperazin-1-yl)-3-fluorobenzonitrile | ++++ |
| 280 | 3-(6-((1-(1-(1-cyclobutylethyl)piperidin-4-yl)-1H-pyrazol-4-yl)methyl)-2-oxobenzo[cd]indol-1(2H)-yl)piperidine-2,6-dione | ++++ |
| 281 | 3-(6-((1-(1-(1-cyclobutylethyl)piperidin-4-yl)-1H-pyrazol-4-yl)methyl)-2-oxobenzo[cd]indol-1(2H)-yl)piperidine-2,6-dione | ++++ |
| 282 | 3-(6-((1-(1-(1-cyclopropylethyl)piperidin-4-yl)-1H-pyrazol-4-yl)methyl)-2-oxobenzo[cd]indol-1(2H)-yl)piperidine-2,6-dione | ++++ |

TABLE 2-continued

| # | Structure | IC$_{50}$ (nM) |
|---|---|---|
| 283 | 3-(6-((1-(1-(1-cyclopropylethyl)piperidin-4-yl)-1H-pyrazol-4-yl)methyl)-2-oxobenzo[cd]indol-1(2H)-yl)piperidine-2,6-dione | ++++ |
| 284 | 3-(6-(4-(1-(4-(2-fluorophenyl)piperazin-1-yl)ethyl)benzyl)-2-oxobenzo[cd]indol-1(2H)-yl)piperidine-2,6-dione | ++++ |
| 285 | 3-(6-(4-(1-(4-(2-fluorophenyl)piperazin-1-yl)ethyl)benzyl)-2-oxobenzo[cd]indol-1(2H)-yl)piperidine-2,6-dione | ++++ |
| 286 | 3-(6-(4-((4-(2-fluorophenyl)piperazin-1-yl)methyl)-3-methylbenzyl)-2-oxobenzo[cd]indol-1(2H)-yl)piperidine-2,6-dione | ++++ |
| 287 | 3-(6-((1-(1-(1-(dimethylamino)cyclobutane-1-carbonyl)piperidin-4-yl)-1H-pyrazol-4-yl)methyl)-2-oxobenzo[cd]indol-1(2H)-yl)piperidine-2,6-dione | ++++ |

TABLE 2-continued

| # | Structure | IC$_{50}$ (nM) |
|---|---|---|
| 288 | 3-(2-oxo-6-((1-(1-(spiro[3.3]heptan-2-yl)piperidin-4-yl)-1H-pyrazol-4-yl)methyl)benzo[cd]indol-1(2H)-yl)piperidine-2,6-dione | ++++ |
| 289 | 3-(6-((1-(1-(1-methylcyclobutane-1-carbonyl)piperidin-4-yl)-1H-pyrazol-4-yl)methyl)-2-oxopyrrolo[4,3,2-ij]isoquinolin-1(2H)-yl)piperidine-2,6-dione | +++ |
| 290 | 3-(6-(3-(1-(1-methylcyclobutane-1-carbonyl)piperidin-4-yl)benzyl)-2-oxobenzo[cd]indol-1(2H)-yl)piperidine-2,6-dione | ++++ |
| 291 | 3-(6-((2-(morpholinomethyl)pyrimidin-5-yl)methyl)-2-oxobenzo[cd]indol-1(2H)-yl)piperidine-2,6-dione | |

TABLE 2-continued

| # | Structure | IC$_{50}$ (nM) |
|---|---|---|
| 292 | tert-butyl 1-(4-(4-(((1-(2,6-dioxopiperidin-3-yl)-2-oxo-1,2-dihydrobenzo[cd]indol-6-yl)methyl)-1H-pyrazol-1-yl)piperidine-1-carbonyl)-3-azabicyclo[3.1.1]heptane-3-carboxylate | ++++ |
| 293 | 4-(4-(((1-(2,6-dioxopiperidin-3-yl)-2-oxo-1,2-dihydrobenzo[cd]indol-6-yl)methyl)-1H-pyrazol-1-yl)-1-((1-methylcyclopropyl)methyl)piperidine-4-carbonitrile | |
| 294 | 1-methyl-3-(6-(((1-(1-((1-methylcyclobutyl)methyl)piperidin-4-yl)-1H-pyrazol-4-yl)methyl)-2-oxobenzo[cd]indol-1(2H)-yl)piperidine-2,6-dione | +++ |

TABLE 2-continued

| # | Structure | IC$_{50}$ (nM) |
|---|-----------|----------------|
| 295 | 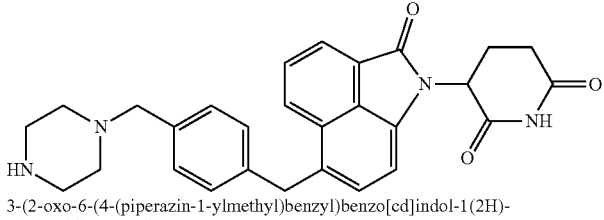 3-(2-oxo-6-(4-(piperazin-1-ylmethyl)benzyl)benzo[cd]indol-1(2H)-yl)piperidine-2,6-dione | |

In the above table: ++++ is < 1 nM; +++ is < 100 nM; ++ is < 999 nM, and + > 999 nM.

All publications and patent applications cited in this specification are herein incorporated by reference as if each individual publication or patent application were specifically and individually indicated to be incorporated by reference.

Although the foregoing invention has been described in some detail by way of illustration and example for the purposes of clarity of understanding, it will be readily apparent to one of ordinary skill in the art in light of the teaching of this invention that certain changes and modification may be made thereto without departing from the spirit or scope of the invention as defined in the claims.

We claim:
1. A compound of Formula:

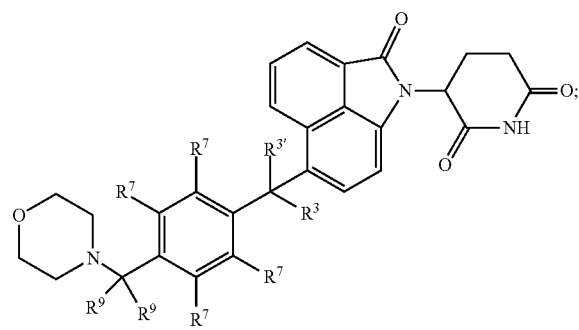

or a pharmaceutically acceptable salt thereof,
wherein:
$R^2$ is independently selected at each occurrence from the group consisting of hydrogen, alkyl, and haloalkyl;
$R^3$ is hydrogen, halogen, alkyl, haloalkyl, —$OR^8$, or —$NR^8R^{8'}$;
$R^{3'}$ is hydrogen;
$R^7$ is independently selected at each occurrence from the group consisting of hydrogen, halogen, hydroxyl, cyano, nitro, alkyl, haloalkyl, alkenyl, alkynyl, cycloalkyl, heterocycle, aryl, heteroaryl, —$OR^8$, —$NR^8R^{8'}$, —$C(O)R^8$, —$C(O)OR^8$, —$C(O)$—$NR^8R^{8'}$, —$OC(O)R^8$, —$NR^8$—$C(O)R^8$, —$S(O)R^8$, —$SO_2R^8$, —$SO_2$—$OR^8$, and —$SO_2$—$NR^8R^{8'}$;
$R^8$ and $R^{8'}$ are independently selected at each occurrence from the group consisting of hydrogen, alkyl, haloalkyl, alkenyl, and alkynyl;
each $R^9$ is independently selected from the group consisting of hydrogen and alkyl.
2. The compound of claim 1, wherein one $R^7$ is hydrogen.

3. The compound of claim 1, wherein two $R^7$s are hydrogen.
4. The compound of claim 3, wherein the remaining $R^7$s are independently selected at each occurrence from the group consisting of alkyl, halogen, and haloalkyl.
5. The compound of claim 1, wherein three $R^7$s are hydrogen.
6. The compound of claim 1, wherein $R^7$ is independently selected at each occurrence from the group consisting of hydrogen, halogen, hydroxyl, alkyl, haloalkyl, alkene, alkyne, heterocycle, aryl, and heteroaryl.
7. The compound of claim 1, wherein $R^7$ is independently selected at each occurrence from the group consisting of hydrogen, alkyl, halogen, and haloalkyl.
8. The compound of claim 1, wherein $R^7$ is independently selected at each occurrence from the group consisting of hydrogen and halogen.
9. The compound of claim 1, wherein all $R^7$s are hydrogen.
10. The compound of claim 1, wherein $R^3$ is hydrogen.
11. The compound of claim 10, wherein both $R^9$s are hydrogen.
12. The compound of claim 10, wherein all $R^7$s are hydrogen.
13. The compound of claim 1, wherein both $R^9$s are hydrogen.
14. The compound of claim 13, wherein all $R^7$s are hydrogen.
15. The compound of claim 13, wherein $R^7$ is independently selected at each occurrence from the group consisting of hydrogen, halogen, hydroxyl, alkyl, haloalkyl, alkene, alkyne, heterocycle, aryl, and heteroaryl.
16. The compound of claim 13, wherein $R^7$ is independently selected at each occurrence from the group consisting of hydrogen, alkyl, halogen, and haloalkyl.
17. The compound of claim 13, wherein $R^7$ is independently selected at each occurrence from the group consisting of hydrogen and halogen.
18. The compound of claim 13, wherein three $R^7$s are hydrogen.
19. The compound of claim 1, wherein the compound is

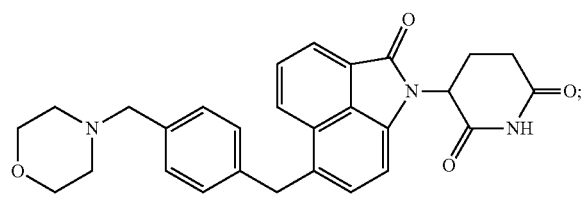 [SMILES: O=C1CCC(N2C(=O)c3cccc4c(Cc5ccc(CN6CCOCC6)cc5)ccc2c34)C(=O)N1]

or a pharmaceutically acceptable salt thereof.

20. A compound of structure:

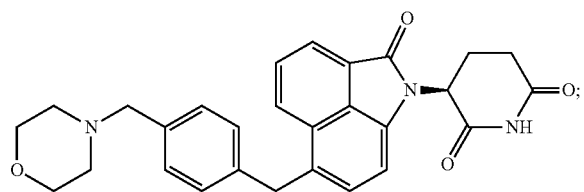 [SMILES: O=C1CC[C@H](N2C(=O)c3cccc4c(Cc5ccc(CN6CCOCC6)cc5)ccc2c34)C(=O)N1]

or a pharmaceutically acceptable salt thereof.

21. The compound of claim 1, wherein the compound is:

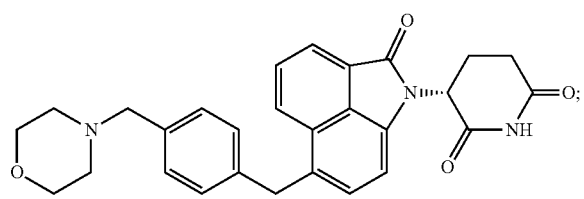 [SMILES: O=C1CC[C@@H](N2C(=O)c3cccc4c(Cc5ccc(CN6CCOCC6)cc5)ccc2c34)C(=O)N1]

or a pharmaceutically acceptable salt thereof.

22. A pharmaceutical composition comprising a compound of claim 1 or a pharmaceutical salt thereof and a pharmaceutically acceptable excipient.

23. A pharmaceutical composition comprising a compound and a pharmaceutically acceptable excipient, wherein the compound is

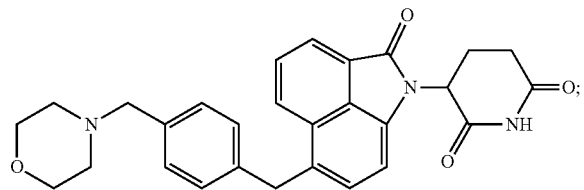 [SMILES: O=C1CCC(N2C(=O)c3cccc4c(Cc5ccc(CN6CCOCC6)cc5)ccc2c34)C(=O)N1]

or a pharmaceutically acceptable salt thereof.

24. The pharmaceutical composition of claim 23, wherein the compound is

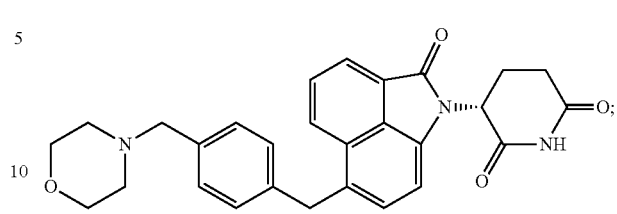

or a pharmaceutically acceptable salt thereof.

25. The pharmaceutical composition of claim 23, wherein the compound is

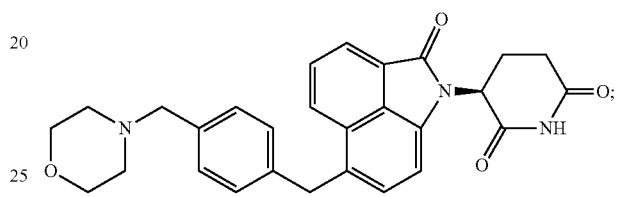

or a pharmaceutically acceptable salt thereof.

26. The pharmaceutical composition of claim 25, wherein the pharmaceutical composition is formulated for oral administration.

27. The pharmaceutical composition of claim 26, wherein the pharmaceutical composition is a tablet.

28. The pharmaceutical composition of claim 26, wherein the pharmaceutical composition is a capsule.

29. The pharmaceutical composition of claim 25, wherein the pharmaceutical composition is formulated for parenteral administration.

30. The pharmaceutical composition of claim 25, wherein the pharmaceutical composition is formulated for intravenous administration.

* * * * *

UNITED STATES PATENT AND TRADEMARK OFFICE
CERTIFICATE OF CORRECTION

PATENT NO. : 11,407,732 B1
APPLICATION NO. : 17/498617
DATED : August 9, 2022
INVENTOR(S) : James A. Henderson et al.

It is certified that error appears in the above-identified patent and that said Letters Patent is hereby corrected as shown below:

In the Claims

In Claim 1, Column 911 Line 60:
$-NR^8-C(O)R^8$
Should read:
$-NR^2-C(O)R^8$.

Signed and Sealed this
Twenty-seventh Day of December, 2022

Katherine Kelly Vidal
*Director of the United States Patent and Trademark Office*